(12) United States Patent
Kurtz et al.

(10) Patent No.: US 11,634,779 B2
(45) Date of Patent: *Apr. 25, 2023

(54) METHODS AND SYSTEMS FOR ANALYZING NUCLEIC ACID MOLECULES

(71) Applicant: The Board of Trustees of the Leland Stanford Junior University, Stanford, CA (US)

(72) Inventors: David M. Kurtz, San Carlos, CA (US); Maximilian Diehn, San Carlos, CA (US); Arash Ash Alizadeh, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/661,730

(22) Filed: May 2, 2022

(65) Prior Publication Data
US 2022/0340980 A1 Oct. 27, 2022

Related U.S. Application Data

(63) Continuation of application No. 17/455,209, filed on Nov. 16, 2021, now Pat. No. 11,447,833, which is a continuation of application No. PCT/US2020/059526, filed on Nov. 6, 2020.

(60) Provisional application No. 62/931,688, filed on Nov. 6, 2019.

(51) Int. Cl.
| | |
|---|---|
| *C12Q 1/6886* | (2018.01) |
| *G16B 30/10* | (2019.01) |
| *G16B 20/20* | (2019.01) |
| *G16B 35/20* | (2019.01) |
| *G16B 30/00* | (2019.01) |
| *C12Q 1/6874* | (2018.01) |
| *G16H 70/60* | (2018.01) |
| *G16H 10/40* | (2018.01) |
| *G16H 50/30* | (2018.01) |
| *G16H 50/70* | (2018.01) |
| *G16H 20/10* | (2018.01) |
| *G16B 40/00* | (2019.01) |
| *G16B 20/10* | (2019.01) |
| *C12N 15/10* | (2006.01) |
| *G16H 50/20* | (2018.01) |
| *C12Q 1/6869* | (2018.01) |
| *G16H 10/60* | (2018.01) |

(52) U.S. Cl.
CPC ....... *C12Q 1/6886* (2013.01); *C12N 15/1089* (2013.01); *C12Q 1/6869* (2013.01); *C12Q 1/6874* (2013.01); *G16B 20/10* (2019.02); *G16B 20/20* (2019.02); *G16B 30/00* (2019.02); *G16B 30/10* (2019.02); *G16B 35/20* (2019.02); *G16B 40/00* (2019.02); *G16H 10/40* (2018.01); *G16H 20/10* (2018.01); *G16H 50/20* (2018.01); *G16H 50/30* (2018.01); *G16H 50/70* (2018.01); *G16H 70/60* (2018.01); *C12Q 2600/112* (2013.01); *C12Q 2600/156* (2013.01); *C12Q 2600/158* (2013.01); *G16H 10/60* (2018.01)

(58) Field of Classification Search
None
See application file for complete search history.

(56) References Cited

U.S. PATENT DOCUMENTS

| | | |
|---|---|---|
| 5,804,396 A | 9/1998 | Plowman |
| 6,171,856 B1 | 1/2001 | Thigpen et al. |
| 9,340,830 B2 | 5/2016 | Lipson et al. |
| 9,598,731 B2 | 3/2017 | Talasaz |
| 9,834,822 B2 | 12/2017 | Talasaz |
| 9,840,743 B2 | 12/2017 | Talasaz |
| 9,850,523 B1 | 12/2017 | Chudova et al. |
| 9,902,992 B2 | 2/2018 | Talasaz et al. |
| 9,920,366 B2 | 3/2018 | Eltoukhy et al. |
| 10,041,127 B2 | 8/2018 | Talasaz |
| 10,450,611 B2 | 10/2019 | West et al. |
| 10,457,955 B2 | 10/2019 | Kumar et al. |
| 10,494,678 B2 | 12/2019 | Talasaz |
| 10,501,808 B2 | 12/2019 | Talasaz |
| 10,501,810 B2 | 12/2019 | Talasaz |
| 10,704,085 B2 | 7/2020 | Talasaz et al. |
| 10,704,086 B2 | 7/2020 | Talasaz et al. |
| 10,738,364 B2 | 8/2020 | Talasaz |
| 11,299,783 B2 | 4/2022 | West et al. |

(Continued)

FOREIGN PATENT DOCUMENTS

| | | |
|---|---|---|
| CN | 113383085 A | 9/2021 |
| DE | 112020005433 T5 | 10/2022 |

(Continued)

OTHER PUBLICATIONS

Corcoran et al. Application of Cell-free DNA Analysis to Cancer Treatment The New England Journal of Medicine vol. 379, pp. 1754-1765 (Year: 2018).*

(Continued)

*Primary Examiner* — John S Brusca
(74) *Attorney, Agent, or Firm* — KPPB LLP

(57) ABSTRACT

Processes and materials to detect cancer from a biopsy are described. In some cases, cell-free nucleic acids can be sequenced, and the sequencing result can be utilized to detect sequences derived from a neoplasm. Detection of somatic variants occurring in phase can indicate the presence of cancer in a diagnostic scan and a clinical intervention can be performed.

14 Claims, 86 Drawing Sheets

Specification includes a Sequence Listing.

(56) References Cited

U.S. PATENT DOCUMENTS

| | | | |
|---|---|---|---|
| 11,384,394 | B2 | 7/2022 | Bartha et al. |
| 11,447,833 | B2 * | 9/2022 | Kurtz ................ G16B 30/10 |
| 2002/0015718 | A1 | 2/2002 | Kruse et al. |
| 2014/0296081 | A1 | 10/2014 | Diehn et al. |
| 2015/0376700 | A1 | 12/2015 | Schnall-Levin et al. |
| 2016/0032396 | A1 | 2/2016 | Diehn et al. |
| 2017/0107576 | A1 | 4/2017 | Babiarz et al. |
| 2018/0251848 | A1 | 9/2018 | Diehn et al. |
| 2019/0264257 | A1 | 8/2019 | Desharnais et al. |
| 2020/0131505 | A1 | 4/2020 | Green et al. |
| 2021/0025005 | A1 | 1/2021 | Babiarz et al. |
| 2021/0172022 | A1 | 6/2021 | Kurtz et al. |
| 2021/0366571 | A1 | 11/2021 | Kurtz et al. |
| 2022/0139497 | A1 | 5/2022 | Kurtz et al. |
| 2022/0208303 | A1 | 6/2022 | Kurtz et al. |
| 2022/0251664 | A1 | 8/2022 | Kurtz et al. |

FOREIGN PATENT DOCUMENTS

| | | |
|---|---|---|
| EP | 3561075 A1 | 10/2019 |
| EP | 4055187 A1 | 9/2022 |
| GB | 2595193 A | 11/2021 |
| GB | 2595193 B | 10/2022 |
| HK | 40060652 A | 5/2022 |
| HK | 40064341 A | 6/2022 |
| IN | 202217026392 A | 7/2022 |
| KR | 1020220094218 A | 7/2022 |
| MX | MX/a/2022/005588 | 9/2022 |
| WO | 2016040901 A1 | 3/2016 |
| WO | 2017161175 A1 | 9/2017 |
| WO | 2018231818 A1 | 12/2018 |
| WO | 2021092476 A1 | 5/2021 |
| WO | 2021173722 A2 | 9/2021 |
| WO | 2021173722 A3 | 9/2021 |
| WO | 2021173724 A1 | 9/2021 |

OTHER PUBLICATIONS

Newman et al. Integrated digital error suppression for improved detection of circulating tumor DNA Nature Biotechnology vol. 34, pp. 547-555 (Year: 2016).*

Roberts et al. Hypermutation in human cancer genomes: footprints and mechanisms Nature Reviews Cancer vol. 14, pp. 786-800 (Year: 2014).*

"Format Requirements for eDissertation", Stanford University Registrar's Office: Student Affairs Website, Retrieved from https://registrar.stanford.edu/students/dissertation-and-thesis-submission/preparing-dissertations-electronic-submission/format on Aug. 19, 2021, 5 pgs.

"Pan-cancer analysis of whole genomes", The ICGC/TCGA Pan-Cancer Analysis of Whole Genomes Consortium, Nature, vol. 578, Feb. 5, 2020, pp. 82-93.

"Permission to publish", Stanford Libraries, Special Collections & University Archives, Retrieved from https://library.stanford.edu/spc/using-our-collections/permission-publish on Aug. 30, 2021, 3 pgs.

"Personalized risk assessment and disease monitoring in non-Hodgkin Lymphoma from circulating tumor DNA [electronic resource]", Stanford University Library Searchworks Catalog, Retrieved from https://searchworks.stanford.edu/view/12266090 on Jul. 21, 2021, 2 pgs.

"Reading room policies & procedures", Stanford Libraries, Special Collections & University Archives, Retrieved from https://library.stanford.edu/spc/using-our-collections/reading-room-policies-procedures on Jul. 30, 2021, 3 pgs.

"Special policies: Guidelines to counsel & researchers seeking discovery from Stanford Libraries", Stanford Libraries, Retrieved from https://library.stanford.edu/using/special-policies/guidelines-counsel-researchers-seeking-discovery-stanford-libraries on Jun. 25, 2021, 2 pgs.

"Using our collections", Stanford Libraries, Special Collections & University Archives, Retrieved from https://library.stanford.edu/spc/using-our-collections on Aug. 19, 2021, 3 pgs.

Abbosh et al., "Abstract CT023: Phylogenetic tracking and minimal residual disease detection using ctDNA in early-stage NSCLC: A lung TRACERx study", Cancer Research, Proceedings of AACR Annual Meeting on Apr. 27-28, 2020 and Jun. 22-24, 2020, Philadelphia, PA, Retrieved from: https://cancerres.aacrjournals.org/content/80/16_Supplement/CT023, Published Aug. 2020, Accessed Sep. 14, 2021, 4 pgs.

Abbosh et al., "Early stage NSCLC—challenges to implementing ctDNA-based screening and MRD detection", Nature Reviews Clinical Oncology, vol. 15, Jul. 3, 2018, pp. 577-586.

Abbosh et al., "Phylogenetic ctDNA analysis depicts early-stage lung cancer evolution", Nature, vol. 545, Apr. 26, 2017, pp. 446-451.

Alexandrov et al., "Clock-like mutational processes in human somatic cells", Nature Genetics, vol. 47, Nov. 9, 2015, pp. 1402-1407.

Alexandrov et al., "Signatures of mutational processes in human cancer", Nature, vol. 500, Aug. 14, 2013, pp. 415-421, doi:10.1038/nature12477.

Alexandrov et al., "The repertoire of mutational signatures in human cancer", Nature, vol. 578, Feb. 5, 2020, pp. 94-101.

Alizadeh et al., "Distinct types of diffuse large B-cell lymphoma identified by gene expression profiling", Nature, Feb. 3, 2000, vol. 403, pp. 503-511.

Alkodsi et al., "Distinct subtypes of diffuse large B-cell lymphoma defined by hypermutated genes", Leukemia, vol. 33, Jun. 11, 2019, pp. 2662-2672.

Bell et al., "Chromosome-scale mega-haplotypes enable digital karyotyping of cancer aneuploidy", Nucleic Acids Research, vol. 45, No. 19, Nov. 2, 2017, 13 pgs.

Bettegowda et al., "Detection of Circulating Tumor DNA in Early- and Late-Stage Human Malignancies", Science Translational Medicine, vol. 6, No. 224, Feb. 19, 2014, 11 pgs.

Bianconi et al., "An estimation of the number of cells in the human body", Annals of Human Biology, vol. 40, No. 6, Jul. 5, 2013, pp. 463-471.

Bozdech et al., "Expression profiling of the schizont and trophozoite stages of Plasmodium falciparum with a long-oligonucleotide microarray", Genome Biology, vol. 4, No. R9, Jan. 31, 2003, 15 pgs.

Brenner et al., "Next-generation sequencing diagnostics of bacteremia in sepsis (Next GeneSiS-Trial): Study protocol of a prospective, observational, noninterventional, multicenter, clinical trial", Medicine, vol. 97, No. 6, Feb. 2018, 8 pgs.

Burns et al., "Evidence for APOBEC3B mutagenesis in multiple human cancers", Nature Genetics, vol. 45, Jul. 14, 2013, pp. 977-983.

Chabon et al., "Circulating tumour DNA profiling reveals heterogeneity of EGFR inhibitor resistance mechanisms in lung cancer patients", Nature Communications, vol. 7, No. 11815, Jun. 10, 2016, 14 pgs.

Chabon et al., "Methods and Systems for Analyzing Nucleic Acid Molecules", U.S. Appl. No. 17/661,034, filed Apr. 27, 2022, 554 pgs.

Chaudhuri et al., "Early Detection of Molecular Residual Disease in Localized Lung Cancer by Circulating Tumor DNA Profiling", Cancer Discovery, vol. 7, No. 12, Dec. 2017, pp. 1394-1403, first published online Sep. 24, 2017, DOI: 10.1158/2159-8290/CD-17-0716.

Cibulskis et al., "Sensitive detection of somatic point mutations in impure and heterogeneous cancer samples", Nature Biotechnology, vol. 31, Feb. 10, 2013, pp. 213-219.

De Vlaminck et al., "Circulating Cell-Free DNA Enables Noninvasive Diagnosis of Heart Transplant Rejection", Science Translational Medicine, vol. 6, No. 241, Jun. 18, 2014, 8 pgs.

De Vlaminck et al., "Noninvasive monitoring of infection and rejection after lung transplantation", PNAS, vol. 112, No. 43, Oct. 27, 2015, pp. 13336-13341.

De Yebenes et al., "Activation-induced deaminase: light and darksides", Trends in Molecular Medicine, vol. 12, No. 9, Sep. 1, 2006, pp. 432-439.

Deng et al., "TNER: a novel background error suppression method for mutation detection in circulating tumor DNA", BMC Bioinformatics, vol. 19, No. 387, Oct. 20, 2018, 7 pgs.

(56) References Cited

OTHER PUBLICATIONS

Dewey et al., "Phased Whole-Genome Genetic Risk in a Family Quartet Using a Major Allele Reference Sequence", PLoS Genetics, Sep. 15, 2011, vol. 7, Issue 9, 15 pgs.
Diaz et al., "Performance of Streck cfDNA Blood Collection Tubes for Liquid Biopsy Testing", PLoS One, vol. 11, No. 11, Nov. 10, 2016, 18 pgs.
Diehl et al., "Circulating mutant DNA to assess tumor dynamics", Nature Medicine, vol. 14, Jul. 31, 2008, pp. 985-990.
Dou et al., "Detecting Somatic Mutations in Normal Cells", Trends Genet. Jul. 2018, 34(7): 545-557. doi:10.1016/j.tig.2018.04.003.
Fan et al., "Noninvasive diagnosis of fetal aneuploidy by shotgun sequencing DNA from maternal blood", Proceedings of the National Academy of Sciences USA, Oct. 21, 2008, vol. 105, No. 42, pp. 16266-16271.
Garcia-Murillas et al., "Mutation tracking in circulating tumor DNA predicts relapse in early breast cancer", Science Translational Medicine, vol. 7, No. 302, Aug. 26, 2015, 11 pgs.
Hawkins et al., "Indel-correcting DNA barcodes for high-throughput sequencing", Proceedings of the National Academy of Sciences of the United States of America, Jul. 3, 2018, vol. 115, No. 27, pp. E6217-E6226.
Jaeger et al., "Improved predictions of secondary structures for RNA", Proceedings of the National Academy of Sciences, vol. 86, No. 20, Oct. 1, 1989, pp. 7706-7710.
Jiang et al., "Lengthening and shortening of plasma DNA in hepatocellular carcinoma patients", Proceedings of the National Academy of Sciences, vol. 112, No. 11, Feb. 2, 2015, pp. E1317-E1325.
Kalinich et al., "Cancer detection: Seeking signals in blood", Science, vol. 359, No. 6378, Feb. 23, 2018, pp. 866-867.
Kennedy et al., "Detecting ultralow-frequency mutations by Duplex Sequencing", Nature Protocols, vol. 9, Oct. 9, 2014, pp. 2586-2606.
Khodabakhshi et al., "Recurrent targets of aberrant somatic hypermutation in lymphoma", Oncotarget, vol. 3, No. 11, Nov. 2012, pp. 1308-1319.
Kim et al., "Strelka2: fast and accurate calling of germline and somatic variants", Nature Methods, vol. 15, Jul. 16, 2018, pp. 591-594.
Koboldt et al., "VarScan 2: Somatic mutation and copy No. alteration discovery in cancer by exome sequencing", Genome Research, Feb. 2, 2012, vol. 22, pp. 568-576, www.genome.org/cgi/doi/10.1101/gr.129684.111.
Kurtz, "Personalized Risk Assessment and Disease Monitoring in Non-Hodgkin Lymphoma From Circulating Tumor DNA", ProQuest, Dec. 2017, 258 pgs.
Kurtz et al., "Circulating Tumor DNA Measurements As Early Outcome Predictors in Diffuse Large B-Cell Lymphoma", Journal of Clinical Oncology: Official Journal of the American Society of Clinical Oncology, vol. 36, No. 28, Oct. 1, 2018, pp. 2845-2853.
Kurtz et al., "Methods and Systems for Analyzing Nucleic Acid Molecules", U.S. Appl. No. 17/308,958, filed May 5, 2021, 434 pgs.
Kurtz et al., "Methods and Systems for Analyzing Nucleic Acid Molecules", U.S. Appl. No. 17/820,200, filed Aug. 16, 2022, 387 pgs.
Kurtz et al., "Methods for Preparing Nucleic Acid Libraries for Sequencing", U.S. Appl. No. 17/661,730, filed May 2, 2022, 355 pgs.
Kurtz et al., "Noninvasive monitoring of diffuse large B-cell lymphoma by immunoglobulin high-throughput sequencing", Blood, vol. 125, No. 24, Jun. 11, 2015, pp. 3679-3687.
Kurtz et al., "Phased Variant Enrichment for Enhanced Minimal Residual Disease Detection from Cell-Free DNA", Blood, vol. 134, Supp. 1, Nov. 13, 2019, pp. 552.
Kurtz et al., "Reply to J. Wang et al.", Journal of Clinical Oncology: Official Journal of the American Society of Clinical Oncology, vol. 37, No. 9, Mar. 20, 2019, pp. 755-757.
Lenz et al., "Aberrant immunoglobulin class switch recombination and switch translocations in activated B cell-like diffuse large B cell lymphoma", The Journal of Experimental Medicine, vol. 204, No. 3, Mar. 19, 2007, pp. 633-643.
Li et al., "Fast and accurate short read alignment with Burrows-Wheeler transform", Bioinformatics, May 18, 2009, vol. 25, No. 14, pp. 1754-1760, doi:10.1093/bioinformatics/btp324.
Lieber, "Mechanisms of human lymphoid chromosomal translocations", Nature Reviews Cancer, vol. 16, May 25, 2016, pp. 387-398.
Lo et al., "Prenatal Diagnosis of Fetal RhD Status by Molecular Analysis of Maternal Plasma", The New England Journal of Medicine, vol. 339, No. 24, Dec. 10, 1998, pp. 1734-1738.
Lo et al., "Presence of fetal DNA in maternal plasma and serum", The Lancet, vol. 350, Aug. 16, 1997, pp. 485-487.
Lu et al., "BCL6 breaks occur at different AID sequence motifs in Ig-BCL6 and non-Ig-BCL6 rearrangements", Blood, vol. 121, No. 22, May 30, 2013, pp. 4551-4554.
Morin et al., "Mutational and structural analysis of diffuse large B-cell lymphoma using whole-genome sequencing", Blood, vol. 122, No. 7, Aug. 15, 2013, pp. 1256-1265.
Nakamura et al., "Analysis of the immunoglobulin heavy chain gene variable region of CD5-positive and -negative diffuse large B cell lymphoma", Leukemia, vol. 15, Mar. 1, 2001, pp. 452-457.
Neelapu et al., "Axicabtagene Ciloleucel CAR T-Cell Therapy in Refractory Large B-Cell Lymphoma", The New England Journal of Medicine, vol. 377, No. 26, Dec. 28, 2017, pp. 2531-2544.
Newman et al., "An ultrasensitive method for quantitating circulating tumor DNA with broad patient coverage", Nature Medicine, Apr. 6, 2014, vol. 20, pp. 548-554, https://doi.org/10.1038/nm.3519.
Newman et al., "An ultrasensitive method for quantitating circulating tumor DNA with broad patient coverage", PMC PubMed Central, HHS Public Access, Author manuscript, PMID: 24705333, Nov. 1, 2014, 65 pgs.
Papageorgiou et al., "Fetal-specific DNA methylation ratio permits noninvasive prenatal diagnosis of trisomy 21", Nature Medicine, vol. 17, Mar. 6, 2011, pp. 510-513.
Pasqualucci et al., "Analysis of the coding genome of diffuse large B-cell Tymphoma", Nature Genetics, vol. 43, Jul. 31, 2011, pp. 830-837.
Pasqualucci et al., "Hypermutation of multiple proto-oncogenes in B-cell diffuse large-cell lymphomas", Nature, vol. 412, Jul. 19, 2001, pp. 341-346.
Phallen et al., "Direct detection of early-stage cancers using circulating tumor DNA", Science Translational Medicine, vol. 9, No. 403, Aug. 16, 2017, 12 pgs.
Puente et al., "Non-coding recurrent mutations in chronic lymphocytic leukaemia", Nature, vol. 526, Jul. 22, 2015, pp. 519-524.
Qian et al., "B Cell Super-Enhancers and Regulatory Clusters Recruit AID Tumorigenic Activity", Cell, vol. 159, Dec. 18, 2014, pp. 1524-1537.
Reinert et al., "Analysis of Plasma Cell-Free DNA by Ultradeep Sequencing in Patients With Stages I to III Colorectal Cancer", JAMA Oncology, vol. 5, No. 8, May 9, 2019, pp. 1124-1131.
Richter et al., "Recurrent mutation of the ID3 gene in Burkitt lymphoma identified by integrated genome, exome and transcriptome sequencing", Nature Genetics, vol. 44, Nov. 11, 2012, pp. 1316-1320.
Robbiani et al., "AID Is Required for the Chromosomal Breaks in c-myc that Lead to c-myc/IgH Translocations", Cell, vol. 135, No. 6, Dec. 12, 2008, pp. 1028-1038.
Roschewski et al., "Circulating tumour DNA and CT monitoring in patients with untreated diffuse large B-cell lymphoma: a correlative biomarker study", The Lancet Oncology, vol. 16, No. 5, May 1, 2015, pp. 541-549.
Rosenthal et al., "deconstructSigs: delineating mutational processes in single tumors distinguishes DNA repair deficiencies and patterns of carcinoma evolution", Genome Biology, vol. 17, No. 31, Feb. 22, 2016, 11 pgs.
Rowley, "Chromosome studies in the non-Hodgkin's lymphomas: the role of the 14;18 translocation", Journal of Clinical Oncology: Official Journal of the American Society of Clinical Oncology, vol. 6, No. 5, May 1988, pp. 919-925.

(56) References Cited

OTHER PUBLICATIONS

Scherer et al., "Distinct biological subtypes and patterns of genome evolution in lymphoma revealed by circulating tumor DNA", Science Translational Medicine, Nov. 9, 2016, vol. 8, No. 364, 364ra155, 11 pgs.
Scherer et al., "High-throughput sequencing for noninvasive disease detection in hematologic malignancies", Blood, vol. 130, No. 4, Jul. 27, 2017, pp. 440-452.
Schmitt et al., "Detection of ultra-rare mutations by next-generation sequencing", Proceedings of the National Academy of Sciences, vol. 109, No. 36, Sep. 4, 2012, pp. 14508-14513.
Schmitz et al., "Burkitt lymphoma pathogenesis and therapeutic targets from structural and functional genomics", Nature, vol. 490, Aug. 12, 2012, pp. 116-120.
Schmitz et al., "Genetics and Pathogenesis of Diffuse Large B-Cell Lymphoma", The New England Journal of Medicine, Apr. 12, 2018, vol. 378, No. 15, pp. 1396-1407, DOI: 10.1056/NEJMoa1801445.
Sozzi et al., "Analysis of Circulating Tumor DNA in Plasma at Diagnosis and during Follow-Up of Lung Cancer Patients", Cancer Research, vol. 61, No. 12, Jun. 15, 2001, pp. 4675-4678.
Steidl et al., "MHC class II transactivator CIITA is a recurrent gene fusion partner in lymphoid cancers", Nature, vol. 471, Mar. 2, 2011, pp. 377-381.
Sugimoto et al., "Improved Thermodynamic Parameters and Helix Initiation Factor to Predict Stability of DNA Duplexes", Nucleic Acids Research, vol. 24, No. 22, Nov. 1, 1996, pp. 4501-4505.
Thierry et al., "Clinical validation of the detection of KRAS and BRAF mutations from circulating tumor DNA", Nature Medicine, vol. 20, Mar. 23, 2014, pp. 430-435.
Tie et al., "Circulating tumor DNA analysis detects minimal residual disease and predicts recurrence in patients with stage II colon cancer", Science Translational Medicine, vol. 8, No. 346, Jul. 6, 2016, 10 pgs.
Van Der Auwera et al., "From FastQ data to high confidence variant calls: the Genome Analysis Toolkit best practices pipeline", Current Protocols in Bioinformatics, vol. 43, No. 1110, Oct. 15, 2013, pp. 11.10.1-11.10.33, doi: 10.1002/0471250953.bi1110s43.
Vaque et al., "B-cell lymphoma mutations: improving diagnostics and enabling targeted therapies", Haematologica, vol. 99, No. 2, Feb. 2014, pp. 222-231.
Wang et al., "Diagnosis of Pneumocystis jirovecii pneumonia with serum cell-free DNA in non-HIV-infected immunocompromised patients", Oncotarget, vol. 8, No. 42, Sep. 22, 2017, pp. 71946-71953.
Corrected Notice of Allowability for U.S. Appl. No. 17/455,209, dated Aug. 2, 2022, 2 pgs.
International Preliminary Report on Patentability for International Application No. PCT/US2020/059526, Report dated May 10, 2022, dated May 19, 2022, 09 Pgs.
International Search Report and Written Opinion for International Application No. PCT/US2022/071759, search completed Jun. 6, 2022, dated Jun. 29, 2022, 13 Pgs.
International Search Report and Written Opinion for International Application No. PCT/US2021/019478, Search completed Jun. 28, 2021, dated Aug. 25, 2021, 20 Pgs.
International Search Report and Written Opinion for International Application No. PCT/US2021/019481, Search completed Jun. 11, 2021, dated Jul. 15, 2021, 19 Pgs.
International Search Report and Written Opinion for International Application PCT/US2020/059526, Report Completed Jan. 22, 2021, dated Jan. 22, 2021, 21 pgs.
Invitation to Pay Additional Fees received for PCT Application No. PCT/US2020/059526, dated Dec. 15, 2020, 2 Pages.
Librarian view of catalog entry for "Personalized risk assessment and disease monitoring in non-Hodgkin lymphoma from circulating tumor DNA, David Kurtz", Date catalogued: Dec. 11, 2017, Accessed on Aug. 19, 2021, 2 pgs.
Notice of Allowance for U.S. Appl. No. 17/455,209, dated Apr. 18, 2022, 10 pgs.
Office Action for U.S. Appl. No. 17/107,668, dated Jun. 17, 2021, 27 pgs.
Office Action for U.S. Appl. No. 17/107,668, dated Oct. 21, 2021, 40 pgs.
Office Action for U.S. Appl. No. 17/646,472, dated Aug. 29, 2022, 41 pgs.
Office Action for U.S. Appl. No. 17/661,730, dated Aug. 22, 2022, 10 pgs.
Response to Jun. 17, 2021 Office Action for U.S. Appl. No. 17/107,668, filed Sep. 17, 2021, 79 pgs.
Response to Oct. 21, 2021 Office Action for U.S. Appl. No. 17/107,668, filed Apr. 21, 2022, 101 pgs.
Restriction Requirement for U.S. Appl. No. 17/107,668, dated Apr. 26, 2021, 9 pgs.
Supplemental Notice of Allowability for U.S. Appl. No. 17/455,209, dated Jun. 13, 2022, 2 pgs.
"Copyright Reminder: Dissertations", Stanford Libraries, Retrieved from https://library.stanford.edu/using/copyright-reminder/common-situations/dissertations on Aug. 18, 2021, 2 pgs.
"Dissertations and theses", Stanford Libraries, Robin Li and Melissa Ma Science Library, Retrieved from https://library.stanford.edu/science/collections/chemistry-and-chemical-engineering-collection/dissertations-and-theses on Sep. 11, 2021, 4 pgs.
"Dissertations and theses", Stanford Libraries, Special Collections & University Archives, Retrieved from https://library.stanford.edu/using/copyright-reminder/common-situations/dissertations on Jun. 21, 2021, 3 pgs.
"eDissertation Requirements for Submission", Stanford University Registrar's Office: Student Affairs Website, Retrieved from https://registrar.stanford.edu/students/dissertation-and-thesis-submission/preparing-dissertations-electronic-submission on Jun. 24, 2021, 3 pgs.
"Embargo and Restriction Options", ProQuest, Retrieved from https://support.proquest.com/articledetail?id=kA0400000004JJCCA2 on Sep. 15, 2021, 4 pgs.
Notice of Allowance for U.S. Appl. No. 17/646,473, dated Nov. 9, 2022, 10 pgs.
Office Action for U.S. Appl. No. 17/646,473, dated Jun. 22, 2022, 18 pgs.
Office Action for U.S. Appl. No. 17/646,473, dated Oct. 17, 2022, 11 pgs.
Kurtz et al., "Methods and Systems for Analyzing Nucleic Acid Molecules", U.S. Appl. No. 18/056,652, filed Nov. 17, 2022, 1237 pgs.
Kurtz et al., "Methods and Systems for Analyzing Nucleic Acid Molecules", U.S. Appl. No. 18/056,656, filed Nov. 17, 2022, 1240 pgs.

* cited by examiner

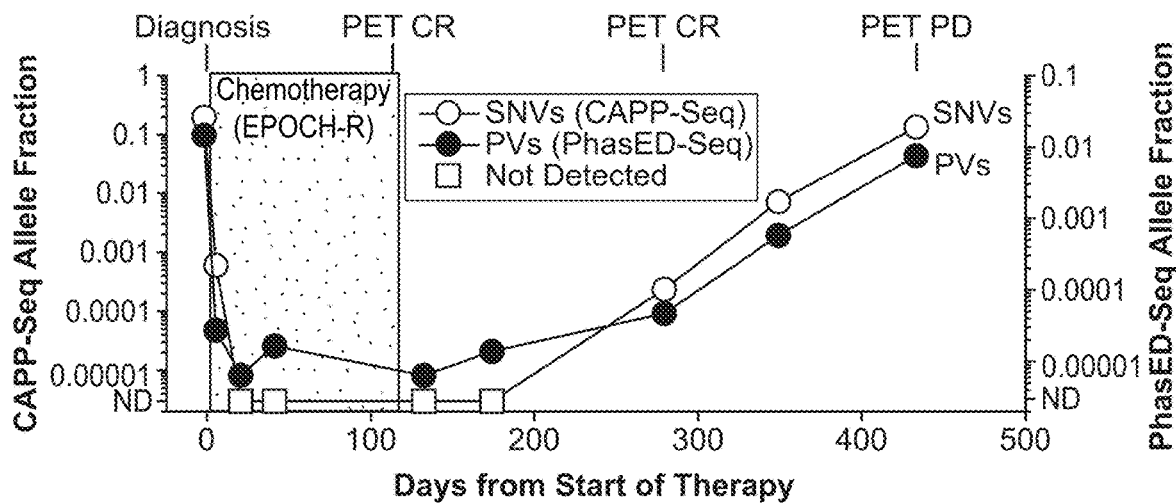
FIG. 4A
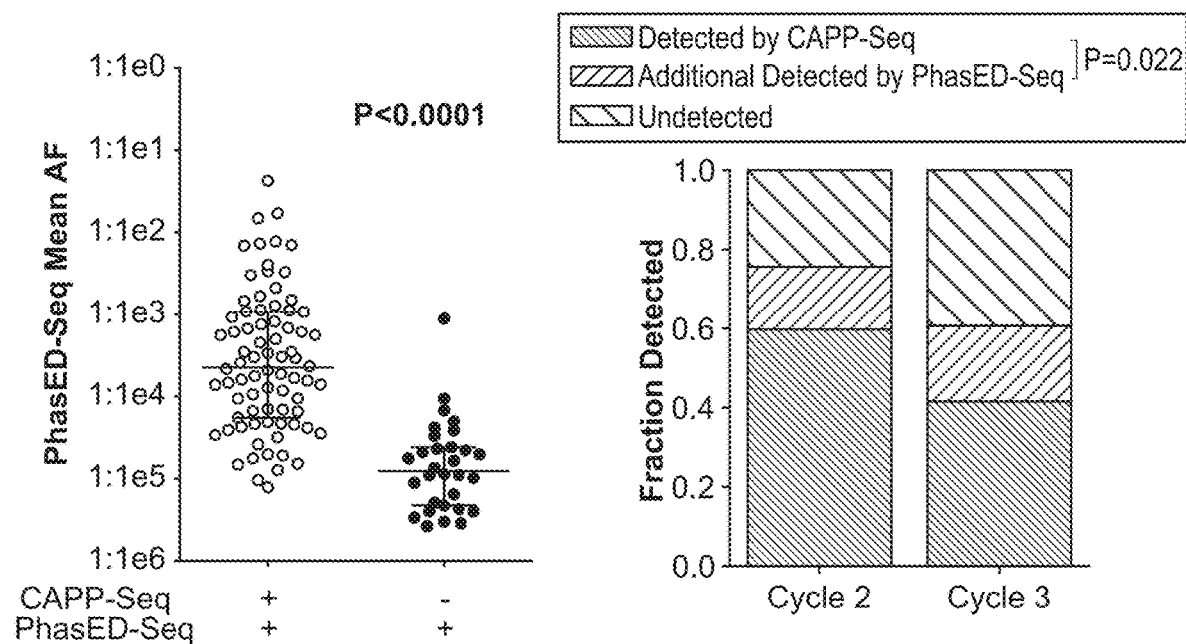
FIG. 4B
FIG. 4C

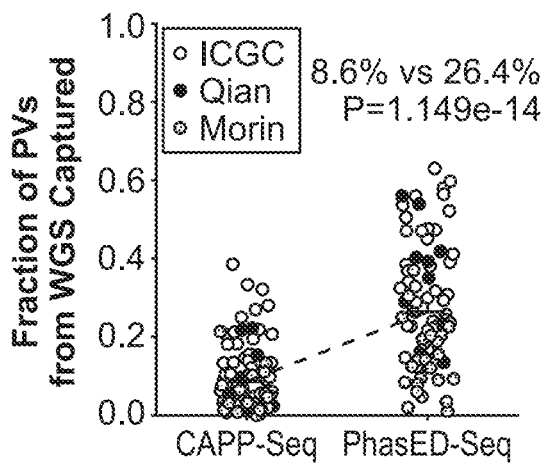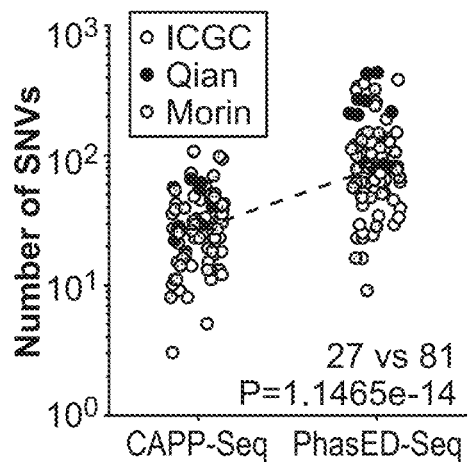
FIG. 9A
FIG. 9B
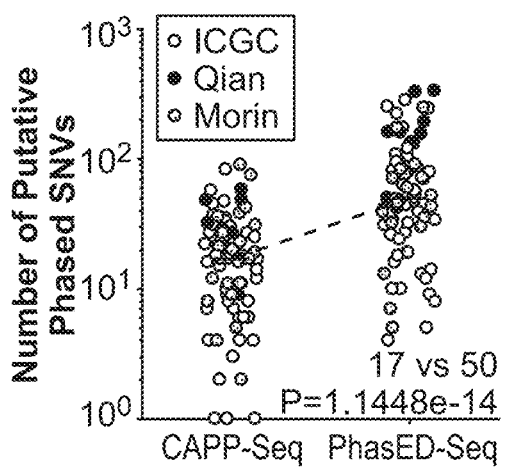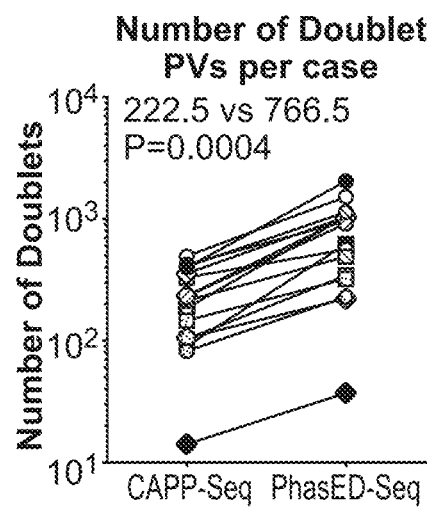
FIG. 9C
FIG. 9D
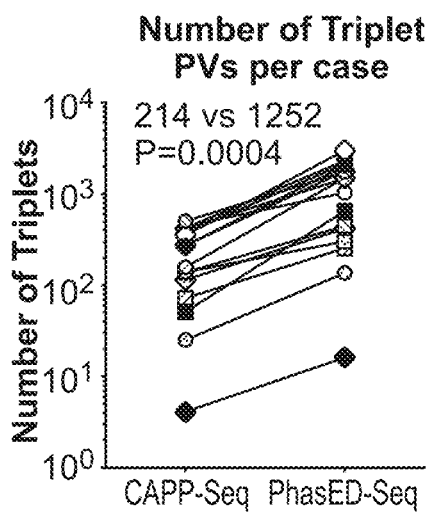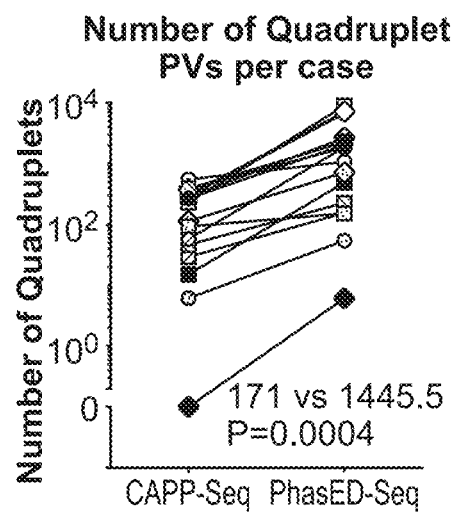
FIG. 9E
FIG. 9F

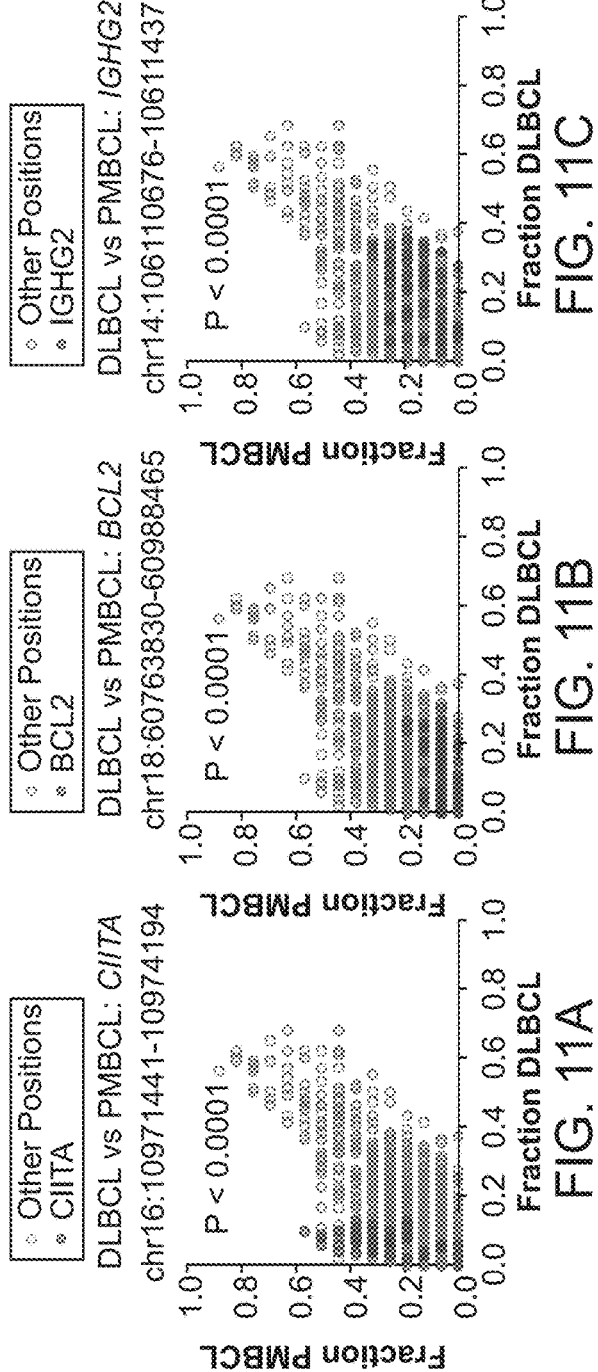
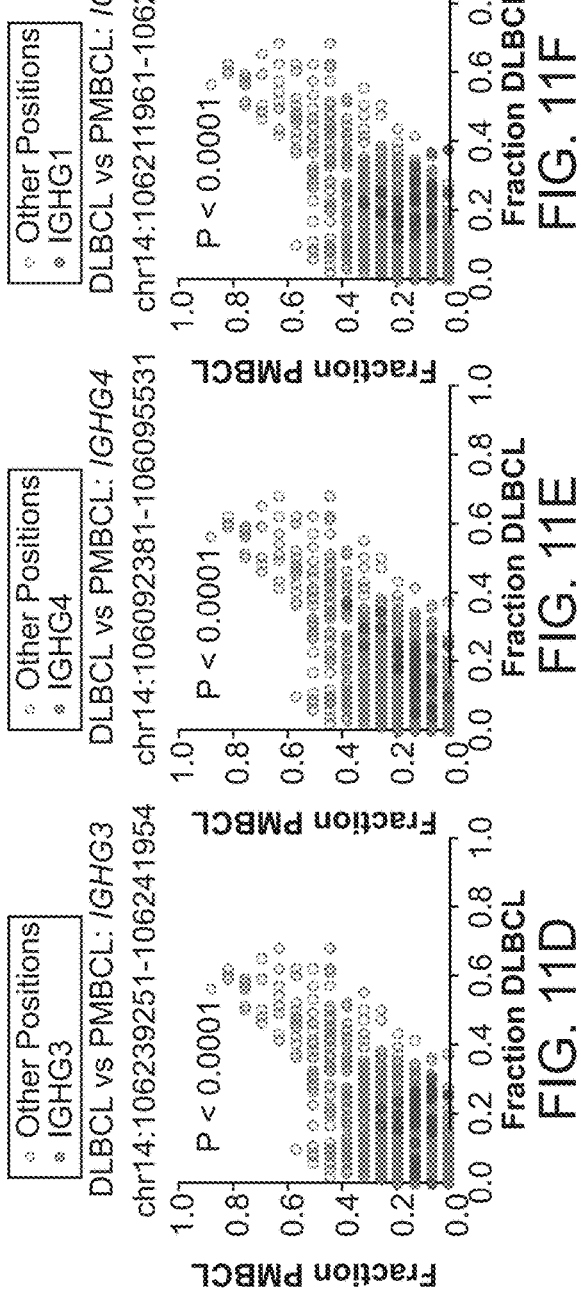
FIG. 11A  FIG. 11B  FIG. 11C
FIG. 11D  FIG. 11E  FIG. 11F

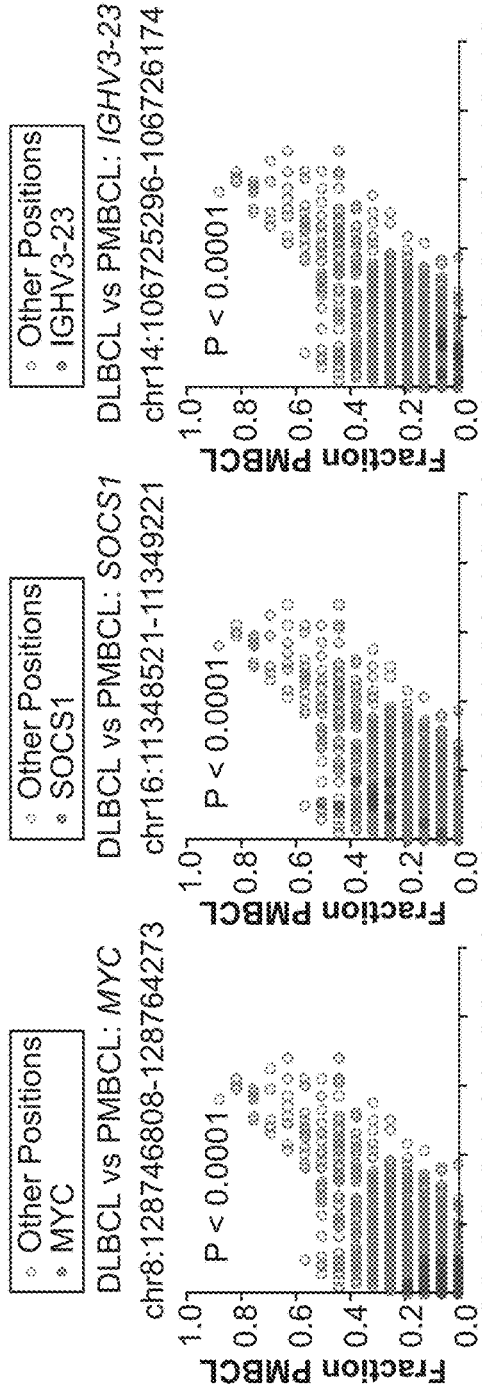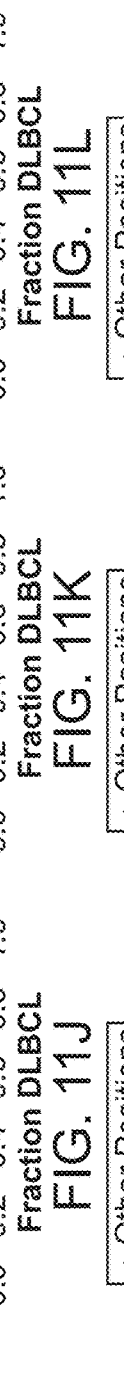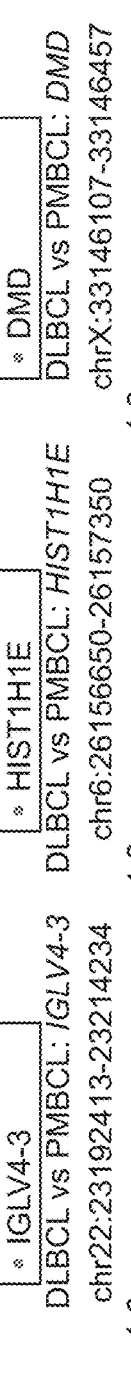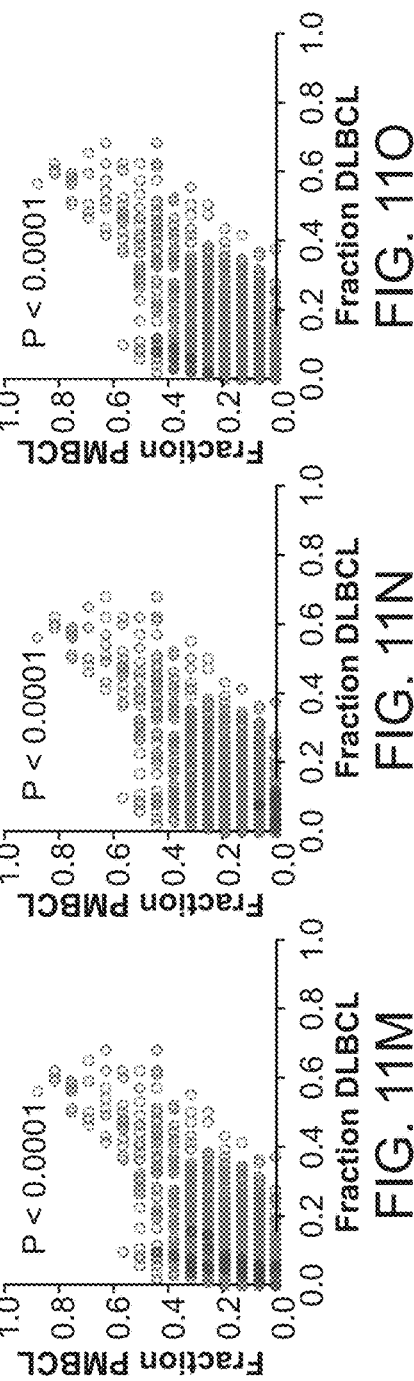

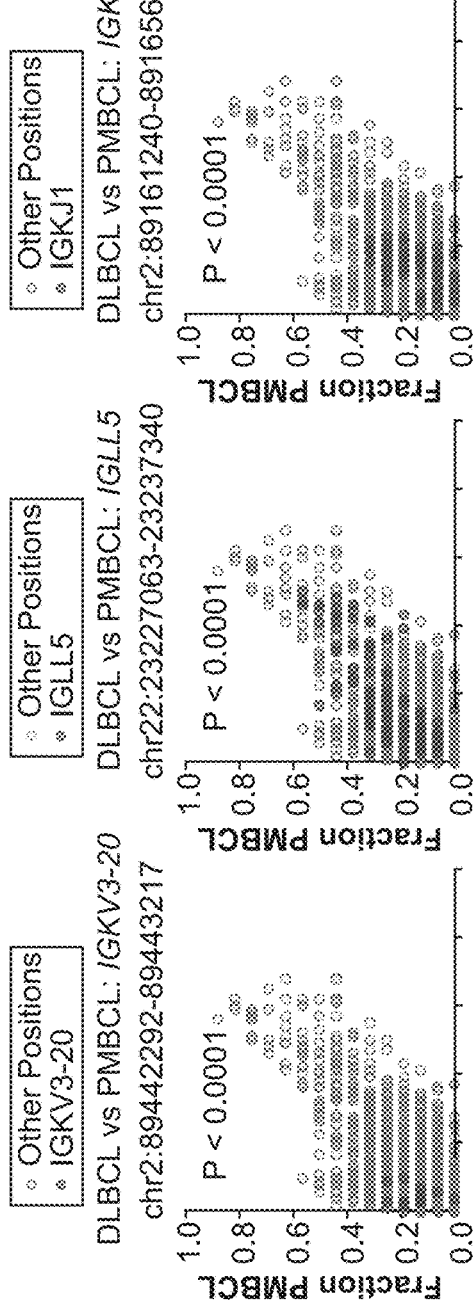
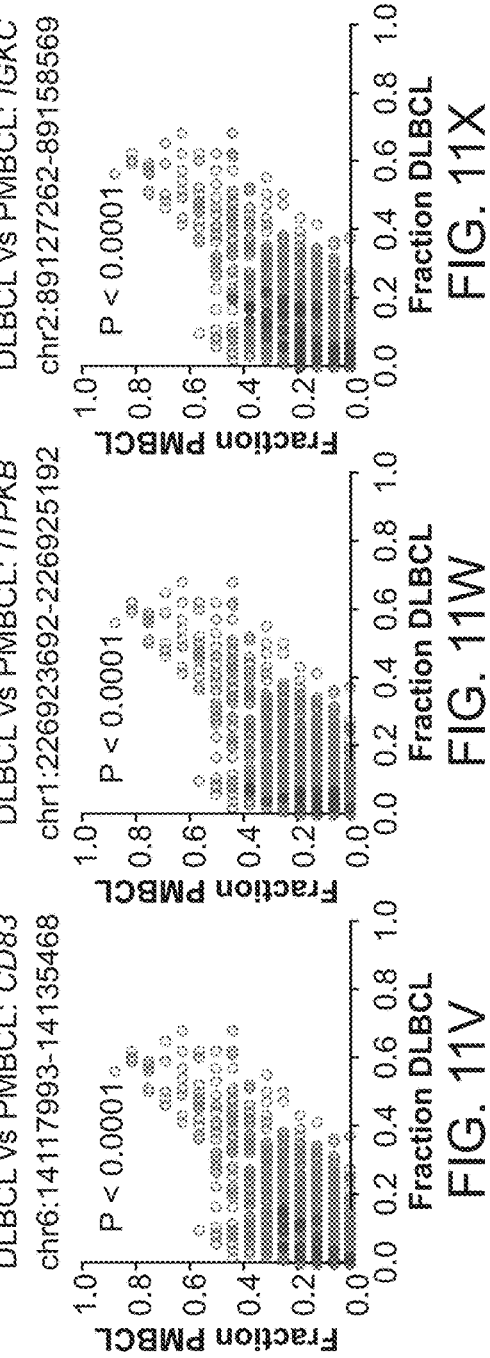

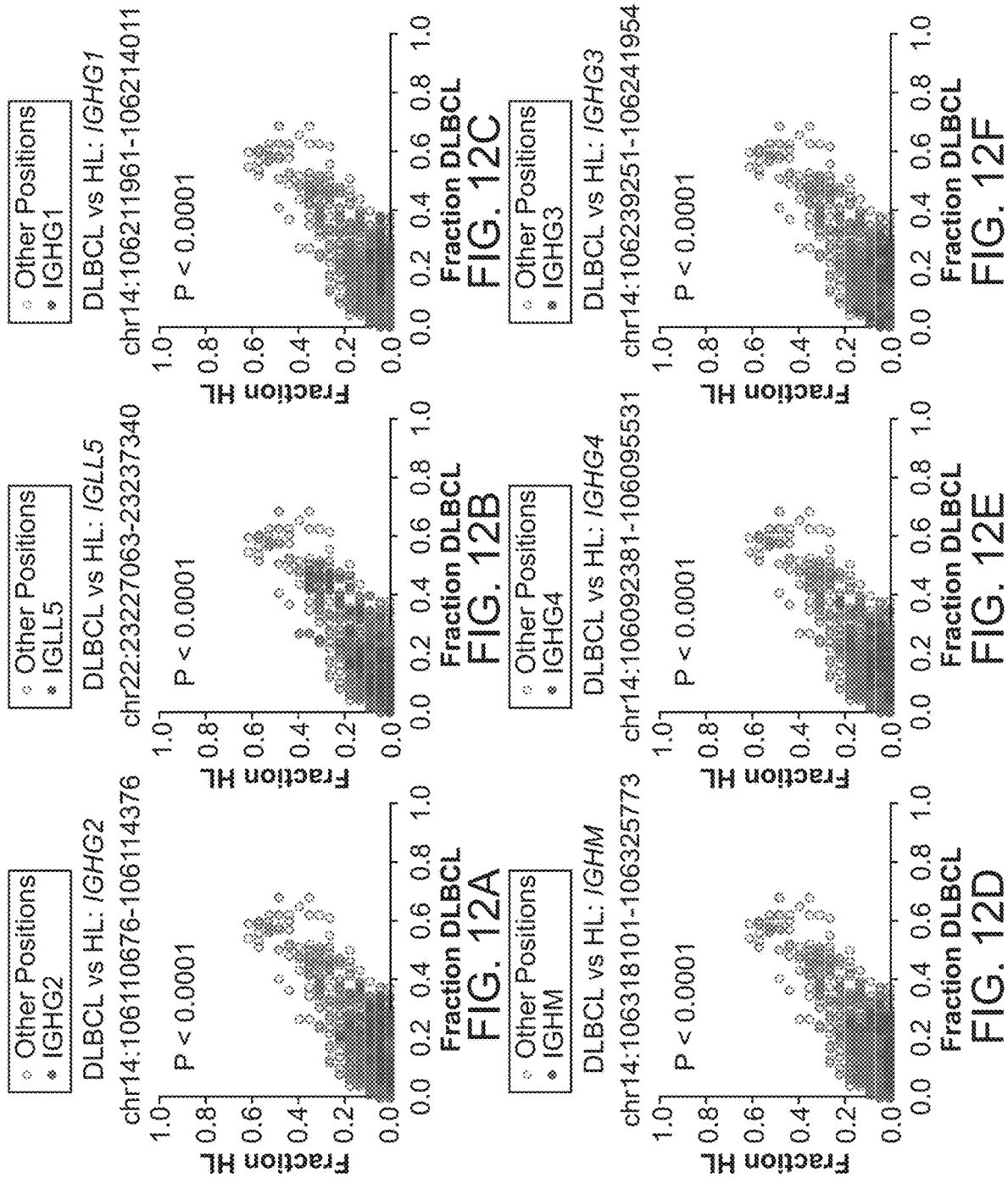

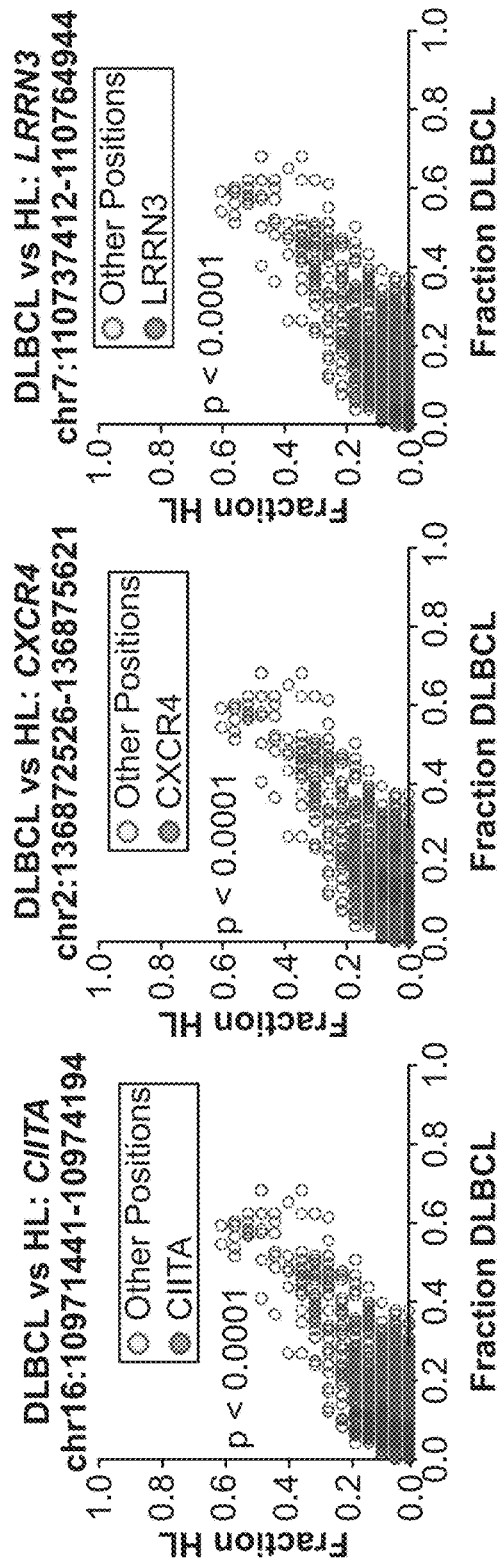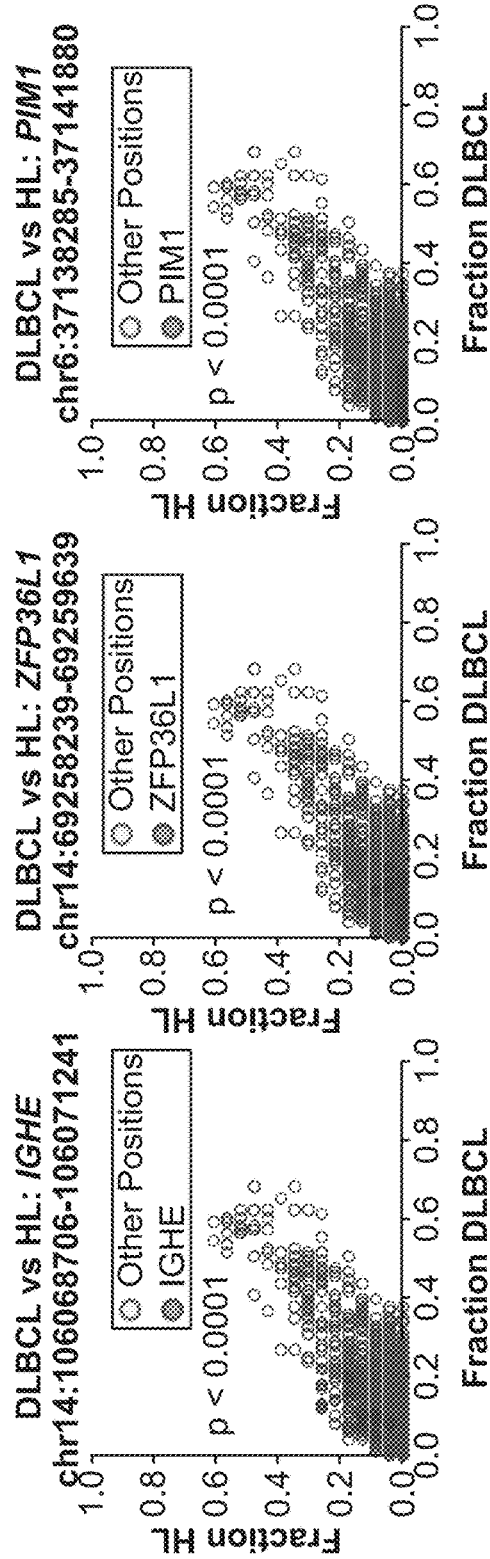
FIG. 12J  FIG. 12K  FIG. 12L
FIG. 12M  FIG. 12N  FIG. 12O

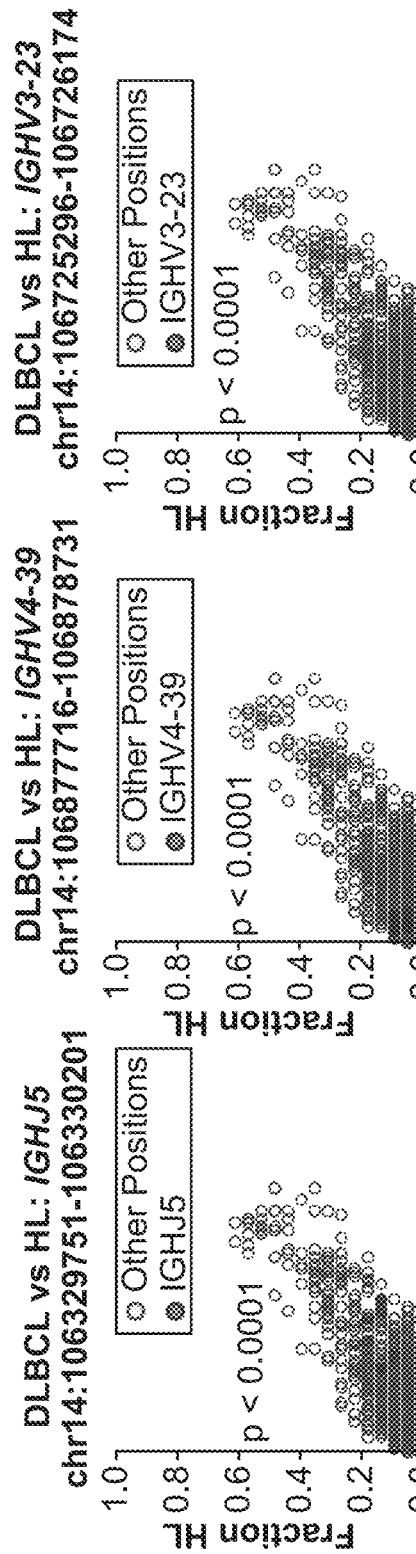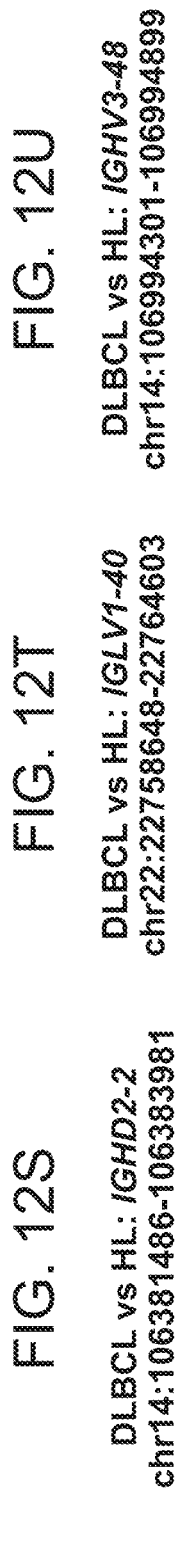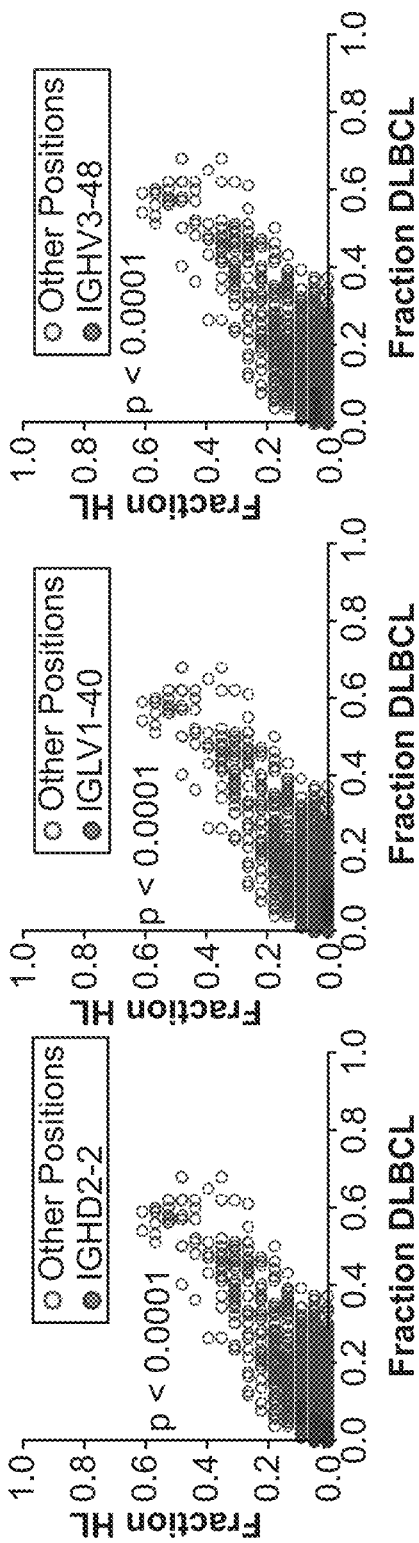
FIG. 12S FIG. 12T FIG. 12U
FIG. 12V FIG. 12W FIG. 12X

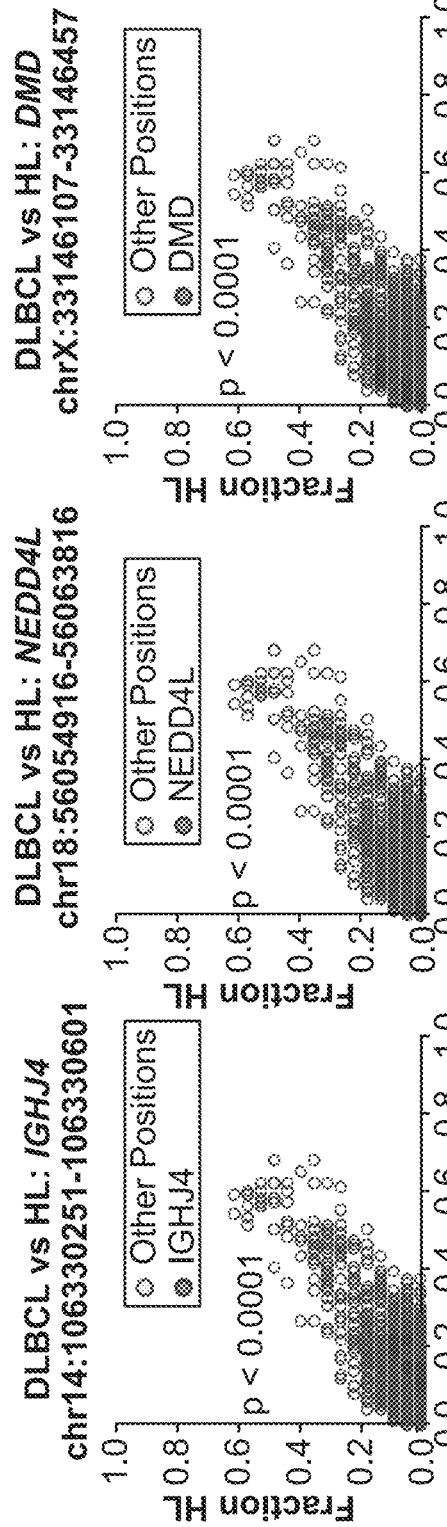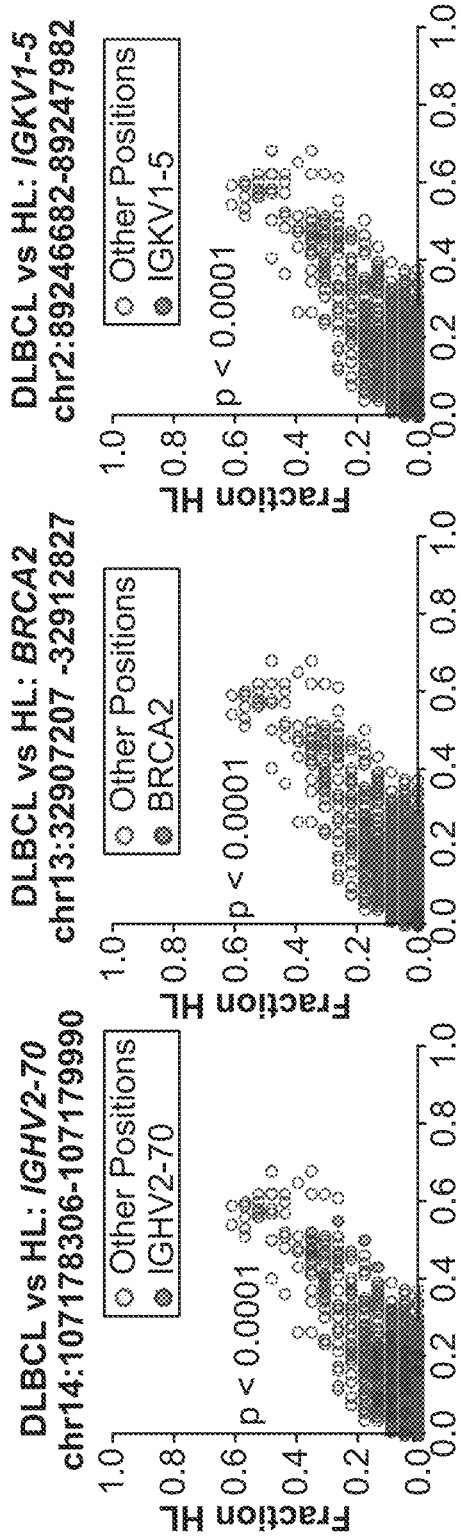

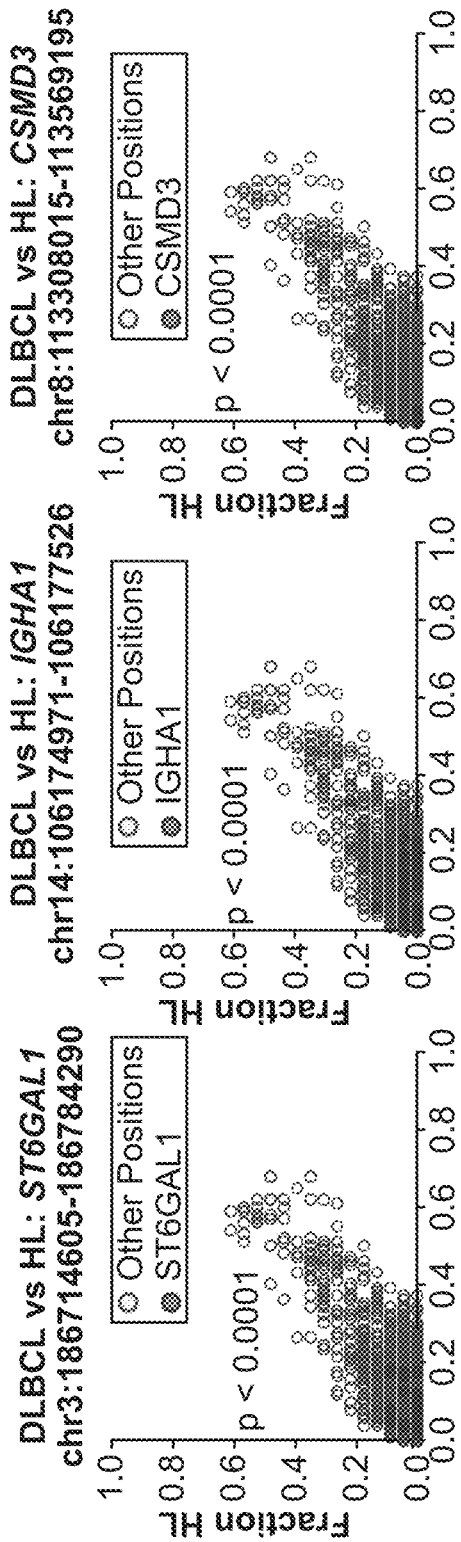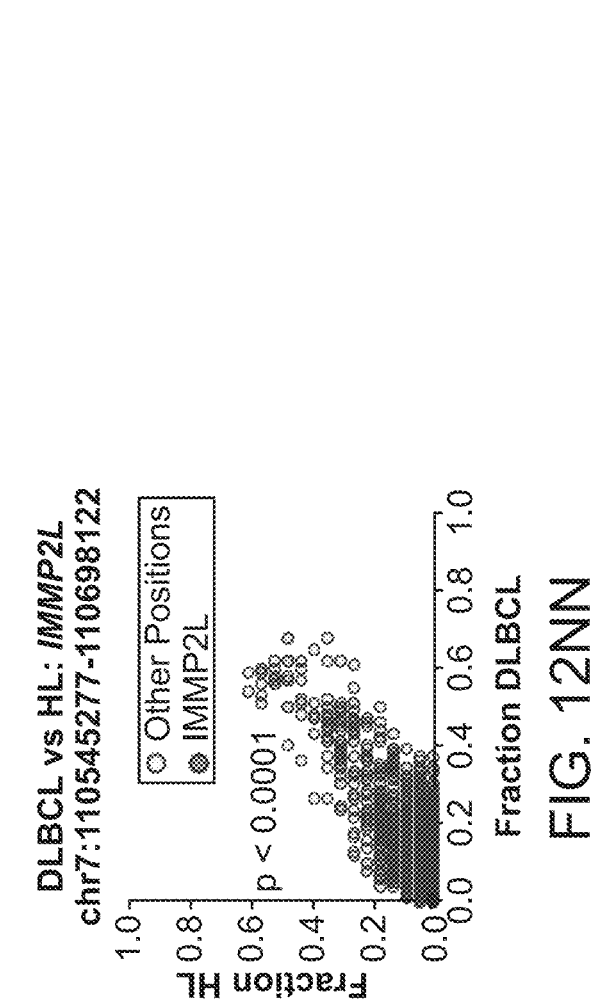
FIG. 12KK  FIG. 12LL  FIG. 12MM  FIG. 12NN

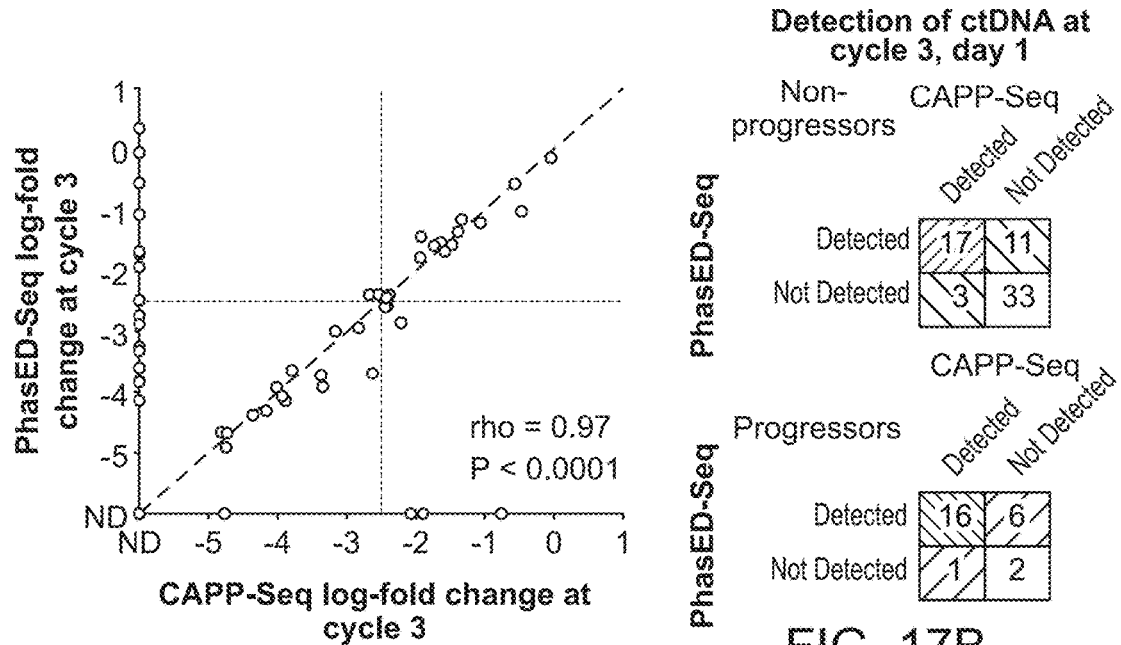
FIG. 17A
FIG. 17B
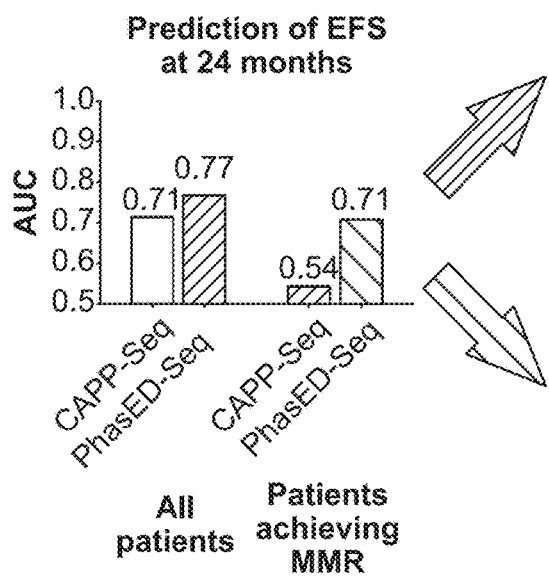
FIG. 17C
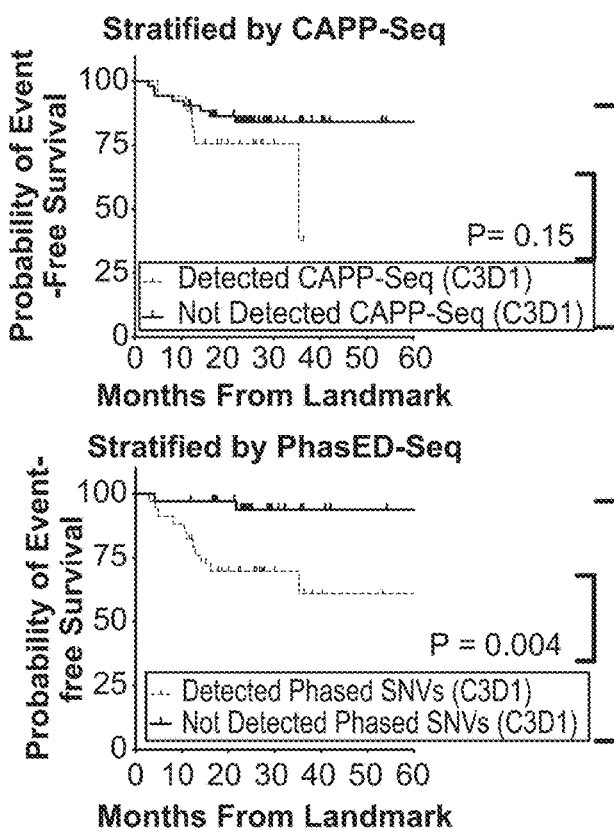
FIG. 17D

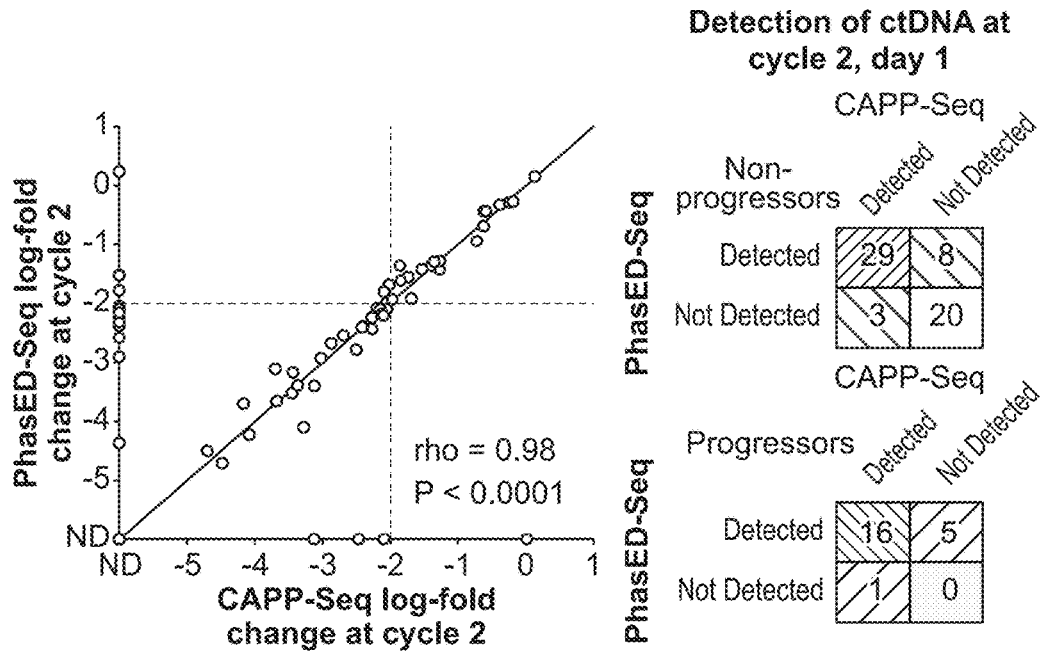
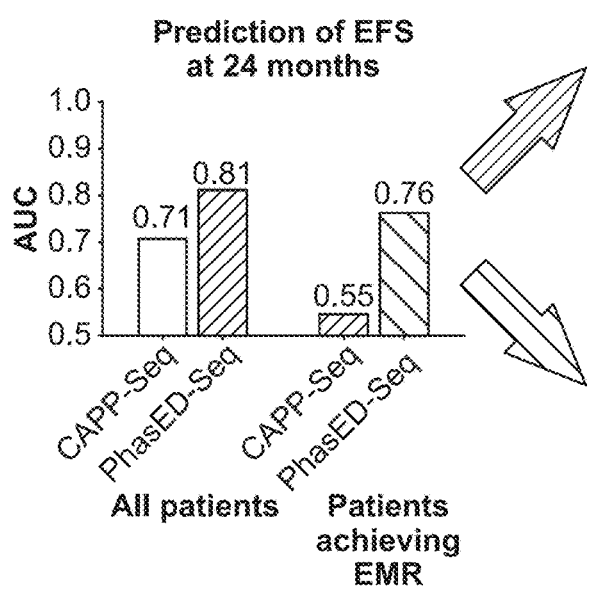
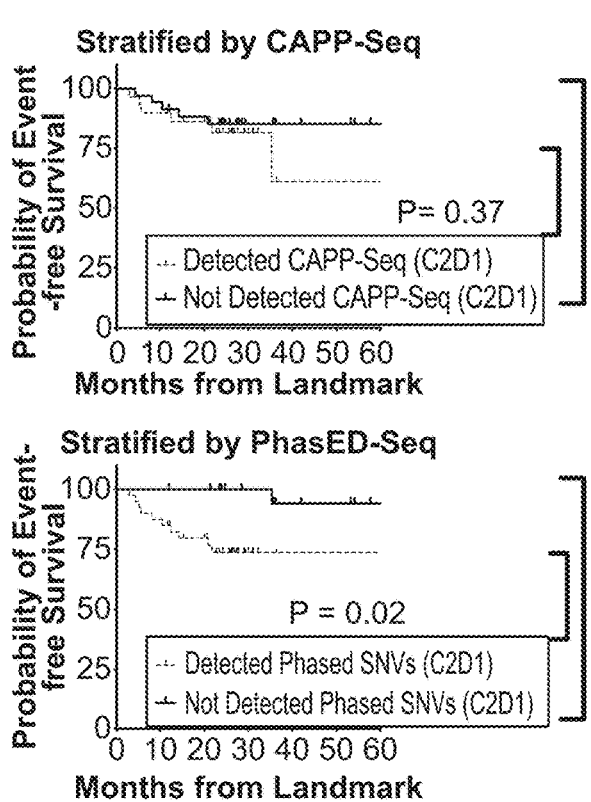
FIG. 18A
FIG. 18B
FIG. 18C
FIG. 18D

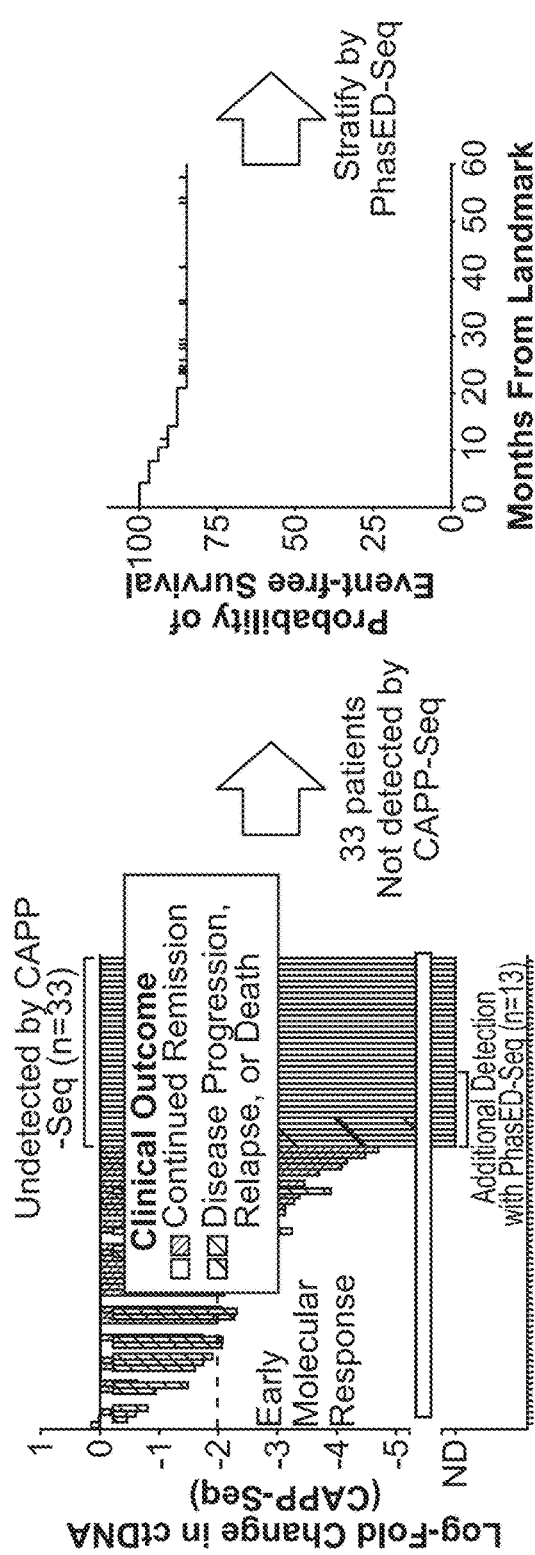
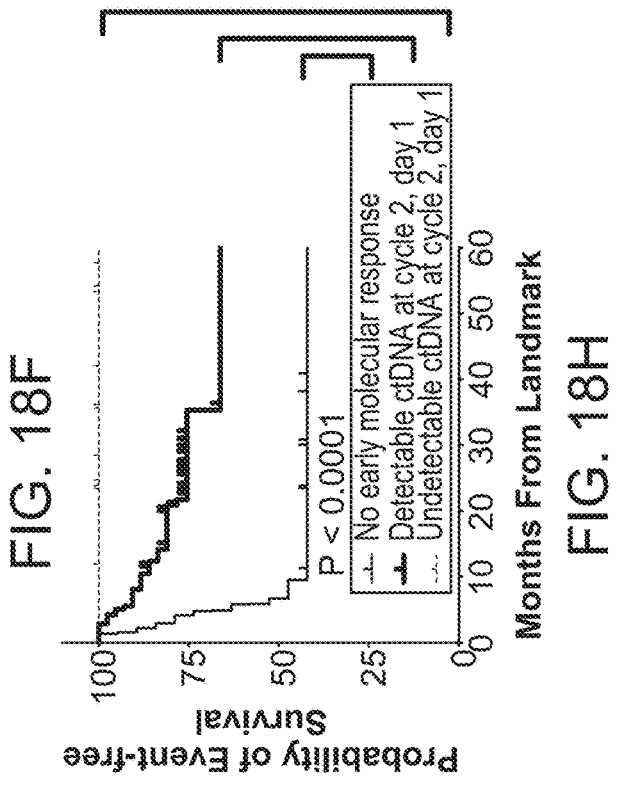
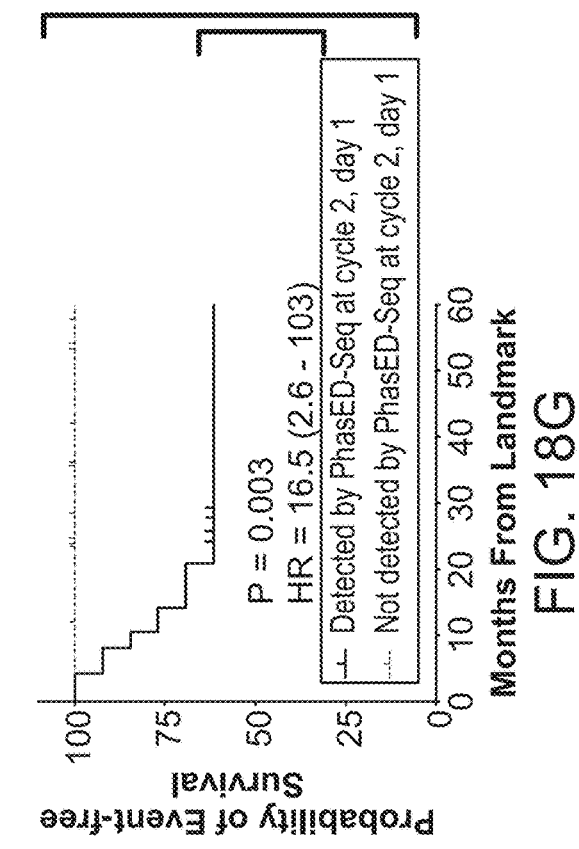
FIG. 18E
FIG. 18F
FIG. 18G
FIG. 18H

2542 — Identifying the subject for treatment of the condition, wherein the subject has been determined to have the condition based on identification of one or more cell-free nucleic acid molecules from a plurality of cell-free nucleic acid molecules from the subject,
wherein each of the one or more cell-free nucleic acid molecules identified comprises a plurality of phased variants relative to a reference genomic sequence that are separated by at least one nucleotide, and
wherein a presence of the plurality of phased variants is indicative of the condition of the subject.

2544 — Subjecting the subject to the treatment based on the identification.

2562 — Providing a mixture comprising (1) a set of nucleic acid probes and (2) a plurality of cell-free nucleic acid molecules from a subject,
wherein an individual nucleic acid probe of the set of nucleic acid probes is designed to hybridize to a target cell-free nucleic acid molecule comprising a plurality of phased variants relative to a reference genomic sequence that are separated by at least one nucleotide, and
wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2564 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants.

2566 — Analyzing the identified one or more cell-free nucleic acid molecules to determine a condition of the subject.

2572 — Providing a mixture comprising (1) a set of nucleic acid probes and (2) a plurality of cell-free nucleic acid molecules from a subject, wherein an individual nucleic acid probe of the set of nucleic acid probes is designed to hybridize to a target cell-free nucleic acid molecule comprising a plurality of phased variants relative to a reference genomic sequence, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2574 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules.

2576 — Analyzing the identified one or more cell-free nucleic acid molecules to determine a condition of the subject.

SEQUENCE LISTING

<160> NUMBER OF SEQ ID NOS: 1358

<210> SEQ ID NO 1
<211> LENGTH: 100
<212> TYPE: DNA
<213> ORGANISM: Homo sapiens

<400> SEQUENCE: 1
tctcttctgg cccacagccg cagcaatggc gctgagttcc tctgctggag ttcatcctgc      60
tagctgggtt cccgagctgc cggtctgagc ctgaggcatg                           100

<210> SEQ ID NO 2
<211> LENGTH: 100
<212> TYPE: DNA
<213> ORGANISM: Homo sapiens

<400> SEQUENCE: 2
gagcctcctg gagactgggg gcctcctccc tggagatcca cccccaaaac cgacgtcttg      60
aggctggtga gcccccgagc ctcctctccg tctgctcgca                           100

<210> SEQ ID NO 3
<211> LENGTH: 100
<212> TYPE: DNA
<213> ORGANISM: Homo sapiens

<400> SEQUENCE: 3
gatcccagtt ctgaccccag ggcctccac agatctcttc cccatgcccc tgtcctggcc       60
gttgctggct ccggcgtcca gcccgtcccc tgctgcctgg                           100

<210> SEQ ID NO 4
<211> LENGTH: 100
<212> TYPE: DNA
<213> ORGANISM: Homo sapiens

<400> SEQUENCE: 4
ccatgttgct ggcttacttg gcatttccca tgatctcaca ctgctggctt atttggcatt      60
tcccatgatc ccctgctgct ggtttacttg gcattcccta                           100

<210> SEQ ID NO 5
<211> LENGTH: 100
<212> TYPE: DNA
<213> ORGANISM: Homo sapiens

<400> SEQUENCE: 5
tgatcccatg ttgctggttt acttagcatt tcccatgatc ccatgttgct ggcttacttg      60
gcatttccca tgataccatg ttgctggctt acttggcatt                           100

<210> SEQ ID NO 6
<211> LENGTH: 100
<212> TYPE: DNA
<213> ORGANISM: Homo sapiens

<400> SEQUENCE: 6
atagattaga ggaaggaatt ctagatgaaa ttaagtaaat gagttattta agtcaactaa      60
tacaagtcct caaaactttg attatataga gagctaaact                           100

<210> SEQ ID NO 7
<211> LENGTH: 100
<212> TYPE: DNA
<213> ORGANISM: Homo sapiens

```
<400> SEQUENCE: 7
gataaatata gacaaatata gtgagcctat aaattaaagc tatactatga tgaaaaaata      60
aatgaataat tgtgaaatag ccaaaaatac taaaatacag                           100

<210> SEQ ID NO 8
<211> LENGTH: 100
<212> TYPE: DNA
<213> ORGANISM: Homo sapiens

<400> SEQUENCE: 8
aatgaataat tgtgaaatag ccaaaaatac taaaatacag ctataaggtt aaaaataaat      60
ctgaataaaa aatgtaggag ggaaaagtga ttaccttacc                           100

<210> SEQ ID NO 9
<211> LENGTH: 100
<212> TYPE: DNA
<213> ORGANISM: Homo sapiens

<400> SEQUENCE: 9
gacatgcatc aaatgtaaac aaatgattac agccatttta taaaaagtca tattctttaa      60
aacatttttt gtcatcatta aaaattaaaa ggcaataaag                           100

<210> SEQ ID NO 10
<211> LENGTH: 100
<212> TYPE: DNA
<213> ORGANISM: Homo sapiens

<400> SEQUENCE: 10
tgtcattgtc gtgaaacagt acgtgatctt aagggaagaa acatctcact agagtttgca      60
caagttcctt cttcttctaa ctgtagatct ggtggcaaag                           100

<210> SEQ ID NO 11
<211> LENGTH: 100
<212> TYPE: DNA
<213> ORGANISM: Homo sapiens

<400> SEQUENCE: 11
gaggagcccc tgggtcccca ggtctgggaa gtgtagttga agagaagatg gtattttcag      60
ttctgcctac ttctagaaca ggcaaattca gagaagaatt                           100

<210> SEQ ID NO 12
<211> LENGTH: 100
<212> TYPE: DNA
<213> ORGANISM: Homo sapiens

<400> SEQUENCE: 12
agtagaaaaa aagggcgtcg tgctggattc tccttctgga tggtacatga cagtggatgc      60
cctcagtttt tcagagaaat tactctcatc tgaatttgat                           100

<210> SEQ ID NO 13
<211> LENGTH: 100
<212> TYPE: DNA
<213> ORGANISM: Homo sapiens

<400> SEQUENCE: 13
ctggagaggt tgttcgtggc tccatctgga aaaggttcac aactgctaca ttttagtcct      60
acaataaaat tattcagatg taaatgaaaa agtaactaaa                           100
```

```
<210> SEQ ID NO 14
<211> LENGTH: 100
<212> TYPE: DNA
<213> ORGANISM: Homo sapiens

<400> SEQUENCE: 14
acccgagacc tctcactgag cccgagccgc gcgcgacatg agccacggga agggaaccga      60
catgctcccg gagatcgccg ccgccgtgggg cttcctctcc                          100

<210> SEQ ID NO 15
<211> LENGTH: 100
<212> TYPE: DNA
<213> ORGANISM: Homo sapiens

<400> SEQUENCE: 15
agcctcctga ggacccgggg ctgcgtgagc gagcagaggc ttaaggtctt cagcggggcg      60
ctccaggagg cactcacagg tgagcgcatg ccaggggcc                            100

<210> SEQ ID NO 16
<211> LENGTH: 100
<212> TYPE: DNA
<213> ORGANISM: Homo sapiens

<400> SEQUENCE: 16
tggcgccacc gggggtcggc cccatccctg ccagggccgt ctttcttcta ctcctgcggc      60
agggtgaccc acgggagcag ctttgggact cggtggccct                           100

<210> SEQ ID NO 17
<211> LENGTH: 100
<212> TYPE: DNA
<213> ORGANISM: Homo sapiens

<400> SEQUENCE: 17
cctccgaccc ccggggcggc ccgcagtccc cagtttcctg ggtcctcctc cccagccctg      60
tgctcgggtc tcggccgtgg cggttctgat ggggcgcgcc                           100

<210> SEQ ID NO 18
<211> LENGTH: 100
<212> TYPE: DNA
<213> ORGANISM: Homo sapiens

<400> SEQUENCE: 18
cctctacgct ctcggaggcg cagaccctgg tcctggagtg ccagcccgag tccccagctt      60
atgcccctgt ctcattacgg gctcgtctcc ctcgctggac                           100

<210> SEQ ID NO 19
<211> LENGTH: 100
<212> TYPE: DNA
<213> ORGANISM: Homo sapiens

<400> SEQUENCE: 19
cctcgagatc ttaagaccct cgatggatgt tgttgcgggc cgcccggtcg gccgaggggt      60
cccgatgagg gaagaaggtg cagtcgagcc ttttcaacaa                           100

<210> SEQ ID NO 20
<211> LENGTH: 100
<212> TYPE: DNA
<213> ORGANISM: Homo sapiens

<400> SEQUENCE: 20
```

```
tttggagtcc cagtgcggtt cttcctgccg gtcggggtgc gctgtgcctg gggtagtcca        60
ctggttgctg actggcttca agttggaatt tgggccccct                            100
```

<210> SEQ ID NO 21
<211> LENGTH: 100
<212> TYPE: DNA
<213> ORGANISM: Homo sapiens

<400> SEQUENCE: 21

```
ttgtgttatc tttggttccc cttagccatc tgccacctat tgtggtaggg aggagagcct        60
cgtagctcgt gaccctgccg tgcgggcctt caagttggga                            100
```

<210> SEQ ID NO 22
<211> LENGTH: 100
<212> TYPE: DNA
<213> ORGANISM: Homo sapiens

<400> SEQUENCE: 22

```
ggtgaagaga taagcagccc gctcgctggc tggggagaga cctctctccc agctgtttct        60
agctggttac tgtcagtttt gggaagcgat agccatctcg                            100
```

<210> SEQ ID NO 23
<211> LENGTH: 100
<212> TYPE: DNA
<213> ORGANISM: Homo sapiens

<400> SEQUENCE: 23

```
gaacgcaccc acacagaccc tgccttctga ggaaaacaga tgtttcatca aaacaaccca        60
gttttcactc ccttaggcac tgctaaggaa ggttctctga                            100
```

<210> SEQ ID NO 24
<211> LENGTH: 100
<212> TYPE: DNA
<213> ORGANISM: Homo sapiens

<400> SEQUENCE: 24

```
ctcttctgaa ggaagcagag ggaacacagg gtgggaggtc cagtgacttg ctgtggaccc        60
aacaatgttg gcagccttcc tggccctgaa acttcagctc                            100
```

<210> SEQ ID NO 25
<211> LENGTH: 100
<212> TYPE: DNA
<213> ORGANISM: Homo sapiens

<400> SEQUENCE: 25

```
acaggtctcc agaggccctg cctggacatg ccagtcccag tcacaccctt cccttgcttt        60
gggggtgtgc caaaagcaat acactggcca ctagagagta                            100
```

<210> SEQ ID NO 26
<211> LENGTH: 100
<212> TYPE: DNA
<213> ORGANISM: Homo sapiens

<400> SEQUENCE: 26

```
ccctagagct ctagaatccc ctcccaacac gcacacacac acacacacac actctctctc        60
tcacacacac acactcagtc acacacacac acacacacac                            100
```

<210> SEQ ID NO 27

<211> LENGTH: 100
<212> TYPE: DNA
<213> ORGANISM: Homo sapiens

<400> SEQUENCE: 27
ctttcagatc tttcgcagcg tcccaacagg gcaaaggctc cagcattctg ccagaaggaa    60
ttcccgcctc cacattcccg gtccccggct gtgctgaggg                          100

<210> SEQ ID NO 28
<211> LENGTH: 100
<212> TYPE: DNA
<213> ORGANISM: Homo sapiens

<400> SEQUENCE: 28
gctgccccca agcaagccca gcgttgggga ccctccctcc actctgtcgg agagctgcca    60 acgcccccg cccacggggg ccccacttcg ggcctcctca                           100

<210> SEQ ID NO 29
<211> LENGTH: 100
<212> TYPE: DNA
<213> ORGANISM: Homo sapiens

<400> SEQUENCE: 29
gggcctacgg aggccagggc cctgggcagc ctggaccagc tcagggaatc agaggactct    60
gcgctttgca cgctcacagt cgtctcctct ggccttttgc                          100

<210> SEQ ID NO 30
<211> LENGTH: 100
<212> TYPE: DNA
<213> ORGANISM: Homo sapiens

<400> SEQUENCE: 30
ccacttcagg ctccccagag cccggcatgc cacagggcag atatcctttc cccatcttcc    60 caggggttc tccatcgcgg ggcccgcccc tttctggggc                           100

<210> SEQ ID NO 31
<211> LENGTH: 100
<212> TYPE: DNA
<213> ORGANISM: Homo sapiens

<400> SEQUENCE: 31
tgggcttgtc tcactgccca gaaactgccc ctgcctctcc accagggcct ctgggggctg    60
caggtcctca agctcacggg ctctcccaga cggctcagtg                          100

<210> SEQ ID NO 32
<211> LENGTH: 100
<212> TYPE: DNA
<213> ORGANISM: Homo sapiens

<400> SEQUENCE: 32
agggcaagat cctgtggacg gtgtggccca gtggatgtaa ctctcgctgc cacttccgtg    60
gccatcgtta agctagctcc gaacagcccc aatgagggag                          100

<210> SEQ ID NO 33
<211> LENGTH: 100
<212> TYPE: DNA
<213> ORGANISM: Homo sapiens

<400> SEQUENCE: 33
ctaggcagct ccgagttccc ggggtaggag agccccttt gtcaatttcc atagctgtgg    60

| | |
|---|---|
| gtgagccaca gcggggactg gcagggatac ccttctccat | 100 |

<210> SEQ ID NO 34
<211> LENGTH: 100
<212> TYPE: DNA
<213> ORGANISM: Homo sapiens

<400> SEQUENCE: 34

| | |
|---|---|
| ccttacaaaa gcggatggac cctgagcctc tgatcctgta ggggcagccc ggccgggaag | 60 |
| aggtggcatt cctttcttca cctgcgagga gcataggctg | 100 |

<210> SEQ ID NO 35
<211> LENGTH: 100
<212> TYPE: DNA
<213> ORGANISM: Homo sapiens

<400> SEQUENCE: 35

| | |
|---|---|
| ggccctcctt tcctcccgga gtcggttcct gaagtctctg gacattgctc cccccaggac | 60 |
| tttgtcctcc gttcctcgct ccgggcgccc tgaaccagga | 100 |

<210> SEQ ID NO 36
<211> LENGTH: 100
<212> TYPE: DNA
<213> ORGANISM: Homo sapiens

<400> SEQUENCE: 36

| | |
|---|---|
| cccttccagg gggctgactg ctgctgcgga aggggcacgg ggagggcgag cgagccctgc | 60 |
| ccaaacgcgg gctgcggggc gcttgaatgg cggagctctg | 100 |

<210> SEQ ID NO 37
<211> LENGTH: 100
<212> TYPE: DNA
<213> ORGANISM: Homo sapiens

<400> SEQUENCE: 37

| | |
|---|---|
| tgcctggatg tgcgcctcaa acatgcccac tttctggttc acctgcacgt tctgcaactc | 60 |
| gcgctgcaag atccgcagct tcctcttggc ctcctccggc | 100 |

<210> SEQ ID NO 38
<211> LENGTH: 100
<212> TYPE: DNA
<213> ORGANISM: Homo sapiens

<400> SEQUENCE: 38

| | |
|---|---|
| cctggcgggg agagggtacc ggctgccacc acctgctgcc ggtcccctcg caggcgacca | 60 |
| gcccaacttg ggctgctcac gctactgccg ctgctgccgc | 100 |

<210> SEQ ID NO 39
<211> LENGTH: 100
<212> TYPE: DNA
<213> ORGANISM: Homo sapiens

<400> SEQUENCE: 39

| | |
|---|---|
| tgccactgcc gctgctacta ttcagcctgc gccggccgct ccgccagccc ccggggctcc | 60 |
| ggggctcctc gggggacagc gactcggctg gggggaagag | 100 |

<210> SEQ ID NO 40
<211> LENGTH: 100
<212> TYPE: DNA

<213> ORGANISM: Homo sapiens

<400> SEQUENCE: 40
gaaagaggcg cctctcccgg ggctgaaaac gctgccgggg ctcagcactg ccctcctcgg    60
gggcggggc gtctcgctgc cactgggccc cgggccgccg                          100

<210> SEQ ID NO 41
<211> LENGTH: 100
<212> TYPE: DNA
<213> ORGANISM: Homo sapiens

<400> SEQUENCE: 41
ccgctcttca tctcgttggc gctattcatg atcaccaggc tattgagcgc atagcagtac    60
acagccatag tactgggtcc cgcgctgccc gccgccgcgg                          100

<210> SEQ ID NO 42
<211> LENGTH: 100
<212> TYPE: DNA
<213> ORGANISM: Homo sapiens

<400> SEQUENCE: 42
ctcccgctcc tgctccgccg ccggcgcctc ctcctcccgg cgctcccggc tcagccccgg    60
aggcccggca gccgcggctc cgcgcgcaga tggggcggca                          100

<210> SEQ ID NO 43
<211> LENGTH: 100
<212> TYPE: DNA
<213> ORGANISM: Homo sapiens

<400> SEQUENCE: 43
aagtgcgaag gaagtgtcag gctggatgtc aaaatgaaca ccttggagaa ctggatgatg    60
gaacagacgg taaaaatcag ctaaacatca gagaaaatgg                          100

<210> SEQ ID NO 44
<211> LENGTH: 100
<212> TYPE: DNA
<213> ORGANISM: Homo sapiens

<400> SEQUENCE: 44
aggaagaggt caaaactgtg aacaggaact agaagaaagt gtagcagaaa aagacttgtc    60
acaaacttcg agagatttgg agaaaatgat gtcaaaacac                          100

<210> SEQ ID NO 45
<211> LENGTH: 100
<212> TYPE: DNA
<213> ORGANISM: Homo sapiens

<400> SEQUENCE: 45
atcttcctca agcccatgct gagtatctct gatttggtta atttcttggt aagtgttcca    60
agtacagaca acaaagcaga aaagcactga ttacagggaa                          100

<210> SEQ ID NO 46
<211> LENGTH: 100
<212> TYPE: DNA
<213> ORGANISM: Homo sapiens

<400> SEQUENCE: 46
tatgcagaat gatccttcag atcatgtgaa cgctataatt aaatgttgct accaaatccc    60
cactacccttt tctcccacct agaaaaagtt aatgcatgaa                         100

<210> SEQ ID NO 47
<211> LENGTH: 100
<212> TYPE: DNA
<213> ORGANISM: Homo sapiens

<400> SEQUENCE: 47
ttcagtatga gcaaattgtg atttataaaa acaaacaaac aaacaaacaa acaaaaccca    60
ccctattcac tccgtagggg aataaagctt tcttgcatta                         100

<210> SEQ ID NO 48
<211> LENGTH: 100
<212> TYPE: DNA
<213> ORGANISM: Homo sapiens

<400> SEQUENCE: 48
aacaaacaaa acccacccta ttcactccgt aggggaataa agctttcttg cattaagtca    60
cgcatcatgg gggtaggaaa aaagcacagt actgaaagaa                          100

<210> SEQ ID NO 49
<211> LENGTH: 100
<212> TYPE: DNA
<213> ORGANISM: Homo sapiens

<400> SEQUENCE: 49
gtgaagtgat ccaaatgtag cccagagatc ctaaagaaaa aacgatgctc atgtgttaca    60
aaacaaaatt ttaaggcaat cagtgaggaa tcacagacaa                          100

<210> SEQ ID NO 50
<211> LENGTH: 100
<212> TYPE: DNA
<213> ORGANISM: Homo sapiens

<400> SEQUENCE: 50
atttccttag tgcttttatc aaggttgaat ctgaatataa attactagag gaaagcaaat    60
cagatttcac atctgaaaat taaaaacaaa attcttagct                          100

<210> SEQ ID NO 51
<211> LENGTH: 100
<212> TYPE: DNA
<213> ORGANISM: Homo sapiens

<400> SEQUENCE: 51
aggcaacaaa atgagatcct gtccctagaa aacatttcaa aaaattaaca gcatggtgac    60
gcacacttgt agccctagct acttgggagg ctgagtggga                          100

<210> SEQ ID NO 52
<211> LENGTH: 100
<212> TYPE: DNA
<213> ORGANISM: Homo sapiens

<400> SEQUENCE: 52
aagaacttaa gcagactagg atataaagta taggagcgta ttgtgtacag gaacgggaaa    60
tactgtttcc tggatctttt gtttcactta cgcacacacc                          100

<210> SEQ ID NO 53
<211> LENGTH: 100
<212> TYPE: DNA
<213> ORGANISM: Homo sapiens

<400> SEQUENCE: 53
cacacccgcc agtagtgtac caggttgcga tggaaatctc tctcttctg tggatgagtt    60 tgtggaagcc cttgctccag catgccctcc ttcctgccca    100

<210> SEQ ID NO 54
<211> LENGTH: 100
<212> TYPE: DNA
<213> ORGANISM: Homo sapiens

<400> SEQUENCE: 54
cccctggacc attccttccc ttcacagcac tgtcccatgg gtaggccaca gcccagcaca    60
ggccccagcc tggcggctgc agcaggagcc ccatcccagg    100

<210> SEQ ID NO 55
<211> LENGTH: 100
<212> TYPE: DNA
<213> ORGANISM: Homo sapiens

<400> SEQUENCE: 55
gcctgagggg ccatgcgggg gtctgggtgg gagtgggaac cgctgaggaa ggtgaaggga    60
aatatggtga gatgacaggc ccgctgtcag ggagagtggg    100

<210> SEQ ID NO 56
<211> LENGTH: 100
<212> TYPE: DNA
<213> ORGANISM: Homo sapiens

<400> SEQUENCE: 56
aggagccctg gagtgcccta cctctgtggg gctggaactc cctgtatccg agctagggtc    60
ttccacacgc atgctactac cccaagtgcc acagctggag    100

<210> SEQ ID NO 57
<211> LENGTH: 100
<212> TYPE: DNA
<213> ORGANISM: Homo sapiens

<400> SEQUENCE: 57
tcatctccca ctggataaca gtgttgtcgg gaacttccat ccagcactgg cggacactcc    60
cgtcgcagct gctcctgact gagcaagtca tttaagggg    100

<210> SEQ ID NO 58
<211> LENGTH: 100
<212> TYPE: DNA
<213> ORGANISM: Homo sapiens

<400> SEQUENCE: 58
tccttggcac tcataagcac tcacagaatg gggctggcag tgcgcccggc ctccctggga    60
tgggtccaga atggtaggaa gcgcagtccg ggagggaccc    100

<210> SEQ ID NO 59
<211> LENGTH: 100
<212> TYPE: DNA
<213> ORGANISM: Homo sapiens

<400> SEQUENCE: 59
actgcttaga gctctcagcc ctagatggcg tatcacagtt aatgctctat aaaacccatc    60
atggcttttc cctagtaagc ctcaaatcgc tgcaagcaag    100

```
<210> SEQ ID NO 60
<211> LENGTH: 100
<212> TYPE: DNA
<213> ORGANISM: Homo sapiens

<400> SEQUENCE: 60
gcttcatata tgagagtttc tgctgtctcc tggagccatc tcacccaaag ccactgactc      60
tgggagacca gcccaggcca caaaccagca aagcaccagt                           100

<210> SEQ ID NO 61
<211> LENGTH: 100
<212> TYPE: DNA
<213> ORGANISM: Homo sapiens

<400> SEQUENCE: 61
tatagttaga gctgcattat aaagtggcca gaggacattt ctttgcagtg agatgtgtat      60
cgtgaacgtt tggggcctgt gctcgcctag tcctcatctt                           100

<210> SEQ ID NO 62
<211> LENGTH: 100
<212> TYPE: DNA
<213> ORGANISM: Homo sapiens

<400> SEQUENCE: 62
tgcttttcta ggtacacaaa gccatcccat ggctgcaaat gttagctggg ctgggctccc      60
tacttgcctc aagccccttc atagacccett caggcacatg                          100

<210> SEQ ID NO 63
<211> LENGTH: 100
<212> TYPE: DNA
<213> ORGANISM: Homo sapiens

<400> SEQUENCE: 63
cttttctctg gacgtttaca gacaggtcct cagaggtcag agcaggttgt cctagggagc      60
agggaggctt cctagggagg tcagactcca aatagtggat                           100

<210> SEQ ID NO 64
<211> LENGTH: 100
<212> TYPE: DNA
<213> ORGANISM: Homo sapiens

<400> SEQUENCE: 64
atggcaaaaa tgcagctgca gactcatgag gagtcgccct gggctgccac tagggctccc      60
acagtgtgcg ctgccaacct gctgcccgtg cagaaactct                           100

<210> SEQ ID NO 65
<211> LENGTH: 100
<212> TYPE: DNA
<213> ORGANISM: Homo sapiens

<400> SEQUENCE: 65
caactgtgcc ctgcactgtt agggcccttg tcaaaacaac acatttctca gtgattctga      60
gactctttct cttatctata gaagtcataa ctcaagagta                           100

<210> SEQ ID NO 66
<211> LENGTH: 100
<212> TYPE: DNA
<213> ORGANISM: Homo sapiens

<400> SEQUENCE: 66
```

```
aaatcatacc aatattttac ataaacccta gaattttttat agatctatta tttcttttta    60
gagtacatat tggaagtaac ttcacaagga acattttctt                          100
```

<210> SEQ ID NO 67
<211> LENGTH: 100
<212> TYPE: DNA
<213> ORGANISM: Homo sapiens

<400> SEQUENCE: 67

```
tctggtcaaa ccactccaca aataaagtgg actgatcctc ttgactctat gtgtaagtgc    60
ccattgtgtg tgcacagagc tggtgagaac ggccatggtg                          100
```

<210> SEQ ID NO 68
<211> LENGTH: 100
<212> TYPE: DNA
<213> ORGANISM: Homo sapiens

<400> SEQUENCE: 68

```
ctaggtgggg gtggtgttgg tggagttgga ctagattatc tgggatcatg cgaaatggaa    60
attcatttct agctggctgg cttcagaagg tgccatctcc                          100
```

<210> SEQ ID NO 69
<211> LENGTH: 100
<212> TYPE: DNA
<213> ORGANISM: Homo sapiens

<400> SEQUENCE: 69

```
tatttttata tgaagcgtgc tttggaactc agggcaacga agggtgggtg tgctgcacaa    60
ggacagcaga agagtgagct gactggtccc tgaaatcgca                          100
```

<210> SEQ ID NO 70
<211> LENGTH: 100
<212> TYPE: DNA
<213> ORGANISM: Homo sapiens

<400> SEQUENCE: 70

```
gttggaaagt ggattaccag tgcagtagaa ctcttcacgg aggcctggac catcaggtct    60
aatggtgttg ttccaggtgg gtggtcatgt ggagcaaaaa                          100
```

<210> SEQ ID NO 71
<211> LENGTH: 100
<212> TYPE: DNA
<213> ORGANISM: Homo sapiens

<400> SEQUENCE: 71

```
tatttgaaat cagcgagcac gtacctgaga gatgactttt ccacttgggc tagtctcttg    60
atatttctgg tcctgtttct tcatctgtaa actgggttag                          100
```

<210> SEQ ID NO 72
<211> LENGTH: 100
<212> TYPE: DNA
<213> ORGANISM: Homo sapiens

<400> SEQUENCE: 72

```
aaggagacca agaagcgtat ttaaaatctt gatgttttga gtttcttcct agcttccccc    60
tattccttaa taaagttcta aattgttttg ttggagctct                          100
```

<210> SEQ ID NO 73
<211> LENGTH: 100

<212> TYPE: DNA
<213> ORGANISM: Homo sapiens

<400> SEQUENCE: 73

```
ttgcagccat tctgagggct ttgcatgctt ttctgacctt gcagtaaact caatgcttta    60
ggcaaagaat ggccacgtca tccgaccccc tcagagttta                         100
```

<210> SEQ ID NO 74
<211> LENGTH: 100
<212> TYPE: DNA
<213> ORGANISM: Homo sapiens

<400> SEQUENCE: 74

```
gaattcagaa caggtctgaa gaagaccagg cagcggctga gtcaaggaaa gcctccgtcc    60
gcttttattt cccctgtgcc tcttccagga ctgtgctggg                         100
```

<210> SEQ ID NO 75
<211> LENGTH: 100
<212> TYPE: DNA
<213> ORGANISM: Homo sapiens

<400> SEQUENCE: 75

```
ataacaggct cccgggggtt actttggctg ggctgggcta aaacctccct gcagagcagg    60
ccctgagccc tgcctctgcg cctgggtggt gtcagcccct                         100
```

<210> SEQ ID NO 76
<211> LENGTH: 100
<212> TYPE: DNA
<213> ORGANISM: Homo sapiens

<400> SEQUENCE: 76

```
ccaccttctg actgttccag caactctcta agccctccca aaggcctcaa ggcctgtaac    60
catatgcagc aattttcagc cataccagga gaggtcaact                         100
```

<210> SEQ ID NO 77
<211> LENGTH: 100
<212> TYPE: DNA
<213> ORGANISM: Homo sapiens

<400> SEQUENCE: 77

```
gtaatcttgg ccacctgcct aagaggaagt ggctagcttc acttctgacc ctcagcaact    60
gccaggtggc ctcttggaaa tccccctctg ggggattcca                         100
```

<210> SEQ ID NO 78
<211> LENGTH: 100
<212> TYPE: DNA
<213> ORGANISM: Homo sapiens

<400> SEQUENCE: 78

```
cccgttgggt gggagagcag tagttaaaat gtaaaataag aatcttttgc tgggagaagt    60
caacagatag ggagaagtca gctgataaca gaaatagttt                         100
```

<210> SEQ ID NO 79
<211> LENGTH: 100
<212> TYPE: DNA
<213> ORGANISM: Homo sapiens

<400> SEQUENCE: 79

```
taaaactaac ttcactgtta accaagcagt tcaacatgaa agactgaatc tcttatgttt    60
```

| aatattttct tctcttttaa tcttcataac taattttttt | 100 |

```
<210> SEQ ID NO 80
<211> LENGTH: 100
<212> TYPE: DNA
<213> ORGANISM: Homo sapiens

<400> SEQUENCE: 80
```

| cagataattg tataaaataa ccatggtagc aaaataatgt gatcactgga aaataagcag | 60 |
| ggaaaaacat gctatgaaga tactcctatc tgggtgaatt | 100 |

```
<210> SEQ ID NO 81
<211> LENGTH: 100
<212> TYPE: DNA
<213> ORGANISM: Homo sapiens

<400> SEQUENCE: 81
```

| cttgatagct ttacattttt catctggcat ttaaacatta aacagttaat gtatttgaca | 60 |
| tgaaaattat ttcaagttat cttattagtt ttaatagagt | 100 |

```
<210> SEQ ID NO 82
<211> LENGTH: 100
<212> TYPE: DNA
<213> ORGANISM: Homo sapiens

<400> SEQUENCE: 82
```

| ttaaaagtg tttaaaagag ttttcaaaag gctctaaaat cattttgaaa tagtttaaaa | 60 |
| cagttttgaa tcgttgtaag ttagttttaa tagagcttta | 100 |

```
<210> SEQ ID NO 83
<211> LENGTH: 100
<212> TYPE: DNA
<213> ORGANISM: Homo sapiens

<400> SEQUENCE: 83
```

| aaaaggcct aaaatagtcc tatcaagttg ttgcagacca aaataatctc cttaaatatc | 60 |
| acttttgaga tcagctgggg taaacgacag caacacaatg | 100 |

```
<210> SEQ ID NO 84
<211> LENGTH: 100
<212> TYPE: DNA
<213> ORGANISM: Homo sapiens

<400> SEQUENCE: 84
```

| acaaatcatt aaactatttt agagattatg aaattaaaat actcagatta aaattttcct | 60 |
| atcacagaat taaggtactg gaaaatatgt ttaagttttt | 100 |

```
<210> SEQ ID NO 85
<211> LENGTH: 100
<212> TYPE: DNA
<213> ORGANISM: Homo sapiens

<400> SEQUENCE: 85
```

| attaatcaca ttgctatagg tttagatatt ttgtacaact gaaataaaat cacacactgg | 60 |
| cagctacatt tttgaaagtt aaaaacatgg tcacgaatat | 100 |

```
<210> SEQ ID NO 86
<211> LENGTH: 100
<212> TYPE: DNA
<213> ORGANISM: Homo sapiens
```

```
<400> SEQUENCE: 86
atcttatttt aaaatcagtt aatataccct aatggtattt aatgccaaat tcaaagtgaa      60
ttgatcaagc cctcagtggc caggtcatgg gtgtgatttt                            100

<210> SEQ ID NO 87
<211> LENGTH: 100
<212> TYPE: DNA
<213> ORGANISM: Homo sapiens

<400> SEQUENCE: 87
tactctgaaa gaattacata tttctttctt tttggttgag cttttgttat ttaaatacat      60
ttgatgagag gatattgaaa taattaaata gcactgaaaa                            100

<210> SEQ ID NO 88
<211> LENGTH: 100
<212> TYPE: DNA
<213> ORGANISM: Homo sapiens

<400> SEQUENCE: 88
aaaaaaagct ttaaattatt tacaatcccc taatggaaat tttcactaat gagatatcat      60
aatgaatgtg aattttattt ctgaaatctc taataaatca                            100

<210> SEQ ID NO 89
<211> LENGTH: 100
<212> TYPE: DNA
<213> ORGANISM: Homo sapiens

<400> SEQUENCE: 89
aagctttaaa ttatttacaa tcccctaatg gaaattttca ctaatgagat atcataatga      60
atgtgaattt tatttctgaa atctctaata aatcagtctt                            100

<210> SEQ ID NO 90
<211> LENGTH: 100
<212> TYPE: DNA
<213> ORGANISM: Homo sapiens

<400> SEQUENCE: 90
ctccctggtt ttcccagctc agcgcccatt acgtttctgt tctctttccc ttagtggcat      60
tatttgtatc actgtgcatc aggaaagctg gctacggcag                            100

<210> SEQ ID NO 91
<211> LENGTH: 100
<212> TYPE: DNA
<213> ORGANISM: Homo sapiens

<400> SEQUENCE: 91
catcaatcgg gcagacacag ggtggccacg gccactagcg gcaaggcggc tgccccaaga      60
gcgcggtggc atggccacca aagccactca atcgagaaag                            100

<210> SEQ ID NO 92
<211> LENGTH: 100
<212> TYPE: DNA
<213> ORGANISM: Homo sapiens

<400> SEQUENCE: 92
accgcggctc tgtctacagc tcgcggtgcc acggccttct tggcagaata aaaatgtaga      60
caagtaataa cagaggataa tgaaagaaca tactctttaa                            100
```

<210> SEQ ID NO 93
<211> LENGTH: 100
<212> TYPE: DNA
<213> ORGANISM: Homo sapiens

<400> SEQUENCE: 93
aatatttcct attttttca cagacccacg gtcattaaaa aatgcaatta tttacttttt    60
ttcatttaaa cacatttctt tgagattgag cttttgggaa                         100

<210> SEQ ID NO 94
<211> LENGTH: 100
<212> TYPE: DNA
<213> ORGANISM: Homo sapiens

<400> SEQUENCE: 94
taaccacctt tccaccatta caataagaga taatttcacg tttagtctaa tgtacaaatt    60 ggattttaa aaaatgagct ctatctgtga agcccttatt                          100

<210> SEQ ID NO 95
<211> LENGTH: 100
<212> TYPE: DNA
<213> ORGANISM: Homo sapiens

<400> SEQUENCE: 95
aaaatgagct ctatctgtga agcccttatt cctatagaat gtgtcttttt gagtttatta    60
cttattacag actctaaaaa caacattgct gctgattttc                         100

<210> SEQ ID NO 96
<211> LENGTH: 100
<212> TYPE: DNA
<213> ORGANISM: Homo sapiens

<400> SEQUENCE: 96
aagtaagctg cctcttctac atagcaaata ggtacacttc acttttccct gattttctt    60 agggcgtgct attgattttt attgttgtct gacaaaataa                         100

<210> SEQ ID NO 97
<211> LENGTH: 100
<212> TYPE: DNA
<213> ORGANISM: Homo sapiens

<400> SEQUENCE: 97
tttatcaaac aaaagggaga aagactaaaa aatgtatttt tccacttttc tgtatcatgc    60
ataatcagca acaaccaata caatatttgg caagagtgaa                         100

<210> SEQ ID NO 98
<211> LENGTH: 100
<212> TYPE: DNA
<213> ORGANISM: Homo sapiens

<400> SEQUENCE: 98
caaaaataaa tttactttg ctccttagaa atacaagggt tcctttttag ttacactttt    60
tttttttact ttgtgtcatt cagtttagag caatttaatc                         100

<210> SEQ ID NO 99
<211> LENGTH: 100
<212> TYPE: DNA
<213> ORGANISM: Homo sapiens

<400> SEQUENCE: 99

```
tttttttctc caaatccatt tttgaagctg agtttaactt ttgcaaccca tggcaaatct    60
taaatgccct catttaccaa tctttaccaa actcctattt                         100

<210> SEQ ID NO 100
<211> LENGTH: 100
<212> TYPE: DNA
<213> ORGANISM: Homo sapiens

<400> SEQUENCE: 100
aagcctctaa aagtcaatac tggccatcag acccaaattt cagaagacaa tagtgaaaaa    60
ttacttacgt ttaatctcca gtcgtgtccc ttggccgaag                         100

<210> SEQ ID NO 101
<211> LENGTH: 100
<212> TYPE: DNA
<213> ORGANISM: Homo sapiens

<400> SEQUENCE: 101
gtgatccaca gtgttaactt aattactttc cccttaacaa aaatctcttt tcgctgttaa    60
tatcactaac ctgaccgatg cagagaaaat cttgcaattg                         100

<210> SEQ ID NO 102
<211> LENGTH: 100
<212> TYPE: DNA
<213> ORGANISM: Homo sapiens

<400> SEQUENCE: 102
agatgcctca cttaactggc tagcgcttgg ctgttcctta agatgaacta attttctatc    60
ccttactcat ctgactttt gaaagaatct ggtactcttt                          100

<210> SEQ ID NO 103
<211> LENGTH: 100
<212> TYPE: DNA
<213> ORGANISM: Homo sapiens

<400> SEQUENCE: 103
ggaattgacc tgagctaata tctcaaacac aaaaacgctc caaatttaaa accttataag    60
aaaaagcatt aggaaagtgc acttacgttt gatctccacc                         100

<210> SEQ ID NO 104
<211> LENGTH: 100
<212> TYPE: DNA
<213> ORGANISM: Homo sapiens

<400> SEQUENCE: 104
ttggtccctc cgccgaaagt gagccacagt gagggatctc acccttcccc ctcaacaaaa    60
acctctcttg aagccaatca tatgagatag gctgcttgtt                         100

<210> SEQ ID NO 105
<211> LENGTH: 100
<212> TYPE: DNA
<213> ORGANISM: Homo sapiens

<400> SEQUENCE: 105
cagagaaaaa tctagctatt tcttccccat tcccccatg aatcctattc tcctctcaaa     60
cccaatgatt cgtctatttg ctcagctttt taagttcatt                         100

<210> SEQ ID NO 106
```

-continued

```
<211> LENGTH: 100
<212> TYPE: DNA
<213> ORGANISM: Homo sapiens

<400> SEQUENCE: 106
ttctggtgtc ctgctattta cttctgggtc accaggttta ttcaaccaaa atatcacaaa     60
acttgcacaa atgatacaat ggcactaaaa tctcacgaat                          100

<210> SEQ ID NO 107
<211> LENGTH: 100
<212> TYPE: DNA
<213> ORGANISM: Homo sapiens

<400> SEQUENCE: 107
aattgagaca gatgtactta cgtttgatat ccactttggt cccagggccg aaagtgaatc     60
acagtgattc gtcttaactt ttcccttttac aaaaacctcc                         100

<210> SEQ ID NO 108
<211> LENGTH: 100
<212> TYPE: DNA
<213> ORGANISM: Homo sapiens

<400> SEQUENCE: 108
ctgaaagctc agcaagcctc tttcccccaa tgaagttatt ttgatttaga aatcttaaaa     60
attagccaca agctagcgtc ctgtggaaca atttcccctc                          100

<210> SEQ ID NO 109
<211> LENGTH: 100
<212> TYPE: DNA
<213> ORGANISM: Homo sapiens

<400> SEQUENCE: 109
ctctgtacct aacctgggaa tgaagtttgt tagatccctg gcatccgact aatgaaaatc     60
cacacaaagg aacacaaagt aaactaatta gcaacagtga                          100

<210> SEQ ID NO 110
<211> LENGTH: 100
<212> TYPE: DNA
<213> ORGANISM: Homo sapiens

<400> SEQUENCE: 110
agaatcagtg gaaaaaagta cttacgtttg atctccagct tggtcccctg gccaaaagtg     60
tacacacaat ggttcctctt aacttccctc ctatacaaaa                          100

<210> SEQ ID NO 111
<211> LENGTH: 100
<212> TYPE: DNA
<213> ORGANISM: Homo sapiens

<400> SEQUENCE: 111 actcccttc tgacaattga ccaaggctct gtccagaaca tgttatgttc cccaggacat      60
ttctgaagct attacttaga caagttattc tcacccaatg                          100

<210> SEQ ID NO 112
<211> LENGTH: 100
<212> TYPE: DNA
<213> ORGANISM: Homo sapiens

<400> SEQUENCE: 112
actgaatctt gcttgctctt caaagaaaat gtgcaatcaa ttctcgagtt tgactacaga    60
```

```
cttatcttta tcttttccct gaaggatatc agaggctgat                          100
```

<210> SEQ ID NO 113
<211> LENGTH: 100
<212> TYPE: DNA
<213> ORGANISM: Homo sapiens

<400> SEQUENCE: 113

```
tgcagagtca ccttatagat cacttcatag acacagggaa cagaagacac agacaactga    60
ggaagcaaag tttaaattct actcacgttt gatttccacc                         100
```

<210> SEQ ID NO 114
<211> LENGTH: 100
<212> TYPE: DNA
<213> ORGANISM: Homo sapiens

<400> SEQUENCE: 114

```
ttggtccctt ggccgaacgt ccaccacagt gagagctctc cattgtcttg ctgaacaaaa    60
acccttctca ccaaagggga acagagtcct gggtcagctg                         100
```

<210> SEQ ID NO 115
<211> LENGTH: 100
<212> TYPE: DNA
<213> ORGANISM: Homo sapiens

<400> SEQUENCE: 115

```
atcaacttaa ggctcataac tttgaaatgc attttgaaat gtagctccag atggtatacg    60
aaaccaaagt gaagactaat agagtagaaa agtagacttt                         100
```

<210> SEQ ID NO 116
<211> LENGTH: 100
<212> TYPE: DNA
<213> ORGANISM: Homo sapiens

<400> SEQUENCE: 116

```
acttggttgg tttgtctgtt ttcacagcac aggaagagct cagctcttac tgagctggac    60
caggcgcatg ccatctttgg agctgccatg gagtcccagt                         100
```

<210> SEQ ID NO 117
<211> LENGTH: 100
<212> TYPE: DNA
<213> ORGANISM: Homo sapiens

<400> SEQUENCE: 117

```
gttccatagt gtttccatag taatctcatc aacaacactg aagacctttt cagtattttc    60
ttttgagtcc agctccattt ttgcagcctt gtatctctct                         100
```

<210> SEQ ID NO 118
<211> LENGTH: 100
<212> TYPE: DNA
<213> ORGANISM: Homo sapiens

<400> SEQUENCE: 118

```
ccgcgcccag ccgagtgcct gtttattttt acctgctttc agattctctt ctacccttct    60
aaattataag ctgtttgatg ttttatttgc cctgtatttg                         100
```

<210> SEQ ID NO 119
<211> LENGTH: 100
<212> TYPE: DNA

<213> ORGANISM: Homo sapiens

<400> SEQUENCE: 119

```
ggaggctccg tccagtatct ttacttagca aatgcttaac aaacattttc agaataaata     60
aaaaaaaata cctaattgaa agtcaataat agatcagaga                          100
```

<210> SEQ ID NO 120
<211> LENGTH: 100
<212> TYPE: DNA
<213> ORGANISM: Homo sapiens

<400> SEQUENCE: 120

```
tgctatcata gaccaaagac taatactgac tgccacaaca gtaaccttta caacagaaat     60
cataactaca attctaaaga ttaggggtag gtttatttga                          100
```

<210> SEQ ID NO 121
<211> LENGTH: 100
<212> TYPE: DNA
<213> ORGANISM: Homo sapiens

<400> SEQUENCE: 121

```
ttctgtcact ggcagctttg ctagttgcct tgaatagcag aattagcatt tggtctcacc     60
agaagatgag aaggagagg gatcaagtta gaggtggaga                           100
```

<210> SEQ ID NO 122
<211> LENGTH: 100
<212> TYPE: DNA
<213> ORGANISM: Homo sapiens

<400> SEQUENCE: 122

```
gttaacattg gcaagtgaaa tttaatgtgc aaaatagctg accaagggca tagtcctttt     60
ttaaagggga cacaaagtga ttttctctgc agacatacac                          100
```

<210> SEQ ID NO 123
<211> LENGTH: 100
<212> TYPE: DNA
<213> ORGANISM: Homo sapiens

<400> SEQUENCE: 123

```
gcaataccaa tcataaaggg tgacatttat tgagcactta ctaagtgcca gacattgtac     60
atggatcatc acatttaatt attcccaaga ctctatgaac                          100
```

<210> SEQ ID NO 124
<211> LENGTH: 100
<212> TYPE: DNA
<213> ORGANISM: Homo sapiens

<400> SEQUENCE: 124

```
tgagcactta ctaagtgcca gacattgtac atggatcatc acatttaatt attcccaaga     60
ctctatgaac taggaactaa tattatcccc tactttgtag                          100
```

<210> SEQ ID NO 125
<211> LENGTH: 100
<212> TYPE: DNA
<213> ORGANISM: Homo sapiens

<400> SEQUENCE: 125

```
gtgcaaaaac ttgagggcag agaggtcaag gaactggctt atggcagtaa gtggcagagc     60
tgtgacctaa actcagatcc catgttttta actgaactat                          100
```

<210> SEQ ID NO 126
<211> LENGTH: 100
<212> TYPE: DNA
<213> ORGANISM: Homo sapiens

<400> SEQUENCE: 126

```
atgcagatta tactccagga gtaaagtcac tcaacggaag caacaagcgt gacagggaat      60
gctgggatgg gggaaggtaa aaggaactcc ttagactggg                            100
```

<210> SEQ ID NO 127
<211> LENGTH: 100
<212> TYPE: DNA
<213> ORGANISM: Homo sapiens

<400> SEQUENCE: 127

```
ataagtgtgt acagacgtat gtataagact acacatggaa atattgttta aagagtgaaa      60
aataactaaa atcctcatta ataggagttt ggttaaactg                            100
```

<210> SEQ ID NO 128
<211> LENGTH: 100
<212> TYPE: DNA
<213> ORGANISM: Homo sapiens

<400> SEQUENCE: 128

```
tgctagagct ttacaatgta gcacaaagca gacattaagg ggaagacgta gacttctata      60
tagttacgtg gaaggtgttt gtgaaaatgc aggtcactga                            100
```

<210> SEQ ID NO 129
<211> LENGTH: 100
<212> TYPE: DNA
<213> ORGANISM: Homo sapiens

<400> SEQUENCE: 129

```
agagtatgtg tggtgagata tcatgatccc atctacattg aatatatatg tatataaata      60
cgggctgaat tttaaaagac ataaattgtg cttggtagtt                            100
```

<210> SEQ ID NO 130
<211> LENGTH: 100
<212> TYPE: DNA
<213> ORGANISM: Homo sapiens

<400> SEQUENCE: 130

```
aaatacgggc tgaattttaa aagacataaa ttgtgcttgg tagttatctc ctgggattgc      60
agaggaggaa caatgacact ttatgccatc tcctcctact                            100
```

<210> SEQ ID NO 131
<211> LENGTH: 100
<212> TYPE: DNA
<213> ORGANISM: Homo sapiens

<400> SEQUENCE: 131

```
cttctgtatg gtgatgtgaa tatattcatt ttatagtttt tagaaataat aaaactgtac      60
taattttgaa aaacagtaaa ctctgacatt gcctattagc                            100
```

<210> SEQ ID NO 132
<211> LENGTH: 100
<212> TYPE: DNA
<213> ORGANISM: Homo sapiens

```
<400> SEQUENCE: 132
attctcgata ttcctgtgca atgcataaac ataacttttt aaaagatatg tacacacatg    60
tgtgagtttt ctttgtcaaa tacttttcta taatctttaa                          100

<210> SEQ ID NO 133
<211> LENGTH: 100
<212> TYPE: DNA
<213> ORGANISM: Homo sapiens

<400> SEQUENCE: 133
atcaagcatg ccaaaaaggt aaaagctttc ctgtttcagt gtaggagata gtcgtctgca    60
aaggaaagag atgtagggga tagaaacagg aatgaaaaag                          100

<210> SEQ ID NO 134
<211> LENGTH: 100
<212> TYPE: DNA
<213> ORGANISM: Homo sapiens

<400> SEQUENCE: 134
atgactgagc tgttcgaggg acttatgttc ctaagtgagc taattggaaa tctaatatga    60
acagtgcaac cgataacta ttgtaaagca gtatttgtaa                           100

<210> SEQ ID NO 135
<211> LENGTH: 100
<212> TYPE: DNA
<213> ORGANISM: Homo sapiens

<400> SEQUENCE: 135
acaataaaag atgattatca taagtaccat tgttgcaaaa actatttat tgatcacatg    60 cagtggtgat ctgtaggaat gattgttgtg atgtttgctg                          100

<210> SEQ ID NO 136
<211> LENGTH: 100
<212> TYPE: DNA
<213> ORGANISM: Homo sapiens

<400> SEQUENCE: 136
taacataaaa tgaaacatgg aagtggctg agatctttag gatgtgtgtg gttcattttt     60
tgaaagcaaa tgttgtctca gaagcatctg tgagactctg                          100

<210> SEQ ID NO 137
<211> LENGTH: 100
<212> TYPE: DNA
<213> ORGANISM: Homo sapiens

<400> SEQUENCE: 137
ccaggatcca ccgttctaca aaatatctgt gatggacatt gataagattg atctgttgag    60
gaaaggcaag gtgtcagtaa gatagtctga gagcttcttg                          100

<210> SEQ ID NO 138
<211> LENGTH: 100
<212> TYPE: DNA
<213> ORGANISM: Homo sapiens

<400> SEQUENCE: 138
gatttcatgt aaaagagtgc tggaaataga atttcttggg gaacattcca actaactcat    60
cactgaaggt gctttacatt gaaccctcag caaagttaga                          100
```

```
<210> SEQ ID NO 139
<211> LENGTH: 100
<212> TYPE: DNA
<213> ORGANISM: Homo sapiens

<400> SEQUENCE: 139
ttatcagaaa aaaaatataa actgctgtgg aggggacagg aaggaaagtc agggagggag      60
gggggcaagg agagaaagag cgagagagag gagagaaaga                          100

<210> SEQ ID NO 140
<211> LENGTH: 100
<212> TYPE: DNA
<213> ORGANISM: Homo sapiens

<400> SEQUENCE: 140
agagaggaga gagagagcac aagtacacac ttcaatgcac atctataaat catcctgaaa      60
actactgata aattatttta gcaatgttcc tcagatgtaa                          100

<210> SEQ ID NO 141
<211> LENGTH: 100
<212> TYPE: DNA
<213> ORGANISM: Homo sapiens

<400> SEQUENCE: 141
catttcaaga aatatcattt ttgcttttta tttggcataa tttactagcc aatttaggaa      60
gttcccctca catcagtaac atacagtaca tcacccagta                          100

<210> SEQ ID NO 142
<211> LENGTH: 100
<212> TYPE: DNA
<213> ORGANISM: Homo sapiens

<400> SEQUENCE: 142
tgtcagagga cacaatggca taagtttgcc ttttgcaagg tttgagggat ggccatttcc      60
ctacctgact caggaaagtc tgtagctgat atccatcttc                          100

<210> SEQ ID NO 143
<211> LENGTH: 100
<212> TYPE: DNA
<213> ORGANISM: Homo sapiens

<400> SEQUENCE: 143
aagtttgtgg ttctttctct ctatatatat atttgagctc agcagtcatg ctggagtcca      60
gagtaggtga ttctttctgc tttagcttga ctcctcctta                          100

<210> SEQ ID NO 144
<211> LENGTH: 100
<212> TYPE: DNA
<213> ORGANISM: Homo sapiens

<400> SEQUENCE: 144
tatatatttg agctcagcag tcatgctgga gtccagagta ggtgattctt tctgctttag      60
cttgactcct ccttaagatt gtaactctct cagttttaca                          100

<210> SEQ ID NO 145
<211> LENGTH: 100
<212> TYPE: DNA
<213> ORGANISM: Homo sapiens

<400> SEQUENCE: 145
```
ttttttgtca gacgtaagct gacattccac aaggagagga ggaaattctg tggttcacat    60
ccagtggtgc ttggaacctg attggttgtc attcttccag                         100

<210> SEQ ID NO 146
<211> LENGTH: 100
<212> TYPE: DNA
<213> ORGANISM: Homo sapiens

<400> SEQUENCE: 146
ctagtttgtc acgagtggat atctgtcctg gattcccaag gatcaaggct gccccattag    60
ccaggaagta gggagataga ggaggtcact tgagaaagag                         100

<210> SEQ ID NO 147
<211> LENGTH: 100
<212> TYPE: DNA
<213> ORGANISM: Homo sapiens

<400> SEQUENCE: 147
ctgcttcttt gccgcctcca ggttgtgtct gtttcctctc atatctgaag acagatgtgc    60
tggcagaagc aaagtccttt gtccggccac gtgcaaatgc                         100

<210> SEQ ID NO 148
<211> LENGTH: 100
<212> TYPE: DNA
<213> ORGANISM: Homo sapiens

<400> SEQUENCE: 148
atgggacata aatatgaaca gagattcttg tcccactcta gaaaatgtag atgttcatct    60
tgtttccaag gggacagtaa ggctgcaggt gttttttgac                         100

<210> SEQ ID NO 149
<211> LENGTH: 100
<212> TYPE: DNA
<213> ORGANISM: Homo sapiens

<400> SEQUENCE: 149
cttttgtact cactggttgt ttttgcatag gcccctccag gccacgacca gctgtttgga    60
ttttataaac gggccgtttg cattgtgaac tgagctacaa                         100

<210> SEQ ID NO 150
<211> LENGTH: 100
<212> TYPE: DNA
<213> ORGANISM: Homo sapiens

<400> SEQUENCE: 150
caggcaggca gggcagcaa gatggtgttg cagacccagg tcttcatttc tctgttgctc     60
tggatctctg gtgaggaatt aaaaagtgcc acagtctttt                         100

<210> SEQ ID NO 151
<211> LENGTH: 100
<212> TYPE: DNA
<213> ORGANISM: Homo sapiens

<400> SEQUENCE: 151
cagagtaata tctgtgtaga aataaaaaaa attaagatat agttggaaat aatgactatt    60
tccaatatgg atccaattat ctgctgactt ataatactac                         100

<210> SEQ ID NO 152
<211> LENGTH: 100

<212> TYPE: DNA
<213> ORGANISM: Homo sapiens

<400> SEQUENCE: 152
attaagatat agttggaaat aatgactatt tccaatatgg atccaattat ctgctgactt    60
ataatactac tagaaagcaa atttaaatga catatttcaa                          100

<210> SEQ ID NO 153
<211> LENGTH: 100
<212> TYPE: DNA
<213> ORGANISM: Homo sapiens

<400> SEQUENCE: 153
ttatatctga dacagcgtgt ataagtttat gtataatcat tgtccattac tgactacagg    60
tgcctacggg gacatcgtga tgacccagtc tccagactcc                          100

<210> SEQ ID NO 154
<211> LENGTH: 100
<212> TYPE: DNA
<213> ORGANISM: Homo sapiens

<400> SEQUENCE: 154
ctggctgtgt ctctgggcga gagggccacc atcaactgca agtccagcca gagtgtttta    60
tacagctcca acaataagaa ctacttagct tggtaccagc                          100

<210> SEQ ID NO 155
<211> LENGTH: 100
<212> TYPE: DNA
<213> ORGANISM: Homo sapiens

<400> SEQUENCE: 155
agaaaccagg acagcctcct aagctgctca tttactgggc atctacccgg gaatccgggg    60
tccctgaccg attcagtggc agcgggtctg ggacagattt                          100

<210> SEQ ID NO 156
<211> LENGTH: 100
<212> TYPE: DNA
<213> ORGANISM: Homo sapiens

<400> SEQUENCE: 156
cactctcacc atcagcagcc tgcaggctga agatgtggca gtttattact gtcagcaata    60
ttatagtact cctcccacag tgcttcagcc tcgaacacaa                          100

<210> SEQ ID NO 157
<211> LENGTH: 100
<212> TYPE: DNA
<213> ORGANISM: Homo sapiens

<400> SEQUENCE: 157
acctcctccc catacgctgg gccagtaggt ctttgctgca gcagctgctt cctctgcaca    60
cagcccccaa catgcatgct tcctctgtgt gttggggagg                          100

<210> SEQ ID NO 158
<211> LENGTH: 100
<212> TYPE: DNA
<213> ORGANISM: Homo sapiens

<400> SEQUENCE: 158
aatacatgaa aacaactacc gaaatgttat gaaattatag tttagtagaa ctaacaagtg    60

```
cattaatgca aagaaaagt agggctcagt aatcagggaa                    100

<210> SEQ ID NO 159
<211> LENGTH: 100
<212> TYPE: DNA
<213> ORGANISM: Homo sapiens

<400> SEQUENCE: 159
ccaagtgtgc attgtaaaag tgcagcctct ctaacactgg gtttcatcac aagtaacaga    60
acaggatgcc tgatgcaggg aaaaaagaaa ggcaattgtt                         100

<210> SEQ ID NO 160
<211> LENGTH: 100
<212> TYPE: DNA
<213> ORGANISM: Homo sapiens

<400> SEQUENCE: 160
gatctctggt aagagaaaca cttcctctcc tctgtgccac caagtcccct gcatatccac    60
aaaaataata tattttcata aggaattgat tttcctcatt                         100

<210> SEQ ID NO 161
<211> LENGTH: 100
<212> TYPE: DNA
<213> ORGANISM: Homo sapiens

<400> SEQUENCE: 161
ctctgcaaat atgatgcatt tgatttatgt tttttacttt gctccataat cagataccag    60
ggcagaaacg acactcacgc agtctccagc attcatgtca                         100

<210> SEQ ID NO 162
<211> LENGTH: 100
<212> TYPE: DNA
<213> ORGANISM: Homo sapiens

<400> SEQUENCE: 162
gcgactccag gagacaaagt caacatctcc tgcaaagcca gccaagacat tgatgatgat    60
atgaactggt accaacagaa accaggagaa gctgctattt                         100

<210> SEQ ID NO 163
<211> LENGTH: 100
<212> TYPE: DNA
<213> ORGANISM: Homo sapiens

<400> SEQUENCE: 163
tcattattca agaagctact actctcgttc ctggaatccc acctcgattc agtggcagcg    60
ggtatggaac agattttacc ctcacaatta ataacataga                         100

<210> SEQ ID NO 164
<211> LENGTH: 100
<212> TYPE: DNA
<213> ORGANISM: Homo sapiens

<400> SEQUENCE: 164
atctgaggat gctgcatatt acttctgtct acaacatgat aatttccctc tcacagtgat    60
acaccctgtt acaaaaacct ccaagttctc tcagtgggat                         100

<210> SEQ ID NO 165
<211> LENGTH: 100
<212> TYPE: DNA
```

<400> SEQUENCE: 165
gccctctgtc ctggagacac ggccaaggag gctggagact gggtcagcac aatgtcccca    60
ttgcagcctg aaatgataaa gacagataaa ttatatcaga                          100

<210> SEQ ID NO 166
<211> LENGTH: 100
<212> TYPE: DNA
<213> ORGANISM: Homo sapiens

<400> SEQUENCE: 166
tatactgaga ctgtccccat gtaggccatg cattggtgac acttgtaacc acagtcatat    60
gcaacatctt gagtaaccag aaaacaaaag ataactgggg                          100

<210> SEQ ID NO 167
<211> LENGTH: 100
<212> TYPE: DNA
<213> ORGANISM: Homo sapiens

<400> SEQUENCE: 167
aacttacaac ctacaatgag tgccctaaat ccaacaacca agaatccaga gacacaaaaa    60
acaatgatgg ccacatgagt ttgcccgatg tttccctata                          100

<210> SEQ ID NO 168
<211> LENGTH: 100
<212> TYPE: DNA
<213> ORGANISM: Homo sapiens

<400> SEQUENCE: 168
taccaacacc atcagagtgt ggctgcatct gaggaccact ctcagctgat agaggcatca    60
ggaggagcag ctggggcagc cctgcctcac acatctgctt                          100

<210> SEQ ID NO 169
<211> LENGTH: 100
<212> TYPE: DNA
<213> ORGANISM: Homo sapiens

<400> SEQUENCE: 169
ggggtttatg ttcgggtgtg taacactgtg ggagaataac tattatactg ttggcagtaa    60
taagttgcaa aatcatcagg ctgcaggctg ctgatggtga                          100

<210> SEQ ID NO 170
<211> LENGTH: 100
<212> TYPE: DNA
<213> ORGANISM: Homo sapiens

<400> SEQUENCE: 170
gccgctgaac cttgatggga ccccactttc taaactagac gccttataga tcaggagctt    60
aggggctttc cctggtttct gctgatacca ggccaaccag                          100

<210> SEQ ID NO 171
<211> LENGTH: 100
<212> TYPE: DNA
<213> ORGANISM: Homo sapiens

<400> SEQUENCE: 171
ctactaatac tctgactggc ccggcaagtg atggtgactc tgtctcctac agatgcagac    60
agggtggaag gagactgggt catctggatg tcacatttgg                          100

```
<210> SEQ ID NO 172
<211> LENGTH: 100
<212> TYPE: DNA
<213> ORGANISM: Homo sapiens

<400> SEQUENCE: 172
ggatgtcaca tttggcacct gagattggaa atagaaacac aaatattcat actattgatc    60
atattatagg aagactccc tgaataacca ggcagtactg                           100

<210> SEQ ID NO 173
<211> LENGTH: 100
<212> TYPE: DNA
<213> ORGANISM: Homo sapiens

<400> SEQUENCE: 173
agcacactgg gctgagtaaa ttcctagtgt tctccttcct tacctgggag ccagagcagc    60
aggagcccca ggagctgagc ggggaccctc atgtccatgc                          100

<210> SEQ ID NO 174
<211> LENGTH: 100
<212> TYPE: DNA
<213> ORGANISM: Homo sapiens

<400> SEQUENCE: 174
gggactattt tattatgaga aacaattttt aggtattttt ttgagaattt taaatattcc    60
tcaggagccg atagagtaat gtatttcatt ggtgtatcag                          100

<210> SEQ ID NO 175
<211> LENGTH: 100
<212> TYPE: DNA
<213> ORGANISM: Homo sapiens

<400> SEQUENCE: 175
gattatttag gagaatattc ttgtttgtag gaaacacata gtaaatgtt agatggtagg     60 attctcaagt cttcaaaaga ctctcataag attccgggta                          100

<210> SEQ ID NO 176
<211> LENGTH: 100
<212> TYPE: DNA
<213> ORGANISM: Homo sapiens

<400> SEQUENCE: 176
tattcttgtt tgtaggaaac acatagtaaa atgttagatg gtaggattct caagtcttca    60
aaagactctc ataagattcc gggtagggaa gggggtaatt                          100

<210> SEQ ID NO 177
<211> LENGTH: 100
<212> TYPE: DNA
<213> ORGANISM: Homo sapiens

<400> SEQUENCE: 177
tgtaagtatt aggtaatggt gttatgcctt tgttcttact agtattagat caagcaattt    60
attacagata tacaaagatg ataccgtgtt gtctccatgc                          100

<210> SEQ ID NO 178
<211> LENGTH: 100
<212> TYPE: DNA
<213> ORGANISM: Homo sapiens

<400> SEQUENCE: 178
```

```
atgcagcact cacagatcca ccactatcaa gaactgcagg tctctttaat acccagagac    60
taaatgaggt gcaccttatt cttgttttgg gtaccttcat                         100

<210> SEQ ID NO 179
<211> LENGTH: 100
<212> TYPE: DNA
<213> ORGANISM: Homo sapiens

<400> SEQUENCE: 179
ttgggtgtgt aacactgtgg gagggtaact ataatactgt tgacagtaat aagttgcaaa    60
atcttcagac tgcaggcagc tgatggtgag agtgaaatct                         100

<210> SEQ ID NO 180
<211> LENGTH: 100
<212> TYPE: DNA
<213> ORGANISM: Homo sapiens

<400> SEQUENCE: 180
ctgactcgcc cgacaagtga tggtgactct gtctcctgta gatgcagaga atgaggatgg    60
agactgggtc atccggatgg cacatctggc acctgagatt                         100

<210> SEQ ID NO 181
<211> LENGTH: 100
<212> TYPE: DNA
<213> ORGANISM: Homo sapiens

<400> SEQUENCE: 181
ctttcccctg gagacaaaga cagggtgcct ggagactgcg tcaacacaat ttctccggtg    60
gtatctgaga ttggaaataa aacagaaaag tcacccatgt                         100

<210> SEQ ID NO 182
<211> LENGTH: 100
<212> TYPE: DNA
<213> ORGANISM: Homo sapiens

<400> SEQUENCE: 182
aatctaaatc aaacccattg tcttcccaga agagccagaa ttattgcttt atattgagct    60
ttaattattg tattgactga gcagagttgc caggtaacag                         100

<210> SEQ ID NO 183
<211> LENGTH: 100
<212> TYPE: DNA
<213> ORGANISM: Homo sapiens

<400> SEQUENCE: 183
gacttgagag ggttttcact gacatgcaaa accatcccat gttcccctca cctgggagcc    60
agagtagcag gaggaagaga agctgcgctg gggtttccat                         100

<210> SEQ ID NO 184
<211> LENGTH: 100
<212> TYPE: DNA
<213> ORGANISM: Homo sapiens

<400> SEQUENCE: 184
agctcttctc cagagctctg acccaggcat tgatatgggc tctggactgc agggcggctg    60
ggagggacat gcaaagcagc tggggcgggt gctgggcttg                         100

<210> SEQ ID NO 185
```

```
<211> LENGTH: 100
<212> TYPE: DNA
<213> ORGANISM: Homo sapiens

<400> SEQUENCE: 185
cagctgcaga gacaatctgc ctcccctttc tgctctcagc agcccatgcc caggtgatca      60
ggccagaaaa ggccgttggc tcagtctgag ggtagaactt                           100

<210> SEQ ID NO 186
<211> LENGTH: 100
<212> TYPE: DNA
<213> ORGANISM: Homo sapiens

<400> SEQUENCE: 186
ctcccctgcg gccacagaat ttaacccctg tgtcctcttg tctcaccatc acctagattg      60
agccacagaa tgtttggtac aagtctgtta gaaacaaaat                           100

<210> SEQ ID NO 187
<211> LENGTH: 100
<212> TYPE: DNA
<213> ORGANISM: Homo sapiens

<400> SEQUENCE: 187
agaaggctgt ggtttcattt ttctctttct gctccaactt gtgcccagtc agctccctaa      60
atgcatgatg gatcaggttg aaaggaagag tctattacaa                           100

<210> SEQ ID NO 188
<211> LENGTH: 100
<212> TYPE: DNA
<213> ORGANISM: Homo sapiens

<400> SEQUENCE: 188
ctttatcttc cggatatact tgtatttact tgttagtgat ctttcctgag ggtccagaag      60
ctgtctcatt ctttgcagaa attaaaagag taacattcaa                           100

<210> SEQ ID NO 189
<211> LENGTH: 100
<212> TYPE: DNA
<213> ORGANISM: Homo sapiens

<400> SEQUENCE: 189
ttaacctcag cactgtgggt gtgaggactt tcacaactgc acagataagt gagacctggg      60
ctccaaatcc tcagggtagt gataccattt ccctaaagac                           100

<210> SEQ ID NO 190
<211> LENGTH: 100
<212> TYPE: DNA
<213> ORGANISM: Homo sapiens

<400> SEQUENCE: 190
agaagatggt tttgtccatg caggcaaaga actatttctt gggtgatcct ctaaactatc      60
cagtcttttt attctgtata gctggtatag tttacccta                            100

<210> SEQ ID NO 191
<211> LENGTH: 100
<212> TYPE: DNA
<213> ORGANISM: Homo sapiens

<400> SEQUENCE: 191
ggctatatat gtatttgttc atatttcaaa aatacacagt ttcaaaatgg aactcaaggg      60
```

```
atccaaggct caaagggtc tccagaagac cccacaccat                     100
```

<210> SEQ ID NO 192
<211> LENGTH: 100
<212> TYPE: DNA
<213> ORGANISM: Homo sapiens

<400> SEQUENCE: 192

```
cccctttctg tgtcagtctt ccccagagca cagatccttg tttctgcttg aatcttcctc    60
actctcacag atctgatcat cacatgcccc actctggagg                         100
```

<210> SEQ ID NO 193
<211> LENGTH: 100
<212> TYPE: DNA
<213> ORGANISM: Homo sapiens

<400> SEQUENCE: 193

```
acaacatgtg catgtccaat acaggaaagg aacacacata ggagtgtagt gagaccccca    60
gagatcactg ttgttagagg cagtggggcc ccagaactca                         100
```

<210> SEQ ID NO 194
<211> LENGTH: 100
<212> TYPE: DNA
<213> ORGANISM: Homo sapiens

<400> SEQUENCE: 194

```
ggagcagcag cgggtggaga ccccatgggc tggccgagac aagaggactc ctcagccagt    60
cctcctgacc tgagacaggt ctcaggaatg tgcggaggac                         100
```

<210> SEQ ID NO 195
<211> LENGTH: 100
<212> TYPE: DNA
<213> ORGANISM: Homo sapiens

<400> SEQUENCE: 195

```
acaccgggac atacatttcc cttcatgctc ccaacataca catgcaaaca tacacagacc    60
catacaggca cgcgcgagca gccatgcccc accccctccc                         100
```

<210> SEQ ID NO 196
<211> LENGTH: 100
<212> TYPE: DNA
<213> ORGANISM: Homo sapiens

<400> SEQUENCE: 196

```
ccaacacaca cacgtataaa agtgtgtgta tatgggcaaa ctgctcgcat ccccaaatgg    60
caggctcttt ccctagaggc gcccagtccg cggcggggag                         100
```

<210> SEQ ID NO 197
<211> LENGTH: 100
<212> TYPE: DNA
<213> ORGANISM: Homo sapiens

<400> SEQUENCE: 197

```
aagctcactc actggggcca ttgactggga tccagtctgt ggccatgtca tggtttctat    60
ttttgaggtt atagctaatg agcaacatga ggttaagaca                         100
```

<210> SEQ ID NO 198
<211> LENGTH: 100
<212> TYPE: DNA

<213> ORGANISM: Homo sapiens

<400> SEQUENCE: 198
cacttttcat aaggcccag ccagcatcat aaatatgtgt gtgagcatgt tcacactcag    60
gttatgtctt ctttatgtgc accctctacc acacacacac                        100

<210> SEQ ID NO 199
<211> LENGTH: 100
<212> TYPE: DNA
<213> ORGANISM: Homo sapiens

<400> SEQUENCE: 199
gccaagaacc acgactctct aattttactt cccagcaggt attcagtgca taatagttcc    60
tacttagaag tatcatattt gcccaaacac aaggtgatac                        100

<210> SEQ ID NO 200
<211> LENGTH: 100
<212> TYPE: DNA
<213> ORGANISM: Homo sapiens

<400> SEQUENCE: 200
ccaaaatgag gtaagtttcc tgttttctca gtgagatctt ttgttgttgt tgttgttgtt    60
gttgttttgt tgtcgatgtt gttgtttttg gttttggtct                        100

<210> SEQ ID NO 201
<211> LENGTH: 100
<212> TYPE: DNA
<213> ORGANISM: Homo sapiens

<400> SEQUENCE: 201
ccgggtcgtc cagccccggg ccgccgcggc tgcccactac acccacgcca accgcccgca    60
agcagcgctg cagggctcc gctgggcgac acgccaggct                         100

<210> SEQ ID NO 202
<211> LENGTH: 100
<212> TYPE: DNA
<213> ORGANISM: Homo sapiens

<400> SEQUENCE: 202
ctgtcccaca gggtgctggg gagcgactgg gcggctccgc cgcgagcgtc tttgaattgc    60
gcgccgctgc aggaaaccaa aaactcccta gcaagagggt                        100

<210> SEQ ID NO 203
<211> LENGTH: 100
<212> TYPE: DNA
<213> ORGANISM: Homo sapiens

<400> SEQUENCE: 203
ttcaaaaggt ttctggaaac caccgacggt taaacatcac aactggactc ggagagagcc    60
aaacggtttc cccacttgca cctgccagtc ttcgcggcgg                        100

<210> SEQ ID NO 204
<211> LENGTH: 100
<212> TYPE: DNA
<213> ORGANISM: Homo sapiens

<400> SEQUENCE: 204
cgacctggca gcccaggtgc ggtcttaacc gccccgccc ctcacccgt acccgctcct    60 atccccggag cgcaaatctc agggctggca gctgcgcggt                        100

<210> SEQ ID NO 205
<211> LENGTH: 100
<212> TYPE: DNA
<213> ORGANISM: Homo sapiens

<400> SEQUENCE: 205
ggaaggtttt cccccctcaaa cccaaagcgc gcgggcggat caactcctag ctgctgccac    60
cactcgatcc cctcagagga tcggcgcggt gggtccaccc                         100

<210> SEQ ID NO 206
<211> LENGTH: 100
<212> TYPE: DNA
<213> ORGANISM: Homo sapiens

<400> SEQUENCE: 206
gcctctcccg ccctctgcct actgtgctgg gagactggca cagctccgtc ggccgcacag    60
agtttaacaa acacgcaccc agtgtcaaga acagtcacca                         100

<210> SEQ ID NO 207
<211> LENGTH: 100
<212> TYPE: DNA
<213> ORGANISM: Homo sapiens

<400> SEQUENCE: 207
ggcgcttaac cccgaagtta aagcgggcgc aatctcctcc tgggaactca gcccaggcac    60
gccgccctcc gcctctaaat tcagacaatg taactcgctc                         100

<210> SEQ ID NO 208
<211> LENGTH: 100
<212> TYPE: DNA
<213> ORGANISM: Homo sapiens

<400> SEQUENCE: 208
caagacatcc ccgcttcccc aaggaagaga ccggtggtct gagtcccgag gcagcgcgca    60
cgccttctct gcacttgtgc acagaatgtt cttacgtttg                         100

<210> SEQ ID NO 209
<211> LENGTH: 100
<212> TYPE: DNA
<213> ORGANISM: Homo sapiens

<400> SEQUENCE: 209
caaacagcgt gcaagccgcc gcgcgcggcg ggactcaagg gggagacaca tgcagccact    60
ggaacgctct ttccagtcgt ttctcctcga ctcacagaga                         100

<210> SEQ ID NO 210
<211> LENGTH: 100
<212> TYPE: DNA
<213> ORGANISM: Homo sapiens

<400> SEQUENCE: 210
aaaagattcc aatcctgctc cccccccacc caccccgcact atataggcat ggtcaagaaa    60
actcctttcg gtgacccttt tttggagtac gggtacctcc                         100

<210> SEQ ID NO 211
<211> LENGTH: 100
<212> TYPE: DNA
<213> ORGANISM: Homo sapiens

<400> SEQUENCE: 211
aatgtcctgg ccgcttctgc ccgctcggag aggggctgcg ctctaagttc aaacgtttgt    60
acatttatga caaagcaggt tgaaactgga cttacactga                          100

<210> SEQ ID NO 212
<211> LENGTH: 100
<212> TYPE: DNA
<213> ORGANISM: Homo sapiens

<400> SEQUENCE: 212
tcccctccat ggtaaccgct ggttctccag atgcggtggc tactggagca ctcaggccct    60
cggcgtcact ttgctacctg ctgccgcagc caacaaactg                          100

<210> SEQ ID NO 213
<211> LENGTH: 100
<212> TYPE: DNA
<213> ORGANISM: Homo sapiens

<400> SEQUENCE: 213
cccattgctg acatacttac tccctgagag tggctcttca tgcacctcca aggggttgct    60
ctccggtcca tccagtgtct tgctcacccc ctgtggtgaa                          100

<210> SEQ ID NO 214
<211> LENGTH: 100
<212> TYPE: DNA
<213> ORGANISM: Homo sapiens

<400> SEQUENCE: 214
agttctccac catctccctc tccggagggt gagctgggct gcttggcgag gggcacctcc    60
cctctggggc ctgagctggg ctctgggctt tggtttctcc                          100

<210> SEQ ID NO 215
<211> LENGTH: 100
<212> TYPE: DNA
<213> ORGANISM: Homo sapiens

<400> SEQUENCE: 215
cagccggagc actgcacaca tccccagtcc ccggtttctc attctccagt gacgcgtgat    60
ccccacgtgc gttttttgca tctctggcat cctcggtgct                          100

<210> SEQ ID NO 216
<211> LENGTH: 100
<212> TYPE: DNA
<213> ORGANISM: Homo sapiens

<400> SEQUENCE: 216
atttgcaggt tatatcctgg atggtggcac gacagcgcct ggaacacaga aggttgggag    60
gcgtgacgct catcaggaag gctctttttgg ggagccagga                         100

<210> SEQ ID NO 217
<211> LENGTH: 100
<212> TYPE: DNA
<213> ORGANISM: Homo sapiens

<400> SEQUENCE: 217
agagtccccc agaagcccac ttggcaccct atctataaca agttgctctt taagaatcat    60
gggaactcca gaatcatttt cacaaatacc ttccactcat                          100

```
<210> SEQ ID NO 218
<211> LENGTH: 100
<212> TYPE: DNA
<213> ORGANISM: Homo sapiens

<400> SEQUENCE: 218
gattcaatta aatggcagaa acacaaacc ttccgttccc actggcaaac tgggtctagc      60
taactgagca cagctagcac aaggcaggcc ccctgctagc                          100

<210> SEQ ID NO 219
<211> LENGTH: 100
<212> TYPE: DNA
<213> ORGANISM: Homo sapiens

<400> SEQUENCE: 219
agggcaagtg gcggcccggt ccccaaggcc caggggagcc tctgcagctc cctggaagga    60
cggtcaagtg aacagagagc tggctgccat ctgggttctt                          100

<210> SEQ ID NO 220
<211> LENGTH: 100
<212> TYPE: DNA
<213> ORGANISM: Homo sapiens

<400> SEQUENCE: 220
atgagatcac cagtttatcg taactagagg cctctcccat ctaaagcatc tttgtaactg    60
ctttcccttt ccccacactg cctacacata aagaagcccc                          100

<210> SEQ ID NO 221
<211> LENGTH: 100
<212> TYPE: DNA
<213> ORGANISM: Homo sapiens

<400> SEQUENCE: 221
taatttgtaa caagtcattt gacaactcca gaagagggc cacatccttt ttctctatgt      60
ctgttgatta acaaagacaa cattatgttt ccaacaccag                          100

<210> SEQ ID NO 222
<211> LENGTH: 100
<212> TYPE: DNA
<213> ORGANISM: Homo sapiens

<400> SEQUENCE: 222
tcagaccaag ggggaaaaaa gtccccatga cttcagtaat tttccatcct ttggaacaag    60
gaaatataca caaaaggttt actatagaat gtaagcattg                          100

<210> SEQ ID NO 223
<211> LENGTH: 100
<212> TYPE: DNA
<213> ORGANISM: Homo sapiens

<400> SEQUENCE: 223
aactgttcaa gattgggctc tcacactaac acacctcttc cttgcaactt gcacccaatt    60
tgactctggt cctaggcatg ctgacctgaa atagttgctg                          100

<210> SEQ ID NO 224
<211> LENGTH: 100
<212> TYPE: DNA
<213> ORGANISM: Homo sapiens

<400> SEQUENCE: 224
```

```
gctgcggcaa gcaccacgcg gtggcaggag aattcctgaa tgtccacaca caagatgaca    60
tctgtcagag cgttttccat tcgcagggtt tccaggccat                         100

<210> SEQ ID NO 225
<211> LENGTH: 100
<212> TYPE: DNA
<213> ORGANISM: Homo sapiens

<400> SEQUENCE: 225
tctgaagaat taaggagagt cccgcgtcgt caaatttgac cttttcccca tttaagatct    60
cgaccaagtc tcctgttttc tgggagggct catctgtaga                         100

<210> SEQ ID NO 226
<211> LENGTH: 100
<212> TYPE: DNA
<213> ORGANISM: Homo sapiens

<400> SEQUENCE: 226
aggtgccagg ggcccttcca aactcttctc gaccacatca cccatggtcc aggcgcccct    60
ttgtcctgcc atcaacatcg agactgaagg agcgcccaag                         100

<210> SEQ ID NO 227
<211> LENGTH: 100
<212> TYPE: DNA
<213> ORGANISM: Homo sapiens

<400> SEQUENCE: 227
ccttcctgtt ggccactaca tacgtgtccc ccgcttcttg cccctctctg cttgggtccc    60
tgctacactg gtatcctgca cttttccacct tgtattgcca                        100

<210> SEQ ID NO 228
<211> LENGTH: 100
<212> TYPE: DNA
<213> ORGANISM: Homo sapiens

<400> SEQUENCE: 228
gtttgtttcc aaggccatct ccactttgag cttgttcatg accacctcac acagcacact    60
tggtctgtgt ggtggtttga ggggttctgt ctgtacactg                         100

<210> SEQ ID NO 229
<211> LENGTH: 100
<212> TYPE: DNA
<213> ORGANISM: Homo sapiens

<400> SEQUENCE: 229
tgctttggct gtgttggagg cgggcaggtg ggaaggaaga aatgtattct tggggagatt    60 tgttttaga gacatgagac atggaaaata gttaagtaat                          100

<210> SEQ ID NO 230
<211> LENGTH: 100
<212> TYPE: DNA
<213> ORGANISM: Homo sapiens

<400> SEQUENCE: 230
aatataatat gggaggcatg gactatcaga ggaggcaggc aggactgccc aacctcctca    60
ctgggcacgt tacgctactt cctcctgacc tctatagtcc                         100

<210> SEQ ID NO 231
<211> LENGTH: 100
```

```
<212> TYPE: DNA
<213> ORGANISM: Homo sapiens

<400> SEQUENCE: 231
ctatcattgc cctttcttac cttgatatcc taaaaagctg gtggtctgtc ttctctatct    60
tttgtcctgg tcagttatcc taactatttt gtgtctgttt                          100

<210> SEQ ID NO 232
<211> LENGTH: 100
<212> TYPE: DNA
<213> ORGANISM: Homo sapiens

<400> SEQUENCE: 232
ctgtggatta gtaaacgggg tccccacccc cactccacaa ggagaacatc tggcacccag    60
aagtcactga gagaatagct gttgctttgg tagaattctg                          100

<210> SEQ ID NO 233
<211> LENGTH: 100
<212> TYPE: DNA
<213> ORGANISM: Homo sapiens

<400> SEQUENCE: 233
cctctgagtg gcttgttctt ttcccagacg gagaggtctc ctgacagcag ctctcttctt    60
tttctttttt ttttttttg agacagagtt ttgctcttgc                           100

<210> SEQ ID NO 234
<211> LENGTH: 100
<212> TYPE: DNA
<213> ORGANISM: Homo sapiens

<400> SEQUENCE: 234
ctcctgtacc ctgtgggcct gagagaggag acaatgggac aagaagaccc agtggcttcc    60
ttggaagctt ttgtgctagc tggagagaga agacctactt                          100

<210> SEQ ID NO 235
<211> LENGTH: 100
<212> TYPE: DNA
<213> ORGANISM: Homo sapiens

<400> SEQUENCE: 235
cctatatgcc tagcaacagt ccacactgac tggactgcaa ccaggacatt tccagattac    60
tcagtggggc ttatcttgaa ataatagttg atgccatttg                          100

<210> SEQ ID NO 236
<211> LENGTH: 100
<212> TYPE: DNA
<213> ORGANISM: Homo sapiens

<400> SEQUENCE: 236
ttaaatatat tatatatacc atctaagggt cttacatgcc ttctctcatt tgatcttcat    60
ggcaaaccct gtgaggtatg accaccaacc accattttac                          100

<210> SEQ ID NO 237
<211> LENGTH: 100
<212> TYPE: DNA
<213> ORGANISM: Homo sapiens

<400> SEQUENCE: 237
ctcagaactc aggctcccag agtttaagtt gctcacagga gcccagaaag taagcgacag    60
```

```
aggtgggatt tggttctagg tgtttgccac cagcacttta                    100

<210> SEQ ID NO 238
<211> LENGTH: 100
<212> TYPE: DNA
<213> ORGANISM: Homo sapiens

<400> SEQUENCE: 238
aatcaccaaa gctttctgga agctccaact tttcttctca agatactgaa agacaggtat    60
ctggatgggt tggcagggcg ggtgggaggt gggcgagatt                   100

<210> SEQ ID NO 239
<211> LENGTH: 100
<212> TYPE: DNA
<213> ORGANISM: Homo sapiens

<400> SEQUENCE: 239
tccatcaaca acgggtctaa aaccagcgat ggtgagctgg gtgattttga tggaacccct    60
gccatacagt ctattaatat cataattgga gctaaaattt                   100

<210> SEQ ID NO 240
<211> LENGTH: 100
<212> TYPE: DNA
<213> ORGANISM: Homo sapiens

<400> SEQUENCE: 240
aatcatgatg gcaatcatga gttctggggc ttcttgattt gggccagcag acacagtctc    60
agtcactagt tctccgaatc agagaaagga tgccttcagg                   100

<210> SEQ ID NO 241
<211> LENGTH: 100
<212> TYPE: DNA
<213> ORGANISM: Homo sapiens

<400> SEQUENCE: 241
ctgtgtcttc acatggcttt tcctctgtgc gtggtggaaa gagagagctc tgcgggtctc    60
ttcttgttgt aaggacactg gccccattgg attagggccc                   100

<210> SEQ ID NO 242
<211> LENGTH: 100
<212> TYPE: DNA
<213> ORGANISM: Homo sapiens

<400> SEQUENCE: 242
caccacatga cacatttaat cctaattacc tccctcacag ccctatttcc aaacagggta    60
ttagtcacat tagggattag ggcttcaaca taggaattct                   100

<210> SEQ ID NO 243
<211> LENGTH: 100
<212> TYPE: DNA
<213> ORGANISM: Homo sapiens

<400> SEQUENCE: 243
gggggcacac aattcagtct ataacagagg gaaaacagat ttgagaagaa aaaagtccaa    60
aatatgcaca gtggtaatat ctgaagatgt gcgtgcgtgc                   100

<210> SEQ ID NO 244
<211> LENGTH: 100
<212> TYPE: DNA
<213> ORGANISM: Homo sapiens
```

<400> SEQUENCE: 244
tcaagggctc agcaaacgac aacttaagca tttagagtcc catccctatc caccaaaccc    60
agaataagtt agtcttttca agaaagcatt ggtataaaac                          100

<210> SEQ ID NO 245
<211> LENGTH: 100
<212> TYPE: DNA
<213> ORGANISM: Homo sapiens

<400> SEQUENCE: 245
ccttcaaaac tgaaaagaag aaagggggcaa ttggagaatt cccacttttt ctggctgtct    60
ccttcaagtc gcccagtttt tatgaacagc atctagcctt                          100

<210> SEQ ID NO 246
<211> LENGTH: 100
<212> TYPE: DNA
<213> ORGANISM: Homo sapiens

<400> SEQUENCE: 246
actgtcacta tcaacaaccc ttaaaactag ccaatgcttc ggcctctagt attggaaagt    60
cttccaaata ggatactgga aacttctatt tataagcttg                          100

<210> SEQ ID NO 247
<211> LENGTH: 100
<212> TYPE: DNA
<213> ORGANISM: Homo sapiens

<400> SEQUENCE: 247
gggtggcggg cggggcgggg aggtggagag agagttgcca tctacaggtt tctattttgg    60
cctgaagact caactgcagt cattagagta agggaatgcc                          100

<210> SEQ ID NO 248
<211> LENGTH: 100
<212> TYPE: DNA
<213> ORGANISM: Homo sapiens

<400> SEQUENCE: 248
ttatttatta aaaccacaca caccttgcaa agaaaaaggg aaactggcag tctctgtaga    60
ggaagccggt ggcatcgctc agagccacaa actgtatttc                          100

<210> SEQ ID NO 249
<211> LENGTH: 100
<212> TYPE: DNA
<213> ORGANISM: Homo sapiens

<400> SEQUENCE: 249
taaacagccc tttccctggt tccctctctc ctgccccact ttttttaaaa tccagactgt    60
aaaaaacaca tctactgaca ctcactttac tttaaaaaaa                          100

<210> SEQ ID NO 250
<211> LENGTH: 100
<212> TYPE: DNA
<213> ORGANISM: Homo sapiens

<400> SEQUENCE: 250
gaagagaaaa agtaaagcgt tacaagactt tcctcctgga aactataaac tgaaaaaaaa    60
atccataaaa gattaaatcc tggcgggttg tggggtggcg                          100

```
<210> SEQ ID NO 251
<211> LENGTH: 100
<212> TYPE: DNA
<213> ORGANISM: Homo sapiens

<400> SEQUENCE: 251
ggggccggcg gggagggggc gcggagtgga gattggctct ctgaggtggt caggggccct    60
gtgacagctt gggactttca gcacctggtt tggggtcatt                         100

<210> SEQ ID NO 252
<211> LENGTH: 100
<212> TYPE: DNA
<213> ORGANISM: Homo sapiens

<400> SEQUENCE: 252
tatctgctca actgtcagga ccccccaccc ccaaacccca gccaccaaca caaccatcgt    60
agaagggaac acaacacaga gggtcttttt tcattttttt                         100

<210> SEQ ID NO 253
<211> LENGTH: 100
<212> TYPE: DNA
<213> ORGANISM: Homo sapiens

<400> SEQUENCE: 253
tttttaaaaa atcggtttgg ttgtgttttt gttttccatg ggggagcttt aaaactcatt    60
attgcaacac tagttccatt tttcgccagg gttccaataa                         100

<210> SEQ ID NO 254
<211> LENGTH: 100
<212> TYPE: DNA
<213> ORGANISM: Homo sapiens

<400> SEQUENCE: 254
caagacattt accacggtca ctacatccgg cagcggggtg gccctagct cctgctgccc     60 ccccgccctt tctccccgcc cgcccccgga gctcagccga                         100

<210> SEQ ID NO 255
<211> LENGTH: 100
<212> TYPE: DNA
<213> ORGANISM: Homo sapiens

<400> SEQUENCE: 255
tttctgaggc tccaactcta cccactccct ccccgggccg ccgccgccgc gccttccccc    60
attcttactc cctcgaggag agccacaggt tgcaaatcca                         100

<210> SEQ ID NO 256
<211> LENGTH: 100
<212> TYPE: DNA
<213> ORGANISM: Homo sapiens

<400> SEQUENCE: 256
accaacctcg caatctattt ttgcaaaatc actcacaaag atctcccttt cgcgcccgcg    60
cccgctcctc ccgcgccggg tcccctcagc cacggccaca                         100

<210> SEQ ID NO 257
<211> LENGTH: 100
<212> TYPE: DNA
<213> ORGANISM: Homo sapiens

<400> SEQUENCE: 257
```

```
aagtgccctt ctctcctcct gagtcttgca cataaggaac gcgggctggg gctctgttcg    60
tctttctcct cgcccaaggt aaggacctcg ggaatctgaa                         100

<210> SEQ ID NO 258
<211> LENGTH: 100
<212> TYPE: DNA
<213> ORGANISM: Homo sapiens

<400> SEQUENCE: 258
gcctggcgtc cactacgctc aggcccgcag ttccctttt acagagcttg caccatggga    60
aaaaataaaa taaaatttag gaaagggagg caacagccat                         100

<210> SEQ ID NO 259
<211> LENGTH: 100
<212> TYPE: DNA
<213> ORGANISM: Homo sapiens

<400> SEQUENCE: 259
taaaatttag gaaagggagg caacagccat tgggagccaa cacagagtca cgcagcgccc    60
aaaatacaaa caccgcagcg gccagaaatc ccgccacctt                         100

<210> SEQ ID NO 260
<211> LENGTH: 100
<212> TYPE: DNA
<213> ORGANISM: Homo sapiens

<400> SEQUENCE: 260
tctcgttctc ccaggctgtc ctgtcgaggt tccctgagtc ccccgcaca ctgaaaggca     60 tcgcaggtgc agtgcgcacc cctttcccac ccaccccaag                         100

<210> SEQ ID NO 261
<211> LENGTH: 100
<212> TYPE: DNA
<213> ORGANISM: Homo sapiens

<400> SEQUENCE: 261
aagccctgtc ccgccatcag tctctctcct cgggatgagc agggagagcg cgcggaggtt    60
cccgactccc tcgactacaa ccaagaaaga ataattttca                         100

<210> SEQ ID NO 262
<211> LENGTH: 100
<212> TYPE: DNA
<213> ORGANISM: Homo sapiens

<400> SEQUENCE: 262
aagtgttcaa catccccgcc cccaagctcc ccaaaacaca ggggcaggga acaccaaaac    60
actcggctct cattaggaag atcacggctc tgaaaggaaa                         100

<210> SEQ ID NO 263
<211> LENGTH: 100
<212> TYPE: DNA
<213> ORGANISM: Homo sapiens

<400> SEQUENCE: 263
tagtagacac gatacttcat ctcatctgga tttatgacca aaaaacaaa aacaaaaacc     60 caaagagttc gcttgcattt tttccttcca aatctcggtt                         100

<210> SEQ ID NO 264
```

```
<211> LENGTH: 100
<212> TYPE: DNA
<213> ORGANISM: Homo sapiens

<400> SEQUENCE: 264
aacaaaaacc caaagagttc gcttgcattt tttccttcca aatctcggtt cggctcgaag      60
gcagggaatc taaaagaccg aggccgatgg aagagagcca                          100

<210> SEQ ID NO 265
<211> LENGTH: 100
<212> TYPE: DNA
<213> ORGANISM: Homo sapiens

<400> SEQUENCE: 265
gcggggcgag cgagcgggca gcctcccttt ttgcctcccg gagttaccca gaaggacagg      60
ggaagggaag gaagaagagg cgaggaaaaa gaggagggag                          100

<210> SEQ ID NO 266
<211> LENGTH: 100
<212> TYPE: DNA
<213> ORGANISM: Homo sapiens

<400> SEQUENCE: 266
ggaagcggag gccaggagcg acggagcaag gaaagcagtt tgcaagcgag aaaagaggga      60
aaaaacacag ccgcacgaat ccagagagat cacaagccgt                          100

<210> SEQ ID NO 267
<211> LENGTH: 100
<212> TYPE: DNA
<213> ORGANISM: Homo sapiens

<400> SEQUENCE: 267
acgcaagcag cagcagaaag agcgagagcg cgagcgcgcg tcctctccgc ggtctggggc      60
cagacagccc ccagactagc ccgaatcacc ccccaagcac                          100

<210> SEQ ID NO 268
<211> LENGTH: 100
<212> TYPE: DNA
<213> ORGANISM: Homo sapiens

<400> SEQUENCE: 268
tgtctcgtcc tctctgctcc ggccgccccc taattcccct ccttcctctc ctccacctcc      60
tttccaaaaa ccaaacaac acaagggagg gtggcaaaag                           100

<210> SEQ ID NO 269
<211> LENGTH: 100
<212> TYPE: DNA
<213> ORGANISM: Homo sapiens

<400> SEQUENCE: 269
cctccccaaa ccggccgatt cactcaaaga caacaataat aataataaat acataacaat      60
ctatatccta tggtgggaga gacgtgggac taatcttcgg                          100

<210> SEQ ID NO 270
<211> LENGTH: 100
<212> TYPE: DNA
<213> ORGANISM: Homo sapiens

<400> SEQUENCE: 270
acataacaat ctatatccta tggtgggaga gacgtgggac taatcttcgg catttatttt      60
```

```
aacacctgac agctagaata aataaatata tacatttata                    100
```

<210> SEQ ID NO 271
<211> LENGTH: 100
<212> TYPE: DNA
<213> ORGANISM: Homo sapiens

<400> SEQUENCE: 271

```
aataaatata tacatttata tcaatagata cacatagaaa acttggagcc aaagcatttg    60
gcaagagcgg aaaaaaaaag aattaaaagg taaaataatg                         100
```

<210> SEQ ID NO 272
<211> LENGTH: 100
<212> TYPE: DNA
<213> ORGANISM: Homo sapiens

<400> SEQUENCE: 272

```
atcatgagca gcggcggcgg cagcggcacc agcggcaaca gcggcggcgg cggcagtagc    60
agcagcagcg gcggcagcaa cagcaataat cacctggtgt                         100
```

<210> SEQ ID NO 273
<211> LENGTH: 100
<212> TYPE: DNA
<213> ORGANISM: Homo sapiens

<400> SEQUENCE: 273

```
ccggcctttc ctagaaactt cttgcatcac cacttctaag aacccagtt ctaagaatca    60 acagagctca attctcggaa tttgagcttc ggactttacc                         100
```

<210> SEQ ID NO 274
<211> LENGTH: 100
<212> TYPE: DNA
<213> ORGANISM: Homo sapiens

<400> SEQUENCE: 274

```
actgctacgt ggcaggggag gacttggtgt cagctctccg agattttttac tgcccctggc    60 caaccaaaag ccctcaaagc cacaagattt tttcactggc                         100
```

<210> SEQ ID NO 275
<211> LENGTH: 100
<212> TYPE: DNA
<213> ORGANISM: Homo sapiens

<400> SEQUENCE: 275

```
cggcatattt cgaggtcctc ataagcagag cgtctcggat ttggaggttc cggttcgagg    60
ctcgaggggc ctgaaggtgg ctctccctcc ccgggcccaa                         100
```

<210> SEQ ID NO 276
<211> LENGTH: 100
<212> TYPE: DNA
<213> ORGANISM: Homo sapiens

<400> SEQUENCE: 276

```
gacgatggta tggcctgctc cgccaccatc acgtgggctc ctcctctgtg acgtcggcgc    60
cttcgctgta gcaaagctcg gcctctggaa ttctgagaac                         100
```

<210> SEQ ID NO 277
<211> LENGTH: 100
<212> TYPE: DNA

```
<213> ORGANISM: Homo sapiens

<400> SEQUENCE: 277
gcacaaaagg gagcgagagg tttgaaccac tgggaaaagt atgttatata tatagtaggg    60
ttagagaggc gagtaagaga aaaataaaat aaaataaaca                         100

<210> SEQ ID NO 278
<211> LENGTH: 100
<212> TYPE: DNA
<213> ORGANISM: Homo sapiens

<400> SEQUENCE: 278
aaaataaaat aaacatcaca gctctttcca actagaatat taggcaccac gagaaaata    60 tttgccaagc agttttcggt gggttcattt gctttatttt                        100

<210> SEQ ID NO 279
<211> LENGTH: 100
<212> TYPE: DNA
<213> ORGANISM: Homo sapiens

<400> SEQUENCE: 279
tatttaggac aggggttttt gctgttgttc tgggtttttt tctttctggt gtggtggctt    60 gggattttttg gtttctgtat tttgatggtt tatggatttt                       100

<210> SEQ ID NO 280
<211> LENGTH: 100
<212> TYPE: DNA
<213> ORGANISM: Homo sapiens

<400> SEQUENCE: 280
tgcttctgat ttttgcctt ttgcaagttt gtggtgttac gtaaatcaca ggatcggcat     60
cggttggatt ttttgtacg tgcctttttct ttccctatct                        100

<210> SEQ ID NO 281
<211> LENGTH: 100
<212> TYPE: DNA
<213> ORGANISM: Homo sapiens

<400> SEQUENCE: 281
aatccctcaa gcgttttaaa gatgtattat ttcaatacta atactattga aagaagctta    60 aattttggc catatgtaac aatcccagcc cccactttttt                        100

<210> SEQ ID NO 282
<211> LENGTH: 100
<212> TYPE: DNA
<213> ORGANISM: Homo sapiens

<400> SEQUENCE: 282
attatcatca tcaccaccaa catcctctgc cctggagacc aagagaattc aaacaggtca    60
gcacctctaa ttgctgtata gaacattgac cctactgtct                        100

<210> SEQ ID NO 283
<211> LENGTH: 100
<212> TYPE: DNA
<213> ORGANISM: Homo sapiens

<400> SEQUENCE: 283
cccagttcct gaggatggtg tgataataat acatctcaga gttctgtagt ttcttcacca    60
ctgtgcaggt gtggttggtg ggagcaatgc cctggatgga                        100
```

<210> SEQ ID NO 284
<211> LENGTH: 100
<212> TYPE: DNA
<213> ORGANISM: Homo sapiens

<400> SEQUENCE: 284
taagccaagc tcttgtgtcc tggcagataa acaaggtgaa ccctcaatcc gtgtagcagg      60
agtttccaga caaactcact ttgcatggaa ggacactaac                          100

<210> SEQ ID NO 285
<211> LENGTH: 100
<212> TYPE: DNA
<213> ORGANISM: Homo sapiens

<400> SEQUENCE: 285
ccttccaggt gcatggaaat attttgtagt ttttactgtc tcccccttcc tccactgcct      60 catcttttt gttttttccc ctgtgagact atttgctctg                           100

<210> SEQ ID NO 286
<211> LENGTH: 100
<212> TYPE: DNA
<213> ORGANISM: Homo sapiens

<400> SEQUENCE: 286
cctttccaac actggcctgc cttagggact caccgtctgc actccgcctg cacaggtgga      60
actgagttca gatgagggag aattgctttc cattgttcag                          100

<210> SEQ ID NO 287
<211> LENGTH: 100
<212> TYPE: DNA
<213> ORGANISM: Homo sapiens

<400> SEQUENCE: 287
taggcttttt gtaatttcta gttttgctta cctttcctac tcaccacaca cacaaaacag      60
tgtgagcttt ctcattctag tgcataaaca caggtcggtc                          100

<210> SEQ ID NO 288
<211> LENGTH: 100
<212> TYPE: DNA
<213> ORGANISM: Homo sapiens

<400> SEQUENCE: 288
aatacccaca agtgttccaa aaggtgagct ggcattgctg cccaactggg cattatagtc      60
ccttctgtcc ctgcccatca ggcttgcctt cctcggcaac                          100

<210> SEQ ID NO 289
<211> LENGTH: 100
<212> TYPE: DNA
<213> ORGANISM: Homo sapiens

<400> SEQUENCE: 289
ctttctagct tgaattgtac tgtgactcct tctcacggac cactcccgga gactggtgaa      60
agttgggccc attcttgaag cctctgcttc taaatcatgt                          100

<210> SEQ ID NO 290
<211> LENGTH: 100
<212> TYPE: DNA
<213> ORGANISM: Homo sapiens

```
<400> SEQUENCE: 290
tttccataaa gtctccctca tcgtgcttgc ttccaccttc tcctatttgg aattactggt    60
gggctcttcc actgtcccat agcaagtgtt ctatacattc                        100

<210> SEQ ID NO 291
<211> LENGTH: 100
<212> TYPE: DNA
<213> ORGANISM: Homo sapiens

<400> SEQUENCE: 291
tgaaggcaca tttgaatata tactttgtca tggttgcttg gaaccatgtc gtcttttcca    60
agtaggctgt gaacattcag tggcatggat cataccgtgc                        100

<210> SEQ ID NO 292
<211> LENGTH: 100
<212> TYPE: DNA
<213> ORGANISM: Homo sapiens

<400> SEQUENCE: 292
cccattgttc aaagaaaggc attatggagt ctccaaaagc cattggcagg tggtgtctgt    60
gacttcctta gcctggaaat aaacaaataa acaagcacaa                        100

<210> SEQ ID NO 293
<211> LENGTH: 100
<212> TYPE: DNA
<213> ORGANISM: Homo sapiens

<400> SEQUENCE: 293
aaacaaataa acaagcacaa attagaagtc tttgccctat tactgcacta ttagtattga    60
ttgcgcaaca tcatgcaaaa agtcacttta atttatctgg                        100

<210> SEQ ID NO 294
<211> LENGTH: 100
<212> TYPE: DNA
<213> ORGANISM: Homo sapiens

<400> SEQUENCE: 294
caggtcctat gtaaacacca atacagtcaa gagggcttgg atgggtattt gctttcattt    60
ctaatgaaat ttcaggcctc tagggtagga tatcaaaatt                        100

<210> SEQ ID NO 295
<211> LENGTH: 100
<212> TYPE: DNA
<213> ORGANISM: Homo sapiens

<400> SEQUENCE: 295
ggtagatcat ttgcaattta ttttatccca aacacctcac tttacagtca gagaaactga    60
ggcccagaga agtaaaatga gttgctcaag gtctcagaga                        100

<210> SEQ ID NO 296
<211> LENGTH: 100
<212> TYPE: DNA
<213> ORGANISM: Homo sapiens

<400> SEQUENCE: 296
actgaggccc agagaagtaa aatgagttgc tcaaggtctc agagagcaag aaatagagat    60
gggacttgag cacctagatc tctggtattg ctgtcctgta                        100
```

-continued

```
<210> SEQ ID NO 297
<211> LENGTH: 100
<212> TYPE: DNA
<213> ORGANISM: Homo sapiens

<400> SEQUENCE: 297
gttcatggag ctggcagatg gatacatctg tgacctggga tgatggagag actgctggac      60
ccttcagagg atctcatctc aaggtggggt ttatgtgtaa                           100

<210> SEQ ID NO 298
<211> LENGTH: 100
<212> TYPE: DNA
<213> ORGANISM: Homo sapiens

<400> SEQUENCE: 298
atgatatctg tgtgtttcat tttcctttca taaactaatt taaaaatcct tttggtatca      60
aattttaagc caaaaagtag tgaggggaa catgggtagg                            100

<210> SEQ ID NO 299
<211> LENGTH: 100
<212> TYPE: DNA
<213> ORGANISM: Homo sapiens

<400> SEQUENCE: 299
aatagcttac agcttgccta acaaggttgt tgactgcata agagtcagga gttttgggta      60
agagtgtgtg tgtgtgtgtg tgtgtgtgtg tgtgtgtgag                           100

<210> SEQ ID NO 300
<211> LENGTH: 100
<212> TYPE: DNA
<213> ORGANISM: Homo sapiens

<400> SEQUENCE: 300
cgtactgaat ttgactgctt tattttgtag ggaaggaaac tgatgtgcct agagtagttg      60
agagctttat tcaaactcat tccactgtta ttgagtagtt                           100

<210> SEQ ID NO 301
<211> LENGTH: 100
<212> TYPE: DNA
<213> ORGANISM: Homo sapiens

<400> SEQUENCE: 301
aggatattag accagcaaca tatttgggta gaaactttca tataaaaaag cgtaatcata      60
actatccaat catgtcaact agtaaggctg ctcaggtggg                           100

<210> SEQ ID NO 302
<211> LENGTH: 100
<212> TYPE: DNA
<213> ORGANISM: Homo sapiens

<400> SEQUENCE: 302
ataacacatc aaccttcttt gggattcttc cctcagacat ggttttggtg ggaggagcat      60
ggcaagggag gggcgagctc caaatgcagg gctgctctgt                           100

<210> SEQ ID NO 303
<211> LENGTH: 100
<212> TYPE: DNA
<213> ORGANISM: Homo sapiens

<400> SEQUENCE: 303
```

```
cctcggcgac ctgagcagac acacgagcag agatcagaga cactcttagt gaatgaacct    60
ccctattggc tatattaaag taatgctctg aaaaagttcc                         100

<210> SEQ ID NO 304
<211> LENGTH: 100
<212> TYPE: DNA
<213> ORGANISM: Homo sapiens

<400> SEQUENCE: 304
tatgtatgca tagtctaaag tgatgatttt agaggtagca agacagtgag aatgtcccta    60
catgtgaaat gggcacagtt ttatcaggga agtgtcaata                         100

<210> SEQ ID NO 305
<211> LENGTH: 100
<212> TYPE: DNA
<213> ORGANISM: Homo sapiens

<400> SEQUENCE: 305
gagggttaat gttccacgta gtggctgcaa gaatgataag tggtcatggg gatagcctga    60
cactctagga gcagaaggtg gtgggtatgg atagaactac                         100

<210> SEQ ID NO 306
<211> LENGTH: 100
<212> TYPE: DNA
<213> ORGANISM: Homo sapiens

<400> SEQUENCE: 306
tgatatagca tgaatccaac ctgctgttat ctgcgcaggc ctctctgcag ctgttttgccc   60 tgaagtacat gctgtacgtt tctccagctg atcctgcatg                         100

<210> SEQ ID NO 307
<211> LENGTH: 100
<212> TYPE: DNA
<213> ORGANISM: Homo sapiens

<400> SEQUENCE: 307
actgggtata aacgcctgtc cgctgtgtgc tggacagccc cagacaccct cggcagcctg    60
ctgtgtttgt gtgagacatg ctgtgttagg gatttaagca                         100

<210> SEQ ID NO 308
<211> LENGTH: 100
<212> TYPE: DNA
<213> ORGANISM: Homo sapiens

<400> SEQUENCE: 308
acagctttct catctacatg gacaacctat ttttaaagaa tcttcagaga gtcgttgact    60
ttgttataac tactactata tacgtaattt cagatgatag                         100

<210> SEQ ID NO 309
<211> LENGTH: 100
<212> TYPE: DNA
<213> ORGANISM: Homo sapiens

<400> SEQUENCE: 309
aattgaaaat ttaacttgtt tttctagaaa gagtttatttt tccctataac ttcaaagagt   60
aatggtgggg agtaggacat tctgaaaata agaagaaaca                         100

<210> SEQ ID NO 310
<211> LENGTH: 100
```

```
<212> TYPE: DNA
<213> ORGANISM: Homo sapiens

<400> SEQUENCE: 310
tgtcaaatga atttctgact tccagctagg catatggaat aaaggtcttt attccagtga    60
cctctgctca ttggaaaact ttgggctggt agatttcatg                         100

<210> SEQ ID NO 311
<211> LENGTH: 100
<212> TYPE: DNA
<213> ORGANISM: Homo sapiens

<400> SEQUENCE: 311
tctcttgcat tcttaacttg caatttagta ctgtttatat tctgcttgaa ggttagagac    60
attcgactaa atggtctttt ctccacattg ctgtcattca                         100

<210> SEQ ID NO 312
<211> LENGTH: 100
<212> TYPE: DNA
<213> ORGANISM: Homo sapiens

<400> SEQUENCE: 312
ttaatgtcct ggtcctggac tttactcatt gaccacagga caagtggctc aactctctcc    60
tgccactacc caggctgtta gtcctgttgg gaggctcagg                         100

<210> SEQ ID NO 313
<211> LENGTH: 100
<212> TYPE: DNA
<213> ORGANISM: Homo sapiens

<400> SEQUENCE: 313
gcccaactca ctcatctgta actctcatct ccattcagct gcagcctcta cagcccctgg    60 ttatacccctg gatcttatca ttgcttcgct ctattttacc                        100

<210> SEQ ID NO 314
<211> LENGTH: 100
<212> TYPE: DNA
<213> ORGANISM: Homo sapiens

<400> SEQUENCE: 314
tcctaaatcg taaaaattaa aaccagcctc ggaacacaac ccctcattct tccagcactc    60
tctctcattc aggtaactcc tattctactt ttcttcagca                         100

<210> SEQ ID NO 315
<211> LENGTH: 100
<212> TYPE: DNA
<213> ORGANISM: Homo sapiens

<400> SEQUENCE: 315
ttgttttttt ttactttacc ttaatttctc tttttggact aagatgttaa aatgtttctt    60
aatgtgactg tctccgaaac tgttttgtgt ctaccactca                         100

<210> SEQ ID NO 316
<211> LENGTH: 100
<212> TYPE: DNA
<213> ORGANISM: Homo sapiens

<400> SEQUENCE: 316
tcctagtggc agtcattgat cctttttcttg ttgcgagtgt ttgagtgtgg gtgtgtgtga   60
```

```
gtgtgtatat gtatttgtag agggaaaaac aagagagagg                          100
```

<210> SEQ ID NO 317
<211> LENGTH: 100
<212> TYPE: DNA
<213> ORGANISM: Homo sapiens

<400> SEQUENCE: 317

```
tgtgagtgtg tatatgtatt tgtagaggga aaacaagag agagggaaac agacattgga     60
gccacctttc ccccactagc cacgtacctg ttgaaccttc                          100
```

<210> SEQ ID NO 318
<211> LENGTH: 100
<212> TYPE: DNA
<213> ORGANISM: Homo sapiens

<400> SEQUENCE: 318

```
aagcctctct atagaatcag atatacacaa gcacagtgac agaactacat gtgtcctaca    60
gtccagcttt taagatatga taaaaactct tgtattcaca                          100
```

<210> SEQ ID NO 319
<211> LENGTH: 100
<212> TYPE: DNA
<213> ORGANISM: Homo sapiens

<400> SEQUENCE: 319

```
gagctaaatg gcaataacca taggagattg catattgcta cattatgtaa agacagagtc    60
ccaagaaaat agtgagaact cagtttgatg tatgatgtga                          100
```

<210> SEQ ID NO 320
<211> LENGTH: 100
<212> TYPE: DNA
<213> ORGANISM: Homo sapiens

<400> SEQUENCE: 320

```
tatgtgatat cttactttac atggctaaca gttgacattc tttgtggatt ctatattgtc    60
taaggctaca gaagagccat atgataaatt catcggcaac                          100
```

<210> SEQ ID NO 321
<211> LENGTH: 100
<212> TYPE: DNA
<213> ORGANISM: Homo sapiens

<400> SEQUENCE: 321

```
cagtgaaaag gcttgggccg cttttgtttt cacctgcttt tgttgaacaa atttgatttc    60
cggagtcagt cattttactg tcaagacatt tcttcggcat                          100
```

<210> SEQ ID NO 322
<211> LENGTH: 100
<212> TYPE: DNA
<213> ORGANISM: Homo sapiens

<400> SEQUENCE: 322

```
tctgcaacag gtaaggattt tgcttcctta aaagtatttc tttggtgtca aaagaaattt    60
ttctaatttt atttagcttt tactctaggc caaacatcgt                          100
```

<210> SEQ ID NO 323
<211> LENGTH: 100
<212> TYPE: DNA
<213> ORGANISM: Homo sapiens

<400> SEQUENCE: 323
aatgactctg agctacctgc tgtaaggtgt agaatcaatt tacaggggga cgggggtcgg    60
gggggtgagt gttgctttga tattcactgc ccctcaccac                          100

<210> SEQ ID NO 324
<211> LENGTH: 100
<212> TYPE: DNA
<213> ORGANISM: Homo sapiens

<400> SEQUENCE: 324
agtcctaaca agattttga aacatgaaaa gttacaatag ttggctttttt ggttttccag    60 atattctaga gaatgcatat gcttgtgact gtggctgagc                          100

<210> SEQ ID NO 325
<211> LENGTH: 100
<212> TYPE: DNA
<213> ORGANISM: Homo sapiens

<400> SEQUENCE: 325
tcaactgtat gggtagttta aatactaccc aaggtttgat gaagtaaatc taaagatgct    60
ctaagttgtg caaatatgaa ttttaaagtt gtctagttca                          100

<210> SEQ ID NO 326
<211> LENGTH: 100
<212> TYPE: DNA
<213> ORGANISM: Homo sapiens

<400> SEQUENCE: 326
gaaaagaaac agaaccgaag tctaaatgat gtagatttca atctggaatt tctagcttgt    60
gtttttcacc tattgccaat gttaatgacc atttcccaaa                          100

<210> SEQ ID NO 327
<211> LENGTH: 100
<212> TYPE: DNA
<213> ORGANISM: Homo sapiens

<400> SEQUENCE: 327
agtgctctat gatgtataac atgtattttt taattaaatt taatctttct tctgaggtgg    60
tttgatttgg agatatgcta cgaggtacca gtcagtagcc                          100

<210> SEQ ID NO 328
<211> LENGTH: 100
<212> TYPE: DNA
<213> ORGANISM: Homo sapiens

<400> SEQUENCE: 328
tgagttgtaa ctaaacaaag tttgggaaat caccggtttt aggtgcttta ctaaatgaaa    60
gttgccattg acgtattcaa gcaggcaaca agtagttggt                          100

<210> SEQ ID NO 329
<211> LENGTH: 100
<212> TYPE: DNA
<213> ORGANISM: Homo sapiens

<400> SEQUENCE: 329
gtccccttat tggttctaag ctggtgccgt ggaggatata agagaaatat tttaaaaatc    60
tctactttga aggaccctat aatctggtag ttgtgataag                          100

```
<210> SEQ ID NO 330
<211> LENGTH: 100
<212> TYPE: DNA
<213> ORGANISM: Homo sapiens

<400> SEQUENCE: 330
tttaaaaatc tctactttga aggaccctat aatctggtag ttgtgataag aagtaaaatt      60
taggaagcaa tgcaagatga gaattcagtg atgagtgggg                          100

<210> SEQ ID NO 331
<211> LENGTH: 100
<212> TYPE: DNA
<213> ORGANISM: Homo sapiens

<400> SEQUENCE: 331
cagcacaggc ttgaagagtt ctgtgaattc catggagggg gcctgggggc aaactggagt      60
tgtcaggaag atctgggctt tggaagaatg cgaagtgtcg                          100

<210> SEQ ID NO 332
<211> LENGTH: 100
<212> TYPE: DNA
<213> ORGANISM: Homo sapiens

<400> SEQUENCE: 332
gtagaaggag aagggggcagg tgatttcaga ctgggaggac cttgtgggca aaggcacaaa     60
ggcgagactg acctggagat gataaggcca gttgaagaga                          100

<210> SEQ ID NO 333
<211> LENGTH: 100
<212> TYPE: DNA
<213> ORGANISM: Homo sapiens

<400> SEQUENCE: 333
acattgcagg aaatcagatt agacagttag ggtgtggaca caaaagcgag gaccttgcag      60
gcactgggga gaagtgaccc cattcaatag tccttggtct                          100

<210> SEQ ID NO 334
<211> LENGTH: 100
<212> TYPE: DNA
<213> ORGANISM: Homo sapiens

<400> SEQUENCE: 334
ccttctgccc tgcggctgcg cttcctcggc tctcacggca ccagcagaat tccatgtgag      60
agggagcttg tcgagcgtgg cctcttccca cttggggctg                          100

<210> SEQ ID NO 335
<211> LENGTH: 100
<212> TYPE: DNA
<213> ORGANISM: Homo sapiens

<400> SEQUENCE: 335
ctttctgcat ccctgtgcct ggctgtgggc ctccatttgc cctctactgt cttcccttag      60
gacatcattt atgcagagaa aggttcgtgt ggctcggggt                          100

<210> SEQ ID NO 336
<211> LENGTH: 100
<212> TYPE: DNA
<213> ORGANISM: Homo sapiens

<400> SEQUENCE: 336
```

```
ggacgttgtt tagagagtca gtagatcata ataattcaga cactttttt ctggaccata    60 aaatatctga acccatataa taacaaacat acagcacggt                       100

<210> SEQ ID NO 337
<211> LENGTH: 100
<212> TYPE: DNA
<213> ORGANISM: Homo sapiens

<400> SEQUENCE: 337
gaataagaac ccaactttg agccagatca ctttgcatgg aatccccatt ctatcattct    60
atcatttctg ggctgtggga acctcagaca agttacttaa                       100

<210> SEQ ID NO 338
<211> LENGTH: 100
<212> TYPE: DNA
<213> ORGANISM: Homo sapiens

<400> SEQUENCE: 338
cttcttcaat gctcagatta aaaaaaaaat tcacaaaata tctctaataa cagtaataat    60
aactgaaaat acctacctca gagggttgtc gtagagatca                        100

<210> SEQ ID NO 339
<211> LENGTH: 100
<212> TYPE: DNA
<213> ORGANISM: Homo sapiens

<400> SEQUENCE: 339
aaaattcaca aaatatctct aataacagta ataataactg aaaataccta cctcagaggg    60
ttgtcgtaga gatcaaatga gataaaaata tgtaaagcat                        100

<210> SEQ ID NO 340
<211> LENGTH: 100
<212> TYPE: DNA
<213> ORGANISM: Homo sapiens

<400> SEQUENCE: 340
gtagcctagt gcctgactga aaaaaaaatc tctcaataga tgcaactctt atgattctta    60
ttaaggactt ggctattgcc acaaatgaag gtgttatgag                        100

<210> SEQ ID NO 341
<211> LENGTH: 100
<212> TYPE: DNA
<213> ORGANISM: Homo sapiens

<400> SEQUENCE: 341
ccctggctta agagcaagaa gcctgcaaag ctaactctcc taatcccaac attccttcc    60 agggaaagta gggtgacagg tggaggctgg gaattaacgt                        100

<210> SEQ ID NO 342
<211> LENGTH: 100
<212> TYPE: DNA
<213> ORGANISM: Homo sapiens

<400> SEQUENCE: 342
tttttgagca ccaaatatgg acaaggcaca ggggttgggt gttttctag tgagaataca    60 tatgaaagaa ggaaaacaaa cttggaaacc gctattttaa                        100

<210> SEQ ID NO 343
```

```
<211> LENGTH: 100
<212> TYPE: DNA
<213> ORGANISM: Homo sapiens

<400> SEQUENCE: 343
gccatttggt aacagtttct ctagcttatg agatgagaga ggtcctctca gtatccgctg     60
cattacttgt gggcctcctt ggttgacgtc gctctctgaa                          100

<210> SEQ ID NO 344
<211> LENGTH: 100
<212> TYPE: DNA
<213> ORGANISM: Homo sapiens

<400> SEQUENCE: 344
cgcttggggt ggaattctag aggtgctttt cattagaggc agagagcatg acctttcttc     60
cttgcccagt ttaaattaaa ttattttatc ttacaatgtg                          100

<210> SEQ ID NO 345
<211> LENGTH: 100
<212> TYPE: DNA
<213> ORGANISM: Homo sapiens

<400> SEQUENCE: 345
ttaattttag tgctagcaag gcacagctaa aattccattt ctacttagga gtggggatca     60
ttgtggcagt gagtgcttat ttgggtttgg gatgcttgga                          100

<210> SEQ ID NO 346
<211> LENGTH: 100
<212> TYPE: DNA
<213> ORGANISM: Homo sapiens

<400> SEQUENCE: 346
tctgggtgaa agccaggatt aaaaagcatc ctccttcccc attccactct ctaggttata     60 aatattttt tggattaaaa gcctccttta aaaaaatgca                           100

<210> SEQ ID NO 347
<211> LENGTH: 100
<212> TYPE: DNA
<213> ORGANISM: Homo sapiens

<400> SEQUENCE: 347
aatccacctg gcatgttaat tgtgcagggg attcctaatt atgtgtgcag atgacgtgag     60
tcacacggtg atagtgttcc ttctagagtc ccactggtgt                          100

<210> SEQ ID NO 348
<211> LENGTH: 100
<212> TYPE: DNA
<213> ORGANISM: Homo sapiens

<400> SEQUENCE: 348
actaggcgtt catcctgtgt aatttgaaaa tatgtcacac gtggtgatga gaatctatt     60 gaggaacatg ggcagtttga ataatatat gcaatgtatg                           100

<210> SEQ ID NO 349
<211> LENGTH: 100
<212> TYPE: DNA
<213> ORGANISM: Homo sapiens

<400> SEQUENCE: 349
actagtttat ataatgaaag gaagtattta aaaagataga atgacataga ctaatctaat    60
```

```
tgagaaatat gaaagtctaa cagaaatgat tgcttgtgaa                           100
```

<210> SEQ ID NO 350
<211> LENGTH: 100
<212> TYPE: DNA
<213> ORGANISM: Homo sapiens

<400> SEQUENCE: 350

```
attttatgaa gaaatccaca gataaattct ccaccttgat ctatgtaatc cgaaatttag     60
atgttaaaaa tatgttgatt ctgaaaattt atatttattc                          100
```

<210> SEQ ID NO 351
<211> LENGTH: 100
<212> TYPE: DNA
<213> ORGANISM: Homo sapiens

<400> SEQUENCE: 351

```
tttggtatga ataggtcaaa acaagtcacc attaactgac aggaagcaca gaattctcaa     60
tttagttttg gcaaagacat tattttataa atatgagttt                          100
```

<210> SEQ ID NO 352
<211> LENGTH: 100
<212> TYPE: DNA
<213> ORGANISM: Homo sapiens

<400> SEQUENCE: 352

```
ttaaatgatt cttatgaaga aactagcacc aaagtgaatg cactctgcaa ataactccca     60
gcttctctga atttcaaaag cagccactaa atattattag                          100
```

<210> SEQ ID NO 353
<211> LENGTH: 100
<212> TYPE: DNA
<213> ORGANISM: Homo sapiens

<400> SEQUENCE: 353

```
caaatcaatt tagctgaaag cgatgaatta cagaagtaaa tctttaggta caaagtagac     60
agctgacaca catgtagcat atacacacta gtgatctgcc                          100
```

<210> SEQ ID NO 354
<211> LENGTH: 100
<212> TYPE: DNA
<213> ORGANISM: Homo sapiens

<400> SEQUENCE: 354

```
ttccttcttt accaacatag agtttcccat gagccctgaa tccggggcac ttttgctaac     60
ttcccctgca gcggcgacgc tgccactccc agtgcccccg                          100
```

<210> SEQ ID NO 355
<211> LENGTH: 100
<212> TYPE: DNA
<213> ORGANISM: Homo sapiens

<400> SEQUENCE: 355

```
cagtggaagg ggctcgcgcc acctccattg ctcttggccc caaagccata gaggtgcccc     60
ccggaagggg cctggctgcc actgccattc tggtggccct                          100
```

<210> SEQ ID NO 356
<211> LENGTH: 100
<212> TYPE: DNA

<213> ORGANISM: Homo sapiens

<400> SEQUENCE: 356

```
gaagcaggtc gtgcttgtcc ttcctggatt tccccgcatc cttatcccgc ttggcgcctc      60
ggctgctctg gcttttacct ggcttctcct ctttgctttt                           100
```

<210> SEQ ID NO 357
<211> LENGTH: 100
<212> TYPE: DNA
<213> ORGANISM: Homo sapiens

<400> SEQUENCE: 357

```
cccacaggag cctgcccccg cggtggcggc agaggtgctg gtgctggtac tattgctgtt      60
tgggttgccg ctgccgccgc tgctcacact ttgacccagc                           100
```

<210> SEQ ID NO 358
<211> LENGTH: 100
<212> TYPE: DNA
<213> ORGANISM: Homo sapiens

<400> SEQUENCE: 358

```
gctgaattca tgccagttgc ctctccaggg cgcccttgga cttcctgcct cttgccagtg      60
ctgctgatct cgggaatccc atacaaggca gcagaaggca                           100
```

<210> SEQ ID NO 359
<211> LENGTH: 100
<212> TYPE: DNA
<213> ORGANISM: Homo sapiens

<400> SEQUENCE: 359

```
gagatttatt agcatcctta gaagttttac tccttttcac ttttgatttg ctggtctctt      60
tgtgtgaatt cccctgggga gcagaggcct gaacagaagc                           100
```

<210> SEQ ID NO 360
<211> LENGTH: 100
<212> TYPE: DNA
<213> ORGANISM: Homo sapiens

<400> SEQUENCE: 360

```
aaatttagg ccatcagcta aggctgcggt agcaccagcc ccactggagg ccggacctcc      60
acaatccttg gagttgctgc tactagtggt ggtggtggaa                           100
```

<210> SEQ ID NO 361
<211> LENGTH: 100
<212> TYPE: DNA
<213> ORGANISM: Homo sapiens

<400> SEQUENCE: 361

```
ttattcatct caaatttctg tctgtccttc tccaaatcag cgtccaaatc aattattaaa      60
tttccaaccc cgatttccca atcatcgcca ctgtcataag                           100
```

<210> SEQ ID NO 362
<211> LENGTH: 100
<212> TYPE: DNA
<213> ORGANISM: Homo sapiens

<400> SEQUENCE: 362

```
tatcaactgt atttggatcc acaccttttc ctgcagtaga aatgttcact gacatcctga      60
agatgagctc tctagaataa aaatccgatg aacttttctt                           100
```

<210> SEQ ID NO 363
<211> LENGTH: 100
<212> TYPE: DNA
<213> ORGANISM: Homo sapiens

<400> SEQUENCE: 363
ttcctcagga atttgagctg gggatctgca tcctggccat tgcagtcctt tagcatcctc    60
gccgcgccct gagcgcgctg gaggctcgca ggctgcgccc                          100

<210> SEQ ID NO 364
<211> LENGTH: 100
<212> TYPE: DNA
<213> ORGANISM: Homo sapiens

<400> SEQUENCE: 364
tcccagggct gatgccgcgt cctgctccgc cgttctggga cgtcgggac aaaagtggag     60 gagacgggag agcccgggca gaaaaagcag gacgcgcgtc                          100

<210> SEQ ID NO 365
<211> LENGTH: 100
<212> TYPE: DNA
<213> ORGANISM: Homo sapiens

<400> SEQUENCE: 365
ccaggtgccc acctcttcgc tttgaggcgg gggcggtggg atggaatatg ggtgcgcgag    60
gtcggggctg gtaactctcg gaggggcacg gcctccacgc                          100

<210> SEQ ID NO 366
<211> LENGTH: 100
<212> TYPE: DNA
<213> ORGANISM: Homo sapiens

<400> SEQUENCE: 366
tgggagggat gaatggacgc tgggccccgg caaatgaggc gctgtgggtc cccaggaagt    60
ggggtaccag gctctactcc caccccggcc tctgaaacgc                          100

<210> SEQ ID NO 367
<211> LENGTH: 100
<212> TYPE: DNA
<213> ORGANISM: Homo sapiens

<400> SEQUENCE: 367
ggccaggagg ggtggcggct gggtggggag agagggtgca agacgagcgg cgcgtgtcgg    60
gagcctttgg gctgcgggtg cgttacagga gagcaggcgg                          100

<210> SEQ ID NO 368
<211> LENGTH: 100
<212> TYPE: DNA
<213> ORGANISM: Homo sapiens

<400> SEQUENCE: 368
gtaggagcct tcgcgggggc cgagctcgga aggcggacgg ctgtgcccgc ccaggggatg    60
cgcccgggcc ggccgcgaag gtgccttctt ccgggggccc                          100

<210> SEQ ID NO 369
<211> LENGTH: 100
<212> TYPE: DNA
<213> ORGANISM: Homo sapiens

```
<400> SEQUENCE: 369
ggacgaccct dacacggcac gcgcgcgctt cgcagcctca aagactccgg ggcctcgtgg      60
tcactggcgc aggggatcgg ggcggggtgc ccggagtgcg                            100

<210> SEQ ID NO 370
<211> LENGTH: 100
<212> TYPE: DNA
<213> ORGANISM: Homo sapiens

<400> SEQUENCE: 370
cccgcagtgc agagcagagc gggcggagga ccccgggcgc gggcgcggac ggcacgcggg      60
gcatgaacct ggagggcggc ggccgaggcg gagagttcgg                            100

<210> SEQ ID NO 371
<211> LENGTH: 100
<212> TYPE: DNA
<213> ORGANISM: Homo sapiens

<400> SEQUENCE: 371
catgagcgcg gtgagctgcg gcaacgggaa gctccgccag tggctgatcg accagatcga      60
cagcggcaag taccccgggc tggtgtggga gaacgaggag                            100

<210> SEQ ID NO 372
<211> LENGTH: 100
<212> TYPE: DNA
<213> ORGANISM: Homo sapiens

<400> SEQUENCE: 372
aagagcatct tccgcatccc ctggaagcac gcgggcaagc aggactacaa ccgcgaggag      60
gacgccgcgc tcttcaaggt ctccggcctc gggagccggc                            100

<210> SEQ ID NO 373
<211> LENGTH: 100
<212> TYPE: DNA
<213> ORGANISM: Homo sapiens

<400> SEQUENCE: 373
cccgcgcgcc acagctctgc agctcgtggc agcggcgcag cgctccagcc atgtcgcgcg      60
gcctccagct tctgctcctg agctgcggta gggctcgcga                            100

<210> SEQ ID NO 374
<211> LENGTH: 100
<212> TYPE: DNA
<213> ORGANISM: Homo sapiens

<400> SEQUENCE: 374
gcgcctgtct cgcctgtcgc ccccgcccc tccacgacac cccctcccgt cggtcgcttg       60
ctcacgacgc gctctctctt tcttgtagcc tacagcctgg                            100

<210> SEQ ID NO 375
<211> LENGTH: 100
<212> TYPE: DNA
<213> ORGANISM: Homo sapiens

<400> SEQUENCE: 375
ctcccgcgac gccggaggtg aaggtggctt gctccgaaga tgtggacttg ccctgcaccg      60 cccccctggga tccgcaggtt ccctacacgg tctcctgggt                           100
```

```
<210> SEQ ID NO 376
<211> LENGTH: 100
<212> TYPE: DNA
<213> ORGANISM: Homo sapiens

<400> SEQUENCE: 376
caaggtaggt gctgcgatac ccacgggctg gggtttggtg ggctcatttg aagacagcag    60
gaaccatctc ccctaggctg gcgaccctct gtggctgcca                         100

<210> SEQ ID NO 377
<211> LENGTH: 100
<212> TYPE: DNA
<213> ORGANISM: Homo sapiens

<400> SEQUENCE: 377 ggtggggcg aggggcgtct cccgcagctg aacttggagt acccagcctc ccgtcgcgcc    60
tcccccaccc catccgcatc caggtacagg gccgaattag                         100

<210> SEQ ID NO 378
<211> LENGTH: 100
<212> TYPE: DNA
<213> ORGANISM: Homo sapiens

<400> SEQUENCE: 378
gttttgctct ccgcagacct caatcccctt cctgtcactg aaggtggcct gagatgaatg    60
atccacttaa gatgttttgg aagggcagag actctcattt                         100

<210> SEQ ID NO 379
<211> LENGTH: 100
<212> TYPE: DNA
<213> ORGANISM: Homo sapiens

<400> SEQUENCE: 379
ggattaattc tggaggccac ctgtggttgt gggccagcag gtcaggaaga aagcaacagg    60
gacctagatt tgggcattgg acaggggaa tgtctccaga                          100

<210> SEQ ID NO 380
<211> LENGTH: 100
<212> TYPE: DNA
<213> ORGANISM: Homo sapiens

<400> SEQUENCE: 380
ctctccagtt cctatattct aatacccctc cgccgccaaa taaaatttgg cgtctggcca    60
cagctctttt agtgggtatc tgggtggctc ttaaaagagc                         100

<210> SEQ ID NO 381
<211> LENGTH: 100
<212> TYPE: DNA
<213> ORGANISM: Homo sapiens

<400> SEQUENCE: 381
ctttggggtt aggtgttaag acgcttactt ggaatgttta cttggagctg gtgtacttgg    60
tgacggcctt ggtgccctcc gacacggcgt gcttggccag                         100

<210> SEQ ID NO 382
<211> LENGTH: 100
<212> TYPE: DNA
<213> ORGANISM: Homo sapiens

<400> SEQUENCE: 382
```

```
ctccggcccc tgccgagaag actcccgtga agaagaaggc ccgcaagtct gcaggtgcgg      60
ccaagcgcaa agcgtctggg cccccggtgt ccgagctcat                           100
```

<210> SEQ ID NO 383
<211> LENGTH: 100
<212> TYPE: DNA
<213> ORGANISM: Homo sapiens

<400> SEQUENCE: 383

```
tactaaagct gttgccgcct ccaaggagcg cagcggcgta tctttggccg ctctcaagaa      60
agcgctggca gccgctggct atgacgtgga gaagaacaac                           100
```

<210> SEQ ID NO 384
<211> LENGTH: 100
<212> TYPE: DNA
<213> ORGANISM: Homo sapiens

<400> SEQUENCE: 384

```
agccgcatca agctgggtct caagagcctg gtgagcaagg gcaccctggt gcagaccaag      60
ggcaccggcg cgtcgggttc cttcaaactc aacaagaagg                           100
```

<210> SEQ ID NO 385
<211> LENGTH: 100
<212> TYPE: DNA
<213> ORGANISM: Homo sapiens

<400> SEQUENCE: 385

```
cggcctctgg ggaagccaag cctaaggcta aaaaggcagg cgcggccaag gccaagaagc      60
cagcaggagc ggcgaagaag cccaagaagg cgacggggc                            100
```

<210> SEQ ID NO 386
<211> LENGTH: 100
<212> TYPE: DNA
<213> ORGANISM: Homo sapiens

<400> SEQUENCE: 386

```
ggccaccccc aagaagagcg ccaagaagac cccaaagaag gcgaagaagc cggctgcagc      60
tgctggagcc aaaaaagcga aaagcccgaa aaaggcgaaa                           100
```

<210> SEQ ID NO 387
<211> LENGTH: 100
<212> TYPE: DNA
<213> ORGANISM: Homo sapiens

<400> SEQUENCE: 387

```
gcagccaagc caaaaaaggc gcccaagagc ccagcgaagg ccaaagcagt taaacccaag      60
gcggctaaac caaagaccgc caagcccaag gcagccaagc                           100
```

<210> SEQ ID NO 388
<211> LENGTH: 100
<212> TYPE: DNA
<213> ORGANISM: Homo sapiens

<400> SEQUENCE: 388

```
caaagaaggc ggcagccaag aaaaagtaga agttcctttt ggccaactgc ttagaagccc      60
aacacaaccc aaaggctctt ttcagagcca cccaccgctc                           100
```

<210> SEQ ID NO 389
<211> LENGTH: 100

```
<212> TYPE: DNA
<213> ORGANISM: Homo sapiens

<400> SEQUENCE: 389
tcagtaaaag agctgttgca ctattagggg gcgtggctcg ggaaaacgct gctaagcagg    60
ggcgggtctc ccgggaacaa agtcggggag aggagtggga                         100

<210> SEQ ID NO 390
<211> LENGTH: 100
<212> TYPE: DNA
<213> ORGANISM: Homo sapiens

<400> SEQUENCE: 390
ctccttagcc agactcgatt acaagcactg catgcattac tcagtgtgat aagatcatga    60
taatcccttt aaaaagatcg cccgaattta agcctggatt                         100

<210> SEQ ID NO 391
<211> LENGTH: 100
<212> TYPE: DNA
<213> ORGANISM: Homo sapiens

<400> SEQUENCE: 391
aggaacacgt gtttacagct ctaatatcga taatttaagt ggctcttaaa agagcctttg    60
gggttgggct ttaagacgct tacttggcaa gtttacttag                         100

<210> SEQ ID NO 392
<211> LENGTH: 100
<212> TYPE: DNA
<213> ORGANISM: Homo sapiens

<400> SEQUENCE: 392
cgctggtgta cttggtgacg gccttggtgc cctcggacac ggcgtgcttg gccaactccc    60
cgggcagcag caggcgcacg gccgtctgga tctccctgga                         100

<210> SEQ ID NO 393
<211> LENGTH: 100
<212> TYPE: DNA
<213> ORGANISM: Homo sapiens

<400> SEQUENCE: 393
ccccggctcc ggctcctgcg gcagctcctc tgggcaccgt ccctgcgccg acatcctgga    60
ggttgggatg ctcttgtcca aaatcaactc gcttgcccac                         100

<210> SEQ ID NO 394
<211> LENGTH: 100
<212> TYPE: DNA
<213> ORGANISM: Homo sapiens

<400> SEQUENCE: 394
ctgcgcgccg cgccctgcaa cgacctgcac gccaccaagc tggcgcccgg tgagagcacc    60
ccccgcctcc ggcccgggga tgcggggcgg cggcgggatc                         100

<210> SEQ ID NO 395
<211> LENGTH: 100
<212> TYPE: DNA
<213> ORGANISM: Homo sapiens

<400> SEQUENCE: 395
tcctgggtgg ggagctggcg gctcgcgggc cggcactgag tccccgtgct tccccctttc    60
```
ctaggcaagg agaaggagcc cctggagtcg cagtaccagg         100

<210> SEQ ID NO 396
<211> LENGTH: 100
<212> TYPE: DNA
<213> ORGANISM: Homo sapiens

<400> SEQUENCE: 396
tgggcccgct actgggcagc ggcggcttcg gctcggtcta ctcaggcatc cgcgtctccg    60
acaacttgcc ggtgagtggg cgccccgcgg tggggagggc                         100

<210> SEQ ID NO 397
<211> LENGTH: 100
<212> TYPE: DNA
<213> ORGANISM: Homo sapiens

<400> SEQUENCE: 397
gcgccgggcg gggggcgcac gggcgtgctt tagcccggac gagggaacct gacggagacc    60
ctgggcttcc aggtggccat caaacacgtg gagaaggacc                         100

<210> SEQ ID NO 398
<211> LENGTH: 100
<212> TYPE: DNA
<213> ORGANISM: Homo sapiens

<400> SEQUENCE: 398
ggatttccga ctggggagag ctggtgagtg ccctgcagga gcgaccccca ggatgagtgg    60
gtggggtgag gggcgccccc gactcccgcc ctaacgcggc                         100

<210> SEQ ID NO 399
<211> LENGTH: 100
<212> TYPE: DNA
<213> ORGANISM: Homo sapiens

<400> SEQUENCE: 399
cccctcgccc ctgcagccta atggcactcg agtgcccatg gaagtggtcc tgctgaagaa    60
ggtgagctcg ggtttctccg gcgtcattag gctcctggac                         100

<210> SEQ ID NO 400
<211> LENGTH: 100
<212> TYPE: DNA
<213> ORGANISM: Homo sapiens

<400> SEQUENCE: 400
tggttcgaga ggcccgacag tttcgtcctg atcctggaga ggcccgagcc ggtgcaagat    60
ctcttcgact tcatcacgga aaggggagcc ctgcaagagg                         100

<210> SEQ ID NO 401
<211> LENGTH: 100
<212> TYPE: DNA
<213> ORGANISM: Homo sapiens

<400> SEQUENCE: 401
agctggcccg cagcttcttc tggcaggtgc tggaggccgt gcggcactgc cacaactgcg    60
gggtgctcca ccgcgacatc aaggacgaaa acatccttat                         100

<210> SEQ ID NO 402
<211> LENGTH: 100
<212> TYPE: DNA
<213> ORGANISM: Homo sapiens

<400> SEQUENCE: 402
cgacctcaat cgcggcgagc tcaagctcat cgacttcggg tcgggggcgc tgctcaagga    60
caccgtctac acggacttcg atggtgagcc aggcccggga                          100

<210> SEQ ID NO 403
<211> LENGTH: 100
<212> TYPE: DNA
<213> ORGANISM: Homo sapiens

<400> SEQUENCE: 403
gggagctgcc caggtgactc ggcccggccc ggcccagtcc ggaggcctcg gccagtctcc    60
cgcgccagcc ttttgtaaag gtcattgggc cgcctggctc                          100

<210> SEQ ID NO 404
<211> LENGTH: 100
<212> TYPE: DNA
<213> ORGANISM: Homo sapiens

<400> SEQUENCE: 404
gatgctagcc ggggtgggac gcaggagagc ctcccagcgt agtaaagccg gggattttca    60
gccagctgaa cctgtaatgt ttctggcatg attttattct                          100

<210> SEQ ID NO 405
<211> LENGTH: 100
<212> TYPE: DNA
<213> ORGANISM: Homo sapiens

<400> SEQUENCE: 405
tcaagtggaa ttcagttagt tccaggcttt cccgatgaat aagaggttgt gggcaaccgg    60
cggtagccca gattttttcta aagtctgacc cagtttcccc                         100

<210> SEQ ID NO 406
<211> LENGTH: 100
<212> TYPE: DNA
<213> ORGANISM: Homo sapiens

<400> SEQUENCE: 406
ctctaaacag acaaaagcaa aatatctcat taggcatcat ctccgccaag gttcccacta    60
ggcaggaaag gatttttatc taaagtaatt acccttttta                          100

<210> SEQ ID NO 407
<211> LENGTH: 100
<212> TYPE: DNA
<213> ORGANISM: Homo sapiens

<400> SEQUENCE: 407
gttaaataca ctcaacagat gaaatttaca gagagtgaga gactgcagca ctagacagcg    60
aaggtgaaaa ccaggaacgc cgcgtctcgc cgcccgcggg                          100

<210> SEQ ID NO 408
<211> LENGTH: 100
<212> TYPE: DNA
<213> ORGANISM: Homo sapiens

<400> SEQUENCE: 408
cccgccggga gactgcgggt ccgtctcgcg ggtggggcgc cccggtccct ctcgtttcct    60
ggaggccaca ggtcacggcg acggcggtga ccgggagagc                          100

```
<210> SEQ ID NO 409
<211> LENGTH: 100
<212> TYPE: DNA
<213> ORGANISM: Homo sapiens

<400> SEQUENCE: 409
cgggtctgac agctgctgcg gctcgcgcgg acgcgcgcct cctgcagccc gccctcccca     60
tgcctgactt attactctct gctcctcctc cctctgctgt                          100

<210> SEQ ID NO 410
<211> LENGTH: 100
<212> TYPE: DNA
<213> ORGANISM: Homo sapiens

<400> SEQUENCE: 410
tccaaaacac ccttcgacgc cagcaaaata caatgcgcct cggccgccgt aaacagccgg     60
gagggagagc acacattcgg cgcggcgcgg ccgccggctc                          100

<210> SEQ ID NO 411
<211> LENGTH: 100
<212> TYPE: DNA
<213> ORGANISM: Homo sapiens

<400> SEQUENCE: 411
ggctcccacc cccttcccgt tcctagaaaa tgccataaaa gcgggcaggg cgcggggagg     60
gcggctgcgc gcccggcggc cggggctccc ttcccgcgcc                          100

<210> SEQ ID NO 412
<211> LENGTH: 100
<212> TYPE: DNA
<213> ORGANISM: Homo sapiens

<400> SEQUENCE: 412
tatgaaacag ccagtgctac gtctccttta taccaaaact ggtagcctga agagctctca     60
ggcttaccta taaacgatgt tcagtgaatg caggtagccc                          100

<210> SEQ ID NO 413
<211> LENGTH: 100
<212> TYPE: DNA
<213> ORGANISM: Homo sapiens

<400> SEQUENCE: 413
aaggcactgg ctatttcagc agcatagaaa cgagcccgtg gttccaggaa gcagcgttcc     60
ctctggagat ggtagaacaa ctgcaggaga cagaacaaag                          100

<210> SEQ ID NO 414
<211> LENGTH: 100
<212> TYPE: DNA
<213> ORGANISM: Homo sapiens

<400> SEQUENCE: 414
tcattctggg ttgcaaatga atttaattag ttttgacata cacagcaaaa gaacaactgc     60
aggaagtggc cccaagtaat ctattaacta taaacctgac                          100

<210> SEQ ID NO 415
<211> LENGTH: 100
<212> TYPE: DNA
<213> ORGANISM: Homo sapiens

<400> SEQUENCE: 415
```

```
aggttgaagg aaatgctaat tctggtaaca ttctccccac caaaaatctt tgaaaacttt    60
tttctcaaac taaaacaaag caggctgtgc agagacacta                         100
```

<210> SEQ ID NO 416
<211> LENGTH: 100
<212> TYPE: DNA
<213> ORGANISM: Homo sapiens

<400> SEQUENCE: 416

```
agagttgact tctatccccc ctgctcacct ctccaccatt aatgtagtct aggacaaagt    60
acaatttgtc agcagtctgg aaagagaagt gaaggcccac                         100
```

<210> SEQ ID NO 417
<211> LENGTH: 100
<212> TYPE: DNA
<213> ORGANISM: Homo sapiens

<400> SEQUENCE: 417

```
caggaaaggg tgcttcacat tcttcaacag aacattccgc tccgacataa tatgcttctc    60
ctaggaaaat gacgattcag atttagtggc atgtttcaac                         100
```

<210> SEQ ID NO 418
<211> LENGTH: 100
<212> TYPE: DNA
<213> ORGANISM: Homo sapiens

<400> SEQUENCE: 418

```
gaggacatga aggaagtgta ccaaaagatc ttcagatttg aaattacctt tccaaaactg    60 cccttttccga tcactttcaa gaagtgaaag tcagatggtt                        100
```

<210> SEQ ID NO 419
<211> LENGTH: 100
<212> TYPE: DNA
<213> ORGANISM: Homo sapiens

<400> SEQUENCE: 419

```
tagcatgagg attggacgac gggccaaggt tgatttgctg agaaggactt ggctagaaaa    60
aaaaaaaaag aatttctttt aataccattg cttcaaagga                         100
```

<210> SEQ ID NO 420
<211> LENGTH: 100
<212> TYPE: DNA
<213> ORGANISM: Homo sapiens

<400> SEQUENCE: 420

```
aatttctttt aataccattg cttcaaagga agacatctat aacataaacg atgtagaaaa    60
tgttacatct acaaatgact gatgcaaatg accatacatc                         100
```

<210> SEQ ID NO 421
<211> LENGTH: 100
<212> TYPE: DNA
<213> ORGANISM: Homo sapiens

<400> SEQUENCE: 421

```
aataaaataa tactctgact caatacttaa atatttatat cacttgttat gccataatga    60
agcattcctg ccttgatact aatttctaga aatgctattt                         100
```

<210> SEQ ID NO 422

```
<211> LENGTH: 100
<212> TYPE: DNA
<213> ORGANISM: Homo sapiens

<400> SEQUENCE: 422
taatccatta atgtaggaat actaactgac tcccttacag ttctccacag atgcacggca    60
catacaaaaa cttactggag gagaagggtt ggcattcata                         100

<210> SEQ ID NO 423
<211> LENGTH: 100
<212> TYPE: DNA
<213> ORGANISM: Homo sapiens

<400> SEQUENCE: 423
agctcaggct cctgaggttg ggagatcttc aagatggact gaacttcagg gctgcaggga    60
ataaagggca cgatttagaa tccagctcgc cactaggggg                         100

<210> SEQ ID NO 424
<211> LENGTH: 100
<212> TYPE: DNA
<213> ORGANISM: Homo sapiens

<400> SEQUENCE: 424
cacaccaaca tcaaaagtga gtttctggct ctaccgactt ctacccggat aattcactgt    60
ttaaactgaa ataccccaa tacattagtc agttaaagaa                          100

<210> SEQ ID NO 425
<211> LENGTH: 100
<212> TYPE: DNA
<213> ORGANISM: Homo sapiens

<400> SEQUENCE: 425
aataataaac cccattaaat acagaaataa ggattgttgc tcatggagaa aggccgtgaa    60
ttcggccaac acgaaccatt tatcttacat ctccagttca                         100

<210> SEQ ID NO 426
<211> LENGTH: 100
<212> TYPE: DNA
<213> ORGANISM: Homo sapiens

<400> SEQUENCE: 426
agccaaatca gcaaattaac tttaatgttt aaaatgtgtc aaatatatta gaatttaagg    60
agaaatgaga tccccacccc agaagaagtc ttcgccttcc                         100

<210> SEQ ID NO 427
<211> LENGTH: 100
<212> TYPE: DNA
<213> ORGANISM: Homo sapiens

<400> SEQUENCE: 427
cgataaacgc cgtgatgaga atgtttaccg ctggcaaatt caaactatac tagttatttc    60
ctcaaatccg gtcaaactta ctgtttgcat gcataggagt                         100

<210> SEQ ID NO 428
<211> LENGTH: 100
<212> TYPE: DNA
<213> ORGANISM: Homo sapiens

<400> SEQUENCE: 428
tattggcaat cttctgaata aagtcgttca gacccatcct cctctgcttc atgaaagctg    60
```

```
tggatgaagg aggagaaata aagaaacgtt tagacggctt              100
```

<210> SEQ ID NO 429
<211> LENGTH: 100
<212> TYPE: DNA
<213> ORGANISM: Homo sapiens

<400> SEQUENCE: 429

```
cataacgtcc ggcgccacac acactaatct gatccgggac tttcaaaaaa tttccacttt   60
gcgtctcctg gagcagaagt cccgcaagat tcctgcactc                       100
```

<210> SEQ ID NO 430
<211> LENGTH: 100
<212> TYPE: DNA
<213> ORGANISM: Homo sapiens

<400> SEQUENCE: 430

```
accgatgaga attgccacca tgccctcat cctggagtaa gtgagggtgc ccttagcagc    60
ctcagttttc accgtcatca ccaccgcggg gagacagaaa                       100
```

<210> SEQ ID NO 431
<211> LENGTH: 100
<212> TYPE: DNA
<213> ORGANISM: Homo sapiens

<400> SEQUENCE: 431

```
gacgttagcg ctcaaagacc ggctcggcgt atgctgcgcc aggccgcgcg ctcggcctta   60 taaaaaggc accgccgcgg gggcggggcc tgcgcgacag                        100
```

<210> SEQ ID NO 432
<211> LENGTH: 100
<212> TYPE: DNA
<213> ORGANISM: Homo sapiens

<400> SEQUENCE: 432

```
agggtgagag gagtcaccag gtaaagatgg gttggaagga cctggcaggc agagcaggga   60
gcaggacccc agtccagggc agcagggaag cgggagtctg                       100
```

<210> SEQ ID NO 433
<211> LENGTH: 100
<212> TYPE: DNA
<213> ORGANISM: Homo sapiens

<400> SEQUENCE: 433

```
ggcagagctg attccaggca gctcagtatt gctggcctgt gcatcctgag acttatccga   60
gtcgcaggtg aagctggtgg gaatcaggca gagtgcagag                       100
```

<210> SEQ ID NO 434
<211> LENGTH: 100
<212> TYPE: DNA
<213> ORGANISM: Homo sapiens

<400> SEQUENCE: 434

```
ctttagctgg ggcagggtta gccaagagcc tgtcatggag ctgctctctg ggcactggga   60
aacataagtc tggaggcttt ggctgcagct gcagataaag                       100
```

<210> SEQ ID NO 435
<211> LENGTH: 100
<212> TYPE: DNA

```
<213> ORGANISM: Homo sapiens

<400> SEQUENCE: 435 atgcagggc ctctgacgat gggggcctta gtcatctcag aggtggtgca gagggtagaa    60
gcctgactgg ggtcagagat gaggaaggag agggtcagaa                         100

<210> SEQ ID NO 436
<211> LENGTH: 100
<212> TYPE: DNA
<213> ORGANISM: Homo sapiens

<400> SEQUENCE: 436
acagtgattc taaaccaatt tggttgaggc agaagatact aatggccgag gggaggagag    60
agggagcgta ggctctaaag gggaagcttg ttaggaatga                          100

<210> SEQ ID NO 437
<211> LENGTH: 100
<212> TYPE: DNA
<213> ORGANISM: Homo sapiens

<400> SEQUENCE: 437
agacagaggc gcaggcacag ccctttcatc agctgaccag gagtgctcgg cccggcctgc    60
caggaacctc ttatcaaact ccaccggctg cctgcatcta                          100

<210> SEQ ID NO 438
<211> LENGTH: 100
<212> TYPE: DNA
<213> ORGANISM: Homo sapiens

<400> SEQUENCE: 438
caattcaagt ccatggctaa ccttctgtta gagacagaaa ttctgctgca gccagcaagt    60
ttgctggtgt acagggcacc gcttcatggg cctagtagga                          100

<210> SEQ ID NO 439
<211> LENGTH: 100
<212> TYPE: DNA
<213> ORGANISM: Homo sapiens

<400> SEQUENCE: 439
agcgaagctg aaaggcaact tccgaaagcc agtctcctct cccaaacgcc ctttaatatc    60
tccccagttg gatctggggc gcctgtggtt tcggaccctt                          100

<210> SEQ ID NO 440
<211> LENGTH: 100
<212> TYPE: DNA
<213> ORGANISM: Homo sapiens

<400> SEQUENCE: 440
aggagctctg agaactggtg tgtgtggtcg gaagccatct gagtctccct gtgatttgga    60 cttttttaaga aacttctaag ttgtattact atacccttta                         100

<210> SEQ ID NO 441
<211> LENGTH: 100
<212> TYPE: DNA
<213> ORGANISM: Homo sapiens

<400> SEQUENCE: 441
ttcccttgtc atatgacttc catcctcagc actacaatat tatcattaat gtttaaatca    60
ttgtcaagtc tgtgattgcc ttagagattt attaagaata                          100
```

<210> SEQ ID NO 442
<211> LENGTH: 100
<212> TYPE: DNA
<213> ORGANISM: Homo sapiens

<400> SEQUENCE: 442
acatgctagg attaggaaag tttaactttt taccatcctt aaaattagat ttttgaaaac    60
tgtcttatcc ccattaaaga aaaaaataaa aaggatgaat                        100

<210> SEQ ID NO 443
<211> LENGTH: 100
<212> TYPE: DNA
<213> ORGANISM: Homo sapiens

<400> SEQUENCE: 443
tatacatacc tgcacatata tacagcatat gtatatgtgt ctgtattata tgtattaaat    60
gaaagattat ccacattttg ttctttagga tcttcagcag                        100

<210> SEQ ID NO 444
<211> LENGTH: 100
<212> TYPE: DNA
<213> ORGANISM: Homo sapiens

<400> SEQUENCE: 444
ctctcttccc atcacaatag aaaggcctga gctaacattt ccatttctgc aaaaggcaga    60
ttttgttcaa ttaaaaatta taatgcctta aatttccaca                        100

<210> SEQ ID NO 445
<211> LENGTH: 100
<212> TYPE: DNA
<213> ORGANISM: Homo sapiens

<400> SEQUENCE: 445
gacatttaag agacttcgtt ttcactgtga taaacaggtt tgatttggac ttataacttt    60
tttctaaaat tatcaaatta ataacgacta taatgaaata                        100

<210> SEQ ID NO 446
<211> LENGTH: 100
<212> TYPE: DNA
<213> ORGANISM: Homo sapiens

<400> SEQUENCE: 446
gaggcaaata ttttagagga ttcattcctt ggggtaacat tgttctata atttatagtc    60 tcataatgtt gagagattaa agcatttaaa taacattgtc                        100

<210> SEQ ID NO 447
<211> LENGTH: 100
<212> TYPE: DNA
<213> ORGANISM: Homo sapiens

<400> SEQUENCE: 447
aactaacttt cagcttacct ttcttaagga aaaaaacaa aaaaatgtta aaaatagaca     60
tgtatttttc aaacatacaa ttcatgtttt tatgtcatta                        100

<210> SEQ ID NO 448
<211> LENGTH: 100
<212> TYPE: DNA
<213> ORGANISM: Homo sapiens

<400> SEQUENCE: 448
aagagatgtg agggacttat aaataatatt aagataacag gaattaaagt ctcggtgtgt    60
gaaaatactg tatatctagg atgcacataa aaactgccct    100

<210> SEQ ID NO 449
<211> LENGTH: 100
<212> TYPE: DNA
<213> ORGANISM: Homo sapiens

<400> SEQUENCE: 449
tacagatctt gcagggaaaa gtacctgact atactgtata agacttctgc tgtaccattt    60
aatcatacca aaaaaaatgg aatcaacaca caaatagatt    100

<210> SEQ ID NO 450
<211> LENGTH: 100
<212> TYPE: DNA
<213> ORGANISM: Homo sapiens

<400> SEQUENCE: 450
tcttttccac tgttctcaat ttaaaaataa ttggagaaat gtgtgctttg tttagaagag    60
taaaggaaaa cattcattca atagtaccat gcagaatgat    100

<210> SEQ ID NO 451
<211> LENGTH: 100
<212> TYPE: DNA
<213> ORGANISM: Homo sapiens

<400> SEQUENCE: 451
cagaaaaata gaaagattat catcggattt gggaatcaaa gacagctcag caaaatacta    60
ggacatggct catataagat ggaataagcc tggaaataca    100

<210> SEQ ID NO 452
<211> LENGTH: 100
<212> TYPE: DNA
<213> ORGANISM: Homo sapiens

<400> SEQUENCE: 452
ctttagggga tagctctgca aggggagagg ttcgggactg tggcgcgcac tgcgcgctgc    60
gccaggtttc cgcaccaaga cccctttaac tcaagactgc    100

<210> SEQ ID NO 453
<211> LENGTH: 100
<212> TYPE: DNA
<213> ORGANISM: Homo sapiens

<400> SEQUENCE: 453
ctcccgcttt gtgtgccccg ctccagcagc ctcccgcgac gatgcccctc aacgttagct    60
tcaccaacag gaactatgac ctcgactacg actcggtgca    100

<210> SEQ ID NO 454
<211> LENGTH: 100
<212> TYPE: DNA
<213> ORGANISM: Homo sapiens

<400> SEQUENCE: 454
gccgtatttc tactgcgacg aggaggagaa cttctaccag cagcagcagc agagcgagct    60 gcagccccccg cgcccagcg aggatatctg gaagaaattc    100

```
<210> SEQ ID NO 455
<211> LENGTH: 100
<212> TYPE: DNA
<213> ORGANISM: Homo sapiens

<400> SEQUENCE: 455
gagctgctgc ccaccccgcc cctgtccect agccgccgct ccgggctctg ctcgccctcc      60
tacgttgcgg tcacacccett ctcccttcgg ggagacaacg                          100

<210> SEQ ID NO 456
<211> LENGTH: 100
<212> TYPE: DNA
<213> ORGANISM: Homo sapiens

<400> SEQUENCE: 456
acggcggtgg cgggagcttc tccacggccg accagctgga gatggtgacc gagctgctgg      60
gaggagacat ggtgaaccag agtttcatct gcgacccgga                          100

<210> SEQ ID NO 457
<211> LENGTH: 100
<212> TYPE: DNA
<213> ORGANISM: Homo sapiens

<400> SEQUENCE: 457
cgacgagacc ttcatcaaaa acatcatcat ccaggactgt atgtggagcg gcttctcggc      60
cgccgccaag ctcgtctcag agaagctggc ctcctaccag                          100

<210> SEQ ID NO 458
<211> LENGTH: 100
<212> TYPE: DNA
<213> ORGANISM: Homo sapiens

<400> SEQUENCE: 458
gctgcgcgca aagacagcgg cagcccgaac cccgcccgcg ccacagcgt ctgctccacc      60 tccagcttgt acctgcagga tctgagcgcc gccgcctcag                          100

<210> SEQ ID NO 459
<211> LENGTH: 100
<212> TYPE: DNA
<213> ORGANISM: Homo sapiens

<400> SEQUENCE: 459
agtgcatcga cccctcggtg gtcttcccct accctctcaa cgacagcagc tcgcccaagt      60
cctgcgcctc gcaagactcc agcgccttct ctccgtcctc                          100

<210> SEQ ID NO 460
<211> LENGTH: 100
<212> TYPE: DNA
<213> ORGANISM: Homo sapiens

<400> SEQUENCE: 460
ggattctctg ctctcctcga cggagtcctc cccgcagggc agccccgagc ccctggtgct      60
ccatgaggag acaccgccca ccaccagcag cgactctggt                          100

<210> SEQ ID NO 461
<211> LENGTH: 100
<212> TYPE: DNA
<213> ORGANISM: Homo sapiens

<400> SEQUENCE: 461
```

```
gctccccatc tgtccccaca gttgctcctt ggctgagcca agggcttgct cacctctcag    60
agcattgccc taactggttt gttttgggct tacattgcaa                         100
```

<210> SEQ ID NO 462
<211> LENGTH: 100
<212> TYPE: DNA
<213> ORGANISM: Homo sapiens

<400> SEQUENCE: 462

```
gatcaggtcc tccccagagc caggctggag tccgaggcag aaaaggctgt ggagggcact    60
ggggtcacca cagactggaa accggttggg cgcaggcccc                         100
```

<210> SEQ ID NO 463
<211> LENGTH: 100
<212> TYPE: DNA
<213> ORGANISM: Homo sapiens

<400> SEQUENCE: 463

```
aaaccttgag gaatcgtttg ggctgggacc agaacagggg gctcctctgc acagagctcc    60
ccaccgcttt ggtggattac ttcagactca gaaaattgac                         100
```

<210> SEQ ID NO 464
<211> LENGTH: 100
<212> TYPE: DNA
<213> ORGANISM: Homo sapiens

<400> SEQUENCE: 464

```
acaaagagaa actgacctgc ccgcagccag ccctggctgc ctacacaagc tttcccctgc    60
ttgccaggcc actcagcact gcgtggcaga cacggacatg                         100
```

<210> SEQ ID NO 465
<211> LENGTH: 100
<212> TYPE: DNA
<213> ORGANISM: Homo sapiens

<400> SEQUENCE: 465

```
ctcgccccgg gaagctcacc ttcactccag ccgggtctct gctgcctttg ttaaataggg    60
gacctgcggc taggaaagct ggatcccagg ctgttgggat                         100
```

<210> SEQ ID NO 466
<211> LENGTH: 100
<212> TYPE: DNA
<213> ORGANISM: Homo sapiens

<400> SEQUENCE: 466

```
ggggggggagc ggggtgggag gaccaggcat ggggacggct cctagcccgg gagcaactcc   60
ctgacctgaa gcccgcagag accccgagcg gcacccgagc                         100
```

<210> SEQ ID NO 467
<211> LENGTH: 100
<212> TYPE: DNA
<213> ORGANISM: Homo sapiens

<400> SEQUENCE: 467

```
cgaggctgcc gaagcctgtc accttcctcc agcctggctc tgcagcaaac agaaaggaaa    60
cgcgattcgt tccacttgga atttccttga aatctccgaa                         100
```

<210> SEQ ID NO 468
<211> LENGTH: 100

```
<212> TYPE: DNA
<213> ORGANISM: Homo sapiens

<400> SEQUENCE: 468
tctaatccgg cgttaactca ccgtgagagg agcgctcatc tcacaggagg ctgtggtaat      60
gggtgaattg gcaggatccc tgcgggccag gcagccaggc                          100

<210> SEQ ID NO 469
<211> LENGTH: 100
<212> TYPE: DNA
<213> ORGANISM: Homo sapiens

<400> SEQUENCE: 469
ttttcgtttc ttatcctctt tttttaaagg ggagaagcca tgagaaaagg cgtcctgcag      60
agaaggaccc aatggggtct ttaagggtct ctgtatgaac                          100

<210> SEQ ID NO 470
<211> LENGTH: 100
<212> TYPE: DNA
<213> ORGANISM: Homo sapiens

<400> SEQUENCE: 470
tggccggctc ctaagcagaa gctgaactca gaaaccgcta cttccttgat ttttcaaagc      60 ccctcctca actccaggac gcctttggag ccctagcccc                           100

<210> SEQ ID NO 471
<211> LENGTH: 100
<212> TYPE: DNA
<213> ORGANISM: Homo sapiens

<400> SEQUENCE: 471
tgtcgccgcc ggagccttga aaggctgcag ctcgctgccc aagctacgcg ttgccggagg      60
cgggattccc aggtgcctca gcccgggcgg ccaagtgcgt                          100

<210> SEQ ID NO 472
<211> LENGTH: 100
<212> TYPE: DNA
<213> ORGANISM: Homo sapiens

<400> SEQUENCE: 472
tgtttcaggt ccctgcctg ggatccctgc actttgcaaa gttagctgcg cggctgcaga      60
ggtccgagat ccttccggcc ttagtacctg acccacggtc                          100

<210> SEQ ID NO 473
<211> LENGTH: 100
<212> TYPE: DNA
<213> ORGANISM: Homo sapiens

<400> SEQUENCE: 473
cggcaccccc aacccggtcc cggcgggaga gtgagagaag cgagctcgcc gcctacttac      60
tatgcatgga tgcaaacggg tcgtgcttac agtgtatttc                          100

<210> SEQ ID NO 474
<211> LENGTH: 100
<212> TYPE: DNA
<213> ORGANISM: Homo sapiens

<400> SEQUENCE: 474
catcggggcg ctccagactg caggccggcc cacgccgccg cctcccggcg ccaaggggct      60
```

```
gcccagggcg atagggagc ctcgccacca ggccaggcac              100

<210> SEQ ID NO 475
<211> LENGTH: 100
<212> TYPE: DNA
<213> ORGANISM: Homo sapiens

<400> SEQUENCE: 475
tgtgcgagct gggctcagaa aacactgctg gagcttcggg gtctctctca gagcctccct    60
gctggagacc gcccggagct gcgcggagag gcgggaaatg                         100

<210> SEQ ID NO 476
<211> LENGTH: 100
<212> TYPE: DNA
<213> ORGANISM: Homo sapiens

<400> SEQUENCE: 476
gtgctagcgc acccgggcta ggagcgggtg cccaactccg gctggcttcc ctccctggct    60
ggctcaagca gcagctccgg gcccagcccg gggtagctgc                         100

<210> SEQ ID NO 477
<211> LENGTH: 100
<212> TYPE: DNA
<213> ORGANISM: Homo sapiens

<400> SEQUENCE: 477
ggccaaggcg cccgcggctt cggggggcata gcgtaggggc ccgcctccgg gacagccagc    60 agccccggc cccaggaagg agcagctttg aggaggccgc                          100

<210> SEQ ID NO 478
<211> LENGTH: 100
<212> TYPE: DNA
<213> ORGANISM: Homo sapiens

<400> SEQUENCE: 478
cggaacaatc ggcccttgac ttcactcagg gggcggagag acccgggggc tgccaggctg    60
gttccgcggc ctcgatgctt ctgaggtccc tcctcgaccc                         100

<210> SEQ ID NO 479
<211> LENGTH: 100
<212> TYPE: DNA
<213> ORGANISM: Homo sapiens

<400> SEQUENCE: 479
cacacaggca acaactttt ggacacaaac tcatatattt ttacatcttt taaaaataca    60
tatactgtaa tgaacacact gagtcccta tataaacaca                         100

<210> SEQ ID NO 480
<211> LENGTH: 100
<212> TYPE: DNA
<213> ORGANISM: Homo sapiens

<400> SEQUENCE: 480
caggccctaa cttgcagacc cccggaagga cgccagcgtg aacattcaga aacagagaaa    60
aacacagaca aactcacaga tatttggact gatgcagaag                         100

<210> SEQ ID NO 481
<211> LENGTH: 100
<212> TYPE: DNA
<213> ORGANISM: Homo sapiens
```

<400> SEQUENCE: 481
acagtttgaa gtgtgagcct gaacatgttt gatctaaggt ctggaggaag atgtgaagca    60
aatctgacct aaaaaaaatt ataggaaaaa agcaaattgt    100

<210> SEQ ID NO 482
<211> LENGTH: 100
<212> TYPE: DNA
<213> ORGANISM: Homo sapiens

<400> SEQUENCE: 482
tctggatttg tttcaccaag gaacaagtaa gcagagaacc agacactgga gaaaaaaagg    60
agtcaggaag tagacaagga aatgttaaaa gaaataatag    100

<210> SEQ ID NO 483
<211> LENGTH: 100
<212> TYPE: DNA
<213> ORGANISM: Homo sapiens

<400> SEQUENCE: 483
gataactgaa agaatgtagc ttccagattg ctagctatca gcagatagat agaaacttt    60 atacagcctt taaatcttcc ctagaaacct ttttaaaagt    100

<210> SEQ ID NO 484
<211> LENGTH: 100
<212> TYPE: DNA
<213> ORGANISM: Homo sapiens

<400> SEQUENCE: 484
caagggcctg ccaggatgag aacgggcaaa cctggccaag gtgacccat tagggactac    60 cctcctaggg acagcactca gggccgttcc caatcacccc    100

<210> SEQ ID NO 485
<211> LENGTH: 100
<212> TYPE: DNA
<213> ORGANISM: Homo sapiens

<400> SEQUENCE: 485
ggatttcctg tcctgctcgt ctcctgccac acctcctttt gatctacccc caagacaccc    60
ctaccttttt attctgtgaa aatttactca tgctgtgggc    100

<210> SEQ ID NO 486
<211> LENGTH: 100
<212> TYPE: DNA
<213> ORGANISM: Homo sapiens

<400> SEQUENCE: 486
cctgctggaa atgccctcct actgtttccc caaaccccgt cagaaattcc acggggaaac    60
tcccttccct tctgctgcag gcaccgtcac tgtgtctctc    100

<210> SEQ ID NO 487
<211> LENGTH: 100
<212> TYPE: DNA
<213> ORGANISM: Homo sapiens

<400> SEQUENCE: 487
agctctgccc cccagcctct gagtaccacc ttatcctagc ccttagctac tggcttgtca    60
ttgtctcttt acgttctcag cctcccacag aagcctggga    100

<210> SEQ ID NO 488
<211> LENGTH: 100
<212> TYPE: DNA
<213> ORGANISM: Homo sapiens

<400> SEQUENCE: 488
aggcacactc gccctggtc tccaaggctc tgggtcctca gactggctga gtactgggga    60
ccaaggtcac ccaagaagcc ctgagtggcc ctcttgaggg                         100

<210> SEQ ID NO 489
<211> LENGTH: 100
<212> TYPE: DNA
<213> ORGANISM: Homo sapiens

<400> SEQUENCE: 489
ttagcagagc ttctctctgt ccaagacagg tcaggctctc tccctggcc ccagctccac    60 cgtcactcag aggagtggcc taaacaaacg ctgcaggtga                         100

<210> SEQ ID NO 490
<211> LENGTH: 100
<212> TYPE: DNA
<213> ORGANISM: Homo sapiens

<400> SEQUENCE: 490
ggctcccgag cccctgacat ggatgtttat ggaagaggac tcttggcatc agcacctggg    60
caaggtgggt agaggcagga gtgggcaaat gggaaagtct                         100

<210> SEQ ID NO 491
<211> LENGTH: 100
<212> TYPE: DNA
<213> ORGANISM: Homo sapiens

<400> SEQUENCE: 491
ggagagccgt ttgagattca ccaggtgaat gaaccccggt ttttttctgg gtaacaggtc    60
gaatgtgaat tacttatttt cacaagctct tgacatgttc                         100

<210> SEQ ID NO 492
<211> LENGTH: 100
<212> TYPE: DNA
<213> ORGANISM: Homo sapiens

<400> SEQUENCE: 492
cgtcaaattg ctgttcccca aagagtggac tctggtgaca tataagtgtg tgggaccatt    60
gcatcttacc ccagagatcc actcctgatc tggcattatt                         100

<210> SEQ ID NO 493
<211> LENGTH: 100
<212> TYPE: DNA
<213> ORGANISM: Homo sapiens

<400> SEQUENCE: 493
caaaatctgc tgaattcaaa acgatcctgt acttcctgct caccaggtct gaaagaaaa    60 aagaaaaaag aagaaggaaa gactacacct gacaaaagac                         100

<210> SEQ ID NO 494
<211> LENGTH: 100
<212> TYPE: DNA
<213> ORGANISM: Homo sapiens

<400> SEQUENCE: 494

```
ttcacggttt ctctttagtt ttatctgaaa tacatttgta agcttagggt gcaatttgga    60
ttaaaacagt tttctttagt gtcaataatg gcctttacta                          100

<210> SEQ ID NO 495
<211> LENGTH: 100
<212> TYPE: DNA
<213> ORGANISM: Homo sapiens

<400> SEQUENCE: 495
gagtgaatgg atatttttcc attctggatt atcgtttaat cgaaactttg tttcctgtgg    60 aaattttttct ggtttaagtt atttgatttg ggagataaat                         100

<210> SEQ ID NO 496
<211> LENGTH: 100
<212> TYPE: DNA
<213> ORGANISM: Homo sapiens

<400> SEQUENCE: 496
catgtaactt aataaacttt ggcatcctgg ttaactgaaa ttgcttcatt caatatttga    60
agactgaaat ctgtattgtt gcctgtacct aaattatggg                          100

<210> SEQ ID NO 497
<211> LENGTH: 100
<212> TYPE: DNA
<213> ORGANISM: Homo sapiens

<400> SEQUENCE: 497
ggacagacag ggagagatga ctgagttaga tgagacgagg gggcgggctg ggggtgcgag    60
aaggaagctt ggcaaggaga ctaggtctag ggggaccaca                          100

<210> SEQ ID NO 498
<211> LENGTH: 100
<212> TYPE: DNA
<213> ORGANISM: Homo sapiens

<400> SEQUENCE: 498
gtggggcagg ctgcatggaa aatatccgca gggtccccca ggcagaacag ccacgctcca    60
ggccaggctg tccctactgc ctggtggagg gggaacttga                          100

<210> SEQ ID NO 499
<211> LENGTH: 100
<212> TYPE: DNA
<213> ORGANISM: Homo sapiens

<400> SEQUENCE: 499
cctctgggag ggcgccgctc ttgcatagct gagcgagccc gggtgcgctg gtctgtgtgg    60
aaggaggaag gcagggagag gtagaagggg tggaggagtc                          100

<210> SEQ ID NO 500
<211> LENGTH: 100
<212> TYPE: DNA
<213> ORGANISM: Homo sapiens

<400> SEQUENCE: 500
ggggcaggcg gagcttgagg aaaccgcaga taagttttttt tctctttgaa agatagagat    60
taatacaact acttaaaaaa tatagtcaat aggttactaa                          100

<210> SEQ ID NO 501
```

```
<210> SEQ ID NO 501
<211> LENGTH: 100
<212> TYPE: DNA
<213> ORGANISM: Homo sapiens

<400> SEQUENCE: 501
gatattgctt agcgttaagt ttttaacgta attttaatag cttaagattt taagagaaaa    60
tatgaagact tagaagagta gcatgaggaa ggaaaagata                          100

<210> SEQ ID NO 502
<211> LENGTH: 100
<212> TYPE: DNA
<213> ORGANISM: Homo sapiens

<400> SEQUENCE: 502
aaaggtttct aaaacatgac ggaggttgag atgaagcttc ttcatggagt aaaaaatgta    60
tttaaaagaa aattgagaga aaggactaca gagccccgaa                          100

<210> SEQ ID NO 503
<211> LENGTH: 100
<212> TYPE: DNA
<213> ORGANISM: Homo sapiens

<400> SEQUENCE: 503
ttaataccaa tagaagggca atgcttttag attaaaatga aggtgactta aacagcttaa    60
agtttagttt aaaagttgta ggtgattaaa ataatttgaa                          100

<210> SEQ ID NO 504
<211> LENGTH: 100
<212> TYPE: DNA
<213> ORGANISM: Homo sapiens

<400> SEQUENCE: 504
ttggagaagt atagaagata gaaaaatata aagccaaaaa ttggataaaa tagcactgaa    60
aaaatgagga aattattggt aaccaattta ttttaaaagc                          100

<210> SEQ ID NO 505
<211> LENGTH: 100
<212> TYPE: DNA
<213> ORGANISM: Homo sapiens

<400> SEQUENCE: 505
ccatcaattt aatttctggt ggtgcagaag ttagaaggta aagcttgaga agatgagggt    60
gtttacgtag accagaacca atttagaaga atacttgaag                          100

<210> SEQ ID NO 506
<211> LENGTH: 100
<212> TYPE: DNA
<213> ORGANISM: Homo sapiens

<400> SEQUENCE: 506
ctagaagggg aagttggtta aaaatcacat caaaaagcta ctaaaaggac tggtgtaatt    60
taaaaaaaac taaggcagaa ggcttttgga agagttagaa                          100

<210> SEQ ID NO 507
<211> LENGTH: 100
<212> TYPE: DNA
<213> ORGANISM: Homo sapiens

<400> SEQUENCE: 507
tggtgtaaga gatgtgccag cggctggccg aggggcgctt agggctagag cccggggcgc    60
```

-continued tgcagaggtt gagagtcagt gggtggggcg cagttatcaa        100

<210> SEQ ID NO 508
<211> LENGTH: 100
<212> TYPE: DNA
<213> ORGANISM: Homo sapiens

<400> SEQUENCE: 508
acaccagggc ccaaaagcag gctctagata ggttccaggt gctcaatttc tatttcacgt        60
ttggagtgag ccagtggaat tgtgaagttg tggcattttg        100

<210> SEQ ID NO 509
<211> LENGTH: 100
<212> TYPE: DNA
<213> ORGANISM: Homo sapiens

<400> SEQUENCE: 509
attcggttgc caagagttat cactgggcct ttgcaggtgc caaataaatt tcaggacaga        60
gcctaaggca gagctctggc acaggaagga agtaaaacgt        100

<210> SEQ ID NO 510
<211> LENGTH: 100
<212> TYPE: DNA
<213> ORGANISM: Homo sapiens

<400> SEQUENCE: 510
ttaatgagca aatggacgca tgtttccaag cggtggtagg aagacagcag ttttggttg         60 tcttcctggt gatcagcatg gaaacctagt agtgctctta        100

<210> SEQ ID NO 511
<211> LENGTH: 100
<212> TYPE: DNA
<213> ORGANISM: Homo sapiens

<400> SEQUENCE: 511
ctctgatcaa tacattgtcg aaggcatgta cctgatgcta acgtaacaat aatattaaat        60
attgacttta tttgctatta tttattgcta acattaagta        100

<210> SEQ ID NO 512
<211> LENGTH: 100
<212> TYPE: DNA
<213> ORGANISM: Homo sapiens

<400> SEQUENCE: 512
ctgctacctg ctatgtgcta ggtttgtctc tgaagacttt acatgtattt ttcacgttta        60
attatcataa tcttaagaag caggtaccat aattatctcc        100

<210> SEQ ID NO 513
<211> LENGTH: 100
<212> TYPE: DNA
<213> ORGANISM: Homo sapiens

<400> SEQUENCE: 513
gggaaaaaga atgacgaaag gcaagacagt ggagcaagtg aggacacgct tcaccgagcc        60
agatctccac tcctcccagg gtatccacag ggacaagtca        100

<210> SEQ ID NO 514
<211> LENGTH: 100
<212> TYPE: DNA

<213> ORGANISM: Homo sapiens

<400> SEQUENCE: 514

```
cacctggcag aaagctaagt cactcagcta gaaacaggcc cagggaattc aacagaaggc    60
tgaagagcca ctgcttatgg aaataaagcc cctcctgtaa                          100
```

<210> SEQ ID NO 515
<211> LENGTH: 100
<212> TYPE: DNA
<213> ORGANISM: Homo sapiens

<400> SEQUENCE: 515

```
agaactgcat ggcttttccc tcccaacccc aaacccatcc cacatctggc ttttgttgtg    60
tgaatcataa actgccctt cttcaccaca gtgattcatg                           100
```

<210> SEQ ID NO 516
<211> LENGTH: 100
<212> TYPE: DNA
<213> ORGANISM: Homo sapiens

<400> SEQUENCE: 516

```
aatcctctcc cactgtggat ctgtaaaatc tagacaggtc agtcagctcc cgcccttaa     60
gagtttattt tccattctgt ggaagaagca gataaggaga                          100
```

<210> SEQ ID NO 517
<211> LENGTH: 100
<212> TYPE: DNA
<213> ORGANISM: Homo sapiens

<400> SEQUENCE: 517

```
gctgctgtcc ttaggagaca tcctttagag gaagctggaa gacacgggtt caggccctgc    60
atcctcctct gagttgctat gtgactggga acaggatact                          100
```

<210> SEQ ID NO 518
<211> LENGTH: 100
<212> TYPE: DNA
<213> ORGANISM: Homo sapiens

<400> SEQUENCE: 518

```
tcacctctcc attctttctc tccttttctc ttagggtcgg aatatggaac tagacaggaa    60
agtactttgg aggttttctt accgtaagga ggctggcatt                          100
```

<210> SEQ ID NO 519
<211> LENGTH: 100
<212> TYPE: DNA
<213> ORGANISM: Homo sapiens

<400> SEQUENCE: 519

```
gggccctcca cccagcctca gttctatggg ggacgtggag tcaggcgatg atgtcctctg    60
aggcagcgtc catctcccct taacattaag gaataaggcc                          100
```

<210> SEQ ID NO 520
<211> LENGTH: 100
<212> TYPE: DNA
<213> ORGANISM: Homo sapiens

<400> SEQUENCE: 520

```
agagggttct cgctcatttg ggaaaataaa aaaagcagga atggggcgct ggaaattcta    60
taagcttttc cccaccactc acaaaaacac agctgtgaaa                          100
```

<210> SEQ ID NO 521
<211> LENGTH: 100
<212> TYPE: DNA
<213> ORGANISM: Homo sapiens

<400> SEQUENCE: 521
ataaatacca cccccaaac caagggtcta gggccaccaa cagtcctcct cctcctcctc    60
ctcctccttc tcctcctcgt cctccagatc cagctgccaa                        100

<210> SEQ ID NO 522
<211> LENGTH: 100
<212> TYPE: DNA
<213> ORGANISM: Homo sapiens

<400> SEQUENCE: 522
ccttctcctc ctcgtcctcc agatccagct gccaacagca tccccgctc ctgaagaaat    60 gcaccgccca aagggaacg gcgaaagggg gaagaagtcc                         100

<210> SEQ ID NO 523
<211> LENGTH: 100
<212> TYPE: DNA
<213> ORGANISM: Homo sapiens

<400> SEQUENCE: 523
aggggacccc cggcctctgg ccgagagctt gggtgggggc ctcggccgtc gccactcacc    60
cggggagggg aaaagctcca gatcgacttt ttccgtcttg                         100

<210> SEQ ID NO 524
<211> LENGTH: 100
<212> TYPE: DNA
<213> ORGANISM: Homo sapiens

<400> SEQUENCE: 524
atgatggtga gagtcggctt gagatcgacg gccgccttca tggtgccagg agtgggggac    60
gtacgggatg gtagcaagtt tgcagttact gttgtttttc                         100

<210> SEQ ID NO 525
<211> LENGTH: 100
<212> TYPE: DNA
<213> ORGANISM: Homo sapiens

<400> SEQUENCE: 525
tttttaatga ggattagtaa caggggaag gggacggggg aaatccgact ttcttcccaa    60
aaatctcaaa ttcccgctgc ctttctttcc cccgcgcccg                         100

<210> SEQ ID NO 526
<211> LENGTH: 100
<212> TYPE: DNA
<213> ORGANISM: Homo sapiens

<400> SEQUENCE: 526
gacggtgcgc gcccggcact ccaggggaag ttggcacttt gcggcgaagt gagcgcgctc    60
gggtcccagc ctcgcccgcg ccgcgcccgc tcctcctgcc                         100

<210> SEQ ID NO 527
<211> LENGTH: 100
<212> TYPE: DNA
<213> ORGANISM: Homo sapiens

<400> SEQUENCE: 527
gagtgagtag caaatattca tttatgaccc agtttttgtc caccctcagg cggggcatag    60
gactacagac atttttctag attacagcta ggatattatt                         100

<210> SEQ ID NO 528
<211> LENGTH: 100
<212> TYPE: DNA
<213> ORGANISM: Homo sapiens

<400> SEQUENCE: 528
cctgagttta tgacaatgaa atggtttgag aaggcaatat tgtggggctt tcagagaggt    60
ttgctgagtg gctaggtgca tgcatgggtt taaccattaa                         100

<210> SEQ ID NO 529
<211> LENGTH: 100
<212> TYPE: DNA
<213> ORGANISM: Homo sapiens

<400> SEQUENCE: 529 cttcccttttt tgccttttta ttataagctg gttttgtctg tggctgtttt tttctttttaa   60 aattaattaa aacttctcaa aatttctaaa agtaaacaag                         100

<210> SEQ ID NO 530
<211> LENGTH: 100
<212> TYPE: DNA
<213> ORGANISM: Homo sapiens

<400> SEQUENCE: 530
gcattctcta catacatcta catacatatt ttgcatttta aaaattggaa tatttgtcat    60
ttttctgtat tacccaaaag tatataaaca gttaccagag                         100

<210> SEQ ID NO 531
<211> LENGTH: 100
<212> TYPE: DNA
<213> ORGANISM: Homo sapiens

<400> SEQUENCE: 531
atttatgtga gaagacagtt gtcacattac agatgtcaga ttagctataa aattgtttca    60
ttctagaaac ctaatatggt aaaaataaac cttacttatt                         100

<210> SEQ ID NO 532
<211> LENGTH: 100
<212> TYPE: DNA
<213> ORGANISM: Homo sapiens

<400> SEQUENCE: 532
tagccattta tcagacaatt gcttttgttc agccagtttc ttgttctagc agtataaata    60 ttcttttttat agaaagttac ttggtttgag aaataaacat                        100

<210> SEQ ID NO 533
<211> LENGTH: 100
<212> TYPE: DNA
<213> ORGANISM: Homo sapiens

<400> SEQUENCE: 533
ataagcttaa ggtaggctag agatgaaaaa tttcagactt gtgtttgttt tggatttatt    60 gtacccttttc tactattatc tgagaaagct atttaggagt                        100

```
<210> SEQ ID NO 534
<211> LENGTH: 100
<212> TYPE: DNA
<213> ORGANISM: Homo sapiens

<400> SEQUENCE: 534
ttaagaaata gtctagtttt aaaatagcaa tggtttgccg gacacagtgg ctcacccctg    60
taatcccagc attttgggag gccgaggtgg gcagattgct                         100

<210> SEQ ID NO 535
<211> LENGTH: 100
<212> TYPE: DNA
<213> ORGANISM: Homo sapiens

<400> SEQUENCE: 535
gaatttgcca gttttcaata ttctgattca ctctgttaag ctagtaaggc agtctttaaa    60
ttacacagtc tgtgtgttat tttactactg ctcagagggc                         100

<210> SEQ ID NO 536
<211> LENGTH: 100
<212> TYPE: DNA
<213> ORGANISM: Homo sapiens

<400> SEQUENCE: 536
attggagaag gttcccttgt gattagaact gttcatgttg agacatgaat cataaggcat    60
tccaaagttg gtttaaggtg tgtctgcttt agacactgtg                         100

<210> SEQ ID NO 537
<211> LENGTH: 100
<212> TYPE: DNA
<213> ORGANISM: Homo sapiens

<400> SEQUENCE: 537
cccaggacta ttcttttgct ccagttttgc cttttgatta aatcaatatt atacctgagt    60
tttataaact actaagaatt tgttccccTT cctcactgtg                         100

<210> SEQ ID NO 538
<211> LENGTH: 100
<212> TYPE: DNA
<213> ORGANISM: Homo sapiens

<400> SEQUENCE: 538
attttcttgc agtattttct tagaagagtc aactttaata acttacccca aagtgcacgt    60
tcttgatatt atgaacttgc tattgttgtc ttcccagttt                         100

<210> SEQ ID NO 539
<211> LENGTH: 100
<212> TYPE: DNA
<213> ORGANISM: Homo sapiens

<400> SEQUENCE: 539
tattgtagtt tttggaaggg ctcgttctgc ccaagagaag ttcctcctta cagctgattc    60
ggctgtctac catttgcacg ttggtgctgt tttgagtgct                         100

<210> SEQ ID NO 540
<211> LENGTH: 100
<212> TYPE: DNA
<213> ORGANISM: Homo sapiens

<400> SEQUENCE: 540
```

```
acctcctgct ggtgaggctt catacagcac acagatggag ccatcctctc caattctgta    60
ggacacttca tagggtcaa cccagagtgt gagttcactt                           100

<210> SEQ ID NO 541
<211> LENGTH: 100
<212> TYPE: DNA
<213> ORGANISM: Homo sapiens

<400> SEQUENCE: 541
gggagaagcc tgaacagctc ctgactgctc agtccaatcc gctgtgctgc ctgtccaatc    60
agaggatcca ttttatggtt gatgcgaata caacggtaac                          100

<210> SEQ ID NO 542
<211> LENGTH: 100
<212> TYPE: DNA
<213> ORGANISM: Homo sapiens

<400> SEQUENCE: 542
ccgatccctt gcatggcttt tctgggaacc agtgatgttt ataatgttct atagaagaaa    60
agaagaacag agaaacaacg cttaggatcg ttagctccca                          100

<210> SEQ ID NO 543
<211> LENGTH: 100
<212> TYPE: DNA
<213> ORGANISM: Homo sapiens

<400> SEQUENCE: 543
ctgcggattc ctcctacccc aggctccttt gaggagcgaa aatgaaaact atcaactttt    60
taaaatgtcc aggattgcat ccgttgttgt gcatgtgcgg                          100

<210> SEQ ID NO 544
<211> LENGTH: 100
<212> TYPE: DNA
<213> ORGANISM: Homo sapiens

<400> SEQUENCE: 544
ggatggaaaa agcgggcagg gttttagaaa taacacagta gtaccggaca aaacaatctc    60
caggaaccaa ccggttgagc cgccaaaaca ggaatcaggc                          100

<210> SEQ ID NO 545
<211> LENGTH: 100
<212> TYPE: DNA
<213> ORGANISM: Homo sapiens

<400> SEQUENCE: 545
gcgcagcctc ggccagtcgg gaagccactg gcacctatgg ccaggcgaga aactgtttac    60
tttctccacc ccaccccaga tgcacacaat ggagttgatg                          100

<210> SEQ ID NO 546
<211> LENGTH: 100
<212> TYPE: DNA
<213> ORGANISM: Homo sapiens

<400> SEQUENCE: 546
gctttggaga tgagaagcgc caccggactg ttaaccccga agggaagaaa aacaagcaac    60
cctaaaccac gctctgggca gggctgttaa ttgtgccggt                          100

<210> SEQ ID NO 547
<211> LENGTH: 100
```

<212> TYPE: DNA
<213> ORGANISM: Homo sapiens

<400> SEQUENCE: 547
acgcaacggt tggagggggc tgaggaaagg ggacgtcgaa cccaccccag ccccacggct    60
cctttgtccc caaatccgcc gacggtcctc ggaccgcagc                          100

<210> SEQ ID NO 548
<211> LENGTH: 100
<212> TYPE: DNA
<213> ORGANISM: Homo sapiens

<400> SEQUENCE: 548
tcccgcctcg gtgggcttaa gtttctttgt tgtgcgtgtt gtcttctcct ctccgttttg    60
ccagctgggg ggaagggggc gccctccgtc cagcccctaa                          100

<210> SEQ ID NO 549
<211> LENGTH: 100
<212> TYPE: DNA
<213> ORGANISM: Homo sapiens

<400> SEQUENCE: 549
agcctcgcgg ggaaccgctg ttagcggcca cccagcgcaa ccacaccggt cccgcggcgg    60
ggcccaagcg cgaccggccc cggggcgctg ccgaggttcc                          100

<210> SEQ ID NO 550
<211> LENGTH: 100
<212> TYPE: DNA
<213> ORGANISM: Homo sapiens

<400> SEQUENCE: 550
cgcagccccg acggccggac tctgacccag ggatgtgggg cccgcgtccc tccgacgccc    60
tcgccctgct cacctgccag cagctcctgc aggtctggc                           100

<210> SEQ ID NO 551
<211> LENGTH: 100
<212> TYPE: DNA
<213> ORGANISM: Homo sapiens

<400> SEQUENCE: 551
tgaaggtctg cagctgtcgc tcgctcgtga gccccttggt gcggagaaac ttggagatga    60
aggacacggc ggcggcgatc tcgcctatca tggtggcggc                          100

<210> SEQ ID NO 552
<211> LENGTH: 100
<212> TYPE: DNA
<213> ORGANISM: Homo sapiens

<400> SEQUENCE: 552
ccgggtgtag aagggatgca tgggggcggc gtgcggggc ggcccggggc ggctggggct     60
cggcggcgcg gccccgacgg cggagcagcc accccgggct                          100

<210> SEQ ID NO 553
<211> LENGTH: 100
<212> TYPE: DNA
<213> ORGANISM: Homo sapiens

<400> SEQUENCE: 553
acgccgcacc cctcccccgt gcgttctgcg gccacccagg ccttccagga caccgtggag    60
agggaacaag ggggcaggga cgccccttc ggcaggagcc 100

<210> SEQ ID NO 554
<211> LENGTH: 100
<212> TYPE: DNA
<213> ORGANISM: Homo sapiens

<400> SEQUENCE: 554
gtcggagaag ggggcccaga ccggagggag gcgagaagcc ccactgaagc cgggcgcagg 60
gtctgggacg cagttgggag tgcaaagggc tggctgagag 100

<210> SEQ ID NO 555
<211> LENGTH: 100
<212> TYPE: DNA
<213> ORGANISM: Homo sapiens

<400> SEQUENCE: 555
ccgcaggagc agcaggctgt ggcccaggcc tcctgggtga caggccctgt ctggcgggga 60
agagggacca agagacaaca cggaagaggc tggacctcga 100

<210> SEQ ID NO 556
<211> LENGTH: 100
<212> TYPE: DNA
<213> ORGANISM: Homo sapiens

<400> SEQUENCE: 556
acaggggcgg ctgcctcact ccctacctga gccagccgag ggggccaagg actttagagc 60
tgtttcctcc ggcataagag agacacttgc tttccagggc 100

<210> SEQ ID NO 557
<211> LENGTH: 100
<212> TYPE: DNA
<213> ORGANISM: Homo sapiens

<400> SEQUENCE: 557 agcaccctt atcggagaag gctctacagg gaagggtct ttgcagcctg gatggccatc 60
ccacattcct ttaacggagg tctctaggcc tcagagagaa 100

<210> SEQ ID NO 558
<211> LENGTH: 100
<212> TYPE: DNA
<213> ORGANISM: Homo sapiens

<400> SEQUENCE: 558
cccagagtta gaaaggaggc cagacggtcc ttgctgtccc cctggggaga gaggaagttg 60
ccgcctgctg ccaggcccag gaggagctgg gcctgcaata 100

<210> SEQ ID NO 559
<211> LENGTH: 100
<212> TYPE: DNA
<213> ORGANISM: Homo sapiens

<400> SEQUENCE: 559 gtggggacc tggcccctga ggcagtggcg gccatgtcac ggccaggcca cggtgggctg 60
atgcctgtga atggtctggg cttcccaccg cagaacgtgg 100

<210> SEQ ID NO 560
<211> LENGTH: 100
<212> TYPE: DNA
<213> ORGANISM: Homo sapiens

<400> SEQUENCE: 560
cccgggtggt ggtgtgggag tggctgaatg agcacagccg ctggcggccc tacacggcca    60
ccgtgtgcca ccacattgag aacgtgctga aggaggacgc                          100

<210> SEQ ID NO 561
<211> LENGTH: 100
<212> TYPE: DNA
<213> ORGANISM: Homo sapiens

<400> SEQUENCE: 561
tcgcggttcc gtggtcctgg ggcaggtgga cgcccagctt gtgccctaca tcatcgacct    60
gcagtccatg caccagtttc gccaggacac aggtgagcag                          100

<210> SEQ ID NO 562
<211> LENGTH: 100
<212> TYPE: DNA
<213> ORGANISM: Homo sapiens

<400> SEQUENCE: 562
acacccaccc catgccaccc gccccgccga gccatcacta ccttgcagcg taggatgctg    60
aaaatcccag taaatctgct gatgccaaat cccttcccca                          100

<210> SEQ ID NO 563
<211> LENGTH: 100
<212> TYPE: DNA
<213> ORGANISM: Homo sapiens

<400> SEQUENCE: 563
tctccctgcc tcacctccag aaaaacaggg cagtctaacc ttgtccagtt taagacttgg    60
attccaatgc agcctctgag caagctgtag ggccttgagc                          100

<210> SEQ ID NO 564
<211> LENGTH: 100
<212> TYPE: DNA
<213> ORGANISM: Homo sapiens

<400> SEQUENCE: 564
gggtagatca atatctctca cagctgagtg aggattaaat aaaattgtgc tcactgagca    60
cagaacctag aacagcagta gcatgggatt gtagaataag                          100

<210> SEQ ID NO 565
<211> LENGTH: 100
<212> TYPE: DNA
<213> ORGANISM: Homo sapiens

<400> SEQUENCE: 565
ggctttacat gcacttcctc atttgatttt tcccaagaat cacaggcagt aagtctgtgt    60
attgttgtat tattatgagt cccattttat agatgaagaa                          100

<210> SEQ ID NO 566
<211> LENGTH: 100
<212> TYPE: DNA
<213> ORGANISM: Homo sapiens

<400> SEQUENCE: 566
tttatagatg aagaaaccga gtctcccaga agctgagtga tttaaactca gagctgggat    60
ttaaacccag gcggttgagt tccagaacca aagttcttaa                          100

<210> SEQ ID NO 567
<211> LENGTH: 100
<212> TYPE: DNA
<213> ORGANISM: Homo sapiens

<400> SEQUENCE: 567
ctggtatcct atactggctc caagtgttgg tttgtggggt ggagtcgtgc tggtggtaat    60
taattgggga tgggggcgt tggtggtgtt gatggtgggg                          100

<210> SEQ ID NO 568
<211> LENGTH: 100
<212> TYPE: DNA
<213> ORGANISM: Homo sapiens

<400> SEQUENCE: 568
tgaggtggca atgatggagg agacagtgtt agcggttgtg ttggtggtga ctcagtgata    60
gtattgatgg tggtggggtc ttggtgacaa tggagggatg                         100

<210> SEQ ID NO 569
<211> LENGTH: 100
<212> TYPE: DNA
<213> ORGANISM: Homo sapiens

<400> SEQUENCE: 569
tgttggtgac attgatagtt gtgttggtgg tggtgctgga agtggtgtga tggggtggtg    60
atgatggaga aaatgagaga atgatgttgg tggcagtctt                         100

<210> SEQ ID NO 570
<211> LENGTH: 100
<212> TYPE: DNA
<213> ORGANISM: Homo sapiens

<400> SEQUENCE: 570
cgtggccatg tggtgtggct ggtagccctg tgtgtggctg ttacttagtg gtattggtga    60
tcctgttgtg gttgtaatga tggtgatgtt gatggttgcg                         100

<210> SEQ ID NO 571
<211> LENGTH: 100
<212> TYPE: DNA
<213> ORGANISM: Homo sapiens

<400> SEQUENCE: 571
ttggtggtaa tgtgatggct gatgatggag ataaaatcga tgaggtccca ctctcaggcc    60
tactctcttt tgttctggag atttgtcatc gttggggaga                         100

<210> SEQ ID NO 572
<211> LENGTH: 100
<212> TYPE: DNA
<213> ORGANISM: Homo sapiens

<400> SEQUENCE: 572
tgaaatggct gctgtcgggc tgtcatctcc aggcccgggg cgctgacatt tgggccactc    60
tcggtctccc tcttcattct gggcgcgcat tagctctggt                         100

<210> SEQ ID NO 573
<211> LENGTH: 100
<212> TYPE: DNA
<213> ORGANISM: Homo sapiens

<400> SEQUENCE: 573

```
ccggccggtt ccgctgcagc tgaacagcaa gatgcggcac ccaggttacc ctgatcatcg    60
cagatttctc cccggggctc tgttctgagg cctcaaaagt                         100
```

<210> SEQ ID NO 574
<211> LENGTH: 100
<212> TYPE: DNA
<213> ORGANISM: Homo sapiens

<400> SEQUENCE: 574

```
gctccttgta gatgggacca ggggtcattt gggcagtagc agcgcctggt ctcagtctgg    60
tactgaagtc aggaatggct taaggtgaaa tcgtggtcct                         100
```

<210> SEQ ID NO 575
<211> LENGTH: 100
<212> TYPE: DNA
<213> ORGANISM: Homo sapiens

<400> SEQUENCE: 575

```
ctggtgaagc tcagcgaaga ccccctcgcc ttgtttatga caagagaact tctgggggcg    60
ggaggaagag tccctgttac gatgctgatc atcattgagc                         100
```

<210> SEQ ID NO 576
<211> LENGTH: 100
<212> TYPE: DNA
<213> ORGANISM: Homo sapiens

<400> SEQUENCE: 576

```
ttttgctgag cagaaaactc tttagtactc aaggtcgaga gtctctggtg gtctgcctgg    60
caccaggcac cttcctacaa ccctagtttt ccaaaaggac                         100
```

<210> SEQ ID NO 577
<211> LENGTH: 100
<212> TYPE: DNA
<213> ORGANISM: Homo sapiens

<400> SEQUENCE: 577

```
aaagcctggg gcaggcgacg tcctagctcg catttgaaca gggccgcggg ccagcagaga    60
tgcgcgatgc ccaactcttt ccaagagcac ctcgcgtccc                         100
```

<210> SEQ ID NO 578
<211> LENGTH: 100
<212> TYPE: DNA
<213> ORGANISM: Homo sapiens

<400> SEQUENCE: 578

```
gaaccggtgc cttcaactcg gagaagtcaa gagacccgca agaaacttgc acgactgcac    60
ccgccgccgc gctctggggg ctgggcaggg gcagctgggc                         100
```

<210> SEQ ID NO 579
<211> LENGTH: 100
<212> TYPE: DNA
<213> ORGANISM: Homo sapiens

<400> SEQUENCE: 579

```
tggctcccgg ggaacgcgac ccccccgcgc cccgcagacc ggctgtctcc catggacccc    60
tcggcacctg cagcctccga ggaagggtca gcgcgcgtgt                         100
```

<210> SEQ ID NO 580

```
<211> LENGTH: 100
<212> TYPE: DNA
<213> ORGANISM: Homo sapiens

<400> SEQUENCE: 580 gggggctcg ggccagccga tgttttggc cagaagccgt tcgtcctggg ccgcggctgc      60
ctctccacac cgggagctcg tgtttgtttt gcggagggag                         100

<210> SEQ ID NO 581
<211> LENGTH: 100
<212> TYPE: DNA
<213> ORGANISM: Homo sapiens

<400> SEQUENCE: 581
ctgttgtttt tgttctctgc accggggaga gggggacttg gtggcggccg cgcgtggttt   60
tcgggatcac attagcgtcc gcccggcgtg gcccggtcga                         100

<210> SEQ ID NO 582
<211> LENGTH: 100
<212> TYPE: DNA
<213> ORGANISM: Homo sapiens

<400> SEQUENCE: 582
cattaagggg atcgaacctt tccgcggcct cgtcggggtc tgctcggaat cggcccctgg   60
gccaggcccg aggcgcaagc agatcgccag gttgggtcag                         100

<210> SEQ ID NO 583
<211> LENGTH: 100
<212> TYPE: DNA
<213> ORGANISM: Homo sapiens

<400> SEQUENCE: 583
agttgttgaa aactccccgc tgcctgattt caactttatt attttttcc cacgccttca    60 ctggggtccc ggagggagag gagccgccgc aacgctggct                         100

<210> SEQ ID NO 584
<211> LENGTH: 100
<212> TYPE: DNA
<213> ORGANISM: Homo sapiens

<400> SEQUENCE: 584
agtagcgcct cggtctctaa aagccactgg gggcgagcct ccggtgtggc ggtgtcacaa   60
gttagctgtc ctttctgagt caaacccaac aaaaaaggca                         100

<210> SEQ ID NO 585
<211> LENGTH: 100
<212> TYPE: DNA
<213> ORGANISM: Homo sapiens

<400> SEQUENCE: 585
agaggaaaat caataaagtc cacgtgctcc ccggcctcct atggaaaggg ctggctgcga   60
tggccggatg cccggccgtg ggctgggttt ggctccagtg                         100

<210> SEQ ID NO 586
<211> LENGTH: 100
<212> TYPE: DNA
<213> ORGANISM: Homo sapiens

<400> SEQUENCE: 586
ggacaaagaa tttcagaac cgtgagaagg ggaggctttc caaagttgag atccaagtcg    60
```

```
tcggtgtctc gggagctccc ctggtacaca gggtgcccgg                 100
```

<210> SEQ ID NO 587
<211> LENGTH: 100
<212> TYPE: DNA
<213> ORGANISM: Homo sapiens

<400> SEQUENCE: 587

```
tgcccgactg gagccattta aaaatggcag aaacagctgc aggccaacac acacacgctg    60
gaaaacaacc cgcagccccc tctactgtgg gattccccgc                        100
```

<210> SEQ ID NO 588
<211> LENGTH: 100
<212> TYPE: DNA
<213> ORGANISM: Homo sapiens

<400> SEQUENCE: 588

```
gggaagcccg gagttgctcc cctccttgcc tcagcccctg tgcaaagaaa gaactggtgt    60
ctgtgcctgg gtcccttctg tcgccggcct ggaggttggg                        100
```

<210> SEQ ID NO 589
<211> LENGTH: 100
<212> TYPE: DNA
<213> ORGANISM: Homo sapiens

<400> SEQUENCE: 589

```
aaacagccgg caagccgcct ttctctgctc gaggaggcgt ggtggggcct cctactccag    60
gttcccggct ggacagaggc tcctgcaccc tgacagctgc                        100
```

<210> SEQ ID NO 590
<211> LENGTH: 100
<212> TYPE: DNA
<213> ORGANISM: Homo sapiens

<400> SEQUENCE: 590

```
ggaggccttc cagcccgctg accccgcggg gaccaggcct gtagttggag cttgagggc    60 tgtacctctg cgcctccctg ggtttgggga acaacacat                         100
```

<210> SEQ ID NO 591
<211> LENGTH: 100
<212> TYPE: DNA
<213> ORGANISM: Homo sapiens

<400> SEQUENCE: 591

```
cgtgtcctct gaagacctca ggctttggga tctcatggtc cagcttccag ttcacttcgt    60
tgccgcgacc ttgggcatat cattgtcact tctctaacca                        100
```

<210> SEQ ID NO 592
<211> LENGTH: 100
<212> TYPE: DNA
<213> ORGANISM: Homo sapiens

<400> SEQUENCE: 592

```
tggtgacccg gggttttgtg cttggcttcc aggtcccctc gggttattga ggacgattga    60
ggtcatgcct ccgagagcac cgcgccctgg gcgcaggagg                        100
```

<210> SEQ ID NO 593
<211> LENGTH: 100
<212> TYPE: DNA

<213> ORGANISM: Homo sapiens

<400> SEQUENCE: 593
aatgcaaatt taacagggca ccctgtattt tacccagagg gaagccgaag tgtttggcag    60
atcatttggc cccatgagcc ttgggtgggt ttctcctcag                         100

<210> SEQ ID NO 594
<211> LENGTH: 100
<212> TYPE: DNA
<213> ORGANISM: Homo sapiens

<400> SEQUENCE: 594
ccctagtgac ccctaaaatt acccccccga cccacccact gtccctgat gcttccccca    60 ccccggaaa aagctgtggc ctccctctca tttggggcag                          100

<210> SEQ ID NO 595
<211> LENGTH: 100
<212> TYPE: DNA
<213> ORGANISM: Homo sapiens

<400> SEQUENCE: 595
gctgcctcct gttctctttt tctggtgttt cagcaaggca ggccagtgga ggtgaggtga    60
ccagaagatg gctaaaggga aaacaaaatg gtgggcctct                         100

<210> SEQ ID NO 596
<211> LENGTH: 100
<212> TYPE: DNA
<213> ORGANISM: Homo sapiens

<400> SEQUENCE: 596
ccagggtttg ggggccctgt gctggtggag gagagaagac cccagggcga tggtaggaga    60
cgaaagcttg ggctgcagcg taagcttgga ggcccgctgc                         100

<210> SEQ ID NO 597
<211> LENGTH: 100
<212> TYPE: DNA
<213> ORGANISM: Homo sapiens

<400> SEQUENCE: 597
ggtggctcac gcctgtaatc ccagagcttt gggaggctga gacaggagga ttgcttgagc    60
ccaggagttt gagaccagcc tgggtctcaa accaaaaaaa                         100

<210> SEQ ID NO 598
<211> LENGTH: 100
<212> TYPE: DNA
<213> ORGANISM: Homo sapiens

<400> SEQUENCE: 598
taaatataat tttaacgcca atctgagaaa aatgacttat tagctgtgtg attttgagca    60
atgctcttaa cctcccccat gaaggatggt gtgagaacga                         100

<210> SEQ ID NO 599
<211> LENGTH: 100
<212> TYPE: DNA
<213> ORGANISM: Homo sapiens

<400> SEQUENCE: 599
acagaattgt agcacgtgta tcagtctggt acacaatgtc ctatgaaggt tagctttatt    60
atcaccatca ttattattgc agaaagactt tcagttcaga                         100

<210> SEQ ID NO 600
<211> LENGTH: 100
<212> TYPE: DNA
<213> ORGANISM: Homo sapiens

<400> SEQUENCE: 600
ataagacagc acagttacag agacctggtt ttattttcca gcttcttaac tgagtcatct    60
ttcagctcct tttaattaaa aagaaaaaac aatcagagat                         100

<210> SEQ ID NO 601
<211> LENGTH: 100
<212> TYPE: DNA
<213> ORGANISM: Homo sapiens

<400> SEQUENCE: 601
tcaaagacct ggcagaaatg acttcccaac cccagatgcc cccagcagca gtatttagca    60
gtcatacaat tgcctgaaat gaagaatgag taatctggat                         100

<210> SEQ ID NO 602
<211> LENGTH: 100
<212> TYPE: DNA
<213> ORGANISM: Homo sapiens

<400> SEQUENCE: 602
gagtcggccc tgaaatcgac ctgcaactta cccggaacgt gagctgtctc tctctgacct    60
ctgctggctg cttcacctgg agtctgagtc cgactcatgt                         100

<210> SEQ ID NO 603
<211> LENGTH: 100
<212> TYPE: DNA
<213> ORGANISM: Homo sapiens

<400> SEQUENCE: 603
agcacttcac tgtccgcgtt agtttagcct tcactgtcag caactcgtca ccttgtcctc    60
ttgcagcgaa ggtttggaat cccatcacgg gtgtgcagtg                         100

<210> SEQ ID NO 604
<211> LENGTH: 100
<212> TYPE: DNA
<213> ORGANISM: Homo sapiens

<400> SEQUENCE: 604
gttagtcctg agatcatggt ggtgctagga gaacctgcca accaatacag aaagttgtca    60
cgaatagaaa cctaagctct ggccgggtgc ggtggttcaa                         100

<210> SEQ ID NO 605
<211> LENGTH: 100
<212> TYPE: DNA
<213> ORGANISM: Homo sapiens

<400> SEQUENCE: 605
agatatactg ttctagacat gtgtctgaaa ggaatcctgc aaattctgtc ttattgaaca    60
ggcataaggt gtcacgtcag gcgtaaggtg tcacagcagg                         100

<210> SEQ ID NO 606
<211> LENGTH: 100
<212> TYPE: DNA
<213> ORGANISM: Homo sapiens -continued

```
<400> SEQUENCE: 606
cgtaaggcgt cacgtcaggc gtaaggtgtc acagcaggcg taaggcatca cgtcaggcgt    60
aaggcgtcac gtcaggcgta aggtgtcaca agctcggtga                         100

<210> SEQ ID NO 607
<211> LENGTH: 100
<212> TYPE: DNA
<213> ORGANISM: Homo sapiens

<400> SEQUENCE: 607
acgtcagggg tgtgccttgt gttctctgtt cgttgctttc agaagcagca gcatgtggca    60
gcatctctgt gcctatgacg atattgcagt gaatatgaga                         100

<210> SEQ ID NO 608
<211> LENGTH: 100
<212> TYPE: DNA
<213> ORGANISM: Homo sapiens

<400> SEQUENCE: 608
aattgtacat ttcaacaaca taaataagct gttcaagact gtctcccatg cctccaaaac    60
aaataaaaac cccccacaac tcaaatgcat ataagctgtt                         100

<210> SEQ ID NO 609
<211> LENGTH: 100
<212> TYPE: DNA
<213> ORGANISM: Homo sapiens

<400> SEQUENCE: 609
actatagtat aatggtgagt tatagccagt gtatgatggg attgttgata gaataatgca    60
tattagagct tttagttcaa aaatttgaga tagtgattca                         100

<210> SEQ ID NO 610
<211> LENGTH: 100
<212> TYPE: DNA
<213> ORGANISM: Homo sapiens

<400> SEQUENCE: 610
gaaagaaaaa aaggaatgat tatcatgaat tctgtttatt agaattctgt ttattaaaga    60
gttaaagata tgtttatttt ttttatcttt attatcatta                         100

<210> SEQ ID NO 611
<211> LENGTH: 100
<212> TYPE: DNA
<213> ORGANISM: Homo sapiens

<400> SEQUENCE: 611
aattctaatg ttggtcccTT aggatcagca gggggggacc gggaatctgt aactgcaacc    60
accccaccga gaggattaca ggaacccagt cgagagctgg                         100

<210> SEQ ID NO 612
<211> LENGTH: 100
<212> TYPE: DNA
<213> ORGANISM: Homo sapiens

<400> SEQUENCE: 612
ttcccaacaa tgaggttcat ttaaaaagtc gtgaggggg aggggggcca aagaaagaaa    60
tagatcaaag agcgggagag tcgagaaaag aaggaagaaa                         100
```

-continued

```
<210> SEQ ID NO 613
<211> LENGTH: 100
<212> TYPE: DNA
<213> ORGANISM: Homo sapiens

<400> SEQUENCE: 613
tgttggggag cgctggcagc cgggctggca agtggagttt gggaatgtgc agggagggaa      60
ggaagctgaa aaattcaaac tttttaaatg ctactcttca                          100

<210> SEQ ID NO 614
<211> LENGTH: 100
<212> TYPE: DNA
<213> ORGANISM: Homo sapiens

<400> SEQUENCE: 614
gctcctcggc gtccctgcac cccaaccctg cagccctggg gcgttggcag ctgcaccaac      60
aggagcagca agctgggaaa acagagcaac atgacccgac                          100

<210> SEQ ID NO 615
<211> LENGTH: 100
<212> TYPE: DNA
<213> ORGANISM: Homo sapiens

<400> SEQUENCE: 615
gtgttaagag aaggcaaaac acttcagcaa ttaaaaagta gcccagcagc ttcacccttt      60
caaattggga gggggaggtt ggaaagaaat ttaacaacat                          100

<210> SEQ ID NO 616
<211> LENGTH: 100
<212> TYPE: DNA
<213> ORGANISM: Homo sapiens

<400> SEQUENCE: 616
ccatagactt ttgctatgta catttaaacc gcagtcctgg aacattccga gtttaaaact      60 tgcttttca acactggctg acaagcaaca tgttttaagg                           100

<210> SEQ ID NO 617
<211> LENGTH: 100
<212> TYPE: DNA
<213> ORGANISM: Homo sapiens

<400> SEQUENCE: 617 agcccccat taaatcctta ctcgcgggac tctcgagttc aagccagcat tttgtcgcca       60 cctcccccc caaccccgcc cgcaatcgat gagccgcaat                           100

<210> SEQ ID NO 618
<211> LENGTH: 100
<212> TYPE: DNA
<213> ORGANISM: Homo sapiens

<400> SEQUENCE: 618
gcctcggcaa acaggtaag cgggtcaacc tgaatgcctc tttcaccca aagtttgctg       60 cacgatcggc tatcgcggga agaagcccaa cggagctagg                          100

<210> SEQ ID NO 619
<211> LENGTH: 100
<212> TYPE: DNA
<213> ORGANISM: Homo sapiens

<400> SEQUENCE: 619
```

```
gcggactcaa gccccactgc aaacttgttc tgcaacatct ttttgaatca caacttggcc      60
tttcttcctc gcatatcccc agctccccc aaagagtgga                             100
```

<210> SEQ ID NO 620
<211> LENGTH: 100
<212> TYPE: DNA
<213> ORGANISM: Homo sapiens

<400> SEQUENCE: 620

```
ggaaaacatt gtcccgagac tcacttcccc gagggacctc ccactcccaa ccccacgggt      60
gggtaatgcc gctggacaga cctagggcgc agactgggaa                            100
```

<210> SEQ ID NO 621
<211> LENGTH: 100
<212> TYPE: DNA
<213> ORGANISM: Homo sapiens

<400> SEQUENCE: 621

```
cccgatcaga ccagcaaacc tgggatccag cagcacgtta cgtaaaacag gatcgcccaa      60
aacttgtccc aatcccagcc ctccccccga agccccgggg                            100
```

<210> SEQ ID NO 622
<211> LENGTH: 100
<212> TYPE: DNA
<213> ORGANISM: Homo sapiens

<400> SEQUENCE: 622

```
ctgccctgcc aggcaaactt cgcccctcaa aaccctggcc tccagattca catgtaatcc      60
ccgccagcaa ctgttgaaac tcaaagggtg ggaaggacgg                            100
```

<210> SEQ ID NO 623
<211> LENGTH: 100
<212> TYPE: DNA
<213> ORGANISM: Homo sapiens

<400> SEQUENCE: 623

```
ggccaaattc cttcaaactt gggagaaatg ccggaggaga aaagaatcat ctcgctgcac      60
cactttcccc attgccttcc aagacccaaa cttttggggg                            100
```

<210> SEQ ID NO 624
<211> LENGTH: 100
<212> TYPE: DNA
<213> ORGANISM: Homo sapiens

<400> SEQUENCE: 624

```
ttctttctta aggcaaaaga aaagactttt ttgaaaagca aatgctccgc cccccttttac     60 cttgcataaa acttcgctca agtcgaagat ggtggcagac                            100
```

<210> SEQ ID NO 625
<211> LENGTH: 100
<212> TYPE: DNA
<213> ORGANISM: Homo sapiens

<400> SEQUENCE: 625

```
acgagggtgg tggtcatcct gtgcgttcgc gcgagccagg ggcgaggatc tggtgtgtcg      60
cgaaggtccc ggtgcgggga aggcgcagcc tctcctgtct                            100
```

<210> SEQ ID NO 626
<211> LENGTH: 100

```
<212> TYPE: DNA
<213> ORGANISM: Homo sapiens

<400> SEQUENCE: 626
ttattttttt atattaagat ttattctaaa ttttgattct tctaaatata gtatatattt    60
agtatatata taatgcacct ctcttaccta atgatcattt                         100

<210> SEQ ID NO 627
<211> LENGTH: 100
<212> TYPE: DNA
<213> ORGANISM: Homo sapiens

<400> SEQUENCE: 627
ctaaataatc ataacaacat cgagtaaaac tatgtaataa cacatattat tattaagata    60
agtataagaa atataataat aaattgtccc tgttctaaaa                         100

<210> SEQ ID NO 628
<211> LENGTH: 100
<212> TYPE: DNA
<213> ORGANISM: Homo sapiens

<400> SEQUENCE: 628
ggtaattata taatgctgaa tgtgtcagag gcattcgaac cagagtgact ccattttgag    60
tgagggctag gaaaatgagg ctgagacttg ctgggatgca                         100

<210> SEQ ID NO 629
<211> LENGTH: 100
<212> TYPE: DNA
<213> ORGANISM: Homo sapiens

<400> SEQUENCE: 629
tttaattttt atgctttctt cagtgtatgt ttggagagag tttgaacatt ttttgactct    60
ttttcattga gtaaatccaa atacttgtaa aagacttatc                         100

<210> SEQ ID NO 630
<211> LENGTH: 100
<212> TYPE: DNA
<213> ORGANISM: Homo sapiens

<400> SEQUENCE: 630
tatttcttta acaaaaactt aacatggatt aaggacccat cttaaggcat cacacattaa    60
aaaagtcaat attgattcaa taccggcgct tatactacga                         100

<210> SEQ ID NO 631
<211> LENGTH: 100
<212> TYPE: DNA
<213> ORGANISM: Homo sapiens

<400> SEQUENCE: 631
catcacttgt taaatttgtt ttctaaataa agcccagagg tagtggaaaa tacttcacac    60
tctaggccag tgtttgctat gcctggttga ccctaaactg                         100

<210> SEQ ID NO 632
<211> LENGTH: 100
<212> TYPE: DNA
<213> ORGANISM: Homo sapiens

<400> SEQUENCE: 632
ttgagggttc ttttttaaaaa tacagatttc tgggacccac ctgagatgat tccgataatc    60
```

```
ggccatatgg atgagtcact tagagatacc catttttaag                            100

<210> SEQ ID NO 633
<211> LENGTH: 100
<212> TYPE: DNA
<213> ORGANISM: Homo sapiens

<400> SEQUENCE: 633
gattaggacc ccgaagccca gaaaatgcct gctgtagtca acattatagt cacactccac      60
aggcactggg tccacccctt tgaccgacat tcctttgcgg                           100

<210> SEQ ID NO 634
<211> LENGTH: 100
<212> TYPE: DNA
<213> ORGANISM: Homo sapiens

<400> SEQUENCE: 634
ttttcccacc cttcttccct gcctggagaa ctcctattca tcctccagag cccggctcaa      60
agtggcttca tctgtgggga tcctccctgc cccatagtga                           100

<210> SEQ ID NO 635
<211> LENGTH: 100
<212> TYPE: DNA
<213> ORGANISM: Homo sapiens

<400> SEQUENCE: 635
gtgctccttg agtcctcgcc cttcctaggg catcccaagc tcccaggggc tgcccctgct      60
gcctcgccat ccgctccaaa gctggctgta cctcgatggt                           100

<210> SEQ ID NO 636
<211> LENGTH: 100
<212> TYPE: DNA
<213> ORGANISM: Homo sapiens

<400> SEQUENCE: 636
taagggcagc caggcgtgct gcttctcgtc caaatacacg aacttctccc aggcccacag      60
gcggtccggg tggtcggtga ctgcctcccc gagtgtcggg                           100

<210> SEQ ID NO 637
<211> LENGTH: 100
<212> TYPE: DNA
<213> ORGANISM: Homo sapiens

<400> SEQUENCE: 637
aggaatcaga tttcaaaatg aatatgtata agaaaagaac cggggatcag tgatcaggaa      60
cagggatcca tgatctggtc cagggctcag cggtcaggaa                           100

<210> SEQ ID NO 638
<211> LENGTH: 100
<212> TYPE: DNA
<213> ORGANISM: Homo sapiens

<400> SEQUENCE: 638
ccctggcctg gagtcccaag tccccagccc atcctgcccc tggagcccag tttagcttgg      60
tcttgaagtc tgctctaggt accccaaaa tcacagtatc                            100

<210> SEQ ID NO 639
<211> LENGTH: 100
<212> TYPE: DNA
<213> ORGANISM: Homo sapiens
```

```
<400> SEQUENCE: 639
cagccccgct ctgcccaccg ggacagccaa gttcagctga gactggccta ccggggagt     60 cgccctctga agttcactct aagccagcct ggttcagcct                         100

<210> SEQ ID NO 640
<211> LENGTH: 100
<212> TYPE: DNA
<213> ORGANISM: Homo sapiens

<400> SEQUENCE: 640
ggcccaggtc agcccaggac ctcccttgc aggcagcaaa ctcttatttc agtccagcca    60
gctcaaccag cttgcttctg actcagctcc tcttagccag                        100

<210> SEQ ID NO 641
<211> LENGTH: 100
<212> TYPE: DNA
<213> ORGANISM: Homo sapiens

<400> SEQUENCE: 641
ttagctcagc aaagctggac ctaaagtagc cacctcaccc cagcttcatc cagatgaata    60
cagtccagat cagcttagtc agttaagcct agcctagcta                        100

<210> SEQ ID NO 642
<211> LENGTH: 100
<212> TYPE: DNA
<213> ORGANISM: Homo sapiens

<400> SEQUENCE: 642
gttaaatcca gttacgacca gctcaactaa tcctgctcag gcctgctcag cccagcccag    60
ctgaacccag tttagccgag gccaggccag cccagctgaa                        100

<210> SEQ ID NO 643
<211> LENGTH: 100
<212> TYPE: DNA
<213> ORGANISM: Homo sapiens

<400> SEQUENCE: 643
tacagttgcc cagtctagct cagcccagtc cagcactgcc cagtttagct gagctcagcc    60
tggcccagcc cagctcatat cagcccatct cagctgaacc                        100

<210> SEQ ID NO 644
<211> LENGTH: 100
<212> TYPE: DNA
<213> ORGANISM: Homo sapiens

<400> SEQUENCE: 644
agtttgaccc agtctaaccc aaccccgctc agctgaaccc agcccagccc agcccagccc    60
agccaaaccc agtttagcct agctcagctc agcccatttc                        100

<210> SEQ ID NO 645
<211> LENGTH: 100
<212> TYPE: DNA
<213> ORGANISM: Homo sapiens

<400> SEQUENCE: 645
cctgtcctag gggtggcagg cagtctgcac ccagcctagc cctgcccagc gtggggtctc    60
tgaccttctt ggtcttgggc ccagccaaga ttcccagccc                        100
```

<210> SEQ ID NO 646
<211> LENGTH: 100
<212> TYPE: DNA
<213> ORGANISM: Homo sapiens

<400> SEQUENCE: 646
ttctagcttt cctgtgtccc catgcaggga agggatgcct agagtccacg cagtgaccaa    60
gaagcttggt tgatgctgtg agggtggccc aggagtcccc    100

<210> SEQ ID NO 647
<211> LENGTH: 100
<212> TYPE: DNA
<213> ORGANISM: Homo sapiens

<400> SEQUENCE: 647
cacctgctgt ccttggtcct ggctgagagg agggccctac ggccagctct gctgaccctg    60
ccctgggctc tggtgatgct gccggcctgg acaagcccct    100

<210> SEQ ID NO 648
<211> LENGTH: 100
<212> TYPE: DNA
<213> ORGANISM: Homo sapiens

<400> SEQUENCE: 648
gagctcaggt cggtcgtgcc catcctggca tcaccccaca gccggttctg ccgcatcccg    60
tcatgttcct cgtgctccca gcccggtcgt cctggaggcc    100

<210> SEQ ID NO 649
<211> LENGTH: 100
<212> TYPE: DNA
<213> ORGANISM: Homo sapiens

<400> SEQUENCE: 649
tgagcatgag tggggcgggc agaggcctcc gggtgaggag acagatgggg cctgccttgc    60
tgccctgggc tggggctgca cagccggggt gcgtccaggc    100

<210> SEQ ID NO 650
<211> LENGTH: 100
<212> TYPE: DNA
<213> ORGANISM: Homo sapiens

<400> SEQUENCE: 650
aggagggctg agcctggctt ccagcagaca ccctccctcc ctgagctggc ctctcaccaa    60
ctgtcttgtc caccttggtg ttgctgggct tgtgatctac    100

<210> SEQ ID NO 651
<211> LENGTH: 100
<212> TYPE: DNA
<213> ORGANISM: Homo sapiens

<400> SEQUENCE: 651
accaactgtc ttgtccacct tggtgttgct gggcttgtga tctacgttgc aggtgtaggt    60
ctgggtgccg aagttgctgg agggcacggt caccacgctg    100

<210> SEQ ID NO 652
<211> LENGTH: 100
<212> TYPE: DNA
<213> ORGANISM: Homo sapiens

<400> SEQUENCE: 652
ggactgtagg acagccggga aggtgtgcac gccgctggtc agagcgcctg agttccacga    60
caccgtcacc ggttcgggga agtagtcctt gaccaggcag                         100

<210> SEQ ID NO 653
<211> LENGTH: 100
<212> TYPE: DNA
<213> ORGANISM: Homo sapiens

<400> SEQUENCE: 653
tgctacactg ccctgcacca cctccactca gcttcattgt gctggtggcc ctggctcctg    60
gcagcccatc ttgctccttc tggggcgcca gcctcagagg                         100

<210> SEQ ID NO 654
<211> LENGTH: 100
<212> TYPE: DNA
<213> ORGANISM: Homo sapiens

<400> SEQUENCE: 654
ccttcctgcc tagggtccgc tggggccagc cctgggaccc tcctggtctc aagcacacat    60 tcccctgca gccacacctg cccctgcctg agagctcagc                          100

<210> SEQ ID NO 655
<211> LENGTH: 100
<212> TYPE: DNA
<213> ORGANISM: Homo sapiens

<400> SEQUENCE: 655
cccgagccct ggaatgcctt cccttctcca tcccagctca cccttgccaa ctgctcagtg    60
ggatgggctc acactccctt cctggcacca ggaggctgca                         100

<210> SEQ ID NO 656
<211> LENGTH: 100
<212> TYPE: DNA
<213> ORGANISM: Homo sapiens

<400> SEQUENCE: 656
ctgcactttc accagccctc agctgtctgc tgccagcaac tacccagctc ctgccaaaat    60
ctaggagctg agtgatgcct cccaccggcc ctgctcacct                         100

<210> SEQ ID NO 657
<211> LENGTH: 100
<212> TYPE: DNA
<213> ORGANISM: Homo sapiens

<400> SEQUENCE: 657
gtggttgcct tgccctgagc tctagtgcct gtccctgct cgtcctgcct cccaccggcc    60
ctgctcacct gtggctgctc tgctctgatt ccctgaggct                         100

<210> SEQ ID NO 658
<211> LENGTH: 100
<212> TYPE: DNA
<213> ORGANISM: Homo sapiens

<400> SEQUENCE: 658
aagcctcagt cctgctcacc ttctgatgct ctcctctgtc ccctgagctc caggggctgt    60
cccctgctcg tcctgcctcc tacctgcccc tgcttacctg                         100

<210> SEQ ID NO 659

```
<211> LENGTH: 100
<212> TYPE: DNA
<213> ORGANISM: Homo sapiens

<400> SEQUENCE: 659
agggtgctct gccctggtgc tctgagctcc aggggctgtc ccctgctcct cctgcttcct      60
accagcccct gctcacctgt ggctgctctg ccctggtccc                           100

<210> SEQ ID NO 660
<211> LENGTH: 100
<212> TYPE: DNA
<213> ORGANISM: Homo sapiens

<400> SEQUENCE: 660
ctctgccctg gtcccctgag ctccaggggc ttccccctgc tcttcctgcc cccaccagcc      60
cctgttcacc ttcagatgcc ctcccctggt cccctgaagt                           100

<210> SEQ ID NO 661
<211> LENGTH: 100
<212> TYPE: DNA
<213> ORGANISM: Homo sapiens

<400> SEQUENCE: 661
cccagagctg cccctgttc ctcctgcctc ccaccagccc gtgctcacct gccgctgctc       60
tgccctggtc ccgagttcca ggggctgcac cctgttcgcc                           100

<210> SEQ ID NO 662
<211> LENGTH: 100
<212> TYPE: DNA
<213> ORGANISM: Homo sapiens

<400> SEQUENCE: 662
cacctcccac tagccatgct cagctcttga tgctctgtcc tggtcccctg agctccagga      60
gctgtcccct actcgtcctg ccacccacca gccctgctc                            100

<210> SEQ ID NO 663
<211> LENGTH: 100
<212> TYPE: DNA
<213> ORGANISM: Homo sapiens

<400> SEQUENCE: 663
acctgaggca cctgaggctg ctctgccctg gtccctgag ctccagggtc ttccccctgc       60
tcatcctgcc tcccacctgc ccttgttcac cttcagttgc                           100

<210> SEQ ID NO 664
<211> LENGTH: 100
<212> TYPE: DNA
<213> ORGANISM: Homo sapiens

<400> SEQUENCE: 664
tctgccctgg tctgctgagc tccaggaggt gcccctgct ccttctgccc ccacctgccc       60
tgctcacctg tggctgctcg gtcctggtac cctgaactcc                           100

<210> SEQ ID NO 665
<211> LENGTH: 100
<212> TYPE: DNA
<213> ORGANISM: Homo sapiens

<400> SEQUENCE: 665 gcccctgct ccttctgccc ccacctgccc tgctcacctg tggctgctcg gtcctggtac       60
```

```
cctgaactcc aatgcctgcc ccctgctcac tctgccctcc                          100
```

<210> SEQ ID NO 666
<211> LENGTH: 100
<212> TYPE: DNA
<213> ORGANISM: Homo sapiens

<400> SEQUENCE: 666

```
ctcaacccgg gcagcaatgt cactcaggtc actgttgccc cctgcctgt cctggcaccc      60 tctgtccagg tttgggctgt ttttctggcc tcattttgt                           100
```

<210> SEQ ID NO 667
<211> LENGTH: 100
<212> TYPE: DNA
<213> ORGANISM: Homo sapiens

<400> SEQUENCE: 667

```
tgtccagtca ggtctcccca acagagcccc ttgcccttgc ccatgtgccc ctcctgggtg     60
agctcccaga tcctcccgtc cctgcactgc tcctgctctg                          100
```

<210> SEQ ID NO 668
<211> LENGTH: 100
<212> TYPE: DNA
<213> ORGANISM: Homo sapiens

<400> SEQUENCE: 668

```
gaagcctctc cagaacctca gctcctcagt ggcctctgct ctgctgggtc agctccctga    60
acgcacggag cctcaccct ccctcgccc caggcctgct                             100
```

<210> SEQ ID NO 669
<211> LENGTH: 100
<212> TYPE: DNA
<213> ORGANISM: Homo sapiens

<400> SEQUENCE: 669

```
gcactctggg cctttctggg cctccctgga ctcttccctc ctcccatctg tgcactcagc    60
acagctctcc cctccactcc gctgctgacc acagccctgc                          100
```

<210> SEQ ID NO 670
<211> LENGTH: 100
<212> TYPE: DNA
<213> ORGANISM: Homo sapiens

<400> SEQUENCE: 670

```
cctttctggg cctccctgga ctcttccctc ctcccatctg tgcactcagc acagctctcc    60
cctccactcc gctgctgacc acagccctgc tccccgccag                          100
```

<210> SEQ ID NO 671
<211> LENGTH: 100
<212> TYPE: DNA
<213> ORGANISM: Homo sapiens

<400> SEQUENCE: 671

```
cccacggcca gcactgctga ccctgccctg ggctccagtg atgctgctgg cctggacaag    60
cccctccgtt cacctggggc ctctcctcct ccctcgttct                          100
```

<210> SEQ ID NO 672
<211> LENGTH: 100
<212> TYPE: DNA

-continued

<213> ORGANISM: Homo sapiens

<400> SEQUENCE: 672

```
actgcctcct cagctcaggt gggtcctgcc catgctggca tcaccccacg gccggctctg    60
ccgcatcccg tcaggttcct cgtgctccca gcctggtcgt                         100
```

<210> SEQ ID NO 673
<211> LENGTH: 100
<212> TYPE: DNA
<213> ORGANISM: Homo sapiens

<400> SEQUENCE: 673

```
catggaggcc tcagtcagcc tctggtgtgt cctgccctgt tggcttggaa gccctgccc     60
acggtccccg tcatcttgca ctgggtgggc gttggtgcct                         100
```

<210> SEQ ID NO 674
<211> LENGTH: 100
<212> TYPE: DNA
<213> ORGANISM: Homo sapiens

<400> SEQUENCE: 674

```
agctcagccc agcctagtcc agcccagccc agcacaggtc agcccagctt agcttagccc    60
aggtcagtcc agctcagctc agtccactta agctcaccca                         100
```

<210> SEQ ID NO 675
<211> LENGTH: 100
<212> TYPE: DNA
<213> ORGANISM: Homo sapiens

<400> SEQUENCE: 675

```
ggtcagctcc gtccagctca gcccagccta gcccagctta gcccagccca gcccaacaca    60
ggtcagccca gctcagccta gcccagccca gctcagcaca                         100
```

<210> SEQ ID NO 676
<211> LENGTH: 100
<212> TYPE: DNA
<213> ORGANISM: Homo sapiens

<400> SEQUENCE: 676

```
ggtcagacca gctcagtaca gctcaggtca gcccagacca gtccaaccca gcccagcgca    60
gtccaaccca gcccagctca gctcatccaa gcctagctca                         100
```

<210> SEQ ID NO 677
<211> LENGTH: 100
<212> TYPE: DNA
<213> ORGANISM: Homo sapiens

<400> SEQUENCE: 677

```
gctcagccca gcccaggtca gcctagccca gccgaaccca gctcagccca ggtcaaccca    60
attcagctca gctcagccca ggtcaaccca accaagctca                         100
```

<210> SEQ ID NO 678
<211> LENGTH: 100
<212> TYPE: DNA
<213> ORGANISM: Homo sapiens

<400> SEQUENCE: 678

```
gctcagccta gcccagtcca gctcagccca gctcagctca gcccagtcca gctcaatcca    60
cctaagctca cccagctcag cccagtctgg ctcagcttag                         100
```

<210> SEQ ID NO 679
<211> LENGTH: 100
<212> TYPE: DNA
<213> ORGANISM: Homo sapiens

<400> SEQUENCE: 679
gtcagcccag cccagcctag cccagatcag tccagcttag cccagcccag gtcagcccag    60
cccaggtcag cccagctcag ctcagcccag cccagctcag                         100

<210> SEQ ID NO 680
<211> LENGTH: 100
<212> TYPE: DNA
<213> ORGANISM: Homo sapiens

<400> SEQUENCE: 680
cccagcccag ctcagcgcag cccagcctag ctcaccccag ccaggtccag cttagcccag    60
ctcagcccag cccaactcag ctcagcccag ctcagcccaa                         100

<210> SEQ ID NO 681
<211> LENGTH: 100
<212> TYPE: DNA
<213> ORGANISM: Homo sapiens

<400> SEQUENCE: 681
tctgagctcc aggggctgcc cacctgctcc tcctgcttcc caccggccct gctcacctgc    60
agctgctctg ccctggctcc ctgaggctga gcctcagtcc                         100

<210> SEQ ID NO 682
<211> LENGTH: 100
<212> TYPE: DNA
<213> ORGANISM: Homo sapiens

<400> SEQUENCE: 682
tgctcacctt ctgatgctct ccccttgtcc cctgagctcc aggggctgac ccctgatctt    60
tctgcttcct acctgcccct gctcacctgt ggctgctctg                         100

<210> SEQ ID NO 683
<211> LENGTH: 100
<212> TYPE: DNA
<213> ORGANISM: Homo sapiens

<400> SEQUENCE: 683
ccctgatccc ctgagctcca ggagctgcct cctgctcttc ctgcctccca cctgcccctg    60
ctcacctgca gatctgccct ggctctctga ggtccagggg                         100

<210> SEQ ID NO 684
<211> LENGTH: 100
<212> TYPE: DNA
<213> ORGANISM: Homo sapiens

<400> SEQUENCE: 684
ctgccccctg ctcgcccacc tcccaccagc catgctgacg ttgtgatgct ctgccctggt    60
ctcctgaggt ccagggctg tccctgctt attctgcctc                          100

<210> SEQ ID NO 685
<211> LENGTH: 100
<212> TYPE: DNA
<213> ORGANISM: Homo sapiens

```
<400> SEQUENCE: 685
ccacctgccc cttctcacct gaggctcttc tgccctggtg ctctgagctc caaaagctgc    60
ccacttgctc ctcctgcttc ctaccagccc ctgctctcct                         100

<210> SEQ ID NO 686
<211> LENGTH: 100
<212> TYPE: DNA
<213> ORGANISM: Homo sapiens

<400> SEQUENCE: 686
gtggatgatc tgccctggct ctctgagctc caggggctgc ccacctgctc cccatgcttc    60
ccacctgccc ctgctgacct gcggctgctc tgccttggct                         100

<210> SEQ ID NO 687
<211> LENGTH: 100
<212> TYPE: DNA
<213> ORGANISM: Homo sapiens

<400> SEQUENCE: 687
ccctgagctc caggagcttc cccctgctca tcctgccccc cactggcccc tgttcacctt    60
cagatgccct ccctggtccc ctgaagtcca ggagctgccc                         100

<210> SEQ ID NO 688
<211> LENGTH: 100
<212> TYPE: DNA
<213> ORGANISM: Homo sapiens

<400> SEQUENCE: 688
cctgttcctc ccgcctccca ccagcccgtg ctcacctgcg gctgctctgc cctggtcccc    60
tgagttccag gggctgcccc ctgctcgccc acctcccact                         100

<210> SEQ ID NO 689
<211> LENGTH: 100
<212> TYPE: DNA
<213> ORGANISM: Homo sapiens

<400> SEQUENCE: 689
agccatgctc acctcctgat gctctgtcct ggtcccctga gctccagggg ctgccccctg    60
cttgcccatc tcccactagc catgctcacc ttctgatgct                         100

<210> SEQ ID NO 690
<211> LENGTH: 100
<212> TYPE: DNA
<213> ORGANISM: Homo sapiens

<400> SEQUENCE: 690
ctgccctggt ccctgagct ccagggtctt ccccctgctc atcctgccgc ccaccagccc     60
ctgctcacct gaggctgctc tgccctggtc ccctgagctc                         100

<210> SEQ ID NO 691
<211> LENGTH: 100
<212> TYPE: DNA
<213> ORGANISM: Homo sapiens

<400> SEQUENCE: 691 ccctgagct ccagggtctt ccccctgctc atcctgccgc ccaccagccc ctgctcacct     60
gaggctgctc tgccctggtc ccctgagctc caggaggtgc                         100
```

<210> SEQ ID NO 692
<211> LENGTH: 100
<212> TYPE: DNA
<213> ORGANISM: Homo sapiens

<400> SEQUENCE: 692

```
ttctgccccc acctgccctg ctcacctgtg gctgcttggt cctggtccct gagctccaat      60
gcctgctccc tgctcactct gccctccctc aacccgggca                           100
```

<210> SEQ ID NO 693
<211> LENGTH: 100
<212> TYPE: DNA
<213> ORGANISM: Homo sapiens

<400> SEQUENCE: 693

```
gcaatgtcac tcaggtcact gttgccccc tgcctgtcct ggcaccctct gtccaggttt       60
gggctgtttt tctgccctca tttttgattt tgcagcactt                           100
```

<210> SEQ ID NO 694
<211> LENGTH: 100
<212> TYPE: DNA
<213> ORGANISM: Homo sapiens

<400> SEQUENCE: 694

```
cctctgtcca ggtttgggct gttttttctgc cctcattttt gatttgcag cacttggcgt      60
gttccctatg ctgtggagca gccccagtgt ccagtcaggt                           100
```

<210> SEQ ID NO 695
<211> LENGTH: 100
<212> TYPE: DNA
<213> ORGANISM: Homo sapiens

<400> SEQUENCE: 695

```
agtgtccagt caggtctccc caacagagcc ccttgccctt gcccatgtgc ccctcctgaa      60
tgagctcccg gatcctcctg tccctgcact gctcctgctc                           100
```

<210> SEQ ID NO 696
<211> LENGTH: 100
<212> TYPE: DNA
<213> ORGANISM: Homo sapiens

<400> SEQUENCE: 696

```
tggaagcctc tctggaacct cagctcctca gtggcctctg ctctgctggg tcagttccct      60
gaacgcacgg agcctcagcc cttcccctcg ccccaggcct                           100
```

<210> SEQ ID NO 697
<211> LENGTH: 100
<212> TYPE: DNA
<213> ORGANISM: Homo sapiens

<400> SEQUENCE: 697

```
gctgcactct gggcctttct gggcctccct ggactcttcc cttctcccgc ccgtgcactc      60
agcacagctc tcccctcctc tccactgctg accacagccc                           100
```

<210> SEQ ID NO 698
<211> LENGTH: 100
<212> TYPE: DNA
<213> ORGANISM: Homo sapiens

<400> SEQUENCE: 698

```
tgctccccgc cagcaggtgc cccaacccca tcagctggct ctgagcccag ccctgtgcc    60 tccctgtcc ctgcctctgc ctctgggctc cttggcttcc                        100
```

<210> SEQ ID NO 699
<211> LENGTH: 100
<212> TYPE: DNA
<213> ORGANISM: Homo sapiens

<400> SEQUENCE: 699

```
acctgctgtc cttggtcctg gctgagagga gggccccacg gccagcactg ctgaccctgc    60
cctgggctcc ggtgatgctg ccggcctgga caagcccctc                        100
```

<210> SEQ ID NO 700
<211> LENGTH: 100
<212> TYPE: DNA
<213> ORGANISM: Homo sapiens

<400> SEQUENCE: 700

```
cgttcacctg gggcctctcc tcctccctcg ctctgctgcc tcctgagctc aggtcggtcg    60
tgcccatcct ggcatcaccc cacggccggc tctgccgcat                        100
```

<210> SEQ ID NO 701
<211> LENGTH: 100
<212> TYPE: DNA
<213> ORGANISM: Homo sapiens

<400> SEQUENCE: 701

```
ccagtcatgt tcctcgtgct cccagcccgg tcgtcctgga ggcctcagtc agcctctggt    60
gtgtcctgcc ctgttggctt ggaagcccct gcccacggtc                        100
```

<210> SEQ ID NO 702
<211> LENGTH: 100
<212> TYPE: DNA
<213> ORGANISM: Homo sapiens

<400> SEQUENCE: 702

```
cccgtcgtct cgcactgggt gggcatcggt gcctgaaggc tgcccacctc ccccgtgctg    60
gctccgcttg ggcctccatg tggggccggc ctcgaccca                         100
```

<210> SEQ ID NO 703
<211> LENGTH: 100
<212> TYPE: DNA
<213> ORGANISM: Homo sapiens

<400> SEQUENCE: 703

```
cactgcactt tcaccagccc tcagctgtct gctgccggca actacccagc tcctgccaaa    60
gtctaggagc tgcgtgctgc ctcccaccgt ccctgctcac                        100
```

<210> SEQ ID NO 704
<211> LENGTH: 100
<212> TYPE: DNA
<213> ORGANISM: Homo sapiens

<400> SEQUENCE: 704

```
ctgtggctgc tctgccctgg tgctctgagc tccaggagat gcccctgct cctcctgccc     60 cccacctgcc cctgctcacc tgcagcggct ctgccctggt                        100
```

<210> SEQ ID NO 705
<211> LENGTH: 100

```
<212> TYPE: DNA
<213> ORGANISM: Homo sapiens

<400> SEQUENCE: 705
gagctccaag agctgccccc tgctcctcct gtcccctgac cctgctcctg tttgcctatg    60
gctgctctgc ccttgtcccc tgagctccag gagctgcccc                         100

<210> SEQ ID NO 706
<211> LENGTH: 100
<212> TYPE: DNA
<213> ORGANISM: Homo sapiens

<400> SEQUENCE: 706
tgctcattct gccgcccacc tgccctgtt cacctgtggc tgctcttccc tggtcctctg     60
agctccatga gctgcccctt gctcctcctg ctttccacca                         100

<210> SEQ ID NO 707
<211> LENGTH: 100
<212> TYPE: DNA
<213> ORGANISM: Homo sapiens

<400> SEQUENCE: 707 gccctgctc acctaccgat gatcttcccc ggctctctga gctccagggg ctgcccacct    60
gctaccctg cttcccacca gccctgctta cctgcagctg                          100

<210> SEQ ID NO 708
<211> LENGTH: 100
<212> TYPE: DNA
<213> ORGANISM: Homo sapiens

<400> SEQUENCE: 708
ctctgccctg gctggcagag ctgcagaagc tgcccctgc tctgcaacct cccaccggcc    60
cttctcatct tctgatgttc tccctgttc cctgagctcc                          100

<210> SEQ ID NO 709
<211> LENGTH: 100
<212> TYPE: DNA
<213> ORGANISM: Homo sapiens

<400> SEQUENCE: 709
aggagctgcc ccctactcgt tctacctccc accaacccgt gctcacctgc gactgctctg    60
ccctggtccc ctgagctcca ggggctgccc cctgctcgcc                         100

<210> SEQ ID NO 710
<211> LENGTH: 100
<212> TYPE: DNA
<213> ORGANISM: Homo sapiens

<400> SEQUENCE: 710
tgccctgatc ccctgagctc caggactgcc ccctgctcgt cctgcccctc acctgcccct    60
gctcacctga ggctgctctg ccctggtccc ctgagctaaa                         100

<210> SEQ ID NO 711
<211> LENGTH: 100
<212> TYPE: DNA
<213> ORGANISM: Homo sapiens

<400> SEQUENCE: 711
ggggctgccc cttactcatc ctgcctccca ccagcccctg ctcaccttct gatgccctcc    60
```

```
cctggtcccc tgagctccag gggctgcccc ctgctcgtcc                           100
```

<210> SEQ ID NO 712
<211> LENGTH: 100
<212> TYPE: DNA
<213> ORGANISM: Homo sapiens

<400> SEQUENCE: 712

```
gggctgcccc ctgctcgtcc tgcctcccac cagccctgc tcacctgcag ctacactgcc    60
ctggttccct gagctccagg agctgccacc tgcttgtcct                          100
```

<210> SEQ ID NO 713
<211> LENGTH: 100
<212> TYPE: DNA
<213> ORGANISM: Homo sapiens

<400> SEQUENCE: 713

```
gccttccacc agccctgct cacctgcagc tacactgccc tggttccctg agctccggga    60
gctgccgcct gcttgtcctg cctcccacca gccctgctc                           100
```

<210> SEQ ID NO 714
<211> LENGTH: 100
<212> TYPE: DNA
<213> ORGANISM: Homo sapiens

<400> SEQUENCE: 714

```
acctgtggct acactgccct ggtgccctga gctccaggag ctgcccctg cttgcccatc    60 ttccactgag ccctgctcac tgcaactgc tctgccctgg                           100
```

<210> SEQ ID NO 715
<211> LENGTH: 100
<212> TYPE: DNA
<213> ORGANISM: Homo sapiens

<400> SEQUENCE: 715

```
ctctatgagc tccaggggct gcccctgct ggtcctgcct cccacctgcc ctgcgcacct    60
gtggctgcct cctcacctgt ggctgctctg ccctggtccc                          100
```

<210> SEQ ID NO 716
<211> LENGTH: 100
<212> TYPE: DNA
<213> ORGANISM: Homo sapiens

<400> SEQUENCE: 716

```
ctgagctcca gggtcttcct cctgctcatc ctgcccctcc accggctcct gttcaccttc    60
agatgctctc ccgtggtccc ctgagctcca ggagctgccc                          100
```

<210> SEQ ID NO 717
<211> LENGTH: 100
<212> TYPE: DNA
<213> ORGANISM: Homo sapiens

<400> SEQUENCE: 717

```
cctgttcttc ctgcctccca cctgccctgt gcacctgtgg ctgcttggtc ctggtcccct    60
gaactccaat gcctgccccc tgctcactct gccctccctc                          100
```

<210> SEQ ID NO 718
<211> LENGTH: 100
<212> TYPE: DNA
<213> ORGANISM: Homo sapiens

<400> SEQUENCE: 718
aacctggggc agcaacgtca ctcggtccac tgttgccccc ctgcctgtcc tggcaccctc    60
tgtccaggtt taggctgttt ttcttgcctc attttttgttt                        100

<210> SEQ ID NO 719
<211> LENGTH: 100
<212> TYPE: DNA
<213> ORGANISM: Homo sapiens

<400> SEQUENCE: 719
tggcaccctc tgtccaggtt taggctgttt ttcttgcctc attttttgttt ttgcagcact    60 tggcgtgttc cctatgctgt ggagcagccc cagtgtccag                        100

<210> SEQ ID NO 720
<211> LENGTH: 100
<212> TYPE: DNA
<213> ORGANISM: Homo sapiens

<400> SEQUENCE: 720
tccagtcagg tctccccaac agagcccctt gcccttgccc atgtgcccct cctggatgag    60
ctcccggatc ctcccgtccc tgcactgctc ctgctctgga                        100

<210> SEQ ID NO 721
<211> LENGTH: 100
<212> TYPE: DNA
<213> ORGANISM: Homo sapiens

<400> SEQUENCE: 721
agcctctcca gaacctcagc tcctcagtgg cctctgctct gctgggtcag ttccctgaac    60
gcacggagcc tcagcccctc ccctcgcccc aggcctgctg                        100

<210> SEQ ID NO 722
<211> LENGTH: 100
<212> TYPE: DNA
<213> ORGANISM: Homo sapiens

<400> SEQUENCE: 722
cactctgggc ctttctgggc ctccctggac tcttccctcc tcccgcccgt gcactcagca    60
cagctctccc ctcctctccg ctgctgacca cagccctgct                        100

<210> SEQ ID NO 723
<211> LENGTH: 100
<212> TYPE: DNA
<213> ORGANISM: Homo sapiens

<400> SEQUENCE: 723
gaccacagcc ctgctcccgg ccagcaggtg ccccaacccc atcagctggc tctgagccca    60 gccctgtgc ctcccctgtc cctgcctctg cctctgggct                         100

<210> SEQ ID NO 724
<211> LENGTH: 100
<212> TYPE: DNA
<213> ORGANISM: Homo sapiens

<400> SEQUENCE: 724
gctctgctcc cagctcacct gctgtccttg gtcctggctg agaggagggc cctacggcca    60
gctctgctga ccctgccctg ggctccggtg atgctgccgg                        100

<210> SEQ ID NO 725
<211> LENGTH: 100
<212> TYPE: DNA
<213> ORGANISM: Homo sapiens

<400> SEQUENCE: 725
cctggacaag cccctcggtt cacctggggc ctctcctcct ccctctctct gctgcctcct    60
gagctcaggt cggtcatgcc catcctggca tcaccccatg                         100

<210> SEQ ID NO 726
<211> LENGTH: 100
<212> TYPE: DNA
<213> ORGANISM: Homo sapiens

<400> SEQUENCE: 726
gctggctctg ccccatcccg tcatgttcct cacactccca gcccggtcgt cctggaggcc    60
tcagtcagcc tctggtgtgt cctgccctgt tggcttggaa                         100

<210> SEQ ID NO 727
<211> LENGTH: 100
<212> TYPE: DNA
<213> ORGANISM: Homo sapiens

<400> SEQUENCE: 727
gggtagagcc cacctcgtgg cctgcaagcc agccagcccc tgccggtcga gaaggaagcc    60
tgtgtgagag cacacaactg gaggccgggc ggggaagaga                         100

<210> SEQ ID NO 728
<211> LENGTH: 100
<212> TYPE: DNA
<213> ORGANISM: Homo sapiens

<400> SEQUENCE: 728
aacacgtgcc aacaggccac gcaggccagg accccagacc cggaggcagc gcccctttga    60
gttcctctct ctggtctccg atgttcttct gttgggatca                         100

<210> SEQ ID NO 729
<211> LENGTH: 100
<212> TYPE: DNA
<213> ORGANISM: Homo sapiens

<400> SEQUENCE: 729
tttcacctac aggcaacaga gacagtgtga aatgctttcc ctgtggtcgg gaagggagcc    60
ggggcagaga tgacccagtg gggtggtgtg ggggcctccg                         100

<210> SEQ ID NO 730
<211> LENGTH: 100
<212> TYPE: DNA
<213> ORGANISM: Homo sapiens

<400> SEQUENCE: 730
ctttgcacac cacgtgttcg tctgtgccct gcatgacgtc cttggaaggc agcagcacct    60
gtgaggtggc tgcgtacttg ccccctctca ggactgatgg                         100

<210> SEQ ID NO 731
<211> LENGTH: 100
<212> TYPE: DNA
<213> ORGANISM: Homo sapiens

<400> SEQUENCE: 731

```
gaagccccgg gtgctgctga tgtcagagtt gttcttgtat ttccaggaga aagtgatgga    60
gtcgggaagg aagtcctgtg cgaggcagcc aacggccacg                         100

<210> SEQ ID NO 732
<211> LENGTH: 100
<212> TYPE: DNA
<213> ORGANISM: Homo sapiens

<400> SEQUENCE: 732
ctgctcgtat ccgacgggga attctcacag gagacgaggg ggaaaagggt tggggcggat    60
gcactccctg aggacccgca ggacaaaaga gaaagggagg                         100

<210> SEQ ID NO 733
<211> LENGTH: 100
<212> TYPE: DNA
<213> ORGANISM: Homo sapiens

<400> SEQUENCE: 733
actccagcta ccctgaagtc tccccaggca gacaacccag gcctgggagt gagtataggg    60
agggtgggtg tgatggggaa cgcagtgtag actcagctga                         100

<210> SEQ ID NO 734
<211> LENGTH: 100
<212> TYPE: DNA
<213> ORGANISM: Homo sapiens

<400> SEQUENCE: 734
ggctatccat ctatgtccaa caagatcatg aagattggcc cagtgccatg tcctccagtt    60
catcccagcc caggccagct caatccagtt catcccagcc                         100

<210> SEQ ID NO 735
<211> LENGTH: 100
<212> TYPE: DNA
<213> ORGANISM: Homo sapiens

<400> SEQUENCE: 735
caggccagct caatccagcc cagcccaccc caccccagct cagcaaagcc aagctcagct    60
cagcccaact cagatgagct cagaccagct cagcccagcc                         100

<210> SEQ ID NO 736
<211> LENGTH: 100
<212> TYPE: DNA
<213> ORGANISM: Homo sapiens

<400> SEQUENCE: 736
cagctcagct cagcccaacc cagcccagct cgctcaacct tgctcggctc agcttagccc    60
agcccagccc agctcaatcc agcctggctc agcccagccc                         100

<210> SEQ ID NO 737
<211> LENGTH: 100
<212> TYPE: DNA
<213> ORGANISM: Homo sapiens

<400> SEQUENCE: 737
agcccagttt ggctcaaccc agcttggctc agcccaggtc agcctggctc aactcagccc    60
agcccagccc agctctgctc aacccagctc tgctcaactc                         100

<210> SEQ ID NO 738
```

```
<211> LENGTH: 100
<212> TYPE: DNA
<213> ORGANISM: Homo sapiens

<400> SEQUENCE: 738
agcccagctc atcccagctc agccagccc agcctagctt agctcaaccc agctcagctc      60
agttcagctc agccctgctc agcacagcac agcagagccc                          100

<210> SEQ ID NO 739
<211> LENGTH: 100
<212> TYPE: DNA
<213> ORGANISM: Homo sapiens

<400> SEQUENCE: 739
agcccggatc ggctcaaccc agcttagctc agcccaggtc agcccagctt aactcagccc      60
aggtcagccc agcttaactc agcccagccc agcccagctc                          100

<210> SEQ ID NO 740
<211> LENGTH: 100
<212> TYPE: DNA
<213> ORGANISM: Homo sapiens

<400> SEQUENCE: 740
tcagcccagt tcagcccagc tcagcccagc ccagcctagc ttggctcaac acagctcagc      60
tcagccagcc cagaccagct cagctcagcc cagtccagct                          100

<210> SEQ ID NO 741
<211> LENGTH: 100
<212> TYPE: DNA
<213> ORGANISM: Homo sapiens

<400> SEQUENCE: 741
caacccagcc cagcccaacc cagctcggct taacccagct cggctcagcc cagatcagcc      60
tggctcaact cagcccagcc cagctcaacc cagcccagtt                          100

<210> SEQ ID NO 742
<211> LENGTH: 100
<212> TYPE: DNA
<213> ORGANISM: Homo sapiens

<400> SEQUENCE: 742
cagctcagct gagcccagcc cagcccagtc cggctcagct cagccccgcc ccactcagcc      60
cagctcagct cagcccagct cagcccagct cagcttagcc                          100

<210> SEQ ID NO 743
<211> LENGTH: 100
<212> TYPE: DNA
<213> ORGANISM: Homo sapiens

<400> SEQUENCE: 743
cagcccagat catcccagct cagctcagct cagctcggct tagcccagct caacctggcc      60
cagcctggtc caggtcagcc cagcctggac cacccagccc                          100

<210> SEQ ID NO 744
<211> LENGTH: 100
<212> TYPE: DNA
<213> ORGANISM: Homo sapiens

<400> SEQUENCE: 744
agctcagctc agcccagctc atcctggttc agctcagctc aacccggctc agcccaggtc      60
```

```
tgctcaaccc agcccaaatc agctcagccc agcccaggtc                              100
```

<210> SEQ ID NO 745
<211> LENGTH: 100
<212> TYPE: DNA
<213> ORGANISM: Homo sapiens

<400> SEQUENCE: 745

```
atcccagctc agcccagcac agcctacttc agctcagctc agctcagcct aggtcagctc        60
agttgaggtc agctcaactc agcccaatcc agcctggctc                              100
```

<210> SEQ ID NO 746
<211> LENGTH: 100
<212> TYPE: DNA
<213> ORGANISM: Homo sapiens

<400> SEQUENCE: 746

```
agcccagctc accctagctc agcttagctc agcccaactc aacccagccc agccttgccc        60
aacccagctc agctcagccc agcccaggtt agcccagccc                              100
```

<210> SEQ ID NO 747
<211> LENGTH: 100
<212> TYPE: DNA
<213> ORGANISM: Homo sapiens

<400> SEQUENCE: 747

```
agcctcggct tagctctgct cagctcggcc ctgctcgcct cagcccgttc agcccagttc        60
agctcagctc agctcagccc agctcagccc agccctggtt                              100
```

<210> SEQ ID NO 748
<211> LENGTH: 100
<212> TYPE: DNA
<213> ORGANISM: Homo sapiens

<400> SEQUENCE: 748

```
agctcagccc agctaagctc agctcggctt ggctctgctg agcttggccc agcttggctt        60
agcctgatac aacctgctca gcccagttca gctcggctca                              100
```

<210> SEQ ID NO 749
<211> LENGTH: 100
<212> TYPE: DNA
<213> ORGANISM: Homo sapiens

<400> SEQUENCE: 749

```
gcccagcgta gctcagctca gctgagccca gcccaggtta gctcagcccc agtccaggtc        60
agctcaactc agcccaaacc agcctggctc ggcccagctc                              100
```

<210> SEQ ID NO 750
<211> LENGTH: 100
<212> TYPE: DNA
<213> ORGANISM: Homo sapiens

<400> SEQUENCE: 750

```
accctagttc agcttagctc agcccagccc agccctgccc aacccagctc agctcagccc        60
agcccaggtt agcccagccc agcctcggct tagctctgct                              100
```

<210> SEQ ID NO 751
<211> LENGTH: 100
<212> TYPE: DNA

<213> ORGANISM: Homo sapiens

<400> SEQUENCE: 751
agcccagccc aggttagccc agcccagcct cggcttagct ctgctcagct cggcccagcc     60
caggttagcc cagcccagcc tcggcttagc tctgctcagc                           100

<210> SEQ ID NO 752
<211> LENGTH: 100
<212> TYPE: DNA
<213> ORGANISM: Homo sapiens

<400> SEQUENCE: 752
tcggccctgc tcgcctcagc ccgttcagcc cagttcagct cagctcagct cagcccagct     60
cagcccagcc ctggttagct cagcccagct aagctcagct                           100

<210> SEQ ID NO 753
<211> LENGTH: 100
<212> TYPE: DNA
<213> ORGANISM: Homo sapiens

<400> SEQUENCE: 753
cggctcagct ctgctgagct cggcccagct tggctcagcc cgacacagcc tgctcagccc     60
agttcagctc ggctcagccc agcccagccc agcgtagctc                           100

<210> SEQ ID NO 754
<211> LENGTH: 100
<212> TYPE: DNA
<213> ORGANISM: Homo sapiens

<400> SEQUENCE: 754
agctgagccc agcccaggtt agctcagccc cagcccaggt tagctcagcc cagctcagct     60
ctgcccaggt tagctcagcc ccagtccagg ttagctcagc                           100

<210> SEQ ID NO 755
<211> LENGTH: 100
<212> TYPE: DNA
<213> ORGANISM: Homo sapiens

<400> SEQUENCE: 755
ccagctcagc tctgcccagg ttagctcagc cccagtccag gttagctcag cccagctcag     60
ccttgcccag gttagctcag cccagctaag ctcaacttgg                           100

<210> SEQ ID NO 756
<211> LENGTH: 100
<212> TYPE: DNA
<213> ORGANISM: Homo sapiens

<400> SEQUENCE: 756
ctcagctcag cctagcttgg ctcagcccag cacagcacgc tcaacccggt tcagcttggc     60
tcagcccagc ccagcccagc ctagctcagc tcagccccgc                           100

<210> SEQ ID NO 757
<211> LENGTH: 100
<212> TYPE: DNA
<213> ORGANISM: Homo sapiens

<400> SEQUENCE: 757
ccagctcagc gcagcccagc tcagctcagc tcagcctagc cttgctcggc ccagctcagc     60
tcagcccagc tcagcctagc cttgctcagc ccagctcagc                           100

<210> SEQ ID NO 758
<211> LENGTH: 100
<212> TYPE: DNA
<213> ORGANISM: Homo sapiens

<400> SEQUENCE: 758
tcagcccagc cctgcccagc tcagcccagc ttagtgcagc caagcccagc tcagctcagc    60
tcacctggtg caacttagcc cagctcagct cagctcagct                          100

<210> SEQ ID NO 759
<211> LENGTH: 100
<212> TYPE: DNA
<213> ORGANISM: Homo sapiens

<400> SEQUENCE: 759
caacccagtt caactcagcc cagttcagct cagctcagcc cagttcagcc ttgtttagtc    60
taggtcagct taggtcagtt ttgcccatct gagtccattt                          100

<210> SEQ ID NO 760
<211> LENGTH: 100
<212> TYPE: DNA
<213> ORGANISM: Homo sapiens

<400> SEQUENCE: 760
ctgaaagctg gatggagttg tcatggccag aaatggtcag cccaccagac ctgcttgtct    60
cagctaaagc catctcattg ccaggttcct gcacagccag                          100

<210> SEQ ID NO 761
<211> LENGTH: 100
<212> TYPE: DNA
<213> ORGANISM: Homo sapiens

<400> SEQUENCE: 761
gctggcttcc atcttttgtc tccctctact tgataccccca gttccctgca gtcctgcccc   60
agcgccacct gggttttggt tccaaagcat taccaatcat                          100

<210> SEQ ID NO 762
<211> LENGTH: 100
<212> TYPE: DNA
<213> ORGANISM: Homo sapiens

<400> SEQUENCE: 762
taccaccctc cactacctgg gtggaatatt tctttgctgc tttaaagtca ttaaaacatc    60
ttgagaatga gaccaagaat ttaggagcct gtgctgtgat                          100

<210> SEQ ID NO 763
<211> LENGTH: 100
<212> TYPE: DNA
<213> ORGANISM: Homo sapiens

<400> SEQUENCE: 763
aaaaatgagc aggtcccctt gctctagaag tggcagcata tcttctgcac caagaggagg    60
gtattgagat gctcagagcc tccaccttcc cggagcatcc                          100

<210> SEQ ID NO 764
<211> LENGTH: 100
<212> TYPE: DNA
<213> ORGANISM: Homo sapiens

```
<400> SEQUENCE: 764
cctcccttct gagtctgcag taaacccctg cctttaaatt ccctctagat aacagtcatc      60
attggaaaca accaagaaat gcattttatc tgaatttgcc                          100

<210> SEQ ID NO 765
<211> LENGTH: 100
<212> TYPE: DNA
<213> ORGANISM: Homo sapiens

<400> SEQUENCE: 765
acttaaaatt ctgccattta ccataaatcg ctttggaagg catgggctac tttcaagggt      60
gcgatgatga cctacagtca atgacttaga caagggcgat                          100

<210> SEQ ID NO 766
<211> LENGTH: 100
<212> TYPE: DNA
<213> ORGANISM: Homo sapiens

<400> SEQUENCE: 766
gccagtgggg cttggtatgt tctcaagcat cattacccat gccatcccca ttcagaggtt      60
gtggagcagc tcgtgcgacc tctccttcaa atgggcttta                          100

<210> SEQ ID NO 767
<211> LENGTH: 100
<212> TYPE: DNA
<213> ORGANISM: Homo sapiens

<400> SEQUENCE: 767
gggaaagtta aatgggagtg acccagacaa tggtcactca aaagactcac ataaatgagt      60
ctcctgctct tcatcaagca attaagacca gttccccttc                          100

<210> SEQ ID NO 768
<211> LENGTH: 100
<212> TYPE: DNA
<213> ORGANISM: Homo sapiens

<400> SEQUENCE: 768
tagtggaaat aagacgtcaa atacaaagtt ttaagagaag caaatgcagc agcggcggct      60
gcctgtctct taccatgtcg ggcgcctggt cactgcgagc                          100

<210> SEQ ID NO 769
<211> LENGTH: 100
<212> TYPE: DNA
<213> ORGANISM: Homo sapiens

<400> SEQUENCE: 769
cttgcaaagc tttggcatgg aatcattcct ccaagtccat taacaagggc tggggcctga      60
gcagccagtc ggcccggcag cagaagccac gcatcccagc                          100

<210> SEQ ID NO 770
<211> LENGTH: 100
<212> TYPE: DNA
<213> ORGANISM: Homo sapiens

<400> SEQUENCE: 770
tctgggtagt ccggggagac ccaaagccca ggccgggcct ggcagccacc ctcccagagc      60
ctccgctagg ccagtcctgc tgacgccgca tcggtgattc                          100
```

```
<210> SEQ ID NO 771
<211> LENGTH: 100
<212> TYPE: DNA
<213> ORGANISM: Homo sapiens

<400> SEQUENCE: 771
ggaacagaat ctgtccttct aaggtgtctc cacagtcctg tcttcagcac tatctgattg      60
agttttctct tatgccacca actaacatgc ttaactgaaa                          100

<210> SEQ ID NO 772
<211> LENGTH: 100
<212> TYPE: DNA
<213> ORGANISM: Homo sapiens

<400> SEQUENCE: 772
taattcagga taatgatgca cattttacct aaaacttatc ctaaagtgag tagttgaaaa      60
gtggtcttga aaaatactaa aatgaaggcc actctatcag                          100

<210> SEQ ID NO 773
<211> LENGTH: 100
<212> TYPE: DNA
<213> ORGANISM: Homo sapiens

<400> SEQUENCE: 773
aatatcaaag tgtttctcct taatcacaaa gagaaaacga gttaacctaa aaagattgtg      60
aacacagtca ttatgaaaat aatgctctga ggtatcgaaa                          100

<210> SEQ ID NO 774
<211> LENGTH: 100
<212> TYPE: DNA
<213> ORGANISM: Homo sapiens

<400> SEQUENCE: 774
aagtatttga gattagttat cacatgaagg gataacaagc taatttaaaa aacttttga       60 atacagtcat aaactctccc taagactgtt taatttctta                          100

<210> SEQ ID NO 775
<211> LENGTH: 100
<212> TYPE: DNA
<213> ORGANISM: Homo sapiens

<400> SEQUENCE: 775
aacatcttac tttaaaaatg aatgcagttt agaagttgat atgctgtttg cacaaactag      60
cagttgataa gctaagattg gaaatgaaat tcagatagtt                          100

<210> SEQ ID NO 776
<211> LENGTH: 100
<212> TYPE: DNA
<213> ORGANISM: Homo sapiens

<400> SEQUENCE: 776
aaaaaaagcc ttttcagttt cggtcagcct cgccttattt tagaaacgca aattgtccag      60
gtgttgtttt gctcagtaga gcactttcag atctgggcct                          100

<210> SEQ ID NO 777
<211> LENGTH: 100
<212> TYPE: DNA
<213> ORGANISM: Homo sapiens

<400> SEQUENCE: 777
```

```
gggcaaaacc acctcttcac aaccagaagt gataaattta ccaattgtgt tttttttgctt    60 cctaaaatag actctcgcgg tgacctgctt cctgccacct                          100
```

<210> SEQ ID NO 778
<211> LENGTH: 100
<212> TYPE: DNA
<213> ORGANISM: Homo sapiens

<400> SEQUENCE: 778

```
gctgtgggtg ccggagaccc ccatgcagcc atcttgactc taattcatca tctgcttcca    60
gcttcgctca attaattaaa aaaataaact tgatttatga                          100
```

<210> SEQ ID NO 779
<211> LENGTH: 100
<212> TYPE: DNA
<213> ORGANISM: Homo sapiens

<400> SEQUENCE: 779

```
tggtcaaaac gcagtcccgc atcggggccg acagcactgt gctagtattt cttagctgag    60
cttgctttgg cctcaattcc agacacatat cactcatggg                          100
```

<210> SEQ ID NO 780
<211> LENGTH: 100
<212> TYPE: DNA
<213> ORGANISM: Homo sapiens

<400> SEQUENCE: 780

```
tgttaatcaa atgataagaa tttcaaatac ttggacagtt aaaaaaatta atatacttga    60
aaatctctca cattttttaag tcataatttt cttaaccatt                         100
```

<210> SEQ ID NO 781
<211> LENGTH: 100
<212> TYPE: DNA
<213> ORGANISM: Homo sapiens

<400> SEQUENCE: 781

```
tttctcagaa gccacttcaa acatatcctg tcttttaaca gtaagcatgc ctcctaagat    60
aaacaatcct tttctcttgg aaaccagctt caaggcactg                          100
```

<210> SEQ ID NO 782
<211> LENGTH: 100
<212> TYPE: DNA
<213> ORGANISM: Homo sapiens

<400> SEQUENCE: 782

```
aggtcctgga gcctccctaa gccctgtca ggacggcagc caccgtttct gggctacccc     60
tgcccccaac cctgctctca tcaagaccgg ggctacgcgt                          100
```

<210> SEQ ID NO 783
<211> LENGTH: 100
<212> TYPE: DNA
<213> ORGANISM: Homo sapiens

<400> SEQUENCE: 783

```
ccctcctggc tggattcacc cactccgaca gttctctttc cagccaataa agaatttaag    60
atgcaggttg acacacagcg cacctcataa ttctaaagaa                          100
```

<210> SEQ ID NO 784
<211> LENGTH: 100

```
<212> TYPE: DNA
<213> ORGANISM: Homo sapiens

<400> SEQUENCE: 784
aatatttcac gattcgctgc tgtgcagcga tcttgcagtc ctacagacac cgctcctgag    60
acacattcct cagccatcac taagacccct ggtttgttca                         100

<210> SEQ ID NO 785
<211> LENGTH: 100
<212> TYPE: DNA
<213> ORGANISM: Homo sapiens

<400> SEQUENCE: 785
ggcatctcgt ccaaatgtgg ctccccaagc ccccaggctc agttactcca tcagacgcac    60
ccaacctgag tcccattttc caaaggcatc ggaaaatcca                         100

<210> SEQ ID NO 786
<211> LENGTH: 100
<212> TYPE: DNA
<213> ORGANISM: Homo sapiens

<400> SEQUENCE: 786
cagaggctcc cagatcctca aggcacccca gtgcccgtcc cctcctggcc agtccgccca    60
ggtcccctcg gaacatgccc cgaggaccaa cctgcaatgc                         100

<210> SEQ ID NO 787
<211> LENGTH: 100
<212> TYPE: DNA
<213> ORGANISM: Homo sapiens

<400> SEQUENCE: 787
tcaggaaacc ccacaggcag tagcagaaaa caaaggccct agagtggcca ttcttacctg    60
aggagacggt gaccgtggtc cctttgcccc agacgtccat                         100

<210> SEQ ID NO 788
<211> LENGTH: 100
<212> TYPE: DNA
<213> ORGANISM: Homo sapiens

<400> SEQUENCE: 788
gtagtagtag tagtagtaat cacaatggca gaatgtccat cctcaccccca caaaaaccca    60 gccacccaga gaccttctgt ctccgggcgt cacatggaag                         100

<210> SEQ ID NO 789
<211> LENGTH: 100
<212> TYPE: DNA
<213> ORGANISM: Homo sapiens

<400> SEQUENCE: 789
ctgactgtcc gtggccctgt cctgcccttc tcatggaacc ctctgctggc ctcccacgta    60
ccccacattc tggcctgacc cctcagaagc cagaccactg                         100

<210> SEQ ID NO 790
<211> LENGTH: 100
<212> TYPE: DNA
<213> ORGANISM: Homo sapiens

<400> SEQUENCE: 790
tcggcctggg aagtccaact gcaagcagac ggctgctaag tcaccccccag gagtccaaaa    60
```
accccggggg gcacccgtcc cagagagcgg gtgccttgga    100

<210> SEQ ID NO 791
<211> LENGTH: 100
<212> TYPE: DNA
<213> ORGANISM: Homo sapiens

<400> SEQUENCE: 791
gcgggacaga gtcccaccac gcaatcatca cgacagcccc tgagaatgct ccaggtgaag    60
cggagagagg tcaccccaga ccagccgaag gagcccccca    100

<210> SEQ ID NO 792
<211> LENGTH: 100
<212> TYPE: DNA
<213> ORGANISM: Homo sapiens

<400> SEQUENCE: 792
gctgccgaca tctgtggccg gacttgggga ggacaggctg ggttcccatt cgaagggtcc    60
ctctccccgg ctttctttcc tgacctccaa aatgcctcca    100

<210> SEQ ID NO 793
<211> LENGTH: 100
<212> TYPE: DNA
<213> ORGANISM: Homo sapiens

<400> SEQUENCE: 793
agactctgac cctgagaccc tggcaagctg agtctcccta agtggactca gagaggggt    60 ggtgaggact cacctgagga gacggtgacc agggttccct    100

<210> SEQ ID NO 794
<211> LENGTH: 100
<212> TYPE: DNA
<213> ORGANISM: Homo sapiens

<400> SEQUENCE: 794
ggccccaggg gtcgaaccag ttgtcacatt gtgacaacaa tgccaggacc ccaggcaaga    60
actggcgccc cgctacgtcc ctgggaccct ctcagactga    100

<210> SEQ ID NO 795
<211> LENGTH: 100
<212> TYPE: DNA
<213> ORGANISM: Homo sapiens

<400> SEQUENCE: 795
gcccggggag ggcccggggg ttgttgggca ttggacccca gaggcctagg gtggccctgg    60
ccacagagag acccgtgctg ctgggctcag gaggaaggag    100

<210> SEQ ID NO 796
<211> LENGTH: 100
<212> TYPE: DNA
<213> ORGANISM: Homo sapiens

<400> SEQUENCE: 796
catctggagc ccttgcccct cgtctgtgtg gccgctgttg cctcagggca tcctcctgag    60 cccccccagga tgctccgggg ctctcttggc aggagaccca    100

<210> SEQ ID NO 797
<211> LENGTH: 100
<212> TYPE: DNA
<213> ORGANISM: Homo sapiens

<400> SEQUENCE: 797
gcacccttat tccccccag aaatgcagca aaacccttca gagttaaagc aggagagagg          60
ttgtgaggac tcacctgagg agacggtgac cagggttccc                              100

<210> SEQ ID NO 798
<211> LENGTH: 100
<212> TYPE: DNA
<213> ORGANISM: Homo sapiens

<400> SEQUENCE: 798
tggccccagt agtcaaagta gtcacattgt gggaggcccc attaagggt gcacaaaaac          60 ctgactctcc gactgtcccg ggccggccgt ggcagccagc                              100

<210> SEQ ID NO 799
<211> LENGTH: 100
<212> TYPE: DNA
<213> ORGANISM: Homo sapiens

<400> SEQUENCE: 799
cccgtgtccc aaggtcattt tgtccccagc acaagcatga ctctgcccac cctttgcccc          60
agcagcagag tcccagttcc caaagaaagg ccttctgctg                              100

<210> SEQ ID NO 800
<211> LENGTH: 100
<212> TYPE: DNA
<213> ORGANISM: Homo sapiens

<400> SEQUENCE: 800
aacgtggtcc caaacagccg gagaaggagc cccggagggc cccacatggc ccagcgcaga          60
ccaaggagcc cccggacatt atctcccagc tccaggacag                              100

<210> SEQ ID NO 801
<211> LENGTH: 100
<212> TYPE: DNA
<213> ORGANISM: Homo sapiens

<400> SEQUENCE: 801
aggacgctgg gcccagagaa aggaggcaga aggaaagcca tcttacctga agagacggtg          60
accattgtcc cttggcccca gatatcaaaa gcatcacaca                              100

<210> SEQ ID NO 802
<211> LENGTH: 100
<212> TYPE: DNA
<213> ORGANISM: Homo sapiens

<400> SEQUENCE: 802
gggacacagt ccctgttcct gcccagacac aaacctgtgc ccgtgcagga cactcgaatg          60
ggtcacatgg cccaagcaca gagcagaggc agccggcgtc                              100

<210> SEQ ID NO 803
<211> LENGTH: 100
<212> TYPE: DNA
<213> ORGANISM: Homo sapiens

<400> SEQUENCE: 803
cctgtcccca gccacacaga cccccgggct gagacccagg cagggagggg tgacgttccc          60
agggagacgg tggccgggct gccctggccc cagtgctcca                              100

<210> SEQ ID NO 804
<211> LENGTH: 100
<212> TYPE: DNA
<213> ORGANISM: Homo sapiens

<400> SEQUENCE: 804
agcacttgta gccacactaa agcgcaggcc tggtccccgg cacatgaaca gccagcgccc    60
agccccagcc caggctctgc ccacaacttc tccttcccgt                         100

<210> SEQ ID NO 805
<211> LENGTH: 100
<212> TYPE: DNA
<213> ORGANISM: Homo sapiens

<400> SEQUENCE: 805
ccctgccctc ggcctgcttg ctacctgtgg agggtccctg acggggctga agcccagcgg    60
ggtccctgcc tgtccttggg ggctccagct ggccccaggg                         100

<210> SEQ ID NO 806
<211> LENGTH: 100
<212> TYPE: DNA
<213> ORGANISM: Homo sapiens

<400> SEQUENCE: 806
ctaagtgaca gcagggctct ggcatgcagc ccatggcgga gaccccaggg atggcagctg    60
gtgtggcctc aggccagacc caggccggct gcagacccca                         100

<210> SEQ ID NO 807
<211> LENGTH: 100
<212> TYPE: DNA
<213> ORGANISM: Homo sapiens

<400> SEQUENCE: 807
gatacctggc ctggtgcctg gacagagaag actgggaggg ggctgcagtg ggactcacct    60
gaggagacag tgaccagggt gccacggccc cagagatcga                         100

<210> SEQ ID NO 808
<211> LENGTH: 100
<212> TYPE: DNA
<213> ORGANISM: Homo sapiens

<400> SEQUENCE: 808
agtaccagta gcacagcctc tgccctcctg cttctcccat acaaaaacac accctccgcc    60
ctcctgccga cctcctttgc tgagcacctg tccccaagtc                         100

<210> SEQ ID NO 809
<211> LENGTH: 100
<212> TYPE: DNA
<213> ORGANISM: Homo sapiens

<400> SEQUENCE: 809
tgaagccaaa gcccttgcct ggcccagtac acctggctcc ccgctatccc cagacagcag    60
actcacctga ggagacggtg accagggtgc cctggcccca                         100

<210> SEQ ID NO 810
<211> LENGTH: 100
<212> TYPE: DNA
<213> ORGANISM: Homo sapiens

<400> SEQUENCE: 810
gtgctggaag tattcagcca cggtgagtca gccctgagcc aggggctaca gaaacccaca    60
gcccggggtc ccgggggagc atggtttttg tagagctgcc                         100

<210> SEQ ID NO 811
<211> LENGTH: 100
<212> TYPE: DNA
<213> ORGANISM: Homo sapiens

<400> SEQUENCE: 811
aatcactgtg tccccagtta gcacagtggt tctcagctca gccaaaaccc tgcggctggt    60 aggggggcctg tggggctggg ggctgatgtg gctgcggtct                        100

<210> SEQ ID NO 812
<211> LENGTH: 100
<212> TYPE: DNA
<213> ORGANISM: Homo sapiens

<400> SEQUENCE: 812
tgctgggtct gtcctctgtg ggaggggctg ctacccaggc ccaggactgc agtggagggc    60
tcactgaggg gcttttgggt ctggcctgag ccgctgtggg                         100

<210> SEQ ID NO 813
<211> LENGTH: 100
<212> TYPE: DNA
<213> ORGANISM: Homo sapiens

<400> SEQUENCE: 813
gctctcaggt ctactgcggg gacactcggg tctgccctg gcttaggtgg acagtgtccg     60
tgcccacctg tgccctgagg ctccatttca ggctgatatc                         100

<210> SEQ ID NO 814
<211> LENGTH: 100
<212> TYPE: DNA
<213> ORGANISM: Homo sapiens

<400> SEQUENCE: 814
tgtctgtatt gtccctaccc gctgcatggc catgtccttt tgggtttata aattgccccc    60
aaatcacgca ggcatcattc aggcttttta tattccctgg                         100

<210> SEQ ID NO 815
<211> LENGTH: 100
<212> TYPE: DNA
<213> ORGANISM: Homo sapiens

<400> SEQUENCE: 815
tattccctgg gccaccaggt gcctccaccc agaaagctga gatgtgggag gttctagagt    60
cattctgcaa ccctggatga gcccctgcag cctcagtgct                         100

<210> SEQ ID NO 816
<211> LENGTH: 100
<212> TYPE: DNA
<213> ORGANISM: Homo sapiens

<400> SEQUENCE: 816
actgaggttc cagcaagacc tggagcaggt gcagatgagg cctgaggcca ggtgaagccc    60
aggccaggtg aggtccaggc cagtgaggcc caggtcagat                         100

<210> SEQ ID NO 817

```
<211> LENGTH: 100
<212> TYPE: DNA
<213> ORGANISM: Homo sapiens

<400> SEQUENCE: 817
gaggcccagg tcaggtgaag cccaggtcag gtgaaaccca ggtcaggtga ggcccagatc    60
atgtgagctc aggacaggca aggtccaagt caggtgaggc                         100

<210> SEQ ID NO 818
<211> LENGTH: 100
<212> TYPE: DNA
<213> ORGANISM: Homo sapiens

<400> SEQUENCE: 818
cgagctcagg tgaagcccag aggtgaggtc taggccaggt gaggtccagg ccaggtgagg    60
tccaggtcag gtgaggccca ggtcaggcaa ggctgaggta                         100

<210> SEQ ID NO 819
<211> LENGTH: 100
<212> TYPE: DNA
<213> ORGANISM: Homo sapiens

<400> SEQUENCE: 819
tccaggtcag gtgaggccca ggtcaggcaa ggctgaggta gatgtatgag acttctgtaa    60
ttttcagttg gtgccaaccc tgcctggtgt ccctgcccct                         100

<210> SEQ ID NO 820
<211> LENGTH: 100
<212> TYPE: DNA
<213> ORGANISM: Homo sapiens

<400> SEQUENCE: 820
cctcccagcc catgctctgt gcctgccaga tggcggcccc tgcacaggtg ctgctggctg    60
tggaggagct gggctctgcc tccctgtgca tgggcgtccc                         100

<210> SEQ ID NO 821
<211> LENGTH: 100
<212> TYPE: DNA
<213> ORGANISM: Homo sapiens

<400> SEQUENCE: 821
gcctgcagcc tgtccgggga tgcccaggga ggtgagtgcc accacatatc aggcctttc    60 tctttaaagt catttctttg gggatacatc atcaatgtct                         100

<210> SEQ ID NO 822
<211> LENGTH: 100
<212> TYPE: DNA
<213> ORGANISM: Homo sapiens

<400> SEQUENCE: 822
tctaaacaca gctgtgtgca ttttcctctt cttgcaattt agaattttaa ctgctgtttt    60
caaggtactg taatgtattt gttctcttct tgttaggaga                         100

<210> SEQ ID NO 823
<211> LENGTH: 100
<212> TYPE: DNA
<213> ORGANISM: Homo sapiens

<400> SEQUENCE: 823
cttgccaacc ctgtgtgtct cagttcatac cctcttcctt ccccagtaga agtaacgacc    60
```

```
actgtgttta tgtgatcatc cttttcttga ttttccttat                    100
```

<210> SEQ ID NO 824
<211> LENGTH: 100
<212> TYPE: DNA
<213> ORGANISM: Homo sapiens

<400> SEQUENCE: 824

```
tgtgatcatc cttttcttga ttttccttat agttttccta gtggaaagtt tatcccttaa    60
gaagatagtt cattttgccg gctgtaaatt ttatttagaa                         100
```

<210> SEQ ID NO 825
<211> LENGTH: 100
<212> TYPE: DNA
<213> ORGANISM: Homo sapiens

<400> SEQUENCE: 825

```
ctgccatcgt ttatttgcct gttttccttc agatggctgt ttgcttcatt ctcagtttgg    60
ggctatgaca aacatatgtt ctgcacatct ttgcccatga                         100
```

<210> SEQ ID NO 826
<211> LENGTH: 100
<212> TYPE: DNA
<213> ORGANISM: Homo sapiens

<400> SEQUENCE: 826

```
ggctctcagg gagggctctg gagctggcat tgcctgcagg gctctgcttt gttgcaggga    60
gttcctgcca aggcttttca gagtgtctgt gcccagcctg                         100
```

<210> SEQ ID NO 827
<211> LENGTH: 100
<212> TYPE: DNA
<213> ORGANISM: Homo sapiens

<400> SEQUENCE: 827

```
aaggtacaca ctgtactttg cccttgcatc aggcactttc cttgtgcttg cttctgtgtg    60
gctccacatt ctggagaatt tattcagatc tgtgctgcaa                         100
```

<210> SEQ ID NO 828
<211> LENGTH: 100
<212> TYPE: DNA
<213> ORGANISM: Homo sapiens

<400> SEQUENCE: 828

```
cttcccacac tgtcctcctg ggctcactcc cagccatcga tcttgaacac cagtttatgg    60
aactatctgc acaggaaagc agaaacagca aaaggccctg                         100
```

<210> SEQ ID NO 829
<211> LENGTH: 100
<212> TYPE: DNA
<213> ORGANISM: Homo sapiens

<400> SEQUENCE: 829

```
ttgcgtggac cctgttttg gtcaagggaa gtacttgctg gtgaaggaga cctcccctcc    60
tttctttctc aggagccccc tctgatgccg ttgcctggtg                         100
```

<210> SEQ ID NO 830
<211> LENGTH: 100
<212> TYPE: DNA

<213> ORGANISM: Homo sapiens

<400> SEQUENCE: 830
tttctcaggg ctggtgctgg gggctcagca gtgtctgccc tgttccaggt gggaatgtgg    60
gtctgttctg tttccacgcg gtgttctggg ccgccagtg                          100

<210> SEQ ID NO 831
<211> LENGTH: 100
<212> TYPE: DNA
<213> ORGANISM: Homo sapiens

<400> SEQUENCE: 831
cagcagtgtc tgccctgttc caggtgggaa tgtgggtctg ttctgtttcc acgcggtgtt    60
ctggggccgc cagtgagggg ctcgggatgt cagcggctgg                         100

<210> SEQ ID NO 832
<211> LENGTH: 100
<212> TYPE: DNA
<213> ORGANISM: Homo sapiens

<400> SEQUENCE: 832
tctctgtccc tatggtctgg gctccggttc actgctcccc tgccctccag gtcggtcact    60
gactcagtta ctatccagcg ggctccgtgg ctgttcagtg                         100

<210> SEQ ID NO 833
<211> LENGTH: 100
<212> TYPE: DNA
<213> ORGANISM: Homo sapiens

<400> SEQUENCE: 833
gggagcaaat ggagagggaa gtggcagcgg cccgagtgcc aggcggtccc ggtttggggt    60
tgatctttgt ggaacagctc cctggcccgt gtgtaagtgg                         100

<210> SEQ ID NO 834
<211> LENGTH: 100
<212> TYPE: DNA
<213> ORGANISM: Homo sapiens

<400> SEQUENCE: 834
tcgggggagg cacggaggtc tggagctaca agcggtggca ggaaggcagg tcccagtctt    60
gggggtctgg agcttatctt cttcctgtga actgagtgtg                         100

<210> SEQ ID NO 835
<211> LENGTH: 100
<212> TYPE: DNA
<213> ORGANISM: Homo sapiens

<400> SEQUENCE: 835
atggaggacc tgcctcggat gacacccta tcttaagaag gtcatggtgg gttccagctg     60
ggaggaaggg aagtgggcca cctcctgggg gtcttccacc                         100

<210> SEQ ID NO 836
<211> LENGTH: 100
<212> TYPE: DNA
<213> ORGANISM: Homo sapiens

<400> SEQUENCE: 836
gtcttccacc cccaccacct cagcctgggg cctctgtgat tcctctctgc acagacccca    60
aagtctgtgc tgccgcaggg caggaaggaa gggcctgtgg                         100

<210> SEQ ID NO 837
<211> LENGTH: 100
<212> TYPE: DNA
<213> ORGANISM: Homo sapiens

<400> SEQUENCE: 837
tcgaggttgg ggccacagtg gtgttcccta agcccgagtc tggtctcatg gcccgccccg    60
cagcaggtcc tgagtgaggg acagagaccg gggcgggstc                         100

<210> SEQ ID NO 838
<211> LENGTH: 100
<212> TYPE: DNA
<213> ORGANISM: Homo sapiens

<400> SEQUENCE: 838
tttggtcctg gtggactctg gggtggattc cagtggggag tcatcagggt cggtgtcccc    60
cagggtactg gggtgtctct gctcctggag tcggctctgg                         100

<210> SEQ ID NO 839
<211> LENGTH: 100
<212> TYPE: DNA
<213> ORGANISM: Homo sapiens

<400> SEQUENCE: 839
cctgggtttt tgtacaggag gtgccctggg ctgtgtcttt gtggtctgtg tgcacagtaa    60
tatgtggctg tgtccacagg gtccatgttg gtcattgtaa                         100

<210> SEQ ID NO 840
<211> LENGTH: 100
<212> TYPE: DNA
<213> ORGANISM: Homo sapiens

<400> SEQUENCE: 840
gtgtccttgg tgatggtgag cctgctcttc agagatgggc tgtagcgctt atcatcattc    60
caataaatga gtgcaagcca ctccagggcc tttcctgggg                         100

<210> SEQ ID NO 841
<211> LENGTH: 100
<212> TYPE: DNA
<213> ORGANISM: Homo sapiens

<400> SEQUENCE: 841
gctgacggat ccagcccaca cccactccac tagtgctgag tgagaaccca gagaaggtgc    60
aggtcagcgt gagggtctgt gtgggtttca ccagcgtagg                         100

<210> SEQ ID NO 842
<211> LENGTH: 100
<212> TYPE: DNA
<213> ORGANISM: Homo sapiens

<400> SEQUENCE: 842
ctgtggagaa agcataagaa gatgaagccc acaaacaaga aaactgatgt ttcacccgtg    60
aaggagtccc tgaccacagc actcacatga agggatggtc                         100

<210> SEQ ID NO 843
<211> LENGTH: 100
<212> TYPE: DNA
<213> ORGANISM: Homo sapiens

<400> SEQUENCE: 843
agcagcagga gcgtggagca aagtgtgtcc atggtggggc acaggagtca ctgagctggg    60
acctgtgctc ggcttttca acccagagga gggtggagct                          100

<210> SEQ ID NO 844
<211> LENGTH: 100
<212> TYPE: DNA
<213> ORGANISM: Homo sapiens

<400> SEQUENCE: 844
aagtgtgtcc atggtggggc acaggagtca ctgagctggg acctgtgctc ggcttttca    60 acccagagga gggtggagct ggtggagatt tgcattcccc                         100

<210> SEQ ID NO 845
<211> LENGTH: 100
<212> TYPE: DNA
<213> ORGANISM: Homo sapiens

<400> SEQUENCE: 845
agatttgcat tcccctcatc tgtgccctac tctatgggat ggagtcaggt ttcaggactc    60
aggagggtgt tgcatctgtg gtgaggacca gtgatagtaa                         100

<210> SEQ ID NO 846
<211> LENGTH: 100
<212> TYPE: DNA
<213> ORGANISM: Homo sapiens

<400> SEQUENCE: 846
catgatcagt gtaattcaga tggcattaat ctaaggctgg gcaagtagat tctgagtaga    60
agtctttgca gaagtcatga ttatgaggtc atgttggtct                         100

<210> SEQ ID NO 847
<211> LENGTH: 100
<212> TYPE: DNA
<213> ORGANISM: Homo sapiens

<400> SEQUENCE: 847
gcccttcaca gagtccacat agtatttctc acttccatct tgctttatgt tggccaccca    60
ctccagcccc ttccctggag cctggcggac ccagctcatc                         100

<210> SEQ ID NO 848
<211> LENGTH: 100
<212> TYPE: DNA
<213> ORGANISM: Homo sapiens

<400> SEQUENCE: 848
tgagtcctct gtgctcagtg ctgatcacca agtggaaagg ccttggagtc cagggctaag    60
gctcctctct gagacctgca gggtcagggt tgggttggtt                         100

<210> SEQ ID NO 849
<211> LENGTH: 100
<212> TYPE: DNA
<213> ORGANISM: Homo sapiens

<400> SEQUENCE: 849
ttcatcagta gagggagggc cctatttgca tgtctcctac tatataagaa gctctagtgg    60
gatgctggag gaataggctg tacccatata agaagacggt                         100

```
<210> SEQ ID NO 850
<211> LENGTH: 100
<212> TYPE: DNA
<213> ORGANISM: Homo sapiens

<400> SEQUENCE: 850
agggccctat tgcatgtct cctactatat aagaagctct agtgggatgc tggaggaata     60
ggctgtaccc atataagaag acggtgctct gcagaagttt                         100

<210> SEQ ID NO 851
<211> LENGTH: 100
<212> TYPE: DNA
<213> ORGANISM: Homo sapiens

<400> SEQUENCE: 851
gctgacaatg atggtatttg gaaaatatgc tgtcttatga aattgtgctg tgataaacac    60
tttgccctga tcaccctatt acattttta aaaaatgtgt                         100

<210> SEQ ID NO 852
<211> LENGTH: 100
<212> TYPE: DNA
<213> ORGANISM: Homo sapiens

<400> SEQUENCE: 852
caaacacaga gacaacctag tcagaaactg ccacatatat tcactgctta tctcactcac    60
gtccactcaa tgtctctagt tctccataaa tcaccttta                         100

<210> SEQ ID NO 853
<211> LENGTH: 100
<212> TYPE: DNA
<213> ORGANISM: Homo sapiens

<400> SEQUENCE: 853
taatagcaac aaggaaaacc cagctcagcc caaactccat ggtgagtcct ctgtgttcag    60
tgctgatcac cgaatggaaa ctcctgggaa ttctggggct                        100

<210> SEQ ID NO 854
<211> LENGTH: 100
<212> TYPE: DNA
<213> ORGANISM: Homo sapiens

<400> SEQUENCE: 854
gtcctctgtg ttcagtgctg atcaccgaat ggaaactcct gggaattctg ggctggggc    60 tcttctccca gagctgcagg gtctgggctc ggctggtttt                        100

<210> SEQ ID NO 855
<211> LENGTH: 100
<212> TYPE: DNA
<213> ORGANISM: Homo sapiens

<400> SEQUENCE: 855
tatcagcaga gggagggccc tatttgcatg tctcctacta tatagcaagc tctagtggga    60
cgctggagga gagggcagtg cccagagcag atgagagggt                        100

<210> SEQ ID NO 856
<211> LENGTH: 100
<212> TYPE: DNA
<213> ORGANISM: Homo sapiens

<400> SEQUENCE: 856
```

```
cccggaaaac actggaggta atcctatctc tcaggaaaat ataacttcag attatgtgat    60
tgtgacttga tgatcaatta gcagtcatca tcttatttaa                        100
```

<210> SEQ ID NO 857
<211> LENGTH: 100
<212> TYPE: DNA
<213> ORGANISM: Homo sapiens

<400> SEQUENCE: 857

```
tgtttacata tttgcagaat atattcagtg caagtgtcaa tgttacattt ttagagaaga    60
tgaattacat acataacaga gcagttgtgc aatgtgtcca                        100
```

<210> SEQ ID NO 858
<211> LENGTH: 100
<212> TYPE: DNA
<213> ORGANISM: Homo sapiens

<400> SEQUENCE: 858

```
actcacactt aatctctcta gttctccata aatcaccttt taaaatagca gcaaggaaaa    60
tccagctcag cccaaactcc atggtgagtc ctctgtgttc                        100
```

<210> SEQ ID NO 859
<211> LENGTH: 100
<212> TYPE: DNA
<213> ORGANISM: Homo sapiens

<400> SEQUENCE: 859

```
gatgctattt aatagcccaa ttcctgaccc aggatgagaa agagcaaata catgacacat    60
ggacgacaca attgtagaag ctgagggttc aagccgtaat                        100
```

<210> SEQ ID NO 860
<211> LENGTH: 100
<212> TYPE: DNA
<213> ORGANISM: Homo sapiens

<400> SEQUENCE: 860

```
cctgttagag gccacgcatc ccctacccat ccctgaactc tgtgttgaca gagcttcccc    60
cactggagaa caagctcccc caggacacgc acctcactta                        100
```

<210> SEQ ID NO 861
<211> LENGTH: 100
<212> TYPE: DNA
<213> ORGANISM: Homo sapiens

<400> SEQUENCE: 861

```
ggcccttcac ggagtctgcg tagtatgtgc taccaccact accactaata gctgagaccc    60
actccagccc cttccctgga gcctggcgga cccagctcat                        100
```

<210> SEQ ID NO 862
<211> LENGTH: 100
<212> TYPE: DNA
<213> ORGANISM: Homo sapiens

<400> SEQUENCE: 862

```
ggcatagctg ctaaaggtga atccagaggc tgcacaggag agtctcaggg acccccagg     60 ctgtaccaag cctcccccag actccaacag ctgcacctca                        100
```

<210> SEQ ID NO 863
<211> LENGTH: 100

-continued

```
<212> TYPE: DNA
<213> ORGANISM: Homo sapiens

<400> SEQUENCE: 863
actgtttctc tcactcttat ccattcacac tcaattttc tatttctcca tgaattacct      60
tttaaaatag ccacaagaaa aagccagctc agcccaaact                          100

<210> SEQ ID NO 864
<211> LENGTH: 100
<212> TYPE: DNA
<213> ORGANISM: Homo sapiens

<400> SEQUENCE: 864
ccatggtgag ttctctctgt tcagtcctga tcaccaaatg aaaacacctg aaaatcccag      60
ggctgggctc ctctctcaga gctgcagggt cagggctggg                          100

<210> SEQ ID NO 865
<211> LENGTH: 100
<212> TYPE: DNA
<213> ORGANISM: Homo sapiens

<400> SEQUENCE: 865
tttgcatatc tcctactata tagtaagctc tggggtgaga ggcctttgga gatagtgggg      60
ctcagagcat gtcagaatgt cctcggggag atctgtgata                          100

<210> SEQ ID NO 866
<211> LENGTH: 100
<212> TYPE: DNA
<213> ORGANISM: Homo sapiens

<400> SEQUENCE: 866
ttgaaagcat tgggaaattg tgctttccta ttgtcagttt gttttgtgat aaacttaaac      60
cttaaaacct aaaaatctta taattttgta attttattt                           100

<210> SEQ ID NO 867
<211> LENGTH: 100
<212> TYPE: DNA
<213> ORGANISM: Homo sapiens

<400> SEQUENCE: 867
gaggtaccat agatctacat aaactgcata tttttaaagt tagcaccaat catcttttat      60
ttttacatac gcagagaaac catggtatat agtatcaata                          100

<210> SEQ ID NO 868
<211> LENGTH: 100
<212> TYPE: DNA
<213> ORGANISM: Homo sapiens

<400> SEQUENCE: 868
ttatttccat gttaaagatg aaaaattatc agcaaaagca caggtgggtt ttacaatgtc      60
cccagtgctc acttttggtc agagtgagcc tgggcatctg                          100

<210> SEQ ID NO 869
<211> LENGTH: 100
<212> TYPE: DNA
<213> ORGANISM: Homo sapiens

<400> SEQUENCE: 869
tcctacataa tgacagtgta cacatctttc cattgctgtt ttactcaatt actcaaccca      60
```

```
tttctaaac agatttaaac ttcataaatc ctgtcatctc                          100
```

<210> SEQ ID NO 870
<211> LENGTH: 100
<212> TYPE: DNA
<213> ORGANISM: Homo sapiens

<400> SEQUENCE: 870

```
ctcagcctca gcacagctgc ctcattcctc agggtttctg acgctctcag gatgtgggtt    60
ttcacactgt gtctgttgca cagtaataca cggccgtgtc                         100
```

<210> SEQ ID NO 871
<211> LENGTH: 100
<212> TYPE: DNA
<213> ORGANISM: Homo sapiens

<400> SEQUENCE: 871

```
gctcagctcc atgtaggctg tgtctgtaga tgtgtcctcg gtcatggtga ctctgccctg    60
gaacttctgt gcgtagattg tttcaccatc ttcaggatca                         100
```

<210> SEQ ID NO 872
<211> LENGTH: 100
<212> TYPE: DNA
<213> ORGANISM: Homo sapiens

<400> SEQUENCE: 872

```
ttcaggatca aaacctccca tccactcaag cccttttcca ggagcctgtc gcacccagtg    60
catggataat tcagtgaggg tgtatccgga aaccttgcag                         100
```

<210> SEQ ID NO 873
<211> LENGTH: 100
<212> TYPE: DNA
<213> ORGANISM: Homo sapiens

<400> SEQUENCE: 873

```
gagaccttca ctgaggcccc aggcttcttc acctcagccc cagactgtac cagctggacc    60
tgggcgtggg tgcctgtgga gaggacagag gagtggatga                         100
```

<210> SEQ ID NO 874
<211> LENGTH: 100
<212> TYPE: DNA
<213> ORGANISM: Homo sapiens

<400> SEQUENCE: 874

```
gacaccactt aactggaccc agtcccctca tcagccctgg aactcaggat tctcttgcct    60
gtagctgctg ccaccaagaa gaggatcctc caggtgcagt                         100
```

<210> SEQ ID NO 875
<211> LENGTH: 100
<212> TYPE: DNA
<213> ORGANISM: Homo sapiens

<400> SEQUENCE: 875

```
gagggtggga atctgggaga gcaaggggct tcccataagt gttctgataa aaatcctctt    60
tgtttagggg gaaagtgatg attttttttga atgatagaga                        100
```

<210> SEQ ID NO 876
<211> LENGTH: 100
<212> TYPE: DNA
<213> ORGANISM: Homo sapiens

```
<400> SEQUENCE: 876
atacatcacc caaacattta aaatgtatt gtgtaaagaa gtgtaaatgg catctcagcc    60
atttacacac tgcaagacac acagcttatt agtgtgcctg                        100

<210> SEQ ID NO 877
<211> LENGTH: 100
<212> TYPE: DNA
<213> ORGANISM: Homo sapiens

<400> SEQUENCE: 877
tggtgaatcg gcccttcacg gagtctgcat agtatttatt acttccatca tatgatataa    60
ctgccaccca ctccagcccc ttgcctggag cctggcggac                        100

<210> SEQ ID NO 878
<211> LENGTH: 100
<212> TYPE: DNA
<213> ORGANISM: Homo sapiens

<400> SEQUENCE: 878
acaatcactt gagttcagac acaccaggat tcacttaatg ttattttag ttcagaacct    60 ctatcaggtt tagagggaat cgctctgtcc cagggagtgg                        100

<210> SEQ ID NO 879
<211> LENGTH: 100
<212> TYPE: DNA
<213> ORGANISM: Homo sapiens

<400> SEQUENCE: 879
atcttacaat agcaaaacgg tcttagaaaa cccaacataa tctacagcga gacctcagca    60
tggcaagcaa ggaatcacta aagccaccag ggagatccgg                        100

<210> SEQ ID NO 880
<211> LENGTH: 100
<212> TYPE: DNA
<213> ORGANISM: Homo sapiens

<400> SEQUENCE: 880
cactaaagcc accagggaga tccggatgca ctgatacgat ccagaaacat agcgagtccg    60
ggaactgatg cggactttga ggcagcctct ttttttttt                         100

<210> SEQ ID NO 881
<211> LENGTH: 100
<212> TYPE: DNA
<213> ORGANISM: Homo sapiens

<400> SEQUENCE: 881
gatggtgaat cggcccttca cggagtctgc atagtattta ttacttccat cataccatat    60
aactgccacc cactccagcc ccttgcctgg agcctggcgg                        100

<210> SEQ ID NO 882
<211> LENGTH: 100
<212> TYPE: DNA
<213> ORGANISM: Homo sapiens

<400> SEQUENCE: 882
acccagtgca tgccatagct actgaaggtg aatccagacg ctgcacagga gagtctcagg    60
gacctcccag gctggaccac gcctccccca gactccacca                        100
```

<210> SEQ ID NO 883
<211> LENGTH: 100
<212> TYPE: DNA
<213> ORGANISM: Homo sapiens

<400> SEQUENCE: 883
ctcgactctt gagggacggg ttgtagttgg tgcttccact atgattgatt tccccaatcc    60
actccagccc cttccctggg ggctggcgga tccagctcca                         100

<210> SEQ ID NO 884
<211> LENGTH: 100
<212> TYPE: DNA
<213> ORGANISM: Homo sapiens

<400> SEQUENCE: 884
ggctggcgga tccagctcca gtagtaacca ctgaaggacc caccatagac agcgcaggtg    60
agggacaggg tctccgaagg cttcaacagt cctgcgcccc                         100

<210> SEQ ID NO 885
<211> LENGTH: 100
<212> TYPE: DNA
<213> ORGANISM: Homo sapiens

<400> SEQUENCE: 885
actgctgtag ctgcacctgg acaggaccc ctgtgaacag agaaacccac agtgagccct     60
gggatcagag gcagcatctc atatcttcat atccgcattc                         100

<210> SEQ ID NO 886
<211> LENGTH: 100
<212> TYPE: DNA
<213> ORGANISM: Homo sapiens

<400> SEQUENCE: 886
ctgagacact cacatctggg agctgccacc aggaggagga agaaccacag gtgtttcatg    60
ttcttgtgca ggaggtccat gactctcaga aagcacttcc                         100

<210> SEQ ID NO 887
<211> LENGTH: 100
<212> TYPE: DNA
<213> ORGANISM: Homo sapiens

<400> SEQUENCE: 887
gaggatttgc atgtgggtgg tgcctttgta tggataggta aaaagggatg agggaggccc    60
cagtcttttg ggctcaccct gggaggtgta tgctggctgt                         100

<210> SEQ ID NO 888
<211> LENGTH: 100
<212> TYPE: DNA
<213> ORGANISM: Homo sapiens

<400> SEQUENCE: 888
agttctcttc ctgtggcctc ccctcaccaa acccagagtc ctcttcttcc aggtaggaaa    60
tgtgctgaag gagctggtct gggagacaag tgtgatcatg                         100

<210> SEQ ID NO 889
<211> LENGTH: 100
<212> TYPE: DNA
<213> ORGANISM: Homo sapiens

<400> SEQUENCE: 889

```
ggtctgggag acaagtgtga tcatggatca aagacagatt ttggaataca gttaatactg      60
ttctacattt aaagattcat ataacaccaa ccatacaccc                           100

<210> SEQ ID NO 890
<211> LENGTH: 100
<212> TYPE: DNA
<213> ORGANISM: Homo sapiens

<400> SEQUENCE: 890
aggtcaccta aattgtcatt taccccttca gacatattga acagctgct gagtgtaata       60 atcacagtga attgagacaa acctggatcc atgcaatgtg                           100

<210> SEQ ID NO 891
<211> LENGTH: 100
<212> TYPE: DNA
<213> ORGANISM: Homo sapiens

<400> SEQUENCE: 891
tactgtagtt cagaacatcc atcatggtta gaaggatgct acctgtccca ggaagtgggt      60
tatttttaaa tagtacctga gagctgccct tctgagacct                           100

<210> SEQ ID NO 892
<211> LENGTH: 100
<212> TYPE: DNA
<213> ORGANISM: Homo sapiens

<400> SEQUENCE: 892
tttgaaattt gagattgtgt gtgagatctc aggagaaggt agtagaatat atctccatcc      60
ttctcaatgt gtaaccctga gaatatggcc tgacctctaa                           100

<210> SEQ ID NO 893
<211> LENGTH: 100
<212> TYPE: DNA
<213> ORGANISM: Homo sapiens

<400> SEQUENCE: 893
acatttctgt gtgaaaagat gtacattggg gatagcagtg acagcttcag atgaaaactc      60
tatagtacat cagcactgga ggatagtctc atcaccaaga                           100

<210> SEQ ID NO 894
<211> LENGTH: 100
<212> TYPE: DNA
<213> ORGANISM: Homo sapiens

<400> SEQUENCE: 894
ttagtgaaat tacctttcct gggaaccaga gaggacctct gtgagctcta ccctctgaga      60
gaacaaggaa ctctggttct tccctgacag gtcacacctg                           100

<210> SEQ ID NO 895
<211> LENGTH: 100
<212> TYPE: DNA
<213> ORGANISM: Homo sapiens

<400> SEQUENCE: 895
aacaagtggg ctggccttct atgagacgac agagggaaag agacagactc aatatccaga      60
gcgaggtgag ctccttacct acctaccagg tggtctctgg                           100

<210> SEQ ID NO 896
```

```
<211> LENGTH: 100
<212> TYPE: DNA
<213> ORGANISM: Homo sapiens

<400> SEQUENCE: 896
gccatttgtt tgagcagacc cagaagtacc ttcctcaccc tcaggagaat tatgaacatt      60
gagagaaact gagatacttt ttttatttac agggaatatt                          100

<210> SEQ ID NO 897
<211> LENGTH: 100
<212> TYPE: DNA
<213> ORGANISM: Homo sapiens

<400> SEQUENCE: 897
tcatcggcgt gtttacatct acctgggtgt gtacagggat gctaggatgt gctcatacac      60
agaagagcaa gaattatatt tcgtggaaag aaaaccaaag                          100

<210> SEQ ID NO 898
<211> LENGTH: 100
<212> TYPE: DNA
<213> ORGANISM: Homo sapiens

<400> SEQUENCE: 898
agcttctgaa tttgtaggta ttgtttgctg caaatgtgtc aggtcactag atcatgttat      60
gctgctagaa gaaaaacttc ccaacattgt catggagaca                          100

<210> SEQ ID NO 899
<211> LENGTH: 100
<212> TYPE: DNA
<213> ORGANISM: Homo sapiens

<400> SEQUENCE: 899
aaatgcaaaa cagtaaagat tcaactgaga ttcccttgaa aatcaccagt aatgaacagg      60
ccaaaagaaa tcaaccattg tggaaagagt ggtcattaag                          100

<210> SEQ ID NO 900
<211> LENGTH: 100
<212> TYPE: DNA
<213> ORGANISM: Homo sapiens

<400> SEQUENCE: 900
cccagtgtca ccttacacat cctgcaggtc acctcacaca tccaccaggt caccgcacat      60 atacccaca tcacctcaga cacaccctgg tcacctcata                           100

<210> SEQ ID NO 901
<211> LENGTH: 100
<212> TYPE: DNA
<213> ORGANISM: Homo sapiens

<400> SEQUENCE: 901
catacgtcag gtcacctcac gctcacccaa ggtcacctca cacatcccgc aggtcacctc      60
gtaaatcccc caggtcacca catacatgca ccagttcacc                          100

<210> SEQ ID NO 902
<211> LENGTH: 100
<212> TYPE: DNA
<213> ORGANISM: Homo sapiens

<400> SEQUENCE: 902
ctcttgaggg acgggttgta gtaggtgctc ccactataat agatactccc aatccactcc      60
```

```
agccccttcc ctgggggctg gcggatccag ccccagtagt                         100

<210> SEQ ID NO 903
<211> LENGTH: 100
<212> TYPE: DNA
<213> ORGANISM: Homo sapiens

<400> SEQUENCE: 903
aactactact gctgatggag ccaccagaga cagtgcaggt gagggacagg gtctccgaag    60
gcttcaccag tcctgggccc gactcctgca gctgcagctg                         100

<210> SEQ ID NO 904
<211> LENGTH: 100
<212> TYPE: DNA
<213> ORGANISM: Homo sapiens

<400> SEQUENCE: 904
gaacagaaaa acccacagtg agccctggga tcagaggcag cctcccatat ctccatgtct    60
gcatcctaga aacactcaca tctgggagcc gccaccagca                         100

<210> SEQ ID NO 905
<211> LENGTH: 100
<212> TYPE: DNA
<213> ORGANISM: Homo sapiens

<400> SEQUENCE: 905
ggaggaagaa ccacaggtgc ttcattttct tgcacatgag atccatgact ctcagaaagc    60
atttccctta tgagttggac ctgaatttaa ggaaatgtgt                         100

<210> SEQ ID NO 906
<211> LENGTH: 100
<212> TYPE: DNA
<213> ORGANISM: Homo sapiens

<400> SEQUENCE: 906
ggtggcttcc tgtgggcgcc taagtgagga tttgcatggg ggtggtgcgt ttgtacggag    60
cagtgaaaag ggatgagaga ggcgccagtc ttttgagctc                         100

<210> SEQ ID NO 907
<211> LENGTH: 100
<212> TYPE: DNA
<213> ORGANISM: Homo sapiens

<400> SEQUENCE: 907
accctgggag gagaatgctg gctgtgccct ttgagaactc agttctcttc ttgggcctcc    60
cctctccaag cccagagtcc tcttcttcca ggtaaagaga                         100

<210> SEQ ID NO 908
<211> LENGTH: 100
<212> TYPE: DNA
<213> ORGANISM: Homo sapiens

<400> SEQUENCE: 908
tgtgctgaag gagctggtct gagagatgag tgtgatcctg gatcaaggac agattttgga    60
atagggtcag tactgttcaa cccttaaaga ttcatataaa                         100

<210> SEQ ID NO 909
<211> LENGTH: 100
<212> TYPE: DNA
```

```
<213> ORGANISM: Homo sapiens

<400> SEQUENCE: 909
acccaccaca cacccaggcc atctaaatag tcatttaccc tttcagacac attgaaacaa    60
cagctgaatg taataatgac agtgacttca aacaatactg                         100

<210> SEQ ID NO 910
<211> LENGTH: 100
<212> TYPE: DNA
<213> ORGANISM: Homo sapiens

<400> SEQUENCE: 910
atgtttattg tagttcagaa catccaccat ggttacaggg aagctcactg tccctggaag    60
tgggtcattt tttaaaagca cctgagagct gtccttctgt                         100

<210> SEQ ID NO 911
<211> LENGTH: 100
<212> TYPE: DNA
<213> ORGANISM: Homo sapiens

<400> SEQUENCE: 911
aaggtagtgg gacatatctc catacttctc aatgtgtgac cttgaagatg tgtcctgccc    60
tctaaacact tctgattgaa aatatgtaga ttggggatta                         100

<210> SEQ ID NO 912
<211> LENGTH: 100
<212> TYPE: DNA
<213> ORGANISM: Homo sapiens

<400> SEQUENCE: 912
gtggaaatgc cttggaatcc agggctaagg cacctctctg agagctgcag ggtcagggtt    60
gggttggttt tcatcagtag agggagggcc ctatttgcat                         100

<210> SEQ ID NO 913
<211> LENGTH: 100
<212> TYPE: DNA
<213> ORGANISM: Homo sapiens

<400> SEQUENCE: 913
ggacccttga ggagtaggct gtacccagat aagacgacgg tgccctgtag aagtttgctg    60
gcaatgattg catttggaaa atatgctgtc ttattatgaa                         100

<210> SEQ ID NO 914
<211> LENGTH: 100
<212> TYPE: DNA
<213> ORGANISM: Homo sapiens

<400> SEQUENCE: 914
attgtgctgt gataaacact ttgcactaat caccctattt cattttaaat attcatgtaa    60
actatgttct gtaggagaca atattttctc catttacaga                         100

<210> SEQ ID NO 915
<211> LENGTH: 100
<212> TYPE: DNA
<213> ORGANISM: Homo sapiens

<400> SEQUENCE: 915
acactttgca ctaatcaccc tatttcattt taaatattca tgtaaactat gttctgtagg    60
agacaatatt ttctccattt acagaagtgg aagtaaaccc                         100
```

<210> SEQ ID NO 916
<211> LENGTH: 100
<212> TYPE: DNA
<213> ORGANISM: Homo sapiens

<400> SEQUENCE: 916
ctgtatgcat ctaggagctc atgtctggga tgagtgaacc ccggtatctg gccctgtgct    60
cttcatcact gtctctgaca tccccctaaa ccaactccag                          100

<210> SEQ ID NO 917
<211> LENGTH: 100
<212> TYPE: DNA
<213> ORGANISM: Homo sapiens

<400> SEQUENCE: 917
gacaaagctg gatgtgtcta gtgtttttat cagaacccac tttccgtaat aagagcatgt    60
gtggttttgc tgccctccag cactcttctg aaaatatgga                          100

<210> SEQ ID NO 918
<211> LENGTH: 100
<212> TYPE: DNA
<213> ORGANISM: Homo sapiens

<400> SEQUENCE: 918
gagaactagg atccaggcac attaattttc aggtacttct gacattgaac ttattttttc    60
tatctttcta ttactctttc cttgtctaag tttccatttg                          100

<210> SEQ ID NO 919
<211> LENGTH: 100
<212> TYPE: DNA
<213> ORGANISM: Homo sapiens

<400> SEQUENCE: 919
agagagaccc acagtgagcc ctgggatcag aggcacctcc catatcccca tgtctggatc    60
cctgagatac tcacatctgg gagctgccac caggagaagg                          100

<210> SEQ ID NO 920
<211> LENGTH: 100
<212> TYPE: DNA
<213> ORGANISM: Homo sapiens

<400> SEQUENCE: 920
aagaaccaca gatgtttcat gttcttgcac aggaggtcca ggactctcag aaagtatttc    60
ccatgtgagc tggaacctga atttaaggaa atgtgtggtg                          100

<210> SEQ ID NO 921
<211> LENGTH: 100
<212> TYPE: DNA
<213> ORGANISM: Homo sapiens

<400> SEQUENCE: 921
atttgcatgt gggtggtgcc tttgtatgga gaggtgaaaa aggaggaggg aggccccagt    60
cttttgggct cgccctggga gtaggatgct ggctgtgccc                          100

<210> SEQ ID NO 922
<211> LENGTH: 100
<212> TYPE: DNA
<213> ORGANISM: Homo sapiens

<400> SEQUENCE: 922
tttgagaact cagttgtctt cttggggtct ccctctcca agcccagagt cctcttcttt    60
caggtaaaga gacgtgctga aggacctggt ctgggagatg    100

<210> SEQ ID NO 923
<211> LENGTH: 100
<212> TYPE: DNA
<213> ORGANISM: Homo sapiens

<400> SEQUENCE: 923
ctgacagtgg tgaccatggt tgagaacttt tcatctcctc tgtgaggatc aatctgcatt    60
ttctgcatag gagaataggt tttcatatta aaacaatcat    100

<210> SEQ ID NO 924
<211> LENGTH: 100
<212> TYPE: DNA
<213> ORGANISM: Homo sapiens

<400> SEQUENCE: 924
tttaaaaata tgtagaaatg accctagtaa tcacagaatt ccgaacttag gttcagtaga    60
gaaactttaa gaagatgaag tcccacatcg tgacaggaaa    100

<210> SEQ ID NO 925
<211> LENGTH: 100
<212> TYPE: DNA
<213> ORGANISM: Homo sapiens

<400> SEQUENCE: 925
tggagatggt gaatctgccc ttcacagagt ctgcataata tgtgctaccc ccattactac    60
taatagctga aacatattcc agtcccttcc ctggagcctg    100

<210> SEQ ID NO 926
<211> LENGTH: 100
<212> TYPE: DNA
<213> ORGANISM: Homo sapiens

<400> SEQUENCE: 926
gcggacccag tgcatagcat agctactgaa ggtgaatcca gaggctgcac aggagagtct    60
cagggacccc ccaggctgga ccaagccttc cccagactcc    100

<210> SEQ ID NO 927
<211> LENGTH: 100
<212> TYPE: DNA
<213> ORGANISM: Homo sapiens

<400> SEQUENCE: 927
ttctctcact catgtccact cacactcaat atctctattt cctcatgaat cacctttaaa    60
aatagcaaca aggaaaaccc agctcagccc aaactccatc    100

<210> SEQ ID NO 928
<211> LENGTH: 100
<212> TYPE: DNA
<213> ORGANISM: Homo sapiens

<400> SEQUENCE: 928
atgactcttc tgtgttcagt gctgatcacc aaatgaaaac acctgggaat cccagggcgg    60
gggctcctct cccagagctg cggagtcagg gctgggctgg    100

```
<210> SEQ ID NO 929
<211> LENGTH: 100
<212> TYPE: DNA
<213> ORGANISM: Homo sapiens

<400> SEQUENCE: 929
tagggcacat ccttcccatc cactcaagcc cttgtgcatg ggcctggcgc acctagtgca      60
tagagtaact ggtgaaggta ggtgtatcca caagtcttgc                           100

<210> SEQ ID NO 930
<211> LENGTH: 100
<212> TYPE: DNA
<213> ORGANISM: Homo sapiens

<400> SEQUENCE: 930
aggagacttt cactgatgcc ccagccttct tcatctcatc cccagactgc accagctgca      60
cctgggactg ggcacctgtg gagaggacac gggagtggat                           100

<210> SEQ ID NO 931
<211> LENGTH: 100
<212> TYPE: DNA
<213> ORGANISM: Homo sapiens

<400> SEQUENCE: 931
gaaaacttgt tcacagtagc accttcatgg aatgtttgta tcaacgttat agagtgtggc      60
cttttccact ctgtgaattt ggcttatatt acgactcttg                           100

<210> SEQ ID NO 932
<211> LENGTH: 100
<212> TYPE: DNA
<213> ORGANISM: Homo sapiens

<400> SEQUENCE: 932
aatggaatat ttatcttaaa attagagtat gtacttgttt ctactgttct ttttttctca      60
aatatataac ccattttgta aacagcctta aacctaataa                           100

<210> SEQ ID NO 933
<211> LENGTH: 100
<212> TYPE: DNA
<213> ORGANISM: Homo sapiens

<400> SEQUENCE: 933
ctgctcagct ccatgtaggc tgtgctcgtg gatttgtccg cggtaatcgt gactctgccc      60
tggaacttct gtgcgtagtt tgctgtacca aagataggga                           100

<210> SEQ ID NO 934
<211> LENGTH: 100
<212> TYPE: DNA
<213> ORGANISM: Homo sapiens

<400> SEQUENCE: 934
tgatccctcc catccactca agcccttgtc caggggcctg tcgcacccag ctgatagcat      60
agctgctgaa ggtgcctcca gaagccttgc aggagacctt                           100

<210> SEQ ID NO 935
<211> LENGTH: 100
<212> TYPE: DNA
<213> ORGANISM: Homo sapiens

<400> SEQUENCE: 935
```

```
caccgaggac ccaggcttct tcacctcagc cccagactgc accagctgca cctgggactg    60
gacacctgtg gagaggacac aggggtgaat aaaatcctct                         100
```

<210> SEQ ID NO 936
<211> LENGTH: 100
<212> TYPE: DNA
<213> ORGANISM: Homo sapiens

<400> SEQUENCE: 936

```
cctgggactg gacacctgtg gagaggacac aggggtgaat aaaatcctct ttaactaaac    60
caggatccct tcctcagcct taggactagg aagcccctta                         100
```

<210> SEQ ID NO 937
<211> LENGTH: 100
<212> TYPE: DNA
<213> ORGANISM: Homo sapiens

<400> SEQUENCE: 937

```
cctgtagctg ctgccaccac aaagaggaac ctccaggtcc agtccatggt gatgagctgt    60
gctcccaggg gcttcttcag aggaggaatg tggttgttat                         100
```

<210> SEQ ID NO 938
<211> LENGTH: 100
<212> TYPE: DNA
<213> ORGANISM: Homo sapiens

<400> SEQUENCE: 938

```
gtgatgctct cagggcacca atatatctat atttatctca gaagacctca ggttatttgc    60
atatgcatga ggcagggtat ttcacagctc aaagcctgat                         100
```

<210> SEQ ID NO 939
<211> LENGTH: 100
<212> TYPE: DNA
<213> ORGANISM: Homo sapiens

<400> SEQUENCE: 939

```
tttgcatatg catgaggcag ggtatttcac agctcaaagc ctgatctagg atgagaaaga    60
aaacacagat gccacatcag ctgtacaagt gtgggatgct                         100
```

<210> SEQ ID NO 940
<211> LENGTH: 100
<212> TYPE: DNA
<213> ORGANISM: Homo sapiens

<400> SEQUENCE: 940

```
cagaacaaac cccaacccca ggatgcactc ctcactgtga acccacattt tattggccta    60
aagattacct gggttttttg tgggaccatt gctgtctctg                         100
```

<210> SEQ ID NO 941
<211> LENGTH: 100
<212> TYPE: DNA
<213> ORGANISM: Homo sapiens

<400> SEQUENCE: 941

```
acattgagca ggcacctaga cccatcctgg tcccattagg aacactcaga gctcactggt    60
aacactgaaa aggtggccac tcgttaccct acatgagtgt                         100
```

<210> SEQ ID NO 942
<211> LENGTH: 100

<212> TYPE: DNA
<213> ORGANISM: Homo sapiens

<400> SEQUENCE: 942
ccagcaggac ccatggagag ttctgagatc tgctgggcac tcccaagaca gggtccccag    60
cactttcctg agggtcctga cctcccaggt ccttcagtgg                          100

<210> SEQ ID NO 943
<211> LENGTH: 100
<212> TYPE: DNA
<213> ORGANISM: Homo sapiens

<400> SEQUENCE: 943
ttatccattt ctatgtgttc ttttgaaaat gtctactcat gtcctttgct cattttaacg    60
gagttatttg gttcttgttg ctgttgttgt tgtagagttg                          100

<210> SEQ ID NO 944
<211> LENGTH: 100
<212> TYPE: DNA
<213> ORGANISM: Homo sapiens

<400> SEQUENCE: 944
ttgcaaattc ttcatattag ttccctgtca caggcaaagt gtgcaaaagt tttctgtcat    60
tctgtaaatt gcgtattcac tctgttgttg tgaaaaaaat                          100

<210> SEQ ID NO 945
<211> LENGTH: 100
<212> TYPE: DNA
<213> ORGANISM: Homo sapiens

<400> SEQUENCE: 945
tatttaggtt aattaaatct catctgtcta ttttttttta ggtagcagga cctttcatgc    60
tgaatctttg tcaaacagga tacagcttct gcttgcatga                          100

<210> SEQ ID NO 946
<211> LENGTH: 100
<212> TYPE: DNA
<213> ORGANISM: Homo sapiens

<400> SEQUENCE: 946
accactaaca ggggacatgc catttattag taaagaaaaa ggaggaaaac aaggctctga    60
gtcagatggg gatgggaaac gcacgccctg ggcaggaaat                          100

<210> SEQ ID NO 947
<211> LENGTH: 100
<212> TYPE: DNA
<213> ORGANISM: Homo sapiens

<400> SEQUENCE: 947
ggcatctcag ccacactatc ctgttctgca gaagtgggga gggagcacca ctgaaaaaca    60
cctgggttct tgtacaggaa gcgccctggg ctgtgtctct                          100

<210> SEQ ID NO 948
<211> LENGTH: 100
<212> TYPE: DNA
<213> ORGANISM: Homo sapiens

<400> SEQUENCE: 948
gtggtatccg tgcacaataa tacgtggctg tgtccacagg gtccatgttg gtcattgtaa    60
ggaccacctg gttttggag gtgtccttgg agatggtgag 100

<210> SEQ ID NO 949
<211> LENGTH: 100
<212> TYPE: DNA
<213> ORGANISM: Homo sapiens

<400> SEQUENCE: 949
acctggtttt tggaggtgtc cttggagatg gtgagcctgg tcttcagaga tgtgctgtag 60
tatttatcat catcccaatc aatgagtgca agccactcca 100

<210> SEQ ID NO 950
<211> LENGTH: 100
<212> TYPE: DNA
<213> ORGANISM: Homo sapiens

<400> SEQUENCE: 950
gggccttccc tgggggctga cggatccagc tcacacacat tccactagtg ctgagtgaga 60
acccagagaa ggtgcaggtc agtgtgaggg tctgtgtggg 100

<210> SEQ ID NO 951
<211> LENGTH: 100
<212> TYPE: DNA
<213> ORGANISM: Homo sapiens

<400> SEQUENCE: 951
tttcaccagc gcaggaccag actccctcaa ggtgacctgg gataagaccc ctgtggagaa 60
gacataagaa gatgaagccc acaaaggaga gaatagattt 100

<210> SEQ ID NO 952
<211> LENGTH: 100
<212> TYPE: DNA
<213> ORGANISM: Homo sapiens

<400> SEQUENCE: 952
ctgtggagaa gacataagaa gatgaagccc acaaaggaga gaatagattt tttgcttctg 60
aagtactacc tgaccacagc actcacagga cgggacagtc 100

<210> SEQ ID NO 953
<211> LENGTH: 100
<212> TYPE: DNA
<213> ORGANISM: Homo sapiens

<400> SEQUENCE: 953
agtagcagga gcgtggaaca aagtatgtcc atggtggaga gcaggattca ctgagcgagg 60
ccctgtcctc gtcttttgaa cccaggggag ggtggagctg 100

<210> SEQ ID NO 954
<211> LENGTH: 100
<212> TYPE: DNA
<213> ORGANISM: Homo sapiens

<400> SEQUENCE: 954
gtggagattt gcatcccctc atctgagccc tactctatgg ggtgcactca ggtctcagga 60
ctcagtaggg gagtgcatct gtggtgagga gcagtgagcc 100

<210> SEQ ID NO 955
<211> LENGTH: 100
<212> TYPE: DNA
<213> ORGANISM: Homo sapiens

```
<400> SEQUENCE: 955
tactctatgg ggtgcactca ggtctcagga ctcagtaggg gagtgcatct gtggtgagga      60
gcagtgagcc ctcaggtgtg ggggtccacg tgtgctctcc                          100

<210> SEQ ID NO 956
<211> LENGTH: 100
<212> TYPE: DNA
<213> ORGANISM: Homo sapiens

<400> SEQUENCE: 956
atcagggaat ctatctcatt tcagcaccat ggctctcagt caagtcttga cgctcctgct      60
tctacagaca ggatcttctt cgatgctccc gcaccggaca                          100

<210> SEQ ID NO 957
<211> LENGTH: 100
<212> TYPE: DNA
<213> ORGANISM: Homo sapiens

<400> SEQUENCE: 957
tgcaaccttc tggttttagt cctagaggat tagagtagaa atcaagagag ctgccgttcc      60
tcctcccttc aagaataatg atggtgggca tctgggggc                           100

<210> SEQ ID NO 958
<211> LENGTH: 100
<212> TYPE: DNA
<213> ORGANISM: Homo sapiens

<400> SEQUENCE: 958
aaggggctcc ccacaagcat tctgatcaaa atcctctttg attatgggga aaagtgatga      60
atttgtgtaa aaaaattgga gagaataaat aagaaaatac                          100

<210> SEQ ID NO 959
<211> LENGTH: 100
<212> TYPE: DNA
<213> ORGANISM: Homo sapiens

<400> SEQUENCE: 959
agttacaagt aattatgtaa agaagtgtgt gcttagcagt gtgtgtgcac acagctgcat      60
tcctagaggc atgttccatg aaaaatcgat gttgtccttg                          100

<210> SEQ ID NO 960
<211> LENGTH: 100
<212> TYPE: DNA
<213> ORGANISM: Homo sapiens

<400> SEQUENCE: 960
tgccccgtca gttctgtgga gagagtagac tgcatgaatg acttccctttt tctcagccca     60 tgaatgagcg gatgctttgg acaagggaat tggaagactc                          100

<210> SEQ ID NO 961
<211> LENGTH: 100
<212> TYPE: DNA
<213> ORGANISM: Homo sapiens

<400> SEQUENCE: 961
ctgagggagc agcaggctga ctgttgcagc cttgctctgc acctgcactg gatgtggtct      60
ctgtgctcat aaggccgtgg aaactcatca atccaggttc                          100
```

<210> SEQ ID NO 962
<211> LENGTH: 100
<212> TYPE: DNA
<213> ORGANISM: Homo sapiens

<400> SEQUENCE: 962
caaaaagggg ttaaatgatt ttggaaaagt aagtagaaaa taaaagaagg agggagtaag    60
agcggacaga agggaggaag gcaagcaagc aatgatgaac                         100

<210> SEQ ID NO 963
<211> LENGTH: 100
<212> TYPE: DNA
<213> ORGANISM: Homo sapiens

<400> SEQUENCE: 963
tgtgtaaaat tttcactaat taaaagacta ttatattgaa gaggtgccta ttaggcagcc    60
ttttgatgtt aaccatgtaa tatacaccat gaacaacctt                         100

<210> SEQ ID NO 964
<211> LENGTH: 100
<212> TYPE: DNA
<213> ORGANISM: Homo sapiens

<400> SEQUENCE: 964
gaacaacctt gtagaacaca caagagcccc ctcagagaac tggatgggtc aggtctccca    60
tccagttgcc ttaggggtta ggaacgctcc catgttgttc                         100

<210> SEQ ID NO 965
<211> LENGTH: 100
<212> TYPE: DNA
<213> ORGANISM: Homo sapiens

<400> SEQUENCE: 965
tctggttttt gctcctgagg acacaaacag ccagtgtttc ctccccggat gaatagagag    60
gcccctgggg agggtgtgtc tggcagctca ctctgcacct                         100

<210> SEQ ID NO 966
<211> LENGTH: 100
<212> TYPE: DNA
<213> ORGANISM: Homo sapiens

<400> SEQUENCE: 966
gtttcctccc cggatgaata gagaggcccc tggggagggt gtgtctggca gctcactctg    60
cacctgcacc gcggaaggtt ttagatggtc cctctcacac                         100

<210> SEQ ID NO 967
<211> LENGTH: 100
<212> TYPE: DNA
<213> ORGANISM: Homo sapiens

<400> SEQUENCE: 967
aataatacat ggcggcgtcc gaggccttca ggctgctcca ctgcaggtag gcggtgctgc    60
tggagctgtc ggctgagatg gtgacgtggc cttggaagga                         100

<210> SEQ ID NO 968
<211> LENGTH: 100
<212> TYPE: DNA
<213> ORGANISM: Homo sapiens

<400> SEQUENCE: 968

```
tgggctgtat ctggtatcag agttcccagg atagatgctc cccatccact ccagttcttt    60
cccgggcatc tggcgcaccc agtggatcca gtagctggta                          100

<210> SEQ ID NO 969
<211> LENGTH: 100
<212> TYPE: DNA
<213> ORGANISM: Homo sapiens

<400> SEQUENCE: 969
acaggagatc ctcagagact ccccgggtct tttcacctct gctgcagact gcaacagctg    60
cacctcggca aagacacctg tgtgggagac acaaaatttg                          100

<210> SEQ ID NO 970
<211> LENGTH: 100
<212> TYPE: DNA
<213> ORGANISM: Homo sapiens

<400> SEQUENCE: 970
gtgtctggag tatgaaccat gtatcagcac cgaaaggttc tagaagtcag actttcgggc    60
agtgtgtcac taactctcag catgctggcc tggctcggcc                          100

<210> SEQ ID NO 971
<211> LENGTH: 100
<212> TYPE: DNA
<213> ORGANISM: Homo sapiens

<400> SEQUENCE: 971
cacagcaagg tcttctcgcc tcccttggg taaatactga ggggtgcctc tgcaggacgg     60
gacctctgcc agactccact ccatacccag agaagcaggg                          100

<210> SEQ ID NO 972
<211> LENGTH: 100
<212> TYPE: DNA
<213> ORGANISM: Homo sapiens

<400> SEQUENCE: 972
aaaccaaaat tggagtcagc cttgaggtgt agctgttgag ccctcagcag ctggggagag    60
ctggcggatg ctgccctccc cccagtttcc taatggtgtt                          100

<210> SEQ ID NO 973
<211> LENGTH: 100
<212> TYPE: DNA
<213> ORGANISM: Homo sapiens

<400> SEQUENCE: 973
gtttaaaaag ggtcagggga cgggggaaca gatggtggga agagcacagt gcagacacct    60
ggcaccggct ctgaaggcag catggcagct acaccgttgg                          100

<210> SEQ ID NO 974
<211> LENGTH: 100
<212> TYPE: DNA
<213> ORGANISM: Homo sapiens

<400> SEQUENCE: 974
ctgggaaggg tgtgcccctg aagaagtcgt ttacattctc gagtcaattt tcctggagtg    60
tacaatggac ctgtgggaaa gcctgtatga aagggtaatg                          100

<210> SEQ ID NO 975
```

```
<211> LENGTH: 100
<212> TYPE: DNA
<213> ORGANISM: Homo sapiens

<400> SEQUENCE: 975
atgagggacc tagcacagtg tccaatattt tataggaact ggaattgagc tcataggagc    60
tcaattttat tggcattgct gttgttggat ggttaaaggg                         100

<210> SEQ ID NO 976
<211> LENGTH: 100
<212> TYPE: DNA
<213> ORGANISM: Homo sapiens

<400> SEQUENCE: 976
gtggtatccc ttttctcaga ctcccctgaa atgtatggtt tgctttgaac ccagagactg    60
atgacaggtc tgccggtgtg gttgggtgca gccttaagtt                         100

<210> SEQ ID NO 977
<211> LENGTH: 100
<212> TYPE: DNA
<213> ORGANISM: Homo sapiens

<400> SEQUENCE: 977
gctacgggaa agtgttggag ggggagaagt cagaggtaac cttgcccct ccctcaattc    60 cagatgagga aattcaggcc tgaaaaggga aagtgaccac                         100

<210> SEQ ID NO 978
<211> LENGTH: 100
<212> TYPE: DNA
<213> ORGANISM: Homo sapiens

<400> SEQUENCE: 978
ctcaaagtct catgccttgg aggacccagc aggaatccaa gacctctgaa aaggaccggc    60
agggctcttg ccacggctgg gggtgtggtc atggtaacac                         100

<210> SEQ ID NO 979
<211> LENGTH: 100
<212> TYPE: DNA
<213> ORGANISM: Homo sapiens

<400> SEQUENCE: 979
aggttttcca tccatggaag gtacctgagg gattttctct tcctccctag ggccagcatc    60
agaggagtga atagctcagt tagctcatct caggggccat                         100

<210> SEQ ID NO 980
<211> LENGTH: 100
<212> TYPE: DNA
<213> ORGANISM: Homo sapiens

<400> SEQUENCE: 980
gtgccctcgg aggtggtttg ccactttcac ggttggactg agttggagag aaacagagac    60
ccacccaggg gtggggacaa gctccctgca actcaggact                         100

<210> SEQ ID NO 981
<211> LENGTH: 100
<212> TYPE: DNA
<213> ORGANISM: Homo sapiens

<400> SEQUENCE: 981
tgcagatcac ttgcccaagt ggctccctag ctcctggctc ctggcccggg gcctgggact    60
```

```
ctccccgaag tggggctggc cactgtgagg aaccgactgg                          100

<210> SEQ ID NO 982
<211> LENGTH: 100
<212> TYPE: DNA
<213> ORGANISM: Homo sapiens

<400> SEQUENCE: 982
aggcagggac ctcttggatg ccccaggcag ttgggatgcc acttctgata aagcacgtgg    60
tggccacagt aggtgcttgg ttgctccaca gcctggcccg                          100

<210> SEQ ID NO 983
<211> LENGTH: 100
<212> TYPE: DNA
<213> ORGANISM: Homo sapiens

<400> SEQUENCE: 983
agctcagcgc tgcagaaaga aagtgaaagg gaaaaagaac tgcggggagg cggggaggta    60
ggatgaccag cggacgagct gccacagact tgccgcggcc                          100

<210> SEQ ID NO 984
<211> LENGTH: 100
<212> TYPE: DNA
<213> ORGANISM: Homo sapiens

<400> SEQUENCE: 984
ccagagctgg cgggagggag aggccaccag cagcgcgcgc gggagcccgg ggaacagcgg    60
taggtgacca aagtctcctc tgtaacccct aaggtcgggc                          100

<210> SEQ ID NO 985
<211> LENGTH: 100
<212> TYPE: DNA
<213> ORGANISM: Homo sapiens

<400> SEQUENCE: 985
tgagaatcga ggctccgaga ctgtcagcta cttgctcaag gtcacacagc aagtctggga    60
ggatgggggg atggaatatg caaaatgtag ggccgggaaa                          100

<210> SEQ ID NO 986
<211> LENGTH: 100
<212> TYPE: DNA
<213> ORGANISM: Homo sapiens

<400> SEQUENCE: 986
cacctcgttt ccagcatccc cgcaacgact ctgcgcggga accaggagcc gggaacccgg    60
agcttggctt gctgtgccca gagctccggg gccgtgggcg                          100

<210> SEQ ID NO 987
<211> LENGTH: 100
<212> TYPE: DNA
<213> ORGANISM: Homo sapiens

<400> SEQUENCE: 987
ggtggcagga aagcctggcg gcagcttctg cagagaagcc ggagcgcaga ctgggagcgc    60
ggagcagaca cactcccccg gccacccttg gccgactccg                          100

<210> SEQ ID NO 988
<211> LENGTH: 100
<212> TYPE: DNA
```

<213> ORGANISM: Homo sapiens

<400> SEQUENCE: 988
cgcgcccggg atcctgcaga ggtgcgcgcc cttcttgtac gccagacttt ggaccagggc    60
cgccgttccc tgagcttcac tttccctgtt gggtcatatt                        100

<210> SEQ ID NO 989
<211> LENGTH: 100
<212> TYPE: DNA
<213> ORGANISM: Homo sapiens

<400> SEQUENCE: 989
ccatctctaa ctctggaatc ttgggtattg ggctctccag gcggggggcc ctgctcaggg    60
aggcagtagg gagccaaacc tttaaccaga ggatgggata                        100

<210> SEQ ID NO 990
<211> LENGTH: 100
<212> TYPE: DNA
<213> ORGANISM: Homo sapiens

<400> SEQUENCE: 990
agtcctcaac tctcgttgaa catcttggcg aaggtgtgtg ttgttgggag gggtggggga    60
gggatccccc cggactgaac cgatctcttg atctctcact                        100

<210> SEQ ID NO 991
<211> LENGTH: 100
<212> TYPE: DNA
<213> ORGANISM: Homo sapiens

<400> SEQUENCE: 991
tctctacctc gctttggggc cctgagtcac accctctaag gagagaggct aaagcgcccc    60
ggaaagccag cgtgcgaatg ccggggtggg agtgggagat                        100

<210> SEQ ID NO 992
<211> LENGTH: 100
<212> TYPE: DNA
<213> ORGANISM: Homo sapiens

<400> SEQUENCE: 992
tggatctccc tggggtccag gaaagccgga atcggagcca ccatgcttag cttagtctgg    60
aactcttaaa agccgcggtc ctcctgagtc ccacagcccc                        100

<210> SEQ ID NO 993
<211> LENGTH: 100
<212> TYPE: DNA
<213> ORGANISM: Homo sapiens

<400> SEQUENCE: 993
tctccaccct aggtggcaca ggagaggtgg caaaagccta gaagttcaag gcatggctcc    60
ctccccagcc gcagcctgga gtgtctaact ttggcaggaa                        100

<210> SEQ ID NO 994
<211> LENGTH: 100
<212> TYPE: DNA
<213> ORGANISM: Homo sapiens

<400> SEQUENCE: 994
gtcttccgtt tctgctcccc actccagaga aaaataaat aaatactcct ccggagtgag    60
attaaggaaa caggtacttc ttcctcttgg agaaagagga                        100

<210> SEQ ID NO 995
<211> LENGTH: 100
<212> TYPE: DNA
<213> ORGANISM: Homo sapiens

<400> SEQUENCE: 995
cttctccgga gtgagattaa ggaaacaggt acttcttcct cttggagaaa gaggagccaa    60
aggaacttga ctccaacaaa tgatcacctt gcaaaccccc                          100

<210> SEQ ID NO 996
<211> LENGTH: 100
<212> TYPE: DNA
<213> ORGANISM: Homo sapiens

<400> SEQUENCE: 996 ggctcccttta ggggatgacc tggtctccaa caatctcaga gcgtttggag gcagggtctt    60
tggagatgac tgagtgggga atcccaggct ccccacacat                          100

<210> SEQ ID NO 997
<211> LENGTH: 100
<212> TYPE: DNA
<213> ORGANISM: Homo sapiens

<400> SEQUENCE: 997
gaacatcacc tgggatgatc aacctgttca ggatgtaggt tcccgggctc accccaggc     60 ccggttggct aggcctgggg tgaggctgag atcctgcagg                          100

<210> SEQ ID NO 998
<211> LENGTH: 100
<212> TYPE: DNA
<213> ORGANISM: Homo sapiens

<400> SEQUENCE: 998
ttaaaccatc tatcccaggt gactccaatg ttcgtttgtg gggcaaaagt ccctcaagtc    60
agagacactg ggaggcgctg atgtggtctc atctctttac                          100

<210> SEQ ID NO 999
<211> LENGTH: 100
<212> TYPE: DNA
<213> ORGANISM: Homo sapiens

<400> SEQUENCE: 999
caagaggtga aaggggtct gcggcctcgt ctccagccga gggcgggagg cgcctcgccc      60
ctacacccat ccgctccctc caacccaggc cggggagggt                          100

<210> SEQ ID NO 1000
<211> LENGTH: 100
<212> TYPE: DNA
<213> ORGANISM: Homo sapiens

<400> SEQUENCE: 1000
acccacatgg ttccaggcaa gtaataacaa aataacacgg catcccagtt aatgctgcgt    60
gcacggcggg cgctgccggt caaatctgga aggggaagga                          100

<210> SEQ ID NO 1001
<211> LENGTH: 100
<212> TYPE: DNA
<213> ORGANISM: Homo sapiens -continued

<400> SEQUENCE: 1001
gctcaggtag tcgcggagga cggggttgag ggggatgcga gccaggttct cgcggcccac    60
ggtggccacg atgcgctggc ggcacagctc ctgcagcggc    100

<210> SEQ ID NO 1002
<211> LENGTH: 100
<212> TYPE: DNA
<213> ORGANISM: Homo sapiens

<400> SEQUENCE: 1002
cgcacgcggc gctggcgcag cggggccccc agcatgcggc gcggcgccgc cacgtagtgc    60
tccagcagct cgaagaggca gtcgaagctc tcgcggctgc    100

<210> SEQ ID NO 1003
<211> LENGTH: 100
<212> TYPE: DNA
<213> ORGANISM: Homo sapiens

<400> SEQUENCE: 1003
catccaggtg aaagcggccg gcctgaaagt gcacgcggat gctcgtgggt cccgaggcca    60
tcttcacgct aagggcgaaa aagcagttcc gctggcggct    100

<210> SEQ ID NO 1004
<211> LENGTH: 100
<212> TYPE: DNA
<213> ORGANISM: Homo sapiens

<400> SEQUENCE: 1004
gtcgcgcacc aggaaggtgc ccacgggctc ggcgcgcagc cgctcgtgcg ccccgtgcac    60
gctcaggggc ccccagtaga atccgcaggc gtccaggagc    100

<210> SEQ ID NO 1005
<211> LENGTH: 100
<212> TYPE: DNA
<213> ORGANISM: Homo sapiens

<400> SEQUENCE: 1005
gcgctggcgc gcgtgatgcg ccggtaatcg gcgtgcgaac ggaatgtgcg gaagtgcgtg    60
tcgccggggg ccggggccgg daccgcgggg cacggccgcg    100

<210> SEQ ID NO 1006
<211> LENGTH: 100
<212> TYPE: DNA
<213> ORGANISM: Homo sapiens

<400> SEQUENCE: 1006
ggcgcgcggg ggccgcgggc gaggaggagg aagaggagga aggttctggc cgccgtcggg    60
gctctgctgc tgtggagact gcattgtcgg ctgccacctg    100

<210> SEQ ID NO 1007
<211> LENGTH: 100
<212> TYPE: DNA
<213> ORGANISM: Homo sapiens

<400> SEQUENCE: 1007
tttaaaatca cccaaatcaa aataattttta tcttcattaa taaataatca tcagaagttt    60
aactaatttt tactttataa tactaggttt aaaaattctt    100

<210> SEQ ID NO 1008
<211> LENGTH: 100
<212> TYPE: DNA
<213> ORGANISM: Homo sapiens

<400> SEQUENCE: 1008
aatctgaatg cccaagtcgt tgattgtcgt ttgcctgttt ccaaagattg gtagatagat    60 gccttttaa aaatctcatt tttctttaaa tctggtttac                          100

<210> SEQ ID NO 1009
<211> LENGTH: 100
<212> TYPE: DNA
<213> ORGANISM: Homo sapiens

<400> SEQUENCE: 1009
atggaaaacg ttaggagagc tcatataatg aacggcaata gcaaccccct atcttgaaac    60
gcgctctatc atcccactga aattctacca cgtggaataa                         100

<210> SEQ ID NO 1010
<211> LENGTH: 100
<212> TYPE: DNA
<213> ORGANISM: Homo sapiens

<400> SEQUENCE: 1010
tgcttggagg gtcagagttg tggaactgcc caataaccag tcgttactga gggttagttt    60
gtgaaggagg ggacagactg cttctaaaat tctgtttaat                         100

<210> SEQ ID NO 1011
<211> LENGTH: 100
<212> TYPE: DNA
<213> ORGANISM: Homo sapiens

<400> SEQUENCE: 1011
gacagtcaat taagatttct gagtctggct tgagggcctt tgcttccatc acagcccagt    60
cgtccttggc aagagagtct gtatatgggc cacagctcac                         100

<210> SEQ ID NO 1012
<211> LENGTH: 100
<212> TYPE: DNA
<213> ORGANISM: Homo sapiens

<400> SEQUENCE: 1012
aaaagcattg tttgaaaaaa tttattgaaa gaacattgtt tgtaaaatga gtcccaatac    60
ataggacaga ctttcctaag gtgagatgtg ttacttaccc                         100

<210> SEQ ID NO 1013
<211> LENGTH: 100
<212> TYPE: DNA
<213> ORGANISM: Homo sapiens

<400> SEQUENCE: 1013
agagctgtga aaggctttac ggatggaaac tagagactga attttccaga attttaagaa    60
gtctccccaa ccaatggccc cccactttct tttttaaac                          100

<210> SEQ ID NO 1014
<211> LENGTH: 100
<212> TYPE: DNA
<213> ORGANISM: Homo sapiens

<400> SEQUENCE: 1014

```
ggcgtgatct ccgaagccca cagtacactc atccataaag taggaaacac tacaccctcc    60
agtgctgtta gtagtgcttt ctactttatg ggtgactgca                          100

<210> SEQ ID NO 1015
<211> LENGTH: 100
<212> TYPE: DNA
<213> ORGANISM: Homo sapiens

<400> SEQUENCE: 1015
ctgtctgtct gtccgtcggc gtgtactctt caggctgccc aggcctcctg actcctgctc    60
caagagcccc ccagccctcc ttgtggcttc ctaagatccc                          100

<210> SEQ ID NO 1016
<211> LENGTH: 100
<212> TYPE: DNA
<213> ORGANISM: Homo sapiens

<400> SEQUENCE: 1016
ccctcttccc ttccccctaa aggctccacc ccatccccc agtttcagag acactcaggt    60
agagactagg gcctctggag gcctcacctt cagttctgtg                          100

<210> SEQ ID NO 1017
<211> LENGTH: 100
<212> TYPE: DNA
<213> ORGANISM: Homo sapiens

<400> SEQUENCE: 1017 aaccccctggc tggccgcttc cagccacgct agccaccctc cagcgtccaa atgaggcagc    60
cacagctccc ctgccaaggt cttggtctcc agtccacccc                          100

<210> SEQ ID NO 1018
<211> LENGTH: 100
<212> TYPE: DNA
<213> ORGANISM: Homo sapiens

<400> SEQUENCE: 1018
aaccgtgagg tcctgactgc ccagagcctc agtccccacc cttcagcctc cccaccagcc    60
caagatcctg acccccagg gcctaagtcc ccagcctccc                           100

<210> SEQ ID NO 1019
<211> LENGTH: 100
<212> TYPE: DNA
<213> ORGANISM: Homo sapiens

<400> SEQUENCE: 1019
caacagccca gggtcctgac cccccagggc ctcaggccct ggcctcccca ccagcccaag    60
gtcttgaaca caccagggcc tcaattccca gcctccccac                          100

<210> SEQ ID NO 1020
<211> LENGTH: 100
<212> TYPE: DNA
<213> ORGANISM: Homo sapiens

<400> SEQUENCE: 1020
cagctcaagg tcctgactcc cccagagcct cagtcccagc ctccatagca gcccaaggtc    60 ctgaccccc agggcctcag tccccagcca ctccaccagc                           100

<210> SEQ ID NO 1021
<211> LENGTH: 100
```

```
<212> TYPE: DNA
<213> ORGANISM: Homo sapiens

<400> SEQUENCE: 1021
cccaaagtcc tgactcccca gagccttgat tctcggcctc cccaccagcc caaagtcctg    60
actccctcac tgccctgctg ttcccctggc aggagcccaa                         100

<210> SEQ ID NO 1022
<211> LENGTH: 100
<212> TYPE: DNA
<213> ORGANISM: Homo sapiens

<400> SEQUENCE: 1022
ggctatccca acaaaaatgg tggccatgtt gggcggagga agaggctggc gccccttgag    60
acactggtcc cacttctcag cctctgcgta ccctctgcca                         100

<210> SEQ ID NO 1023
<211> LENGTH: 100
<212> TYPE: DNA
<213> ORGANISM: Homo sapiens

<400> SEQUENCE: 1023
tccccgcctt actctccagc cctcctcctt ggacacctct ttccccgcct ggggtcccgg    60
agccatttta ccttccttca ctagagaggg tttcaaggcg                         100

<210> SEQ ID NO 1024
<211> LENGTH: 100
<212> TYPE: DNA
<213> ORGANISM: Homo sapiens

<400> SEQUENCE: 1024
ctaagatttt caagaagtta aacgtagaat taagattgtt ctaattctgg ttgtaaactg    60
ctattttaaa aaacaaaaca aacagaaaac atcaaaaaca                         100

<210> SEQ ID NO 1025
<211> LENGTH: 100
<212> TYPE: DNA
<213> ORGANISM: Homo sapiens

<400> SEQUENCE: 1025
aaacaaacag aaaacatcaa aaacacaaaa agatattaaa acagcaagtc ttttgtacat    60
cactgtagca taagctgctt gaggttgtca tgcagaatag                         100

<210> SEQ ID NO 1026
<211> LENGTH: 100
<212> TYPE: DNA
<213> ORGANISM: Homo sapiens

<400> SEQUENCE: 1026
tatccttcac gtcacggaaa acaaggcgga tgttctccgt gttgatagca gtggtgaagt    60
ggtggtataa gggcttctgt tgctggtccc ggcgtttgtt                         100

<210> SEQ ID NO 1027
<211> LENGTH: 100
<212> TYPE: DNA
<213> ORGANISM: Homo sapiens

<400> SEQUENCE: 1027
ccggaaacat tccaccagga attttggac gtctcttaag cagtggggat cccccttcaaa    60
```

| | |
|---|---|
| ttctaggaaa tagtctttga tgctcacaat ttgcaccttc | 100 |

<210> SEQ ID NO 1028
<211> LENGTH: 100
<212> TYPE: DNA
<213> ORGANISM: Homo sapiens

<400> SEQUENCE: 1028

| | |
|---|---|
| tcctcaagca agtctgtctt gtttaagaac agaattatgg agacattgct gaaaacccgg | 60 |
| ttattgacga ttgtttcaaa aatgttcaga gactctgtaa | 100 |

<210> SEQ ID NO 1029
<211> LENGTH: 100
<212> TYPE: DNA
<213> ORGANISM: Homo sapiens

<400> SEQUENCE: 1029

| | |
|---|---|
| ggcgattggt cagtcgatct tccataagca cctggtcaaa ttcacttgag gaaacaagga | 60 |
| aaagtattga tgtcacactg tcgaaacatt caaaccaacg | 100 |

<210> SEQ ID NO 1030
<211> LENGTH: 100
<212> TYPE: DNA
<213> ORGANISM: Homo sapiens

<400> SEQUENCE: 1030

| | |
|---|---|
| tttcctttct gatctctgac cacctacatc aaccattttg aaaggaacat tttttatttc | 60 |
| aaagtcgtat tcatggatgc ctttggtggg tcttctggca | 100 |

<210> SEQ ID NO 1031
<211> LENGTH: 100
<212> TYPE: DNA
<213> ORGANISM: Homo sapiens

<400> SEQUENCE: 1031

| | |
|---|---|
| agcagaatat cttgttgtga tggaatataa tcctggaaaa gaaaaaactt gttttatacc | 60 |
| tattaatccc gaagtaatgc gaatttttaa tggactacta | 100 |

<210> SEQ ID NO 1032
<211> LENGTH: 100
<212> TYPE: DNA
<213> ORGANISM: Homo sapiens

<400> SEQUENCE: 1032

| | |
|---|---|
| tgtaaatatt tggccaacta agctgagtgg ctaagttctc ctgctgcccg gagcttcttg | 60 |
| gaacatgttt cctttcgca aggggtttcc ctggcttcca | 100 |

<210> SEQ ID NO 1033
<211> LENGTH: 100
<212> TYPE: DNA
<213> ORGANISM: Homo sapiens

<400> SEQUENCE: 1033

| | |
|---|---|
| ggagggccag gaagaaattc gaattggcca ccgctttctc taaaatcact ccgctcaagt | 60 |
| tatcacccct ctgggctccc gaagaccggc tggctggagg | 100 |

<210> SEQ ID NO 1034
<211> LENGTH: 100
<212> TYPE: DNA
<213> ORGANISM: Homo sapiens

<400> SEQUENCE: 1034
ctggagatag tctcaatgct cgaaatgccg taaccgaagc tccccgcggc gccggcactg      60
ggatccaggg agctgctgct acagcgcagc tctggattcc                          100

<210> SEQ ID NO 1035
<211> LENGTH: 100
<212> TYPE: DNA
<213> ORGANISM: Homo sapiens

<400> SEQUENCE: 1035
tggatgtgtt ggatatgtgc agggcgttcc tgggaggagc ggggagggag ggtgctgctg      60
gcggggctgg tctgcgtgtg ctttgcttct ctacaatggc                          100

<210> SEQ ID NO 1036
<211> LENGTH: 100
<212> TYPE: DNA
<213> ORGANISM: Homo sapiens

<400> SEQUENCE: 1036
atgctgcgtg tcggccatgc agaggcatgt cagtgagcag gggctgaggg atctccctaa      60
cggacctgct ttcagagggt cttttcatgc tgggagaacc                          100

<210> SEQ ID NO 1037
<211> LENGTH: 100
<212> TYPE: DNA
<213> ORGANISM: Homo sapiens

<400> SEQUENCE: 1037
ccagagacta aatcatgcag ccaacggggt ggtccccggc ctcaaagcag ggaggggcga      60
ggagctttgt aggcaatgcc atctgctcct gaaacgccgt                          100

<210> SEQ ID NO 1038
<211> LENGTH: 100
<212> TYPE: DNA
<213> ORGANISM: Homo sapiens

<400> SEQUENCE: 1038
cagcctcctt agtagctacc gccttagtaa gtaccactta gtaagtaccg ccttagtaag      60
taccacttag tagctacctc cttagtaagt accacttagt                          100

<210> SEQ ID NO 1039
<211> LENGTH: 100
<212> TYPE: DNA
<213> ORGANISM: Homo sapiens

<400> SEQUENCE: 1039
aagtacctcc ttagtaagta ccacttagta ctaccaccac gcctggctaa tttcgtattt      60
tttttttttt agtagagacg gggtttctcc atattggtca                          100

<210> SEQ ID NO 1040
<211> LENGTH: 100
<212> TYPE: DNA
<213> ORGANISM: Homo sapiens

<400> SEQUENCE: 1040
aggtcaggcg catactgcat gcgggtctcg cggtcgtgct ccagccacag cacggacatc      60
tggaagagcg ccagctccga ctccacgggg ggcggcagcg                          100

<210> SEQ ID NO 1041
<211> LENGTH: 100
<212> TYPE: DNA
<213> ORGANISM: Homo sapiens

<400> SEQUENCE: 1041
agtccagcag ggcgcgcatc tcctcgaagt tgagcagcag cacatcctcc accaggtact    60
tgttggccag cttcttggtc tcctccaggc cgtgcagcgc                         100

<210> SEQ ID NO 1042
<211> LENGTH: 100
<212> TYPE: DNA
<213> ORGANISM: Homo sapiens

<400> SEQUENCE: 1042
ggcgatcttg cacacctgct tgtagttctg caccgagatc tggtcgttga ggaactgcac    60
gcagagcttg gtgacctggg ggatgtgcag gatcttgctg                         100

<210> SEQ ID NO 1043
<211> LENGTH: 100
<212> TYPE: DNA
<213> ORGANISM: Homo sapiens

<400> SEQUENCE: 1043
accgacagca cctcctccac cgtgtccagg gacagggtca cgttggccgt gtagaggtac    60
tcgagcacca ggcgcagccc gatggacgag cagccctgca                         100

<210> SEQ ID NO 1044
<211> LENGTH: 100
<212> TYPE: DNA
<213> ORGANISM: Homo sapiens

<400> SEQUENCE: 1044
gcaccaggtt gttgatggcc cggggggctgg tcagcagctt gtcgtcgggg gaggaagaag    60
gagtcccggg ctcctcctgc ggcggcggct gctgctgctg                         100

<210> SEQ ID NO 1045
<211> LENGTH: 100
<212> TYPE: DNA
<213> ORGANISM: Homo sapiens

<400> SEQUENCE: 1045
tgacggctgc tgctgcggcg gctgctgctg gtccttgggg gcccccaggc cgtcctggcc    60 gccgaccccct cccccgagag gggggtggct ggagaagagc                         100

<210> SEQ ID NO 1046
<211> LENGTH: 100
<212> TYPE: DNA
<213> ORGANISM: Homo sapiens

<400> SEQUENCE: 1046
gagacttcag ccggagctgg ctattccaga gatggacctc agaggattcc ttagtctaat    60
taccttctgg gctggggtag aagatggtgt ctggagggaa                         100

<210> SEQ ID NO 1047
<211> LENGTH: 100
<212> TYPE: DNA
<213> ORGANISM: Homo sapiens

<400> SEQUENCE: 1047

```
gcacagaacc aagttccta  ctgccgcact  agctatgcaa  atactgcagg  gcacctgtgg    60
gctcatgtcc ctcctgcaag aaggtgtggt  cagtccagta                           100
```

<210> SEQ ID NO 1048
<211> LENGTH: 100
<212> TYPE: DNA
<213> ORGANISM: Homo sapiens

<400> SEQUENCE: 1048

```
attcaaaaga cgtacttctg aaataggtgg  agaaatgcat  ttatagcaaa  aagtgctaaa    60
aatatgttaa tagttatgct atttggttca  ccaggttagt                           100
```

<210> SEQ ID NO 1049
<211> LENGTH: 100
<212> TYPE: DNA
<213> ORGANISM: Homo sapiens

<400> SEQUENCE: 1049

```
gtaataaacc ataacaagag agactaaagg  ccgtatctat  atgaccttga  aatctcatct    60
tcagcgggct tattcattca gtaaccaaac  tattttttgta                          100
```

<210> SEQ ID NO 1050
<211> LENGTH: 100
<212> TYPE: DNA
<213> ORGANISM: Homo sapiens

<400> SEQUENCE: 1050

```
aggtgctgag tatttagctt aaagctaaat  aagacacatg  ccctgcccta  tagtaactgc    60
ttggtaatat tcccagtggc ttccatgggc  ctgataattt                           100
```

<210> SEQ ID NO 1051
<211> LENGTH: 100
<212> TYPE: DNA
<213> ORGANISM: Homo sapiens

<400> SEQUENCE: 1051

```
tcttagtact gaattcaaag cactttgtgt  cttgtctgca  ggcccatttg  cccagcagtg    60
gccttgccag gagagaacag gcccatgctc  ctgtcctcat                           100
```

<210> SEQ ID NO 1052
<211> LENGTH: 100
<212> TYPE: DNA
<213> ORGANISM: Homo sapiens

<400> SEQUENCE: 1052

```
caaacaaaca attcaagaag aggatttaaa  ttttagaaat  ttaaattggg  gcattttagt    60
taatcttact tttaaacacc aaacagtggc  atcaatattt                           100
```

<210> SEQ ID NO 1053
<211> LENGTH: 100
<212> TYPE: DNA
<213> ORGANISM: Homo sapiens

<400> SEQUENCE: 1053

```
tgtcaacttt ggtcaaataa gatcagatgt  tcacatcaat  catctacttt  tcttggcctt    60
ttctctattt ggcctcctag tatgagcaca  ctttgtaaaa                           100
```

<210> SEQ ID NO 1054

```
<211> LENGTH: 100
<212> TYPE: DNA
<213> ORGANISM: Homo sapiens

<400> SEQUENCE: 1054
tgtaataaaa acatgtggtg tgcttcttga catctaatcc acttgcagta atttctaggc    60 ttttgctcc tgttaggtcc tataaaataa tgacattagt                          100

<210> SEQ ID NO 1055
<211> LENGTH: 100
<212> TYPE: DNA
<213> ORGANISM: Homo sapiens

<400> SEQUENCE: 1055
atagatacct agatgcaaat ttttttcagc cgaccacaaa attaggtcca ctctgagtgg    60
tgaaaaacaa aagattctaa cattctagca aactggtaaa                          100

<210> SEQ ID NO 1056
<211> LENGTH: 100
<212> TYPE: DNA
<213> ORGANISM: Homo sapiens

<400> SEQUENCE: 1056
ccatacacaa attatagaat acaaagaatg cagccgatgc aaattctgtc actgacaagg    60
tagcaaagcc atagcctgat actcctcagg acacctcatc                          100

<210> SEQ ID NO 1057
<211> LENGTH: 100
<212> TYPE: DNA
<213> ORGANISM: Homo sapiens

<400> SEQUENCE: 1057
acgcccactg ggaacatggc acacactgga gattccagtc caaggacttt ggaatgtcaa    60
cttagctctt tacaaacaca actaagtttt tcagggaaaa                          100

<210> SEQ ID NO 1058
<211> LENGTH: 100
<212> TYPE: DNA
<213> ORGANISM: Homo sapiens

<400> SEQUENCE: 1058
agacttacat tggttttcct cttttggaaa attttaccga ttgatgatgc ccttggtctt    60
ctgtggagtc tattcttcta atcgggttgt tctccaattt                          100

<210> SEQ ID NO 1059
<211> LENGTH: 100
<212> TYPE: DNA
<213> ORGANISM: Homo sapiens

<400> SEQUENCE: 1059
tagtgtacaa cgggcttgtt tcaggggagc ttgtttggga tgcagactgt caagacccaa    60
cctggtatct ggttcataag cagtccctga aacctccctc                          100

<210> SEQ ID NO 1060
<211> LENGTH: 100
<212> TYPE: DNA
<213> ORGANISM: Homo sapiens

<400> SEQUENCE: 1060
cggttccaac aagctgctca agccaggaaa cggtggtcct ggggactcct ggaccttcag    60
```

```
cttgagaaac actgaagggg taccatttac caccacatcc                   100

<210> SEQ ID NO 1061
<211> LENGTH: 100
<212> TYPE: DNA
<213> ORGANISM: Homo sapiens

<400> SEQUENCE: 1061
tactggatta caaacgctag atctttggat ctccacgact agcaagcaag ttaaagactt    60
ttagatggca ggcgttatcg gtcaggttgg gagtgaacgc                        100

<210> SEQ ID NO 1062
<211> LENGTH: 100
<212> TYPE: DNA
<213> ORGANISM: Homo sapiens

<400> SEQUENCE: 1062
tttgtccaga ggaggaggta gggacgccgg gaagcaacaa ctctgatttt atttcgccgg    60
ctccacagcc tcccattgcc ccaggagccc acccgcactc                        100

<210> SEQ ID NO 1063
<211> LENGTH: 100
<212> TYPE: DNA
<213> ORGANISM: Homo sapiens

<400> SEQUENCE: 1063 caaccccgc atctcggacc tgtggcctca gcccagactc acatcaccaa gtgcacctac    60
ccagcctccg ttatcctgga tccaggtgtg caggtgccgg                        100

<210> SEQ ID NO 1064
<211> LENGTH: 100
<212> TYPE: DNA
<213> ORGANISM: Homo sapiens

<400> SEQUENCE: 1064
ttcaggtact cagtcatcca cagggcgatg ttgtccacca ggggcgacat ctcccggttg    60
acgctctcca cacacatgac cccaccgaac tcaaagaagg                        100

<210> SEQ ID NO 1065
<211> LENGTH: 100
<212> TYPE: DNA
<213> ORGANISM: Homo sapiens

<400> SEQUENCE: 1065
ccacaatcct cccccagttc accccgtccc tgaagagctc ctccaccacc gtggcaaagc    60
gtccccgcgc ggtgaagggc gtcaggtgca gctggctgga                        100

<210> SEQ ID NO 1066
<211> LENGTH: 100
<212> TYPE: DNA
<213> ORGANISM: Homo sapiens

<400> SEQUENCE: 1066
catctcggcg aagtcgcggc ggtagcggcg ggagaagtcg tcgccggcct ggcggagggt    60
caggtggacc acaggtggca ccgggctgag cgcaggcccc                        100

<210> SEQ ID NO 1067
<211> LENGTH: 100
<212> TYPE: DNA
```

```
<213> ORGANISM: Homo sapiens

<400> SEQUENCE: 1067
gcggcggcgc cgggggcagc cggggtctgc agcggcgagg tcctggcgac cgggtcccgg    60
gatgcggctg gatggggcgt gtgcccgggc tgggaggaga                         100

<210> SEQ ID NO 1068
<211> LENGTH: 100
<212> TYPE: DNA
<213> ORGANISM: Homo sapiens

<400> SEQUENCE: 1068
agatgcccgg tgcggggcg gccccgggg gcgcggcgcc cacatctccc gcatcccact    60
cgtagcccct ctgcgacagc ttataatgga tgtacttcat                         100

<210> SEQ ID NO 1069
<211> LENGTH: 100
<212> TYPE: DNA
<213> ORGANISM: Homo sapiens

<400> SEQUENCE: 1069
cactatctcc cggttatcgt accctgttct cccagcgtgc gccatccttc ccagaggaaa    60
agcaacgggg gccaacggca cctctcgccc cagctcccac                         100

<210> SEQ ID NO 1070
<211> LENGTH: 100
<212> TYPE: DNA
<213> ORGANISM: Homo sapiens

<400> SEQUENCE: 1070
cccacggccc ccagagaaag aagaggagtt ataatccagc tattttattg gatgtgcttt    60
gcattcttgg acgaggggt gtcttcaatc acgcggaaca                         100

<210> SEQ ID NO 1071
<211> LENGTH: 100
<212> TYPE: DNA
<213> ORGANISM: Homo sapiens

<400> SEQUENCE: 1071
cttgattctg gtgtttcccc cttggcatga gatgcaggaa attttattc caattccttt    60 cggatcttta tttcatgagg cacgttatta ttagtaagta                         100

<210> SEQ ID NO 1072
<211> LENGTH: 100
<212> TYPE: DNA
<213> ORGANISM: Homo sapiens

<400> SEQUENCE: 1072
ttgttaatat cagtctactt cctctgtgat gctgaaaggt taaagaaaaa acaaactaat    60
aagtaaaaaa tcaggtgcgt ttccctgtac acactgagtg                         100

<210> SEQ ID NO 1073
<211> LENGTH: 100
<212> TYPE: DNA
<213> ORGANISM: Homo sapiens

<400> SEQUENCE: 1073
aaagcagggc atacacacta caagtaacac ggctaaaaag aatgtattaa gctgcctgga    60
aattaaattt actcgaatgc actttaagta aaaaatctca                         100
```

<210> SEQ ID NO 1074
<211> LENGTH: 100
<212> TYPE: DNA
<213> ORGANISM: Homo sapiens

<400> SEQUENCE: 1074
aaggtttcca ttgaaagtta cattaaacca atttcctgtg cagagaactt acttgtattt    60
tttaagtaca gcatgatcct ctgtcaagtt tcctttttgt                         100

<210> SEQ ID NO 1075
<211> LENGTH: 100
<212> TYPE: DNA
<213> ORGANISM: Homo sapiens

<400> SEQUENCE: 1075
aaaaccaaaa caaatgcata aggcaacgat cccatcaatc ttcagcactc tccagttata    60
gctgatttga aacttcccaa tgaatcagga gtcgcgggga                         100

<210> SEQ ID NO 1076
<211> LENGTH: 100
<212> TYPE: DNA
<213> ORGANISM: Homo sapiens

<400> SEQUENCE: 1076
gagggagtaa aaattaggag gatttccaga tcgattccca gacttctgct tcacagaaat    60
gtcaatccgc aggaatccca accggagatc tcaagagctc                         100

<210> SEQ ID NO 1077
<211> LENGTH: 100
<212> TYPE: DNA
<213> ORGANISM: Homo sapiens

<400> SEQUENCE: 1077
gagaaaaaaa aaaggcagcg gcggcggcag atgaattaca attttcagtc cggtattcgc    60
agaagtcctg tgatgttttc cccttctcgg caatttacac                         100

<210> SEQ ID NO 1078
<211> LENGTH: 100
<212> TYPE: DNA
<213> ORGANISM: Homo sapiens

<400> SEQUENCE: 1078
tgaaggagcc ggggacggag gcaggaatcc tcttctgatt aaactccgaa cagcaaatgc    60
attttccgaa aagctgctgg ataaatgaag gcaggacgcg                         100

<210> SEQ ID NO 1079
<211> LENGTH: 100
<212> TYPE: DNA
<213> ORGANISM: Homo sapiens

<400> SEQUENCE: 1079
cctggcccgc cggtgccgag cgctagaagc ccgcgctgtg tgtggtgcgg cgaggggtgg    60
ggagaaggag gtggtggggg agggttttat ttttccctc                          100

<210> SEQ ID NO 1080
<211> LENGTH: 100
<212> TYPE: DNA
<213> ORGANISM: Homo sapiens

<400> SEQUENCE: 1080 tttcctaaa aaggatgact gctacgaagt tctccccct ggacccctc ttccgctgca      60 ccccaccggc gcaccccgcc tccgggctgc gcacccttc                          100

<210> SEQ ID NO 1081
<211> LENGTH: 100
<212> TYPE: DNA
<213> ORGANISM: Homo sapiens

<400> SEQUENCE: 1081
gtgtgtgtct cgcctggacc ttttctagcc gtgtatgtgg gagtgtgtgt gtcgcctgga      60
ccctttctag ccgtgtatga gagtgtgtac acgcgcctac                            100

<210> SEQ ID NO 1082
<211> LENGTH: 100
<212> TYPE: DNA
<213> ORGANISM: Homo sapiens

<400> SEQUENCE: 1082
acacacacac gttgtgttac cggcgctcgg ccgccggggg aagacccagg ccaatgccgc      60 ccccaccgc ccccagcagt gggacctcag cgctgccctg                             100

<210> SEQ ID NO 1083
<211> LENGTH: 100
<212> TYPE: DNA
<213> ORGANISM: Homo sapiens

<400> SEQUENCE: 1083
ctgtgaagac aggtgactct gcacgtttta agcaatgtct agggacgccc cgagcgtggt      60
gtttactttc aagtagcttc ctaggtgtcc gcgcactaca                            100

<210> SEQ ID NO 1084
<211> LENGTH: 100
<212> TYPE: DNA
<213> ORGANISM: Homo sapiens

<400> SEQUENCE: 1084
cacgcacgcg catcccgcc cgtgtccacc tgaacaccta gtccgtggcc caggccatgc       60
agaactcagc gctccaggga aggggtttat caagggcttt                            100

<210> SEQ ID NO 1085
<211> LENGTH: 100
<212> TYPE: DNA
<213> ORGANISM: Homo sapiens

<400> SEQUENCE: 1085
acgacagttt aagtcaatgt tttccctctg tccctaacac cttttacact ggtttagtgc      60
tacacgatga ggacttccat atagtaactt tcaggcccac                            100

<210> SEQ ID NO 1086
<211> LENGTH: 100
<212> TYPE: DNA
<213> ORGANISM: Homo sapiens

<400> SEQUENCE: 1086
cgtcctaacg ctggggtggg tgggctccta aaggtctcca cctttgcctc gtagccaatc      60
ctagttggcc gcactttctc aaatgaggta catagataca                            100

<210> SEQ ID NO 1087
<211> LENGTH: 100
<212> TYPE: DNA
<213> ORGANISM: Homo sapiens

<400> SEQUENCE: 1087
gtgtctccat ggagatggca gcaggaccg accccgtgct ggcccgcact ctcggcctcc    60
ttatctggtt taggaatgcg cggtatccac gctcgctcgc                         100

<210> SEQ ID NO 1088
<211> LENGTH: 100
<212> TYPE: DNA
<213> ORGANISM: Homo sapiens

<400> SEQUENCE: 1088
gcgggagcca cgcctcctct ccccccgcc cccgagaccg ccacacgcgc ggggcccca     60 cgtctccaag cggcactgga aggattcctc tccgtcccgc                         100

<210> SEQ ID NO 1089
<211> LENGTH: 100
<212> TYPE: DNA
<213> ORGANISM: Homo sapiens

<400> SEQUENCE: 1089
caggggtccc gcctcgagat tctgggaaga ctggggtgg gggaccagat cgcagcagca    60
gctgcaccgc gagttccgcg cctggccgtg tcgccccacg                         100

<210> SEQ ID NO 1090
<211> LENGTH: 100
<212> TYPE: DNA
<213> ORGANISM: Homo sapiens

<400> SEQUENCE: 1090 aggggggactg tgggctcagc gcgtggggcc cggagcatct gacaaggaca gagacagagg   60 aggggggtgga aatccccggg tgagtcaacc cgtgcctgag                         100

<210> SEQ ID NO 1091
<211> LENGTH: 100
<212> TYPE: DNA
<213> ORGANISM: Homo sapiens

<400> SEQUENCE: 1091 aaggggggcga gttccgacgc tccgcccggc tcggggccac gcgaggtccg cgccacgcgc   60
gccttcaccc acgacccatc cctgagccgg agttgaaaga                          100

<210> SEQ ID NO 1092
<211> LENGTH: 100
<212> TYPE: DNA
<213> ORGANISM: Homo sapiens

<400> SEQUENCE: 1092
ggaggcgtct gagccacgca gtcactttct ctttccttac aaaacaaagc cacgcccccc    60
gccgggggac cggaggaggc aaacaacttg gggaaaccga                          100

<210> SEQ ID NO 1093
<211> LENGTH: 100
<212> TYPE: DNA
<213> ORGANISM: Homo sapiens

<400> SEQUENCE: 1093

```
cccacttttcc ccttctgtcc ctaaagtttt ttcttcctct tgcctccccc agcccttttg      60
aaagctcccc gcgtcgtcct cctgctgccc cggctcctta                            100
```

<210> SEQ ID NO 1094
<211> LENGTH: 100
<212> TYPE: DNA
<213> ORGANISM: Homo sapiens

<400> SEQUENCE: 1094

```
gcagcttctg ggacgcacgg gagggaaaag ccgcgggac cccccccacc ccagcctccc       60
agccgggtga gatttggttg ctgtgtttcc tcctcacttg                            100
```

<210> SEQ ID NO 1095
<211> LENGTH: 100
<212> TYPE: DNA
<213> ORGANISM: Homo sapiens

<400> SEQUENCE: 1095

```
ccaccccagc ctcccagccg ggtgagattt ggttgctgtg tttcctcctc acttgggcat      60
ttaaaaaata ttttaacacg aattgtccgc ggaattttca                            100
```

<210> SEQ ID NO 1096
<211> LENGTH: 100
<212> TYPE: DNA
<213> ORGANISM: Homo sapiens

<400> SEQUENCE: 1096

```
catggcctgg acccctctcc tcctccagct tctcaccctc tgctcaggtg actgcctgtg      60
gaatgccaaa gtgattattg gggacacatg ggatgacttt                            100
```

<210> SEQ ID NO 1097
<211> LENGTH: 100
<212> TYPE: DNA
<213> ORGANISM: Homo sapiens

<400> SEQUENCE: 1097

```
tctcttatat tttaacattg tggggtgggt agtgaaccca gactcacctc tctgtgcctg      60
cctcctctgt tccagggtcc tgggcacagt ctgcgctgac                            100
```

<210> SEQ ID NO 1098
<211> LENGTH: 100
<212> TYPE: DNA
<213> ORGANISM: Homo sapiens

<400> SEQUENCE: 1098

```
ccaggaagcc tcggtgtcag ggaccgtggg acagaaggtc accctctcct gtactggaaa      60
cagcaacaac gttggaagtt atgctgtggg ctggtaccaa                            100
```

<210> SEQ ID NO 1099
<211> LENGTH: 100
<212> TYPE: DNA
<213> ORGANISM: Homo sapiens

<400> SEQUENCE: 1099

```
cagatttctc acggtgctcc caaaactgtg atgtttggaa attctctgcc ctcagggatc      60
cctgaccgct tctctggctc aaagtctggg accacagcct                            100
```

<210> SEQ ID NO 1100
<211> LENGTH: 100

```
<212> TYPE: DNA
<213> ORGANISM: Homo sapiens

<400> SEQUENCE: 1100
ccctgactat ctcgggcctc tagcctgagg acgaggctga ttattactgt tcaacatggg      60
actacagcct cagtgctcac acagtgctgc aggcacatgg                           100

<210> SEQ ID NO 1101
<211> LENGTH: 100
<212> TYPE: DNA
<213> ORGANISM: Homo sapiens

<400> SEQUENCE: 1101
ggaaccgaga caaaaacctg cccttggcct gtcccgaggc tgatcactcc atacttgcct      60
atgacaaaca aagagggtgc ctgtggctga tcgtacagtt                           100

<210> SEQ ID NO 1102
<211> LENGTH: 100
<212> TYPE: DNA
<213> ORGANISM: Homo sapiens

<400> SEQUENCE: 1102
gaaatgttgt ttgctcttgt ccttccttca ggccataatg agcgtctctg ttttcagggt      60
ctctctccca gcctgtgctg actcaatcat cctctgcctc                           100

<210> SEQ ID NO 1103
<211> LENGTH: 100
<212> TYPE: DNA
<213> ORGANISM: Homo sapiens

<400> SEQUENCE: 1103
tcaagctcac ctgcactctg agcagtgggc acagtagcta catcatcgca tggcatcagc      60
agcagccagg gaaggcccct cggtacttga tgaagcttga                           100

<210> SEQ ID NO 1104
<211> LENGTH: 100
<212> TYPE: DNA
<213> ORGANISM: Homo sapiens

<400> SEQUENCE: 1104
aggtagtgga agctacaaca aggggagcgg agttcctgat cgcttctcag gctccagctc      60
tggggctgac cgctacctca ccatctccaa cctccagttt                           100

<210> SEQ ID NO 1105
<211> LENGTH: 100
<212> TYPE: DNA
<213> ORGANISM: Homo sapiens

<400> SEQUENCE: 1105
gaggatgagg ctgattatta ctgtgagacc tgggacagta acactcacac agtgatacag      60
gcagatgagg aagtgggaca aaatcctcaa cctgctgagg                           100

<210> SEQ ID NO 1106
<211> LENGTH: 100
<212> TYPE: DNA
<213> ORGANISM: Homo sapiens

<400> SEQUENCE: 1106
aaggtcacca tctcctgctc tggaagcagc tccaacattg gaataatta tgtatcctgg      60
```
taccagcagc tcccaggaac agcccccaaa ctcctcattt                                  100

<210> SEQ ID NO 1107
<211> LENGTH: 100
<212> TYPE: DNA
<213> ORGANISM: Homo sapiens

<400> SEQUENCE: 1107
atgacaataa taagcgaccc tcagggattc ctgaccgatt ctctggctcc aagtctggca            60
cgtcagccac cctgggcatc accggactcc agactgggga                                 100

<210> SEQ ID NO 1108
<211> LENGTH: 100
<212> TYPE: DNA
<213> ORGANISM: Homo sapiens

<400> SEQUENCE: 1108
tcagccagac tcacctgcac cttgcgcagt ggcatcaatc ttggtagcta caggatattc            60
tggtaccagc agaagccaga gagccctccc cggtatctcc                                 100

<210> SEQ ID NO 1109
<211> LENGTH: 100
<212> TYPE: DNA
<213> ORGANISM: Homo sapiens

<400> SEQUENCE: 1109
tgagctacta ctcagactca agtaagcatc agggctctgg agtccccagc cgcttctctg            60
gatccaaaga tgcttcgagc aatgcaggga ttttagtcat                                 100

<210> SEQ ID NO 1110
<211> LENGTH: 100
<212> TYPE: DNA
<213> ORGANISM: Homo sapiens

<400> SEQUENCE: 1110
agagatctgg gggaagctca gcttcagctg tggtagagaa gacaggattc aggacaatct            60
ccagcatggc cggcttccct ctcctcctca ccctcctcac                                 100

<210> SEQ ID NO 1111
<211> LENGTH: 100
<212> TYPE: DNA
<213> ORGANISM: Homo sapiens

<400> SEQUENCE: 1111
tcactgtgca ggtgacagga tggggaccaa gagaggggcc ctgggaagcc catggggccc            60
tgctttctcc tcttgtctcc tttcgtctct tgtcaatcac                                 100

<210> SEQ ID NO 1112
<211> LENGTH: 100
<212> TYPE: DNA
<213> ORGANISM: Homo sapiens

<400> SEQUENCE: 1112
catgtctgtg tctctctcac ttccagggtc ctgggcccag tctgtgctga ctcagccacc            60
ctcagcgtct gggacccccg ggcagagggt caccatctct                                 100

<210> SEQ ID NO 1113
<211> LENGTH: 100
<212> TYPE: DNA
<213> ORGANISM: Homo sapiens

```
<400> SEQUENCE: 1113
tgttctggaa gcagctccaa catcggaagt aattatgtat actggtacca gcagctccca     60
ggaacggccc ccaaactcct catctatagt aataatcagc                           100

<210> SEQ ID NO 1114
<211> LENGTH: 100
<212> TYPE: DNA
<213> ORGANISM: Homo sapiens

<400> SEQUENCE: 1114
ggccctcagg ggtccctgac cgattctctg gctccaagtc tggcacctca gcctccctgg     60
ccatcagtgg gctccggtcc gaggatgagg ctgattatta                           100

<210> SEQ ID NO 1115
<211> LENGTH: 100
<212> TYPE: DNA
<213> ORGANISM: Homo sapiens

<400> SEQUENCE: 1115
atttgcataa agcagcacac agcacacccc ctccgtgcgg agagctcaat aggagataaa     60
gagccatcag aatccagccc cagctctggc accaggggtc                           100

<210> SEQ ID NO 1116
<211> LENGTH: 100
<212> TYPE: DNA
<213> ORGANISM: Homo sapiens

<400> SEQUENCE: 1116
ccttccaata tcagcaccat ggcctggact cctctctttc tgttcctcct cacttgctgc     60
ccaggttaag agagatttca ataccagcc tttggaggga                            100

<210> SEQ ID NO 1117
<211> LENGTH: 100
<212> TYPE: DNA
<213> ORGANISM: Homo sapiens

<400> SEQUENCE: 1117
tccctttttc tccctttcta attcctaata tatgtctgtt tttttgttt cagggtccaa      60 ttcccaggct gtggtgactc aggagccctc actgactgtg                           100

<210> SEQ ID NO 1118
<211> LENGTH: 100
<212> TYPE: DNA
<213> ORGANISM: Homo sapiens

<400> SEQUENCE: 1118
ggacagtcac tctcacctgt ggctccagca ctggagctgt caccagtggt cattatccct     60
actggttcca gcagaagcct ggccaagccc ccaggacact                           100

<210> SEQ ID NO 1119
<211> LENGTH: 100
<212> TYPE: DNA
<213> ORGANISM: Homo sapiens

<400> SEQUENCE: 1119
gatttatgat acaagcaaca aacactcctg gacacctgcc cggttctcag gctccctcct     60
tgggggcaaa gctgccctga ccctttggg tgcgcagcct                            100
```

<210> SEQ ID NO 1120
<211> LENGTH: 100
<212> TYPE: DNA
<213> ORGANISM: Homo sapiens

<400> SEQUENCE: 1120
gaggatgagg ctgagtatta ctgcttgctc tcctatagtg gtgctcggca cagtgacaga      60
cccatgagag gaaccaagac ataaacctcc ctcggccctt                           100

<210> SEQ ID NO 1121
<211> LENGTH: 100
<212> TYPE: DNA
<213> ORGANISM: Homo sapiens

<400> SEQUENCE: 1121
ggtcagccac ccagcctgat tctgactctt ctggcaaaga tccctgaaaa actttaccct      60
ggtttctgcc ttagcaccca ttaatgtctg tgtttccagg                           100

<210> SEQ ID NO 1122
<211> LENGTH: 100
<212> TYPE: DNA
<213> ORGANISM: Homo sapiens

<400> SEQUENCE: 1122
ttccctctcg caggctgtgc tgactcagcc gtcttccctc tctgcatctc ctggagcatc      60
agccagtctc acctgcacct tgcgcagtgg catcaatgtt                           100

<210> SEQ ID NO 1123
<211> LENGTH: 100
<212> TYPE: DNA
<213> ORGANISM: Homo sapiens

<400> SEQUENCE: 1123
gcatcagcca gtctcacctg caccttgcgc agtggcatca atgttggtac ctacaggata     60
tactggtacc agcagaagcc agggagtcct ccccagtatc                           100

<210> SEQ ID NO 1124
<211> LENGTH: 100
<212> TYPE: DNA
<213> ORGANISM: Homo sapiens

<400> SEQUENCE: 1124
tcctgaggta caaatcagac tcagataagc agcagggctc tggagtcccc agccgcttct     60
ctggatccaa agatgcttcg gccaatgcag ggatttttact                           100

<210> SEQ ID NO 1125
<211> LENGTH: 100
<212> TYPE: DNA
<213> ORGANISM: Homo sapiens

<400> SEQUENCE: 1125
acagatgggg aagtgggaca aaaacctcac cctgctctgg gtcttgctct gtaccaattt     60
ttaaatttta aataactgg cctaggcaca aactatattt                           100

<210> SEQ ID NO 1126
<211> LENGTH: 100
<212> TYPE: DNA
<213> ORGANISM: Homo sapiens

<400> SEQUENCE: 1126

```
gcccagtctg tgctgactca gccaccctca gcgtctggga cccccgggca gagggtcacc    60
atctcttgtt ctggaagcag ctccaacatc ggaagtaata                         100
```

<210> SEQ ID NO 1127
<211> LENGTH: 100
<212> TYPE: DNA
<213> ORGANISM: Homo sapiens

<400> SEQUENCE: 1127

```
ctgtaaactg gtaccagcag ctcccaggaa cggcccccaa actcctcatc tatagtaata    60
atcagcggcc ctcaggggtc cctgaccgat tctctggctc                         100
```

<210> SEQ ID NO 1128
<211> LENGTH: 100
<212> TYPE: DNA
<213> ORGANISM: Homo sapiens

<400> SEQUENCE: 1128

```
tgctgctcag gcctggcctg tggcttctgc tgctgcagct tccttcatgg gtccaggggc    60
atccagggcc ctgcctgaga gtggaggctc ctcctcccct                         100
```

<210> SEQ ID NO 1129
<211> LENGTH: 100
<212> TYPE: DNA
<213> ORGANISM: Homo sapiens

<400> SEQUENCE: 1129

```
tccagcactg gagcagtcac cagtggttac tatccaaact ggttccagca gaaacctgga    60
caagcaccca gggcactgat ttatagtaca agcaacaaac                         100
```

<210> SEQ ID NO 1130
<211> LENGTH: 100
<212> TYPE: DNA
<213> ORGANISM: Homo sapiens

<400> SEQUENCE: 1130

```
ccctccttgg gggcaaagct gccctgacac tgtcaggtgt gcagcctgag gacgaggctg    60
agtattactg cctgctctac tatggtggtg ctcagcacag                         100
```

<210> SEQ ID NO 1131
<211> LENGTH: 100
<212> TYPE: DNA
<213> ORGANISM: Homo sapiens

<400> SEQUENCE: 1131

```
tgacagactc ataagaggaa ccaagacata aacctccctc ggcccttgtg atgtggagat    60
tgtgtgatca tacacaccag ctctcaagac agcctacatg                         100
```

<210> SEQ ID NO 1132
<211> LENGTH: 100
<212> TYPE: DNA
<213> ORGANISM: Homo sapiens

<400> SEQUENCE: 1132

```
acataaacct ccctcggccc ttgtgatgtg gagattgtgt gatcatacac accagctctc    60
aagacagcct acatgtggac cagccataga aaggggaagg                         100
```

<210> SEQ ID NO 1133

```
<211> LENGTH: 100
<212> TYPE: DNA
<213> ORGANISM: Homo sapiens

<400> SEQUENCE: 1133
atagaaaggg gaaggaaagg gtctgaattg atttctatcc ctccttgtgc cctgaagtgg      60
aggaaatgtg agagtgattt gcagtaattg aatgagacaa                          100

<210> SEQ ID NO 1134
<211> LENGTH: 100
<212> TYPE: DNA
<213> ORGANISM: Homo sapiens

<400> SEQUENCE: 1134
agcaaaagtt atttgtttta tatgaaaaaa aaaaacagaa acagcaggat cagatctaaa      60
ggctgagtct aaatgcattt cctccagaca gaagcttctt                          100

<210> SEQ ID NO 1135
<211> LENGTH: 100
<212> TYPE: DNA
<213> ORGANISM: Homo sapiens

<400> SEQUENCE: 1135
cagatctaaa ggctgagtct aaatgcattt cctccagaca gaagcttctt caaacgatgg      60
gctttctgag ctaagagcaa agaaaataaa ctctccacgg                          100

<210> SEQ ID NO 1136
<211> LENGTH: 100
<212> TYPE: DNA
<213> ORGANISM: Homo sapiens

<400> SEQUENCE: 1136
gtatattatt aaagtttatt ttattgagtt actttcaaag caatccatga ctattatata      60
aagtcagaaa gtattaaaaa tcaccaagtt ctctgctaag                          100

<210> SEQ ID NO 1137
<211> LENGTH: 100
<212> TYPE: DNA
<213> ORGANISM: Homo sapiens

<400> SEQUENCE: 1137
ctaccttatc ccatgcaatc aaaataagta cttttcttca tttggatgca ttttttattt      60
ctgtttttaa tatttccaca atggtgatta aacctggtgc                          100

<210> SEQ ID NO 1138
<211> LENGTH: 100
<212> TYPE: DNA
<213> ORGANISM: Homo sapiens

<400> SEQUENCE: 1138
acagggtcag gggaggggtc caggaagccc atgaggccct gctttctcct tctctctcta      60
gaccaagaat caccgtgtct gtgtctctcc tgcttccacg                          100

<210> SEQ ID NO 1139
<211> LENGTH: 100
<212> TYPE: DNA
<213> ORGANISM: Homo sapiens

<400> SEQUENCE: 1139
gtcctgggcc cagtctgtgt tgacgcagcc gccttcagtg tctgcggccc caggacagaa      60
```

```
ggtcaccatc tcctgctctg gaagcagctc cgacatgggg                        100

<210> SEQ ID NO 1140
<211> LENGTH: 100
<212> TYPE: DNA
<213> ORGANISM: Homo sapiens

<400> SEQUENCE: 1140
aattatgcgg tatcctggta ccagcagctc ccaggaacag cccccaaact cctcatctat   60
gaaaataata agcgaccctc agggattcct gaccgattct                        100

<210> SEQ ID NO 1141
<211> LENGTH: 100
<212> TYPE: DNA
<213> ORGANISM: Homo sapiens

<400> SEQUENCE: 1141
ctggctccaa gtctggcacc tcagccaccc tgggcatcac tggcctctgg cctgaggact   60
aggccgatta ttactgctta gcatgggata ccagcctgag                        100

<210> SEQ ID NO 1142
<211> LENGTH: 100
<212> TYPE: DNA
<213> ORGANISM: Homo sapiens

<400> SEQUENCE: 1142
agcttgcaca gtgctccagg ccaatgggga actgagacaa gaaccctctt cctcctccgc   60
caggagggtg agtgcctgca gctgctgctc acacctgacc                        100

<210> SEQ ID NO 1143
<211> LENGTH: 100
<212> TYPE: DNA
<213> ORGANISM: Homo sapiens

<400> SEQUENCE: 1143
tgtagcttct gctgctgtag cttcccccat gggcctcggg gcatccaggg ccttgcctag   60
gagtggaggc tccaccactt ttgtcctcag agtcaggaac                        100

<210> SEQ ID NO 1144
<211> LENGTH: 100
<212> TYPE: DNA
<213> ORGANISM: Homo sapiens

<400> SEQUENCE: 1144
agggacccca ggagacagaa tatcctgctc ctcagcttgg gacacagggt ctctgcactg   60
aaatcgtggg ctgaggtggc aggtccaact gtgtcttcac                        100

<210> SEQ ID NO 1145
<211> LENGTH: 100
<212> TYPE: DNA
<213> ORGANISM: Homo sapiens

<400> SEQUENCE: 1145
ctctgcactg aaatcgtggg ctgaggtggc aggtccaact gtgtcttcac agtccttcct   60
gtgcctgccc atggtgtggg gacggagtga ggaagtgtgg                        100

<210> SEQ ID NO 1146
<211> LENGTH: 100
<212> TYPE: DNA
```

<213> ORGANISM: Homo sapiens

<400> SEQUENCE: 1146

```
tcctcactct cctcgctcac tgcacaggtg actggataca ggtccagggg aggggccctg    60
ggaagcctat ggattcttgc tttctcctgt tgtctctaga                         100
```

<210> SEQ ID NO 1147
<211> LENGTH: 100
<212> TYPE: DNA
<213> ORGANISM: Homo sapiens

<400> SEQUENCE: 1147

```
agccgaataa tgatgcctgt gtctctccca cttccagggt cctgggccca gtctgtgctg    60
acgcagccgc cctcagtgtc tggggcccca gggcagaggg                         100
```

<210> SEQ ID NO 1148
<211> LENGTH: 100
<212> TYPE: DNA
<213> ORGANISM: Homo sapiens

<400> SEQUENCE: 1148

```
tcaccatctc ctgcactggg agcagctcca acatcggggc aggttatgat gtacactggt    60
accagcagct tccaggaaca gccccccaaac tcctcatcta                        100
```

<210> SEQ ID NO 1149
<211> LENGTH: 100
<212> TYPE: DNA
<213> ORGANISM: Homo sapiens

<400> SEQUENCE: 1149

```
ctccaggctg aggatgaggc tgattattac tgccagtcct atgacagcag cctgagtggt    60
tccacagtgc tccaggcccg gggggaactg agacaagaac                         100
```

<210> SEQ ID NO 1150
<211> LENGTH: 100
<212> TYPE: DNA
<213> ORGANISM: Homo sapiens

<400> SEQUENCE: 1150

```
gctcctcact ctcctcactc aggacacagg tgacgcctcc agggaagggg tcttggggac    60
ctctgggctg atccttggtc tcctgctcct caggctcacc                         100
```

<210> SEQ ID NO 1151
<211> LENGTH: 100
<212> TYPE: DNA
<213> ORGANISM: Homo sapiens

<400> SEQUENCE: 1151

```
ttccagggtc ctgggcccag tctgccctga ctcagcctgc ctccgtgtct gggtctcctg    60
gacagtcgat caccatctcc tgcactggaa ccagcagtga                         100
```

<210> SEQ ID NO 1152
<211> LENGTH: 100
<212> TYPE: DNA
<213> ORGANISM: Homo sapiens

<400> SEQUENCE: 1152

```
tgttgggagt tataaccttg tctcctggta ccaacagcac ccaggcaaag cccccaaact    60
catgatttat gagggcagta agcggccctc aggggtttct                         100
```

<210> SEQ ID NO 1153
<211> LENGTH: 100
<212> TYPE: DNA
<213> ORGANISM: Homo sapiens

<400> SEQUENCE: 1153
aatcgcttct ctggctccaa gtctggcaac acggcctccc tgacaatctc tgggctccag    60
gctgaggacg aggctgatta ttactgctgc tcatatgcag                         100

<210> SEQ ID NO 1154
<211> LENGTH: 100
<212> TYPE: DNA
<213> ORGANISM: Homo sapiens

<400> SEQUENCE: 1154
gctgaggacg aggctgatta ttactgctgc tcatatgcag gtagtagcac tttccacagt    60
ggtccaagtt catggggaac tgagaccaaa acctgcccag                         100

<210> SEQ ID NO 1155
<211> LENGTH: 100
<212> TYPE: DNA
<213> ORGANISM: Homo sapiens

<400> SEQUENCE: 1155
ggccttcaga cttcctcctt gctctgaaga tgcttcctca cccggtgcaa gaggcttgct    60
gcagcgcggc cttgagaatt cttctctctc agctccttcc                         100

<210> SEQ ID NO 1156
<211> LENGTH: 100
<212> TYPE: DNA
<213> ORGANISM: Homo sapiens

<400> SEQUENCE: 1156
ctttccacca tgaattccaa caggaaacct gccctgtggt ttcccatcca ggacagggac    60
agcttcctga tgcttgtgtg ctgtggtccc tgaatgtgca                         100

<210> SEQ ID NO 1157
<211> LENGTH: 100
<212> TYPE: DNA
<213> ORGANISM: Homo sapiens

<400> SEQUENCE: 1157
actcttccca gctcttcaaa tgcagggaca gtgacaagga gctgcctgat tggtgcagtc    60
actgcttttt tcagggatgt cttcaccta catgtatcat                          100

<210> SEQ ID NO 1158
<211> LENGTH: 100
<212> TYPE: DNA
<213> ORGANISM: Homo sapiens

<400> SEQUENCE: 1158
catcccctac actgtgggta gaattttagc aactacattc taatggttat cgccacaact    60
ttgatcttag aaataacagt gcagtgaaca tccctatgca                         100

<210> SEQ ID NO 1159
<211> LENGTH: 100
<212> TYPE: DNA
<213> ORGANISM: Homo sapiens

<400> SEQUENCE: 1159
ggctcctttg agttcctgtg tgaatacgac cataggattc atttctaaaa gtgaaattgc    60
gggtcagaaa gatgtgtgtt tgtgattttc acccaatgtt                          100

<210> SEQ ID NO 1160
<211> LENGTH: 100
<212> TYPE: DNA
<213> ORGANISM: Homo sapiens

<400> SEQUENCE: 1160
accagcagaa gccaggccag gcccctgtgc tggtcgtcta tgatgatagc gaccggccct    60
cagggatccc tgagcgattc tctggctcca actctgggaa                          100

<210> SEQ ID NO 1161
<211> LENGTH: 100
<212> TYPE: DNA
<213> ORGANISM: Homo sapiens

<400> SEQUENCE: 1161
cccagcctcg gtcaccctct tgctccagcc ccgggaagcc tgttgataaa gccatgagtg    60
aatctggccc agttcacctg gatctgagcc tttcaggttg                          100

<210> SEQ ID NO 1162
<211> LENGTH: 100
<212> TYPE: DNA
<213> ORGANISM: Homo sapiens

<400> SEQUENCE: 1162
cccttccctc cagcccccctc caggagtctc tacagaagat acatcaggca taaatatggc    60
ctggaagggc cagaatcatc tggtgacttg gggctgttgt                          100

<210> SEQ ID NO 1163
<211> LENGTH: 100
<212> TYPE: DNA
<213> ORGANISM: Homo sapiens

<400> SEQUENCE: 1163
ggtcctgggc ccagtctgcc ctgactcagc ctgcctccgt gtctgggtct cctggacagt    60
cgatcaccat ctcctgcact ggaaccagca gtgacgttgg                          100

<210> SEQ ID NO 1164
<211> LENGTH: 100
<212> TYPE: DNA
<213> ORGANISM: Homo sapiens

<400> SEQUENCE: 1164
aaagccccca aactcatgat ttatgaggtc agtaatcggc cctcagggat ttctaatcgc    60
ttctctggct ccaagtctgg caacacggcc tccctgacca                          100

<210> SEQ ID NO 1165
<211> LENGTH: 100
<212> TYPE: DNA
<213> ORGANISM: Homo sapiens

<400> SEQUENCE: 1165
aggctcagtg cccatagacc ccaagttggc cctgccctga accctgtgca aagcccagac    60
acagtcttag ggtaggaccc ctgggaatgg gctcttgatc                          100

<210> SEQ ID NO 1166
<211> LENGTH: 100
<212> TYPE: DNA
<213> ORGANISM: Homo sapiens

<400> SEQUENCE: 1166
ttcaagcccc ctctcctgtt ttccttgcag tctctgaggc ctcctatgag ctgacacagc    60
caccctcggt gtcagtgtcc ccaggacaaa cggccaggat                         100

<210> SEQ ID NO 1167
<211> LENGTH: 100
<212> TYPE: DNA
<213> ORGANISM: Homo sapiens

<400> SEQUENCE: 1167
agaagtcagg ccaggcccct gtgctggtca tctatgagga cagcaaacga ccctccggga    60
tccctgagag attctctggc tccagctcag ggacaatggc                         100

<210> SEQ ID NO 1168
<211> LENGTH: 100
<212> TYPE: DNA
<213> ORGANISM: Homo sapiens

<400> SEQUENCE: 1168
caccttgact atcagtgggg cccaggtgga ggatgaagct gactactact gttactcaac    60
agacagcagt ggtaatcata gcacagtgac actggcagat                         100

<210> SEQ ID NO 1169
<211> LENGTH: 100
<212> TYPE: DNA
<213> ORGANISM: Homo sapiens

<400> SEQUENCE: 1169
ggggaagtga gacacaaacc ccttcttcat ctattttacc ctctccctcc agccccagga    60
ccgctgtgga ccaacccata agcaggtctg gcagaattca                         100

<210> SEQ ID NO 1170
<211> LENGTH: 100
<212> TYPE: DNA
<213> ORGANISM: Homo sapiens

<400> SEQUENCE: 1170
aggctcacct gggcccagca ctgactcact agactgtgtt tctcccttc cagggtcctg    60 ggcccagtct gccctgactc agcctccctc cgcgtccggg                         100

<210> SEQ ID NO 1171
<211> LENGTH: 100
<212> TYPE: DNA
<213> ORGANISM: Homo sapiens

<400> SEQUENCE: 1171
catctcctgc actggaacca gcagtgacgt tggtggttat aactatgtct cctggtacca    60
acagcaccca ggcaaagccc ccaaactcat gatttatgag                         100

<210> SEQ ID NO 1172
<211> LENGTH: 100
<212> TYPE: DNA
<213> ORGANISM: Homo sapiens

<400> SEQUENCE: 1172

```
gtcagtaagc ggccctcagg ggtccctgat cgcttctctg ctccaagtc tggcaacacg    60 gcctccctga ccgtctctgg gctccaggct gaggatgagg                        100

<210> SEQ ID NO 1173
<211> LENGTH: 100
<212> TYPE: DNA
<213> ORGANISM: Homo sapiens

<400> SEQUENCE: 1173
aggctgagga tgaggctgat tattactgca gctcatatgc aggcagcaac aatttccaca    60
gtgttttaag tcaatgagga agtaagatca aaacctgccc                        100

<210> SEQ ID NO 1174
<211> LENGTH: 100
<212> TYPE: DNA
<213> ORGANISM: Homo sapiens

<400> SEQUENCE: 1174
tcaggctcag aacccatagg atcctgagct gggcctgccc aaacatgagt tcatcccagg    60
cacaacctca ggtgggaccc cctgggaac agattcatca                         100

<210> SEQ ID NO 1175
<211> LENGTH: 100
<212> TYPE: DNA
<213> ORGANISM: Homo sapiens

<400> SEQUENCE: 1175
tttacaagcc tcctctcctg tcctctcttg caagctccta tgagcttaca cagccaccct    60
cagtgtcagt gtcaccagga caggcagcca tgatcacctg                        100

<210> SEQ ID NO 1176
<211> LENGTH: 100
<212> TYPE: DNA
<213> ORGANISM: Homo sapiens

<400> SEQUENCE: 1176
ctcttgagat aacctcaaag atgagtatgt ttactggttc tggcagaagc cagaccaggc    60
ccatactggt gatatatgaa ggcagcaagc ggccctcagg                        100

<210> SEQ ID NO 1177
<211> LENGTH: 100
<212> TYPE: DNA
<213> ORGANISM: Homo sapiens

<400> SEQUENCE: 1177
aatttctgat tttctgagtc cagctcaggg aacatggcca ccctgaccat cagcagggct    60
cagactgagg acgaggctga ctattactgt cacaggtaca                        100

<210> SEQ ID NO 1178
<211> LENGTH: 100
<212> TYPE: DNA
<213> ORGANISM: Homo sapiens

<400> SEQUENCE: 1178
atagaaacag tgatgagccc acagtgacac aggcagatta ggaagtgaga cacaaacccc    60
ttcccaatct gtgtcaccct ctttctccag ccccaggatg                        100

<210> SEQ ID NO 1179
<211> LENGTH: 100
```

```
<212> TYPE: DNA
<213> ORGANISM: Homo sapiens

<400> SEQUENCE: 1179
gggatgagaa gggaccaggg gcctgggatt gagctgtgaa gggaaccaaa aggcaggagg    60
gacagggcag gggctgtcag ctatgactca ggggaggttc                         100

<210> SEQ ID NO 1180
<211> LENGTH: 100
<212> TYPE: DNA
<213> ORGANISM: Homo sapiens

<400> SEQUENCE: 1180
ctgggcctca ggatcctccc tctgaggcca ccaggggcg ggggtggcac atgcctggac     60
ctgggaggtc cctgctgggc ttcaccctgg gtgggtccta                         100

<210> SEQ ID NO 1181
<211> LENGTH: 100
<212> TYPE: DNA
<213> ORGANISM: Homo sapiens

<400> SEQUENCE: 1181
atgcctggac ctgggaggtc cctgctgggc ttcaccctgg gtgggtccta ggagctcctt    60
cctcctaagt cccctaaag agacagaggc attctggggt                          100

<210> SEQ ID NO 1182
<211> LENGTH: 100
<212> TYPE: DNA
<213> ORGANISM: Homo sapiens

<400> SEQUENCE: 1182
cctaaatctg tcatgccccc ataaatgcat ttctacgagg gccaataaat gaactccagg    60
tttatccaag cagcagcttc aggcgtctgc agacacagag                         100

<210> SEQ ID NO 1183
<211> LENGTH: 100
<212> TYPE: DNA
<213> ORGANISM: Homo sapiens

<400> SEQUENCE: 1183
cggggaggaa ttagccaacc tgaggcaccc tagaagggct gaagggggct gaagggact     60 gaagggtccc tgtggggcct gtggtcctgg ggaggggaga                         100

<210> SEQ ID NO 1184
<211> LENGTH: 100
<212> TYPE: DNA
<213> ORGANISM: Homo sapiens

<400> SEQUENCE: 1184
gctggggtgt ctcccagcca ctctgggccc tgtcctgaca cttctcccac aaagaaggga    60
agggaaatcc tgggacccca cagccaggac caaccgtgaa                         100

<210> SEQ ID NO 1185
<211> LENGTH: 100
<212> TYPE: DNA
<213> ORGANISM: Homo sapiens

<400> SEQUENCE: 1185
ccacaggaca ggaaggacag ggaccccaa ggctggctcc atttcccagg cactgtcatg     60
```

```
ggctgagtct caggaaatcc aagtcaagga gtttcaatcc                            100

<210> SEQ ID NO 1186
<211> LENGTH: 100
<212> TYPE: DNA
<213> ORGANISM: Homo sapiens

<400> SEQUENCE: 1186
ccaaggaaac agaagtctac gggcccaggc ccaggtgagg gtggggtaag aagaggagct       60
taggatgcag atttgcatgg aggccccgcc ctcctctgag                            100

<210> SEQ ID NO 1187
<211> LENGTH: 100
<212> TYPE: DNA
<213> ORGANISM: Homo sapiens

<400> SEQUENCE: 1187
gcatcagggt aagacaaggc tgggggcagg cccagtgctg gggtctcagg aggcagcgct       60
ctggggacgt ctccaccatg gcctgggctc tgctcctcct                            100

<210> SEQ ID NO 1188
<211> LENGTH: 100
<212> TYPE: DNA
<213> ORGANISM: Homo sapiens

<400> SEQUENCE: 1188
ctcagggcac aggtgacgcc tccagggaag gggcctcggg gacccttggg ctgatccttg       60
gtctcctgct cctcaggctc acctgggccc agcactgact                            100

<210> SEQ ID NO 1189
<211> LENGTH: 100
<212> TYPE: DNA
<213> ORGANISM: Homo sapiens

<400> SEQUENCE: 1189
ttgggagtta tgactatgtc tcctggtacc aacagcaccc aggcacagtc cccaaaccca       60
tgatctacaa tgtcaatact cagccctcag gggtccctga                            100

<210> SEQ ID NO 1190
<211> LENGTH: 100
<212> TYPE: DNA
<213> ORGANISM: Homo sapiens

<400> SEQUENCE: 1190
tcgtttctct ggctccaagt ctggcaatac ggcctccatg accatctctg gactccaggc       60
tgaggacgag gctgattatt agtgctgctc atatacaagc                            100

<210> SEQ ID NO 1191
<211> LENGTH: 100
<212> TYPE: DNA
<213> ORGANISM: Homo sapiens

<400> SEQUENCE: 1191
tgaggacgag gctgattatt agtgctgctc atatacaagc agtgccactt aaccacagtg       60
gtccaagttc ttggggaact gagacgaaaa cctgccctgg                            100

<210> SEQ ID NO 1192
<211> LENGTH: 100
<212> TYPE: DNA
<213> ORGANISM: Homo sapiens
```

<400> SEQUENCE: 1192
cctgggctct caggctccct ttttgctctg aagatgtttc ctcacccagt gcaacgggct    60
tcctgaagca cagccttgag aattcttctc cctcagcaac                         100

<210> SEQ ID NO 1193
<211> LENGTH: 100
<212> TYPE: DNA
<213> ORGANISM: Homo sapiens

<400> SEQUENCE: 1193
tctcttttcc caccatgaaa tccaaaggaa acctgctctg tggtttctca tccaggacag    60
ggacagcttc cttttgcttg tgtgttgtgg tccctgagtg                         100

<210> SEQ ID NO 1194
<211> LENGTH: 100
<212> TYPE: DNA
<213> ORGANISM: Homo sapiens

<400> SEQUENCE: 1194
ggtgcaactc ttcctagctt tttaaattat gggagggtga caatgagctc cctgactggt    60
gcagtccctg ctgttttcag gaacatcctc atcctaaatg                         100

<210> SEQ ID NO 1195
<211> LENGTH: 100
<212> TYPE: DNA
<213> ORGANISM: Homo sapiens

<400> SEQUENCE: 1195
catctgaatc tcccactgtg tgcagaccaa tctggacaga tgttattagg gggagtttcc    60
agaagccaca tcttactcaa ctctgtatcc accacactct                         100

<210> SEQ ID NO 1196
<211> LENGTH: 100
<212> TYPE: DNA
<213> ORGANISM: Homo sapiens

<400> SEQUENCE: 1196
tgcctcagcc atggcatgga tccctctctt cctcggcgtc cttgcttact gcacaggtgc    60
tgcccctagg gtcctagcca ctggtccagt cccagggctc                         100

<210> SEQ ID NO 1197
<211> LENGTH: 100
<212> TYPE: DNA
<213> ORGANISM: Homo sapiens

<400> SEQUENCE: 1197
tgggtccagc ctggccctga ctctgagctc agcagggccc ccgcctgtgg tgggcaggat    60
gctcatgacc ctgctgcagg tggatgggct cggcggggct                         100

<210> SEQ ID NO 1198
<211> LENGTH: 100
<212> TYPE: DNA
<213> ORGANISM: Homo sapiens

<400> SEQUENCE: 1198
tgggcaggat gctcatgacc ctgctgcagg tggatgggct cggcggggct gaaatccccc    60
cacacagtgc tcatgtgctc acactgcctt agggctcttt                         100

<210> SEQ ID NO 1199
<211> LENGTH: 100
<212> TYPE: DNA
<213> ORGANISM: Homo sapiens

<400> SEQUENCE: 1199
catccctgga tctgtgtcca ggccaggcac gtgggaagat ttacttggag ttcagctcct    60
cagtttcaag ccttttctct cccgttttct ctcctgtagg                         100

<210> SEQ ID NO 1200
<211> LENGTH: 100
<212> TYPE: DNA
<213> ORGANISM: Homo sapiens

<400> SEQUENCE: 1200
atccgtggcc tcctatgagc tgactcagcc accctcagtg tccgtgtccc caggacagac    60
agccagcatc acctgctctg gagataaatt gggggataaa                         100

<210> SEQ ID NO 1201
<211> LENGTH: 100
<212> TYPE: DNA
<213> ORGANISM: Homo sapiens

<400> SEQUENCE: 1201
caggacagac agccagcatc acctgctctg gagataaatt gggggataaa tatgcttgct    60
ggtatcagca gaagccaggc cagtcccctg tgctggtcat                         100

<210> SEQ ID NO 1202
<211> LENGTH: 100
<212> TYPE: DNA
<213> ORGANISM: Homo sapiens

<400> SEQUENCE: 1202
ctatcaagat agcaagcggc cctcagggat ccctgagcga ttctctggct ccaactctgg    60
gaacacagcc actctgacca tcagcgggac ccaggctatg                         100

<210> SEQ ID NO 1203
<211> LENGTH: 100
<212> TYPE: DNA
<213> ORGANISM: Homo sapiens

<400> SEQUENCE: 1203
gatgaggctg actattactg tcaggcgtgg gacagcagca ctgcacacag tgacacaggc    60
agatgcggaa gtgagacaga aaccagccac ctcggcctgg                         100

<210> SEQ ID NO 1204
<211> LENGTH: 100
<212> TYPE: DNA
<213> ORGANISM: Homo sapiens

<400> SEQUENCE: 1204
ctcacaagac ccttccctct ctcctgccct gtcacactga gcaggaggga gccttccatg    60
tggaatggaa gtttccagtc ctatccctgc ccttatgttc                         100

<210> SEQ ID NO 1205
<211> LENGTH: 100
<212> TYPE: DNA
<213> ORGANISM: Homo sapiens

<400> SEQUENCE: 1205

```
ctgagagacg ggagcaagtt cctgcccacc tctaggctca gcttatccca gaataaactg    60
agctagtcat tttgatgatc aaatgccagc tcccaaaaga                         100

<210> SEQ ID NO 1206
<211> LENGTH: 100
<212> TYPE: DNA
<213> ORGANISM: Homo sapiens

<400> SEQUENCE: 1206
ccccagaaac cctgatatct aagtagcacc gactctatta gtatcaaggg agactagccc    60
tagggtggaa tcattttagt gtctcagaag gcacagggca                         100

<210> SEQ ID NO 1207
<211> LENGTH: 100
<212> TYPE: DNA
<213> ORGANISM: Homo sapiens

<400> SEQUENCE: 1207
atggaaagtg tttatgaggt ttcaggatat gcacgtgagc agttaaaggc aggtcttaca    60
aggaaggaac ctactagaat tggggcccat ctgtgacatc                         100

<210> SEQ ID NO 1208
<211> LENGTH: 100
<212> TYPE: DNA
<213> ORGANISM: Homo sapiens

<400> SEQUENCE: 1208
acatccctct gctttgggag agaagggcca gggcggacc cagagagctc tgcagaggca     60
ccacagaccc tcagcagggg gtctgccaaa caggacagct                         100

<210> SEQ ID NO 1209
<211> LENGTH: 100
<212> TYPE: DNA
<213> ORGANISM: Homo sapiens

<400> SEQUENCE: 1209
ggacttggct gcttctgccc aggcctggat ccagcccttg cacatctcag ggcaggggat    60
aggcctgggt ggccagagct gcagctgcac ctgctgggga                         100

<210> SEQ ID NO 1210
<211> LENGTH: 100
<212> TYPE: DNA
<213> ORGANISM: Homo sapiens

<400> SEQUENCE: 1210
ggcctagtcc agtcctccag ggtccccaga cagactcgga tttccgactg cagccaccat    60
ggaaggatgt ggtctgcggt gacgatgtct atccagaggc                         100

<210> SEQ ID NO 1211
<211> LENGTH: 100
<212> TYPE: DNA
<213> ORGANISM: Homo sapiens

<400> SEQUENCE: 1211
ccgaatatcc aaggagccca agatcagagg caggaatagg ccaagctccc cagtggagaa    60
gctgtgctgg accaggggtt tcccagggcc ctcccttgtg                         100

<210> SEQ ID NO 1212
```

```
<211> LENGTH: 100
<212> TYPE: DNA
<213> ORGANISM: Homo sapiens

<400> SEQUENCE: 1212
ccctgaatga tgtctgttag ggcacctaca ccctgttact gctcagtgcc ttgcctattt      60
tgaaggacag ggatgtgtgg tgattatttg tataatccag                          100

<210> SEQ ID NO 1213
<211> LENGTH: 100
<212> TYPE: DNA
<213> ORGANISM: Homo sapiens

<400> SEQUENCE: 1213
cccccagcac ctggtcctca aaagttaccc aagcaatgtg tataaagatc cagcctggag      60
atctttgaaa accgattcga tgagtcgaac cattaagtca                          100

<210> SEQ ID NO 1214
<211> LENGTH: 100
<212> TYPE: DNA
<213> ORGANISM: Homo sapiens

<400> SEQUENCE: 1214
tgatcaccat cctcaacttc atctctttct tcctcctcct cctcattatc atcaccttca      60
agaactgtta agagtctgag acttcatcct atttgcagac                          100

<210> SEQ ID NO 1215
<211> LENGTH: 100
<212> TYPE: DNA
<213> ORGANISM: Homo sapiens

<400> SEQUENCE: 1215
tcctcctcct cctcattatc atcaccttca agaactgtta agagtctgag acttcatcct      60
atttgcagac taaaaagtaa gcctgccaca gtgccatgga                          100

<210> SEQ ID NO 1216
<211> LENGTH: 100
<212> TYPE: DNA
<213> ORGANISM: Homo sapiens

<400> SEQUENCE: 1216
tgctggcaga agatacaaga ctcctgggtc agagacaacg aataatctgt ttttcacagc      60
aatagcagtt gccaaggtat cagcattgtc ttgcaccagt                          100

<210> SEQ ID NO 1217
<211> LENGTH: 100
<212> TYPE: DNA
<213> ORGANISM: Homo sapiens

<400> SEQUENCE: 1217
tccacaaggt gatgcaaaga gggccaggtg acatctgcat gccagagctc agggatccca      60
aatatttcat acttgacagt aagcatatat ctgtgttttg                          100

<210> SEQ ID NO 1218
<211> LENGTH: 100
<212> TYPE: DNA
<213> ORGANISM: Homo sapiens

<400> SEQUENCE: 1218
ctccaaagag aggcattctc tgtaccttcc gaggttgttc actccacaaa cactcttgaa      60
```

```
aagataatcc acaatcagtg cctttgcccg agagacatgc                          100
```

<210> SEQ ID NO 1219
<211> LENGTH: 100
<212> TYPE: DNA
<213> ORGANISM: Homo sapiens

<400> SEQUENCE: 1219

```
agaaatgcag agatccatag tagaccactg tctcccaaca accatcaact ttatcaatga    60
aatgaagtct caggctattt gtctgttacc atagcccaca                          100
```

<210> SEQ ID NO 1220
<211> LENGTH: 100
<212> TYPE: DNA
<213> ORGANISM: Homo sapiens

<400> SEQUENCE: 1220

```
aaaatgtctg gcttgattgt caccaaatgt atcaaggaag ttaaggagta tctgacacaa    60
aatgtgaacc aagcaattct caaaggagcc tcccaggaaa                          100
```

<210> SEQ ID NO 1221
<211> LENGTH: 100
<212> TYPE: DNA
<213> ORGANISM: Homo sapiens

<400> SEQUENCE: 1221

```
ttcactttag gaagtcctag gaggctcctc tgagagttgc taaaacaaaa cattgagagt    60
cctagagggc tgcagatctg aacttgagca gatattttta                          100
```

<210> SEQ ID NO 1222
<211> LENGTH: 100
<212> TYPE: DNA
<213> ORGANISM: Homo sapiens

<400> SEQUENCE: 1222

```
aagattttgt ggcagaaaaa gaaactggaa agcaagaggg cagaccctca ttgcagttct    60
gtaatgtaag ggggcagagc aggggccttt ctcaccagag                          100
```

<210> SEQ ID NO 1223
<211> LENGTH: 100
<212> TYPE: DNA
<213> ORGANISM: Homo sapiens

<400> SEQUENCE: 1223

```
gatattggac cctgcattca tcttctctgg atggtaattt tctcacctgt aaaacagaga    60
cactggcccc aaggacaccc cacaagtagt tgtgaatccc                          100
```

<210> SEQ ID NO 1224
<211> LENGTH: 100
<212> TYPE: DNA
<213> ORGANISM: Homo sapiens

<400> SEQUENCE: 1224

```
aaagtaagag aagaacaaaa aaagaaccag aatttattca cacccactg agtgcttagc     60
aaacacatgg tttctttaac tctcataagc ttcatgctgc                          100
```

<210> SEQ ID NO 1225
<211> LENGTH: 100
<212> TYPE: DNA

<213> ORGANISM: Homo sapiens

<400> SEQUENCE: 1225
agaggaactc tccccatttt acagataagg aaactgaggc ccagaggtaa cctaggtcta    60
gatagactcc acatttatga cttcaccact cttccttgcc                         100

<210> SEQ ID NO 1226
<211> LENGTH: 100
<212> TYPE: DNA
<213> ORGANISM: Homo sapiens

<400> SEQUENCE: 1226
aaactgaggc ccagaggtaa cctaggtcta gatagactcc acatttatga cttcaccact    60
cttccttgcc tgaaggatat agaatcactc cctgcagggc                         100

<210> SEQ ID NO 1227
<211> LENGTH: 100
<212> TYPE: DNA
<213> ORGANISM: Homo sapiens

<400> SEQUENCE: 1227
tcttgcctga ctcaggaaag ggccacagga tagccagcca ggcttaacca acccagccaa    60
gaaagggctg gtcccaactg gctggagtgc agtgtacagg                         100

<210> SEQ ID NO 1228
<211> LENGTH: 100
<212> TYPE: DNA
<213> ORGANISM: Homo sapiens

<400> SEQUENCE: 1228
gttggtagat gcccctctgg gagagatccc caggggtgac agccatggac cctggaaggg    60
cctgggctag ggacagggac cagagccagt ccagggagag                         100

<210> SEQ ID NO 1229
<211> LENGTH: 100
<212> TYPE: DNA
<213> ORGANISM: Homo sapiens

<400> SEQUENCE: 1229
gacagagcca atggactggg gtgtactgta acagccctgc tggcgagagg gaccagggca    60
ccgtcctcca gggagcccat gctgcaagtc gggccagagg                         100

<210> SEQ ID NO 1230
<211> LENGTH: 100
<212> TYPE: DNA
<213> ORGANISM: Homo sapiens

<400> SEQUENCE: 1230
tgcccctgaa cctgaaggcc aatgagaccc aagacaggcc aagtgggttg tgagacccct    60
gaggagctgg gccctggtcc caggcagcgc tggcccctgc                         100

<210> SEQ ID NO 1231
<211> LENGTH: 100
<212> TYPE: DNA
<213> ORGANISM: Homo sapiens

<400> SEQUENCE: 1231
tgctgctggg tctggccatg gtcgcccatg gcctgctgcg cccaatggtt gcaccgcaaa    60
gcggggaccc agaccctgga gcctcagttg gaagcagccg                         100

<210> SEQ ID NO 1232
<211> LENGTH: 100
<212> TYPE: DNA
<213> ORGANISM: Homo sapiens

<400> SEQUENCE: 1232

```
atccagcctg cggagcctgt ggggcaggta aggggcaaga gattccaggg gatgtggggg      60
tcctgcagca gagctgggaa agggtgacca aggggagaca                           100
```

<210> SEQ ID NO 1233
<211> LENGTH: 100
<212> TYPE: DNA
<213> ORGANISM: Homo sapiens

<400> SEQUENCE: 1233

```
agccagagga gtgaggagga aggttaaccc ctaagagggg cctgggctga cactggcttt      60
agtaatgggt tgatattttg tccatcacag atttgtttga                           100
```

<210> SEQ ID NO 1234
<211> LENGTH: 100
<212> TYPE: DNA
<213> ORGANISM: Homo sapiens

<400> SEQUENCE: 1234

```
attactgttt ttaatatcat attacgatat tattttctt gatttctgag ttttctggcg       60
ccacttaaat tttcaccagg gtcagtgcct caatcaccta                           100
```

<210> SEQ ID NO 1235
<211> LENGTH: 100
<212> TYPE: DNA
<213> ORGANISM: Homo sapiens

<400> SEQUENCE: 1235

```
gtcctagtcc tctgggtagg gaaggaacag aggcagggac aggacatcca caggggtgg       60
tggccactgt ccccacaggg tgcccaggcc tgttcctccc                           100
```

<210> SEQ ID NO 1236
<211> LENGTH: 100
<212> TYPE: DNA
<213> ORGANISM: Homo sapiens

<400> SEQUENCE: 1236

```
cctcctcctc tctgcccatg tgcctcctgc ccagtgaggg caggggccac tccctggaga      60
aggcagcaag ggcttggttt ggtctccccc aaggctgtct                           100
```

<210> SEQ ID NO 1237
<211> LENGTH: 100
<212> TYPE: DNA
<213> ORGANISM: Homo sapiens

<400> SEQUENCE: 1237

```
gttcaccaac ttgcacataa atgcttactg gggccaggct caaggacaca gggagggtgg      60
gatgaaccga ggggagctgt ccagtcattg gaacaggccc                           100
```

<210> SEQ ID NO 1238
<211> LENGTH: 100
<212> TYPE: DNA
<213> ORGANISM: Homo sapiens

<400> SEQUENCE: 1238
acggcccatg tttggagcaa taaagggaga ggggatctcc ctctgggatg atgcccaggc    60
tggtctcaca gatcgagggg cactggctgg tgatgggtgc                         100

<210> SEQ ID NO 1239
<211> LENGTH: 100
<212> TYPE: DNA
<213> ORGANISM: Homo sapiens

<400> SEQUENCE: 1239
tggtctcaca gatcgagggg cactggctgg tgatgggtgc ccccaaaaga cagagcagcg    60
tcagaggaga ggagagcaca ggatgaggct gggagctcct                         100

<210> SEQ ID NO 1240
<211> LENGTH: 100
<212> TYPE: DNA
<213> ORGANISM: Homo sapiens

<400> SEQUENCE: 1240
gggtgactgg gaaggggagg caagaagacc atagggtccg tgcaccattc ccagtccagg    60
acgagtcctt ggatggattt aggtagattg attatcagag                         100

<210> SEQ ID NO 1241
<211> LENGTH: 100
<212> TYPE: DNA
<213> ORGANISM: Homo sapiens

<400> SEQUENCE: 1241
tcagatttgt gtttttggaa aaatcagcac cggattggag gctgatgcga cgcccgatta    60
gaggagggag gagaggggggt gatggccaag tccagggtag                        100

<210> SEQ ID NO 1242
<211> LENGTH: 100
<212> TYPE: DNA
<213> ORGANISM: Homo sapiens

<400> SEQUENCE: 1242
gtggggatcc tggaggaagc cgtgccttgg ggatggggag gacactcaga ttcagagcac    60 ccagggccc agtttcctat gaaatgggag catgaagttg                          100

<210> SEQ ID NO 1243
<211> LENGTH: 100
<212> TYPE: DNA
<213> ORGANISM: Homo sapiens

<400> SEQUENCE: 1243
aagtgagggc tgagcagagg ggagcagaca cgctcgggga ctgtctatgg gcattaaaaa    60
tgtataacca ttttagcaac aggcggcgag tcaaaaaaca                         100

<210> SEQ ID NO 1244
<211> LENGTH: 100
<212> TYPE: DNA
<213> ORGANISM: Homo sapiens

<400> SEQUENCE: 1244
aagtgtgttt atctaaactg ggcaattcca cttctaggaa tttatcctaa gggttggttg    60
ggggaataat caaagctgta accaaatctt tataacaagg                         100

```
<210> SEQ ID NO 1245
<211> LENGTH: 100
<212> TYPE: DNA
<213> ORGANISM: Homo sapiens

<400> SEQUENCE: 1245
gtggttagct cagcattatt agtgatggga gaaaactgga aaaaatccaa atatctacca      60
gaaagggtgt gaaaaaacac aattgtattt gggggactgt                          100

<210> SEQ ID NO 1246
<211> LENGTH: 100
<212> TYPE: DNA
<213> ORGANISM: Homo sapiens

<400> SEQUENCE: 1246
tggctaattt tgattaggat tattattagt ttagagacag agcctcgcta tattgctcag      60
gcctgtctca aattcctaag ctcaagcaat ctttctgcct                          100

<210> SEQ ID NO 1247
<211> LENGTH: 100
<212> TYPE: DNA
<213> ORGANISM: Homo sapiens

<400> SEQUENCE: 1247
actgcacctg acccaactgt gttttttaaag tatatatgca ttttcaaaaa cctgtcagaa     60
aatatagaaa aatgtcaatg gtgtgtctgg ctggctgatg                          100

<210> SEQ ID NO 1248
<211> LENGTH: 100
<212> TYPE: DNA
<213> ORGANISM: Homo sapiens

<400> SEQUENCE: 1248
ggatttcacc taattttaat gtggctttat aattttctgg ttttgtgaag ttgttcacaa     60
aaagagacat ttcttctaat ataattttta atacaacagt                          100

<210> SEQ ID NO 1249
<211> LENGTH: 100
<212> TYPE: DNA
<213> ORGANISM: Homo sapiens

<400> SEQUENCE: 1249
aatgtactca tgtgcattac tcttttttgta atgagtatat tacaaaatgt aatgacttttt    60 gtacattact cttttttcttt gccaaaaaaa aaaaagatta                          100

<210> SEQ ID NO 1250
<211> LENGTH: 100
<212> TYPE: DNA
<213> ORGANISM: Homo sapiens

<400> SEQUENCE: 1250
agcagagaag tatataaagt aaaagcaagt gcttctgctt accatctctc acctcttccc     60
agagatagcc actgtcaggt tggtcaatat acttccagaa                          100

<210> SEQ ID NO 1251
<211> LENGTH: 100
<212> TYPE: DNA
<213> ORGANISM: Homo sapiens

<400> SEQUENCE: 1251
```

| | |
|---|---|
| cttttcctgt gtgtgtgtgt gtccctgaaa acacacacac acacacacac acacacacac | 60 |
| acagttggtg ctgggatttt attttgcaaa agtaagagcc | 100 |

<210> SEQ ID NO 1252
<211> LENGTH: 100
<212> TYPE: DNA
<213> ORGANISM: Homo sapiens

<400> SEQUENCE: 1252

| | |
|---|---|
| cacacacagt tggtgctggg attttatttt gcaaaagtaa gagccatatt ctgcatatta | 60 |
| ccaactttta atctattatt gacactttct gtatcagtcc | 100 |

<210> SEQ ID NO 1253
<211> LENGTH: 100
<212> TYPE: DNA
<213> ORGANISM: Homo sapiens

<400> SEQUENCE: 1253

| | |
|---|---|
| atatggatta accacattca ttgcttataa actttgtttt ataagcaaag tttagatgag | 60 |
| ccagaattta tttccactaa aaaatctaaa tgacaaatga | 100 |

<210> SEQ ID NO 1254
<211> LENGTH: 100
<212> TYPE: DNA
<213> ORGANISM: Homo sapiens

<400> SEQUENCE: 1254

| | |
|---|---|
| tgctgcagtg gaaatttgtg tgtgtgtgtg tgtgtgtgtg tgtgtgtgtg tgtgtgtgtg | 60 |
| tgtatgtgta caaagtgcac ttatatatct ccccaggata | 100 |

<210> SEQ ID NO 1255
<211> LENGTH: 100
<212> TYPE: DNA
<213> ORGANISM: Homo sapiens

<400> SEQUENCE: 1255

| | |
|---|---|
| tgacctgggt gtttttcttt ttctctgtag gatgttaata gtatcttgtg tcatgctagg | 60 |
| atgtctagga cagagggcaa tacaatgagg ggaaggcatt | 100 |

<210> SEQ ID NO 1256
<211> LENGTH: 100
<212> TYPE: DNA
<213> ORGANISM: Homo sapiens

<400> SEQUENCE: 1256

| | |
|---|---|
| ctgcgatgtc cccaggcctc tggcttgaag agtaacttgc tgaagtgagg actctgtgga | 60 |
| ggagcaagtt atacagaaag aagtttagtt gtgatctgtt | 100 |

<210> SEQ ID NO 1257
<211> LENGTH: 100
<212> TYPE: DNA
<213> ORGANISM: Homo sapiens

<400> SEQUENCE: 1257

| | |
|---|---|
| gagttggagg tgtctacagg gcatccaagc agacataggt tgaggaggca gaatatatgt | 60 |
| gaatctggag ccaagaagag aggtaagggc tggaaatagg | 100 |

<210> SEQ ID NO 1258
<211> LENGTH: 100

```
<212> TYPE: DNA
<213> ORGANISM: Homo sapiens

<400> SEQUENCE: 1258
gatctaagac ccctggacag ttgtgagtgt gcacaatgag ggtcagatgc agagaaaatt    60
aggagactac agagagcaga acccagggtg gggatctggg                        100

<210> SEQ ID NO 1259
<211> LENGTH: 100
<212> TYPE: DNA
<213> ORGANISM: Homo sapiens

<400> SEQUENCE: 1259
agtcagcagt tgggcatggg cctggtagaa agggaagcca aggaggagga gaggggcag    60 tctcagacac caaggagggg agagtgacta gaaagaaaac                        100

<210> SEQ ID NO 1260
<211> LENGTH: 100
<212> TYPE: DNA
<213> ORGANISM: Homo sapiens

<400> SEQUENCE: 1260
cttcttgcag agacataggg gatggggaag aactgcagac tgaactgggg caaaggactg    60
ttggccttaa ccagagagat ttgagggaga gatgaggctg                        100

<210> SEQ ID NO 1261
<211> LENGTH: 100
<212> TYPE: DNA
<213> ORGANISM: Homo sapiens

<400> SEQUENCE: 1261
agagccaggg gatcctgcca tgtcccagca taaaaacagt acctgacaca gatgggtgct    60
tgggagctgt tgtcggatga atgagtggac agatgcatgg                        100

<210> SEQ ID NO 1262
<211> LENGTH: 100
<212> TYPE: DNA
<213> ORGANISM: Homo sapiens

<400> SEQUENCE: 1262
atggacggat ggatggaagg atgatagatt gatggacaaa cagatgaaca gatgaatagc    60
tggatggaca actggatgga tgggtagaca gaatgatctc                        100

<210> SEQ ID NO 1263
<211> LENGTH: 100
<212> TYPE: DNA
<213> ORGANISM: Homo sapiens

<400> SEQUENCE: 1263
agagatcaga aaaagcttca tgcactaagt gggactgaac cgcgtctcca tgggtagaaa    60
gcagaggaat ctccacttga gtcaggaatg acccagtgct                        100

<210> SEQ ID NO 1264
<211> LENGTH: 100
<212> TYPE: DNA
<213> ORGANISM: Homo sapiens

<400> SEQUENCE: 1264
ctcaatccag ggagaaagcc agcctggctt cactggggac acttgtgtgg gggactcaga    60
``` ggcccttaa atgaggccag acgaggttgg acaggtccaa 100

<210> SEQ ID NO 1265
<211> LENGTH: 100
<212> TYPE: DNA
<213> ORGANISM: Homo sapiens

<400> SEQUENCE: 1265
gccaactcag cactcctctg ccacactgca caggagggga tgtgtcactc agggagttgc 60
tgggacctat gggtcccagt gttgtcatca gcaccgacag 100

<210> SEQ ID NO 1266
<211> LENGTH: 100
<212> TYPE: DNA
<213> ORGANISM: Homo sapiens

<400> SEQUENCE: 1266
cctcagagag gaaagacaca cactggggta actccaaggc tgtgtgtggc acttgccttg 60
gacagcagac aggcacaggg acacctctag ggggctggcc 100

<210> SEQ ID NO 1267
<211> LENGTH: 100
<212> TYPE: DNA
<213> ORGANISM: Homo sapiens

<400> SEQUENCE: 1267
acccccctgc ctcatgtcta ggtcccagcc ccgcccactg caaccctgtg cccgtcatgc 60
ccagcaggct cctgctccag cccagccccc agagagcaga 100

<210> SEQ ID NO 1268
<211> LENGTH: 100
<212> TYPE: DNA
<213> ORGANISM: Homo sapiens

<400> SEQUENCE: 1268
cactgcaacc ctgtgcccgt catgcccagc aggctcctgc tccagcccag cccccagaga 60 gcagaccccca ggtgctggcc ccgggggttt tggtctgagc 100

<210> SEQ ID NO 1269
<211> LENGTH: 100
<212> TYPE: DNA
<213> ORGANISM: Homo sapiens

<400> SEQUENCE: 1269
ctcagtcact gtgttatgtc ttcggaactg ggaccaaggt caccgtccta ggtaagtggc 60
tctcaacctt tcccagcctg tctcacccctc tgctgtccct 100

<210> SEQ ID NO 1270
<211> LENGTH: 100
<212> TYPE: DNA
<213> ORGANISM: Homo sapiens

<400> SEQUENCE: 1270
ggaaaatctg ttttctctct ctggggcttc ctcccctctg tcctcccagc cttaagcact 60
gacccttacc tttctccatg gggcctggag gaggtgcatt 100

<210> SEQ ID NO 1271
<211> LENGTH: 100
<212> TYPE: DNA
<213> ORGANISM: Homo sapiens

```
<400> SEQUENCE: 1271
agtctccggg taaccggcag gaagggcctc cacagtggga gcagccggat gcagcctggt    60 cccgggcct gagctgggat tgggcagggt cagggctcct                          100

<210> SEQ ID NO 1272
<211> LENGTH: 100
<212> TYPE: DNA
<213> ORGANISM: Homo sapiens

<400> SEQUENCE: 1272
cctctcttcc agggcagatg tctgagtgag ggacagaggc tggttctgat gagggggccct   60 gcagtgtcct tagggacatt gcccagtgac tcctggggtc                          100

<210> SEQ ID NO 1273
<211> LENGTH: 100
<212> TYPE: DNA
<213> ORGANISM: Homo sapiens

<400> SEQUENCE: 1273
ggacagaggc tggttctgat gaggggccct gcagtgtcct tagggacatt gcccagtgac    60
tcctggggtc aaggacagag gctgctgggg tgggcctggg                          100

<210> SEQ ID NO 1274
<211> LENGTH: 100
<212> TYPE: DNA
<213> ORGANISM: Homo sapiens

<400> SEQUENCE: 1274
agctgctgag tctcatagtc tagggagca gccccaagaa cagctgaggg tctaggctga     60
ggactggatg ccaatccagc ctgggagggc cacacggcct                          100

<210> SEQ ID NO 1275
<211> LENGTH: 100
<212> TYPE: DNA
<213> ORGANISM: Homo sapiens

<400> SEQUENCE: 1275
tctcatagtc tagggagca gccccaagaa cagctgaggg tctaggctga ggactggatg     60
ccaatccagc ctgggagggc cacacggcct ggtgacacag                          100

<210> SEQ ID NO 1276
<211> LENGTH: 100
<212> TYPE: DNA
<213> ORGANISM: Homo sapiens

<400> SEQUENCE: 1276
aggtcacccc aagggagac caatggaggg cacagagagg gctctgggtc taggctgcag     60
ctctgtggcc tgtgctgggt catgaggaca tggggacaca                          100

<210> SEQ ID NO 1277
<211> LENGTH: 100
<212> TYPE: DNA
<213> ORGANISM: Homo sapiens

<400> SEQUENCE: 1277
tgtgctgggt catgaggaca tggggacaca gagggacggg tgagactggg tgaggtgcca    60
gaatccaacc ctcccaggac agtcaccaga aaggagacag                          100
```

<210> SEQ ID NO 1278
<211> LENGTH: 100
<212> TYPE: DNA
<213> ORGANISM: Homo sapiens

<400> SEQUENCE: 1278

```
tctcttaggg cagagatgtg tctgtccctg gagccccgtc acctctgggg cccagtgtct      60
ctctgttcac ggatcggcct cctgccttcc tcaaagggca                           100
```

<210> SEQ ID NO 1279
<211> LENGTH: 100
<212> TYPE: DNA
<213> ORGANISM: Homo sapiens

<400> SEQUENCE: 1279

```
tgttagactc aggaaatgac cagaggggag tgaatgaggg gtgcagagaa ctccatggct      60
accaggtgaa gtttggggtc atcacaggct gctggggtgg                           100
```

<210> SEQ ID NO 1280
<211> LENGTH: 100
<212> TYPE: DNA
<213> ORGANISM: Homo sapiens

<400> SEQUENCE: 1280

```
catagtctgt gggagcagcc ccaggaacag ctgaggtgaa gggttctgtg gtcgggcttg      60
tggagacagg aaacatctca gagcctcaga ggagccctga                           100
```

<210> SEQ ID NO 1281
<211> LENGTH: 100
<212> TYPE: DNA
<213> ORGANISM: Homo sapiens

<400> SEQUENCE: 1281

```
ggcttgtcta ggtggagccc actccttgcc aggagagcca agtgggctgg gctggggcag      60
agcccggtgc ctgtgaggga taggaagctc cagttcaaag                           100
```

<210> SEQ ID NO 1282
<211> LENGTH: 100
<212> TYPE: DNA
<213> ORGANISM: Homo sapiens

<400> SEQUENCE: 1282

```
caggcttggg tctccccaca cactgcctgc caggacagtc ctacaggatg agcaggggac      60
ccacagttca cggaggaggc tctaggtcct ggaagaataa                           100
```

<210> SEQ ID NO 1283
<211> LENGTH: 100
<212> TYPE: DNA
<213> ORGANISM: Homo sapiens

<400> SEQUENCE: 1283

```
agtgggtgat ggaggggggt atagggatgg aaatgaggga tccagggtc aaggccagat       60
tctaaactca gactccagag atcagagaag aaggaacaca                           100
```

<210> SEQ ID NO 1284
<211> LENGTH: 100
<212> TYPE: DNA
<213> ORGANISM: Homo sapiens

<400> SEQUENCE: 1284

```
gcctgccctg ggtatatgga gaaattgagg ctgtagagga gagggctgg gccaggacac      60 ctgtgaaagg tgacttggga gggctcctag gaaggcacag                           100
```

<210> SEQ ID NO 1285
<211> LENGTH: 100
<212> TYPE: DNA
<213> ORGANISM: Homo sapiens

<400> SEQUENCE: 1285

```
tgaaagcccc actgctatga ccaggtagcc gggacgtggg gtggatgcca gaaaagactc      60
cacggaataa gagagagccc aggacagcag gcaggctctc                            100
```

<210> SEQ ID NO 1286
<211> LENGTH: 100
<212> TYPE: DNA
<213> ORGANISM: Homo sapiens

<400> SEQUENCE: 1286

```
cgatccccc aggcccttgc cccatacacg ggctccagaa cacacatttg gctggaacag       60
cctgagggac caaaaggccc cagtatccca cagagctgag                            100
```

<210> SEQ ID NO 1287
<211> LENGTH: 100
<212> TYPE: DNA
<213> ORGANISM: Homo sapiens

<400> SEQUENCE: 1287

```
gagccaggcc agaaaagtaa ccccagagtt cgctgtgcag gggagacaca gagctctctt      60
tatctgtcag gatggcagga ggggacaggg tcagggcgct                            100
```

<210> SEQ ID NO 1288
<211> LENGTH: 100
<212> TYPE: DNA
<213> ORGANISM: Homo sapiens

<400> SEQUENCE: 1288

```
gagggtcaga tgtcggtgtt gggggccaag gccccgagag atctcaggac aggtggtcag      60
gtgtctaagg taaaacagct ccccgtgcag atcagggcat                            100
```

<210> SEQ ID NO 1289
<211> LENGTH: 100
<212> TYPE: DNA
<213> ORGANISM: Homo sapiens

<400> SEQUENCE: 1289

```
atgcaggaca gtccggagag ggaaatcagg agaagtgaag gggtctctgg ggagcccaga      60
tgtgggctag aggcagaagt aagggtgaag agcacctatg                            100
```

<210> SEQ ID NO 1290
<211> LENGTH: 100
<212> TYPE: DNA
<213> ORGANISM: Homo sapiens

<400> SEQUENCE: 1290

```
agtcaatgtc atggtctcag caggaacaca gttgaaaatc cccattccac acaagaccgt      60
ttagcaggaa aggagtccat acttgtgctg ccaccaggat                            100
```

<210> SEQ ID NO 1291

<211> LENGTH: 100
<212> TYPE: DNA
<213> ORGANISM: Homo sapiens

<400> SEQUENCE: 1291

```
gtcctgagaa gccttggaga atgaaacata caggtgcatt tcctagactt gacaatgcac    60
gttagccaag taaaggcaat gaaaagttct ctactaggga                         100
```

<210> SEQ ID NO 1292
<211> LENGTH: 100
<212> TYPE: DNA
<213> ORGANISM: Homo sapiens

<400> SEQUENCE: 1292

```
tttgtttgtt tctgtatctt gtctcaactt gtggtcagcc tttctccctg catcccaggc    60
ctgagcaagg acctctgccc tccctgttca gacccttgct                         100
```

<210> SEQ ID NO 1293
<211> LENGTH: 100
<212> TYPE: DNA
<213> ORGANISM: Homo sapiens

<400> SEQUENCE: 1293

```
tgcctcagca ggtcactaca accacttcac ctctgaccgc aggggcaggg gactagatag    60
aatgacctac tgagcctcgt ctgtctgtct gtctgtctgt                         100
```

<210> SEQ ID NO 1294
<211> LENGTH: 100
<212> TYPE: DNA
<213> ORGANISM: Homo sapiens

<400> SEQUENCE: 1294

```
ctgtttgtct ctctgtctgt ctgacaggcg caggctgggt ctctaagcct tgttctgttc    60
tggcctcctc agtctgggtt cttgtcggaa cagctttgcc                         100
```

<210> SEQ ID NO 1295
<211> LENGTH: 100
<212> TYPE: DNA
<213> ORGANISM: Homo sapiens

<400> SEQUENCE: 1295

```
cttgggttac ctgggttcca tctcctgggg aattgggaac aaggggtctg agggaggcac    60
ctcctgggag actttagaag gacccagtgc cctcggggct                         100
```

<210> SEQ ID NO 1296
<211> LENGTH: 100
<212> TYPE: DNA
<213> ORGANISM: Homo sapiens

<400> SEQUENCE: 1296

```
agagttcgct gtgcagggga gacacagagc tctctttatc tgtcaggatg gcaggagggg    60
acagggtcag ggcgctgagg gtcagatgtc ggtgttgggg                         100
```

<210> SEQ ID NO 1297
<211> LENGTH: 100
<212> TYPE: DNA
<213> ORGANISM: Homo sapiens

<400> SEQUENCE: 1297

```
gccaaggccc cgagagatct caggacaggt ggtcaggtgt ctaaggtaaa acagctcccc    60
```

```
gtgcagatca ggacatagtg gaaaacaccc tgaccccct                    100
```

<210> SEQ ID NO 1298
<211> LENGTH: 100
<212> TYPE: DNA
<213> ORGANISM: Homo sapiens

<400> SEQUENCE: 1298

```
gcctggcata gaccttcaga cacagagccc ctgaacaagg gcaccccaac acctcatcat    60
atactgaggt cagggctcc ccaggtggac accaggactc                          100
```

<210> SEQ ID NO 1299
<211> LENGTH: 100
<212> TYPE: DNA
<213> ORGANISM: Homo sapiens

<400> SEQUENCE: 1299

```
agaatattcc gtgagaaggt ggccccacag cgctgggtca cacgccatcc cccaagacag    60
gcaggacacc acagacaggg tggtgggtct cagaaaactc                         100
```

<210> SEQ ID NO 1300
<211> LENGTH: 100
<212> TYPE: DNA
<213> ORGANISM: Homo sapiens

<400> SEQUENCE: 1300

```
aggccctaaa cgtggatgct taccaattcc tccactggag gaagacctca gagcagatgc    60
ccaggacagg gacttctggt agggacggtg actgggacgg                         100
```

<210> SEQ ID NO 1301
<211> LENGTH: 100
<212> TYPE: DNA
<213> ORGANISM: Homo sapiens

<400> SEQUENCE: 1301

```
gtgcctgttt gtcagggaaa acccactgga gagtcagatc ccccagataa cttctcacga    60
catggagact ctttcgaaca gacaaagctc cacgttcagc                         100
```

<210> SEQ ID NO 1302
<211> LENGTH: 100
<212> TYPE: DNA
<213> ORGANISM: Homo sapiens

<400> SEQUENCE: 1302

```
tcagggagta aaaaaaaaat gcctcaaatg gaggcctttg atctactgga atccagcccc    60
caggactgac accctgtctc accaggcagc ccagaggggt                         100
```

<210> SEQ ID NO 1303
<211> LENGTH: 100
<212> TYPE: DNA
<213> ORGANISM: Homo sapiens

<400> SEQUENCE: 1303

```
cagggtccac cagaaggcat ctcagaacca gccagcagtg gccctgattg tcagcaggac    60
cccagggagg ggggtggcca ggacagggct ctgaagcccc                         100
```

<210> SEQ ID NO 1304
<211> LENGTH: 100
<212> TYPE: DNA

-continued

<213> ORGANISM: Homo sapiens

<400> SEQUENCE: 1304

```
caccccagga ccttccctgg gcagaacgag ttggtgaggg agtgatgagc aaccacaggc    60
ctcctaactt cccaagctgg cgattctgag aggcctcaag                         100
```

<210> SEQ ID NO 1305
<211> LENGTH: 100
<212> TYPE: DNA
<213> ORGANISM: Homo sapiens

<400> SEQUENCE: 1305

```
gctgagacac ggttcagcct tttaggccct cctgaacgtg tcccctgtct ccacagcctg    60
ggaatgcact ctcttttgac ccagaaatcc tgctcataag                         100
```

<210> SEQ ID NO 1306
<211> LENGTH: 100
<212> TYPE: DNA
<213> ORGANISM: Homo sapiens

<400> SEQUENCE: 1306

```
ctgtcattgt acaacacatc atttcacttt gtttttcaaa catagtgaat tctttcctaa    60
ttaaagaaga aaagagtata aagagaaagt ttccagtgca                         100
```

<210> SEQ ID NO 1307
<211> LENGTH: 100
<212> TYPE: DNA
<213> ORGANISM: Homo sapiens

<400> SEQUENCE: 1307

```
gtataaagag aaagttttcca gtgcagcctg gagatctgta ctggttgtat ctggaattcc    60
agactcagcc ttgcatttca catagcagat agatgatgat                         100
```

<210> SEQ ID NO 1308
<211> LENGTH: 100
<212> TYPE: DNA
<213> ORGANISM: Homo sapiens

<400> SEQUENCE: 1308

```
gatggagaag gagaagaaga aggaggagga ggaggaaaga aggaagaaga agaagaagag    60
gaggaggaag aagaagacga agggaagaag aagaaggatg                         100
```

<210> SEQ ID NO 1309
<211> LENGTH: 100
<212> TYPE: DNA
<213> ORGANISM: Homo sapiens

<400> SEQUENCE: 1309

```
tccaggtctg ccaggtgtag gggaggtgtg actggttcca tcatggaccg gttcctccat    60
ggaccggttc ctccgtggac cggttccgcc atggaccggt                         100
```

<210> SEQ ID NO 1310
<211> LENGTH: 100
<212> TYPE: DNA
<213> ORGANISM: Homo sapiens

<400> SEQUENCE: 1310

```
tccgccatgg accactcctg ccctggacca ctcctgccct ggaccggttc tgccgtggac    60
tggttcccgc cgtggaccag ttcccgctgt atactggttc                         100
```

<210> SEQ ID NO 1311
<211> LENGTH: 100
<212> TYPE: DNA
<213> ORGANISM: Homo sapiens

<400> SEQUENCE: 1311
tgccctggac tggttcccgc tgtggactgg ttccttgggg ctctaagtgc ggaagggccc    60
agagctggtc cctgcccagc gccctgctag ggctgtgtcc                          100

<210> SEQ ID NO 1312
<211> LENGTH: 100
<212> TYPE: DNA
<213> ORGANISM: Homo sapiens

<400> SEQUENCE: 1312
tcgtactcgt gcgcctcgct tcggtgagcc ccagggcccc tgcctccttc ctcctgccgt    60
cctgcctccg tcccgccct ttcatcatcc gcgtccctgt                           100

<210> SEQ ID NO 1313
<211> LENGTH: 100
<212> TYPE: DNA
<213> ORGANISM: Homo sapiens

<400> SEQUENCE: 1313
gaaggcattc cctaaatccg agcccgagtg gttctccccg ggaaggctac tttggggagc    60 tgggggatg cgaaacaccc tagatactgg ataatggggt                           100

<210> SEQ ID NO 1314
<211> LENGTH: 100
<212> TYPE: DNA
<213> ORGANISM: Homo sapiens

<400> SEQUENCE: 1314
ggggaaatcg atgatttaag aacaaaaccg aaaaactggc gttttgccgt gccgctcgga    60
ggggacatta aaaatttct tagtgtttgc ccgcaaaggt                           100

<210> SEQ ID NO 1315
<211> LENGTH: 100
<212> TYPE: DNA
<213> ORGANISM: Homo sapiens

<400> SEQUENCE: 1315
tagtgtttgc ccgcaaaggt attgtgcgtt gccttggagg ctgagatatg ggggaataga    60
caagtccttt gttctgaggt tcatcttccg agccccgagc                          100

<210> SEQ ID NO 1316
<211> LENGTH: 100
<212> TYPE: DNA
<213> ORGANISM: Homo sapiens

<400> SEQUENCE: 1316
ctcctcccag cctcggacgg ctgcgcgggc tgcatctgtg cagcctggcg gcggcgggc     60 tgtgctatga catctttaca gtccttcttg cagagacatg                          100

<210> SEQ ID NO 1317
<211> LENGTH: 100
<212> TYPE: DNA
<213> ORGANISM: Homo sapiens

<400> SEQUENCE: 1317
tgtgccaggg atgccgaatt gccgggagag caggcaagac cggcttcggg gcgcgcggcg    60
gccgctttgt gtgcggggct gcattgtgac gcgggcgatg                         100

<210> SEQ ID NO 1318
<211> LENGTH: 100
<212> TYPE: DNA
<213> ORGANISM: Homo sapiens

<400> SEQUENCE: 1318
aagccggtag ggcggtggtc ggaagctcca gccgcggccg ccgcctttgt gagaggacta    60
gaaagccgga tccggcccgc atccttgcgg agaggccgcg                         100

<210> SEQ ID NO 1319
<211> LENGTH: 100
<212> TYPE: DNA
<213> ORGANISM: Homo sapiens

<400> SEQUENCE: 1319
gctaggaaat ggaaacgctt ttcctacctg ggctccattt taggaattct tgccgatttt    60
tcccacttga atttggaagt ggctttcctc ttctttcctt                         100

<210> SEQ ID NO 1320
<211> LENGTH: 100
<212> TYPE: DNA
<213> ORGANISM: Homo sapiens

<400> SEQUENCE: 1320
gtcctagcca gcctttaatt ttaaacgctg taattaacaa ttcgcagtgg tcaatttcct    60
ttattctgca agattcggct ttgagaggca tccgccctct                         100

<210> SEQ ID NO 1321
<211> LENGTH: 100
<212> TYPE: DNA
<213> ORGANISM: Homo sapiens

<400> SEQUENCE: 1321
ttggtccaca gcgttttgaa atatggggag gaggggcgcg gggggtgtcg cctctttttc    60
tgtagaaaga ggaagctcgt gagcgcggaa cggcagcagt                         100

<210> SEQ ID NO 1322
<211> LENGTH: 100
<212> TYPE: DNA
<213> ORGANISM: Homo sapiens

<400> SEQUENCE: 1322
aagtgcagtt cccagcccag agacagcggg gcgggtggct cttcctcacg ctcgctcttg    60
gcttgctccc tgcagctttt cctccgcaac catgtctgac                         100

<210> SEQ ID NO 1323
<211> LENGTH: 100
<212> TYPE: DNA
<213> ORGANISM: Homo sapiens

<400> SEQUENCE: 1323
aaacccgata tggctgagat cgagaaattc gataagtcga aactgaagaa gacagagacg    60
caagagaaaa atccactgcc ttccaaagaa agtgagctcc                         100

```
<210> SEQ ID NO 1324
<211> LENGTH: 100
<212> TYPE: DNA
<213> ORGANISM: Homo sapiens

<400> SEQUENCE: 1324
agacgcaaga gaaaaatcca ctgccttcca aagaaagtga gctccgaccc accccatct      60 ttagaaaggc tgggtgggag cggccggtgg gagggcggga                          100

<210> SEQ ID NO 1325
<211> LENGTH: 100
<212> TYPE: DNA
<213> ORGANISM: Homo sapiens

<400> SEQUENCE: 1325
tttatagaaa ggcatatgga acaggagtca tccaaatata tcccaggggt tgcaaattga    60
ccaaaagagt cacctttagg gaagcctgct tctgaatgct                          100

<210> SEQ ID NO 1326
<211> LENGTH: 100
<212> TYPE: DNA
<213> ORGANISM: Homo sapiens

<400> SEQUENCE: 1326
tgtggaattt atcattcttc tgaatggctg ttgcatttat ctgcagcttt tactcaccag    60
atgagacctc agacatttca aattctgcgg aggctggcta                          100

<210> SEQ ID NO 1327
<211> LENGTH: 100
<212> TYPE: DNA
<213> ORGANISM: Homo sapiens

<400> SEQUENCE: 1327
cacaccttca taggaaagct ttttgctgat ttccctgttg gtacttttct cttacacatt    60
ctatggggta tggtaaacct ggaggtagag tcatagccaa                          100

<210> SEQ ID NO 1328
<211> LENGTH: 100
<212> TYPE: DNA
<213> ORGANISM: Homo sapiens

<400> SEQUENCE: 1328
gcacagataa agcaggcaca gaatctctga ccagcctcac aaaagcagac aaacacacaa    60 tcttttttgca cctgtttctt ccactccggt tgccgtgaat                         100

<210> SEQ ID NO 1329
<211> LENGTH: 100
<212> TYPE: DNA
<213> ORGANISM: Homo sapiens

<400> SEQUENCE: 1329
tagaaatggt tcaaccagtc caatatcaat atagctgctt attactctat tcacttactt    60
caaagtggca tttgttttga gtaagacttt atttaattct                          100

<210> SEQ ID NO 1330
<211> LENGTH: 100
<212> TYPE: DNA
<213> ORGANISM: Homo sapiens

<400> SEQUENCE: 1330
```
taccgttagc ttgaaaccat agagatcttc tctctatttg ccctacttcc ttcaaaagtc    60
aaatgacctc ctacaaataa aagacgttct tattttcatt    100

<210> SEQ ID NO 1331
<211> LENGTH: 150
<212> TYPE: DNA
<213> ORGANISM: Homo sapiens

<400> SEQUENCE: 1331
cgactacgac tcggtgcagc cgtatttcta ctgcgacgag gaggagaact tctaccagca    60
gcagcagcag agcgagctgc agccccggc gcccagcgag gatatctgga agaaattcga    120
gctgctgccc accccgcccc tgtcccctag    150

<210> SEQ ID NO 1332
<211> LENGTH: 150
<212> TYPE: DNA
<213> ORGANISM: Homo sapiens

<400> SEQUENCE: 1332
cgactacgac tcggtgcagc cgtagttcta ctgcgacgag gaggaaaact tctaccagca    60
gcagcagcag agcgagctgc agcccctggc gcccagcgag gatatctgga agaacttcga    120
gctgctgccc accccgcccc tgtcccctag    150

<210> SEQ ID NO 1333
<211> LENGTH: 150
<212> TYPE: DNA
<213> ORGANISM: Homo sapiens

<400> SEQUENCE: 1333
cgactacgac tcggtgcagc cgtagttcta ctgcgacgag gaggaatact tctaccagca    60
gcagccgcag agcgagctgc agcccctggc gcccagcgag ggtatctgga agaacttcga    120
gctactgccc accccgcccc tgtcccctag    150

<210> SEQ ID NO 1334
<211> LENGTH: 150
<212> TYPE: DNA
<213> ORGANISM: Homo sapiens

<400> SEQUENCE: 1334
cgactacgac tcgttgcagc cgtagttcta ctgcgacgag gaggaatact tctaccagca    60
gcagccgcag agcgagctgc agcgcctggc gcccagcgag ggtatctgga agaacttcga    120
gctacagccc accccgcccc tgtcccctag    150

<210> SEQ ID NO 1335
<211> LENGTH: 150
<212> TYPE: DNA
<213> ORGANISM: Homo sapiens

<400> SEQUENCE: 1335
cgactacgac tcgttgcagc cgtagatcta ctgcgacgag gaggaatact tctacctgca    60
gcagccgcag agcgagctgc agcgcctggc gcccagcgag cgtatctgga agaacttcga    120
gctacagccc accccgccct tgtcccctag    150

<210> SEQ ID NO 1336
<211> LENGTH: 150
<212> TYPE: DNA
<213> ORGANISM: Homo sapiens

<400> SEQUENCE: 1336
cgacaacgac tcgttgcacc cgtagatcta ctgcgacgag gaggaatact tctacctgca        60
gcagccgcag agcgagctgc agcgcctggc gcccagcgag cgtatctgaa agaacttcga       120
gctacagccc acgccgccct tgtcccctag                                        150

<210> SEQ ID NO 1337
<211> LENGTH: 150
<212> TYPE: DNA
<213> ORGANISM: Homo sapiens

<400> SEQUENCE: 1337
cgacaacgac tcgttgcacc cgtagatcta ctgcgacgag gaggaatact tctacctgca        60
gcagccgcag agcgagctgc agcgcctggc gcccagcgag cgtatctgaa agaacttcga       120
gctacagccc acgccgccct tgtcccctag                                        150

<210> SEQ ID NO 1338
<211> LENGTH: 150
<212> TYPE: DNA
<213> ORGANISM: Homo sapiens

<400> SEQUENCE: 1338
gctcacctgt acaaatctgg ctccgcaggt ttcgcatttg tagggcttct ctccagagtg        60
aattcgagtg tgggttttca ggttggctgg ccggttgaac tgggccccac agatgttgca       120
acgatagggt ttctcaccta ttaccaagaa                                        150

<210> SEQ ID NO 1339
<211> LENGTH: 150
<212> TYPE: DNA
<213> ORGANISM: Homo sapiens

<400> SEQUENCE: 1339
gctcacctgt acaaatctgc ctccgcaggt ttcgcatttg tagggctcct ctccagagtg        60
aattcgagtg tgggttttca ggttggctgg gcggttgaac tgggccccac agatgttgca       120
acgctagggt ttctcaccta ttaccaagaa                                        150

<210> SEQ ID NO 1340
<211> LENGTH: 150
<212> TYPE: DNA
<213> ORGANISM: Homo sapiens

<400> SEQUENCE: 1340
gctcacctgt acaaatctgc ctccgcaggt ttcgcctttg tagggctcct ctccagagtg        60
aattcgagtg taggttttca agttggctgg gcggttgaac tgggccccac ggatgttgca       120
acgctagggt ttctcaccta ttaccaagaa                                        150

<210> SEQ ID NO 1341
<211> LENGTH: 150
<212> TYPE: DNA
<213> ORGANISM: Homo sapiens

<400> SEQUENCE: 1341
gctcacctgt acaaatctgc ctccgccggt ttcgcctttt tagggctcct ctccagagtg        60
aattcgagtg taggttttca agttggctgg gcggttgaac tgggccccac ggatgttgca       120
acgctagggt ttctcaccta tttccaagaa                                        150

<210> SEQ ID NO 1342
<211> LENGTH: 150
<212> TYPE: DNA
<213> ORGANISM: Homo sapiens

<400> SEQUENCE: 1342

```
gctcacctgt acaagtctgc ctccgccggt tacgcctttt tagggctcct ctccagagtg    60
aattcgagtg taggttttca agttggctgg gcggttgaac tgggctccac ggatgttgca   120
acgctaggga ttctcaccta tttccaagaa                                    150
```

<210> SEQ ID NO 1343
<211> LENGTH: 150
<212> TYPE: DNA
<213> ORGANISM: Homo sapiens

<400> SEQUENCE: 1343

```
gctcacctgg acaagtctgc ctccgccggt tacgactttt tagggctcct ctccagagtg    60
aattcgagtg taggctttca agttggctgg gcggttgaac tgggctccac ggctgttgca   120
acgctaggga ttctcaccta tttccaagaa                                    150
```

<210> SEQ ID NO 1344
<211> LENGTH: 150
<212> TYPE: DNA
<213> ORGANISM: Homo sapiens

<400> SEQUENCE: 1344

```
gctcacctgg acaagtctgc ctccgccggt tacgactttt tagggcacct ctccagagtg    60
aattcgagtg taggctttca agttggctgg gagcttgaac tgggctgcac ggctgttgca   120
acgctaggga ttctcaccta tttccaagaa                                    150
```

<210> SEQ ID NO 1345
<211> LENGTH: 150
<212> TYPE: DNA
<213> ORGANISM: Homo sapiens

<400> SEQUENCE: 1345

```
ctaggggaca ggggcggggt gggcagcagc tcgaatttct tccagatatc ctcgctgggc    60
gccgggggct gcagctcgct ctgctgctgc tgctggtaga agttctcctc ctcgtcgcag   120
tagaaatacg gctgcaccga gtcgtagtcg                                    150
```

<210> SEQ ID NO 1346
<211> LENGTH: 150
<212> TYPE: DNA
<213> ORGANISM: Homo sapiens

<400> SEQUENCE: 1346

```
ctaggggaca ggggcggggt gggcagcagc tcgaagttct tccagatatc ctcgctgggc    60
gccaggggct gcagctcgct ctgctgctgc tgctggtaga agttttcctc ctcgtcgcag   120
tagaactacg gctgcaccga gtcgtagtcg                                    150
```

<210> SEQ ID NO 1347
<211> LENGTH: 150
<212> TYPE: DNA
<213> ORGANISM: Homo sapiens

<400> SEQUENCE: 1347

```
ctaggggaca ggggcggggt gggcagtagc tcgaagttct tccagatacc ctcgctgggc    60
```

```
gccagggget gcagctcgct ctgcggctgc tgctggtaga agtattcctc ctcgtcgcag    120
tagaactacg gctgcaccga gtcgtagtcg                                    150
```

<210> SEQ ID NO 1348
<211> LENGTH: 150
<212> TYPE: DNA
<213> ORGANISM: Homo sapiens

<400> SEQUENCE: 1348

```
ctagggaca ggggcggggt gggctgtagc tcgaagttct tccagatacc ctcgctgggc     60
gccaggcgct gcagctcgct ctgcggctgc tgctggtaga agtattcctc ctcgtcgcag    120
tagaactacg gctgcaacga gtcgtagtcg                                    150
```

<210> SEQ ID NO 1349
<211> LENGTH: 150
<212> TYPE: DNA
<213> ORGANISM: Homo sapiens

<400> SEQUENCE: 1349

```
ctagggaca agggcggggt gggctgtagc tcgaagttct tccagatacg ctcgctgggc     60
gccaggcgct gcagctcgct ctgcggctgc tgcaggtaga agtattcctc ctcgtcgcag    120
tagatctacg gctgcaacga gtcgtagtcg                                    150
```

<210> SEQ ID NO 1350
<211> LENGTH: 150
<212> TYPE: DNA
<213> ORGANISM: Homo sapiens

<400> SEQUENCE: 1350

```
ctagggaca agggcggcgt gggctgtagc tcgaagttct ttcagatacg ctcgctgggc     60
gccaggcgct gcagctcgct ctgcggctgc tgcaggtaga agtattcctc ctcgtcgcag    120
tagatctacg ggtgcaacga gtcgttgtcg                                    150
```

<210> SEQ ID NO 1351
<211> LENGTH: 150
<212> TYPE: DNA
<213> ORGANISM: Homo sapiens

<400> SEQUENCE: 1351

```
ctaggcgaca agggcggcgt gggctgtagc tcgaagttct ttcagatacg ctcggtgggc     60
gccaggcgct gcagcacgct ctgcggctgc tgcaggtaga agtattcctc ctcgtcgcag    120
tagatctacg ggtgcaacga gtcgctgtcg                                    150
```

<210> SEQ ID NO 1352
<211> LENGTH: 150
<212> TYPE: DNA
<213> ORGANISM: Homo sapiens

<400> SEQUENCE: 1352

```
ttcttggtaa taggtgagaa accctatcgt tgcaacatct gtggggccca gttcaaccgg     60
ccagccaacc tgaaaaccca cactcgaatt cactctggag agaagcccta caaatgcgaa    120
acctgcggag ccagatttgt acaggtgagc                                    150
```

<210> SEQ ID NO 1353
<211> LENGTH: 150
<212> TYPE: DNA

<213> ORGANISM: Homo sapiens

<400> SEQUENCE: 1353

```
ttcttggtaa taggtgagaa accctagcgt tgcaacatct gtggggccca gttcaaccgc    60
ccagccaacc tgaaaaccca cactcgaatt cactctggag aggagcccta caaatgcgaa   120
acctgcggag gcagatttgt acaggtgagc                                    150
```

<210> SEQ ID NO 1354
<211> LENGTH: 150
<212> TYPE: DNA
<213> ORGANISM: Homo sapiens

<400> SEQUENCE: 1354

```
ttcttggtaa taggtgagaa accctagcgt tgcaacatcc gtggggccca gttcaaccgc    60
ccagccaact tgaaaaccta cactcgaatt cactctggag aggagcccta caaaggcgaa   120
acctgcggag gcagatttgt acaggtgagc                                    150
```

<210> SEQ ID NO 1355
<211> LENGTH: 150
<212> TYPE: DNA
<213> ORGANISM: Homo sapiens

<400> SEQUENCE: 1355

```
ttcttggaaa taggtgagaa accctagcgt tgcaacatcc gtggggccca gttcaaccgc    60
ccagccaact tgaaaaccta cactcgaatt cactctggag aggagcccta aaaaggcgaa   120
accggcggag gcagatttgt acaggtgagc                                    150
```

<210> SEQ ID NO 1356
<211> LENGTH: 150
<212> TYPE: DNA
<213> ORGANISM: Homo sapiens

<400> SEQUENCE: 1356

```
ttcttggaaa taggtgagaa tccctagcgt tgcaacatcc gtggagccca gttcaaccgc    60
ccagccaact tgaaaaccta cactcgaatt cactctggag aggagcccta aaaaggcgta   120
accggcggag gcagacttgt acaggtgagc                                    150
```

<210> SEQ ID NO 1357
<211> LENGTH: 150
<212> TYPE: DNA
<213> ORGANISM: Homo sapiens

<400> SEQUENCE: 1357

```
ttcttggaaa taggtgagaa tccctagcgt tgcaacagcc gtggagccca gttcaaccgc    60
ccagccaact tgaaagccta cactcgaatt cactctggag aggagcccta aaaagtcgta   120
accggcggag gcagacttgt ccaggtgagc                                    150
```

<210> SEQ ID NO 1358
<211> LENGTH: 150
<212> TYPE: DNA
<213> ORGANISM: Homo sapiens -continued

```
<400> SEQUENCE: 1358
ttcttggaaa taggtgagaa tccctagcgt tgcaacagcc gtgcagccca gttcaagctc      60
ccagccaact tgaaagccta cactcgaatt cactctggag aggtgcccta aaaagtcgta     120
accggcggag gcagacttgt ccaggtgagc                                     150
```

METHODS AND SYSTEMS FOR ANALYZING NUCLEIC ACID MOLECULES

CROSS-REFERENCE

This application is a continuation of U.S. patent application Ser. No. 17/455,209, filed Nov. 16, 2021, which is a continuation of PCT Patent Application No. PCT/US2020/059526, filed Nov. 6, 2020, which claims the benefit of U.S. Provisional Patent Application No. 62/931,688, filed Nov. 6, 2019, the disclosures of which are entirely incorporated herein by reference in their entirety.

GOVERNMENT RIGHTS

This invention was made with Government support under CA233975, CA241076, and CA188298 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Nov. 3, 2020, is named 58626-702_601_SL.txt and is 307,199 bytes in size.

BACKGROUND

Noninvasive blood tests that can detect somatic alterations (e.g., mutated nucleic acids) based on the analysis of cell-free nucleic acids (e.g., cell-free deoxyribonucleic acid (cfDNA) and cell-free ribonucleic acid (cfRNA)) are attractive candidates for cancer screening applications due to the relative ease of obtaining biological specimens (e.g., biological fluids). Circulating tumor nucleic acids (e.g., ctDNA or ctRNA; i.e., nucleic acids derived from cancerous cells) can be sensitive and specific biomarkers in numerous cancer subtypes. However, current methods for minimal residual disease (MRD) detection from ctDNA can be limited by one or more factors, such as low input DNA amounts and high background error rates.

Recent approaches have improved ctDNA MRD performance by tracking multiple somatic mutations with error-suppressed sequencing, resulting in detection limits as low as 4 parts in 100,000 from limited cfDNA input. Detection of residual disease during or after treatment is a powerful tool, with detectable MRD representing an adverse prognostic sign even during radiographic remission. However, current limits of detection may be insufficient to universally detect residual disease in patients destined for disease relapse or progression. This 'loss of detection' is exemplified in diffuse large B-cell lymphoma (DLBCL), where ctDNA detection after two cycles of curative-intent therapy is a strong prognostic marker. Despite this, almost one-third of patients experiencing disease progression do not have detectable ctDNA at this landmark, representing 'false-negative' tests. Similar false-negative rates in colon cancer and breast cancer have been observed.

SUMMARY

The present disclosure provides methods and systems for analyzing cell-free nucleic acids (e.g., cfDNA, cfRNA) from a subject. Methods and systems of the present disclosure can utilize sequencing results derived from the subject to detect cancer-derived nucleic acids (e.g., ctDNA, ctRNA) for, e.g., disease diagnosis, disease monitoring, or determining treatments for the subject. Methods and systems of the present disclosure can exhibit enhanced sensitivity, specificity and/or reliability of detection of cancer-derived nucleic acids.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence, wherein at least about 10% of the one or more cell-free nucleic acid molecules comprises a first phased variant of the plurality of phased variants and a second phased variant of the plurality of phased variants that are separated by at least one nucleotide; and (c) analyzing, by the computer system, the identified one or more cell-free nucleic acid molecules to determine a condition of the subject.

In some embodiments of any one of the methods disclosed herein, the at least about 10% of the cell-free nucleic acid molecules comprise at least about 20%, at least about 30%, at least about 40%, at least about 50%, at least about 60%, at least about 70%, at least about 80%, at least about 90%, or about 100% of the one or more cell-free nucleic acid molecules.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence that are separated by at least one nucleotide; and (c) analyzing, by the computer system, the identified one or more cell-free nucleic acid molecules to determine a condition of the subject.

In one aspect, the present disclosure provides a method comprising: (a) obtaining sequencing data derived from a plurality of cell-free nucleic acid molecules that is obtained or derived from a subject; (b) processing the sequencing data to identify one or more cell-free nucleic acid molecules of the plurality of cell-free nucleic acid molecules with a limit of detection of less than about 1 out of 50,000 observations from the sequencing data; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 observations from the sequencing data.

In some embodiments of any one of the methods disclosed herein, each of the one or more cell-free nucleic acid molecules comprises a plurality of phased variants relative to a reference genomic sequence. In some embodiments of any one of the methods disclosed herein, a first phased variant of the plurality of phased variants and a second phased variant of the plurality of phased variants are separated by at least one nucleotide.

In some embodiments of any one of the methods disclosed herein, the processes (a) to (c) are performed by a computer system.

In some embodiments of any one of the methods disclosed herein, the sequencing data is generated based on nucleic acid amplification. In some embodiments of any one of the methods disclosed herein, the sequencing data is generated based on polymerase chain reaction. In some embodiments of any one of the methods disclosed herein, the sequencing data is generated based on amplicon sequencing.

In some embodiments of any one of the methods disclosed herein, the sequencing data is generated based on next-generation sequencing (NGS). Alternatively, in some embodiments of any one of the methods disclosed herein, the sequencing data is generated based on non-hybridization-based NGS.

In some embodiments of any one of the methods disclosed herein, the sequencing data is generated without use of molecular barcoding of at least a portion of the plurality of cell-free nucleic acid molecules. In some embodiments of any one of the methods disclosed herein, the sequencing data is obtained without use of sample barcoding of at least a portion of the plurality of cell-free nucleic acid molecules.

In some embodiments of any one of the methods disclosed herein, the sequencing data is obtained without in silico removal or suppression of (i) background error or (ii) sequencing error.

In one aspect, the present disclosure provides a method of treating a condition of a subject, the method comprising: (a) identifying the subject for treatment of the condition, wherein the subject has been determined to have the condition based on identification of one or more cell-free nucleic acid molecules from a plurality of cell-free nucleic acid molecules that is obtained or derived from the subject, wherein each of the one or more cell-free nucleic acid molecules identified comprises a plurality of phased variants relative to a reference genomic sequence that are separated by at least one nucleotide, and wherein a presence of the plurality of phased variants is indicative of the condition of the subject; and (b) subjecting the subject to the treatment based on the identification in (a).

In one aspect, the present disclosure provides a method of monitoring a progress of a condition of a subject, the method comprising: (a) determining a first state of the condition of the subject based on identification of a first set of one or more cell-free nucleic acid molecules from a first plurality of cell-free nucleic acid molecules that is obtained or derived from the subject; (b) determining a second state of the condition of the subject based on identification of a second set of one or more cell-free nucleic acid molecules from a second plurality of cell-free nucleic acid molecules that is obtained or derived from the subject, wherein the second plurality of cell-free nucleic acid molecules are obtained from the subject subsequent to obtaining the first plurality of cell-free nucleic acid molecules from the subject; and (c) determining the progress of the condition based on the first state of the condition and the second state of the condition, wherein each of the one or more cell-free nucleic acid molecules comprises a plurality of phased variants relative to a reference genomic sequence that are separated by at least one nucleotide.

In some embodiments of any one of the methods disclosed herein, the progress of the condition is worsening of the condition.

In some embodiments of any one of the methods disclosed herein, the progress of the condition is at least a partial remission of the condition.

In some embodiments of any one of the methods disclosed herein, a presence of the plurality of phased variants is indicative of the first state or the second state of the condition of the subject.

In some embodiments of any one of the methods disclosed herein, the second plurality of cell-free nucleic acid molecules is obtained from the subject at least about 1 week, at least about 2 weeks, at least about 3 weeks, at least about 4 weeks, at least about 2 months, or at least about 3 months subsequent to obtaining the first plurality of cell-free nucleic acid molecules from the subject.

In some embodiments of any one of the methods disclosed herein, the subject is subjected to a treatment for the condition (i) prior to obtaining the second plurality of cell-free nucleic acid molecules from the subject and (ii) subsequent to obtaining the first plurality of cell-free nucleic acid molecules from the subject.

In some embodiments of any one of the methods disclosed herein, the progress of the condition is indicative of minimal residual disease of the condition of the subject. In some embodiments of any one of the methods disclosed herein, the progress of the condition is indicative of tumor burden or cancer burden of the subject.

In some embodiments of any one of the methods disclosed herein, the one or more cell-free nucleic acid molecules are captured from among the plurality of cell-free nucleic acid molecules with a set of nucleic acid probes, wherein the set of nucleic acid probes is configured to hybridize to at least a portion of cell-free nucleic acid molecules comprising one or more genomic regions associated with the condition.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence that are separated by at least one nucleotide, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants; and (c) analyzing the identified one or more cell-free nucleic acid molecules to determine a condition of the subject.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 cell-free nucleic acid molecules of the plurality of cell-free nucleic acid molecules.

In some embodiments of any one of the methods disclosed herein, a first phased variant of the plurality of phased variants and a second phased variant of the plurality of phased variants are separated by at least one nucleotide.

In some embodiments of any one of the methods disclosed herein, the activatable reporter agent is activated upon hybridization of the individual nucleic acid probe to the plurality of phased variants.

In some embodiments of any one of the methods disclosed herein, the activatable reporter agent is activated upon dehybridization of at least a portion of the individual nucleic acid probe that has been hybridized to the plurality of phased variants.

In some embodiments of any one of the methods disclosed herein, the method further comprises mixing (1) the set of nucleic acid probes and (2) the plurality of cell-free nucleic acid molecules.

In some embodiments of any one of the methods disclosed herein, the activatable reporter agent is a fluorophore.

In some embodiments of any one of the methods disclosed herein, analyzing the identified one or more cell-free nucleic acid molecules comprises analyzing (i) the identified one or more cell-free nucleic acid molecules and (ii) other cell-free nucleic acid molecules of the plurality of cell-free nucleic acid molecules that do not comprise the plurality of phased variants as different variables.

In some embodiments of any one of the methods disclosed herein, the analyzing of the identified one or more cell-free nucleic acid molecules is not based on other cell-free nucleic acid molecules of the plurality of cell-free nucleic acid molecules that do not comprise the plurality of phased variants.

In some embodiments of any one of the methods disclosed herein, a number of the plurality of phased variants from the identified one or more cell-free nucleic acid molecules is indicative of the condition of the subject. In some embodiments, a ratio of (i) the number of the plurality of phased variants from the one or more cell-free nucleic acid molecules and (ii) a number of single nucleotide variants (SNVs) from the one or more cell-free nucleic acid molecules is indicative of the condition of the subject.

In some embodiments of any one of the methods disclosed herein, a frequency of the plurality of phased variants in the identified one or more cell-free nucleic acid molecules is indicative of the condition of the subject. In some embodiments, the frequency is indicative of a diseased cell associated with the condition. In some embodiments, the condition is diffuse large B-cell lymphoma, and wherein the frequency is indicative of whether the one or more cell-free nucleic acid molecules are derived from germinal center B-cell (GCB) or activated B-cell (ABC).

In some embodiments of any one of the methods disclosed herein, genomic origin of the identified one or more cell-free nucleic acid molecules is indicative of the condition of the subject.

In some embodiments of any one of the methods disclosed herein, the first and second phased variants are separated by at least 2, at least 3, at least 4, at least 5, at least 6, at least 7, or at least 8 nucleotides. In some embodiments of any one of the methods disclosed herein, the first and second phased variants are separated by at most about 180, at most about 170, at most about 160, at most about 150, or at most about 140 nucleotides.

In some embodiments of any one of the methods disclosed herein, at least about 10%, at least about 20%, at least about 30%, at least about 40%, or at least about 50% of the one or more cell-free nucleic acid molecules comprising a plurality of phased variants comprises a single nucleotide variant (SNV) that is at least 2 nucleotides away from an adjacent SNV.

In some embodiments of any one of the methods disclosed herein, the plurality of phased variants comprises at least 3, at least 4, at least 5, at least 10, at least 15, at least 20, or at least 25 phased variants within the same cell-free nucleic acid molecule.

In some embodiments of any one of the methods disclosed herein, the one or more cell-free nucleic acid molecules identified comprises at least 2, at least 3, at least 4, at least 5, at least 10, at least 50, at least 100, at least 500, or at least 1,000 cell-free nucleic acid molecules.

In some embodiments of any one of the methods disclosed herein, the reference genomic sequence is derived from a reference cohort. In some embodiments, the reference genomic sequence comprises a consensus sequence from the reference cohort. In some embodiments, the reference genomic sequence comprises at least a portion of hg19 human genome, hg18 genome, hg17 genome, hg16 genome, or hg38 genome.

In some embodiments of any one of the methods disclosed herein, the reference genomic sequence is derived from a sample of the subject.

In some embodiments of any one of the methods disclosed herein, the sample is a healthy sample. In some embodiments, the sample comprises a healthy cell. In some embodiments, the healthy cell comprises a healthy leukocyte.

In some embodiments of any one of the methods disclosed herein, the sample is a diseased sample. In some embodiments, the diseased sample comprises a diseased cell. In some embodiments, the diseased cell comprises a tumor cell. In some embodiments, the diseased sample comprises a solid tumor.

In some embodiments of any one of the methods disclosed herein, the set of nucleic acid probes is designed based on the plurality of phased variants that are identified by comparing (i) sequencing data from a solid tumor, lymphoma, or blood tumor of the subject and (ii) sequencing data from a healthy cell of the subject or a healthy cohort. In some embodiments, the healthy cell is from the subject. In some embodiments, the healthy cell is from the healthy cohort.

In some embodiments of any one of the methods disclosed herein, the set of nucleic acid probes are designed to hybridize to at least a portion of sequences of genomic loci associated with the condition. In some embodiments, the genomic loci associated with the condition are known to exhibit aberrant somatic hypermutation when the subject has the condition.

In some embodiments of any one of the methods disclosed herein, the set of nucleic acid probes are designed to hybridize to at least about 5%, at least about 10%, at least about 20%, at least about 30%, at least about 40%, at least about 50%, at least about 60%, at least about 70%, at least about 80%, at least about 90%, or about 100% of (i) the genomic regions identified in Table 1, (ii) the genomic regions identified in Table 3, or (iii) the genomic regions identified to have a plurality of phased variants in Table 3.

In some embodiments of any one of the methods disclosed herein, each nucleic acid probe of the set of nucleic acid probes has at least about 70%, at least about 80%, at least about 90% sequence identity, at least about 95% sequence identity, or about 100% sequence identity to a probe sequence selected from Table 6.

In some embodiments of any one of the methods disclosed herein, the set of nucleic acid probes comprises at least about 5%, at least about 10%, at least about 20%, at least about 30%, at least about 40%, at least about 50%, at least about 60%, at least about 70%, at least about 80%, or at least about 90% of probe sequences in Table 6.

In some embodiments of any one of the methods disclosed herein, the method further comprises determining that the subject has the condition or determining a degree or status of the condition of the subject, based on the identified one or more cell-free nucleic acid molecules comprising the plurality of phased variants. In some embodiments, the method further comprises determining that the one or more cell-free nucleic acid molecules are derived from a sample associated with the condition, based on performing a statistical model analysis of the identified one or more cell-free nucleic acid molecules. In some embodiments, the statistical model analysis comprises a Monte Carlo statistical analysis.

In some embodiments of any one of the methods disclosed herein, the method further comprises monitoring a progress of the condition of the subject based on the identified one or more cell-free nucleic acid molecules.

In some embodiments of any one of the methods disclosed herein, the method further comprises performing a different procedure to confirm the condition of the subject. In some embodiments, the different procedure comprises a blood test, genetic test, medical imaging, physical exam, or tissue biopsy.

In some embodiments of any one of the methods disclosed herein, the method further comprises determining a treatment for the condition of the subject based on the identified one or more cell-free nucleic acid molecules.

In some embodiments of any one of the methods disclosed herein, the subject has been subjected to a treatment for the condition prior to (a).

In some embodiments of any one of the methods disclosed herein, the treatment comprises chemotherapy, radiotherapy, chemoradiotherapy, immunotherapy, adoptive cell therapy, hormone therapy, targeted drug therapy, surgery, transplant, transfusion, or medical surveillance.

In some embodiments of any one of the methods disclosed herein, the plurality of cell-free nucleic acid molecules comprise a plurality of cell-free deoxyribonucleic acid (DNA) molecules.

In some embodiments of any one of the methods disclosed herein, condition comprises a disease.

In some embodiments of any one of the methods disclosed herein, the plurality of cell-free nucleic acid molecules are derived from a bodily sample of the subject. In some embodiments, the bodily sample comprises plasma, serum, blood, cerebrospinal fluid, lymph fluid, saliva, urine, or stool.

In some embodiments of any one of the methods disclosed herein, the subject is a mammal. In some embodiments of any one of the methods disclosed herein, the subject is a human.

In some embodiments of any one of the methods disclosed herein, the condition comprises neoplasm, cancer, or tumor. In some embodiments, the condition comprises a solid tumor. In some embodiments, the condition comprises a lymphoma. In some embodiments, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any one of the methods disclosed herein, the plurality of phased variants have been previously identified as tumor-derived from sequencing a prior tumor sample or cell-free nucleic acid sample.

In one aspect, the present disclosure provides a composition comprising a bait set comprising a set of nucleic acid probes designed to capture cell-free DNA molecules derived from at least about 5% of genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to pull down cell-free DNA molecules derived from at least about 10%, at least about 20%, at least about 30%, at least about 40%, at least about 50%, at least about 60%, at least about 70%, at least about 80%, at least about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to capture the one or more cell-free DNA molecules derived from at most about 10%, at most about 20%, at most about 30%, at most about 40%, at most about 50%, at most about 60%, at most about 70%, at most about 80%, at most about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the bait set comprises at most 5, at most 10, at most 50, at most 100, at most 500, at most 1000, or at most 2000 nucleic acid probes.

In some embodiments of any of the compositions disclosed herein, an individual nucleic acid probe of the set of nucleic acid probes comprises a pull-down tag.

In some embodiments of any of the compositions disclosed herein, the pull-down tag comprises a nucleic acid barcode.

In some embodiments of any of the compositions disclosed herein, the pull-down tag comprises biotin.

In some embodiments of any of the compositions disclosed herein, each of the cell-free DNA molecules is between about 100 nucleotides and about 180 nucleotides in length.

In some embodiments of any of the compositions disclosed herein, the genomic regions are associated with a condition.

In some embodiments of any of the compositions disclosed herein, the genomic regions exhibit aberrant somatic hypermutation when a subject has the condition.

In some embodiments of any of the compositions disclosed herein, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any of the compositions disclosed herein, the composition further comprises a plurality of cell-free DNA molecules obtained or derived from a subject.

In one aspect, the present disclosure provides a method to perform a clinical procedure on an individual, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) performing a clinical procedure on the individual to confirm the presence of the B-cell cancer, based upon determining that the cell-free nucleic acid sequencing result contains nucleic acid sequences likely derived from the B-cell cancer.

In some embodiments of any of the compositions disclosed herein, the biopsy is one of blood, serum, cerebrospinal fluid, lymph fluid, urine, or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the clinical is procedure is a blood test, medical imaging, or a physical exam.

In one aspect, the present disclosure provides a method to treat an individual for a B-cell cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) treating the individual to curtail the B-cell cancer, based upon determining that the cell-free nucleic acid sequencing result contains nucleic acid sequences derived from the B-cell cancer.

In some embodiments of any of the compositions disclosed herein, the biopsy is one of blood, serum, cerebrospinal fluid, lymph fluid, urine or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the treatment is chemotherapy, radiotherapy, immunotherapy, hormone therapy, targeted drug therapy, or medical surveillance.

In one aspect, the present disclosure provides a method to detect cancerous minimal residual disease in an individual and to treat the individual for a cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, wherein the liquid or waste biopsy is sourced after a series of treatments in order to detect minimal residual disease, and wherein the targeting sequencing is performed utilizing nucleic acid probes to pull down sequences of genomic loci determined to contain a plurality of variants in phase, as determined by a prior sequencing result on a prior biopsy derived from the cancer; (b) identifying or having identified at least one set of the plurality of variants in phase within the cell-free nucleic acid sequencing result; and (c) treating the individual to curtail the cancer, based upon determining that the cell-free nucleic acid sequencing result contains nucleic acid sequences derived from the cancer.

In some embodiments of any of the compositions disclosed herein, the liquid or waste biopsy is one of blood, serum, cerebrospinal fluid, lymph fluid, urine or stool.

In some embodiments of any of the compositions disclosed herein, the treatment is chemotherapy, radiotherapy, immunotherapy, hormone therapy, targeted drug therapy, or medical surveillance.

In one aspect, the present disclosure provides a computer program product comprising a non-transitory computer-readable medium having computer-executable code encoded therein, the computer-executable code adapted to be executed to implement any one of the methods disclosed herein.

In one aspect, the present disclosure provides a system comprising one or more computer processors and computer memory coupled thereto, wherein the computer memory comprises machine executable code that, upon execution by the one or more computer processors, implements any one of the methods disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A. is a cartoon depicting the difference between detection of a single nucleotide variant (SNV) (top) and multiple variants 'in-phase' (phased variants, PVs; bottom) on individual cell-free DNA molecules. In theory, detection of a PV is a more specific event than detection of an isolated SNV. FIG. 1B. is a scatter plot showing the distribution of the number of PVs from WGS data for 24 different histologies of cancer, normalized by the total number of SNVs. Bars show the median value and interquartile range. (FL-NHL, follicular lymphoma; DLBCL-NHL, diffuse large B-cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma.) FIG. 1C. is a heatmap demonstrating the enrichment in single base substitution (SBS) mutational signatures for PVs versus single SNVs across multiple cancer types. Blue represents signatures which are enriched in PVs in specific histologies; darker gray represents signatures where un-phased, single SNVs are enriched; and red represents SNVs occurring in isolation. Only signatures which have a significant difference between PVs and unphased SNVs after correcting for multiple hypotheses are shown; other signatures are grey. Signatures associated with smoking, AID/AICDA, and APOBEC are indicated. FIG. 1D. demonstrate bar plots showing the distribution of PVs occurring in stereotyped regions across the genome in B-lymphoid malignancies and lung adenocarcinoma. In this plot, the genome was divided into 1000 bp bins, and the fraction of samples of a given histology with a PV in each 1000 bp bin was calculated. Only bins that have at least a 2 percent recurrence frequency in any cancer subtype are shown. Key genomic loci are also labeled. FIG. 1E. is a comparison of duplex sequencing to phased variant sequencing. A schema comparing error-suppressed sequencing by duplex sequencing vs. recovery of phased variants. In duplex sequencing, recovery of a single SNV observed on both strands of an original DNA double-helix (i.e., in trans) is required. This requires independent recovery of two molecules by sequencing as the plus and minus strands of the original DNA molecule go through library preparation and PCR independently. In contrast, recovery of PVs requires multiple SNVs observed on the same single strand of DNA (i.e., in cis). Thus, recovery of only the plus or the minus strand (rather than both) is sufficient for identification of PVs.

FIG. 2A is a schematic of the design for PhasED-Seq. WGS data from DLBCL tumor samples were aggregated (left), and areas of recurrent putative PVs were identified (middle). An assay capturing the genomic regions most recurrently containing PVs was then designed (right), resulting in an ~7500× enrichment in PVs compared to WGS. The top right panel shows the in silico expected number of PVs per case per kilobase of panel size (y-axis) for increasing panel sizes (x-axis). The dashed line shows the selected regions in the PhasED-Seq panel. The bottom right panel shows the total number of expected PVs per case (y-axis, assessed in silico from WGS data, for increasing panel sizes (y-axis). The dark area shows the selected regions in the PhasED-Seq panel. FIG. 2B illustrate two panels showing the yield of SNVs (left) and PVs (right) for sequencing tumor DNA and matched germline by a previously established lymphoma CAPP-Seq panel or PhasED-Seq; values are assessed in silico by limiting WGS to the targeted space of interest. PVs reported in the right panel include doublet, triplet, and quadruplet phased events. FIG. 2C shows the yield of SNVs (left) and PVs (right) from experimental sequencing of tumor and/or cell-free DNA from CAPP-Seq versus PhasED-Seq, similar to FIG. 2B. FIG. 2D is a scatterplot showing the frequency of PVs by genomic location (in 1000 bp bins) for patients with DLBCL, identified either by WGS or identified by PhasED-Seq. PVs in IGH, BCL2, MYC, and BCL6 are highlighted. FIG. 2E illustrate scatterplots comparing the frequency of PVs by genomic location (in 50 bp bins) for patients with different types of lymphomas. The colored circles show the relative frequency of PVs in 50 bp bins from a specific gene of interest; the other (gray) circles show the relative frequency of PVs in 50 bp bins from the remainder of the PhasED-Seq sequencing panel. FIG. 2F illustrate volcano plots summarizing the difference in relative frequency of PVs in specific genetic loci between types of lymphoma, including ABC-DLBCL vs. GCB-DLBCL (dark Gray, left); PMBCL vs DLBCL (dark gray, middle); and HL vs. DLBCL (dark gray, right). The x-axis demonstrates the relative enrichment in PVs in a specific locus, while the y-axis demonstrates the statistical significance of this association. (Example 10).

FIG. 3A illustrates bar plot showing the performance of hybrid capture sequencing for recovery of synthetic 150 bp oligonucleotides from two loci (MYC and BCL6) with increasing degree of mutation/non-reference bases. Error bars represent the 95% confidence interval (n=3 replicates of each condition in distinct samples). FIG. 3B illustrates plot demonstrating the background error-rate (Example 10) for different types of error-suppression from 12 healthy control cell-free DNA samples sequenced on the PhasED-Seq panel. 'PhasED-Seq 2×' or 'doublets' represents detection of two mutations in-phase on the same DNA molecule; 'PhasED-Seq 3×' or 'triplets' represents detection of three mutations in-phase on the same DNA molecule. FIG. 3C illustrates bar plot showing the depth of unique molecular recovery (e.g., depth after barcode-mediated PCR duplicate removal) from sequencing data from 12 cell-free DNA samples for different types of error-suppression, including barcode deduplication, duplex sequencing, and recovery of PVs of increasing maximal distance between SNVs in-phase. FIG. 3D illustrates bar plot showing the cumulative fraction of PVs that have a maximal distance between SNVs less than the number of base-pairs shown on the x-axis. FIG. 3E illustrates a plot demonstrating the results of a limiting dilution series simulating cell-free DNA samples containing patient-specific tumor fractions of $1 \times 10^{-3}$ to $0.5 \times 10^{-6}$; cfDNA from 3 independent patients samples were used in each dilution. The same sequencing data was analyzed using a variety of error-suppression methods for recovery of expected tumor fractions, including iDES, duplex sequencing, and PhasED-Seq (both for recovery of doublet and triplet molecules). Points and error-bars represent the mean, minimum, and maximum across the three patient-specific tumor mutations considered. The difference between observed and expected tumor fractions for sample <1:10,000 were compared via paired t-test. *, P<0.05, , P<0.005, *, P<0.0005. FIG. 3F illustrates plot demonstrating the background signal for detection of tumor-specific alleles in 12 unrelated, healthy cell-free DNA samples, and the healthy cfDNA sample used for limiting dilution series (n=13 total samples). In each sample, tumor-specific SNVs or PVs from the 3 patient samples utilized in the limiting dilution experiment shown in FIG. 3E, for a total of 39 assessments were assessed. Bars represent the arithmetic mean across all 39 assessments; statistical comparison performed by Wilcoxon rank-sum test. *, P<0.05, , P<0.005, *, P<0.0005. FIG. 3G illustrates plot showing the theoretical rate of detection for a sample with a given number of PV-containing regions, according to simple binomial sampling. This plot is produced by assuming a unique sequencing depth of 5000× (line), along with a varying number of independent 150 bp PV-containing regions, from 3 regions (blue) to 67 regions (purple). Confidence envelopes consider depth from 4000-6000×; a 5% false-positive rate is also assumed.

FIG. 3H illustrates plot showing the observed rate of detection (y-axis) for sample of a given true tumor fraction (x-axis), with varying numbers of PV-containing regions. For each number of tumor-reporter regions ranging from 3 to 67, this number of 150 bp windows was randomly sampled from each of 3 patient-specific PV reporter lists 25 times and used to assess tumor-detection at each dilution. Filled-in points represent 'wet' dilution series experiments, while open points represent in silico dilution experiments. Points and error-bars represent the mean, minimum, and maximum across the three patient-specific PV reporter lists used in the original sampling.

FIGS. 4A-4G illustrate clinical application of PhasED-Seq for ultra-sensitive disease detection and response monitoring in DLBCL. FIG. 4A illustrates plot showing ctDNA levels for a patient with DLBCL responding to, and subsequently relapsing after, first-line immuno-chemotherapy. Levels measured by CAPP-Seq are shown in darker gray circles while levels measured by PhasED-Seq are shown in lighter gray circles. Open circles represent undetectable levels by CAPP-Seq. FIG. 4B illustrates a univariate scatter plot showing the mean tumor allele fraction measured by PhasED-Seq for clinical samples at time-points of minimal disease (i.e., after 1 or 2 cycles of therapy). The plot is divided by samples detected vs undetected by standard CAPP-Seq; P-value from Wilcoxon rank-sum test. FIG. 4C illustrates bar plot showing the fraction of DLBCL patients who have detectable ctDNA by CAPP-Seq after 1 or 2 cycles of treatment (dark gray bars), as well as the fraction of additional patients with detectable disease when adding PhasED-Seq to standard CAPP-Seq (medium gray bars). P-value represents a Fisher's Exact Test for detection by CAPP-Seq alone versus the combination of PhasED-Seq and CAPP-Seq in 171 samples after 1 or 2 cycles of treatment. FIG. 4D illustrates a waterfall plot showing the change in ctDNA levels measured by CAPP-Seq after 2 cycles of first-line therapy in patients with DLBCL. Patients with undetectable ctDNA by CAPP-Seq are shown as "ND" ("not detected"), in darker colors. The colors of the bars also indicate the eventual clinical outcomes for these patients.

FIG. 4E illustrates a Kaplan-Meier plot showing the event-free survival for 52 DLBCL patients with undetectable ctDNA measured by CAPP-Seq after 2 cycles. FIG. 4F illustrates a Kaplan-Meier plot showing the event-free survival of 52 patients shown in FIG. 4E (undetectable ctDNA by CAPP-Seq) stratified by ctDNA detection via PhasED-Seq at this same time-point (cycle 3, day 1). FIG. 4G illustrates a Kaplan-Meier plot showing the event-free survival for 89 patients with DLBCL stratified by ctDNA at cycle 3, day 1 separated into 3 strata—patients failing to achieve a major molecular response (dark gray), patients with a major molecular response who still have detectable ctDNA by PhasED-Seq and/or CAPP-Seq (light grey), and patients who have a stringent molecular remission (undetectable ctDNA by PhasED-Seq and CAPP-Seq; medium gray).

FIG. 5A-C illustrate Univariate scatter plots showing the number of SNVs (FIG. 5A), PVs (FIG. 5B), and PVs, controlling for total number of SNVs (FIG. 5C), from WGS data for 24 different histologies of cancer. Bars show the median value and interquartile range. (FL-NHL, follicular lymphoma; DLBCL-NHL, diffuse large B cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma).

FIG. 8A. illustrates bar plot showing the number of independent 1000 bp regions across the genome that recurrently contain PVs for DLBCL, FL, BL, and CLL (n=68, 74, 36, and 151 respectively). FIG. 8B-D illustrate plots showing the frequency of PVs for multiple lymphoid malignancies with relationships to specific genetic loci, including FIG. 8B: BCL2, FIG. 8C: MYC, and FIG. 8D: ID3. The location of the transcript for a given gene is shown below the plot in grey; exons are shown in darker gray. * indicates a region with significantly more PVs in a given cancer histology compared to all other histologies by Fisher's Exact Test (P<0.05). FIG. 8E, similar to FIG. 8B-D, these plots show the frequency of PVs across lymphoma subtypes. Here, it is shown the IGH locus, consisting of IGHV, IGHD, and IGHJ parts, for ABC and GCB subtype DLBCLs (n=25 and 25, respectively). Coding regions for Ig parts, including Ig-constant regions and V-genes, are shown. (DLBCL, diffuse large B-cell lymphoma; FL, follicular lymphoma; BL, Burkitt lymphoma; CLL, chronic lymphocytic leukemia).

FIGS. 9A-9K illustrate performance of PhasED-Seq for recovery of PVs across lymphomas. FIG. 9A illustrates univariate scatter plot showing the fraction of all PVs across the genome identified by WGS (n=79) that were recovered by previously reported lymphoma CAPP-Seq panel[8] (left) compared to PhasED-Seq (right). FIG. 9B illustrates the expected yield of SNVs per case identified from WGS using a previously established lymphoma CAPP-Seq panel or the PhasED-Seq panel. FIG. 9C illustrates the expected yield of PVs per case identified from WGS using a previously established lymphoma CAPP-Seq panel or the PhasED-Seq panel. Data from three independent publicly available cohorts are shown in FIGS. 9A-9C. FIG. 9D-9F illustrate plots showing the improvement in recovery of PVs by PhasED-Seq compared to CAPP-Seq in 16 patients sequenced by both assays. This includes improvement in d) two SNVs in phase (e.g., 2× or 'doublet PVs'), e) three SNVs in phase (3× or 'triplet PVs') and f) four SNVs in phase (e.g., 4× or 'quadruplet PVs'). FIGS. 9G-9K. illustrate panels showing the number of SNVs and PVs identified for patients with different types of lymphomas. These panels show the number of g) SNVs, h) doublet PVs, i) triplet PVs, j) quadruplet PVs, and k) all PVs. *, P<0.05; , P<0.01; *, P<0.001. (DLBCL, diffuse large B-cell lymphoma; GCB, germinal center B-cell like DLBCL; ABC, activated B-cell like DLBCL; PMBCL, primary mediastinal B-cell lymphoma; HL, Hodgkin lymphoma).

FIG. 14A shows a plot of the theoretical energy of binding for typical 150-mers across the genome with increasing fraction of bases mutated from the reference genome. Mutations were spread throughout the 150-mer either clustered to one end of the sequence, clustered in the middle of the sequence, or randomly throughout the sequence. Point and error-bars represent the median and interquartile ranges from 10,000 in silico simulations. FIG. 14B illustrates a plot showing two histograms of summary metrics of the mutation rate of 151-bp windows across the PhasED-Seq panel across all patients in this study. The light gray histogram shows the maximum percent mutated in any 151-bp window for all patients in this study; the dark gray histogram shows the 95$^{th}$ percentile mutation rate across all mutated 151-bp windows. FIG. 14C is a plot showing the percentile of mutation rate across all mutated 151-bp windows across all patients in this study. FIG. 14D illustrates heatmaps showing the relative error rate (as log 10 (error rate)) for single SNVs (left, "RED"), doublet PVs (middle, "YELLOW"), and triplet PVs (right, "BLUE"). FIG. 14D demonstrates that analysis based on the plurality of phased variants (e.g., double or triplet PVs) yields a lower error rate than analysis based on single SNVs. In addition, FIG. 14D demonstrates that analysis using a higher number of phased variant sets (e.g., triplet PVs labeled as "BLUE") yields a lower error rate than analysis based on a lower number of phased variant sets (e.g., doublet PVs labeled as "YELLOW"). The error rate of single SNVs from sequencing with multiple error suppression methods is shown, including barcode deduplication, iDES, and duplex sequencing. Error rates are summarized by the type of mutation. In the case of triplet PVs, the x and y-axis of the heatmap represent the first and second type of base alteration in the PV; the third alteration is averaged over all 12 possible base changes. FIG. 14E illustrates a plot showing the error rate for doublet/ 2× PVs as a function of the genomic distance between the component SNVs.

FIG. 15 illustrates the detection-rate of ctDNA from pretreatment samples across 107 patients with large-B cell lymphomas by standard CAPP-Seq (green), as well as PhasED-Seq using doublets (light blue), triplets (medium blue), and quadruplets (dark blue). The specificity of ctDNA detection is also shown. In the lower two plots, the false-detection rate in 40 withheld healthy control cfDNA samples is shown. The size of each bar in these two plots shows the detection-rate for patient-specific cfDNA mutations in these 40-withheld controls, across all 107 cases. FIG. 16A illustrates table summarizing the sensitivity and specificity for ctDNA detection in pretreatment samples by CAPP-Seq and PhasED-Seq using doublets, triplets, and quadruplets, shown in panel A. Sensitivity is calculated across all 107 cases, while specificity is calculated across the 40 withheld control samples, assessing for each of the 107 independent patient-specific mutation lists, for a total of 4280 independent tests. FIG. 16B illustrates a scatterplot showing the quantity of ctDNA (measured as log 10 (haploid genome equivalents/mL)) as measured by CAPP-Seq vs. PhasED-Seq in individual samples. Samples taken prior to cycle 1 of RCHOP therapy (i.e., pretreatment), prior to cycle 2, and prior to cycle 3, are shown in independent colors (blue, green, and red respectively; 278 total samples). Undetectable levels fall on the axes. Spearman correlation and P-value are shown.

FIGS. 17A-17D illustrate detection of ctDNA after two cycles of systemic therapy. FIG. 17A illustrates a scatter plot showing the log-fold change in ctDNA after 2 cycles of therapy (i.e., the Major Molecular Response or MMR) measured by CAPP-Seq or PhasED-Seq for patients receiving RCHOP therapy. Dotted lines show the previously established threshold of a 2.5-log reduction in ctDNA for MMR. Undetectable samples fall on the axes; the correlation coefficient represents a Spearman rho for the 33 samples detected by both CAPP-Seq and PhasED-Seq. FIG. 17B illustrates 2 by 2 tables summarizing the detection rate of ctDNA samples after 2 cycles of therapy by PhasED-Seq vs CAPP-Seq. Patients with eventual disease progression are shown in bottom panel, while patients without eventual disease progression are shown in upper panel. FIG. 17C illustrates bar-plots showing the area under the receiver operator curve (AUC) for classification of patients for event-free survival at 24 months based on CAPP-Seq (light colors) or PhasED-Seq (dark colors) after 2 cycles of therapy. Classification of all patient (n=89, left) and only patients achieving a MMR (n=69, right) are both shown. FIG. 17D illustrates Kaplan-Meier plots showing the event-free survival of 69 patients achieving a MMR stratified by ctDNA detection with CAPP-Seq (top) or PhasED-Seq (bottom).

FIGS. 18A-18H illustrate detection of ctDNA after one cycle of systemic therapy. FIG. 18A illustrates scatterplot showing the log-fold change in ctDNA after 1 cycle of therapy (i.e., the Early Molecular Response or EMR) measured by CAPP-Seq or PhasED-Seq for patients receiving RCHOP therapy. Dotted lines show the previously established threshold of a 2-log reduction in ctDNA for EMR. Undetectable samples fall on the axes; the correlation coefficient represents a Spearman rho for the 45 samples detected by both CAPP-Seq and PhasED-Seq. FIG. 18B illustrates 2 by 2 tables summarizing the detection rate of ctDNA samples after 1 cycle of therapy by PhasED-Seq vs CAPP-Ceq. Patients with eventual disease progression are shown in red, while patients without eventual disease progression are shown in blue. FIG. 18C illustrates bar-plots showing the area under the receiver operator curve (AUC) for classification of patients for event-free survival at 24 months based on CAPP-Seq (light colors) or PhasED-Seq (dark colors) after 1 cycle of therapy. Classification of all patient (n=82, left) and only patients achieving an EMR (n=63, right) are both shown. FIG. 18D illustrates Kaplan-Meier plots showing the event-free survival of 63 patients achieving an EMR stratified by ctDNA detection with CAPP-Seq (top) or PhasED-Seq (bottom). FIG. 18E illustrates waterfall plot showing the change in ctDNA levels measured by CAPP-Seq after 1 cycle of first-line therapy in patients with DLBCL. Patients with undetectable ctDNA by CAPP-Seq are shown as "ND" ("not detected"), in darker colors. The colors of the bars also indicate the eventual clinical outcomes for these patients. FIG. 18F illustrates a Kaplan-Meier plot showing the event-free survival for 33 DLBCL patients with undetectable ctDNA measured by CAPP-Seq after 1 cycle of therapy. FIG. 18G illustrates a Kaplan-Meier plot showing the event-free survival of 33 patients shown in FIG. 18F (undetectable ctDNA by CAPP-Seq) stratified by ctDNA detection via PhasED-Seq at this same time-point (cycle 2, day 1). FIG. 18H illustrates a Kaplan-Meier plot showing the event-free survival for 82 patients with DLBCL stratified by ctDNA at cycle 2, day 1 separated into 3 strata—patients failing to achieve an early molecular response, patients with an early molecular response who still have detectable ctDNA by PhasED-Seq and/or CAPP-Seq, and patients who have a stringent molecular remission (undetectable ctDNA by PhasED-Seq and CAPP-Seq).

FIG. 25D shows an example flowchart of a method for treating a condition of a subject based on one or more cell-free nucleic acid molecules comprising a plurality of variants.

FIGS. 25F and 25G show example flowcharts of methods for determining a condition of a subject based on one or more cell-free nucleic acid molecules comprising a plurality of variants.

DETAILED DESCRIPTION

Figure 1A:
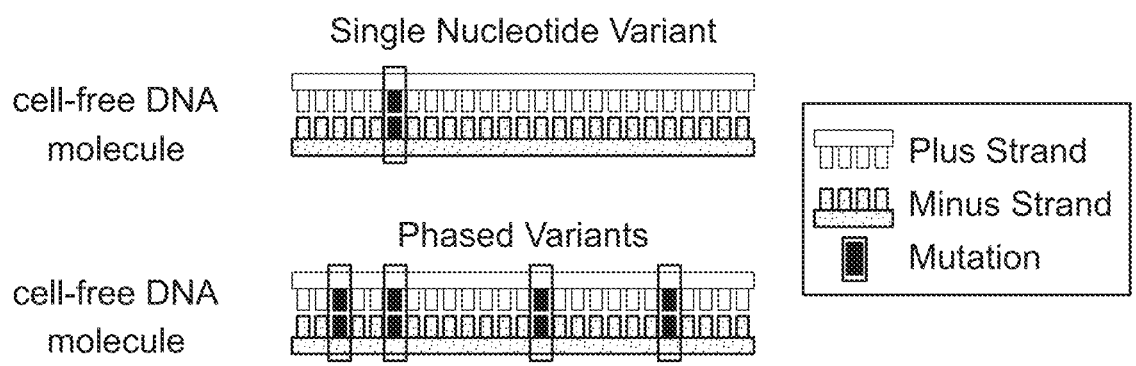
FIGS. 1A-1E illustrate discovery of phased variants and their mutational signatures via analysis of whole-genome sequencing data.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "about" or "approximately" generally mean within an acceptable error range for the particular value, which may depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value may be assumed.

The term "phased variants," "variants in phase," "PV," or "somatic variants in phase," as used interchangeably herein, generally refers to two or more mutations (e.g., SNVs or indels) that occur in cis (i.e., on the same strand of a nucleic acid molecule) within a single cell-free nucleic acid molecule. In some cases, a cell-free nucleic acid molecule can be a cell-free deoxyribonucleic acid (cfDNA) molecule. In some cases, a cfDNA molecule can be derived from a diseased tissue, such as a tumor (e.g., a circulating tumor DNA (ctDNA) molecule).

The term "biological sample" or "bodily sample," as used interchangeably herein, generally refers to a tissue or fluid sample derived from a subject. A biological sample can be directly obtained from the subject. Alternatively, a biological sample can be derived from the subject (e.g., by processing an initial biological sample obtained from the subject). The biological sample can be or can include one or more nucleic acid molecules, such as DNA or ribonucleic acid (RNA) molecules. The biological sample can be derived from any organ, tissue or biological fluid. A biological sample can comprise, for example, a bodily fluid or a solid tissue sample. An example of a solid tissue sample is a tumor sample, e.g., from a solid tumor biopsy. Non-limiting examples of bodily fluids include blood, serum, plasma, tumor cells, saliva, urine, cerebrospinal fluid, lymphatic fluid, prostatic fluid, seminal fluid, milk, sputum, stool, tears, and derivatives of these. In some cases, one or more cell-free nucleic acid molecules as disclosed herein can be derived from a biological sample.

The term "subject," as used herein, generally refers to any animal, mammal, or human. A subject can have, potentially have, or be suspected of having one or more conditions, such as a disease. In some cases, a condition of the subject can be cancer, a symptom(s) associated with cancer, or asymptomatic with respect to cancer or undiagnosed (e.g., not diagnosed for cancer). In some cases, the subject can have cancer, the subject can show a symptom(s) associated with cancer, the subject can be free from symptoms associated with cancer, or the subject may not be diagnosed with cancer. In some examples, the subject is a human.

The term "cell-free DNA" or "cfDNA," as used interchangeably herein, generally refers to DNA fragments circulating freely in a blood stream of a subject. Cell-free DNA fragments can have dinucleosomal protection (e.g., a fragment size of at least 240 base pairs ("bp")). These cfDNA fragments with dinucleosomal protection were likely not cut between the nucleosome, resulting in a longer fragment length (e.g., with a typical size distribution centered around 334 bp). Cell-free DNA fragments can have mononucleosomal protection (e.g., a fragment size of less than 240 base pairs ("bp")). These cfDNA fragments with mononucleosomal protection were likely cut between the nucleosome, resulting in a shorter fragment length (e.g., with a typical size distribution centered around 167 bp).

The term "sequencing data," as used herein, generally refers to "raw sequence reads" and/or "consensus sequences" of nucleic acids, such as cell-free nucleic acids or derivatives thereof. Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences can be produced by voting (wherein each majority nucleotide, e.g., the most commonly observed nucleotide at a given base position, among the sequences is the consensus nucleotide) or other approaches such as comparing to a reference genome. In some cases, consensus sequences can be produced by tagging original parent molecules with unique or non-unique molecular tags, which allow tracking of the progeny sequences (e.g., after amplification) by tracking of the tag and/or use of sequence read internal information.

The term "reference genomic sequence," as used herein, generally refers to a nucleotide sequence against which a subject's nucleotide sequences are compared.

The term "genomic region," as used herein, generally refers to any region (e.g., range of base pair locations) of a genome, e.g., an entire genome, a chromosome, a gene, or an exon. A genomic region can be a contiguous or a non-contiguous region. A "genetic locus" (or "locus") can be a portion or entirety of a genomic region (e.g., a gene, a portion of a gene, or a single nucleotide of a gene).

The term "likelihood," as used herein, generally refers to a probability, a relative probability, a presence or an absence, or a degree.

The term "liquid biopsy," as used herein, generally refers to a non-invasive or minimally invasive laboratory test or assay (e.g., of a biological sample or cell-free nucleic acids). The "liquid biopsy" assays can report detections or measurements (e.g., minor allele frequencies, gene expression, or protein expression) of one or more marker genes associated with a condition of a subject (e.g., cancer or tumor-associated marker genes).

A. Introduction

Modifications (e.g., mutations) of genomic DNA can be manifested in a formation and/or progression of one or more conditions (e.g., a disease, such as cancer or tumor) of a subject. The present disclosure provides methods and systems for analyzing cell-free nucleic acid molecules, such as cfDNA, from a subject to determine the presence or absence of a condition of the subject, prognosis of a diagnosed condition of the subject, progress of the condition of the subject over time, therapeutic treatment of a diagnosed condition of the subject, or predicted treatment outcome for a condition of the subject.

Analysis of cell-free nucleic acids, such as cfDNA, have been developed with broad applications in, e.g., prenatal testing, organ transplantation, infectious disease, and oncology. In the context of detecting or monitoring a disease of a subject, such as cancer, circulating tumor DNA (ctDNA) can be a sensitive and specific biomarker in numerous cancer types. In some cases, ctDNA can be used to detect the presence of minimal residual disease (MRD) or tumor burden after treatment, such as chemotherapies or surgical resection of solid tumors. However, the limit of detection (LOD) for ctDNA analysis can be restricted by a number of factors including (i) low input DNA amounts from a typical blood collection and (ii) background error rates from sequencing.

In some cases, ctDNA-based cancer detection can be improved by tracking multiple somatic mutations with error-suppressed sequencing, e.g., with LOD of about 2 parts in 100,000 from cfDNA input while using off-the-shelf panels or personalized assays. However, in some cases, current LOD of ctDNA of interest can be insufficient to universally detect MRD in patients destined for disease relapse or progression. For example, such 'loss of detection' can be exemplified in diffuse large B-cell lymphoma (DLBCL). For DLBCL, interim ctDNA detection after only two cycles of curative-intent therapy can represent a major molecular response (MMR), and can be a strong prognostic marker for ultimate clinical outcomes. Despite this, nearly one-third of patients ultimately experiencing disease progression do not have detectable ctDNA at this interim landmark using available techniques (e.g., Cancer Personalized Profiling by Deep Sequencing (CAPP-Seq)), thus representing 'false-negative' measurements. Such high false-negative rates have also been observed in DLBCL patients by alternative methods, such as monitoring ctDNA through immunoglobulin gene rearrangements. Therefore, there exists a need for improved methods of ctDNA-based cancer detection with greater sensitivity.

Somatic variants detected on both of the complementary strands of parental DNA duplexes can be used to lower the LOD of ctDNA detection, thereby advantageously increasing the sensitivity of ctDNA detection. Such 'duplex sequencing' can reduce background error profile due to the requirement of two concordant events for detection of a single nucleotide variant (SNV). However, the duplex sequencing approach alone can be limited by inefficient recovery of DNA duplexes as recovery of both original strands can occur in a minority of all recovered molecules. Thus, duplex sequencing may be suboptimal and inefficient for real-world ctDNA detection with limited amount of starting sample, where input DNA from practical blood volumes (e.g., between about 4,000 to about 8,000 genomes per standard 10 milliliter (mL) blood collection tube) is limited and maximal recovery of genomes is essential.

Thus, there remains a significant unmet need for detection and analysis of ctDNA with low LOD (e.g., thereby yielding high sensitivity) for determining, for example, presence or absence of a disease of a subject, prognosis of the disease, treatment for the disease, and/or predicted outcome of the treatment.

B. Methods and Systems for Determining or Monitoring a Condition

The present disclosure describes methods and systems for detecting and analyzing cell free nucleic acids with a plurality of phased variants as a characteristic of a condition of a subject. In some aspects, the cell-free nucleic acid molecules can comprise cfDNA molecules, such as ctDNA molecules. The methods and systems disclosed herein can utilize sequencing data derived from a plurality of cell-free nucleic acid molecules of the subject to identify a subset of the plurality of cell-free nucleic acid molecules having the plurality of phased variants, thereby to determine the condition of the subject. The methods and systems disclosed herein can directly detect and, in some cases, pull down (or capture) such subset of the plurality of cell-free nucleic acid molecules that exhibit the plurality of phased variants, thereby to determine the condition of the subject with or without sequencing. The methods and systems disclosed herein can reduce background error rate often involved during detection and analysis of cell-free nucleic acid molecules, such as cfDNA.

In some aspects, methods and systems for cell-free nucleic acid sequencing and detection of cancer are provided. In some embodiments, cell-free nucleic acids (e.g., cfDNA or cfRNA) can be extracted from a liquid biopsy of an individual and prepared for sequencing. Sequencing results of the cell-free nucleic acids can be analyzed to detect somatic variants in phase (i.e., phased variants, as disclosed herein) as an indication of circulating-tumor nucleic acid (ctDNA or ctRNA) sequences (i.e., sequences that derived or are originated from nucleic acids of a cancer cell). Accordingly, in some cases, cancer can be detected in the individual by extracting a liquid biopsy from the individual and sequencing the cell-free nucleic acids derived from that liquid biopsy to detect circulating-tumor nucleic acid sequences, and the presence of circulating-tumor nucleic acid sequences can indicate that the individual has a cancer (e.g., a specific type of cancer). In some cases, a clinical intervention and/or treatment can be determined and/or performed on the individual based on the detection of the cancer.

As disclosed herein, a presence of somatic variants in phase can be a strong indication that the nucleic acids containing such phased variants are derived from a bodily sample with a condition, such as a cancerous cell (or alternatively, that the nucleic acids are from derived from a bodily sample obtained or derived from a subject with a condition, such as cancer). Detection of phased somatic variants can enhance the signal-to-noise ratio of cell-free nucleic acid detection methods (e.g., by reducing or eliminating spurious "noise" signals) as it may be unlikely that phased mutations would occur within a small genetic window that is approximately the size of a typical cell-free nucleic acid molecule (e.g., about 170 bp or less).

In some aspects, a number of genomic regions can be used as hotspots for detection of phased variants, especially in various cancers, e.g., lymphomas. In some cases, enzymes (e.g., AID, Apobec3a) can stereotypically mutagenize DNA in specific genes and locations, leading to development of particular cancers. Accordingly, cell-free nucleic acids derived from such hotspot genomic regions can be captured or targeted (e.g., with or without deep sequencing) for cancer detection and/or monitoring. Alternatively, capture or targeted sequencing can performed on regions in which phased variants have been previously detected from a cancerous source (e.g., tumor) of a particular individual in order to detect cancer in that individual.

In some aspects, capture sequencing on cell-free nucleic acids can be performed as a screening diagnostic. In some cases, a screening diagnostic can be developed and used to detect circulating-tumor nucleic acids for cancers that have stereotypical regions of phased variants. In some cases, capture sequencing on cell-free nucleic acids is performed as a diagnostic to detect MRD or tumor burden to determine if a particular disease is present during or after treatment. In some cases, capture sequencing on cell-free nucleic acids can be performed as a diagnostic to determine progress (e.g., progression or regression) of a treatment.

In some aspects, cell-free nucleic acid sequencing results can be analyzed to detect whether phased somatic single nucleotide variants (SNVs) or other mutations or variants (e.g., indels) exist within the cell-free nucleic acid sample. In some cases, the presence of particular somatic SNVs or other variants can be indicative of circulating-tumor nucleic acid sequences, and thus indicative of a tumor present in the subject. In some cases, a minimum of two variants can be detected in phase on a cell-free nucleic acid molecule. In some cases, a minimum of three variants can be detected in phase on a cell-free nucleic acid molecule. In some cases, a minimum of four variants can be detected in phase on a cell-free nucleic acid molecule. In some cases, a minimum of five or more variants can be detected in phase on a cell-free nucleic acid molecule. In some cases, the greater number of phased variants detected on a cell-free nucleic acid molecule, the greater the likelihood that the cell-free nucleic acid molecule is derived from cancer, as opposed to detecting an innocuous sequence of somatic variants that arise from molecular preparation of the sequence library or random biological errors. Accordingly, the likelihood of false-positive detection can decrease with detection of more variants in phase within a molecule (e.g., thereby increasing specificity of detection).

In some aspects, a cell-free nucleic acid sequencing result can be analyzed to detect whether an insertion or deletion of one or more nucleobases (i.e., indel) exist within the cell-free nucleic acid sample, e.g., relative to a reference genomic sequence. Without wishing to be bound by theory, in some cases, presence of indels in a cell-free nucleic acid molecule (e.g., cfDNA) can be indicative of a condition of a subject, e.g., a disease such as cancer. In some cases, a genetic variation as a result of an indel can be treated as a variant or mutation, and thus two indels can be treated a two phased variants, as disclosed herein. In some examples, within a cell-free nucleic acid molecule, a first genetic variation from a first indel (a first phase variant) and a second genetic variation from a second indel (a second phase variant) can be separated from each other by at least 1 nucleotide.

Within a single cell-free nucleic acid molecule (e.g., a single cfDNA molecule), as disclosed herein, a first phased variant can be a SNV and a second phased variant can be a part of a different small nucleotide polymorphism, e.g., another SNV or a part of a multi-nucleotide variant (MNV). A multi-nucleotide variant can be a cluster of two or more (e.g., at least 2, 3, 4, 5, or more) adjacent variants existing within the same stand of nucleic acid molecule. In some cases, the first phased variant and the second phased variant can be parts of the same MNV within the single cell-free nucleic acid molecule. In some cases, the first phased variant and the second phased variant can be from two different MNVs within the single cell-free nucleic acid molecule.

In some aspects, a statistical method can be utilized to calculate the likelihood that detected phased variants are from a cancer and not random or artificial (e.g., from sample prep or sequencing error). In some cases, a Monte Carlo sampling method can be utilized to determine the likelihood that detected phased variants are from a cancer and not random or artificial.

Aspects of the present disclosure provide identification or detection of cell-free nucleic acids (e.g., cfDNA molecule) with a plurality of phased variants, e.g., from a liquid biopsy of a subject. In some cases, a first phased variant of the plurality of phased variants and a second phased variant of the plurality of phased variants can be directly adjacent to each other (e.g., neighboring SNVs). In some cases, a first phased variant of the plurality of phased variants and a second phased variant of the plurality of phased variants can be separated by at least one nucleotide. The spacing between the first phased variant and the second phased variant can be limited by the length of the cell-free nucleic acid molecule.

Within a single cell-free nucleic acid molecule (e.g., a single cfDNA molecule), as disclosed herein, a first phased variant and a second phased variant can be separated from each other by at least or up to about 1 nucleotide, at least or up to about 2 nucleotides, at least or up to about 3 nucleotides, at least or up to about 4 nucleotides, at least or up to about 5 nucleotides, at least or up to about 6 nucleotides, at least or up to about 7 nucleotides, at least or up to about 8 nucleotides, at least or up to about 9 nucleotides, at least or up to about 10 nucleotides, at least or up to about 11 nucleotides, at least or up to about 12 nucleotides, at least or up to about 13 nucleotides, at least or up to about 14 nucleotides, at least or up to about 15 nucleotides, at least or up to about 20 nucleotides, at least or up to about 25 nucleotides, at least or up to about 30 nucleotides, at least or up to about 35 nucleotides, at least or up to about 40 nucleotides, at least or up to about 45 nucleotides, at least or up to about 50 nucleotides, at least or up to about 60 nucleotides, at least or up to about 70 nucleotides, at least or up to about 80 nucleotides, at least or up to about 90 nucleotides, at least or up to about 100 nucleotides, at least or up to about 110 nucleotides, at least or up to about 120 nucleotides, at least or up to about 130 nucleotides, at least or up to about 140 nucleotides, at least or up to about 150 nucleotides, at least or up to about 160 nucleotides, at least or up to about 170 nucleotides, or at least or up to about 180 nucleotides. Alternatively or in addition to, within a single cell-free nucleic acid molecule, a first phased variant and a second phased variant may not or need not be separated by one or more nucleotides and thus can be directly adjacent to one another.

A single cell-free nucleic acid molecule (e.g., a single cfDNA molecule), as disclosed herein, can comprise at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants within the same molecule.

From a plurality of cell-free nucleic acid molecules obtained (e.g., from a liquid biopsy of a subject), two or more (e.g., 10 or more, 1,000 or more, 10,000 or more) cell-free nucleic acid molecules can be identified to have an average of at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants per each cell-free nucleic acid molecule identified to comprise a plurality of phased variants.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, at least or up to 1,000, at least or up to 5,000, at least or up to, 10,000, at least or up to 50,000, or at least or up to 100,000 cell-free nucleic acid molecules can be identified, such that each identified cell-free nucleic acid molecule comprises the plurality of phased variants, as disclosed herein.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, or at least or up to 1,000 cell-free nucleic acid molecules can be identified from a target genomic region (e.g., a target genomic locus), such that each identified cell-free nucleic acid molecule comprises the plurality of phased variants, as disclosed herein.

Figure 1B:
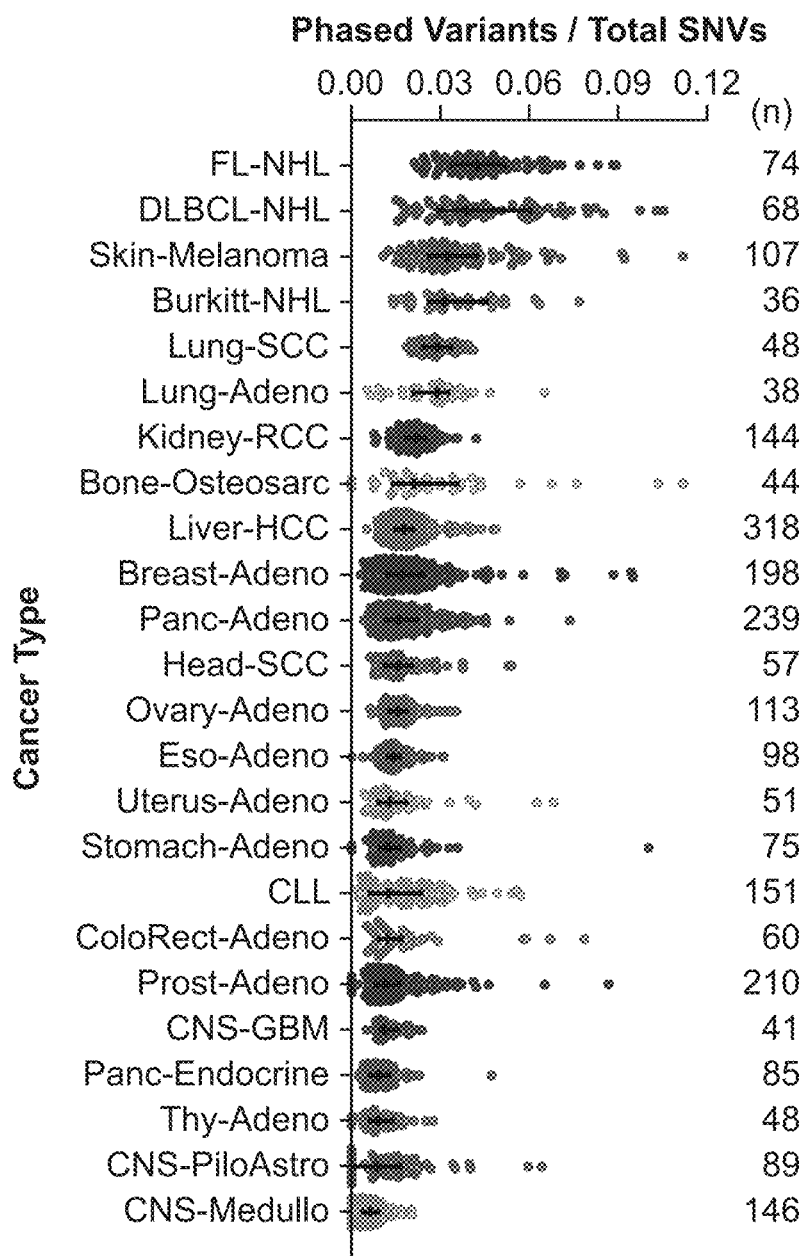
Figure 1C:
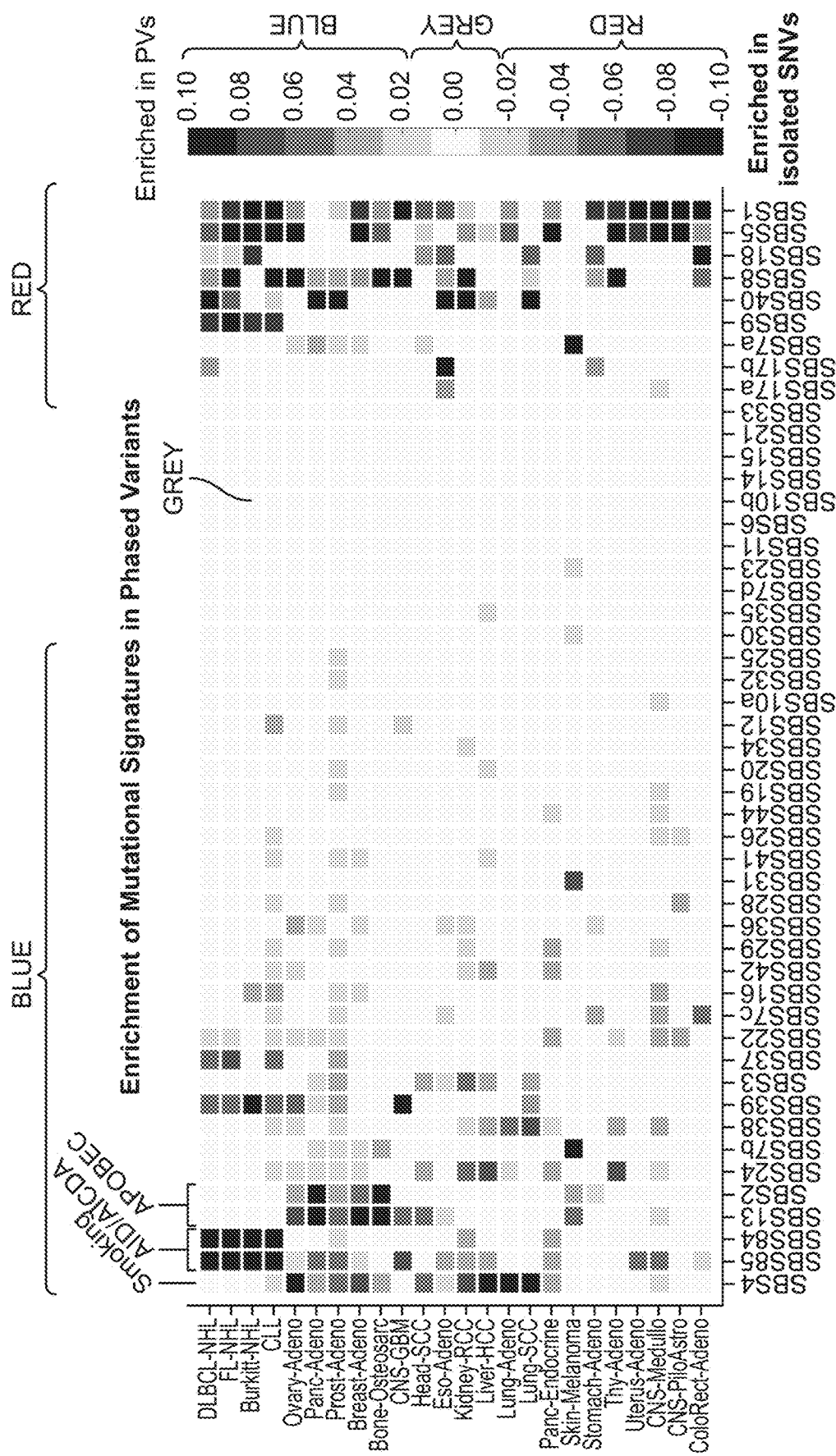
Figure 1D:
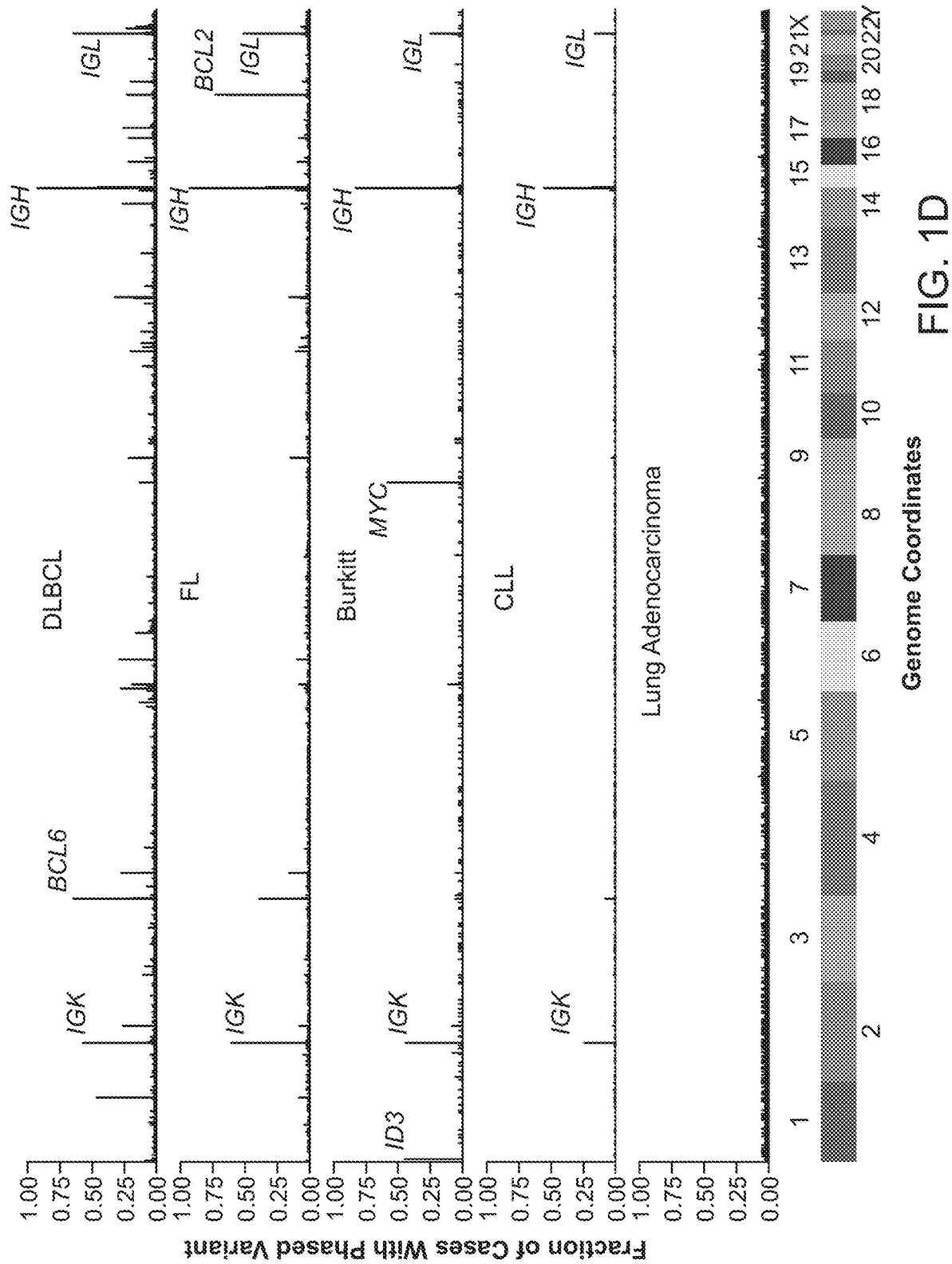
Figure 1E:
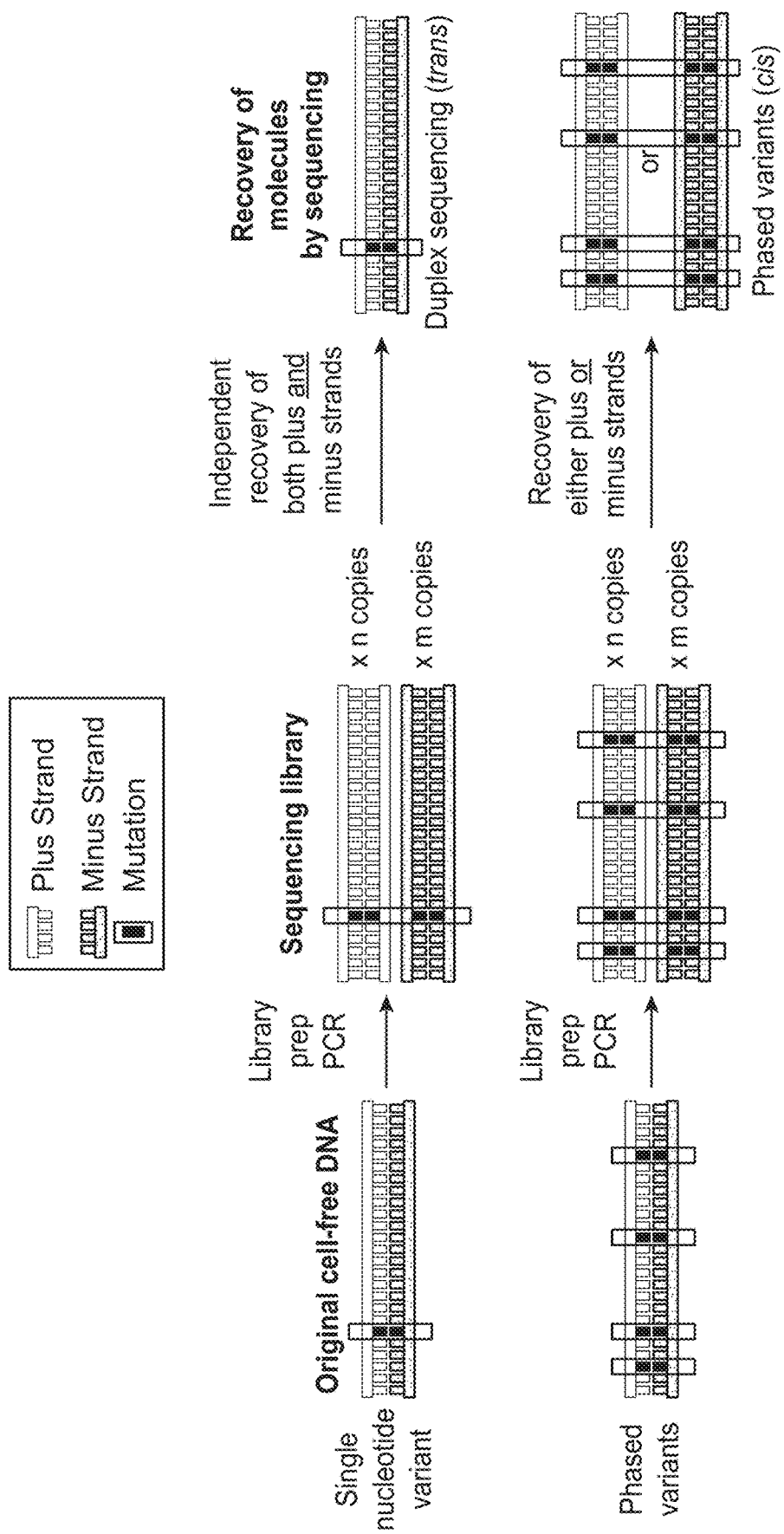

FIGS. 1A and 1E schematically illustrate examples of (i) a cfDNA molecule comprising a SNV and (ii) another cfDNA molecule comprising a plurality of phased variants. Each variant identified within the cfDNA can indicate a presence of one more genetic mutations in the cell that the cfDNA is originated from. In alternative embodiments, one or more of the phased variants may be an insertion or deletion (indel) instead of an SNV.

Figure 25A:
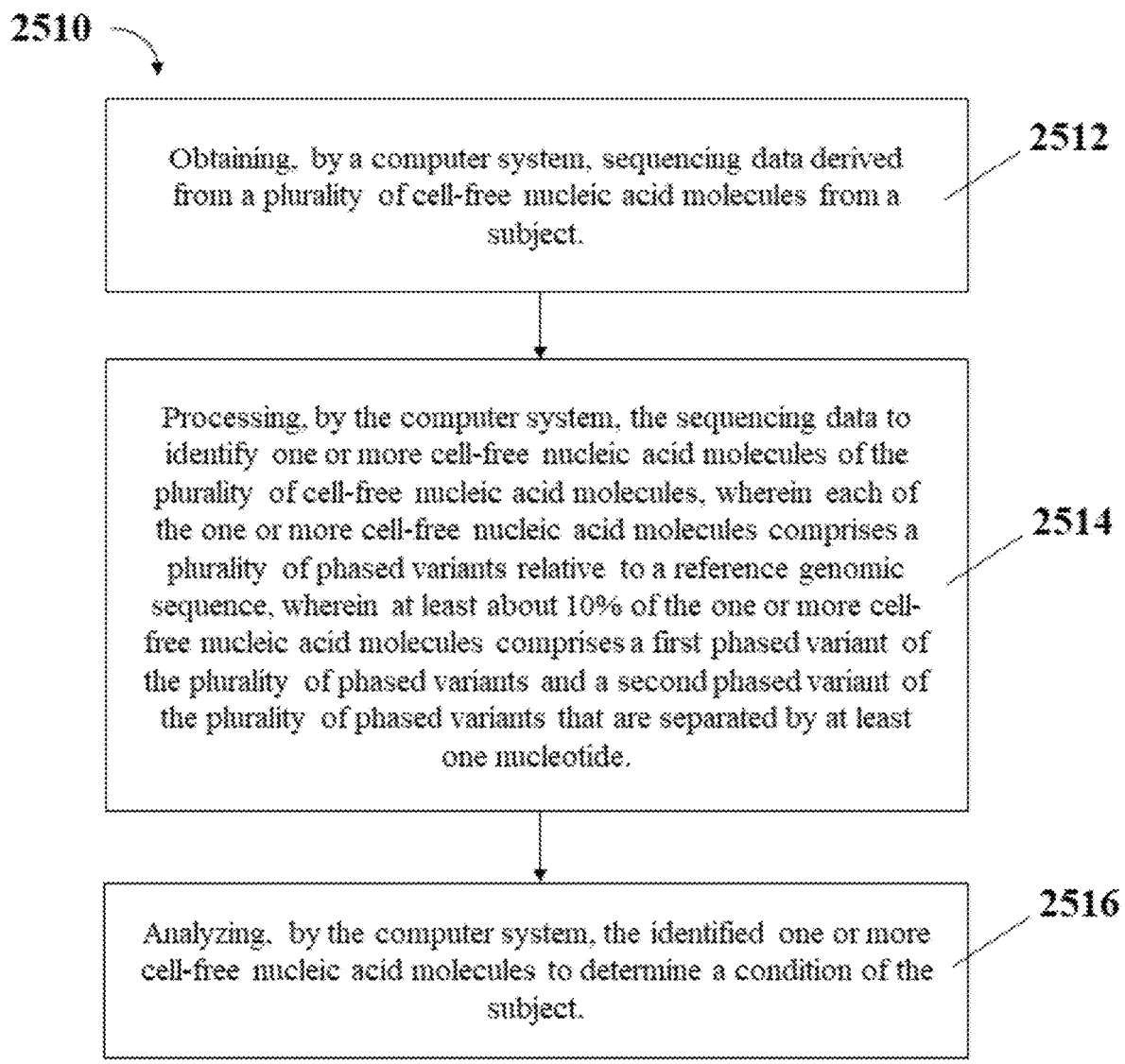
FIGS. 25A-25C show example flowcharts of methods for determining a condition of a subject based on one or more cell-free nucleic acid molecules comprising a plurality of variants.

In one aspect, the present disclosure provides a method for determining a condition of a subject, as shown by flowchart 2510 in FIG. 25A. The method can comprise (a) obtaining, by a computer system, sequencing data derived from a plurality of cell-free nucleic acid molecules that is obtained or derived from the subject (process 2512). The method can further comprise (b) processing, by the computer system, the sequencing data to identify one or more cell-free nucleic acid molecules of the plurality of cell-free nucleic acid molecules, wherein each of the one or more cell-free nucleic acid molecules identified comprises a plurality of phased variants relative to a reference genomic sequence (process 2514). In some cases, at least a portion of the one or more cell-free nucleic acid molecules can comprise a first phased variant of the plurality of phased variants and a second phased variant of the plurality of phased variants that are separated by at least one nucleotide, as disclosed herein. The method can optionally comprise (c) analyzing, by the computer system, at least a portion of the identified one or more cell-free nucleic acid molecules to determine the condition of the subject (process 2516).

In some cases, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 60%, at least or up to about 70%, at least or up to about 80%, at least or up to about 90%, at least or up to about 95%, at least or up to about 99%, or about 100% of the one or more cell-free nucleic acid molecules can comprise a first phased variant of the plurality of phased variants and a second phased variant of the plurality of phased variants that are separated by at least one nucleotide, as disclosed herein. In some examples, a plurality of phased variants within a single cfDNA molecule can comprise (i) a first plurality of phased variants that are separated by at least one nucleotide from one another and (ii) a second plurality of phased variants that are adjacent to one another (e.g., two phased variants within a MNV). In some examples, a plurality of phased variants within a single cfDNA molecule can consist of phased variants that are separate by at least one nucleotide from one another.

Figure 25B:
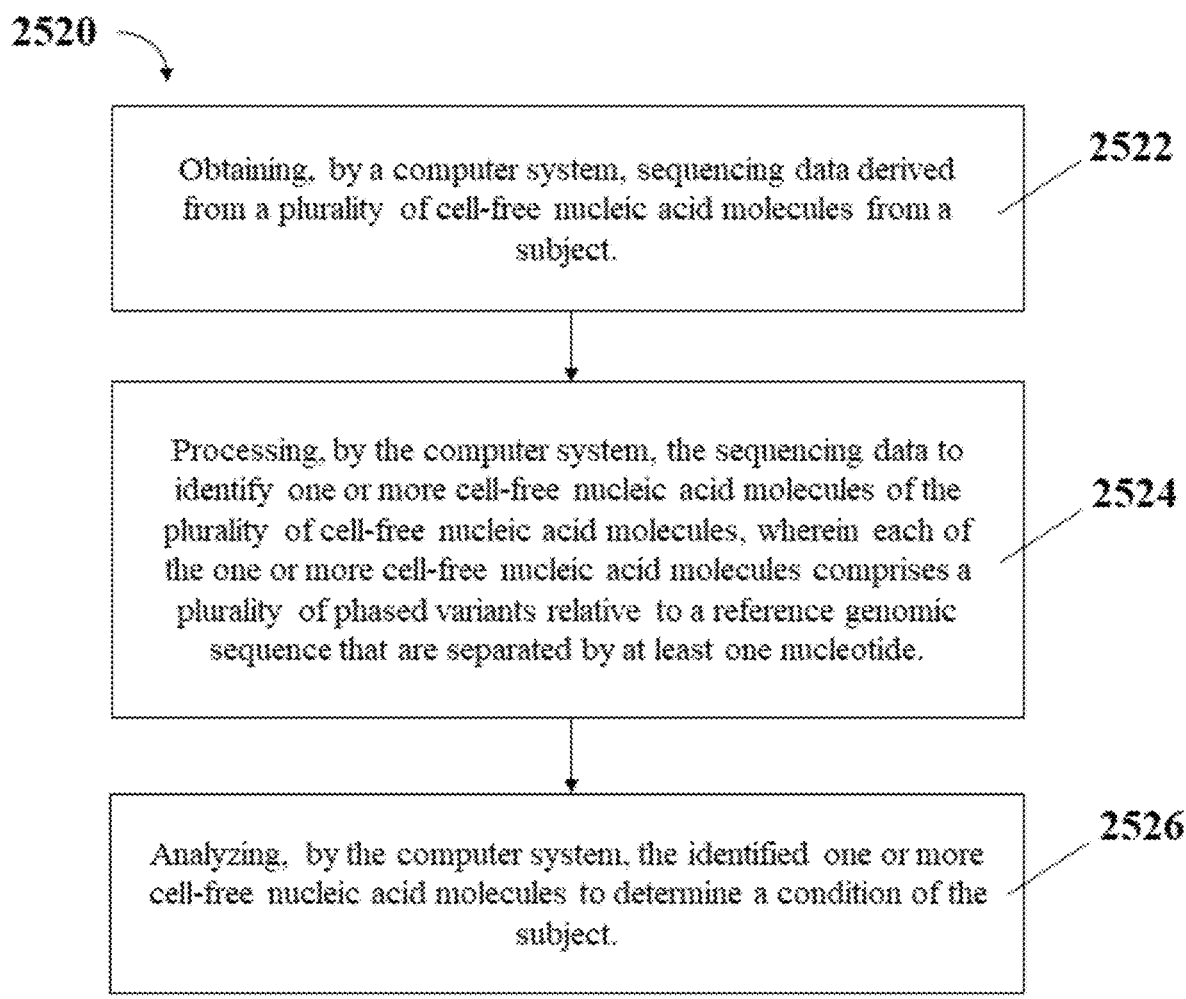

In one aspect, the present disclosure provides a method for determining a condition of the subject, as shown by flowchart 2520 in FIG. 25B. The method can comprise (a) obtaining, by a computer system, sequencing data derived from a plurality of cell-free nucleic acid molecules that is obtained or derived from a subject (process 2522). The method can further comprise (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence (process 2524). In some cases, a first phased variant of the plurality of phased variant and a second phased variant of the plurality of phased variant can be separated by at least one nucleotide, as disclosed herein. The method can optionally comprise (c) analyzing, by the computer system, at least a portion of the identified one or more cell-free nucleic acid molecules to determine the condition of the subject (process 2526).

Figure 25C:
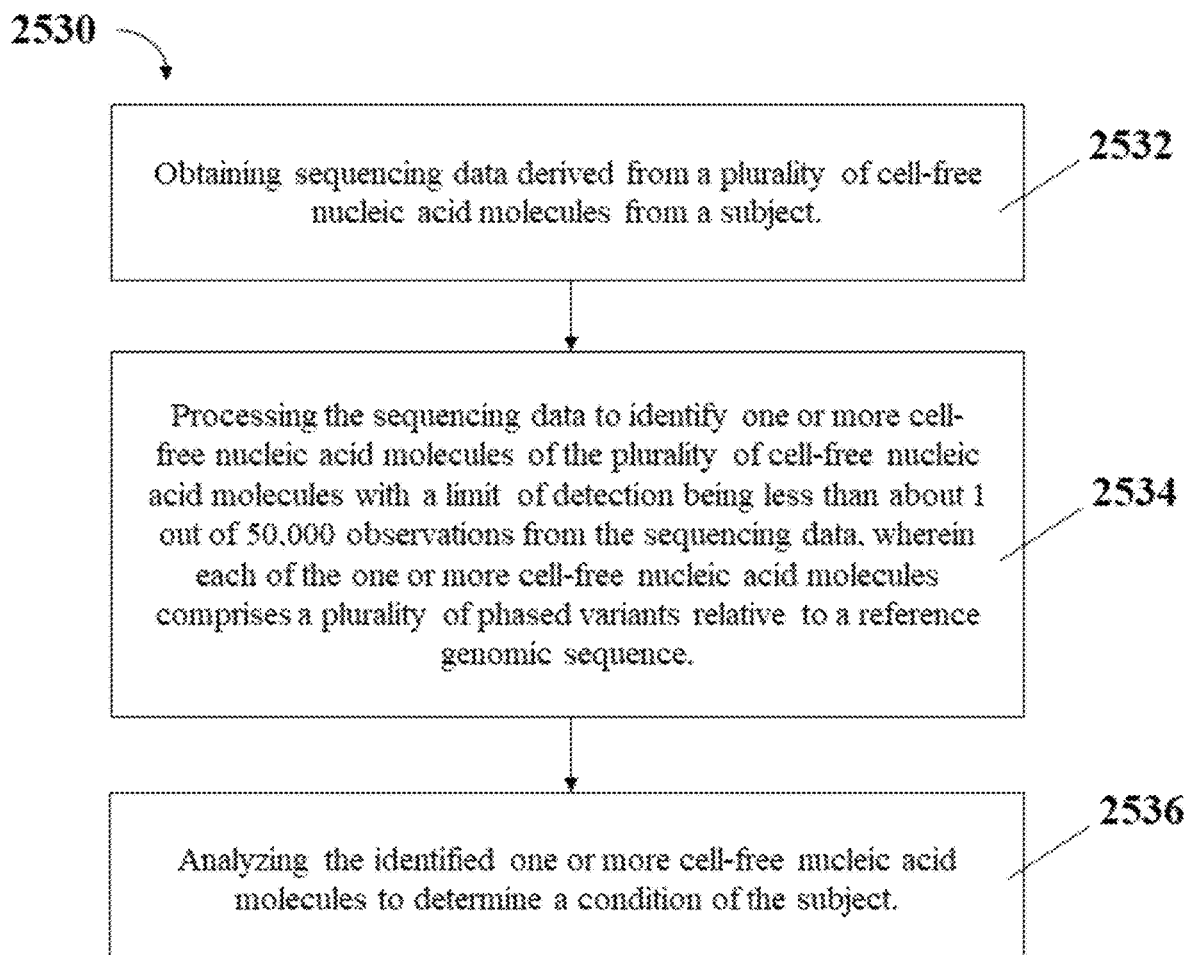

In one aspect, the present disclosure provides a method for determining a condition of a subject, as shown by flowchart 2530 in FIG. 25C. The method can comprise (a) obtaining sequencing data derived from a plurality of cell-free nucleic acid molecules that is obtained or derived from the subject (process 2532). The method can further comprise (b) processing the sequencing data to identify one or more cell-free nucleic acid molecules of the plurality of cell-free nucleic acid molecules with a LOD being less than about 1 out of 50,000 observations (or cell-free nucleic acid molecules) from the sequencing data (process 2534). In some cases, each of the one or more cell-free nucleic acid molecules comprises a plurality of phased variants relative to a reference genomic sequence. The method can optionally comprise (c) analyzing at least a portion of the identified one or more cell-free nucleic acid molecules to determine the condition of the subject (process 2536).

In some cases, the LOD of the operation of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, or less than 1 out of 2,000,000 observations from the sequencing data.

In some cases, at least one cell-free nucleic acid molecule of the identified one or more cell-free nucleic acid molecules can comprise a first phased variant of the plurality of phased variants and a second phased variant of the plurality of phased variants that are separated by at least one nucleotide, as disclosed herein.

In some cases, one or more of the operations (a) through (c) of the subject method can be performed by a computer system. In an example, all of the operations (a) through (c) of the subject method can be performed by the computer system.

The sequencing data, as disclosed herein, can be obtained from one or more sequencing methods. A sequencing method can be a first-generation sequencing method (e.g., Maxam-Gilbert sequencing, Sanger sequencing). A sequencing method can be a high-throughput sequencing method, such as next-generation sequencing (NGS) (e.g., sequencing by synthesis). A high-throughput sequencing method can sequence simultaneously (or substantially simultaneously) at least about 10,000, at least about 100,000, at least about 1 million, at least about 10 million, at least about 100 million, at least about 1 billion, or more polynucleotide molecules (e.g., cell-free nucleic acid molecules or derivatives thereof). NGS can be any generation number of sequencing technologies (e.g., second-generation sequencing technologies, third-generation sequencing technologies, fourth-generation sequencing technologies, etc.). Non-limiting examples of high-throughput sequencing methods include massively parallel signature sequencing, polony sequencing, pyrosequencing, sequencing-by-synthesis, combinatorial probe anchor synthesis (cPAS), sequencing-by-ligation (e.g., sequencing by oligonucleotide ligation and detection (SOLiD) sequencing), semiconductor sequencing (e.g., Ion Torrent semiconductor sequencing), DNA nanoball sequencing, and single-molecule sequencing, sequencing-by-hybridization.

In some embodiments of any one of the methods disclosed herein, the sequencing data can be obtained based on any of the disclosed sequencing methods that utilizes nucleic acid amplification (e.g., polymerase chain reaction (PCR)). Non-limiting examples of such sequencing methods can include 454 pyrosequencing, polony sequencing, and SoLiD sequencing. In some cases, amplicons (e.g., derivatives of the plurality of cell-free nucleic acid molecules that is obtained or derived from the subject, as disclosed herein) that correspond to a genomic region of interest (e.g., a genomic region associated with a disease) can be generated by PCR, optionally pooled, and subsequently sequenced to generating sequencing data. In some examples, because the regions of interest are amplified into amplicons by PCR before being sequenced, the nucleic acid sample is already enriched for the region of interest, and thus any additional pooling (e.g., hybridization) may not and need not be needed prior to sequencing (e.g., non-hybridization based NGS). Alternatively, pooling via hybridization can further be performed for additional enrichment prior to sequencing. Alternatively, the sequencing data can be obtained without generating PCR copies, e.g., via cPAS sequencing.

A number of embodiments utilize capture hybridization techniques to perform targeted sequencing. When performing sequencing on cell-free nucleic acids, in order to enhance resolution on particular genomic loci, library products can be captured by hybridization prior to sequencing. Capture hybridization can be particularly useful when trying to detect rare and/or somatic phased variants from a sample at particular genomic loci. In some situations, detection of rare and/or somatic phased variants is indicative of the source of nucleic acids, including nucleic acids derived from a cancer source. Accordingly, capture hybridization is a tool that can enhance detection of circulating-tumor nucleic acids within cell-free nucleic acids.

Various types of cancers repeatedly experience aberrant somatic hypermutation in particular genomic loci. For instance, the enzyme activation-induced deaminase induces aberrant somatic hypermutation in B-cells, which leads to various B-cell lymphomas, including (but not limited to) diffuse large B-cell lymphoma (DLBCL), follicular lymphoma (FL), Burkitt lymphoma (BL), and B-cell chronic lymphocytic leukemia (CLL). Accordingly, in numerous embodiments, probes are designed to pull down (or capture) genomic loci known to experience aberrant somatic hypermutation in a lymphoma. FIG. 1D and Table 1 describe a number of regions that experience aberrant somatic hypermutation in DLBCL, FL, BL and CLL. Provided in Table 6 is list of nucleic acid probes that can be utilized to pull down (or capture) genomic loci to detect aberrant somatic hypermutation in B-cell cancers.

Capture sequencing can also be performed utilizing personalized nucleic acid probes designed to detect the existence of an individual's cancer. An individual having a cancer can have their cancer biopsied and sequenced to detect somatic phased variants that have accumulated in the cancer. Based on the sequencing result, in accordance with a number of embodiments, nucleic acid probes are designed and synthesized capable of pulling down the genomic loci inclusive of the positions of where the phased variants. These personalized designed and synthesized nucleic acid probes can be utilized to detect circulating-tumor nucleic acids from a liquid biopsy of that individual. Accordingly, the personalized nucleic acid probes can be useful for determining treatment response and/or detecting MRD after treatment.

In some embodiments of any one of the methods disclosed herein, the sequencing data can be obtained based on any sequencing method that utilizes adapters. Nucleic acid samples (e.g., the plurality of cell-free nucleic acid molecules from the subject, as disclosed herein) can be conjugated with one or more adapters (or adapter sequences) for recognizing (e.g., via hybridization) of the sample or any derivatives thereof (e.g., amplicons). In some examples, the nucleic acid samples can be tagged with a molecular barcode, e.g., such that each cell-free nucleic acid molecule of the plurality of cell-free nucleic acid molecules can have a unique barcode. Alternatively or in addition to, the nucleic acid samples can be tagged with a sample barcode, e.g., such that the plurality of cell-free nucleic acid molecules from the subject (e.g., a plurality of cell-free nucleic acid molecules obtained from a specific bodily tissue of the subject) can have the same barcode.

In alternative embodiments, the methods of identifying one or more cell-free nucleic acid molecules comprising the plurality of phased variants, as disclosed herein, can be performed without molecular barcoding, without sample barcoding, or without molecular barcoding and sample barcoding, at least in part due to high specificity and low LOD achieved by relying on identifying the phased variants as opposed to, e.g., a single SNV.

In some embodiments of any one of the methods disclosed herein, the sequencing data can be obtained and analyzed without in silico removal or suppression of (i) background error and/or (ii) sequencing error, at least in part due to high specificity and low LOD achieved by relying on identifying the phased variants as opposed to, e.g., a single SNV or indel.

In some embodiments of any one of the methods disclosed herein, using the plurality of variants as a condition to identify target cell-free nucleic acid molecules with specific mutations of interest without in silico methods of error suppression can yield a background error-rate that is lower than that of (i) barcode-deduplication, (ii) integrated digital error suppression, or (iii) duplex sequencing by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 400-fold, at least about 600-fold, at least about 800-fold, or at least about 1,000-fold. This approach may advantageously increase signal-to-noise ratio (thereby increasing sensitivity and/or specificity) of identifying target cell-free nucleic acid molecules with specific mutations of interest.

In some embodiments of any one of the methods disclosed herein, increasing a minimum number of phased variants (e.g., increasing from at least two phased variants to at least three phased variants) per cell-free nucleic acid molecule required as a condition to identify target cell-free nucleic acid molecules with specific mutations of interest can reduce the background error-rate by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold. This approach may advantageously increase signal-to-noise ratio (thereby increasing sensitivity and/or specificity) of identifying target cell-free nucleic acid molecules with specific mutations of interest.

In one aspect, the present disclosure provides a method of treating a condition of a subject, as shown in flowchart 2540 in FIG. 25D. The method can comprise (a) identifying the subject for treatment of the condition, wherein the subject has been determined to have the condition based on identification of one or more cell-free nucleic acid molecules from a plurality of cell-free nucleic acid molecules that is obtained or derived from the subject (Process 2542). Each of the identified one or more cell-free nucleic acid molecules can comprise a plurality of phased variants relative to a reference genomic sequence. At least a portion (e.g., partial or all) of the plurality of phased variants can be separated by at least one nucleotide, such that a first phased variant of the plurality of phased variants and a second phased variant of the plurality of phased variants are separated by at least one nucleotide, as disclosed herein. In some cases, a presence of the plurality of phased variants is indicative of the condition (e.g., a disease, such as cancer) of the subject. The method can further comprise (b) subjecting the subject to the treatment based on the step (a) (process 2544). Examples of such treatment of the condition of the subject are disclosed elsewhere in the present disclosure.

Figure 25E:
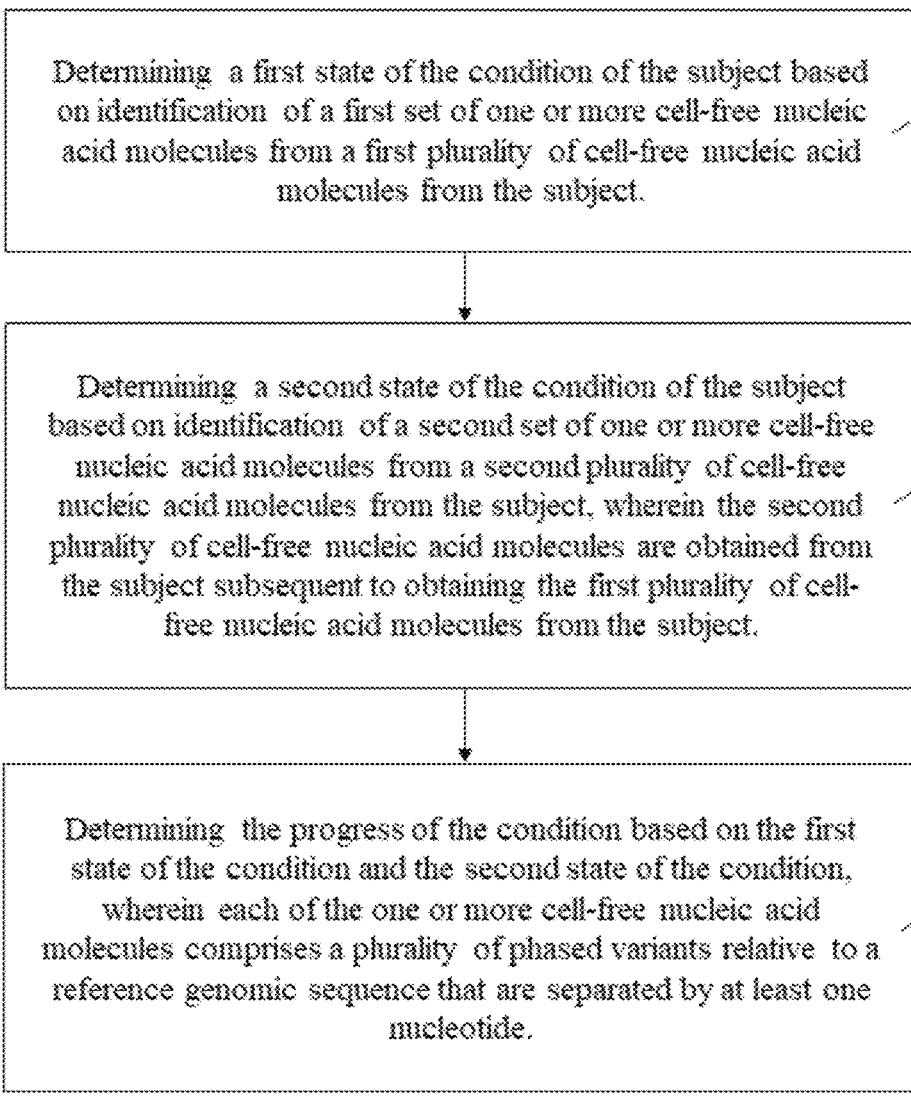
FIG. 25E shows an example flowchart of a method for determining a progress (e.g., progression or regression) of a condition of a subject based on one or more cell-free nucleic acid molecules comprising a plurality of variants.

In one aspect, the present disclosure provides a method of monitoring a progress (e.g., progression or regression) of a condition of a subject, as shown in flowchart 2550 in FIG. 25E. The method can comprise (a) determining a first state of the condition of the subject based on identification of a first set of one or more cell-free nucleic acid molecules from a first plurality of cell-free nucleic acid molecules that is obtained or derived from the subject (process 2552). The method can further comprise (b) determining a second state of the condition of the subject based on identification of a second set of one or more cell-free nucleic acid molecules from a second plurality of cell-free nucleic acid molecules that is obtained or derived from the subject (process 2554). The second plurality of cell-free nucleic acid molecules can be obtained from the subject subsequent to obtaining the first plurality of cell-free nucleic acid molecules from the subject. The method can optionally comprise (c) determining the progress (e.g., progression or regression) of the condition based at least in part on the first state of the condition and the second state of the condition (process 2556). In some cases, each of the one or more cell-free nucleic acid molecules identified (e.g., each of the first set of one or more cell-free nucleic acid molecules identified, each of the second set of one or more cell-free nucleic acid molecules identified) can comprise a plurality of phased variants relative to a reference genomic sequence. At least a portion (e.g., partial or all) of the one or more cell-free nucleic acid molecules identified can be separated by at least one nucleotide, as disclosed herein. In some cases, presence of the plurality of phased variants can be indicative of a state of the condition of the subject.

In some cases, the first plurality of cell-free nucleic acid molecules from the subject can be obtained (e.g., via blood biopsy) and analyzed to determine (e.g., diagnose) a first state of the condition (e.g., a disease, such as cancer) of the subject. The first plurality of cell-free nucleic acid molecules can be analyzed via any of the methods disclosed herein (e.g., with or without sequencing) to identify the first set of one or more cell-free nucleic acid molecules comprising the plurality of phased variants, and the presence or characteristics of the first set of one or more cell-free nucleic acid molecules can be used to determine the first state of the condition (e.g., an initial diagnosis) of the subject. Based on the determined first state of the condition, the subject can be subjected to one or more treatments (e.g., chemotherapy) as disclosed herein. Subsequent to the one or more treatments, the second plurality of cell-free nucleic acid molecules can be obtained from the subject.

In some cases, the subject can be subjected to at least or up to about 1 treatment, at least or up to about 2 treatments, at least or up to about 3 treatments, at least or up to about 4 treatments, at least or up to about 5 treatments, at least or up to about 6 treatments, at least or up to about 7 treatments, at least or up to about 8 treatments, at least or up to about 9 treatments, or at least or up to about 10 treatments based on the determined first state of the condition. In some cases, the subject can be subjected to a plurality of treatments based on the determined first state of the condition, and a first treatment of the plurality of treatments and a second treatment of the plurality of treatments can be separated by at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 12 months, at least or up to about 2 years, at least or up to about 3 years, at least or up to about 4 years, at least or up to about 5 years, or at least or up to about 10 years. The plurality of treatments for the subject can be the same. Alternatively, the plurality of treatments can be different by drug type (e.g., different chemotherapeutic drugs), drug dosage (e.g., increasing dosage, decreasing dosage), presence or absence of a co-therapeutic agent (e.g., chemotherapy and immunotherapy), modes of administration (e.g., intravenous vs oral administrations), frequency of administration (e.g., daily, weekly, monthly), etc.

In some cases, the subject may not and need not be treated for the condition between determination of the first state of the condition and determination of the second state of the condition. For example, without any intervening treatment, the second plurality of cell-free nucleic acid molecules may be contained (e.g., via liquid biopsy) from the subject to confirm whether the subject still exhibits indications of the first state of the condition.

In some cases, the second plurality of cell-free nucleic acid molecules from the subject can be obtained (e.g., via blood biopsy) at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 6 months, at least or up to about 12 months, at least or up to about 2 years, at least or up to about 3 years, at least or up to about 4 years, at least or up to about 5 years, or at least or up to about 10 years after obtaining the first plurality of cell-free nucleic acid molecules from the subject.

In some cases, at least or up to about 2, at least or up to about 3, at least or up to about 4, at least or up to about 5, at least or up to about 6, at least or up to about 7, at least or up to about 8, at least or up to about 9, or at least or up to about 10 different samples comprising a plurality of nucleic acid molecules (e.g., at least the first plurality of cell-free nucleic acid molecules and the second plurality of cell-free nucleic acid molecules) can be obtained over time (e.g., once every month for 6 months, once every two months for a year, once every three months for a year, once every 6 months for one or more years, etc.) to monitor the progress of the condition of the subject, as disclosed herein.

In some cases, the step of determining the progress of the condition based on the first state of the condition and the second state of the condition can comprise comparing one or more characteristics of the first state and the second state of the condition, such as, for example, (i) a total number of cell-free nucleic acid molecules identified to comprise the plurality of phased variants in each state (e.g., per equal weight or volume of the biological sample of origin, per equal number of initial cell-free nucleic acid molecules analyzed, etc.), (ii) an average number of the plurality of phased variants per each cell-free nucleic acid molecule identified to comprise a plurality of phased variants (i.e., two or more phased variants), or (iii) a number of cell-free nucleic acid molecules identified to comprise the plurality of phased variants divided by a total number of cell-free nucleic acid molecules that comprise a mutation that overlaps with some of the plurality of phased variants (i.e., phased variant allele frequency). Based on such comparison, MRD of the condition (e.g., cancer or tumor) of the subject can be determined. For example, tumor burden or cancer burden of the subject can be determined based on such comparison.

In some cases, the progress of the condition can be progression or worsening of the condition. In an example, the worsening of the condition can comprise developing of a cancer from an earlier stage to a later stage, such as from stage I cancer to stage III cancer. In another example, the worsening of the condition can comprise increasing size (e.g., volume) of a solid tumor. Yet in a different example, the worsening of the condition can comprise cancer metastasis from once location to another location within the subject's body.

In some examples, (i) a total number of cell-free nucleic acid molecules identified to comprise the plurality of phased variants from the second state of the condition of the subject can be higher than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be higher than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can be regression or at least a partial remission of the condition. In an example, the at least the partial remission of the condition can comprise downstaging of a cancer from a later stage to an earlier stage, such as from stage IV cancer to stage II cancer. Alternatively, the at least the partial remission of the condition can be full remission from cancer. In another example, the at least the partial remission of the condition can comprise decreasing size (e.g., volume) of a solid tumor.

In some examples, (i) a total number of cell-free nucleic acid molecules identified to comprise the plurality of phased variants from the second state of the condition of the subject can be lower than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be lower than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can remain substantially the same between the two states of the condition of the subject. In some examples, (i) a total number of cell-free nucleic acid molecules identified to comprise the plurality of phased variants from the second state of the condition of the subject can be about the same as (ii) a total number of cell-free nucleic acid molecules identified to comprise the plurality of phased variants from the first state of the condition of the subject. In some examples, (i) an average number of the plurality of phased variants per each cell-free nucleic acid molecule identified to comprise a plurality of phased variants from the second state of the condition of the subject can about the same as (ii) an average number of the plurality of phased variants per each cell-free nucleic acid molecule identified to comprise a plurality of phased variants from the first state of the condition of the subject.

In some embodiments of any one of the methods disclosed herein, the one or more cell-free nucleic acid molecules comprising the plurality of phased variants can be identified from the plurality of cell-free nucleic acid molecules by one or more sequencing methods. Alternatively or in addition to, the one or more cell-free nucleic acid molecules comprising the plurality of phased variants can be identified by being pulled down from (or captured from among) the plurality of cell-free nucleic acid molecules with a set of nucleic acid probes. The pull down (or capture) method via the set of nucleic acid probes can be sufficient to identify the one or more cell-free nucleic acid molecules of interest without sequencing. In some cases, the set of nucleic acid probes can be configured to hybridize to at least a portion of cell-free nucleic acid (e.g., cfDNA) molecules from one or more genomic regions associated with the condition of the subject. As such, a presence of one or more cell-free nucleic acid molecules that have been pulled down by the set of nucleic acid probes can be an indication that the one or more cell-free nucleic acid molecules are derived from the condition (e.g., ctDNA or ctRNA). Additional details of the set of nucleic probes are disclosed elsewhere the present disclosure.

In some embodiments of any one of the methods disclosed herein, based the sequencing data derived from the plurality of cell-free nucleic acid molecules (e.g., cfDNA) that is obtained or derived from the subject, (i) the one or more cell-free nucleic acid molecules identified to comprise the plurality of phased variants can be separated, in silico, from (ii) one or more other cell-free nucleic acid molecules that are not identified to comprise the plurality of phased variants (or one or more other cell-free nucleic acid molecules that do not comprise the plurality of phased variants). In some cases, the method can further comprise generating an additional data comprising sequencing information of only (i) the one or more cell-free nucleic acid molecules identified to comprise the plurality of phased variants. In some cases, the method can further comprise generating a different data comprising sequencing information of only (ii) the one or more other cell-free nucleic acid molecules that are not identified to comprise the plurality of phased variants (or the one or more other cell-free nucleic acid molecules that do not comprise the plurality of phased variants).

In one aspect, the present disclosure provides a method for determining a condition of the subject, as shown by flowchart 2560 in FIG. 25F. The method can comprise (a) providing a mixture comprising (1) a set of nucleic acid probes and (2) a plurality of cell-free nucleic acid molecules obtained or derived from the subject (process 2562). In some cases, an individual nucleic acid probe of the set of nucleic acid probes can be designed to hybridize to a target cell-free nucleic acid molecule comprising a plurality of phased variants relative to a reference genomic sequence that are separated by at least one nucleotide. As such, a first phased variant of the plurality of phased variants and a second phased variant of the plurality of phased variants can be separated by at least one nucleotide, as disclosed herein. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2564). Each of the one or more cell-free nucleic acid molecules can comprise the plurality of phased variants. The method can optionally comprise (c) analyzing at least a portion of the identified one or more cell-free nucleic acid molecules to determine the condition of the subject (process 2566).

In one aspect, the present disclosure provides a method for determining a condition of the subject, as shown by flowchart 2570 in FIG. 25G. The method can comprise (a) providing a mixture comprising (1) a set of nucleic acid probes and (2) a plurality of cell-free nucleic acid molecules obtained or derived from the subject (process 2572). In some cases, an individual nucleic acid probe of the set of nucleic acid probes can be designed to hybridize to a target cell-free nucleic acid molecule comprising a plurality of phased variants relative to a reference genomic sequence. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2574). Each of the one or more cell-free nucleic acid molecules can comprise the plurality of phased variants, and a LOD of the identification step can be less than about 1 out of 50,000 cell-free nucleic acid molecules of the plurality of cell-free nucleic acid molecules, as disclosed herein. The method can optionally comprise (c) analyzing at least a portion of the identified one or more cell-free nucleic acid molecules to determine the condition of the subject (process 2576).

In some cases, a first phased variant of the plurality of phased variants and a second phased variant of the plurality of phased variants are separated by at least one nucleotide, as disclosed herein.

In some cases, the LOD of the step of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, less than 1 out of 2,000,000, less than 1 out of 2,500,000, less than 1 out of 3,000,000, less than 1 out of 4,000,000, or less than 1 out of 5,000,000 cell-free nucleic acid molecules of the plurality of cell-free nucleic acid molecules. Generally, a detection method with a lower LOD has a greater sensitivity of such detection.

In some embodiments of any one of the methods disclosed herein, the method can further comprise mixing (1) the set of nucleic acid probes and (2) the plurality of cell-free nucleic acid molecules.

In some embodiments of any one of the methods disclosed herein, the activatable reporter agent of a nucleic acid probe can be activated upon hybridization of the individual nucleic acid probe to the plurality of phased variants. Non-limiting examples of such nucleic acid probe can include a molecular beacon, eclipse probe, amplifluor probe, scorpions PCR primer, and light upon extension fluorogenic PCR primer (LUX primer).

Figure 26A:
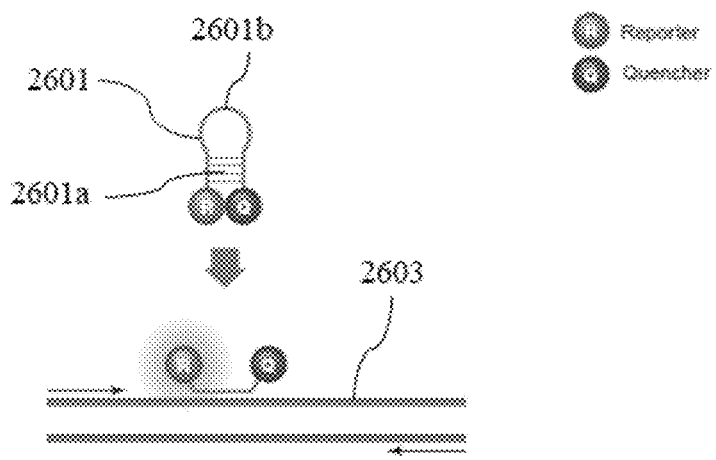
FIGS. 26A and 26B schematically illustrate different fluorescent probes for identifying one or more cell-free nucleic acid molecules comprising a plurality of phased variants.

For example, the nucleic acid probe can be a molecular beacon, as shown in FIG. 26A. The molecular beacon can be fluorescently labeled (e.g., dye-labeled) oligonucleotide probe that comprises complementarity to a target cell-free nucleic acid molecule 2603 in a region that comprises the plurality of phased variants. The molecular beacon can have a length between about 25 nucleotides to about 50 nucleotides. The molecular beacon can also be designed to be partially self-complimentary, such that it form a hairpin structure with a stem 2601a and a loop 2601b. The 5' and 3' ends of the molecular beacon probe can have complementary sequences (e.g., about 5-6 nucleotides) that form the stem structure 2601a. The loop portion 2601b of the hairpin can be designed to specifically hybridize to a portion (e.g., about 15-30 nucleotides) of the target sequence comprising two or more phased variants. The hairpin can be designed to hybridize to a portion that comprises at least 2, 3, 4, 5, or more phased variants. A fluorescent reporter molecule can be attached to the 5' end of the molecular beacon probe, and a quencher that quenches fluorescence of the fluorescent reporter can be attached to the 3' end of the molecular beacon probe. Formation of the hairpin therefore can bring the fluorescent reporter and quencher together, such that no fluorescence is emitted. However, during annealing operation of amplification reaction of the plurality of cell-free nucleic acid molecules that is obtained or derived from the subject, the loop portion of the molecular beacon can bind to its target sequence, causing the stem to denature. Thus, the reporter and quencher can be separated, abolishing quenching, and the fluorescent reporter is activated and detectable. Because fluorescence of the fluorescent reporter is emitted from the molecular beacon probe only when the probe is bound to the target sequence, the amount or level of fluorescence detected can be proportional to the amount of target in the reaction (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the activatable reporter agent can be activated upon dehybridization of at least a portion of the individual nucleic acid probe that has been hybridized to the plurality of phased variants. In other words, once the individual nucleic acid probe is hybridized to target cell-free nucleic acid molecule's portion that comprises the plurality of phased variants, dehybridization of at least a portion of the individual nucleic acid prob and the target cell-free nucleic acid can activate the activatable reporter agent. Non-limiting examples of such nucleic acid probe can include a hydrolysis probe (e.g., TaqMan prob), dual hybridization probes, and QZyme PCR primer.

Figure 26B:
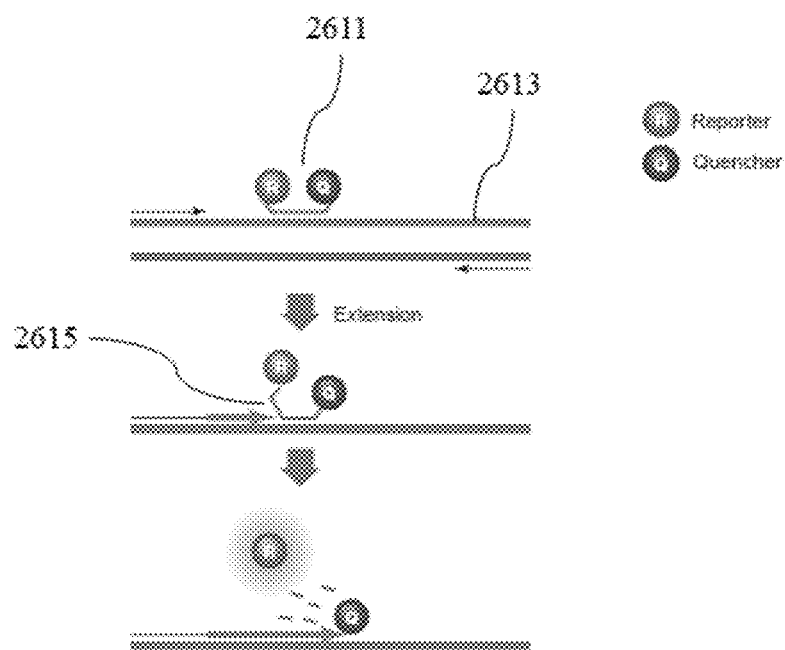

For example, the nucleic acid probe can be a hydrolysis probe, as shown in FIG. 26B. The hydrolysis probe 2611 can be a fluorescently labeled oligonucleotide probe that can specifically hybridize to a portion (e.g., between about 10 and about 25 nucleotides) of the target cell-free nucleic acid molecule 2613, wherein the hybridized portion comprises two or more phased variants. The hydrolysis probe 2611 can be labeled with a fluorescent reporter at the 5' end and a quencher at the 3' end. When the hydrolysis probe is intact (e.g., not cleaved), the fluorescence of the reporter is quenched due to its proximity to the quencher (FIG. 26B). During annealing operation of amplification reaction of the plurality of cell-free nucleic acid molecules obtained or derived from the subject, 5'→3' exonuclease activity of certain thermostable polymerases (e.g., Taq or Tth) The amplification reaction of the plurality of cell-free nucleic acid molecules obtained or derived from the subject can include a combined annealing/extension operation during which the hydrolysis probe hybridizes to the target cell-free nucleic acid molecule, and the dsDNA-specific 5'→3' exonuclease activity of a thermostable polymerase (e.g., Taq or Tth) cleaves off the fluorescent reporter from the hydrolysis probe. As a result, the fluorescent reporter is separated from the quencher, resulting in a fluorescence signal that is proportional to the amount of target in the sample (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the reporter agent can comprise a fluorescent reporter. Non-limiting examples of a fluorescent reporter include fluorescein amidite (FAM, 2-[3-(dimethylamino)-6-dimethyliminio-xanthen-9-yl]benzoate TAMRA, (2E)-2-[(2E,4E)-5-(2-tert-butyl-9-ethyl-6,8,8-trimethyl-pyrano[3,2-g]quinolin-1-ium-4-yl)penta-2,4-dienylidene]-1-(6-hydroxy-6-oxo-hexyl)-3,3-dimethyl-indoline-5-sulfonate Dy 750, 6-carboxy-2',4,4',5',7,7'-hexachlorofluorescein, 4,5,6,7-Tetrachlorofluorescein TET™, sulforhodamine 101 acid chloride succinimidyl ester Texas Red-X, ALEXA Dyes, Bodipy Dyes, cyanine Dyes, Rhodamine 123 (hydrochloride), Well RED Dyes, MAX, and TEX 613. In some cases, the reporter agent further comprises a quencher, as disclosed herein. Non-limiting examples of a quencher can include Black Hole Quencher, Iowa Black Quencher, and 4-dimethylaminoazobenzene-4'-sulfonyl chloride (DABCYL).

In some embodiments of any one of the methods disclosed herein, any PCR reaction utilizing the set of nucleic acid probes can be performed using real-time PCR (qPCR). Alternatively, the PCR reaction utilizing the set of nucleic acid probes can be performed using digital PCR (dPCR).

Figure 24:
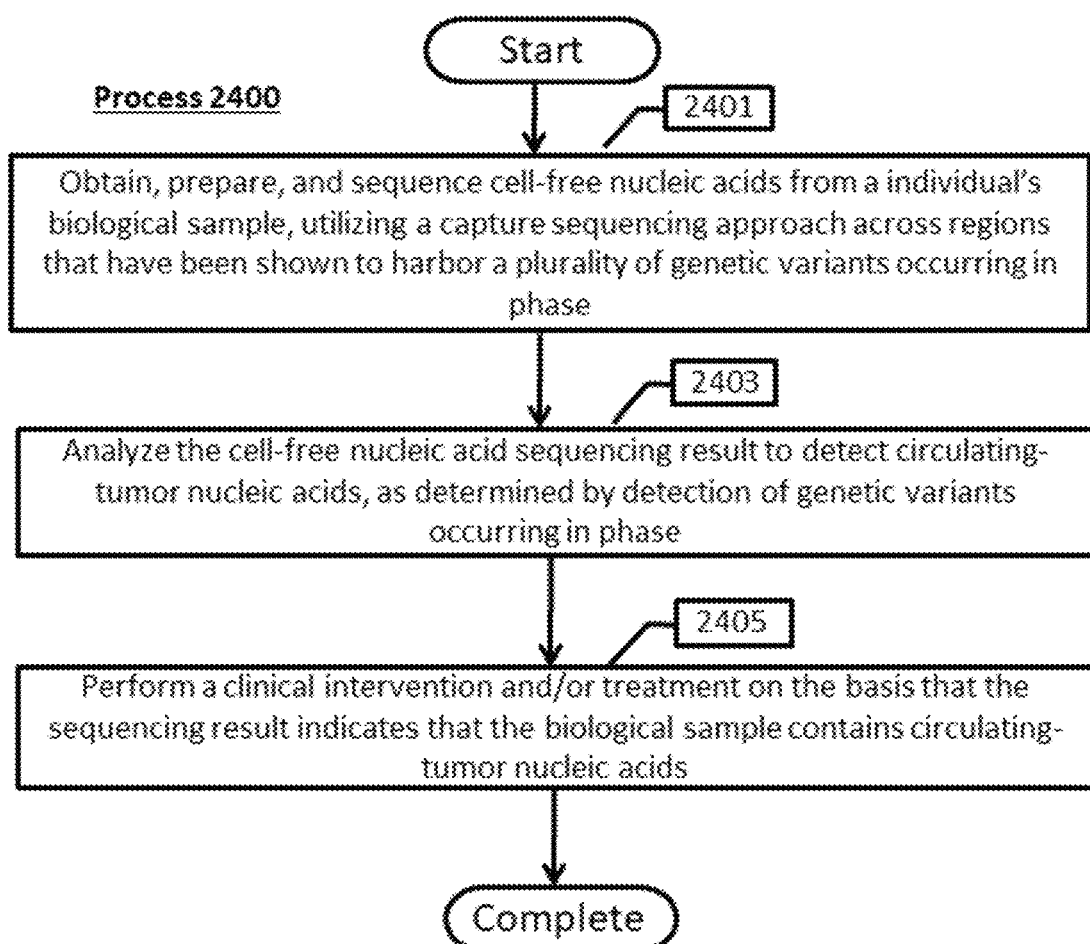
FIG. 24 illustrates a flow diagram of a process to perform a clinical intervention and/or treatment on an individual based on detecting circulating-tumor nucleic acid sequences in a sequencing result in accordance with an embodiment.

Provided in FIG. 24 is an example flowchart of a process to perform a clinical intervention and/or treatment based on detecting circulating-tumor nucleic acids in an individual's biological sample. In several embodiments, detection of circulating-tumor nucleic acids is determined by the detection of somatic variants in phase in a cell-free nucleic acid sample. In many embodiments, detection of circulating-tumor nucleic acids indicates cancer is present, and thus appropriate clinical intervention and/or treatment can be performed.

Referring to FIG. 24, process 2400 can begin with obtaining, preparing, and sequencing (2401) cell-free nucleic acids obtained from a non-invasive biopsy (e.g., liquid or waste biopsy), utilizing a capture sequencing approach across regions shown to harbor a plurality of genetic mutations or variants occurring in phase. In several embodiments, cfDNA and/or cfRNA is extracted from plasma, blood, lymph, saliva, urine, stool, and/or other appropriate bodily fluid. Cell-free nucleic acids can be isolated and purified by any appropriate means. In some embodiments, column purification is utilized (e.g., QIAamp Circulating Nucleic Acid Kit from Qiagen, Hilden, Germany). In some embodiments, isolated RNA fragments can be converted into complementary DNA for further downstream analysis.

In some embodiments, a biopsy is extracted prior to any indication of cancer. In some embodiments, a biopsy is extracted to provide an early screen in order to detect a cancer. In some embodiments, a biopsy is extracted to detect if residual cancer exists after a treatment. In some embodiments, a biopsy is extracted during treatment to determine whether the treatment is providing the desired response. Screening of any particular cancer can be performed. In some embodiments, screening is performed to detect a cancer that develops somatic phased variants in stereotypical regions in the genome, such as (for example) lymphoma. In some embodiments, screening is performed to detect a cancer in which somatic phased variants were discovered utilizing a prior extracted cancer biopsy.

In some embodiments, a biopsy is extracted from an individual with a determined risk of developing cancer, such as those with a familial history of the disorder or have determined risk factors (e.g., exposure to carcinogens). In many embodiments, a biopsy is extracted from any individual within the general population. In some embodiments, a biopsy is extracted from individuals within a particular age group with higher risk of cancer, such as, for example, aging individuals above the age of 50. In some embodiments, a biopsy is extracted from an individual diagnosed with and treated for a cancer.

In some embodiments, extracted cell-free nucleic acids are prepared for sequencing. Accordingly, cell-free nucleic acids are converted into a molecular library for sequencing. In some embodiments, adapters and/or primers are attached onto cell-free nucleic acids to facilitate sequencing. In some embodiments, targeted sequencing of particular genomic loci is to be performed, and thus particular sequences corresponding to the particular loci are captured via hybridization prior to sequencing (e.g., capture sequencing). In some embodiments, capture sequencing is performed utilizing a set of probes that pull down (or capture) regions that have been discovered to commonly harbor phased variants for a particular cancer (e.g., lymphoma). In some embodiments, capture sequencing is performed utilizing a set of probes that pull down (or capture) regions that have been discovered to harbor phased variants as determined prior by sequencing a biopsy of the cancer. More detailed discussion of capture sequencing and probes is provided in the section entitled "Capture Sequencing."

In some embodiments, any appropriate sequencing technique can be utilized that can detect phased variants indicative of circulating-tumor nucleic acids. Sequencing techniques include (but are not limited to) 454 sequencing, Illumina sequencing, SOLiD sequencing, Ion Torrent sequencing, single-read sequencing, paired-end sequencing, etc.

Process 2400 analyzes (2403) the cell-free nucleic acid sequencing result to detect circulating-tumor nucleic acid sequences, as determined by detection of somatic variants occurring in phase. Because cancers are actively growing and expanding, neoplastic cells are often releasing biomolecules (especially nucleic acids) into the vasculature, lymph, and/or waste systems. In addition, due to biophysical constraints in their local environment, neoplastic cells are often rupturing, releasing their inner cell contents into the vasculature, lymph, and/or waste systems. Accordingly, it is possible to detect distal primary tumors and/or metastases from a liquid or waste biopsy.

Detection of circulating-tumor nucleic acid sequences indicates that a cancer is present in the individual being examined. Accordingly, based on detection of circulating-tumor nucleic acids, a clinical intervention and/or treatment may be performed (2405). In a number of embodiments, a clinical procedure is performed, such as (for example) a blood test, genetic test, medical imaging, physical exam, a tumor biopsy, or any combination thereof. In several embodiments, diagnostics are preformed to determine the particular stage of cancer. In a number of embodiments, a treatment is performed, such as (for example) chemotherapy, radiotherapy, chemoradiotherapy, immunotherapy, hormone therapy, targeted drug therapy, surgery, transplant, transfusion, medical surveillance, or any combination thereof. In some embodiments, an individual is assessed and/or treated by medical professional, such as a doctor, physician, physician's assistant, nurse practitioner, nurse, caretaker, dietician, or similar.

Various embodiments of the present disclosure are directed towards utilizing detection of cancer to perform clinical interventions. In a number of embodiments, an individual has a liquid or waste biopsy screened and processed by methods described herein to indicate that the individual has cancer and thus an intervention is to be performed. Clinical interventions include clinical procedures and treatments. Clinical procedures include (but are not limited to) blood tests, genetic test, medical imaging, physical exams, and tumor biopsies. Treatments include (but are not limited to) chemotherapy, radiotherapy, chemoradiotherapy, immunotherapy, hormone therapy, targeted drug therapy, surgery, transplant, transfusion, and medical surveillance. In several embodiments, diagnostics are performed to determine the particular stage of cancer. In some embodiments, an individual is assessed and/or treated by medical professional, such as a doctor, physician, physician's assistant, nurse practitioner, nurse, caretaker, dietician, or similar.

In several embodiments as described herein a cancer can be detected utilizing a sequencing result of cell-free nucleic acids derived from blood, serum, cerebrospinal fluid, lymph fluid, urine or stool. In many embodiments, cancer is detected when a sequencing result has one or more somatic variants present in phase within a short genetic window, such as the length of a cell-free molecule (e.g., about 170 bp). In numerous embodiments, a statistical method is utilized to determine whether the presence of phased variants is derived from a cancerous source (as opposed to molecular artifact or other biological source). Various embodiments utilize a Monte Carlo sampling method as the statistical method to determine whether a sequencing result of cell-free nucleic acids includes sequences of circulating-tumor nucleic acids based on a score as determined by the presence of phased variants. Accordingly, in a number of embodiments, cell-free nucleic acids are extracted, processed, and sequenced, and the sequencing result is analyzed to detect cancer. This process is especially useful in a clinical setting to provide a diagnostic scan.

An exemplary procedure for a diagnostic scan of an individual for a B-cell cancer is as follows:
(a) extract liquid or waste biopsy from individual,
(b) prepare and perform targeted sequencing of cell-free nucleic acids from biopsy utilizing nucleic acid probes specific for the B-cell cancer,
(c) detect phased variants in a sequencing results that are indicative of circulating-tumor nucleic acid sequences, and
(d) perform clinical intervention based on detection of circulating-tumor nucleic acid sequences.

An exemplary procedure for a personalized diagnostic scan of an individual for a cancer that has been previously sequenced to detect phased variants in particular genomic loci is as follows:
extract cancer biopsy from individual
sequence cancer biopsy to detect phased variants that have accumulated in the cancer
(a) design and synthesize nucleic acid probes for genomic loci that include the positions of the detected phased variants,
(b) extract liquid or waste biopsy from individual,
(c) prepare and perform targeted sequencing of cell-free nucleic acids from biopsy utilizing the designed and synthesized nucleic acid probes,
(d) detect phased variants in a sequencing results that are indicative of circulating-tumor nucleic acid sequences, and
(e) perform clinical intervention based on detection of circulating-tumor nucleic acid sequences.

In some embodiments of any one of the methods disclosed herein, at least a portion of the identified one or more cell-free nucleic acid molecules comprising the plurality of phased variants can be further analyzed for determining the condition of the subject. In such analysis, (i) the identified one or more cell-free nucleic acid molecules and (ii) other cell-free nucleic acid molecules of the plurality of cell-free nucleic acid molecules that do not comprise the plurality of phased variants can be analyzed as different variables. In some cases, a ratio of (i) a number the identified one or more cell-free nucleic acid molecules and (ii) a number of the other cell-free nucleic acid molecules of the plurality of cell-free nucleic acid molecules that do not comprise the plurality of phased variants can be used a factor to determine the condition of the subject. In some cases, comparison of (i) a position(s) of the identified one or more cell-free nucleic acid molecules relative to the reference genomic sequence and (ii) a position(s) of the other cell-free nucleic acid molecules of the plurality of cell-free nucleic acid molecules that do not comprise the plurality of phased variants relative to the reference genomic sequence can be used a factor to determine the condition of the subject.

Alternatively, in some cases, the analysis of the identified one or more cell-free nucleic acid molecules comprising the plurality of phased variants for determining the condition of the subject may not and need not be based on the other cell-free nucleic acid molecules of the plurality of cell-free nucleic acid molecules that do not comprise the plurality of phased variants. As disclosed herein, non-limiting examples of information or characteristics of the one or more cell-free nucleic acid molecules comprising the plurality of phased variants can include (i) a total number of such cell-free nucleic acid molecules and (ii) an average number of the plurality of phased variations per each nucleic acid molecule in the population of identified cell-free nucleic acid molecules.

Thus, in some embodiments of any one of the methods disclosed herein, a number of the plurality of phased variants from the one or more cell-free nucleic acid molecules that have been identified to have the plurality of phased variants can be indicative of the condition of the subject. In some cases, a ratio of (i) the number of the plurality of phased variants from the one or more cell-free nucleic acid molecules and (ii) a number of single nucleotide variants from the one or more cell-free nucleic acid molecules can be indicative of the condition of the subject. For instance, a particular condition (e.g., follicular lymphoma) can exhibit a signature ratio that is different than that of another condition (e.g., breast cancer). In some examples, for cancer or solid tumor, the ratio as disclosed herein can be between about 0.01 and about 0.20. In some examples, for cancer or solid tumor, the ratio as disclosed herein can be about 0.01, about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, or about 0.20. In some examples, for cancer or solid tumor, the ratio as disclosed herein can be at least or up to about 0.01, at least or up to about 0.02, at least or up to about 0.03, at least or up to about 0.04, at least or up to about 0.05, at least or up to about 0.06, at least or up to about 0.07, at least or up to about 0.08, at least or up to about 0.09, at least or up to about 0.10, at least or up to about 0.11, at least or up to about 0.12, at least or up to about 0.13, at least or up to about 0.14, at least or up to about 0.15, at least or up to about 0.16, at least or up to about 0.17, at least or up to about 0.18, at least or up to about 0.19, or at least or up to about 0.20.

In some embodiments of any one of the methods disclosed herein, a frequency of the plurality of phased variants in the one or more cell-free nucleic acid molecules that have been identified can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule that is associated with a particular gene (e.g., BCL2, PIM1) can be indicative of the condition of the subject. The size of the bin can be about 30, about 40, about 50, about 60, about 70, or about 80.

In some examples, a first condition (e.g., Hodgkin lymphoma or HL) can exhibit a first average frequency and a second condition (e.g., DLBCL) can exhibit a different average frequency, thereby allowing identification and/or determination of whether the subject has or is suspected of having a particular condition. In some examples, a first sub-type of a disease can exhibit a first average frequency and a second sub-type of the same disease can exhibit a different average frequency, thereby allowing identification and/or determination of whether the subject has or is suspected of having a particular sub-type of the disease. For example, the subject can have DLBCL, and one or more cell-free nucleic acid molecules derived from germinal center B-cell (GCB) DLBCL or activated B-cell (ABC) DLBCL can have different average frequency of the plurality of phased variant per a predetermined bin length, as disclosed herein.

In some example, a condition of the subject may have a predetermined number of phased variants spanning predetermined genomic loci (i.e., a predetermined frequency of phased variants). When the predetermined frequency of phased variants match a frequency of the plurality of phased variants in the one or more cell-free nucleic acid molecules that have been identified from a plurality of cell-free nucleic acid molecules from the subject, it may indicate that the subject has such condition.

In some embodiments of any one of the methods disclosed herein, the one or more cell-free nucleic acid molecules identified to comprise the plurality of phased variants can be analyzed to determine their genomic origin (e.g., which gene locus they are from). The genomic origin of the one or more cell-free nucleic acid molecules that have been identified can be indicative of the condition of the subject, as different disease can have the plurality of phased variants in different signature genes. For example, a subject can have GCB DLBCL, and one or more cell-free nucleic acid molecules originated from GCBs of the subject can have the phased variants prevalent in BCL2 gene, while one or more cell-free nucleic acid molecules originated from ABCs of the same subject may not comprise as many phased variants in the BCL2 gene as those from GCBs. On the other hand, a subject can have ABC DLBCL, and one or more cell-free nucleic acid molecules originated from ABCs of the subject can have the phased variants prevalent in PIM1 gene, while one or more cell-free nucleic acid molecules originated from GCBs of the same subject may not comprise as many phased variants in the PIM1 gene as those from ABCs.

In some embodiments of any one of the methods disclosed herein, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the one or more cell-free nucleic acid molecules comprising the plurality of phased variants can comprise a single nucleotide variant (SNV) that is at least 2 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 3 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 4 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 5 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 6 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 7 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 8 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 9 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 10 nucleotides away from an adjacent SNV.

C. Reference Genomic Sequence

In some embodiments of any one of the methods disclosed herein, the reference genomic sequence can be at least a portion of a nucleic acid sequence database (i.e., a reference genome), which database is assembled from genetic data and intended to represent the genome of a reference cohort. In some cases, a reference cohort can be a collection of individuals from a specific or varying genotype, haplotype, demographics, sex, nationality, age, ethnicity, relatives, physical condition (e.g., healthy or having been diagnosed to have the same or different condition, such as a specific type of cancer), or other groupings. A reference genomic sequence as disclosed herein can be a mosaic (or a consensus sequence) of the genomes of two or more individuals. The reference genomic sequence can comprise at least a portion of a publicly available reference genome or a private reference genome. Non-limiting examples of a human reference genome include hg19, hg18, hg17, hg16, and hg38.

In some examples, the reference genomic sequence can comprise at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, at least or up to about 500 kb, at least or up to about 600 kb, at least or up to about 700 kb, at least or up to about 800 kb, at least or up to about 900 kb, at least or up to about 1,000 kb, at least or up to about 2,000 kb, at least or up to about 3,000 kb, at least or up to about 4,000 kb, at least or up to about 5,000 kb, at least or up to about 6,000 kb, at least or up to about 7,000 kb, at least or up to about 8,000 kb, at least or up to about 9,000 kb, at least or up to about 10,000 kb, at least or up to about 20,000 kb, at least or up to about 30,000 kb, at least or up to about 40,000 kb, at least or up to about 50,000 kb, at least or up to about 60,000 kb, at least or up to about 70,000 kb, at least or up to about 80,000 kb, at least or up to about 90,000 kb, or at least or up to about 100,000 kb.

In some cases, the reference genomic sequence can be whole reference genome or a portion (e.g., a portion relevant to the condition of interest) of the genome. For example, the reference genomic sequence can consist of at least 1, 2, 3, 4, 5, or more genes that experience aberrant somatic hypermutation under certain types of cancer. In some cases, the reference genomic sequence can be a whole chromosomal sequence, or a fragment thereof. In some cases, the reference genomic sequence can comprise two or more (e.g., at least 2, 3, 4, 5, or more) different portions of the reference genome that are not adjacent to one another (e.g., within the same chromosome or from different chromosomes).

In some embodiments of any one of the methods disclosed herein, the reference genomic sequence can be at least a portion of a reference genome of a selected individual, such as a healthy individual or the subject of any of the methods as disclosed herein.

In some cases, the reference genomic sequence can be derived from an individual who is not the subject (e.g., a healthy control individual). Alternatively, in some cases, the reference genomic sequence can be derived from a sample of the subject. In some examples, the sample can be a healthy sample of the subject. The healthy sample of the subject can be any subject cell that is healthy, e.g., a healthy leukocyte. By comparing sequencing data of the plurality of cell-free nucleic acid molecules (e.g., cfDNA molecules) of the subject against at least a portion of the genomic sequence of a healthy cell of the same subject, one or more cell-free nucleic acid molecules that comprise the plurality of phased variants can be identified and analyzed, as disclosed herein. In some examples, the sample can be a diseased sample of the subject, such as a diseased cell (e.g., a tumor cell) or a solid tumor. The reference genomic sequence can be obtained from sequencing at least a portion of a diseased cell of the subject or from sequencing a plurality of cell-free nucleic acid molecules obtained from the solid tumor of the subject. Once the subject is diagnosed to have a particular condition (e.g., a disease), the reference genomic sequence of the subject that comprises the plurality of phased variants can be used to determine whether the subject still exhibits the same phased variants at future time points. In this context, any new phased variants identified between the "diseased" reference genomic sequence of the subject and new cell-free nucleic acid molecules obtained or derived from the subject can indicate a reduced degree of aberrant somatic hypermutation in particular genomic loci (e.g., at least a partial remission).

In various embodiments, diagnostic scans can be performed for any neoplasm type, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CIVIL), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

In a number of embodiments, a diagnostic scan is utilized to provide an early detection of cancer. In some embodiments, a diagnostic scan detects cancer in individuals having stage I, II, or III cancer. In some embodiments, a diagnostic scan is utilized to detect MRD or tumor burden. In some embodiments, a diagnostic scan is utilized to determine progress (e.g., progression or regression) of treatment. Based on the diagnostic scan, a clinical procedure and/or treatment may be performed.

D. Nucleic Acid Probes

In some embodiments of any one of the methods disclosed herein, the set of nucleic acid probes can be designed based on the any of the subject reference genomic sequences of the present disclosure. In some cases, the set of nucleic acid probes can be designed based on the plurality of phased variants that have been identified by comparing (i) sequencing data from a solid tumor of the subject and (ii) sequencing data from a healthy cell of the subject or a healthy cohort, as disclosed herein. The set of nucleic acid probes can be designed based on the plurality of phased variants that have been identified by comparing (i) sequencing data from a solid tumor of the subject and (ii) sequencing data from a healthy cell of the subject. The set of nucleic acid probes can be designed based on the plurality of phased variants that have been identified by comparing (i) sequencing data from a solid tumor of the subject and (ii) sequencing data from a healthy cell of a healthy cohort.

In some embodiments of any one of the methods disclosed herein, the set of nucleic acid probes are designed to hybridize to sequences of genomic loci associated with the condition. As disclosed herein, the genomic loci associated with the condition can be determined to experience or exhibit aberrant somatic hypermutation when the subject has the condition. Alternatively, the set of nucleic acid probes are designed to hybridize to sequences of stereotyped regions.

In some embodiments of any one of the methods disclosed herein, the set of nucleic acid probes can be designed to hybridize to at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, the set of nucleic acid probes can be designed to hybridize to at least a portion of cell-free nucleic acid (e.g., cfDNA) molecules derived from at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, each nucleic acid probe of the set of nucleic acid probes can have at least about 50%, at least about 55%, at least about 60%, at least about 65%, at least about 70%, at least about 75%, at least about 80%, at least about 85%, at least about 90% sequence identity, at least about 95% sequence identity, at least about 99%, or about 100% sequence identity to a probe sequence selected from Table 6.

In some embodiments of any one of the methods disclosed herein, the set of nucleic acid probes can comprise at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% of probe sequences in Table 6.

In some embodiments of any one of the methods disclosed herein, the set of nucleic acid probes can be designed to cover one or more target genomic regions comprising at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, or at least or up to about 500 kb.

In some embodiments of any one of the methods disclosed herein, a target genomic region (e.g., a target genomic locus) of the one or more target genomic regions can comprise at most about 200 nucleobases, at most about 300 nucleobases, 400 nucleobases, at most about 500 nucleobases, at most about 600 nucleobases, at most about 700 nucleobases, at most about 800 nucleobases, at most about 900 nucleobases, at most about 1 kb, at most about 2 kb, at most about 3 kb, at most about 4 kb, at most about 5 kb, at most about 6 kb, at most about 7 kb, at most about 8 kb, at most about 9 kb, at most about 10 kb, at most about 11 kb, at most about 12 kb, at most about 13 kb, at most about 14 kb, at most about 15 kb, at most about 16 kb, at most about 17 kb, at most about 18 kb, at most about 19 kb, at most about 20 kb, at most about 25 kb, at most about 30 kb, at most about 35 kb, at most about 40 kb, at most about 45 kb, at most about 50 kb, or at most about 100 kb.

In some embodiments of any one of the methods disclosed herein, the set of nucleic acid probes can comprise at least or up to about 10, at least or up to about 20, at least or up to about 30, at least or up to about 40, at least or up to about 50, at least or up to about 60, at least or up to about 70, at least or up to about 80, at least or up to about 90, at least or up to about 100, at least or up to about 200, at least or up to about 300, at least or up to about 400, at least or up to about 500, at least or up to about 600, at least or up to about 700, at least or up to about 800, at least or up to about 900, at least or up to about 1,000, at least or up to about 2,000, at least or up to about 3,000, at least or up to about 4,000, or at least or up to about 5,000 different nucleic acid probes designed to hybridize to different target nucleic acid sequences.

In some embodiments of any one of the methods disclosed herein, the set of nucleic acid probes can have a length of at least or up to about 50, at least or up to about 55, at least or up to about 60, at least or up to about 65, at least or up to about 70, at least or up to about 75, at least or up to about 80, at least or up to about 85, at least or up to about 90, at least or up to about 95, or at least or up to about 100 nucleotides.

In one aspect, the present disclosure provides a composition comprising a bait set comprising any one of the set of nucleic acid probes disclosed herein. The composition comprising such bait set can be used for any of the methods disclosed herein. In some cases, the set of nucleic acid probes can be designed to pull down (or capture) cfDNA molecules. In some cases, the set of nucleic acid probes can be designed to pull down (or capture) cfRNA molecules.

In some embodiments, the bait set can comprise a set of nucleic acid probes designed to pull down cell-free nucleic acid (e.g., cfDNA) molecules derived from genomic regions set forth in Table 1. The set of nucleic acid probes can be designed to pull down cell-free nucleic acid molecules derived from at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the genomic regions set forth in Table 1. In some cases, the set of nucleic acid probes can be designed to pull down cfDNA molecules. In some cases, the set of nucleic acid probes can be designed to pull down cfRNA molecules.

In some embodiments of any one of the compositions disclosed herein, an individual nucleic acid probe (or each nucleic acid probe) of the set of nucleic acid probes can comprise a pull-down tag. The pull-down tag can be used to enrich a sample (e.g., a sample comprising the plurality of nucleic acid molecules obtained or derived from the subject) for a specific subset (e.g., for cell-free nucleic acid molecules comprising the plurality of phased variants as disclosed herein).

In some cases, pull-down tag can comprise a nucleic acid barcode (e.g., on either or both sides of the nucleic acid probe). By utilizing beads or substrates comprising nucleic acid sequences having complementarity to the nucleic acid barcode, the nucleic acid barcode can be used to pull-down and enrich for any nucleic acid probe that is hybridized to a target cell-free nucleic acid molecule. Alternatively or in addition to, the nucleic acid barcode can be used to identify the target cell-free nucleic acid molecule from any sequencing data (e.g., sequencing by amplification) obtained by using any of the set of nucleic acid probes disclosed herein.

In some cases, the pull-down tag can comprise an affinity target moiety that can be specifically recognized and bound by an affinity binding moiety. The affinity binding moiety specifically can bind the affinity target moiety to form an affinity pair. In some cases, by utilizing beads or substrates comprising the affinity binding moiety, the affinity target moiety can be used to pull-down and enrich for any nucleic acid probe that is hybridized to a target cell-free nucleic acid molecule. Alternatively, the pull-down tag can comprise the affinity binding moiety, while the beads/substrates can comprise the affinity target moiety. Non-limiting examples of the affinity pair can include biotin/avidin, antibody/antigen, biotin/streptavidin, metal/chelator, ligand/receptor, nucleic acid and binding protein, and complementary nucleic acids. In an example, the pull-down tag can comprise biotin.

In some embodiments of any one of the compositions disclosed herein, a length of a target cell-free nucleic acid (e.g., cfDNA) molecule that is to be pulled down by any subject nucleic acid probe can be about 100 nucleotides to about 200 nucleotides. The length of the target cell-free nucleic acid molecule can be at least about 100 nucleotides.

The length of the target cell-free nucleic acid molecule can be at most about 200 nucleotides. The length of the target cell-free nucleic acid molecule can be about 100 nucleotides to about 110 nucleotides, about 100 nucleotides to about 120 nucleotides, about 100 nucleotides to about 130 nucleotides, about 100 nucleotides to about 140 nucleotides, about 100 nucleotides to about 150 nucleotides, about 100 nucleotides to about 160 nucleotides, about 100 nucleotides to about 170 nucleotides, about 100 nucleotides to about 180 nucleotides, about 100 nucleotides to about 190 nucleotides, about 100 nucleotides to about 200 nucleotides, about 110 nucleotides to about 120 nucleotides, about 110 nucleotides to about 130 nucleotides, about 110 nucleotides to about 140 nucleotides, about 110 nucleotides to about 150 nucleotides, about 110 nucleotides to about 160 nucleotides, about 110 nucleotides to about 170 nucleotides, about 110 nucleotides to about 180 nucleotides, about 110 nucleotides to about 190 nucleotides, about 110 nucleotides to about 200 nucleotides, about 120 nucleotides to about 130 nucleotides, about 120 nucleotides to about 140 nucleotides, about 120 nucleotides to about 150 nucleotides, about 120 nucleotides to about 160 nucleotides, about 120 nucleotides to about 170 nucleotides, about 120 nucleotides to about 180 nucleotides, about 120 nucleotides to about 190 nucleotides, about 120 nucleotides to about 200 nucleotides, about 130 nucleotides to about 140 nucleotides, about 130 nucleotides to about 150 nucleotides, about 130 nucleotides to about 160 nucleotides, about 130 nucleotides to about 170 nucleotides, about 130 nucleotides to about 180 nucleotides, about 130 nucleotides to about 190 nucleotides, about 130 nucleotides to about 200 nucleotides, about 140 nucleotides to about 150 nucleotides, about 140 nucleotides to about 160 nucleotides, about 140 nucleotides to about 170 nucleotides, about 140 nucleotides to about 180 nucleotides, about 140 nucleotides to about 190 nucleotides, about 140 nucleotides to about 200 nucleotides, about 150 nucleotides to about 160 nucleotides, about 150 nucleotides to about 170 nucleotides, about 150 nucleotides to about 180 nucleotides, about 150 nucleotides to about 190 nucleotides, about 150 nucleotides to about 200 nucleotides, about 160 nucleotides to about 170 nucleotides, about 160 nucleotides to about 180 nucleotides, about 160 nucleotides to about 190 nucleotides, about 160 nucleotides to about 200 nucleotides, about 170 nucleotides to about 180 nucleotides, about 170 nucleotides to about 190 nucleotides, about 170 nucleotides to about 200 nucleotides, about 180 nucleotides to about 190 nucleotides, about 180 nucleotides to about 200 nucleotides, or about 190 nucleotides to about 200 nucleotides. The length of the target cell-free nucleic acid molecule can be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, or about 200 nucleotides. In some examples, the length of the target cell-free nucleic acid molecule can range between about 100 nucleotides and about 180 nucleotides.

In some embodiments of any one of the compositions disclosed herein, the genomic regions can be associated with a condition. The genomic regions can be determined to exhibit aberrant somatic hypermutation when a subject has the condition. For example, the condition can comprise B-cell lymphoma or a sub-type thereof, such as diffuse large B-cell lymphoma, follicular lymphoma, Burkitt lymphoma, and B-cell chronic lymphocytic leukemia. Additional details of the condition are provided below.

In some embodiments of any one of the compositions disclosed herein, the composition further comprises the plurality of cell-free nucleic acid (e.g., cfDNA) molecules obtained or derived from the subject.

E. Diagnostic or Therapeutic Applications

A number of embodiments are directed towards performing a diagnostic scan on cell-free nucleic acids of an individual and then based on results of the scan indicating cancer, performing further clinical procedures and/or treating the individual. In accordance with various embodiments, numerous types of neoplasms can be detected.

In some embodiments of any one of the methods disclosed herein, the method can comprise determining that the subject has the condition or determining a degree or status of the condition of the subject, based on the one or more cell-free nucleic acid molecules comprising the plurality of phased variants. In some cases, the method can further comprise determining that the one or more cell-free nucleic acid molecules (each identified to comprise a plurality of phased variants) are derived from a sample associated with the condition (e.g., cancer), based on a statistical model analysis (i.e., molecular analysis). For example, the method can comprise using one or more algorithms (e.g., Monte Carlos simulation) to determine a first probability of a cell-free nucleic acid identified to have a plurality of phased variants being associated with or originated from a first condition (e.g., 80%) and a second probability of the same cell-free nucleic acid being associated with or originated from a second condition (or from a healthy cell) (e.g., 20%). In some cases, the method can comprise determining a likelihood or probability that the subject has one or more conditions based on analysis of the one or more cell-free nucleic acid molecules each identified to comprise a plurality of phased variants (i.e., macro- or global analysis). For example, the method can comprise using one or more algorithms (e.g., comprising one or more mathematical models as disclosed herein, such as binomial sampling) to analyze a plurality of cell-free nucleic acid molecules each identified to comprise a plurality of phased variants, thereby to determine a first probability of the subject having a first condition (e.g., 80%) and a second probability of the subject having a second condition (or being healthy) (e.g., 20%).

The statistical model analysis as disclosed herein can be an approximate solution by a numerical approximation such as a binomial model, a ternary model, a Monte Carlo simulation, or a finite difference method. In an example, the statistical model analysis as used herein can be a Monte Carlo statistical analysis. In another example, the statistical model analysis as used herein can be a binomial or ternary model analysis.

In some embodiments of any one of the methods disclosed herein, the method can comprise monitoring a progress of the condition of the subject based on the one or more cell-free nucleic acid molecules identified, such that each of the identified cell-free nucleic acid molecule comprises a plurality of phased variants. In some cases, the progress of the condition can be worsening of the condition, as described in the present disclosure (e.g., developing from stage I cancer to stage III cancer). In some cases, the progress of the condition can be at least a partial remission of the condition, as described in the present disclosure (e.g., downstaging from stage IV cancer to stage II cancer). Alternatively, in some cases, the progress of the condition can remain substantially the same between two different time points, as described in the present disclosure. In an example, the method can comprise determining likelihoods or probabilities of different progresses of the condition of the subject. For example, the method can comprise using one or more algorithms (e.g., comprising one or more mathematical models as disclosed herein, such as binomial sampling) to determine a first probability of the subject's condition being worse than before (e.g., 20%), a second probability of at least partial remission of the condition (e.g., 70%), and a third probability that the subject's condition is the same as before (e.g., 10%).

In some embodiments of any one of the methods disclosed herein, the method can comprise comprising performing a different procedure (e.g., follow-up diagnostic procedures) to confirm the condition of the subject, which condition has been determined and/or monitored progress thereof, as provided in the present disclosure. Non-limiting examples of a different procedure can include physical exam, medical imaging, genetic test, mammography, endoscopy, stool sampling, pap test, alpha-fetoprotein blood test, CA-125 test, prostate-specific antigen (PSA) test, biopsy extraction, bone marrow aspiration, and tumor marker detection tests. Medical imaging includes (but is not limited to) X-ray, magnetic resonance imaging (MM), computed tomography (CT), ultrasound, and positron emission tomography (PET). Endoscopy includes (but is not limited to) bronchoscopy, colonoscopy, colposcopy, cystoscopy, esophagoscopy, gastroscopy, laparoscopy, neuroendoscopy, proctoscopy, and sigmoidoscopy.

In some embodiments of any one of the methods disclosed herein, the method can comprise determining a treatment for the condition of the subject based on the one or more cell-free nucleic acid molecules identified, each identified cell-free nucleic acid molecule comprising a plurality of phased variants. In some cases, the treatment can be determined based on (i) the determined condition of the subject and/or (ii) the determined progress of the condition of the subject. In addition, the treatment can be determined based on one or more additional factors of the following: sex, nationality, age, ethnicity, and other physical conditions of the subject. In some examples, the treatment can be determined based on one or more features of the plurality of phased variants of the identified cell-free nucleic acid molecules, as disclosed herein.

In some embodiments of any one of the methods disclosed herein, the subject may not have been subjected to any treatment for the condition, e.g., the subject may not have been diagnosed with the condition (e.g., a lymphoma). In some embodiments of any one of the methods disclosed herein, the subject may been subjected to a treatment for the condition prior to any subject method of the present disclosure. In some cases, the methods disclosed herein can be performed to monitor progress of the condition that the subject has been diagnosed with, thereby to (i) determine efficacy of the previous treatment and (ii) assess whether to keep the treatment, modify the treatment, or cancel the treatment in favor of a new treatment.

In some embodiments of any one of the methods disclosed herein, non-limiting examples of a treatment (e.g., prior treatment, new treatment to be determined based on the methods of the present disclosure, etc.) can include chemotherapy, radiotherapy, chemoradiotherapy, immunotherapy, adoptive cell therapy (e.g., chimeric antigen receptor (CAR) T cell therapy, CAR NK cell therapy, modified T cell receptor (TCR) T cell therapy, etc.) hormone therapy, targeted drug therapy, surgery, transplant, transfusion, or medical surveillance.

In some embodiments of any one of the methods disclosed herein, the condition can comprise a disease. In some embodiments of any one of the methods disclosed herein, the condition can comprise neoplasm, cancer, or tumor. In an example, the condition can comprise a solid tumor. In another example, the condition can comprise a lymphoma, such as B-cell lymphoma (BCL). Non-limiting examples of BCL can include diffuse large B-cell lymphoma (DLBCL), follicular lymphoma (FL), Burkitt lymphoma (BL), B-cell chronic lymphocytic leukemia (CLL), Marginal zone B-cell lymphoma (MZL), and Mantle cell lymphoma (MCL).

As disclosed herein, a treatment for a condition of subject can comprise administering the subject with one or more therapeutic agents. The one or more therapeutic drugs can be administered to the subject by one or more of the following: orally, intraperitoneally, intravenously, intraarterially, transdermally, intramuscularly, liposomally, via local delivery by catheter or stent, subcutaneously, intraadiposally, and intrathecally.

Non-limiting examples of the therapeutic drugs can include cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, anti-PD1 antibodies (e.g., Pembrolizumab) platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like.

Non-limiting examples of a cytotoxic agent can include radioactive isotopes (e.g., At211, I131, I125, Y90, Re186, Re188, Sm153, Bi212, P32, and radioactive isotopes of Lu), chemotherapeutic agents, e.g., methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin.

Non-limiting examples of a chemotherapeutic agent can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolmelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics; dynemicin, including dynemicin A; an espiramicina; as well as neocarzinostatin chromophore and related chromoprotein enediyne antibiotic chromophores), aclacinomycins, actinomycin, anthramycin, azaserine, bleomycins, cactinomycin, carabicin, carminomycin, carzinophilin, chromomycins, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Examples of a chemotherapeutic agent can also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD) leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Examples of a chemotherapeutic agent can also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, feMzumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Examples of a chemotherapeutic agent can also include "tyrosine kinase inhibitors" such as an EGFR-targeting agent (e.g., small molecule, antibody, etc.); small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties); PD-0183805 (Warner-Lamber); antisense molecules (e.g., those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®).

Examples of a chemotherapeutic agent can also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Examples of a chemotherapeutic agent can also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate: immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell costimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa/β2 blockers such as Anti-lymphotoxin alpha (LTa); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above.

In accordance with many embodiments, once a diagnosis of cancer is indicated, a number of treatments can be performed, including (but not limited to) surgery, resection, chemotherapy, radiation therapy, immunotherapy, targeted therapy, hormone therapy, stem cell transplant, and blood transfusion. In some embodiments, an anti-cancer and/or chemotherapeutic agent is administered, including (but not limited to) alkylating agents, platinum agents, taxanes, *vinca* agents, anti-estrogen drugs, aromatase inhibitors, ovarian suppression agents, endocrine/hormonal agents, bisphophonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, daunorubicin, doxorubicin, epirubicin, idarubicin, valrubicin mitoxantrone, bevacizumab, cetuximab, ipilimumab, ado-trastuzumab emtansine, afatinib, aldesleukin, alectinib, alemtuzumab, atezolizumab, avelumab, axtinib, belimumab, belinostat, bevacizumab, blinatumomab, bortezomib, bosutinib, brentuximab vedotin, brigatinib, cabozantinib, canakinumab, carfilzomib, certinib, cetuximab, cobimetinib, crizotinib, dabrafenib, daratumumab, dasatinib, denosumab, dinutuximab, durvalumab, elotuzumab, enasidenib, erlotinib, everolimus, gefitinib, ibritumomab tiuxetan, ibrutinib, idelalisib, imatinib, ipilimumab, ixazomib, lapatinib, lenvatinib, midostaurin, necitumumab, neratinib, nilotinib, niraparib, nivolumab, obinutuzumab, ofatumumab, olaparib, olaratumab, osimertinib, palbociclib, panitumumab, panobinostat, pembrolizumab, pertuzumab, ponatinib, ramucirumab, regorafenib, ribociclib, rituximab, romidepsin, rucaparib, ruxolitinib, siltuximab, sipuleucel-T, sonidegib, sorafenib, temsirolimus, tocilizumab, tofacitinib, tositumomab, trametinib, trastuzumab, vandetanib, vemurafenib, venetoclax, vismodegib, vorinostat, and ziv-aflibercept. In accordance with various embodiments, an individual may be treated, by a single medication or a combination of medications described herein. A common treatment combination is cyclophosphamide, methotrexate, and 5-fluorouracil (CMF).

In some embodiments of any one of the methods disclosed herein, any of the cell-free nucleic acid molecules (e.g., cfDNA, cfRNA) can be derived from a cell. For example, a cell sample or tissue sample may be obtained from a subject and processed to remove all cells from the sample, thereby producing cell-free nucleic acid molecules derived from the sample.

In some embodiments of any one of the methods disclosed herein, a reference genomic sequence can be derived from a cell of an individual. The individual can be a healthy control or the subject who is being subjected to the methods disclosed herein for determining or monitoring progress of a condition.

A cell can be a healthy cell. Alternatively, a cell can be a diseased cell. A diseased cell can have altered metabolic, gene expression, and/or morphologic features. A diseased cell can be a cancer cell, a diabetic cell, and an apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

A cell can be a mammalian cell or derived from a mammalian cell. A cell can be a rodent cell or derived from a rodent cell. A cell can be a human cell or derived from a human cell. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a pluripotent stem cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a microbe cell or derived from a microbe cell. A cell can be a fungi cell or derived from a fungi cell. A cell can be from a specific organ or tissue.

Non-limiting examples of a cell(s) can include lymphoid cells, such as B cell, T cell (Cytotoxic T cell, Natural Killer T cell, Regulatory T cell, T helper cell), Natural killer cell, cytokine induced killer (CIK) cells; myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffin cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula *densa* cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Leydig cell of testes, Theca interna cell of ovarian follicle, Corpus *luteum* cell of ruptured ovarian follicle, Granulosa lutein cells, Theca lutein cells, Juxtaglomerular cell (renin secretion), Macula *densa* cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

In some embodiments of any one of the methods disclosed herein, the condition can be a cancer or tumor. Non-limiting examples of such condition can include Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, and Wilms' tumor.

In accordance with various embodiments, numerous types of neoplasms can be detected, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CIVIL), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

Many embodiments are directed to diagnostic or companion diagnostic scans performed during cancer treatment of an individual. When performing diagnostic scans during treatment, the ability of agent to treat the cancer growth can be monitored. Most anti-cancer therapeutic agents result in death and necrosis of neoplastic cells, which should release higher amounts nucleic acids from these cells into the samples being tested. Accordingly, the level of circulating-tumor nucleic acids can be monitored over time, as the level should increase during early treatments and begin to decrease as the number of cancerous cells are decreased. In some embodiments, treatments are adjusted based on the treatment effect on cancer cells. For instance, if the treatment isn't cytotoxic to neoplastic cells, a dosage amount may be increased or an agent with higher cytotoxicity can be administered. In the alternative, if cytotoxicity of cancer cells is good but unwanted side effects are high, a dosage amount can be decreased or an agent with less side effects can be administered.

Various embodiments are also directed to diagnostic scans performed after treatment of an individual to detect residual disease and/or recurrence of cancer. If a diagnostic scan indicates residual and/or recurrence of cancer, further diagnostic tests and/or treatments may be performed as described herein. If the cancer and/or individual is susceptible to recurrence, diagnostic scans can be performed frequently to monitor any potential relapse.

F. Computer Systems

In one aspect, the present disclosure provides a computer program product comprising a non-transitory computer-readable medium having computer-executable code encoded therein, the computer-executable code adapted to be executed to implement any one of the preceding methods.

The present disclosure provides computer systems that are programmed to implement methods of the disclosure. The system can, in some cases, include components such as a processor, an input module for inputting sequencing data or data derived therefrom, a computer-readable medium containing instructions that, when executed by the processor, perform an algorithm on the input regarding one or more cell-free nucleic acids molecules, and an output module providing one or more indicia associated with the condition.

Figure 27:
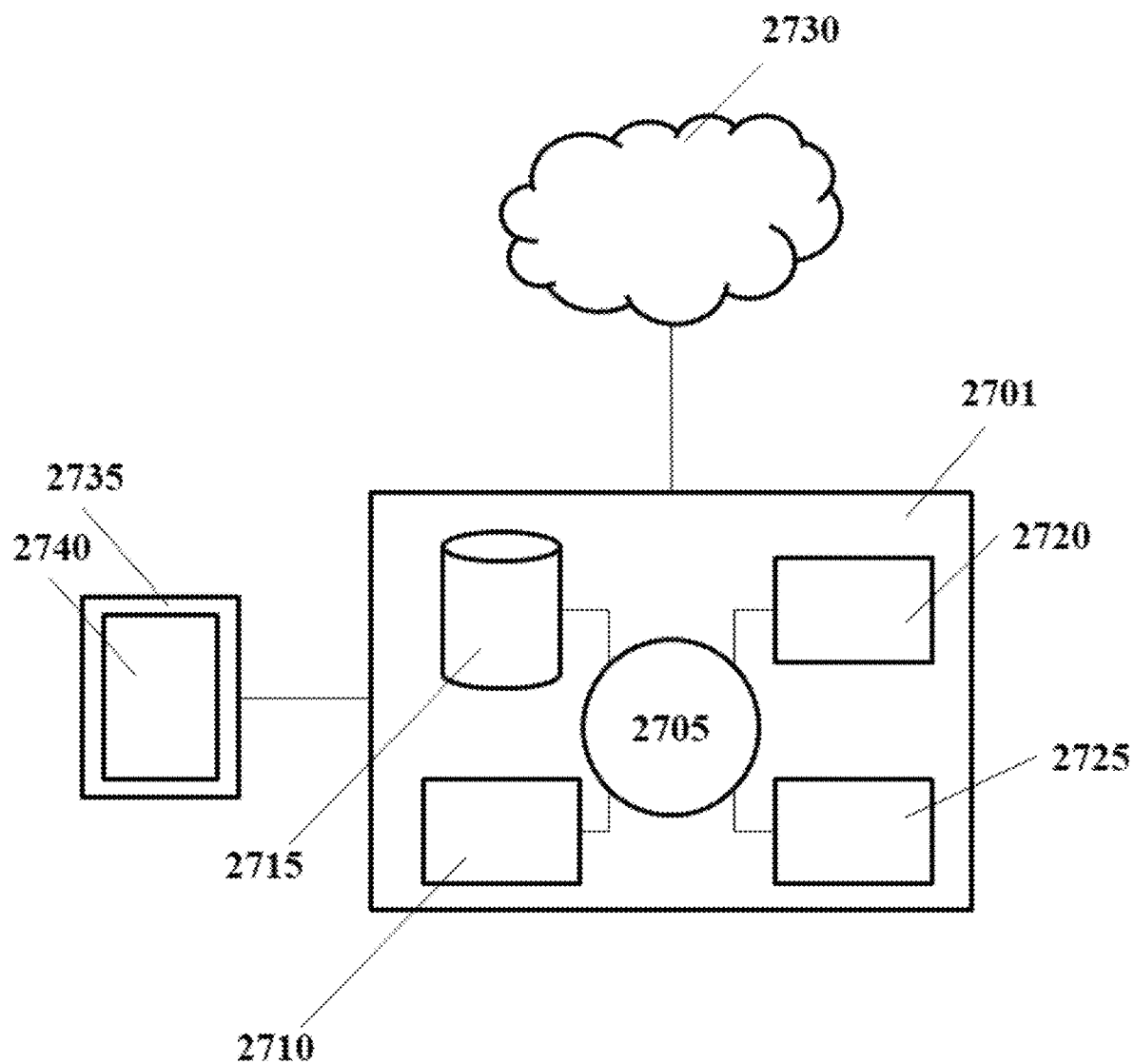
FIG. 27 shows a computer system that is programmed or otherwise configured to implement methods provided herein.

FIG. 27 shows a computer system 2701 that is programmed or otherwise configured to implement partial or all of the methods disclosed herein. The computer system 2701 can regulate various aspects of the present disclosure, such as, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules. The computer system 2701 can be an electronic device of a user or a computer system that is remotely located with respect to the electronic device. The electronic device can be a mobile electronic device.

The computer system 2701 includes a central processing unit (CPU, also "processor" and "computer processor" herein) 2705, which can be a single core or multi core processor, or a plurality of processors for parallel processing. The computer system 2701 also includes memory or memory location 2710 (e.g., random-access memory, read-only memory, flash memory), electronic storage unit 2715

(e.g., hard disk), communication interface 2720 (e.g., network adapter) for communicating with one or more other systems, and peripheral devices 2725, such as cache, other memory, data storage and/or electronic display adapters. The memory 2710, storage unit 2715, interface 2720 and peripheral devices 2725 are in communication with the CPU 2705 through a communication bus (solid lines), such as a motherboard. The storage unit 2715 can be a data storage unit (or data repository) for storing data. The computer system 2701 can be operatively coupled to a computer network ("network") 2730 with the aid of the communication interface 2720. The network 2730 can be the Internet, an internet and/or extranet, or an intranet and/or extranet that is in communication with the Internet. The network 2730 in some cases is a telecommunication and/or data network. The network 2730 can include one or more computer servers, which can enable distributed computing, such as cloud computing. The network 2730, in some cases with the aid of the computer system 2701, can implement a peer-to-peer network, which may enable devices coupled to the computer system 2701 to behave as a client or a server.

The CPU 2705 can execute a sequence of machine-readable instructions, which can be embodied in a program or software. The instructions may be stored in a memory location, such as the memory 2710. The instructions can be directed to the CPU 2705, which can subsequently program or otherwise configure the CPU 2705 to implement methods of the present disclosure. Examples of operations performed by the CPU 2705 can include fetch, decode, execute, and writeback.

The CPU 2705 can be part of a circuit, such as an integrated circuit. One or more other components of the system 2701 can be included in the circuit. In some cases, the circuit is an application specific integrated circuit (ASIC).

The storage unit 2715 can store files, such as drivers, libraries and saved programs. The storage unit 2715 can store user data, e.g., user preferences and user programs. The computer system 2701 in some cases can include one or more additional data storage units that are external to the computer system 2701, such as located on a remote server that is in communication with the computer system 2701 through an intranet or the Internet.

The computer system 2701 can communicate with one or more remote computer systems through the network 2730. For instance, the computer system 2701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2701 via the network 2730.

Methods as described herein can be implemented by way of machine (e.g., computer processor) executable code stored on an electronic storage location of the computer system 2701, such as, for example, on the memory 2710 or electronic storage unit 2715. The machine executable or machine readable code can be provided in the form of software. During use, the code can be executed by the processor 2705. In some cases, the code can be retrieved from the storage unit 2715 and stored on the memory 2710 for ready access by the processor 2705. In some situations, the electronic storage unit 2715 can be precluded, and machine-executable instructions are stored on memory 2710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2701 can include or be in communication with an electronic display 2735 that comprises a user interface (UI) 2740 for providing, for example, (i) analysis of any of the identified cell-free nucleic acid molecules, (ii) a determined condition of the subject based at least in part on the identified cell-free nucleic acid molecules, (iii) a determined progress of the condition of the subject based at least in part on the identified cell-free nucleic acid molecules, (iv) the identified subject suspected of having the condition based at least in part on the identified cell-free nucleic acid molecules, or (v) a determined treatment of the condition of the subject based at least in part on the identified cell-free nucleic acid molecules. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2705. The algorithm can, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules.

EXAMPLES

The following illustrative examples are representative of embodiments of the stimulation, systems, and methods described herein and are not meant to be limiting in any way.

Example 1: Genomic Distribution of Phased Variants

Described is an alternative to duplex sequencing for reducing the background error rate that involves detection of 'phased variants' (PVs), where two or more mutations occur in cis (i.e., on the same strand of DNA FIG. 1A and FIG. 1E). Similar to duplex sequencing, this method provides lower error profiles due to the concordant detection of two separate non-reference events in individual molecules. However, unlike duplex sequencing, both events occur on the same sequencing read-pair, thereby increasing the efficiency of genome recovery. Phased mutations are present in diverse cancer types, but occur in stereotyped portions of the genome in B-cell malignancies, likely due to on-target and aberrant somatic hypermutation (aSHM) driven by activation-induced deaminase (AID). The most common regions of aSHM in B-cell non-Hodgkin lymphomas (NHL) are identified. Described herein is phased variant Enrichment and Detection Sequencing (PhasED-Seq), a novel method to detect ctDNA through phased variants to tumor fractions on the order of parts per million. Described herein is demonstration that PhasED-Seq can meaningfully improve detection of ctDNA in clinical samples both during therapy and prior to disease relapse.

To identify malignancies where PVs may potentially improve disease detection, the frequency of PVs across cancer types were assessed. Publicly available whole-genome sequencing data was analyzed to identify sets of variants occurring at a distance of <170 bp apart, which represents the typical length of a single cfDNA fragment consisting of a single core nucleosome and associated linker. The frequency of these 'putative phased variants,'' (Example 10) controlling for the total number of SNVs, from 2538 tumors across 24 cancer histologies including solid tumors and hematological malignancies (FIG. 1B, FIG. 5, and Table 1) was identified and summarized. PVs were most significantly enriched in two B-cell lymphomas (DLBCL and follicular lymphoma, FL, P<0.05 vs all other histologies), a group of diseases with hypermutation driven by AID/AICDA.

Example 2: Mutational Mechanisms Underlying PVs

Figure 6A:
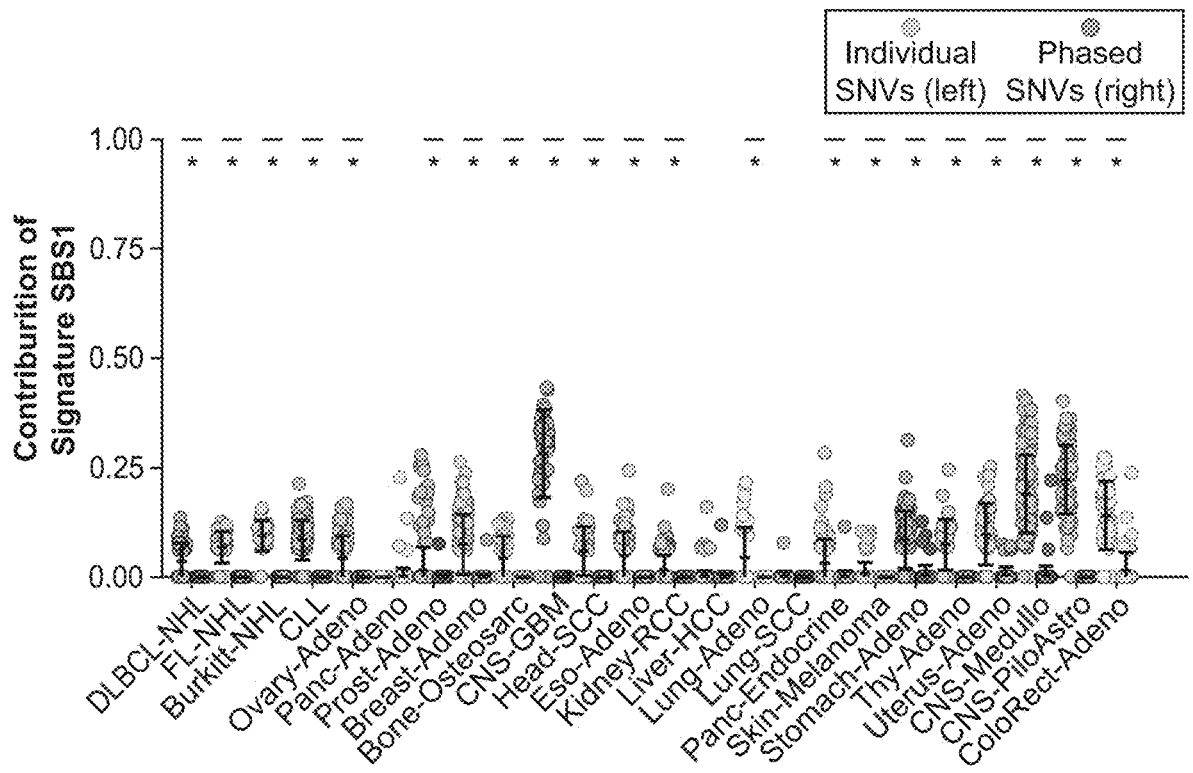
FIGS. 6A-6WW illustrate contribution of mutational signatures in phased and un-phased SNVs in WGS (FIGS. 6A-6WW.) Scatterplots showing the contribution of established single base substitution (SBS) mutational signatures to SNVs seen in PVs, shown in dark colors, and SNVs seen outside of possible phased relationships, shown in light colors, from WGS. This is presented for 49 SBS mutational signatures across 24 subtypes of cancer. Mutational signatures that show a significant difference in contribution between phased and un-phased SNVs after multiple hypothesis testing correction are indicated with a *. These figures represent the raw data summarized in FIG. 1C.
Figure 6B:
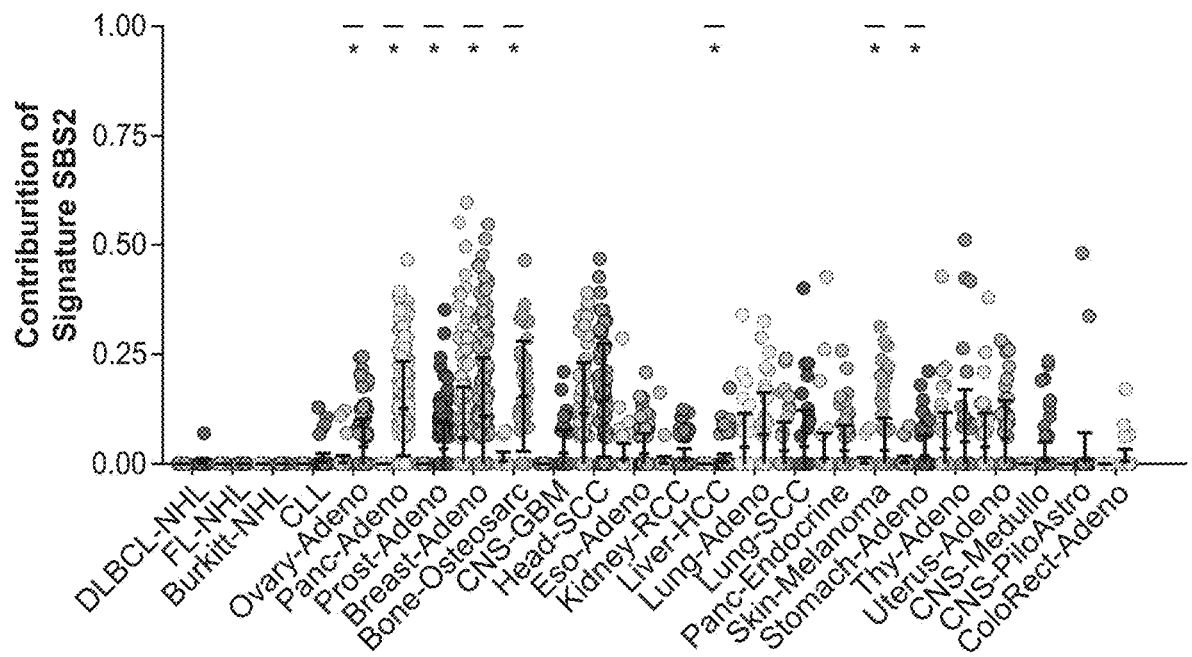
Figure 6C:
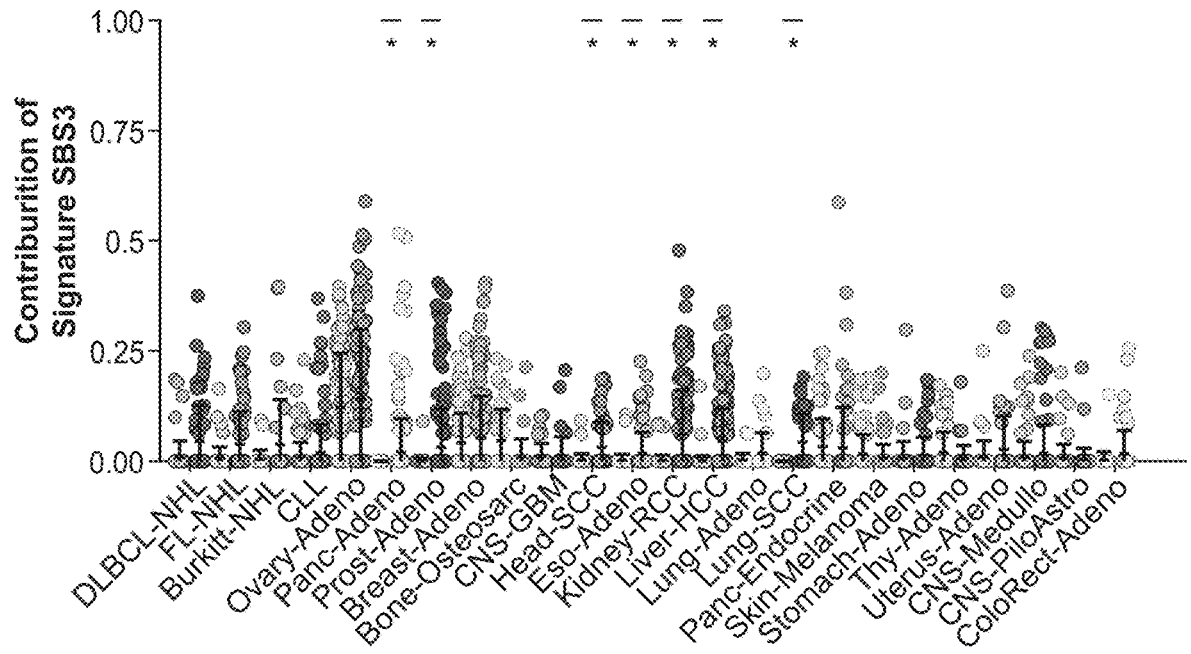
Figure 6D:
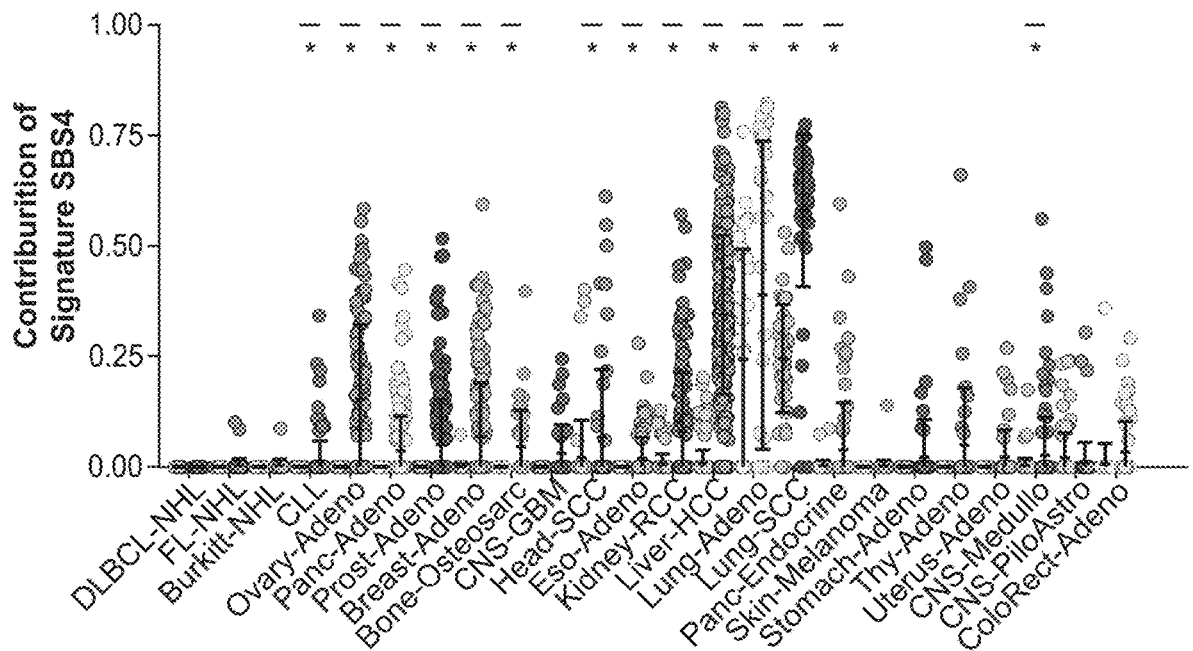
Figure 6E:
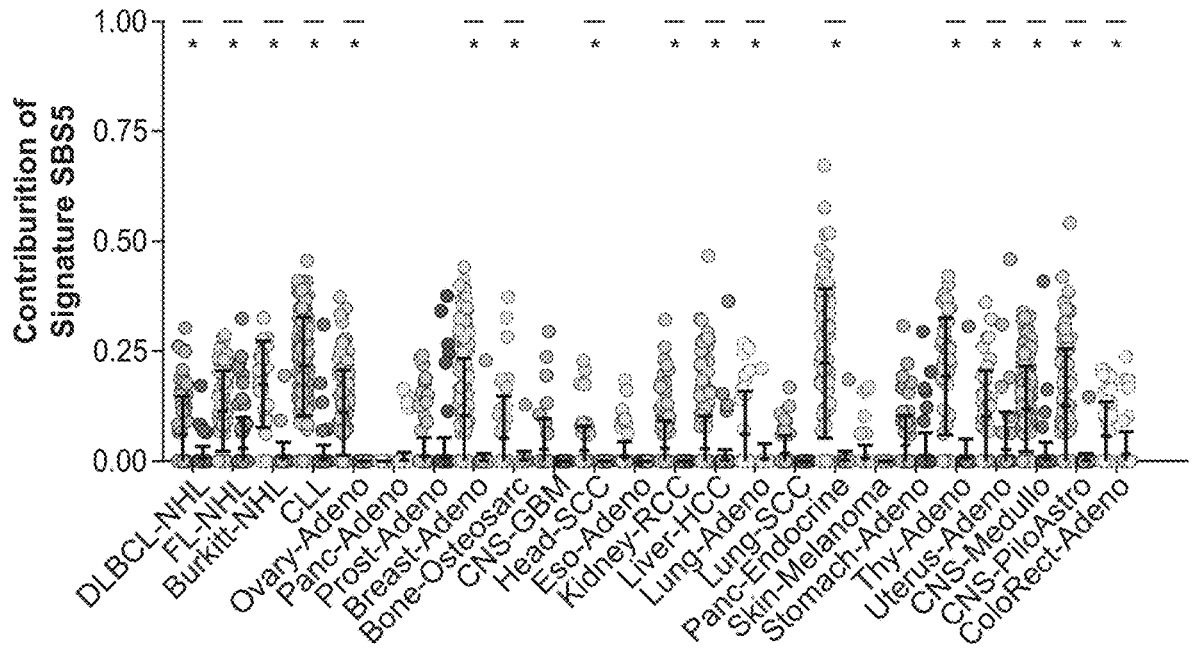
Figure 6F:
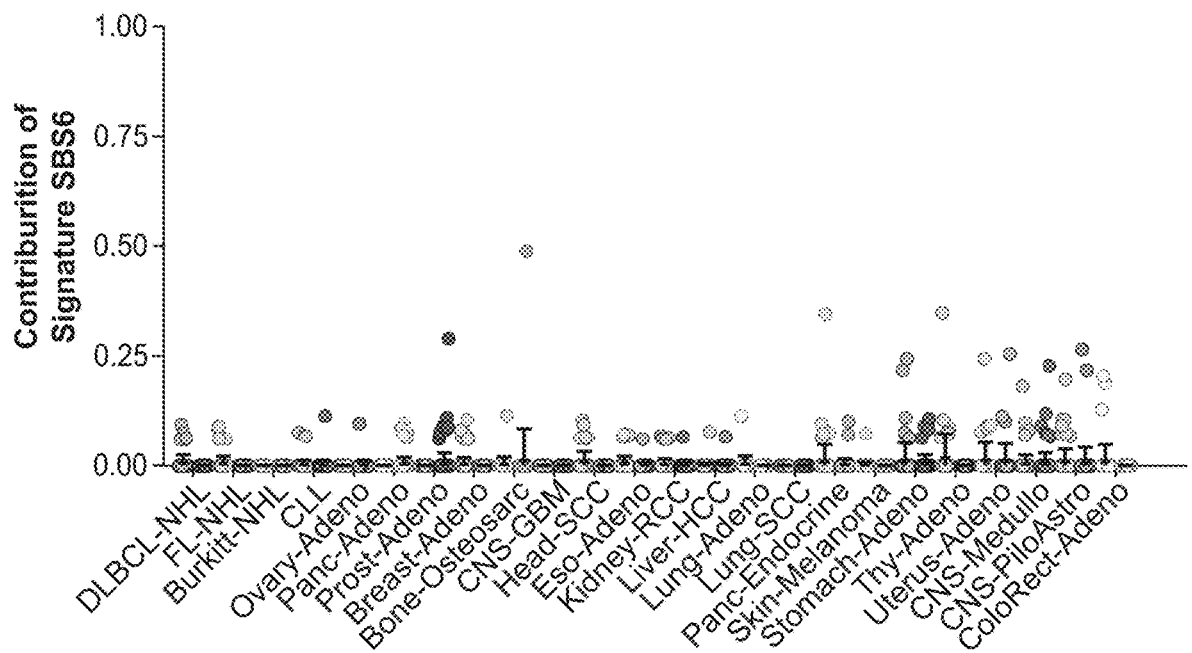
Figure 6G:
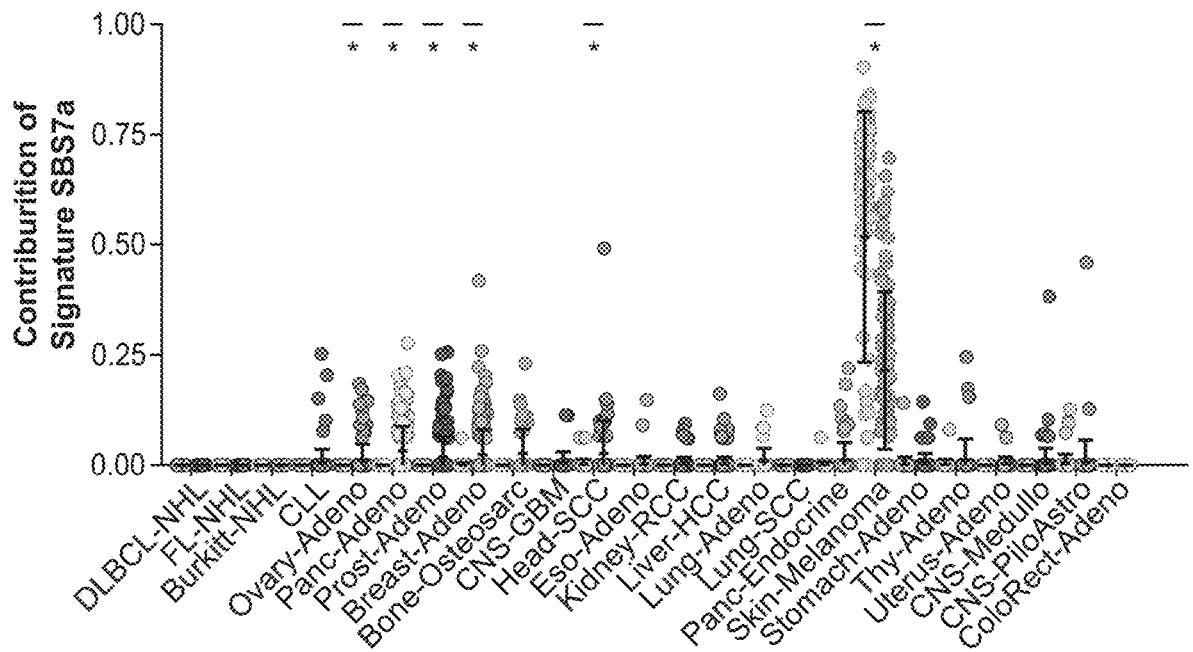
Figure 6H:
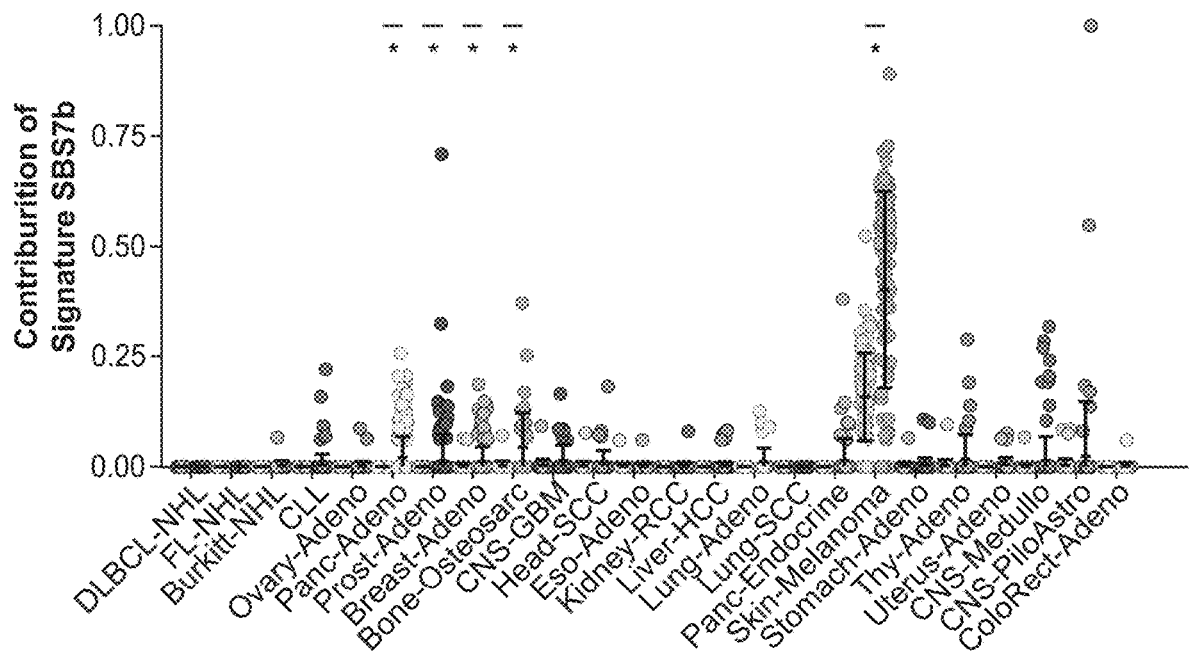
Figure 6I:
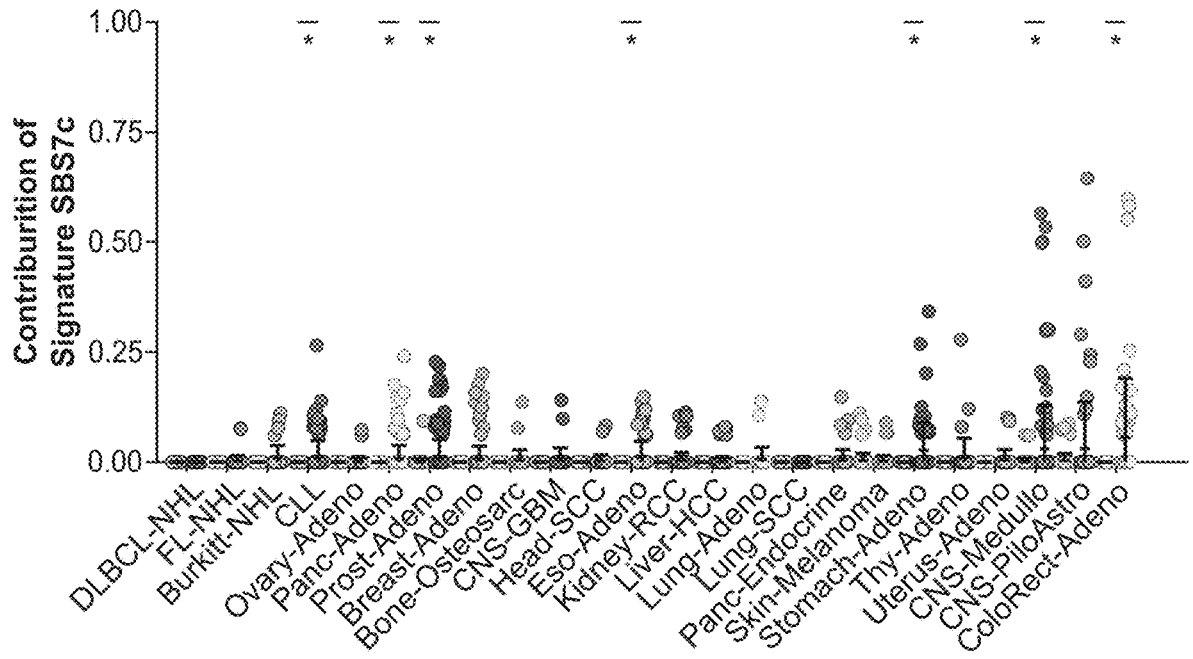
Figure 6J:
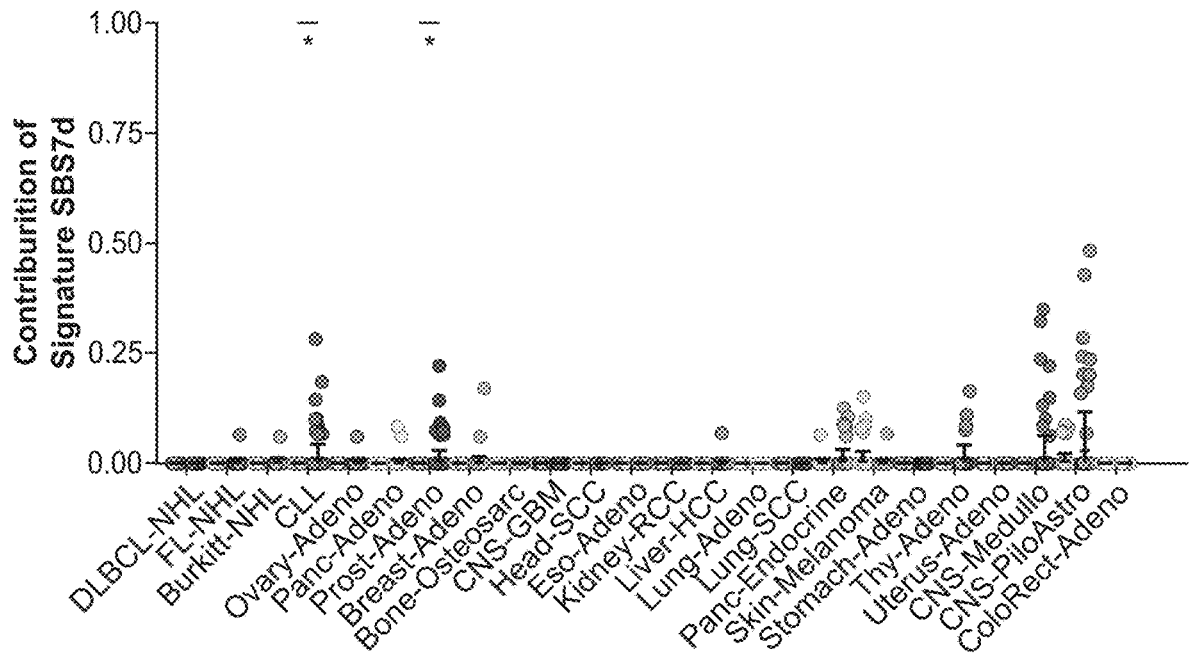
Figure 6K:
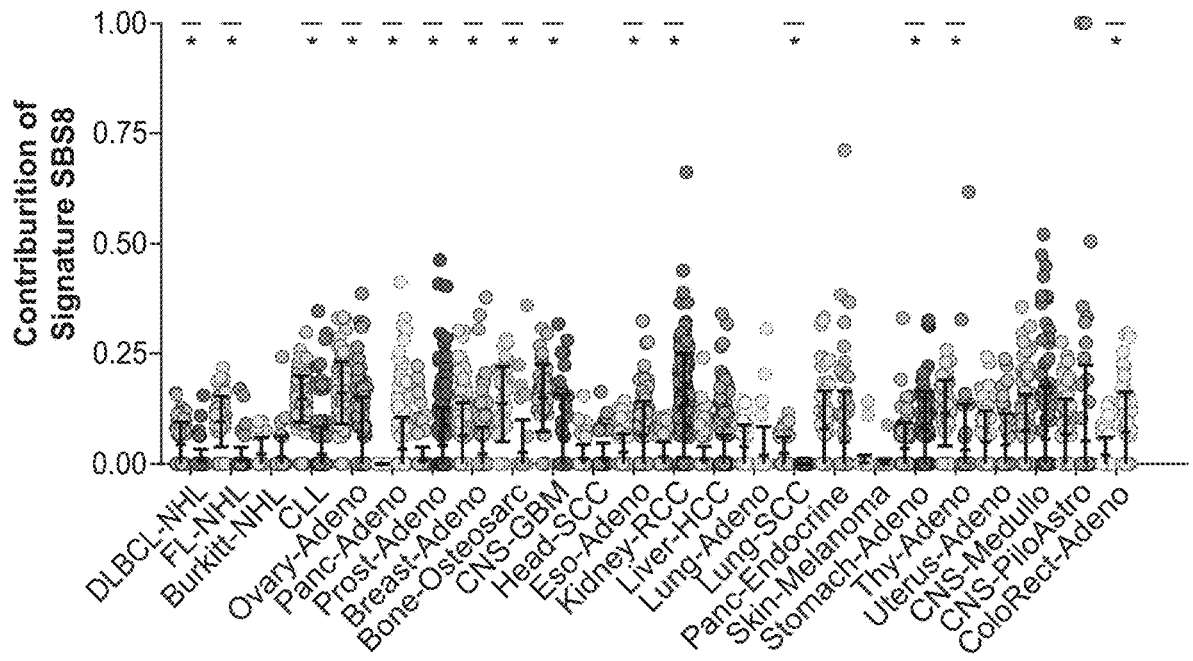
Figure 6L:
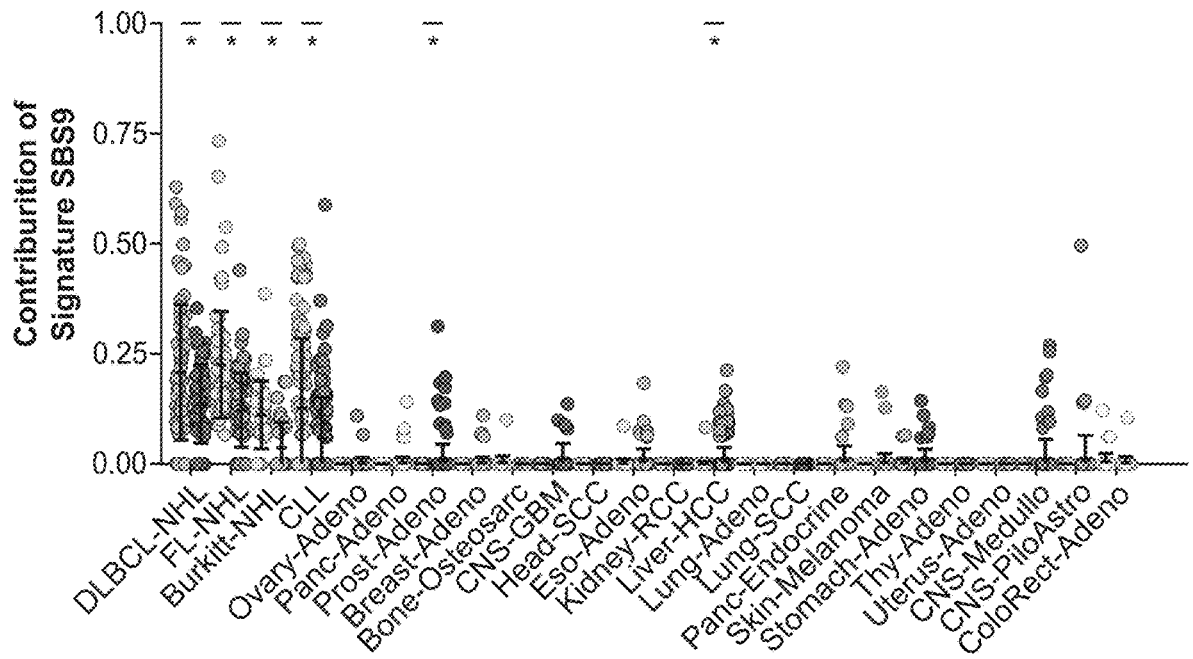
Figure 6M:
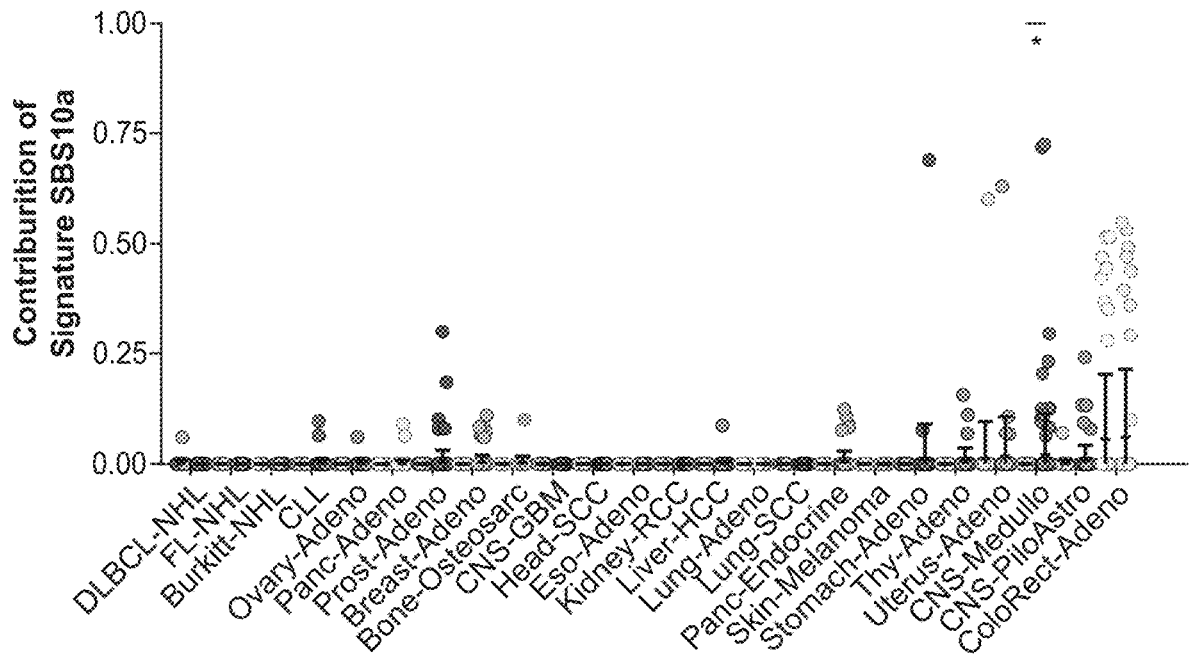
Figure 6N:
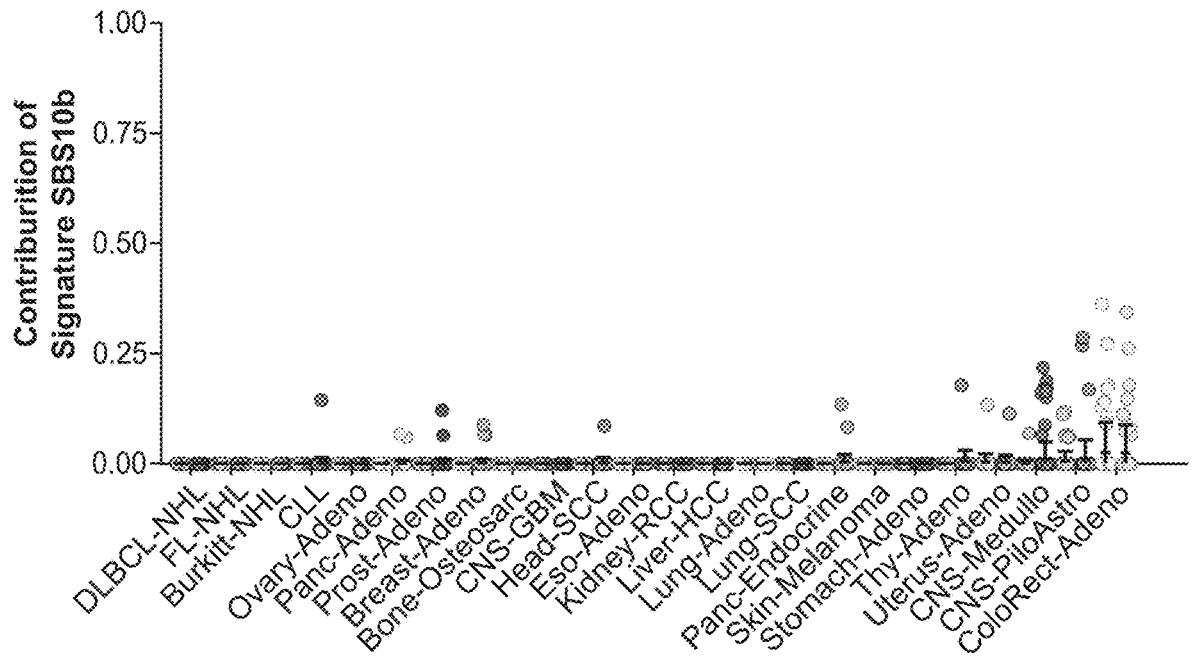
Figure 6O:
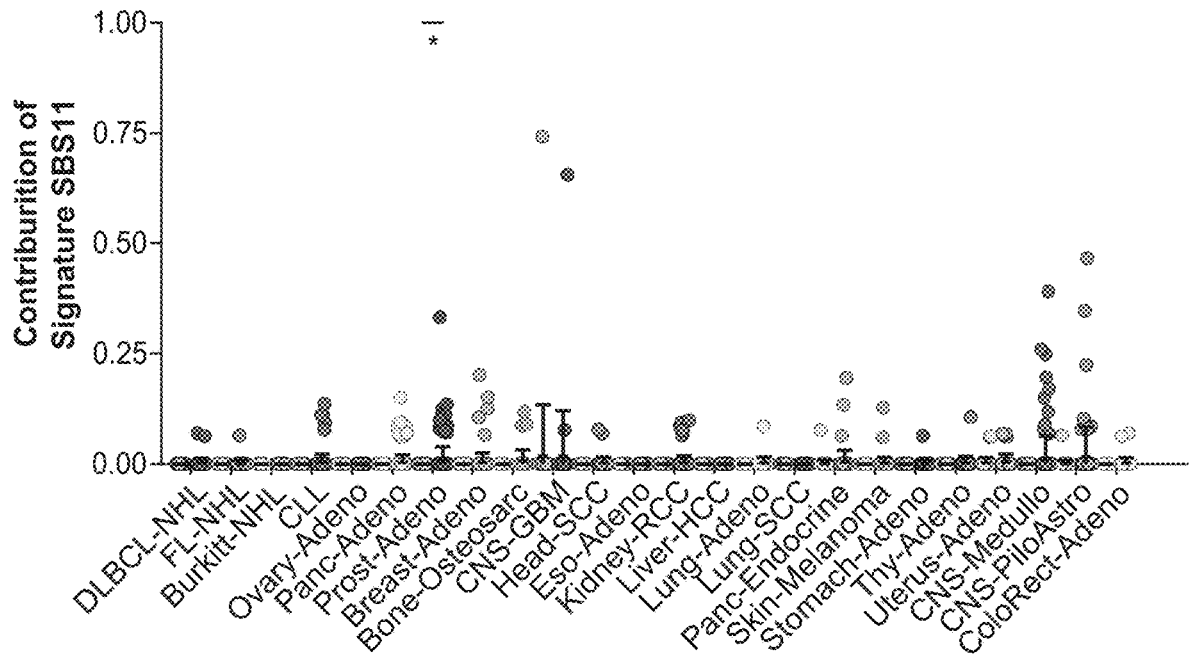
Figure 6P:
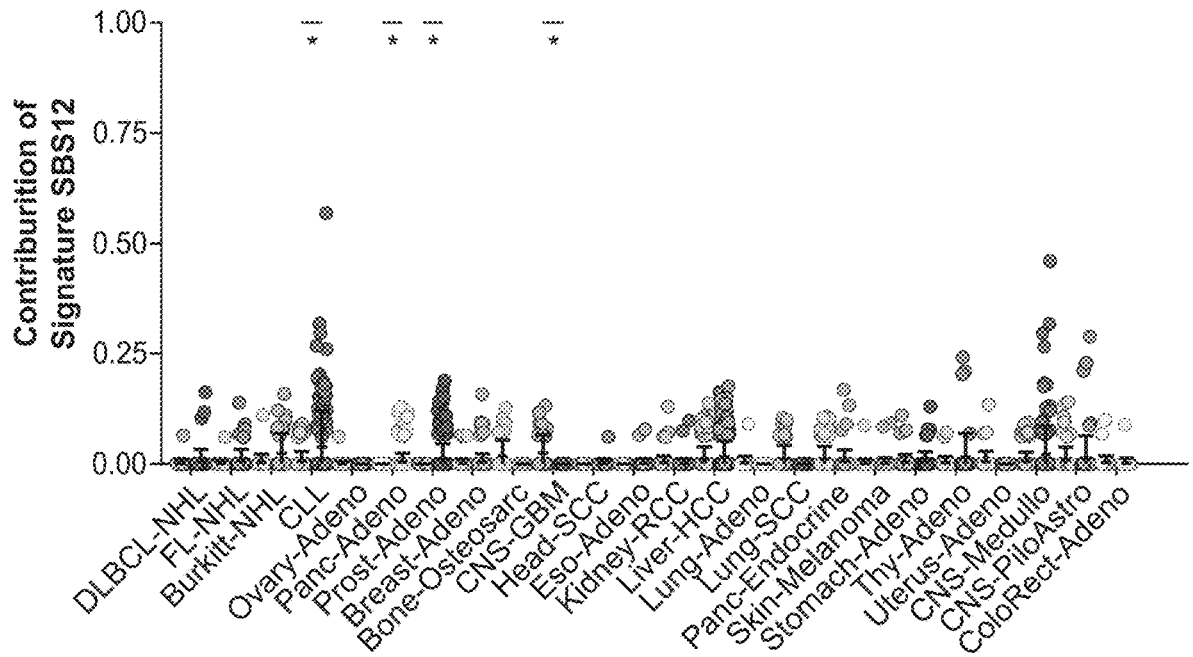
Figure 6Q:
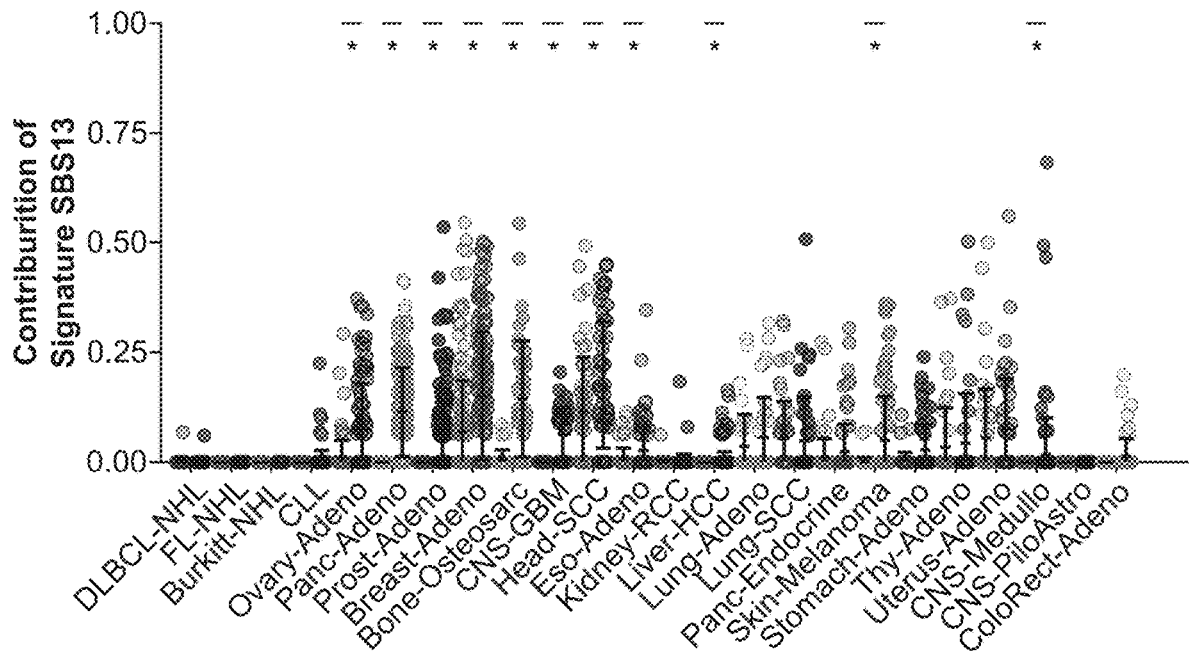
Figure 6R:
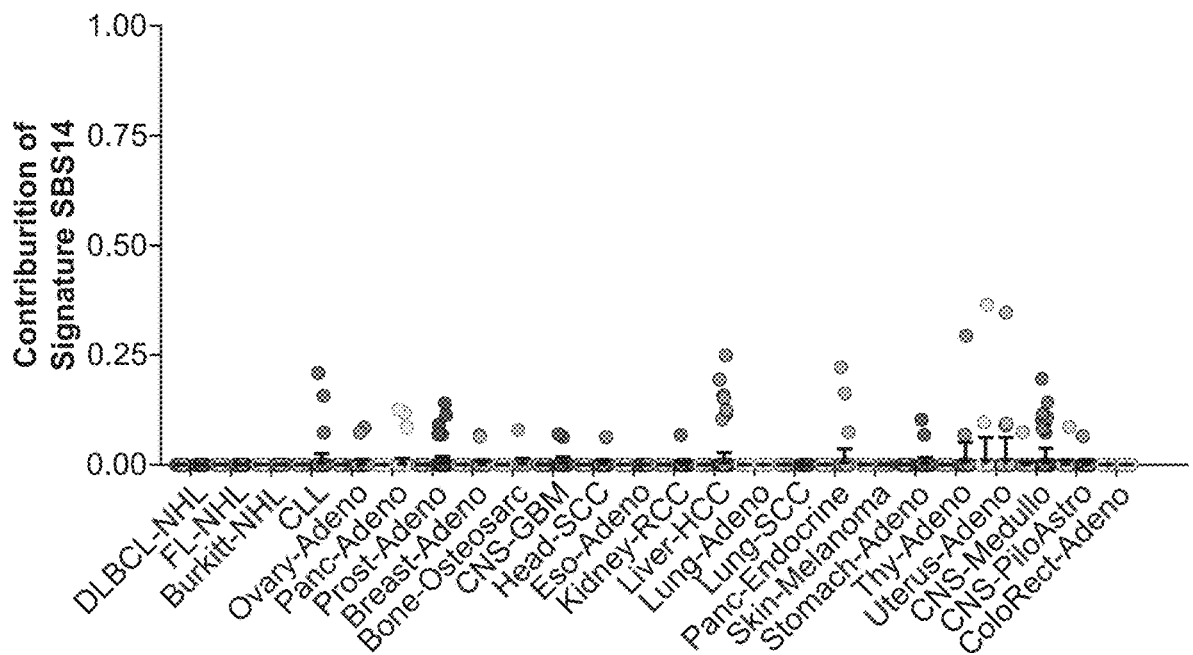
Figure 6S:
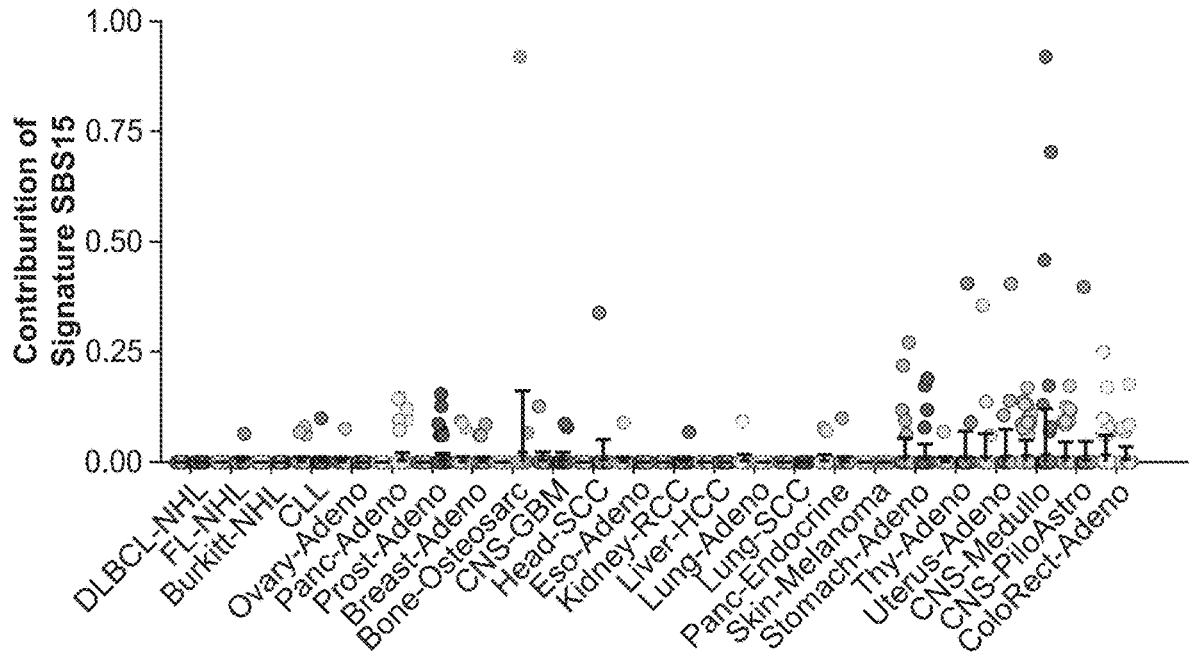
Figure 6T:
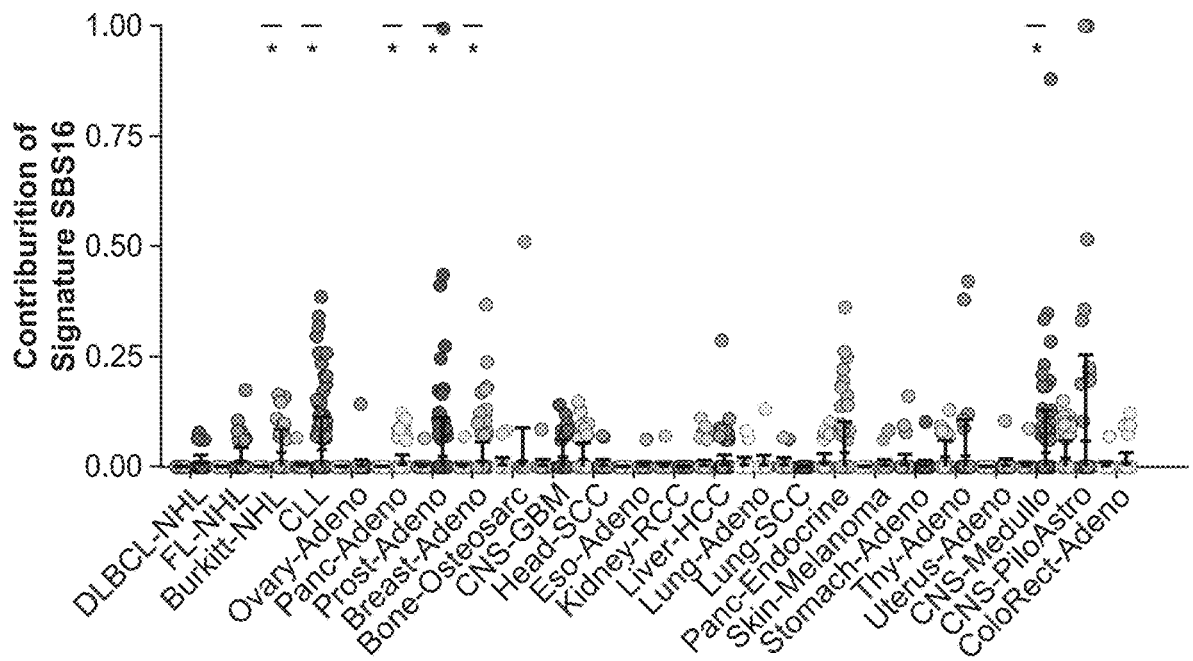
Figure 6U:
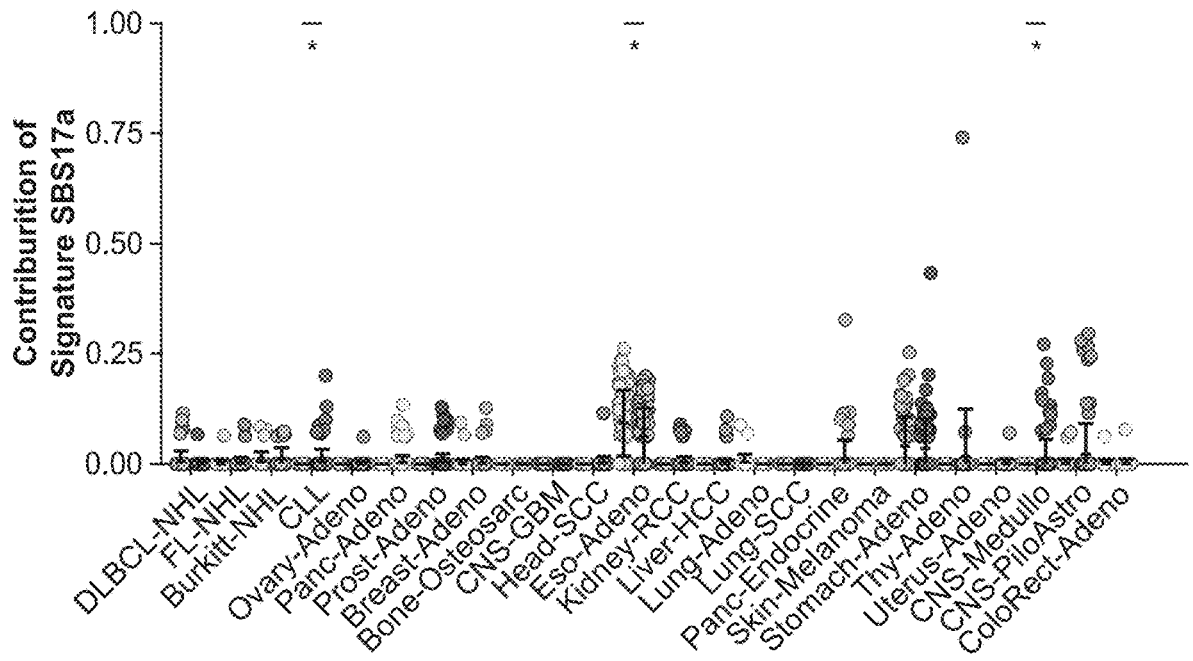
Figure 6V:
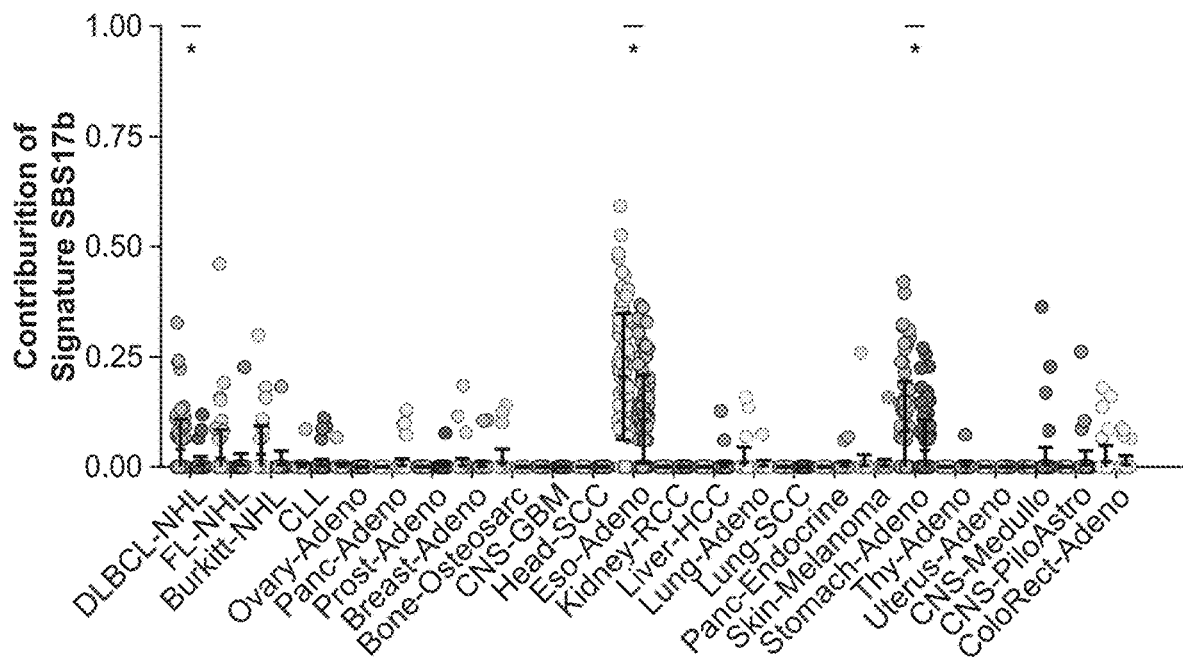
Figure 6W:
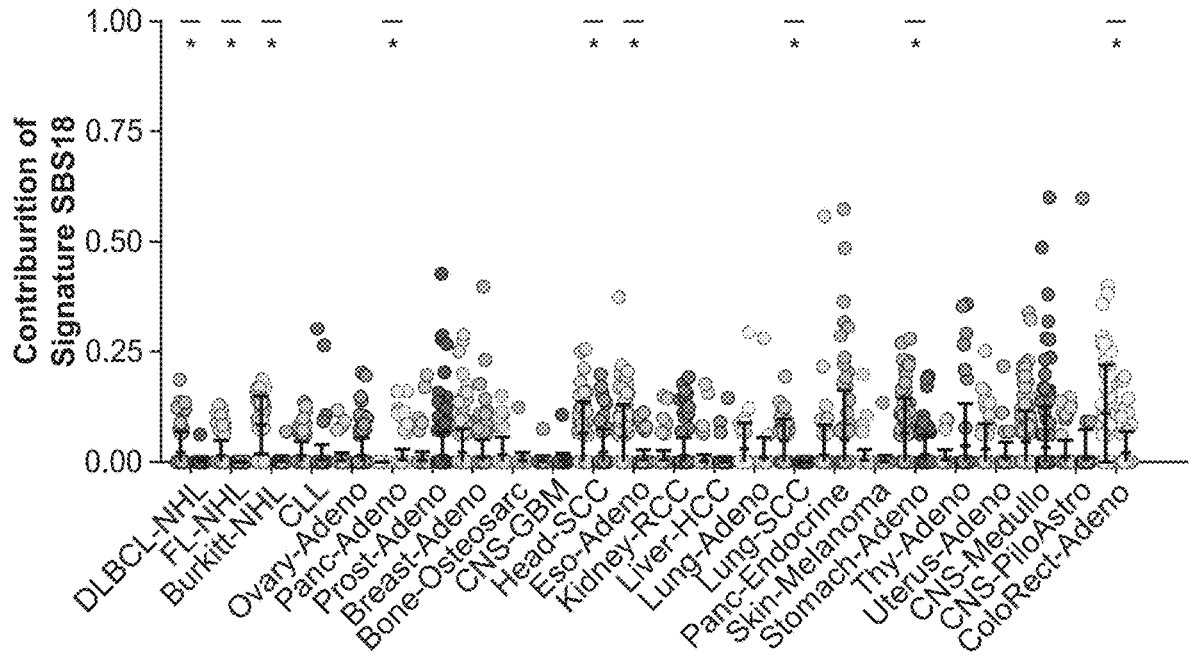
Figure 6X:
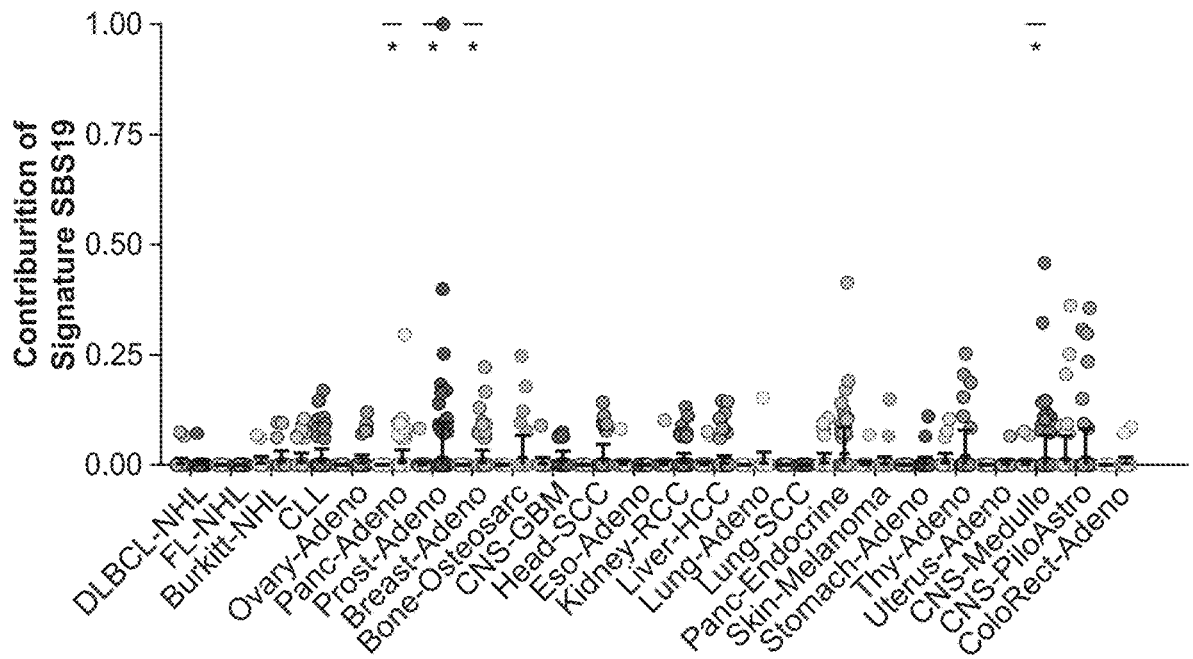
Figure 6Y:
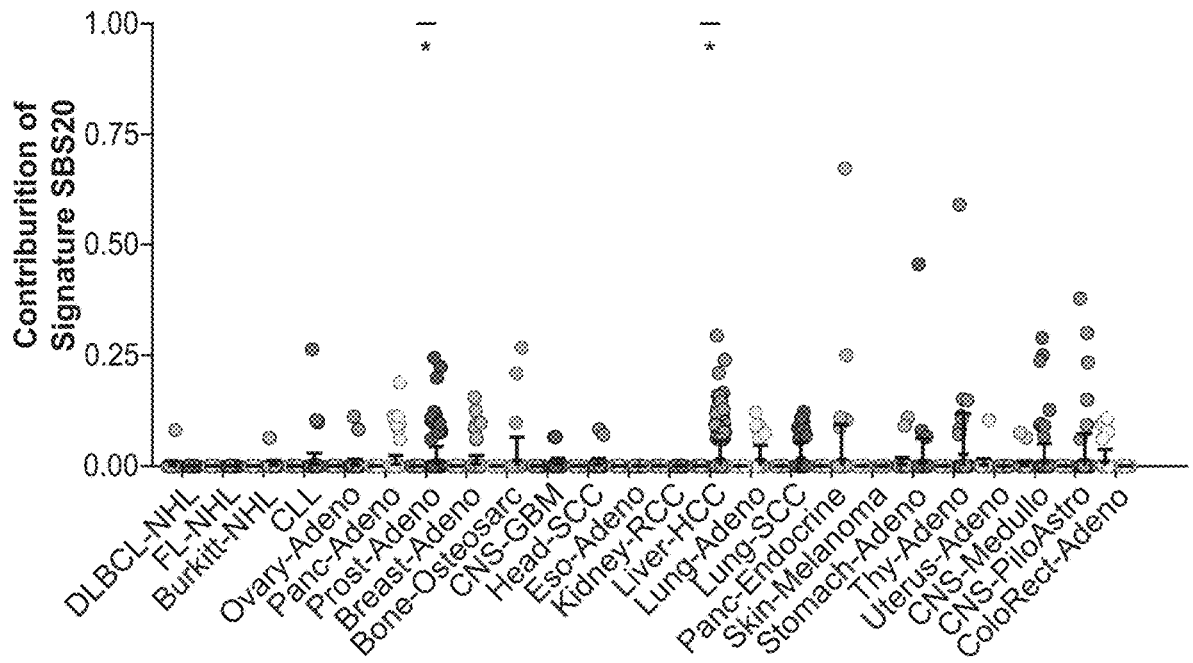
Figure 6Z:
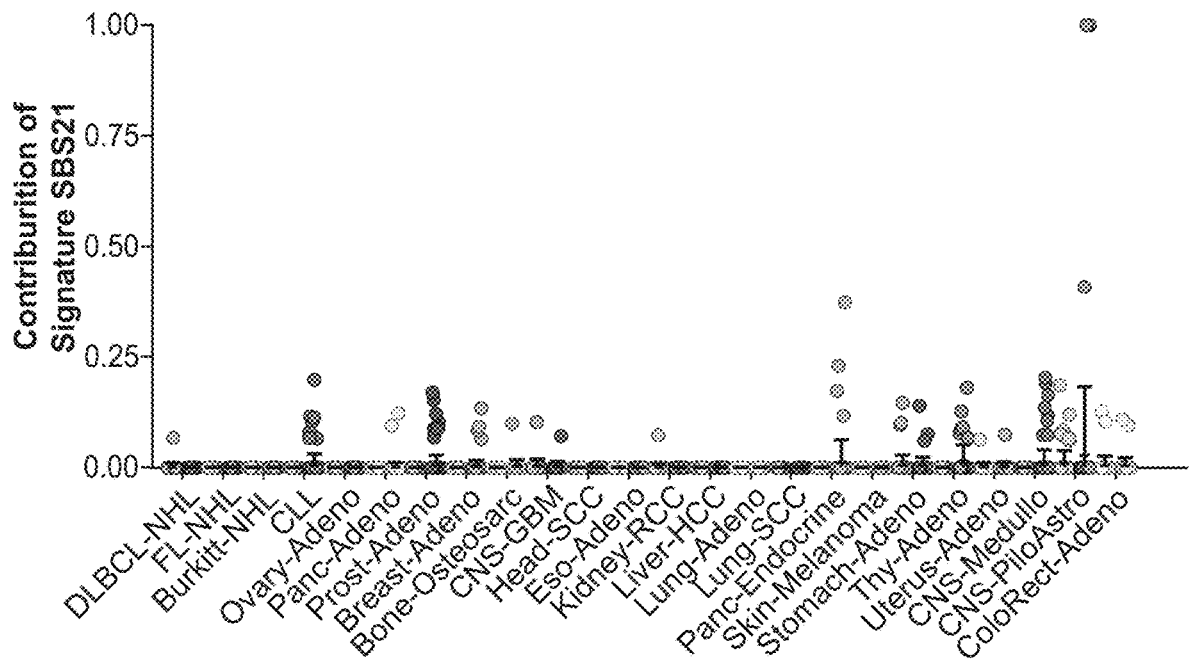
Figure 6A:
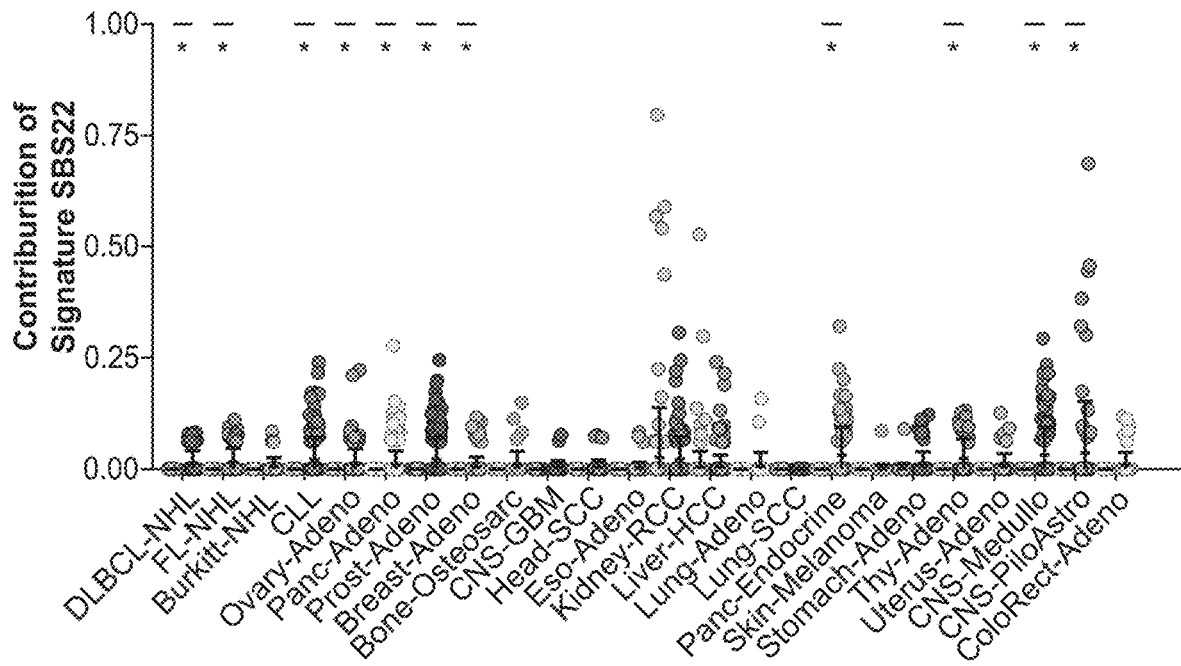
Figure 6B:
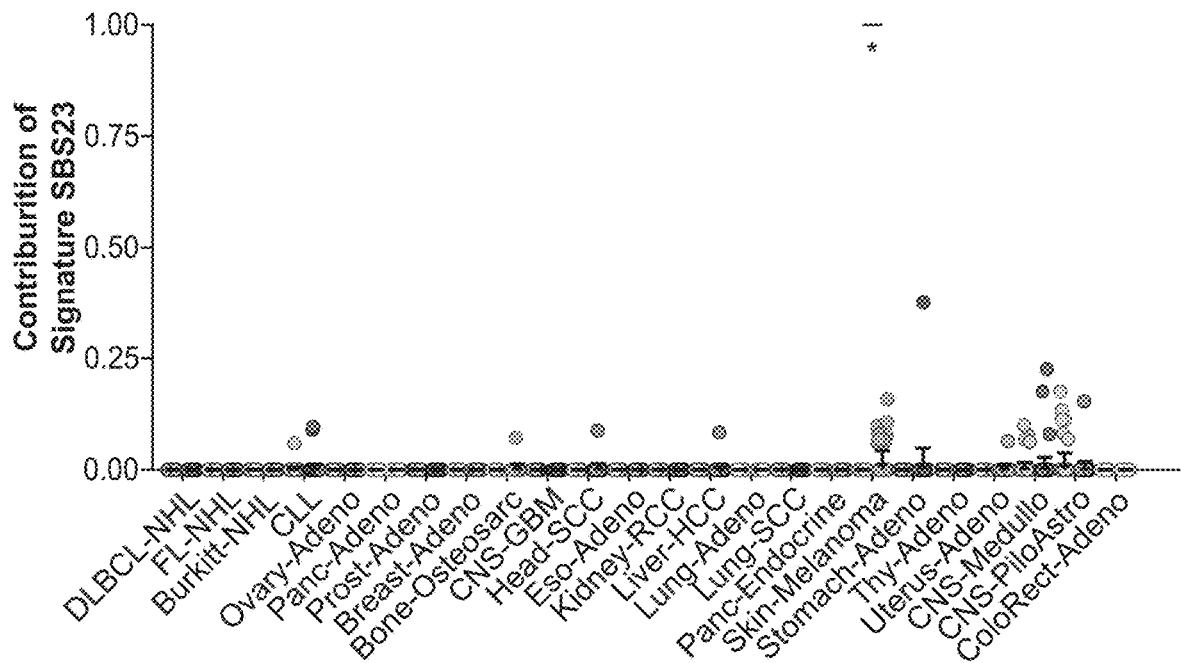
Figure 6C:
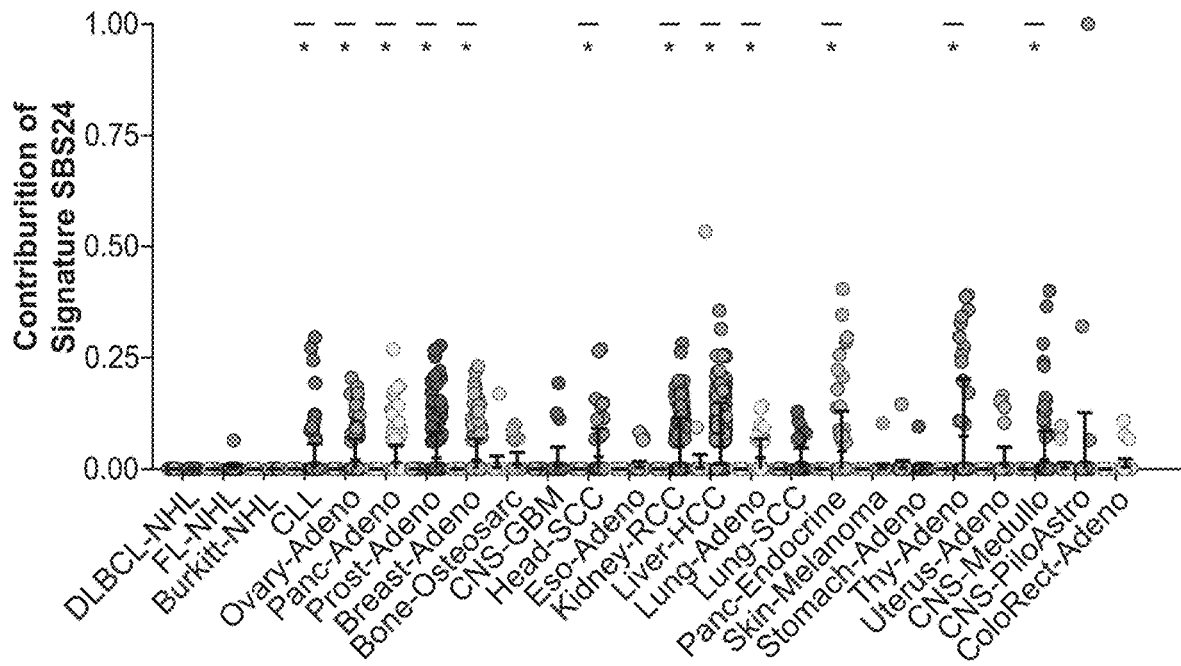
Figure 6D:
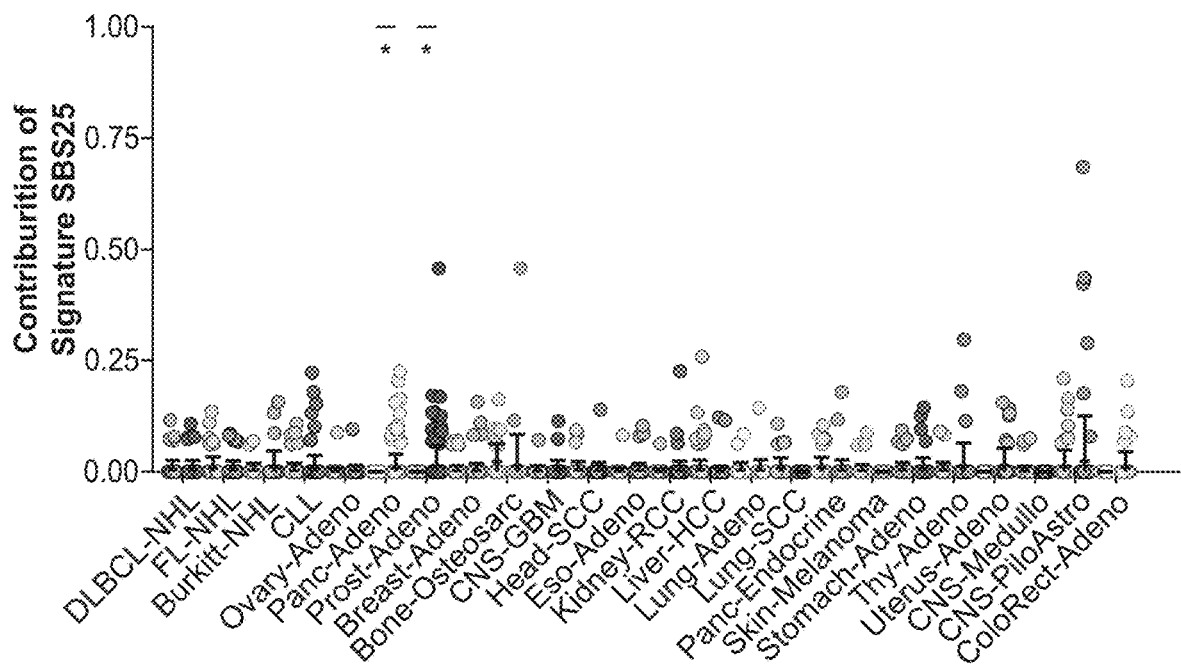
Figure 6E:
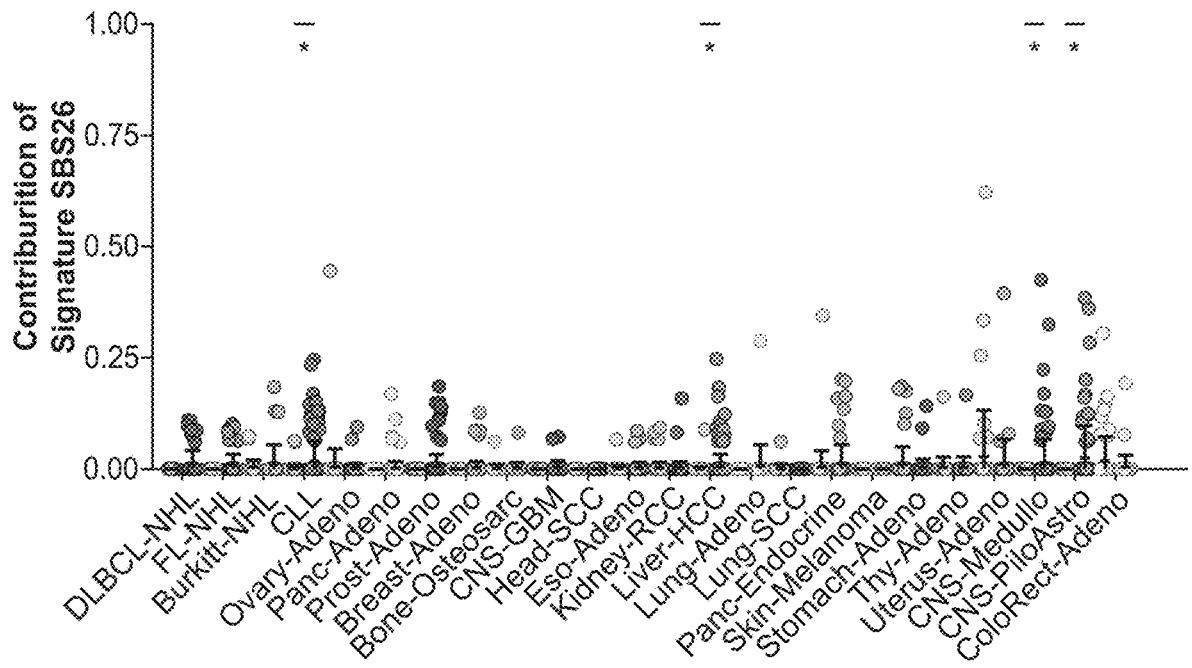
Figure 6F:
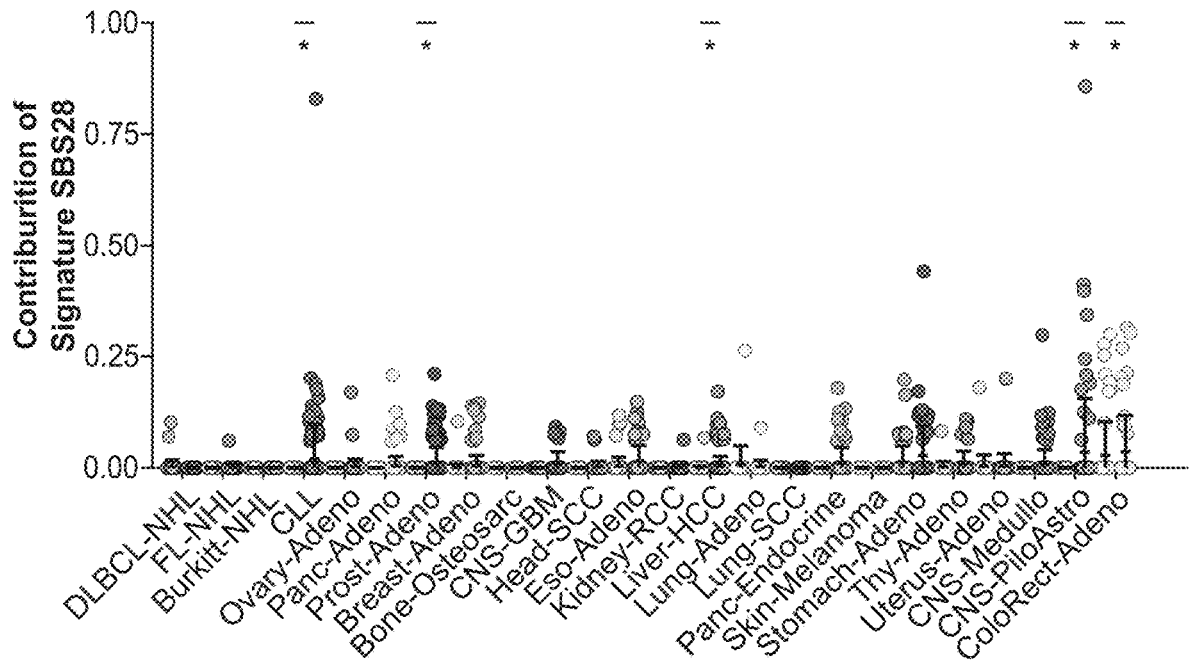
Figure 6G:
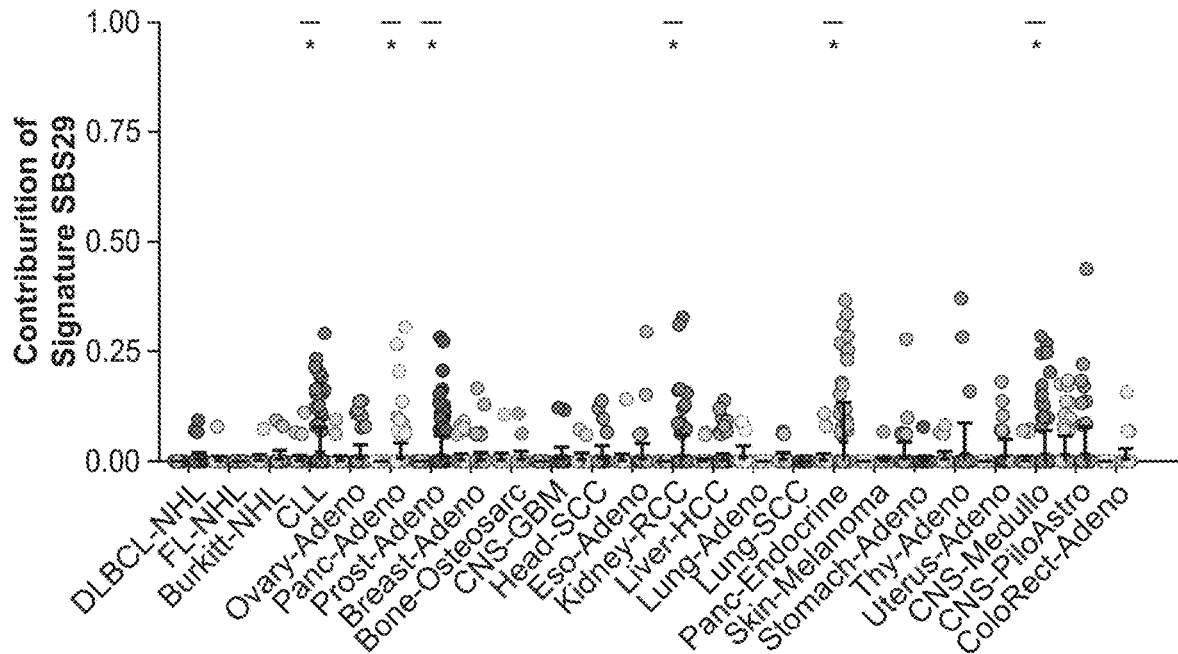
Figure 6H:
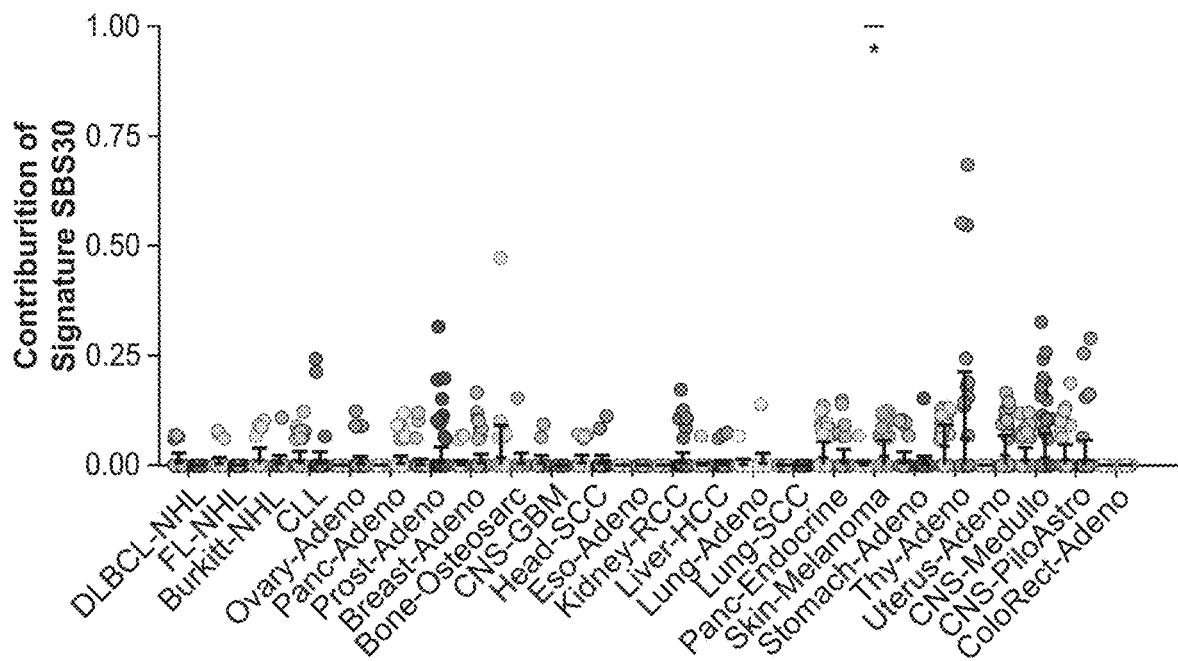
Figure 6I:
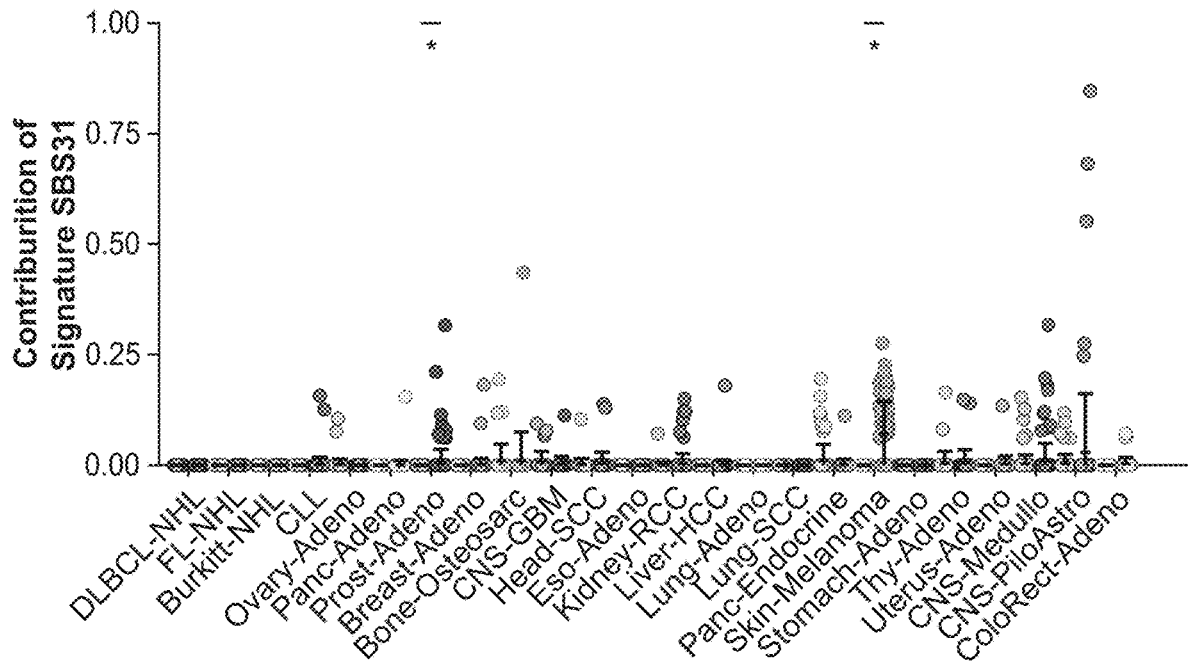
Figure 6J:
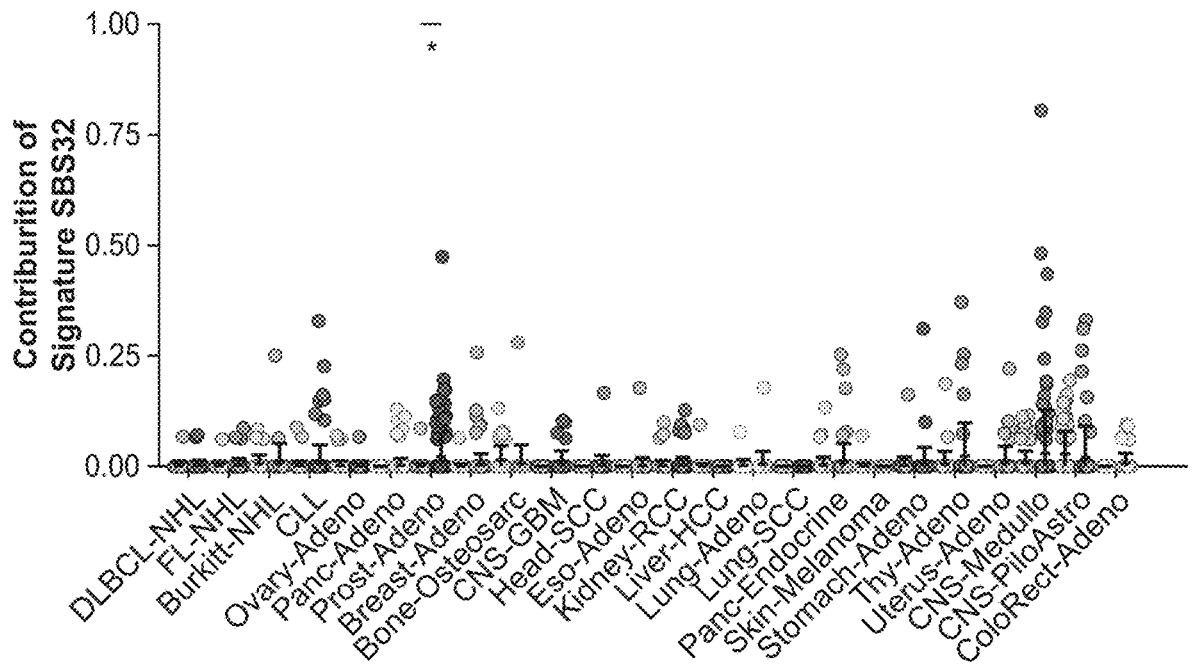
Figure 6K:
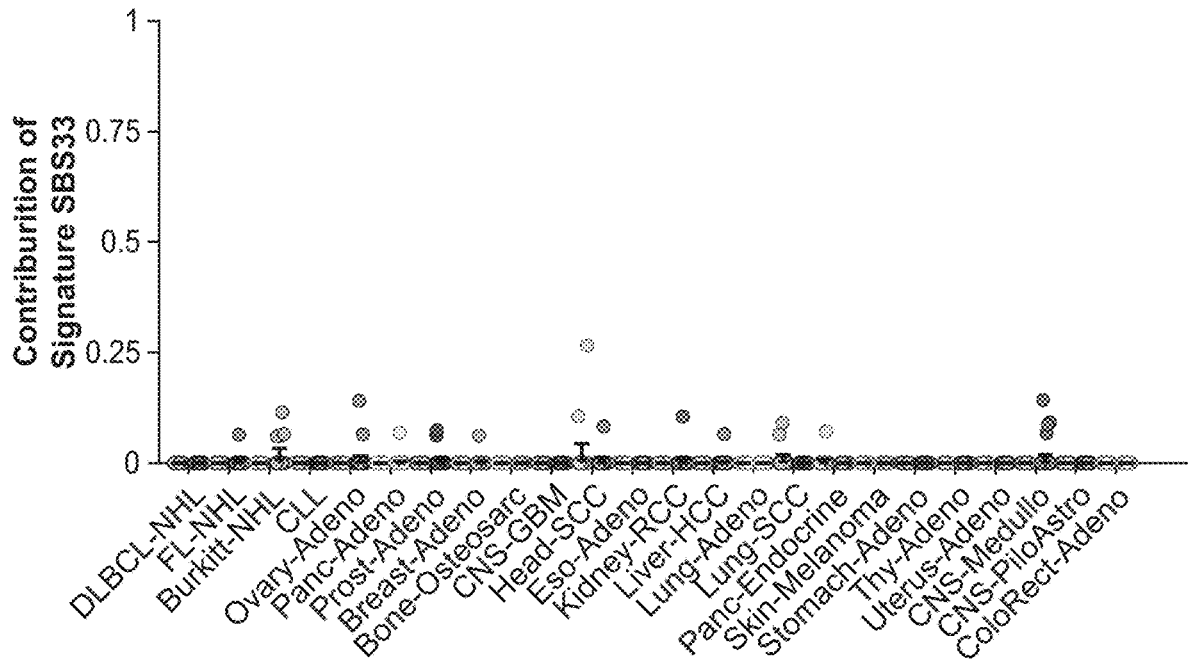
Figure 6L:
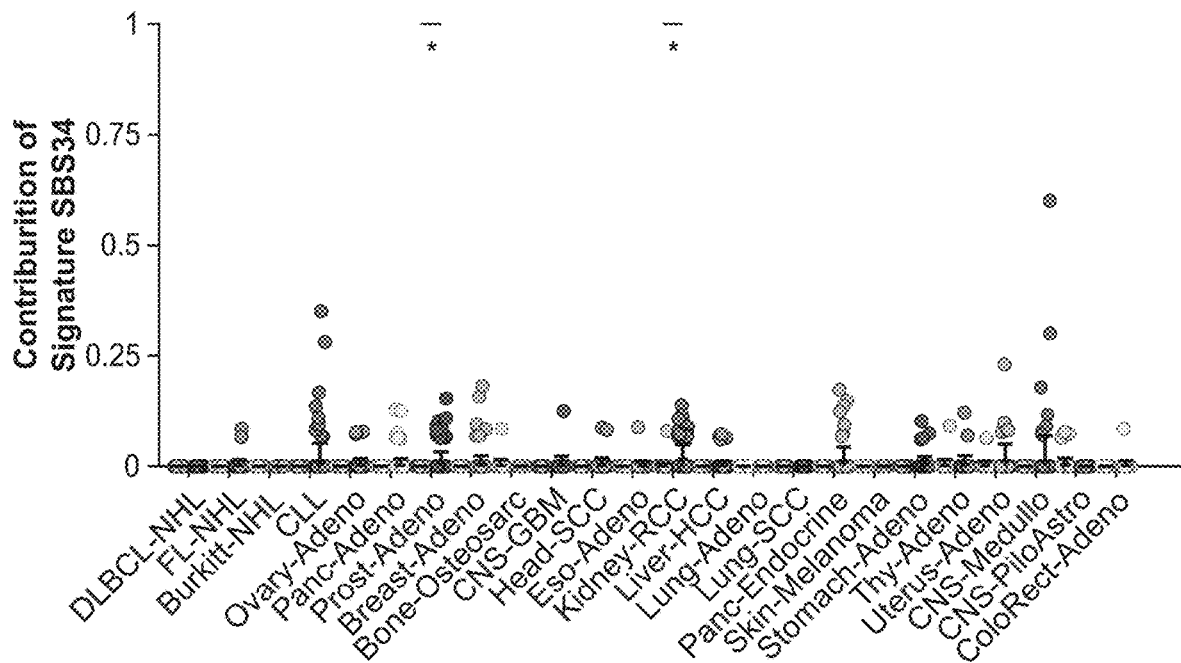
Figure 6M:
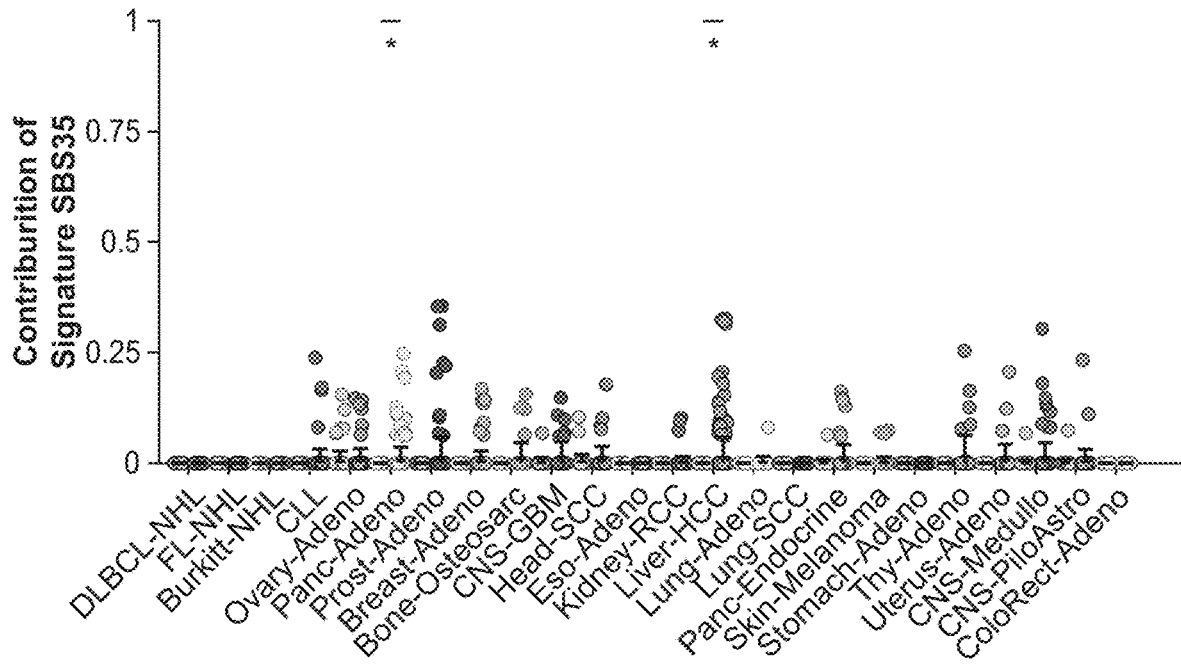
Figure 6N:
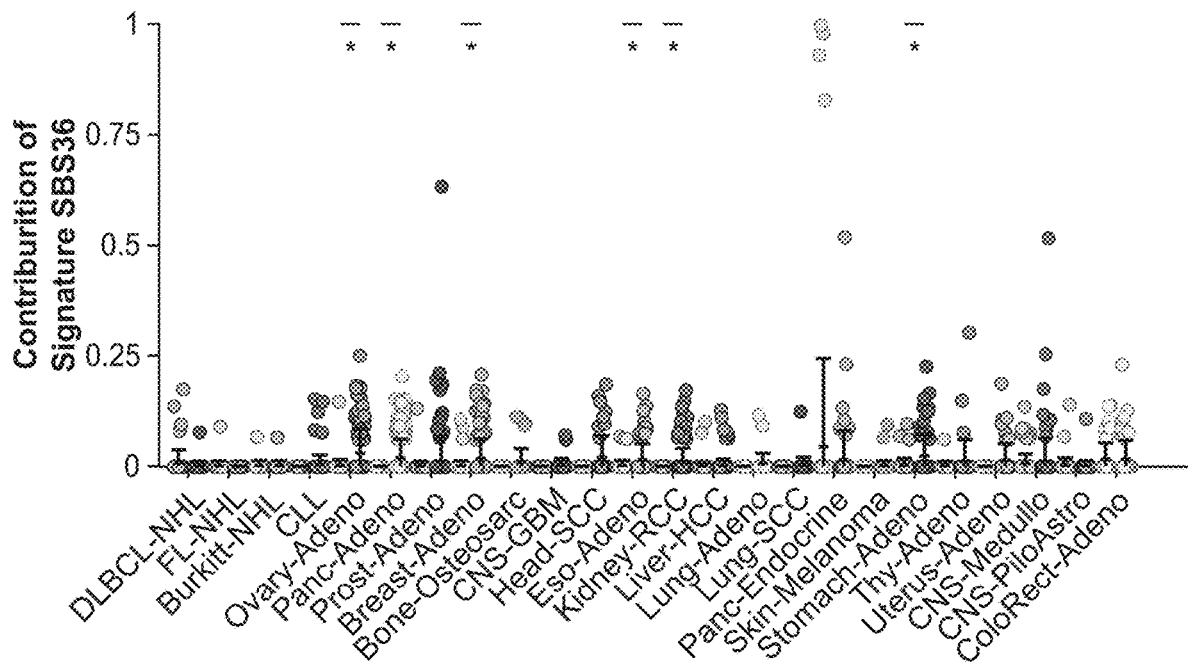
Figure 6O:
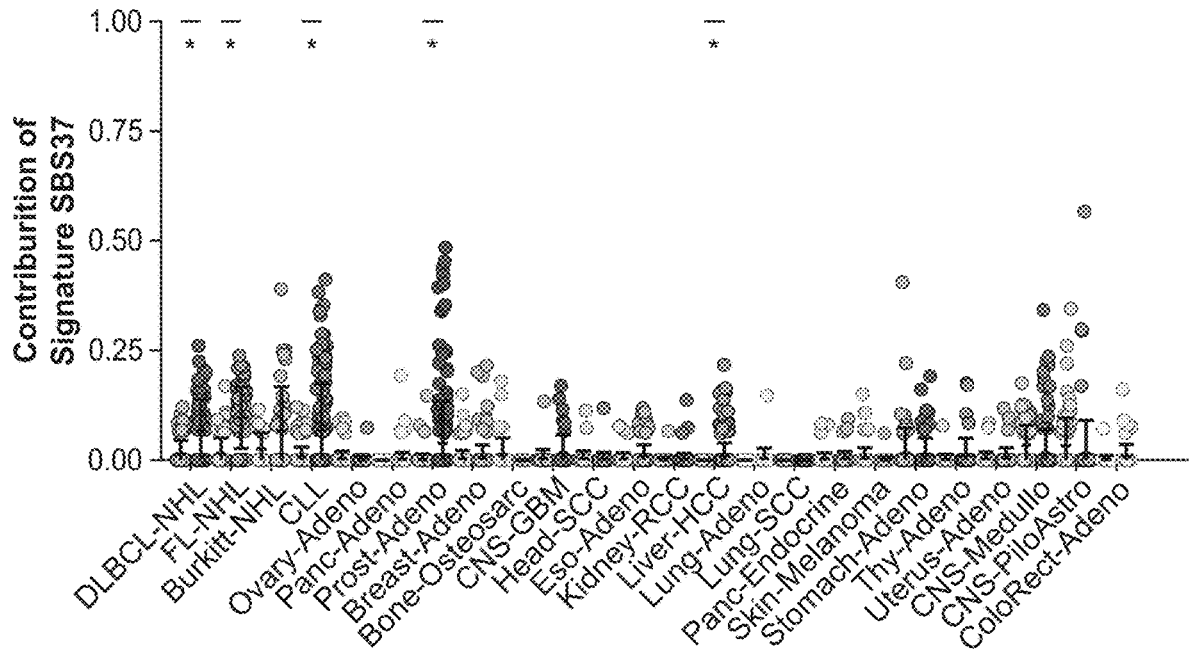
Figure 6P:
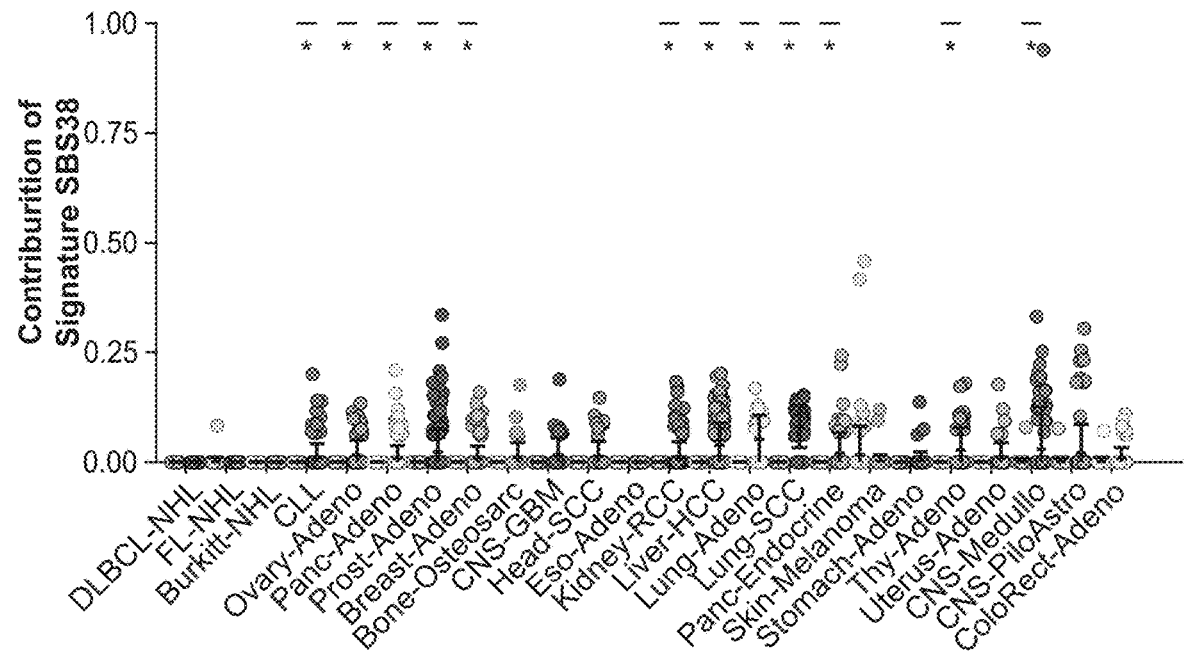
Figure 6Q:
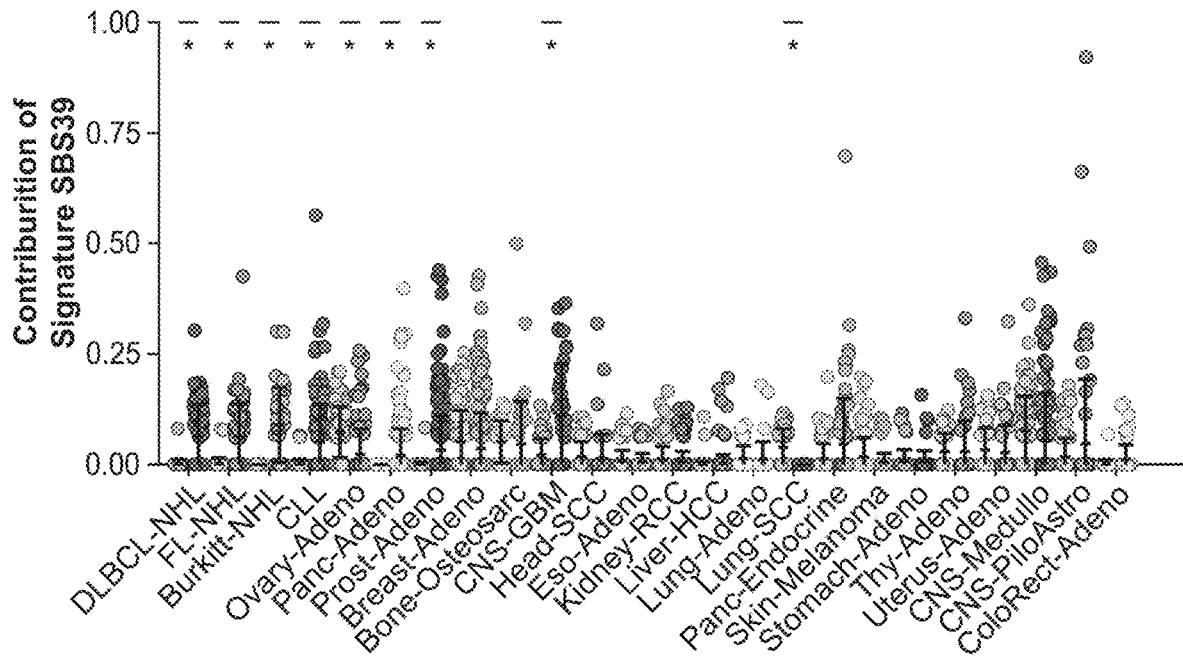
Figure 6R:
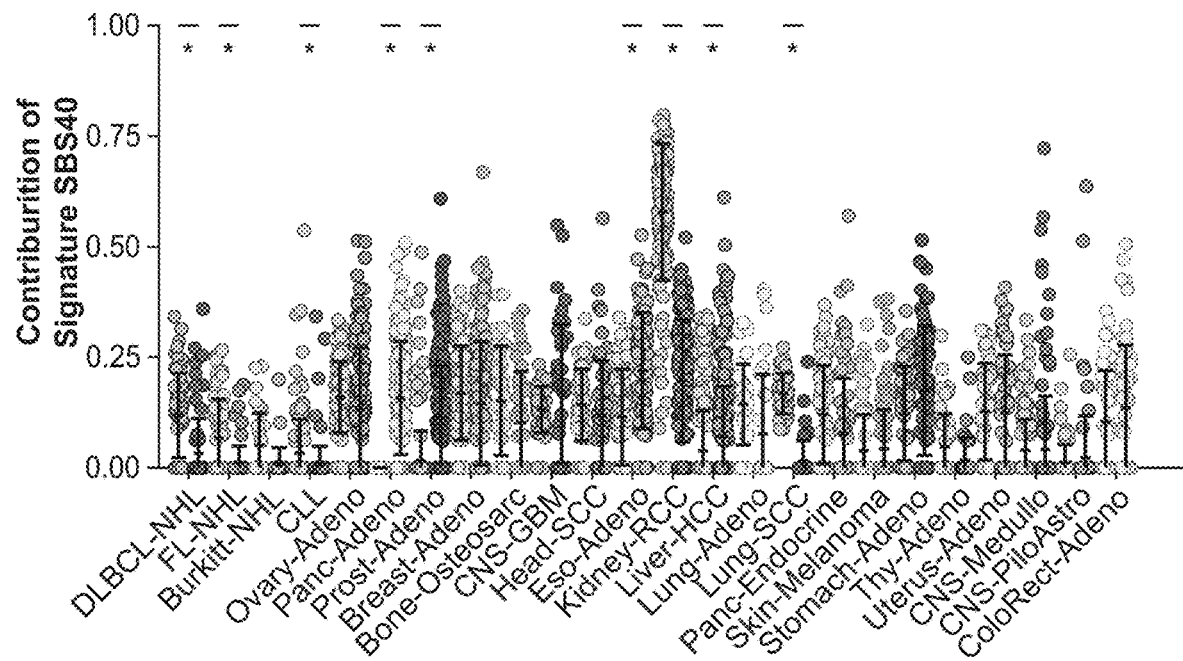
Figure 6S:
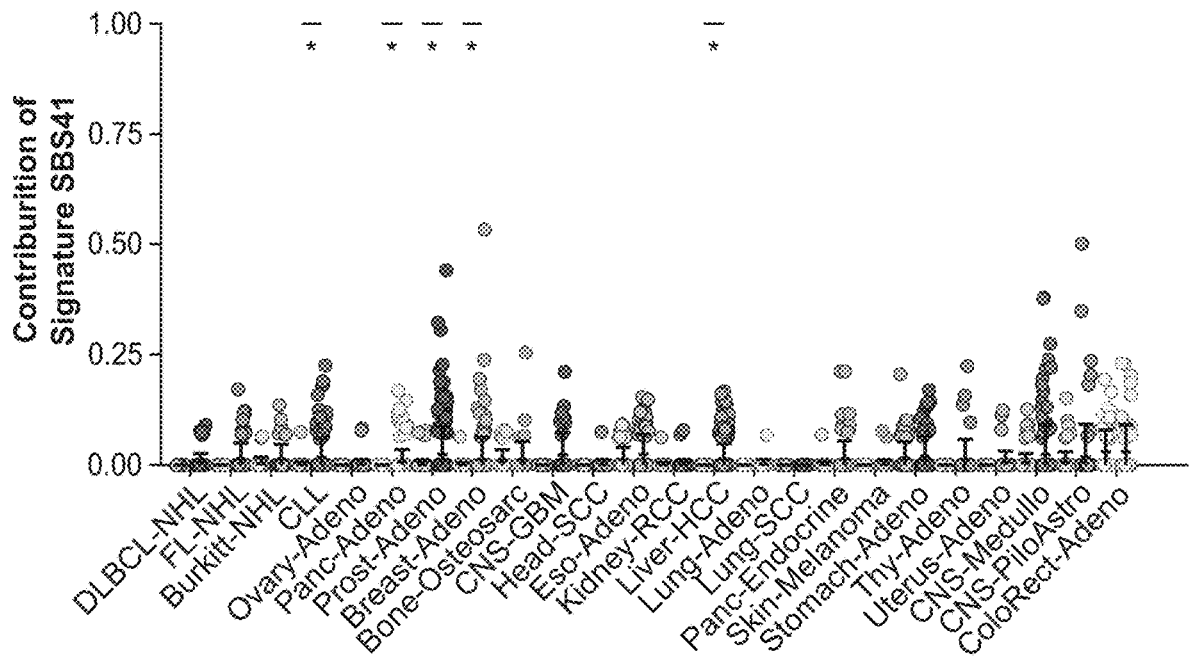
Figure 6T:
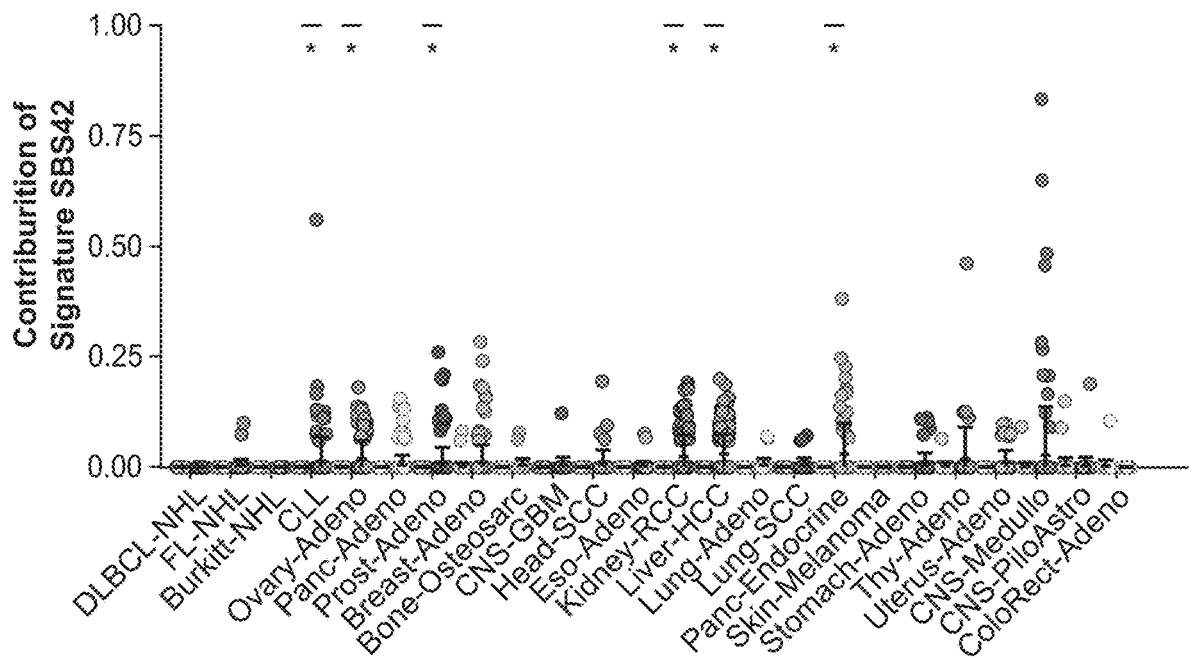
Figure 6U:
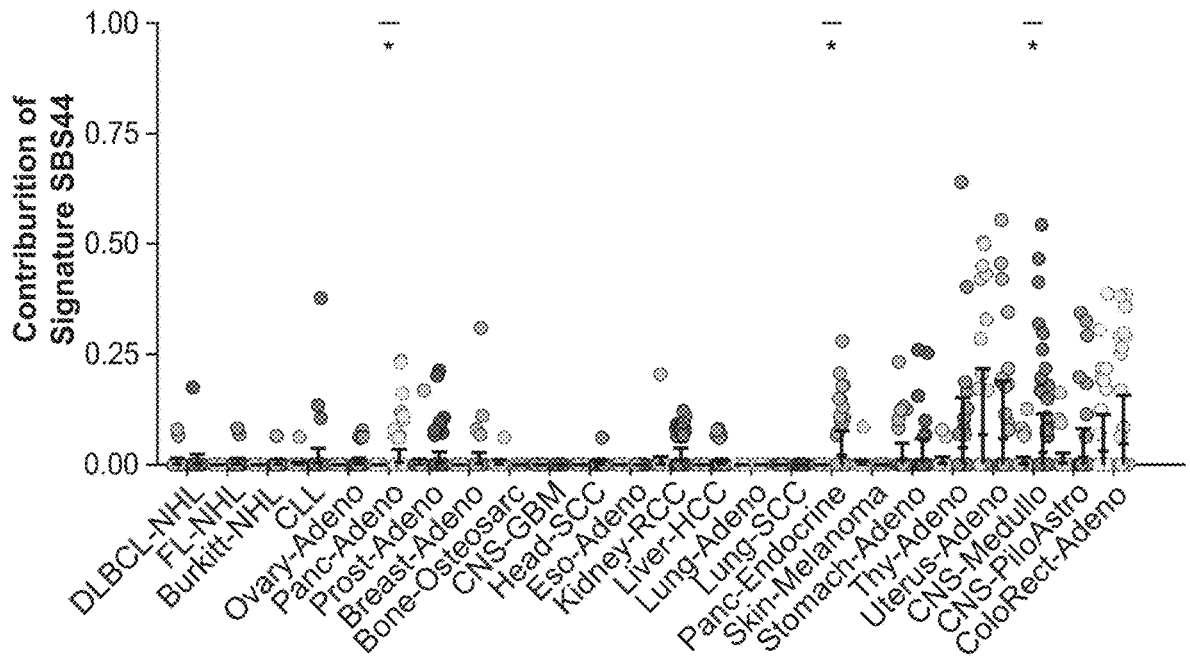
Figure 6V:
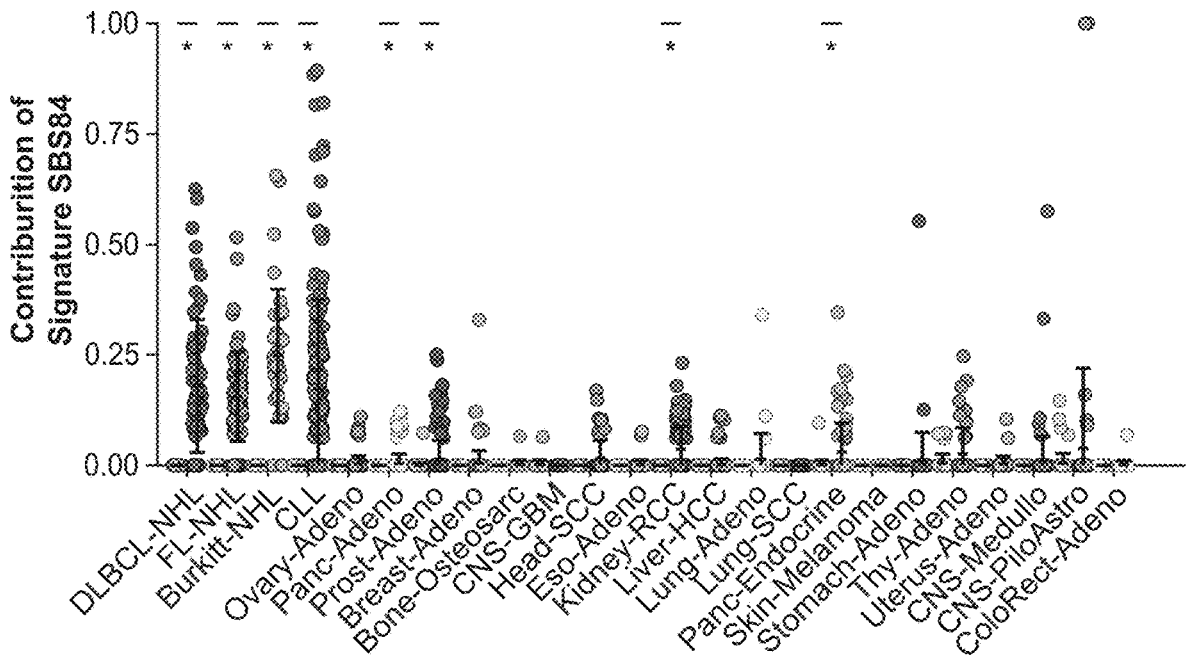
Figure 6W:
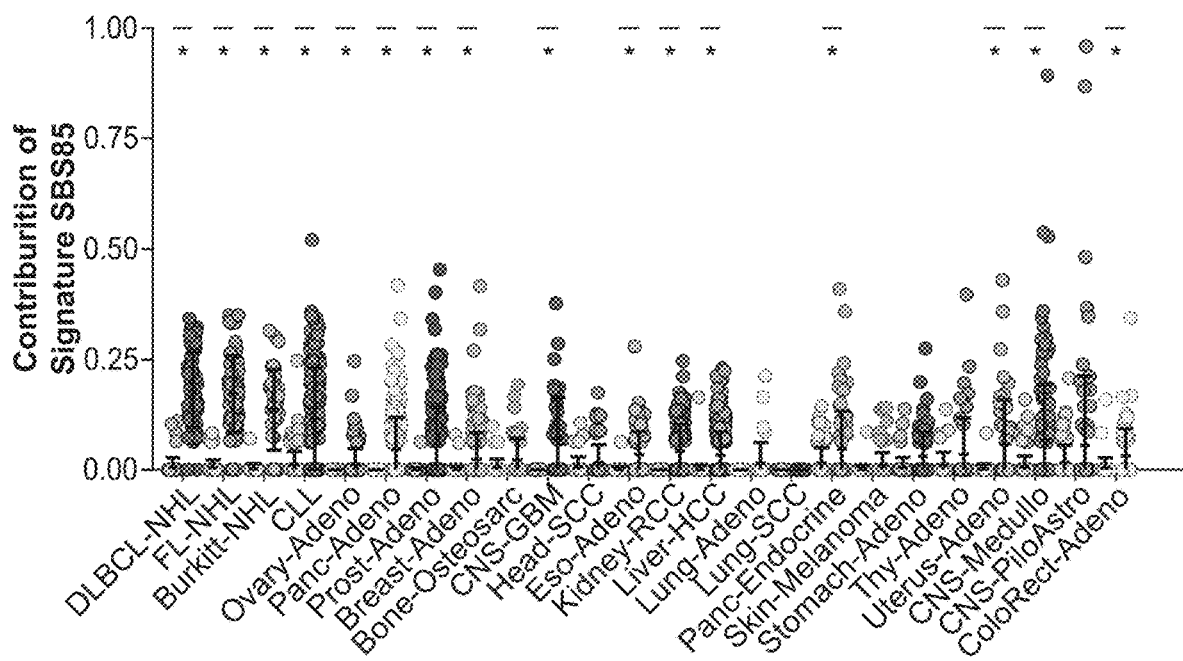

To investigate the origin of PVs, the single base substitution (SBS) mutational signatures contributing to SNVs occurring within 170 bp of another SNV, and SNVs occurring in isolation (e.g., not having another SNV within 170 bp) (Example 10) were compared. As expected, PVs were highly enriched in several mutational signatures associated with clustered mutations. Signatures of clustered mutations associated with activity of AID (SBS84 and SBS85) were significantly enriched in PVs from B-cell lymphomas and CLL, while signatures associated with activity of APOBEC3B (SBS2 and SBS13)—another mechanism of kataegis hypermutation—were significantly enriched in PVs from multiple solid cancer histologies, including ovarian, pancreatic, prostate, and breast adenocarcinomas (FIG. 1C and FIGS. 6A-6WW). Signatures of clustered mutations associated with activity of AID (SBS84 and SBS85) were enriched in PVs found in lymphomas and CLL, while signatures associated with activity of APOBEC3B (SBS2 and SBS13) were significantly enriched in breast cancer (FIG. 1C and FIGS. 6A-6WW). PVs from multiple tumor types were also associated with SBS4, a signature associated with tobacco use. Furthermore, among PVs across multiple tumor histologies, it was observed that novel enrichments in several other signatures without clearly associated mechanisms (e.g., SBS24, SBS37, SBS38, and SBS39). In contrast, aging-associated mutational signatures such as SBS1 and SBS5 were significantly enriched in isolated SNVs.

Example 3: PVs Occur in Stereotyped Genomic Regions in Lymphoid Cancers

Figure 7:
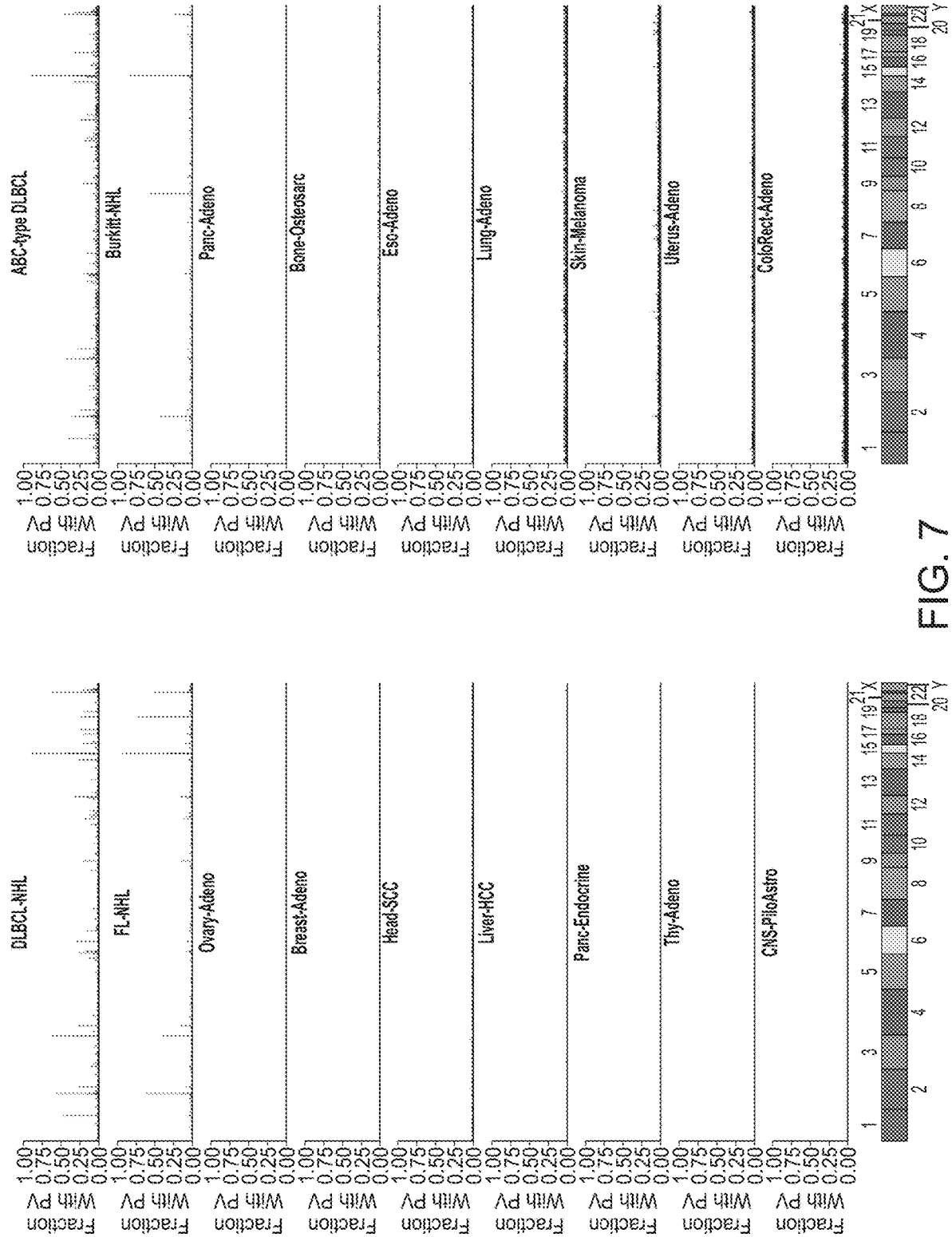
FIG. 7 illustrates distribution of PVs in stereotyped regions across the genome. Bar plots show the distribution of PVs occurring in stereotyped regions across the genome of multiple cancer types. In this plot, the genome was divided into 1000 bp bins, and the fraction of samples of a given histology with a PV in each 1000 bp bin was calculated. Only bins that have at least a 2 percent recurrence frequency in any cancer subtype are shown. Histologies shown are as in FIG. 1E; activated B-cell (ABC) and germinal center B-cell (GCB) subtypes of DLBCL are also shown.
Figure 7:
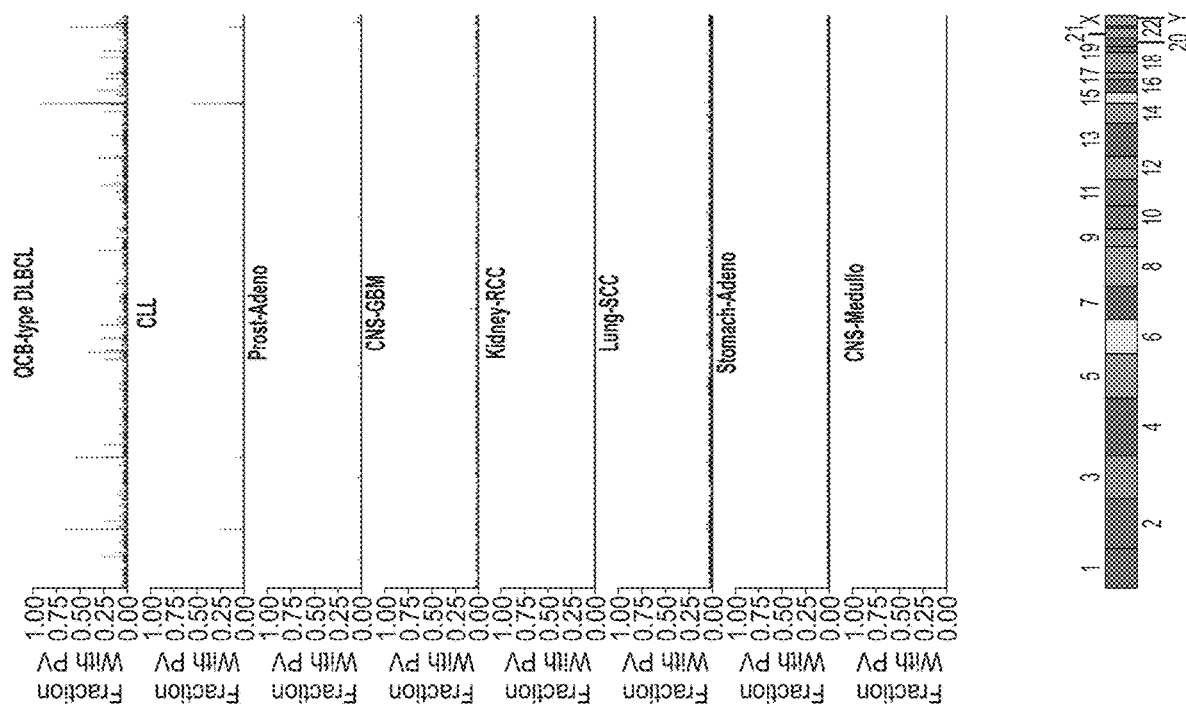

To assess the genomic distribution of putative PVs, these events were first binned into 1-kb regions to visualize their frequency across tumor types. It was observed that a strikingly stereotyped distribution of PVs in individual lymphoid neoplasms (e.g., DLBCL, FL, Burkitt lymphoma (BL), and chronic lymphocytic leukemia (CLL); FIG. 1D and FIG. 7). In contrast, non-lymphoid cancers generally did not exhibit substantial recurrence of clustered PVs in stereotyped regions. This lack of stereotype in the position of PVs was true even when considering melanomas and lung cancers, diseases with frequent PVs.

Figure 8A:
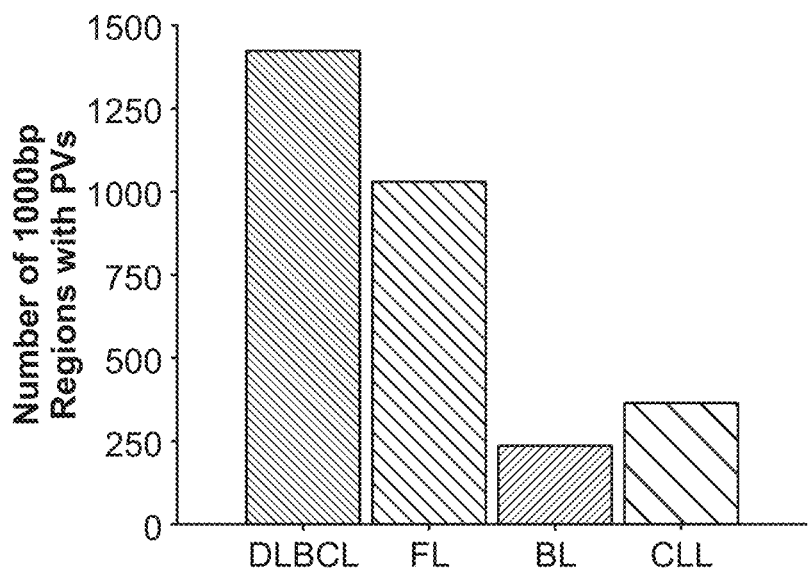
FIGS. 8A-8E illustrate quantity and genomic location of PVs from WGS in lymphoid malignancies.

Notably, the majority of hypermutated regions were shared between all three lymphoma subtypes, with the highest densities seen in known targets of aSHM including BCL2, BCL6, and MYC, as well as the immunoglobulin (Ig) loci encoding the heavy and light chains IGH, IGK, and IGL (Table 2). Strikingly, certain regions within Ig loci were densely mutated in nearly all lymphoma patients as well as in patients with CLL (FIG. 1D). Among lymphoma subtypes, DLBCL tumors harbored the most 1-kb regions recurrently containing PVs (FIG. 8A), consistent with the highest number of recurrently mutated genes being observed in this tumor type. In total, 1639 unique 1-kb regions recurrently containing PVs in B-lymphoid malignancies were identified. Among these lymphoma-associated 1-kb regions, nearly one-third fell into genomic areas previously associated with physiological or aberrant SHM in B-cells. Specifically, 19% (315/1639) were located in Ig regions, while 13% (218/1639) were in portions of 68 previously identified targets of aSHM (Table 2). While most PVs fell into noncoding regions of the genome, additional recurrently affected loci not previously described as targets of aSHM, including XBP1, LPP, and AICDA, among others, were also identified.

Figure 8B:
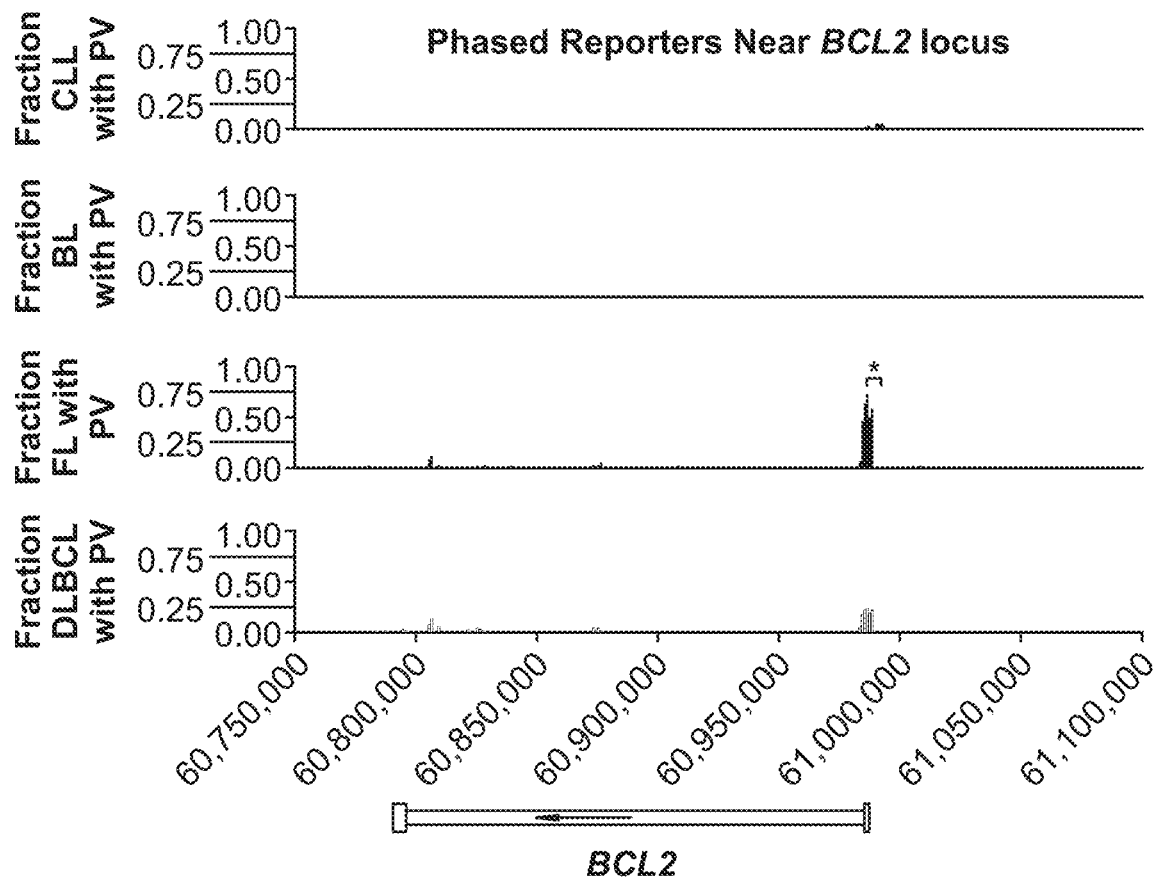
Figure 8C:
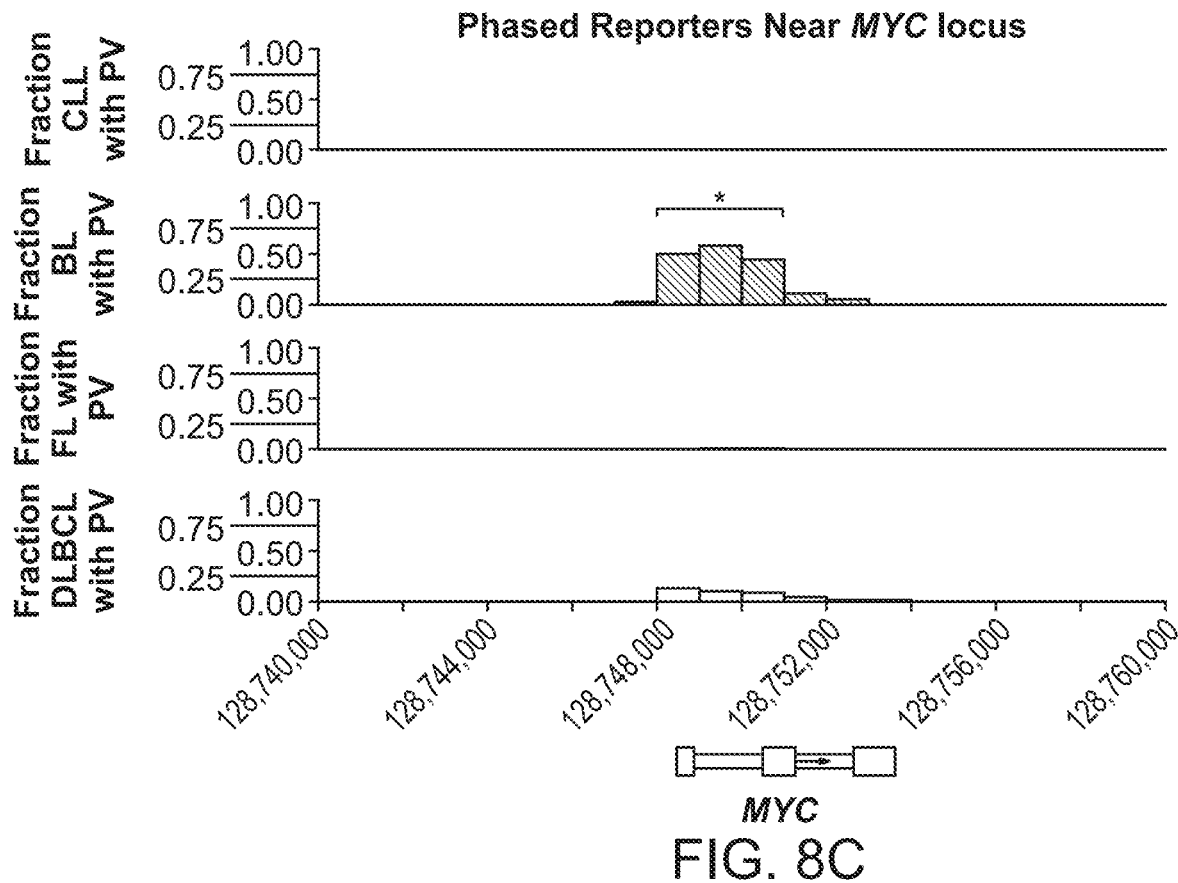
Figure 8D:
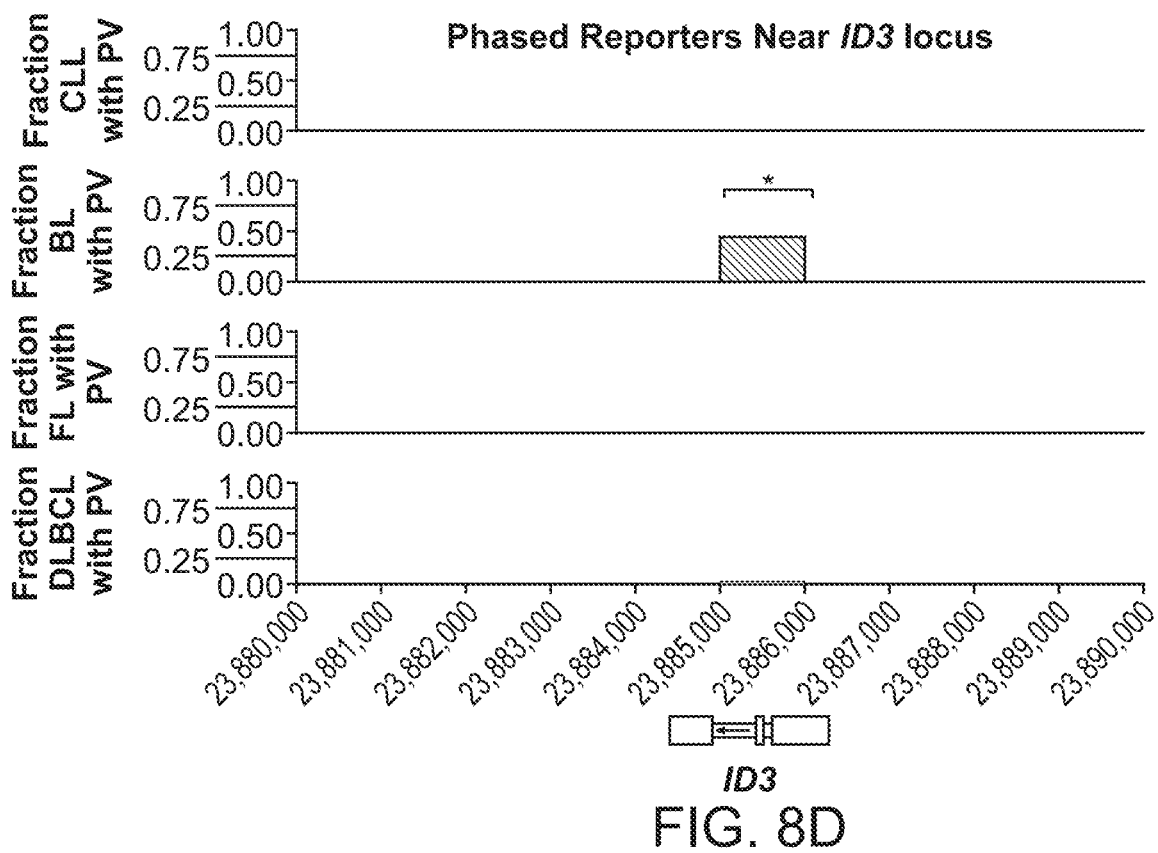
Figure 8E:
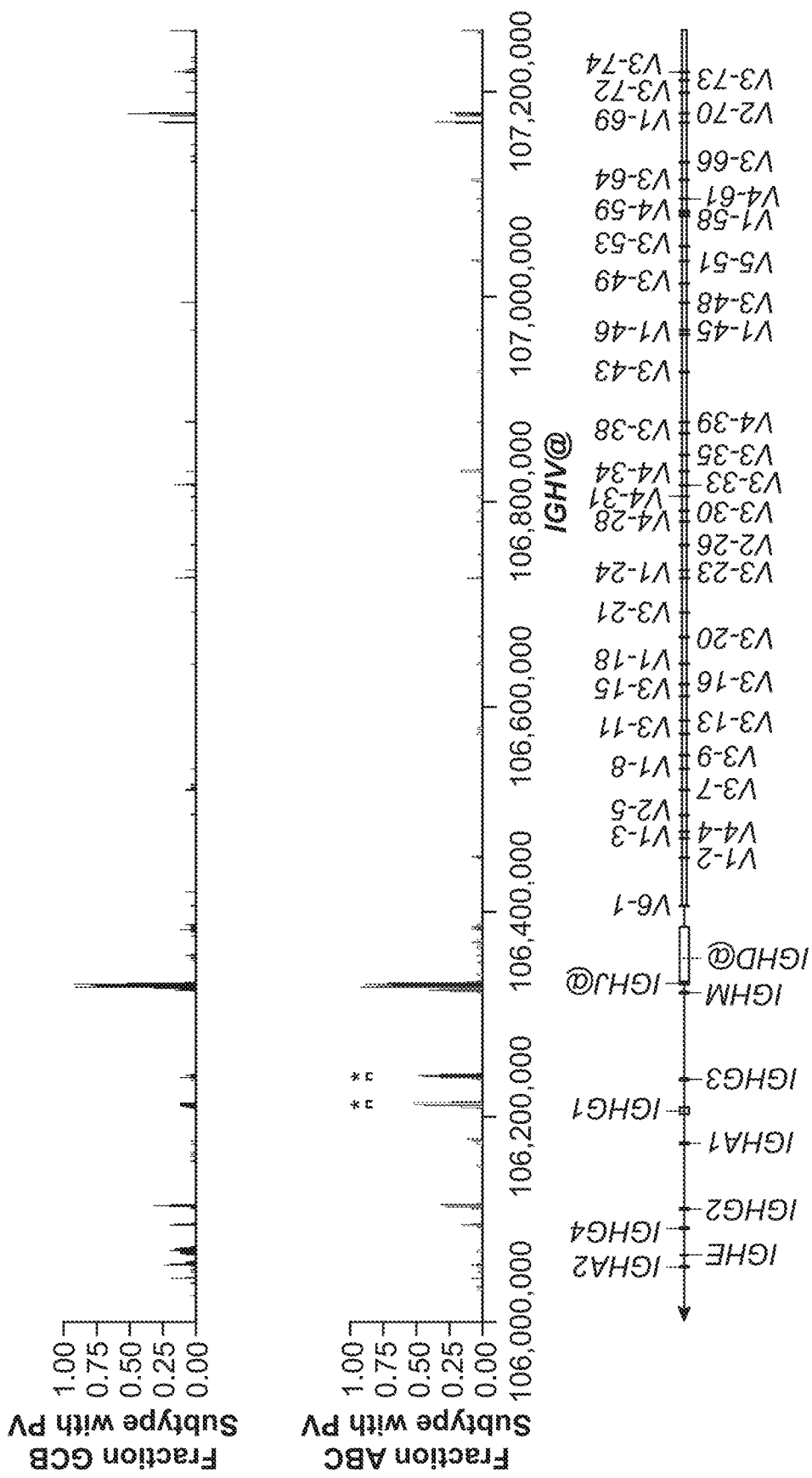

The distribution of PVs within each lymphoid malignancy correlated with oncogenic features associated with the distinct pathophysiology of the corresponding disease. For example, cases of FL—where more than 90% of tumors harbor oncogenic BCL2 fusions—were significantly more likely to contain phased variants in BCL2 than other lymphoid malignancies (FIG. 1D and FIG. 8B). Similarly, significantly more Burkitt lymphomas (BL) harbored PVs in MYC and ID3, two driver genes strongly associated with the BL pathogenesis, than other lymphoid malignancies (FIG. 1D and FIGS. 8C-8D). DLBCL molecular subtypes associated with distinct cell-of-origin also demonstrated distinct distributions of PVs (Table 2). Specifically, while germinal center B-cell like (GCB) and activated B-cell like (ABC) DLBCLs harbored similar frequencies of PVs overall (median 798 vs 516, P=0.37), significant enrichment for PVs in the telomeric IGH class-switch regions (Sγ1, and Sγ3) in ABC-DLBCLs, consistent with previous reports 41 (FIG. 8E), was found. Conversely, GCB-DLBCLs harbored more phased haplotypes in centromeric IGH class switch regions (Sα2 and Sε) and in BCL2.

Example 4: Design and Validation of PhasED-Seq Panel for Lymphoma

Figure 2A:
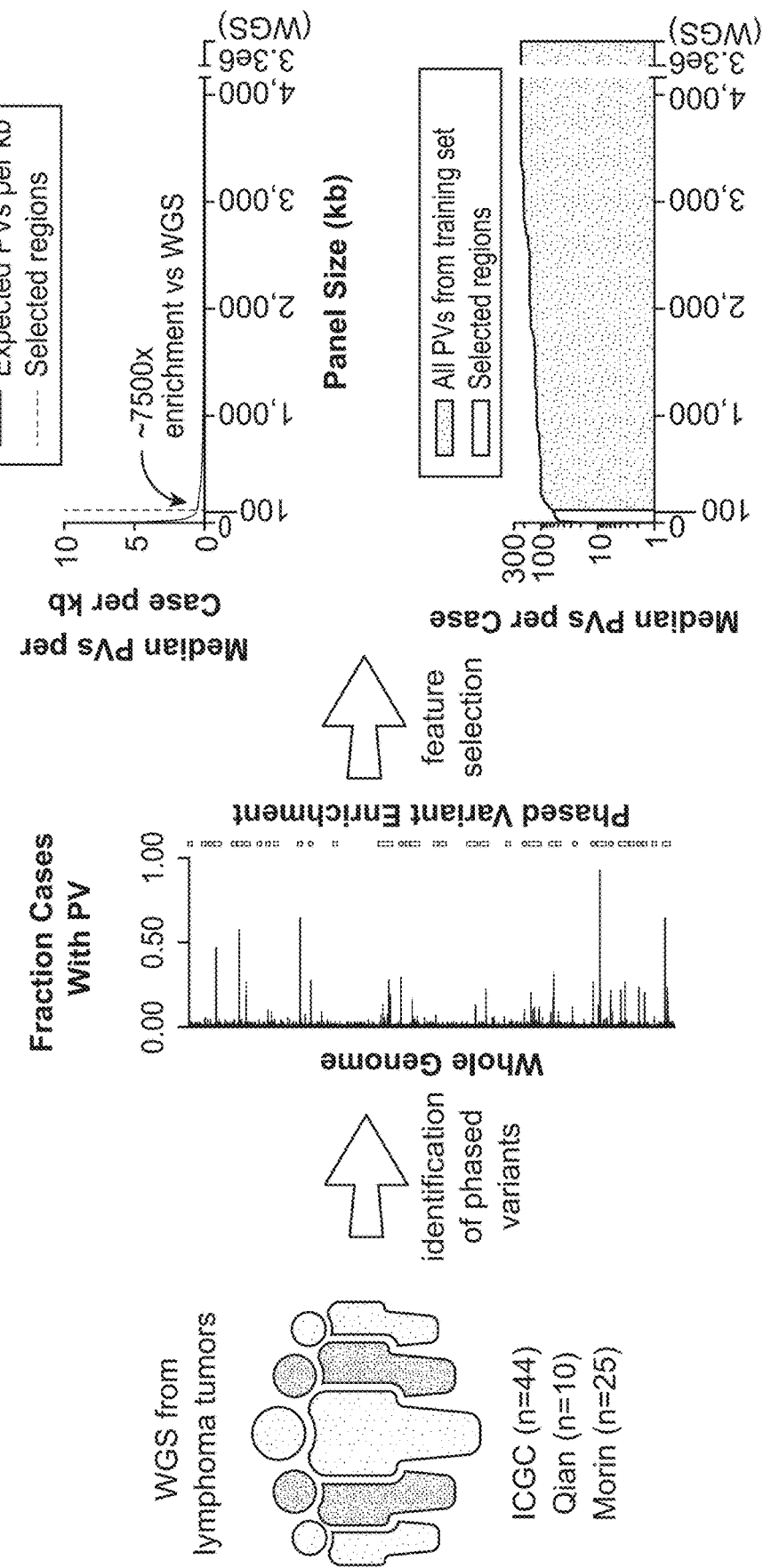
FIGS. 2A-2F illustrate design, validation, and application of phased variant enrichment sequencing.
Figure 9G:
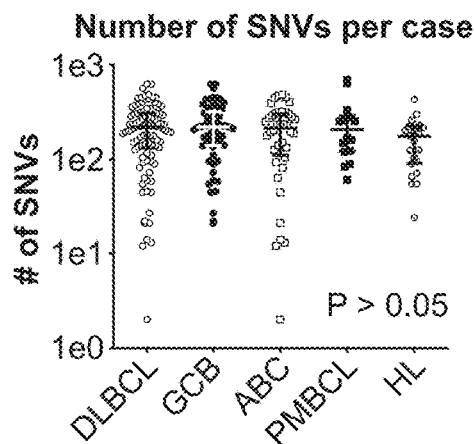
Figure 9H:
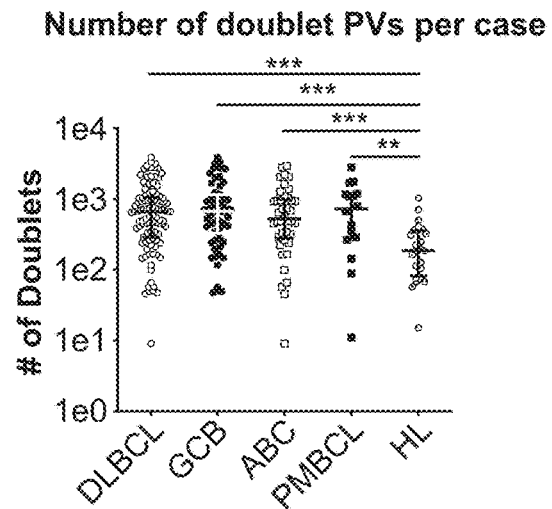
Figure 9I:
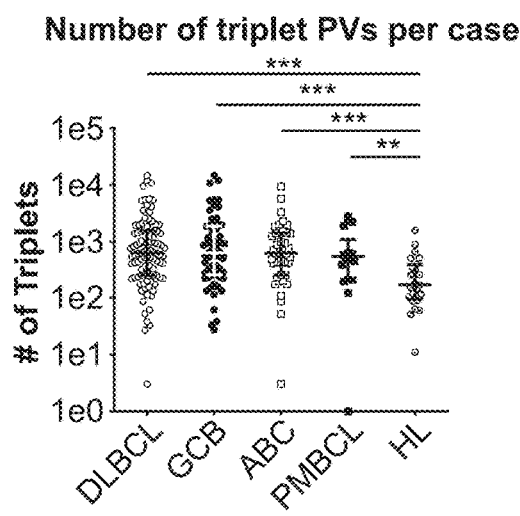
Figure 9J:
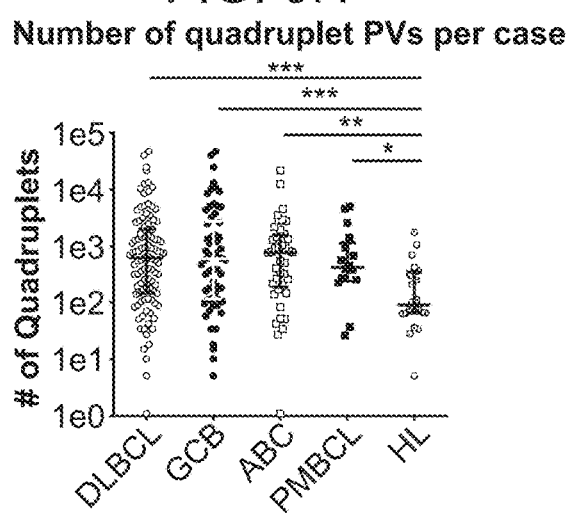
Figure 9K:
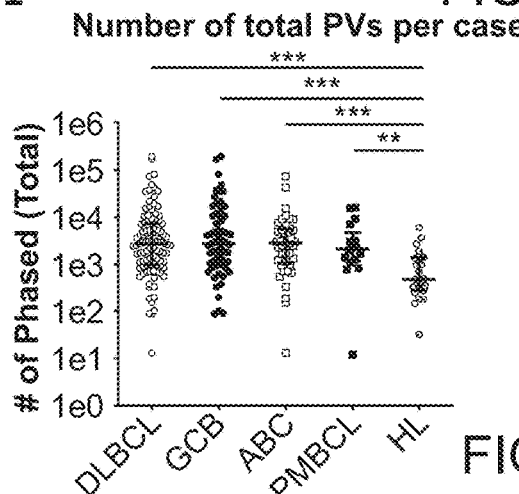
Figure 10A:
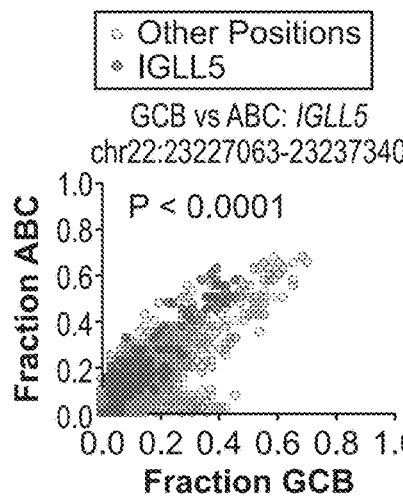
FIGS. 10A-10Y illustrate location-specific differences in PVs between ABC-DLBCL and GCB-DLBC (FIGS. 10A-10Y.) Similar to FIG. 2D, these scatterplots compare the frequency of PVs by genomic location (in 50 bp bins) for patients with different types of lymphomas; in this figure, the difference between ABC-DLBCL and GCB-DLBCL is shown. The red circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between ABC-DLBCL and GCB-DLBCL are shown. P-values represent a Wilcoxon rank-sum test of 50 bp bins from a given gene against all other 50 bp bins; see Example 10.
Figure 10B:
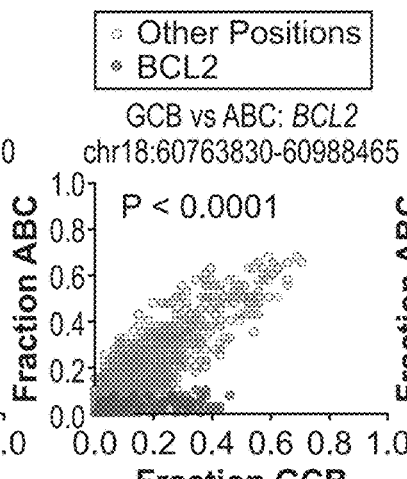
Figure 10C:
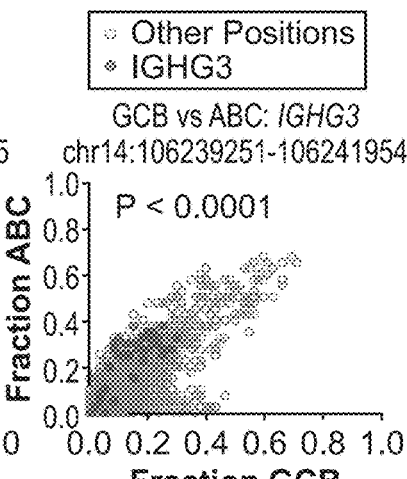
Figure 10D:
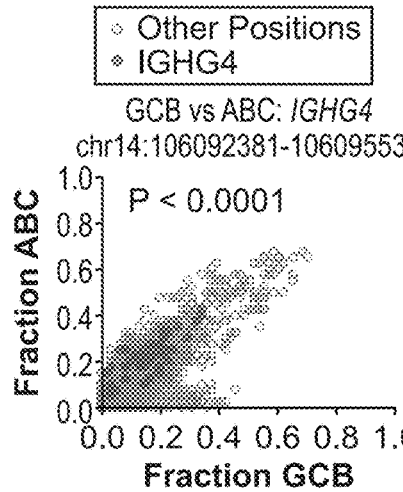
Figure 10E:
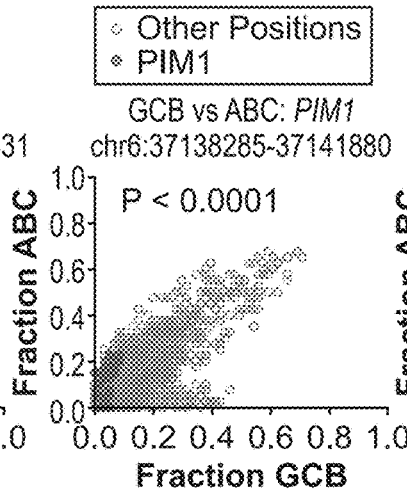
Figure 10F:
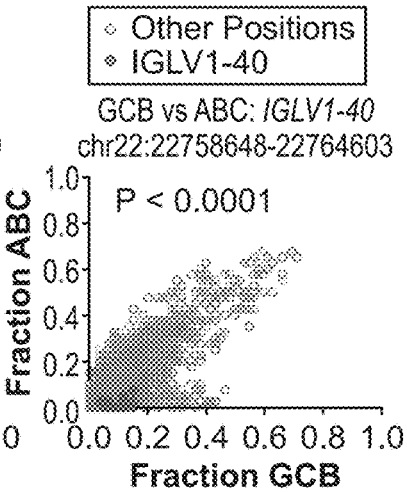
Figure 10G:
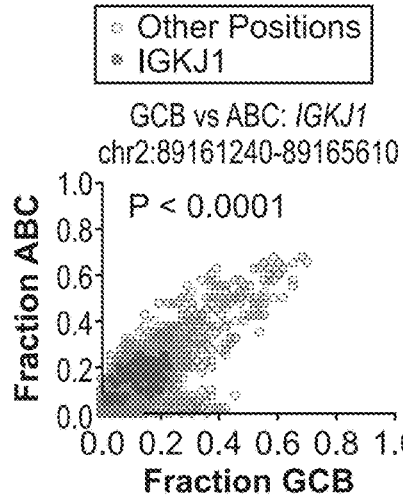
Figure 10H:
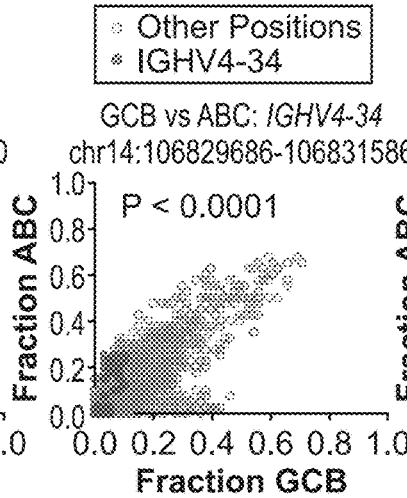
Figure 10I:
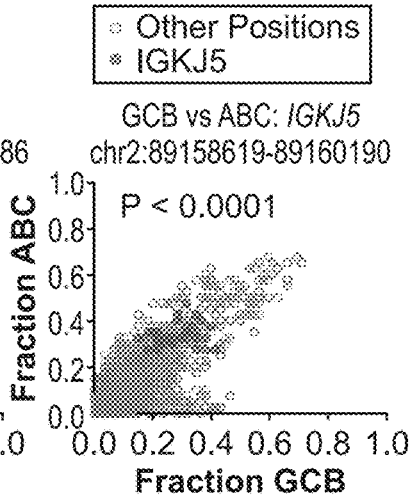
Figures 10J, 10K, 10L, 10M, 10N, 10O, 10P, 10Q, 10R:
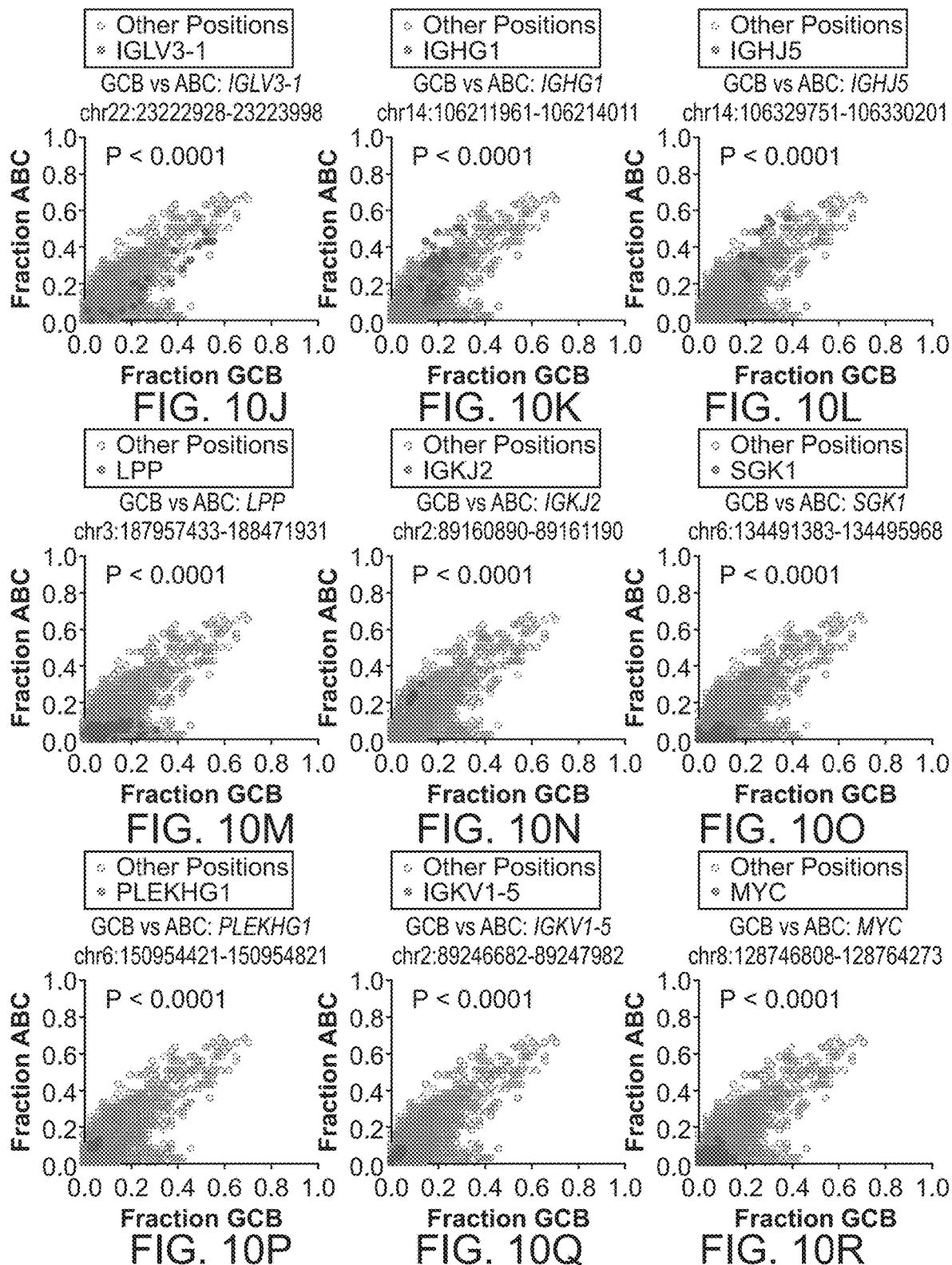
Figure 10S:
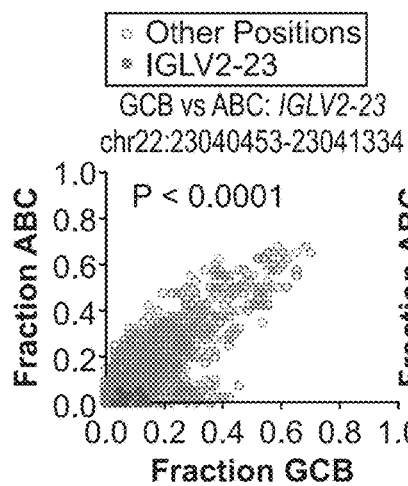
Figure 10T:
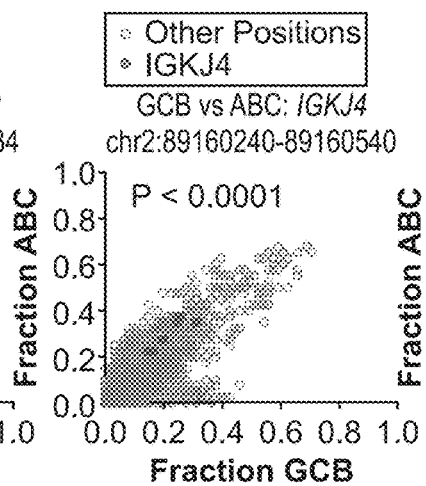
Figure 10U:
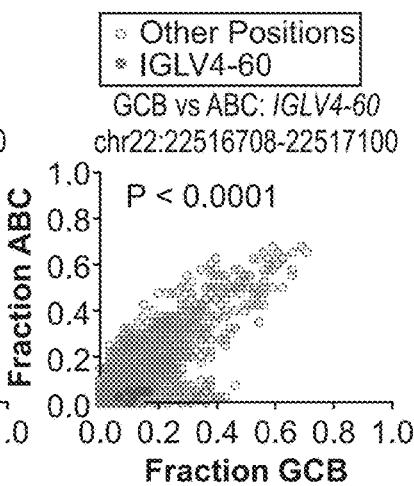
Figure 10V:
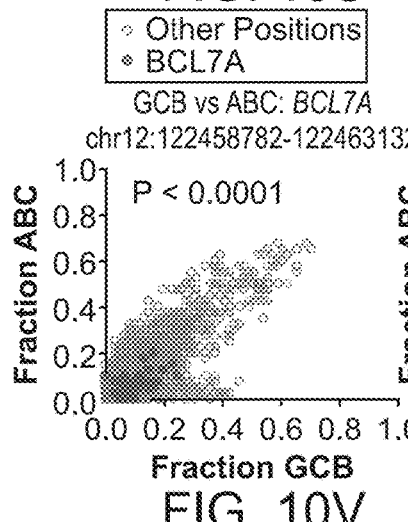
Figure 10W:
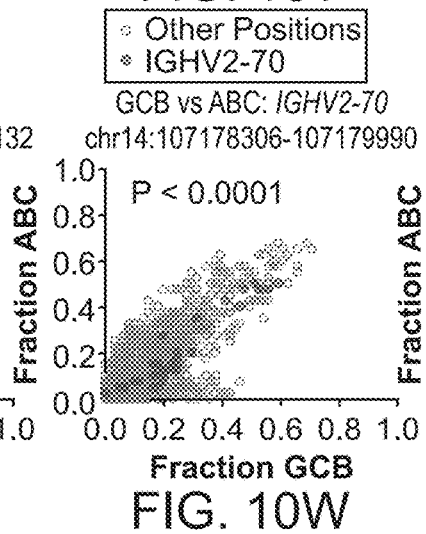
Figure 10X:
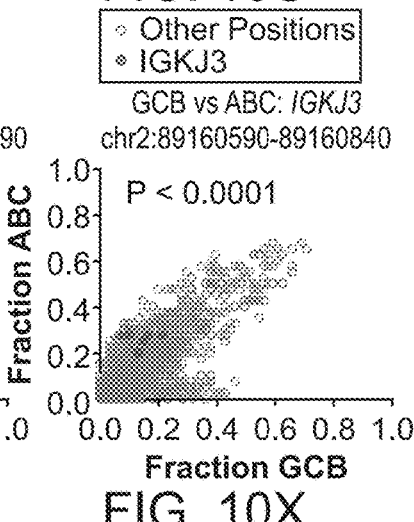
Figure 10Y:
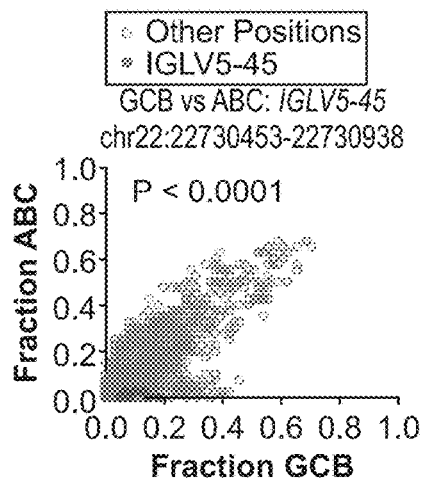

To validate these PV-rich regions and assess their utility for disease detection from ctDNA, a sequencing panel targeting putative PVs identified within WGS from three independent cohorts of patients with DLBCL, as well as in patients with CLL (FIG. 2A and Example 10) was designed. This final Phased variant Enrichment and Detection Sequencing (PhasED-Seq) panel targeted ~115 kb of genomic space focused on PVs, along with an additional ~200 kb targeting genes that are recurrently mutated in B-NHLs (Table 3). While the 115 kb of space dedicated to PV-capture targets only 0.0035% of the human genome, it captures 26% of phased variants observed in mature B-cell neoplasms profiled by WGS (FIG. 9A), thus yielding a 7500-fold PV enrichment by PhasED-Seq over WGS.

Figure 2B:
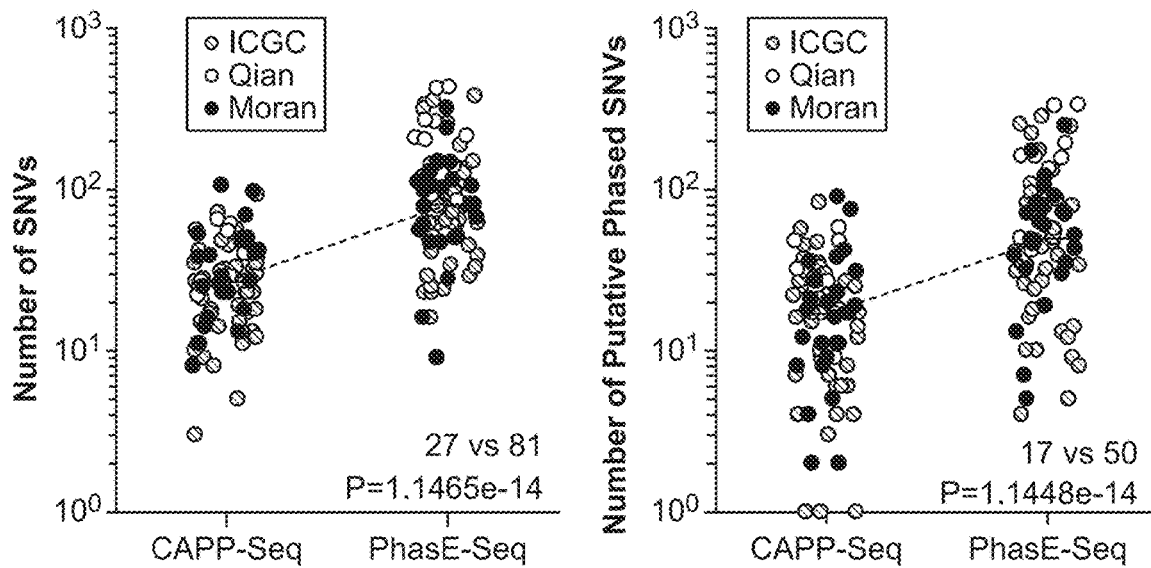
Figure 2C:
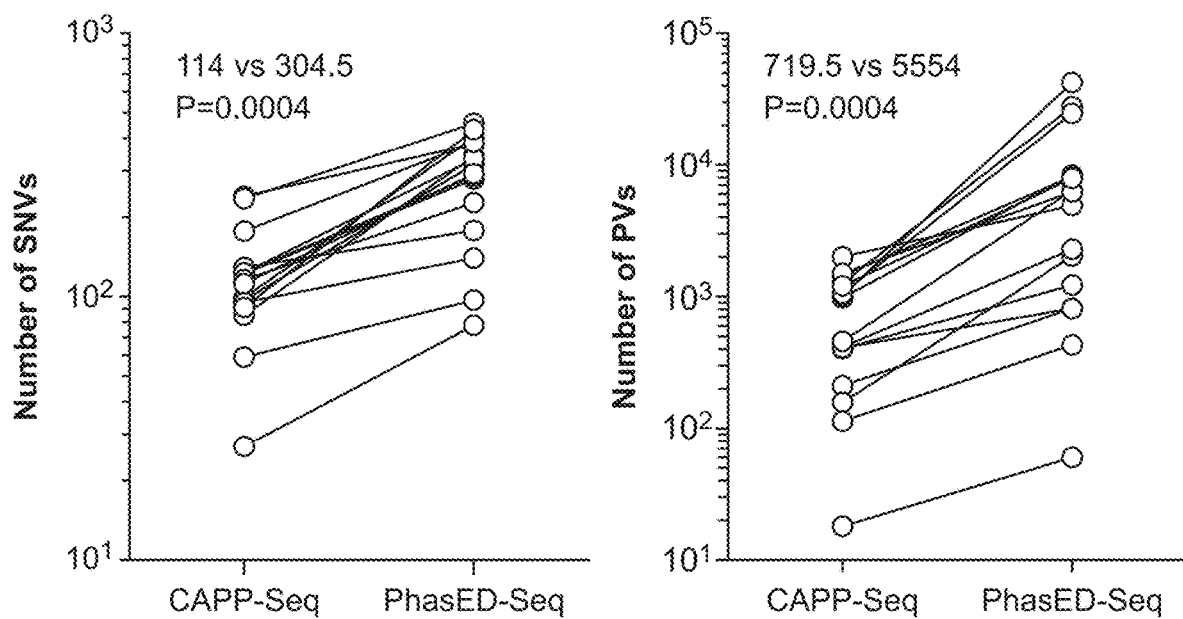
Figure 2D:
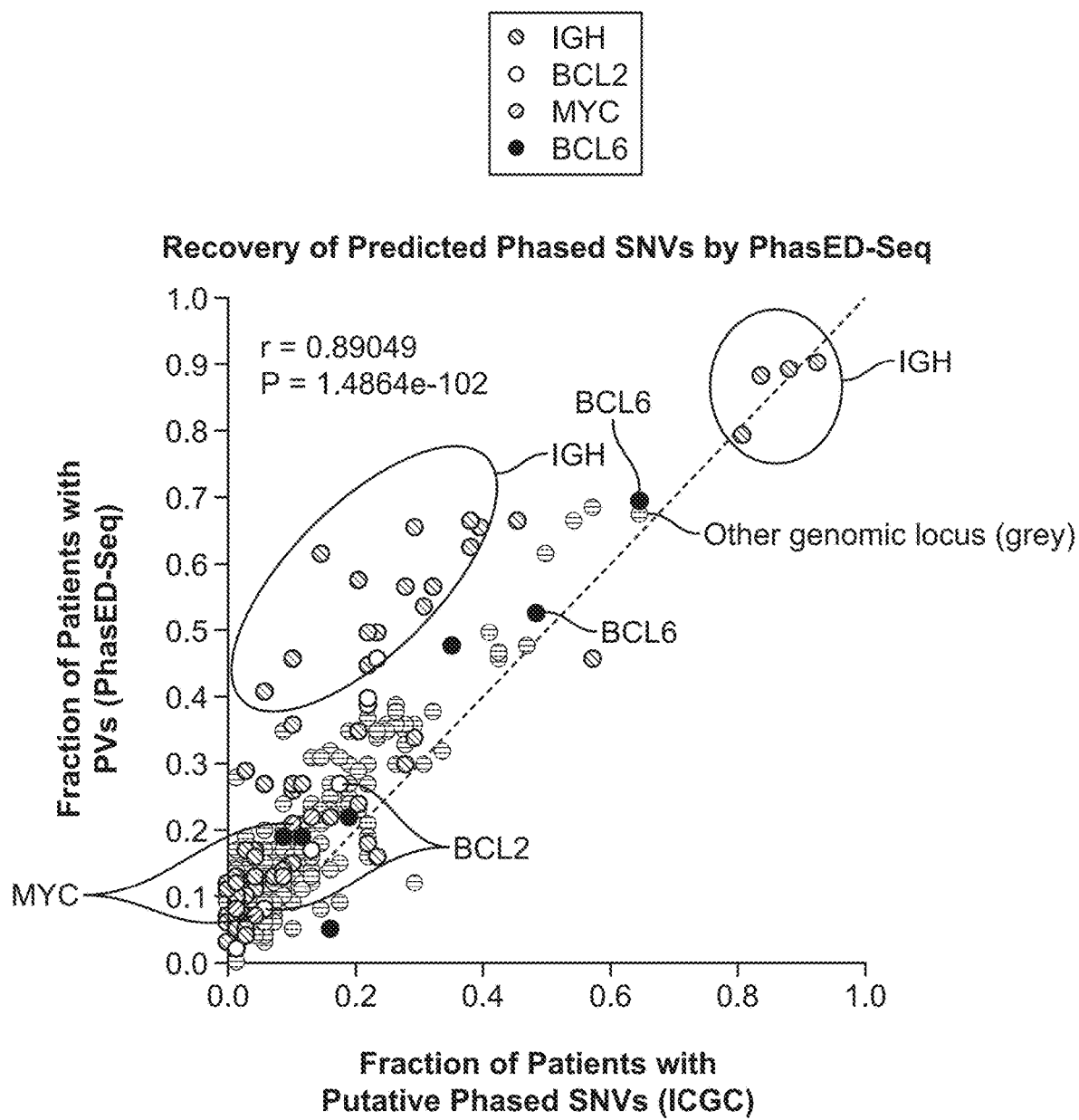

Expected SNV and PV recovery was compared to previously reported CAPP-Seq selector designed to maximize SNVs per patient in B-cell lymphomas (FIG. 9A-C). When considering diverse B-NHLs with available WGS data, PhasED-Seq recovered 3.0× more SNVs (81 vs. 27) and 2.9× more PVs (50 vs. 17) in the median case than previous CAPP-Seq panel. This observation highlights the importance of including non-coding portions of the genome for maximal mutation recovery. To validate these yield improvements experimentally, 16 pretreatment tumor or plasma DNA samples from patients with DLBCL (Table 4) were profiled. Both CAPP-Seq and PhasED-Seq panels were applied to each specimen in parallel and then sequenced them to high unique molecular depths (FIG. 2B). Compared to the expected enrichment established from WGS, similar improvements in yield of SNVs by PhasED-Seq compared to CAPP-Seq (2.7×; median 304.5 vs. 114) were observed. However, when enumerating PVs observed in individual sequenced DNA fragments, an improvement in favor of PhasED-Seq beyond the expected improvement from WGS (7.7×; median 5554 vs 719.5 PVs/case) was found. This improvement is potentially due to either 1) the higher sequencing depth in targeted sequencing which leads to improvement in rare allele detection, or 2) enumeration of higher order PVs in targeted sequencing with PhasED-Seq or CAPP-Seq, which was not accounted for in the WGS design (i.e., >2 SNVs per fragment; FIGS. 9D-9F). Furthermore, across 1-kb windows in the panel, robust correlation between the frequency of putative PVs in WGS data and PVs from targeted sequencing by PhasED-Seq across 101 DLBCL samples (FIG. 2C) was observed, further validating the frequency and distribution of PVs in B-cell malignancies.

Example 5: Differences in Phased Variants Between Lymphoma Subtypes

Figure 2E:
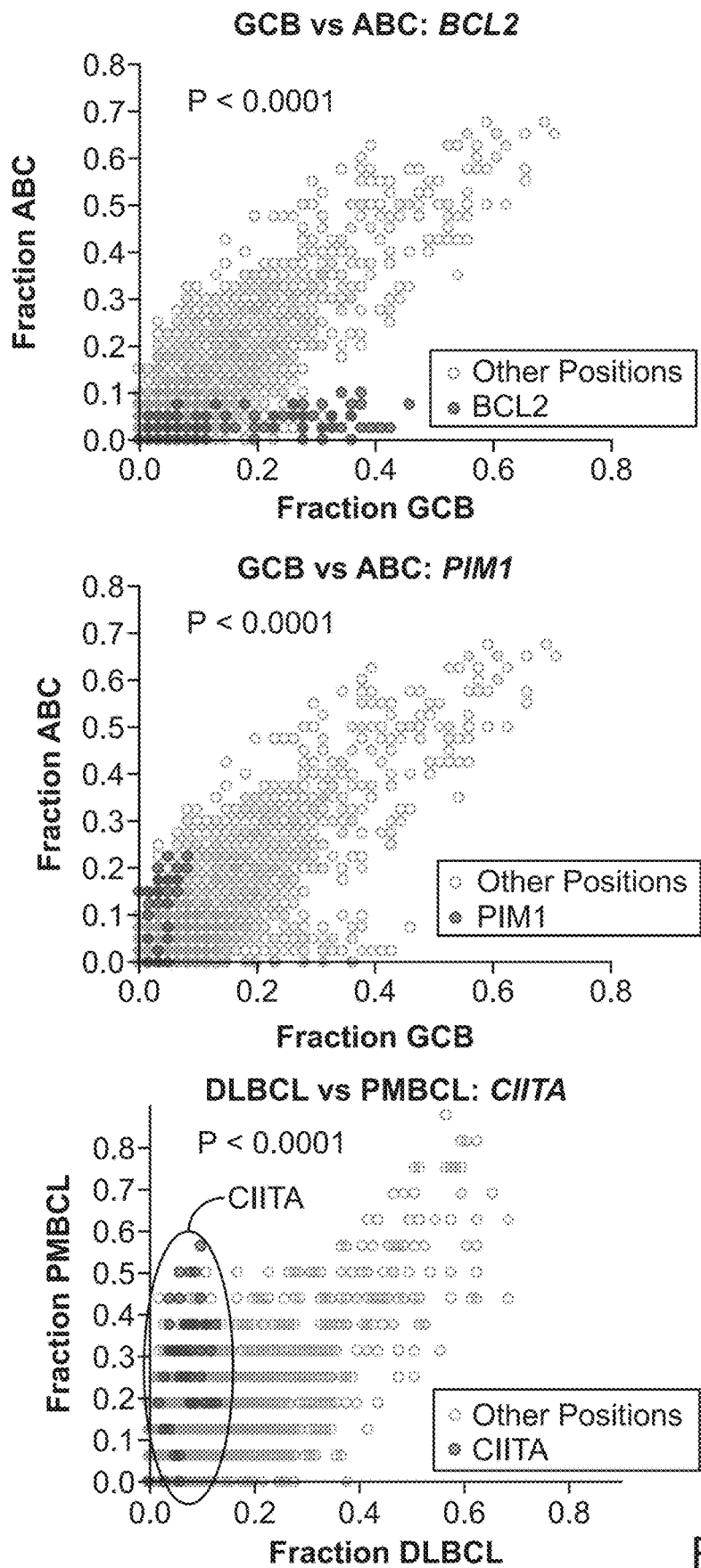
Figure 2F:
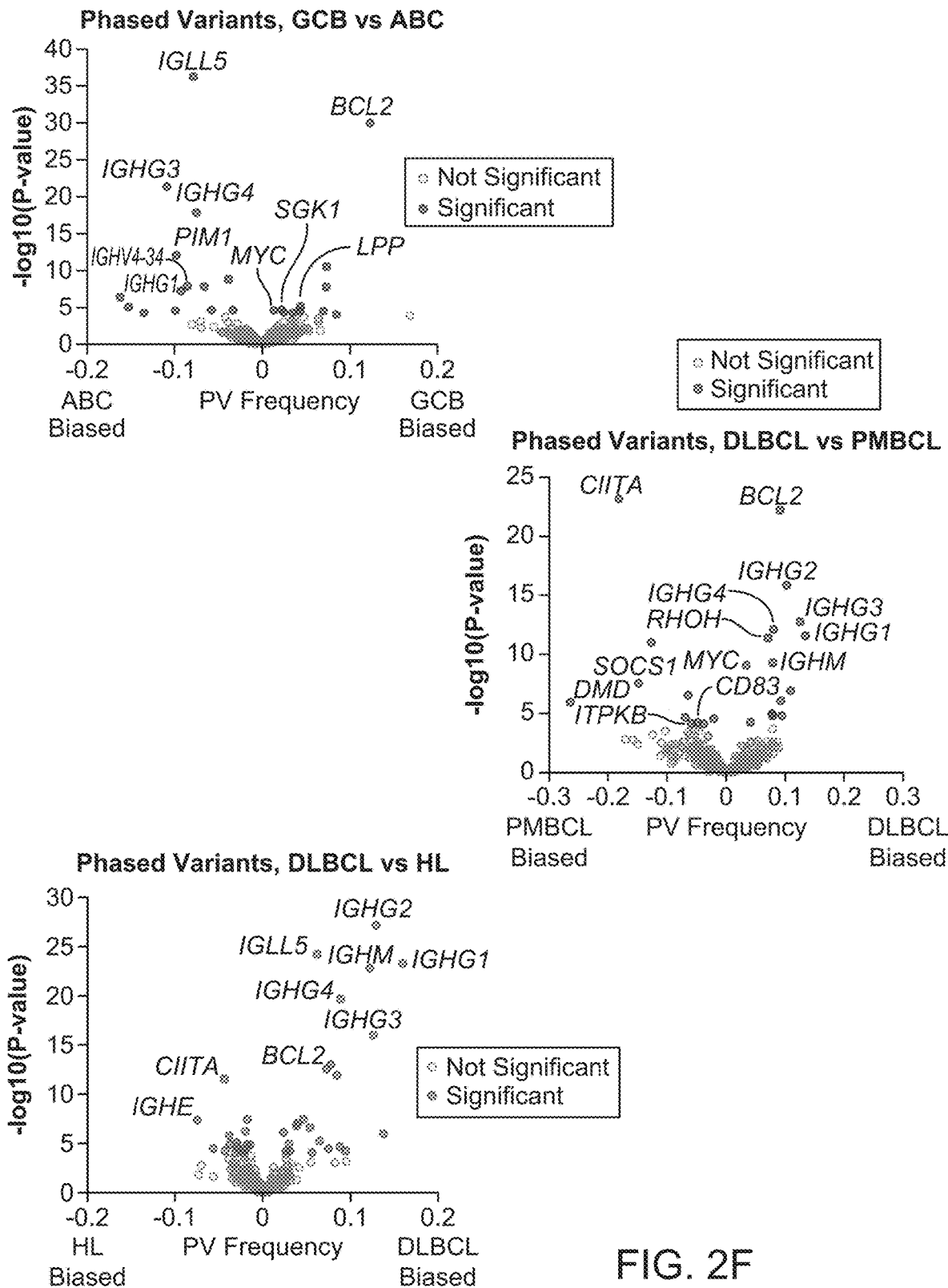
Figures 11G, 11H, 11I:
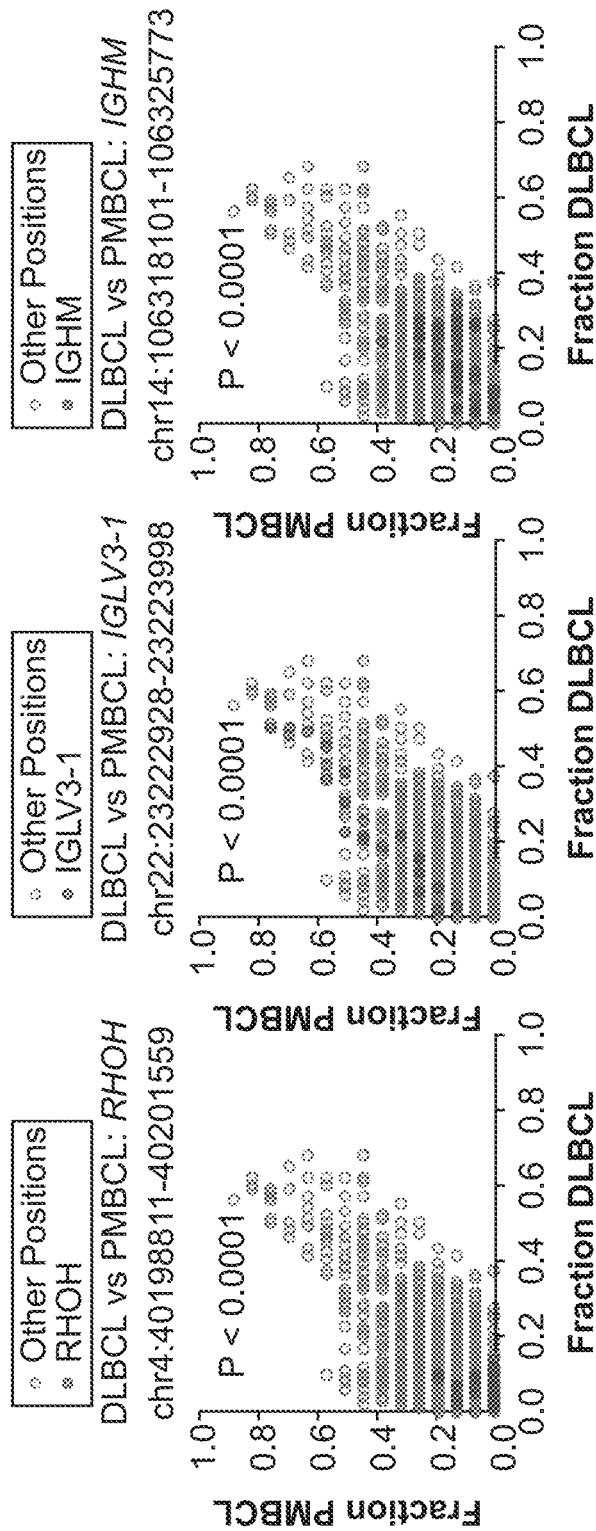
FIGS. 11A-11X illustrate Location-specific differences in PVs between DLBCL and PMBCL (FIGS. 11A-11X). Similar to FIG. 2D, these scatterplots compare the frequency of PVs by genomic location (in 50 bp bins) for patients with different types of lymphomas; in this figure, the difference between DLBCL and PMBCL is shown. The blue circles show the relative frequency of PVs in 50 bp bins from a specific gene of interest; the other (gray) circles show the relative frequency of PVs in 50 bp bins from the remainder of the PhasED-Seq sequencing panel. Only genes with a statistically significant difference in PVs between DLBCL and PMBCL are shown. P-values represent a Wilcoxon rank-sum test of 50 bp bins from a given gene against all other 50 bp bins; see Example 10.
Figures 11P, 11Q, 11R:
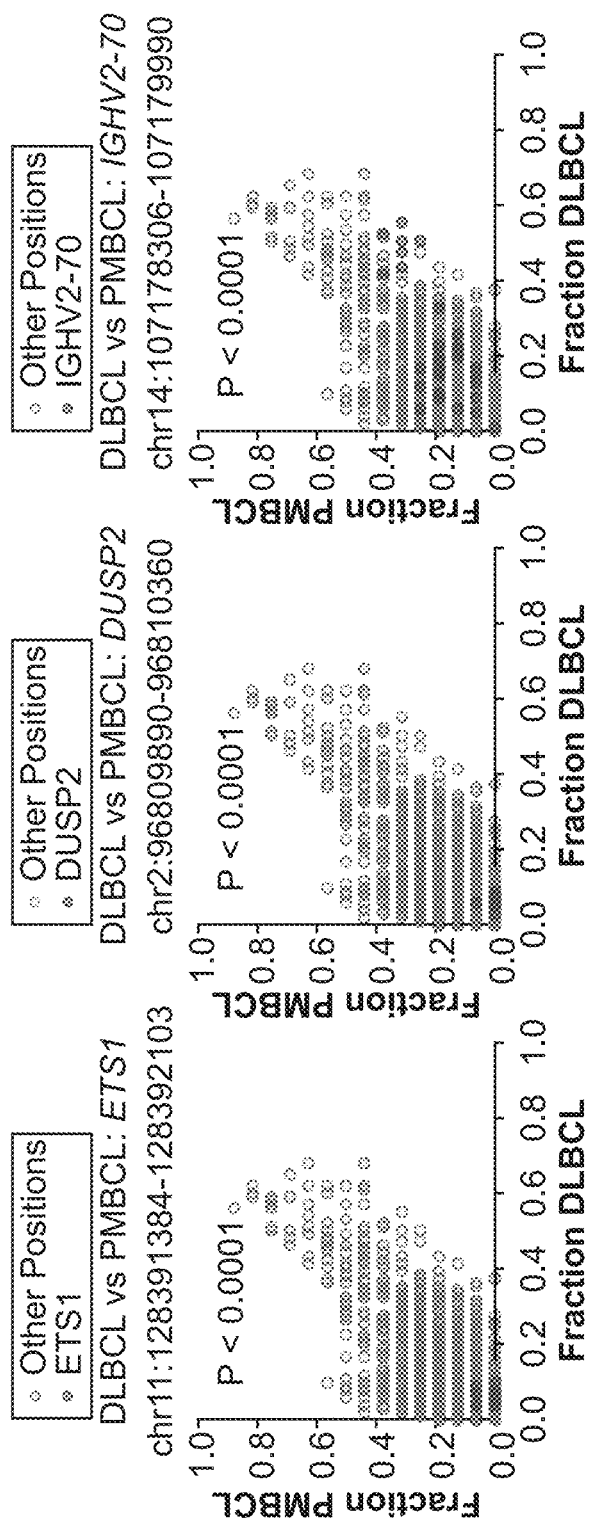
Figures 12G, 12H, 12I:
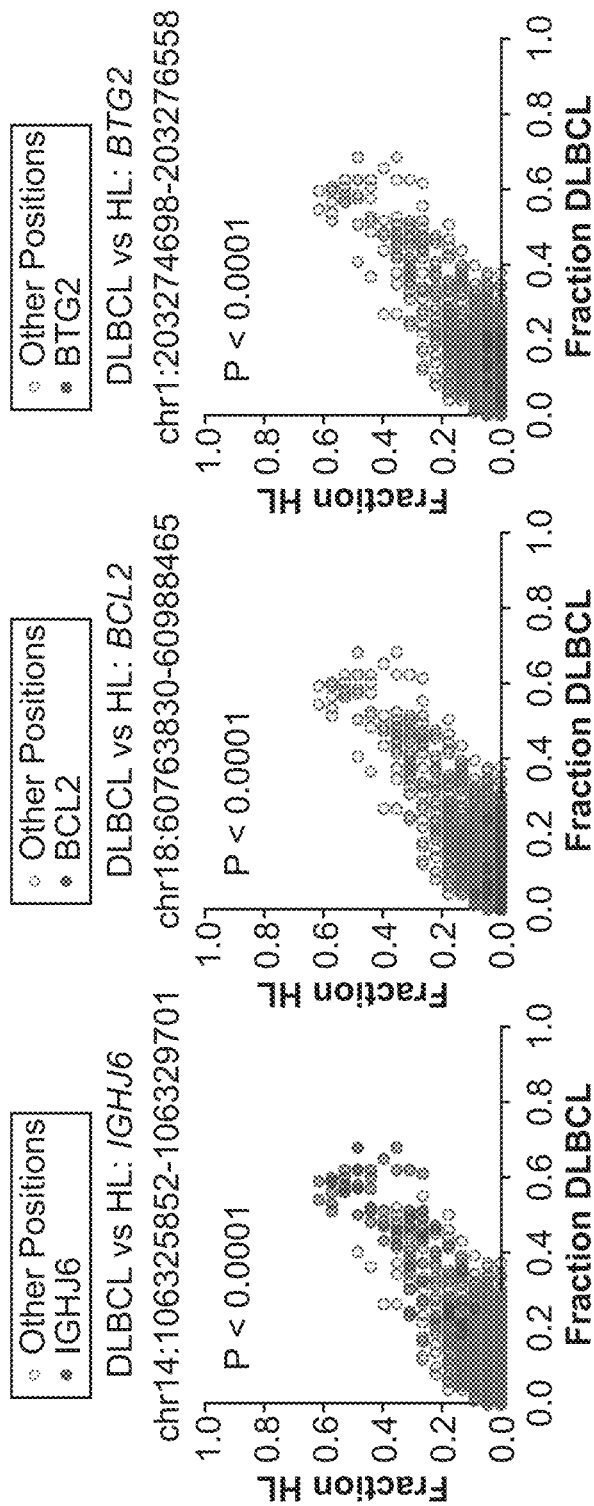
FIGS. 12A-12NN illustrate Location-specific differences in PVs between DLBCL and HL. Similar to FIG. 2D, scatterplots of FIGS. 12A-12NN compare the frequency of PVs by genomic location (in 50 bp bins) for patients with different types of lymphomas; in this figure, the difference between DLBCL and HL is shown. The green circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between DLBCL and HL are shown. P-values represent a Wilcoxon rank sum test of 50 bp bins from a given gene against all other 50 bp bins; see Example 10.
Figures 12P, 12Q, 12R:
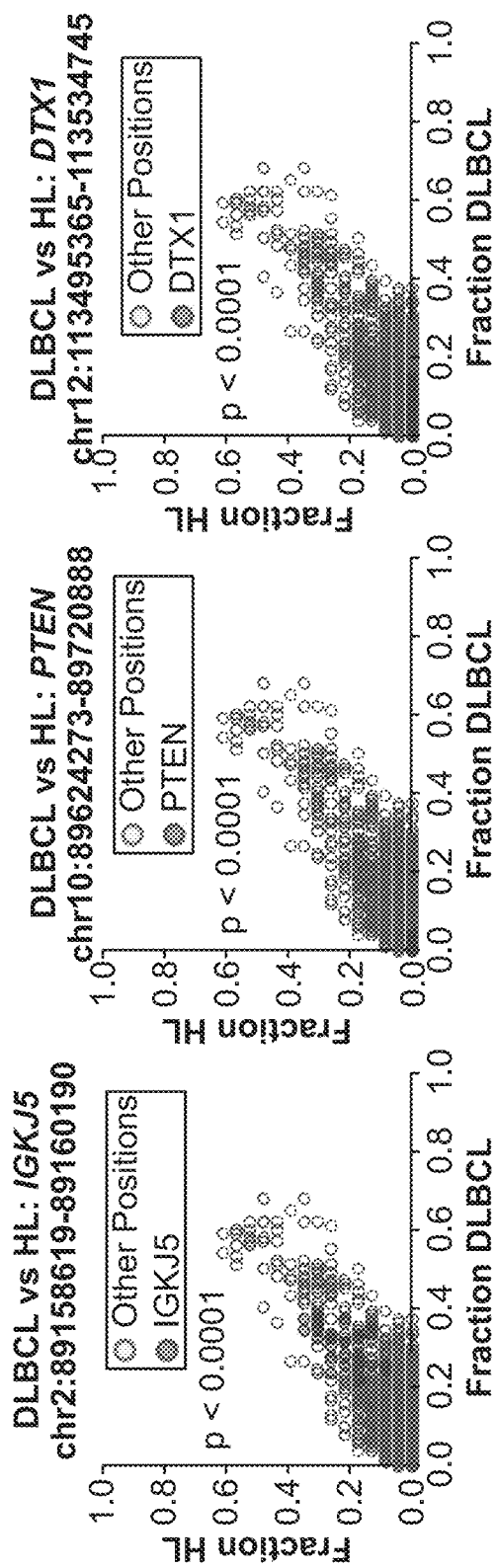
Figures 12A, 12Y, 12Z:
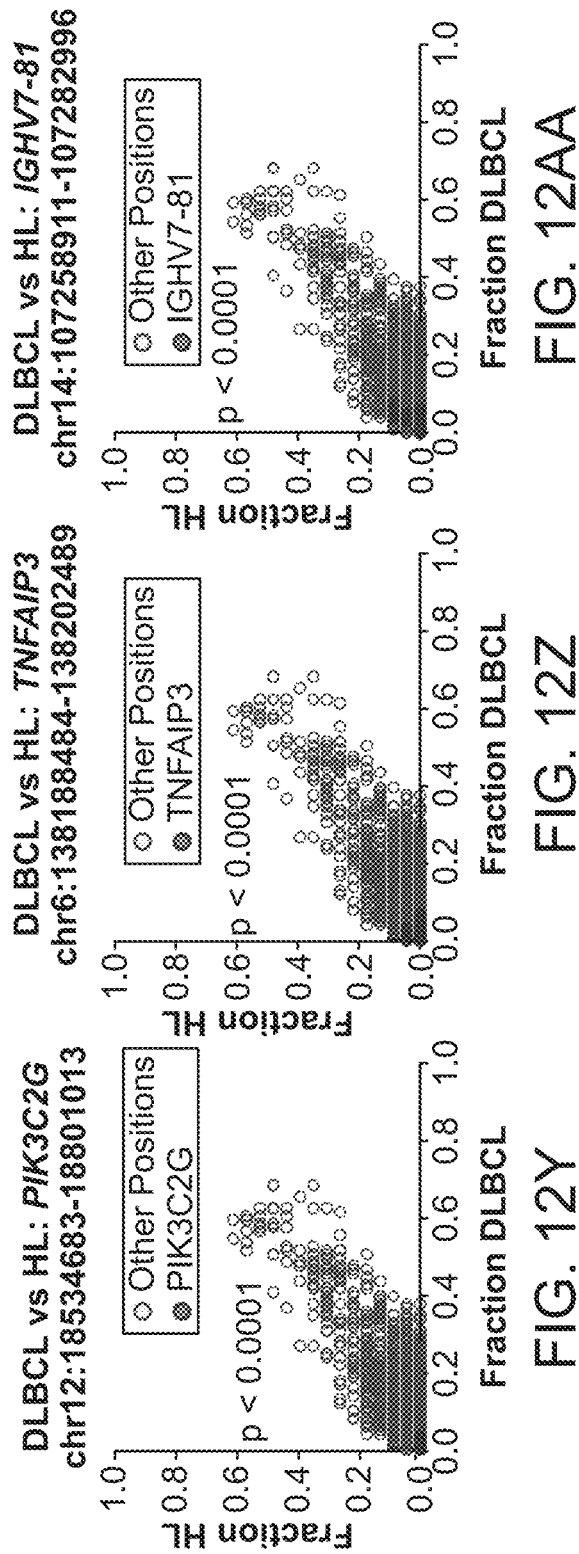
Figures 12H, 12I, 12J:
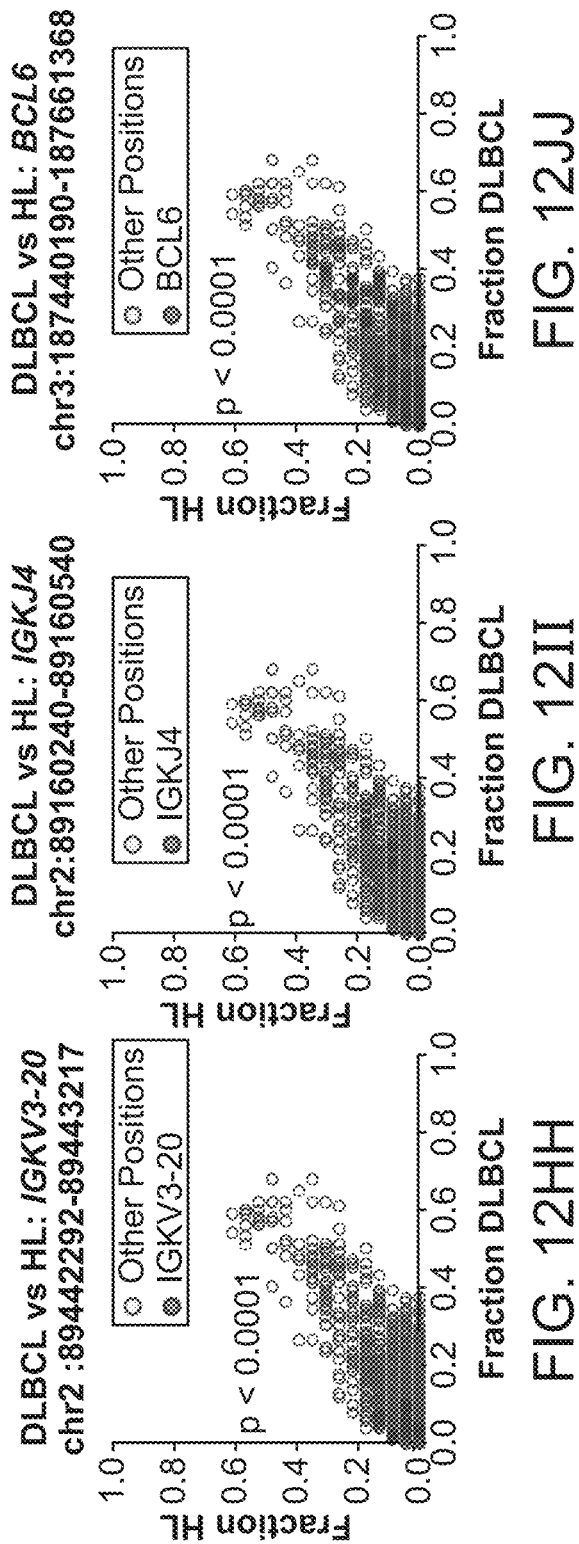
Figure 13:
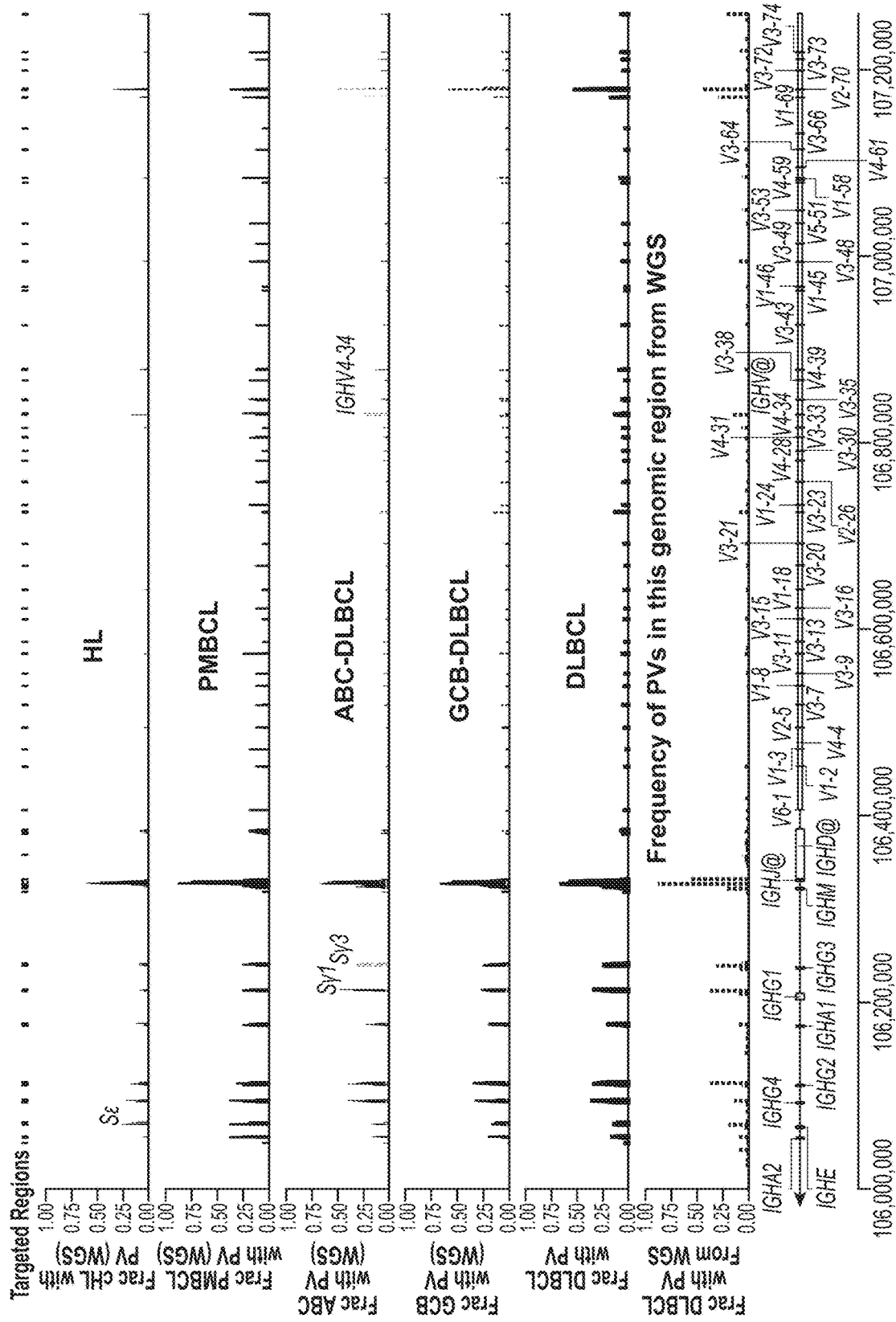
FIG. 13 illustrates differences in PVs between lymphoma types in mutations in the IGH locus. This figure shows the frequency of PVs from PhasED-Seq across the @IGH locus for different types of B-cell lymphomas. The bottom track shows the structure of the @IGH locus and gene-parts, including Ig-constant genes and V-genes. The next (outlined) track shows the frequency of PVs in this genomic region from WGS data (ICGC cohort). The remainder of the tracks show the frequency of PVs from PhasED-Seq targeted sequencing data, including 1) DLBCL, GCB-DLBCL, ABC-DLBCL, PMBCL, and HL. The regions targeted by the PhasED-Seq panel are shown at the top. Selected immunoglobulin parts with PVs enriched in specific histologies are labeled (i.e., IGHV4-34, Sε, Sγ3 and Sγ1).

Having validated the PhasED-Seq panel, the biological differences in PVs between various B-cell malignancies, including DLBCL (n=101), primary mediastinal B-cell lymphoma (PMBCL) (n=16), and classical Hodgkin lymphoma (cHL) (n=23) were examined. The number of SNVs identified per case was not significantly different between lymphoma subtypes (FIGS. 9G-9K). However, when considering mutational haplotypes, cHL had a significantly lower burden of PVs than either DLBCL or PMBCL. In addition to this quantitative disparity, differences in the genomic locations of PVs between different B-cell lymphoma subtypes were also observed (FIGS. 2D-2E and FIGS. 10-12). This included previously established biological associations in DLBCL subtypes, including more frequent PVs in BCL2 in GCB-type than ABC-type DLBCL, with the opposite association seen for PIM1. More frequent PVs in CIITA in PMBCL compared with DLBCL, a gene in which breakpoints are common in PMBCL, was also observed. Relative enrichments were also observed throughout the IGH locus, with more frequent PVs seen in Sγ3 and Sγ1 regions in ABC-DLBCL (compared with GCB-DLBCL) and interestingly, more frequent PVs in the Sε locus in cHL compared with DLBCL (FIG. 2E and FIG. 13). In total, after correcting for testing multiple hypotheses, significant relative enrichments in 25 genetic loci between ABC- and GCB-DLBCL, 24 between DLBCL and PMBCL, and 40 between DLBCL and cHL were found (FIG. 10-12).

Example 6: Recovery of Phased Variants Through PhasED-Seq

Figure 3A:
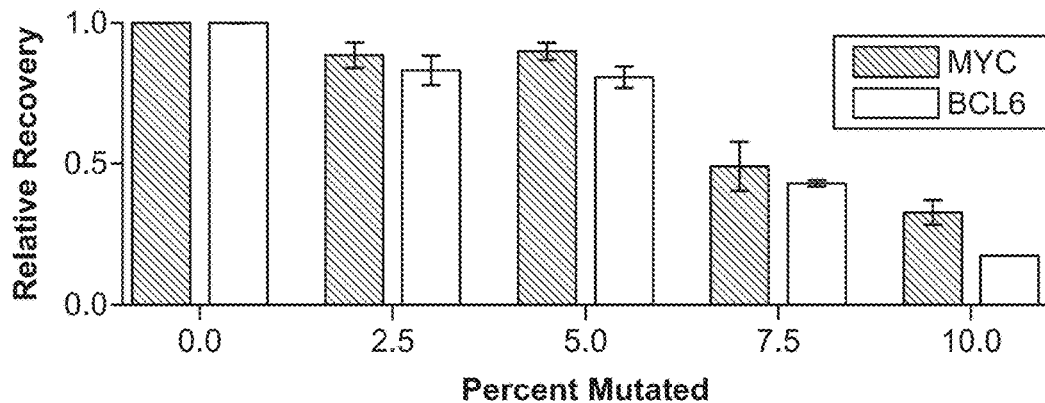
FIGS. 3A-3H illustrate technical performance of PhasED-Seq for disease detection.
Figure 14B:
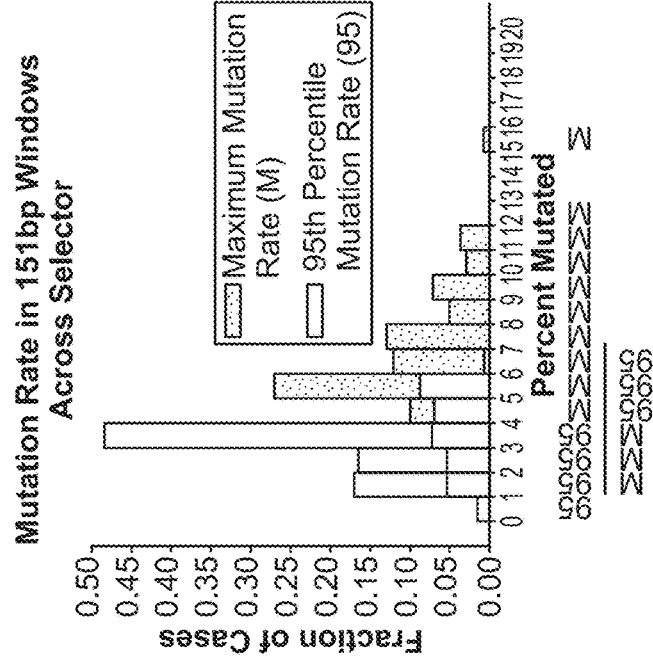
FIGS. 14A-14E illustrate Technical aspects of PhasED-Seq by hybrid-capture sequencing.
Figure 14A:
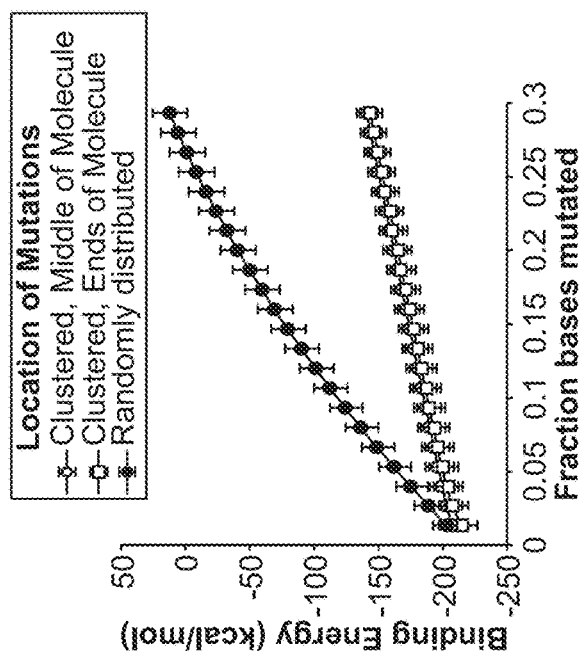
Figure 14C:
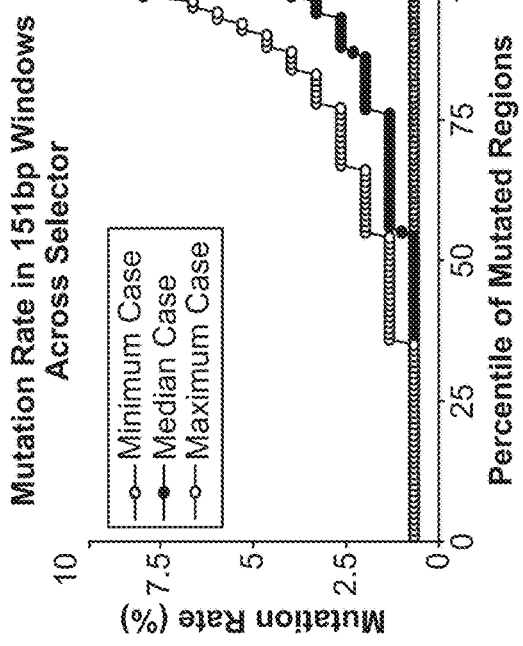

To facilitate detection of ctDNA using PVs, efficient recovery of DNA molecules is desired. Hybrid-capture sequencing is potentially sensitive to DNA mismatches, with increasing mutations decreasing hybridization efficiency. Indeed, AID hotspots can contain a 5-10% local mutation rate, with even higher rates in certain regions of IGH. To empirically assess the effect of mutation rate on capture efficiency, DNA hybridization of 150-mers with varying mutation rates in silico was simulated. As expected, predicted binding energy decreased with an increasing number of mutations (FIG. 14A). Notably, randomly distributed mutations had a greater effect on binding energy than clustered mutations. To assess the effect of this decreased binding affinity, 150-mer DNA oligonucleotides with 0 to 10% difference from the reference sequence in MYC and BCL6, two loci that are targets of aSHM were synthesized. To assess the worst-case scenario for hybridization, non-reference bases were randomly distributed rather than in clusters (Example 10). An equimolar mixture of these oligonucleotides were then captured with PhasED-Seq panel. Concordant with the in silico predictions, increased mutational rates resulted in decreased capture efficiency (FIG. 3A). Molecules with a 5% mutation rate were captured with 85% efficiency relative to fully-wildtype counterparts, while molecules with 10% mutation were captured with only 27% relative efficiency. To assess the prevalence of this degree of mutation in human tumors, the distribution of variants in panel in 140 patients with B-cell lymphomas, calculating the fraction of mutated bases in overlapping 151-bp windows (Example 10) was examined. Only 7% (10/140) of patients had any 151-bp window exceeding 10% mutation rate (FIG. 14B-C). Indeed, in the experiment with synthetic oligonucleotides, a 5% mutation rate was recovered nearly as efficiently as the wild-type sequence. In over half of all cases considered, no locus had >5% mutation rate at any window, while in all cases >90% of windows had <5% mutations. Overall, these observations indicate that the majority of phased mutations are recoverable by efficient hybrid capture, despite hybridization biases.

Example 7: Error Profile and Limit of Detection for Phased Variant Sequencing

Figure 3B:
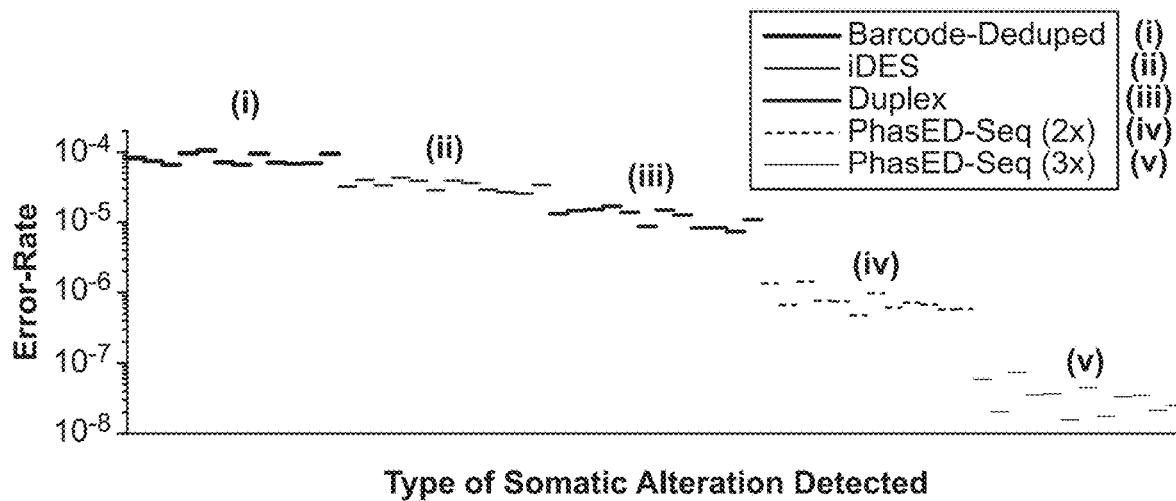
Figure 3C:
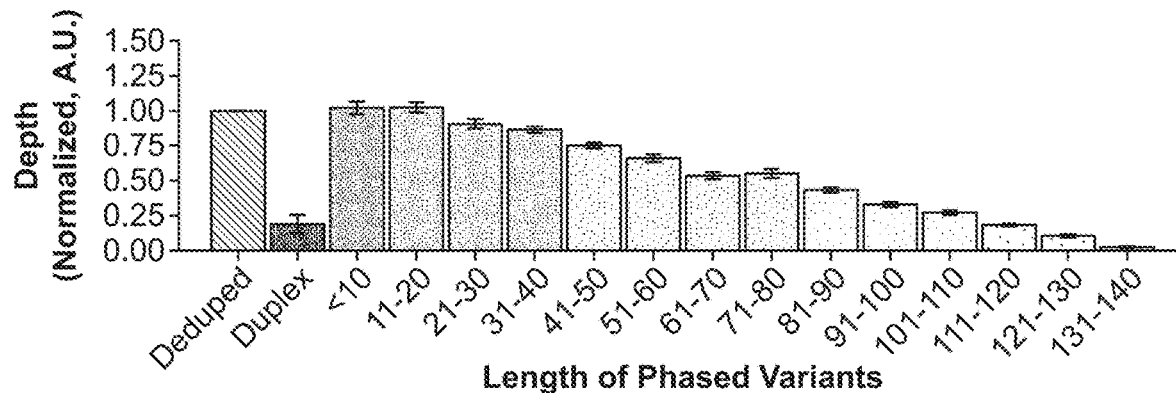
Figure 3D:
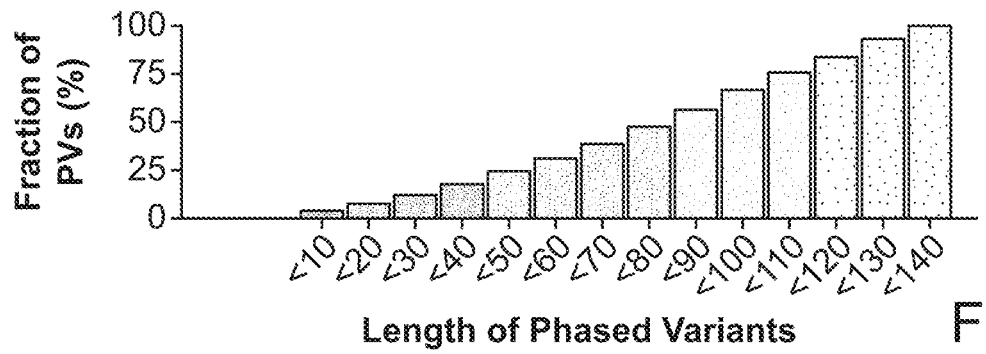
Figure 14D:
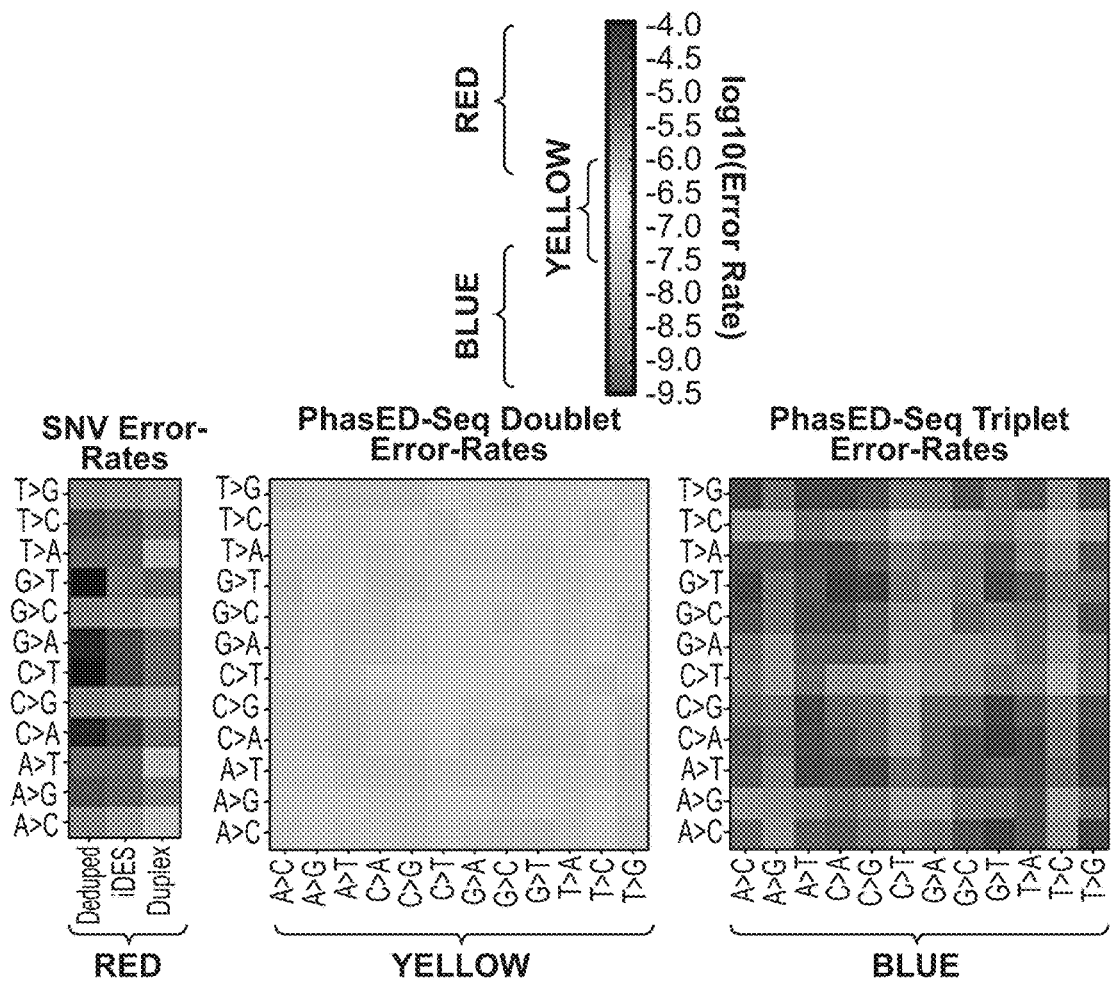
Figure 14E:
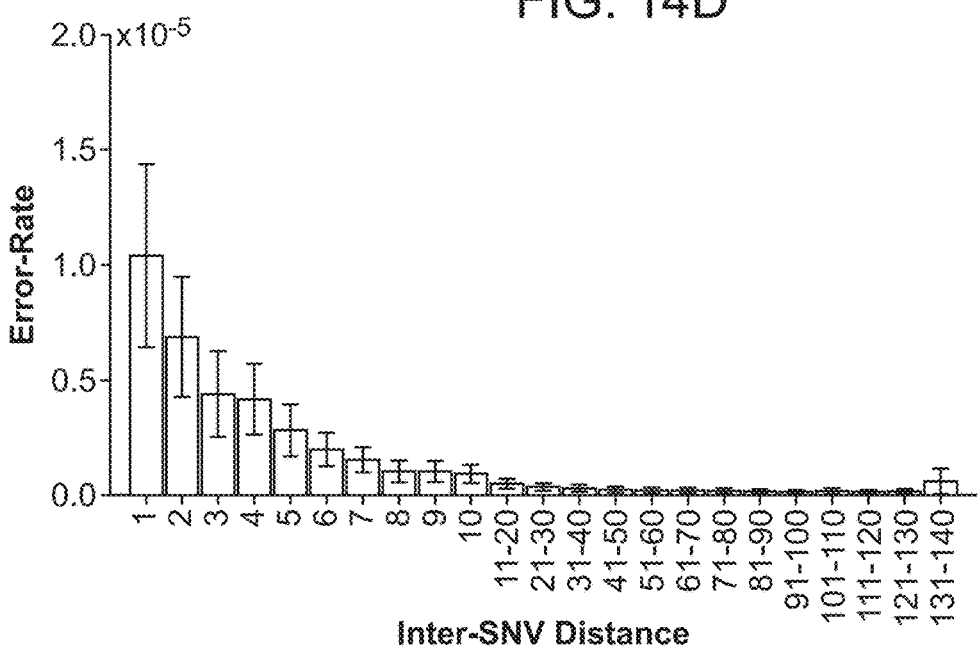

Previous methods for highly error-suppressed sequencing applied to cfDNA have utilized either a combination of molecular and in silico methods for error suppression (e.g., integrated digital error suppression, iDES) or duplex molecular recovery. However, each of these has limitations, either for detecting events at ultra-low tumor fractions or for efficient recovery of original DNA molecules, which are important considerations for cfDNA analysis where input DNA is limited. The error profile and recovery of input genomes from plasma cfDNA samples form 12 heathy adults by PhasED-Seq were compared with both iDES-CAPP-Seq and duplex sequencing. While iDES-enhanced CAPP-Seq had a lower background error profile than barcode-deduplication alone, duplex sequencing offered the lowest background error rate for non-reference single nucleotide substitutions (FIG. 3B, $3.3 \times 10^{-5}$ vs. $1.2 \times 10^{-5}$, P<0.0001). However, the rate of phased errors—e.g., multiple non-reference bases occurring on the same sequencing fragment—was significantly lower than the rate of single errors in either iDES-enhanced CAPP-Seq or duplex sequencing data. This was true for the incidence of both two (2× or 'doublet' PVs) or three (3× or 'triplet' PVs) substitutions on the same DNA molecule (FIG. 3B, $8.0 \times 10^{-7}$ and $3.4 \times 10^{-8}$ respectively, P<0.0001). Phased errors containing C to T or T to C transition substitutions were more common than other types of PVs (FIG. 14D). Notably, the rate doublet PVs errors in cfDNA was also correlated with distance between positions, with the highest PV error-rate consisting of neighboring SNVs (e.g., DNVs) and decreasing error rate with increasing distance between constituent variants (FIG. 14E). When considering unique molecular depth, duplex sequencing recovered only 19% of all unique cfDNA fragments (FIG. 3C). In contrast, the unique depth of PVs within a genomic distance of <20 bp was nearly identical to the depth of individual positions (e.g., molecules covering individual SNVs). Similarly, PVs up to 80 bps in size had depth greater than 50% of the median unique molecular depth for a sample. Importantly, almost half (48%) of all PVs were within 80 bp of each other, demonstrating their utility for disease detection from input-limited cfDNA samples (FIG. 3D).

Figure 3E:
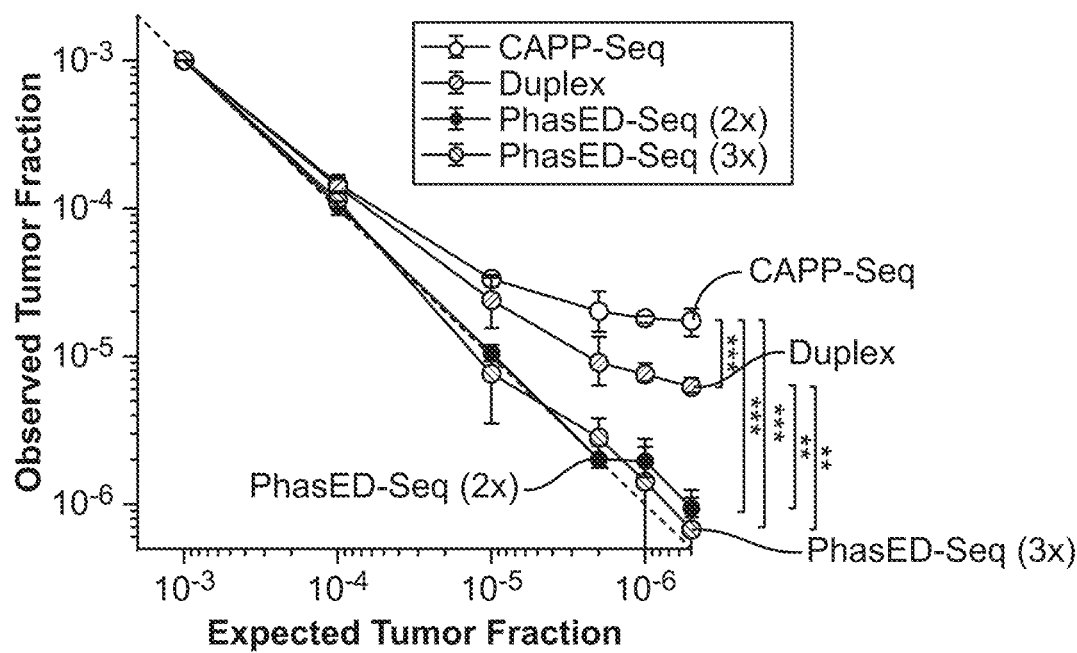
Figure 3F:
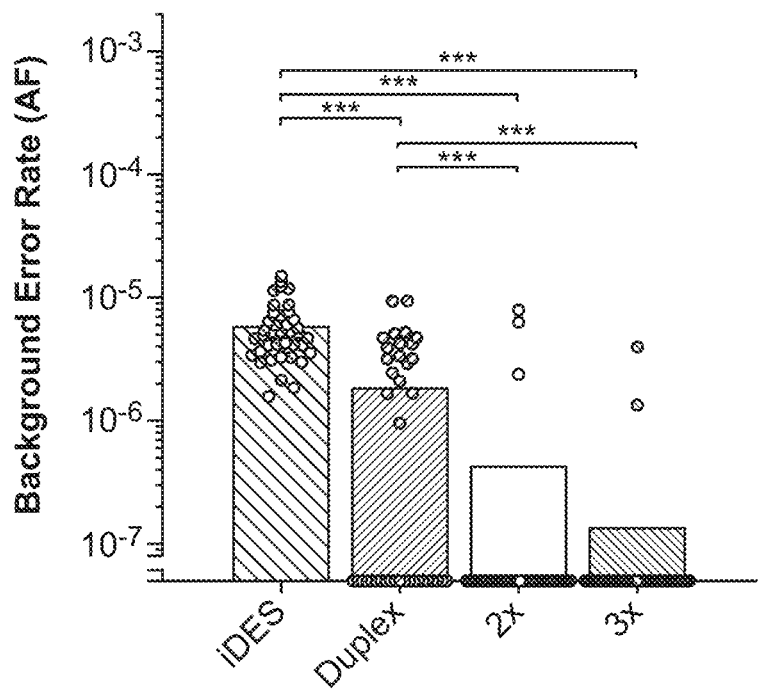
Figure 23A:
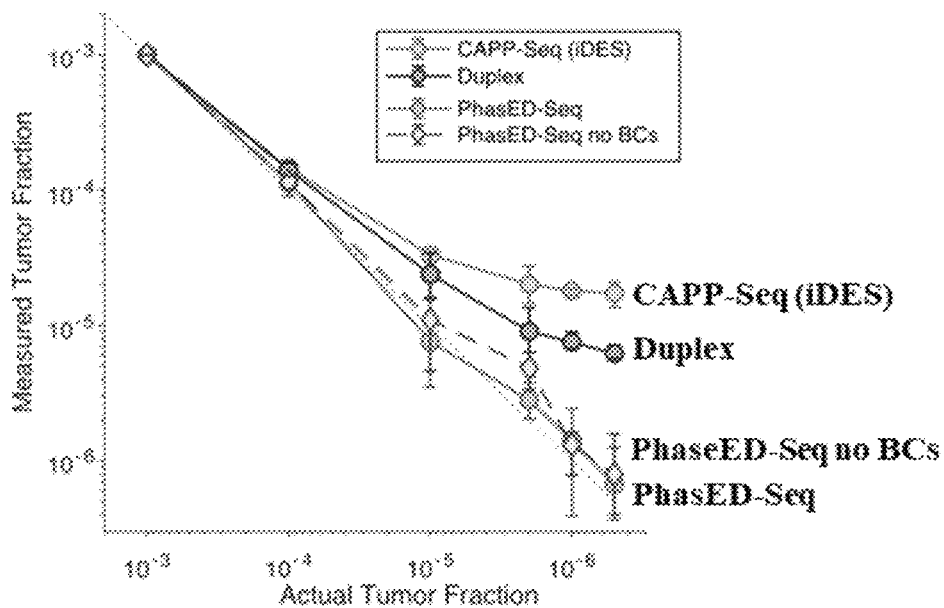
FIGS. 23A-23B illustrate that the method describe herein (e.g. method depicted yielding FIG. 3E and FIG. 3F) does not require barcode meditated error suppression.
Figure 23B:
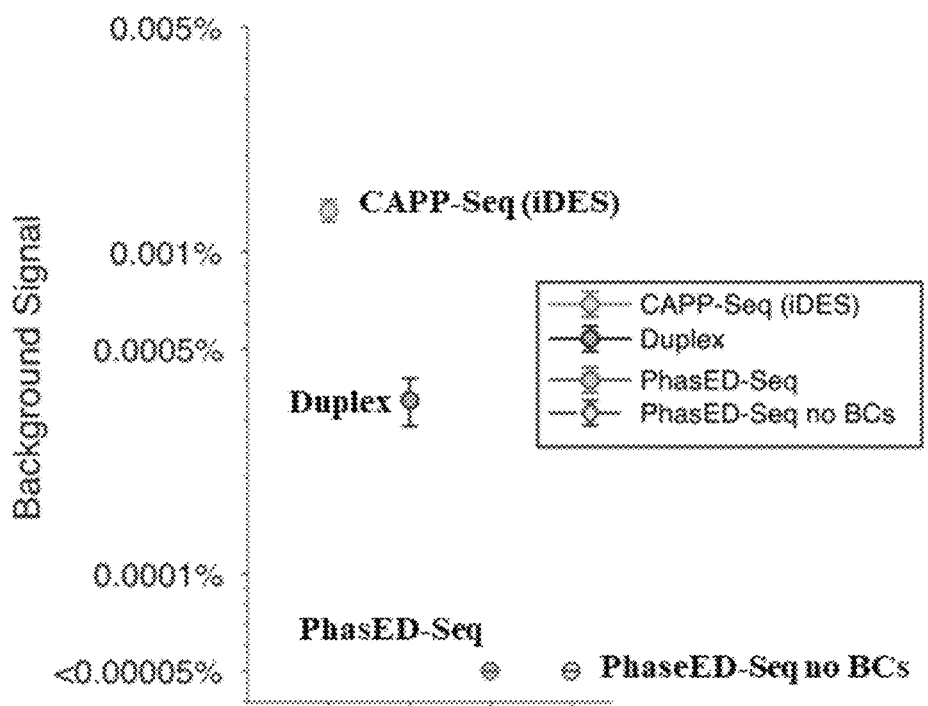

To quantitatively compare the performance of PhasED-Seq to alternative methods for ctDNA detection, limiting dilutions of ctDNA from 3 lymphoma patients into healthy control cfDNA were generated, resulting in expected tumor fractions between 0.1% and 0.00005% (1 part in 2,000,000; (Example 10). The expected tumor fraction was compared to the estimated tumor content in each of these dilutions using PhasED-Seq to track tumor-derived PVs, as well as to error-suppressed detection methods depending on individual SNVs (e.g. iDES-enhanced CAPP-Seq or duplex sequencing; FIG. 3E). All methods performed equally well down to tumor fractions of 0.01% (1 part in 10,000). However, below this level (e.g., 0.001%, 0.0002%, 0.0001%, and 0.00005%), both PhasED-Seq and duplex sequencing significantly outperformed iDES-enhanced CAPP-Seq (P<0.0001 for duplex, '2×' PhasED-Seq, and '3×' PhasED-Seq; FIG. 3E). In addition, when compared to duplex-sequencing, tracking either 2 or 3 variants in-phase (e.g., 2× and 3× PhasED-Seq) more accurately identified expected tumor content, with superior linearity down to 1 part in 2,000,000 (P=0.005 for duplex vs 2× PhasED-Seq, P=0.002 for 3× PhasED-Seq) (Example 10). Specificity of PVs by looking for evidence of tumor-derived SNVs or PVs in cfDNA samples from 12 unrelated healthy control subjects and the healthy control used for the limiting dilution was assessed. Here again, both 2×- or 3×-PhasED-Seq showed significantly lower background signal levels than did CAPP-Seq and duplex sequencing (FIG. 3F). This lower error rate and background from PVs improves the detection limit for ctDNA disease detection. In some instances, the method of sequencing-based cfDNA assays described herein (e.g. the method depicted in FIG. 3E and FIG. 3F) does not require molecular barcodes to achieve exquisite error-suppression and low limits of detection. Signal assessed by the method without barcode used limiting dilution series from 1:1,000 to 5:10,000,000, and 'blank' controls (FIGS. 23A-23B).

Figure 3G:
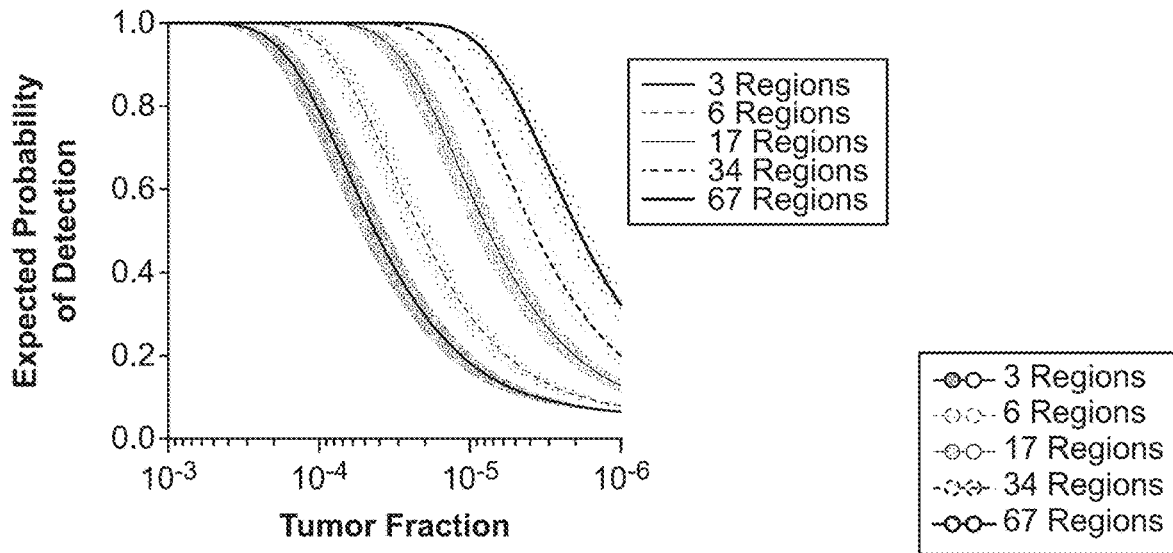
Figure 3H:
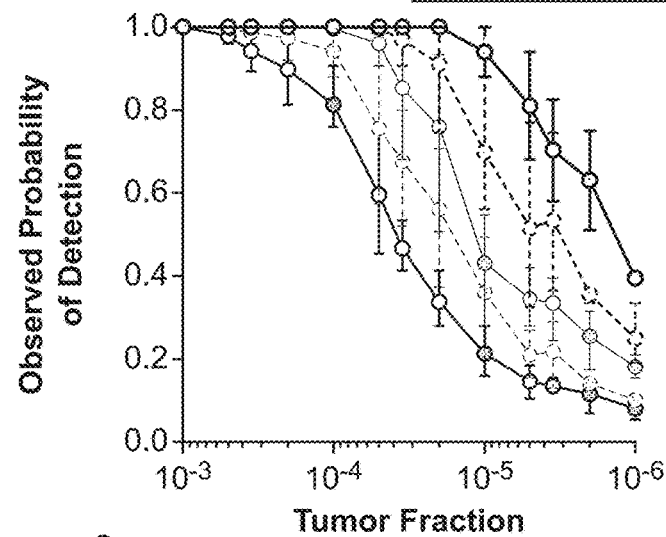
Figure 3I:
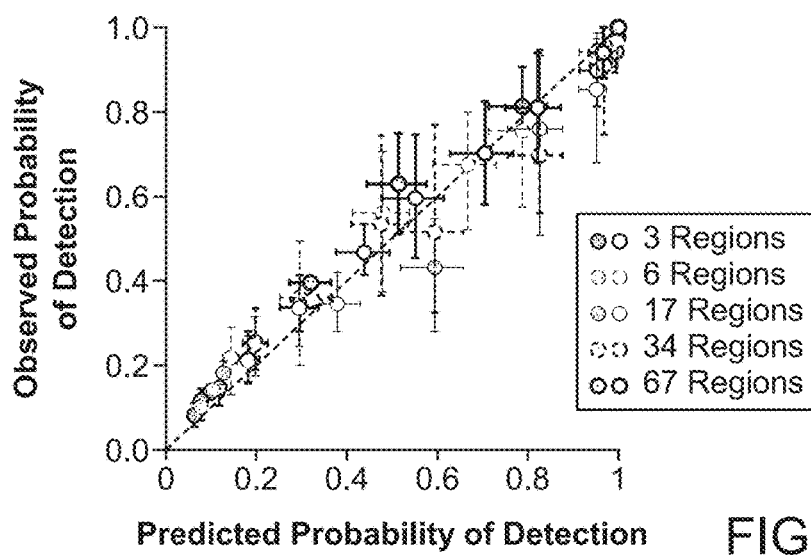
FIG. 3I illustrates scatter plot compares the predicted vs observed rate of detection for samples from the dilution series shown in panels FIG. 3G and FIG. 3H. Additional details of this experiment are provided in Example 10.

This dilution series was used to assess the limit of detection for a given number of PVs (FIGS. 3G-3I). When considering a set of PVs within 150 base pair (bp) regions, the probability of detection for a given sample may be accurately modelled by binomial sampling, considering both the depth of sequencing and the number of 150 bp regions with PVs (Example 10).

Example 8: Improvements in Detection of Low-Burden Minimal Residual Disease

To test the utility of the lower LOD afforded by PhasED-Seq for detection of ultra-low burden MRD from cfDNA, Serial cell-free DNA samples were sequenced from a patient undergoing front-line therapy for DLBCL (FIG. 4A). Using CAPP-Seq, this patient had undetectable ctDNA after only one cycle of therapy, with multiple subsequent samples during and after treatment also remaining undetectable. This patient had subsequent re-emergence of detectable ctDNA >250 days after the start of therapy, with eventual clinical and radiographic disease progression 5 months later, indicating falsely negative serial measurements with CAPP-Seq. Strikingly, all four of the plasma samples that were undetectable by CAPP-Seq during and after treatment had detectable ctDNA levels by PhasED-Seq, with mean allelic fractions as low as 6 parts in 1,000,000. This increased sensitivity improved the lead-time of disease detection by ctDNA compared to radiographic surveillance from 5 with CAPP-Seq to 10 months with PhasED-Seq.

Figures 4D, 4E, 4F, 4G:
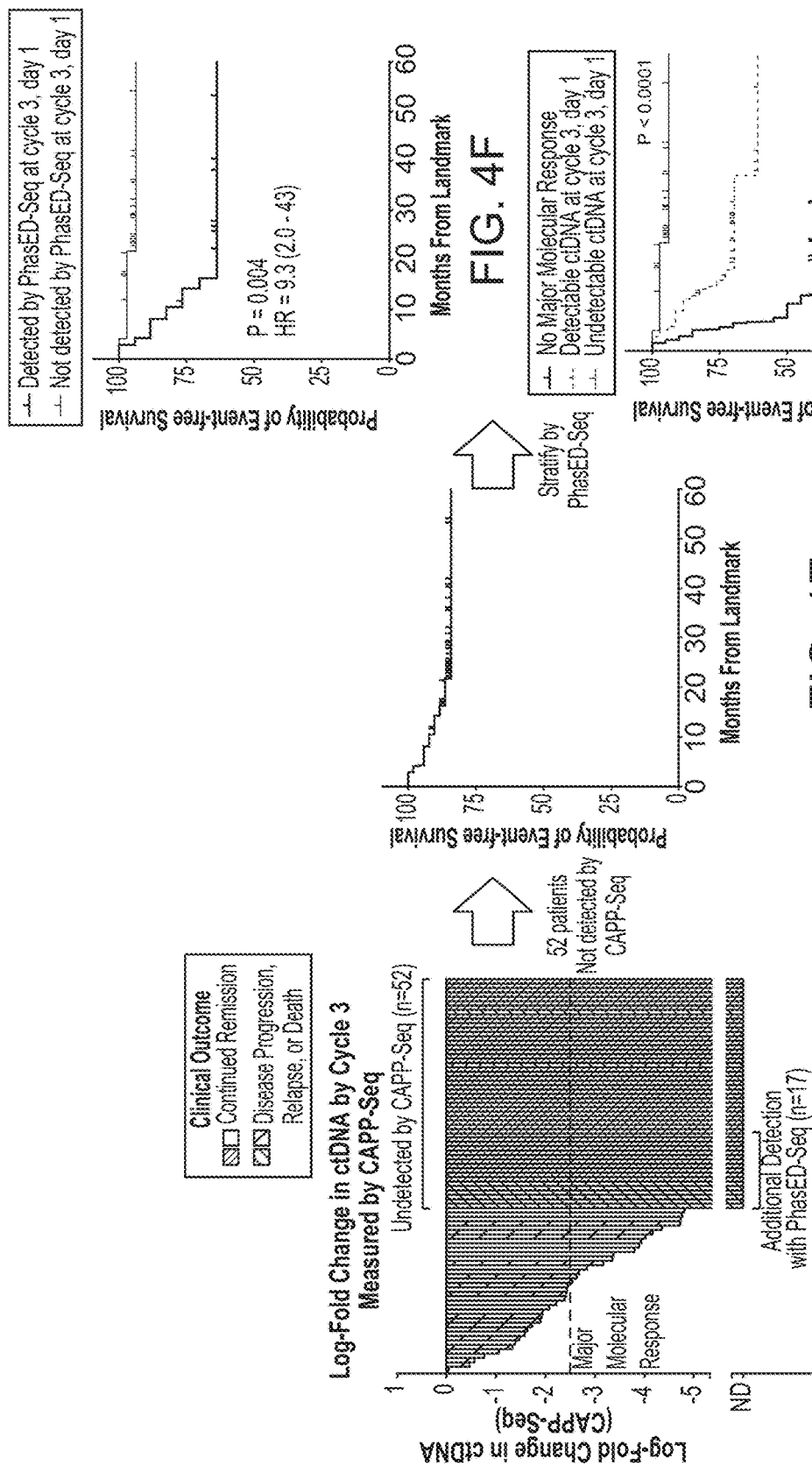
Figure 15:
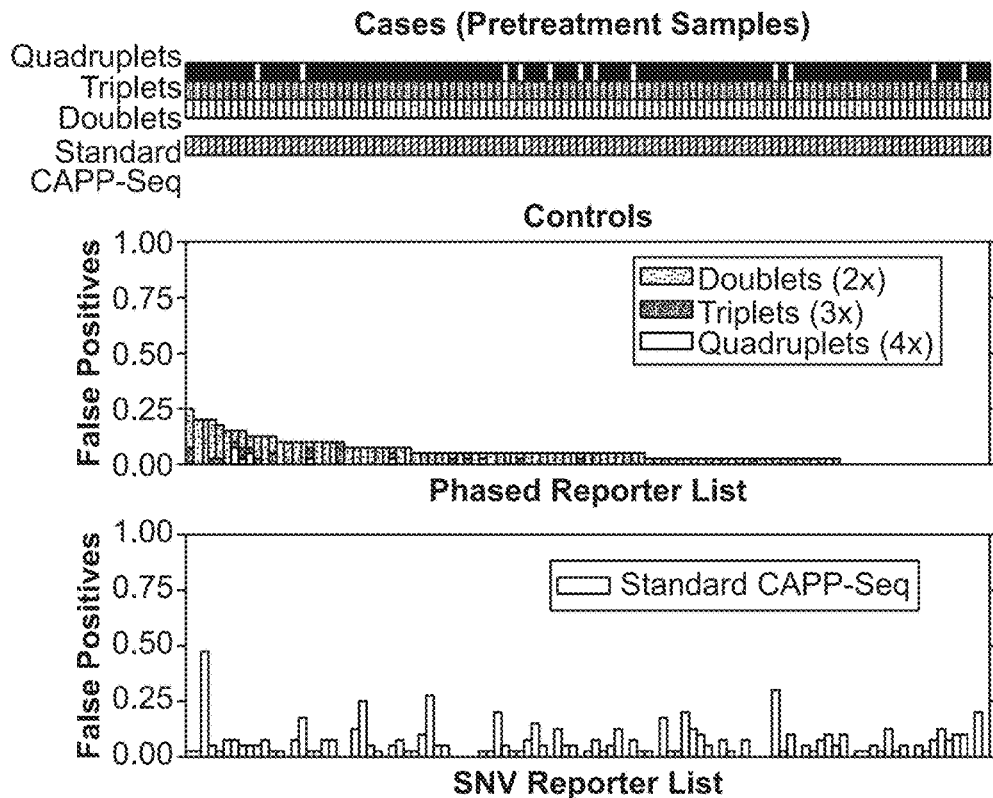
FIGS. 15 and 16A-16B illustrate comparison of ctDNA quantitation by PhasED-Seq to CAPP-Seq and clinical applications.
Figure 16A:
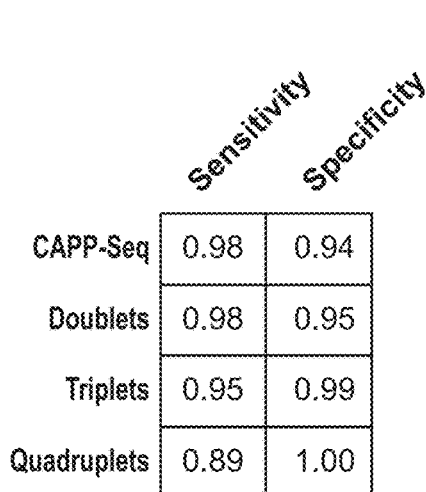
Figure 16B:
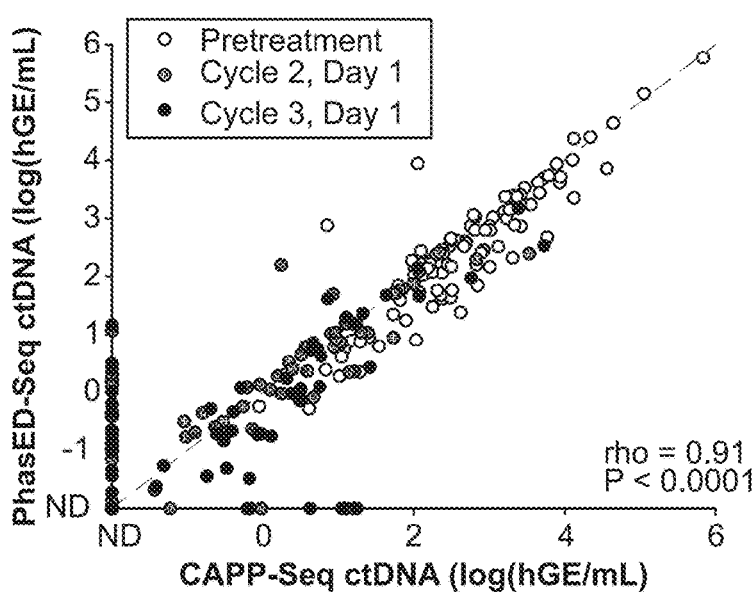

Next, the performance of PhasED-Seq ctDNA detection in a cohort of 107 patients with large B-cell lymphomas and blood samples available after 1 or 2 cycles of standard immuno-chemotherapy was next assessed. Importantly, ctDNA levels measured by PhasED-Seq were highly correlated with those measured by CAPP-Seq. In total, 443 tumor, germ-line, and cell-free DNA samples, including cfDNA prior to therapy (n=107) and after 1 or 2 cycles of treatment (n=82 and 89), were assessed. Prior to therapy, patient-specific PVs were detectable by PhaseED-Seq in 98% of samples, with 95% specificity in cfDNA from healthy controls (FIGS. 15 and 16A). Importantly, ctDNA levels measured by PhasED-Seq were highly correlated with those measured by CAPP-Seq, considering both pretreatment and post treatment samples (Spearman rho=0.91, FIG. 16B). Next, quantitative levels of ctDNA measured by PhasED-Seq and CAPP-Seq from cfDNA samples after initiation of therapy were compared. In total, 72% (78/108) of samples with detectable ctDNA by PhasED-Seq after 1 or 2 cycles were also detected by conventional CAPP-Seq (FIG. 4B). Among 108 samples detected by PhasED-Seq, disease burden was significantly lower for those with undetectable (28%) vs. detectable (72%) ctDNA levels using conventional CAPP-Seq, with a >10× difference in median ctDNA levels (tumor fraction $2.2 \times 10^{-4}$ vs $1.2 \times 10^{-5}$, P<0.001, FIG. 4B). In total, an additional 16% (13/82) of samples after 1 cycle of therapy and 19% (17/89) of samples after 2 cycles of therapy had detectable ctDNA when comparing PhasED-Seq with CAPP-Seq (FIG. 4C).

ctDNA molecular response criteria was previously described for DLBCL patients using CAPP-Seq, including Major Molecular Response (MMR), defined as a 2.5-log reduction in ctDNA after 2 cycles of therapy 22. While MMR at this time-point is prognostic for outcomes, many patients have undetectable ctDNA by CAPP-Seq at this landmark (FIGS. 4D-4E). Importantly, even in patients with undetectable ctDNA by CAPP-Seq, detection of occult ultra-low ctDNA levels by PhasED-Seq was prognostic for outcomes including event-free and overall survival (FIG. 4D). Indeed, in the 89 patients with a sample available from this time-point, 58% (52/89) had undetectable ctDNA by CAPP-Seq at their interim MMR assessment, after completing 2 of 6 planned cycles of therapy. Using PhasED-Seq, 33% (17/52) of samples not detected by CAPP-Seq had evidence of ctDNA as evidenced by PVs, with levels as low as 3:1,000,000 (FIGS. 17A-17D)—these 17 cases additionally detected by PhasED-Seq represent potential false negative tests by CAPP-Seq. Similar results were seen at the Early Molecular Response (EMR) time-point (i.e., after 1 cycle of therapy, FIGS. 18A-18H).

While detection of ctDNA in DLBCL after 1 or 2 cycles of therapy is a known adverse prognostic marker outcomes for patients with undetectable ctDNA at these time-points are heterogeneous (FIG. 4E and FIG. 18F). Importantly, even in patients with undetectable ctDNA by CAPP-Seq after 1 or 2 cycles of therapy, detection of ultra-low ctDNA levels by PhasED-Seq was strongly prognostic for outcomes including event-free survival (FIG. 4F, FIGS. 17C-D, FIGS. 18C-D, and FIG. 18G). When combining detection by PhasED-Seq with previously described MMR threshold, patients could be stratified into three groups—patients not achieving MMR, patients achieving MMR but with persistent ctDNA, and patients with undetectable ctDNA (FIG. 4G). Interestingly, while patients not achieving MMR were at especially high risk for early events despite additional planned first line therapy (e.g., within the first year of treatment), patients with persistent low levels of ctDNA appeared to have a higher risk of later relapse or progression events. In contrast, patients with undetectable ctDNA after 2 cycles of therapy by PhasED-Seq had overwhelmingly favorable outcomes, with 95% being event-free and 97% overall survival at 5 years. Similar results were seen at the EMR time-point after 1 cycle of therapy (FIG. 18H).

Example 9: Exemplary Embodiments of Mutation Detection Using Next Generation Sequencing (NGS) when the Mutation is not a Single Base Substation, but Rather a Pair of Mutations In many instances, a limitation of cfDNA tracking may be the limitation on the number of molecules available for detection. Additionally, there are multiple potential limitations on tracking tumor molecules from cell-free DNA, including not only the sequencing error profile, but also the number of molecules available for detection. The number of molecules available for detection—here termed the number of "evaluable fragments"—can be thought of as both a function of the number of recovered unique genomes (e.g., unique depth of sequencing) and the number of somatic mutations being tracked. More specifically, the number of evaluable fragments is equal to: $EF=d*n$.

Where d=the unique molecular depth considered and n=the number of somatic alterations tracked. For the typical cell-free DNA samples, less than 10,000 unique genomes are often recovered (d), requiring any sensitive method to track multiple alterations (n). Furthermore, as stated above, the major limitation for duplex sequencing is difficulty recovering sufficient unique molecular depth (d); thus, from a typical plasma sample with duplex depth of ~1,500×, even if following 100 somatic alterations, there are only 150,000 evaluable fragments. Thus, in this scenario, sensitivity is limited by the number of molecules available for detection. In contrast, other methods such as iDES-enhanced CAPP-Seq consider all molecules recovered. Here, as many as 5,000-6,000× unique haploid genomes can be recovered. Therefore, the number of evaluable fragments, tracking the same 100 somatic alterations, may be 500,000-600,000×. However, the error profile of single-stranded sequencing, even with error suppression, allows detection to levels of at best 1 part in 50,000. Therefore, methods aiming to improve on the detection limits for ctDNA must overcome both the error-profile of sequencing and the recovery of sufficient evaluable fragments to utilize said lower error-profiles.

To remedy this apparent deficiency, the method of PhasED-Seq, as described in the instant disclosure, allows for lymphoid malignancies and was applicable to other cancer histologies, (e.g., using a "personalized" approach). For a personalized approach, customized hybrid-capture oligonucleotides (or primers for PCR amplicons) were used to capture personalized somatic mutations identified from whole exome or genome sequencing. The PCAWG dataset assessed for SNVs occurring within 170 bp of each other in genomic space was re-analyzed. It was found that in 14 of 24 cancer histologies considered, the median case contained >100 possible phased variants, including in several solid tumors such as Melanoma (median 2072), lung squamous cell carcinoma (1268), lung adenocarcinoma (644.5), and colorectal adenocarcinoma (216.5).

Figure 19:
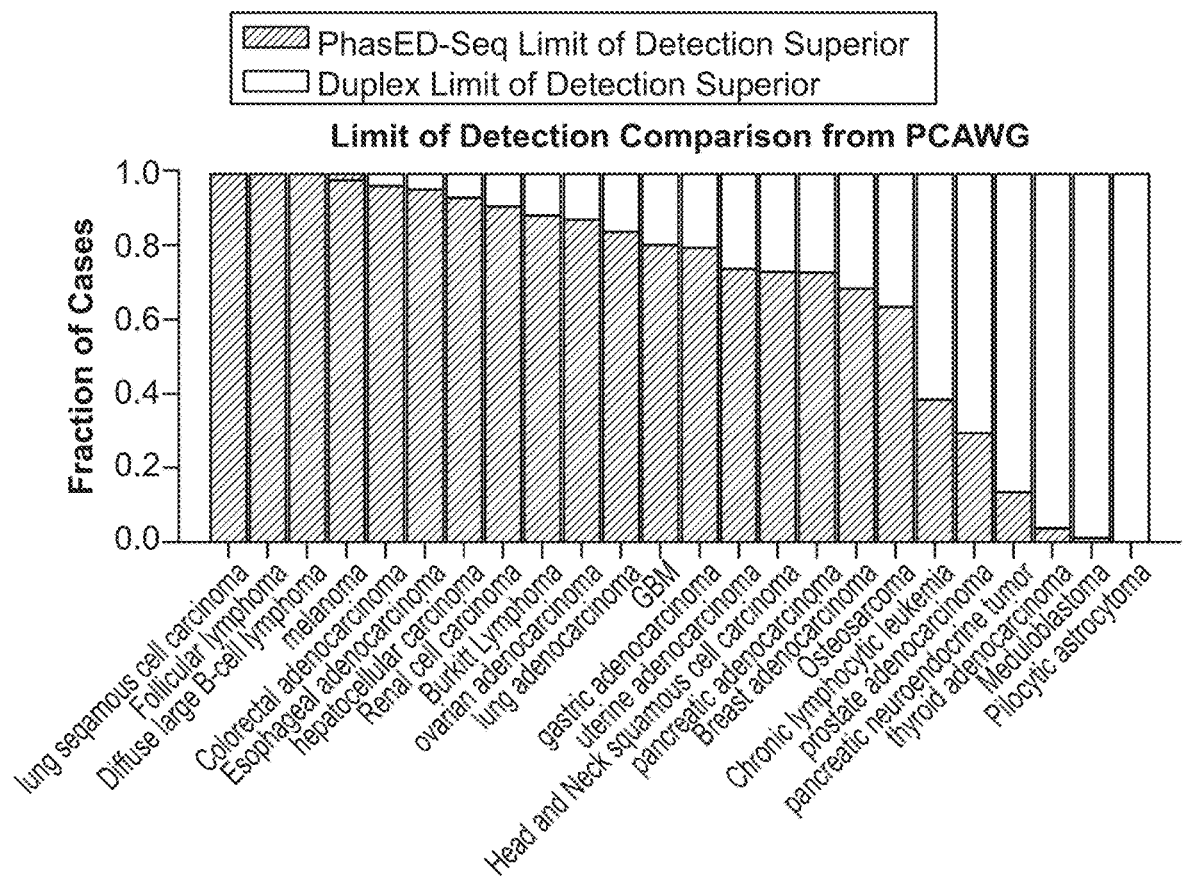
FIG. 19 illustrates a fraction of patients where PhasED-Seq would achieve a lower LOD than duplex sequencing tracking SNVs based on PCAWG data (whole genome sequencing) from which the number of SNVs and phased variants (PVs) in different tumor types was quantified.
Figure 20:
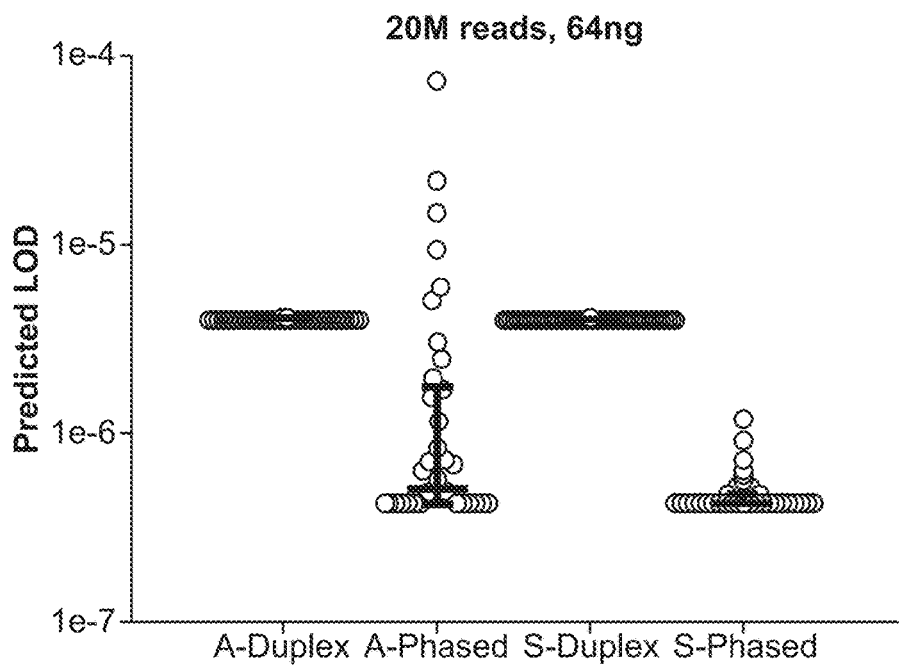
FIG. 20 illustrates improved LODs achieved in lung cancers (adenocarcinoma, abbreviated 'A', and squamous cell carcinoma, abbreviated S'), compared to duplex sequencing of whole genome sequencing data.

Next, the expected limit of detection in all cases in the PCAWG dataset using either duplex sequencing or PhasED-Seq was assessed. Again, the limit of detection was defined by the expected number of evaluable fragments, and thus depends on both the number of variants tracked and the expected depth of sequencing. Utilizing the data from optimized hybrid capture conditions, a model to predict the expected deduplicated (single-stranded) and duplex (double-stranded) molecular depth with a given DNA input and number of sequencing reads was constructed. Using this, along with the number of SNVs or possible PVs from the PCAWG dataset, for each case, which method would lead to a greater number of evaluable fragments, and therefore a superior limit of detection was assessed. The results of this exercise, assuming 64 nanograms (ng) of total cfDNA input and a total of 20 million sequencing reads are shown in FIG. 19. Notably, in the majority of cancer types (18/24 histologies), PhasED-Seq had a lower limit of detection than duplex sequencing. This importantly included not only B-cell lymphomas, but common solid tumors, including lung squamous cell carcinoma and adenocarcinoma, colorectal adenocarcinoma, esophageal and gastric adenocarcinoma, and breast adenocarcinoma, among others. Indeed, taking lung cancers as a specific example, an almost 10-fold lower limit of detection was found for the median squamous cell and adenocarcinoma lung cancer case using PhasED-Seq compared to duplex sequencing (FIG. 20). Both PhasED-Seq and duplex sequencing using a personalized approach had a lower limit of detection than non-personalized approaches (e.g., iDES-enhanced CAPP-Seq).

Figure 21:
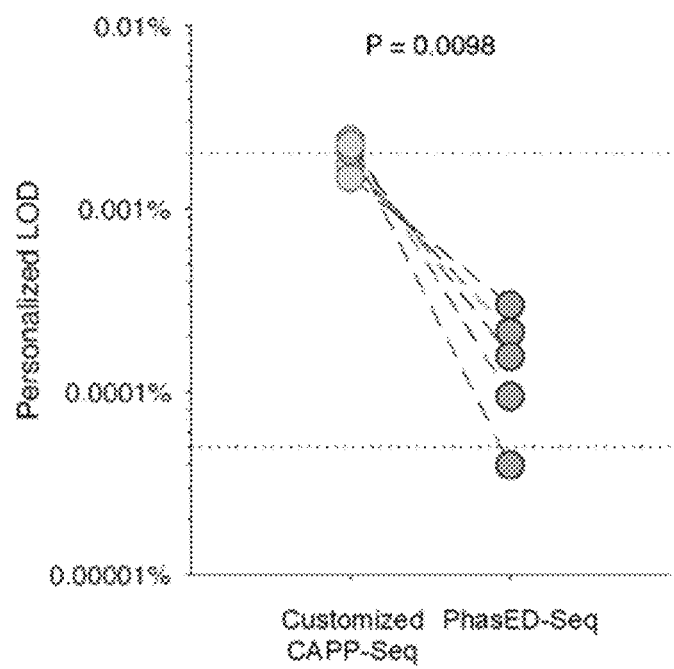
FIG. 21 illustrates empiric data from an experiment where WGS was performed on tumor tissue and custom panels were designed for 5 patients with solid tumors (5 lung cancers) to examine and compare the LODs of custom CAPP-Seq vs PhasED-Seq, showing a ~10× lower LOD using PhasED-Seq in 5/5 patients.

To further confirm the applicability of phased variants and PhasED-Seq in diverse solid tumors, WGS (20-30×) was performed on paired tumor and normal DNA to identify PVs from five solid tumor patients predicted to have low ctDNA burden prior to treatment (lung cancer (n=5)). After identifying putative PVs in each case, a set of personalized hybrid capture oligonucleotides was subsequently designed to performed targeted resequencing of tumor and normal DNA to validate candidate PVs. Finally, plasma samples were sequenced from all 5 patients to high unique molecular depth using personalized PhasED-Seq to detect ctDNA. Considering these five lung cancer cases the PhasED-Seq approach achieved a ~10-fold improvement in analytical sensitivity, achieving a median LOD of 0.00018% compared to 0.0019% using customized CAPP-Seq (FIG. 21).

Figure 22A:
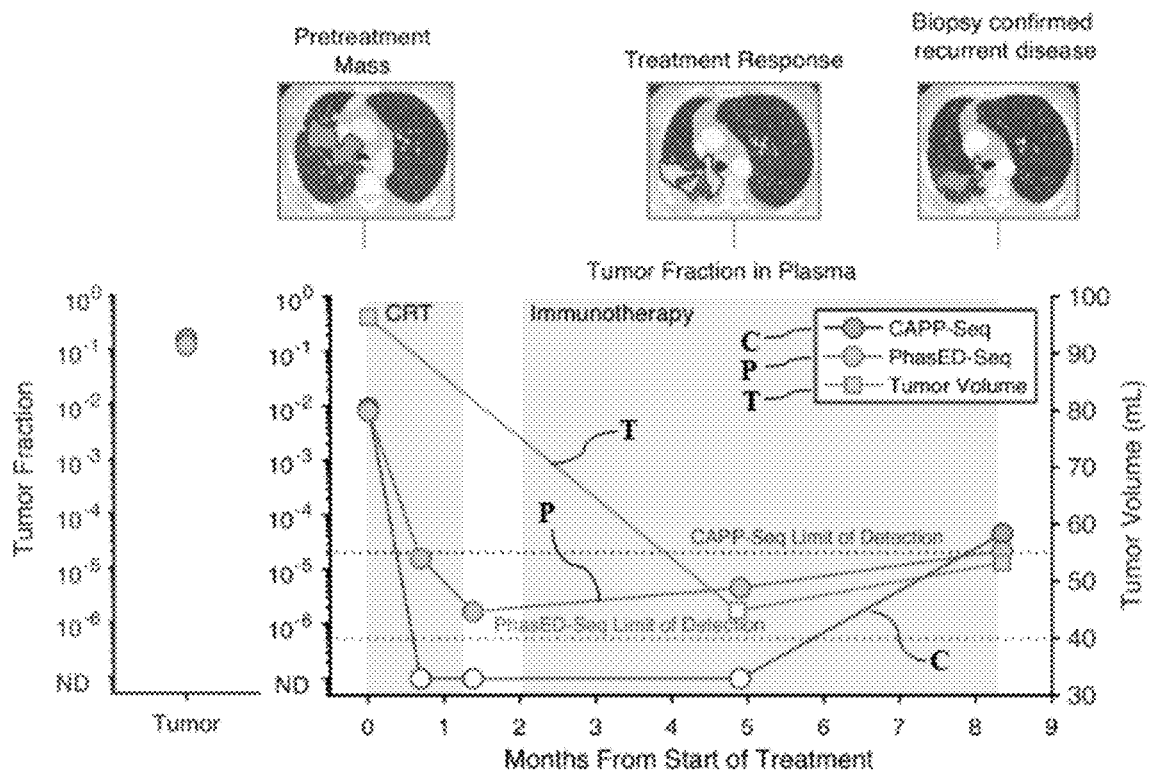
FIG. 22A illustrates proof of principle example patient vignette comparing using custom CAPP-Seq and PhasED-Seq for disease surveillance in lung cancer showing earlier detection of relapse using PhasED-Seq.
Figure 22B:
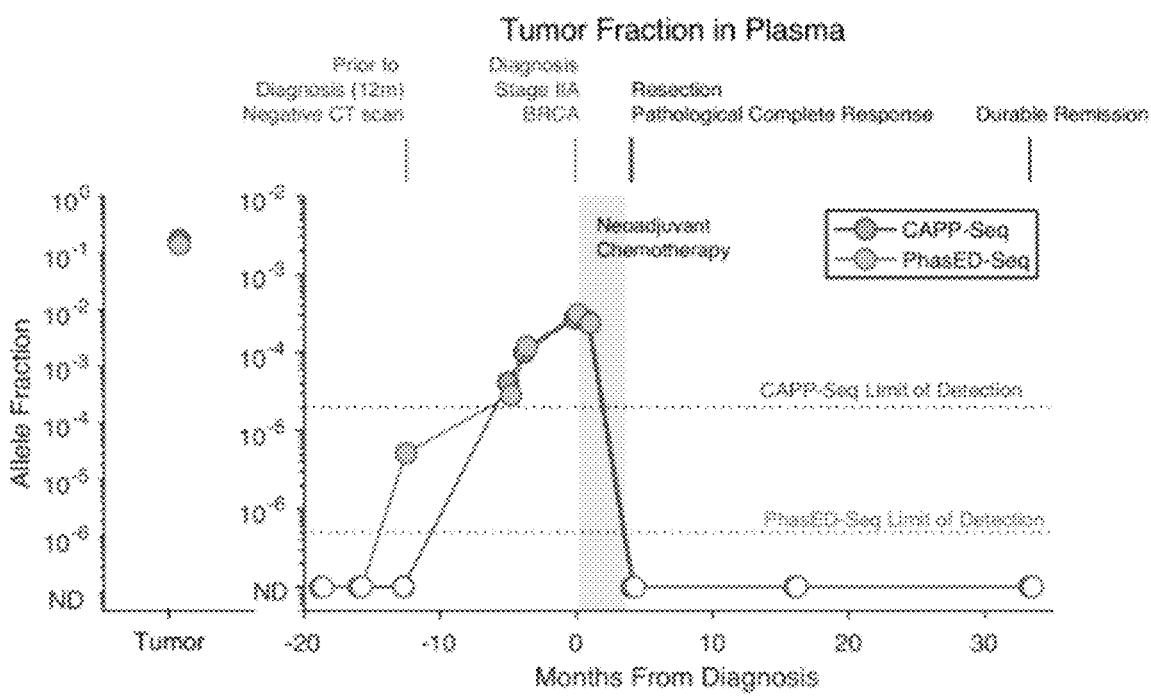
FIG. 22B illustrates proof of principle example patient vignette comparing using custom CAPP-Seq and PhasED-Seq for early detection of disease in breast cancer, showing earlier detection of disease with PhasED-Seq.

To demonstrate the clinical significance of this improved limit of detection for ctDNA from PhasED-Seq in solid tumors, serial plasma samples from a patient with stage 3 adenocarcinoma of the lung treated with chemoradiotherapy with curative intent (LUP814) were analyzed using both CAPP-Seq and PhasED-Seq. As outlined above, both CAPP-Seq and PhasED-Seq quantified a similar level of ctDNA prior to therapy (~1% tumor fraction). However, 3 subsequent samples after beginning therapy had undetectable ctDNA by standard CAPP-Seq, including samples during and after chemoradiation and during adjuvant immunotherapy with Durvalumab. Despite the lack of detectable disease by CAPP-Seq, the patient had biopsy-confirmed recurrent disease after an initial radiographic response. However, when analyzing these same samples with PhasED-Seq, molecular residual disease in 3/3 (100%) of samples was detected, with mean tumor fraction as low as 0.00016% (1.6 parts per million). Furthermore, the trend in ctDNA quantitation mirrored the patient's disease course, with an initial response to chemoradiotherapy but disease progression during immunotherapy. Importantly, this patient's disease remained detectable at all timepoints, with detectable disease at the completion of chemoradiotherapy 8 months prior to the patient's biopsy-confirmed disease progression (FIG. 22).

Figures 5A, 5B:
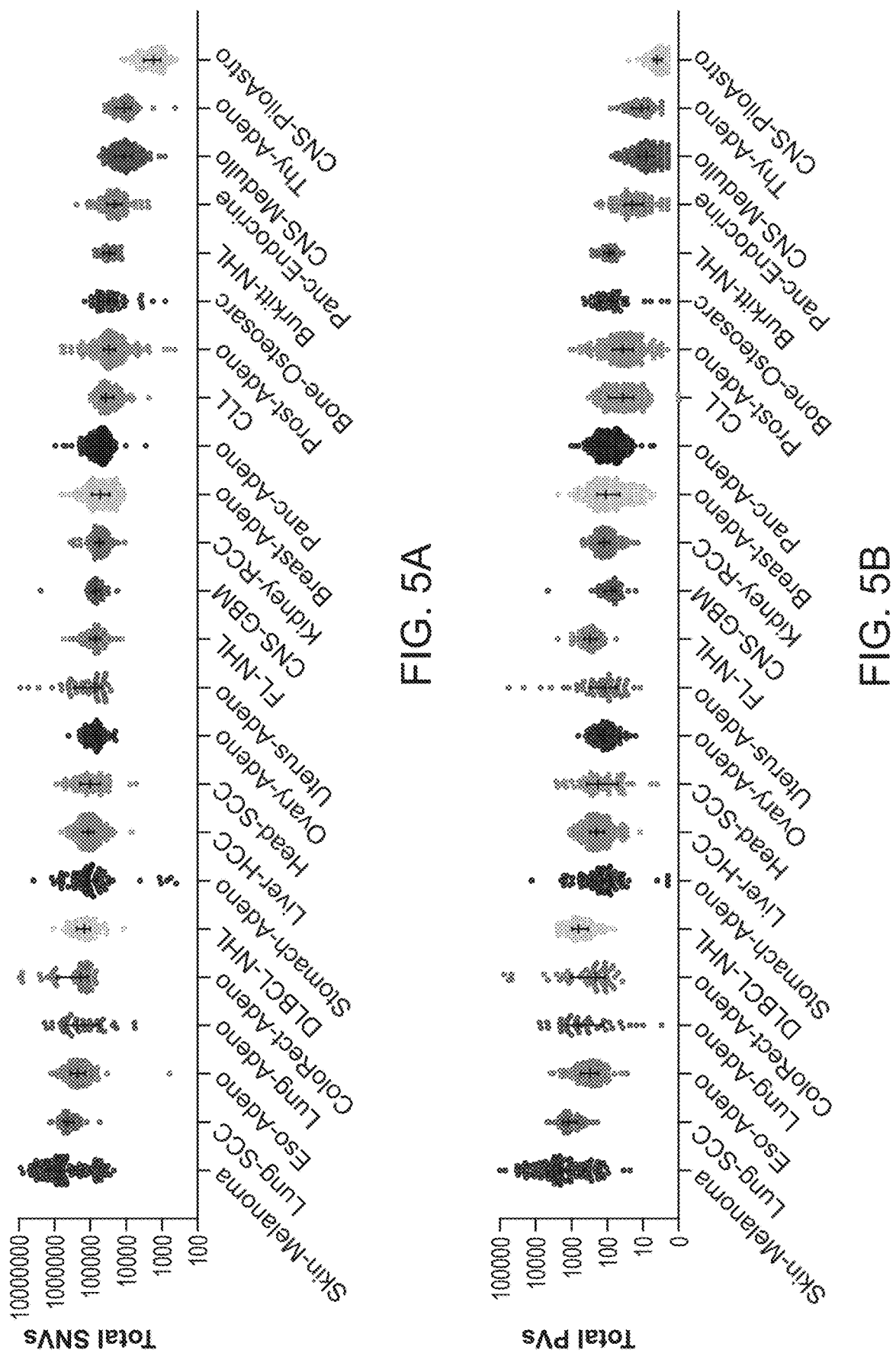
FIGS. 5A-5C illustrate enumeration of SNVs and PVs in diverse cancers from WGS.
Figure 5C:
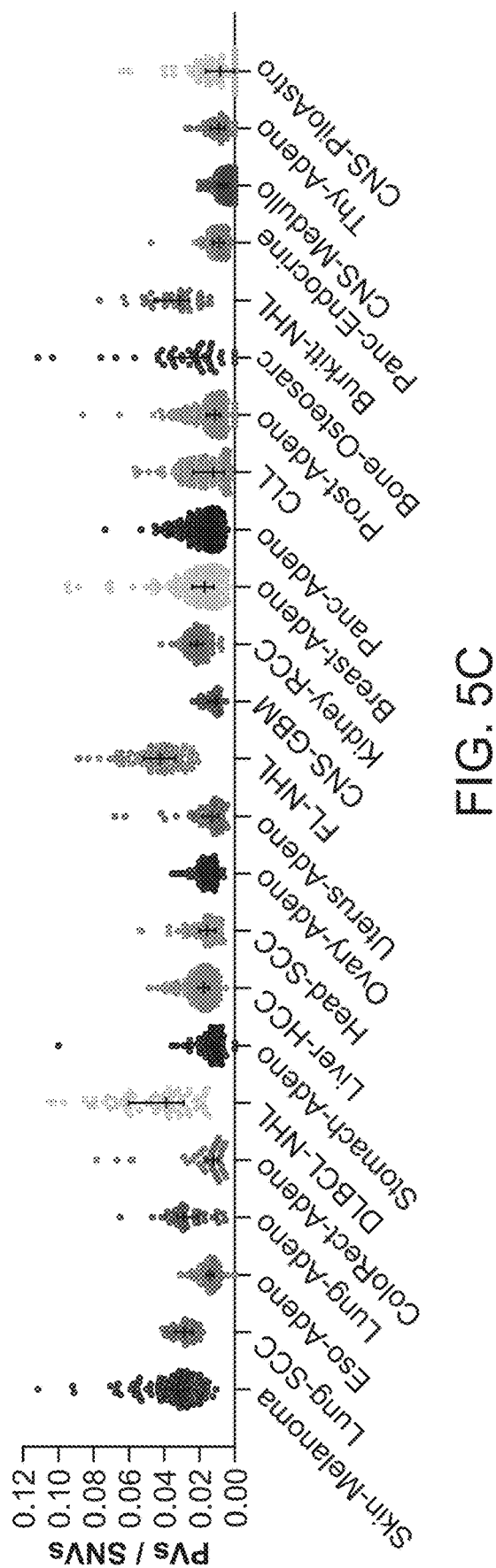

Example 10: Methods of Phased Variant Enrichment for Enhanced Disease Detection from Cell-Free DNA 10(a): Whole-Genome Sequencing Analysis 10(a)(1): Whole-Genome Sequencing Data Putative Phased Variant Identification Whole-genome sequencing data were obtained from two sources. Data for lymphoid malignancies (diffuse large B-cell lymphoma, DLBCL; follicular lymphoma, FL; Burkitt lymphoma, BL; chronic lymphocytic leukemia, CLL) were downloaded from the International Cancer Genome Consortium (ICGC) data portal on May 7, 2018. Data from all other histologies were part of the pan-Cancer analysis of whole genomes (PCAWG) and downloaded on Nov. 11, 2019. Only cancer histologies with at least 35 available cases were considered; details of the dataset considered are provided in Table 1. All samples had somatic mutations called from WGS using matched tumor and normal genotyping. Queries were limited to base substitutions obtained from WGS (single, double, triple, and oligo nucleotide variants; SNVs, DNVs, TNVs, and ONVs). Having thus identified the cases and variants of interest, the number of putative phased variants (PVs) in each tumor was next identified. To function as a PV on a single cell-free DNA (cfDNA) molecule, two variants, such as two single nucleotide variants (SNVs) generally must occur within a genomic distance less than the length of a typical cfDNA molecule (~170 bp). Therefore, putative PVs were defined as two variants occurring on the same chromosome within a genomic distance of <170 bp. DNVs, TNVs, and ONVs were considered as the set of their respective component SNVs. The number of SNVs as well as the identity of putative PVs for each case are detailed in Table 1. The raw number of SNVs and putative PVs, as well as the number of putative PVs controlling for the number of SNVs, is shown in FIG. 5A-C.

10(a)(2): Mutational Signatures of Phased Variants from WGS

To assess the mutational processes associated with phased and non-phased mutations across different cancer types/subtypes, the mutational signatures of single base substitutions (SBS) were enumerated for each WGS case described above using the R package 'deconstructSigs'. The list of SNVs for each patient was first divided into two groups: 1) SNVs contained within a possible PV; that is, with an adjacent or 'nearest neighbor' SNV <170 bp away, and 2) isolated SNVs (i.e., non-phased), defined as those occurring ≥170 bp in distance from the closest adjacent SNV. 'DeconstructSigs' was then applied using the 49 SBS signatures described in COSMIC (excluding signatures linked to possible sequencing artefacts) to assess the contribution of each SBS signature to both candidate phased SNVs and un-phased SNVs for each patient. To compare the contribution of each SBS signature to phased and isolated SNVs, a Wilcoxon signed rank test was performed to compare the relative contribution of each SBS signature between these two categories for each cancer type (FIGS. 6A-6WW). To account for multiple hypotheses, Bonferroni's correction was applied, by considering any SBS signature that differed in contribution to phased vs. un-phased SNVs to be significant if the Wilcoxon signed rank test resulted in a P-value of <0.05/49 or 0.001. The distributions of these comparisons, along with significance testing, are depicted in FIGS. 6A-6WW. A summary of this analysis is also shown in FIG. 1C using a heat-map display, where the 'heat' represents the difference between the mean contribution of the SBS signature to phased variants to the mean contribution to isolated/un-phased variants.

10(a)(3): Genomic Distribution of Phased Variants from WGS

The recurrence frequency for PVs was assessed in each cancer type across the genome within each tumor type. Specifically, the human genome (build GRCh37/hg19) was first divided into 1-kb bins (3,095,689 total bins); then, for each sample, the number of PVs (as defined above) contained in each 1-kb bin was counted. For this analysis, any PV with at least one of its constituent SNVs falling within the 1-kb bin of interest was included. The fraction of patients whose tumors harbored a PV for each cancer type within each genomic bin was then calculated. To identify 1-kb bins recurrently harboring PVs across patients, the fraction of patients containing PVs in each 1-kb bin vs. genomic coordinates (FIG. 1D and FIG. 7) was plotted; for this analysis, only bins where at least 2% of samples contained a PV in at least one cancer subtype were plotted.

10(a)(4): Identification of Recurrent 1-Kb Bins with Phased Variants

To identify 1-kb bins that recurrently contain PVs in B-lymphoid malignancies, WGS data was utilized from the following diseases: DLBCL, FL, BL, and CLL. Any 1-kb bin where >1 sample from these tumor types was considered to recurrently contain PVs from B-lymphoid malignancies. The genomic coordinates of 1-kb bins containing recurrent PVs in lymphoid malignancies are enumerated in Table 2, and are plotted in FIG. 8A.

10(b): Design of PhasED-Seq Panel for B-Lymphoid Malignancies

10(b)(1): Identification of Recurrent PVs from WGS Data at Higher Resolution

Given the prevalence of recurrent putative PVs from WGS data in B-cell malignancies, a targeted sequencing approach was designed for their hybridization-mediated capture—Phased variant Enrichment Sequencing (PhasED-Seq)—to enrich these specific PV events from tumor or cell-free DNA. In addition to the ICGC data described above, WGS data was also utilized from other sources in this design, including both B-cell NHLs as well as CLL.

Previous experience with targeted sequencing from cfDNA in NHLs was also examined. Pairs of SNVs occurring at a distance of <170 bp apart in each B-cell tumor sample were identified. Then, genomic "windows" that contained PVs was identified as follows: for each chromosome, the PVs were sorted by genomic coordinates relative to reference genome. Then, the lowest (i.e., left-most) position was identified for any PV in any patient; this defined the left-hand (5') coordinate seeding a desired window of interest, to be captured from the genome. This window was then extended by growing its 3' end to capture successive PVs until a gap of ≥340 bp was reached, with 340-bp chosen as capturing two successive chromatosomal sized fragments of ~170-bp. When such a gap was reached, a new window was started, and this iterative process of adding neighboring PVs was repeated again until the next gap of ≥340 bp was reached. This resulted in a BED file of genomic windows containing all possible PVs from all samples considered. Finally, each window was additionally padded by 50 bp on each side, to enable efficient capture from flanking sequences in rare scenarios when repetitive or poorly mapping intervening sequences might preclude their direct targeting for enrichment.

Having identified the regions of interest containing putative PVs, each window was then into 170 bp segments (e.g., the approximate size of a chromatosomal cfDNA molecule). Then, the number of cases containing a PV was enumerated in each case. For each 170 bp region, the region in final sequencing panel design was included if one or more of the following criteria was met: 1) at least one patient contained a PV in the 170 bp region in 3 of 5 independent data-sets, 2) at least one patient contained a PV in the region in 2 of 5 independent data-sets if one dataset was prior CAPP-Seq experience, or 3) at least one patient contained a PV in the region in 2 of 5 independent data-sets, with a total of at least 3 patients containing a PV in the region. This resulted in 691 'tiles', with each tile representing a 170 bp genomic region. These tiles, along with an additional ~200 kb of genomic space targeting driver genes recurrently mutated in B-NHL, were combined into a unified targeted sequencing panel as previously described for both tumor and cfDNA genotyping using NimbleDesign (Roche NimbleGen). The final coordinates of this panel are provided in Table 3.

10(b)(2): Comparison of PhasED-Seq and CAPP-Seq Performance in PV Yield

To evaluate the performance of PhasED-Seq for capturing both SNVs and PVs compared to previously reported CAPP-Seq selector for B-cell lymphomas, the predicted number of both SNVs and PVs that may be recovered with each panel by limiting WGS in silico to the capture targets of each approach (FIG. 9A-C) was quantified. The predicted number of variants was then compared using the Wilcoxon signed rank test. Both CAPP-Seq and PhasED-Seq were also performed on 16 samples from patients with DLBCL. In these samples, tumor or plasma DNA, along with matched germline DNA, was sequenced. The resulting number of variants were again compared by the Wilcoxon signed rank text (FIG. 2B, and FIGS. 9D-9E). The sequencing depth for the samples included in this analysis are provided in Tables 4.

10(c): Identification of Phased Variants from Targeted Sequencing Data

10(c)(1): Patient Enrollment and Clinical Sample Collection

Patients with B-cell lymphomas undergoing front-line therapy were enrolled on this study from six centers across North America and Europe, including Stanford University, MD Anderson Cancer Center, the National Cancer Institute, University of Eastern Piedmont (Italy), Essen University Hospital (Germany), and CHU Dijon (France). In total, 343 cell-free DNA, 73 tumor, and 183 germ-line samples from 183 patients were included in this study. All patient samples were collected with written informed consent for research use and were approved by the corresponding Institutional Review Boards in accordance with the Declaration of Helsinki. Cell-free, tumor, and germ-line DNA were isolated as previously described. All radiographic imaging was performed as part of standard clinical care.

10(c)(2): Library Preparation and Sequencing

To generate sequencing libraries and targeted sequencing data, CAPP-Seq was applied as previously described. Briefly, cell-free, tumor, and germ-line DNA were used to construct sequencing libraries through end repair, A-tailing, and adapter ligation following the KAPA Hyper Prep Kit manufacturer's instructions with ligation performed overnight at 4° C. CAPP-Seq adapters with unique molecular identifiers (UMIDs) were used for barcoding of unique DNA duplexes and subsequent deduplication of sequencing read pairs. Hybrid capture was then performed (SeqCap EZ Choice; NimbleGen) using the PhasED-Seq panel described above. Affinity capture was performed according to the manufacturer's protocol, with all 47° C. hybridizations conducted on an Eppendorf thermal cycler. Following enrichment, libraries were sequenced using an Illumina HiSeq4000 instrument with 2×150 bp paired-end (PE) reads.

10(c)(3): Pre-Processing and Alignment

FASTQ files were de-multiplexed and UMIDs were extracted using a custom pipeline as previously described. Following demultiplexing, reads were aligned to the human genome (build GRCh37/hg19) using BWA ALN. Molecular barcode-mediated error suppression and background polishing (i.e., integrated digital error suppression; iDES) were then performed as previously described.

10(c)(4): Identification of Phased Variants and Allelic Quantitation

After generating UMID error-suppressed alignment files (e.g., BAM files), PVs were identified from each sample as follows. First, matched germ-line sequencing of uninvolved peripheral blood mononuclear cells (PBMCs) was performed to identify patient-specific constitutional single nucleotide polymorphisms (SNPs). These were defined as non-reference positions with a variant allele fraction (VAF) above 40% with a depth of at least 10, or a VAF of above 0.25% with a depth of at least 100. Next, PVs were identified from read-level data for a sample of interest. Following UMID-mediated error suppression, each individual paired-end (PE) read and identified all non-reference positions were using 'samtools calmd'. PE data was used rather than single reads to identify variants occurring on the same template DNA molecule, which may subsequently fall into either read 1 or read 2. Any read-pair containing ≥2 non-reference positions was considered to represent a possible somatic PV. For reads with >2 non-reference positions, each permutation of size ≥2 was considered independently: i.e., if 4 non-reference positions were identified in a read-pair, all combinations of 2 SNVs (i.e., 'doublet' phased variants) and all combinations of 3 SNVs (i.e., 'triplet' phased variants) were independently considered. PVs containing putative germ-line SNPs were also removed as follows: if in a given n-mer (i.e., n SNVs in phase on a given molecule)≥n−1 of the component variants were identified as germ-line SNPs, the PV was redacted. This filtering strategy ensures that for any remaining PV, at least 2 of the component SNVs were not seen in the germ-line, as relevant for both sensitivity and specificity.

Putative somatic PVs were filtered using a heuristic blacklisting approach in considering sequencing data from 170 germ-line DNA samples serving as controls. In each of these samples, PVs were identified on read-pairs as described above, but without filtering for matched germ-line. Any PV that occurred in one or greater paired-end read, in one or more of these control samples, was included in the blacklist and removed from patient-specific somatic PV lists.

To calculate the VAF of each PV, a numerator representing the number of DNA molecules containing a PV of interest was calculated over a denominator representing the total number of DNA molecules that covered the genomic region of interest. That is, the numerator is simply the total number of deduplicated read-pairs that contain a given PV while the denominator is the number of read-pairs that span the genomic locus of a given PV.

10(c)(5): Genotyping Phased Variants from Pretreatment Samples

The above strategy resulted in a list of PVs of ≥1 read-depth in each sample. To identify PVs serving as tumor-specific somatic reporters for disease monitoring, for each case a 'best genotyping' specimen—either DNA from a tumor tissue biopsy (preferred), or pretreatment cell-free DNA was identified. After identifying all possible PVs in the 'best genotyping sample', the list for specificity was further filtered as follows. For any n-mer PV set, if ≥n−1 of the constituent SNVs were present as germ-line SNPs in the 170 control samples described above, the PV was removed. Furthermore, only PVs that meet the following criteria were considered: 1) AF >1%; 2) depth of the PV locus of ≥100 read-pairs, and 3) at least one component SNV must be in the on-target space. Finally, 4) any PV meeting these criteria was assessed for read-support in a cohort of 12 healthy control cfDNA samples. If any read-support was present in >1 of these 12 samples, the PV was removed. For genotyping from cell-free DNA samples identified as low tumor fraction by SNVs (i.e., <1% mean AF across all SNVs), the AF threshold for determining PVs was relaxed to >0.2%. This filtering resulted in the PV lists used for disease monitoring and MRD detection.

10(c)(6). Determination of Tumor Fraction in a Sample from Phased Variants

For evaluation of a sample for minimal residual disease (MRD) detection with prior knowledge of the tumor genotype, the presence of any PV identified in the best pretreatment genotyping sample in the MRD sample of interest can be assessed. Given a list of k possible tumor-derived PVs observed in the best genotyping sample, all read-pairs covering at least 1 of the k possible PVs were determined. This value, d, can be thought of as the aggregated 'informative depth' across all PVs spanned by cfDNA molecules in a PhasED-Seq experiment. It was then assessed how many of these d read-pairs actually contained 1 or more of the k possible PVs—this value, x, represents the number of tumor-derived molecules containing somatic PVs in a given sample. The number of tumor-derived molecules containing PVs divided by the informative depth—x/d—is therefore the phased-variant tumor fraction (PVAF) in a given sample. For detection of MRD in each sample, PVAF was calculated independently for doublet, triplet, and quadruplet PVs.

10(c)(7): Monte Carlo Simulation for Empirical Significance of PV Detection within a Specimen To assess the statistical significance of the detection of tumor-derived PVs in any sample, an empiric significance testing approach was implemented. A test statistic f was first defined as follows—from a given list of k possible tumor-derived PVs observed in the best genotyping sample, the arithmetic mean of allele fractions was calculated across all k PVs (allele fraction defined as the number of read-pairs containing an individual PV (xi) over the number of read-pairs spanning the PV positions (d)):

$$f = \frac{\sum_{i=1}^{k} \frac{x_i}{d_i}}{k} \quad (1)$$

to assess the hypothesis that f is not significantly different from the background error-rate of similar PVs assessed from the same sample. A Monte Carlo approach was used to develop a null distribution and perform statistical testing as follows:

1. Given a set of k PVs, $\{pv_1 \ldots pv_i \ldots pv_k\}$, an 'alternate' list of PVs, $\{pv'_1 \ldots pv'_i \ldots pv'_k\}$, was generated such that for each alternate PV had the same type of base change and distance between SNVs as the test PV. For example, if a doublet PV, chr14:106329929 C>T and chr14:106329977 G>A, was identified in the genotyping sample and searched for an alternate two positions at the same genomic distance (here, 48 bp) with reference bases C and G, and assessed for read-pairs with the same types of base changes (i.e., C>T and G>A), using the heuristic search scheme below.
2. For each tumor $pv_i$ in the set of k, 50 such alternates were identified. This was performed with a random search algorithm to scan the genomic space and identify alternates. To find these 50 alternates, a random position on the same chromosome as the test $pv_i$ was identified and then searched for the same types of reference bases at the same genomic distance as described above. Synteny of observed/alternate PVs was used to control for regional variation in SHM/aSHM as well as copy number variation, as potential confounders of the null distribution. Alternate positions that were identified as a germ-line SNP, defined as having AF >5%, were excluded.
3. After identifying 50 such alternates for each $pv_i$, 10,000 random permutations of 1 alternate were generated for each of the k original PVs and calculated the phased-variant fraction f' for these alternate lists in the sample of interest being evaluated for presence of MRD, as described above.
4. An empiric P-value was calculated, defined as the fraction of times the true phased-variant fraction f is observed to be less than or equal to the alternate f' across the 10,000 random PV lists as an empirical measure of significance of MRD significance in the blood sample of interest.

While this resulting comparison is a measure of the significance for PV detection of tumor-reporter list compared to the empirically defined background PV error-rate within the sample of interest, its relationship to specificity of detection across cases and control samples was also evaluated, as described below.

10(c)(8): Assessment of Specificity of PhasED-Seq

To determine the specificity of disease and MRD detection through PhasED-Seq, patient-specific PVs from 107 patients with DLBCL were first identified using pretreatment tumor or plasma DNA along with paired germ-line samples. 40 independent plasma DNA samples were then assessed from healthy individuals for presence of these patient-specific PVs, using the Monte Carlo approach outlined above. A threshold for P-values was empirically determined from Monte Carlo such that 95% specificity was achieved for disease detection from doublet, triplet, and quadruplet PVs. The P-value threshold yielding 95% specificity for each size of PV was as follows: <0.041 for doublets, <1 for triplets, and <1 for quadruplets. The results of this specificity in control cfDNA analysis is shown in FIGS. 15 and 16.

10(c)(9): Calculation of Error Rates

To assess the error profile of both isolated SNVs and PVs, the non-reference base observation rate of each type of variant was examined across all reads. For isolated SNVs, the error-rate for each possible base change $e_{n1>n1'}$ was calculated as the fraction of on-target bases with reference allele n1 that are mutated to alternate allele n1', when considering all possible base-changes of the reference allele. Positions with a non-reference allele rate exceeding 5% were classified as probable germ-line events, and excluded from the error-rate analysis. A global error rate, defined as the rate of mutation from the hg19 reference allele to any alternate allele, was also calculated.

For phased variants, a similar calculation was performed. For the error-rate of a given type of phased variant composed of k constituent base-changes $\{e_{n1>n1'} \ldots e_{nk>nk'}\}$, the error-rate was calculated by determining both the number of instances of the type of base change (i.e., the numerator), as well as the number of possible instances for the base change (i.e., the denominator). To calculate the numerator, N, the number of occurrences of the PV of interest over all read-pairs was counted in a given sample. For example, to calculate the error-rate of C>T and G>A phased doublets, the number of read-pairs that include both a reference C mutated to a T as well as a reference G mutated to an A was first counted.

To calculate the denominator, D, the number of possible instances of this type of phased variant was also calculated; this was performed first for each read-pair i, and then summed over all read pairs. A PV with k components can be summarized as having certain set of reference bases $p_A$, $p_C$, $p_G$, $p_T$, where $p_N$ is the number of each reference base in the PV. Similarly, a given read pair contains a certain set of reference bases $b_A$, $b_C$, $b_G$, $b_T$, where $b_N$ is the number of each reference base in the read pair. Therefore, for each read pair in a given sample, the number of possible occurrences of PV type of interest can be calculated combinatorically as:

$$D_i = \binom{b_A}{p_A}\binom{b_C}{p_C}\binom{b_G}{p_G}\binom{b_T}{p_T} \quad (2)$$

For example, consider a read-pair with 40 reference As, 50 reference Cs, 45 reference Gs, and 35 reference Ts. The number of positions for a C>T and G>A PV is:

$$D_i = \binom{40}{0}\binom{50}{1}\binom{45}{1}\binom{35}{0} = 2250 \quad (3)$$

The aggregated denominator, D, for error rate calculation is then simply the sum of this value over all read pairs. The error rate for this type of PV is then simply N/D.

10(d): Differences in Phased Variants Between Lymphoma Subtypes

To compare the distribution of phased variants in different types of lymphomas, tumor-specific PVs were identified in 101 DLBCL, 16 PMBCL, and 23 cHL patients via sequencing of tumor biopsy specimens and/or pre-treatment cell-free DNA and paired germ-line specimens. After identifying these tumor-specific PVs, their distribution was the assessed across the targeted sequencing panel. The panel was first divided into 50 bp bins; for each patient, it was then determined if each patient had evidence of a PV within the 50 bp bin, defined as having at least one component of the PV within the bin. The nearest gene to each 50 bp bin was further determined, based on GENCODEv19 annotation of the reference genome.

To assess how the distribution of PVs between subtypes of lymphoma varies at the level of specific genes, the distribution of PVs was examined across the 50 bp bins spanning each gene (or nearest gene). For example, consider a given gene with n such 50 bp bins represented in targeted sequencing panel. For each bin, it was first determined the fraction of patients, f in each type of lymphoma with a PV falling within the 50 bp bin—i.e., determining if $\{f_{type1,1}, \ldots f_{type1,n}\}$ and $\{f_{type2,1}, \ldots f_{type2,n}\}$ Then, any two histologies were then compared for the fraction of cases harboring PVs in the set of 50 bp bins assigned to each gene. These comparisons are depicted for individual genes on gene-specific plots in FIG. 2D and FIGS. 10-12.

The enrichment in PVs was statistically compared in a specific lymphoma type or subtype vs. another by calculating the difference in the fraction of patients which contain a PV in each 50 bp bin across all bins assigned to a gene (i.e., overlapping a given gene or with a given nearest gene). Specifically, for any comparison between two lymphoma types (type$_1$ and type$_2$), this set of differences in PV-rate was first identified between histologies $\{f_{type1,1}-f_{type2,1}, \ldots f_{type1,n}-f_{type2,n}\}$. This set of gene-specific differences in frequency of PVs was the compared between types of lymphoma against the distribution of all other 50 bp bins in the sequencing panel by the Wilcoxon rank sum test. For this test, the set of n 50 bp bins assigned to a given gene was compared to all other 50 bp bins (i.e., 6755-n, since there are 6755 50 bp bins in sequencing panel). This P-value, along with the mean difference in fraction of patients with a PV in each bin for each gene between histologies, is depicted as a volcano plot in FIG. 2E. To account for the global difference in rate of PVs between different histologies, the mean difference in fraction of patients with a PV between histologies was centered on 0 by subtracting the mean difference across all genes.

10(e): Hybridization Bias

To assess the effect of mutations on hybridization efficiency, the affinity of mutated molecules to wildtype capture baits in silico was first estimated by considering DNA fragments harboring 0-30% mutations across the entire fragment. For each mutation condition across this range, 10,000 regions were first randomly sampled, each 150 bp in length, from across the whole genome. These 150-mers were then mutated in silico to simulate the desired mutation rate in 3 different ways: 1) mutating 'clustered' or contiguous bases starting from the ends of a sequence, 2) mutating clustered bases started from the middle of the sequence, or 3) mutating bases selected at random positions throughout the sequence. The energy.c package was then used to calculate the theoretical binding energy (kcal/mol) between the mutated and wild-type sequences, in relying on a nearest-neighbor model employing established thermodynamic parameters (FIG. 14A).

This in silico experiment was then replicated by testing the effects of same mutation rates in vitro. Specifically, oligonucleotides (IDT) were synthesized and annealed to form DNA duplexes harboring 0-10% mutations at defined positions relative to the human reference genome sequence. These synthetic DNA molecules were then captured together at equimolar concentrations and quantified the relative capture efficiency of mutated duplexes compared to the wild-type, unmutated species (FIG. 3A). Two sets of oligonucleotide sequences were selected from coding regions of BCL6 and MYC to capture AID-mediated aberrant somatic hypermutations associated with each gene (Table 5); the preserved mappability of the mutated species was ensured by BWA ALN. These synthetic oligonucleotide duplexes were then subjected to library preparation, then captured and sequenced using PhasED-Seq, performed in triplicate using distinct samples. This allowed assessment of the relative efficiency of hybrid capture and molecular recovery as directly compared to wildtype molecules identical to the reference genome.

10(f): Assessment of Limit of Detection with Limiting Dilution Series

To empirically define the analytical sensitivity of PhasED-Seq, a limited dilution series of cell-free DNA from 3 patients that were spiked into healthy control cell-free DNA at defined concentrations was utilized. The dilution series contained samples with an expected mean tumor fraction of 0.1%, 0.01%, 0.001%, 0.0002%, 0.0001%, and 0.00005% or ranging from 1 part in 1,000 to 1 part in 2,000,000. The sequencing characteristics and ctDNA quantification via CAPP-Seq, duplex sequencing, and PhasED-Seq are provided. To compare the performance of each method, the difference was calculated, δ, between the observed and expected tumor fraction for each patient i at each dilution concentration j:

$$\delta_{i,j} = \text{tum} \overline{\text{orfr}} \text{ac}_{i,j} - \text{tumorfrac}_{i,j} \tag{4}$$

This value was calculated for patients i={1,2,3} and concentrations j={0.001%, 0.0002%, 0.0001%, 0.00005%} for each ctDNA detection method (CAPP-Seq, duplex, doublet PhasED-Seq, and triplet PhasED-Seq). The performance of each method was then compared to each other by paired t-test across this set of patients and concentrations.

10(g): Model to Predict the Probability of Detection for a Given Set of Phased Variants To build a mathematical model to predict the probability of detection for a given sample of interest, it began with the common assumption that cfDNA detection can be considered a random process based on binomial sampling. However, unlike SNVs occurring at large genomic distances apart from one another, detection of PVs can be highly inter-dependent, especially when PVs are degenerate (i.e., when two PVs share component SNVs) or occur in close proximity. To account for this, only PVs occurring >150 bp apart from each other was considered as independent 'tumor reporters'. The number of 'tumor reporters' to allow for disease detection in a given sample can thus be determined as follows. The PhasED-Seq panel was broken apart into 150 bp bins. Each PV in a given patient's reporter list was then turned into a BED coordinate, consisting of the start position (defined as the left-most component SNV) and end position (defined as the right-most component SNV). For each PV, the 150 bp bin from the PhasED-Seq selector panel containing the PV was determined; if a PV spanned two or more 150 bp bins, it was assigned to both bins. The number of independent tumor reporters was then defined as the number of separate 150 bp bins containing a tumor-specific PV.

A mathematical model was then developed comparing the expected probability of detection for a given sample at a given tumor fraction with a given number of independent tumor reporters (e.g., 150 bp bins). With a given number of tumor reporters r, at a given tumor fraction f, with a given sequencing depth d, the probability of detecting 1 or more cell-free DNA molecule containing a tumor-specific PV containing can be defined as:

$$Pr(\text{detection}) = 1 - Pr(\text{nondetection}) \quad (5)$$

$$= 1 - \binom{d*r}{0} f^0 (1-f)^{d*r} \quad (6)$$

based on simple binomial sampling. However, as ctDNA detection method was trained to have a 5% false positive rate, this false positive rate term was added to the model as well:

$$Pr(\text{dectection}) = 1 - Pr(\text{nondetection}) + 0.05 * Pr(\text{nondetection}) \quad (7)$$

$$Pr(\text{detection}) = 1 - 0.95 * Pr(\text{nondetection}) \quad (8)$$

$$= 1 - 0.95 * \binom{d*r}{0} f^0 (1-f)^{d*r} \quad (9)$$

FIG. 3G shows the results of this model for a range of tumor reporters r from 3 to 67 at depth d of 5000. The confidence envelope on this plot shows solutions for a range of depth d from 4000 to 6000.

To empirically validate this model assessing the probability of disease detection, samples from limiting dilution series were utilized. In this dilution series, 3 patient cfDNA samples, each containing patient-specific PVs, were spiked into healthy control cfDNA. For each list of patient specific PVs, 25 random subsamplings of the 150 bp bins containing patient-specific PVs were performed to generate reporter lists containing variable numbers of tumor-specific reporters. A maximum bin number of 67 was selected to allow sampling from all 3 patient-specific PV lists, followed by scaling down the number of bins by 2× or 3× per operation. This resulted in reporter lists containing patient-specific PVs from 3, 6, 17, 34, or 67 independent 150 bp bins. Disease detection was then assessed using each of these patient-specific PV lists of increasing size in each of 'wet' limiting dilution samples from 1:1,000 to 1:1,000,000 (FIG. 3H, closed circles). In silico mixtures was further created using sequencing reads from limiting dilution samples with varying expected tumor-content, and again assessed for the probability of disease detection using patient-specific sub-sampled PV reporter lists of varying lengths (open circles). For this experiment, both the 'wet' and 'in-silico' dilution bam files were down-sampled to achieve a depth of ~4000-6000× to correspond with modeled depth. The final mean and standard deviation of depth across all down-sampled bam files was 4214×±789. The probability of detection was summarized across all tests at a given expected tumor fraction, for a given patient-specific PV list. For each given dilution, multiple independently sampled sets of reads were considered to allow superior estimation of the true probability of detection. Specifically, the following number of replicates at each dilution indicated was considered in Table 7.

TABLE 7

Replicates at each dilution for predicting the probability of detection for a given set of phased variants.

| Dilution | Replicates | Number of Tests (Replicates * 25) | Wet or In silico |
| --- | --- | --- | --- |
| 1:1,000 | 1 | 25 | Wet |
| 5:10,000 | 3 | 75 | In silico |
| 3.5:10,000 | 3 | 75 | In silico |
| 2:10,000 | 3 | 75 | In silico |
| 1:10,000 | 3 | 75 | Wet |
| 5:100,000 | 3 | 75 | In silico |
| 3.5:100,000 | 3 | 75 | In silico |
| 2:100,000 | 3 | 75 | In silico |
| 1:100,000 | 3 | 75 | Wet |
| 5:1,000,000 | 8 | 200 | In silico |
| 3.5:1,000,000 | 8 | 200 | In silico |
| 2:1,000,000 | 8 | 200 | Wet |
| 1:1,000,000 | 8 | 200 | Wet |

The total number of tests, for each patient-specific PV list, is therefore the number of randomly subsampled PV lists (e.g., 25) times the number of independently downsampled bam files; this number is provided in the table above. In FIG. 3H, the points and error-bars represent the mean, minimum, and maximum across all three patients. The concordance between the predicted probability of disease detection from theoretical mathematical model and wet and in silico samples validating this model, is shown in FIG. 3I.

10(h): Statistical Analyses & Software Availability

All P-values reported in this manuscript are 2-sided unless otherwise noted. Comparisons of matched samples and populations were performed using the Wilcoxon signed rank test; comparisons of samples drawn from unrelated populations were performed using the Wilcoxon rank-sum test. Comparisons of paired samples were performed by paired t-test. Survival probabilities were estimated using the Kaplan-Meier method; survival of groups of patients based on ctDNA levels were compared using the log-rank test. Other statistical tests are noted in the manuscript text where utilized. All analyses were performed with the use of MAT-LAB, version 2018b, R Statistical Software version 3.4.1, and GraphPad Prism, version 8.0.2. The contribution of known mutational processes to phased and isolated SNVs from WGS was assessed with the deconstruct Sigs R package using the COSMIC signature set (v2) as described. Calculation of AUC accounting for survival and censorship was performed using the R 'survivalROC' package version 1.0.3 with default settings. An executable version of the PhasED-Seq software, developed in C++ 17, is available at phasedseq(dot)stanford(dot)edu.

Example 11

Additional details of the tables described throughout the present disclosure are provided herein:

TABLE 1: 1000 bp regions of interest throughout the genome containing putative phased variants (PV) in various lymphoid neoplasms. Only regions containing >1 subject with a PV are shown. Coordinates are in hg19. Regions from genes that were previously identified as targets of activation-induced deaminase (AID) are labeled. Regions that contain PVs in >5% of subjects in any histology (BL, CLL, DLBCL, FL) are also labeled. BL, Burkitt lymphoma; CLL, chronic lymphocytic leukemia; DLBCL, diffuse large B-cell lymphoma; FL, follcicular lymphoma.

TABLE 2: 1000 bp regions of interest throughout the genome containing putative phased variants (PV) in the ABC and GCB subtypes of DLBCL. Only regions containing >1 subject with a PV are shown. Coordinates are in hg19. Regions from genes that were previously identified as targets of AID are labeled. ABC, activated B-cell subtype; GCB, germinal center B-cell subtype.

TABLE 3: Regions used for the PhasED-Seq capture reagent described in this paper focused on lymphoid malignancies. Coordinates are in hg19. The closest gene and the reason for inclusion (Phased Variants vs general DLBCL genotyping) is also shown.

TABLE 4: Enrichment of PVs at genetic loci throughout the PhasED-Seq targeted sequencing panel for different types of B-cell lymphomas (DLBCL including ABC and GCB subtypes, PMBCL, and cHL). The PhasED-Seq selector was binned into 50 bp bins in hg19 coordinates, and each bin was labelled by gene or nearest gene. The mean of the fraction of cases of a given histology with a PV across all 50 bp bins is shown. Significance was determined by rank-sum (Mann-Whitney U) test of 50 bp bins for a given gene against the remainder of the sequencing panel. Uncorrected P-values are shown; multiple-hypothesis testing correction was performed by Bonferroni method. DLBCL, diffuse large B-cell lymphoma; PMBCL, primary mediastinal B-cell lymphoma; cHL, classical Hodgkin lymphoma; ABC, activated B-cell DLBCL; GCB, germinal center B-cell DLBCL.

TABLE 5: Sequences of oligonucleotides synthesized to assess hybridization and molecular recovery bias with increasing mutational burden (SEQ ID NOs. 1331-1358).

TABLE 6: Nucleic acid probes for Capture Sequencing of B-cell Cancers (SEQ ID NOs. 0001-1330).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

TABLE 1

| # | Chromosome | Region Start | Region End | BL | CLL | DLBCL | FL |
|---|---|---|---|---|---|---|---|
| 1 | chr1 | 756000 | 757000 | 0.028 | 0.000 | 0.015 | 0.000 |
| 2 | chr1 | 1963000 | 1964000 | 0.028 | 0.000 | 0.015 | 0.000 |
| 3 | chr1 | 2052000 | 2053000 | 0.028 | 0.000 | 0.000 | 0.014 |
| 4 | chr1 | 3789000 | 3790000 | 0.000 | 0.000 | 0.029 | 0.000 |
| 5 | chr1 | 6613000 | 6614000 | 0.000 | 0.000 | 0.044 | 0.014 |
| 6 | chr1 | 6614000 | 6615000 | 0.000 | 0.000 | 0.088 | 0.027 |
| 7 | chr1 | 6661000 | 6662000 | 0.000 | 0.000 | 0.029 | 0.014 |
| 8 | chr1 | 6662000 | 6663000 | 0.000 | 0.000 | 0.044 | 0.014 |
| 9 | chr1 | 9129000 | 9130000 | 0.000 | 0.000 | 0.044 | 0.000 |
| 10 | chr1 | 10894000 | 10895000 | 0.028 | 0.000 | 0.000 | 0.014 |
| 11 | chr1 | 17019000 | 17020000 | 0.028 | 0.000 | 0.000 | 0.014 |
| 12 | chr1 | 17231000 | 17232000 | 0.000 | 0.000 | 0.015 | 0.014 |
| 13 | chr1 | 19935000 | 19936000 | 0.000 | 0.000 | 0.029 | 0.000 |
| 14 | chr1 | 21091000 | 21092000 | 0.000 | 0.000 | 0.015 | 0.014 |
| 15 | chr1 | 23885000 | 23886000 | 0.444 | 0.000 | 0.015 | 0.000 |
| 16 | chr1 | 28408000 | 28409000 | 0.000 | 0.000 | 0.029 | 0.000 |
| 17 | chr1 | 32373000 | 32374000 | 0.000 | 0.000 | 0.029 | 0.000 |
| 18 | chr1 | 36722000 | 36723000 | 0.000 | 0.012 | 0.015 | 0.000 |
| 19 | chr1 | 46576000 | 46577000 | 0.000 | 0.000 | 0.015 | 0.014 |
| 20 | chr1 | 51965000 | 51966000 | 0.000 | 0.006 | 0.015 | 0.000 |
| 21 | chr1 | 51978000 | 51979000 | 0.000 | 0.000 | 0.029 | 0.000 |
| 22 | chr1 | 51983000 | 51984000 | 0.000 | 0.006 | 0.029 | 0.000 |
| 23 | chr1 | 72393000 | 72394000 | 0.000 | 0.000 | 0.015 | 0.014 |
| 24 | chr1 | 73719000 | 73720000 | 0.000 | 0.000 | 0.029 | 0.000 |
| 25 | chr1 | 77315000 | 77316000 | 0.028 | 0.006 | 0.000 | 0.000 |
| 26 | chr1 | 81306000 | 81307000 | 0.000 | 0.000 | 0.015 | 0.014 |
| 27 | chr1 | 81527000 | 81528000 | 0.000 | 0.000 | 0.029 | 0.000 |
| 28 | chr1 | 82009000 | 82010000 | 0.028 | 0.000 | 0.015 | 0.000 |
| 29 | chr1 | 84106000 | 84107000 | 0.000 | 0.006 | 0.015 | 0.000 |
| 30 | chr1 | 87524000 | 87525000 | 0.000 | 0.006 | 0.015 | 0.000 |
| 31 | chr1 | 94551000 | 94552000 | 0.000 | 0.000 | 0.029 | 0.000 |
| 32 | chr1 | 94552000 | 94553000 | 0.000 | 0.000 | 0.029 | 0.000 |
| 33 | chr1 | 103696000 | 103697000 | 0.000 | 0.000 | 0.000 | 0.027 |
| 34 | chr1 | 116979000 | 116980000 | 0.000 | 0.000 | 0.044 | 0.041 |
| 35 | chr1 | 149784000 | 149785000 | 0.000 | 0.000 | 0.015 | 0.014 |
| 36 | chr1 | 149821000 | 349822000 | 0.000 | 0.000 | 0.044 | 0.000 |
| 37 | chr1 | 149857000 | 149858000 | 0.000 | 0.000 | 0.015 | 0.014 |
| 38 | chr1 | 149858000 | 149859000 | 0.000 | 0.000 | 0.059 | 0.000 |

TABLE 1-continued

| | | | | | | | |
|---|---|---|---|---|---|---|---|
| 39 | chr1 | 160616000 | 160617000 | 0.000 | 0.000 | 0.015 | 0.014 |
| 40 | chr1 | 162711000 | 162712000 | 0.000 | 0.000 | 0.015 | 0.014 |
| 41 | chr1 | 163684000 | 163685000 | 0.000 | 0.000 | 0.015 | 0.014 |
| 42 | chr1 | 167598000 | 167599000 | 0.000 | 0.000 | 0.044 | 0.014 |
| 43 | chr1 | 167599000 | 167600000 | 0.000 | 0.000 | 0.029 | 0.014 |
| 44 | chr1 | 167600000 | 167601000 | 0.000 | 0.000 | 0.044 | 0.000 |
| 45 | chr1 | 174333000 | 174334000 | 0.000 | 0.000 | 0.015 | 0.014 |
| 46 | chr1 | 187263000 | 187264000 | 0.000 | 0.000 | 0.044 | 0.000 |
| 47 | chr1 | 187283000 | 187284000 | 0.000 | 0.000 | 0.029 | 0.000 |
| 48 | chr1 | 187892000 | 187893000 | 0.028 | 0.000 | 0.015 | 0.000 |
| 49 | chr1 | 195282000 | 195283000 | 0.000 | 0.000 | 0.015 | 0.014 |
| 50 | chr1 | 198591000 | 198592000 | 0.000 | 0.000 | 0.029 | 0.000 |
| 51 | chr1 | 198608000 | 198609000 | 0.000 | 0.000 | 0.029 | 0.000 |
| 52 | chr1 | 198609000 | 198610000 | 0.000 | 0.000 | 0.029 | 0.000 |
| 53 | chr1 | 202004000 | 202005000 | 0.028 | 0.000 | 0.029 | 0.000 |
| 54 | chr1 | 203273000 | 203274000 | 0.000 | 0.000 | 0.029 | 0.000 |
| 55 | chr1 | 203274000 | 203275000 | 0.000 | 0.000 | 0.176 | 0.014 |
| 56 | chr1 | 203275000 | 203276000 | 0.028 | 0.006 | 0.471 | 0.081 |
| 57 | chr1 | 203276000 | 203277000 | 0.028 | 0.000 | 0.059 | 0.000 |
| 58 | chr1 | 205780000 | 205781000 | 0.000 | 0.000 | 0.000 | 0.027 |
| 59 | chr1 | 205781000 | 205782000 | 0.000 | 0.000 | 0.000 | 0.027 |
| 60 | chr1 | 206283000 | 206284000 | 0.000 | 0.000 | 0.015 | 0.014 |
| 61 | chr1 | 206286000 | 206287000 | 0.000 | 0.000 | 0.029 | 0.014 |
| 62 | chr1 | 217044000 | 217045000 | 0.000 | 0.000 | 0.029 | 0.000 |
| 63 | chr1 | 226924000 | 226925000 | 0.000 | 0.000 | 0.029 | 0.000 |
| 64 | chr1 | 226925000 | 226926000 | 0.000 | 0.000 | 0.044 | 0.000 |
| 65 | chr1 | 226926000 | 226927000 | 0.000 | 0.000 | 0.029 | 0.000 |
| 66 | chr1 | 229974000 | 229975000 | 0.028 | 0.000 | 0.015 | 0.027 |
| 67 | chr1 | 235131000 | 235132000 | 0.000 | 0.000 | 0.000 | 0.027 |
| 68 | chr1 | 235141000 | 235142000 | 0.000 | 0.000 | 0.015 | 0.014 |
| 69 | chr1 | 239787000 | 238788000 | 0.000 | 0.000 | 0.029 | 0.000 |
| 70 | chr1 | 248088000 | 248089000 | 0.028 | 0.000 | 0.015 | 0.000 |
| 71 | chr2 | 630000 | 631000 | 0.000 | 0.000 | 0.000 | 0.027 |
| 72 | chr2 | 1484000 | 1485000 | 0.000 | 0.000 | 0.000 | 0.027 |
| 73 | chr2 | 7991000 | 7992000 | 0.056 | 0.000 | 0.000 | 0.000 |
| 74 | chr2 | 12173000 | 12174000 | 0.000 | 0.000 | 0.044 | 0.000 |
| 75 | cht2 | 12175000 | 12176000 | 0.000 | 0.000 | 0.029 | 0.000 |
| 76 | chr2 | 12249000 | 12250000 | 0.000 | 0.000 | 0.029 | 0.000 |
| 77 | chr2 | 14113000 | 14114000 | 0.000 | 0.000 | 0.000 | 0.027 |
| 78 | chr2 | 17577000 | 17578000 | 0.000 | 0.000 | 0.015 | 0.014 |
| 79 | chr2 | 19253000 | 19254000 | 0.000 | 0.000 | 0.029 | 0.000 |
| 80 | chr2 | 24802000 | 24803000 | 0.000 | 0.000 | 0.029 | 0.000 |
| 81 | chr2 | 31478000 | 31479000 | 0.000 | 0.000 | 0.015 | 0.014 |
| 82 | chr2 | 41728000 | 41729000 | 0.000 | 0.000 | 0.015 | 0.014 |
| 83 | chr2 | 45404000 | 45405000 | 0.000 | 0.000 | 0.000 | 0.027 |
| 84 | chr2 | 47923000 | 47924000 | 0.000 | 0.000 | 0.015 | 0.014 |
| 85 | chr2 | 47944000 | 47945000 | 0.000 | 0.000 | 0.029 | 0.000 |
| 86 | chr2 | 51360000 | 51361000 | 0.000 | 0.000 | 0.015 | 0.014 |
| 87 | chr2 | 51655000 | 51656000 | 0.000 | 0.000 | 0.000 | 0.027 |
| 88 | chr2 | 56565000 | 56566000 | 0.000 | 0.000 | 0.029 | 0.000 |
| 89 | chr2 | 57800000 | 57801000 | 0.000 | 0.000 | 0.015 | 0.014 |
| 90 | chr2 | 60779000 | 60780000 | 0.000 | 0.000 | 0.029 | 0.027 |
| 91 | chr2 | 60780000 | 60781000 | 0.000 | 0.000 | 0.029 | 0.000 |
| 92 | chr2 | 63802000 | 63803000 | 0.000 | 0.000 | 0.000 | 0.027 |
| 93 | chr2 | 63827000 | 63828000 | 0.000 | 0.000 | 0.015 | 0.014 |
| 94 | chr2 | 64319000 | 64320000 | 0.000 | 0.000 | 0.044 | 0.000 |
| 95 | chr2 | 65593000 | 65594000 | 0.000 | 0.000 | 0.044 | 0.054 |
| 96 | chr2 | 67002000 | 67003000 | 0.028 | 0.000 | 0.029 | 0.000 |
| 97 | chr2 | 70315000 | 70316000 | 0.083 | 0.000 | 0.000 | 0.000 |
| 98 | chr2 | 79502000 | 79503000 | 0.028 | 0.000 | 0.015 | 0.000 |
| 99 | chr2 | 79644000 | 79645000 | 0.000 | 0.000 | 0.000 | 0.027 |
| 100 | chr2 | 81818000 | 81819000 | 0.000 | 0.000 | 0.000 | 0.027 |
| 101 | chr2 | 82310000 | 82311000 | 0.028 | 0.000 | 0.015 | 0.000 |
| 102 | chr2 | 82948000 | 82949000 | 0.000 | 0.000 | 0.029 | 0.000 |
| 103 | chr2 | 85335000 | 85336000 | 0.000 | 0.000 | 0.000 | 0.027 |
| 104 | chr2 | 88905000 | 88906000 | 0.000 | 0.000 | 0.059 | 0.000 |
| 105 | chr2 | 88906000 | 88907000 | 0.000 | 0.006 | 0.074 | 0.014 |
| 106 | chr2 | 88907000 | 88908000 | 0.000 | 0.000 | 0.059 | 0.000 |
| 107 | chr2 | 89052000 | 89053000 | 0.000 | 0.006 | 0.035 | 0.000 |
| 108 | chr2 | 89065000 | 89066000 | 0.000 | 0.000 | 0.015 | 0.027 |
| 109 | chr2 | 89066000 | 89067000 | 0.000 | 0.000 | 0.015 | 0.014 |
| 110 | chr2 | 89095000 | 99096000 | 0.000 | 0.000 | 0.015 | 0.014 |
| 111 | chr2 | 89127000 | 89128000 | 0.000 | 0.006 | 0.147 | 0.041 |
| 112 | chr2 | 89128000 | 89129000 | 0.028 | 0.006 | 0.176 | 0.041 |
| 113 | chr2 | 89129000 | 89130000 | 0.000 | 0.000 | 0.044 | 0.041 |
| 114 | chr2 | 89130000 | 89131000 | 0.000 | 0.000 | 0.044 | 0.000 |
| 115 | chr2 | 89131000 | 89132000 | 0.000 | 0.000 | 0.029 | 0.000 |
| 116 | chr2 | 89132000 | 89133000 | 0.000 | 0.006 | 0.015 | 0.014 |
| 117 | chr2 | 89133000 | 89134000 | 0.000 | 0.000 | 0.029 | 0.041 |
| 118 | chr2 | 89137000 | 99138000 | 0.000 | 0.000 | 0.044 | 0.014 |

TABLE 1-continued

| | | | | | | | |
|---|---|---|---|---|---|---|---|
| 119 | chr2 | 89138000 | 89139000 | 0.000 | 0.000 | 0.015 | 0.014 |
| 120 | chr2 | 89139000 | 89140000 | 0.000 | 0.000 | 0.044 | 0.014 |
| 121 | chr2 | 89140000 | 89141000 | 0.000 | 0.000 | 0.088 | 0.054 |
| 122 | chr2 | 89141000 | 89142000 | 0.000 | 0.006 | 0.103 | 0.027 |
| 123 | chr2 | 89142000 | 89143000 | 0.000 | 0.000 | 0.088 | 0.000 |
| 124 | chr2 | 89143000 | 89144000 | 0.000 | 0.000 | 0.029 | 0.000 |
| 125 | chr2 | 89144000 | 89145000 | 0.000 | 0.000 | 0.015 | 0.014 |
| 126 | chr2 | 89145000 | 89146000 | 0.000 | 0.000 | 0.029 | 0.014 |
| 127 | chr2 | 89146000 | 89147000 | 0.000 | 0.000 | 0.029 | 0.014 |
| 128 | chr2 | 89153000 | 89154000 | 0.000 | 0.000 | 0.029 | 0.000 |
| 129 | chr2 | 89155000 | 89156000 | 0.000 | 0.000 | 0.059 | 0.014 |
| 130 | chr2 | 89156000 | 89157000 | 0.000 | 0.000 | 0.103 | 0.014 |
| 131 | chr2 | 89157000 | 89158000 | 0.000 | 0.000 | 0.250 | 0.149 |
| 132 | chr2 | 89158000 | 89159000 | 0.028 | 0.019 | 0.426 | 0.270 |
| 133 | chr2 | 89159000 | 89160000 | 0.222 | 0.180 | 0.574 | 0.473 |
| 134 | chr2 | 89160000 | 89161000 | 0.444 | 0.242 | 0.500 | 0.608 |
| 135 | chr2 | 89161000 | 89162000 | 0.222 | 0.081 | 0.265 | 0.405 |
| 136 | chr2 | 89162000 | 89163000 | 0.056 | 0.012 | 0.221 | 0.108 |
| 137 | chr2 | 89163000 | 89164000 | 0.000 | 0.068 | 0.235 | 0.176 |
| 138 | chr2 | 89164000 | 89165000 | 0.028 | 0.137 | 0.294 | 0.216 |
| 139 | chr2 | 89165000 | 89166000 | 0.083 | 0.143 | 0.279 | 0.216 |
| 140 | chr2 | 89166000 | 89167000 | 0.028 | 0.012 | 0.044 | 0.027 |
| 141 | chr2 | 89169000 | 89170000 | 0.000 | 0.000 | 0.015 | 0.014 |
| 142 | chr2 | 89184000 | 89185000 | 0.000 | 0.006 | 0.015 | 0.054 |
| 143 | chr2 | 89185000 | 89186000 | 0.028 | 0.056 | 0.162 | 0.135 |
| 144 | chr2 | 89196000 | 89197000 | 0.000 | 0.000 | 0.059 | 0.014 |
| 145 | chr2 | 89197000 | 89198000 | 0.000 | 0.000 | 0.000 | 0.027 |
| 146 | chr2 | 89214000 | 89215000 | 0.000 | 0.012 | 0.000 | 0.000 |
| 147 | chr2 | 89246000 | 89247000 | 0.000 | 0.031 | 0.029 | 0.027 |
| 148 | chr2 | 89247000 | 89248000 | 0.028 | 0.019 | 0.118 | 0.054 |
| 149 | chr2 | 89248000 | 89249000 | 0.028 | 0.000 | 0.044 | 0.000 |
| 150 | chr2 | 89266000 | 89267000 | 0.000 | 0.000 | 0.015 | 0.014 |
| 151 | chr2 | 89291000 | 89292000 | 0.000 | 0.019 | 0.029 | 0.000 |
| 152 | chr2 | 89292000 | 89293000 | 0.000 | 0.025 | 0.044 | 0.000 |
| 153 | chr2 | 69326000 | 89327000 | 0.000 | 0.019 | 0.000 | 0.041 |
| 154 | chr2 | 89327000 | 89328000 | 0.000 | 0.012 | 0.015 | 0.027 |
| 155 | chr2 | 89442000 | 89443000 | 0.111 | 0.050 | 0.074 | 0.122 |
| 156 | chr2 | 89443000 | 89444000 | 0.000 | 0.000 | 0.015 | 0.041 |
| 157 | chr2 | 89476000 | 89477000 | 0.028 | 0.000 | 0.000 | 0.014 |
| 158 | chr2 | 89513000 | 89514000 | 0.000 | 0.000 | 0.029 | 0.000 |
| 159 | chr2 | 89521000 | 89522000 | 0.028 | 0.000 | 0.015 | 0.014 |
| 160 | chr2 | 89533000 | 89534000 | 0.028 | 0.000 | 0.044 | 0.014 |
| 161 | chr2 | 89534000 | 89535000 | 0.000 | 0.000 | 0.029 | 0.014 |
| 162 | chr2 | 89544000 | 89545000 | 0.028 | 0.012 | 0.059 | 0.014 |
| 163 | chr2 | 89545000 | 89546000 | 0.000 | 0.006 | 0.029 | 0.000 |
| 164 | chr2 | 90259000 | 90260000 | 0.000 | 0.000 | 0.015 | 0.014 |
| 165 | chr2 | 90260000 | 90261000 | 0.000 | 0.000 | 0.059 | 0.014 |
| 166 | chr2 | 96809000 | 96810000 | 0.000 | 0.000 | 0.044 | 0.000 |
| 167 | chr2 | 96810000 | 96811000 | 0.000 | 0.000 | 0.044 | 0.014 |
| 168 | chr2 | 96811000 | 96812000 | 0.000 | 0.000 | 0.029 | 0.000 |
| 169 | chr2 | 98611000 | 98612000 | 0.000 | 0.000 | 0.015 | 0.014 |
| 170 | chr2 | 100757000 | 100758000 | 0.000 | 0.000 | 0.029 | 0.027 |
| 171 | chr2 | 100758000 | 100759000 | 0.000 | 0.000 | 0.044 | 0.014 |
| 172 | chr2 | 106144000 | 106145000 | 0.000 | 0.000 | 0.029 | 0.000 |
| 173 | chr2 | 111878000 | 111879000 | 0.000 | 0.000 | 0.029 | 0.014 |
| 174 | chr2 | 111679000 | 111880000 | 0.000 | 0.000 | 0.044 | 0.014 |
| 175 | chr2 | 112305000 | 112306000 | 0.000 | 0.000 | 0.015 | 0.014 |
| 176 | chr2 | 116234000 | 116235000 | 0.000 | 0.000 | 0.015 | 0.014 |
| 177 | chr2 | 116439000 | 116440000 | 0.028 | 0.000 | 0.000 | 0.014 |
| 178 | chr2 | 124697000 | 124698000 | 0.028 | 0.000 | 0.015 | 0.000 |
| 179 | chr2 | 125235000 | 125236000 | 0.000 | 0.000 | 0.029 | 0.000 |
| 180 | chr2 | 127538000 | 127539000 | 0.028 | 0.000 | 0.015 | 0.000 |
| 181 | chr2 | 136874000 | 136875000 | 0.000 | 0.000 | 0.191 | 0.014 |
| 182 | chr2 | 136675000 | 136876000 | 0.083 | 0.019 | 0.265 | 0.081 |
| 183 | chr2 | 136996000 | 136997000 | 0.000 | 0.000 | 0.029 | 0.000 |
| 184 | chr2 | 137082000 | 137083000 | 0.000 | 0.000 | 0.015 | 0.014 |
| 185 | chr2 | 140951000 | 140952000 | 0.000 | 0.000 | 0.029 | 0.000 |
| 186 | chr2 | 141335000 | 141336000 | 0.000 | 0.000 | 0.015 | 0.014 |
| 187 | chr2 | 141770000 | 141771000 | 0.000 | 0.000 | 0.029 | 0.000 |
| 188 | chr2 | 146445000 | 146446000 | 0.000 | 0.000 | 0.029 | 0.000 |
| 189 | chr2 | 146446000 | 146447000 | 0.000 | 0.000 | 0.029 | 0.014 |
| 190 | chr2 | 156443000 | 156444000 | 0.000 | 0.000 | 0.029 | 0.000 |
| 191 | chr2 | 172590000 | 172591000 | 0.000 | 0.000 | 0.029 | 0.000 |
| 192 | chr2 | 176581000 | 176582000 | 0.028 | 0.000 | 0.000 | 0.014 |
| 193 | chr2 | 179880000 | 179881000 | 0.000 | 0.000 | 0.015 | 0.014 |
| 194 | chr2 | 180358000 | 180359000 | 0.000 | 0.000 | 0.029 | 0.000 |
| 195 | chr2 | 189259000 | 189206000 | 0.000 | 0.000 | 0.015 | 0.014 |
| 196 | chr2 | 189432000 | 189433000 | 0.028 | 0.000 | 0.000 | 0.014 |
| 197 | chr2 | 194115000 | 194116000 | 0.000 | 0.000 | 0.015 | 0.014 |
| 198 | chr2 | 197035000 | 197036000 | 0.000 | 0.000 | 0.044 | 0.014 |

TABLE 1-continued

| | | | | | | | |
|---|---|---|---|---|---|---|---|
| 199 | chr2 | 197041000 | 197042000 | 0.000 | 0.000 | 0.029 | 0.000 |
| 200 | chr2 | 215999000 | 216000000 | 0.000 | 0.006 | 0.015 | 0.000 |
| 201 | chr2 | 216973000 | 216974000 | 0.028 | 0.000 | 0.000 | 0.014 |
| 202 | chr2 | 217247000 | 217248000 | 0.028 | 0.000 | 0.000 | 0.014 |
| 203 | chr2 | 225386000 | 225387000 | 0.000 | 0.000 | 0.029 | 0.000 |
| 204 | chr2 | 225524000 | 225525000 | 0.000 | 0.000 | 0.029 | 0.000 |
| 205 | chr2 | 233478000 | 233479000 | 0.028 | 0.000 | 0.015 | 0.000 |
| 206 | chr2 | 233980000 | 233981000 | 0.028 | 0.000 | 0.029 | 0.000 |
| 207 | chr2 | 240641000 | 240642000 | 0.028 | 0.000 | 0.000 | 0.027 |
| 208 | chr2 | 241125000 | 241126000 | 0.000 | 0.000 | 0.000 | 0.027 |
| 209 | chr3 | 8739000 | 8740000 | 0.000 | 0.000 | 0.000 | 0.027 |
| 210 | chr3 | 16407000 | 16408000 | 0.000 | 0.000 | 0.000 | 0.027 |
| 211 | chr3 | 16409000 | 16410000 | 0.028 | 0.000 | 0.000 | 0.041 |
| 212 | chr3 | 16419000 | 16420000 | 0.000 | 0.006 | 0.044 | 0.000 |
| 213 | chr3 | 16172000 | 16473000 | 0.000 | 0.000 | 0.015 | 0.014 |
| 214 | chr3 | 16495000 | 16496000 | 0.000 | 0.000 | 0.029 | 0.000 |
| 215 | chr3 | 16552000 | 16553000 | 0.000 | 0.012 | 0.029 | 0.014 |
| 216 | chr3 | 16554000 | 16555000 | 0.000 | 0.000 | 0.103 | 0.027 |
| 217 | chr3 | 16555000 | 16556000 | 0.000 | 0.000 | 0.029 | 0.000 |
| 218 | chr3 | 21658000 | 21659000 | 0.000 | 0.000 | 0.029 | 0.000 |
| 219 | chr3 | 25691000 | 25692000 | 0.000 | 0.000 | 0.029 | 0.000 |
| 220 | chr3 | 31969000 | 31970000 | 0.000 | 0.000 | 0.029 | 0.000 |
| 221 | chr3 | 31993000 | 31994000 | 0.000 | 0.000 | 0.044 | 0.000 |
| 222 | chr3 | 32001000 | 32002000 | 0.000 | 0.000 | 0.044 | 0.000 |
| 223 | chr3 | 32022000 | 32023000 | 0.000 | 0.000 | 0.088 | 0.014 |
| 224 | chr3 | 32023000 | 32024000 | 0.000 | 0.000 | 0.029 | 0.000 |
| 225 | chr3 | 50128000 | 50129000 | 0.000 | 0.000 | 0.029 | 0.000 |
| 226 | chr3 | 54913000 | 54914000 | 0.000 | 0.006 | 0.015 | 0.000 |
| 227 | chr3 | 56074000 | 56075000 | 0.028 | 0.000 | 0.000 | 0.014 |
| 228 | chr3 | 59577000 | 59578000 | 0.000 | 0.000 | 0.029 | 0.000 |
| 229 | chr3 | 60351000 | 60352000 | 0.000 | 0.000 | 0.044 | 0.000 |
| 230 | chr3 | 60356000 | 60357000 | 0.028 | 0.000 | 0.000 | 0.014 |
| 231 | chr3 | 60357000 | 60358000 | 0.000 | 0.000 | 0.015 | 0.014 |
| 232 | chr3 | 60358000 | 60359000 | 0.000 | 0.000 | 0.015 | 0.014 |
| 233 | chr3 | 60359000 | 60360000 | 0.000 | 0.000 | 0.029 | 0.000 |
| 234 | chr3 | 60389000 | 60390000 | 0.000 | 0.000 | 0.015 | 0.027 |
| 235 | chr3 | 60392000 | 60393000 | 0.000 | 0.000 | 0.029 | 0.000 |
| 236 | chr3 | 60395000 | 60396000 | 0.000 | 0.000 | 0.000 | 0.027 |
| 237 | chr3 | 60404000 | 60405000 | 0.000 | 0.000 | 0.029 | 0.000 |
| 238 | chr3 | 60436000 | 60437000 | 0.000 | 0.000 | 0.000 | 0.027 |
| 239 | chr3 | 60437000 | 60438000 | 0.000 | 0.000 | 0.029 | 0.000 |
| 240 | chr3 | 60477000 | 60478000 | 0.000 | 0.000 | 0.029 | 0.000 |
| 241 | chr3 | 60485000 | 60486000 | 0.000 | 0.000 | 0.015 | 0.014 |
| 242 | chr3 | 60515000 | 60516000 | 0.000 | 0.000 | 0.015 | 0.014 |
| 243 | chr3 | 60535000 | 60536000 | 0.000 | 0.006 | 0.015 | 0.000 |
| 244 | chr3 | 60602000 | 60603000 | 0.000 | 0.000 | 0.029 | 0.014 |
| 245 | chr3 | 60613000 | 60614000 | 0.000 | 0.000 | 0.029 | 0.014 |
| 246 | chr3 | 60614000 | 60615000 | 0.000 | 0.000 | 0.029 | 0.000 |
| 247 | chr3 | 60632000 | 60633000 | 0.000 | 0.000 | 0.000 | 0.027 |
| 248 | chr3 | 60635000 | 60636000 | 0.000 | 0.000 | 0.029 | 0.000 |
| 249 | chr3 | 60640000 | 60641000 | 0.000 | 0.000 | 0.000 | 0.027 |
| 250 | chr3 | 60647000 | 60648000 | 0.000 | 0.000 | 0.015 | 0.014 |
| 251 | chr3 | 60648000 | 60649000 | 0.000 | 0.000 | 0.015 | 0.014 |
| 252 | chr3 | 60652000 | 60653000 | 0.000 | 0.000 | 0.000 | 0.027 |
| 253 | chr3 | 60660000 | 60661000 | 0.000 | 0.000 | 0.029 | 0.014 |
| 254 | chr3 | 60665000 | 60666000 | 0.000 | 0.000 | 0.015 | 0.027 |
| 255 | chr3 | 60666000 | 60667000 | 0.000 | 0.000 | 0.015 | 0.014 |
| 256 | chr3 | 60671000 | 60672000 | 0.000 | 0.000 | 0.000 | 0.041 |
| 257 | chr3 | 60673000 | 60674000 | 0.000 | 0.000 | 0.044 | 0.000 |
| 258 | chr3 | 60675000 | 60676000 | 0.000 | 0.000 | 0.015 | 0.014 |
| 259 | chr3 | 60678000 | 60679000 | 0.000 | 0.000 | 0.044 | 0.000 |
| 260 | chr3 | 60683000 | 60684000 | 0.000 | 0.000 | 0.015 | 0.027 |
| 261 | chr3 | 60684000 | 60685000 | 0.000 | 0.000 | 0.015 | 0.041 |
| 262 | chr3 | 60688000 | 60689000 | 0.000 | 0.000 | 0.015 | 0.014 |
| 263 | chr3 | 60717000 | 60718000 | 0.000 | 0.000 | 0.000 | 0.027 |
| 264 | chr3 | 60740000 | 60741000 | 0.000 | 0.000 | 0.029 | 0.000 |
| 265 | chr3 | 60774000 | 60775000 | 0.000 | 0.000 | 0.029 | 0.000 |
| 266 | chr3 | 60792000 | 60793000 | 0.000 | 0.000 | 0.000 | 0.027 |
| 267 | chr3 | 60806000 | 60807000 | 0.028 | 0.000 | 0.000 | 0.014 |
| 268 | chr3 | 60812000 | 60813000 | 0.000 | 0.000 | 0.000 | 0.027 |
| 269 | chr3 | 60860000 | 60861000 | 0.000 | 0.000 | 0.000 | 0.027 |
| 270 | chr3 | 71551000 | 71552000 | 0.000 | 0.000 | 0.000 | 0.027 |
| 271 | chr3 | 78274000 | 78275000 | 0.000 | 0.000 | 0.015 | 0.014 |
| 272 | chr3 | 80273000 | 80274000 | 0.000 | 0.006 | 0.015 | 0.000 |
| 273 | chr3 | 83094000 | 83095000 | 0.028 | 0.000 | 0.015 | 0.000 |
| 274 | chr3 | 83924000 | 83925000 | 0.028 | 0.000 | 0.000 | 0.014 |
| 275 | chr3 | 84293000 | 84294000 | 0.000 | 0.000 | 0.015 | 0.014 |
| 276 | chr3 | 85260000 | 85261000 | 0.000 | 0.000 | 0.044 | 0.000 |
| 277 | chr3 | 85261000 | 85262000 | 0.000 | 0.000 | 0.029 | 0.000 |
| 278 | chr3 | 85799000 | 85800000 | 0.000 | 0.000 | 0.029 | 0.000 |

TABLE 1-continued

| | | | | | | | |
|---|---|---|---|---|---|---|---|
| 279 | chr3 | 86226000 | 86227000 | 0.000 | 0.000 | 0.029 | 0.000 |
| 280 | chr3 | 88146000 | 88147000 | 0.000 | 0.000 | 0.029 | 0.000 |
| 281 | chr3 | 94709000 | 94710000 | 0.000 | 0.000 | 0.029 | 0.000 |
| 282 | chr3 | 95460000 | 95461000 | 0.028 | 0.000 | 0.015 | 0.000 |
| 283 | chr3 | 95724000 | 95725000 | 0.000 | 0.000 | 0.029 | 0.000 |
| 284 | chr3 | 101569000 | 101570000 | 0.028 | 0.000 | 0.015 | 0.000 |
| 285 | chr3 | 111851000 | 111852000 | 0.000 | 0.000 | 0.044 | 0.000 |
| 286 | chr3 | 111852000 | 111833000 | 0.000 | 0.000 | 0.059 | 0.000 |
| 287 | chr3 | 122377000 | 122378000 | 0.028 | 0.000 | 0.044 | 0.000 |
| 288 | chr3 | 150478000 | 150479000 | 0.000 | 0.000 | 0.029 | 0.000 |
| 289 | chr3 | 150479000 | 150480000 | 0.000 | 0.000 | 0.029 | 0.000 |
| 290 | chr3 | 150480000 | 150481000 | 0.000 | 0.000 | 0.015 | 0.014 |
| 291 | chr3 | 163237000 | 163238000 | 0.000 | 0.000 | 0.000 | 0.027 |
| 292 | chr3 | 163238000 | 163239000 | 0.000 | 0.000 | 0.029 | 0.000 |
| 293 | chr3 | 163615000 | 163616000 | 0.000 | 0.000 | 0.029 | 0.000 |
| 294 | chr3 | 183270000 | 183271000 | 0.000 | 0.000 | 0.029 | 0.000 |
| 295 | chr3 | 183271000 | 183272000 | 0.000 | 0.000 | 0.029 | 0.014 |
| 296 | chr3 | 183272000 | 183273000 | 0.000 | 0.000 | 0.029 | 0.014 |
| 297 | chr3 | 183273000 | 183274000 | 0.000 | 0.019 | 0.044 | 0.027 |
| 298 | chr3 | 186648000 | 186649000 | 0.000 | 0.000 | 0.044 | 0.014 |
| 299 | chr3 | 186714000 | 186715000 | 0.000 | 0.006 | 0.132 | 0.027 |
| 300 | chr3 | 186715000 | 186716000 | 0.000 | 0.000 | 0.044 | 0.014 |
| 301 | chr3 | 186739000 | 186740000 | 0.000 | 0.006 | 0.074 | 0.014 |
| 302 | chr3 | 186740000 | 186741000 | 0.056 | 0.006 | 0.074 | 0.027 |
| 303 | chr3 | 186742000 | 186743000 | 0.000 | 0.000 | 0.029 | 0.000 |
| 304 | chr3 | 186783000 | 186784000 | 0.000 | 0.050 | 0.338 | 0.041 |
| 305 | chr3 | 186784000 | 186785000 | 0.000 | 0.025 | 0.044 | 0.000 |
| 306 | chr3 | 187458000 | 187459000 | 0.000 | 0.000 | 0.029 | 0.000 |
| 307 | chr3 | 187459000 | 187460000 | 0.000 | 0.000 | 0.029 | 0.000 |
| 308 | chr3 | 187460000 | 187461000 | 0.000 | 0.000 | 0.088 | 0.041 |
| 309 | chr3 | 187461000 | 187462000 | 0.000 | 0.006 | 0.353 | 0.122 |
| 310 | chr3 | 187462000 | 187463000 | 0.056 | 0.081 | 0.647 | 0.392 |
| 311 | chr3 | 187463000 | 187464000 | 0.000 | 0.037 | 0.485 | 0.230 |
| 312 | chr3 | 187464000 | 187465000 | 0.028 | 0.000 | 0.162 | 0.000 |
| 313 | chr3 | 187468000 | 187469000 | 0.028 | 0.000 | 0.044 | 0.000 |
| 314 | chr3 | 187635000 | 187636000 | 0.000 | 0.000 | 0.029 | 0.000 |
| 315 | chr3 | 187636000 | 187637000 | 0.000 | 0.000 | 0.000 | 0.027 |
| 316 | chr3 | 187653000 | 187654000 | 0.000 | 0.000 | 0.044 | 0.014 |
| 317 | chr3 | 187658000 | 187659000 | 0.000 | 0.000 | 0.029 | 0.000 |
| 318 | chr3 | 187660000 | 187661000 | 0.000 | 0.019 | 0.118 | 0.054 |
| 319 | chr3 | 187661000 | 187662000 | 0.000 | 0.012 | 0.191 | 0.081 |
| 320 | chr3 | 187664000 | 187665000 | 0.000 | 0.000 | 0.044 | 0.000 |
| 321 | chr3 | 187686000 | 187687000 | 0.028 | 0.000 | 0.029 | 0.014 |
| 322 | chr3 | 187687000 | 187688000 | 0.000 | 0.006 | 0.000 | 0.014 |
| 323 | chr3 | 187693000 | 187694000 | 0.000 | 0.000 | 0.015 | 0.014 |
| 324 | chr3 | 187696000 | 187622000 | 0.000 | 0.006 | 0.059 | 0.000 |
| 325 | chr3 | 187697000 | 187698000 | 0.000 | 0.000 | 0.044 | 0.000 |
| 326 | chr3 | 187803000 | 187804000 | 0.000 | 0.000 | 0.029 | 0.000 |
| 327 | chr3 | 187806000 | 187807000 | 0.000 | 0.000 | 0.059 | 0.014 |
| 328 | chr3 | 187937000 | 187958000 | 0.000 | 0.006 | 0.132 | 0.014 |
| 329 | chr3 | 187958000 | 187959000 | 0.028 | 0.025 | 0.221 | 0.095 |
| 330 | chr3 | 187959000 | 187960000 | 0.000 | 0.012 | 0.118 | 0.000 |
| 331 | chr3 | 187960000 | 187961000 | 0.000 | 0.000 | 0.029 | 0.000 |
| 332 | chr3 | 188222000 | 188223000 | 0.000 | 0.000 | 0.029 | 0.000 |
| 333 | chr3 | 188298000 | 188299000 | 0.000 | 0.000 | 0.015 | 0.014 |
| 334 | chr3 | 188299000 | 188300000 | 0.000 | 0.006 | 0.088 | 0.027 |
| 335 | chr3 | 188471000 | 188472000 | 0.000 | 0.006 | 0.191 | 0.068 |
| 336 | chr3 | 188472000 | 188473000 | 0.000 | 0.000 | 0.044 | 0.027 |
| 337 | chr4 | 50000 | 51000 | 0.000 | 0.000 | 0.029 | 0.000 |
| 338 | chr4 | 51000 | 52000 | 0.000 | 0.000 | 0.044 | 0.014 |
| 339 | chr4 | 54000 | 55000 | 0.000 | 0.000 | 0.029 | 0.000 |
| 340 | chr4 | 290000 | 291000 | 0.056 | 0.000 | 0.000 | 0.000 |
| 341 | chr4 | 385000 | 386000 | 0.000 | 0.000 | 0.029 | 0.000 |
| 342 | chr4 | 550000 | 551000 | 0.000 | 0.000 | 0.000 | 0.027 |
| 343 | chr4 | 2207000 | 2708000 | 0.028 | 0.000 | 0.015 | 0.000 |
| 344 | chr4 | 5206000 | 5207000 | 0.000 | 0.000 | 0.029 | 0.000 |
| 345 | chr4 | 25963000 | 25864000 | 0.000 | 0.000 | 0.059 | 0.014 |
| 346 | chr4 | 25964000 | 25865000 | 0.000 | 0.006 | 0.044 | 0.027 |
| 347 | chr4 | 25865000 | 25866000 | 0.000 | 0.000 | 0.074 | 0.027 |
| 348 | chr4 | 29657000 | 29658000 | 0.000 | 0.000 | 0.015 | 0.014 |
| 349 | chr4 | 30356000 | 30357000 | 0.000 | 0.006 | 0.015 | 0.000 |
| 350 | chr4 | 33419000 | 33419000 | 0.000 | 0.000 | 0.029 | 0.000 |
| 351 | chr4 | 33449000 | 33450000 | 0.028 | 0.000 | 0.015 | 0.000 |
| 352 | chr4 | 39348000 | 39349000 | 0.000 | 0.000 | 0.015 | 0.014 |
| 353 | chr4 | 39974000 | 39975000 | 0.000 | 0.000 | 0.000 | 0.027 |
| 354 | chr4 | 40194000 | 40195000 | 0.000 | 0.000 | 0.044 | 0.027 |
| 355 | chr4 | 40195000 | 40196000 | 0.000 | 0.000 | 0.015 | 0.027 |
| 356 | chr4 | 40196000 | 40197000 | 0.000 | 0.000 | 0.074 | 0.014 |
| 357 | chr4 | 40197000 | 40198000 | 0.000 | 0.000 | 0.015 | 0.027 |
| 358 | chr4 | 40198000 | 40199000 | 0.000 | 0.000 | 0.088 | 0.041 |

TABLE 1-continued

| | | | | | | | |
|---|---|---|---|---|---|---|---|
| 359 | chr4 | 40199000 | 40200000 | 0.056 | 0.000 | 0.279 | 0.162 |
| 360 | chr4 | 40200000 | 40201000 | 0.000 | 0.006 | 0.118 | 0.041 |
| 361 | chr4 | 40201000 | 40202000 | 0.000 | 0.000 | 0.088 | 0.041 |
| 362 | chr4 | 40202000 | 40203000 | 0.000 | 0.000 | 0.029 | 0.014 |
| 363 | chr4 | 40204000 | 40205000 | 0.000 | 0.000 | 0.029 | 0.000 |
| 364 | chr4 | 45308000 | 45309000 | 0.000 | 0.000 | 0.029 | 0.000 |
| 365 | chr4 | 46360000 | 46361000 | 0.000 | 0.000 | 0.015 | 0.014 |
| 366 | chr4 | 62375000 | 62376000 | 0.000 | 0.000 | 0.029 | 0.000 |
| 367 | chr4 | 62530000 | 62531000 | 0.000 | 0.000 | 0.029 | 0.000 |
| 368 | chr4 | 62911000 | 62912000 | 0.000 | 0.000 | 0.029 | 0.000 |
| 369 | chr4 | 63120000 | 63121000 | 0.000 | 0.000 | 0.029 | 0.000 |
| 370 | chr4 | 64015000 | 64016000 | 0.000 | 0.000 | 0.029 | 0.000 |
| 371 | chr4 | 65038000 | 65039000 | 0.000 | 0.000 | 0.015 | 0.014 |
| 372 | chr4 | 65165000 | 65166000 | 0.000 | 0.000 | 0.015 | 0.014 |
| 373 | chr4 | 65966000 | 65967000 | 0.000 | 0.006 | 0.000 | 0.014 |
| 374 | chr4 | 66827000 | 66828000 | 0.000 | 0.000 | 0.029 | 0.000 |
| 375 | chr4 | 71531000 | 71532000 | 0.000 | 0.000 | 0.015 | 0.041 |
| 376 | chr4 | 71532000 | 71533000 | 0.000 | 0.000 | 0.000 | 0.027 |
| 377 | chr4 | 74456000 | 74457000 | 0.000 | 0.000 | 0.029 | 0.000 |
| 378 | chr4 | 74483000 | 74484000 | 0.000 | 0.006 | 0.015 | 0.000 |
| 379 | chr4 | 74484000 | 74485000 | 0.000 | 0.000 | 0.044 | 0.000 |
| 380 | chr4 | 74485000 | 74486000 | 0.000 | 0.000 | 0.088 | 0.000 |
| 381 | chr4 | 91886000 | 91887000 | 0.000 | 0.000 | 0.015 | 0.014 |
| 382 | chr4 | 92787000 | 92788000 | 0.000 | 0.000 | 0.029 | 0.000 |
| 383 | chr4 | 113206000 | 113207000 | 0.000 | 0.000 | 0.029 | 0.000 |
| 384 | chr4 | 114466000 | 114467000 | 0.000 | 0.000 | 0.029 | 0.000 |
| 385 | chr4 | 114681000 | 114682000 | 0.000 | 0.000 | 0.044 | 0.000 |
| 386 | chr4 | 117928000 | 117929000 | 0.000 | 0.000 | 0.029 | 0.000 |
| 387 | chr4 | 123637000 | 123638000 | 0.000 | 0.000 | 0.000 | 0.027 |
| 388 | chr4 | 125227000 | 125228000 | 0.000 | 0.000 | 0.015 | 0.014 |
| 389 | chr4 | 127371000 | 127372000 | 0.000 | 0.000 | 0.029 | 0.000 |
| 390 | chr4 | 133455000 | 133456000 | 0.000 | 0.000 | 0.000 | 0.027 |
| 391 | chr4 | 134538000 | 134539000 | 0.000 | 0.000 | 0.015 | 0.014 |
| 392 | chr4 | 134743000 | 134744000 | 0.000 | 0.000 | 0.029 | 0.000 |
| 393 | chr4 | 134867000 | 134868000 | 0.000 | 0.000 | 0.029 | 0.000 |
| 394 | chr4 | 134949000 | 134950000 | 0.000 | 0.000 | 0.029 | 0.000 |
| 395 | chr4 | 135064000 | 135065000 | 0.000 | 0.000 | 0.015 | 0.014 |
| 396 | chr4 | 135077000 | 135078000 | 0.000 | 0.000 | 0.029 | 0.000 |
| 397 | chr4 | 136799000 | 136800000 | 0.028 | 0.006 | 0.000 | 0.000 |
| 398 | chr4 | 136867000 | 136868000 | 0.000 | 0.000 | 0.015 | 0.014 |
| 399 | chr4 | 140236000 | 140237000 | 0.000 | 0.000 | 0.015 | 0.014 |
| 400 | chr4 | 151723000 | 151724000 | 0.000 | 0.000 | 0.029 | 0.000 |
| 401 | chr4 | 151950000 | 151951000 | 0.000 | 0.000 | 0.000 | 0.027 |
| 402 | chr4 | 152125000 | 152126000 | 0.028 | 0.000 | 0.029 | 0.000 |
| 403 | chr4 | 157246000 | 157247900 | 0.000 | 0.000 | 0.015 | 0.014 |
| 404 | chr4 | 164532000 | 164533000 | 0.000 | 0.000 | 0.000 | 0.027 |
| 405 | chr4 | 178732000 | 178733000 | 0.028 | 0.000 | 0.000 | 0.014 |
| 406 | chr4 | 178805000 | 178086000 | 0.000 | 0.000 | 0.029 | 0.000 |
| 407 | chr4 | 179898000 | 179099000 | 0.000 | 0.000 | 0.029 | 0.000 |
| 408 | chr4 | 180886000 | 180886000 | 0.000 | 0.006 | 0.029 | 0.000 |
| 409 | chr4 | 181554000 | 181555000 | 0.000 | 0.000 | 0.029 | 0.000 |
| 410 | chr4 | 182122000 | 182123000 | 0.000 | 0.000 | 0.015 | 0.014 |
| 411 | chr5 | 436000 | 437000 | 0.028 | 0.000 | 0.000 | 0.014 |
| 412 | chr5 | 3982000 | 3983000 | 0.000 | 0.000 | 0.029 | 0.000 |
| 413 | chr5 | 17218000 | 17219000 | 0.000 | 0.000 | 0.029 | 0.000 |
| 414 | chr5 | 17219000 | 17220000 | 0.000 | 0.000 | 0.029 | 0.000 |
| 415 | chr5 | 18514000 | 18515000 | 0.028 | 0.000 | 0.000 | 0.014 |
| 416 | chr5 | 22356000 | 22357000 | 0.000 | 0.000 | 0.029 | 0.000 |
| 417 | chr5 | 22517000 | 22518000 | 0.000 | 0.000 | 0.015 | 0.014 |
| 418 | chr5 | 24632000 | 24633000 | 0.000 | 0.000 | 0.029 | 0.000 |
| 419 | chr5 | 25275000 | 25276000 | 0.000 | 0.000 | 0.015 | 0.014 |
| 420 | chr5 | 25541000 | 25542000 | 0.000 | 0.000 | 0.029 | 0.000 |
| 421 | chr5 | 26119000 | 26120000 | 0.000 | 0.000 | 0.015 | 0.014 |
| 422 | chr5 | 26450000 | 26451000 | 0.000 | 0.000 | 0.029 | 0.000 |
| 423 | chr5 | 29224000 | 29225000 | 0.000 | 0.000 | 0.029 | 0.000 |
| 424 | chr5 | 29492000 | 29493000 | 0.000 | 0.000 | 0.029 | 0.000 |
| 425 | chr5 | 29648000 | 29649000 | 0.000 | 0.000 | 0.029 | 0.000 |
| 426 | chr5 | 51521000 | 51522000 | 0.000 | 0.000 | 0.044 | 0.014 |
| 427 | chr5 | 83841000 | 83842000 | 0.000 | 0.000 | 0.029 | 0.000 |
| 428 | chr5 | 88177000 | 88178000 | 0.000 | 0.000 | 0.029 | 0.000 |
| 429 | chr5 | 88178000 | 88179000 | 0.000 | 0.000 | 0.015 | 0.014 |
| 430 | chr5 | 914170000 | 91418000 | 0.000 | 0.000 | 0.000 | 0.027 |
| 431 | chr5 | 103678000 | 103679000 | 0.000 | 0.000 | 0.015 | 0.014 |
| 432 | chr5 | 123696000 | 123697000 | 0.000 | 0.000 | 0.000 | 0.027 |
| 433 | chr5 | 124079000 | 124080000 | 0.000 | 0.000 | 0.029 | 0.014 |
| 434 | chr5 | 124080000 | 124081000 | 0.000 | 0.000 | 0.029 | 0.014 |
| 435 | chr5 | 127594000 | 127595000 | 0.000 | 0.000 | 0.015 | 0.014 |
| 436 | chr5 | 127875000 | 127876000 | 0.000 | 0.000 | 0.000 | 0.027 |
| 437 | chr5 | 131825000 | 131826000 | 0.000 | 0.000 | 0.074 | 0.000 |
| 438 | chr5 | 131826000 | 131827000 | 0.000 | 0.000 | 0.029 | 0.000 |

TABLE 1-continued

| | | | | | | | |
|---|---|---|---|---|---|---|---|
| 439 | chr5 | 149791000 | 149792000 | 0.000 | 0.000 | 0.132 | 0.014 |
| 440 | chr5 | 149792000 | 141093000 | 0.000 | 0.000 | 0.015 | 0.014 |
| 441 | chr5 | 158380000 | 158381000 | 0.028 | 0.000 | 0.015 | 0.000 |
| 442 | chr5 | 158479000 | 158480000 | 0.000 | 0.000 | 0.029 | 0.000 |
| 443 | chr5 | 158526000 | 158527000 | 0.028 | 0.000 | 0.044 | 0.000 |
| 444 | chr5 | 158527000 | 158528000 | 0.000 | 0.000 | 0.029 | 0.000 |
| 445 | chr5 | 158528000 | 158529000 | 0.000 | 0.000 | 0.059 | 0.000 |
| 446 | chr5 | 164247000 | 164248000 | 0.000 | 0.000 | 0.029 | 0.000 |
| 447 | chr5 | 164441000 | 164442000 | 0.028 | 0.000 | 0.015 | 0.000 |
| 448 | chr5 | 165932000 | 165933000 | 0.000 | 0.000 | 0.015 | 0.014 |
| 449 | chr5 | 173300000 | 173301000 | 0.000 | 0.000 | 0.000 | 0.027 |
| 450 | chr5 | 179166000 | 179167000 | 0.000 | 0.000 | 0.015 | 0.027 |
| 451 | chr5 | 180102000 | 180103000 | 0.000 | 0.000 | 0.015 | 0.014 |
| 452 | chr6 | 392000 | 393000 | 0.000 | 0.000 | 0.074 | 0.000 |
| 453 | chr6 | 393000 | 394000 | 0.000 | 0.000 | 0.074 | 0.000 |
| 454 | chr6 | 14118000 | 14119000 | 0.000 | 0.000 | 0.279 | 0.041 |
| 455 | chr6 | 14119000 | 14120000 | 0.000 | 0.000 | 0.044 | 0.027 |
| 456 | chr6 | 18111000 | 18112000 | 0.028 | 0.000 | 0.044 | 0.000 |
| 457 | chr6 | 18387000 | 18388000 | 0.000 | 0.000 | 0.000 | 0.027 |
| 458 | chr6 | 18388000 | 18389000 | 0.000 | 0.000 | 0.000 | 0.027 |
| 459 | chr6 | 19573000 | 19574000 | 0.000 | 0.000 | 0.029 | 0.000 |
| 460 | chr6 | 22873000 | 22874000 | 0.000 | 0.000 | 0.015 | 0.014 |
| 461 | chr6 | 26031000 | 26032000 | 0.000 | 0.000 | 0.000 | 0.027 |
| 462 | chr6 | 26032000 | 26033000 | 0.000 | 0.000 | 0.000 | 0.027 |
| 463 | chr6 | 26056000 | 26057000 | 0.000 | 0.000 | 0.059 | 0.027 |
| 464 | chr6 | 26123000 | 26121000 | 0.000 | 0.000 | 0.059 | 0.014 |
| 465 | chr6 | 26124000 | 26125000 | 0.000 | 0.000 | 0.074 | 0.000 |
| 466 | chr6 | 26125000 | 26126000 | 0.000 | 0.000 | 0.015 | 0.014 |
| 467 | chr6 | 26156000 | 26157000 | 0.000 | 0.000 | 0.074 | 0.014 |
| 468 | chr6 | 26157000 | 26158000 | 0.000 | 0.000 | 0.029 | 0.014 |
| 469 | chr6 | 26216000 | 26217000 | 0.000 | 0.000 | 0.029 | 0.000 |
| 470 | chr6 | 26234000 | 26235000 | 0.000 | 0.000 | 0.044 | 0.000 |
| 471 | chr6 | 27101000 | 27102000 | 0.000 | 0.000 | 0.029 | 0.000 |
| 472 | chr6 | 27114000 | 27115000 | 0.000 | 0.000 | 0.059 | 0.014 |
| 473 | chr6 | 27792000 | 27793000 | 0.000 | 0.000 | 0.044 | 0.014 |
| 474 | chr6 | 27833000 | 27834000 | 0.000 | 0.000 | 0.015 | 0.014 |
| 475 | chr6 | 27860000 | 27861000 | 0.000 | 0.000 | 0.029 | 0.027 |
| 476 | chr6 | 27861000 | 27862000 | 0.000 | 0.000 | 0.015 | 0.014 |
| 477 | chr6 | 29778000 | 29779000 | 0.028 | 0.000 | 0.000 | 0.014 |
| 478 | chr6 | 29700000 | 29781000 | 0.000 | 0.000 | 0.015 | 0.014 |
| 479 | chr6 | 29911000 | 29912000 | 0.000 | 0.000 | 0.044 | 0.000 |
| 480 | chr6 | 29927000 | 29928000 | 0.000 | 0.000 | 0.015 | 0.014 |
| 481 | chr6 | 31324000 | 31325000 | 0.000 | 0.000 | 0.029 | 0.014 |
| 482 | chr6 | 31325000 | 31326000 | 0.028 | 0.000 | 0.000 | 0.014 |
| 483 | chr6 | 31543000 | 31544000 | 0.000 | 0.000 | 0.029 | 0.000 |
| 484 | chr6 | 31549000 | 31550000 | 0.000 | 0.006 | 0.191 | 0.068 |
| 485 | chr6 | 31550000 | 31551000 | 0.000 | 0.000 | 0.044 | 0.000 |
| 486 | chr6 | 32440000 | 32441000 | 0.000 | 0.000 | 0.044 | 0.027 |
| 487 | chr6 | 32451000 | 32452000 | 0.056 | 0.000 | 0.000 | 0.000 |
| 488 | chr6 | 32452000 | 32453000 | 0.028 | 0.000 | 0.015 | 0.000 |
| 489 | chr6 | 32455000 | 32456000 | 0.028 | 0.000 | 0.015 | 0.000 |
| 490 | chr6 | 32457000 | 32458000 | 0.000 | 0.000 | 0.000 | 0.027 |
| 491 | chr6 | 32498000 | 32499000 | 0.000 | 0.000 | 0.000 | 0.027 |
| 492 | chr6 | 32505000 | 32506000 | 0.000 | 0.000 | 0.029 | 0.014 |
| 493 | chr6 | 32511000 | 32512000 | 0.000 | 0.000 | 0.000 | 0.041 |
| 494 | chr6 | 32522000 | 32523000 | 0.028 | 0.000 | 0.015 | 0.027 |
| 495 | chr6 | 32525000 | 32526000 | 0.000 | 0.000 | 0.029 | 0.014 |
| 496 | chr6 | 32526000 | 32527000 | 0.000 | 0.000 | 0.000 | 0.041 |
| 497 | chr6 | 32527000 | 32528000 | 0.000 | 0.000 | 0.000 | 0.027 |
| 498 | chr6 | 32548000 | 32549000 | 0.000 | 0.000 | 0.029 | 0.014 |
| 499 | chr6 | 32552000 | 32553000 | 0.056 | 0.000 | 0.015 | 0.027 |
| 500 | chr6 | 32557000 | 32558000 | 0.028 | 0.000 | 0.000 | 0.041 |
| 501 | chr6 | 32609000 | 32610000 | 0.028 | 0.000 | 0.059 | 0.014 |
| 502 | chr6 | 32630000 | 32631000 | 0.000 | 0.000 | 0.015 | 0.014 |
| 503 | chr6 | 32632000 | 32633000 | 0.111 | 0.000 | 0.029 | 0.027 |
| 504 | chr6 | 32727000 | 32728000 | 0.056 | 0.000 | 0.015 | 0.000 |
| 505 | chr6 | 32729000 | 32730000 | 0.056 | 0.000 | 0.029 | 0.014 |
| 506 | chr6 | 33048000 | 33049000 | 0.000 | 0.000 | 0.015 | 0.014 |
| 507 | chr6 | 34179000 | 34180000 | 0.000 | 0.000 | 0.029 | 0.000 |
| 508 | chr6 | 37138000 | 37139000 | 0.000 | 0.000 | 0.191 | 0.081 |
| 509 | chr6 | 37139000 | 37340000 | 0.000 | 0.000 | 0.088 | 0.041 |
| 510 | chr6 | 37140000 | 37141000 | 0.000 | 0.000 | 0.029 | 0.014 |
| 511 | chr6 | 58001000 | 58002000 | 0.000 | 0.000 | 0.015 | 0.014 |
| 512 | chr6 | 67923000 | 67924000 | 0.000 | 0.000 | 0.015 | 0.014 |
| 513 | chr6 | 77256000 | 77257000 | 0.000 | 0.000 | 0.029 | 0.000 |
| 514 | chr6 | 81437000 | 81438000 | 0.000 | 0.000 | 0.015 | 0.014 |
| 515 | chr6 | 88468000 | 88469000 | 0.000 | 0.000 | 0.015 | 0.014 |
| 516 | chr6 | 88630000 | 88631000 | 0.000 | 0.000 | 0.044 | 0.014 |
| 517 | chr6 | 88876000 | 88877000 | 0.028 | 0.000 | 0.015 | 0.000 |
| 518 | chr6 | 89323000 | 89324000 | 0.000 | 0.000 | 0.029 | 0.014 |

TABLE 1-continued

| | | | | | | | |
|---|---|---|---|---|---|---|---|
| 519 | chr6 | 89338000 | 89339000 | 0.000 | 0.000 | 0.029 | 0.000 |
| 520 | chr6 | 89348000 | 89349000 | 0.000 | 0.000 | 0.044 | 0.000 |
| 521 | chr6 | 89470000 | 89473000 | 0.000 | 0.000 | 0.029 | 0.000 |
| 522 | chr6 | 89471000 | 89172000 | 0.000 | 0.000 | 0.029 | 0.000 |
| 523 | chr6 | 90061000 | 90062000 | 0.000 | 0.000 | 0.059 | 0.000 |
| 524 | chr6 | 90062000 | 90063000 | 0.000 | 0.000 | 0.029 | 0.000 |
| 525 | chr6 | 90994000 | 90995000 | 0.000 | 0.000 | 0.029 | 0.014 |
| 526 | chr6 | 91004000 | 91005000 | 0.000 | 0.000 | 0.059 | 0.014 |
| 527 | chr6 | 91005000 | 91006000 | 0.000 | 0.019 | 0.294 | 0.095 |
| 528 | chr6 | 91006000 | 91007000 | 0.000 | 0.006 | 0.118 | 0.027 |
| 529 | chr6 | 91007000 | 91008000 | 0.000 | 0.012 | 0.029 | 0.000 |
| 530 | chr6 | 94822000 | 94823000 | 0.028 | 0.000 | 0.015 | 0.000 |
| 531 | chr6 | 107704000 | 107705000 | 0.028 | 0.000 | 0.000 | 0.014 |
| 532 | chr6 | 112885000 | 112886000 | 0.000 | 0.000 | 0.015 | 0.014 |
| 533 | chr6 | 118244000 | 118245000 | 0.000 | 0.000 | 0.015 | 0.014 |
| 534 | chr6 | 121288000 | 121289000 | 0.000 | 0.000 | 0.000 | 0.027 |
| 535 | chr6 | 121489000 | 121490000 | 0.000 | 0.000 | 0.029 | 0.000 |
| 536 | chr6 | 123504000 | 123505000 | 0.000 | 0.006 | 0.015 | 0.000 |
| 537 | chr6 | 127313000 | 127314000 | 0.000 | 0.006 | 0.015 | 0.000 |
| 538 | chr6 | 133785000 | 133786000 | 0.000 | 0.000 | 0.029 | 0.000 |
| 539 | chr6 | 134491000 | 134492000 | 0.000 | 0.000 | 0.029 | 0.000 |
| 540 | chr6 | 134492000 | 134493000 | 0.000 | 0.000 | 0.044 | 0.014 |
| 541 | chr6 | 154493000 | 134494000 | 0.000 | 0.000 | 0.029 | 0.000 |
| 542 | chr6 | 134494000 | 174495000 | 0.000 | 0.000 | 0.029 | 0.000 |
| 543 | chr6 | 134495000 | 134496000 | 0.000 | 0.000 | 0.162 | 0.041 |
| 544 | chr6 | 134496000 | 134497000 | 0.000 | 0.000 | 0.029 | 0.000 |
| 545 | chr6 | 142046000 | 142047000 | 0.000 | 0.000 | 0.059 | 0.000 |
| 546 | chr6 | 147860000 | 147861000 | 0.028 | 0.000 | 0.015 | 0.000 |
| 547 | chr6 | 150954000 | 150955000 | 0.000 | 0.000 | 0.044 | 0.014 |
| 548 | chr6 | 159238000 | 159239000 | 0.000 | 0.012 | 0.044 | 0.014 |
| 549 | chr6 | 159239000 | 159240000 | 0.000 | 0.000 | 0.029 | 0.014 |
| 550 | chr6 | 159240000 | 159241000 | 0.000 | 0.000 | 0.029 | 0.014 |
| 551 | chr6 | 159464000 | 159465000 | 0.000 | 0.000 | 0.015 | 0.014 |
| 552 | chr6 | 159465000 | 159466000 | 0.000 | 0.000 | 0.029 | 0.000 |
| 553 | chr6 | 161265000 | 161266000 | 0.028 | 0.000 | 0.000 | 0.027 |
| 554 | chr6 | 161833000 | 161834000 | 0.028 | 0.000 | 0.000 | 0.027 |
| 555 | chr6 | 162712000 | 162713000 | 0.000 | 0.000 | 0.029 | 0.000 |
| 556 | chr6 | 164941000 | 164932000 | 0.000 | 0.000 | 0.029 | 0.000 |
| 557 | chr6 | 168813000 | 168814000 | 0.028 | 0.000 | 0.015 | 0.000 |
| 558 | chr7 | 1898000 | 1899000 | 0.000 | 0.000 | 0.029 | 0.000 |
| 559 | chr7 | 1963000 | 1964000 | 0.028 | 0.000 | 0.015 | 0.000 |
| 560 | chr7 | 2080000 | 2081000 | 0.000 | 0.000 | 0.015 | 0.014 |
| 561 | chr7 | 5568000 | 5569000 | 0.000 | 0.000 | 0.059 | 0.014 |
| 562 | chr7 | 5569000 | 5570000 | 0.000 | 0.000 | 0.059 | 0.014 |
| 563 | chr7 | 5570000 | 5571000 | 0.000 | 0.000 | 0.015 | 0.027 |
| 564 | chr7 | 9933000 | 9934000 | 0.000 | 0.000 | 0.029 | 0.014 |
| 565 | chr7 | 13017000 | 13018000 | 0.028 | 0.000 | 0.015 | 0.000 |
| 566 | chr7 | 13346000 | 13347000 | 0.000 | 0.000 | 0.000 | 0.027 |
| 567 | chr7 | 15459000 | 15460000 | 0.000 | 0.000 | 0.000 | 0.027 |
| 568 | chr7 | 16382000 | 16383000 | 0.000 | 0.000 | 0.015 | 0.014 |
| 569 | chr7 | 28600000 | 28601000 | 0.028 | 0.000 | 0.015 | 0.000 |
| 570 | chr7 | 40846000 | 40847000 | 0.000 | 0.000 | 0.015 | 0.041 |
| 571 | chr7 | 50349000 | 50350000 | 0.000 | 0.000 | 0.059 | 0.014 |
| 572 | chr7 | 50350000 | 50351000 | 0.000 | 0.000 | 0.044 | 0.000 |
| 573 | chr7 | 53335000 | 53336000 | 0.000 | 0.000 | 0.000 | 0.027 |
| 574 | chr7 | 57713000 | 57714000 | 0.000 | 0.000 | 0.029 | 0.000 |
| 575 | chr7 | 62475000 | 62476000 | 0.000 | 0.000 | 0.015 | 0.027 |
| 576 | chr7 | 70669000 | 70670000 | 0.000 | 0.000 | 0.029 | 0.000 |
| 577 | chr7 | 71553000 | 71554000 | 0.000 | 0.000 | 0.015 | 0.014 |
| 578 | chr7 | 79847000 | 79848000 | 0.000 | 0.000 | 0.015 | 0.014 |
| 579 | chr7 | 80694000 | 80695000 | 0.000 | 0.000 | 0.029 | 0.000 |
| 580 | chr7 | 81556000 | 81557000 | 0.000 | 0.000 | 0.000 | 0.027 |
| 581 | chr7 | 84127000 | 84128000 | 0.028 | 0.000 | 0.015 | 0.000 |
| 582 | chr7 | 84247000 | 84248000 | 0.000 | 0.000 | 0.029 | 0.000 |
| 583 | chr7 | 84257000 | 84258000 | 0.028 | 0.000 | 0.015 | 0.000 |
| 584 | chr7 | 86914000 | 86915000 | 0.000 | 0.000 | 0.015 | 0.014 |
| 585 | chr7 | 90356000 | 90357000 | 0.000 | 0.000 | 0.029 | 0.000 |
| 586 | chr7 | 93304000 | 93305000 | 0.000 | 0.000 | 0.029 | 0.000 |
| 587 | chr7 | 93682000 | 93683000 | 0.000 | 0.000 | 0.015 | 0.014 |
| 588 | chr7 | 102644000 | 102645000 | 0.028 | 0.000 | 0.000 | 0.014 |
| 589 | chr7 | 105699000 | 105700000 | 0.000 | 0.000 | 0.015 | 0.027 |
| 590 | chr7 | 110521000 | 110522000 | 0.000 | 0.000 | 0.029 | 0.000 |
| 591 | chr7 | 110543000 | 110544000 | 0.000 | 0.000 | 0.029 | 0.000 |
| 592 | chr7 | 110545000 | 110546000 | 0.000 | 0.000 | 0.015 | 0.014 |
| 593 | chr7 | 110597000 | 110598000 | 0.000 | 0.000 | 0.015 | 0.014 |
| 594 | chr7 | 110601000 | 110602000 | 0.000 | 0.000 | 0.029 | 0.000 |
| 595 | chr7 | 110602000 | 110603000 | 0.000 | 0.000 | 0.029 | 0.000 |
| 596 | chr7 | 110609000 | 110610000 | 0.000 | 0.000 | 0.029 | 0.000 |
| 597 | chr7 | 119610000 | 119611000 | 0.000 | 0.000 | 0.044 | 0.000 |
| 598 | chr7 | 110617000 | 110618000 | 0.000 | 0.000 | 0.029 | 0.000 |

TABLE 1-continued

| | | | | | | | |
|---|---|---|---|---|---|---|---|
| 599 | chr7 | 110618000 | 119619000 | 0.000 | 0.000 | 0.044 | 0.000 |
| 600 | chr7 | 110619000 | 110620000 | 0.000 | 0.000 | 0.029 | 0.000 |
| 601 | chr7 | 110621000 | 110622000 | 0.000 | 0.000 | 0.029 | 0.000 |
| 602 | chr7 | 110628000 | 110629000 | 0.000 | 0.000 | 0.024 | 0.000 |
| 603 | chr7 | 110629000 | 110630000 | 0.000 | 0.000 | 0.015 | 0.027 |
| 604 | chr7 | 110631000 | 110632000 | 0.000 | 0.000 | 0.044 | 0.000 |
| 605 | chr7 | 119632000 | 110633000 | 0.000 | 0.000 | 0.029 | 0.014 |
| 606 | chr7 | 110636000 | 110637000 | 0.000 | 0.000 | 0.029 | 0.014 |
| 607 | chr7 | 110637000 | 110638000 | 0.000 | 0.000 | 0.029 | 0.014 |
| 608 | chr7 | 110638000 | 110639000 | 0.000 | 0.000 | 0.029 | 0.027 |
| 609 | chr7 | 110639000 | 110640000 | 0.000 | 0.000 | 0.044 | 0.000 |
| 610 | chr7 | 110641000 | 110642000 | 0.000 | 0.000 | 0.029 | 0.000 |
| 611 | chr7 | 110650000 | 110651000 | 0.000 | 0.000 | 0.029 | 0.000 |
| 612 | chr7 | 110651000 | 110652000 | 0.000 | 0.000 | 0.029 | 0.014 |
| 613 | chr7 | 110666000 | 110667000 | 0.000 | 0.006 | 0.000 | 0.027 |
| 614 | chr7 | 110671000 | 110672000 | 0.000 | 0.000 | 0.029 | 0.000 |
| 615 | chr7 | 110677000 | 110678000 | 0.000 | 0.000 | 0.029 | 0.014 |
| 616 | chr7 | 110679000 | 110680000 | 0.000 | 0.000 | 0.029 | 0.000 |
| 617 | chr7 | 110680000 | 110681000 | 0.000 | 0.000 | 0.074 | 0.000 |
| 618 | chr7 | 110685000 | 110686000 | 0.000 | 0.000 | 0.029 | 0.000 |
| 619 | chr7 | 110686000 | 110687000 | 0.028 | 0.000 | 0.044 | 0.027 |
| 620 | chr7 | 110688000 | 110689000 | 0.000 | 0.000 | 0.029 | 0.000 |
| 621 | chr7 | 110699000 | 110700000 | 0.000 | 0.000 | 0.059 | 0.000 |
| 622 | chr7 | 110700000 | 110701000 | 0.000 | 0.000 | 0.029 | 0.000 |
| 623 | chr7 | 110709000 | 110710000 | 0.000 | 0.000 | 0.029 | 0.000 |
| 624 | chr7 | 110711000 | 110712000 | 0.000 | 0.000 | 0.044 | 0.000 |
| 625 | chr7 | 110714000 | 110715000 | 0.000 | 0.000 | 0.015 | 0.014 |
| 626 | chr7 | 110727000 | 110728000 | 0.000 | 0.000 | 0.029 | 0.000 |
| 627 | chr7 | 110728000 | 110729000 | 0.000 | 0.000 | 0.015 | 0.014 |
| 628 | chr7 | 110729000 | 110730000 | 0.000 | 0.000 | 0.029 | 0.014 |
| 629 | chr7 | 110734000 | 110735000 | 0.000 | 0.000 | 0.015 | 0.014 |
| 630 | chr7 | 110737000 | 110738000 | 0.000 | 0.000 | 0.015 | 0.027 |
| 631 | chr7 | 110740000 | 110741000 | 0.000 | 0.000 | 0.029 | 0.027 |
| 632 | chr7 | 110744000 | 110745000 | 0.000 | 0.000 | 0.029 | 0.000 |
| 633 | chr7 | 110746000 | 110747000 | 0.000 | 0.000 | 0.029 | 0.014 |
| 634 | chr7 | 110747000 | 110748000 | 0.000 | 0.000 | 0.029 | 0.000 |
| 635 | chr7 | 110748000 | 110749000 | 0.000 | 0.000 | 0.029 | 0.000 |
| 636 | chr7 | 110755000 | 110756000 | 0.000 | 0.000 | 0.044 | 0.000 |
| 637 | chr7 | 110764000 | 110765000 | 0.000 | 0.000 | 0.029 | 0.000 |
| 638 | chr7 | 110767000 | 110768000 | 0.000 | 0.000 | 0.029 | 0.014 |
| 639 | chr7 | 110769000 | 110770000 | 0.000 | 0.000 | 0.044 | 0.000 |
| 640 | chr7 | 110771000 | 110772000 | 0.000 | 0.000 | 0.029 | 0.014 |
| 641 | chr7 | 110779000 | 110780000 | 0.000 | 0.000 | 0.015 | 0.027 |
| 642 | chr7 | 110780000 | 110781000 | 0.000 | 0.000 | 0.029 | 0.000 |
| 643 | chr7 | 110783000 | 110784000 | 0.000 | 0.000 | 0.044 | 0.000 |
| 644 | chr7 | 110785000 | 110786000 | 0.000 | 0.000 | 0.029 | 0.000 |
| 645 | chr7 | 110801000 | 110802000 | 0.000 | 0.000 | 0.015 | 0.027 |
| 646 | chr7 | 110802000 | 110803000 | 0.000 | 0.000 | 0.029 | 0.000 |
| 647 | chr7 | 110810000 | 110811000 | 0.000 | 0.000 | 0.029 | 0.000 |
| 648 | chr7 | 110816000 | 110817000 | 0.000 | 0.000 | 0.044 | 0.000 |
| 649 | chr7 | 110821000 | 110822000 | 0.000 | 0.000 | 0.029 | 0.000 |
| 650 | chr7 | 110824000 | 110825000 | 0.000 | 0.000 | 0.029 | 0.000 |
| 651 | chr7 | 110827000 | 110828000 | 0.000 | 0.000 | 0.015 | 0.014 |
| 652 | chr7 | 110836000 | 110837000 | 0.000 | 0.000 | 0.044 | 0.000 |
| 653 | chr7 | 110847000 | 110848000 | 0.000 | 0.000 | 0.020 | 0.000 |
| 654 | chr7 | 111567000 | 111568000 | 0.028 | 0.000 | 0.000 | 0.014 |
| 655 | chr7 | 119056000 | 119057000 | 0.000 | 0.000 | 0.015 | 0.014 |
| 656 | chr7 | 121380000 | 121381000 | 0.000 | 0.006 | 0.015 | 0.014 |
| 657 | chr7 | 123887000 | 123888000 | 0.000 | 0.000 | 0.029 | 0.000 |
| 658 | chr7 | 125262000 | 125263000 | 0.000 | 0.000 | 0.015 | 0.014 |
| 659 | chr7 | 145723000 | 145724000 | 0.000 | 0.000 | 0.029 | 0.000 |
| 660 | chr7 | 148508000 | 148509000 | 0.000 | 0.000 | 0.000 | 0.041 |
| 661 | chr7 | 155127000 | 155128000 | 0.000 | 0.000 | 0.000 | 0.027 |
| 662 | chr7 | 157162000 | 157163000 | 0.056 | 0.000 | 0.000 | 0.000 |
| 663 | chr7 | 158684000 | 158685000 | 0.000 | 0.000 | 0.015 | 0.014 |
| 664 | chr8 | 1646000 | 1647000 | 0.000 | 0.000 | 0.015 | 0.027 |
| 665 | chr8 | 5558000 | 5559000 | 0.000 | 0.000 | 0.029 | 0.000 |
| 666 | chr8 | 5612000 | 5613000 | 0.000 | 0.000 | 0.000 | 0.027 |
| 667 | chr8 | 8602000 | 8603000 | 0.000 | 0.000 | 0.029 | 0.014 |
| 668 | chr8 | 8706000 | 8707000 | 0.000 | 0.000 | 0.029 | 0.000 |
| 669 | chr8 | 8717000 | 8718000 | 0.000 | 0.000 | 0.029 | 0.000 |
| 670 | chr8 | 11352000 | 11353000 | 0.000 | 0.000 | 0.029 | 0.014 |
| 671 | chr8 | 14080000 | 14081000 | 0.000 | 0.000 | 0.015 | 0.014 |
| 672 | chr8 | 14796000 | 14797000 | 0.000 | 0.006 | 0.015 | 0.000 |
| 673 | chr8 | 16090000 | 16091000 | 0.000 | 0.000 | 0.015 | 0.014 |
| 674 | chr8 | 16187000 | 16188000 | 0.028 | 0.000 | 0.015 | 0.000 |
| 675 | chr8 | 23101000 | 23102000 | 0.000 | 0.000 | 0.015 | 0.014 |
| 676 | chr8 | 24207000 | 24208000 | 0.000 | 0.000 | 0.029 | 0.000 |
| 677 | chr8 | 29155000 | 29156000 | 0.028 | 0.000 | 0.000 | 0.014 |
| 678 | chr8 | 35657000 | 35658000 | 0.000 | 0.000 | 0.029 | 0.000 |

TABLE 1-continued

| | | | | | | | |
|---|---|---|---|---|---|---|---|
| 679 | chr8 | 38759000 | 38760000 | 0.000 | 0.000 | 0.029 | 0.000 |
| 680 | chr8 | 54986000 | 54987000 | 0.000 | 0.000 | 0.029 | 0.000 |
| 681 | chr8 | 60031000 | 60032000 | 0.000 | 0.000 | 0.015 | 0.014 |
| 682 | chr8 | 67525000 | 67526000 | 0.000 | 0.000 | 0.015 | 0.014 |
| 683 | chr8 | 77105000 | 77106000 | 0.000 | 0.000 | 0.029 | 0.000 |
| 684 | chr8 | 78400000 | 78401000 | 0.000 | 0.000 | 0.029 | 0.000 |
| 685 | chr8 | 90322000 | 90323000 | 0.000 | 0.000 | 0.029 | 0.000 |
| 686 | chr8 | 93199000 | 93200000 | 0.000 | 0.000 | 0.029 | 0.000 |
| 687 | chr8 | 94618000 | 94619000 | 0.028 | 0.000 | 0.015 | 0.000 |
| 688 | chr8 | 110586000 | 110587000 | 0.000 | 0.000 | 0.015 | 0.014 |
| 689 | chr8 | 126687000 | 126688000 | 0.028 | 0.000 | 0.015 | 0.014 |
| 690 | chr8 | 128748000 | 129749000 | 0.500 | 0.000 | 0.132 | 0.000 |
| 691 | chr8 | 128749000 | 128750000 | 0.583 | 0.000 | 0.103 | 0.014 |
| 692 | chr8 | 128750000 | 128751000 | 0.444 | 0.000 | 0.088 | 0.014 |
| 693 | chr8 | 128751000 | 128752000 | 0.111 | 0.000 | 0.044 | 0.000 |
| 694 | chr8 | 128752000 | 128753000 | 0.056 | 0.000 | 0.015 | 0.000 |
| 695 | chr8 | 137918000 | 137919000 | 0.028 | 0.000 | 0.015 | 0.000 |
| 696 | chr8 | 138274000 | 138275000 | 0.000 | 0.000 | 0.000 | 0.027 |
| 697 | chr8 | 143183000 | 143184000 | 0.028 | 0.000 | 0.015 | 0.000 |
| 698 | chr8 | 144123000 | 144124000 | 0.000 | 0.000 | 0.029 | 0.000 |
| 699 | chr9 | 6411000 | 6412000 | 0.000 | 0.000 | 0.029 | 0.000 |
| 700 | chr9 | 6413000 | 6414000 | 0.000 | 0.000 | 0.015 | 0.014 |
| 701 | chr9 | 6414000 | 6415000 | 0.000 | 0.000 | 0.029 | 0.014 |
| 702 | chr9 | 9928000 | 9929000 | 0.000 | 0.000 | 0.000 | 0.027 |
| 703 | chr9 | 13965000 | 13966000 | 0.000 | 0.000 | 0.029 | 0.000 |
| 704 | chr9 | 22824000 | 22825000 | 0.000 | 0.000 | 0.029 | 0.000 |
| 705 | chr9 | 25260000 | 25261000 | 0.000 | 0.000 | 0.029 | 0.000 |
| 706 | chr9 | 29890000 | 29891000 | 0.000 | 0.000 | 0.015 | 0.014 |
| 707 | chr9 | 30656000 | 30657000 | 0.000 | 0.000 | 0.015 | 0.014 |
| 708 | chr9 | 37003000 | 37004000 | 0.000 | 0.006 | 0.015 | 0.000 |
| 709 | chr9 | 37005000 | 37006000 | 0.000 | 0.000 | 0.015 | 0.014 |
| 710 | chr9 | 37024000 | 37025000 | 0.000 | 0.000 | 0.044 | 0.027 |
| 711 | chr9 | 37025000 | 37026000 | 0.000 | 0.000 | 0.132 | 0.054 |
| 712 | chr9 | 37026000 | 37027000 | 0.000 | 0.006 | 0.221 | 0.108 |
| 713 | chr9 | 37027000 | 37028000 | 0.000 | 0.000 | 0.029 | 0.014 |
| 714 | chr9 | 37033000 | 37034000 | 0.000 | 0.000 | 0.041 | 0.014 |
| 715 | chr9 | 37034000 | 37035000 | 0.000 | 0.000 | 0.074 | 0.041 |
| 716 | chr9 | 37035000 | 37036000 | 0.000 | 0.000 | 0.015 | 0.014 |
| 717 | chr9 | 37196000 | 37197000 | 0.000 | 0.000 | 0.029 | 0.014 |
| 718 | chr9 | 37197000 | 37198000 | 0.000 | 0.000 | 0.029 | 0.000 |
| 719 | chr9 | 37293000 | 37294000 | 0.000 | 0.000 | 0.029 | 0.027 |
| 720 | chr9 | 37294000 | 37295000 | 0.000 | 0.000 | 0.044 | 0.027 |
| 721 | chr9 | 37327000 | 37328000 | 0.000 | 0.000 | 0.015 | 0.014 |
| 722 | chr9 | 37336000 | 37337000 | 0.000 | 0.000 | 0.044 | 0.014 |
| 723 | chr9 | 37337000 | 37338000 | 0.000 | 0.012 | 0.015 | 0.041 |
| 724 | chr9 | 37338000 | 37339000 | 0.000 | 0.000 | 0.029 | 0.014 |
| 725 | chr9 | 37369000 | 37370000 | 0.000 | 0.000 | 0.029 | 0.000 |
| 726 | chr9 | 37371000 | 37372000 | 0.028 | 0.025 | 0.118 | 0.068 |
| 727 | chr9 | 37372000 | 37373000 | 0.000 | 0.000 | 0.015 | 0.014 |
| 728 | chr9 | 37383000 | 37384000 | 0.000 | 0.000 | 0.059 | 0.027 |
| 729 | chr9 | 37384000 | 37385000 | 0.000 | 0.000 | 0.059 | 0.054 |
| 730 | chr9 | 37385000 | 37386000 | 0.000 | 0.000 | 0.029 | 0.014 |
| 731 | chr9 | 37387000 | 37388000 | 0.000 | 0.000 | 0.059 | 0.014 |
| 732 | chr9 | 37397000 | 37398000 | 0.000 | 0.000 | 0.044 | 0.000 |
| 733 | chr9 | 37398000 | 37399000 | 0.000 | 0.000 | 0.029 | 0.000 |
| 734 | chr9 | 37399000 | 37400000 | 0.000 | 0.000 | 0.029 | 0.000 |
| 735 | chr9 | 37402000 | 37403000 | 0.000 | 0.006 | 0.029 | 0.000 |
| 736 | chr9 | 37406000 | 37407000 | 0.000 | 0.000 | 0.015 | 0.014 |
| 737 | chr9 | 37407000 | 37408000 | 0.000 | 0.000 | 0.132 | 0.149 |
| 738 | chr9 | 37408000 | 37409000 | 0.000 | 0.006 | 0.029 | 0.027 |
| 739 | chr9 | 37410000 | 37411000 | 0.000 | 0.000 | 0.029 | 0.000 |
| 740 | chr9 | 37424000 | 37425000 | 0.000 | 0.000 | 0.044 | 0.000 |
| 741 | chr9 | 37425000 | 37426000 | 0.000 | 0.000 | 0.029 | 0.000 |
| 742 | chr9 | 112811000 | 112812000 | 0.000 | 0.000 | 0.059 | 0.014 |
| 743 | chr9 | 117037000 | 117038000 | 0.056 | 0.000 | 0.000 | 0.014 |
| 744 | chr9 | 119779000 | 119780000 | 0.000 | 0.000 | 0.044 | 0.000 |
| 745 | chr9 | 126232000 | 126233000 | 0.056 | 0.000 | 0.000 | 0.000 |
| 746 | chr9 | 130741000 | 130742000 | 0.000 | 0.000 | 0.059 | 0.000 |
| 747 | chr9 | 130742000 | 130743000 | 0.000 | 0.000 | 0.059 | 0.027 |
| 748 | chr9 | 132767000 | 132768000 | 0.000 | 0.000 | 0.015 | 0.014 |
| 749 | chr9 | 132785000 | 132786000 | 0.000 | 0.000 | 0.029 | 0.000 |
| 750 | chr9 | 132803000 | 132804000 | 0.000 | 0.000 | 0.015 | 0.014 |
| 751 | chr9 | 132804000 | 132803000 | 0.000 | 0.000 | 0.029 | 0.027 |
| 752 | chr9 | 134551000 | 134552000 | 0.000 | 0.000 | 0.029 | 0.000 |
| 753 | chr9 | 138874000 | 138875000 | 0.056 | 0.000 | 0.029 | 0.014 |
| 754 | chr10 | 3333000 | 3334000 | 0.000 | 0.000 | 0.000 | 0.027 |
| 755 | chr10 | 5707000 | 5708000 | 0.000 | 0.000 | 0.029 | 0.014 |
| 756 | chr10 | 5728000 | 5729000 | 0.000 | 0.006 | 0.015 | 0.000 |
| 757 | chr10 | 15393000 | 15194000 | 0.028 | 0.000 | 0.015 | 0.000 |
| 758 | chr10 | 20796000 | 20797000 | 0.000 | 0.006 | 0.015 | 0.000 |

TABLE 1-continued

| | | | | | | | |
|---|---|---|---|---|---|---|---|
| 759 | chr10 | 35424000 | 35425000 | 0.000 | 0.000 | 0.029 | 0.000 |
| 760 | chr10 | 56678000 | 56679000 | 0.000 | 0.000 | 0.000 | 0.027 |
| 761 | chr10 | 63440000 | 63441000 | 0.028 | 0.000 | 0.015 | 0.000 |
| 762 | chr10 | 63659000 | 63660000 | 0.000 | 0.000 | 0.044 | 0.014 |
| 763 | chr10 | 63660000 | 63661000 | 0.000 | 0.000 | 0.059 | 0.014 |
| 764 | chr10 | 63662000 | 63663000 | 0.000 | 0.000 | 0.029 | 0.014 |
| 765 | chr10 | 63720000 | 63721000 | 0.000 | 0.000 | 0.029 | 0.000 |
| 766 | chr10 | 63803000 | 63804000 | 0.000 | 0.000 | 0.000 | 0.027 |
| 767 | chr10 | 63809000 | 63810000 | 0.000 | 0.000 | 0.015 | 0.014 |
| 768 | chr10 | 63810000 | 63811000 | 0.000 | 0.000 | 0.000 | 0.027 |
| 769 | chr10 | 67907000 | 67908000 | 0.000 | 0.006 | 0.015 | 0.000 |
| 770 | chr10 | 68474000 | 68475000 | 0.000 | 0.000 | 0.000 | 0.027 |
| 771 | chr10 | 98510000 | 98511000 | 0.000 | 0.000 | 0.029 | 0.000 |
| 772 | chr10 | 101384000 | 101385000 | 0.028 | 0.000 | 0.015 | 0.014 |
| 773 | chr10 | 108276000 | 108277000 | 0.000 | 0.000 | 0.029 | 0.000 |
| 774 | chr10 | 113473000 | 113474000 | 0.028 | 0.000 | 0.015 | 0.000 |
| 775 | chr10 | 113636000 | 113637000 | 0.000 | 0.000 | 0.029 | 0.000 |
| 776 | chr10 | 116458000 | 116459000 | 0.000 | 0.000 | 0.044 | 0.000 |
| 777 | chr10 | 121623000 | 121624000 | 0.000 | 0.000 | 0.029 | 0.000 |
| 778 | chr10 | 132973000 | 132974000 | 0.000 | 0.000 | 0.015 | 0.027 |
| 779 | chr10 | 134326000 | 134327000 | 0.028 | 0.000 | 0.015 | 0.000 |
| 780 | chr11 | 871000 | 872000 | 0.028 | 0.000 | 0.029 | 0.000 |
| 781 | chr11 | 1149000 | 1150000 | 0.028 | 0.000 | 0.015 | 0.000 |
| 782 | chr11 | 25065000 | 25066000 | 0.000 | 0.000 | 0.029 | 0.000 |
| 783 | chr11 | 25289000 | 25290000 | 0.000 | 0.000 | 0.029 | 0.000 |
| 784 | chr11 | 27216000 | 27217000 | 0.028 | 0.000 | 0.029 | 0.014 |
| 785 | chr11 | 28849000 | 28850000 | 0.000 | 0.000 | 0.000 | 0.027 |
| 786 | chr11 | 29253000 | 29254000 | 0.000 | 0.000 | 0.029 | 0.000 |
| 787 | chr11 | 29900000 | 29901000 | 0.000 | 0.000 | 0.029 | 0.000 |
| 788 | chr11 | 40626000 | 40627000 | 0.000 | 0.000 | 0.029 | 0.000 |
| 789 | chr11 | 40845000 | 40846000 | 0.000 | 0.000 | 0.029 | 0.000 |
| 790 | chr11 | 40868000 | 40869000 | 0.000 | 0.000 | 0.029 | 0.000 |
| 791 | chr11 | 41066000 | 41067000 | 0.000 | 0.000 | 0.029 | 0.000 |
| 792 | chr11 | 41844000 | 41845000 | 0.028 | 0.000 | 0.015 | 0.000 |
| 793 | chr11 | 57171000 | 57172000 | 0.000 | 0.000 | 0.029 | 0.014 |
| 794 | chr11 | 60224000 | 60225000 | 0.000 | 0.000 | 0.074 | 0.014 |
| 795 | chr11 | 65190000 | 65191000 | 0.000 | 0.000 | 0.074 | 0.027 |
| 796 | chr11 | 65191000 | 65192000 | 0.000 | 0.000 | 0.103 | 0.014 |
| 797 | chr11 | 65266000 | 65267000 | 0.000 | 0.000 | 0.029 | 0.014 |
| 798 | chr11 | 65267000 | 65268000 | 0.000 | 0.000 | 0.103 | 0.000 |
| 799 | chr11 | 85963000 | 85964000 | 0.000 | 0.000 | 0.029 | 0.000 |
| 800 | chr11 | 92261000 | 92262000 | 0.000 | 0.000 | 0.029 | 0.000 |
| 801 | chr11 | 102117000 | 102118000 | 0.000 | 0.000 | 0.000 | 0.027 |
| 802 | chr11 | 102188000 | 102189000 | 0.000 | 0.012 | 0.206 | 0.108 |
| 803 | chr11 | 102189000 | 102190000 | 0.000 | 0.000 | 0.059 | 0.000 |
| 804 | chr11 | 107497000 | 107498000 | 0.028 | 0.000 | 0.015 | 0.000 |
| 805 | chr11 | 108781000 | 108782000 | 0.000 | 0.000 | 0.015 | 0.014 |
| 806 | chr11 | 108974000 | 108976000 | 0.000 | 0.000 | 0.015 | 0.014 |
| 807 | chr11 | 109066000 | 109067000 | 0.028 | 0.000 | 0.015 | 0.000 |
| 808 | chr11 | 111248000 | 111249000 | 0.000 | 0.000 | 0.029 | 0.014 |
| 809 | chr11 | 111249000 | 111250000 | 0.000 | 0.012 | 0.103 | 0.081 |
| 810 | chr11 | 115761000 | 115762000 | 0.028 | 0.000 | 0.015 | 0.041 |
| 811 | chr11 | 118723000 | 118724000 | 0.000 | 0.000 | 0.029 | 0.000 |
| 812 | chr11 | 126496000 | 126497000 | 0.028 | 0.000 | 0.015 | 0.014 |
| 813 | chr11 | 128390000 | 128391000 | 0.000 | 0.000 | 0.044 | 0.014 |
| 814 | chr11 | 128391000 | 128392000 | 0.000 | 0.000 | 0.118 | 0.014 |
| 815 | chr12 | 6554000 | 6555000 | 0.000 | 0.000 | 0.029 | 0.000 |
| 816 | chr12 | 8762000 | 8763000 | 0.000 | 0.000 | 0.015 | 0.014 |
| 817 | chr12 | 8763000 | 8764000 | 0.000 | 0.000 | 0.044 | 0.041 |
| 818 | chr12 | 8764000 | 8765000 | 0.000 | 0.000 | 0.029 | 0.068 |
| 819 | chr12 | 8765000 | 8766000 | 0.000 | 0.000 | 0.015 | 0.027 |
| 820 | chr12 | 9823000 | 9824000 | 0.000 | 0.000 | 0.015 | 0.014 |
| 821 | chr12 | 11710000 | 11711000 | 0.000 | 0.000 | 0.029 | 0.000 |
| 822 | chr12 | 11803000 | 11804000 | 0.000 | 0.000 | 0.015 | 0.014 |
| 823 | chr12 | 14923000 | 14924000 | 0.000 | 0.000 | 0.015 | 0.014 |
| 824 | chr12 | 16717000 | 16718000 | 0.000 | 0.000 | 0.000 | 0.027 |
| 825 | chr12 | 23805000 | 23806000 | 0.000 | 0.000 | 0.029 | 0.000 |
| 826 | chr12 | 25149000 | 25150000 | 0.000 | 0.000 | 0.029 | 0.000 |
| 827 | chr12 | 25151000 | 25152000 | 0.000 | 0.000 | 0.015 | 0.014 |
| 828 | chr12 | 25174000 | 25175000 | 0.000 | 0.000 | 0.044 | 0.000 |
| 829 | chr12 | 25205000 | 25206000 | 0.000 | 0.006 | 0.015 | 0.000 |
| 830 | chr12 | 25206000 | 25207000 | 0.000 | 0.006 | 0.103 | 0.014 |
| 831 | chr12 | 25207000 | 25208000 | 0.000 | 0.006 | 0.118 | 0.014 |
| 832 | chr12 | 25208000 | 25209000 | 0.000 | 0.000 | 0.029 | 0.014 |
| 833 | chr12 | 25665000 | 25666000 | 0.028 | 0.000 | 0.015 | 0.000 |
| 834 | chr12 | 38920000 | 38921000 | 0.000 | 0.000 | 0.029 | 0.000 |
| 835 | chr12 | 48027000 | 48028000 | 0.028 | 0.000 | 0.059 | 0.027 |
| 836 | chr12 | 57496000 | 57497000 | 0.000 | 0.000 | 0.015 | 0.014 |
| 837 | chr12 | 69203000 | 69204000 | 0.000 | 0.006 | 0.015 | 0.000 |
| 838 | chr12 | 76202000 | 76203000 | 0.000 | 0.000 | 0.000 | 0.027 |

TABLE 1-continued

| | | | | | | | |
|---|---|---|---|---|---|---|---|
| 839 | chr12 | 79270000 | 79271000 | 0.000 | 0.000 | 0.029 | 0.027 |
| 840 | chr12 | 82572000 | 82573000 | 0.000 | 0.000 | 0.015 | 0.014 |
| 841 | chr12 | 84837000 | 84838000 | 0.000 | 0.000 | 0.000 | 0.027 |
| 842 | chr12 | 86114000 | 86115000 | 0.000 | 0.000 | 0.029 | 0.000 |
| 843 | chr12 | 86115000 | 86116000 | 0.000 | 0.000 | 0.029 | 0.000 |
| 844 | chr12 | 92538000 | 92539000 | 0.000 | 0.000 | 0.088 | 0.027 |
| 845 | chr12 | 92539000 | 92540000 | 0.000 | 0.000 | 0.074 | 0.014 |
| 846 | chr12 | 96030000 | 96031000 | 0.028 | 0.000 | 0.015 | 0.000 |
| 847 | chr12 | 110171000 | 110172000 | 0.000 | 0.006 | 0.015 | 0.000 |
| 848 | chr12 | 110980000 | 110981000 | 0.000 | 0.000 | 0.015 | 0.014 |
| 849 | chr12 | 113493000 | 113494000 | 0.000 | 0.000 | 0.059 | 0.000 |
| 850 | chr12 | 113494000 | 113495000 | 0.000 | 0.000 | 0.176 | 0.041 |
| 851 | chr12 | 113495000 | 113496000 | 0.000 | 0.000 | 0.162 | 0.068 |
| 852 | chr12 | 113496000 | 113497000 | 0.000 | 0.000 | 0.132 | 0.054 |
| 853 | chr12 | 113497000 | 113498000 | 0.000 | 0.000 | 0.074 | 0.000 |
| 854 | chr12 | 113499000 | 113500000 | 0.000 | 0.000 | 0.029 | 0.000 |
| 855 | chr12 | 113512000 | 113513000 | 0.000 | 0.000 | 0.029 | 0.000 |
| 856 | chr12 | 115966000 | 115967000 | 0.000 | 0.000 | 0.000 | 0.027 |
| 857 | chr12 | 122432000 | 122433000 | 0.000 | 0.000 | 0.029 | 0.000 |
| 858 | chr12 | 122433000 | 122434000 | 0.000 | 0.000 | 0.059 | 0.014 |
| 859 | chr12 | 122447000 | 127448000 | 0.000 | 0.000 | 0.000 | 0.027 |
| 860 | chr12 | 122458000 | 122459000 | 0.000 | 0.006 | 0.118 | 0.068 |
| 861 | chr12 | 122459000 | 122460000 | 0.000 | 0.006 | 0.324 | 0.108 |
| 862 | chr12 | 122460000 | 122463000 | 0.000 | 0.000 | 0.176 | 0.081 |
| 863 | chr12 | 122461000 | 122462000 | 0.000 | 0.006 | 0.279 | 0.162 |
| 864 | chr12 | 122462000 | 122463000 | 0.000 | 0.012 | 0.191 | 0.027 |
| 865 | chr12 | 122463000 | 122464000 | 0.000 | 0.012 | 0.132 | 0.054 |
| 866 | chr12 | 124054000 | 124055000 | 0.028 | 0.000 | 0.015 | 0.014 |
| 867 | chr12 | 127965000 | 127966000 | 0.000 | 0.000 | 0.000 | 0.027 |
| 868 | chr12 | 131303000 | 131304000 | 0.056 | 0.000 | 0.015 | 0.014 |
| 869 | chr12 | 131649000 | 131650000 | 0.000 | 0.000 | 0.000 | 0.027 |
| 870 | chr12 | 133306000 | 133307000 | 0.028 | 0.000 | 0.015 | 0.027 |
| 871 | chr13 | 21913000 | 21914000 | 0.000 | 0.000 | 0.029 | 0.000 |
| 872 | chr13 | 32116000 | 32117000 | 0.028 | 0.000 | 0.015 | 0.000 |
| 873 | chr13 | 35498000 | 35499000 | 0.000 | 0.000 | 0.015 | 0.027 |
| 874 | chr13 | 38371000 | 38372000 | 0.028 | 0.000 | 0.015 | 0.000 |
| 875 | chr13 | 38630000 | 38631000 | 0.000 | 0.000 | 0.029 | 0.000 |
| 876 | chr13 | 41156000 | 41157000 | 0.000 | 0.000 | 0.029 | 0.000 |
| 877 | chr13 | 41240000 | 41241000 | 0.028 | 0.000 | 0.029 | 0.000 |
| 878 | chr13 | 46958000 | 46959000 | 0.000 | 0.000 | 0.029 | 0.000 |
| 879 | chr13 | 46959000 | 46960000 | 0.000 | 0.000 | 0.029 | 0.000 |
| 880 | chr13 | 46960000 | 46961000 | 0.000 | 0.000 | 0.088 | 0.027 |
| 881 | chr13 | 46961000 | 46962000 | 0.000 | 0.000 | 0.015 | 0.014 |
| 882 | chr13 | 46962000 | 46963000 | 0.000 | 0.000 | 0.015 | 0.014 |
| 883 | chr13 | 55239000 | 55240000 | 0.000 | 0.000 | 0.029 | 0.000 |
| 884 | chr13 | 55386000 | 55387000 | 0.000 | 0.000 | 0.029 | 0.000 |
| 885 | chr13 | 55598000 | 55599000 | 0.000 | 0.000 | 0.029 | 0.000 |
| 886 | chr13 | 57222000 | 57223000 | 0.000 | 0.000 | 0.029 | 0.000 |
| 887 | chr13 | 61343000 | 61344000 | 0.028 | 0.000 | 0.015 | 0.000 |
| 888 | chr13 | 62830000 | 62831000 | 0.000 | 0.000 | 0.000 | 0.027 |
| 889 | chr13 | 63049000 | 63050000 | 0.000 | 0.000 | 0.029 | 0.000 |
| 890 | chr13 | 63157000 | 63158000 | 0.028 | 0.000 | 0.015 | 0.000 |
| 891 | chr13 | 63214000 | 63215000 | 0.028 | 0.000 | 0.015 | 0.000 |
| 892 | chr13 | 64802000 | 64803000 | 0.000 | 0.000 | 0.015 | 0.014 |
| 893 | chr13 | 65637000 | 95638000 | 0.000 | 0.000 | 0.029 | 0.000 |
| 894 | chr13 | 68656000 | 68657000 | 0.000 | 0.000 | 0.000 | 0.027 |
| 895 | chr13 | 69418000 | 69419000 | 0.000 | 0.000 | 0.029 | 0.014 |
| 896 | chr13 | 70956000 | 70957000 | 0.000 | 0.012 | 0.015 | 0.000 |
| 897 | chr13 | 74542000 | 74543000 | 0.000 | 0.000 | 0.029 | 0.000 |
| 898 | chr13 | 75983000 | 75984000 | 0.000 | 0.000 | 0.074 | 0.014 |
| 899 | chr13 | 75984000 | 75985000 | 0.000 | 0.000 | 0.118 | 0.027 |
| 900 | chr13 | 83450000 | 83451000 | 0.000 | 0.000 | 0.029 | 0.000 |
| 901 | chr13 | 84641000 | 84642000 | 0.000 | 0.000 | 0.015 | 0.014 |
| 902 | chr13 | 87793000 | 87794000 | 0.000 | 0.000 | 0.015 | 0.014 |
| 903 | chr13 | 91480000 | 91481000 | 0.000 | 0.000 | 0.000 | 0.027 |
| 904 | chr13 | 106081000 | 106082000 | 0.000 | 0.000 | 0.015 | 0.014 |
| 905 | chr13 | 114786000 | 114787000 | 0.000 | 0.000 | 0.015 | 0.027 |
| 906 | chr13 | 114916000 | 114917000 | 0.028 | 0.000 | 0.000 | 0.014 |
| 907 | chr14 | 22948000 | 22949000 | 0.000 | 0.000 | 0.029 | 0.000 |
| 908 | chr14 | 22949000 | 22950000 | 0.000 | 0.000 | 0.044 | 0.000 |
| 909 | chr14 | 22950000 | 22951000 | 0.000 | 0.000 | 0.029 | 0.000 |
| 910 | chr14 | 22977000 | 22978000 | 0.000 | 0.000 | 0.015 | 0.014 |
| 911 | chr14 | 27286000 | 27287000 | 0.000 | 0.000 | 0.029 | 0.000 |
| 912 | chr14 | 28645000 | 28646000 | 0.000 | 0.000 | 0.000 | 0.027 |
| 913 | chr14 | 49407000 | 49408000 | 0.000 | 0.000 | 0.000 | 0.041 |
| 914 | chr14 | 50864000 | 50865000 | 0.000 | 0.000 | 0.029 | 0.000 |
| 915 | chr14 | 54812000 | 54813000 | 0.000 | 0.000 | 0.000 | 0.027 |
| 916 | chr14 | 55348000 | 55349000 | 0.000 | 0.000 | 0.029 | 0.000 |
| 917 | chr14 | 59827000 | 59828000 | 0.000 | 0.000 | 0.029 | 0.000 |
| 918 | chr14 | 63143000 | 63144000 | 0.000 | 0.000 | 0.015 | 0.014 |

TABLE 1-continued

| | | | | | | | |
|---|---|---|---|---|---|---|---|
| 919 | chr14 | 64194000 | 64195000 | 0.000 | 0.000 | 0.015 | 0.014 |
| 920 | chr14 | 69258000 | 69259000 | 0.000 | 0.000 | 0.191 | 0.027 |
| 921 | chr14 | 69259000 | 69260000 | 0.000 | 0.012 | 0.265 | 0.068 |
| 922 | chr14 | 78418000 | 78419000 | 0.000 | 0.000 | 0.029 | 0.000 |
| 923 | chr14 | 81685000 | 81686000 | 0.028 | 0.000 | 0.015 | 0.000 |
| 924 | chr14 | 84420000 | 84421000 | 0.000 | 0.006 | 0.015 | 0.000 |
| 925 | chr14 | 91883000 | 91884000 | 0.000 | 0.000 | 0.015 | 0.014 |
| 926 | chr14 | 94941000 | 94942000 | 0.000 | 0.006 | 0.029 | 0.014 |
| 927 | chr14 | 94942000 | 94943000 | 0.000 | 0.000 | 0.118 | 0.014 |
| 928 | chr14 | 96179000 | 96180000 | 0.028 | 0.037 | 0.132 | 0.108 |
| 929 | chr14 | 96180000 | 96181000 | 0.028 | 0.025 | 0.088 | 0.054 |
| 930 | chr14 | 101597000 | 101598000 | 0.000 | 0.000 | 0.000 | 0.027 |
| 931 | chr14 | 102285000 | 102286000 | 0.000 | 0.000 | 0.015 | 0.014 |
| 932 | chr14 | 105954000 | 105955000 | 0.000 | 0.000 | 0.044 | 0.014 |
| 933 | chr14 | 106031000 | 106032000 | 0.000 | 0.000 | 0.015 | 0.014 |
| 934 | chr14 | 106042000 | 106043000 | 0.000 | 0.019 | 0.103 | 0.041 |
| 935 | chr14 | 106048000 | 106049000 | 0.000 | 0.006 | 0.015 | 0.000 |
| 936 | chr14 | 106054000 | 106055000 | 0.000 | 0.000 | 0.029 | 0.014 |
| 937 | chr14 | 106055000 | 106056000 | 0.056 | 0.000 | 0.103 | 0.027 |
| 938 | chr14 | 106056000 | 106057000 | 0.056 | 0.006 | 0.074 | 0.027 |
| 939 | chr14 | 106057000 | 106058000 | 0.000 | 0.000 | 0.059 | 0.000 |
| 940 | chr14 | 106058000 | 106059000 | 0.000 | 0.000 | 0.029 | 0.000 |
| 941 | chr14 | 106066000 | 106067000 | 0.000 | 0.000 | 0.059 | 0.000 |
| 942 | chr14 | 106067000 | 106068000 | 0.000 | 0.000 | 0.044 | 0.014 |
| 943 | chr14 | 106068000 | 106069000 | 0.000 | 0.000 | 0.103 | 0.027 |
| 944 | chr14 | 106069000 | 106070000 | 0.000 | 0.006 | 0.206 | 0.216 |
| 945 | chr14 | 106070000 | 106071000 | 0.000 | 0.000 | 0.088 | 0.068 |
| 946 | chr14 | 106071000 | 106072000 | 0.000 | 0.000 | 0.074 | 0.068 |
| 947 | chr14 | 106072000 | 106073000 | 0.000 | 0.000 | 0.029 | 0.014 |
| 948 | chr14 | 106082000 | 106083000 | 0.000 | 0.000 | 0.015 | 0.027 |
| 949 | chr14 | 106092000 | 106093000 | 0.000 | 0.000 | 0.029 | 0.000 |
| 950 | chr14 | 106094000 | 106095000 | 0.000 | 0.006 | 0.147 | 0.027 |
| 951 | chr14 | 106095000 | 106096000 | 0.000 | 0.000 | 0.103 | 0.081 |
| 952 | chr14 | 106110000 | 106111000 | 0.000 | 0.000 | 0.074 | 0.014 |
| 953 | chr14 | 106111000 | 106112000 | 0.000 | 0.000 | 0.015 | 0.014 |
| 954 | chr14 | 106112000 | 106113000 | 0.000 | 0.056 | 0.294 | 0.257 |
| 955 | chr14 | 106113000 | 106114000 | 0.028 | 0.068 | 0.397 | 0.284 |
| 956 | chr14 | 106114000 | 106115000 | 0.000 | 0.000 | 0.279 | 0.122 |
| 957 | chr14 | 106146000 | 106147000 | 0.000 | 0.000 | 0.029 | 0.000 |
| 958 | chr14 | 106151000 | 106152000 | 0.000 | 0.006 | 0.015 | 0.014 |
| 959 | chr14 | 106152000 | 106153000 | 0.000 | 0.006 | 0.015 | 0.027 |
| 960 | chr14 | 106161000 | 106162000 | 0.000 | 0.000 | 0.015 | 0.014 |
| 961 | chr14 | 106173000 | 106174000 | 0.028 | 0.006 | 0.029 | 0.027 |
| 962 | chr14 | 106174000 | 106175000 | 0.000 | 0.006 | 0.029 | 0.000 |
| 963 | chr14 | 106175000 | 106176000 | 0.028 | 0.006 | 0.059 | 0.014 |
| 964 | chr14 | 106176000 | 106177000 | 0.139 | 0.031 | 0.103 | 0.068 |
| 965 | chr14 | 106177000 | 106178000 | 0.000 | 0.019 | 0.059 | 0.027 |
| 966 | chr14 | 106178000 | 106179000 | 0.000 | 0.006 | 0.059 | 0.014 |
| 967 | chr14 | 106208000 | 106209000 | 0.000 | 0.000 | 0.103 | 0.027 |
| 968 | chr14 | 106209000 | 106210000 | 0.000 | 0.006 | 0.118 | 0.054 |
| 969 | chr14 | 106210000 | 106211000 | 0.000 | 0.000 | 0.118 | 0.068 |
| 970 | chr14 | 106211000 | 106212000 | 0.000 | 0.056 | 0.235 | 0.149 |
| 971 | chr14 | 106212000 | 106213000 | 0.028 | 0.106 | 0.309 | 0.270 |
| 972 | chr14 | 106213000 | 106214000 | 0.056 | 0.068 | 0.382 | 0.216 |
| 973 | chr14 | 106214000 | 106215000 | 0.000 | 0.000 | 0.147 | 0.000 |
| 974 | chr14 | 106237000 | 106238000 | 0.000 | 0.000 | 0.088 | 0.000 |
| 975 | chr14 | 106238000 | 106239000 | 0.000 | 0.000 | 0.176 | 0.027 |
| 976 | chr14 | 106239000 | 106240000 | 0.056 | 0.062 | 0.206 | 0.135 |
| 977 | chr14 | 106240000 | 106241000 | 0.028 | 0.130 | 0.324 | 0.230 |
| 978 | chr14 | 106241000 | 106242000 | 0.000 | 0.025 | 0.221 | 0.081 |
| 979 | chr14 | 106242000 | 106243000 | 0.000 | 0.000 | 0.044 | 0.014 |
| 980 | chr14 | 106321000 | 106322000 | 0.000 | 0.000 | 0.059 | 0.000 |
| 981 | chr14 | 106322000 | 106323000 | 0.000 | 0.006 | 0.221 | 0.054 |
| 982 | chr14 | 106323000 | 106324000 | 0.056 | 0.062 | 0.235 | 0.162 |
| 983 | chr14 | 106324000 | 106325000 | 0.250 | 0.193 | 0.221 | 0.284 |
| 984 | chr14 | 106325000 | 106326000 | 0.694 | 0.335 | 0.279 | 0.365 |
| 985 | chr14 | 106326000 | 106327000 | 0.833 | 0.540 | 0.838 | 0.838 |
| 986 | chr14 | 106327000 | 106328000 | 0.333 | 0.335 | 0.926 | 0.905 |
| 987 | chr14 | 106328000 | 106329000 | 0.250 | 0.248 | 0.809 | 0.730 |
| 988 | chr14 | 106329000 | 106330000 | 0.694 | 0.441 | 0.882 | 0.932 |
| 989 | chr14 | 106330000 | 106331000 | 0.694 | 0.298 | 0.574 | 0.649 |
| 990 | chr14 | 106331000 | 106332000 | 0.028 | 0.012 | 0.044 | 0.027 |
| 991 | chr14 | 106338000 | 106339000 | 0.028 | 0.006 | 0.000 | 0.000 |
| 992 | chr14 | 106350000 | 106351000 | 0.000 | 0.006 | 0.029 | 0.000 |
| 993 | chr14 | 106352000 | 106353000 | 0.000 | 0.000 | 0.029 | 0.000 |
| 994 | chr14 | 106353000 | 106354000 | 0.000 | 0.006 | 0.029 | 0.000 |
| 995 | chr14 | 106354000 | 106355000 | 0.000 | 0.006 | 0.015 | 0.000 |
| 996 | chr14 | 106355000 | 106356000 | 0.000 | 0.000 | 0.044 | 0.000 |
| 997 | chr14 | 106357000 | 106358000 | 0.028 | 0.000 | 0.059 | 0.000 |
| 998 | chr14 | 106358000 | 106359000 | 0.000 | 0.006 | 0.029 | 0.000 |

TABLE 1-continued

| | | | | | | | |
|---|---|---|---|---|---|---|---|
| 999 | chr14 | 106362000 | 106363000 | 0.028 | 0.006 | 0.000 | 0.000 |
| 1000 | chr14 | 106564000 | 106565000 | 0.000 | 0.000 | 0.029 | 0.000 |
| 1001 | chr14 | 106367000 | 106368000 | 0.000 | 0.000 | 0.029 | 0.000 |
| 1002 | chr14 | 106370000 | 106371000 | 0.000 | 0.012 | 0.044 | 0.014 |
| 1003 | chr14 | 106371000 | 106372000 | 0.000 | 0.012 | 0.029 | 0.014 |
| 1004 | chr14 | 106372000 | 106373000 | 0.000 | 0.006 | 0.015 | 0.000 |
| 1005 | chr14 | 106375000 | 106376000 | 0.000 | 0.019 | 0.015 | 0.000 |
| 1006 | chr14 | 106376000 | 106377000 | 0.000 | 0.012 | 0.015 | 0.000 |
| 1007 | chr14 | 106380000 | 106381000 | 0.000 | 0.031 | 0.000 | 0.000 |
| 1008 | chr14 | 106381000 | 106382000 | 0.000 | 0.031 | 0.000 | 0.000 |
| 1009 | chr14 | 106382000 | 106383000 | 0.000 | 0.037 | 0.044 | 0.014 |
| 1010 | chr14 | 106383000 | 106384000 | 0.000 | 0.000 | 0.044 | 0.014 |
| 1011 | chr14 | 106384000 | 106385000 | 0.000 | 0.012 | 0.014 | 0.014 |
| 1012 | chr14 | 106385000 | 106386000 | 0.000 | 0.000 | 0.029 | 0.014 |
| 1013 | chr14 | 106387000 | 106388000 | 0.000 | 0.000 | 0.029 | 0.014 |
| 1014 | chr14 | 106405000 | 106406000 | 0.000 | 0.006 | 0.015 | 0.014 |
| 1015 | chr14 | 106406000 | 106407000 | 0.000 | 0.006 | 0.015 | 0.014 |
| 1016 | chr14 | 106419000 | 106420000 | 0.000 | 0.006 | 0.015 | 0.000 |
| 1017 | chr14 | 106452000 | 106453000 | 0.000 | 0.006 | 0.029 | 0.000 |
| 1018 | chr14 | 106453000 | 106454000 | 0.000 | 0.006 | 0.044 | 0.000 |
| 1019 | chr14 | 106454000 | 106455000 | 0.000 | 0.000 | 0.029 | 0.000 |
| 1020 | chr14 | 106494000 | 106495000 | 0.000 | 0.019 | 0.000 | 0.014 |
| 1021 | chr14 | 106518000 | 106519000 | 0.028 | 0.037 | 0.000 | 0.054 |
| 1022 | chr14 | 106519000 | 106520000 | 0.000 | 0.012 | 0.000 | 0.027 |
| 1023 | chr14 | 106539000 | 106540000 | 0.000 | 0.031 | 0.015 | 0.000 |
| 1024 | chr14 | 106552000 | 106553000 | 0.000 | 0.006 | 0.029 | 0.014 |
| 1025 | chr14 | 106573000 | 106574000 | 0.000 | 0.019 | 0.029 | 0.068 |
| 1026 | chr14 | 106574000 | 106575000 | 0.000 | 0.006 | 0.029 | 0.041 |
| 1027 | chr14 | 106578000 | 106579000 | 0.000 | 0.000 | 0.015 | 0.027 |
| 1028 | chr14 | 106579000 | 106580000 | 0.000 | 0.000 | 0.015 | 0.027 |
| 1029 | chr14 | 106610000 | 106611000 | 0.056 | 0.012 | 0.029 | 0.000 |
| 1030 | chr14 | 106641000 | 106642000 | 0.000 | 0.019 | 0.015 | 0.000 |
| 1031 | chr14 | 106642000 | 106643000 | 0.000 | 0.012 | 0.015 | 0.000 |
| 1032 | chr14 | 106691000 | 106692000 | 0.000 | 0.012 | 0.029 | 0.027 |
| 1033 | chr14 | 106692000 | 106693000 | 0.000 | 0.006 | 0.015 | 0.041 |
| 1034 | chr14 | 106725000 | 106726000 | 0.083 | 0.068 | 0.103 | 0.135 |
| 1035 | chr14 | 106726000 | 106727000 | 0.028 | 0.019 | 0.088 | 0.095 |
| 1036 | chr14 | 106733000 | 106734000 | 0.028 | 0.006 | 0.015 | 0.027 |
| 1037 | chr14 | 106757000 | 106758000 | 0.056 | 0.000 | 0.015 | 0.000 |
| 1038 | chr14 | 106758000 | 106759000 | 0.056 | 0.000 | 0.000 | 0.000 |
| 1039 | chr14 | 106791000 | 106792000 | 0.056 | 0.006 | 0.015 | 0.000 |
| 1040 | chr14 | 106804000 | 106805000 | 0.000 | 0.006 | 0.029 | 0.000 |
| 1041 | chr14 | 106805000 | 106806000 | 0.000 | 0.006 | 0.044 | 0.014 |
| 1042 | chr14 | 106806000 | 106807000 | 0.000 | 0.006 | 0.015 | 0.000 |
| 1043 | chr14 | 106815000 | 106816000 | 0.000 | 0.012 | 0.044 | 0.027 |
| 1044 | chr14 | 106816000 | 106817000 | 0.000 | 0.006 | 0.074 | 0.014 |
| 1045 | chr14 | 106817000 | 106818000 | 0.000 | 0.000 | 0.029 | 0.000 |
| 1046 | chr14 | 106829000 | 106830000 | 0.167 | 0.050 | 0.162 | 0.135 |
| 1047 | chr14 | 106830000 | 106831000 | 0.028 | 0.043 | 0.118 | 0.135 |
| 1048 | chr14 | 106877000 | 106878000 | 0.056 | 0.006 | 0.015 | 0.041 |
| 1049 | chr14 | 106878000 | 106879000 | 0.028 | 0.012 | 0.044 | 0.041 |
| 1050 | chr14 | 106967000 | 106968000 | 0.056 | 0.000 | 0.015 | 0.000 |
| 1051 | chr14 | 106994000 | 106995000 | 0.028 | 0.012 | 0.088 | 0.122 |
| 1052 | chr14 | 106995000 | 106996000 | 0.000 | 0.000 | 0.000 | 0.027 |
| 1053 | chr14 | 107034000 | 107035000 | 0.028 | 0.000 | 0.000 | 0.014 |
| 1054 | chr14 | 107035000 | 197036000 | 0.000 | 0.006 | 0.029 | 0.014 |
| 1055 | chr14 | 107048000 | 197049000 | 0.028 | 0.006 | 0.000 | 0.000 |
| 1056 | chr14 | 107049000 | 107050000 | 0.000 | 0.012 | 0.044 | 0.027 |
| 1057 | chr14 | 107083000 | 107084000 | 0.000 | 0.006 | 0.044 | 0.054 |
| 1058 | chr14 | 107084000 | 107085000 | 0.009 | 0.006 | 0.029 | 0.027 |
| 1059 | chr14 | 107095000 | 107096000 | 0.000 | 0.006 | 0.015 | 0.000 |
| 1060 | chr14 | 107113000 | 107114000 | 0.000 | 0.000 | 0.029 | 0.000 |
| 1061 | chr14 | 107114000 | 107115000 | 0.000 | 0.000 | 0.029 | 0.000 |
| 1062 | chr14 | 107169000 | 107170000 | 0.056 | 0.068 | 0.206 | 0.041 |
| 1063 | chr14 | 107170000 | 107171000 | 0.028 | 0.075 | 0.294 | 0.095 |
| 1064 | chr14 | 107176000 | 107177000 | 0.028 | 0.006 | 0.118 | 0.027 |
| 1065 | chr14 | 107177000 | 107178000 | 0.000 | 0.000 | 0.044 | 0.027 |
| 1066 | chr14 | 107178000 | 107179000 | 0.056 | 0.161 | 0.456 | 0.284 |
| 1067 | chr14 | 107179000 | 107180000 | 0.056 | 0.180 | 0.382 | 0.338 |
| 1068 | chr14 | 107183000 | 107184000 | 0.000 | 0.006 | 0.029 | 0.000 |
| 1069 | chr14 | 107199000 | 107200000 | 0.000 | 0.012 | 0.015 | 0.000 |
| 1070 | chr14 | 107218000 | 107219000 | 0.028 | 0.012 | 0.015 | 0.000 |
| 1071 | chr14 | 107219000 | 107220000 | 0.000 | 0.012 | 0.074 | 0.027 |
| 1072 | chr14 | 107221000 | 107222000 | 0.000 | 0.000 | 0.059 | 0.000 |
| 1073 | chr14 | 107232000 | 107233000 | 0.000 | 0.000 | 0.029 | 0.000 |
| 1074 | chr14 | 107253000 | 107254000 | 0.000 | 0.000 | 0.044 | 0.014 |
| 1075 | chr14 | 107258000 | 107259000 | 0.000 | 0.000 | 0.015 | 0.014 |
| 1076 | chr14 | 107259000 | 107260000 | 0.000 | 0.025 | 0.235 | 0.027 |
| 1077 | chr15 | 45003000 | 45004000 | 0.000 | 0.000 | 0.044 | 0.000 |
| 1078 | chr15 | 45007000 | 45008000 | 0.000 | 0.000 | 0.044 | 0.000 |

TABLE 1-continued

| | | | | | | | |
|---|---|---|---|---|---|---|---|
| 1079 | chr15 | 45814000 | 45815000 | 0.000 | 0.000 | 0.015 | 0.014 |
| 1080 | chr15 | 59664000 | 59665000 | 0.000 | 0.000 | 0.044 | 0.041 |
| 1081 | chr15 | 65588000 | 65589000 | 0.028 | 0.000 | 0.000 | 0.014 |
| 1082 | chr15 | 78332000 | 78333000 | 0.028 | 0.000 | 0.000 | 0.014 |
| 1083 | chr15 | 83227000 | 83228000 | 0.000 | 0.000 | 0.029 | 0.000 |
| 1084 | chr15 | 86226000 | 86227000 | 0.000 | 0.000 | 0.044 | 0.000 |
| 1085 | chr15 | 86233000 | 86234000 | 0.000 | 0.000 | 0.029 | 0.014 |
| 1086 | chr15 | 86245000 | 86246000 | 0.000 | 0.000 | 0.059 | 0.000 |
| 1087 | chr16 | 368000 | 369000 | 0.000 | 0.000 | 0.015 | 0.014 |
| 1088 | chr16 | 3788000 | 3789000 | 0.000 | 0.000 | 0.015 | 0.014 |
| 1089 | chr16 | 10971000 | 10972000 | 0.000 | 0.000 | 0.162 | 0.041 |
| 1090 | chr16 | 10972000 | 10973000 | 0.000 | 0.000 | 0.191 | 0.081 |
| 1091 | chr16 | 10973000 | 10974000 | 0.000 | 0.000 | 0.162 | 0.095 |
| 1092 | chr16 | 10974000 | 10975000 | 0.000 | 0.000 | 0.059 | 0.000 |
| 1093 | chr16 | 11348000 | 11349000 | 0.000 | 0.000 | 0.191 | 0.027 |
| 1094 | chr16 | 11349000 | 11350000 | 0.000 | 0.000 | 0.221 | 0.041 |
| 1095 | chr16 | 21167000 | 21168000 | 0.000 | 0.000 | 0.015 | 0.014 |
| 1096 | chr16 | 27325000 | 27326000 | 0.000 | 0.000 | 0.029 | 0.041 |
| 1097 | chr16 | 27326000 | 27327000 | 0.000 | 0.000 | 0.088 | 0.041 |
| 1098 | chr16 | 27327000 | 27328000 | 0.000 | 0.000 | 0.029 | 0.000 |
| 1099 | chr16 | 27414000 | 27415000 | 0.000 | 0.000 | 0.029 | 0.000 |
| 1100 | chr16 | 29248000 | 29249000 | 0.000 | 0.000 | 0.029 | 0.000 |
| 1101 | chr16 | 31910000 | 31911000 | 0.000 | 0.000 | 0.015 | 0.014 |
| 1102 | chr16 | 46821000 | 46822000 | 0.000 | 0.000 | 0.015 | 0.014 |
| 1103 | chr16 | 50985000 | 50986000 | 0.000 | 0.000 | 0.015 | 0.014 |
| 1104 | chr16 | 64351000 | 64352000 | 0.000 | 0.000 | 0.029 | 0.014 |
| 1105 | chr16 | 78398000 | 78399000 | 0.000 | 0.000 | 0.000 | 0.027 |
| 1106 | chr16 | 78615000 | 78616000 | 0.000 | 0.000 | 0.015 | 0.014 |
| 1107 | chr16 | 78753000 | 78754000 | 0.000 | 0.000 | 0.015 | 0.014 |
| 1108 | chr16 | 78811000 | 78812000 | 0.000 | 0.000 | 0.000 | 0.027 |
| 1109 | chr16 | 79988000 | 79989000 | 0.000 | 0.000 | 0.015 | 0.014 |
| 1110 | chr16 | 81836000 | 81837000 | 0.000 | 0.000 | 0.029 | 0.000 |
| 1111 | chr16 | 85932000 | 85933000 | 0.000 | 0.000 | 0.059 | 0.027 |
| 1112 | chr16 | 85933000 | 85934000 | 0.000 | 0.012 | 0.221 | 0.081 |
| 1113 | chr16 | 85934000 | 85935000 | 0.000 | 0.006 | 0.015 | 0.027 |
| 1114 | chr16 | 85936000 | 85937000 | 0.000 | 0.000 | 0.029 | 0.000 |
| 1115 | chr16 | 88441000 | 88442000 | 0.000 | 0.000 | 0.015 | 0.014 |
| 1116 | chr17 | 3598000 | 3599000 | 0.000 | 0.000 | 0.029 | 0.014 |
| 1117 | chr17 | 17286000 | 17287000 | 0.000 | 0.000 | 0.029 | 0.000 |
| 1118 | chr17 | 21194000 | 21195000 | 0.000 | 0.000 | 0.015 | 0.041 |
| 1119 | chr17 | 29646000 | 29647000 | 0.000 | 0.000 | 0.029 | 0.014 |
| 1120 | chr17 | 38020000 | 38021000 | 0.000 | 0.000 | 0.029 | 0.014 |
| 1121 | chr17 | 43662000 | 43663000 | 0.000 | 0.000 | 0.029 | 0.000 |
| 1122 | chr17 | 56408000 | 56409000 | 0.000 | 0.006 | 0.059 | 0.027 |
| 1123 | chr17 | 56409000 | 56410000 | 0.000 | 0.000 | 0.265 | 0.027 |
| 1124 | chr17 | 57916000 | 57917000 | 0.000 | 0.000 | 0.029 | 0.014 |
| 1125 | chr17 | 57917000 | 57918000 | 0.000 | 0.000 | 0.029 | 0.000 |
| 1126 | chr17 | 62007000 | 62008000 | 0.000 | 0.000 | 0.029 | 0.000 |
| 1127 | chr17 | 62008000 | 62009000 | 0.000 | 0.000 | 0.044 | 0.014 |
| 1128 | chr17 | 63067000 | 63068000 | 0.000 | 0.000 | 0.015 | 0.014 |
| 1129 | chr17 | 65676000 | 65677000 | 0.000 | 0.000 | 0.029 | 0.000 |
| 1130 | chr17 | 69365000 | 69366000 | 0.000 | 0.000 | 0.015 | 0.014 |
| 1131 | chr17 | 70083000 | 70084000 | 0.028 | 0.000 | 0.000 | 0.014 |
| 1132 | chr17 | 74733000 | 74734000 | 0.000 | 0.000 | 0.000 | 0.027 |
| 1133 | chr17 | 75447000 | 75448000 | 0.000 | 0.000 | 0.044 | 0.000 |
| 1134 | chr17 | 75448000 | 75449000 | 0.000 | 0.000 | 0.044 | 0.000 |
| 1135 | chr17 | 76775000 | 76776000 | 0.000 | 0.000 | 0.000 | 0.027 |
| 1136 | chr17 | 80928000 | 80929000 | 0.000 | 0.000 | 0.029 | 0.000 |
| 1137 | chr17 | 80976000 | 80977000 | 0.000 | 0.000 | 0.015 | 0.014 |
| 1138 | chr18 | 2709000 | 2710000 | 0.000 | 0.000 | 0.029 | 0.000 |
| 1139 | chr18 | 3600000 | 3601000 | 0.000 | 0.000 | 0.015 | 0.014 |
| 1140 | chr18 | 12062000 | 12063000 | 0.000 | 0.000 | 0.000 | 0.041 |
| 1141 | chr18 | 27771000 | 27772000 | 0.000 | 0.000 | 0.029 | 0.000 |
| 1142 | chr18 | 28066000 | 28067000 | 0.000 | 0.000 | 0.029 | 0.000 |
| 1143 | chr18 | 30349000 | 30350000 | 0.000 | 0.000 | 0.000 | 0.027 |
| 1144 | chr18 | 36806000 | 36807000 | 0.000 | 0.000 | 0.029 | 0.000 |
| 1145 | chr18 | 37751000 | 37752000 | 0.000 | 0.000 | 0.015 | 0.014 |
| 1146 | chr18 | 38672000 | 38673000 | 0.028 | 0.000 | 0.000 | 0.014 |
| 1147 | chr18 | 42168000 | 42169000 | 0.028 | 0.000 | 0.000 | 0.014 |
| 1148 | chr18 | 51952000 | 51953000 | 0.000 | 0.000 | 0.029 | 0.000 |
| 1149 | chr18 | 52447000 | 52448000 | 0.000 | 0.000 | 0.015 | 0.014 |
| 1150 | chr18 | 52988000 | 52989000 | 0.000 | 0.000 | 0.029 | 0.000 |
| 1151 | chr18 | 54653000 | 54654000 | 0.000 | 0.000 | 0.000 | 0.027 |
| 1152 | chr18 | 60794000 | 60795000 | 0.000 | 0.000 | 0.029 | 0.000 |
| 1153 | chr18 | 60805000 | 60806000 | 0.000 | 0.000 | 0.074 | 0.081 |
| 1154 | chr18 | 60806000 | 60807000 | 0.000 | 0.006 | 0.132 | 0.122 |
| 1155 | chr18 | 60809000 | 60810000 | 0.000 | 0.000 | 0.059 | 0.027 |
| 1156 | chr18 | 60821000 | 60822000 | 0.000 | 0.000 | 0.029 | 0.000 |
| 1157 | chr18 | 60825000 | 60826000 | 0.000 | 0.000 | 0.044 | 0.027 |
| 1158 | chr18 | 60826000 | 60827000 | 0.000 | 0.000 | 0.029 | 0.000 |

TABLE 1-continued

| | | | | | | | |
|---|---|---|---|---|---|---|---|
| 1159 | chr18 | 60828000 | 60829000 | 0.000 | 0.000 | 0.015 | 0.027 |
| 1160 | chr18 | 60873000 | 60874000 | 0.000 | 0.000 | 0.044 | 0.027 |
| 1161 | chr18 | 60875000 | 60876000 | 0.000 | 0.000 | 0.044 | 0.027 |
| 1162 | chr18 | 60876000 | 60877000 | 0.000 | 0.000 | 0.015 | 0.054 |
| 1163 | chr18 | 60983000 | 60984000 | 0.000 | 0.006 | 0.059 | 0.068 |
| 1164 | chr18 | 60984000 | 60985000 | 0.000 | 0.012 | 0.176 | 0.459 |
| 1165 | chr18 | 60985000 | 60986000 | 0.000 | 0.000 | 0.221 | 0.635 |
| 1166 | chr18 | 60986000 | 60987000 | 0.000 | 0.019 | 0.235 | 0.730 |
| 1167 | chr18 | 60987000 | 60988000 | 0.000 | 0.019 | 0.191 | 0.500 |
| 1168 | chr18 | 60988000 | 60989000 | 0.000 | 0.012 | 0.221 | 0.595 |
| 1169 | chr18 | 61810000 | 61811000 | 0.000 | 0.000 | 0.015 | 0.014 |
| 1170 | chr18 | 63080000 | 63081000 | 0.000 | 0.000 | 0.029 | 0.000 |
| 1171 | chr18 | 63791000 | 63792000 | 0.028 | 0.000 | 0.015 | 0.000 |
| 1172 | chr18 | 63875000 | 63876000 | 0.000 | 0.000 | 0.029 | 0.000 |
| 1173 | chr18 | 64643000 | 64644000 | 0.000 | 0.000 | 0.029 | 0.000 |
| 1174 | chr18 | 65863000 | 65864000 | 0.000 | 0.000 | 0.000 | 0.027 |
| 1175 | chr18 | 66328000 | 66329000 | 0.000 | 0.000 | 0.015 | 0.014 |
| 1176 | chr18 | 70462000 | 70463000 | 0.000 | 0.000 | 0.015 | 0.014 |
| 1177 | chr18 | 73767000 | 73768000 | 0.000 | 0.000 | 0.015 | 0.014 |
| 1178 | chr18 | 76515000 | 76516000 | 0.000 | 0.000 | 0.029 | 0.014 |
| 1179 | chr18 | 76724000 | 76725000 | 0.000 | 0.000 | 0.015 | 0.014 |
| 1180 | chr18 | 76725000 | 76726000 | 0.000 | 0.000 | 0.015 | 0.014 |
| 1181 | chr19 | 1612000 | 1613000 | 0.056 | 0.000 | 0.000 | 0.000 |
| 1182 | chr19 | 2476000 | 2477000 | 0.000 | 0.000 | 0.029 | 0.000 |
| 1183 | chr19 | 10304000 | 10305000 | 0.000 | 0.000 | 0.059 | 0.000 |
| 1184 | chr19 | 10305000 | 10306000 | 0.000 | 0.000 | 0.044 | 0.000 |
| 1185 | chr19 | 10335000 | 10336000 | 0.000 | 0.000 | 0.015 | 0.014 |
| 1186 | chr19 | 10340000 | 10341000 | 0.000 | 0.000 | 0.118 | 0.041 |
| 1187 | chr19 | 10341000 | 10342000 | 0.000 | 0.012 | 0.206 | 0.054 |
| 1188 | chr19 | 16030000 | 16031000 | 0.028 | 0.000 | 0.015 | 0.000 |
| 1189 | chr19 | 16436000 | 16437000 | 0.000 | 0.000 | 0.029 | 0.014 |
| 1190 | chr19 | 20889000 | 20890000 | 0.000 | 0.006 | 0.015 | 0.000 |
| 1191 | chr19 | 21073000 | 21074000 | 0.000 | 0.000 | 0.015 | 0.027 |
| 1192 | chr19 | 21092000 | 21093000 | 0.000 | 0.000 | 0.029 | 0.000 |
| 1193 | chr19 | 23841000 | 23842000 | 0.000 | 0.000 | 0.015 | 0.027 |
| 1194 | chr19 | 29256000 | 29257000 | 0.000 | 0.000 | 0.029 | 0.000 |
| 1195 | chr19 | 44183000 | 44184000 | 0.000 | 0.000 | 0.029 | 0.000 |
| 1196 | chr19 | 50399000 | 50400000 | 0.000 | 0.000 | 0.029 | 0.000 |
| 1197 | chr19 | 53419000 | 53420000 | 0.028 | 0.000 | 0.015 | 0.014 |
| 1198 | chr20 | 15470000 | 15471000 | 0.028 | 0.006 | 0.000 | 0.000 |
| 1199 | chr20 | 23359000 | 23360000 | 0.056 | 0.000 | 0.000 | 0.000 |
| 1200 | chr20 | 23912000 | 23913000 | 0.000 | 0.000 | 0.000 | 0.027 |
| 1201 | chr20 | 46131000 | 46132000 | 0.000 | 0.000 | 0.059 | 0.014 |
| 1202 | chr20 | 49127000 | 49128000 | 0.000 | 0.000 | 0.029 | 0.014 |
| 1203 | chr20 | 49648000 | 49649000 | 0.000 | 0.000 | 0.029 | 0.000 |
| 1204 | chr20 | 61607000 | 61608000 | 0.000 | 0.000 | 0.000 | 0.027 |
| 1205 | chr21 | 21597000 | 21598000 | 0.000 | 0.000 | 0.029 | 0.000 |
| 1206 | chr21 | 23458000 | 23459000 | 0.000 | 0.000 | 0.029 | 0.000 |
| 1207 | chr21 | 24998000 | 24999000 | 0.000 | 0.000 | 0.029 | 0.000 |
| 1208 | chr21 | 26935000 | 26936000 | 0.000 | 0.000 | 0.015 | 0.014 |
| 1209 | chr21 | 35779000 | 35780000 | 0.000 | 0.000 | 0.000 | 0.027 |
| 1210 | chr21 | 38779000 | 38780000 | 0.000 | 0.000 | 0.000 | 0.027 |
| 1211 | chr21 | 43254000 | 43255000 | 0.000 | 0.000 | 0.029 | 0.000 |
| 1212 | chr21 | 44612000 | 44613000 | 0.000 | 0.000 | 0.000 | 0.027 |
| 1213 | chr21 | 45381000 | 45382000 | 0.000 | 0.000 | 0.029 | 0.000 |
| 1214 | chr21 | 46058000 | 46059000 | 0.000 | 0.000 | 0.015 | 0.027 |
| 1215 | chr22 | 19050000 | 19051000 | 0.000 | 0.006 | 0.000 | 0.027 |
| 1216 | chr22 | 20212000 | 20213000 | 0.000 | 0.000 | 0.029 | 0.014 |
| 1217 | chr22 | 20708000 | 20709000 | 0.000 | 0.000 | 0.029 | 0.000 |
| 1218 | chr22 | 21994000 | 21995000 | 0.028 | 0.000 | 0.015 | 0.000 |
| 1219 | chr22 | 22379000 | 22380000 | 0.000 | 0.000 | 0.029 | 0.027 |
| 1220 | chr22 | 22380000 | 22381000 | 0.000 | 0.012 | 0.044 | 0.068 |
| 1221 | chr22 | 22381000 | 22382000 | 0.000 | 0.012 | 0.015 | 0.027 |
| 1222 | chr22 | 22385000 | 22386000 | 0.028 | 0.031 | 0.029 | 0.068 |
| 1223 | chr22 | 22452000 | 22453000 | 0.000 | 0.012 | 0.015 | 0.014 |
| 1224 | chr22 | 22453000 | 22454000 | 0.000 | 0.012 | 0.015 | 0.014 |
| 1225 | chr22 | 22516000 | 22517000 | 0.000 | 0.025 | 0.015 | 0.054 |
| 1226 | chr22 | 22517000 | 22518000 | 0.000 | 0.019 | 0.000 | 0.014 |
| 1227 | chr22 | 22550000 | 22551000 | 0.056 | 0.006 | 0.044 | 0.054 |
| 1228 | chr22 | 22569000 | 22570000 | 0.000 | 0.006 | 0.015 | 0.014 |
| 1229 | chr22 | 22676000 | 22677000 | 0.028 | 0.000 | 0.015 | 0.000 |
| 1230 | chr22 | 22677000 | 22678000 | 0.083 | 0.012 | 0.015 | 0.014 |
| 1231 | chr22 | 22707000 | 22708000 | 0.028 | 0.006 | 0.044 | 0.014 |
| 1232 | chr22 | 22712000 | 22713000 | 0.083 | 0.012 | 0.088 | 0.041 |
| 1233 | chr22 | 22723000 | 22724000 | 0.000 | 0.006 | 0.015 | 0.027 |
| 1234 | chr22 | 22724000 | 22725000 | 0.028 | 0.012 | 0.088 | 0.041 |
| 1235 | chr22 | 22730000 | 22731000 | 0.000 | 0.006 | 0.059 | 0.054 |
| 1236 | chr22 | 22731000 | 22732000 | 0.000 | 0.006 | 0.029 | 0.000 |
| 1237 | chr22 | 22735000 | 22736000 | 0.028 | 0.037 | 0.059 | 0.068 |
| 1238 | chr22 | 22749000 | 22750000 | 0.000 | 0.006 | 0.059 | 0.027 |

TABLE 1-continued

| | | | | | | | |
|---|---|---|---|---|---|---|---|
| 1239 | chr22 | 22758000 | 22759000 | 0.028 | 0.006 | 0.029 | 0.014 |
| 1240 | chr22 | 22759000 | 22760000 | 0.056 | 0.006 | 0.044 | 0.027 |
| 1241 | chr22 | 22764000 | 22765000 | 0.111 | 0.006 | 0.044 | 0.068 |
| 1242 | chr22 | 23028000 | 23029000 | 0.000 | 0.006 | 0.015 | 0.000 |
| 1243 | chr22 | 23029000 | 23030000 | 0.028 | 0.062 | 0.132 | 0.108 |
| 1244 | chr22 | 23035000 | 23036000 | 0.000 | 0.000 | 0.015 | 0.014 |
| 1245 | chr22 | 23039000 | 23040000 | 0.000 | 0.000 | 0.000 | 0.027 |
| 1246 | chr22 | 23040000 | 23041000 | 0.000 | 0.043 | 0.103 | 0.054 |
| 1247 | chr22 | 23041000 | 23042000 | 0.000 | 0.006 | 0.044 | 0.000 |
| 1248 | chr22 | 23055000 | 23056000 | 0.028 | 0.056 | 0.059 | 0.014 |
| 1249 | chr22 | 23063000 | 23064000 | 0.000 | 0.000 | 0.074 | 0.041 |
| 1250 | chr22 | 23090000 | 23091000 | 0.000 | 0.000 | 0.059 | 0.041 |
| 1251 | chr22 | 23100000 | 23101000 | 0.000 | 0.019 | 0.044 | 0.054 |
| 1252 | chr22 | 23101000 | 23102000 | 0.028 | 0.031 | 0.074 | 0.081 |
| 1253 | chr22 | 23114000 | 23115000 | 0.000 | 0.000 | 0.015 | 0.027 |
| 1254 | chr22 | 23134000 | 23135000 | 0.000 | 0.000 | 0.029 | 0.014 |
| 1255 | chr22 | 23154000 | 23155000 | 0.000 | 0.019 | 0.074 | 0.027 |
| 1256 | chr22 | 23161000 | 23162000 | 0.000 | 0.006 | 0.000 | 0.014 |
| 1257 | chr22 | 23162000 | 23163000 | 0.000 | 0.012 | 0.000 | 0.014 |
| 1258 | chr22 | 23165000 | 23166000 | 0.000 | 0.012 | 0.000 | 0.041 |
| 1259 | chr22 | 23192000 | 23193000 | 0.000 | 0.006 | 0.088 | 0.041 |
| 1260 | chr22 | 23197000 | 23198000 | 0.000 | 0.006 | 0.015 | 0.000 |
| 1261 | chr22 | 23198000 | 23199000 | 0.000 | 0.025 | 0.147 | 0.068 |
| 1262 | chr22 | 23199000 | 23200000 | 0.000 | 0.031 | 0.221 | 0.068 |
| 1263 | chr22 | 23203000 | 23204000 | 0.000 | 0.000 | 0.029 | 0.000 |
| 1264 | chr22 | 23204000 | 23205000 | 0.056 | 0.000 | 0.059 | 0.041 |
| 1265 | chr22 | 23205000 | 23206000 | 0.000 | 0.000 | 0.015 | 0.027 |
| 1266 | chr22 | 23207000 | 23208000 | 0.000 | 0.000 | 0.029 | 0.000 |
| 1267 | chr22 | 23209000 | 23210000 | 0.000 | 0.000 | 0.029 | 0.000 |
| 1268 | chr22 | 23213000 | 23214000 | 0.000 | 0.000 | 0.088 | 0.027 |
| 1269 | chr22 | 23214000 | 23215000 | 0.000 | 0.000 | 0.074 | 0.027 |
| 1270 | chr22 | 23219000 | 23220000 | 0.000 | 0.000 | 0.044 | 0.000 |
| 1271 | chr22 | 23220000 | 23221000 | 0.000 | 0.000 | 0.059 | 0.000 |
| 1272 | chr22 | 23222000 | 23223000 | 0.000 | 0.006 | 0.147 | 0.014 |
| 1273 | chr22 | 23223000 | 23224000 | 0.083 | 0.149 | 0.544 | 0.432 |
| 1274 | chr22 | 23224000 | 23225000 | 0.000 | 0.000 | 0.118 | 0.027 |
| 1275 | chr22 | 23226000 | 23227000 | 0.000 | 0.000 | 0.029 | 0.000 |
| 1276 | chr22 | 23227000 | 23228000 | 0.028 | 0.056 | 0.412 | 0.257 |
| 1277 | chr22 | 23228000 | 23229000 | 0.028 | 0.019 | 0.309 | 0.095 |
| 1278 | chr22 | 23229000 | 23230000 | 0.000 | 0.000 | 0.118 | 0.041 |
| 1279 | chr22 | 23230000 | 23231000 | 0.222 | 0.161 | 0.647 | 0.514 |
| 1280 | chr22 | 23231000 | 23232000 | 0.250 | 0.155 | 0.647 | 0.514 |
| 1281 | chr22 | 23232000 | 23233000 | 0.000 | 0.012 | 0.426 | 0.162 |
| 1282 | chr22 | 23233000 | 23234000 | 0.000 | 0.006 | 0.162 | 0.054 |
| 1283 | chr22 | 23234000 | 23235000 | 0.056 | 0.000 | 0.147 | 0.041 |
| 1284 | chr22 | 23235000 | 23736000 | 0.056 | 0.031 | 0.176 | 0.068 |
| 1285 | chr22 | 23236000 | 23237000 | 0.111 | 0.043 | 0.250 | 0.095 |
| 1286 | chr22 | 23237000 | 23238000 | 0.083 | 0.006 | 0.103 | 0.054 |
| 1287 | chr22 | 23241000 | 23242000 | 0.028 | 0.012 | 0.074 | 0.000 |
| 1288 | chr22 | 23242000 | 23243000 | 0.028 | 0.050 | 0.147 | 0.108 |
| 1289 | chr22 | 23243000 | 23244000 | 0.000 | 0.000 | 0.029 | 0.000 |
| 1290 | chr22 | 23244000 | 23245000 | 0.000 | 0.012 | 0.015 | 0.014 |
| 1291 | chr22 | 23247000 | 23248000 | 0.111 | 0.099 | 0.088 | 0.122 |
| 1292 | chr22 | 23248000 | 23249000 | 0.000 | 0.012 | 0.015 | 0.027 |
| 1293 | chr22 | 23249000 | 23250000 | 0.000 | 0.006 | 0.029 | 0.027 |
| 1294 | chr22 | 23260000 | 23261000 | 0.000 | 0.025 | 0.015 | 0.000 |
| 1295 | chr22 | 23261000 | 23262000 | 0.000 | 0.012 | 0.015 | 0.014 |
| 1296 | chr22 | 23263000 | 23264000 | 0.000 | 0.006 | 0.044 | 0.014 |
| 1297 | chr22 | 23264000 | 23265000 | 0.000 | 0.006 | 0.044 | 0.027 |
| 1298 | chr22 | 23273000 | 23274000 | 0.000 | 0.000 | 0.044 | 0.000 |
| 1299 | chr22 | 23277000 | 23278000 | 0.000 | 0.000 | 0.029 | 0.014 |
| 1300 | chr22 | 23278000 | 23279000 | 0.000 | 0.006 | 0.059 | 0.014 |
| 1301 | chr22 | 23281000 | 23282000 | 0.000 | 0.000 | 0.029 | 0.014 |
| 1302 | chr22 | 23282000 | 23283000 | 0.000 | 0.006 | 0.147 | 0.027 |
| 1303 | chr22 | 23284000 | 23285000 | 0.000 | 0.000 | 0.029 | 0.000 |
| 1304 | chr22 | 23523000 | 23524000 | 0.000 | 0.000 | 0.015 | 0.041 |
| 1305 | chr22 | 23524000 | 23525000 | 0.000 | 0.000 | 0.029 | 0.014 |
| 1306 | chr22 | 27236000 | 27237000 | 0.028 | 0.000 | 0.029 | 0.000 |
| 1307 | chr22 | 29195000 | 29196000 | 0.000 | 0.000 | 0.088 | 0.000 |
| 1308 | chr22 | 29196000 | 29197000 | 0.000 | 0.000 | 0.059 | 0.041 |
| 1309 | chr22 | 31826000 | 31827000 | 0.000 | 0.000 | 0.029 | 0.000 |
| 1310 | chr22 | 32982000 | 32983000 | 0.028 | 0.000 | 0.015 | 0.000 |
| 1311 | chr22 | 39852000 | 39853000 | 0.000 | 0.000 | 0.029 | 0.000 |
| 1312 | chr22 | 39854000 | 39855000 | 0.000 | 0.000 | 0.029 | 0.000 |
| 1313 | chr22 | 43360000 | 43361000 | 0.000 | 0.000 | 0.029 | 0.000 |
| 1314 | chr22 | 47186000 | 47187000 | 0.000 | 0.000 | 0.029 | 0.000 |
| 1315 | chr22 | 47738000 | 47739000 | 0.000 | 0.000 | 0.000 | 0.027 |
| 1316 | chr22 | 50336000 | 50337000 | 0.028 | 0.000 | 0.015 | 0.000 |
| 1317 | chrX | 228000 | 229000 | 0.000 | 0.000 | 0.000 | 0.027 |
| 1318 | chrX | 1514000 | 1515000 | 0.000 | 0.000 | 0.015 | 0.014 |

TABLE 1-continued

| | | | | | | | |
|---|---|---|---|---|---|---|---|
| 1319 | chrX | 1611000 | 1612000 | 0.000 | 0.000 | 0.029 | 0.000 |
| 1320 | chrX | 12993000 | 12994000 | 0.000 | 0.000 | 0.235 | 0.041 |
| 1321 | chrX | 12994000 | 12995000 | 0.000 | 0.000 | 0.221 | 0.027 |
| 1322 | chrX | 13419000 | 13420000 | 0.028 | 0.000 | 0.029 | 0.027 |
| 1323 | chrX | 27031000 | 27032000 | 0.000 | 0.000 | 0.059 | 0.000 |
| 1324 | chrX | 32315000 | 32316000 | 0.000 | 0.000 | 0.000 | 0.027 |
| 1325 | chrX | 32317000 | 32318000 | 0.028 | 0.000 | 0.000 | 0.014 |
| 1326 | chrX | 33144000 | 33145000 | 0.000 | 0.000 | 0.029 | 0.014 |
| 1327 | chrX | 33145000 | 33346000 | 0.000 | 0.000 | 0.044 | 0.027 |
| 1328 | chrX | 33146000 | 33147000 | 0.000 | 0.000 | 0.162 | 0.068 |
| 1329 | chrX | 41366000 | 41367000 | 0.000 | 0.000 | 0.015 | 0.027 |
| 1330 | chrX | 42802000 | 42803000 | 0.000 | 0.000 | 0.074 | 0.027 |
| 1331 | chrX | 48775000 | 48776000 | 0.000 | 0.000 | 0.044 | 0.014 |
| 1332 | chrX | 48776000 | 48777000 | 0.000 | 0.000 | 0.029 | 0.014 |
| 1333 | chrX | 64071000 | 64072000 | 0.000 | 0.000 | 0.059 | 0.014 |
| 1334 | chrX | 67030000 | 67031000 | 0.028 | 0.000 | 0.015 | 0.000 |
| 1335 | chrX | 80258000 | 80259000 | 0.000 | 0.000 | 0.000 | 0.027 |
| 1336 | chrX | 81172000 | 81173000 | 0.000 | 0.000 | 0.015 | 0.027 |
| 1337 | chrX | 87742000 | 87743000 | 0.000 | 0.000 | 0.029 | 0.000 |
| 1338 | chrX | 87831000 | 87832000 | 0.000 | 0.000 | 0.000 | 0.027 |
| 1339 | chrX | 88263000 | 88264000 | 0.000 | 0.000 | 0.000 | 0.027 |
| 1340 | chrX | 88458000 | 88459000 | 0.000 | 0.000 | 0.029 | 0.000 |
| 1341 | chrX | 92647000 | 92648000 | 0.000 | 0.000 | 0.000 | 0.027 |
| 1342 | chrX | 93279000 | 93280000 | 0.000 | 0.000 | 0.015 | 0.014 |
| 1343 | chrX | 94079000 | 94080000 | 0.000 | 0.000 | 0.015 | 0.014 |
| 1344 | chrX | 104006000 | 104007000 | 0.000 | 0.000 | 0.015 | 0.014 |
| 1345 | chrX | 104269000 | 104270000 | 0.000 | 0.000 | 0.015 | 0.014 |
| 1346 | chrX | 106132000 | 106133000 | 0.000 | 0.000 | 0.000 | 0.027 |
| 1347 | chrX | 113095000 | 113096000 | 0.000 | 0.006 | 0.015 | 0.000 |
| 1348 | chrX | 115676000 | 115677000 | 0.000 | 0.000 | 0.015 | 0.014 |
| 1349 | chrX | 124996000 | 124997000 | 0.000 | 0.000 | 0.029 | 0.000 |
| 1350 | chrX | 125708000 | 125709000 | 0.000 | 0.000 | 0.029 | 0.000 |
| 1351 | chrX | 128565000 | 128566000 | 0.000 | 0.000 | 0.015 | 0.014 |
| 1352 | chrX | 129643000 | 129644000 | 0.000 | 0.000 | 0.015 | 0.027 |
| 1353 | chrX | 134903000 | 134904000 | 0.000 | 0.000 | 0.029 | 0.014 |
| 1354 | chrX | 140846000 | 140847000 | 0.000 | 0.000 | 0.029 | 0.000 |
| 1355 | chrX | 143750000 | 143751000 | 0.000 | 0.000 | 0.000 | 0.027 |
| 1356 | chrX | 145016000 | 145017000 | 0.028 | 0.000 | 0.000 | 0.027 |

| # | ClosestGene | Fisher_p_DLBCL_vs_FL | Fisher_p_DLBCL_vs_BL | Fisher_p_DLBCL_vs_CLL | Previously Identified | over5pctInAny Histology |
|---|---|---|---|---|---|---|
| 1 | AL669831.1 | 0.47887 | 1.00000 | 0.29694 | 0 | 0 |
| 2 | GABRD | 0.47887 | 1.00000 | 0.29694 | 0 | 0 |
| 3 | PRKCZ | 1.00000 | 0.34615 | 1.00000 | 0 | 0 |
| 4 | DFFB | 0.22755 | 0.54294 | 0.08726 | 0 | 0 |
| 5 | NOL9 | 0.34948 | 0.54966 | 0.02537 | 1 | 0 |
| 6 | NOL9 | 0.15270 | 0.09031 | 0.00058 | 1 | 1 |
| 7 | KLHL21 | 0.60686 | 0.54294 | 0.08726 | 0 | 0 |
| 8 | KLHL21 | 0.34948 | 0.54966 | 0.02537 | 0 | 0 |
| 9 | SLC2A5 | 0.10727 | 0.54966 | 0.02537 | 0 | 0 |
| 10 | C1orf127 | 1.00000 | 0.34615 | 1.00000 | 0 | 0 |
| 11 | AL137798.1 | 1.00000 | 0.34615 | 1.00000 | 0 | 0 |
| 12 | CROCC | 1.00000 | 1.00000 | 0.29694 | 0 | 0 |
| 13 | MINOS1-NBL1 | 0.22755 | 0.54294 | 0.08726 | 0 | 0 |
| 14 | HP1BP3 | 1.00000 | 1.00000 | 0.29694 | 0 | 0 |
| 15 | ID3 | 0.47887 | 0.00000 | 0.29694 | 1 | 1 |
| 16 | EYA3 | 0.22755 | 0.54294 | 0.08726 | 0 | 0 |
| 17 | PTP4A2 | 0.22755 | 0.54294 | 0.08726 | 0 | 0 |
| 18 | THRAP3 | 0.47887 | 1.00000 | 1.00000 | 0 | 0 |
| 19 | PIK3R3 | 1.00000 | 1.00000 | 0.29694 | 0 | 0 |
| 20 | EPS15 | 0.47887 | 1.00000 | 0.50663 | 0 | 0 |
| 21 | EPS15 | 0.22755 | 0.54294 | 0.08726 | 0 | 0 |
| 22 | EPS15 | 0.22755 | 0.54294 | 0.21104 | 0 | 0 |
| 23 | NEGR1 | 1.00000 | 1.00000 | 0.29694 | 0 | 0 |
| 24 | LRRIQ3 | 0.22755 | 0.54294 | 0.08726 | 0 | 0 |
| 25 | ST6GALNAC5 | 1.00000 | 0.34615 | 1.00000 | 0 | 0 |
| 26 | LPHN2 | 1.00000 | 1.00000 | 0.29694 | 0 | 0 |
| 27 | LPHN2 | 0.22755 | 0.54294 | 0.08726 | 0 | 0 |
| 28 | LPHN2 | 0.47887 | 1.00000 | 0.29694 | 0 | 0 |
| 29 | TTLL7 | 0.47887 | 1.00000 | 0.50663 | 0 | 0 |
| 30 | HS2ST1; HS2ST1LOC339524; | 0.47887 | 1.00000 | 0.50663 | 0 | 0 |
| 31 | ABCA4 | 0.22755 | 0.54294 | 0.08726 | 0 | 0 |
| 32 | ABCA4 | 0.22755 | 0.54294 | 0.08726 | 0 | 0 |
| 33 | COL11A1 | 0.49735 | 1.00000 | 1.00000 | 0 | 0 |
| 34 | ATP1A1 | 1.00000 | 0.54966 | 0.02537 | 0 | 0 |
| 35 | HIST2H3D | 1.00000 | 1.00000 | 0.29694 | 1 | 0 |
| 36 | HIST2H2AA4 | 0.10727 | 0.54966 | 0.02537 | 1 | 0 |

TABLE 1-continued

| | | | | | | |
|---|---|---|---|---|---|---|
| 37 | HIST2H2BE | 1.00000 | 1.00000 | 0.29694 | 1 | 0 |
| 38 | HIST2H2AC; HIST2H2BE; | 0.05016 | 0.29551 | 0.00730 | 0 | 1 |
| 39 | SFAMF1 | 1.00000 | 1.00000 | 0.29694 | 0 | 0 |
| 40 | DDR2 | 1.00000 | 1.00000 | 0.29694 | 0 | 0 |
| 41 | NUF2 | 1.00000 | 1.00000 | 0.29694 | 0 | 0 |
| 42 | RCSD1 | 0.34948 | 0.54966 | 0.02537 | 0 | 0 |
| 43 | RCSD1 | 0.60686 | 0.54294 | 0.08726 | 0 | 0 |
| 44 | RCSD1 | 0.10727 | 0.54966 | 0.02537 | 0 | 0 |
| 45 | RABGAP1L | 1.00000 | 1.00000 | 0.29694 | 0 | 0 |
| 46 | PLA2G4A | 0.10727 | 0.54966 | 0.02537 | 0 | 0 |
| 47 | PLA2G4A | 0.22755 | 0.54294 | 0.08726 | 0 | 0 |
| 48 | PLA2G4A | 0.47887 | 1.00000 | 0.29694 | 0 | 0 |
| 49 | KCNT2 | 1.00000 | 1.00000 | 0.29694 | 0 | 0 |
| 50 | PTPRC | 0.22755 | 0.54294 | 0.08726 | 0 | 0 |
| 51 | PTPRC | 0.22755 | 0.54294 | 0.08726 | 0 | 0 |
| 52 | PTPRC | 0.22755 | 0.54294 | 0.08726 | 0 | 0 |
| 53 | ELF3 | 0.22755 | 1.00000 | 0.08726 | 0 | 0 |
| 54 | BTG2 | 0.22755 | 0.54294 | 0.08726 | 1 | 0 |
| 55 | BTG2 | 0.00078 | 0.00730 | 0.00000 | 1 | 1 |
| 56 | BTG2 | 0.00000 | 0.00000 | 0.00000 | 1 | 1 |
| 57 | BTG2 | 0.05016 | 0.65667 | 0.00730 | 1 | 1 |
| 58 | SLC41A1 | 0.49735 | 1.00000 | 1.00000 | 0 | 0 |
| 59 | SLC41A1 | 0.49735 | 1.00000 | 1.00000 | 0 | 0 |
| 60 | CTSE | 1.00000 | 1.00000 | 0.29694 | 0 | 0 |
| 61 | CTSE | 0.60686 | 0.54294 | 0.08726 | 0 | 0 |
| 62 | ESRRG | 0.22755 | 0.54294 | 0.08726 | 0 | 0 |
| 63 | ITPKB | 0.22755 | 0.54294 | 0.08726 | 1 | 0 |
| 64 | ITPKB | 0.10727 | 0.54966 | 0.02537 | 1 | 0 |
| 65 | ITPKB | 0.22755 | 0.54294 | 0.08726 | 1 | 0 |
| 66 | URB2 | 1.00000 | 1.00000 | 0.29694 | 0 | 0 |
| 67 | TOMM20 | 0.49735 | 1.00000 | 1.00000 | 0 | 0 |
| 68 | TOMM20 | 1.00000 | 1.00000 | 0.29694 | 0 | 0 |
| 69 | MTRNR2L11 | 0.22755 | 0.54294 | 0.08726 | 0 | 0 |
| 70 | OR2T8 | 0.47887 | 1.00000 | 0.29694 | 0 | 0 |
| 71 | TMEM18 | 0.49735 | 1.00000 | 1.00000 | 0 | 0 |
| 72 | TPO | 0.49735 | 1.00000 | 1.00000 | 0 | 0 |
| 73 | RNF144A | 1.00000 | 0.11763 | 1.00000 | 0 | 1 |
| 74 | LPIN1 | 0.10727 | 0.54966 | 0.02537 | 0 | 0 |
| 75 | LPIN1 | 0.22755 | 0.54294 | 0.08726 | 0 | 0 |
| 76 | LPIN1 | 0.22755 | 0.54294 | 0.08726 | 0 | 0 |
| 77 | FAM84A | 0.49735 | 1.00000 | 1.00000 | 0 | 0 |
| 78 | RAD51AP2 | 1.00000 | 1.00000 | 0.29694 | 0 | 0 |
| 79 | OSR1 | 0.22755 | 0.54294 | 0.08726 | 0 | 0 |
| 80 | NCOA1 | 0.22755 | 0.54294 | 0.08726 | 0 | 0 |
| 81 | EHD3 | 1.00000 | 1.00000 | 0.29694 | 0 | 0 |
| 82 | C2orf91 | 1.00000 | 1.00000 | 0.29694 | 0 | 0 |
| 83 | SIX2 | 0.49735 | 1.00000 | 1.00000 | 0 | 0 |
| 84 | MSH6 | 1.00000 | 1.00000 | 0.29694 | 0 | 0 |
| 85 | MSH6 | 0.22755 | 0.54294 | 0.08726 | 0 | 0 |
| 86 | NRXN1 | 1.00000 | 1.00000 | 0.29694 | 0 | 0 |
| 87 | NRXN1 | 0.49735 | 1.00000 | 1.00000 | 0 | 0 |
| 88 | CCDC85A | 0.22755 | 0.54294 | 0.08726 | 0 | 0 |
| 89 | VRK2 | 1.00000 | 1.00000 | 0.29694 | 0 | 0 |
| 90 | BCL11A | 1.00000 | 0.54294 | 0.08726 | 0 | 0 |
| 91 | BCL11A | 0.22755 | 0.54294 | 0.08726 | 0 | 0 |
| 92 | WDPCP | 0.49735 | 1.00000 | 1.00000 | 0 | 0 |
| 93 | MDH1 | 1.00000 | 1.00000 | 0.29694 | 0 | 0 |
| 94 | PELI1 | 0.10727 | 0.54966 | 0.02537 | 0 | 0 |
| 95 | SPRED2 | 1.00000 | 0.54966 | 0.02537 | 1 | 1 |
| 96 | MEIS1 | 0.22755 | 1.00000 | 0.08726 | 0 | 0 |
| 97 | PCBP1 | 1.00000 | 0.03921 | 1.00000 | 0 | 1 |
| 98 | REG3A | 0.47887 | 1.00000 | 0.29694 | 0 | 0 |
| 99 | CTNNA2 | 0.49735 | 1.00000 | 1.00000 | 0 | 0 |
| 100 | CTNNA2 | 0.49735 | 1.00000 | 1.00000 | 0 | 0 |
| 101 | CTNNA2 | 0.47887 | 1.00000 | 0.29694 | 0 | 0 |
| 102 | SUCLG1 | 0.22755 | 0.54294 | 0.08726 | 0 | 0 |
| 103 | TCF7L1 | 0.49735 | 1.00000 | 1.00000 | 0 | 0 |
| 104 | EIF2AK3 | 0.05016 | 0.29551 | 0.00730 | 0 | 1 |
| 105 | EIF2AK3 | 0.10420 | 0.16101 | 0.00953 | 0 | 1 |
| 106 | EIF2AK3 | 0.05016 | 0.29551 | 0.00730 | 0 | 1 |
| 107 | RPIA | 0.47887 | 1.00000 | 0.50663 | 0 | 0 |
| 108 | RPIA | 1.00000 | 1.00000 | 0.29694 | 0 | 0 |
| 109 | RPIA | 1.00000 | 1.00000 | 0.29694 | 0 | 0 |
| 110 | RPIA | 1.00000 | 1.00000 | 0.29694 | 0 | 0 |
| 111 | IGKC | 0.03985 | 0.01404 | 0.00003 | 0 | 1 |
| 112 | IGKC | 0.01224 | 0.03142 | 0.00000 | 0 | 1 |
| 113 | IGKC | 1.00000 | 0.54966 | 0.02537 | 0 | 0 |
| 114 | IGKC | 0.10727 | 0.54966 | 0.02537 | 0 | 0 |
| 115 | IGKC | 0.22755 | 0.54294 | 0.08726 | 0 | 0 |

TABLE 1-continued

| | | | | | | |
|---|---|---|---|---|---|---|
| 116 | IGKC | 1.00000 | 1.00000 | 0.50663 | 0 | 0 |
| 117 | IGKC | 1.00000 | 0.54294 | 0.08726 | 0 | 0 |
| 118 | IGKC | 0.34948 | 0.54966 | 0.02537 | 0 | 0 |
| 119 | IGKC | 1.00000 | 1.00000 | 0.29694 | 0 | 0 |
| 120 | IGKC | 0.34948 | 0.54966 | 0.02537 | 0 | 0 |
| 121 | IGKC | 0.52007 | 0.09031 | 0.00058 | 0 | 1 |
| 122 | IGKC | 0.08710 | 0.09269 | 0.00099 | 0 | 1 |
| 123 | IGKC | 0.01070 | 0.09031 | 0.00058 | 0 | 1 |
| 124 | IGKC | 0.22755 | 0.54294 | 0.08726 | 0 | 0 |
| 125 | IGKC | 1.00000 | 1.00000 | 0.29694 | 0 | 0 |
| 126 | IGKC | 0.60686 | 0.54294 | 0.08726 | 0 | 0 |
| 127 | IGKC | 0.60686 | 0.54294 | 0.08726 | 0 | 0 |
| 128 | IGKC | 0.22755 | 0.54294 | 0.08726 | 0 | 0 |
| 129 | IGKC | 0.19371 | 0.29551 | 0.00730 | 0 | 1 |
| 130 | IGKC | 0.02808 | 0.09269 | 0.00016 | 0 | 1 |
| 131 | IGKC | 0.14439 | 0.00048 | 0.00000 | 0 | 1 |
| 132 | IGKC | 0.05462 | 0.00001 | 0.00000 | 0 | 1 |
| 133 | IGKJ5; | 0.24418 | 0.00083 | 0.00000 | 0 | 1 |
| 134 | IGKJ3; JGKJ4; IGKJ5; | 0.23729 | 0.68125 | 0.00019 | 0 | 1 |
| 135 | IGKJ1; IGKJ2; | 0.10957 | 0.81234 | 0.00049 | 0 | 1 |
| 136 | IGKJ1 | 0.10913 | 0.04835 | 0.00000 | 0 | 1 |
| 137 | IGKJ1 | 0.41068 | 0.00098 | 0.00117 | 0 | 1 |
| 138 | IGKJ1 | 0.33637 | 0.00075 | 0.00821 | 0 | 1 |
| 139 | IGKJ1 | 0.43812 | 0.02316 | 0.02379 | 0 | 1 |
| 140 | IGKJ1 | 0.67043 | 1.00000 | 0.15671 | 0 | 0 |
| 141 | IGKJ1 | 1.00000 | 1.00000 | 0.29694 | 0 | 0 |
| 142 | IGKV4-1 | 0.36833 | 1.00000 | 0.50663 | 0 | 1 |
| 143 | IGKV4-1 | 0.81354 | 0.05349 | 0.01836 | 0 | 1 |
| 144 | IGKV5-2 | 0.19371 | 0.29551 | 0.00730 | 0 | 1 |
| 145 | IGKV5-2 | 0.49735 | 1.00000 | 1.00000 | 0 | 0 |
| 146 | IGKV5-2 | 1.00000 | 1.00000 | 1.00000 | 0 | 0 |
| 147 | IGKV1-5 | 1.00000 | 0.54294 | 1.00000 | 0 | 0 |
| 148 | IGKV1-5 | 0.23086 | 0.15803 | 0.00321 | 0 | 1 |
| 149 | IGKV1-5 | 0.10727 | 1.00000 | 0.02537 | 0 | 0 |
| 150 | IGKV1-6 | 1.00000 | 1.00000 | 0.29694 | 0 | 0 |
| 151 | IGKV1-8 | 0.22755 | 0.54294 | 0.63492 | 0 | 0 |
| 152 | IGKV1-8 | 0.10727 | 0.54966 | 0.42650 | 0 | 0 |
| 153 | IGKV3-11 | 0.24603 | 1.00000 | 0.55662 | 0 | 0 |
| 154 | IGKV3-11 | 1.00000 | 1.00000 | 1.00000 | 0 | 0 |
| 155 | IGKV3-20 | 0.40586 | 0.71556 | 0.53493 | 0 | 1 |
| 156 | ICKV3-20 | 0.62100 | 1.00000 | 0.29694 | 0 | 0 |
| 157 | IGKV2-24 | 1.00000 | 0.34615 | 1.00000 | 0 | 0 |
| 158 | IGKV1-27 | 0.22755 | 0.54294 | 0.08726 | 0 | 0 |
| 159 | IGKV2-28 | 1.00000 | 1.00000 | 0.29694 | 0 | 0 |
| 160 | IGKV2-30 | 0.34948 | 1.00000 | 0.02537 | 0 | 0 |
| 161 | IGKV2-30 | 0.60686 | 0.54294 | 0.08726 | 0 | 0 |
| 162 | IGKV2-30 | 0.19371 | 0.65667 | 0.06548 | 0 | 1 |
| 163 | IGKV2-30 | 0.22755 | 0.54294 | 0.21104 | 0 | 0 |
| 164 | IGKV1D-8 | 1.00000 | 1.00000 | 0.29694 | 0 | 0 |
| 165 | IGKV1D-8 | 0.19371 | 0.29551 | 0.00730 | 0 | 1 |
| 166 | DUSP2 | 0.10727 | 0.54966 | 0.02537 | 1 | 0 |
| 167 | DUSP2 | 0.34948 | 0.54966 | 0.02537 | 1 | 0 |
| 168 | DUSP2 | 0.22755 | 0.54294 | 0.08726 | 1 | 0 |
| 169 | TMEM131 | 1.00000 | 1.00000 | 0.29694 | 0 | 0 |
| 170 | AFF3 | 1.00000 | 0.54294 | 0.08726 | 0 | 0 |
| 171 | AFF3 | 0.34948 | 0.54966 | 0.02537 | 0 | 0 |
| 172 | FHL2 | 0.22755 | 0.54294 | 0.08726 | 0 | 0 |
| 173 | BCL2L11 | 0.60686 | 0.54294 | 0.08726 | 0 | 0 |
| 174 | BCL2L11 | 0.34948 | 0.54966 | 0.02537 | 0 | 0 |
| 175 | ANAPC1 | 1.00000 | 1.00000 | 0.29694 | 0 | 0 |
| 176 | DPP10 | 1.00000 | 1.00000 | 0.29694 | 0 | 0 |
| 177 | DPP10 | 1.00000 | 0.34615 | 1.00000 | 0 | 0 |
| 178 | CNTNAP5 | 0.47887 | 1.00000 | 0.29694 | 0 | 0 |
| 179 | CNTNAP5 | 0.22755 | 0.54294 | 0.08726 | 0 | 0 |
| 180 | GYPC | 0.47887 | 1.00000 | 0.29694 | 0 | 0 |
| 181 | CXCR4 | 0.00036 | 0.00372 | 0.00000 | 1 | 1 |
| 182 | CXCR4 | 0.00626 | 0.03882 | 0.00000 | 1 | 1 |
| 183 | CXCR4 | 0.22755 | 0.54294 | 0.08726 | 1 | 0 |
| 184 | CXCR4 | 1.00000 | 1.00000 | 0.29694 | 1 | 0 |
| 185 | LRP1B | 0.22755 | 0.54294 | 0.08726 | 0 | 0 |
| 186 | LRP1B | 1.00000 | 1.00000 | 0.29694 | 0 | 0 |
| 187 | LRP1B | 0.22755 | 0.54294 | 0.08726 | 0 | 0 |
| 188 | ZEB2 | 0.22755 | 0.54294 | 0.08726 | 0 | 0 |
| 189 | ZEB2 | 0.60686 | 0.54294 | 0.08726 | 0 | 0 |
| 190 | KCNJ3 | 0.22755 | 0.54294 | 0.08726 | 0 | 0 |
| 191 | DYNC1I2 | 0.22755 | 0.54294 | 0.08726 | 0 | 0 |
| 192 | KIAA1715 | 1.00000 | 0.34615 | 1.00000 | 0 | 0 |
| 193 | CCDC141 | 1.00000 | 1.00000 | 0.29694 | 0 | 0 |
| 194 | ZNF385B | 0.22755 | 0.54294 | 0.08726 | 0 | 0 |

TABLE 1-continued

| | | | | | | |
|---|---|---|---|---|---|---|
| 195 | GULP1 | 1.00000 | 1.00000 | 0.29694 | 0 | 0 |
| 196 | GULP1 | 1.00000 | 0.34615 | 1.00000 | 0 | 0 |
| 197 | TMEFF2 | 1.00000 | 1.00000 | 0.29694 | 0 | 0 |
| 198 | STK17B | 0.34948 | 0.54966 | 0.02537 | 0 | 0 |
| 199 | STK17B | 0.22755 | 0.54294 | 0.08726 | 0 | 0 |
| 200 | ABCA12 | 0.47887 | 1.00000 | 0.50663 | 0 | 0 |
| 201 | XRCC5 | 1.00000 | 0.34615 | 1.00000 | 0 | 0 |
| 202 | 4-Mar-19 | 1.00000 | 0.34615 | 1.00000 | 0 | 0 |
| 203 | CUL3 | 0.22755 | 0.54294 | 0.08726 | 0 | 0 |
| 204 | CUL3 | 0.22755 | 0.54294 | 0.00726 | 0 | 0 |
| 205 | EFHD1 | 0.47887 | 1.00000 | 0.29694 | 0 | 0 |
| 206 | INPP5D | 0.22755 | 1.00000 | 0.08726 | 0 | 0 |
| 207 | AC093802.1 | 0.49735 | 0.34615 | 1.00000 | 0 | 0 |
| 208 | OTOS | 0.49735 | 1.00000 | 1.00000 | 0 | 0 |
| 209 | CAV3 | 0.49735 | 1.00000 | 1.00000 | 0 | 0 |
| 210 | RFTN1 | 0.49735 | 1.00000 | 1.00000 | 1 | 0 |
| 211 | RFTN1 | 0.24603 | 0.34615 | 1.00000 | 1 | 0 |
| 212 | RFTN1 | 0.10727 | 0.54966 | 0.07959 | 1 | 0 |
| 213 | RFTN1 | 1.00000 | 1.00000 | 0.29694 | 1 | 0 |
| 214 | RFTN1 | 0.22755 | 0.54294 | 0.08726 | 1 | 0 |
| 215 | RFTN1 | 0.60686 | 0.54294 | 0.58408 | 1 | 0 |
| 216 | RFTN1 | 0.08710 | 0.09269 | 0.00016 | 1 | 1 |
| 217 | RFTN1 | 0.22755 | 0.54294 | 0.08726 | 1 | 0 |
| 218 | ZNF385D | 0.22755 | 0.54294 | 0.08726 | 0 | 0 |
| 219 | TOP2B | 0.22755 | 0.54294 | 0.08726 | 0 | 0 |
| 220 | OSBPL10 | 0.22755 | 0.54294 | 0.08726 | 1 | 0 |
| 221 | OSBPL10 | 0.10727 | 0.54966 | 0.02537 | 1 | 0 |
| 222 | OSBPL10 | 0.10727 | 0.54966 | 0.02537 | 1 | 0 |
| 223 | OSBPL10 | 0.05468 | 0.09031 | 0.00058 | 1 | 1 |
| 224 | OSBPL10 | 0.22755 | 0.54294 | 0.08726 | 1 | 0 |
| 225 | RBM5 | 0.22755 | 0.54294 | 0.08726 | 0 | 0 |
| 226 | CACNA2D3 | 0.47887 | 1.00000 | 0.50663 | 0 | 0 |
| 227 | ERC2 | 1.00000 | 0.34615 | 1.00000 | 0 | 0 |
| 228 | FHIT | 0.22755 | 0.54294 | 0.08726 | 0 | 0 |
| 229 | FHIT | 0.10727 | 0.54966 | 0.02537 | 0 | 0 |
| 230 | FHIT | 1.00000 | 0.34615 | 1.00000 | 0 | 0 |
| 231 | FHIT | 1.00000 | 1.00000 | 0.29694 | 0 | 0 |
| 232 | FHIT | 1.00000 | 1.00000 | 0.29694 | 0 | 0 |
| 233 | FHIT | 0.22755 | 0.54294 | 0.08726 | 0 | 0 |
| 234 | FHIT | 1.00000 | 1.00000 | 0.29694 | 0 | 0 |
| 235 | FHIT | 0.22755 | 0.54294 | 0.08726 | 0 | 0 |
| 236 | FHIT | 0.49735 | 1.00000 | 1.00000 | 0 | 0 |
| 237 | FHIT | 0.22755 | 0.54294 | 0.08726 | 0 | 0 |
| 238 | FHIT | 0.49735 | 1.00000 | 1.00000 | 0 | 0 |
| 239 | FHIT | 0.22755 | 0.54294 | 0.08726 | 0 | 0 |
| 240 | FHIT | 0.22755 | 0.54294 | 0.08726 | 0 | 0 |
| 241 | FHIT | 1.00000 | 1.00000 | 0.29694 | 0 | 0 |
| 242 | FHIT | 1.00000 | 1.00000 | 0.29694 | 0 | 0 |
| 243 | FHIT | 0.47887 | 1.00000 | 0.50663 | 0 | 0 |
| 244 | FHIT | 0.60686 | 0.54294 | 0.08726 | 0 | 0 |
| 245 | FHIT | 0.60686 | 0.54294 | 0.08726 | 0 | 0 |
| 246 | FHIT | 0.22755 | 0.54294 | 0.08726 | 0 | 0 |
| 247 | FHIT | 0.49735 | 1.00000 | 1.00000 | 0 | 0 |
| 248 | FHIT | 0.22755 | 0.54294 | 0.08726 | 0 | 0 |
| 249 | FHIT | 0.49735 | 1.00000 | 1.00000 | 0 | 0 |
| 250 | FHIT | 1.00000 | 1.90000 | 0.29694 | 0 | 0 |
| 251 | FHIT | 1.00000 | 1.00000 | 0.29694 | 0 | 0 |
| 252 | FHIT | 0.49735 | 1.00000 | 1.00000 | 0 | 0 |
| 253 | FHIT | 0.60686 | 0.54294 | 0.08726 | 0 | 0 |
| 254 | FHIT | 1.00000 | 1.00000 | 0.29694 | 0 | 0 |
| 255 | FHIT | 1.00000 | 1.00000 | 0.29694 | 0 | 0 |
| 256 | FHIT | 0.24603 | 1.00000 | 1.00000 | 0 | 0 |
| 257 | FHIT | 0.10727 | 0.54966 | 0.02537 | 0 | 0 |
| 258 | FHIT | 1.00000 | 1.00000 | 0.29694 | 0 | 0 |
| 259 | FHIT | 0.10727 | 0.54966 | 0.02537 | 0 | 0 |
| 260 | FHIT | 1.00000 | 1.00000 | 0.29694 | 0 | 0 |
| 261 | FHIT | 0.62100 | 1.00000 | 0.29694 | 0 | 0 |
| 262 | FHIT | 1.00000 | 1.00000 | 0.29694 | 0 | 0 |
| 263 | FHIT | 0.49735 | 1.00000 | 1.00000 | 0 | 0 |
| 264 | FHIT | 0.22755 | 0.54294 | 0.08726 | 0 | 0 |
| 265 | FHIT | 0.22755 | 0.54294 | 0.08726 | 0 | 0 |
| 266 | FHIT | 0.49735 | 1.00000 | 1.00000 | 0 | 0 |
| 267 | FHIT | 1.00000 | 0.34615 | 1.00000 | 0 | 0 |
| 268 | FHIT | 0.49735 | 1.00000 | 1.00000 | 0 | 0 |
| 269 | FHIT | 0.49735 | 1.00000 | 1.00000 | 0 | 0 |
| 270 | EIF4E3 | 0.49735 | 1.00000 | 1.00000 | 0 | 0 |
| 271 | ROBO1 | 1.00000 | 1.00000 | 0.29694 | 0 | 0 |
| 272 | ROBO1 | 0.47887 | 1.00000 | 0.50663 | 0 | 0 |
| 273 | GBE1 | 0.47887 | 1.00000 | 0.29694 | 0 | 0 |
| 274 | CADM2 | 1.00000 | 0.34615 | 1.00000 | 0 | 0 |

TABLE 1-continued

| | | | | | | |
|---|---|---|---|---|---|---|
| 275 | CADM2 | 1.00000 | 1.00000 | 0.29694 | 0 | 0 |
| 276 | CADM2 | 0.10727 | 0.54966 | 0.02537 | 0 | 0 |
| 277 | CADM2 | 0.22755 | 0.54294 | 0.08726 | 0 | 0 |
| 278 | CADM2 | 0.22755 | 0.54294 | 0.08726 | 0 | 0 |
| 279 | CADM2 | 0.22755 | 0.54294 | 0.08726 | 0 | 0 |
| 280 | CGGBP1 | 0.22755 | 0.54294 | 0.08726 | 0 | 0 |
| 281 | NSUN3 | 0.22755 | 0.54294 | 0.08726 | 0 | 0 |
| 282 | MTRNR2L12 | 0.47887 | 1.00000 | 0.29694 | 0 | 0 |
| 283 | MTRNR2L12 | 0.22755 | 0.54294 | 0.08726 | 0 | 0 |
| 284 | NFKBIZ | 0.47887 | 1.00000 | 0.29694 | 0 | 0 |
| 285 | GCSAM | 0.10727 | 0.54966 | 0.02537 | 0 | 0 |
| 286 | GCSAM | 0.05016 | 0.29551 | 0.00730 | 0 | 1 |
| 287 | PARP14 | 0.10727 | 1.00000 | 0.02537 | 0 | 0 |
| 288 | SIAH2 | 0.22755 | 0.54294 | 0.08726 | 0 | 0 |
| 289 | SIAH2 | 0.22755 | 0.54294 | 0.08726 | 0 | 0 |
| 290 | SIAH2 | 1.00000 | 1.00000 | 0.29694 | 0 | 0 |
| 291 | SI | 0.49735 | 1.00000 | 1.00000 | 0 | 0 |
| 292 | SI | 0.22755 | 0.54294 | 0.08726 | 0 | 0 |
| 293 | SI | 0.22755 | 0.54294 | 0.08726 | 0 | 0 |
| 294 | KLHL6 | 0.22755 | 0.54294 | 0.08726 | 0 | 0 |
| 295 | KLHL6 | 0.60686 | 0.54294 | 0.08726 | 0 | 0 |
| 296 | KLHL6 | 0.60686 | 0.54294 | 0.08726 | 0 | 0 |
| 297 | KLHL6 | 0.67043 | 0.54966 | 0.36534 | 0 | 0 |
| 298 | ADIPOQ | 0.34948 | 0.54966 | 0.02537 | 0 | 0 |
| 299 | ST6GAL1 | 0.02624 | 0.02564 | 0.00009 | 1 | 1 |
| 300 | ST6GAL1 | 0.34948 | 0.54966 | 0.02537 | 1 | 0 |
| 301 | ST6GAL1 | 0.10420 | 0.16101 | 0.00953 | 1 | 1 |
| 302 | ST6GAL1 | 0.25970 | 1.00000 | 0.00953 | 1 | 1 |
| 303 | ST6GAL1 | 0.22755 | 0.54294 | 0.08726 | 1 | 0 |
| 304 | ST6GAL1 | 0.00001 | 0.00001 | 0.00000 | 1 | 1 |
| 305 | ST6GAL1 | 0.10727 | 0.54966 | 0.42650 | 1 | 0 |
| 306 | BCL6 | 0.22755 | 0.54294 | 0.08726 | 1 | 0 |
| 307 | BCL6 | 0.22755 | 0.54294 | 0.08726 | 1 | 0 |
| 308 | BCL6 | 0.31126 | 0.09031 | 0.00058 | 1 | 1 |
| 309 | BCL6 | 0.00137 | 0.00001 | 0.00000 | 1 | 1 |
| 310 | BCL6 | 0.00266 | 0.00000 | 0.00000 | 1 | 1 |
| 311 | BCL6 | 0.00164 | 0.00000 | 0.00000 | 1 | 1 |
| 312 | BCL6 | 0.00019 | 0.05349 | 0.00000 | 1 | 1 |
| 313 | BCL6 | 0.10727 | 0.54966 | 0.02537 | 1 | 0 |
| 314 | BCL6 | 0.22755 | 0.54294 | 0.08726 | 1 | 0 |
| 315 | BCL6 | 0.49735 | 1.00000 | 1.00000 | 1 | 0 |
| 316 | BCL6 | 0.34948 | 0.54966 | 0.02537 | 1 | 0 |
| 317 | BCL6 | 0.22755 | 0.54294 | 0.08726 | 1 | 0 |
| 318 | BCL6 | 0.23086 | 0.04825 | 0.00321 | 1 | 1 |
| 319 | BCL6 | 0.08249 | 0.00372 | 0.00000 | 1 | 1 |
| 320 | BCL6 | 0.10727 | 0.54966 | 0.02537 | 1 | 0 |
| 321 | AC022498.1 | 0.60686 | 1.00000 | 0.08726 | 0 | 0 |
| 322 | AC022498.1 | 1.00000 | 1.00000 | 1.00000 | 0 | 0 |
| 323 | AC022498.1 | 1.00000 | 1.00000 | 0.29694 | 0 | 0 |
| 324 | AC022498.1 | 0.05016 | 0.29551 | 0.02818 | 0 | 1 |
| 325 | AC022498.1 | 0.10727 | 0.54966 | 0.02537 | 0 | 0 |
| 326 | AC022498.1 | 0.22755 | 0.54294 | 0.08726 | 0 | 0 |
| 327 | AC022498.1 | 0.19371 | 0.29551 | 0.00730 | 0 | 1 |
| 328 | AC022498.1 | 0.00701 | 0.02564 | 0.00009 | 0 | 1 |
| 329 | AC022498.1 | 0.06156 | 0.00936 | 0.00000 | 0 | 1 |
| 330 | AC022498.1 | 0.00220 | 0.04825 | 0.00116 | 0 | 1 |
| 331 | AC022498.1 | 0.22755 | 0.54294 | 0.08726 | 0 | 0 |
| 332 | LPP | 0.22755 | 0.54294 | 0.08726 | 0 | 0 |
| 333 | LPP | 1.00000 | 1.00000 | 0.29694 | 0 | 0 |
| 334 | LPP | 0.15270 | 0.09031 | 0.00311 | 0 | 1 |
| 335 | LPP | 0.04150 | 0.00372 | 0.00000 | 0 | 1 |
| 336 | LPP | 0.67043 | 0.54966 | 0.02537 | 0 | 0 |
| 337 | ZNF595; ZNF718; | 0.22755 | 0.54294 | 0.08726 | 0 | 0 |
| 338 | ZNF595; ZNF718; | 0.34948 | 0.54966 | 0.02537 | 0 | 0 |
| 339 | ZNF595; ZNF718; | 0.22755 | 0.54294 | 0.08726 | 0 | 0 |
| 340 | ZNF732 | 1.00000 | 0.11763 | 1.00000 | 0 | 1 |
| 341 | ZNF141 | 0.22755 | 0.54294 | 0.08726 | 0 | 0 |
| 342 | PIGG | 0.49735 | 1.00000 | 1.00000 | 0 | 0 |
| 343 | FAM193A | 0.47887 | 1.00000 | 0.29694 | 0 | 0 |
| 344 | STK32B | 0.22755 | 0.54294 | 0.08726 | 0 | 0 |
| 345 | SEL1L3 | 0.19371 | 0.29551 | 0.00730 | 0 | 1 |
| 346 | SEL1L3 | 0.67043 | 0.54966 | 0.07959 | 0 | 0 |
| 347 | SEL1L3 | 0.25970 | 0.16101 | 0.00208 | 0 | 1 |
| 348 | PCDH7 | 1.00000 | 1.00000 | 0.29694 | 0 | 0 |
| 349 | PCDH7 | 0.47887 | 1.00000 | 0.50663 | 0 | 0 |
| 350 | PCDH7 | 0.22755 | 0.54294 | 0.08726 | 0 | 0 |
| 351 | PCDH7 | 0.47887 | 1.00000 | 0.29694 | 0 | 0 |

TABLE 1-continued

| | | | | | | |
|---|---|---|---|---|---|---|
| 352 | RFC1 | 1.00000 | 1.00000 | 0.29694 | 0 | 0 |
| 353 | PDS5A | 0.49735 | 1.00000 | 1.00000 | 0 | 0 |
| 354 | N4BP2 | 0.67043 | 0.54966 | 0.02537 | 0 | 0 |
| 355 | N4BP2 | 1.00000 | 1.00000 | 0.29694 | 0 | 0 |
| 356 | N4BP2 | 0.10420 | 0.16101 | 0.00208 | 0 | 1 |
| 357 | N4BP2 | 1.00000 | 1.00000 | 0.29694 | 0 | 0 |
| 358 | N4BP2 | 0.31126 | 0.09031 | 0.00058 | 0 | 1 |
| 359 | N4BP2 | 0.10628 | 0.00895 | 0.00000 | 0 | 1 |
| 360 | RHOH | 0.11795 | 0.04825 | 0.00030 | 1 | 1 |
| 361 | RHOH | 0.31126 | 0.09031 | 0.00058 | 1 | 1 |
| 362 | RHOH | 0.60686 | 0.54294 | 0.08726 | 1 | 0 |
| 363 | RHOH | 0.22755 | 0.54294 | 0.08726 | 1 | 0 |
| 364 | GNPDA2 | 0.22755 | 0.54294 | 0.08726 | 0 | 0 |
| 365 | GABRA2 | 1.00000 | 1.00000 | 0.29694 | 0 | 0 |
| 366 | LPHN3 | 0.22755 | 0.54294 | 0.08726 | 0 | 0 |
| 367 | LPHN3 | 0.22755 | 0.54294 | 0.08726 | 0 | 0 |
| 368 | LPHN3 | 0.22755 | 0.54294 | 0.08726 | 0 | 0 |
| 369 | LPHN3 | 0.22755 | 0.54294 | 0.08726 | 0 | 0 |
| 370 | LPHN3 | 0.22755 | 0.54294 | 0.08726 | 0 | 0 |
| 371 | TECRL | 1.00000 | 1.00000 | 0.29694 | 0 | 0 |
| 372 | TECRL | 1.00000 | 1.00000 | 0.29694 | 0 | 0 |
| 373 | EPHA5 | 1.00000 | 1.00000 | 1.00000 | 0 | 0 |
| 374 | EPHA5 | 0.22755 | 0.54294 | 0.08726 | 0 | 0 |
| 375 | IGJ | 0.62100 | 1.00000 | 0.29694 | 0 | 0 |
| 376 | IGJ | 0.49735 | 1.00000 | 1.00000 | 0 | 0 |
| 377 | RASSF6 | 0.22755 | 0.54294 | 0.08726 | 0 | 0 |
| 378 | RASSF6 | 0.47887 | 1.00000 | 0.50663 | 0 | 0 |
| 379 | RASSF6 | 0.10727 | 0.54966 | 0.02537 | 0 | 0 |
| 380 | RASSF6 | 0.01070 | 0.09031 | 0.00058 | 0 | 1 |
| 381 | CCSER1 | 1.00000 | 1.00000 | 0.29694 | 0 | 0 |
| 382 | CCSER1 | 0.22755 | 0.54294 | 0.08726 | 0 | 0 |
| 383 | TIFA | 0.22755 | 0.54294 | 0.08726 | 0 | 0 |
| 384 | CAMK2D | 0.22755 | 0.54294 | 0.08726 | 0 | 0 |
| 385 | CAMK2D | 0.10727 | 0.54966 | 0.02537 | 0 | 0 |
| 386 | TRAM1L1 | 0.22755 | 0.54294 | 0.08726 | 0 | 0 |
| 387 | BBS12 | 0.49735 | 1.00000 | 1.00000 | 0 | 0 |
| 388 | ANKRD50 | 1.00000 | 1.00000 | 0.29694 | 0 | 0 |
| 389 | FAT4 | 0.22755 | 0.54294 | 0.08726 | 0 | 0 |
| 390 | PCDH10 | 0.49735 | 1.00000 | 1.00000 | 0 | 0 |
| 391 | PCDH10 | 1.00000 | 1.00000 | 0.29694 | 0 | 0 |
| 392 | PABPC4L | 0.22755 | 0.54294 | 0.08726 | 0 | 0 |
| 393 | PABPC4L | 0.22755 | 0.54294 | 0.08726 | 0 | 0 |
| 394 | PABPC4L | 0.22755 | 0.54294 | 0.08726 | 0 | 0 |
| 395 | PABPC4L | 1.00000 | 1.00000 | 0.29694 | 0 | 0 |
| 396 | PABPC4L | 0.22755 | 0.54294 | 0.08726 | 0 | 0 |
| 397 | PCDH18 | 1.00000 | 0.34615 | 1.00000 | 0 | 0 |
| 398 | PCDH18 | 1.00000 | 1.00000 | 0.29694 | 0 | 0 |
| 399 | NAA15 | 1.00000 | 1.00000 | 0.29694 | 0 | 0 |
| 400 | LRBA | 0.22755 | 0.54294 | 0.08726 | 0 | 0 |
| 401 | LRBA | 0.49735 | 1.00000 | 1.00000 | 0 | 0 |
| 402 | SH3D19 | 0.22755 | 1.00000 | 0.08726 | 0 | 0 |
| 403 | CTSO | 1.00000 | 1.00000 | 0.29694 | 0 | 0 |
| 404 | 1-Mar-19 | 0.49735 | 1.00000 | 1.00000 | 0 | 0 |
| 405 | AGA | 1.00000 | 0.34615 | 1.00000 | 0 | 0 |
| 406 | AGA | 0.22755 | 0.54294 | 0.08726 | 0 | 0 |
| 407 | AGA | 0.22755 | 0.54294 | 0.08726 | 0 | 0 |
| 408 | TENM3 | 0.22755 | 0.54294 | 0.21104 | 0 | 0 |
| 409 | TENM3 | 0.22755 | 0.54294 | 0.08726 | 0 | 0 |
| 410 | TENM3 | 1.00000 | 1.00000 | 0.29694 | 0 | 0 |
| 411 | AHRR | 1.00000 | 0.34615 | 1.00000 | 0 | 0 |
| 412 | IRX1 | 0.22755 | 0.54294 | 0.08726 | 0 | 0 |
| 413 | BASP1 | 0.22755 | 0.54294 | 0.08726 | 0 | 0 |
| 414 | BASP1 | 0.22755 | 0.54294 | 0.08726 | 0 | 0 |
| 415 | CDH18 | 1.00000 | 0.34615 | 1.00000 | 0 | 0 |
| 416 | CDH12 | 0.22755 | 0.54294 | 0.08726 | 0 | 0 |
| 417 | CDH12 | 1.00000 | 1.00000 | 0.29694 | 0 | 0 |
| 418 | CDH10 | 0.22755 | 0.54294 | 0.08726 | 0 | 0 |
| 419 | CDH10 | 1.00000 | 1.00000 | 0.29694 | 0 | 0 |
| 420 | CDH10 | 0.22755 | 0.54294 | 0.08726 | 0 | 0 |
| 421 | CDH9 | 1.00000 | 1.00000 | 0.29694 | 0 | 0 |
| 422 | CDH9 | 0.22755 | 0.54294 | 0.08726 | 0 | 0 |
| 423 | CDH6 | 0.22755 | 0.54294 | 0.08726 | 0 | 0 |
| 424 | CDH6 | 0.22755 | 0.54294 | 0.08726 | 0 | 0 |
| 425 | CDH6 | 0.22755 | 0.54294 | 0.08726 | 0 | 0 |
| 426 | CTD-2203A3.1 | 0.34948 | 0.54966 | 0.02537 | 0 | 0 |
| 427 | EDIL3 | 0.22755 | 0.54294 | 0.08726 | 0 | 0 |
| 428 | MEF2C | 0.22755 | 0.54294 | 0.08726 | 0 | 0 |
| 429 | MEF2C | 1.00000 | 1.00000 | 0.29694 | 0 | 0 |
| 430 | ARRDC3 | 0.49735 | 1.00000 | 1.00000 | 0 | 0 |
| 431 | NUDT12 | 1.00000 | 1.00000 | 0.29694 | 0 | 0 |

TABLE 1-continued

| | | | | | | |
|---|---|---|---|---|---|---|
| 432 | ZNF608 | 0.49735 | 1.00000 | 1.00000 | 1 | 0 |
| 433 | ZNF608 | 0.60686 | 0.54294 | 0.08726 | 1 | 0 |
| 434 | ZNF608 | 0.60686 | 0.54294 | 0.08726 | 1 | 0 |
| 435 | FBN2 | 1.00000 | 1.00000 | 0.29694 | 0 | 0 |
| 436 | FBN2 | 0.49735 | 1.00000 | 1.00000 | 0 | 0 |
| 437 | IRF1 | 0.02326 | 0.16101 | 0.00208 | 0 | 1 |
| 438 | IRF1 | 0.22755 | 0.54294 | 0.08726 | 0 | 0 |
| 439 | CD74 | 0.00701 | 0.02564 | 0.00001 | 1 | 1 |
| 440 | CD74 | 1.00000 | 1.00000 | 0.29694 | 1 | 0 |
| 441 | EBF1 | 0.47887 | 1.00000 | 0.29694 | 0 | 0 |
| 442 | EBF1 | 0.22755 | 0.54294 | 0.08726 | 0 | 0 |
| 443 | EBF1 | 0.10727 | 1.00000 | 0.02537 | 0 | 0 |
| 444 | EBF1 | 0.22755 | 0.54294 | 0.08726 | 0 | 0 |
| 445 | EBF1 | 0.05016 | 0.29551 | 0.00730 | 0 | 1 |
| 446 | MAT2B | 0.22755 | 0.54294 | 0.08726 | 0 | 0 |
| 447 | MAT2B | 0.47887 | 1.00000 | 0.29694 | 0 | 0 |
| 448 | TENM2 | 1.00000 | 1.00000 | 0.29694 | 0 | 0 |
| 449 | CPEB4 | 0.49735 | 1.00000 | 1.00000 | 0 | 0 |
| 450 | MAML1 | 1.00000 | 1.00000 | 0.29694 | 0 | 0 |
| 451 | FLT4 | 1.00000 | 1.00000 | 0.29694 | 0 | 0 |
| 452 | IRF4 | 0.02326 | 0.16101 | 0.00208 | 1 | 1 |
| 453 | IRF4 | 0.02326 | 0.16101 | 0.00208 | 1 | 1 |
| 454 | CD83 | 0.00011 | 0.00013 | 0.00000 | 1 | 1 |
| 455 | CD83 | 0.67043 | 0.54966 | 0.02537 | 1 | 0 |
| 456 | NHLRC1 | 0.10727 | 1.00000 | 0.02537 | 0 | 0 |
| 457 | RNF144B | 0.49735 | 1.00000 | 1.00000 | 1 | 0 |
| 458 | RNF144B | 0.49735 | 1.00000 | 1.00000 | 1 | 0 |
| 459 | ID4 | 0.22755 | 0.54294 | 0.08726 | 0 | 0 |
| 460 | HDGFL1 | 1.00000 | 1.00000 | 0.29694 | 0 | 0 |
| 461 | HIST1H3B | 0.49735 | 1.00000 | 1.00000 | 1 | 0 |
| 462 | HIST1H3B | 0.49735 | 1.00000 | 1.00000 | 1 | 0 |
| 463 | HIST1H3C | 0.42627 | 0.29551 | 0.00730 | 1 | 1 |
| 464 | HIST1H2BC | 0.19371 | 0.29551 | 0.00730 | 1 | 1 |
| 465 | HIST1H2AC; HIST1H2BC; | 0.02326 | 0.16101 | 0.00208 | 0 | 1 |
| 466 | HIST1H2AC | 1.00000 | 1.00000 | 0.29694 | 1 | 0 |
| 467 | HIST1H1E | 0.10420 | 0.16101 | 0.00208 | 1 | 1 |
| 468 | HIST1H1E | 0.60686 | 0.54294 | 0.08726 | 1 | 0 |
| 469 | HIST1H2BG | 0.22755 | 0.54294 | 0.08726 | 1 | 0 |
| 470 | HIST1H1D | 0.10727 | 0.54966 | 0.02537 | 0 | 0 |
| 471 | HIST1H2AG | 0.22755 | 0.54294 | 0.08726 | 1 | 0 |
| 472 | HIST1H2AH; HIST1H2BK; | 0.19371 | 0.29551 | 0.00730 | 0 | 1 |
| 473 | HIST1H4J | 0.34948 | 0.54966 | 0.02537 | 0 | 0 |
| 474 | HIST1H2AL | 1.00000 | 1.00000 | 0.29694 | 1 | 0 |
| 475 | HIST1H2AM | 1.00000 | 0.54294 | 0.08726 | 1 | 0 |
| 476 | HIST1H2BO | 1.00000 | 1.00000 | 0.29694 | 1 | 0 |
| 477 | LOC554223 | 1.00000 | 0.34615 | 1.00000 | 0 | 0 |
| 478 | HLA-G | 1.00000 | 1.00000 | 0.29694 | 0 | 0 |
| 479 | HLA-A | 0.10727 | 0.54966 | 0.02537 | 0 | 0 |
| 480 | HLA-A | 1.00000 | 1.00000 | 0.29694 | 0 | 0 |
| 481 | HLA-B | 0.60686 | 0.54294 | 0.08726 | 1 | 0 |
| 482 | HLA-B | 1.00000 | 0.34615 | 1.00000 | 1 | 0 |
| 483 | TNF | 0.22755 | 0.54294 | 0.08726 | 1 | 0 |
| 484 | LTB | 0.04150 | 0.00372 | 0.00000 | 1 | 1 |
| 485 | LTB | 0.10727 | 0.54966 | 0.02537 | 1 | 0 |
| 486 | HLA-DRA | 0.67043 | 0.54966 | 0.02537 | 0 | 0 |
| 487 | HLA-DRB5 | 1.00000 | 0.11763 | 1.00000 | 0 | 1 |
| 488 | HLA-DRB5 | 0.47887 | 1.00000 | 0.29694 | 0 | 0 |
| 489 | HLA-DRB5 | 0.47887 | 1.00000 | 0.29694 | 0 | 0 |
| 490 | HLA-DRB5 | 0.49735 | 1.00000 | 1.00000 | 0 | 0 |
| 491 | HLA-DRB5 | 0.49735 | 1.00000 | 1.00000 | 0 | 0 |
| 492 | HLA-DRB5 | 0.60686 | 0.54294 | 0.08726 | 0 | 0 |
| 493 | HLA-DRB5 | 0.24603 | 1.00000 | 1.00000 | 0 | 0 |
| 494 | HLA-DRB1 | 1.00000 | 1.00000 | 0.29694 | 0 | 0 |
| 495 | HLA-DRB1 | 0.60686 | 0.54294 | 0.08726 | 0 | 0 |
| 496 | HLA-DRB1 | 0.24603 | 1.00000 | 1.00000 | 0 | 0 |
| 497 | HLA-DRB1 | 0.49735 | 1.00000 | 1.00000 | 0 | 0 |
| 498 | HLA-DRB1 | 0.60686 | 0.54294 | 0.08726 | 0 | 0 |
| 499 | HLA-DRB1 | 1.00000 | 0.27446 | 0.29694 | 0 | 1 |
| 500 | HLA-DRB1 | 0.24603 | 0.34615 | 1.00000 | 0 | 0 |
| 501 | HLA-DQA1 | 0.19371 | 0.65667 | 0.00730 | 0 | 1 |
| 502 | HLA-DQB1 | 1.00000 | 1.00000 | 0.29694 | 0 | 0 |
| 503 | HLA-DQB1 | 1.00000 | 0.17874 | 0.08726 | 0 | 1 |
| 504 | HLA-DQB2 | 0.47887 | 0.27446 | 0.29694 | 0 | 1 |
| 505 | HLA-DQB2 | 0.60686 | 0.60763 | 0.08726 | 0 | 1 |
| 506 | HLA-DPB1 | 1.00000 | 1.00000 | 0.29694 | 0 | 0 |
| 507 | HMGA1 | 0.22755 | 0.54294 | 0.08726 | 0 | 0 |
| 508 | PIM1 | 0.08249 | 0.00372 | 0.00000 | 1 | 1 |
| 509 | PIM1 | 0.31126 | 0.09031 | 0.00058 | 1 | 1 |

TABLE 1-continued

| | | | | | | |
|---|---|---|---|---|---|---|
| 510 | PIM1 | 0.60686 | 0.54294 | 0.08726 | 1 | 0 |
| 511 | PRIM2 | 1.00000 | 1.00000 | 0.29694 | 0 | 0 |
| 512 | BAI3 | 1.00000 | 1.00000 | 0.29694 | 0 | 0 |
| 513 | IMPG1 | 0.22755 | 0.54294 | 0.08726 | 0 | 0 |
| 514 | BCKDHB | 1.00000 | 1.00000 | 0.29694 | 0 | 0 |
| 515 | AKIRIN2 | 1.00000 | 1.00000 | 0.29694 | 0 | 0 |
| 516 | SPACA1 | 0.34948 | 0.54966 | 0.02537 | 0 | 0 |
| 517 | CNR1 | 0.47887 | 1.00000 | 0.29694 | 0 | 0 |
| 518 | RNGTT | 0.60686 | 0.54294 | 0.08726 | 0 | 0 |
| 519 | RNGTT | 0.22755 | 0.54294 | 0.08726 | 0 | 0 |
| 520 | RNGTT | 0.10727 | 0.54966 | 0.02537 | 0 | 0 |
| 521 | RNGTT | 0.22755 | 0.54294 | 0.08726 | 0 | 0 |
| 522 | RNGTT | 0.22755 | 0.54294 | 0.08726 | 0 | 0 |
| 523 | UBE2J1 | 0.05016 | 0.29551 | 0.00730 | 1 | 1 |
| 524 | UBE2J1 | 0.22755 | 0.54294 | 0.08726 | 1 | 0 |
| 525 | MAP3K7 | 0.60686 | 0.54294 | 0.08726 | 0 | 0 |
| 526 | MAP3K7 | 0.19371 | 0.29551 | 0.00730 | 0 | 1 |
| 527 | MAP3K7 | 0.00279 | 0.00011 | 0.00000 | 0 | 1 |
| 528 | MAP3K7 | 0.04838 | 0.04825 | 0.00030 | 0 | 1 |
| 529 | MAP3K7 | 0.22755 | 0.54294 | 0.58408 | 0 | 0 |
| 530 | EPHA7 | 0.47887 | 1.00000 | 0.29694 | 0 | 0 |
| 531 | PDSS2 | 1.00000 | 0.34615 | 1.00000 | 0 | 0 |
| 532 | RFPL4B | 1.00000 | 1.00000 | 0.29694 | 0 | 0 |
| 533 | SLC35F1 | 1.00000 | 1.00000 | 0.29694 | 0 | 0 |
| 534 | C6orf170 | 0.49735 | 0.34615 | 1.00000 | 0 | 0 |
| 535 | C6orf170 | 0.22755 | 0.54294 | 0.08726 | 0 | 0 |
| 536 | TRDN | 0.47887 | 1.00000 | 0.50663 | 0 | 0 |
| 537 | RSPO3 | 0.47887 | 1.00000 | 0.50663 | 0 | 0 |
| 538 | EYA4 | 0.22755 | 0.54294 | 0.08726 | 0 | 0 |
| 539 | SGK1 | 0.22755 | 0.54294 | 0.08726 | 1 | 0 |
| 540 | SGK1 | 0.34948 | 0.54966 | 0.02537 | 1 | 0 |
| 541 | SGK1 | 0.22755 | 0.54294 | 0.08726 | 1 | 0 |
| 542 | SGK1 | 0.22755 | 0.54294 | 0.08726 | 1 | 0 |
| 543 | SGK1 | 0.02233 | 0.01471 | 0.00000 | 1 | 1 |
| 544 | SGK1 | 0.22755 | 0.54294 | 0.08726 | 1 | 0 |
| 545 | NMBR | 0.05016 | 0.29551 | 0.00730 | 0 | 1 |
| 546 | SAMD5 | 0.47887 | 1.00000 | 0.29694 | 0 | 0 |
| 547 | PLEKHG1 | 0.34948 | 0.54966 | 0.02537 | 0 | 0 |
| 548 | EZR | 0.34948 | 0.54966 | 0.15671 | 0 | 0 |
| 549 | EZR | 0.60686 | 0.54294 | 0.08726 | 0 | 0 |
| 550 | EZR | 0.60686 | 0.54294 | 0.08726 | 0 | 0 |
| 551 | TAGAP | 1.00000 | 1.00000 | 0.29694 | 0 | 0 |
| 552 | TAGAP | 0.22755 | 0.54294 | 0.08726 | 0 | 0 |
| 553 | PLG | 0.49735 | 0.34615 | 1.00000 | 0 | 0 |
| 554 | PARK2 | 0.49735 | 0.34615 | 1.00000 | 0 | 0 |
| 555 | PARK2 | 0.22755 | 0.54294 | 0.08726 | 0 | 0 |
| 556 | C6orf118 | 0.22755 | 0.54294 | 0.08726 | 0 | 0 |
| 557 | SMOC2 | 0.47887 | 1.00000 | 0.29694 | 0 | 0 |
| 558 | AC110781.3 | 0.22755 | 0.54294 | 0.08726 | 0 | 0 |
| 559 | MAD1L1 | 0.47887 | 1.00000 | 0.29694 | 0 | 0 |
| 560 | MAD1L1 | 1.00000 | 1.00000 | 0.29694 | 0 | 0 |
| 561 | ACTB | 0.19371 | 0.29551 | 0.00730 | 1 | 1 |
| 562 | ACTB | 0.19371 | 0.29551 | 0.00730 | 1 | 1 |
| 563 | ACTB | 1.00000 | 1.00000 | 0.29694 | 1 | 0 |
| 564 | NDUFA4 | 0.60686 | 0.54294 | 0.08726 | 0 | 0 |
| 565 | ARL4A | 0.47887 | 1.00000 | 0.29694 | 0 | 0 |
| 566 | ETV1 | 0.49735 | 1.00000 | 1.00000 | 0 | 0 |
| 567 | AGMO | 0.49735 | 1.00000 | 1.00000 | 0 | 0 |
| 568 | ISPD | 1.00000 | 1.00000 | 0.29694 | 0 | 0 |
| 569 | CREB5 | 0.47887 | 1.00000 | 0.29694 | 0 | 0 |
| 570 | C7orf10 | 0.62100 | 1.00000 | 0.29694 | 0 | 0 |
| 571 | IKZF1 | 0.19371 | 0.29551 | 0.00730 | 0 | 1 |
| 572 | IKZF1 | 0.10727 | 0.54966 | 0.02537 | 0 | 0 |
| 573 | POM121L12 | 0.49735 | 1.00000 | 1.00000 | 0 | 0 |
| 574 | ZNF716 | 0.22755 | 0.54294 | 0.08726 | 0 | 0 |
| 575 | AC006455.1 | 1.00000 | 1.00000 | 0.29694 | 0 | 0 |
| 576 | WBSCR17 | 0.22755 | 0.54294 | 0.08726 | 0 | 0 |
| 577 | CALN1 | 1.00000 | 1.00000 | 0.29694 | 0 | 0 |
| 578 | GNAI1 | 1.00000 | 1.00000 | 0.29694 | 0 | 0 |
| 579 | AC005008.2 | 0.22755 | 0.54294 | 0.08726 | 0 | 0 |
| 580 | CACNA2D1 | 0.49735 | 1.00000 | 1.00000 | 0 | 0 |
| 581 | SEMA3A | 0.47887 | 1.00000 | 0.29694 | 0 | 0 |
| 582 | SEMA3D | 0.22755 | 0.54294 | 0.08726 | 0 | 0 |
| 583 | SEMA3D | 0.47887 | 1.00000 | 0.29694 | 0 | 0 |
| 584 | CROT | 1.00000 | 1.00000 | 0.29694 | 0 | 0 |
| 585 | CDK14 | 0.22755 | 0.54294 | 0.08726 | 0 | 0 |
| 586 | CALCR | 0.22755 | 0.54294 | 0.08726 | 0 | 0 |
| 587 | BET1 | 1.00000 | 1.00000 | 0.29694 | 0 | 0 |
| 588 | FBXL13 | 1.00000 | 0.34615 | 1.00000 | 0 | 0 |
| 589 | CDHR3 | 1.00000 | 1.00000 | 0.29694 | 0 | 0 |

TABLE 1-continued

| | | | | | | |
|---|---|---|---|---|---|---|
| 590 | IMMP2L | 0.22755 | 0.54294 | 0.08726 | 0 | 0 |
| 591 | IMMP2L | 0.22755 | 0.54294 | 0.08726 | 0 | 0 |
| 592 | IMMP2L | 1.00000 | 1.00000 | 0.29694 | 0 | 0 |
| 593 | IMMP2L | 1.00000 | 1.00000 | 0.29694 | 0 | 0 |
| 594 | IMMP2L | 0.22755 | 0.54294 | 0.08726 | 0 | 0 |
| 595 | IMMP2L | 0.22755 | 0.54294 | 0.08726 | 0 | 0 |
| 596 | IMMP2L | 0.22755 | 0.54294 | 0.08726 | 0 | 0 |
| 597 | IMMP2L | 0.10727 | 0.54966 | 0.02537 | 0 | 0 |
| 598 | IMMP2L | 0.22755 | 0.54294 | 0.08726 | 0 | 0 |
| 599 | IMMP2L | 0.10727 | 0.54966 | 0.02537 | 0 | 0 |
| 600 | IMMP2L | 0.22755 | 0.54294 | 0.08726 | 0 | 0 |
| 601 | IMMP2L | 0.22755 | 0.54294 | 0.08726 | 0 | 0 |
| 602 | IMMP2L | 0.22755 | 0.54294 | 0.08726 | 0 | 0 |
| 603 | IMMP2L | 1.00000 | 1.00000 | 0.29694 | 0 | 0 |
| 604 | IMMP2L | 0.10727 | 0.54966 | 0.02537 | 0 | 0 |
| 605 | IMMP2L | 0.60686 | 0.54294 | 0.08726 | 0 | 0 |
| 606 | IMMP2L | 0.60686 | 0.54294 | 0.08726 | 0 | 0 |
| 607 | IMMP2L | 0.60686 | 0.54294 | 0.08726 | 0 | 0 |
| 608 | IMMP2L | 1.00000 | 0.54294 | 0.08726 | 0 | 0 |
| 609 | IMMP2L | 0.10727 | 0.54966 | 0.02537 | 0 | 0 |
| 610 | IMMP2L | 0.22755 | 0.54294 | 0.08726 | 0 | 0 |
| 611 | IMMP2L | 0.22755 | 0.54294 | 0.08726 | 0 | 0 |
| 612 | IMMP2L | 0.60686 | 0.54294 | 0.08726 | 0 | 0 |
| 613 | IMMP2L | 0.49735 | 1.00000 | 1.00000 | 0 | 0 |
| 614 | IMMP2L | 0.22755 | 0.54294 | 0.08726 | 0 | 0 |
| 615 | IMMP2L | 0.60686 | 0.54294 | 0.08726 | 0 | 0 |
| 616 | IMMP2L | 0.22755 | 0.54294 | 0.08726 | 0 | 0 |
| 617 | IMMP2L | 0.02326 | 0.16101 | 0.00208 | 0 | 1 |
| 618 | LRRN3 | 0.22755 | 0.54294 | 0.08726 | 0 | 0 |
| 619 | LRRN3 | 0.67043 | 1.00000 | 0.02537 | 0 | 0 |
| 620 | LRRN3 | 0.22755 | 0.54294 | 0.08726 | 0 | 0 |
| 621 | LRRN3 | 0.05016 | 0.29551 | 0.00730 | 0 | 1 |
| 622 | LRRN3 | 0.22755 | 0.54294 | 0.08726 | 0 | 0 |
| 623 | LRRN3 | 0.22755 | 0.54294 | 0.08726 | 0 | 0 |
| 624 | LRRN3 | 0.10727 | 0.54966 | 0.02537 | 0 | 0 |
| 625 | LRRN3 | 1.00000 | 1.00000 | 0.29694 | 0 | 0 |
| 626 | LRRN3 | 0.22755 | 0.54294 | 0.08726 | 0 | 0 |
| 627 | LRRN3 | 1.00000 | 1.00000 | 0.29694 | 0 | 0 |
| 628 | LRRN3 | 0.60686 | 0.54294 | 0.08726 | 0 | 0 |
| 629 | LRRN3 | 1.00000 | 1.00000 | 0.29694 | 0 | 0 |
| 630 | LRRN3 | 1.00000 | 1.00000 | 0.29694 | 0 | 0 |
| 631 | LRRN3 | 1.00000 | 0.54294 | 0.08726 | 0 | 0 |
| 632 | LRRN3 | 0.22755 | 0.54294 | 0.08726 | 0 | 0 |
| 633 | LRRN3 | 0.60686 | 0.54294 | 0.08726 | 0 | 0 |
| 634 | LRRN3 | 0.22755 | 0.54294 | 0.08726 | 0 | 0 |
| 635 | LRRN3 | 0.22755 | 0.54294 | 0.08726 | 0 | 0 |
| 636 | LRRN3 | 0.10727 | 0.54966 | 0.02537 | 0 | 0 |
| 637 | LRRN3 | 0.22755 | 0.54294 | 0.08726 | 0 | 0 |
| 638 | LRRN3 | 0.60686 | 0.54294 | 0.08726 | 0 | 0 |
| 639 | LRRN3 | 0.10727 | 0.54966 | 0.02537 | 0 | 0 |
| 640 | LRRN3 | 0.60686 | 0.54294 | 0.08726 | 0 | 0 |
| 641 | LRRN3 | 1.00000 | 1.00000 | 0.29694 | 0 | 0 |
| 642 | LRRN3 | 0.22755 | 0.54294 | 0.08726 | 0 | 0 |
| 643 | LRRN3 | 0.10727 | 0.54966 | 0.02537 | 0 | 0 |
| 644 | LRRN3 | 0.22755 | 0.54294 | 0.08726 | 0 | 0 |
| 645 | LRRN3 | 1.00000 | 1.00000 | 0.29694 | 0 | 0 |
| 646 | LRRN3 | 0.22755 | 0.54294 | 0.08726 | 0 | 0 |
| 647 | LRRN3 | 0.22755 | 0.54294 | 0.08726 | 0 | 0 |
| 648 | LRRN3 | 0.10727 | 0.54966 | 0.02537 | 0 | 0 |
| 649 | LRRN3 | 0.22755 | 0.54294 | 0.08726 | 0 | 0 |
| 650 | LRRN3 | 0.22755 | 0.54294 | 0.08726 | 0 | 0 |
| 651 | LRRN3 | 1.00000 | 1.00000 | 0.29694 | 0 | 0 |
| 652 | LRRN3 | 0.10727 | 0.54966 | 0.02537 | 0 | 0 |
| 653 | LRRN3 | 0.22755 | 0.54294 | 0.08726 | 0 | 0 |
| 654 | DOCK4 | 1.00000 | 0.34615 | 1.00000 | 0 | 0 |
| 655 | KCND2 | 1.00000 | 1.00000 | 0.29694 | 0 | 0 |
| 656 | PTPRZ1 | 1.00000 | 1.00000 | 0.50663 | 0 | 0 |
| 657 | TMEM229A | 0.22755 | 0.54294 | 0.08726 | 0 | 0 |
| 658 | POT1 | 1.00000 | 1.00000 | 0.29694 | 0 | 0 |
| 659 | CNTNAP2 | 0.22755 | 0.54294 | 0.08726 | 0 | 0 |
| 660 | EZH2 | 0.24603 | 1.00000 | 1.00000 | 0 | 0 |
| 661 | BLACE | 0.49735 | 1.00000 | 1.00000 | 0 | 0 |
| 662 | DNAJB6 | 1.00000 | 0.11763 | 1.00000 | 0 | 1 |
| 663 | WDR60 | 1.00000 | 1.00000 | 0.29694 | 0 | 0 |
| 664 | DLGAP2 | 1.00000 | 1.00000 | 0.29694 | 0 | 0 |
| 665 | MCPH1 | 0.22755 | 0.54294 | 0.08726 | 0 | 0 |
| 666 | MCPH1 | 0.49735 | 1.00000 | 1.00000 | 0 | 0 |
| 667 | MFHAS1 | 0.60686 | 0.54294 | 0.08726 | 0 | 0 |
| 668 | MFHAS1 | 0.22755 | 0.54294 | 0.08726 | 0 | 0 |
| 669 | MFHAS1 | 0.22755 | 0.54294 | 0.08726 | 0 | 0 |

TABLE 1-continued

| | | | | | | |
|---|---|---|---|---|---|---|
| 670 | BLK | 0.60686 | 0.54294 | 0.08726 | 0 | 0 |
| 671 | SGCZ | 1.00000 | 1.00000 | 0.29694 | 0 | 0 |
| 672 | SGCZ | 0.47887 | 1.00000 | 0.50663 | 0 | 0 |
| 673 | MSR1 | 1.00000 | 1.00000 | 0.29694 | 0 | 0 |
| 674 | MSR1 | 0.47887 | 1.00000 | 0.29694 | 0 | 0 |
| 675 | CHMP7 | 1.00000 | 1.00000 | 0.29694 | 0 | 0 |
| 676 | ADAM28 | 0.22755 | 0.54294 | 0.08726 | 0 | 0 |
| 677 | KIF13B | 1.00000 | 0.34615 | 1.00000 | 0 | 0 |
| 678 | AC012215.1 | 0.22755 | 0.54294 | 0.08726 | 0 | 0 |
| 679 | PLEKHA2 | 0.22755 | 0.54294 | 0.08726 | 0 | 0 |
| 680 | LYPLA1 | 0.22755 | 0.54294 | 0.08726 | 0 | 0 |
| 681 | TOX | 1.00000 | 1.00000 | 0.29694 | 0 | 0 |
| 682 | MYBL1 | 1.00000 | 1.00000 | 0.29694 | 0 | 0 |
| 683 | ZFHX4 | 0.22755 | 0.54294 | 0.08726 | 0 | 0 |
| 684 | PEX2 | 0.22755 | 0.54294 | 0.08726 | 0 | 0 |
| 685 | RIPK2 | 0.22755 | 0.54294 | 0.08726 | 0 | 0 |
| 686 | RUNX1T1 | 0.22755 | 0.54294 | 0.08726 | 0 | 0 |
| 687 | FAM92A1 | 0.47887 | 1.00000 | 0.29694 | 0 | 0 |
| 688 | SYBU | 1.00000 | 1.00000 | 0.29694 | 0 | 0 |
| 689 | TRIB1 | 1.00000 | 1.00000 | 0.29694 | 0 | 0 |
| 690 | MYC | 0.00099 | 0.00010 | 0.00001 | 1 | 1 |
| 691 | MYC | 0.02808 | 0.00000 | 0.00016 | 1 | 1 |
| 692 | MYC | 0.05468 | 0.00007 | 0.00058 | 1 | 1 |
| 693 | MYC | 0.10727 | 0.23165 | 0.02537 | 1 | 1 |
| 694 | MYC | 0.47887 | 0.27446 | 0.29694 | 1 | 1 |
| 695 | FAM135B | 0.47887 | 1.00000 | 0.29694 | 0 | 0 |
| 696 | FAM135B | 0.49735 | 1.00000 | 1.00000 | 0 | 0 |
| 697 | TSNARE1 | 0.47887 | 1.00000 | 0.29694 | 0 | 0 |
| 698 | C8orf31 | 0.22755 | 0.54294 | 0.08726 | 0 | 0 |
| 699 | UHRF2 | 0.22755 | 0.54294 | 0.08726 | 0 | 0 |
| 700 | UHRF2 | 1.00000 | 1.00000 | 0.29694 | 0 | 0 |
| 701 | UHRF2 | 0.60686 | 0.54294 | 0.08726 | 0 | 0 |
| 702 | PTPRD | 0.49735 | 1.00000 | 1.00000 | 0 | 0 |
| 703 | NFIB | 0.22755 | 0.54294 | 0.08726 | 0 | 0 |
| 704 | DMRTA1 | 0.22755 | 0.54294 | 0.08726 | 0 | 0 |
| 705 | TUSC1 | 0.22755 | 0.54294 | 0.08726 | 0 | 0 |
| 706 | LINGO2 | 1.00000 | 1.00000 | 0.29694 | 0 | 0 |
| 707 | ACO1 | 1.00000 | 1.00000 | 0.29694 | 0 | 0 |
| 708 | PAX5 | 0.47887 | 1.00000 | 0.50663 | 1 | 0 |
| 709 | PAX5 | 1.00000 | 1.00000 | 0.29694 | 1 | 0 |
| 710 | PAX5 | 0.67043 | 0.54966 | 0.02537 | 1 | 0 |
| 711 | PAX5 | 0.14640 | 0.02564 | 0.00001 | 1 | 1 |
| 712 | PAX5 | 0.10913 | 0.00107 | 0.00000 | 1 | 1 |
| 713 | PAX5 | 0.60686 | 0.54294 | 0.08726 | 1 | 0 |
| 714 | PAX5 | 0.34948 | 0.54966 | 0.02537 | 1 | 0 |
| 715 | PAX5 | 0.47996 | 0.16101 | 0.00208 | 1 | 1 |
| 716 | PAX5 | 1.00000 | 1.00000 | 0.29694 | 1 | 0 |
| 717 | ZCCHC7 | 0.60686 | 0.54294 | 0.08726 | 0 | 0 |
| 718 | ZCCHC7 | 0.22755 | 0.54294 | 0.08726 | 0 | 0 |
| 719 | ZCCHC7 | 1.00000 | 0.54294 | 0.08726 | 0 | 0 |
| 720 | ZCCHC7 | 0.67043 | 0.54966 | 0.02537 | 0 | 0 |
| 721 | ZCCHC7 | 1.00000 | 1.00000 | 0.29694 | 0 | 0 |
| 722 | ZCCHC7 | 0.34948 | 0.54966 | 0.02537 | 0 | 0 |
| 723 | ZCCHC7 | 0.62100 | 1.00000 | 1.00000 | 0 | 0 |
| 724 | ZCCHC7 | 0.60686 | 0.54294 | 0.08726 | 0 | 0 |
| 725 | ZCCHC7 | 0.22755 | 0.54294 | 0.08726 | 0 | 0 |
| 726 | ZCCHC7 | 0.38669 | 0.15803 | 0.00732 | 0 | 1 |
| 727 | ZCCHC7 | 1.00000 | 1.00000 | 0.29694 | 0 | 0 |
| 728 | ZCCHC7 | 0.42627 | 0.29551 | 0.00730 | 0 | 1 |
| 729 | ZCCHC7 | 1.00000 | 0.29551 | 0.00730 | 0 | 1 |
| 730 | ZCCHC7 | 0.60686 | 0.54294 | 0.08726 | 0 | 0 |
| 731 | ZCCHC7 | 0.19371 | 0.29551 | 0.00730 | 0 | 1 |
| 732 | GRHPR | 0.10727 | 0.54966 | 0.02537 | 0 | 0 |
| 733 | GRHPR | 0.22755 | 0.54294 | 0.08726 | 0 | 0 |
| 734 | GRHPR | 0.22755 | 0.54294 | 0.08726 | 0 | 0 |
| 735 | GRHPR | 0.22755 | 0.54294 | 0.21104 | 0 | 0 |
| 736 | GRHPR | 1.00000 | 1.00000 | 0.29694 | 0 | 0 |
| 737 | GRHPR | 0.81382 | 0.02564 | 0.00001 | 0 | 1 |
| 738 | GRHPR | 1.00000 | 0.54294 | 0.21104 | 0 | 0 |
| 739 | GRHPR | 0.22755 | 0.54294 | 0.08726 | 0 | 0 |
| 740 | GRHPR | 0.10727 | 0.54966 | 0.02537 | 0 | 0 |
| 741 | GRHPR | 0.22755 | 0.54294 | 0.08726 | 0 | 0 |
| 742 | AKAP2 | 0.19371 | 0.29551 | 0.00730 | 0 | 1 |
| 743 | COL27A1 | 1.00000 | 0.11763 | 1.00000 | 0 | 1 |
| 744 | ASTN2 | 0.10727 | 0.54966 | 0.02537 | 0 | 0 |
| 745 | DENND1A | 1.00000 | 0.11763 | 1.00000 | 0 | 1 |
| 746 | FAM102A | 0.05016 | 0.29551 | 0.00730 | 1 | 1 |
| 747 | FAM102A | 0.42627 | 0.29551 | 0.00730 | 1 | 1 |
| 748 | FNBP1 | 1.00000 | 1.00000 | 0.29694 | 0 | 0 |
| 749 | FNBP1 | 0.22755 | 0.54294 | 0.08726 | 0 | 0 |

TABLE 1-continued

| | | | | | | |
|---|---|---|---|---|---|---|
| 750 | FNBP1 | 1.00000 | 1.00000 | 0.29694 | 0 | 0 |
| 751 | FNBP1 | 1.00000 | 0.54294 | 0.08726 | 0 | 0 |
| 752 | RAPGEF1 | 0.22755 | 0.54294 | 0.08726 | 0 | 0 |
| 753 | UBAC1 | 0.60686 | 0.60763 | 0.08726 | 0 | 1 |
| 754 | PITRM1 | 0.49735 | 1.00000 | 1.00000 | 0 | 0 |
| 755 | ASB13 | 0.60686 | 0.54294 | 0.08726 | 0 | 0 |
| 756 | ASB13 | 0.47887 | 1.00900 | 0.50663 | 0 | 0 |
| 757 | FAM171A1 | 0.47887 | 1.00000 | 0.29694 | 0 | 0 |
| 758 | PLXDC2 | 0.47887 | 1.00000 | 0.50663 | 0 | 0 |
| 759 | CREM | 0.22755 | 0.54294 | 0.08726 | 0 | 0 |
| 760 | PCDH15 | 0.49735 | 1.00000 | 1.00000 | 0 | 0 |
| 761 | C10orf107 | 0.47887 | 1.00000 | 0.29694 | 0 | 0 |
| 762 | ARID5B | 0.34948 | 0.54966 | 0.02537 | 1 | 0 |
| 763 | ARID5B | 0.19371 | 0.29551 | 0.00730 | 1 | 1 |
| 764 | ARID5B | 0.60686 | 0.54294 | 0.08726 | 1 | 0 |
| 765 | ARID5B | 0.22755 | 0.54294 | 0.08726 | 1 | 0 |
| 766 | ARID5B | 0.49735 | 1.00000 | 1.00000 | 1 | 0 |
| 767 | ARID5B | 1.00000 | 1.00000 | 0.29694 | 1 | 0 |
| 768 | ARID5B | 0.49735 | 1.00000 | 1.00000 | 1 | 0 |
| 769 | CTNNA3 | 0.47887 | 1.00000 | 0.50663 | 0 | 0 |
| 770 | CTNNA3 | 0.49735 | 1.00000 | 1.00000 | 0 | 0 |
| 771 | PIK3AP1 | 0.22755 | 0.54294 | 0.08726 | 0 | 0 |
| 772 | SLC25A28 | 1.00000 | 1.00000 | 0.29694 | 0 | 0 |
| 773 | SORCS1 | 0.22755 | 0.54294 | 0.08726 | 0 | 0 |
| 774 | GPAM | 0.47887 | 1.00000 | 0.29694 | 0 | 0 |
| 775 | GPAM | 0.22755 | 0.54294 | 0.08726 | 0 | 0 |
| 776 | ABLIM1 | 0.10727 | 0.54966 | 0.02537 | 0 | 0 |
| 777 | MCMBP | 0.22755 | 0.54294 | 0.08726 | 0 | 0 |
| 778 | TCERG1L | 1.00000 | 1.00000 | 0.29694 | 0 | 0 |
| 779 | INPP5A | 0.47887 | 1.00000 | 0.29694 | 0 | 0 |
| 780 | CHID1 | 0.22755 | 1.00000 | 0.08726 | 0 | 0 |
| 781 | MUC5AC | 0.47887 | 1.00000 | 0.29694 | 0 | 0 |
| 782 | LUZP2 | 0.22755 | 0.54294 | 0.08726 | 0 | 0 |
| 783 | LUZP2 | 0.22755 | 0.54294 | 0.08726 | 0 | 0 |
| 784 | BBOX1 | 0.60686 | 1.00000 | 0.08726 | 0 | 0 |
| 785 | METTL15 | 0.49735 | 1.00000 | 1.00000 | 0 | 0 |
| 786 | KCNA4 | 0.22755 | 0.54294 | 0.08726 | 0 | 0 |
| 787 | KCNA4 | 0.22755 | 0.54294 | 0.08726 | 0 | 0 |
| 788 | LRRC4C | 0.22755 | 0.54294 | 0.08726 | 0 | 0 |
| 789 | LRRC4C | 0.22755 | 0.54294 | 0.08726 | 0 | 0 |
| 790 | LRRC4C | 0.22755 | 0.54294 | 0.08726 | 0 | 0 |
| 791 | LRRC4C | 0.22755 | 0.54294 | 0.08726 | 0 | 0 |
| 792 | API5 | 0.47887 | 1.00000 | 0.29694 | 0 | 0 |
| 793 | SLC43A3 | 0.60686 | 0.54294 | 0.08726 | 0 | 0 |
| 794 | MS4A1 | 0.10420 | 0.16101 | 0.00208 | 1 | 1 |
| 795 | FRMD8 | 0.25970 | 0.16101 | 0.00208 | 0 | 1 |
| 796 | FRMD8 | 0.02808 | 0.09269 | 0.00016 | 0 | 1 |
| 797 | SCYL1 | 0.60686 | 0.54294 | 0.08726 | 0 | 0 |
| 798 | SCYL1 | 0.00488 | 0.09269 | 0.00016 | 0 | 1 |
| 799 | EED | 0.22755 | 0.54294 | 0.08726 | 0 | 0 |
| 800 | FAT3 | 0.22755 | 0.54294 | 0.08726 | 0 | 0 |
| 801 | YAP1 | 0.49735 | 1.00000 | 1.00000 | 0 | 0 |
| 802 | BIRC3 | 0.16270 | 0.00197 | 0.00000 | 1 | 1 |
| 803 | BIRC3 | 0.05016 | 0.29551 | 0.00730 | 1 | 1 |
| 804 | ELMOD1 | 0.47887 | 1.00000 | 0.29694 | 0 | 0 |
| 805 | DDX10 | 1.00000 | 1.00000 | 0.29694 | 0 | 0 |
| 806 | DDX10 | 1.00000 | 1.00000 | 0.29694 | 0 | 0 |
| 807 | C11orf87 | 0.47887 | 1.00000 | 0.29694 | 0 | 0 |
| 808 | POU2AF1 | 0.60686 | 0.54294 | 0.08726 | 1 | 0 |
| 809 | POU2AF1 | 0.77363 | 0.09269 | 0.00337 | 1 | 1 |
| 810 | CADM1 | 0.62100 | 1.00000 | 0.29694 | 0 | 0 |
| 811 | CXCR5 | 0.22755 | 0.54294 | 0.08726 | 0 | 0 |
| 812 | KIRREL3 | 1.00000 | 1.00000 | 0.29694 | 0 | 0 |
| 813 | ETS1 | 0.34948 | 0.54966 | 0.02537 | 1 | 0 |
| 814 | ETS1 | 0.01415 | 0.04825 | 0.00004 | 1 | 1 |
| 815 | CD27 | 0.22755 | 0.54294 | 0.08726 | 0 | 0 |
| 816 | AICDA | 1.00000 | 1.00000 | 0.29694 | 0 | 0 |
| 817 | AICDA | 1.00000 | 0.54966 | 0.02537 | 0 | 0 |
| 818 | AICDA | 0.44431 | 0.54294 | 0.08726 | 0 | 1 |
| 819 | AICDA | 1.00000 | 1.00000 | 0.29694 | 0 | 0 |
| 820 | CLEC2D | 1.00000 | 1.00000 | 0.29694 | 0 | 0 |
| 821 | ETV6 | 0.22755 | 0.54294 | 0.08726 | 1 | 0 |
| 822 | ETV6 | 1.00000 | 1.00000 | 0.29694 | 1 | 0 |
| 823 | HIST4H4 | 1.00000 | 1.00000 | 0.29694 | 1 | 0 |
| 824 | LMO3 | 0.49735 | 1.00000 | 1.00000 | 0 | 0 |
| 825 | SOX5 | 0.22755 | 0.54294 | 0.08726 | 0 | 0 |
| 826 | C12orf77 | 0.22755 | 0.54294 | 0.08726 | 0 | 0 |
| 827 | C12orf77 | 1.00000 | 1.00000 | 0.29694 | 0 | 0 |
| 828 | C12orf77 | 0.10727 | 0.54966 | 0.02537 | 0 | 0 |
| 829 | LRMP | 0.47887 | 1.00000 | 0.50663 | 1 | 0 |

TABLE 1-continued

| | | | | | | |
|---|---|---|---|---|---|---|
| 830 | LRMP | 0.02808 | 0.09269 | 0.00099 | 1 | 1 |
| 831 | LRMP | 0.01415 | 0.04825 | 0.00030 | 1 | 1 |
| 832 | LRMP | 0.60686 | 0.54294 | 0.08726 | 1 | 0 |
| 833 | IFLTD1 | 0.47887 | 1.00000 | 0.29694 | 0 | 0 |
| 834 | CPNE8 | 0.22755 | 0.54294 | 0.08726 | 0 | 0 |
| 835 | RPAP3 | 0.42627 | 0.65667 | 0.00730 | 0 | 1 |
| 836 | STAT6 | 1.00000 | 1.00000 | 0.29694 | 0 | 0 |
| 837 | MDM2 | 0.47887 | 1.00000 | 0.50663 | 0 | 0 |
| 838 | PHLDA1 | 0.49735 | 1.00000 | 1.00000 | 0 | 0 |
| 839 | SYT1 | 1.00000 | 0.54294 | 0.08726 | 0 | 0 |
| 840 | CCDC59 | 1.00000 | 1.00000 | 0.29694 | 0 | 0 |
| 841 | SLC6A15 | 0.49735 | 1.00000 | 1.00000 | 0 | 0 |
| 842 | RASSF9 | 0.22755 | 0.54294 | 0.08726 | 0 | 0 |
| 843 | RASSF9 | 0.22755 | 0.54294 | 0.08726 | 0 | 0 |
| 844 | BTG1 | 0.15270 | 0.09031 | 0.00058 | 1 | 1 |
| 845 | BTG1 | 0.10420 | 0.16101 | 0.00208 | 1 | 1 |
| 846 | NTN4 | 0.47887 | 1.00000 | 0.29694 | 0 | 0 |
| 847 | FAM222A | 0.47887 | 1.00000 | 0.50663 | 0 | 0 |
| 848 | PPTC7 | 1.00000 | 1.00000 | 0.29694 | 0 | 0 |
| 849 | DTX1 | 0.05016 | 0.29551 | 0.00730 | 1 | 1 |
| 850 | DTX1 | 0.01224 | 0.00730 | 0.00000 | 1 | 1 |
| 851 | DTX1 | 0.11004 | 0.01471 | 0.00000 | 1 | 1 |
| 852 | DTX1 | 0.14640 | 0.02564 | 0.00001 | 1 | 1 |
| 853 | DTX1 | 0.02326 | 0.16101 | 0.00208 | 1 | 1 |
| 854 | DTX1 | 0.22755 | 0.54294 | 0.08726 | 1 | 0 |
| 855 | DTX1 | 0.22755 | 0.54294 | 0.08726 | 1 | 0 |
| 856 | MED13L | 0.49735 | 1.00000 | 1.00000 | 0 | 0 |
| 857 | WDR66 | 0.22755 | 0.54294 | 0.08726 | 0 | 0 |
| 858 | WDR66 | 0.19371 | 0.29551 | 0.00730 | 0 | 1 |
| 859 | WDR66 | 0.49735 | 1.00000 | 1.00000 | 0 | 0 |
| 860 | BCL7A | 0.38669 | 0.04825 | 0.00030 | 1 | 1 |
| 861 | BCL7A | 0.00197 | 0.00003 | 0.00000 | 1 | 1 |
| 862 | BCL7A | 0.12879 | 0.00730 | 0.00000 | 1 | 1 |
| 863 | BCL7A | 0.10628 | 0.00013 | 0.00000 | 1 | 1 |
| 864 | BCL7A | 0.00186 | 0.00372 | 0.00000 | 1 | 1 |
| 865 | BCL7A | 0.14640 | 0.02564 | 0.00038 | 1 | 1 |
| 866 | TMED2 | 1.00000 | 1.00000 | 0.29694 | 0 | 0 |
| 867 | TMEM132C | 0.49735 | 1.00000 | 1.00000 | 0 | 0 |
| 868 | STX2 | 1.00000 | 0.27446 | 0.29694 | 0 | 1 |
| 869 | GPR133 | 0.49735 | 1.00000 | 1.00000 | 0 | 0 |
| 870 | ANKLE2 | 1.00000 | 1.00000 | 0.29694 | 0 | 0 |
| 871 | ZDHHC20 | 0.22755 | 0.54294 | 0.08726 | 0 | 0 |
| 872 | RXFP2 | 0.47887 | 1.00000 | 0.29694 | 0 | 0 |
| 873 | NBEA | 1.00000 | 1.00000 | 0.29694 | 0 | 0 |
| 874 | TRPC4 | 0.47887 | 1.00000 | 0.29694 | 0 | 0 |
| 875 | TRPC4 | 0.22755 | 0.54294 | 0.08726 | 0 | 0 |
| 876 | FOXO1 | 0.22755 | 0.54294 | 0.08726 | 1 | 0 |
| 877 | FOXO1 | 0.22755 | 1.00000 | 0.08726 | 1 | 0 |
| 878 | KIAA0226L | 0.22755 | 0.54294 | 0.08726 | 0 | 0 |
| 879 | KIAA0226L | 0.22755 | 0.54294 | 0.08726 | 0 | 0 |
| 880 | KIAA0226L | 0.15270 | 0.09031 | 0.00058 | 0 | 1 |
| 881 | KIAA0226L | 1.00000 | 1.00000 | 0.29694 | 0 | 0 |
| 882 | KIAA0226L | 1.00000 | 1.00000 | 0.29694 | 0 | 0 |
| 883 | OLFM4 | 0.22755 | 0.54294 | 0.08726 | 0 | 0 |
| 884 | OLFM4 | 0.22755 | 0.54294 | 0.08726 | 0 | 0 |
| 885 | OLFM4 | 0.22755 | 0.54294 | 0.08726 | 0 | 0 |
| 886 | PRR20A; PRR20DPRR20BPRR20E; | 0.22755 | 0.54294 | 0.08726 | 0 | 0 |
| 887 | TDRD3 | 0.47887 | 1.00000 | 0.29694 | 0 | 0 |
| 888 | PCDH20 | 0.49735 | 1.00000 | 1.00000 | 0 | 0 |
| 889 | PCDH20 | 0.22755 | 0.54294 | 0.08726 | 0 | 0 |
| 890 | AL445989.1 | 0.47887 | 1.00000 | 0.29694 | 0 | 0 |
| 891 | AL445989.1 | 0.47887 | 1.00000 | 0.29694 | 0 | 0 |
| 892 | AL445989.1 | 1.00000 | 1.00000 | 0.29694 | 0 | 0 |
| 893 | PCDH9 | 0.22755 | 0.54294 | 0.08726 | 0 | 0 |
| 894 | PCDH9 | 0.49735 | 1.00000 | 1.00000 | 0 | 0 |
| 895 | KLHL1 | 0.60686 | 0.54294 | 0.08726 | 0 | 0 |
| 896 | KLHL1 | 0.47887 | 1.00000 | 1.00000 | 0 | 0 |
| 897 | KLF12 | 0.22755 | 0.54294 | 0.08726 | 0 | 0 |
| 898 | TBC1D4 | 0.10420 | 0.16101 | 0.00208 | 0 | 1 |
| 899 | TBC1D4 | 0.04838 | 0.04825 | 0.00004 | 0 | 1 |
| 900 | SLITRK1 | 0.22755 | 0.54294 | 0.08726 | 0 | 0 |
| 901 | SLITRK1 | 1.00000 | 1.00000 | 0.29694 | 0 | 0 |
| 902 | SLITRK5 | 1.00000 | 1.00000 | 0.29694 | 0 | 0 |
| 903 | GPC5 | 0.49735 | 1.00000 | 1.00000 | 0 | 0 |
| 904 | DAOA | 1.00000 | 1.00000 | 0.29694 | 0 | 0 |
| 905 | RASA3 | 1.00000 | 1.00000 | 0.29694 | 0 | 0 |
| 906 | RASA3 | 1.00000 | 0.34615 | 1.00000 | 0 | 0 |
| 907 | TRAJ56 | 0.22755 | 0.54294 | 0.08726 | 0 | 0 |
| 908 | TRAJ56 | 0.10727 | 0.54966 | 0.02537 | 0 | 0 |

TABLE 1-continued

| | | | | | | |
|---|---|---|---|---|---|---|
| 909 | TRAJ54 | 0.22755 | 0.54294 | 0.08726 | 0 | 0 |
| 910 | TRAJ33 | 1.00000 | 1.00000 | 0.29694 | 0 | 0 |
| 911 | NOVA1 | 0.22755 | 0.54294 | 0.08726 | 0 | 0 |
| 912 | FOXG1 | 0.49735 | 1.00000 | 1.00000 | 0 | 0 |
| 913 | RPS29 | 0.24603 | 1.00000 | 1.00000 | 0 | 0 |
| 914 | CDKL1 | 0.22755 | 0.54294 | 0.08726 | 0 | 0 |
| 915 | CDKN3 | 0.49735 | 1.00000 | 1.00000 | 0 | 0 |
| 916 | GCH1 | 0.22755 | 0.54294 | 0.08726 | 0 | 0 |
| 917 | DAAM1 | 0.22755 | 0.54294 | 0.08726 | 0 | 0 |
| 918 | KCNH5 | 1.00000 | 1.00000 | 0.29694 | 0 | 0 |
| 919 | SGPP1 | 1.00000 | 1.00000 | 0.29694 | 0 | 0 |
| 920 | ZFP36L1 | 0.00186 | 0.00372 | 0.00000 | 1 | 1 |
| 921 | ZFP36L1 | 0.00244 | 0.00024 | 0.00000 | 1 | 1 |
| 922 | ADCK1 | 0.22755 | 0.54294 | 0.08726 | 0 | 0 |
| 923 | GTF2A1 | 0.47887 | 1.00000 | 0.29694 | 0 | 0 |
| 924 | FLRT2 | 0.47887 | 1.00000 | 0.50663 | 0 | 0 |
| 925 | CCDC88C | 1.00000 | 1.00000 | 0.29694 | 0 | 0 |
| 926 | SERPINA9 | 0.60686 | 0.54294 | 0.21104 | 1 | 0 |
| 927 | SERPINA9 | 0.01415 | 0.04825 | 0.00004 | 1 | 1 |
| 928 | TCL1A | 0.79702 | 0.15881 | 0.01566 | 1 | 1 |
| 929 | TCL1A | 0.52007 | 0.41714 | 0.06858 | 1 | 1 |
| 930 | AL117190.3 | 0.49735 | 1.00000 | 1.00000 | 0 | 0 |
| 931 | PPP2R5C | 1.00000 | 1.00000 | 0.29694 | 0 | 0 |
| 932 | CRIP1 | 0.34948 | 0.54966 | 0.02537 | 0 | 0 |
| 933 | IGHA2 | 1.00000 | 1.00000 | 0.29694 | 0 | 0 |
| 934 | IGHA2 | 0.19468 | 0.09269 | 0.00855 | 0 | 1 |
| 935 | IGHA2 | 0.47887 | 1.00000 | 0.50663 | 0 | 0 |
| 936 | IGHA2 | 0.60686 | 0.54294 | 0.08726 | 0 | 0 |
| 937 | IGHA2 | 0.08710 | 0.49207 | 0.00016 | 0 | 1 |
| 938 | IGHA2 | 0.25970 | 1.00000 | 0.00953 | 0 | 1 |
| 939 | IGHA2 | 0.05016 | 0.29551 | 0.00730 | 0 | 1 |
| 940 | IGHA2 | 0.22755 | 0.54294 | 0.08726 | 0 | 0 |
| 941 | IGHE | 0.05016 | 0.29551 | 0.00730 | 0 | 1 |
| 942 | IGHE | 0.34948 | 0.54966 | 0.02537 | 0 | 0 |
| 943 | IGHE | 0.08710 | 0.09269 | 0.00016 | 0 | 1 |
| 944 | IGHE | 1.00000 | 0.00197 | 0.00000 | 0 | 1 |
| 945 | IGHE | 0.75773 | 0.09031 | 0.00058 | 0 | 1 |
| 946 | IGHE | 1.00000 | 0.16101 | 0.00208 | 0 | 1 |
| 947 | IGHE | 0.60686 | 0.54294 | 0.08726 | 0 | 0 |
| 948 | IGHG4 | 1.00000 | 1.00000 | 0.29694 | 0 | 0 |
| 949 | IGHG4 | 0.22755 | 0.54294 | 0.08726 | 0 | 0 |
| 950 | IGHG4 | 0.01393 | 0.01404 | 0.00003 | 0 | 1 |
| 951 | IGHG4 | 0.77363 | 0.09269 | 0.00016 | 0 | 1 |
| 952 | IGHG2 | 0.10420 | 0.16101 | 0.00208 | 0 | 1 |
| 953 | IGHG2 | 1.00000 | 1.00000 | 0.29694 | 0 | 0 |
| 954 | IGHG2 | 0.70749 | 0.00011 | 0.00000 | 0 | 1 |
| 955 | IGHG2 | 0.16121 | 0.00002 | 0.00000 | 0 | 1 |
| 956 | IGHG2 | 0.02111 | 0.00013 | 0.00000 | 0 | 1 |
| 957 | IGHA1 | 0.22755 | 0.54294 | 0.08726 | 0 | 0 |
| 958 | IGHA1 | 1.00000 | 1.00000 | 0.50663 | 0 | 0 |
| 959 | IGHA1 | 1.00000 | 1.00000 | 0.50663 | 0 | 0 |
| 960 | IGHA1 | 1.00000 | 1.00000 | 0.29694 | 0 | 0 |
| 961 | IGHA1 | 1.00000 | 1.00000 | 0.21104 | 0 | 0 |
| 962 | IGHA1 | 0.22755 | 0.54294 | 0.21104 | 0 | 0 |
| 963 | IGHA1 | 0.19371 | 0.65667 | 0.02818 | 0 | 1 |
| 964 | IGHA1 | 0.55139 | 0.74810 | 0.04551 | 0 | 1 |
| 965 | IGHA1 | 0.42627 | 0.29551 | 0.20027 | 0 | 1 |
| 966 | IGHA1 | 0.19371 | 0.29551 | 0.02818 | 0 | 1 |
| 967 | IGHG1 | 0.08710 | 0.09269 | 0.00016 | 0 | 1 |
| 968 | IGHG1 | 0.23086 | 0.04825 | 0.00030 | 0 | 1 |
| 969 | IGHG1 | 0.38669 | 0.04825 | 0.00004 | 0 | 1 |
| 970 | IGHG1 | 0.20587 | 0.00098 | 0.00025 | 0 | 1 |
| 971 | IGHG1 | 0.71144 | 0.00070 | 0.00035 | 0 | 1 |
| 972 | IGHG1 | 0.04243 | 0.00034 | 0.00000 | 0 | 1 |
| 973 | IGHG1 | 0.00044 | 0.01404 | 0.00000 | 0 | 1 |
| 974 | IGHG3 | 0.01070 | 0.09031 | 0.00058 | 0 | 1 |
| 975 | IGHG3 | 0.00370 | 0.00730 | 0.00000 | 0 | 1 |
| 976 | IGHG3 | 0.27339 | 0.04910 | 0.00349 | 0 | 1 |
| 977 | IGHG3 | 0.25971 | 0.00034 | 0.00136 | 0 | 1 |
| 978 | IGHG3 | 0.03144 | 0.00107 | 0.00000 | 0 | 1 |
| 979 | IGHG3 | 0.34948 | 0.54966 | 0.02537 | 0 | 0 |
| 980 | IGHM | 0.05016 | 0.29551 | 0.00730 | 0 | 1 |
| 981 | IGHM | 0.00556 | 0.00107 | 0.00000 | 0 | 1 |
| 982 | IGHM | 0.29797 | 0.02782 | 0.00040 | 0 | 1 |
| 983 | IGHM | 0.44266 | 0.80827 | 0.71834 | 0 | 1 |
| 984 | IGHM | 0.28848 | 0.00006 | 0.44111 | 0 | 1 |
| 985 | IGHJ6 | 1.00000 | 1.00000 | 0.00001 | 0 | 1 |
| 986 | IGHJ6 | 0.76698 | 0.00000 | 0.00000 | 0 | 1 |
| 987 | IGHJ6 | 0.32171 | 0.00000 | 0.00000 | 0 | 1 |
| 988 | IGHJ6 | 0.38669 | 0.03086 | 0.00000 | 0 | 1 |

TABLE 1-continued

| | | | | | | |
|---|---|---|---|---|---|---|
| 989 | IGHJ3; IGHJ4; IGHJ5; | 0.39187 | 0.29080 | 0.00017 | 0 | 1 |
| 990 | IGHD7-27; IGHJ1; IGHJ2; | 0.67043 | 1.00000 | 0.15671 | 0 | 0 |
| 991 | IGHD7-27 | 1.00000 | 0.34615 | 1.00000 | 0 | 0 |
| 992 | IGHD4-23 | 0.22755 | 0.54294 | 0.21104 | 0 | 0 |
| 993 | IGHD3-22 | 0.22755 | 0.54294 | 0.08726 | 0 | 0 |
| 994 | IGHD2-21 | 0.22755 | 0.54294 | 0.21104 | 0 | 0 |
| 995 | IGHD2-21 | 0.47887 | 1.00000 | 0.50663 | 0 | 0 |
| 996 | IGHD2-21 | 0.10727 | 0.54966 | 0.02537 | 0 | 0 |
| 997 | IGHD1-20; IGHD6-19; | 0.05016 | 0.65667 | 0.00730 | 0 | 1 |
| 998 | IGHD5-18 | 0.22755 | 0.54294 | 0.21104 | 0 | 0 |
| 999 | IGHD3-16 | 1.00000 | 0.34615 | 1.00000 | 0 | 0 |
| 1000 | IGHD2-15 | 0.22755 | 0.54294 | 0.08726 | 0 | 0 |
| 1001 | IGHD6-13 | 0.22755 | 0.54294 | 0.08726 | 0 | 0 |
| 1002 | IGHD3-10; IGHD3-9; | 0.34948 | 0.54966 | 0.15671 | 0 | 0 |
| 1003 | IGHD3-9 | 0.60686 | 0.54294 | 0.58408 | 0 | 0 |
| 1004 | IGHD2-8 | 0.47887 | 1.00000 | 0.50663 | 0 | 0 |
| 1005 | IGHD1-7 | 0.47887 | 1.00000 | 1.00000 | 0 | 0 |
| 1006 | IGHD6-6 | 0.47887 | 1.00000 | 1.00000 | 0 | 0 |
| 1007 | IGHD3-3 | 1.00000 | 1.00000 | 0.52529 | 0 | 0 |
| 1008 | IGHD2-2 | 1.00000 | 1.00000 | 0.52529 | 0 | 0 |
| 1009 | IGHD2-2 | 0.34948 | 0.54966 | 0.72719 | 0 | 0 |
| 1010 | IGHD2-2 | 0.34948 | 0.54966 | 0.02537 | 0 | 0 |
| 1011 | IGHD1-1 | 0.34948 | 0.54966 | 0.15671 | 0 | 0 |
| 1012 | IGHD1-1 | 0.60686 | 0.54294 | 0.08726 | 0 | 0 |
| 1013 | KIAA0125 | 0.60686 | 0.54294 | 0.08726 | 0 | 0 |
| 1014 | IGHV6-1 | 1.00000 | 1.00000 | 0.50663 | 0 | 0 |
| 1015 | IGHV6-1 | 1.00000 | 1.00000 | 0.50663 | 0 | 0 |
| 1016 | IGHV6-1 | 0.47887 | 1.00000 | 0.50663 | 0 | 0 |
| 1017 | IGHV1-2 | 0.22755 | 0.54294 | 0.21104 | 0 | 0 |
| 1018 | IGHV1-2 | 0.10727 | 0.54966 | 0.07959 | 0 | 0 |
| 1019 | IGHV1-2 | 0.22755 | 0.54294 | 0.08726 | 0 | 0 |
| 1020 | IGHV2-5 | 1.00000 | 1.00000 | 0.55662 | 0 | 0 |
| 1021 | IGHV3-7 | 0.12104 | 0.34615 | 0.18288 | 0 | 1 |
| 1022 | IGHV3-7 | 0.49735 | 1.00000 | 1.00000 | 0 | 0 |
| 1023 | IGHV1-8 | 0.47887 | 1.00000 | 0.67240 | 0 | 0 |
| 1024 | IGHV3-9 | 0.60686 | 0.54294 | 0.21104 | 0 | 0 |
| 1025 | IGHV3-11 | 0.44431 | 0.54294 | 0.63492 | 0 | 1 |
| 1026 | IGHV3-11 | 1.00000 | 0.54294 | 0.21104 | 0 | 0 |
| 1027 | IGHV3-11 | 1.00000 | 1.00000 | 0.29694 | 0 | 0 |
| 1028 | IGHV3-11 | 1.00000 | 1.00000 | 0.29694 | 0 | 0 |
| 1029 | IGHV3-15 | 0.22755 | 0.60763 | 0.58408 | 0 | 1 |
| 1030 | IGHV1-18 | 0.47887 | 1.00000 | 1.00000 | 0 | 0 |
| 1031 | IGHV1-18 | 0.47887 | 1.00000 | 1.00000 | 0 | 0 |
| 1032 | IGHV3-21 | 1.00000 | 0.54294 | 0.58408 | 0 | 0 |
| 1033 | IGHV3-21 | 0.62100 | 1.00000 | 0.50663 | 0 | 0 |
| 1034 | IGHV3-23 | 0.61250 | 1.00000 | 0.42238 | 0 | 1 |
| 1035 | IGHV3-23 | 1.00000 | 0.41714 | 0.02173 | 0 | 1 |
| 1036 | IGHV1-24 | 1.00000 | 1.00000 | 0.50663 | 0 | 0 |
| 1037 | IGHV2-26 | 0.47887 | 0.27446 | 0.29694 | 0 | 1 |
| 1038 | IGHV2-26 | 1.00000 | 0.11763 | 1.00000 | 0 | 1 |
| 1039 | IGHV3-30 | 0.47887 | 0.27446 | 0.50663 | 0 | 1 |
| 1040 | IGHV4-31 | 0.22755 | 0.52294 | 0.21104 | 0 | 0 |
| 1041 | IGHV4-31 | 0.34948 | 0.54966 | 0.07959 | 0 | 0 |
| 1042 | IGHV4-31 | 0.47887 | 1.00000 | 0.50663 | 0 | 0 |
| 1043 | IGHV3-33 | 0.67043 | 0.54966 | 0.15671 | 0 | 0 |
| 1044 | IGHV3-33 | 0.10420 | 0.16101 | 0.00953 | 0 | 1 |
| 1045 | IGHV3-33 | 0.22755 | 0.54294 | 0.08726 | 0 | 0 |
| 1046 | IGHV4-34 | 0.81354 | 1.00000 | 0.00804 | 0 | 1 |
| 1047 | IGHV4-34 | 0.80514 | 0.15803 | 0.07447 | 0 | 1 |
| 1048 | IGHV4-39 | 0.62100 | 0.27446 | 0.50663 | 0 | 1 |
| 1049 | IGHV4-39 | 1.00000 | 1.00000 | 0.15671 | 0 | 0 |
| 1050 | IGHV1-46 | 0.47887 | 0.27446 | 0.29694 | 0 | 1 |
| 1051 | IGHV3-48 | 0.59201 | 0.41714 | 0.00949 | 0 | 1 |
| 1052 | IGHV3-48 | 0.49735 | 1.00000 | 1.00000 | 0 | 0 |
| 1053 | IGHV5-51 | 1.00000 | 0.34615 | 1.00000 | 0 | 0 |
| 1054 | IGHV5-51 | 0.60686 | 0.54294 | 0.21104 | 0 | 0 |
| 1055 | IGHV3-53 | 1.00000 | 0.34615 | 1.00000 | 0 | 0 |
| 1056 | IGHV3-53 | 0.67043 | 0.54966 | 0.15671 | 0 | 0 |
| 1057 | IGHV4-59 | 1.00000 | 0.54966 | 0.07959 | 0 | 1 |
| 1058 | IGHV4-59 | 1.00000 | 0.54294 | 0.21104 | 0 | 0 |
| 1059 | IGHV4-61 | 0.47887 | 1.00000 | 0.50663 | 0 | 0 |
| 1060 | IGHV3-64 | 0.22755 | 0.54294 | 0.08726 | 0 | 0 |
| 1061 | IGHV3-64 | 0.22755 | 0.54294 | 0.08726 | 0 | 0 |
| 1062 | IGHV1-69 | 0.00346 | 0.04910 | 0.00442 | 0 | 1 |
| 1063 | IGHV1-69 | 0.00279 | 0.00075 | 0.00004 | 0 | 1 |
| 1064 | IGHV2-70 | 0.04838 | 0.15803 | 0.00030 | 0 | 1 |

TABLE 1-continued

| | | | | | | |
|---|---|---|---|---|---|---|
| 1065 | IGHV2-70 | 0.67043 | 0.54966 | 0.02537 | 0 | 0 |
| 1066 | IGHV2-70 | 0.03781 | 0.00002 | 0.00001 | 0 | 1 |
| 1067 | IGHV2-70 | 0.60350 | 0.00034 | 0.00206 | 0 | 1 |
| 1068 | IGHV2-70 | 0.22755 | 0.54294 | 0.21104 | 0 | 0 |
| 1069 | IGHV3-72 | 0.47887 | 1.00000 | 1.00000 | 0 | 0 |
| 1070 | IGHV3-74 | 0.47887 | 1.00000 | 1.00000 | 0 | 0 |
| 1071 | IGHV3-74 | 0.25970 | 0.16101 | 0.02559 | 0 | 1 |
| 1072 | IGHV3-74 | 0.05016 | 0.29551 | 0.00730 | 0 | 1 |
| 1073 | IGHV3-74 | 0.22775 | 0.54294 | 0.08726 | 0 | 0 |
| 1074 | IGHV7-81 | 0.34948 | 0.54966 | 0.02537 | 0 | 0 |
| 1075 | IGHV7-81 | 1.00000 | 1.00000 | 0.29694 | 0 | 0 |
| 1076 | IGHV7-81 | 0.00021 | 0.00098 | 0.00000 | 0 | 1 |
| 1077 | B2M | 0.10727 | 0.54966 | 0.02537 | 0 | 0 |
| 1078 | B2M | 0.10727 | 0.54966 | 0.02537 | 0 | 0 |
| 1079 | SLC30A4 | 1.00000 | 1.00000 | 0.29694 | 0 | 0 |
| 1080 | MYO1E | 1.00000 | 0.54966 | 0.02537 | 0 | 0 |
| 1081 | PARP16 | 1.00000 | 0.34615 | 1.00000 | 0 | 0 |
| 1082 | TBC1D2B | 1.00000 | 0.34615 | 1.00000 | 0 | 0 |
| 1083 | CPEB1 | 0.22755 | 0.54294 | 0.08726 | 0 | 0 |
| 1084 | AKAP13 | 0.10727 | 0.54966 | 0.02537 | 0 | 0 |
| 1085 | AKAP13 | 0.60686 | 0.54294 | 0.08726 | 0 | 0 |
| 1086 | AKAP13 | 0.05016 | 0.29551 | 0.00730 | 0 | 1 |
| 1087 | AXIN1 | 1.00000 | 1.00000 | 0.29694 | 0 | 0 |
| 1088 | CREBBP | 1.00000 | 1.00000 | 0.29694 | 0 | 0 |
| 1089 | CIITA | 0.02233 | 0.01471 | 0.00000 | 1 | 1 |
| 1090 | CIITA | 0.08249 | 0.00372 | 0.00000 | 1 | 1 |
| 1091 | CIITA | 0.31342 | 0.01471 | 0.00000 | 1 | 1 |
| 1092 | CIITA | 0.05016 | 0.29551 | 0.00730 | 1 | 1 |
| 1093 | SOCS1 | 0.00186 | 0.00372 | 0.00000 | 1 | 1 |
| 1094 | SOCS1 | 0.00179 | 0.00107 | 0.00000 | 1 | 1 |
| 1095 | DNAH3 | 1.00000 | 1.00000 | 0.29694 | 0 | 0 |
| 1096 | CTD-3203P2.2 | 1.00000 | 0.54294 | 0.08726 | 0 | 0 |
| 1097 | CTD-3203P2.2 | 0.31126 | 0.09031 | 0.00058 | 0 | 1 |
| 1098 | IL4R | 0.22755 | 0.54294 | 0.08726 | 0 | 0 |
| 1099 | IL21R | 0.22755 | 0.54294 | 0.08726 | 0 | 0 |
| 1100 | 61E3.4 | 0.22755 | 0.54294 | 0.08776 | 0 | 0 |
| 1101 | ZNF267 | 1.00000 | 1.00000 | 0.29694 | 0 | 0 |
| 1102 | C16orf87 | 1.00000 | 1.00000 | 0.29694 | 0 | 0 |
| 1103 | CYLD | 1.00000 | 1.00000 | 0.29694 | 0 | 0 |
| 1104 | CDH11 | 0.60686 | 0.54294 | 0.08726 | 0 | 0 |
| 1105 | WWOX | 0.49735 | 1.00000 | 1.00000 | 0 | 0 |
| 1106 | WWOX | 1.00000 | 1.00000 | 0.29694 | 0 | 0 |
| 1107 | WWOX | 1.00000 | 1.00000 | 0.29694 | 0 | 0 |
| 1108 | WWOX | 0.49735 | 1.00000 | 1.00000 | 0 | 0 |
| 1109 | MAF | 1.00000 | 1.00000 | 0.29694 | 0 | 0 |
| 1110 | PLCG2 | 0.22755 | 0.54294 | 0.08726 | 0 | 0 |
| 1111 | IRF8 | 0.42627 | 0.29551 | 0.00730 | 1 | 1 |
| 1112 | IRF8 | 0.03144 | 0.00107 | 0.00000 | 1 | 1 |
| 1113 | IRF8 | 1.00000 | 1.00000 | 0.50663 | 1 | 0 |
| 1114 | IRF8 | 0.22755 | 0.54294 | 0.08726 | 1 | 0 |
| 1115 | ZNF469 | 1.00000 | 1.00000 | 0.29694 | 0 | 0 |
| 1116 | P2RX5; P2RX5-TAX1BP3P2RX5; | 0.60686 | 0.54294 | 0.08726 | 0 | 0 |
| 1117 | SMCR9 | 0.22755 | 0.54294 | 0.08726 | 0 | 0 |
| 1118 | MAP2K3 | 0.62100 | 1.00000 | 0.29694 | 0 | 0 |
| 1119 | EVI2A | 0.60686 | 0.54294 | 0.08726 | 0 | 0 |
| 1120 | IKZF3 | 0.60686 | 0.54294 | 0.08726 | 0 | 0 |
| 1121 | PLEKHM1 | 0.22755 | 0.54294 | 0.08726 | 0 | 0 |
| 1122 | BZRAP1 | 0.42627 | 0.29551 | 0.02818 | 0 | 1 |
| 1123 | BZRAP1 | 0.00005 | 0.00024 | 0.00000 | 0 | 1 |
| 1124 | VMP1 | 0.60686 | 0.54294 | 0.08726 | 1 | 0 |
| 1125 | VMP1 | 0.22755 | 0.54294 | 0.08726 | 1 | 0 |
| 1126 | CD79B | 0.22755 | 0.54294 | 0.08726 | 0 | 0 |
| 1127 | CD79B | 0.34948 | 0.54966 | 0.02537 | 0 | 0 |
| 1128 | GNA13 | 1.00000 | 1.00000 | 0.29694 | 0 | 0 |
| 1129 | PITPNC1 | 0.22755 | 0.54294 | 0.08726 | 0 | 0 |
| 1130 | AC007461.1 | 1.00000 | 1.00000 | 0.29694 | 0 | 0 |
| 1131 | SOX9 | 1.00000 | 0.34615 | 1.00000 | 0 | 0 |
| 1132 | SRSF2 | 0.49735 | 1.00000 | 1.00000 | 0 | 0 |
| 1133 | 9-Sep-19 | 0.10727 | 0.54966 | 0.02537 | 0 | 0 |
| 1134 | 9-Sep-19 | 0.10727 | 0.54966 | 0.02537 | 0 | 0 |
| 1135 | CYTH1 | 0.49735 | 1.00000 | 1.00000 | 0 | 0 |
| 1136 | B3GNTL1 | 0.22755 | 0.54294 | 0.08726 | 0 | 0 |
| 1137 | B3GNTL1 | 1.00000 | 1.00000 | 0.29694 | 0 | 0 |
| 1138 | SMCHD1 | 0.22755 | 0.54294 | 0.08726 | 0 | 0 |
| 1139 | DLGAP1 | 1.00000 | 1.00000 | 0.29694 | 0 | 0 |
| 1140 | ANKRD62 | 0.24603 | 1.00000 | 1.00000 | 0 | 0 |
| 1141 | DSC3 | 0.22755 | 0.54294 | 0.08726 | 0 | 0 |

TABLE 1-continued

| | | | | | | |
|---|---|---|---|---|---|---|
| 1142 | DSC3 | 0.22755 | 0.54294 | 0.08726 | 0 | 0 |
| 1143 | AC012123.1; KLHL14; | 0.49735 | 1.00000 | 1.00000 | 0 | 0 |
| 1144 | CELF4 | 0.22755 | 0.54294 | 0.08726 | 0 | 0 |
| 1145 | PIK3C3 | 1.00000 | 1.00000 | 0.29694 | 0 | 0 |
| 1146 | PIK3C3 | 1.00000 | 0.34615 | 1.00000 | 0 | 0 |
| 1147 | SETBP1 | 1.00000 | 0.34615 | 1.00000 | 0 | 0 |
| 1148 | C18orf54 | 0.22755 | 0.54294 | 0.08726 | 0 | 0 |
| 1149 | RAB27B | 1.00000 | 1.00000 | 0.29694 | 0 | 0 |
| 1150 | TCF4 | 0.22755 | 0.54294 | 0.08726 | 0 | 0 |
| 1151 | WDR7 | 0.49735 | 1.00000 | 1.00000 | 0 | 0 |
| 1152 | BCL2 | 0.22755 | 0.54294 | 0.08726 | 1 | 0 |
| 1153 | BCL2 | 1.00000 | 0.16101 | 0.00208 | 1 | 1 |
| 1154 | BCL2 | 1.00000 | 0.02564 | 0.00009 | 1 | 1 |
| 1155 | BCL2 | 0.42627 | 0.29551 | 0.00730 | 1 | 1 |
| 1156 | BCL2 | 0.22755 | 0.54294 | 0.08726 | 1 | 0 |
| 1157 | BCL2 | 0.67043 | 0.54966 | 0.02537 | 1 | 0 |
| 1158 | BCL2 | 0.22755 | 0.54294 | 0.08726 | 1 | 0 |
| 1159 | BCL2 | 1.00000 | 1.00000 | 0.29694 | 1 | 0 |
| 1160 | BCL2 | 0.67043 | 0.54966 | 0.02537 | 1 | 0 |
| 1161 | BCL2 | 0.67043 | 0.54966 | 0.02537 | 1 | 0 |
| 1162 | BCL2 | 0.36833 | 1.00000 | 0.29694 | 1 | 1 |
| 1163 | BCL2 | 1.00000 | 0.29551 | 0.02818 | 1 | 1 |
| 1164 | BCL2 | 0.00034 | 0.00730 | 0.00001 | 1 | 1 |
| 1165 | BCL2 | 0.00000 | 0.00107 | 0.00000 | 1 | 1 |
| 1166 | BCL2 | 0.00000 | 0.00098 | 0.00000 | 1 | 1 |
| 1167 | BCL2 | 0.00019 | 0.00372 | 0.00001 | 1 | 1 |
| 1168 | BCL2 | 0.00001 | 0.00107 | 0.00000 | 1 | 1 |
| 1169 | SERPNB8 | 1.00000 | 1.00000 | 0.29694 | 0 | 0 |
| 1170 | CDH7 | 0.22755 | 0.54294 | 0.08726 | 0 | 0 |
| 1171 | CDH7 | 0.47887 | 1.00000 | 0.29694 | 0 | 0 |
| 1172 | CDH19 | 0.22755 | 0.54294 | 0.08726 | 0 | 0 |
| 1173 | CDH19 | 0.22755 | 0.54294 | 0.08726 | 0 | 0 |
| 1174 | TMX3 | 0.49735 | 1.00000 | 1.00000 | 0 | 0 |
| 1175 | TMX3 | 1.00000 | 1.00000 | 0.29694 | 0 | 0 |
| 1176 | NETO1 | 1.00000 | 1.00000 | 0.29694 | 0 | 0 |
| 1177 | ZNF516 | 1.00000 | 1.00000 | 0.29694 | 0 | 0 |
| 1178 | SALL3 | 0.60686 | 0.54294 | 0.08726 | 0 | 0 |
| 1179 | SALL3 | 1.00000 | 1.00000 | 0.29694 | 0 | 0 |
| 1180 | SALL3 | 1.00000 | 1.00000 | 0.29694 | 0 | 0 |
| 1181 | TCF3 | 1.00000 | 0.11763 | 1.00000 | 0 | 1 |
| 1182 | GADD45B | 0.22755 | 0.54294 | 0.08726 | 1 | 0 |
| 1183 | DNMT1 | 0.05016 | 0.29551 | 0.00730 | 0 | 1 |
| 1184 | DNMT1 | 0.10727 | 0.54966 | 0.02537 | 0 | 0 |
| 1185 | S1PR2 | 1.00000 | 1.00000 | 0.29694 | 1 | 0 |
| 1186 | S1PR2 | 0.11795 | 0.04825 | 0.00004 | 1 | 1 |
| 1187 | S1PR2 | 0.01013 | 0.00197 | 0.00000 | 1 | 1 |
| 1188 | CYP4F11 | 0.47887 | 1.00000 | 0.29694 | 0 | 0 |
| 1189 | KLF2 | 0.60686 | 0.54294 | 0.08726 | 1 | 0 |
| 1190 | ZNF626 | 0.47887 | 1.00000 | 0.50663 | 0 | 0 |
| 1191 | ZNF85 | 1.00000 | 1.00000 | 0.29694 | 0 | 0 |
| 1192 | ZNF85 | 0.22755 | 0.54294 | 0.08726 | 0 | 0 |
| 1193 | ZNF675 | 1.00000 | 1.00000 | 0.29694 | 0 | 0 |
| 1194 | UQCRFS1 | 0.22755 | 0.54294 | 0.08726 | 0 | 0 |
| 1195 | PLAUR | 0.22755 | 0.54294 | 0.08726 | 0 | 0 |
| 1196 | IL4I1 | 0.22755 | 0.54294 | 0.08726 | 0 | 0 |
| 1197 | ZNF321P; ZNF816; ZNF816-ZNF321PZNF321PZNF816-ZNF321P; | 1.00000 | 1.00000 | 0.29694 | 0 | 0 |
| 1198 | MACROD2 | 1.00000 | 0.34615 | 1.00000 | 0 | 0 |
| 1199 | NAPB | 1.00000 | 0.11763 | 1.00000 | 0 | 1 |
| 1200 | CST5 | 0.49735 | 1.00000 | 1.00000 | 0 | 0 |
| 1201 | NCOA3 | 0.19371 | 0.29551 | 0.00730 | 1 | 1 |
| 1202 | PTPN1 | 0.60686 | 0.54294 | 0.08726 | 0 | 0 |
| 1203 | KCNG1 | 0.22755 | 0.54294 | 0.08726 | 0 | 0 |
| 1204 | SLC17A9 | 0.49735 | 1.00000 | 1.00000 | 0 | 0 |
| 1205 | NCAM2 | 0.22755 | 0.54294 | 0.08726 | 0 | 0 |
| 1206 | NCAM2 | 0.22755 | 0.54294 | 0.08726 | 0 | 0 |
| 1207 | MRPL39 | 0.22755 | 0.54294 | 0.08726 | 0 | 0 |
| 1208 | MRPL39 | 1.00000 | 1.00000 | 0.29694 | 0 | 0 |
| 1209 | SMIM11 | 0.49735 | 1.00000 | 1.00000 | 0 | 0 |
| 1210 | DYRK1A | 0.49735 | 1.00000 | 1.00000 | 0 | 0 |
| 1211 | PRDM15 | 0.22755 | 0.54294 | 0.08726 | 0 | 0 |
| 1212 | CRYAA | 0.49735 | 1.00000 | 1.00000 | 0 | 0 |
| 1213 | AGPAT3 | 0.22755 | 0.54294 | 0.08726 | 0 | 0 |
| 1214 | KRTAP10-10 | 1.00000 | 1.00000 | 0.29694 | 0 | 0 |
| 1215 | DGCR2 | 0.49735 | 1.00000 | 1.00000 | 0 | 0 |
| 1216 | RTN4R | 0.60686 | 0.54294 | 0.08726 | 0 | 0 |
| 1217 | FAM230A | 0.22755 | 0.54294 | 0.08726 | 0 | 0 |
| 1218 | SDF2L1 | 0.47887 | 1.00000 | 0.29694 | 0 | 0 |

TABLE 1-continued

| | | | | | |
|---|---|---|---|---|---|
| 1219 | IGLV4-69 | 1.00000 | 0.54294 | 0.08726 | 0 | 0 |
| 1220 | IGLV4-69 | 0.72064 | 0.54966 | 0.15671 | 0 | 1 |
| 1221 | IGLV4-69 | 1.00000 | 1.00000 | 1.00000 | 0 | 0 |
| 1222 | IGLV4-69 | 0.44431 | 1.00000 | 1.00000 | 0 | 1 |
| 1223 | IGLV8-61 | 1.00000 | 1.00000 | 1.00000 | 0 | 0 |
| 1224 | IGLV8-61 | 1.00000 | 1.00000 | 1.00000 | 0 | 0 |
| 1225 | IGLV4-60 | 0.36833 | 1.00000 | 1.00000 | 0 | 1 |
| 1226 | IGLV4-60 | 1.00000 | 1.00000 | 0.55662 | 0 | 0 |
| 1227 | IGLV6-57 | 1.00000 | 1.00000 | 0.07959 | 0 | 1 |
| 1228 | IGLV10-54 | 1.00000 | 1.00000 | 0.50663 | 0 | 0 |
| 1229 | IGLV1-51 | 0.47887 | 1.00000 | 0.29694 | 0 | 0 |
| 1230 | IGLV1-51 | 1.00000 | 0.11840 | 1.00000 | 0 | 1 |
| 1231 | IGLV5-48 | 0.34948 | 1.00000 | 0.07959 | 0 | 0 |
| 1232 | IGLV1-47 | 0.31126 | 1.00000 | 0.00949 | 0 | 1 |
| 1233 | IGVL7-46 | 1.00000 | 1.00000 | 0.50663 | 0 | 0 |
| 1234 | IGLV5-46 | 0.31126 | 0.41714 | 0.00949 | 0 | 1 |
| 1235 | IGLV5-45 | 1.00000 | 0.29551 | 0.02818 | 0 | 1 |
| 1236 | IGLV5-45 | 0.22755 | 0.54294 | 0.21104 | 0 | 0 |
| 1237 | IGLV1-44 | 1.00000 | 0.65667 | 0.48849 | 0 | 1 |
| 1238 | IGLV7-43 | 0.42627 | 0.29551 | 0.02818 | 0 | 1 |
| 1239 | IGLV1-40 | 0.60686 | 1.00000 | 0.21104 | 0 | 0 |
| 1240 | IGLV1-40 | 0.67043 | 1.00000 | 0.07959 | 0 | 1 |
| 1241 | IGLV1-40 | 0.72064 | 0.23165 | 0.07959 | 0 | 1 |
| 1242 | IGLV3-25 | 0.47887 | 1.00000 | 0.50663 | 0 | 0 |
| 1243 | IGLV3-25 | 0.79702 | 0.15881 | 0.11274 | 0 | 1 |
| 1244 | IGLV2-23 | 1.00000 | 1.00000 | 0.29694 | 0 | 0 |
| 1245 | IGLV2-23 | 0.49735 | 1.00000 | 1.00000 | 0 | 0 |
| 1246 | IGLV2-23 | 0.35266 | 0.09269 | 0.12716 | 0 | 1 |
| 1247 | IGLV2-23 | 0.10727 | 0.54966 | 0.07959 | 0 | 0 |
| 1248 | IGLV3-21 | 0.19371 | 0.65667 | 1.00000 | 0 | 1 |
| 1249 | IGLV3-19 | 0.47996 | 0.16101 | 0.00208 | 0 | 1 |
| 1250 | IGLV3-16 | 0.70990 | 0.29551 | 0.00730 | 0 | 1 |
| 1251 | IGLV2-14 | 1.00000 | 0.54966 | 0.36534 | 0 | 1 |
| 1252 | IGLV2-14 | 1.00000 | 0.66188 | 0.16714 | 0 | 1 |
| 1253 | IGLV3-12 | 1.00000 | 1.00000 | 0.29694 | 0 | 0 |
| 1254 | IGLV2-11 | 0.60686 | 0.54294 | 0.08726 | 0 | 0 |
| 1255 | IGLV3-10 | 0.25970 | 0.16101 | 0.05242 | 0 | 1 |
| 1256 | IGLV3-9 | 1.00000 | 1.00000 | 1.00000 | 0 | 0 |
| 1257 | IGLV3-9 | 1.00000 | 1.00000 | 1.00000 | 0 | 0 |
| 1258 | IGLV2-8 | 0.24603 | 1.00000 | 1.00000 | 0 | 0 |
| 1259 | IGLV4-3 | 0.31126 | 0.09031 | 0.00311 | 0 | 1 |
| 1260 | IGLV4-3 | 0.47887 | 1.00000 | 0.50663 | 0 | 0 |
| 1261 | IGLV4-3 | 0.17231 | 0.01404 | 0.00108 | 0 | 1 |
| 1262 | IGLV4-3 | 0.01424 | 0.00107 | 0.00002 | 0 | 1 |
| 1263 | IGLV4-3 | 0.22755 | 0.54294 | 0.08726 | 0 | 0 |
| 1264 | IGLV4-3 | 0.70990 | 1.00000 | 0.00730 | 0 | 1 |
| 1265 | IGLV4-3 | 1.00000 | 1.00000 | 0.29694 | 0 | 0 |
| 1266 | IGLV4-3 | 0.22755 | 0.54294 | 0.08726 | 0 | 0 |
| 1267 | IGLV4-3 | 0.22755 | 0.54294 | 0.08726 | 0 | 0 |
| 1268 | IGLV4-3 | 0.15270 | 0.09031 | 0.00058 | 0 | 1 |
| 1269 | IGLV4-3 | 0.25970 | 0.16101 | 0.00208 | 0 | 1 |
| 1270 | IGLV3-1 | 0.10727 | 0.54966 | 0.02537 | 0 | 0 |
| 1271 | IGLV3-1 | 0.05016 | 0.29551 | 0.00730 | 0 | 1 |
| 1272 | IGLV3-1 | 0.00342 | 0.01404 | 0.00003 | 0 | 1 |
| 1273 | IGLV3-1 | 0.23940 | 0.00000 | 0.00000 | 0 | 1 |
| 1274 | IGLV3-1 | 0.04838 | 0.04825 | 0.00004 | 0 | 1 |
| 1275 | IGLV3-1 | 0.22755 | 0.54294 | 0.08726 | 0 | 0 |
| 1276 | IGLL5 | 0.07371 | 0.00001 | 0.00000 | 0 | 1 |
| 1277 | IGLL5 | 0.00152 | 0.00070 | 0.00000 | 0 | 1 |
| 1278 | IGLL5 | 0.11795 | 0.04825 | 0.00004 | 0 | 1 |
| 1279 | IGLL5 | 0.12719 | 0.00007 | 0.00000 | 0 | 1 |
| 1280 | IGLL5 | 0.12719 | 0.00017 | 0.00000 | 0 | 1 |
| 1281 | IGLL5 | 0.00075 | 0.00000 | 0.00000 | 0 | 1 |
| 1282 | IGLJ1 | 0.05410 | 0.01471 | 0.00001 | 0 | 1 |
| 1283 | IGLJ1 | 0.03985 | 0.20979 | 0.00000 | 0 | 1 |
| 1284 | IGLJ1; IGLL5; | 0.06843 | 0.13046 | 0.00035 | 0 | 1 |
| 1285 | IGLJ1; IGLL5; | 0.02356 | 0.12484 | 0.00001 | 0 | 1 |
| 1286 | IGLC1; IGLL5; | 0.35266 | 1.00000 | 0.00099 | 0 | 1 |
| 1287 | IGLJ2 | 0.02326 | 0.66188 | 0.02559 | 0 | 1 |
| 1288 | IGLC2 | 0.61516 | 0.09212 | 0.02792 | 0 | 1 |
| 1289 | IGLC2 | 0.22755 | 0.54294 | 0.08726 | 0 | 0 |
| 1290 | IGLC2 | 1.00000 | 1.00000 | 1.00000 | 0 | 0 |
| 1291 | IGLJ3 | 0.59201 | 0.73481 | 1.00000 | 0 | 1 |
| 1292 | IGLC3 | 1.00000 | 1.00000 | 1.00000 | 0 | 0 |
| 1293 | IGLC3 | 1.00000 | 0.54294 | 0.21104 | 0 | 0 |
| 1294 | IGLJ6 | 0.47887 | 1.00000 | 1.00000 | 0 | 0 |
| 1295 | IGLJ6 | 1.00000 | 1.00000 | 1.00000 | 0 | 0 |
| 1296 | IGLJ7 | 0.34948 | 0.54966 | 0.07959 | 0 | 0 |
| 1297 | IGLC7 | 0.67043 | 0.54966 | 0.07959 | 0 | 0 |
| 1298 | IGLC7 | 0.10727 | 0.54966 | 0.02537 | 0 | 0 |

TABLE 1-continued

| | | | | | | |
|---|---|---|---|---|---|---|
| 1299 | IGLC7 | 0.60686 | 0.54294 | 0.08726 | 0 | 0 |
| 1300 | IGLC7 | 0.19371 | 0.29551 | 0.02818 | 0 | 1 |
| 1301 | IGLC7 | 0.60686 | 0.54294 | 0.08726 | 0 | 0 |
| 1302 | IGLC7 | 0.01393 | 0.01404 | 0.00003 | 0 | 1 |
| 1303 | IGLC7 | 0.22755 | 0.54294 | 0.08726 | 0 | 0 |
| 1304 | BCR | 0.62100 | 1.00000 | 0.29694 | 0 | 0 |
| 1305 | BCR | 0.60686 | 0.54294 | 0.08726 | 0 | 0 |
| 1306 | CRYBA4 | 0.22755 | 1.00000 | 0.08726 | 0 | 0 |
| 1307 | XBP1 | 0.01070 | 0.09031 | 0.00058 | 0 | 1 |
| 1308 | XBP1 | 0.70990 | 0.29551 | 0.00730 | 0 | 1 |
| 1309 | DRG1 | 0.22755 | 0.54294 | 0.08726 | 0 | 0 |
| 1310 | SYN3 | 0.47887 | 1.00000 | 0.29694 | 0 | 0 |
| 1311 | TAB1 | 0.22755 | 0.54294 | 0.08726 | 0 | 0 |
| 1312 | TAB1 | 0.22755 | 0.54294 | 0.08726 | 0 | 0 |
| 1313 | PACSIN2 | 0.22755 | 0.54294 | 0.08726 | 0 | 0 |
| 1314 | TBC1D22A | 0.22755 | 0.54294 | 0.08726 | 0 | 0 |
| 1315 | LL22NC03-75H12.2 | 0.49735 | 1.00000 | 1.00000 | 0 | 0 |
| 1316 | CRELD2 | 0.47887 | 1.00000 | 0.29694 | 0 | 0 |
| 1317 | GTPBP6 | 0.49735 | 1.00000 | 1.00000 | 0 | 0 |
| 1318 | SLC25A6 | 1.00000 | 1.00000 | 0.29694 | 0 | 0 |
| 1319 | P2RY8 | 0.22755 | 0.54294 | 0.08726 | 1 | 0 |
| 1320 | TMSB4X | 0.00091 | 0.00098 | 0.00000 | 1 | 1 |
| 1321 | TMSB4X | 0.00045 | 0.00107 | 0.00000 | 1 | 1 |
| 1322 | ATXN3L | 1.00000 | 1.00000 | 0.08726 | 0 | 0 |
| 1323 | DCAF8L2 | 0.05016 | 0.29551 | 0.00730 | 0 | 1 |
| 1324 | DMD | 0.49735 | 1.00000 | 1.00000 | 1 | 0 |
| 1325 | DMD | 1.00000 | 0.34615 | 1.00000 | 1 | 0 |
| 1326 | DMD | 0.60686 | 0.54294 | 0.08726 | 1 | 0 |
| 1327 | DMD | 0.67043 | 0.54966 | 0.02537 | 1 | 0 |
| 1328 | DMD | 0.11004 | 0.01471 | 0.00000 | 1 | 1 |
| 1329 | CASK | 1.00000 | 1.00000 | 0.29694 | 0 | 0 |
| 1330 | MAOA | 0.25970 | 0.16101 | 0.00208 | 0 | 1 |
| 1331 | PIM2 | 0.34948 | 0.54966 | 0.02537 | 1 | 0 |
| 1332 | PIM2 | 0.60686 | 0.54294 | 0.08726 | 1 | 0 |
| 1333 | ZC4H2 | 0.19371 | 0.29551 | 0.00730 | 0 | 1 |
| 1334 | AR | 0.47887 | 1.00000 | 0.29694 | 0 | 0 |
| 1335 | HMGN5 | 0.49735 | 1.00000 | 1.00000 | 0 | 0 |
| 1336 | SH3BGRL | 1.00000 | 1.00000 | 0.29694 | 0 | 0 |
| 1337 | CPXCR1 | 0.22755 | 0.54294 | 0.08726 | 0 | 0 |
| 1338 | CPXCR1 | 0.49735 | 1.00000 | 1.00000 | 0 | 0 |
| 1339 | CPXCR1 | 0.49735 | 1.00000 | 1.00000 | 0 | 0 |
| 1340 | CPXCR1 | 0.22755 | 0.54294 | 0.08726 | 0 | 0 |
| 1341 | NAP1L3 | 0.49735 | 1.00000 | 1.00000 | 0 | 0 |
| 1342 | FAM133A | 1.00000 | 1.00000 | 0.29694 | 0 | 0 |
| 1343 | FAM133A | 1.00000 | 1.00000 | 0.29694 | 0 | 0 |
| 1344 | IL1RAPL2 | 1.00000 | 1.00000 | 0.29694 | 0 | 0 |
| 1345 | IL1RAPL2 | 1.00000 | 1.00000 | 0.29694 | 0 | 0 |
| 1346 | RIPPLY1 | 0.49735 | 1.00000 | 1.00000 | 0 | 0 |
| 1347 | HTR2C | 0.47887 | 1.00000 | 0.50663 | 0 | 0 |
| 1348 | CXorf61 | 1.00000 | 1.00000 | 0.29694 | 0 | 0 |
| 1349 | DCAF12L2 | 0.22755 | 0.54294 | 0.08726 | 0 | 0 |
| 1350 | DCAF12L2 | 0.22755 | 0.54294 | 0.08726 | 0 | 0 |
| 1351 | SMARCA1 | 1.00000 | 1.00000 | 0.29694 | 0 | 0 |
| 1352 | RBMX2 | 1.00000 | 1.00000 | 0.29694 | 0 | 0 |
| 1353 | CT45A3; CT45A4; | 0.60686 | 0.54294 | 0.08726 | 0 | 0 |
| 1354 | SPANXD; SPANXE; | 0.22755 | 0.54294 | 0.08726 | 0 | 0 |
| 1355 | SPANXN1 | 0.49735 | 1.00000 | 1.00000 | 0 | 0 |
| 1356 | TMEM257 | 0.49735 | 0.34615 | 1.00000 | 0 | 0 |

TABLE 2

| # | Chromosome | Region Start | Region End | ABC-subtype | GCB-subtype | ClosestGene | p_ABC_vs_GCB | Previously-Identified |
|---|---|---|---|---|---|---|---|---|
| 1 | chr1 | 756000 | 757000 | 0.040 | 0.000 | AL669831.1 | 1.00000 | 0 |
| 2 | chr1 | 1963000 | 1964000 | 0.000 | 0.000 | GABRD | 1.00000 | 0 |
| 3 | chr1 | 2052000 | 2053000 | 0.000 | 0.040 | PRKCZ | 1.00000 | 0 |
| 4 | chr1 | 3789000 | 3790000 | 0.000 | 0.000 | DFFB | 1.00000 | 0 |
| 5 | chr1 | 6613000 | 6614000 | 0.000 | 0.000 | NOL9 | 1.00000 | 1 |
| 6 | chr1 | 6614000 | 6615000 | 0.120 | 0.040 | NOL9 | 0.60921 | 1 |
| 7 | chr1 | 6661000 | 6662000 | 0.000 | 0.000 | KLHL21 | 1.00000 | 0 |
| 8 | chr1 | 6662000 | 6663000 | 0.120 | 0.000 | KLHL21 | 0.23469 | 0 |
| 9 | chr1 | 9129000 | 9130000 | 0.000 | 0.080 | SLC2A5 | 0.48980 | 0 |
| 10 | chr1 | 10894000 | 10895000 | 0.040 | 0.000 | C1orf127 | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 11 | chr1 | 17019000 | 17020000 | 0.000 | 0.000 | AL137798.1 | 1.00000 | 0 |
| 12 | chr1 | 17231000 | 17232000 | 0.040 | 0.000 | CROCC | 1.00000 | 0 |
| 13 | chr1 | 19935000 | 19936000 | 0.080 | 0.000 | MINOS1-NBL1 | 0.48980 | 0 |
| 14 | chr1 | 21091000 | 21092000 | 0.040 | 0.000 | HP1BP3 | 1.00000 | 0 |
| 15 | chr1 | 23885000 | 23886000 | 0.080 | 0.040 | ID3 | 1.00000 | 1 |
| 16 | chr1 | 28408000 | 28409000 | 0.040 | 0.040 | EYA3 | 1.00000 | 0 |
| 17 | chr1 | 32373000 | 32374000 | 0.000 | 0.040 | PTP4A2 | 1.00000 | 0 |
| 18 | chr1 | 36722000 | 36723000 | 0.040 | 0.000 | THRAP3 | 1.00000 | 0 |
| 19 | chr1 | 46576000 | 46577000 | 0.040 | 0.000 | PIK3R3 | 1.00000 | 0 |
| 20 | chr1 | 51965000 | 51966000 | 0.040 | 0.040 | EPS15 | 1.00000 | 0 |
| 21 | chr1 | 51978000 | 51979000 | 0.040 | 0.080 | EPS15 | 1.00000 | 0 |
| 22 | chr1 | 51983000 | 51984000 | 0.040 | 0.000 | EPS15 | 1.00000 | 0 |
| 23 | chr1 | 72393000 | 72394000 | 0.040 | 0.000 | NEGR1 | 1.00000 | 0 |
| 24 | chr1 | 73719000 | 73720000 | 0.040 | 0.040 | LRR1Q3 | 1.00000 | 0 |
| 25 | chr1 | 77315000 | 77316000 | 0.000 | 0.040 | ST6GALNAC5 | 1.00000 | 0 |
| 26 | chr1 | 81306000 | 81307000 | 0.040 | 0.000 | LPHN2 | 1.00000 | 0 |
| 27 | chr1 | 81527000 | 81528000 | 0.000 | 0.000 | LPHN2 | 1.00000 | 0 |
| 28 | chr1 | 82009000 | 82010000 | 0.000 | 0.000 | LPHN2 | 1.00000 | 0 |
| 29 | chr1 | 84106000 | 84107000 | 0.040 | 0.000 | TTLL7 | 1.00000 | 0 |
| 30 | chr1 | 87524000 | 87525000 | 0.000 | 0.040 | HS2ST1; HS2ST1LOC339524; | 1.00000 | 0 |
| 31 | chr1 | 94551000 | 94552000 | 0.000 | 0.040 | ABCA4 | 1.00000 | 0 |
| 32 | chr1 | 94552000 | 94553000 | 0.000 | 0.040 | ABCA4 | 1.00000 | 0 |
| 33 | chr1 | 103696000 | 103697000 | 0.000 | 0.000 | COL11A1 | 1.00000 | 0 |
| 34 | chr1 | 116979000 | 116980000 | 0.000 | 0.040 | ATP1A1 | 1.00000 | 0 |
| 35 | chr1 | 149784000 | 149785000 | 0.040 | 0.040 | HIST2H3D | 1.00000 | 1 |
| 36 | chr1 | 149821000 | 149822000 | 0.040 | 0.000 | HIST2H2AA4 | 1.00000 | 1 |
| 37 | chr1 | 149857000 | 149858000 | 0.000 | 0.040 | HIST2H2BE | 1.00000 | 1 |
| 38 | chr1 | 149858000 | 149859000 | 0.080 | 0.040 | HIST2H2AC; HIST2H2BE; | 1.00000 | 0 |
| 39 | chr1 | 160616000 | 160617000 | 0.040 | 0.040 | SLAMF1 | 1.00000 | 0 |
| 40 | chr1 | 162711000 | 162712000 | 0.040 | 0.000 | DDR2 | 1.00000 | 0 |
| 41 | chr1 | 163684000 | 163685000 | 0.040 | 0.000 | NUF2 | 1.00000 | 0 |
| 42 | chr1 | 167598000 | 167599000 | 0.080 | 0.000 | RCSD1 | 0.48980 | 0 |
| 43 | chr1 | 167599000 | 167600000 | 0.040 | 0.000 | RCSD1 | 1.00000 | 0 |
| 44 | chr1 | 167600000 | 167601000 | 0.040 | 0.040 | RCSD1 | 1.00000 | 0 |
| 45 | chr1 | 174333000 | 174334000 | 0.040 | 0.000 | RABGAP1L | 1.00000 | 0 |
| 46 | chr1 | 187263000 | 187264000 | 0.000 | 0.000 | PLA2G4A | 1.00000 | 0 |
| 47 | chr1 | 187283000 | 187284000 | 0.040 | 0.000 | PLA2G4A | 1.00000 | 0 |
| 48 | chr1 | 187892000 | 187893000 | 0.040 | 0.000 | PLA2G4A | 1.00000 | 0 |
| 49 | chr1 | 195282000 | 195283000 | 0.000 | 0.040 | KCNT2 | 1.00000 | 0 |
| 50 | chr1 | 198591000 | 198592000 | 0.000 | 0.040 | PTPRC | 1.00000 | 0 |
| 51 | chr1 | 198608000 | 198609000 | 0.040 | 0.000 | PTPRC | 1.00000 | 0 |
| 52 | chr1 | 198609000 | 198610000 | 0.080 | 0.000 | PTPRC | 0.48980 | 0 |
| 53 | chr1 | 202004000 | 202005000 | 0.040 | 0.040 | ELF3 | 1.00000 | 0 |
| 54 | chr1 | 203273000 | 203274000 | 0.040 | 0.000 | BTG2 | 1.00000 | 1 |
| 55 | chr1 | 203274000 | 203275000 | 0.160 | 0.160 | BTG2 | 1.00000 | 1 |
| 56 | chr1 | 203275000 | 203276000 | 0.400 | 0.280 | BTG2 | 0.55122 | 1 |
| 57 | chr1 | 203276000 | 203277000 | 0.080 | 0.040 | BTG2 | 1.00000 | 1 |
| 58 | chr1 | 205780000 | 205781000 | 0.000 | 0.000 | SLC41A1 | 1.00000 | 0 |
| 59 | chr1 | 205781000 | 205782000 | 0.000 | 0.000 | SLC41A1 | 1.00000 | 0 |
| 60 | chr1 | 206283000 | 206284000 | 0.000 | 0.040 | CTSE | 1.00000 | 0 |
| 61 | chr1 | 206286000 | 206287000 | 0.040 | 0.000 | CTSE | 1.00000 | 0 |
| 62 | chr1 | 217044000 | 217045000 | 0.040 | 0.000 | ESRRG | 1.00000 | 0 |
| 63 | chr1 | 226924000 | 226925000 | 0.080 | 0.120 | ITPKB | 1.00000 | 1 |
| 64 | chr1 | 226925000 | 226926000 | 0.120 | 0.000 | ITPKB | 0.23469 | 1 |
| 65 | chr1 | 226926000 | 226927000 | 0.120 | 0.000 | ITPKB | 0.23469 | 1 |
| 66 | chr1 | 229974000 | 229975000 | 0.040 | 0.040 | URB2 | 1.00000 | 0 |
| 67 | chr1 | 235131000 | 235132000 | 0.000 | 0.000 | TOMM20 | 1.00000 | 0 |
| 68 | chr1 | 235141000 | 235142000 | 0.040 | 0.000 | TOMM20 | 1.00000 | 0 |
| 69 | chr1 | 238787000 | 238788000 | 0.040 | 0.000 | MTRNR2L11 | 1.00000 | 0 |
| 70 | chr1 | 248088000 | 248089000 | 0.040 | 0.000 | OR2T8 | 1.00000 | 0 |
| 71 | chr2 | 630000 | 631000 | 0.000 | 0.000 | TMEM18 | 1.00000 | 0 |
| 72 | chr2 | 1484000 | 1485000 | 0.000 | 0.000 | TPO | 1.00000 | 0 |
| 73 | chr2 | 7991000 | 7992000 | 0.000 | 0.040 | RNF144A | 1.00000 | 0 |
| 74 | chr2 | 12173000 | 12174000 | 0.000 | 0.040 | LPIN1 | 1.00000 | 0 |
| 75 | chr2 | 12175000 | 12176000 | 0.000 | 0.000 | LPIN1 | 1.00000 | 0 |
| 76 | chr2 | 12249000 | 12250000 | 0.000 | 0.040 | LPIN1 | 1.00000 | 0 |
| 77 | chr2 | 14113000 | 14114000 | 0.000 | 0.000 | FAM84A | 1.00000 | 0 |
| 78 | chr2 | 17577000 | 17578000 | 0.000 | 0.040 | RAD51AP2 | 1.00000 | 0 |
| 79 | chr2 | 19253000 | 19254000 | 0.000 | 0.000 | OSR1 | 1.00000 | 0 |
| 80 | chr2 | 24802000 | 24803000 | 0.040 | 0.000 | NCOA1 | 1.00000 | 0 |
| 81 | chr2 | 31478000 | 31479000 | 0.040 | 0.000 | EHD3 | 1.00000 | 0 |
| 82 | chr2 | 41728000 | 41729000 | 0.040 | 0.000 | C2orf91 | 1.00000 | 0 |
| 83 | chr2 | 45404000 | 45405000 | 0.000 | 0.000 | SIX2 | 1.00000 | 0 |
| 84 | chr2 | 47923000 | 47924000 | 0.000 | 0.040 | MSH6 | 1.00000 | 0 |
| 85 | chr2 | 47944000 | 47945000 | 0.000 | 0.000 | MSH6 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 86 | chr2 | 51360000 | 51361000 | 0.040 | 0.000 | NRXN1 | 1.00000 | 0 |
| 87 | chr2 | 51655000 | 51656000 | 0.000 | 0.000 | NRXN1 | 1.00000 | 0 |
| 88 | chr2 | 56565000 | 56566000 | 0.040 | 0.000 | CCDC85A | 1.00000 | 0 |
| 89 | chr2 | 57800000 | 57801000 | 0.040 | 0.000 | VRK2 | 1.00000 | 0 |
| 90 | chr2 | 60779000 | 60780000 | 0.000 | 0.040 | BCL11A | 1.00000 | 0 |
| 91 | chr2 | 60780000 | 60781000 | 0.080 | 0.000 | BCL11A | 0.48980 | 0 |
| 92 | chr2 | 63802000 | 63803000 | 0.000 | 0.000 | WDPCP | 1.00000 | 0 |
| 93 | chr2 | 63827000 | 63828000 | 0.000 | 0.040 | MDH1 | 1.00000 | 0 |
| 94 | chr2 | 64319000 | 64320000 | 0.000 | 0.040 | PELI1 | 1.00000 | 0 |
| 95 | chr2 | 65593000 | 65594000 | 0.000 | 0.040 | SPRED2 | 1.00000 | 1 |
| 96 | chr2 | 67002000 | 67003000 | 0.040 | 0.040 | MEIS1 | 1.00000 | 0 |
| 97 | chr2 | 70315000 | 70316000 | 0.040 | 0.000 | PCBP1 | 1.00000 | 0 |
| 98 | chr2 | 79502000 | 79503000 | 0.000 | 0.000 | REG3A | 1.00000 | 0 |
| 99 | chr2 | 79644000 | 79645000 | 0.000 | 0.000 | CTNNA2 | 1.00000 | 0 |
| 100 | chr2 | 81818000 | 81819000 | 0.000 | 0.000 | CTNNA2 | 1.00000 | 0 |
| 101 | chr2 | 82310000 | 82311000 | 0.000 | 0.000 | CTNNA2 | 1.00000 | 0 |
| 102 | chr2 | 82948000 | 82949000 | 0.000 | 0.040 | SUCLG1 | 1.00000 | 0 |
| 103 | chr2 | 85335000 | 85336000 | 0.000 | 0.000 | TCF7L1 | 1.00000 | 0 |
| 104 | chr2 | 88905000 | 88906000 | 0.080 | 0.000 | EIF2AK3 | 0.48980 | 0 |
| 105 | chr2 | 88906000 | 88907000 | 0.160 | 0.040 | EIF2AK3 | 0.34868 | 0 |
| 106 | chr2 | 88907000 | 88908000 | 0.040 | 0.040 | EIF2AK3 | 1.00000 | 0 |
| 107 | chr2 | 89052000 | 89053000 | 0.000 | 0.080 | RPIA | 0.48980 | 0 |
| 108 | chr2 | 89065000 | 89066000 | 0.000 | 0.000 | RPIA | 1.00000 | 0 |
| 109 | chr2 | 89066000 | 89067000 | 0.040 | 0.000 | RPIA | 1.00000 | 0 |
| 110 | chr2 | 89095000 | 89096000 | 0.000 | 0.040 | RPIA | 1.00000 | 0 |
| 111 | chr2 | 89127000 | 89128000 | 0.120 | 0.080 | IGKC | 1.00000 | 0 |
| 112 | chr2 | 89128000 | 89129000 | 0.160 | 0.160 | IGKC | 1.00000 | 0 |
| 113 | chr2 | 89129000 | 89130000 | 0.120 | 0.000 | IGKC | 0.23469 | 0 |
| 114 | chr2 | 89130000 | 89131000 | 0.080 | 0.000 | IGKC | 0.48980 | 0 |
| 115 | chr2 | 89131000 | 89132000 | 0.040 | 0.040 | IGKC | 1.00000 | 0 |
| 116 | chr2 | 89132000 | 89133000 | 0.040 | 0.000 | IGKC | 1.00000 | 0 |
| 117 | chr2 | 89133000 | 89134000 | 0.000 | 0.040 | IGKC | 1.00000 | 0 |
| 118 | chr2 | 89137000 | 89138000 | 0.000 | 0.040 | IGKC | 1.00000 | 0 |
| 119 | chr2 | 89138000 | 89139000 | 0.040 | 0.000 | IGKC | 1.00000 | 0 |
| 120 | chr2 | 89139000 | 89140000 | 0.040 | 0.040 | IGKC | 1.00000 | 0 |
| 121 | chr2 | 89140000 | 89141000 | 0.040 | 0.120 | IGKC | 0.60921 | 0 |
| 122 | chr2 | 89141000 | 89142000 | 0.080 | 0.120 | IGKC | 1.00000 | 0 |
| 123 | chr2 | 89142000 | 89143000 | 0.040 | 0.200 | IGKC | 0.18946 | 0 |
| 124 | chr2 | 89143000 | 89144000 | 0.000 | 0.080 | IGKC | 0.48980 | 0 |
| 125 | chr2 | 89144000 | 89145000 | 0.040 | 0.040 | IGKC | 1.00000 | 0 |
| 126 | chr2 | 89145000 | 89146000 | 0.040 | 0.000 | IGKC | 1.00000 | 0 |
| 127 | chr2 | 89146000 | 89147000 | 0.000 | 0.000 | IGKC | 1.00000 | 0 |
| 128 | chr2 | 89153000 | 89154000 | 0.000 | 0.000 | IGKC | 1.00000 | 0 |
| 129 | chr2 | 89155000 | 89156000 | 0.080 | 0.080 | IGKC | 1.00000 | 0 |
| 130 | chr2 | 89156000 | 89157000 | 0.120 | 0.000 | IGKC | 0.23469 | 0 |
| 131 | chr2 | 89157000 | 89158000 | 0.240 | 0.160 | IGKC | 0.72520 | 0 |
| 132 | chr2 | 89158000 | 89159000 | 0.240 | 0.280 | IGKC | 1.00000 | 0 |
| 133 | chr2 | 89159000 | 89160000 | 0.360 | 0.640 | IGKJ5 | 0.08874 | 0 |
| 134 | chr2 | 89160000 | 89161000 | 0.320 | 0.680 | IGKJ3; IGKJ4; IGKJ5; | 0.02271 | 0 |
| 135 | chr2 | 89161000 | 89162000 | 0.240 | 0.320 | IGKJl; IGKJ2; | 0.75361 | 0 |
| 136 | chr2 | 89162000 | 89163000 | 0.200 | 0.200 | IGKJ1 | 1.00000 | 0 |
| 137 | chr2 | 89163000 | 89164000 | 0.120 | 0.240 | IGKJ1 | 0.46349 | 0 |
| 138 | chr2 | 89164000 | 89165000 | 0.160 | 0.280 | IGKJ1 | 0.49620 | 0 |
| 139 | chr2 | 89165000 | 89166000 | 0.160 | 0.360 | IGKJ1 | 0.19633 | 0 |
| 140 | chr2 | 89166000 | 89167000 | 0.000 | 0.040 | IGKJ1 | 1.00000 | 0 |
| 141 | chr2 | 89169000 | 89170000 | 0.000 | 0.040 | IGKJ1 | 1.00000 | 0 |
| 142 | chr2 | 89184000 | 89185000 | 0.000 | 0.000 | IGKV4-1 | 1.00000 | 0 |
| 143 | chr2 | 89185000 | 89186000 | 0.120 | 0.320 | IGKV4-1 | 0.17062 | 0 |
| 144 | chr2 | 89196000 | 89197000 | 0.000 | 0.160 | IGKV5-2 | 0.10986 | 0 |
| 145 | chr2 | 89197000 | 89198000 | 0.000 | 0.040 | IGKV5-2 | 1.00000 | 0 |
| 146 | chr2 | 89214000 | 89215000 | 0.000 | 0.040 | IGKV5-2 | 1.00000 | 0 |
| 147 | chr2 | 89246000 | 89247000 | 0.040 | 0.000 | IGKV1-5 | 1.00000 | 0 |
| 148 | chr2 | 89247000 | 89248000 | 0.160 | 0.000 | IGKV1-5 | 0.10986 | 0 |
| 149 | chr2 | 89248000 | 89249000 | 0.040 | 0.000 | IGKV1-5 | 1.00000 | 0 |
| 150 | chr2 | 89266000 | 89267000 | 0.000 | 0.040 | IGKV1-6 | 1.00000 | 0 |
| 151 | chr2 | 89291000 | 89292000 | 0.040 | 0.040 | IGKV1-8 | 1.00000 | 0 |
| 152 | chr2 | 89292000 | 89293000 | 0.000 | 0.040 | IGKV1-8 | 1.00000 | 0 |
| 153 | chr2 | 89326000 | 89327000 | 0.040 | 0.000 | IGKV3-11 | 1.00000 | 0 |
| 154 | chr2 | 89327000 | 89328000 | 0.040 | 0.000 | IGKV3-11 | 1.00000 | 0 |
| 155 | chr2 | 89442000 | 89443000 | 0.040 | 0.160 | IGKV3-20 | 0.34868 | 0 |
| 156 | chr2 | 89443000 | 89444000 | 0.000 | 0.000 | IGKV3-20 | 1.00000 | 0 |
| 157 | chr2 | 89476000 | 89477000 | 0.000 | 0.000 | IGKV2-24 | 1.00000 | 0 |
| 158 | chr2 | 89513000 | 89514000 | 0.040 | 0.000 | IGKV1-27 | 1.00000 | 0 |
| 159 | chr2 | 89521000 | 89522000 | 0.040 | 0.040 | IGKV2-28 | 1.00000 | 0 |
| 160 | chr2 | 89533000 | 89534000 | 0.040 | 0.000 | IGKV2-30 | 1.00000 | 0 |
| 161 | chr2 | 89534000 | 89535000 | 0.080 | 0.000 | IGKV2-30 | 0.48980 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 162 | chr2 | 89544000 | 89545000 | 0.000 | 0.080 | IGKV2-30 | 0.48980 | 0 |
| 163 | chr2 | 89545000 | 89546000 | 0.040 | 0.000 | IGKV2-30 | 1.00000 | 0 |
| 164 | chr2 | 90259000 | 90260000 | 0.040 | 0.000 | IGKV1D-8 | 1.00000 | 0 |
| 165 | chr2 | 90260000 | 90261000 | 0.120 | 0.000 | IGKV1D-8 | 0.23469 | 0 |
| 166 | chr2 | 96809000 | 96810000 | 0.040 | 0.080 | DUSP2 | 1.00000 | 1 |
| 167 | chr2 | 96810000 | 96811000 | 0.080 | 0.120 | DUSP2 | 1.00000 | 1 |
| 168 | chr2 | 96811000 | 96812000 | 0.000 | 0.080 | DUSP2 | 0.48980 | 1 |
| 169 | chr2 | 98611000 | 98612000 | 0.000 | 0.040 | TMEM131 | 1.00000 | 0 |
| 170 | chr2 | 100757000 | 100758000 | 0.080 | 0.000 | AFF3 | 0.48980 | 0 |
| 171 | chr2 | 100758000 | 100759000 | 0.120 | 0.000 | AFF3 | 0.23469 | 0 |
| 172 | chr2 | 106144000 | 106145000 | 0.000 | 0.080 | FHL2 | 0.48980 | 0 |
| 173 | chr2 | 111878000 | 111879000 | 0.000 | 0.120 | BCL2L11 | 0.23469 | 0 |
| 174 | chr2 | 111879000 | 111880000 | 0.040 | 0.120 | BCL2L11 | 0.60921 | 0 |
| 175 | chr2 | 112305000 | 112306000 | 0.000 | 0.040 | ANAPC1 | 1.00000 | 0 |
| 176 | chr2 | 116234000 | 116235000 | 0.040 | 0.000 | DPP10 | 1.00000 | 0 |
| 177 | chr2 | 116439000 | 116440000 | 0.040 | 0.000 | DPP10 | 1.00000 | 0 |
| 178 | chr2 | 124697000 | 124698000 | 0.000 | 0.040 | CNTNAP5 | 1.00000 | 0 |
| 179 | chr2 | 125235000 | 125236000 | 0.000 | 0.000 | CNTNAP5 | 1.00000 | 0 |
| 180 | chr2 | 127538000 | 127539000 | 0.000 | 0.000 | GYPC | 1.00000 | 0 |
| 181 | chr2 | 136874000 | 136875000 | 0.200 | 0.120 | CXCR4 | 0.70194 | 1 |
| 182 | chr2 | 136875000 | 136876000 | 0.240 | 0.240 | CXCR4 | 1.00000 | 1 |
| 183 | chr2 | 136996000 | 136997000 | 0.000 | 0.040 | CXCR4 | 1.00000 | 1 |
| 184 | chr2 | 137082000 | 137083000 | 0.040 | 0.000 | CXCR4 | 1.00000 | 1 |
| 185 | chr2 | 140951000 | 140952000 | 0.040 | 0.000 | LRP1B | 1.00000 | 0 |
| 186 | chr2 | 141335000 | 141336000 | 0.040 | 0.000 | LRP1B | 1.00000 | 0 |
| 187 | chr2 | 141770000 | 141771000 | 0.000 | 0.000 | LRP1B | 1.00000 | 0 |
| 188 | chr2 | 146445000 | 146446000 | 0.000 | 0.000 | ZEB2 | 1.00000 | 0 |
| 189 | chr2 | 146446000 | 146447000 | 0.000 | 0.080 | ZEB2 | 0.48980 | 0 |
| 190 | chr2 | 156443000 | 156444000 | 0.000 | 0.000 | KCNJ3 | 1.00000 | 0 |
| 191 | chr2 | 172590000 | 172591000 | 0.040 | 0.000 | DYNC1I2 | 1.00000 | 0 |
| 192 | chr2 | 176581000 | 176582000 | 0.000 | 0.000 | KIAA1715 | 1.00000 | 0 |
| 193 | chr2 | 179880000 | 179881000 | 0.000 | 0.040 | CCDC141 | 1.00000 | 0 |
| 194 | chr2 | 180358000 | 180359000 | 0.040 | 0.000 | ZNF385B | 1.00000 | 0 |
| 195 | chr2 | 189285000 | 189286000 | 0.040 | 0.000 | GULP1 | 1.00000 | 0 |
| 196 | chr2 | 189432000 | 189433000 | 0.000 | 0.040 | GULP1 | 1.00000 | 0 |
| 197 | chr2 | 194115000 | 194116000 | 0.040 | 0.000 | TMEFF2 | 1.00000 | 0 |
| 198 | chr2 | 197035000 | 197036000 | 0.040 | 0.080 | STK17B | 1.00000 | 0 |
| 199 | chr2 | 197041000 | 197042000 | 0.080 | 0.000 | STK17B | 0.48980 | 0 |
| 200 | chr2 | 215999000 | 216000000 | 0.040 | 0.000 | ABCA12 | 1.00000 | 0 |
| 201 | chr2 | 216973000 | 216974000 | 0.000 | 0.000 | XRCC5 | 1.00000 | 0 |
| 202 | chr2 | 217247000 | 217248000 | 0.000 | 0.000 | 4-Mar-19 | 1.00000 | 0 |
| 203 | chr2 | 225386000 | 225387000 | 0.040 | 0.000 | CUL3 | 1.00000 | 0 |
| 204 | chr2 | 225524000 | 225525000 | 0.000 | 0.040 | CUL3 | 1.00000 | 0 |
| 205 | chr2 | 233478000 | 233479000 | 0.040 | 0.000 | EFHD1 | 1.00000 | 0 |
| 206 | chr2 | 233980000 | 233981000 | 0.000 | 0.080 | INPP5D | 0.48980 | 0 |
| 207 | chr2 | 240641000 | 240642000 | 0.000 | 0.000 | AC093802.1 | 1.00000 | 0 |
| 208 | chr2 | 241125000 | 241126000 | 0.000 | 0.000 | OTOS | 1.00000 | 0 |
| 209 | chr3 | 8739000 | 8740000 | 0.000 | 0.000 | CAV3 | 1.00000 | 0 |
| 210 | chr3 | 16407000 | 16408000 | 0.000 | 0.000 | RFTN1 | 1.00000 | 1 |
| 211 | chr3 | 16409000 | 16410000 | 0.000 | 0.000 | RFTN1 | 1.00000 | 1 |
| 212 | chr3 | 16419000 | 16420000 | 0.040 | 0.080 | RFTN1 | 1.00000 | 1 |
| 213 | chr3 | 16472000 | 16473000 | 0.040 | 0.000 | RFTN1 | 1.00000 | 1 |
| 214 | chr3 | 16495000 | 16496000 | 0.000 | 0.080 | RETN1 | 0.48980 | 1 |
| 215 | chr3 | 16552000 | 16553000 | 0.000 | 0.080 | RFTN1 | 0.48980 | 1 |
| 216 | chr3 | 16554000 | 16555000 | 0.120 | 0.120 | RFTN1 | 1.00000 | 1 |
| 217 | chr3 | 16555000 | 16556000 | 0.000 | 0.040 | RFTN1 | 1.00000 | 1 |
| 218 | chr3 | 21658000 | 21659000 | 0.040 | 0.000 | ZNF385D | 1.00000 | 0 |
| 219 | chr3 | 25691000 | 25692000 | 0.040 | 0.040 | TOP2B | 1.00000 | 0 |
| 220 | chr3 | 31969000 | 31970000 | 0.000 | 0.040 | OSBPL10 | 1.00000 | 1 |
| 221 | chr3 | 31993000 | 31994000 | 0.040 | 0.000 | OSBPL10 | 1.00000 | 1 |
| 222 | chr3 | 32001000 | 32002000 | 0.080 | 0.040 | OSBPL10 | 1.00000 | 1 |
| 223 | chr3 | 32022000 | 32023000 | 0.120 | 0.080 | OSBPL10 | 1.00000 | 1 |
| 224 | chr3 | 32023000 | 32024000 | 0.080 | 0.000 | OSBPL10 | 0.48980 | 1 |
| 225 | chr3 | 50128000 | 50129000 | 0.000 | 0.040 | RBM5 | 1.00000 | 0 |
| 226 | chr3 | 54913000 | 54914000 | 0.040 | 0.000 | CACNA2D3 | 1.00000 | 0 |
| 227 | chr3 | 56074000 | 56075000 | 0.040 | 0.040 | ERC2 | 1.00000 | 0 |
| 228 | chr3 | 59577000 | 59578000 | 0.000 | 0.000 | FHIT | 1.00000 | 0 |
| 229 | chr3 | 60351000 | 60352000 | 0.000 | 0.040 | FHIT | 1.00000 | 0 |
| 230 | chr3 | 60356000 | 60357000 | 0.000 | 0.000 | FHIT | 1.00000 | 0 |
| 231 | chr3 | 60357000 | 60358000 | 0.040 | 0.000 | FHIT | 1.00000 | 0 |
| 232 | chr3 | 60358000 | 60359000 | 0.040 | 0.000 | FHIT | 1.00000 | 0 |
| 233 | chr3 | 60359000 | 60360000 | 0.000 | 0.000 | FHIT | 1.00000 | 0 |
| 234 | chr3 | 60389000 | 60390000 | 0.000 | 0.040 | FHIT | 1.00000 | 0 |
| 235 | chr3 | 60392000 | 60393000 | 0.040 | 0.000 | FHIT | 1.00000 | 0 |
| 236 | chr3 | 60395000 | 60396000 | 0.000 | 0.000 | FHIT | 1.00000 | 0 |
| 237 | chr3 | 60404000 | 60405000 | 0.040 | 0.000 | FHIT | 1.00000 | 0 |
| 238 | chr3 | 60436000 | 60437000 | 0.000 | 0.000 | FHIT | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 239 | chr3 | 60437000 | 60438000 | 0.000 | 0.040 | FHIT | 1.00000 | 0 |
| 240 | chr3 | 60477000 | 60478000 | 0.040 | 0.040 | FHIT | 1.00000 | 0 |
| 241 | chr3 | 60485000 | 60486000 | 0.040 | 0.000 | FHIT | 1.00000 | 0 |
| 242 | chr3 | 60515000 | 60516000 | 0.000 | 0.040 | FHIT | 1.00000 | 0 |
| 243 | chr3 | 60535000 | 60536000 | 0.040 | 0.000 | FHIT | 1.00000 | 0 |
| 244 | chr3 | 60602000 | 60603000 | 0.000 | 0.000 | FHIT | 1.00000 | 0 |
| 245 | chr3 | 60613000 | 60614000 | 0.000 | 0.040 | FHIT | 1.00000 | 0 |
| 246 | chr3 | 60614000 | 60615000 | 0.000 | 0.040 | FHIT | 1.00000 | 0 |
| 247 | chr3 | 60632000 | 60633000 | 0.000 | 0.000 | FHIT | 1.00000 | 0 |
| 248 | chr3 | 60635000 | 60636000 | 0.000 | 0.000 | FHIT | 1.00000 | 0 |
| 249 | chr3 | 60640000 | 60641000 | 0.000 | 0.000 | FHIT | 1.00000 | 0 |
| 250 | chr3 | 60647000 | 60648000 | 0.000 | 0.040 | FHIT | 1.00000 | 0 |
| 251 | chr3 | 60648000 | 60649000 | 0.000 | 0.040 | FHIT | 1.00000 | 0 |
| 252 | chr3 | 60652000 | 60653000 | 0.000 | 0.000 | FHIT | 1.00000 | 0 |
| 253 | chr3 | 60660000 | 60661000 | 0.040 | 0.000 | FHIT | 1.00000 | 0 |
| 254 | chr3 | 60665000 | 60666000 | 0.000 | 0.040 | FHIT | 1.00000 | 0 |
| 255 | chr3 | 60666000 | 60667000 | 0.000 | 0.040 | FHIT | 1.00000 | 0 |
| 256 | chr3 | 60671000 | 60672000 | 0.000 | 0.000 | FHIT | 1.00000 | 0 |
| 257 | chr3 | 60673000 | 60674000 | 0.040 | 0.000 | FHIT | 1.00000 | 0 |
| 258 | chr3 | 60675000 | 60676000 | 0.000 | 0.040 | FHIT | 1.00000 | 0 |
| 259 | chr3 | 60678000 | 60679000 | 0.000 | 0.040 | FHIT | 1.00000 | 0 |
| 260 | chr3 | 60683000 | 60684000 | 0.000 | 0.000 | FHIT | 1.00000 | 0 |
| 261 | chr3 | 60684000 | 60685000 | 0.000 | 0.040 | FHIT | 1.00000 | 0 |
| 262 | chr3 | 60688000 | 60689000 | 0.040 | 0.000 | FHIT | 1.00000 | 0 |
| 263 | chr3 | 60717000 | 60718000 | 0.000 | 0.000 | FHIT | 1.00000 | 0 |
| 264 | chr3 | 60740000 | 60741000 | 0.040 | 0.000 | FHIT | 1.00000 | 0 |
| 265 | chr3 | 60774000 | 60775000 | 0.040 | 0.040 | FHIT | 1.00000 | 0 |
| 266 | chr3 | 60792000 | 60793000 | 0.000 | 0.000 | FHIT | 1.00000 | 0 |
| 267 | chr3 | 60806000 | 60807000 | 0.040 | 0.000 | FHIT | 1.00000 | 0 |
| 268 | chr3 | 60812000 | 60813000 | 0.000 | 0.000 | FHIT | 1.00000 | 0 |
| 269 | chr3 | 60860000 | 60861000 | 0.000 | 0.000 | FHIT | 1.00000 | 0 |
| 270 | chr3 | 71551000 | 71552000 | 0.040 | 0.000 | EIF4E3 | 1.00000 | 0 |
| 271 | chr3 | 78274000 | 78275000 | 0.000 | 0.040 | ROBO1 | 1.00000 | 0 |
| 272 | chr3 | 80273000 | 80274000 | 0.000 | 0.000 | ROBO1 | 1.00000 | 0 |
| 273 | chr3 | 83094000 | 83095000 | 0.000 | 0.000 | GBE1 | 1.00000 | 0 |
| 274 | chr3 | 83924000 | 83925000 | 0.000 | 0.000 | CADM2 | 1.00000 | 0 |
| 275 | chr3 | 84293000 | 84294000 | 0.000 | 0.040 | CADM2 | 1.00000 | 0 |
| 276 | chr3 | 85260000 | 85261000 | 0.000 | 0.040 | CADM2 | 1.00000 | 0 |
| 277 | chr3 | 85261000 | 85262000 | 0.000 | 0.000 | CADM2 | 1.00000 | 0 |
| 278 | chr3 | 85799000 | 85800000 | 0.040 | 0.000 | CADM2 | 1.00000 | 0 |
| 279 | chr3 | 86226000 | 86227000 | 0.000 | 0.000 | CADM2 | 1.00000 | 0 |
| 280 | chr3 | 88146000 | 88147000 | 0.040 | 0.000 | CGGBP1 | 1.00000 | 0 |
| 281 | chr3 | 94709000 | 94710000 | 0.000 | 0.000 | NSUN3 | 1.00000 | 0 |
| 282 | chr3 | 95460000 | 95461000 | 0.000 | 0.000 | MTRNR2L12 | 1.00000 | 0 |
| 283 | chr3 | 95724000 | 95725000 | 0.080 | 0.000 | MTRNR2L12 | 0.48980 | 0 |
| 284 | chr3 | 101569000 | 101570000 | 0.000 | 0.040 | NFKBIZ | 1.00000 | 0 |
| 285 | chr3 | 111851000 | 111852000 | 0.000 | 0.000 | GCSAM | 1.00000 | 0 |
| 286 | chr3 | 111852000 | 111853000 | 0.040 | 0.040 | GCSAM | 1.00000 | 0 |
| 287 | chr3 | 122377000 | 122378000 | 0.080 | 0.040 | PARP14 | 1.00000 | 0 |
| 288 | chr3 | 150478000 | 150479000 | 0.000 | 0.000 | SIAH2 | 1.00000 | 0 |
| 289 | chr3 | 150479000 | 150480000 | 0.000 | 0.040 | SIAH2 | 1.00000 | 0 |
| 290 | chr3 | 150480000 | 150481000 | 0.000 | 0.120 | SIAH2 | 0.23469 | 0 |
| 291 | chr3 | 163237000 | 163238000 | 0.000 | 0.000 | SI | 1.00000 | 0 |
| 292 | chr3 | 163238000 | 163239000 | 0.000 | 0.000 | SI | 1.00000 | 0 |
| 293 | chr3 | 163615000 | 163616000 | 0.040 | 0.040 | SI | 1.00000 | 0 |
| 294 | chr3 | 183270000 | 183271000 | 0.000 | 0.000 | KLHL6 | 1.00000 | 0 |
| 295 | chr3 | 183271000 | 183272000 | 0.000 | 0.040 | KLHL6 | 1.00000 | 0 |
| 296 | chr3 | 183272000 | 183273000 | 0.000 | 0.120 | KLHL6 | 0.23469 | 0 |
| 297 | chr3 | 183273000 | 183274000 | 0.000 | 0.040 | KLHL6 | 1.00000 | 0 |
| 298 | chr3 | 186648000 | 186649000 | 0.000 | 0.040 | ADIPOQ | 1.00000 | 0 |
| 299 | chr3 | 186714000 | 186715000 | 0.080 | 0.160 | ST6GAL1 | 0.66710 | 1 |
| 300 | chr3 | 186715000 | 186716000 | 0.080 | 0.000 | ST6GAL1 | 0.48980 | 1 |
| 301 | chr3 | 186739000 | 186740000 | 0.120 | 0.040 | ST6GAL1 | 0.60921 | 1 |
| 302 | chr3 | 186740000 | 186741000 | 0.160 | 0.080 | ST6GAL1 | 0.66710 | 1 |
| 303 | chr3 | 186742000 | 186743000 | 0.160 | 0.000 | ST6GAL1 | 1.00000 | 1 |
| 304 | chr3 | 186783000 | 186784000 | 0.160 | 0.240 | ST6GAL1 | 0.72520 | 1 |
| 305 | chr3 | 186784000 | 186785000 | 0.040 | 0.040 | ST6GAL1 | 1.00000 | 1 |
| 306 | chr3 | 187458000 | 187459000 | 0.000 | 0.000 | BCL6 | 1.00000 | 1 |
| 307 | chr3 | 187459000 | 187460000 | 0.000 | 0.000 | BCL6 | 1.00000 | 1 |
| 308 | chr3 | 187460000 | 187461000 | 0.040 | 0.040 | BCL6 | 1.00000 | 1 |
| 309 | chr3 | 187461000 | 187462000 | 0.240 | 0.360 | BCL6 | 0.53803 | 1 |
| 310 | chr3 | 187462000 | 187463000 | 0.440 | 0.560 | BCL6 | 0.57214 | 1 |
| 311 | chr3 | 187463000 | 187464000 | 0.360 | 0.440 | BCL6 | 0.77379 | 1 |
| 312 | chr3 | 187464000 | 187465000 | 0.200 | 0.200 | BCL6 | 1.00000 | 1 |
| 313 | chr3 | 187468000 | 187469000 | 0.120 | 0.000 | BCL6 | 0.23469 | 1 |
| 314 | chr3 | 187635000 | 187636000 | 0.040 | 0.000 | BCL6 | 1.00000 | 1 |
| 315 | chr3 | 187636000 | 187637000 | 0.000 | 0.000 | BCL6 | 1.00000 | 1 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 316 | chr3 | 187653000 | 187654000 | 0.040 | 0.040 | BCL6 | 1.00000 | 1 |
| 317 | chr3 | 187658000 | 187659000 | 0.000 | 0.040 | BCL6 | 1.00000 | 1 |
| 318 | chr3 | 187660000 | 187661000 | 0.040 | 0.160 | BCL6 | 0.34868 | 1 |
| 319 | chr3 | 187661000 | 187662000 | 0.040 | 0.240 | BCL6 | 0.09878 | 1 |
| 320 | chr3 | 187664000 | 187665000 | 0.040 | 0.080 | BCL6 | 1.00000 | 1 |
| 321 | chr3 | 187686000 | 187687000 | 0.040 | 0.000 | AC022498.1 | 1.00000 | 0 |
| 322 | chr3 | 187687000 | 187688000 | 0.000 | 0.040 | AC022498.1 | 1.00000 | 0 |
| 323 | chr3 | 187693000 | 187694000 | 0.040 | 0.040 | AC022498.1 | 1.00000 | 0 |
| 324 | chr3 | 187696000 | 187697000 | 0.040 | 0.000 | AC022498.1 | 1.00000 | 0 |
| 325 | chr3 | 187697000 | 187698000 | 0.040 | 0.000 | AC022498.1 | 1.00000 | 0 |
| 326 | chr3 | 187803000 | 187804000 | 0.000 | 0.000 | AC022498.1 | 1.00000 | 0 |
| 327 | chr3 | 187806000 | 187807000 | 0.080 | 0.080 | AC022498.1 | 1.00000 | 0 |
| 328 | chr3 | 187957000 | 187958000 | 0.120 | 0.160 | AC022498.1 | 1.00000 | 0 |
| 329 | chr3 | 187958000 | 187959000 | 0.240 | 0.280 | AC022498.1 | 1.00000 | 0 |
| 330 | chr3 | 187959000 | 187960000 | 0.120 | 0.040 | AC022498.1 | 0.60921 | 0 |
| 331 | chr3 | 187960000 | 187961000 | 0.000 | 0.040 | AC022498.1 | 1.00000 | 0 |
| 332 | chr3 | 188222000 | 188223000 | 0.000 | 0.000 | LPP | 1.00000 | 0 |
| 333 | chr3 | 188298000 | 188299000 | 0.040 | 0.000 | LPP | 1.00000 | 0 |
| 334 | chr3 | 188299000 | 188300000 | 0.080 | 0.080 | LPP | 1.00000 | 0 |
| 335 | chr3 | 188471000 | 188472000 | 0.120 | 0.240 | LPP | 0.46349 | 0 |
| 336 | chr3 | 188472000 | 188473000 | 0.000 | 0.080 | LPP | 0.48980 | 0 |
| 337 | chr4 | 50000 | 51000 | 0.080 | 0.000 | ZNF595; ZNF718; | 0.48980 | 0 |
| 338 | chr4 | 51000 | 52000 | 0.120 | 0.040 | ZNF595; ZNF718; | 0.60921 | 0 |
| 339 | chr4 | 54000 | 55000 | 0.080 | 0.000 | ZNF595; ZNF718; | 0.48980 | 0 |
| 340 | chr4 | 290000 | 291000 | 0.000 | 0.000 | ZNF732 | 1.00000 | 0 |
| 341 | chr4 | 385000 | 386000 | 0.080 | 0.000 | ZNF141 | 0.48980 | 0 |
| 342 | chr4 | 550000 | 551000 | 0.000 | 0.000 | PIGG | 1.00000 | 0 |
| 343 | chr4 | 2707000 | 2708000 | 0.000 | 0.040 | FAM193A | 1.00000 | 0 |
| 344 | chr4 | 5206000 | 5207000 | 0.080 | 0.000 | STK32B | 0.48980 | 0 |
| 345 | chr4 | 25863000 | 25864000 | 0.080 | 0.040 | SEL1L3 | 1.00000 | 0 |
| 346 | chr4 | 25864000 | 25865000 | 0.000 | 0.040 | SEL1L3 | 1.00000 | 0 |
| 347 | chr4 | 25865000 | 25866000 | 0.040 | 0.000 | SEL1L3 | 1.00000 | 0 |
| 348 | chr4 | 29657000 | 29658000 | 0.040 | 0.000 | PCDH7 | 1.00000 | 0 |
| 349 | chr4 | 30356000 | 30357000 | 0.040 | 0.000 | PCDH7 | 1.00000 | 0 |
| 350 | chr4 | 33418000 | 33419000 | 0.000 | 0.000 | PCDH7 | 1.00000 | 0 |
| 351 | chr4 | 33449000 | 33450000 | 0.000 | 0.040 | PCDH7 | 1.00000 | 0 |
| 352 | chr4 | 39348000 | 39349000 | 0.000 | 0.040 | RFC1 | 1.00000 | 0 |
| 353 | chr4 | 39974000 | 39975000 | 0.000 | 0.000 | PDS5A | 1.00000 | 0 |
| 354 | chr4 | 40194000 | 40195000 | 0.000 | 0.120 | N4BP2 | 0.23469 | 0 |
| 355 | chr4 | 40195000 | 40196000 | 0.000 | 0.040 | N4BP2 | 1.00000 | 0 |
| 356 | chr4 | 40196000 | 40197000 | 0.040 | 0.000 | N4BP2 | 1.00000 | 0 |
| 357 | chr4 | 40197000 | 40199000 | 0.000 | 0.000 | N4BP2 | 1.00000 | 0 |
| 358 | chr4 | 40198000 | 40199000 | 0.120 | 0.080 | N4BP2 | 1.00000 | 0 |
| 359 | chr4 | 40199000 | 40200000 | 0.280 | 0.240 | N4BP2 | 1.00000 | 0 |
| 360 | chr4 | 40200000 | 40201000 | 0.080 | 0.080 | RHOH | 1.00000 | 1 |
| 361 | chr4 | 40201000 | 40202000 | 0.120 | 0.120 | RHOH | 1.00000 | 1 |
| 362 | chr4 | 40202000 | 40203000 | 0.080 | 0.000 | RHOH | 0.48980 | 1 |
| 363 | chr4 | 40204000 | 40205000 | 0.000 | 0.040 | RHOH | 1.00000 | 1 |
| 364 | chr4 | 45308000 | 45309000 | 0.000 | 0.000 | GNPDA2 | 1.00000 | 0 |
| 365 | chr4 | 46360000 | 46361000 | 0.000 | 0.040 | GABRA2 | 1.00000 | 0 |
| 366 | chr4 | 62375000 | 62376000 | 0.000 | 0.000 | LPHN3 | 1.00000 | 0 |
| 367 | chr4 | 62530000 | 62531000 | 0.000 | 0.000 | LPHN3 | 1.00000 | 0 |
| 368 | chr4 | 62911000 | 62912000 | 0.000 | 0.040 | LPHN3 | 1.00000 | 0 |
| 369 | chr4 | 63120000 | 63121000 | 0.040 | 0.040 | LPHN3 | 1.00000 | 0 |
| 370 | chr4 | 64015000 | 64016000 | 0.000 | 0.000 | LPHN3 | 1.00000 | 0 |
| 371 | chr4 | 65038000 | 65039000 | 0.040 | 0.000 | TECRL | 1.00000 | 0 |
| 372 | chr4 | 65165000 | 65166000 | 0.000 | 0.040 | TECRL | 1.00000 | 0 |
| 373 | chr4 | 65966000 | 65967000 | 0.000 | 0.040 | EPHA5 | 1.00000 | 0 |
| 374 | chr4 | 66827000 | 66828000 | 0.000 | 0.080 | EPHA5 | 0.48980 | 0 |
| 375 | chr4 | 71531000 | 71532000 | 0.000 | 0.040 | IGJ | 1.00000 | 0 |
| 376 | chr4 | 71532000 | 71533000 | 0.000 | 0.000 | IGJ | 1.00000 | 0 |
| 377 | chr4 | 74456000 | 74457000 | 0.040 | 0.000 | RASSF6 | 1.00000 | 0 |
| 378 | chr4 | 74483000 | 74484000 | 0.040 | 0.000 | RASSF6 | 1.00000 | 0 |
| 379 | chr4 | 74484000 | 74485000 | 0.040 | 0.000 | RASSF6 | 1.00000 | 0 |
| 380 | chr4 | 74485000 | 74486000 | 0.120 | 0.000 | RASSF6 | 0.23469 | 0 |
| 381 | chr4 | 91886000 | 91887000 | 0.040 | 0.000 | CCSER1 | 1.00000 | 0 |
| 382 | chr4 | 92787000 | 92788000 | 0.000 | 0.040 | CCSER1 | 1.00000 | 0 |
| 383 | chr4 | 113206000 | 113207000 | 0.000 | 0.000 | TIFA | 1.00000 | 0 |
| 384 | chr4 | 114466000 | 114467000 | 0.000 | 0.000 | CAMK2D | 1.00000 | 0 |
| 385 | chr4 | 114681000 | 114682000 | 0.000 | 0.080 | CAMK2D | 0.48980 | 0 |
| 386 | chr4 | 117928000 | 117929000 | 0.040 | 0.000 | TRAM1L1 | 1.00000 | 0 |
| 387 | chr4 | 123637000 | 123638000 | 0.000 | 0.000 | BBS12 | 1.00000 | 0 |
| 388 | chr4 | 125227000 | 125228000 | 0.040 | 0.000 | ANKRD50 | 1.00000 | 0 |
| 389 | chr4 | 127371000 | 127372000 | 0.000 | 0.000 | FAT4 | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 390 | chr4 | 133455000 | 133456000 | 0.000 | 0.000 | PCDH10 | 1.00000 | 0 |
| 391 | chr4 | 134538000 | 134539000 | 0.000 | 0.040 | PCDH10 | 1.00000 | 0 |
| 392 | chr4 | 134743000 | 134744000 | 0.040 | 0.040 | PABPC4L | 1.00000 | 0 |
| 393 | chr4 | 134867000 | 134868000 | 0.000 | 0.000 | PABPC4L | 1.00000 | 0 |
| 394 | chr4 | 134949000 | 134950000 | 0.080 | 0.000 | PABPC4L | 0.48980 | 0 |
| 395 | chr4 | 135064000 | 135065000 | 0.040 | 0.000 | PABPC4L | 1.00000 | 0 |
| 396 | chr4 | 135077000 | 135078000 | 0.000 | 0.000 | PABPC4L | 1.00000 | 0 |
| 397 | chr4 | 136799000 | 136800000 | 0.000 | 0.000 | PCDH18 | 1.00000 | 0 |
| 398 | chr4 | 136867000 | 136868000 | 0.000 | 0.040 | PCDH18 | 1.00000 | 0 |
| 399 | chr4 | 140236000 | 140237000 | 0.040 | 0.000 | NAA15 | 1.00000 | 0 |
| 400 | chr4 | 151723000 | 151724000 | 0.000 | 0.000 | LRBA | 1.00000 | 0 |
| 401 | chr4 | 151950000 | 151951000 | 0.000 | 0.000 | LRBA | 1.00000 | 0 |
| 402 | chr4 | 152125000 | 152126000 | 0.040 | 0.040 | SH3D19 | 1.00000 | 0 |
| 403 | chr4 | 157246000 | 157247000 | 0.040 | 0.000 | CTSO | 1.00000 | 0 |
| 404 | chr4 | 164532000 | 164533000 | 0.000 | 0.000 | 1-Mar-19 | 1.00000 | 0 |
| 405 | chr4 | 178732000 | 178733000 | 0.040 | 0.040 | AGA | 1.00000 | 0 |
| 406 | chr4 | 178885000 | 178886000 | 0.040 | 0.000 | AGA | 1.00000 | 0 |
| 407 | chr4 | 179898000 | 179899000 | 0.000 | 0.040 | AGA | 1.00000 | 0 |
| 408 | chr4 | 180885000 | 180886000 | 0.040 | 0.000 | TENM3 | 1.00000 | 0 |
| 409 | chr4 | 181554000 | 181555000 | 0.040 | 0.040 | TENM3 | 1.00000 | 0 |
| 410 | chr4 | 182122000 | 182123000 | 0.000 | 0.040 | TENM3 | 1.00000 | 0 |
| 411 | chr5 | 436000 | 437000 | 0.000 | 0.000 | AHRR | 1.00000 | 0 |
| 412 | chr5 | 3982000 | 3983000 | 0.040 | 0.000 | IRX1 | 1.00000 | 0 |
| 413 | chr5 | 17218000 | 17219000 | 0.040 | 0.000 | BASP1 | 1.00000 | 0 |
| 414 | chr5 | 17219000 | 17220000 | 0.080 | 0.000 | BASP1 | 0.48980 | 0 |
| 415 | chr5 | 18514000 | 18515000 | 0.040 | 0.000 | CDH18 | 1.00000 | 0 |
| 416 | chr5 | 22356000 | 22357000 | 0.040 | 0.000 | CDH12 | 1.00000 | 0 |
| 417 | chr5 | 22517000 | 22518000 | 0.040 | 0.000 | CDH12 | 1.00000 | 0 |
| 418 | chr5 | 24632000 | 24633000 | 0.000 | 0.000 | CDH10 | 1.00000 | 0 |
| 419 | chr5 | 25275000 | 25276000 | 0.000 | 0.040 | CDH10 | 1.00000 | 0 |
| 420 | chr5 | 25541000 | 25542000 | 0.000 | 0.000 | CDH10 | 1.00000 | 0 |
| 421 | chr5 | 26119000 | 26120000 | 0.000 | 0.080 | CDH9 | 0.48980 | 0 |
| 422 | chr5 | 26450000 | 26451000 | 0.000 | 0.000 | CDH9 | 1.00000 | 0 |
| 423 | chr5 | 29224000 | 29225000 | 0.080 | 0.000 | CDH6 | 0.48980 | 0 |
| 424 | chr5 | 29492000 | 29493000 | 0.000 | 0.000 | CDH6 | 1.00000 | 0 |
| 425 | chr5 | 29648000 | 29649000 | 0.000 | 0.000 | CDH6 | 1.00000 | 0 |
| 426 | chr5 | 51521000 | 51522000 | 0.000 | 0.040 | CTD-2203A3.1 | 1.00000 | 0 |
| 427 | chr5 | 83841000 | 83842000 | 0.040 | 0.000 | EDIL3 | 1.00000 | 0 |
| 428 | chr5 | 88177000 | 88178000 | 0.040 | 0.000 | MEF2C | 1.00000 | 0 |
| 429 | chr5 | 88178000 | 88179000 | 0.040 | 0.000 | MEF2C | 1.00000 | 0 |
| 430 | chr5 | 91417000 | 91418000 | 0.000 | 0.000 | ARRDC3 | 1.00000 | 0 |
| 431 | chr5 | 103678000 | 103679000 | 0.040 | 0.000 | NUDT12 | 1.00000 | 0 |
| 432 | chr5 | 123696000 | 123697000 | 0.000 | 0.000 | ZNF608 | 1.00000 | 1 |
| 433 | chr5 | 124079000 | 124080000 | 0.000 | 0.040 | ZNF608 | 1.00000 | 1 |
| 434 | chr5 | 124080000 | 124081000 | 0.040 | 0.000 | ZNF608 | 1.00000 | 1 |
| 435 | chr5 | 127594000 | 127595000 | 0.000 | 0.040 | FBN2 | 1.00000 | 0 |
| 436 | chr5 | 127875000 | 127876000 | 0.000 | 0.000 | FBN2 | 1.00000 | 0 |
| 437 | chr5 | 131825000 | 131826000 | 0.120 | 0.040 | IRF1 | 0.60921 | 0 |
| 438 | chr5 | 131826000 | 131827000 | 0.040 | 0.040 | IRF1 | 1.00000 | 0 |
| 439 | chr5 | 149791000 | 149792000 | 0.160 | 0.240 | CD74 | 0.72520 | 1 |
| 440 | chr5 | 149792000 | 149793000 | 0.040 | 0.080 | CD74 | 1.00000 | 1 |
| 441 | chr5 | 158380000 | 158381000 | 0.000 | 0.080 | EBF1 | 0.48980 | 0 |
| 442 | chr5 | 158479000 | 158480000 | 0.000 | 0.000 | EBF1 | 1.00000 | 0 |
| 443 | chr5 | 158526000 | 158527000 | 0.040 | 0.080 | EBF1 | 1.00000 | 0 |
| 444 | chr5 | 158527000 | 158528000 | 0.040 | 0.040 | EBF1 | 1.00000 | 0 |
| 445 | chr5 | 158528000 | 158529000 | 0.040 | 0.040 | EBF1 | 1.00000 | 0 |
| 446 | chr5 | 164247000 | 164248000 | 0.040 | 0.040 | MAT2B | 1.00000 | 0 |
| 447 | chr5 | 164441000 | 164442000 | 0.000 | 0.000 | MAT2B | 1.00000 | 0 |
| 448 | chr5 | 165932000 | 165933000 | 0.000 | 0.000 | TENM2 | 1.00000 | 0 |
| 449 | chr5 | 173300000 | 173301000 | 0.000 | 0.000 | CPEB4 | 1.00000 | 0 |
| 450 | chr5 | 179166000 | 179167000 | 0.040 | 0.040 | MAML1 | 1.00000 | 0 |
| 451 | chr5 | 180102000 | 180103000 | 0.040 | 0.000 | FLT4 | 1.00000 | 0 |
| 452 | chr6 | 392000 | 393000 | 0.120 | 0.080 | IRF4 | 1.00000 | 1 |
| 453 | chr6 | 393000 | 394000 | 0.080 | 0.080 | IRF4 | 1.00000 | 1 |
| 454 | chr6 | 14118000 | 14119000 | 0.160 | 0.440 | CD83 | 0.06222 | 1 |
| 455 | chr6 | 14119000 | 14120000 | 0.000 | 0.120 | CD83 | 0.23469 | 1 |
| 456 | chr6 | 18111000 | 18112000 | 0.000 | 0.080 | NHLRC1 | 0.48980 | 0 |
| 457 | chr6 | 18387000 | 18388000 | 0.000 | 0.040 | RNF144B | 1.00000 | 1 |
| 458 | chr6 | 18388000 | 18389000 | 0.000 | 0.040 | RNF144B | 1.00000 | 1 |
| 459 | chr6 | 19573000 | 19574000 | 0.040 | 0.040 | ID4 | 1.00000 | 0 |
| 460 | chr6 | 22873000 | 22874000 | 0.040 | 0.000 | HDGFL1 | 1.00000 | 0 |
| 461 | chr6 | 26031000 | 26032000 | 0.000 | 0.040 | HIST1H3B | 1.00000 | 1 |
| 462 | chr6 | 26032000 | 26033000 | 0.000 | 0.040 | HIST1H3B | 1.00000 | 1 |
| 463 | chr6 | 26056000 | 26057000 | 0.120 | 0.040 | HIST1H1C | 0.60921 | 1 |
| 464 | chr6 | 26123000 | 26124000 | 0.120 | 0.040 | HIST1H2BC | 0.60921 | 1 |
| 465 | chr6 | 26124000 | 26125000 | 0.120 | 0.080 | HIST1H2AC; HIST1H2BC; | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 466 | chr6 | 26125000 | 26126000 | 0.000 | 0.040 | HIST1H2AC | 1.00000 | 1 |
| 467 | chr6 | 26156000 | 26157000 | 0.120 | 0.080 | HIST1H1E | 1.00000 | 1 |
| 468 | chr6 | 26157000 | 26158000 | 0.080 | 0.040 | HIST1H1E | 1.00000 | 1 |
| 469 | chr6 | 26216000 | 26217000 | 0.040 | 0.040 | HIST1H2BG | 1.00000 | 1 |
| 470 | chr6 | 26234000 | 26235000 | 0.080 | 0.040 | HIST1H1D | 1.00000 | 0 |
| 471 | chr6 | 27101000 | 27102000 | 0.040 | 0.040 | HIST1H2AG | 1.00000 | 1 |
| 472 | chr6 | 27114000 | 27115000 | 0.080 | 0.040 | HIST1H2AH; HIST1H2BK; | 1.00000 | 0 |
| 473 | chr6 | 27792000 | 27793000 | 0.120 | 0.040 | HIST1H4J | 0.60921 | 0 |
| 474 | chr6 | 27833000 | 27834000 | 0.040 | 0.000 | HIST1H2AL | 1.00000 | 1 |
| 475 | chr6 | 27860000 | 27861000 | 0.000 | 0.080 | HIST1H2AM | 0.48980 | 1 |
| 476 | chr6 | 27861000 | 27862000 | 0.000 | 0.040 | HIST1H2BO | 1.00000 | 1 |
| 477 | chr6 | 29778000 | 29779000 | 0.000 | 0.040 | LOC554223 | 1.00000 | 0 |
| 478 | chr6 | 29780000 | 29781000 | 0.040 | 0.000 | HLA-G | 1.00000 | 0 |
| 479 | chr6 | 29911000 | 29912000 | 0.080 | 0.040 | HLA-A | 1.00000 | 0 |
| 480 | chr6 | 29927000 | 29928000 | 0.040 | 0.000 | HLA-A | 1.00000 | 0 |
| 481 | chr6 | 31324000 | 31325000 | 0.040 | 0.040 | HLA-B | 1.00000 | 1 |
| 482 | chr6 | 31325000 | 31326000 | 0.000 | 0.000 | HLA-B | 1.00000 | 1 |
| 483 | chr6 | 31543000 | 31544000 | 0.080 | 0.000 | TNF | 0.48980 | 1 |
| 484 | chr6 | 31549000 | 31550000 | 0.200 | 0.240 | LTB | 1.00000 | 1 |
| 485 | chr6 | 31550000 | 31551000 | 0.040 | 0.040 | LTB | 1.00000 | 1 |
| 486 | chr6 | 32440000 | 32441000 | 0.120 | 0.000 | HLA-DRA | 0.23469 | 0 |
| 487 | chr6 | 32451000 | 32452000 | 0.040 | 0.000 | HLA-DRB5 | 1.00000 | 0 |
| 488 | chr6 | 32452000 | 32453000 | 0.080 | 0.000 | HLA-DRB5 | 0.48980 | 0 |
| 489 | chr6 | 32455000 | 32456000 | 0.040 | 0.040 | HLA-DRB5 | 1.00000 | 0 |
| 490 | chr6 | 32457000 | 32458000 | 0.000 | 0.000 | HLA-DRB5 | 1.00000 | 0 |
| 491 | chr6 | 32498000 | 32499000 | 0.000 | 0.040 | HLA-DRB5 | 1.00000 | 0 |
| 492 | chr6 | 32505000 | 32506000 | 0.040 | 0.000 | HLA-DRB5 | 1.00000 | 0 |
| 493 | chr6 | 32511000 | 32512000 | 0.000 | 0.000 | HLA-DRB5 | 1.00000 | 0 |
| 494 | chr6 | 32522000 | 32523000 | 0.040 | 0.000 | HLA-DRB1 | 1.00000 | 0 |
| 495 | chr6 | 32525000 | 32526000 | 0.040 | 0.000 | HLA-DRB1 | 1.00000 | 0 |
| 496 | chr6 | 32526000 | 32527000 | 0.000 | 0.000 | HLA-DRB1 | 1.00000 | 0 |
| 497 | chr6 | 32527000 | 32528000 | 0.000 | 0.000 | HLA-DRB1 | 1.00000 | 0 |
| 498 | chr6 | 32548000 | 32549000 | 0.000 | 0.000 | HLA-DRB1 | 1.00000 | 0 |
| 499 | chr6 | 32552000 | 32553000 | 0.040 | 0.000 | HLA-DRB1 | 1.00000 | 0 |
| 500 | chr6 | 32557000 | 32558000 | 0.000 | 0.080 | HLA-DRB1 | 0.48980 | 0 |
| 501 | chr6 | 32609000 | 32610000 | 0.000 | 0.040 | HLA-DQA1 | 1.00000 | 0 |
| 502 | chr6 | 32630000 | 32631000 | 0.000 | 0.040 | HLA-DQB1 | 1.00000 | 0 |
| 503 | chr6 | 32632000 | 32633000 | 0.080 | 0.040 | HLA-DQB1 | 1.00000 | 0 |
| 504 | chr6 | 32727000 | 32728000 | 0.040 | 0.040 | HLA-DQB2 | 1.00000 | 0 |
| 505 | chr6 | 32729000 | 32730000 | 0.000 | 0.040 | HLA-DQB2 | 1.00000 | 0 |
| 506 | chr6 | 33048000 | 33049000 | 0.000 | 0.040 | HLA-DPB1 | 1.00000 | 0 |
| 507 | chr6 | 34179000 | 34180000 | 0.000 | 0.040 | HMGA1 | 1.00000 | 0 |
| 508 | chr6 | 37138000 | 37139000 | 0.200 | 0.200 | PIM1 | 1.00000 | 1 |
| 509 | chr6 | 37139000 | 37140000 | 0.120 | 0.120 | PIM1 | 1.00000 | 1 |
| 510 | chr6 | 37140000 | 37141000 | 0.040 | 0.000 | PIM1 | 1.00000 | 1 |
| 511 | chr6 | 58001000 | 58002000 | 0.040 | 0.000 | PRIM2 | 1.00000 | 0 |
| 512 | chr6 | 67923000 | 67924000 | 0.040 | 0.000 | BAI3 | 1.00000 | 0 |
| 513 | chr6 | 77256000 | 77257000 | 0.040 | 0.000 | IMPG1 | 1.00000 | 0 |
| 514 | chr6 | 81437000 | 81438000 | 0.040 | 0.000 | BCKDHB | 1.00000 | 0 |
| 515 | chr6 | 88468000 | 88469000 | 0.000 | 0.040 | AKIRIN2 | 1.00000 | 0 |
| 516 | chr6 | 88630000 | 88631000 | 0.040 | 0.080 | SPACA1 | 1.00000 | 0 |
| 517 | chr6 | 88876000 | 88877000 | 0.000 | 0.000 | CNR1 | 1.00000 | 0 |
| 518 | chr6 | 89323000 | 89324000 | 0.000 | 0.000 | RNGTT | 1.00000 | 0 |
| 519 | chr6 | 89338000 | 89339000 | 0.080 | 0.000 | RNGTT | 0.48980 | 0 |
| 520 | chr6 | 89348000 | 89349000 | 0.080 | 0.000 | RNGTT | 0.48980 | 0 |
| 521 | chr6 | 89470000 | 89471000 | 0.080 | 0.000 | RNGTT | 0.48980 | 0 |
| 522 | chr6 | 89471000 | 89472000 | 0.000 | 0.000 | RNGTT | 1.00000 | 0 |
| 523 | chr6 | 90061000 | 90062000 | 0.040 | 0.040 | UBE2J1 | 1.00000 | 1 |
| 524 | chr6 | 90062000 | 90063000 | 0.040 | 0.040 | UBE2J1 | 1.00000 | 1 |
| 525 | chr6 | 90994000 | 90995000 | 0.000 | 0.080 | MAP3K7 | 0.48980 | 0 |
| 526 | chr6 | 91004000 | 91005000 | 0.040 | 0.040 | MAP3K7 | 1.00000 | 0 |
| 527 | chr6 | 91005000 | 91006000 | 0.120 | 0.280 | MAP3K7 | 0.28902 | 0 |
| 528 | chr6 | 91006000 | 91007000 | 0.040 | 0.120 | MAP3K7 | 0.60921 | 0 |
| 529 | chr6 | 91007000 | 91008000 | 0.040 | 0.040 | MAP3K7 | 1.00000 | 0 |
| 530 | chr6 | 94822000 | 94823000 | 0.000 | 0.040 | EPHA7 | 1.00000 | 0 |
| 531 | chr6 | 107704000 | 107705000 | 0.000 | 0.000 | PDSS2 | 1.00000 | 0 |
| 532 | chr6 | 112885000 | 112886000 | 0.040 | 0.000 | RFPL4B | 1.00000 | 0 |
| 533 | chr6 | 113244000 | 118245000 | 0.040 | 0.000 | SLC35F1 | 1.00000 | 0 |
| 534 | chr6 | 121288000 | 121289000 | 0.000 | 0.000 | C6orf170 | 1.00000 | 0 |
| 535 | chr6 | 121489000 | 121490000 | 0.000 | 0.080 | C6orf170 | 0.48980 | 0 |
| 536 | chr6 | 123504000 | 123505000 | 0.040 | 0.000 | TRDN | 1.00000 | 0 |
| 537 | chr6 | 127313000 | 127314000 | 0.040 | 0.000 | RSPO3 | 1.00000 | 0 |
| 538 | chr6 | 133785000 | 133786000 | 0.080 | 0.000 | EYA4 | 0.48980 | 0 |
| 539 | chr6 | 134491000 | 134492000 | 0.000 | 0.080 | SGK1 | 0.48980 | 1 |
| 540 | chr6 | 134492000 | 134493000 | 0.080 | 0.040 | SGK1 | 1.00000 | 1 |
| 541 | chr6 | 134493000 | 134494000 | 0.040 | 0.080 | SGK1 | 1.00000 | 1 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 542 | chr6 | 134494000 | 134495000 | 0.040 | 0.080 | SGK1 | 1.00000 | 1 |
| 543 | chr6 | 134495000 | 134496000 | 0.160 | 0.280 | SGK1 | 0.49620 | 1 |
| 544 | chr6 | 134496000 | 134497000 | 0.000 | 0.200 | SGK1 | 0.05015 | 1 |
| 545 | chr6 | 142046000 | 142047000 | 0.000 | 0.080 | NMBR | 0.48980 | 0 |
| 546 | chr6 | 147860000 | 147861000 | 0.000 | 0.040 | SAMD5 | 1.00000 | 0 |
| 547 | chr6 | 150954000 | 150955000 | 0.040 | 0.040 | PLEKHG1 | 1.00000 | 0 |
| 548 | chr6 | 159238000 | 159239000 | 0.000 | 0.080 | EZR | 0.48980 | 0 |
| 549 | chr6 | 159239000 | 159240000 | 0.040 | 0.000 | EZR | 1.00000 | 0 |
| 550 | chr6 | 159240000 | 159241000 | 0.040 | 0.000 | EZR | 1.00000 | 0 |
| 551 | chr6 | 159464000 | 159465000 | 0.040 | 0.000 | TAGAP | 1.00000 | 0 |
| 552 | chr6 | 159465000 | 159466000 | 0.040 | 0.000 | TAGAP | 1.00000 | 0 |
| 553 | chr6 | 161265000 | 161266000 | 0.000 | 0.040 | PLG | 1.00000 | 0 |
| 554 | chr6 | 161833000 | 161834000 | 0.000 | 0.000 | PARK2 | 1.00000 | 0 |
| 555 | chr6 | 162712000 | 162713000 | 0.000 | 0.000 | PARK2 | 1.00000 | 0 |
| 556 | chr6 | 164941000 | 164942000 | 0.000 | 0.000 | C6orf118 | 1.00000 | 0 |
| 557 | chr6 | 168813000 | 168814000 | 0.000 | 0.000 | SMOC2 | 1.00000 | 0 |
| 558 | chr7 | 1898000 | 1899000 | 0.040 | 0.040 | AC110781.3 | 1.00000 | 0 |
| 559 | chr7 | 1963000 | 1964000 | 0.040 | 0.000 | MAD1L1 | 1.00000 | 0 |
| 560 | chr7 | 2080000 | 2081000 | 0.000 | 0.040 | MAD1L1 | 1.00000 | 0 |
| 561 | chr7 | 5568000 | 5569000 | 0.040 | 0.080 | ACTB | 1.00000 | 1 |
| 562 | chr7 | 5569000 | 5570000 | 0.040 | 0.120 | ACTB | 0.60921 | 1 |
| 563 | chr7 | 5570000 | 5571000 | 0.040 | 0.040 | ACTB | 1.00000 | 1 |
| 564 | chr7 | 9933000 | 9934000 | 0.040 | 0.040 | NDUFA4 | 1.00000 | 0 |
| 565 | chr7 | 13017000 | 13018000 | 0.000 | 0.040 | ARL4A | 1.00000 | 0 |
| 566 | chr7 | 13346000 | 13347000 | 0.000 | 0.000 | ETV1 | 1.00000 | 0 |
| 567 | chr7 | 15459000 | 15460000 | 0.000 | 0.000 | AGMO | 1.00000 | 0 |
| 568 | chr7 | 16382000 | 16383000 | 0.040 | 0.000 | ISPD | 1.00000 | 0 |
| 569 | chr7 | 28600000 | 28601000 | 0.040 | 0.000 | CREB5 | 1.00000 | 0 |
| 570 | chr7 | 40846000 | 40847000 | 0.040 | 0.000 | C7orf10 | 1.00000 | 0 |
| 571 | chr7 | 50349000 | 50350000 | 0.040 | 0.040 | IKZF1 | 1.00000 | 0 |
| 572 | chr7 | 50350000 | 50351000 | 0.080 | 0.040 | IKZF1 | 1.00000 | 0 |
| 573 | chr7 | 53335000 | 53336000 | 0.000 | 0.000 | POM121L12 | 1.00000 | 0 |
| 574 | chr7 | 57713000 | 57714000 | 0.080 | 0.040 | ZNF716 | 1.00000 | 0 |
| 575 | chr7 | 62475000 | 62476000 | 0.040 | 0.040 | AC006455.1 | 1.00000 | 0 |
| 576 | chr7 | 70669000 | 70670000 | 0.040 | 0.000 | WBSCR17 | 1.00000 | 0 |
| 577 | chr7 | 71553000 | 71554000 | 0.000 | 0.040 | CALN1 | 1.00000 | 0 |
| 578 | chr7 | 79847000 | 79848000 | 0.040 | 0.000 | GNAI1 | 1.00000 | 0 |
| 579 | chr7 | 80694000 | 80695000 | 0.040 | 0.000 | AC005008.2 | 1.00000 | 0 |
| 580 | chr7 | 81556000 | 81557000 | 0.000 | 0.000 | CACNA2D1 | 1.00000 | 0 |
| 581 | chr7 | 84127000 | 84128000 | 0.040 | 0.000 | SEMA3A | 1.00000 | 0 |
| 582 | chr7 | 84247000 | 84248000 | 0.000 | 0.040 | SEMA3D | 1.00000 | 0 |
| 583 | chr7 | 84257000 | 84258000 | 0.000 | 0.000 | SEMA3D | 1.00000 | 0 |
| 584 | chr7 | 86914000 | 86915000 | 0.000 | 0.040 | CROT | 1.00000 | 0 |
| 585 | chr7 | 90356000 | 90357000 | 0.000 | 0.040 | CDK14 | 1.00000 | 0 |
| 586 | chr7 | 93304000 | 93305000 | 0.000 | 0.000 | CALCR | 1.00000 | 0 |
| 587 | chr7 | 93682000 | 93683000 | 0.040 | 0.000 | BET1 | 1.00000 | 0 |
| 588 | chr7 | 102644000 | 102645000 | 0.000 | 0.000 | FBXL13 | 1.00000 | 0 |
| 589 | chr7 | 105699000 | 105700000 | 0.000 | 0.040 | CDHR3 | 1.00000 | 0 |
| 590 | chr7 | 110521000 | 110522000 | 0.040 | 0.040 | IMMP2L | 1.00000 | 0 |
| 591 | chr7 | 110543000 | 110544000 | 0.040 | 0.000 | IMMP2L | 1.00000 | 0 |
| 592 | chr7 | 110545000 | 110546000 | 0.040 | 0.000 | IMMP2L | 1.00000 | 0 |
| 593 | chr7 | 110597000 | 110598000 | 0.000 | 0.040 | IMMP2L | 1.00000 | 0 |
| 594 | chr7 | 110601000 | 110602000 | 0.000 | 0.000 | IMMP2L | 1.00000 | 0 |
| 595 | chr7 | 110602000 | 110603000 | 0.040 | 0.000 | IMMP2L | 1.00000 | 0 |
| 596 | chr7 | 110609000 | 110610000 | 0.040 | 0.000 | IMMP2L | 1.00000 | 0 |
| 597 | chr7 | 110610000 | 110611000 | 0.040 | 0.000 | IMMP2L | 1.00000 | 0 |
| 598 | chr7 | 110617000 | 110618000 | 0.040 | 0.000 | IMMP2L | 1.00000 | 0 |
| 599 | chr7 | 110618000 | 110619000 | 0.000 | 0.000 | IMMP2L | 1.00000 | 0 |
| 600 | chr7 | 110619000 | 110620000 | 0.040 | 0.000 | IMMP2L | 1.00000 | 0 |
| 601 | chr7 | 110621000 | 110622000 | 0.000 | 0.040 | IMMP2L | 1.00000 | 0 |
| 602 | chr7 | 110628000 | 111629000 | 0.040 | 0.000 | IMMP2L | 1.00000 | 0 |
| 603 | chr7 | 110629000 | 110630000 | 0.000 | 0.000 | IMMP2L | 1.00000 | 0 |
| 604 | chr7 | 110631000 | 110632000 | 0.000 | 0.040 | IMMP2L | 1.00000 | 0 |
| 605 | chr7 | 110632000 | 110633000 | 0.040 | 0.000 | IMMP2L | 1.00000 | 0 |
| 606 | chr7 | 110636000 | 110637000 | 0.040 | 0.000 | IMMP2L | 1.00000 | 0 |
| 607 | chr7 | 110637000 | 110638000 | 0.000 | 0.000 | IMMP2L | 1.00000 | 0 |
| 608 | chr7 | 110638000 | 110639000 | 0.000 | 0.040 | IMMP2L | 1.00000 | 0 |
| 609 | chr7 | 110639000 | 110640000 | 0.000 | 0.040 | IMMP2L | 1.00000 | 0 |
| 610 | chr7 | 110641000 | 110642000 | 0.000 | 0.000 | IMMP2L | 1.00000 | 0 |
| 611 | chr7 | 110650000 | 110651000 | 0.000 | 0.000 | IMMP2L | 1.00000 | 0 |
| 612 | chr7 | 110651000 | 110652000 | 0.000 | 0.040 | IMMP2L | 1.00000 | 0 |
| 613 | chr7 | 110666000 | 110667000 | 0.000 | 0.000 | IMMP2L | 1.00000 | 0 |
| 614 | chr7 | 110671000 | 110672000 | 0.000 | 0.080 | IMMP2L | 0.48980 | 0 |
| 615 | chr7 | 110677000 | 110678000 | 0.000 | 0.000 | IMMP2L | 1.00000 | 0 |
| 616 | chr7 | 110679000 | 110680000 | 0.000 | 0.000 | IMMP2L | 1.00000 | 0 |
| 617 | chr7 | 110680000 | 110681000 | 0.000 | 0.000 | IMMP2L | 1.00000 | 0 |
| 618 | chr7 | 110685000 | 110686000 | 0.000 | 0.000 | LRRN3 | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 619 | chr7 | 110686000 | 110687000 | 0.000 | 0.040 | LRRN3 | 1.00000 | 0 |
| 620 | chr7 | 110688000 | 110689000 | 0.000 | 0.000 | LRRN3 | 1.00000 | 0 |
| 621 | chr7 | 110699000 | 110700000 | 0.080 | 0.000 | LRRN3 | 0.48980 | 0 |
| 622 | chr7 | 110700000 | 110701000 | 0.040 | 0.000 | LRRN3 | 1.00000 | 0 |
| 623 | chr7 | 110709000 | 110710000 | 0.000 | 0.040 | LRRN3 | 1.00000 | 0 |
| 624 | chr7 | 110711000 | 110712000 | 0.000 | 0.040 | LRRN3 | 1.00000 | 0 |
| 625 | chr7 | 110714000 | 110715000 | 0.000 | 0.040 | LRRN3 | 1.00000 | 0 |
| 626 | chr7 | 110727000 | 110728000 | 0.000 | 0.040 | LRRN3 | 1.00000 | 0 |
| 627 | chr7 | 110728000 | 110729000 | 0.040 | 0.000 | LRRN3 | 1.00000 | 0 |
| 628 | chr7 | 110729000 | 110730000 | 0.000 | 0.040 | LRRN3 | 1.00000 | 0 |
| 629 | chr7 | 110734000 | 110735000 | 0.000 | 0.040 | LRRN3 | 1.00000 | 0 |
| 630 | chr7 | 110737000 | 110738000 | 0.000 | 0.000 | LRRN3 | 1.00000 | 0 |
| 631 | chr7 | 110740000 | 110741000 | 0.040 | 0.080 | LRRN3 | 1.00000 | 0 |
| 632 | chr7 | 110744000 | 110745000 | 0.000 | 0.000 | LRRN3 | 1.00000 | 0 |
| 633 | chr7 | 110746000 | 110747000 | 0.000 | 0.040 | LRRN3 | 1.00000 | 0 |
| 634 | chr7 | 110747000 | 110748000 | 0.000 | 0.000 | LRRN3 | 1.00000 | 0 |
| 635 | chr7 | 110748000 | 110749000 | 0.000 | 0.000 | LRRN3 | 1.00000 | 0 |
| 636 | chr7 | 110755000 | 110756000 | 0.000 | 0.000 | LRRN3 | 1.00000 | 0 |
| 637 | chr7 | 110764000 | 110765000 | 0.000 | 0.000 | LRRN3 | 1.00000 | 0 |
| 638 | chr7 | 110767000 | 110768000 | 0.040 | 0.000 | LRRN3 | 1.00000 | 0 |
| 639 | chr7 | 110769000 | 110770000 | 0.000 | 0.040 | LRRN3 | 1.00000 | 0 |
| 640 | chr7 | 110771000 | 110772000 | 0.040 | 0.040 | LRRN3 | 1.00000 | 0 |
| 641 | chr7 | 110779000 | 110780000 | 0.000 | 0.000 | LRRN3 | 1.00000 | 0 |
| 642 | chr7 | 110780000 | 110781000 | 0.000 | 0.040 | LRRN3 | 1.00000 | 0 |
| 643 | chr7 | 110783000 | 110784000 | 0.000 | 0.040 | LRRN3 | 1.00000 | 0 |
| 644 | chr7 | 110785000 | 110786000 | 0.000 | 0.080 | LRRN3 | 0.48980 | 0 |
| 645 | chr7 | 110801000 | 110802000 | 0.000 | 0.040 | LRRN3 | 1.00000 | 0 |
| 646 | chr7 | 110802000 | 110303000 | 0.000 | 0.040 | LRRN3 | 1.00000 | 0 |
| 647 | chr7 | 110810000 | 110811000 | 0.000 | 0.000 | LRRN3 | 1.00000 | 0 |
| 648 | chr7 | 110316000 | 110817000 | 0.000 | 0.000 | LRRN3 | 1.00000 | 0 |
| 649 | chr7 | 110821000 | 110822000 | 0.000 | 0.040 | LRRN3 | 1.00000 | 0 |
| 650 | chr7 | 110824000 | 110325000 | 0.000 | 0.000 | LRRN3 | 1.00000 | 0 |
| 651 | chr7 | 110827000 | 110828000 | 0.040 | 0.000 | LRRN3 | 1.00000 | 0 |
| 652 | chr7 | 110336000 | 110837000 | 0.040 | 0.040 | LRRN3 | 1.00000 | 0 |
| 653 | chr7 | 110847000 | 110848000 | 0.040 | 0.040 | LRRN3 | 1.00000 | 0 |
| 654 | chr7 | 111567000 | 111568000 | 0.000 | 0.000 | DOCK4 | 1.00000 | 0 |
| 655 | chr7 | 119056000 | 119057000 | 0.040 | 0.000 | KCND2 | 1.00000 | 0 |
| 656 | chr7 | 121380000 | 121381000 | 0.040 | 0.000 | PTPRZ1 | 1.00000 | 0 |
| 657 | chr7 | 123887000 | 123888000 | 0.000 | 0.000 | THEM229A | 1.00000 | 0 |
| 658 | chr7 | 125262000 | 125263000 | 0.000 | 0.040 | POT1 | 1.00000 | 0 |
| 659 | chr7 | 145723000 | 145724000 | 0.000 | 0.000 | CNTNAP2 | 1.00000 | 0 |
| 660 | chr7 | 148508000 | 148509000 | 0.000 | 0.000 | EZH2 | 1.00000 | 0 |
| 661 | chr7 | 155127000 | 155128000 | 0.000 | 0.000 | BLACE | 1.00000 | 0 |
| 662 | chr7 | 157162000 | 157163000 | 0.040 | 0.000 | DNAJB6 | 1.00000 | 0 |
| 663 | chr7 | 158684000 | 158685000 | 0.000 | 0.040 | WDR60 | 1.00000 | 0 |
| 664 | chr8 | 1646000 | 1647000 | 0.000 | 0.040 | DLGAP2 | 1.00000 | 0 |
| 665 | chr8 | 5558000 | 5559000 | 0.000 | 0.040 | MCPH1 | 1.00000 | 0 |
| 666 | chr8 | 5612000 | 5613000 | 0.000 | 0.000 | MCPH1 | 1.00000 | 0 |
| 667 | chr8 | 8602000 | 8603000 | 0.000 | 0.120 | MFHAS1 | 0.23469 | 0 |
| 668 | chr8 | 8706000 | 8707000 | 0.000 | 0.000 | MFHAS1 | 1.00000 | 0 |
| 669 | chr8 | 8717000 | 8718000 | 0.000 | 0.040 | MFHAS1 | 1.00000 | 0 |
| 670 | chr8 | 11352000 | 11353000 | 0.040 | 0.040 | BLK | 1.00000 | 0 |
| 671 | chr8 | 14080000 | 14081000 | 0.000 | 0.040 | SGCZ | 1.00000 | 0 |
| 672 | chr8 | 14796000 | 14797000 | 0.040 | 0.000 | SGCZ | 1.00000 | 0 |
| 673 | chr8 | 16090000 | 16091000 | 0.000 | 0.040 | MSR1 | 1.00000 | 0 |
| 674 | chr8 | 16187000 | 16188000 | 0.000 | 0.080 | MSR1 | 0.48980 | 0 |
| 675 | chr8 | 23101000 | 23102000 | 0.000 | 0.040 | CHMP7 | 1.00000 | 0 |
| 676 | chr8 | 24207000 | 24208000 | 0.000 | 0.000 | ADAM28 | 1.00000 | 0 |
| 677 | chr8 | 29155000 | 29156000 | 0.000 | 0.040 | KIF13B | 1.00000 | 0 |
| 678 | chr8 | 35657000 | 35658000 | 0.000 | 0.000 | AC012215.1 | 1.00000 | 0 |
| 679 | chr8 | 38759000 | 38760000 | 0.040 | 0.000 | PLEKHA2 | 1.00000 | 0 |
| 680 | chr8 | 54986000 | 54987000 | 0.040 | 0.000 | LYPLA1 | 1.00000 | 0 |
| 681 | chr8 | 60031000 | 60032000 | 0.040 | 0.000 | TOX | 1.00000 | 0 |
| 682 | chr8 | 67525000 | 67526000 | 0.040 | 0.000 | MYBL1 | 1.00000 | 0 |
| 683 | chr8 | 77105000 | 77106000 | 0.000 | 0.000 | ZFHX4 | 1.00000 | 0 |
| 684 | chr8 | 78400000 | 78401000 | 0.000 | 0.040 | PEX2 | 1.00000 | 0 |
| 685 | chr8 | 90322000 | 90323000 | 0.040 | 0.000 | RIPK2 | 1.00000 | 0 |
| 686 | chr8 | 93199000 | 93200000 | 0.000 | 0.040 | RUNX1T1 | 1.00000 | 0 |
| 687 | chr8 | 94618000 | 94619000 | 0.000 | 0.040 | FAM92A1 | 1.00000 | 0 |
| 688 | chr8 | 110586000 | 110587000 | 0.000 | 0.040 | SYBU | 1.00000 | 0 |
| 689 | chr8 | 126687000 | 126688000 | 0.000 | 0.000 | TRIB1 | 1.00000 | 0 |
| 690 | chr8 | 128748000 | 128749000 | 0.080 | 0.280 | MYC | 0.13833 | 1 |
| 691 | chr8 | 128749000 | 128750000 | 0.080 | 0.320 | MYC | 0.07375 | 1 |
| 692 | chr8 | 128750000 | 128751000 | 0.080 | 0.120 | MYC | 1.00000 | 1 |
| 693 | chr8 | 128751000 | 128752000 | 0.040 | 0.080 | MYC | 1.00000 | 1 |
| 694 | chr8 | 128752000 | 128753000 | 0.000 | 0.000 | MYC | 1.00000 | 1 |
| 695 | chr8 | 137918000 | 137919000 | 0.000 | 0.040 | FAM135B | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 696 | chr8 | 138274000 | 138275000 | 0.000 | 0.000 | FAM135B | 1.00000 | 0 |
| 697 | chr8 | 143183000 | 143184000 | 0.000 | 0.040 | TSNARE1 | 1.00000 | 0 |
| 698 | chr8 | 144123000 | 144124000 | 0.000 | 0.040 | C8orf31 | 1.00000 | 0 |
| 699 | chr9 | 6411000 | 6412000 | 0.040 | 0.040 | UHRF2 | 1.00000 | 0 |
| 700 | chr9 | 6413000 | 6414000 | 0.040 | 0.040 | UHRF2 | 1.00000 | 0 |
| 701 | chr9 | 6414000 | 6415000 | 0.000 | 0.000 | UHRF2 | 1.00000 | 0 |
| 702 | chr9 | 9928000 | 9929000 | 0.000 | 0.000 | PTPRD | 1.00000 | 0 |
| 703 | chr9 | 13965000 | 13966000 | 0.040 | 0.000 | NFIB | 1.00000 | 0 |
| 704 | chr9 | 22824000 | 22825000 | 0.040 | 0.000 | DMRTA1 | 1.00000 | 0 |
| 705 | chr9 | 25260000 | 25261000 | 0.040 | 0.000 | TUSC1 | 1.00000 | 0 |
| 706 | chr9 | 29890000 | 29891000 | 0.040 | 0.000 | LINGO2 | 1.00000 | 0 |
| 707 | chr9 | 30656000 | 30657000 | 0.000 | 0.040 | ACO1 | 1.00000 | 0 |
| 708 | chr9 | 37003000 | 37004000 | 0.040 | 0.000 | PAX5 | 1.00000 | 1 |
| 709 | chr9 | 37005000 | 37006000 | 0.040 | 0.000 | PAX5 | 1.00000 | 1 |
| 710 | chr9 | 37024000 | 37025000 | 0.040 | 0.040 | PAX5 | 1.00000 | 1 |
| 711 | chr9 | 37025000 | 37026000 | 0.160 | 0.120 | PAX5 | 1.00000 | 1 |
| 712 | chr9 | 37026000 | 37027000 | 0.240 | 0.120 | PAX5 | 0.46349 | 1 |
| 713 | chr9 | 37027000 | 37028000 | 0.080 | 0.040 | PAX5 | 1.00000 | 1 |
| 714 | chr9 | 37033000 | 37034000 | 0.120 | 0.040 | PAX5 | 0.60921 | 1 |
| 715 | chr9 | 37034000 | 37035000 | 0.120 | 0.040 | PAX5 | 0.60921 | 1 |
| 716 | chr9 | 37035000 | 37036000 | 0.000 | 0.040 | PAX5 | 1.00000 | 1 |
| 717 | chr9 | 37196000 | 37197000 | 0.040 | 0.000 | ZCCHC7 | 1.00000 | 0 |
| 718 | chr9 | 37197000 | 37198000 | 0.040 | 0.000 | ZCCHC7 | 1.00000 | 0 |
| 719 | chr9 | 37293000 | 37294000 | 0.000 | 0.000 | ZCCHC7 | 1.00000 | 0 |
| 720 | chr9 | 37294000 | 37295000 | 0.080 | 0.000 | ZCCHC7 | 0.48980 | 0 |
| 721 | chr9 | 37327000 | 37328000 | 0.040 | 0.000 | ZCCHC7 | 1.00000 | 0 |
| 722 | chr9 | 37336000 | 37337000 | 0.080 | 0.000 | ZCCHC7 | 0.48980 | 0 |
| 723 | chr9 | 37337000 | 37338000 | 0.000 | 0.000 | ZCCHC7 | 1.00000 | 0 |
| 724 | chr9 | 37338000 | 37339000 | 0.000 | 0.040 | ZCCHC7 | 1.00000 | 0 |
| 725 | chr9 | 37369000 | 37370000 | 0.040 | 0.000 | ZCCHC7 | 1.00000 | 0 |
| 726 | chr9 | 37371000 | 37372000 | 0.080 | 0.080 | ZCCHC7 | 1.00000 | 0 |
| 727 | chr9 | 37372000 | 37373000 | 0.000 | 0.000 | ZCCHC7 | 1.00000 | 0 |
| 728 | chr9 | 37383000 | 37384000 | 0.080 | 0.080 | ZCCHC7 | 1.00000 | 0 |
| 729 | chr9 | 37384000 | 37385000 | 0.120 | 0.040 | ZCCHC7 | 0.60921 | 0 |
| 730 | chr9 | 37385000 | 37386000 | 0.040 | 0.000 | ZCCHC7 | 1.00000 | 0 |
| 731 | chr9 | 37387000 | 37388000 | 0.080 | 0.040 | ZCCHC7 | 1.00000 | 0 |
| 732 | chr9 | 37397000 | 37398000 | 0.040 | 0.120 | GRHPR | 0.60921 | 0 |
| 733 | chr9 | 37398000 | 37399000 | 0.040 | 0.000 | GRHPR | 1.00000 | 0 |
| 734 | chr9 | 37399000 | 37400000 | 0.080 | 0.000 | GRHPR | 0.48980 | 0 |
| 735 | chr9 | 37402000 | 37403000 | 0.000 | 0.040 | GRHPR | 1.00000 | 0 |
| 736 | chr9 | 37406000 | 37407000 | 0.000 | 0.040 | GRHPR | 1.00000 | 0 |
| 737 | chr9 | 37407000 | 37408000 | 0.200 | 0.080 | GRHPR | 0.41743 | 0 |
| 738 | chr9 | 37408000 | 37409000 | 0.080 | 0.000 | GRHPR | 0.48980 | 0 |
| 739 | chr9 | 37410000 | 37411000 | 0.000 | 0.000 | GRHPR | 1.00000 | 0 |
| 740 | chr9 | 37424000 | 37425000 | 0.040 | 0.040 | GRHPR | 1.00000 | 0 |
| 741 | chr9 | 37425000 | 37426000 | 0.000 | 0.040 | GRHPR | 1.00000 | 0 |
| 742 | chr9 | 112811000 | 112812000 | 0.080 | 0.080 | AKAP2 | 1.00000 | 0 |
| 743 | chr9 | 117037000 | 117038000 | 0.000 | 0.040 | COL27A1 | 1.00000 | 0 |
| 744 | chr9 | 119779000 | 119780000 | 0.040 | 0.000 | ASTN2 | 1.00000 | 0 |
| 745 | chr9 | 126232000 | 126233000 | 0.040 | 0.000 | DENND1A | 1.00000 | 0 |
| 746 | chr9 | 130741000 | 130742000 | 0.040 | 0.000 | FAM102A | 1.00000 | 1 |
| 747 | chr9 | 130742000 | 130743000 | 0.040 | 0.080 | FAM102A | 1.00000 | 1 |
| 748 | chr9 | 132767000 | 132768000 | 0.000 | 0.040 | FNBP1 | 1.00000 | 0 |
| 749 | chr9 | 132785000 | 132786000 | 0.040 | 0.000 | FNBP1 | 1.00000 | 0 |
| 760 | chr9 | 132803000 | 132804000 | 0.000 | 0.040 | FNBP1 | 1.00000 | 0 |
| 751 | chr9 | 132804000 | 132805000 | 0.040 | 0.120 | FNBP1 | 0.60921 | 0 |
| 752 | chr9 | 134551000 | 134552000 | 0.040 | 0.000 | RAPGEF1 | 1.00000 | 0 |
| 753 | chr9 | 138874000 | 138875000 | 0.000 | 0.040 | URAC1 | 1.00000 | 0 |
| 764 | chr10 | 3333000 | 3334000 | 0.000 | 0.000 | PITRM1 | 1.00000 | 0 |
| 755 | chr10 | 5707000 | 5708000 | 0.040 | 0.040 | ASB13 | 1.00000 | 0 |
| 756 | chr10 | 5728000 | 5729000 | 0.000 | 0.040 | ASB13 | 1.00000 | 0 |
| 757 | chr10 | 15393000 | 15394000 | 0.000 | 0.000 | FAM171A1 | 1.00000 | 0 |
| 758 | chr10 | 20796000 | 20797000 | 0.040 | 0.000 | PLXDC2 | 1.00000 | 0 |
| 759 | chr10 | 35424000 | 35425000 | 0.000 | 0.000 | CREM | 1.00000 | 0 |
| 760 | chr10 | 56678000 | 56679000 | 0.000 | 0.000 | PCDH15 | 1.00000 | 0 |
| 761 | chr10 | 63440000 | 63441000 | 0.000 | 0.040 | C10orf107 | 1.00000 | 0 |
| 762 | chr10 | 63659000 | 63660000 | 0.040 | 0.000 | ARID5B | 1.00000 | 1 |
| 763 | chr10 | 63660000 | 63661000 | 0.040 | 0.080 | ARID5B | 1.00000 | 1 |
| 764 | chr10 | 63662000 | 63663000 | 0.000 | 0.000 | ARID5B | 1.00000 | 1 |
| 765 | chr10 | 63720000 | 63721000 | 0.000 | 0.000 | ARID5B | 1.00000 | 1 |
| 766 | chr10 | 63803000 | 63804000 | 0.000 | 0.000 | ARID5B | 1.00000 | 1 |
| 767 | chr10 | 63809000 | 63810000 | 0.000 | 0.080 | ARID5B | 0.48980 | 1 |
| 768 | chr10 | 63810000 | 63811000 | 0.000 | 0.040 | ARID5B | 1.00000 | 1 |
| 769 | chr10 | 67907000 | 67908000 | 0.000 | 0.040 | CTNNA3 | 1.00000 | 0 |
| 770 | chr10 | 68474000 | 68475000 | 0.000 | 0.000 | CTNNA3 | 1.00000 | 0 |
| 771 | chr10 | 98510000 | 98511000 | 0.080 | 0.000 | PIK3AP1 | 0.48980 | 0 |
| 772 | chr10 | 101384000 | 101385000 | 0.000 | 0.000 | SLC25A28 | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 773 | chr10 | 108276000 | 108277000 | 0.040 | 0.000 | SORCS1 | 1.00000 | 0 |
| 774 | chr10 | 113473000 | 113474000 | 0.040 | 0.040 | GPAM | 1.00000 | 0 |
| 775 | chr10 | 113636000 | 113637000 | 0.040 | 0.000 | GPAM | 1.00000 | 0 |
| 776 | chr10 | 116458000 | 116459000 | 0.000 | 0.040 | ABLIM1 | 1.00000 | 0 |
| 777 | chr10 | 121623000 | 121624000 | 0.040 | 0.000 | MCMBP | 1.00000 | 0 |
| 778 | chr10 | 132973000 | 132974000 | 0.040 | 0.000 | TCERG1L | 1.00000 | 0 |
| 779 | chr10 | 134326000 | 134327000 | 0.000 | 0.000 | INPP5A | 1.00000 | 0 |
| 780 | chr11 | 871000 | 872000 | 0.040 | 0.040 | CHID1 | 1.00000 | 0 |
| 781 | chr11 | 1149000 | 1150000 | 0.000 | 0.000 | MUC5AC | 1.00000 | 0 |
| 782 | chr11 | 25065000 | 25066000 | 0.040 | 0.000 | LUZP2 | 1.00000 | 0 |
| 783 | chr11 | 25289000 | 25290000 | 0.040 | 0.040 | LUZP2 | 1.00000 | 0 |
| 784 | chr11 | 27216000 | 27217000 | 0.000 | 0.040 | BBOX1 | 1.00000 | 0 |
| 785 | chr11 | 28849000 | 28850000 | 0.000 | 0.000 | METTL15 | 1.00000 | 0 |
| 786 | chr11 | 29253000 | 29254000 | 0.040 | 0.000 | KCNA4 | 1.00000 | 0 |
| 787 | chr11 | 29900000 | 29901000 | 0.000 | 0.000 | KCNA4 | 1.00000 | 0 |
| 788 | chr11 | 40626000 | 40627000 | 0.000 | 0.000 | LRRC4C | 1.00000 | 0 |
| 789 | chr11 | 40845000 | 40846000 | 0.000 | 0.000 | LRRC4C | 1.00000 | 0 |
| 790 | chr11 | 40868000 | 40869000 | 0.000 | 0.000 | LRRC4C | 1.00000 | 0 |
| 791 | chr11 | 41066000 | 41067000 | 0.000 | 0.000 | LRRC4C | 1.00000 | 0 |
| 792 | chr11 | 41844000 | 41845000 | 0.000 | 0.000 | API5 | 1.00000 | 0 |
| 793 | chr11 | 57171000 | 57172000 | 0.040 | 0.000 | SLC43A3 | 1.00000 | 0 |
| 794 | chr11 | 60224000 | 60225000 | 0.040 | 0.080 | MS4A1 | 1.00000 | 1 |
| 795 | chr11 | 65190000 | 65191000 | 0.080 | 0.120 | FRMD8 | 1.00000 | 0 |
| 796 | chr11 | 65191000 | 65192000 | 0.080 | 0.120 | FRMD8 | 1.00000 | 0 |
| 797 | chr11 | 65266000 | 65267000 | 0.000 | 0.040 | SCYL1 | 1.00000 | 0 |
| 798 | chr11 | 65267000 | 65268000 | 0.120 | 0.040 | SCYL1 | 0.60921 | 0 |
| 799 | chr11 | 85963000 | 85964000 | 0.000 | 0.000 | EED | 1.00000 | 0 |
| 800 | chr11 | 92261000 | 92262000 | 0.000 | 0.040 | FAT3 | 1.00000 | 0 |
| 801 | chr11 | 102117000 | 102118000 | 0.000 | 0.000 | YAP1 | 1.00000 | 0 |
| 802 | chr11 | 102188000 | 102189000 | 0.200 | 0.280 | BIRC3 | 0.74164 | 1 |
| 803 | chr11 | 102189000 | 102190000 | 0.040 | 0.080 | BIRC3 | 1.00000 | 1 |
| 804 | chr11 | 107497000 | 107498000 | 0.000 | 0.000 | ELMOD1 | 1.00000 | 0 |
| 805 | chr11 | 108781000 | 108782000 | 0.000 | 0.040 | DDX10 | 1.00000 | 0 |
| 806 | chr11 | 108975000 | 108976000 | 0.040 | 0.000 | DDX10 | 1.00000 | 0 |
| 807 | chr11 | 109066000 | 109067000 | 0.000 | 0.000 | C11orf87 | 1.00000 | 0 |
| 808 | chr11 | 111248000 | 111249000 | 0.000 | 0.040 | POU2AF1 | 1.00000 | 1 |
| 809 | chr11 | 111249000 | 111250000 | 0.120 | 0.160 | POU2AF1 | 1.00000 | 1 |
| 810 | chr11 | 115761000 | 115762000 | 0.000 | 0.040 | CADM1 | 1.00000 | 0 |
| 811 | chr11 | 118723000 | 118724000 | 0.040 | 0.000 | CXCR5 | 1.00000 | 0 |
| 812 | chr11 | 126496000 | 126497000 | 0.040 | 0.000 | KIRREL3 | 1.00000 | 0 |
| 813 | chr11 | 128390000 | 128391000 | 0.040 | 0.040 | ETS1 | 1.00000 | 1 |
| 814 | chr11 | 128391000 | 128392000 | 0.160 | 0.040 | ETS1 | 0.34868 | 1 |
| 815 | chr12 | 6554000 | 6555000 | 0.000 | 0.040 | CD27 | 1.00000 | 0 |
| 816 | chr12 | 8762000 | 8763000 | 0.040 | 0.000 | AICDA | 1.00000 | 0 |
| 817 | chr12 | 8763000 | 8764000 | 0.080 | 0.040 | AICDA | 1.00000 | 0 |
| 818 | chr12 | 8764000 | 8765000 | 0.080 | 0.000 | AICDA | 0.48980 | 0 |
| 819 | chr12 | 8765000 | 8766000 | 0.040 | 0.000 | AICDA | 1.00000 | 0 |
| 820 | chr12 | 9823000 | 9824000 | 0.040 | 0.000 | CLEC2D | 1.00000 | 0 |
| 821 | chr12 | 11710000 | 11711000 | 0.000 | 0.040 | ETV6 | 1.00000 | 1 |
| 822 | chr12 | 11803000 | 11804000 | 0.040 | 0.000 | ETV6 | 1.00000 | 1 |
| 823 | chr12 | 14923000 | 14924000 | 0.040 | 0.040 | HIST4H4 | 1.00000 | 1 |
| 824 | chr12 | 16717000 | 16718000 | 0.000 | 0.000 | LMO3 | 1.00000 | 0 |
| 825 | chr12 | 23805000 | 23806000 | 0.000 | 0.040 | SOX5 | 1.00000 | 0 |
| 826 | chr12 | 25149000 | 25150000 | 0.000 | 0.040 | C12orf77 | 1.00000 | 0 |
| 827 | chr12 | 25151000 | 25152000 | 0.000 | 0.040 | C12orf77 | 1.00000 | 0 |
| 828 | chr12 | 25174000 | 25175000 | 0.040 | 0.040 | C12orf77 | 1.00000 | 0 |
| 829 | chr12 | 25205000 | 25206000 | 0.040 | 0.040 | LRMP | 1.00000 | 1 |
| 830 | chr12 | 25206000 | 25207000 | 0.080 | 0.120 | LRMP | 1.00000 | 1 |
| 831 | chr12 | 25207000 | 25208000 | 0.080 | 0.120 | LRMP | 1.00000 | 1 |
| 832 | chr12 | 25208000 | 25209000 | 0.000 | 0.040 | LRMP | 1.00000 | 1 |
| 833 | chr12 | 25665000 | 25666000 | 0.000 | 0.000 | IFLTD1 | 1.00000 | 0 |
| 834 | chr12 | 38920000 | 38921000 | 0.000 | 0.000 | CPNE8 | 1.00000 | 0 |
| 835 | chr12 | 48027000 | 48028000 | 0.080 | 0.080 | RPAP3 | 1.00000 | 0 |
| 836 | chr12 | 57496000 | 57497000 | 0.040 | 0.000 | STAT6 | 1.00000 | 0 |
| 837 | chr12 | 69203000 | 69204000 | 0.040 | 0.040 | MDM2 | 1.00000 | 0 |
| 838 | chr12 | 76202000 | 76203000 | 0.000 | 0.000 | PHLDA1 | 1.00000 | 0 |
| 839 | chr12 | 79270000 | 79271000 | 0.000 | 0.000 | SYT1 | 1.00000 | 0 |
| 840 | chr12 | 82572000 | 82573000 | 0.000 | 0.040 | CCDC59 | 1.00000 | 0 |
| 841 | chr12 | 84837000 | 84838000 | 0.000 | 0.000 | SLC6A15 | 1.00000 | 0 |
| 842 | chr12 | 86114000 | 86115000 | 0.040 | 0.000 | RASSF9 | 1.00000 | 0 |
| 843 | chr12 | 86115000 | 86116000 | 0.040 | 0.000 | RASSF9 | 1.00000 | 0 |
| 844 | chr12 | 92538000 | 92539000 | 0.080 | 0.080 | BTG1 | 1.00000 | 1 |
| 845 | chr12 | 92539000 | 92540000 | 0.080 | 0.040 | BTG1 | 1.00000 | 1 |
| 846 | chr12 | 96030000 | 96031000 | 0.000 | 0.040 | NTN4 | 1.00000 | 0 |
| 847 | chr12 | 110171000 | 110172000 | 0.000 | 0.040 | FAM222A | 1.00000 | 0 |
| 848 | chr12 | 110980000 | 110981000 | 0.000 | 0.040 | PPTC7 | 1.00000 | 0 |
| 849 | chr12 | 113493000 | 113494000 | 0.080 | 0.000 | DTX1 | 0.48980 | 1 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 850 | chr12 | 113494000 | 113495000 | 0.240 | 0.040 | DTX1 | 0.09878 | 1 |
| 851 | chr12 | 113495000 | 113496000 | 0.160 | 0.080 | DTX1 | 0.66710 | 1 |
| 852 | chr12 | 113496000 | 113497000 | 0.160 | 0.040 | DTX1 | 0.34868 | 1 |
| 853 | chr12 | 113497000 | 113498000 | 0.080 | 0.040 | DTX1 | 1.00000 | 1 |
| 854 | chr12 | 113499000 | 113500000 | 0.000 | 0.000 | DTX1 | 1.00000 | 1 |
| 855 | chr12 | 113512000 | 113513000 | 0.000 | 0.000 | DTX1 | 1.00000 | 1 |
| 856 | chr12 | 115966000 | 115967000 | 0.000 | 0.000 | MED13L | 1.00000 | 0 |
| 857 | chr12 | 122432000 | 122433000 | 0.040 | 0.000 | WDR66 | 1.00000 | 0 |
| 858 | chr12 | 122433000 | 122434000 | 0.080 | 0.000 | WDR66 | 0.48980 | 0 |
| 859 | chr12 | 122447000 | 122448000 | 0.040 | 0.000 | WDR66 | 1.00000 | 0 |
| 860 | chr12 | 122458000 | 122459000 | 0.080 | 0.120 | BCL7A | 1.00000 | 1 |
| 861 | chr12 | 122459000 | 122460000 | 0.240 | 0.320 | BCL7A | 0.75361 | 1 |
| 862 | chr12 | 122460000 | 122461000 | 0.120 | 0.280 | BCL7A | 0.28902 | 1 |
| 863 | chr12 | 122461000 | 122462000 | 0.240 | 0.240 | BCL7A | 1.00000 | 1 |
| 864 | chr12 | 122462000 | 122463000 | 0.160 | 0.200 | BCL7A | 1.00000 | 1 |
| 865 | chr12 | 122463000 | 122464000 | 0.120 | 0.200 | BCL7A | 0.70194 | 1 |
| 866 | chr12 | 124054000 | 124055000 | 0.000 | 0.080 | TMED2 | 0.48980 | 0 |
| 867 | chr12 | 127965000 | 127966000 | 0.000 | 0.000 | TMEM132C | 1.00000 | 0 |
| 868 | chr12 | 131303000 | 131304000 | 0.000 | 0.120 | STX2 | 0.23469 | 0 |
| 869 | chr12 | 131649000 | 131650000 | 0.000 | 0.000 | GPR133 | 1.00000 | 0 |
| 870 | chr12 | 133306000 | 133307000 | 0.000 | 0.000 | ANKLE2 | 1.00000 | 0 |
| 871 | chr13 | 21913000 | 21914000 | 0.040 | 0.040 | ZDHHC20 | 1.00000 | 0 |
| 872 | chr13 | 32116000 | 32117000 | 0.040 | 0.040 | RXFP2 | 1.00000 | 0 |
| 873 | chr13 | 35498000 | 35499000 | 0.000 | 0.000 | NBEA | 1.00000 | 0 |
| 874 | chr13 | 38371000 | 38372000 | 0.040 | 0.000 | TRPC4 | 1.00000 | 0 |
| 875 | chr13 | 38630000 | 38631000 | 0.040 | 0.000 | TRPC4 | 1.00000 | 0 |
| 876 | chr13 | 41156000 | 41157000 | 0.000 | 0.040 | FOXO1 | 1.00000 | 1 |
| 877 | chr13 | 41240000 | 41241000 | 0.000 | 0.040 | FOXO1 | 1.00000 | 1 |
| 878 | chr13 | 46958000 | 46959000 | 0.000 | 0.000 | KIAA0226L | 1.00000 | 0 |
| 879 | chr13 | 46959000 | 46960000 | 0.040 | 0.000 | KIAA0226L | 1.00000 | 0 |
| 880 | chr13 | 46960000 | 46961000 | 0.160 | 0.040 | KIAA0226L | 0.34868 | 0 |
| 881 | chr13 | 46961000 | 46962000 | 0.000 | 0.040 | KIAA0226L | 1.00000 | 0 |
| 882 | chr13 | 46962000 | 46963000 | 0.000 | 0.040 | KIAA0226L | 1.00000 | 0 |
| 883 | chr13 | 55239000 | 55240000 | 0.040 | 0.000 | OLFM4 | 1.00000 | 0 |
| 884 | chr13 | 55386000 | 55387000 | 0.040 | 0.000 | OLFM4 | 1.00000 | 0 |
| 885 | chr13 | 55598000 | 55599000 | 0.000 | 0.000 | OLFM4 | 1.00000 | 0 |
| 886 | chr13 | 57222000 | 57223000 | 0.000 | 0.040 | PRR20A;PRR20DPRR20BPRR20E;TDRD3 | 1.00000 | 0 |
| 887 | chr13 | 61343000 | 61343000 | 0.000 | 0.000 |  | 1.00000 | 0 |
| 888 | chr13 | 62830000 | 62831000 | 0.000 | 0.000 | PCDH20 | 1.00000 | 0 |
| 889 | chr13 | 63049000 | 63050000 | 0.080 | 0.000 | PCDH20 | 0.48980 | 0 |
| 890 | chr13 | 63157000 | 63158000 | 0.000 | 0.000 | AL445989.1 | 1.00000 | 0 |
| 891 | chr13 | 63214000 | 63215000 | 0.040 | 0.000 | AL445989.1 | 1.00000 | 0 |
| 892 | chr13 | 64802000 | 64803000 | 0.040 | 0.040 | AL445989.1 | 1.00000 | 0 |
| 893 | chr13 | 65637000 | 65638000 | 0.000 | 0.040 | PCDH9 | 1.00000 | 0 |
| 894 | chr13 | 68656000 | 68657000 | 0.000 | 0.000 | PCDH9 | 1.00000 | 0 |
| 895 | chr13 | 69418000 | 69419000 | 0.000 | 0.000 | KLHL1 | 1.00000 | 0 |
| 896 | chr13 | 70956000 | 70957000 | 0.040 | 0.000 | KLHL1 | 1.00000 | 0 |
| 897 | chr13 | 74542000 | 74543000 | 0.000 | 0.040 | KLF12 | 1.00000 | 0 |
| 898 | chr13 | 75983000 | 75984000 | 0.000 | 0.040 | TBC1D4 | 1.00000 | 0 |
| 899 | chr13 | 75984000 | 75985000 | 0.000 | 0.160 | TBC1D4 | 0.10986 | 0 |
| 900 | chr13 | 83450000 | 83451000 | 0.000 | 0.000 | SLITRK1 | 1.00000 | 0 |
| 901 | chr13 | 84641000 | 84642000 | 0.040 | 0.000 | SLITRK1 | 1.00000 | 0 |
| 902 | chr13 | 87793000 | 87794000 | 0.040 | 0.000 | SLITRK5 | 1.00000 | 0 |
| 903 | chr13 | 91480000 | 91481000 | 0.000 | 0.000 | GPC5 | 1.00000 | 0 |
| 904 | chr13 | 106081000 | 106082000 | 0.040 | 0.000 | DAOA | 1.00000 | 0 |
| 905 | chr13 | 114786000 | 114787000 | 0.040 | 0.000 | RASA3 | 1.00000 | 0 |
| 906 | chr13 | 114916000 | 114917000 | 0.000 | 0.000 | RASA3 | 1.00000 | 0 |
| 907 | chr14 | 22948000 | 22949000 | 0.040 | 0.000 | TRAJ56 | 1.00000 | 0 |
| 908 | chr14 | 22949000 | 22950000 | 0.040 | 0.000 | TRAJ56 | 1.00000 | 0 |
| 909 | chr14 | 22950000 | 22951000 | 0.040 | 0.000 | TRAJ54 | 1.00000 | 0 |
| 910 | chr14 | 22977000 | 22978000 | 0.000 | 0.040 | TRAJ33 | 1.00000 | 0 |
| 911 | chr14 | 27286000 | 27287000 | 0.000 | 0.000 | NOVA1 | 1.00000 | 0 |
| 912 | chr14 | 28645000 | 28646000 | 0.000 | 0.000 | FOXG1 | 1.00000 | 0 |
| 913 | chr14 | 49407000 | 49408000 | 0.000 | 0.000 | RPS29 | 1.00000 | 0 |
| 914 | chr14 | 50864000 | 50865000 | 0.000 | 0.000 | CDKL1 | 1.00000 | 0 |
| 915 | chr14 | 54812000 | 54813000 | 0.000 | 0.000 | CDKN3 | 1.00000 | 0 |
| 916 | chr14 | 55348000 | 55349000 | 0.040 | 0.000 | GCH1 | 1.00000 | 0 |
| 917 | chr14 | 59827000 | 59828000 | 0.000 | 0.040 | DAAM1 | 1.00000 | 0 |
| 918 | chr14 | 63143000 | 63144000 | 0.000 | 0.040 | KCNH5 | 1.00000 | 0 |
| 919 | chr14 | 64194000 | 64195000 | 0.000 | 0.040 | SGPP1 | 1.00000 | 0 |
| 920 | chr14 | 69258000 | 69259000 | 0.240 | 0.200 | ZFP36L1 | 1.00000 | 1 |
| 921 | chr14 | 69259000 | 69260000 | 0.360 | 0.240 | ZFP36L1 | 0.53803 | 1 |
| 922 | chr14 | 78418000 | 78419000 | 0.000 | 0.040 | ADCK1 | 1.00000 | 0 |
| 923 | chr14 | 81685000 | 81686000 | 0.000 | 0.040 | GTF2A1 | 1.00000 | 0 |
| 924 | chr14 | 84420000 | 84421000 | 0.040 | 0.000 | FLRT2 | 1.00000 | 0 |
| 925 | chr14 | 91883000 | 91884000 | 0.040 | 0.000 | CCDC88C | 1.00000 | 0 |

TABLE 2-continued

| # | Chromosome | Region Start | Region End | ABC-subtype | GCB-subtype | ClosestGene | p_ABC_vs_GCB | Previously-lyIdentified |
|---|---|---|---|---|---|---|---|---|
| 926 | chr14 | 94941000 | 94942000 | 0.000 | 0.120 | SERPINA9 | 0.23469 | 1 |
| 927 | chr14 | 94942000 | 94943000 | 0.040 | 0.200 | SERPINA9 | 0.18946 | 1 |
| 928 | chr14 | 96179000 | 96180000 | 0.160 | 0.120 | TCL1A | 1.00000 | 1 |
| 929 | chr14 | 96180000 | 96181000 | 0.080 | 0.160 | TCL1A | 0.66710 | 1 |
| 930 | chr14 | 101597000 | 101598000 | 0.000 | 0.000 | AL117190.3 | 1.00000 | 0 |
| 931 | chr14 | 102285000 | 102286000 | 0.040 | 0.000 | PPP2R5C | 1.00000 | 0 |
| 932 | chr14 | 105954000 | 105955000 | 0.040 | 0.040 | CRIP1 | 1.00000 | 0 |
| 933 | chr14 | 106031000 | 106032000 | 0.040 | 0.000 | IGHA2 | 1.00000 | 0 |
| 934 | chr14 | 106042000 | 106043000 | 0.080 | 0.200 | IGHA2 | 0.41743 | 0 |
| 935 | chr14 | 106048000 | 106049000 | 0.040 | 0.040 | IGHA2 | 1.00000 | 0 |
| 936 | chr14 | 106054000 | 106055000 | 0.040 | 0.040 | IGHA2 | 1.00000 | 0 |
| 937 | chr14 | 106055000 | 106056000 | 0.080 | 0.240 | IGHA2 | 0.24672 | 0 |
| 938 | chr14 | 106056000 | 106057000 | 0.040 | 0.200 | IGHA2 | 0.18946 | 0 |
| 939 | chr14 | 106057000 | 106058000 | 0.000 | 0.080 | IGHA2 | 0.48980 | 0 |
| 940 | chr14 | 106058000 | 106059000 | 0.000 | 0.080 | IGHA2 | 0.48980 | 0 |
| 941 | chr14 | 106066000 | 106067000 | 0.000 | 0.120 | IGHE | 0.23469 | 0 |
| 942 | chr14 | 106067000 | 106068000 | 0.000 | 0.120 | IGHE | 0.23469 | 0 |
| 943 | chr14 | 106068000 | 106069000 | 0.040 | 0.120 | IGHE | 0.60921 | 0 |
| 944 | chr14 | 106069000 | 106070000 | 0.040 | 0.200 | IGHE | 0.18946 | 0 |
| 945 | chr14 | 106070000 | 106071000 | 0.000 | 0.160 | IGHE | 0.10986 | 0 |
| 946 | chr14 | 106071000 | 106072000 | 0.000 | 0.160 | IGHE | 0.10986 | 0 |
| 947 | chr14 | 106072000 | 106073000 | 0.000 | 0.120 | IGHE | 0.23469 | 0 |
| 948 | chr14 | 106082000 | 106083000 | 0.000 | 0.000 | IGHG4 | 1.00000 | 0 |
| 949 | chr14 | 106092000 | 106093000 | 0.040 | 0.000 | IGHG4 | 1.00000 | 0 |
| 950 | chr14 | 106094000 | 106095000 | 0.160 | 0.200 | IGHG4 | 1.00000 | 0 |
| 951 | chr14 | 106095000 | 106096000 | 0.080 | 0.160 | IGHG4 | 0.66710 | 0 |
| 952 | chr14 | 106110000 | 106111000 | 0.080 | 0.040 | IGHG2 | 1.00000 | 0 |
| 953 | chr14 | 106111000 | 106112000 | 0.000 | 0.040 | IGHG2 | 1.00000 | 0 |
| 954 | chr14 | 106112000 | 106113000 | 0.280 | 0.200 | IGHG2 | 0.74164 | 0 |
| 955 | chr14 | 106113000 | 106114000 | 0.240 | 0.320 | IGHG2 | 0.75361 | 0 |
| 956 | chr14 | 106114000 | 106115000 | 0.320 | 0.200 | IGHG2 | 0.52019 | 0 |
| 957 | chr14 | 106146000 | 106147000 | 0.000 | 0.000 | IGHA1 | 1.00000 | 0 |
| 958 | chr14 | 106151000 | 106157000 | 0.040 | 0.000 | IGHA1 | 1.00000 | 0 |
| 959 | chr14 | 106152000 | 106153000 | 0.040 | 0.000 | IGHA1 | 1.00000 | 0 |
| 960 | chr14 | 106161000 | 106162000 | 0.000 | 0.040 | IGHA1 | 1.00000 | 0 |
| 961 | chr14 | 106173000 | 106174000 | 0.040 | 0.040 | IGHA1 | 1.00000 | 0 |
| 962 | chr14 | 106174000 | 106175000 | 0.040 | 0.000 | IGHA1 | 1.00000 | 0 |
| 963 | chr14 | 106175000 | 106176000 | 0.040 | 0.000 | IGHA1 | 1.00000 | 0 |
| 964 | chr14 | 106176000 | 106177000 | 0.080 | 0.040 | IGHA1 | 1.00000 | 0 |
| 965 | chr14 | 106177000 | 106178000 | 0.000 | 0.000 | IGHA1 | 1.00000 | 0 |
| 966 | chr14 | 106178000 | 106179000 | 0.120 | 0.000 | IGHA1 | 0.23469 | 0 |
| 967 | chr14 | 106208000 | 106209000 | 0.040 | 0.040 | IGHG1 | 1.00000 | 0 |
| 968 | chr14 | 106209000 | 106210000 | 0.160 | 0.080 | IGHG1 | 0.66710 | 0 |
| 969 | chr14 | 106210000 | 106211000 | 0.160 | 0.120 | IGHG1 | 1.00000 | 0 |
| 970 | chr14 | 106211000 | 106212000 | 0.440 | 0.120 | IGHG1 | 0.02548 | 0 |
| 971 | chr14 | 106212000 | 106213000 | 0.520 | 0.120 | IGHG1 | 0.00544 | 0 |
| 972 | chr14 | 106213000 | 106214000 | 0.520 | 0.120 | IGHG1 | 0.00544 | 0 |
| 973 | chr14 | 106214000 | 106215000 | 0.240 | 0.000 | IGHG1 | 0.02229 | 0 |
| 974 | chr14 | 106237000 | 106238000 | 0.080 | 0.040 | IGHG3 | 1.00000 | 0 |
| 975 | chr14 | 106238000 | 106239000 | 0.320 | 0.120 | IGHG3 | 0.17062 | 0 |
| 976 | chr14 | 106239000 | 106240000 | 0.440 | 0.040 | IGHG3 | 0.00192 | 0 |
| 977 | chr14 | 106240000 | 106241000 | 0.480 | 0.080 | IGHG3 | 0.00361 | 0 |
| 978 | chr14 | 106241000 | 106242000 | 0.320 | 0.040 | IGHG3 | 0.02322 | 0 |
| 979 | chr14 | 106242000 | 106243000 | 0.040 | 0.000 | IGHG3 | 1.00000 | 0 |
| 980 | chr14 | 106321000 | 106322000 | 0.040 | 0.000 | IGHM | 1.00000 | 0 |
| 981 | chr14 | 106322000 | 106323000 | 0.240 | 0.040 | IGHM | 0.09828 | 0 |
| 982 | chr14 | 106323000 | 106324000 | 0.400 | 0.160 | IGHM | 0.11366 | 0 |
| 983 | chr14 | 106324000 | 106325000 | 0.320 | 0.120 | IGHM | 0.17062 | 0 |
| 984 | chr14 | 106325000 | 106326000 | 0.160 | 0.320 | IGHM | 0.32089 | 0 |
| 985 | chr14 | 106326000 | 106327000 | 0.920 | 0.920 | IGHJ6 | 1.00000 | 0 |
| 986 | chr14 | 106327000 | 106328000 | 0.800 | 0.760 | IGHJ6 | 1.00000 | 0 |
| 987 | chr14 | 106328000 | 106329000 | 0.680 | 0.800 | IGHJ6 | 0.52019 | 0 |
| 988 | chr14 | 106329000 | 106330000 | 0.880 | 0.920 | IGHJ6 | 1.00000 | 0 |
| 989 | chr14 | 106330000 | 106331000 | 0.720 | 0.520 | IGHJ3; IGHJ4; IGHJ5; | 0.24363 | 0 |
| 990 | chr14 | 106331000 | 106332000 | 0.120 | 0.080 | IGHD7-27; IGHJ1; IGHJ2; | 1.00000 | 0 |
| 991 | chr14 | 106338000 | 106339000 | 0.040 | 0.000 | IGHD7-27 | 1.00000 | 0 |
| 992 | chr14 | 106350000 | 106351000 | 0.040 | 0.000 | IGHD4-23 | 1.00000 | 0 |
| 993 | chr14 | 106352000 | 106353000 | 0.000 | 0.040 | IGHD3-22 | 1.00000 | 0 |
| 994 | chr14 | 106353000 | 106354000 | 0.000 | 0.000 | IGHD2-21 | 1.00000 | 0 |
| 995 | chr14 | 106354000 | 106355000 | 0.000 | 0.040 | IGHD2-21 | 1.00000 | 0 |
| 996 | chr14 | 106355000 | 106356000 | 0.000 | 0.040 | IGHD2-21 | 1.00000 | 0 |
| 997 | chr14 | 106357000 | 106358000 | 0.040 | 0.080 | IGHD1-20; IGHD6-19; | 1.00000 | 0 |
| 998 | chr14 | 106358000 | 106359000 | 0.000 | 0.040 | IGHD5-18 | 1.00000 | 0 |
| 999 | chr14 | 106362000 | 106363000 | 0.000 | 0.000 | IGHD3-16 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 1000 | chr14 | 106364000 | 106365000 | 0.040 | 0.000 | IGHD2-15 | 1.00000 | 0 |
| 1001 | chr14 | 106367000 | 106368000 | 0.040 | 0.000 | IGHD6-13 | 1.00000 | 0 |
| 1002 | chr14 | 106370000 | 106371000 | 0.080 | 0.000 | IGHD3-10; IGHD3-9; | 0.48980 | 0 |
| 1003 | chr14 | 106371000 | 106372000 | 0.040 | 0.000 | IGHD3-9 | 1.00000 | 0 |
| 1004 | chr14 | 106372000 | 106373000 | 0.040 | 0.000 | IGHD2-8 | 1.00000 | 0 |
| 1005 | chr14 | 106375000 | 106376000 | 0.000 | 0.000 | IGHD1-7 | 1.00000 | 0 |
| 1006 | chr14 | 106376000 | 106377000 | 0.000 | 0.040 | IGHD6-6 | 1.00000 | 0 |
| 1007 | chr14 | 106380000 | 106381000 | 0.000 | 0.040 | IGHD3-3 | 1.00000 | 0 |
| 1008 | chr14 | 106381000 | 106382000 | 0.000 | 0.040 | IGHD2-2 | 1.00000 | 0 |
| 1009 | chr14 | 106382000 | 106383000 | 0.040 | 0.120 | IGHD2-2 | 0.60921 | 0 |
| 1010 | chr14 | 106383000 | 106384000 | 0.080 | 0.040 | IGHD2-2 | 1.00000 | 0 |
| 1011 | chr14 | 106384000 | 106385000 | 0.040 | 0.040 | IGHD1-1 | 1.00000 | 0 |
| 1012 | chr14 | 106385000 | 106386000 | 0.080 | 0.040 | IGHD1-1 | 1.00000 | 0 |
| 1013 | chr14 | 106387000 | 106388000 | 0.040 | 0.080 | KIAA0125 | 1.00000 | 0 |
| 1014 | chr14 | 106405000 | 106406000 | 0.000 | 0.040 | IGHV6-1 | 1.00000 | 0 |
| 1015 | chr14 | 106406000 | 106407000 | 0.000 | 0.040 | IGHV6-1 | 1.00000 | 0 |
| 1016 | chr14 | 106419000 | 106420000 | 0.000 | 0.080 | IGHV6-1 | 0.48980 | 0 |
| 1017 | chr14 | 106452000 | 106453000 | 0.040 | 0.000 | IGHV1-2 | 1.00000 | 0 |
| 1018 | chr14 | 106453000 | 106454000 | 0.080 | 0.000 | IGHV1-2 | 0.48980 | 0 |
| 1019 | chr14 | 106454000 | 106455000 | 0.040 | 0.000 | IGHV1-2 | 1.00000 | 0 |
| 1020 | chr14 | 106494000 | 106495000 | 0.000 | 0.040 | IGHV2-5 | 1.00000 | 0 |
| 1021 | chr14 | 106518000 | 106519000 | 0.000 | 0.080 | IGHV3-7 | 0.48980 | 0 |
| 1022 | chr14 | 106519000 | 106520000 | 0.000 | 0.080 | IGHV3-7 | 0.48980 | 0 |
| 1023 | chr14 | 106539000 | 106540000 | 0.000 | 0.040 | IGHV1-8 | 1.00000 | 0 |
| 1024 | chr14 | 106552000 | 106553000 | 0.000 | 0.000 | IGHV3-9 | 1.00000 | 0 |
| 1025 | chr14 | 106573000 | 106574000 | 0.040 | 0.000 | IGHV3-11 | 1.00000 | 0 |
| 1026 | chr14 | 106574000 | 106575000 | 0.040 | 0.000 | IGHV3-11 | 1.00000 | 0 |
| 1027 | chr14 | 106578000 | 106579000 | 0.040 | 0.000 | IGHV3-11 | 1.00000 | 0 |
| 1028 | chr14 | 106579000 | 106580000 | 0.040 | 0.000 | IGHV3-11 | 1.00000 | 0 |
| 1029 | chr14 | 106610000 | 106611000 | 0.000 | 0.000 | IGHV3-15 | 1.00000 | 0 |
| 1030 | chr14 | 106641000 | 106642000 | 0.040 | 0.040 | IGHV1-18 | 1.00000 | 0 |
| 1031 | chr14 | 106642000 | 106643000 | 0.040 | 0.000 | IGHV1-18 | 1.00000 | 0 |
| 1032 | chr14 | 106691000 | 106692000 | 0.000 | 0.000 | IGHV3-21 | 1.00000 | 0 |
| 1033 | chr14 | 106692000 | 106693000 | 0.000 | 0.040 | IGHV3-21 | 1.00000 | 0 |
| 1034 | chr14 | 106725000 | 106726000 | 0.120 | 0.160 | IGHV3-23 | 1.00000 | 0 |
| 1035 | chr14 | 106726000 | 106727000 | 0.040 | 0.080 | IGHV3-23 | 1.00000 | 0 |
| 1036 | chr14 | 106733000 | 106734000 | 0.000 | 0.080 | IGHV1-24 | 0.48980 | 0 |
| 1037 | chr14 | 106757000 | 106758000 | 0.000 | 0.040 | IGHV2-26 | 1.00000 | 0 |
| 1038 | chr14 | 106758000 | 106759000 | 0.000 | 0.040 | IGHV2-26 | 1.00000 | 0 |
| 1039 | chr14 | 106791000 | 106792000 | 0.040 | 0.040 | IGHV3-30 | 1.00000 | 0 |
| 1040 | chr14 | 106804000 | 106805000 | 0.040 | 0.040 | IGHV4-31 | 1.00000 | 0 |
| 1041 | chr14 | 106805000 | 106806000 | 0.040 | 0.040 | IGHV4-31 | 1.00000 | 0 |
| 1042 | chr14 | 106806000 | 106807000 | 0.000 | 0.000 | IGHV4-31 | 1.00000 | 0 |
| 1043 | chr14 | 106815000 | 106816000 | 0.000 | 0.040 | IGHV3-33 | 1.00000 | 0 |
| 1044 | chr14 | 106816000 | 106817000 | 0.000 | 0.160 | IGHV3-33 | 0.10986 | 0 |
| 1045 | chr14 | 106817000 | 106818000 | 0.000 | 0.080 | IGHV3-33 | 0.48980 | 0 |
| 1046 | chr14 | 106829000 | 106830000 | 0.160 | 0.080 | IGHV4-34 | 0.66710 | 0 |
| 1047 | chr14 | 106830000 | 106831000 | 0.160 | 0.000 | IGHV4-34 | 0.10986 | 0 |
| 1048 | chr14 | 106877000 | 106878000 | 0.040 | 0.080 | IGHV4-39 | 1.00000 | 0 |
| 1049 | chr14 | 106878000 | 106879000 | 0.000 | 0.080 | IGHV4-39 | 0.48980 | 0 |
| 1050 | chr14 | 106967000 | 106968000 | 0.040 | 0.040 | IGHV1-46 | 1.00000 | 0 |
| 1051 | chr14 | 106994000 | 106995000 | 0.000 | 0.120 | IGHV3-48 | 0.23469 | 0 |
| 1052 | chr14 | 106995000 | 106996000 | 0.000 | 0.000 | IGHV3-48 | 1.00000 | 0 |
| 1053 | chr14 | 107034000 | 107035000 | 0.040 | 0.000 | IGHV5-51 | 1.00000 | 0 |
| 1054 | chr14 | 107035000 | 107036000 | 0.080 | 0.000 | IGHV5-51 | 0.48980 | 0 |
| 1055 | chr14 | 107048000 | 107049000 | 0.000 | 0.000 | IGHV3-53 | 1.00000 | 0 |
| 1056 | chr14 | 107049000 | 107050000 | 0.000 | 0.000 | IGHV3-53 | 1.00000 | 0 |
| 1057 | chr14 | 107083000 | 107084000 | 0.040 | 0.040 | IGHV4-59 | 1.00000 | 0 |
| 1058 | chr14 | 107084000 | 107085000 | 0.000 | 0.040 | IGHV4-59 | 1.00000 | 0 |
| 1059 | chr14 | 107095000 | 107096000 | 0.040 | 0.000 | IGHV4-61 | 1.00000 | 0 |
| 1060 | chr14 | 107113000 | 107114000 | 0.080 | 0.000 | IGHV3-64 | 0.48980 | 0 |
| 1061 | chr14 | 107114000 | 107115000 | 0.080 | 0.000 | IGHV3-64 | 0.48980 | 0 |
| 1062 | chr14 | 107169000 | 107170000 | 0.200 | 0.240 | IGHV1-69 | 1.00000 | 0 |
| 1063 | chr14 | 107170000 | 107171000 | 0.360 | 0.280 | IGHV1-69 | 0.76241 | 0 |
| 1064 | chr14 | 107176000 | 107177000 | 0.200 | 0.200 | IGHV2-70 | 1.00000 | 0 |
| 1065 | chr14 | 107177000 | 107178000 | 0.080 | 0.040 | IGHV2-70 | 1.00000 | 0 |
| 1066 | chr14 | 107178000 | 107179000 | 0.200 | 0.520 | IGHV2-70 | 0.03776 | 0 |
| 1067 | chr14 | 107179000 | 107180000 | 0.240 | 0.360 | IGHV2-70 | 0.53803 | 0 |
| 1068 | chr14 | 107183000 | 107184000 | 0.040 | 0.000 | IGHV2-70 | 1.00000 | 0 |
| 1069 | chr14 | 107199000 | 107200000 | 0.000 | 0.080 | IGHV3-72 | 0.48980 | 0 |
| 1070 | chr14 | 107218000 | 107219000 | 0.000 | 0.080 | IGHV3-74 | 0.48980 | 0 |
| 1071 | chr14 | 107219000 | 107220000 | 0.000 | 0.160 | IGHV3-74 | 0.10986 | 0 |
| 1072 | chr14 | 107221000 | 107222000 | 0.000 | 0.080 | IGHV3-74 | 0.48980 | 0 |
| 1073 | chr14 | 107232000 | 107233000 | 0.000 | 0.000 | IGHV3-74 | 1.00000 | 0 |
| 1074 | chr14 | 107253000 | 107254000 | 0.000 | 0.000 | IGHV7-81 | 1.00000 | 0 |
| 1075 | chr14 | 107258000 | 107259000 | 0.000 | 0.040 | IGHV7-81 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 1076 | chr14 | 107259000 | 107260000 | 0.160 | 0.200 | IGHV7-81 | 1.00000 | 0 |
| 1077 | chr15 | 45003000 | 45004000 | 0.040 | 0.040 | B2M | 1.00000 | 0 |
| 1078 | chr15 | 45007000 | 45008000 | 0.000 | 0.000 | B2M | 1.00000 | 0 |
| 1079 | chr15 | 45814000 | 45815000 | 0.000 | 0.040 | SLC30A4 | 1.00000 | 0 |
| 1080 | chr15 | 59664000 | 59665000 | 0.000 | 0.080 | MYO1E | 0.48980 | 0 |
| 1081 | chr15 | 65588000 | 65589000 | 0.040 | 0.000 | PARP16 | 1.00000 | 0 |
| 1082 | chr15 | 78332000 | 78333000 | 0.000 | 0.000 | TBC1D2B | 1.00000 | 0 |
| 1083 | chr15 | 83227000 | 83228000 | 0.000 | 0.040 | CPEB1 | 1.00000 | 0 |
| 1084 | chr15 | 86226000 | 86227000 | 0.040 | 0.040 | AKAP13 | 1.00000 | 0 |
| 1085 | chr15 | 86233000 | 86234000 | 0.040 | 0.000 | AKAP13 | 1.00000 | 0 |
| 1086 | chr15 | 86245000 | 86246000 | 0.080 | 0.120 | AKAP13 | 1.00000 | 0 |
| 1087 | chr16 | 368000 | 369000 | 0.000 | 0.040 | AXIN1 | 1.00000 | 0 |
| 1088 | chr16 | 3788000 | 3789000 | 0.040 | 0.000 | CREBBP | 1.00000 | 0 |
| 1089 | chr16 | 10971000 | 10972000 | 0.080 | 0.120 | CIITA | 1.00000 | 1 |
| 1090 | chr16 | 10972000 | 10973000 | 0.120 | 0.320 | CIITA | 0.17062 | 1 |
| 1091 | chr16 | 10973000 | 10974000 | 0.120 | 0.240 | CIITA | 0.46349 | 1 |
| 1092 | chr16 | 10974000 | 10975000 | 0.080 | 0.120 | CIITA | 1.00000 | 1 |
| 1093 | chr16 | 11348000 | 11349000 | 0.080 | 0.200 | SOCS1 | 0.41743 | 1 |
| 1094 | chr16 | 11349000 | 11350000 | 0.120 | 0.240 | SOCS1 | 0.46349 | 1 |
| 1095 | chr16 | 21167000 | 21168000 | 0.040 | 0.000 | DNAH3 | 1.00000 | 0 |
| 1096 | chr16 | 27325000 | 27326000 | 0.000 | 0.040 | CTD-3203P2.2 | 1.00000 | 0 |
| 1097 | chr16 | 27326000 | 27327000 | 0.080 | 0.080 | CTD-3203P2.2 | 1.00000 | 0 |
| 1098 | chr16 | 27327000 | 27328000 | 0.000 | 0.000 | IL4R | 1.00000 | 0 |
| 1099 | chr16 | 27414000 | 27415000 | 0.040 | 0.000 | IL21R | 1.00000 | 0 |
| 1100 | chr16 | 29248000 | 29249000 | 0.000 | 0.000 | 61E3.4 | 1.00000 | 0 |
| 1101 | chr16 | 31910000 | 31911000 | 0.040 | 0.000 | ZNF267 | 1.00000 | 0 |
| 1102 | chr16 | 46821000 | 46822000 | 0.000 | 0.040 | C16orf87 | 1.00000 | 0 |
| 1103 | chr16 | 50985000 | 50986000 | 0.040 | 0.000 | CYLD | 1.00000 | 0 |
| 1104 | chr16 | 64351000 | 64352000 | 0.000 | 0.040 | CDH11 | 1.00000 | 0 |
| 1105 | chr16 | 78398000 | 78399000 | 0.000 | 0.000 | WWOX | 1.00000 | 0 |
| 1106 | chr16 | 78615000 | 78616000 | 0.040 | 0.000 | WWOX | 1.00000 | 0 |
| 1107 | chr16 | 78753000 | 78754000 | 0.000 | 0.040 | WWOX | 1.00000 | 0 |
| 1108 | chr16 | 78811000 | 78812000 | 0.000 | 0.040 | WWOX | 1.00000 | 0 |
| 1109 | chr16 | 79988000 | 79989000 | 0.000 | 0.040 | MAF | 1.00000 | 0 |
| 1110 | chr16 | 81836000 | 81837000 | 0.040 | 0.000 | PLCG2 | 1.00000 | 0 |
| 1111 | chr16 | 85932000 | 85933000 | 0.040 | 0.040 | IRF8 | 1.00000 | 1 |
| 1112 | chr16 | 85933000 | 85934000 | 0.080 | 0.240 | IRF8 | 0.24672 | 1 |
| 1113 | chr16 | 85934000 | 85935000 | 0.040 | 0.000 | IRF8 | 1.00000 | 1 |
| 1114 | chr16 | 85936000 | 85937000 | 0.000 | 0.000 | IRF8 | 1.00000 | 1 |
| 1115 | chr16 | 88441000 | 88442000 | 0.040 | 0.000 | ZNF469 | 1.00000 | 0 |
| 1116 | chr17 | 3598000 | 3599000 | 0.040 | 0.040 | P2RX5; P2RX5-TAX1BP3P2RX5; | 1.00000 | 0 |
| 1117 | chr17 | 17286000 | 17287000 | 0.080 | 0.000 | SMCR9 | 0.48980 | 0 |
| 1118 | chr17 | 21194000 | 21195000 | 0.000 | 0.040 | MAP2K3 | 1.00000 | 0 |
| 1119 | chr17 | 29646000 | 29647000 | 0.000 | 0.000 | EVI2A | 1.00000 | 0 |
| 1120 | chr17 | 38020000 | 38021000 | 0.000 | 0.040 | IKZF3 | 1.00000 | 0 |
| 1121 | chr17 | 43662000 | 43663000 | 0.040 | 0.000 | PLEKHM1 | 1.00000 | 0 |
| 1122 | chr17 | 56408000 | 56409000 | 0.120 | 0.040 | BZRAP1 | 0.60921 | 0 |
| 1123 | chr17 | 56409000 | 56410000 | 0.360 | 0.200 | BZRAP1 | 0.34513 | 0 |
| 1124 | chr17 | 57916000 | 57917000 | 0.040 | 0.080 | VMP1 | 1.00000 | 1 |
| 1125 | chr17 | 57917000 | 57918000 | 0.040 | 0.080 | VMP1 | 1.00000 | 1 |
| 1126 | chr17 | 62007000 | 62008000 | 0.040 | 0.000 | CD79B | 1.00000 | 0 |
| 1127 | chr17 | 62008000 | 62009000 | 0.040 | 0.000 | CD79B | 1.00000 | 0 |
| 1128 | chr17 | 63067000 | 63068000 | 0.040 | 0.000 | GNA13 | 1.00000 | 0 |
| 1129 | chr17 | 65676000 | 65677000 | 0.040 | 0.000 | PITPNC1 | 1.00000 | 0 |
| 1130 | chr17 | 69365000 | 69366000 | 0.000 | 0.040 | AC007461.1 | 1.00000 | 0 |
| 1131 | chr17 | 70083000 | 70084000 | 0.000 | 0.000 | SOX9 | 1.00000 | 0 |
| 1132 | chr17 | 74733000 | 74734000 | 0.000 | 0.000 | SRSF2 | 1.00000 | 0 |
| 1133 | chr17 | 75447000 | 75448000 | 0.080 | 0.000 | 9-Sep-19 | 0.48980 | 0 |
| 1134 | chr17 | 75448000 | 75449000 | 0.040 | 0.000 | 9-Sep-19 | 1.00000 | 0 |
| 1135 | chr17 | 76775000 | 76776000 | 0.000 | 0.000 | CYTH1 | 1.00000 | 0 |
| 1136 | chr17 | 80928000 | 80929000 | 0.000 | 0.000 | B3GNTL1 | 1.00000 | 0 |
| 1137 | chr17 | 80976000 | 80977000 | 0.000 | 0.040 | B3GNTL1 | 1.00000 | 0 |
| 1138 | chr18 | 2709000 | 2710000 | 0.000 | 0.000 | SMCHD1 | 1.00000 | 0 |
| 1139 | chr18 | 3600000 | 3601000 | 0.040 | 0.000 | DLGAP1 | 1.00000 | 0 |
| 1140 | chr18 | 12062000 | 12063000 | 0.000 | 0.000 | ANKRD62 | 1.00000 | 0 |
| 1141 | chr18 | 27771000 | 27772000 | 0.040 | 0.000 | DSC3 | 1.00000 | 0 |
| 1142 | chr18 | 28066000 | 28067000 | 0.000 | 0.040 | DSC3 | 1.00000 | 0 |
| 1143 | chr18 | 30349000 | 30350000 | 0.000 | 0.000 | AC012123.1; KLHL14; | 1.00000 | 0 |
| 1144 | chr18 | 36806000 | 36807000 | 0.040 | 0.000 | CELF4 | 1.00000 | 0 |
| 1145 | chr18 | 37751000 | 37752000 | 0.000 | 0.040 | PIK3C3 | 1.00000 | 0 |
| 1146 | chr18 | 38672000 | 38673000 | 0.000 | 0.040 | PIK3C3 | 1.00000 | 0 |
| 1147 | chr18 | 42168000 | 42169000 | 0.000 | 0.000 | SETBP1 | 1.00000 | 0 |
| 1148 | chr18 | 51952000 | 51953000 | 0.040 | 0.000 | C18orf54 | 1.00000 | 0 |
| 1149 | chr18 | 52447000 | 52448000 | 0.000 | 0.080 | RAB27B | 0.48980 | 0 |
| 1150 | chr18 | 52988000 | 52989000 | 0.040 | 0.000 | TCF4 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 1151 | chr18 | 54653000 | 54654000 | 0.000 | 0.000 | WDR7 | 1.00000 | 0 |
| 1152 | chr18 | 60794000 | 60795000 | 0.000 | 0.080 | BCL2 | 0.48980 | 1 |
| 1153 | chr18 | 60805000 | 60806000 | 0.000 | 0.000 | BCL2 | 1.00000 | 1 |
| 1154 | chr18 | 60806000 | 60807000 | 0.000 | 0.120 | BCL2 | 0.23469 | 1 |
| 1155 | chr18 | 60809000 | 60810000 | 0.000 | 0.080 | BCL2 | 0.48980 | 1 |
| 1156 | chr18 | 60821000 | 60822000 | 0.000 | 0.040 | BCL2 | 1.00000 | 1 |
| 1157 | chr18 | 60825000 | 60826000 | 0.000 | 0.080 | BCL2 | 0.48980 | 1 |
| 1158 | chr18 | 60826000 | 60827000 | 0.000 | 0.040 | BCL2 | 1.00000 | 1 |
| 1159 | chr18 | 60828000 | 60829000 | 0.000 | 0.000 | BCL2 | 1.00000 | 1 |
| 1160 | chr18 | 60873000 | 60874000 | 0.000 | 0.040 | BCL2 | 1.00000 | 1 |
| 1161 | chr18 | 60875000 | 60876000 | 0.000 | 0.000 | BCL2 | 1.00000 | 1 |
| 1162 | chr18 | 60876000 | 60877000 | 0.000 | 0.040 | BCL2 | 1.00000 | 1 |
| 1163 | chr18 | 60983000 | 60984000 | 0.000 | 0.040 | BCL2 | 1.00000 | 1 |
| 1164 | chr18 | 60984000 | 60985000 | 0.000 | 0.240 | BCL2 | 0.02229 | 1 |
| 1165 | chr18 | 60985000 | 60986000 | 0.040 | 0.320 | BCL2 | 0.02322 | 1 |
| 1166 | chr18 | 60986000 | 60987000 | 0.080 | 0.320 | BCL2 | 0.07375 | 1 |
| 1167 | chr18 | 60987000 | 60988000 | 0.080 | 0.320 | BCL2 | 0.07375 | 1 |
| 1168 | chr18 | 60988000 | 60989000 | 0.080 | 0.280 | BCL2 | 0.13833 | 1 |
| 1169 | chr18 | 61810000 | 61811000 | 0.040 | 0.000 | SERPINB8 | 1.00000 | 0 |
| 1170 | chr18 | 63080000 | 63081000 | 0.000 | 0.000 | CDH7 | 1.00000 | 0 |
| 1171 | chr18 | 63791000 | 63792000 | 0.000 | 0.000 | CDH7 | 1.00000 | 0 |
| 1172 | chr18 | 63875000 | 63876000 | 0.040 | 0.000 | CDH19 | 1.00000 | 0 |
| 1173 | chr18 | 64643000 | 64644000 | 0.000 | 0.000 | CDH19 | 1.00000 | 0 |
| 1174 | chr18 | 65863000 | 65864000 | 0.000 | 0.000 | TMX3 | 1.00000 | 0 |
| 1175 | chr18 | 66328000 | 66329000 | 0.040 | 0.000 | TMX3 | 1.00000 | 0 |
| 1176 | chr18 | 70462000 | 70463000 | 0.000 | 0.040 | NETO1 | 1.00000 | 0 |
| 1177 | chr18 | 73767000 | 73768000 | 0.040 | 0.000 | ZNF516 | 1.00000 | 0 |
| 1178 | chr18 | 76515000 | 76516000 | 0.040 | 0.000 | SALL3 | 1.00000 | 0 |
| 1179 | chr18 | 76724000 | 76725000 | 0.040 | 0.000 | SALL3 | 1.00000 | 0 |
| 1180 | chr18 | 76725000 | 76726000 | 0.040 | 0.000 | SALL3 | 1.00000 | 0 |
| 1181 | chr19 | 1612000 | 1613000 | 0.000 | 0.040 | TCF3 | 1.00000 | 0 |
| 1182 | chr19 | 2476000 | 2477000 | 0.040 | 0.040 | GADD45B | 1.00000 | 1 |
| 1183 | chr19 | 10304000 | 10305000 | 0.040 | 0.080 | DNMT1 | 1.00000 | 0 |
| 1184 | chr19 | 10305000 | 10306000 | 0.000 | 0.080 | DNMT1 | 0.48980 | 0 |
| 1185 | chr19 | 10335000 | 10336000 | 0.000 | 0.040 | S1PR2 | 1.00000 | 1 |
| 1186 | chr19 | 10340000 | 10341000 | 0.080 | 0.160 | S1PR2 | 0.66710 | 1 |
| 1187 | chr19 | 10341000 | 10342000 | 0.120 | 0.280 | S1PR2 | 0.28902 | 1 |
| 1188 | chr19 | 16030000 | 16031000 | 0.000 | 0.000 | CYP4F11 | 1.00000 | 0 |
| 1189 | chr19 | 16436000 | 16437000 | 0.040 | 0.000 | KLF2 | 1.00000 | 1 |
| 1190 | chr19 | 20889000 | 20890000 | 0.000 | 0.040 | ZNF626 | 1.00000 | 0 |
| 1191 | chr19 | 21073000 | 21074000 | 0.040 | 0.000 | ZNF85 | 1.00000 | 0 |
| 1192 | chr19 | 21092000 | 21093000 | 0.000 | 0.040 | ZNF85 | 1.00000 | 0 |
| 1193 | chr19 | 23841000 | 23842000 | 0.040 | 0.000 | ZNF675 | 1.00000 | 0 |
| 1194 | chr19 | 29256000 | 29257000 | 0.040 | 0.000 | UQCRFS1 | 1.00000 | 0 |
| 1195 | chr19 | 44183000 | 44184000 | 0.040 | 0.000 | PLAUR | 1.00000 | 0 |
| 1196 | chr19 | 50399000 | 50400000 | 0.040 | 0.040 | IL4I1 | 1.00000 | 0 |
| 1197 | chr19 | 53419000 | 53420000 | 0.000 | 0.000 | ZNF321P; ZNF816; ZNF816-ZNF321PZNF321PZNF816-ZNF321P; | 1.00000 | 0 |
| 1198 | chr20 | 15470000 | 15471000 | 0.000 | 0.040 | MACROD2 | 1.00000 | 0 |
| 1199 | chr20 | 23359000 | 23360000 | 0.000 | 0.000 | NAPB | 1.00000 | 0 |
| 1200 | chr20 | 23912000 | 23913000 | 0.000 | 0.000 | CST5 | 1.00000 | 0 |
| 1201 | chr20 | 46131000 | 46132000 | 0.040 | 0.120 | NCOA3 | 0.60921 | 1 |
| 1202 | chr20 | 49127000 | 49128000 | 0.000 | 0.000 | PTPN1 | 1.00000 | 0 |
| 1203 | chr20 | 49648000 | 49649000 | 0.040 | 0.000 | KCNG1 | 1.00000 | 0 |
| 1204 | chr20 | 61607000 | 61608000 | 0.000 | 0.000 | SLC17A9 | 1.00000 | 0 |
| 1205 | chr21 | 21597000 | 21598000 | 0.000 | 0.000 | NCAM2 | 1.00000 | 0 |
| 1206 | chr21 | 23458000 | 23459000 | 0.000 | 0.040 | NCAM2 | 1.00000 | 0 |
| 1207 | chr21 | 24998000 | 24999000 | 0.000 | 0.040 | MRPL39 | 1.00000 | 0 |
| 1208 | chr21 | 26935000 | 26936000 | 0.000 | 0.080 | MRPL39 | 0.48980 | 0 |
| 1209 | chr21 | 35779000 | 35780000 | 0.000 | 0.000 | SMIM11 | 1.00000 | 0 |
| 1210 | chr21 | 38779000 | 38780000 | 0.000 | 0.000 | DYRK1A | 1.00000 | 0 |
| 1211 | chr21 | 43254000 | 43255000 | 0.000 | 0.040 | PRDM15 | 1.00000 | 0 |
| 1212 | chr21 | 44612000 | 44613000 | 0.000 | 0.000 | CRYAA | 1.00000 | 0 |
| 1213 | chr21 | 45381000 | 45382000 | 0.040 | 0.000 | AGPAT3 | 1.00000 | 0 |
| 1214 | chr21 | 46058000 | 46059000 | 0.000 | 0.000 | KRTAP10-10 | 1.00000 | 0 |
| 1215 | chr22 | 19050000 | 19051000 | 0.000 | 0.000 | DGCR2 | 1.00000 | 0 |
| 1216 | chr22 | 20212000 | 20213000 | 0.040 | 0.000 | RTN4R | 1.00000 | 0 |
| 1217 | chr22 | 20708000 | 20709000 | 0.040 | 0.040 | FAM230A | 1.00000 | 0 |
| 1218 | chr22 | 21994000 | 21995000 | 0.000 | 0.000 | SDF2L1 | 1.00000 | 0 |
| 1219 | chr22 | 22379000 | 22380000 | 0.040 | 0.040 | IGLV4-69 | 1.00000 | 0 |
| 1220 | chr22 | 22380000 | 22381000 | 0.040 | 0.080 | IGLV4-69 | 1.00000 | 0 |
| 1221 | chr22 | 22381000 | 22382000 | 0.040 | 0.040 | IGLV4-69 | 1.00000 | 0 |
| 1222 | chr22 | 22385000 | 22386000 | 0.040 | 0.080 | IGLV4-69 | 1.00000 | 0 |
| 1223 | chr22 | 22452000 | 22453000 | 0.000 | 0.040 | IGLV8-61 | 1.00000 | 0 |
| 1224 | chr22 | 22453000 | 22454000 | 0.000 | 0.040 | IGLV8-61 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 1225 | chr22 | 22516000 | 22517000 | 0.000 | 0.160 | IGLV4-60 | 0.10986 | 0 |
| 1226 | chr22 | 22517000 | 22518000 | 0.000 | 0.080 | IGLV4-60 | 0.48980 | 0 |
| 1227 | chr22 | 22550000 | 22551000 | 0.160 | 0.000 | IGLV6-57 | 0.10986 | 0 |
| 1228 | chr22 | 22569000 | 22570000 | 0.040 | 0.000 | IGLV10-54 | 1.00000 | 0 |
| 1229 | chr22 | 22676000 | 22677000 | 0.040 | 0.000 | IGLV1-51 | 1.00000 | 0 |
| 1230 | chr22 | 22677000 | 22678000 | 0.040 | 0.000 | IGLV1-51 | 1.00000 | 0 |
| 1231 | chr22 | 22707000 | 22708000 | 0.040 | 0.080 | IGLV5-48 | 1.00000 | 0 |
| 1232 | chr22 | 22712000 | 22713000 | 0.160 | 0.040 | IGLV1-47 | 0.34868 | 0 |
| 1233 | chr22 | 22723000 | 22724000 | 0.000 | 0.000 | IGLV7-46 | 1.00000 | 0 |
| 1234 | chr22 | 22724000 | 22725000 | 0.080 | 0.040 | IGLV7-46 | 1.00000 | 0 |
| 1235 | chr22 | 22730000 | 22731000 | 0.040 | 0.040 | IGLV5-45 | 1.00000 | 0 |
| 1236 | chr22 | 22731000 | 22732000 | 0.000 | 0.000 | IGLV5-45 | 1.00000 | 0 |
| 1237 | chr22 | 22735000 | 22736000 | 0.080 | 0.120 | IGLV1-44 | 1.00000 | 0 |
| 1238 | chr22 | 22749000 | 22750000 | 0.120 | 0.040 | IGLV7-43 | 0.60921 | 0 |
| 1239 | chr22 | 22758000 | 22759000 | 0.080 | 0.040 | IGLV1-40 | 1.00000 | 0 |
| 1240 | chr22 | 22759000 | 22760000 | 0.080 | 0.080 | IGLV1-40 | 1.00000 | 0 |
| 1241 | chr22 | 22764000 | 22765000 | 0.120 | 0.080 | IGLV1-40 | 1.00000 | 0 |
| 1242 | chr22 | 23028000 | 23029000 | 0.000 | 0.040 | IGLV3-25 | 1.00000 | 0 |
| 1243 | chr22 | 23029000 | 23030000 | 0.040 | 0.120 | IGLV3-25 | 0.60921 | 0 |
| 1244 | chr22 | 23035000 | 23036000 | 0.000 | 0.040 | IGLV2-23 | 1.00000 | 0 |
| 1245 | chr22 | 23039000 | 23040000 | 0.000 | 0.000 | IGLV2-23 | 1.00000 | 0 |
| 1246 | chr22 | 23040000 | 23041000 | 0.120 | 0.040 | IGLV2-23 | 0.60921 | 0 |
| 1247 | chr22 | 23041000 | 23042000 | 0.040 | 0.000 | IGLV2-23 | 1.00000 | 0 |
| 1248 | chr22 | 23055000 | 23056000 | 0.040 | 0.000 | IGLV3-21 | 1.00000 | 0 |
| 1249 | chr22 | 23063000 | 23064000 | 0.040 | 0.000 | IGLV3-19 | 1.00000 | 0 |
| 1250 | chr22 | 23090000 | 23091000 | 0.120 | 0.000 | IGLV3-16 | 0.23469 | 0 |
| 1251 | chr22 | 23100000 | 23101000 | 0.040 | 0.000 | IGLV2-14 | 1.00000 | 0 |
| 1252 | chr22 | 23101000 | 23102000 | 0.120 | 0.040 | IGLV2-14 | 0.60921 | 0 |
| 1253 | chr22 | 23114000 | 23115000 | 0.000 | 0.000 | IGLV3-12 | 1.00000 | 0 |
| 1254 | chr22 | 23134000 | 23135000 | 0.000 | 0.000 | IGLV2-11 | 1.00000 | 0 |
| 1255 | chr22 | 23154000 | 23155000 | 0.120 | 0.000 | IGLV3-10 | 0.23469 | 0 |
| 1256 | chr22 | 23161000 | 23162000 | 0.000 | 0.000 | IGLV3-9 | 1.00000 | 0 |
| 1257 | chr22 | 23162000 | 23163000 | 0.000 | 0.000 | IGLV3-9 | 1.00000 | 0 |
| 1258 | chr22 | 23165000 | 23166000 | 0.000 | 0.000 | IGLV2-8 | 1.00000 | 0 |
| 1259 | chr22 | 23192000 | 23193000 | 0.080 | 0.080 | IGLV4-3 | 1.00000 | 0 |
| 1260 | chr22 | 23197000 | 23198000 | 0.040 | 0.000 | IGLV4-3 | 1.00000 | 0 |
| 1261 | chr22 | 23198000 | 23199000 | 0.160 | 0.040 | IGLV4-3 | 0.34868 | 0 |
| 1262 | chr22 | 23199000 | 23200000 | 0.200 | 0.200 | IGLV4-3 | 1.00000 | 0 |
| 1263 | chr22 | 23203000 | 23204000 | 0.000 | 0.000 | IGLV4-3 | 1.00000 | 0 |
| 1264 | chr22 | 23204000 | 23205000 | 0.080 | 0.000 | IGLV4-3 | 0.48980 | 0 |
| 1265 | chr22 | 23205000 | 23206000 | 0.000 | 0.000 | IGLV4-3 | 1.00000 | 0 |
| 1266 | chr22 | 23207000 | 23208000 | 0.000 | 0.040 | IGLV4-3 | 1.00000 | 0 |
| 1267 | chr22 | 23209000 | 23210000 | 0.000 | 0.040 | IGLV4-3 | 1.00000 | 0 |
| 1268 | chr22 | 23213000 | 23214000 | 0.120 | 0.040 | IGLV4-3 | 0.60921 | 0 |
| 1269 | chr22 | 23214000 | 23215000 | 0.040 | 0.040 | IGLV4-3 | 1.00000 | 0 |
| 1270 | chr22 | 23219000 | 23220000 | 0.080 | 0.000 | IGLV3-1 | 0.48980 | 0 |
| 1271 | chr22 | 23220000 | 23221000 | 0.080 | 0.000 | IGLV3-1 | 0.48980 | 0 |
| 1272 | chr22 | 23222000 | 23223000 | 0.040 | 0.120 | IGLV3-1 | 0.60921 | 0 |
| 1273 | chr22 | 23223000 | 23224000 | 0.320 | 0.520 | IGLV3-1 | 0.25159 | 0 |
| 1274 | chr22 | 23224000 | 23225000 | 0.080 | 0.080 | IGLV3-1 | 1.00000 | 0 |
| 1275 | chr22 | 23226000 | 23227000 | 0.120 | 0.000 | IGLV3-1 | 0.23469 | 0 |
| 1276 | chr22 | 23227000 | 23228000 | 0.200 | 0.360 | IGLL5 | 0.34513 | 0 |
| 1277 | chr22 | 23128000 | 23229000 | 0.240 | 0.200 | IGLL5 | 1.00000 | 0 |
| 1278 | chr22 | 23229000 | 23230000 | 0.040 | 0.160 | IGLL5 | 0.34868 | 0 |
| 1279 | chr22 | 23230000 | 23231000 | 0.440 | 0.600 | IGLL5 | 0.39610 | 0 |
| 1280 | chr22 | 23231000 | 23232000 | 0.480 | 0.440 | IGLL5 | 1.00000 | 0 |
| 1281 | chr22 | 23232000 | 23233000 | 0.320 | 0.240 | IGLL5 | 0.75361 | 0 |
| 1282 | chr22 | 23233000 | 23234000 | 0.200 | 0.040 | IGLJ1 | 0.18946 | 0 |
| 1283 | chr22 | 23234000 | 23235000 | 0.200 | 0.080 | IGLJ1 | 0.41743 | 0 |
| 1284 | chr22 | 23235000 | 23236000 | 0.320 | 0.080 | IGLJ1; IGLL5; | 0.07375 | 0 |
| 1285 | chr22 | 23236000 | 23237000 | 0.240 | 0.200 | IGLJ1; IGLL5; | 1.00000 | 0 |
| 1286 | chr22 | 23237000 | 23238000 | 0.040 | 0.160 | IGLC1; IGLL5; | 0.34868 | 0 |
| 1287 | chr22 | 23241000 | 23242000 | 0.040 | 0.040 | IGLJ2 | 1.00000 | 0 |
| 1288 | chr22 | 23242000 | 23243000 | 0.120 | 0.040 | IGLC2 | 0.60921 | 0 |
| 1289 | chr22 | 23243000 | 23244000 | 0.080 | 0.040 | IGLC2 | 1.00000 | 0 |
| 1290 | chr22 | 23244000 | 23245000 | 0.000 | 0.040 | IGLC2 | 1.00000 | 0 |
| 1291 | chr22 | 23247000 | 23248000 | 0.280 | 0.160 | IGLJ3 | 0.49620 | 0 |
| 1292 | chr22 | 23248000 | 23249000 | 0.040 | 0.000 | IGLC3 | 1.00000 | 0 |
| 1293 | chr22 | 23249000 | 23250000 | 0.040 | 0.000 | IGLC3 | 1.00000 | 0 |
| 1294 | chr22 | 23260000 | 23261000 | 0.000 | 0.000 | IGLJ6 | 1.00000 | 0 |
| 1295 | chr22 | 23261000 | 23262000 | 0.000 | 0.000 | IGLJ6 | 1.00000 | 0 |
| 1296 | chr22 | 23263000 | 23264000 | 0.000 | 0.040 | IGLJ7 | 1.00000 | 0 |
| 1297 | chr22 | 23264000 | 23265000 | 0.000 | 0.040 | IGLC7 | 1.00000 | 0 |
| 1298 | chr22 | 23273000 | 23274000 | 0.000 | 0.040 | IGLC7 | 1.00000 | 0 |
| 1299 | chr22 | 23277000 | 23278000 | 0.040 | 0.040 | IGLC7 | 1.00000 | 0 |
| 1300 | chr22 | 23278000 | 23279000 | 0.000 | 0.120 | IGLC7 | 0.23469 | 0 |
| 1301 | chr22 | 23281000 | 23282000 | 0.040 | 0.000 | IGLC7 | 1.00000 | 0 |

TABLE 2-continued

| # | Chromosome | Region Start | Region End | ABC-subtype | GCB-subtype | ClosestGene | p_ABC_vs_GCB | Previously-Identified |
|---|---|---|---|---|---|---|---|---|
| 1302 | chr22 | 23282000 | 23283000 | 0.080 | 0.160 | IGLC7 | 0.66710 | 0 |
| 1303 | chr22 | 23284000 | 23285000 | 0.000 | 0.000 | IGLC7 | 1.00000 | 0 |
| 1304 | chr22 | 23523000 | 23524000 | 0.000 | 0.080 | BCR | 0.48980 | 0 |
| 1305 | chr22 | 23524000 | 23525000 | 0.000 | 0.000 | BCR | 1.00000 | 0 |
| 1306 | chr22 | 27236000 | 27237000 | 0.000 | 0.000 | CRYBA4 | 1.00000 | 0 |
| 1307 | chr22 | 29195000 | 29196000 | 0.040 | 0.040 | XBP1 | 1.00000 | 0 |
| 1308 | chr22 | 29196000 | 29197000 | 0.040 | 0.040 | XBP1 | 1.00000 | 0 |
| 1309 | chr22 | 31826000 | 31827000 | 0.040 | 0.000 | DRG1 | 1.00000 | 0 |
| 1310 | chr22 | 32982000 | 32983000 | 0.000 | 0.040 | SYN3 | 1.00000 | 0 |
| 1311 | chr22 | 39852000 | 39853000 | 0.040 | 0.000 | TAB1 | 1.00000 | 0 |
| 1312 | chr22 | 39854000 | 39855000 | 0.000 | 0.000 | TAB1 | 1.00000 | 0 |
| 1313 | chr22 | 43360000 | 43361000 | 0.000 | 0.000 | PACSIN2 | 1.00000 | 0 |
| 1314 | chr22 | 47186000 | 47187000 | 0.000 | 0.000 | TBC1D22A | 1.00000 | 0 |
| 1315 | chr22 | 47738000 | 47739000 | 0.000 | 0.000 | LL22NC03-75H12.2 | 1.00000 | 0 |
| 1316 | chr22 | 50336000 | 50337000 | 0.000 | 0.000 | CRELD2 | 1.00000 | 0 |
| 1317 | chrX | 228000 | 229000 | 0.000 | 0.000 | GTPBP6 | 1.00000 | 0 |
| 1318 | chrX | 1514000 | 1515000 | 0.000 | 0.040 | SLC25A6 | 1.00000 | 0 |
| 1319 | chrX | 1611000 | 1612000 | 0.040 | 0.040 | P2RY8 | 1.00000 | 1 |
| 1320 | chrX | 12993000 | 12994000 | 0.320 | 0.280 | TMSB4X | 1.00000 | 1 |
| 1321 | chrX | 12994000 | 12995000 | 0.200 | 0.160 | TMSB4X | 1.00000 | 1 |
| 1322 | chrX | 13419000 | 13420000 | 0.000 | 0.040 | ATXN3L | 1.00000 | 0 |
| 1323 | chrX | 27031000 | 27037000 | 0.080 | 0.040 | DCAF8L2 | 1.00000 | 0 |
| 1324 | chrX | 32315000 | 32316000 | 0.000 | 0.000 | DMD | 1.00000 | 1 |
| 1325 | chrX | 32317000 | 32318000 | 0.000 | 0.000 | DMD | 1.00000 | 1 |
| 1326 | chrX | 33144000 | 33145000 | 0.000 | 0.000 | DMD | 1.00000 | 1 |
| 1327 | chrX | 33145000 | 33146000 | 0.000 | 0.040 | DMD | 1.00000 | 1 |
| 1328 | chrX | 33146000 | 33147000 | 0.080 | 0.120 | DMD | 1.00000 | 1 |
| 1329 | chrX | 41366000 | 41367000 | 0.040 | 0.000 | CASK | 1.00000 | 0 |
| 1330 | chrX | 42802000 | 42803000 | 0.080 | 0.120 | MAOA | 1.00000 | 0 |
| 1331 | chrX | 48775000 | 48776000 | 0.120 | 0.040 | PIM2 | 0.60921 | 1 |
| 1332 | chrX | 48776000 | 48777000 | 0.080 | 0.000 | PIM2 | 0.48980 | 1 |
| 1333 | chrX | 64071000 | 64072000 | 0.120 | 0.080 | ZC4H2 | 1.00000 | 0 |
| 1334 | chrX | 67030000 | 67031000 | 0.000 | 0.000 | AR | 1.00000 | 0 |
| 1335 | chrX | 80258000 | 80259000 | 0.000 | 0.000 | HMGN5 | 1.00000 | 0 |
| 1336 | chrX | 81172000 | 81173000 | 0.040 | 0.000 | SH3BGRL | 1.00000 | 0 |
| 1337 | chrX | 87742000 | 87743000 | 0.040 | 0.000 | CPXCR1 | 1.00000 | 0 |
| 1338 | chrX | 87831000 | 87832000 | 0.000 | 0.000 | CPXCR1 | 1.00000 | 0 |
| 1339 | chrX | 88263000 | 88264000 | 0.000 | 0.000 | CPXCR1 | 1.00000 | 0 |
| 1340 | chrX | 88458000 | 88459000 | 0.040 | 0.000 | CPXCR1 | 1.00000 | 0 |
| 1341 | chrX | 92647000 | 92648000 | 0.000 | 0.000 | NAP1L3 | 1.00000 | 0 |
| 1342 | chrX | 93279000 | 93280000 | 0.040 | 0.000 | FAM133A | 1.00000 | 0 |
| 1343 | chrX | 94079000 | 94080000 | 0.040 | 0.000 | FAM133A | 1.00000 | 0 |
| 1344 | chrX | 104006000 | 104007000 | 0.040 | 0.000 | IL1RAPL2 | 1.00000 | 0 |
| 1345 | chrX | 104269000 | 104270000 | 0.040 | 0.000 | IL1RAPL2 | 1.00000 | 0 |
| 1346 | chrX | 106132000 | 106133000 | 0.000 | 0.000 | RIPPLY1 | 1.00000 | 0 |
| 1347 | chrX | 113095000 | 113096000 | 0.000 | 0.040 | HTR2C | 1.00000 | 0 |
| 1348 | chrX | 115676000 | 115677000 | 0.040 | 0.000 | CXorf61 | 1.00000 | 0 |
| 1349 | chrX | 124996000 | 124997000 | 0.000 | 0.000 | DCAF12L2 | 1.00000 | 0 |
| 1350 | chrX | 125708000 | 125709000 | 0.000 | 0.000 | DCAF12L1 | 1.00000 | 0 |
| 1351 | chrX | 128565000 | 128566000 | 0.040 | 0.040 | SMARCA1 | 1.00000 | 0 |
| 1352 | chrX | 129643000 | 129644000 | 0.000 | 0.040 | RBMX2 | 1.00000 | 0 |
| 1353 | chrX | 134903000 | 134904000 | 0.000 | 0.000 | CT45A3; CT45A4; | 1.00000 | 0 |
| 1354 | chrX | 140846000 | 140847000 | 0.040 | 0.000 | SPANXD; SPANXE; | 1.00000 | 0 |
| 1355 | chrX | 143750000 | 143751000 | 0.000 | 0.000 | SPANXN1 | 1.00000 | 0 |
| 1356 | chrX | 145016000 | 145017000 | 0.040 | 0.000 | TMEM257 | 1.00000 | 0 |

TABLE 3

| # | Chromosome | Region Start | Region End | Closest Gene | Reason for Inclusion |
|---|---|---|---|---|---|
| 1 | chr1 | 2306311 | 2306832 | MORN1 | Genotyping |
| 2 | chr1 | 2334441 | 2334664 | RER1 | Genotyping |
| 3 | chr1 | 2334671 | 2335161 | RER1 | Genotyping |
| 4 | chr1 | 2488006 | 2488247 | TNFRSF14 | Phased Variants |
| 5 | chr1 | 2489111 | 2489330 | TNFRSF14 | Genotyping |
| 6 | chr1 | 2489726 | 2489973 | TNFRSF14 | Genotyping |
| 7 | chr1 | 2491206 | 2491455 | TNFRSF14 | Genotyping |
| 8 | chr1 | 2492036 | 2492175 | TNFRSF14 | Genotyping |
| 9 | chr1 | 2493051 | 2493333 | TNFRSF14 | Genotyping |
| 10 | chr1 | 2494241 | 2494376 | TNFRSF14 | Genotyping |
| 11 | chr1 | 2494556 | 2494745 | TNFRSF14 | Genotyping |
| 12 | chr1 | 3547350 | 3547715 | WRAP73 | Genotyping |
| 13 | chr1 | 3747620 | 3747798 | CEP 104 | Genotyping |

TABLE 3-continued

| # | Chromosome | Region Start | Region End | Closest Gene | Reason for Inclusion |
|---|---|---|---|---|---|
| 14 | chr1 | 3800045 | 3800148 | DFFB | Genotyping |
| 15 | chr1 | 3800155 | 3800363 | DFFB | Genotyping |
| 16 | chr1 | 4472438 | 4472621 | AJAP1 | Genotyping |
| 17 | chr1 | 4476348 | 4476627 | AJAP1 | Genotyping |
| 18 | chr1 | 9784432 | 9784540 | PIK3CD | Genotyping |
| 19 | chr1 | 23885407 | 23885541 | ID3 | Genotyping |
| 20 | chr1 | 23885582 | 23885938 | ID3 | Genotyping |
| 21 | chr1 | 27059146 | 27059321 | ARID1A | Genotyping |
| 22 | chr1 | 27101071 | 27101294 | ARID1A | Genotyping |
| 23 | chr1 | 27101401 | 27101613 | ARID1A | Genotyping |
| 24 | chr1 | 27105466 | 27105671 | ARID1A | Genotyping |
| 25 | chr1 | 27106311 | 27106523 | ARID1A | Genotyping |
| 26 | chr1 | 27106711 | 27106920 | ARID1A | Genotyping |
| 27 | chr1 | 29069531 | 29070185 | YTHDF2 | Genotyping |
| 28 | chr1 | 34404022 | 34404171 | CSMD2 | Phased Variants |
| 29 | chr1 | 35472492 | 35472739 | ZMYM6 | Genotyping |
| 30 | chr1 | 61553802 | 61554330 | NFIA | Genotyping |
| 31 | chr1 | 72334891 | 72335045 | NEGR1 | Phased Variants |
| 32 | chr1 | 72335051 | 72335120 | NEGR1 | Phased Variants |
| 33 | chr1 | 85733207 | 85733640 | BCL10 | Phased Variants |
| 34 | chr1 | 85736272 | 85736619 | BCL10 | Genotyping |
| 35 | chr1 | 85741932 | 85742068 | BCL10 | Genotyping |
| 36 | chr1 | 86591437 | 86591909 | COL24A1 | Genotyping |
| 37 | chr1 | 107866871 | 107867579 | NTNG1 | Genotyping |
| 38 | chr1 | 109649126 | 109649304 | C1orf194 | Genotyping |
| 39 | chr1 | 109822181 | 109822805 | PSRC1 | Genotyping |
| 40 | chr1 | 110561141 | 110561757 | AHCYL1 | Genotyping |
| 41 | chr1 | 111441722 | 111442219 | CD53 | Genotyping |
| 42 | chr1 | 111715727 | 111715908 | CEPT1 | Genotyping |
| 43 | chr1 | 117078642 | 117078856 | CD58 | Genotyping |
| 44 | chr1 | 117086927 | 117087172 | CD58 | Genotyping |
| 45 | chr1 | 120457960 | 120459297 | NOTCH2 | Genotyping |
| 46 | chr1 | 160319283 | 160319532 | NCSTN | Genotyping |
| 47 | chr1 | 181452914 | 181453131 | CACNA1E | Genotyping |
| 48 | chr1 | 185833555 | 185833832 | HMCN1 | Genotyping |
| 49 | chr1 | 185972790 | 185973006 | HMCN1 | Genotyping |
| 50 | chr1 | 186062580 | 186062797 | HMCN1 | Genotyping |
| 51 | chr1 | 186083050 | 186083301 | HMCN1 | Genotyping |
| 52 | chr1 | 186143590 | 186143828 | HMCN1 | Genotyping |
| 53 | chr1 | 186158895 | 186159102 | HMCN1 | Genotyping |
| 54 | chr1 | 190067139 | 190068194 | FAM5C | Genotyping |
| 55 | chr1 | 201038552 | 201038756 | CACNA1S | Genotyping |
| 56 | chr1 | 203274697 | 203275926 | BTG2 | Phased Variants |
| 57 | chr1 | 203276207 | 203276586 | BTG2 | Genotyping |
| 58 | chr1 | 226923691 | 226925200 | ITPKB | Phased Variants |
| 59 | chr1 | 227842646 | 227842718 | ZNF678 | Genotyping |
| 60 | chr2 | 1652010 | 1652858 | PXDN | Genotyping |
| 61 | chr2 | 48027958 | 48028159 | MSH6 | Genotyping |
| 62 | chr2 | 48059883 | 48060051 | FBXO11 | Genotyping |
| 63 | chr2 | 48065973 | 48066184 | FBXO11 | Genotyping |
| 64 | chr2 | 55237198 | 55237610 | RTN4 | Genotyping |
| 65 | chr2 | 56149510 | 56150116 | EFEMP1 | Genotyping |
| 66 | chr2 | 58520800 | 58521222 | FANCL | Genotyping |
| 67 | chr2 | 59821914 | 59822083 | BCL11A | Genotyping |
| 68 | chr2 | 60773084 | 60773479 | BCL11A | Genotyping |
| 69 | chr2 | 61118794 | 61118998 | REL | Genotyping |
| 70 | chr2 | 61145504 | 61145785 | REL | Genotyping |
| 71 | chr2 | 61148869 | 61149644 | REL | Genotyping |
| 72 | chr2 | 61441169 | 61441870 | USP34 | Genotyping |
| 73 | chr2 | 61719434 | 61719642 | XPO1 | Genotyping |
| 74 | chr2 | 62934009 | 62934460 | EHBP1 | Genotyping |
| 75 | chr2 | 63217829 | 63218002 | EHBP1 | Genotyping |
| 76 | chr2 | 63335242 | 63335600 | WDPCP | Genotyping |
| 77 | chr2 | 63631157 | 63631817 | WDPCP | Genotyping |
| 78 | chr2 | 63826277 | 63826429 | MDH1 | Genotyping |
| 79 | chr2 | 65258145 | 65258367 | SLC1A4 | Phased Variants |
| 80 | chr2 | 65593035 | 65593153 | SPRED2 | Phased Variants |
| 81 | chr2 | 65593180 | 65593250 | SPRED2 | Phased Variants |
| 82 | chr2 | 77746602 | 77746988 | LRRTM4 | Genotyping |
| 83 | chr2 | 80801235 | 80801513 | CTNNA2 | Genotyping |
| 84 | chr2 | 88906681 | 88906861 | EIF2AK3 | Phased Variants |
| 85 | chr2 | 89127261 | 89127335 | IGKC | Phased Variants |
| 86 | chr2 | 89127461 | 89127946 | IGKC | Phased Variants |
| 87 | chr2 | 89128431 | 89128574 | IGKC | Phased Variants |
| 88 | chr2 | 89131726 | 89132295 | IGKC | Phased Variants |
| 89 | chr2 | 89140556 | 89140755 | IGKC | Phased Variants |
| 90 | chr2 | 89140886 | 89141350 | IGKC | Phased Variants |
| 91 | chr2 | 89157326 | 89157609 | IGKC | Phased Variants |

TABLE 3-continued

| # | Chromosome | Region Start | Region End | Closest Gene | Reason for Inclusion |
|---|---|---|---|---|---|
| 92 | chr2 | 89157626 | 89158011 | IGKC | Phased Variants |
| 93 | chr2 | 89158036 | 89158938 | IGKC | Phased Variants |
| 94 | chr2 | 89158941 | 89159493 | IGKJ5 | Phased Variants |
| 95 | chr2 | 89159511 | 89161445 | IGKJ1 | Phased Variants |
| 96 | chr2 | 89161926 | 89162149 | IGKJ1 | Phased Variants |
| 97 | chr2 | 89162776 | 89163285 | IGKJ1 | Phased Variants |
| 98 | chr2 | 89163306 | 89163837 | IGKJ1 | Phased Variants |
| 99 | chr2 | 89163861 | 89164838 | IGKJ1 | Phased Variants |
| 100 | chr2 | 89164866 | 89165181 | IGKJ1 | Phased Variants |
| 101 | chr2 | 89165191 | 89165644 | IGKJ1 | Phased Variants |
| 102 | chr2 | 89184966 | 89185186 | IGKV4-1 | Phased Variants |
| 103 | chr2 | 89185196 | 89185704 | IGKV4-1 | Phased Variants |
| 104 | chr2 | 89196226 | 89196411 | IGKV5-2 | Phased Variants |
| 105 | chr2 | 89196851 | 89197324 | IGKV5-2 | Phased Variants |
| 106 | chr2 | 89214836 | 89215040 | IGKV5-2 | Phased Variants |
| 107 | chr2 | 89246681 | 89246772 | IGKV1-5 | Phased Variants |
| 108 | chr2 | 89246786 | 89246857 | IGKV1-5 | Phased Variants |
| 109 | chr2 | 89246911 | 89247053 | IGKV1-5 | Phased Variants |
| 110 | chr2 | 89247096 | 89247215 | IGKV1-5 | Phased Variants |
| 111 | chr2 | 89247526 | 89247628 | IGKV1-5 | Phased Variants |
| 112 | chr2 | 89247641 | 89247735 | IGKV1-5 | Phased Variants |
| 113 | chr2 | 89247831 | 89248010 | IGKV1-5 | Phased Variants |
| 114 | chr2 | 89265756 | 89265829 | IGKV1-6 | Genotyping |
| 115 | chr2 | 89265936 | 89266013 | IGKV1-6 | Genotyping |
| 116 | chr2 | 89291906 | 89291981 | IGKV1-8 | Phased Variants |
| 117 | chr2 | 89292131 | 89292217 | IGKV1-8 | Phased Variants |
| 118 | chr2 | 89442291 | 89442561 | IGKV3-20 | Phased Variants |
| 119 | chr2 | 89442616 | 89443259 | IGKV3-20 | Phased Variants |
| 120 | chr2 | 89475781 | 89476009 | IGKV2-24 | Genotyping |
| 121 | chr2 | 89476041 | 89476122 | IGKV2-24 | Genotyping |
| 122 | chr2 | 89544331 | 89544608 | IGKV2-30 | Genotyping |
| 123 | chr2 | 89544656 | 89544899 | IGKV2-30 | Phased Variants |
| 124 | chr2 | 89976276 | 89976426 | IGKV2D-30 | Genotyping |
| 125 | chr2 | 89986776 | 89987023 | IGKV2D-29 | Genotyping |
| 126 | chr2 | 89987031 | 89987108 | IGKV2D-29 | Genotyping |
| 127 | chr2 | 90025206 | 90025289 | IGKV2D-26 | Genotyping |
| 128 | chr2 | 90025296 | 90025378 | IGKV2D-26 | Genotyping |
| 129 | chr2 | 90025471 | 90025554 | IGKV2D-26 | Genotyping |
| 130 | chr2 | 90077981 | 90078054 | IGKV3D-20 | Genotyping |
| 131 | chr2 | 90078136 | 90078222 | IGKV3D-20 | Genotyping |
| 132 | chr2 | 90078251 | 90078335 | IGKV3D-20 | Genotyping |
| 133 | chr2 | 90121891 | 90122008 | IGKV1D-17 | Genotyping |
| 134 | chr2 | 90122021 | 90122157 | IGKV1D-17 | Genotyping |
| 135 | chr2 | 90212016 | 90212093 | IGKV3D-11 | Genotyping |
| 136 | chr2 | 90212196 | 90212278 | IGKV3D-11 | Genotyping |
| 137 | chr2 | 90249151 | 90249275 | IGKV1D-43 | Genotyping |
| 138 | chr2 | 90249346 | 90249419 | IGKV1D-43 | Genotyping |
| 139 | chr2 | 90259931 | 90260059 | IGKV1D-8 | Genotyping |
| 140 | chr2 | 90260181 | 90260258 | IGKV1D-8 | Genotyping |
| 141 | chr2 | 96809889 | 96810144 | DUSP2 | Genotyping |
| 142 | chr2 | 96810164 | 96810374 | DUSP2 | Phased Variants |
| 143 | chr2 | 100758483 | 100758660 | AFF3 | Phased Variants |
| 144 | chr2 | 103148733 | 103148948 | SLC9A4 | Genotyping |
| 145 | chr2 | 117951919 | 117952057 | DDX18 | Phased Variants |
| 146 | chr2 | 136872525 | 136872740 | CXCR4 | Genotyping |
| 147 | chr2 | 136874415 | 136874797 | CXCR4 | Phased Variants |
| 148 | chr2 | 136874920 | 136875662 | CXCR4 | Phased Variants |
| 149 | chr2 | 141245127 | 141245373 | LRP1B | Genotyping |
| 150 | chr2 | 145162401 | 145162624 | ZEB2 | Genotyping |
| 151 | chr2 | 145187091 | 145187638 | ZEB2 | Genotyping |
| 152 | chr2 | 145270956 | 145271394 | ZEB2 | Genotyping |
| 153 | chr2 | 145275631 | 145275744 | ZEB2 | Genotyping |
| 154 | chr2 | 145275756 | 145276174 | ZEB2 | Genotyping |
| 155 | chr2 | 145278026 | 145278305 | ZEB2 | Genotyping |
| 156 | chr2 | 145278311 | 145278659 | ZEB2 | Genotyping |
| 157 | chr2 | 145692901 | 145693081 | ZEB2 | Genotyping |
| 158 | chr2 | 148680516 | 148680692 | ACVR2A | Genotyping |
| 159 | chr2 | 169781120 | 169781352 | ABCB11 | Genotyping |
| 160 | chr2 | 170101185 | 170101401 | LRP2 | Genotyping |
| 161 | chr2 | 198950434 | 198951003 | PLCL1 | Genotyping |
| 162 | chr2 | 242793232 | 242793447 | PDCD1 | Genotyping |
| 163 | chr2 | 242794037 | 242794192 | PDCD1 | Genotyping |
| 164 | chr2 | 242794317 | 242794537 | PDCD1 | Genotyping |
| 165 | chr2 | 242794822 | 242795040 | PDCD1 | Genotyping |
| 166 | chr2 | 242800887 | 242801093 | PDCD1 | Genotyping |
| 167 | chr3 | 7620223 | 7620990 | GRM7 | Genotyping |
| 168 | chr3 | 16419204 | 16419479 | RFTN1 | Phased Variants |
| 169 | chr3 | 38180129 | 38180549 | MYD88 | Genotyping |

TABLE 3-continued

| # | Chromosome | Region Start | Region End | Closest Gene | Reason for Inclusion |
|---|---|---|---|---|---|
| 170 | chr3 | 38181334 | 38181509 | MYD88 | Genotyping |
| 171 | chr3 | 38181854 | 38182099 | MYD88 | Genotyping |
| 172 | chr3 | 38182194 | 38182407 | MYD88 | Genotyping |
| 173 | chr3 | 38182554 | 38182844 | MYD88 | Genotyping |
| 174 | chr3 | 49397608 | 49397717 | RHOA | Genotyping |
| 175 | chr3 | 49397718 | 49397827 | RHOA | Genotyping |
| 176 | chr3 | 49399903 | 49400084 | RHOA | Genotyping |
| 177 | chr3 | 49405833 | 49406013 | RHOA | Genotyping |
| 178 | chr3 | 49412838 | 49413046 | RHOA | Genotyping |
| 179 | chr3 | 64547204 | 64547477 | ADAMTS9 | Genotyping |
| 180 | chr3 | 64579889 | 64580094 | ADAMTS9 | Genotyping |
| 181 | chr3 | 71551101 | 71551497 | EIF4E3 | Phased Variants |
| 182 | chr3 | 140281598 | 140281875 | CLSTN2 | Genotyping |
| 183 | chr3 | 164730700 | 164730888 | SI | Genotyping |
| 184 | chr3 | 165548198 | 165548680 | BCHE | Genotyping |
| 185 | chr3 | 176750699 | 176750928 | TBL1XR1 | Genotyping |
| 186 | chr3 | 176767759 | 176767977 | TBL1XR1 | Genotyping |
| 187 | chr3 | 176769304 | 176769543 | TBL1XR1 | Genotyping |
| 188 | chr3 | 176771659 | 176771732 | TBL1XR1 | Genotyping |
| 189 | chr3 | 183209758 | 183209937 | KLHL6 | Genotyping |
| 190 | chr3 | 183210258 | 183210544 | KLHL6 | Genotyping |
| 191 | chr3 | 183272308 | 183272521 | KLHL6 | Phased Variants |
| 192 | chr3 | 183273063 | 183273456 | KLHL6 | Phased Variants |
| 193 | chr3 | 184580663 | 184580872 | VPS8 | Genotyping |
| 194 | chr3 | 185146278 | 185146873 | MAP3K13 | Genotyping |
| 195 | chr3 | 185197923 | 185198317 | MAP3K13 | Genotyping |
| 196 | chr3 | 185236908 | 185237109 | LIPH | Genotyping |
| 197 | chr3 | 185446223 | 185446389 | C3orf65 | Genotyping |
| 198 | chr3 | 185538773 | 185538951 | IGF2BP2 | Genotyping |
| 199 | chr3 | 185697423 | 185697669 | TRA2B | Genotyping |
| 200 | chr3 | 186714604 | 186715001 | ST6GAL1 | Phased Variants |
| 201 | chr3 | 186782529 | 186782790 | ST6GAL1 | Phased Variants |
| 202 | chr3 | 186783389 | 186784291 | ST6GAL1 | Phased Variants |
| 203 | chr3 | 187440189 | 187440445 | BCL6 | Genotyping |
| 204 | chr3 | 187442669 | 187442920 | BCL6 | Genotyping |
| 205 | chr3 | 187443239 | 187443438 | BCL6 | Genotyping |
| 206 | chr3 | 187446814 | 187447831 | BCL6 | Genotyping |
| 207 | chr3 | 187449434 | 187449655 | BCL6 | Genotyping |
| 208 | chr3 | 187451284 | 187451667 | BCL6 | Genotyping |
| 209 | chr3 | 187460134 | 187460530 | BCL6 | Phased Variants |
| 210 | chr3 | 187460824 | 187461302 | BCL6 | Phased Variants |
| 211 | chr3 | 187461319 | 187461381 | BCL6 | Phased Variants |
| 212 | chr3 | 187461454 | 187461918 | BCL6 | Phased Variants |
| 213 | chr3 | 187461924 | 187462343 | BCL6 | Phased Variants |
| 214 | chr3 | 187462374 | 187462887 | BCL6 | Phased Variants |
| 215 | chr3 | 187462924 | 187462999 | BCL6 | Phased Variants |
| 216 | chr3 | 187463004 | 187463525 | BCL6 | Phased Variants |
| 217 | chr3 | 187463709 | 187463781 | BCL6 | Phased Variants |
| 218 | chr3 | 187463794 | 187464109 | BCL6 | Phased Variants |
| 219 | chr3 | 187619334 | 187619708 | BCL6 | Phased Variants |
| 220 | chr3 | 187660817 | 187661390 | BCL6 | Phased Variants |
| 221 | chr3 | 187957432 | 187957507 | AC022498.1 | Phased Variants |
| 222 | chr3 | 187957512 | 187957754 | AC022498.1 | Phased Variants |
| 223 | chr3 | 187957767 | 187958110 | AC022498.1 | Phased Variants |
| 224 | chr3 | 187958282 | 187958675 | AC022498.1 | Phased Variants |
| 225 | chr3 | 187958787 | 187959184 | AC022498.1 | Phased Variants |
| 226 | chr3 | 187959462 | 187959686 | AC022498.1 | Phased Variants |
| 227 | chr3 | 188299217 | 188299605 | LPP | Phased Variants |
| 228 | chr3 | 188471412 | 188471549 | LPP | Phased Variants |
| 229 | chr3 | 188471567 | 188471937 | LPP | Phased Variants |
| 230 | chr4 | 7728456 | 7728661 | SORCS2 | Genotyping |
| 231 | chr4 | 40198810 | 40199653 | N4BP2 | Phased Variants |
| 232 | chr4 | 40199660 | 40199873 | N4BP2 | Phased Variants |
| 233 | chr4 | 40199990 | 40200211 | N4BP2 | Phased Variants |
| 234 | chr4 | 40200505 | 40200727 | RHOH | Phased Variants |
| 235 | chr4 | 40200730 | 40201571 | RHOH | Phased Variants |
| 236 | chr4 | 80327792 | 80328151 | GK2 | Genotyping |
| 237 | chr4 | 88011077 | 88011285 | AFF1 | Genotyping |
| 238 | chr4 | 106157604 | 106157813 | TET2 | Genotyping |
| 239 | chr4 | 134727698 | 134727916 | PABPC4L | Phased Variants |
| 240 | chr4 | 153249285 | 153249507 | FBXW7 | Genotyping |
| 241 | chr4 | 154624670 | 154625050 | TLR2 | Genotyping |
| 242 | chr4 | 187509884 | 187510410 | FAT1 | Genotyping |
| 243 | chr4 | 187557779 | 187557985 | FAT1 | Genotyping |
| 244 | chr4 | 188924114 | 188924897 | ZFP42 | Genotyping |
| 245 | chr5 | 5182145 | 5182494 | ADAMTS16 | Genotyping |
| 246 | chr5 | 11110990 | 11111137 | CTNND2 | Genotyping |
| 247 | chr5 | 11236740 | 11236956 | CTNND2 | Genotyping |

TABLE 3-continued

| # | Chromosome | Region Start | Region End | Closest Gene | Reason for Inclusion |
|---|---|---|---|---|---|
| 248 | chr5 | 11364700 | 11364923 | CTNND2 | Genotyping |
| 249 | chr5 | 11397080 | 11397377 | CTNND2 | Genotyping |
| 250 | chr5 | 11411600 | 11411807 | CTNND2 | Genotyping |
| 251 | chr5 | 13864465 | 13864696 | DNAH5 | Genotyping |
| 252 | chr5 | 21783415 | 21783668 | CDH12 | Genotyping |
| 253 | chr5 | 54964698 | 54964921 | SLC38A9 | Phased Variants |
| 254 | chr5 | 67590966 | 67591183 | PIK3R1 | Genotyping |
| 255 | chr5 | 75913716 | 75914448 | F2RL2 | Genotyping |
| 256 | chr5 | 83258967 | 83259183 | EDIL3 | Genotyping |
| 257 | chr5 | 112176756 | 112176958 | APC | Genotyping |
| 258 | chr5 | 124079827 | 124080721 | ZNF608 | Phased Variants |
| 259 | chr5 | 131825017 | 131825239 | IRF1 | Genotyping |
| 260 | chr5 | 135381969 | 135382218 | TGFBI | Genotyping |
| 261 | chr5 | 137801487 | 137801637 | EGR1 | Genotyping |
| 262 | chr5 | 137801697 | 137801804 | EGR1 | Genotyping |
| 263 | chr5 | 140208033 | 140208874 | PCDHA6 | Genotyping |
| 264 | chr5 | 158527642 | 158528019 | EBF1 | Phased Variants |
| 265 | chr5 | 176522449 | 176522613 | FGFR4 | Genotyping |
| 266 | chr6 | 392760 | 392967 | IRF4 | Phased Variants |
| 267 | chr6 | 393090 | 393309 | IRF4 | Phased Variants |
| 268 | chr6 | 394815 | 395025 | IRF4 | Genotyping |
| 269 | chr6 | 14117992 | 14118654 | CD83 | Phased Variants |
| 270 | chr6 | 14131732 | 14132021 | CD83 | Genotyping |
| 271 | chr6 | 14133857 | 14133996 | CD83 | Genotyping |
| 272 | chr6 | 14135317 | 14135496 | CD83 | Genotyping |
| 273 | chr6 | 26020709 | 26020958 | HIST1H3A | Genotyping |
| 274 | chr6 | 26032014 | 26032217 | HIST1H3B | Genotyping |
| 275 | chr6 | 26045744 | 26046077 | HIST1H3C | Genotyping |
| 276 | chr6 | 26056034 | 26056315 | HIST1H1C | Genotyping |
| 277 | chr6 | 26056319 | 26056558 | HIST1H1C | Genotyping |
| 278 | chr6 | 26123614 | 26123778 | HIST1H2BC | Phased Variants |
| 279 | chr6 | 26123879 | 26124098 | HIST1H2BC | Genotyping |
| 280 | chr6 | 26124544 | 26124640 | HIST1H2AC | Genotyping |
| 281 | chr6 | 26124714 | 26124889 | HIST1H2AC | Genotyping |
| 282 | chr6 | 26156649 | 26157377 | HIST1H1E | Phased Variants |
| 283 | chr6 | 26158529 | 26158608 | HIST1H2BD | Genotyping |
| 284 | chr6 | 26158739 | 26158835 | HIST1H2BD | Genotyping |
| 285 | chr6 | 26197104 | 26197182 | HIST1H3D | Genotyping |
| 286 | chr6 | 26197189 | 26197465 | HIST1H3D | Genotyping |
| 287 | chr6 | 26216779 | 26216920 | HIST1H2BG | Genotyping |
| 288 | chr6 | 26217214 | 26217431 | HIST1H2AE | Genotyping |
| 289 | chr6 | 26234654 | 26234976 | HIST1H1D | Genotyping |
| 290 | chr6 | 26250459 | 26250537 | HIST1H3F | Genotyping |
| 291 | chr6 | 26250594 | 26250703 | HIST1H3F | Genotyping |
| 292 | chr6 | 26252154 | 26252232 | HIST1H2BH | Genotyping |
| 293 | chr6 | 27100079 | 27100185 | HIST1H2BJ | Genotyping |
| 294 | chr6 | 27100939 | 27101039 | HIST1H2AG | Genotyping |
| 295 | chr6 | 27101159 | 27101300 | HIST1H2AG | Genotyping |
| 296 | chr6 | 27114004 | 27114216 | HIST1H2BK | Phased Variants |
| 297 | chr6 | 27114319 | 27114396 | HIST1H2BK | Genotyping |
| 298 | chr6 | 27114494 | 27114592 | HIST1H2BK | Genotyping |
| 299 | chr6 | 27277284 | 27277495 | POM121L2 | Genotyping |
| 300 | chr6 | 27777783 | 27777900 | HIST1H3H | Genotyping |
| 301 | chr6 | 27777928 | 27778106 | HIST1H3H | Genotyping |
| 302 | chr6 | 27782718 | 27782926 | HIST1H2BM | Genotyping |
| 303 | chr6 | 27799168 | 27799381 | HIST1H4K | Genotyping |
| 304 | chr6 | 27833408 | 27833516 | HIST1H2AL | Genotyping |
| 305 | chr6 | 27834968 | 27835075 | HIST1H1B | Genotyping |
| 306 | chr6 | 27839658 | 27839805 | HIST1H3I | Genotyping |
| 307 | chr6 | 27860479 | 27860659 | HIST1H2AM | Genotyping |
| 308 | chr6 | 27860794 | 27860938 | HIST1H2AM | Genotyping |
| 309 | chr6 | 27861244 | 27861344 | HIST1H2BO | Genotyping |
| 310 | chr6 | 27861399 | 27861485 | HIST1H2BO | Genotyping |
| 311 | chr6 | 37138284 | 37139559 | PIM1 | Phased Variants |
| 312 | chr6 | 37140749 | 37140956 | PIM1 | Genotyping |
| 313 | chr6 | 37141679 | 37141903 | PIM1 | Genotyping |
| 314 | chr6 | 41903611 | 41903834 | CCND3 | Genotyping |
| 315 | chr6 | 41904271 | 41904477 | CCND3 | Genotyping |
| 316 | chr6 | 41904941 | 41905155 | CCND3 | Genotyping |
| 317 | chr6 | 41908071 | 41908365 | CCND3 | Genotyping |
| 318 | chr6 | 41909196 | 41909441 | CCND3 | Genotyping |
| 319 | chr6 | 75965846 | 75966046 | TMEM30A | Genotyping |
| 320 | chr6 | 75969006 | 75969288 | TMEM30A | Genotyping |
| 321 | chr6 | 91004618 | 91004828 | MAP3K7 | Phased Variants |
| 322 | chr6 | 91005793 | 91005998 | MAP3K7 | Phased Variants |
| 323 | chr6 | 94120219 | 94120743 | EPHA7 | Genotyping |
| 324 | chr6 | 106534266 | 106534477 | PRDM1 | Genotyping |
| 325 | chr6 | 106536046 | 106536340 | PRDM1 | Genotyping |

TABLE 3-continued

| # | Chromosome | Region Start | Region End | Closest Gene | Reason for Inclusion |
|---|---|---|---|---|---|
| 326 | chr6 | 106543466 | 106543637 | PRDM1 | Genotyping |
| 327 | chr6 | 106547146 | 106547437 | PRDM1 | Genotyping |
| 328 | chr6 | 106552761 | 106552932 | PRDM1 | Genotyping |
| 329 | chr6 | 106552961 | 106553841 | PRDM1 | Genotyping |
| 330 | chr6 | 106554221 | 106554400 | PRDM1 | Genotyping |
| 331 | chr6 | 106554766 | 106555383 | PRDM1 | Genotyping |
| 332 | chr6 | 108040228 | 108040856 | SCML4 | Genotyping |
| 333 | chr6 | 108041553 | 108042219 | SCML4 | Genotyping |
| 334 | chr6 | 110777718 | 110778244 | SLC22A16 | Genotyping |
| 335 | chr6 | 134491382 | 134491589 | SGK1 | Genotyping |
| 336 | chr6 | 134491892 | 134492111 | SGK1 | Genotyping |
| 337 | chr6 | 134492132 | 134492333 | SGK1 | Genotyping |
| 338 | chr6 | 134492717 | 134492923 | SGK1 | Genotyping |
| 339 | chr6 | 134493307 | 134493474 | SGK1 | Genotyping |
| 340 | chr6 | 134493732 | 134494308 | SGK1 | Phased Variants |
| 341 | chr6 | 134494342 | 134494514 | SGK1 | Genotyping |
| 342 | chr6 | 134494552 | 134494718 | SGK1 | Phased Variants |
| 343 | chr6 | 134494722 | 134494795 | SGK1 | Phased Variants |
| 344 | chr6 | 134494967 | 134495974 | SGK1 | Phased Variants |
| 345 | chr6 | 138188483 | 138188650 | TNFAIP3 | Genotyping |
| 346 | chr6 | 138192338 | 138192683 | TNFAIP3 | Genotyping |
| 347 | chr6 | 138195963 | 138196172 | TNFAIP3 | Genotyping |
| 348 | chr6 | 138196803 | 138197021 | TNFAIP3 | Genotyping |
| 349 | chr6 | 138197108 | 138197313 | TNFAIP3 | Genotyping |
| 350 | chr6 | 138198193 | 138198407 | TNFAIP3 | Genotyping |
| 351 | chr6 | 138199548 | 138200525 | TNFAIP3 | Genotyping |
| 352 | chr6 | 138201178 | 138201404 | TNFAIP3 | Genotyping |
| 353 | chr6 | 138202138 | 138202494 | TNFAIP3 | Genotyping |
| 354 | chr6 | 150954420 | 150954823 | PLEKHG1 | Phased Variants |
| 355 | chr6 | 159238415 | 159238794 | EZR | Phased Variants |
| 356 | chr7 | 2963818 | 2963952 | CARD11 | Genotyping |
| 357 | chr7 | 2963953 | 2964056 | CARD11 | Genotyping |
| 358 | chr7 | 2969593 | 2969738 | CARD11 | Genotyping |
| 359 | chr7 | 2976668 | 2976876 | CARD11 | Genotyping |
| 360 | chr7 | 2977493 | 2977712 | CARD11 | Genotyping |
| 361 | chr7 | 2978258 | 2978502 | CARD11 | Genotyping |
| 362 | chr7 | 2979398 | 2979601 | CARD11 | Genotyping |
| 363 | chr7 | 2983918 | 2984199 | CARD11 | Genotyping |
| 364 | chr7 | 2985403 | 2985610 | CARD11 | Genotyping |
| 365 | chr7 | 2987163 | 2987382 | CARD11 | Genotyping |
| 366 | chr7 | 5569095 | 5569200 | ACTB | Genotyping |
| 367 | chr7 | 5569210 | 5569359 | ACTB | Genotyping |
| 368 | chr7 | 80285799 | 80286074 | CD36 | Genotyping |
| 369 | chr7 | 82387830 | 82388061 | PCLO | Genotyping |
| 370 | chr7 | 82453520 | 82453733 | PCLO | Genotyping |
| 371 | chr7 | 82763800 | 82764050 | PCLO | Genotyping |
| 372 | chr7 | 82784490 | 82784643 | PCLO | Genotyping |
| 373 | chr7 | 106508490 | 106509161 | PIK3CG | Genotyping |
| 374 | chr7 | 110545276 | 110545445 | IMMP2L | Phased Variants |
| 375 | chr7 | 110697971 | 110698144 | LRRN3 | Phased Variants |
| 376 | chr7 | 110737411 | 110737634 | LRRN3 | Phased Variants |
| 377 | chr7 | 110746681 | 110746893 | LRRN3 | Phased Variants |
| 378 | chr7 | 110762936 | 110764629 | LRRN3 | Genotyping |
| 379 | chr7 | 110764636 | 110764981 | LRRN3 | Genotyping |
| 380 | chr7 | 119915406 | 119915800 | KCND2 | Genotyping |
| 381 | chr7 | 122634905 | 122635140 | TAS2R16 | Genotyping |
| 382 | chr7 | 140453012 | 140453121 | BRAF | Genotyping |
| 383 | chr7 | 140453162 | 140453268 | BRAF | Genotyping |
| 384 | chr7 | 146997183 | 146997422 | CNTNAP2 | Genotyping |
| 385 | chr7 | 148506318 | 148506416 | EZH2 | Genotyping |
| 386 | chr7 | 148506448 | 148506551 | EZH2 | Genotyping |
| 387 | chr7 | 148508658 | 148508867 | EZH2 | Genotyping |
| 388 | chr7 | 148513738 | 148513900 | EZH2 | Genotyping |
| 389 | chr7 | 148523533 | 148523743 | EZH2 | Genotyping |
| 390 | chr7 | 151943421 | 151943500 | KMT2C | Phased Variants |
| 391 | chr8 | 623880 | 624090 | ERICH1 | Genotyping |
| 392 | chr8 | 3141724 | 3141942 | CSMD1 | Genotyping |
| 393 | chr8 | 4494931 | 4495105 | CSMD1 | Genotyping |
| 394 | chr8 | 8748687 | 8749284 | MFHAS1 | Genotyping |
| 395 | chr8 | 8750067 | 8750281 | MFHAS1 | Genotyping |
| 396 | chr8 | 18729445 | 18729937 | PSD3 | Genotyping |
| 397 | chr8 | 75898190 | 75898400 | CRISPLD1 | Genotyping |
| 398 | chr8 | 101730376 | 101730457 | PABPC1 | Genotyping |
| 399 | chr8 | 103663491 | 103664160 | KLF10 | Genotyping |
| 400 | chr8 | 104897561 | 104898479 | RIMS2 | Genotyping |
| 401 | chr8 | 113308014 | 113308283 | CSMD3 | Genotyping |
| 402 | chr8 | 113364624 | 113364791 | CSMD3 | Genotyping |
| 403 | chr8 | 113568994 | 113569205 | CSMD3 | Genotyping |

TABLE 3-continued

| # | Chromosome | Region Start | Region End | Closest Gene | Reason for Inclusion |
|---|---|---|---|---|---|
| 404 | chr8 | 116616145 | 116616886 | TRPS1 | Genotyping |
| 405 | chr8 | 122626847 | 122627163 | HAS2 | Genotyping |
| 406 | chr8 | 128492947 | 128493338 | POU5F1B | Genotyping |
| 407 | chr8 | 128746807 | 128748893 | MYC | Genotyping |
| 408 | chr8 | 128748902 | 128749969 | MYC | Genotyping |
| 409 | chr8 | 128750367 | 128751183 | MYC | Phased Variants |
| 410 | chr8 | 128752612 | 128753235 | MYC | Genotyping |
| 411 | chr8 | 128754007 | 128754731 | MYC | Genotyping |
| 412 | chr8 | 128754752 | 128756424 | MYC | Genotyping |
| 413 | chr8 | 128756707 | 128756931 | MYC | Genotyping |
| 414 | chr8 | 128756947 | 128757361 | MYC | Genotyping |
| 415 | chr8 | 128757737 | 128757921 | MYC | Genotyping |
| 416 | chr8 | 128764072 | 128764292 | MYC | Genotyping |
| 417 | chr8 | 128951724 | 128951896 | TMEM75 | Genotyping |
| 418 | chr8 | 130692149 | 130692503 | GSDMC | Genotyping |
| 419 | chr8 | 130760594 | 130761023 | GSDMC | Genotyping |
| 420 | chr8 | 131373024 | 131373443 | ASAP1 | Genotyping |
| 421 | chr8 | 136569669 | 136569842 | KHDRBS3 | Genotyping |
| 422 | chr8 | 136659204 | 136659414 | KHDRBS3 | Genotyping |
| 423 | chr8 | 137101252 | 137101464 | KHDRBS3 | Genotyping |
| 424 | chr8 | 137528187 | 137528570 | KHDRBS3 | Genotyping |
| 425 | chr8 | 138849937 | 138850149 | FAM135B | Genotyping |
| 426 | chr8 | 139600457 | 139601255 | COL22A1 | Genotyping |
| 427 | chr8 | 139601392 | 139601569 | COL22A1 | Genotyping |
| 428 | chr9 | 5450474 | 5450616 | CD274 | Genotyping |
| 429 | chr9 | 5456059 | 5456200 | CD274 | Genotyping |
| 430 | chr9 | 5457054 | 5457446 | CD274 | Genotyping |
| 431 | chr9 | 5462809 | 5463160 | CD274 | Genotyping |
| 432 | chr9 | 5465489 | 5465622 | CD274 | Genotyping |
| 433 | chr9 | 5466724 | 5466867 | CD274 | Genotyping |
| 434 | chr9 | 5467814 | 5468022 | CD274 | Genotyping |
| 435 | chr9 | 5510589 | 5510804 | PDCD1LG2 | Genotyping |
| 436 | chr9 | 5522484 | 5522636 | PDCD1LG2 | Genotyping |
| 437 | chr9 | 5534764 | 5535047 | PDCD1LG2 | Genotyping |
| 438 | chr9 | 5549309 | 5549627 | PDCD1LG2 | Genotyping |
| 439 | chr9 | 5557589 | 5557762 | PDCD1LG2 | Genotyping |
| 440 | chr9 | 5563119 | 5563251 | PDCD1LG2 | Genotyping |
| 441 | chr9 | 5569929 | 5570140 | PDCD1LG2 | Genotyping |
| 442 | chr9 | 13222185 | 13222409 | MPDZ | Genotyping |
| 443 | chr9 | 16435498 | 16436307 | BNC2 | Genotyping |
| 444 | chr9 | 19957356 | 19958178 | SLC24A2 | Genotyping |
| 445 | chr9 | 20820916 | 20821095 | FOCAD | Genotyping |
| 446 | chr9 | 20946676 | 20946849 | FOCAD | Genotyping |
| 447 | chr9 | 21808814 | 21808891 | MTAP | Genotyping |
| 448 | chr9 | 21808894 | 21808973 | MTAP | Genotyping |
| 449 | chr9 | 21859249 | 21859469 | MTAP | Genotyping |
| 450 | chr9 | 21970834 | 21971023 | CDKN2A | Genotyping |
| 451 | chr9 | 21971069 | 21971170 | CDKN2A | Genotyping |
| 452 | chr9 | 21974409 | 21974881 | CDKN2A | Genotyping |
| 453 | chr9 | 21989304 | 21989976 | CDKN2A | Genotyping |
| 454 | chr9 | 21994084 | 21994405 | CDKN2A | Genotyping |
| 455 | chr9 | 22005929 | 22006067 | CDKN2B | Genotyping |
| 456 | chr9 | 22006109 | 22006187 | CDKN2B | Genotyping |
| 457 | chr9 | 22008649 | 22009012 | CDKN2B | Genotyping |
| 458 | chr9 | 24545399 | 24545922 | IZUMO3 | Genotyping |
| 459 | chr9 | 24905444 | 24905729 | IZUMO3 | Genotyping |
| 460 | chr9 | 27950144 | 27950532 | LINGO2 | Genotyping |
| 461 | chr9 | 37024919 | 37025642 | PAX5 | Phased Variants |
| 462 | chr9 | 37025829 | 37025996 | PAX5 | Phased Variants |
| 463 | chr9 | 37026269 | 37027015 | PAX5 | Phased Variants |
| 464 | chr9 | 37033619 | 37033797 | PAX5 | Phased Variants |
| 465 | chr9 | 37293169 | 37293378 | ZCCHC7 | Phased Variants |
| 466 | chr9 | 37371494 | 37371879 | ZCCHC7 | Phased Variants |
| 467 | chr9 | 37384684 | 37384911 | ZCCHC7 | Phased Variants |
| 468 | chr9 | 37407369 | 37407588 | GRHPR | Phased Variants |
| 469 | chr9 | 78686579 | 78686854 | PCSK5 | Genotyping |
| 470 | chr9 | 139390582 | 139390950 | NOTCH1 | Genotyping |
| 471 | chr9 | 139390952 | 139391172 | NOTCH1 | Genotyping |
| 472 | chr9 | 139402662 | 139402868 | NOTCH1 | Genotyping |
| 473 | chr10 | 5755066 | 5755273 | FAM208B | Phased Variants |
| 474 | chr10 | 89500957 | 89501139 | PAPSS2 | Genotyping |
| 475 | chr10 | 89603602 | 89604077 | KLLN | Genotyping |
| 476 | chr10 | 89624272 | 89624350 | PTEN | Genotyping |
| 477 | chr10 | 89653752 | 89653825 | PTEN | Genotyping |
| 478 | chr10 | 89653832 | 89653909 | PTEN | Genotyping |
| 479 | chr10 | 89685272 | 89685379 | PTEN | Genotyping |
| 480 | chr10 | 89690752 | 89690894 | PTEN | Genotyping |
| 481 | chr10 | 89692737 | 89692810 | PTEN | Genotyping |

TABLE 3-continued

| # | Chromosome | Region Start | Region End | Closest Gene | Reason for Inclusion |
|---|---|---|---|---|---|
| 482 | chr10 | 89692877 | 89692951 | PTEN | Genotyping |
| 483 | chr10 | 89692972 | 89693037 | PTEN | Genotyping |
| 484 | chr10 | 89711837 | 89711966 | PTEN | Genotyping |
| 485 | chr10 | 89711982 | 89712058 | PTEN | Genotyping |
| 486 | chr10 | 89717577 | 89717714 | PTEN | Genotyping |
| 487 | chr10 | 89717742 | 89717811 | PTEN | Genotyping |
| 488 | chr10 | 89720637 | 89720904 | PTEN | Genotyping |
| 489 | chr10 | 90074239 | 90074419 | RNLS | Genotyping |
| 490 | chr10 | 90537736 | 90538027 | LIPN | Genotyping |
| 491 | chr10 | 90579966 | 90580319 | LIPM | Genotyping |
| 492 | chr10 | 90699126 | 90699647 | ACTA2 | Genotyping |
| 493 | chr10 | 90773866 | 90774076 | FAS | Genotyping |
| 494 | chr10 | 91092211 | 91092423 | IFIT3 | Genotyping |
| 495 | chr10 | 91358986 | 91359298 | PANK1 | Genotyping |
| 496 | chr10 | 131640289 | 131640505 | EBF3 | Genotyping |
| 497 | chr11 | 58978692 | 58978791 | MPEG1 | Genotyping |
| 498 | chr11 | 58978927 | 58979095 | MPEG1 | Genotyping |
| 499 | chr11 | 58979112 | 58979365 | MPEG1 | Genotyping |
| 500 | chr11 | 65190342 | 65190557 | FRMD8 | Phased Variants |
| 501 | chr11 | 65266552 | 65266924 | SCYL1 | Phased Variants |
| 502 | chr11 | 65267397 | 65267603 | SCYL1 | Phased Variants |
| 503 | chr11 | 65623422 | 65623506 | CFL1 | Genotyping |
| 504 | chr11 | 69346691 | 69346940 | CCND1 | Genotyping |
| 505 | chr11 | 102188381 | 102188945 | BIRC3 | Phased Variants |
| 506 | chr11 | 111234536 | 111235068 | POU2AF1 | Genotyping |
| 507 | chr11 | 111249311 | 111249530 | POU2AF1 | Phased Variants |
| 508 | chr11 | 111613196 | 111613432 | PPP2R1B | Genotyping |
| 509 | chr11 | 111781036 | 111781641 | CRYAB | Genotyping |
| 510 | chr11 | 111904096 | 111904291 | DLAT | Genotyping |
| 511 | chr11 | 112405016 | 112405330 | AP002884.2 | Genotyping |
| 512 | chr11 | 112405341 | 112405621 | AP002884.2 | Genotyping |
| 513 | chr11 | 117101043 | 117101217 | PCSK7 | Genotyping |
| 514 | chr11 | 117712683 | 117712997 | FXYD6 | Genotyping |
| 515 | chr11 | 118754793 | 118755011 | CXCR5 | Phased Variants |
| 516 | chr11 | 118764838 | 118765408 | CXCR5 | Genotyping |
| 517 | chr11 | 118967323 | 118968029 | DPAGT1 | Genotyping |
| 518 | chr11 | 120127163 | 120127588 | POU2F3 | Genotyping |
| 519 | chr11 | 120189028 | 120189629 | POU2F3 | Genotyping |
| 520 | chr11 | 125472640 | 125472915 | STT3A | Genotyping |
| 521 | chr11 | 128391383 | 128391629 | ETS1 | Phased Variants |
| 522 | chr11 | 128391648 | 128392132 | ETS1 | Phased Variants |
| 523 | chr11 | 129739778 | 129740102 | NFRKB | Genotyping |
| 524 | chr11 | 131747549 | 131748030 | NTM | Genotyping |
| 525 | chr11 | 134027789 | 134027980 | NCAPD3 | Genotyping |
| 526 | chr11 | 134118684 | 134118873 | THYN1 | Genotyping |
| 527 | chr11 | 134129469 | 134130211 | ACAD8 | Genotyping |
| 528 | chr11 | 134130464 | 134131097 | ACAD8 | Genotyping |
| 529 | chr11 | 134133389 | 134133972 | ACAD8 | Genotyping |
| 530 | chr12 | 6439713 | 6439920 | TNFRSF1A | Genotyping |
| 531 | chr12 | 15813487 | 15813687 | EPS8 | Genotyping |
| 532 | chr12 | 18534682 | 18534856 | PIK3C2G | Genotyping |
| 533 | chr12 | 18544037 | 18544241 | PIK3C2G | Genotyping |
| 534 | chr12 | 18573807 | 18574017 | PIK3C2G | Genotyping |
| 535 | chr12 | 18699197 | 18699459 | PIK3C2G | Genotyping |
| 536 | chr12 | 18747397 | 18747562 | PIK3C2G | Genotyping |
| 537 | chr12 | 18800762 | 18801046 | PIK3C2G | Genotyping |
| 538 | chr12 | 18891267 | 18891560 | CAPZA3 | Genotyping |
| 539 | chr12 | 25205888 | 25206105 | LRMP | Phased Variants |
| 540 | chr12 | 25206398 | 25206616 | LRMP | Phased Variants |
| 541 | chr12 | 25206748 | 25206877 | LRMP | Phased Variants |
| 542 | chr12 | 25207088 | 25207474 | LRMP | Phased Variants |
| 543 | chr12 | 25398218 | 25398299 | KRAS | Genotyping |
| 544 | chr12 | 48190731 | 48190983 | HDAC7 | Genotyping |
| 545 | chr12 | 49415991 | 49416144 | KMT2D | Genotyping |
| 546 | chr12 | 49418306 | 49418550 | KMT2D | Genotyping |
| 547 | chr12 | 49420531 | 49420750 | KMT2D | Genotyping |
| 548 | chr12 | 49426451 | 49426592 | KMT2D | Genotyping |
| 549 | chr12 | 49427886 | 49428116 | KMT2D | Genotyping |
| 550 | chr12 | 49433331 | 49433507 | KMT2D | Genotyping |
| 551 | chr12 | 49437926 | 49438391 | KMT2D | Genotyping |
| 552 | chr12 | 49444391 | 49444595 | KMT2D | Genotyping |
| 553 | chr12 | 49447196 | 49447491 | KMT2D | Genotyping |
| 554 | chr12 | 57496552 | 57496735 | STAT6 | Genotyping |
| 555 | chr12 | 57498222 | 57498396 | STAT6 | Genotyping |
| 556 | chr12 | 57498912 | 57499150 | STAT6 | Genotyping |
| 557 | chr12 | 86198698 | 86199622 | RASSF9 | Genotyping |
| 558 | chr12 | 92537875 | 92538647 | BTG1 | Phased Variants |
| 559 | chr12 | 92538790 | 92539374 | BTG1 | Phased Variants |

TABLE 3-continued

| # | Chromosome | Region Start | Region End | Closest Gene | Reason for Inclusion |
|---|---|---|---|---|---|
| 560 | chr12 | 113495364 | 113496458 | DTX1 | Phased Variants |
| 561 | chr12 | 113496509 | 113496679 | DTX1 | Phased Variants |
| 562 | chr12 | 113496694 | 113496945 | DTX1 | Phased Variants |
| 563 | chr12 | 113497059 | 113497278 | DTX1 | Phased Variants |
| 564 | chr12 | 113515199 | 113515658 | DTX1 | Genotyping |
| 565 | chr12 | 113515664 | 113515934 | DTX1 | Genotyping |
| 566 | chr12 | 113530924 | 113531055 | DTX1 | Genotyping |
| 567 | chr12 | 113531319 | 113531531 | DTX1 | Genotyping |
| 568 | chr12 | 113531799 | 113531930 | DTX1 | Genotyping |
| 569 | chr12 | 113532569 | 113532781 | DTX1 | Genotyping |
| 570 | chr12 | 113532809 | 113533032 | DTX1 | Genotyping |
| 571 | chr12 | 113533099 | 113533237 | DTX1 | Genotyping |
| 572 | chr12 | 113534494 | 113534778 | DTX1 | Genotyping |
| 573 | chr12 | 122458781 | 122459524 | BCL7A | Phased Variants |
| 574 | chr12 | 122460811 | 122461193 | BCL7A | Phased Variants |
| 575 | chr12 | 122461316 | 122461882 | BCL7A | Phased Variants |
| 576 | chr12 | 122462001 | 122462210 | BCL7A | Phased Variants |
| 577 | chr12 | 122462716 | 122462935 | BCL7A | Phased Variants |
| 578 | chr12 | 122463031 | 122463137 | BCL7A | Phased Variants |
| 579 | chr13 | 32907206 | 32907376 | BRCA2 | Genotyping |
| 580 | chr13 | 32912226 | 32912828 | BRCA2 | Genotyping |
| 581 | chr13 | 41133662 | 41133842 | FOXO1 | Genotyping |
| 582 | chr13 | 41133922 | 41135026 | FOXO1 | Genotyping |
| 583 | chr13 | 41239682 | 41239755 | FOXO1 | Genotyping |
| 584 | chr13 | 41239827 | 41240356 | FOXO1 | Genotyping |
| 585 | chr13 | 41240362 | 41240788 | FOXO1 | Genotyping |
| 586 | chr13 | 46959165 | 46959379 | KIAA0226L | Phased Variants |
| 587 | chr13 | 46961680 | 46962067 | KIAA0226L | Phased Variants |
| 588 | chr13 | 51915233 | 51915552 | SERPINE3 | Genotyping |
| 589 | chr13 | 58207131 | 58209129 | PCDH17 | Genotyping |
| 590 | chr13 | 84453542 | 84455255 | SLITRK1 | Genotyping |
| 591 | chr13 | 113516229 | 113516436 | ATP11A | Phased Variants |
| 592 | chr14 | 23344697 | 23345206 | LRP10 | Genotyping |
| 593 | chr14 | 32615405 | 32615617 | ARHGAP5 | Genotyping |
| 594 | chr14 | 35873671 | 35873838 | NFKBIA | Genotyping |
| 595 | chr14 | 64330252 | 64330462 | SYNE2 | Phased Variants |
| 596 | chr14 | 69258238 | 69259642 | ZFP36L1 | Phased Variants |
| 597 | chr14 | 84420586 | 84420796 | FLRT2 | Phased Variants |
| 598 | chr14 | 96179592 | 96180295 | TCL1A | Phased Variants |
| 599 | chr14 | 106048955 | 106049032 | IGHA2 | Phased Variants |
| 600 | chr14 | 106054695 | 106055541 | IGHA2 | Genotyping |
| 601 | chr14 | 106055740 | 106055827 | IGHA2 | Genotyping |
| 602 | chr14 | 106055910 | 106055995 | IGHA2 | Genotyping |
| 603 | chr14 | 106056035 | 106056121 | IGHA2 | Genotyping |
| 604 | chr14 | 106068705 | 106068911 | IGHE | Phased Variants |
| 605 | chr14 | 106069045 | 106069384 | IGHE | Phased Variants |
| 606 | chr14 | 106071060 | 106071135 | IGHE | Phased Variants |
| 607 | chr14 | 106071190 | 106071271 | IGHE | Phased Variants |
| 608 | chr14 | 106092380 | 106092608 | IGHG4 | Genotyping |
| 609 | chr14 | 106092670 | 106093406 | IGHG4 | Genotyping |
| 610 | chr14 | 106093435 | 106093575 | IGHG4 | Genotyping |
| 611 | chr14 | 106093610 | 106094215 | IGHG4 | Genotyping |
| 612 | chr14 | 106094235 | 106094479 | IGHG4 | Genotyping |
| 613 | chr14 | 106094580 | 106094654 | IGHG4 | Genotyping |
| 614 | chr14 | 106094675 | 106094915 | IGHG4 | Genotyping |
| 615 | chr14 | 106095335 | 106095417 | IGHG4 | Phased Variants |
| 616 | chr14 | 106095480 | 106095560 | IGHG4 | Phased Variants |
| 617 | chr14 | 106110675 | 106110814 | IGHG2 | Phased Variants |
| 618 | chr14 | 106110830 | 106110904 | IGHG2 | Phased Variants |
| 619 | chr14 | 106110950 | 106111025 | IGHG2 | Phased Variants |
| 620 | chr14 | 106111100 | 106111311 | IGHG2 | Genotyping |
| 621 | chr14 | 106111390 | 106112121 | IGHG2 | Genotyping |
| 622 | chr14 | 106112160 | 106112302 | IGHG2 | Genotyping |
| 623 | chr14 | 106112335 | 106113010 | IGHG2 | Phased Variants |
| 624 | chr14 | 106113020 | 106113438 | IGHG2 | Phased Variants |
| 625 | chr14 | 106113450 | 106113625 | IGHG2 | Phased Variants |
| 626 | chr14 | 106113695 | 106113901 | IGHG2 | Phased Variants |
| 627 | chr14 | 106113905 | 106113984 | IGHG2 | Phased Variants |
| 628 | chr14 | 106114175 | 106114414 | IGHG2 | Phased Variants |
| 629 | chr14 | 106174970 | 106175819 | IGHA1 | Genotyping |
| 630 | chr14 | 106175820 | 106176042 | IGHA1 | Genotyping |
| 631 | chr14 | 106176070 | 106176217 | IGHA1 | Genotyping |
| 632 | chr14 | 106176235 | 106176320 | IGHA1 | Genotyping |
| 633 | chr14 | 106176375 | 106176932 | IGHA1 | Phased Variants |
| 634 | chr14 | 106176985 | 106177069 | IGHA1 | Phased Variants |
| 635 | chr14 | 106177425 | 106177536 | IGHA1 | Genotyping |
| 636 | chr14 | 106211960 | 106212864 | IGHG1 | Phased Variants |
| 637 | chr14 | 106212870 | 106212948 | IGHG1 | Phased Variants |

TABLE 3-continued

| # | Chromosome | Region Start | Region End | Closest Gene | Reason for Inclusion |
|---|---|---|---|---|---|
| 638 | chr14 | 106212980 | 106213124 | IGHG1 | Phased Variants |
| 639 | chr14 | 106213125 | 106213200 | IGHG1 | Phased Variants |
| 640 | chr14 | 106213210 | 106213525 | IGHG1 | Phased Variants |
| 641 | chr14 | 106213660 | 106214042 | IGHG1 | Phased Variants |
| 642 | chr14 | 106239250 | 106239357 | IGHG3 | Phased Variants |
| 643 | chr14 | 106239455 | 106239900 | IGHG3 | Phased Variants |
| 644 | chr14 | 106239990 | 106240155 | IGHG3 | Phased Variants |
| 645 | chr14 | 106240170 | 106240815 | IGHG3 | Phased Variants |
| 646 | chr14 | 106240820 | 106240892 | IGHG3 | Phased Variants |
| 647 | chr14 | 106240915 | 106241118 | IGHG3 | Phased Variants |
| 648 | chr14 | 106241200 | 106241278 | IGHG3 | Phased Variants |
| 649 | chr14 | 106241345 | 106241627 | IGHG3 | Phased Variants |
| 650 | chr14 | 106241630 | 106241705 | IGHG3 | Genotyping |
| 651 | chr14 | 106241710 | 106241975 | IGHG3 | Genotyping |
| 652 | chr14 | 106318100 | 106318327 | IGHM | Phased Variants |
| 653 | chr14 | 106322055 | 106322271 | IGHM | Phased Variants |
| 654 | chr14 | 106322905 | 106323129 | IGHM | Phased Variants |
| 655 | chr14 | 106323470 | 106323656 | IGHM | Phased Variants |
| 656 | chr14 | 106323805 | 106323896 | IGHM | Phased Variants |
| 657 | chr14 | 106324010 | 106324087 | IGHM | Phased Variants |
| 658 | chr14 | 106324155 | 106324245 | IGHM | Phased Variants |
| 659 | chr14 | 106324290 | 106324369 | IGHM | Phased Variants |
| 660 | chr14 | 106324490 | 106324577 | IGHM | Phased Variants |
| 661 | chr14 | 106324750 | 106325340 | IGHM | Phased Variants |
| 662 | chr14 | 106325360 | 106325513 | IGHM | Phased Variants |
| 663 | chr14 | 106325515 | 106325791 | IGHM | Phased Variants |
| 664 | chr14 | 106325820 | 106326095 | IGHJ6 | Phased Variants |
| 665 | chr14 | 106326245 | 106326338 | IGHJ6 | Phased Variants |
| 666 | chr14 | 106326450 | 106331808 | IGHD7-27 | Phased Variants |
| 667 | chr14 | 106357890 | 106357967 | IGHD6-19 | Phased Variants |
| 668 | chr14 | 106380360 | 106380541 | IGHD3-3 | Phased Variants |
| 669 | chr14 | 106380550 | 106380901 | IGHD3-3 | Phased Variants |
| 670 | chr14 | 106380910 | 106381109 | IGHD3-3 | Phased Variants |
| 671 | chr14 | 106381275 | 106381351 | IGHD3-3 | Phased Variants |
| 672 | chr14 | 106381485 | 106381633 | IGHD2-2 | Phased Variants |
| 673 | chr14 | 106381655 | 106381724 | IGHD2-2 | Phased Variants |
| 674 | chr14 | 106381890 | 106381968 | IGHD2-2 | Phased Variants |
| 675 | chr14 | 106381990 | 106382161 | IGHD2-2 | Phased Variants |
| 676 | chr14 | 106382325 | 106382403 | IGHD2-2 | Phased Variants |
| 677 | chr14 | 106382905 | 106383014 | IGHD2-2 | Phased Variants |
| 678 | chr14 | 106383030 | 106383140 | IGHD2-2 | Phased Variants |
| 679 | chr14 | 106383980 | 106384142 | IGHD1-1 | Phased Variants |
| 680 | chr14 | 106384630 | 106384702 | IGHD1-1 | Phased Variants |
| 681 | chr14 | 106384720 | 106384798 | IGHD1-1 | Phased Variants |
| 682 | chr14 | 106384825 | 106384957 | IGHD1-1 | Phased Variants |
| 683 | chr14 | 106405615 | 106405963 | IGHV6-1 | Genotyping |
| 684 | chr14 | 106452660 | 106452748 | IGHV1-2 | Genotyping |
| 685 | chr14 | 106452755 | 106452907 | IGHV1-2 | Genotyping |
| 686 | chr14 | 106452940 | 106453023 | IGHV1-2 | Genotyping |
| 687 | chr14 | 106471395 | 106471476 | IGHV1-3 | Genotyping |
| 688 | chr14 | 106471510 | 106471609 | IGHV1-3 | Genotyping |
| 689 | chr14 | 106494090 | 106494168 | IGHV2-5 | Phased Variants |
| 690 | chr14 | 106494210 | 106494365 | IGHV2-5 | Phased Variants |
| 691 | chr14 | 106494445 | 106494553 | IGHV2-5 | Phased Variants |
| 692 | chr14 | 106494565 | 106494640 | IGHV2-5 | Phased Variants |
| 693 | chr14 | 106494650 | 106494806 | IGHV2-5 | Phased Variants |
| 694 | chr14 | 106518495 | 106518570 | IGHV3-7 | Phased Variants |
| 695 | chr14 | 106518855 | 106518962 | IGHV3-7 | Phased Variants |
| 696 | chr14 | 106518970 | 106519111 | IGHV3-7 | Phased Variants |
| 697 | chr14 | 106539175 | 106539315 | IGHV1-8 | Genotyping |
| 698 | chr14 | 106552365 | 106552502 | IGHV3-9 | Genotyping |
| 699 | chr14 | 106573315 | 106573414 | IGHV3-11 | Genotyping |
| 700 | chr14 | 106573445 | 106573524 | IGHV3-11 | Genotyping |
| 701 | chr14 | 106573540 | 106573645 | IGHV3-11 | Phased Variants |
| 702 | chr14 | 106573685 | 106574021 | IGHV3-11 | Phased Variants |
| 703 | chr14 | 106586200 | 106586343 | IGHV3-13 | Genotyping |
| 704 | chr14 | 106610380 | 106610479 | IGHV3-15 | Genotyping |
| 705 | chr14 | 106610480 | 106610557 | IGHV3-15 | Genotyping |
| 706 | chr14 | 106610690 | 106610765 | IGHV3-15 | Phased Variants |
| 707 | chr14 | 106621885 | 106622026 | IGHV3-16 | Genotyping |
| 708 | chr14 | 106622035 | 106622108 | IGHV3-16 | Genotyping |
| 709 | chr14 | 106641655 | 106641789 | IGHV1-18 | Genotyping |
| 710 | chr14 | 106642110 | 106642265 | IGHV1-18 | Phased Variants |
| 711 | chr14 | 106667545 | 106667628 | IGHV3-20 | Genotyping |
| 712 | chr14 | 106667675 | 106667750 | IGHV3-20 | Genotyping |
| 713 | chr14 | 106667805 | 106667882 | IGHV3-20 | Genotyping |
| 714 | chr14 | 106691755 | 106691904 | IGHV3-21 | Genotyping |
| 715 | chr14 | 106725295 | 106725442 | IGHV3-23 | Phased Variants |

TABLE 3-continued

| # | Chromosome | Region Start | Region End | Closest Gene | Reason for Inclusion |
|---|---|---|---|---|---|
| 716 | chr14 | 106725550 | 106725663 | IGHV3-23 | Phased Variants |
| 717 | chr14 | 106725780 | 106725952 | IGHV3-23 | Phased Variants |
| 718 | chr14 | 106725995 | 106726188 | IGHV3-23 | Phased Variants |
| 719 | chr14 | 106732970 | 106733077 | IGHV1-24 | Phased Variants |
| 720 | chr14 | 106733185 | 106733270 | IGHV1-24 | Phased Variants |
| 721 | chr14 | 106733275 | 106733487 | IGHV1-24 | Phased Variants |
| 722 | chr14 | 106757725 | 106757888 | IGHV2-26 | Genotyping |
| 723 | chr14 | 106758470 | 106758653 | IGHV2-26 | Phased Variants |
| 724 | chr14 | 106780610 | 106780752 | IGHV4-28 | Genotyping |
| 725 | chr14 | 106791090 | 106791169 | IGHV3-30 | Phased Variants |
| 726 | chr14 | 106805290 | 106805428 | IGHV4-31 | Genotyping |
| 727 | chr14 | 106805945 | 106806076 | IGHV4-31 | Phased Variants |
| 728 | chr14 | 106806120 | 106806219 | IGHV4-31 | Phased Variants |
| 729 | chr14 | 106815805 | 106815910 | IGHV3-33 | Phased Variants |
| 730 | chr14 | 106829685 | 106829757 | IGHV4-34 | Phased Variants |
| 731 | chr14 | 106829765 | 106829986 | IGHV4-34 | Phased Variants |
| 732 | chr14 | 106830125 | 106830196 | IGHV4-34 | Phased Variants |
| 733 | chr14 | 106830240 | 106830312 | IGHV4-34 | Phased Variants |
| 734 | chr14 | 106830315 | 106830884 | IGHV4-34 | Phased Variants |
| 735 | chr14 | 106831185 | 106831594 | IGHV4-34 | Phased Variants |
| 736 | chr14 | 106845300 | 106845540 | IGHV3-35 | Genotyping |
| 737 | chr14 | 106846385 | 106846557 | IGHV3-35 | Phased Variants |
| 738 | chr14 | 106866380 | 106866461 | IGHV3-38 | Genotyping |
| 739 | chr14 | 106866475 | 106866638 | IGHV3-38 | Genotyping |
| 740 | chr14 | 106877715 | 106877858 | IGHV4-39 | Phased Variants |
| 741 | chr14 | 106877930 | 106878498 | IGHV4-39 | Phased Variants |
| 742 | chr14 | 106878540 | 106878612 | IGHV4-39 | Phased Variants |
| 743 | chr14 | 106878680 | 106878759 | IGHV4-39 | Phased Variants |
| 744 | chr14 | 106926180 | 106926405 | IGHV3-43 | Genotyping |
| 745 | chr14 | 106962965 | 106963167 | IGHV1-45 | Genotyping |
| 746 | chr14 | 106963170 | 106963280 | IGHV1-45 | Genotyping |
| 747 | chr14 | 106967130 | 106967209 | IGHV1-46 | Genotyping |
| 748 | chr14 | 106967315 | 106967397 | IGHV1-46 | Genotyping |
| 749 | chr14 | 106994300 | 106994376 | IGHV3-48 | Phased Variants |
| 750 | chr14 | 106994430 | 106994534 | IGHV3-48 | Phased Variants |
| 751 | chr14 | 106994545 | 106994618 | IGHV3-48 | Phased Variants |
| 752 | chr14 | 106994660 | 106994745 | IGHV3-48 | Phased Variants |
| 753 | chr14 | 106994760 | 106994904 | IGHV3-48 | Phased Variants |
| 754 | chr14 | 107013035 | 107013204 | IGHV3-49 | Genotyping |
| 755 | chr14 | 107034665 | 107034845 | IGHV5-51 | Genotyping |
| 756 | chr14 | 107034955 | 107035097 | IGHV5-51 | Genotyping |
| 757 | chr14 | 107078455 | 107078631 | IGHV1-58 | Genotyping |
| 758 | chr14 | 107083565 | 107083726 | IGHV4-59 | Phased Variants |
| 759 | chr14 | 107083790 | 107083923 | IGHV4-59 | Phased Variants |
| 760 | chr14 | 107113405 | 107113560 | IGHV3-64 | Phased Variants |
| 761 | chr14 | 107113820 | 107113922 | IGHV3-64 | Phased Variants |
| 762 | chr14 | 107114095 | 107114238 | IGHV3-64 | Phased Variants |
| 763 | chr14 | 107136755 | 107136899 | IGHV3-66 | Phased Variants |
| 764 | chr14 | 107169645 | 107169841 | IGHV1-69 | Phased Variants |
| 765 | chr14 | 107169970 | 107170195 | IGHV1-69 | Phased Variants |
| 766 | chr14 | 107170220 | 107170472 | IGHV1-69 | Phased Variants |
| 767 | chr14 | 107170475 | 107170563 | IGHV1-69 | Phased Variants |
| 768 | chr14 | 107170660 | 107170871 | IGHV1-69 | Phased Variants |
| 769 | chr14 | 107178305 | 107178377 | IGHV2-70 | Phased Variants |
| 770 | chr14 | 107178415 | 107178869 | IGHV2-70 | Phased Variants |
| 771 | chr14 | 107178880 | 107179116 | IGHV2-70 | Phased Variants |
| 772 | chr14 | 107179130 | 107179339 | IGHV2-70 | Phased Variants |
| 773 | chr14 | 107179360 | 107180001 | IGHV2-70 | Phased Variants |
| 774 | chr14 | 107199020 | 107199094 | IGHV3-72 | Genotyping |
| 775 | chr14 | 107199095 | 107199173 | IGHV3-72 | Genotyping |
| 776 | chr14 | 107210955 | 107211159 | IGHV3-73 | Genotyping |
| 777 | chr14 | 107218755 | 107218891 | IGHV3-74 | Genotyping |
| 778 | chr14 | 107258910 | 107259078 | IGHV7-81 | Phased Variants |
| 779 | chr14 | 107259100 | 107259206 | IGHV7-81 | Phased Variants |
| 780 | chr14 | 107259235 | 107259444 | IGHV7-81 | Phased Variants |
| 781 | chr14 | 107259555 | 107259635 | IGHV7-81 | Phased Variants |
| 782 | chr14 | 107282770 | 107282884 | IGHV7-81 | Genotyping |
| 783 | chr14 | 107282945 | 107283018 | IGHV7-81 | Genotyping |
| 784 | chr15 | 45003678 | 45003861 | B2M | Genotyping |
| 785 | chr15 | 45007718 | 45007927 | B2M | Genotyping |
| 786 | chr15 | 45008463 | 45008603 | B2M | Genotyping |
| 787 | chr15 | 66727354 | 66727536 | MAP2K1 | Genotyping |
| 788 | chr15 | 66729014 | 66729123 | MAP2K1 | Genotyping |
| 789 | chr15 | 66729139 | 66729292 | MAP2K1 | Genotyping |
| 790 | chr15 | 86312062 | 86312565 | KLHL25 | Genotyping |
| 791 | chr16 | 2812096 | 2812786 | SRRM2 | Genotyping |
| 792 | chr16 | 3779106 | 3779320 | CREBBP | Genotyping |
| 793 | chr16 | 3781171 | 3781464 | CREBBP | Genotyping |

TABLE 3-continued

| # | Chromosome | Region Start | Region End | Closest Gene | Reason for Inclusion |
|---|---|---|---|---|---|
| 794 | chr16 | 3781756 | 3781972 | CREBBP | Genotyping |
| 795 | chr16 | 3786011 | 3786223 | CREBBP | Genotyping |
| 796 | chr16 | 3786591 | 3786885 | CREBBP | Genotyping |
| 797 | chr16 | 3788511 | 3788716 | CREBBP | Genotyping |
| 798 | chr16 | 3789521 | 3789770 | CREBBP | Genotyping |
| 799 | chr16 | 3790376 | 3790580 | CREBBP | Genotyping |
| 800 | chr16 | 3794846 | 3794994 | CREBBP | Genotyping |
| 801 | chr16 | 3808801 | 3809009 | CREBBP | Genotyping |
| 802 | chr16 | 3817706 | 3817915 | CREBBP | Genotyping |
| 803 | chr16 | 3823711 | 3823942 | CREBBP | Genotyping |
| 804 | chr16 | 3824536 | 3824719 | CREBBP | Genotyping |
| 805 | chr16 | 3832716 | 3832942 | CREBBP | Genotyping |
| 806 | chr16 | 3900236 | 3900462 | CREBBP | Genotyping |
| 807 | chr16 | 3900561 | 3900914 | CREBBP | Genotyping |
| 808 | chr16 | 10971440 | 10973882 | CIITA | Phased Variants |
| 809 | chr16 | 10973885 | 10974203 | CIITA | Phased Variants |
| 810 | chr16 | 11348520 | 11349249 | SOCS1 | Phased Variants |
| 811 | chr16 | 30093722 | 30093935 | PPP4C | Genotyping |
| 812 | chr16 | 33523607 | 33523675 | IGHV3OR16-12 | Phased Variants |
| 813 | chr16 | 81946175 | 81946356 | PLCG2 | Genotyping |
| 814 | chr16 | 81953055 | 81953307 | PLCG2 | Genotyping |
| 815 | chr16 | 81962120 | 81962263 | PLCG2 | Genotyping |
| 816 | chr16 | 85933003 | 85933569 | IRF8 | Phased Variants |
| 817 | chr16 | 85936563 | 85936836 | IRF8 | Genotyping |
| 818 | chr16 | 85942563 | 85942821 | IRF8 | Genotyping |
| 819 | chr16 | 85945108 | 85945330 | IRF8 | Genotyping |
| 820 | chr16 | 85946708 | 85946887 | IRF8 | Genotyping |
| 821 | chr16 | 85948018 | 85948170 | IRF8 | Genotyping |
| 822 | chr16 | 85951993 | 85952448 | IRF8 | Genotyping |
| 823 | chr16 | 85953683 | 85953837 | IRF8 | Genotyping |
| 824 | chr16 | 85954723 | 85954937 | IRF8 | Genotyping |
| 825 | chr17 | 5366796 | 5367031 | DHX33 | Genotyping |
| 826 | chr17 | 7576949 | 7577197 | TP53 | Genotyping |
| 827 | chr17 | 7577444 | 7577683 | TP53 | Genotyping |
| 828 | chr17 | 7578129 | 7578336 | TP53 | Genotyping |
| 829 | chr17 | 7578344 | 7578591 | TP53 | Genotyping |
| 830 | chr17 | 7579259 | 7579428 | TP53 | Genotyping |
| 831 | chr17 | 18001529 | 18001704 | DRG2 | Genotyping |
| 832 | chr17 | 18022119 | 18022791 | MYO15A | Genotyping |
| 833 | chr17 | 40467709 | 40467857 | STAT3 | Genotyping |
| 834 | chr17 | 40469104 | 40469321 | STAT3 | Genotyping |
| 835 | chr17 | 40474309 | 40474530 | STAT3 | Genotyping |
| 836 | chr17 | 40474974 | 40475190 | STAT3 | Genotyping |
| 837 | chr17 | 40475254 | 40475394 | STAT3 | Genotyping |
| 838 | chr17 | 40478074 | 40478252 | STAT3 | Genotyping |
| 839 | chr17 | 40485844 | 40486132 | STAT3 | Genotyping |
| 840 | chr17 | 40489754 | 40489903 | STAT3 | Genotyping |
| 841 | chr17 | 40491284 | 40491489 | STAT3 | Genotyping |
| 842 | chr17 | 41847058 | 41847241 | DUSP3 | Genotyping |
| 843 | chr17 | 51900441 | 51900897 | KIF2B | Genotyping |
| 844 | chr17 | 56408574 | 56408755 | BZRAP1 | Phased Variants |
| 845 | chr17 | 56408884 | 56409615 | BZRAP1 | Phased Variants |
| 846 | chr17 | 62006520 | 62006919 | CD79B | Genotyping |
| 847 | chr17 | 62007105 | 62007279 | CD79B | Genotyping |
| 848 | chr17 | 62007410 | 62007761 | CD79B | Genotyping |
| 849 | chr17 | 62008645 | 62008786 | CD79B | Genotyping |
| 850 | chr17 | 62009505 | 62009659 | CD79B | Genotyping |
| 851 | chr17 | 63010240 | 63010308 | GNA13 | Phased Variants |
| 852 | chr17 | 63010315 | 63010973 | GNA13 | Phased Variants |
| 853 | chr17 | 63014313 | 63014461 | GNA13 | Genotyping |
| 854 | chr17 | 63049573 | 63049774 | GNA13 | Genotyping |
| 855 | chr17 | 63052443 | 63052678 | GNA13 | Genotyping |
| 856 | chr17 | 75447868 | 75448421 | 9-Sep | Phased Variants |
| 857 | chr17 | 78343503 | 78343715 | RNF213 | Genotyping |
| 858 | chr17 | 79478953 | 79479026 | ACTG1 | Genotyping |
| 859 | chr18 | 1477565 | 1477666 | ADCYAP1 | Phased Variants |
| 860 | chr18 | 6947104 | 6947347 | LAMA1 | Genotyping |
| 861 | chr18 | 6980464 | 6980680 | LAMA1 | Genotyping |
| 862 | chr18 | 13825915 | 13826461 | MC5R | Genotyping |
| 863 | chr18 | 30349775 | 30350300 | AC012123.1 | Phased Variants |
| 864 | chr18 | 48231684 | 48232112 | MAPK4 | Genotyping |
| 865 | chr18 | 48327694 | 48327901 | MRO | Genotyping |
| 866 | chr18 | 48512954 | 48513347 | ELAC1 | Genotyping |
| 867 | chr18 | 48591759 | 48592011 | SMAD4 | Genotyping |
| 868 | chr18 | 48593364 | 48593571 | SMAD4 | Genotyping |
| 869 | chr18 | 48604604 | 48604852 | SMAD4 | Genotyping |
| 870 | chr18 | 48703169 | 48703965 | MEX3C | Genotyping |
| 871 | chr18 | 53804515 | 53804796 | TXNL1 | Genotyping |

TABLE 3-continued

| # | Chromosome | Region Start | Region End | Closest Gene | Reason for Inclusion |
|---|---|---|---|---|---|
| 872 | chr18 | 55274405 | 55274580 | NARS | Genotyping |
| 873 | chr18 | 55319680 | 55319999 | ATP8B1 | Genotyping |
| 874 | chr18 | 55329690 | 55329857 | ATP8B1 | Genotyping |
| 875 | chr18 | 55359005 | 55359259 | ATP8B1 | Genotyping |
| 876 | chr18 | 56054915 | 56055594 | NEDD4L | Genotyping |
| 877 | chr18 | 56063365 | 56063826 | NEDD4L | Genotyping |
| 878 | chr18 | 60763829 | 60764032 | BCL2 | Genotyping |
| 879 | chr18 | 60764299 | 60764540 | BCL2 | Genotyping |
| 880 | chr18 | 60774414 | 60774660 | BCL2 | Genotyping |
| 881 | chr18 | 60793369 | 60793654 | BCL2 | Genotyping |
| 882 | chr18 | 60795829 | 60796006 | BCL2 | Genotyping |
| 883 | chr18 | 60806264 | 60806836 | BCL2 | Phased Variants |
| 884 | chr18 | 60983784 | 60983991 | BCL2 | Phased Variants |
| 885 | chr18 | 60984454 | 60986731 | BCL2 | Phased Variants |
| 886 | chr18 | 60986844 | 60987047 | BCL2 | Phased Variants |
| 887 | chr18 | 60987964 | 60988511 | BCL2 | Phased Variants |
| 888 | chr18 | 64172116 | 64172531 | CDH19 | Genotyping |
| 889 | chr18 | 64176241 | 64176518 | CDH19 | Genotyping |
| 890 | chr18 | 64239166 | 64239357 | CDH19 | Genotyping |
| 891 | chr18 | 65179856 | 65181824 | DSEL | Genotyping |
| 892 | chr18 | 73944893 | 73945380 | ZNF516 | Genotyping |
| 893 | chr18 | 75683734 | 75684502 | GALR1 | Genotyping |
| 894 | chr18 | 77092820 | 77093034 | ATP9B | Genotyping |
| 895 | chr18 | 77170715 | 77171032 | NFATC1 | Genotyping |
| 896 | chr18 | 77208755 | 77208996 | NFATC1 | Genotyping |
| 897 | chr18 | 77227415 | 77227661 | NFATC1 | Genotyping |
| 898 | chr18 | 77288040 | 77288611 | NFATC1 | Genotyping |
| 899 | chr18 | 77794425 | 77795130 | RBFA | Genotyping |
| 900 | chr19 | 1376440 | 1376662 | MUM1 | Genotyping |
| 901 | chr19 | 6586161 | 6586445 | CD70 | Genotyping |
| 902 | chr19 | 6590026 | 6590238 | CD70 | Genotyping |
| 903 | chr19 | 6590786 | 6591079 | CD70 | Genotyping |
| 904 | chr19 | 8028408 | 8028583 | ELAVL1 | Genotyping |
| 905 | chr19 | 10334563 | 10335187 | S1PR2 | Genotyping |
| 906 | chr19 | 10335308 | 10335585 | S1PR2 | Genotyping |
| 907 | chr19 | 10340823 | 10341376 | S1PR2 | Phased Variants |
| 908 | chr19 | 10341833 | 10341984 | S1PR2 | Genotyping |
| 909 | chr19 | 12902574 | 12902861 | JUNB | Genotyping |
| 910 | chr19 | 19256469 | 19256851 | MEF2B | Genotyping |
| 911 | chr19 | 19257044 | 19257222 | MEF2B | Genotyping |
| 912 | chr19 | 19257339 | 19257480 | MEF2B | Genotyping |
| 913 | chr19 | 19257489 | 19257741 | MEF2B | Genotyping |
| 914 | chr19 | 19257824 | 19258036 | MEF2B | Genotyping |
| 915 | chr19 | 19258484 | 19258662 | MEF2B | Genotyping |
| 916 | chr19 | 19259984 | 19260176 | MEF2B | Genotyping |
| 917 | chr19 | 19261414 | 19261588 | MEF2B | Genotyping |
| 918 | chr19 | 19293309 | 19293478 | MEF2BNB | Genotyping |
| 919 | chr19 | 42599890 | 42600121 | POU2F2 | Genotyping |
| 920 | chr19 | 51525626 | 51525937 | KLK11 | Genotyping |
| 921 | chr19 | 51559441 | 51560040 | KLK13 | Genotyping |
| 922 | chr19 | 51561771 | 51561943 | KLK13 | Genotyping |
| 923 | chr19 | 52381611 | 52381786 | ZNF577 | Genotyping |
| 924 | chr19 | 52403336 | 52403586 | ZNF649 | Genotyping |
| 925 | chr19 | 52961146 | 52961224 | ZNF534 | Genotyping |
| 926 | chr19 | 52961226 | 52961578 | ZNF534 | Genotyping |
| 927 | chr19 | 53598586 | 53599055 | ZNF160 | Genotyping |
| 928 | chr20 | 23028372 | 23028858 | THBD | Genotyping |
| 929 | chr20 | 25003526 | 25003774 | ACSS1 | Genotyping |
| 930 | chr20 | 46131072 | 46131213 | NCOA3 | Phased Variants |
| 931 | chr20 | 46131217 | 46131287 | NCOA3 | Phased Variants |
| 932 | chr21 | 18981233 | 18981504 | BTG3 | Genotyping |
| 933 | chr21 | 28213258 | 28213536 | ADAMTS1 | Genotyping |
| 934 | chr21 | 28216763 | 28217005 | ADAMTS1 | Genotyping |
| 935 | chr22 | 22380472 | 22381038 | IGLV4-69 | Phased Variants |
| 936 | chr22 | 22385622 | 22385767 | IGLV4-69 | Genotyping |
| 937 | chr22 | 22385777 | 22385898 | IGLV4-69 | Genotyping |
| 938 | chr22 | 22453287 | 22453502 | IGLV8-61 | Genotyping |
| 939 | chr22 | 22453527 | 22453608 | IGLV8-61 | Genotyping |
| 940 | chr22 | 22516707 | 22516785 | IGLV4-60 | Phased Variants |
| 941 | chr22 | 22516827 | 22517113 | IGLV4-60 | Phased Variants |
| 942 | chr22 | 22550337 | 22550812 | IGLV6-57 | Genotyping |
| 943 | chr22 | 22556227 | 22556630 | IGLV11-55 | Genotyping |
| 944 | chr22 | 22569332 | 22569655 | IGLV10-54 | Genotyping |
| 945 | chr22 | 22673242 | 22673607 | IGLV5-52 | Genotyping |
| 946 | chr22 | 22677077 | 22677216 | IGLV1-51 | Phased Variants |
| 947 | chr22 | 22677227 | 22677337 | IGLV1-51 | Genotyping |
| 948 | chr22 | 22681927 | 22682007 | IGLV1-50 | Genotyping |
| 949 | chr22 | 22682097 | 22682213 | IGLV1-50 | Genotyping |

TABLE 3-continued

| # | Chromosome | Region Start | Region End | Closest Gene | Reason for Inclusion |
|---|---|---|---|---|---|
| 950 | chr22 | 22697727 | 22698123 | IGLV9-49 | Genotyping |
| 951 | chr22 | 22707427 | 22707509 | IGLV5-48 | Genotyping |
| 952 | chr22 | 22707517 | 22707658 | IGLV5-48 | Phased Variants |
| 953 | chr22 | 22707742 | 22707823 | IGLV5-48 | Genotyping |
| 954 | chr22 | 22712077 | 22712496 | IGLV1-47 | Phased Variants |
| 955 | chr22 | 22712512 | 22712625 | IGLV1-47 | Genotyping |
| 956 | chr22 | 22723897 | 22724189 | IGLV7-46 | Phased Variants |
| 957 | chr22 | 22724207 | 22724494 | IGLV7-46 | Phased Variants |
| 958 | chr22 | 22730452 | 22730552 | IGLV5-45 | Phased Variants |
| 959 | chr22 | 22730607 | 22730756 | IGLV5-45 | Phased Variants |
| 960 | chr22 | 22730887 | 22730955 | IGLV5-45 | Phased Variants |
| 961 | chr22 | 22735417 | 22735604 | IGLV1-44 | Phased Variants |
| 962 | chr22 | 22735792 | 22735878 | IGLV1-44 | Phased Variants |
| 963 | chr22 | 22749602 | 22749701 | IGLV7-43 | Phased Variants |
| 964 | chr22 | 22749732 | 22749853 | IGLV7-43 | Phased Variants |
| 965 | chr22 | 22749857 | 22749939 | IGLV7-43 | Phased Variants |
| 966 | chr22 | 22749942 | 22750074 | IGLV7-43 | Phased Variants |
| 967 | chr22 | 22750092 | 22750342 | IGLV7-43 | Phased Variants |
| 968 | chr22 | 22758647 | 22759294 | IGLV1-40 | Phased Variants |
| 969 | chr22 | 22759297 | 22759377 | IGLV1-40 | Phased Variants |
| 970 | chr22 | 22764167 | 22764309 | IGLV1-40 | Phased Variants |
| 971 | chr22 | 22764367 | 22764450 | IGLV1-40 | Phased Variants |
| 972 | chr22 | 22764552 | 22764634 | IGLV1-40 | Phased Variants |
| 973 | chr22 | 22782037 | 22782325 | IGLV5-37 | Genotyping |
| 974 | chr22 | 22786477 | 22786702 | IGLV1-36 | Genotyping |
| 975 | chr22 | 22786727 | 22786842 | IGLV1-36 | Genotyping |
| 976 | chr22 | 22930852 | 22931173 | IGLV2-33 | Genotyping |
| 977 | chr22 | 22937192 | 22937341 | IGLV3-32 | Genotyping |
| 978 | chr22 | 22937347 | 22937548 | IGLV3-32 | Genotyping |
| 979 | chr22 | 23010977 | 23011143 | IGLV3-27 | Genotyping |
| 980 | chr22 | 23011172 | 23011316 | IGLV3-27 | Genotyping |
| 981 | chr22 | 23029497 | 23029581 | IGLV3-25 | Genotyping |
| 982 | chr22 | 23029622 | 23029778 | IGLV3-25 | Genotyping |
| 983 | chr22 | 23040452 | 23040527 | IGLV2-23 | Phased Variants |
| 984 | chr22 | 23040592 | 23040811 | IGLV2-23 | Phased Variants |
| 985 | chr22 | 23040852 | 23041365 | IGLV2-23 | Phased Variants |
| 986 | chr22 | 23047067 | 23047329 | IGLV3-22 | Genotyping |
| 987 | chr22 | 23055367 | 23055445 | IGLV3-21 | Genotyping |
| 988 | chr22 | 23055497 | 23055577 | IGLV3-21 | Phased Variants |
| 989 | chr22 | 23055727 | 23055857 | IGLV3-21 | Phased Variants |
| 990 | chr22 | 23063307 | 23063661 | IGLV3-19 | Genotyping |
| 991 | chr22 | 23077337 | 23077435 | IGLV2-18 | Genotyping |
| 992 | chr22 | 23077537 | 23077615 | IGLV2-18 | Genotyping |
| 993 | chr22 | 23090122 | 23090205 | IGLV3-16 | Genotyping |
| 994 | chr22 | 23090287 | 23090372 | IGLV3-16 | Genotyping |
| 995 | chr22 | 23101392 | 23101473 | IGLV2-14 | Phased Variants |
| 996 | chr22 | 23101532 | 23101605 | IGLV2-14 | Phased Variants |
| 997 | chr22 | 23101652 | 23101735 | IGLV2-14 | Genotyping |
| 998 | chr22 | 23114792 | 23114874 | IGLV3-12 | Genotyping |
| 999 | chr22 | 23114947 | 23115052 | IGLV3-12 | Genotyping |
| 1000 | chr22 | 23135152 | 23135230 | IGLV2-11 | Genotyping |
| 1001 | chr22 | 23135247 | 23135399 | IGLV2-11 | Genotyping |
| 1002 | chr22 | 23135437 | 23135521 | IGLV2-11 | Genotyping |
| 1003 | chr22 | 23154347 | 23154477 | IGLV3-10 | Phased Variants |
| 1004 | chr22 | 23154597 | 23154815 | IGLV3-10 | Phased Variants |
| 1005 | chr22 | 23161917 | 23162052 | IGLV3-9 | Genotyping |
| 1006 | chr22 | 23162072 | 23162290 | IGLV3-9 | Genotyping |
| 1007 | chr22 | 23165422 | 23165496 | IGLV2-8 | Phased Variants |
| 1008 | chr22 | 23165542 | 23165680 | IGLV2-8 | Phased Variants |
| 1009 | chr22 | 23165727 | 23165811 | IGLV2-8 | Phased Variants |
| 1010 | chr22 | 23192412 | 23192818 | IGLV4-3 | Phased Variants |
| 1011 | chr22 | 23197917 | 23198053 | IGLV4-3 | Phased Variants |
| 1012 | chr22 | 23198067 | 23198475 | IGLV4-3 | Phased Variants |
| 1013 | chr22 | 23198587 | 23198732 | IGLV4-3 | Phased Variants |
| 1014 | chr22 | 23198797 | 23198869 | IGLV4-3 | Phased Variants |
| 1015 | chr22 | 23199022 | 23199127 | IGLV4-3 | Phased Variants |
| 1016 | chr22 | 23199182 | 23199261 | IGLV4-3 | Phased Variants |
| 1017 | chr22 | 23199277 | 23199671 | IGLV4-3 | Phased Variants |
| 1018 | chr22 | 23213857 | 23214141 | IGLV4-3 | Genotyping |
| 1019 | chr22 | 23214167 | 23214249 | IGLV4-3 | Genotyping |
| 1020 | chr22 | 23222927 | 23223065 | IGLV3-1 | Phased Variants |
| 1021 | chr22 | 23223077 | 23223319 | IGLV3-1 | Phased Variants |
| 1022 | chr22 | 23223327 | 23224010 | IGLV3-1 | Phased Variants |
| 1023 | chr22 | 23227062 | 23227279 | IGLL5 | Phased Variants |
| 1024 | chr22 | 23227567 | 23227896 | IGLL5 | Phased Variants |
| 1025 | chr22 | 23227897 | 23228624 | IGLL5 | Phased Variants |
| 1026 | chr22 | 23229332 | 23229550 | IGLL5 | Phased Variants |
| 1027 | chr22 | 23229562 | 23229739 | IGLL5 | Phased Variants |

TABLE 3-continued

| # | Chromosome | Region Start | Region End | Closest Gene | Reason for Inclusion |
|---|---|---|---|---|---|
| 1028 | chr22 | 23230012 | 23231063 | IGLL5 | Phased Variants |
| 1029 | chr22 | 23231072 | 23231764 | IGLL5 | Phased Variants |
| 1030 | chr22 | 23231927 | 23232005 | IGLL5 | Phased Variants |
| 1031 | chr22 | 23232062 | 23232346 | IGLL5 | Phased Variants |
| 1032 | chr22 | 23232362 | 23232465 | IGLL5 | Phased Variants |
| 1033 | chr22 | 23232517 | 23232737 | IGLL5 | Phased Variants |
| 1034 | chr22 | 23234612 | 23235837 | IGLJ1 | Phased Variants |
| 1035 | chr22 | 23235847 | 23236276 | IGLJ1 | Phased Variants |
| 1036 | chr22 | 23236277 | 23236378 | IGLJ1 | Phased Variants |
| 1037 | chr22 | 23236387 | 23236526 | IGLJ1 | Phased Variants |
| 1038 | chr22 | 23236557 | 23236851 | IGLJ1 | Phased Variants |
| 1039 | chr22 | 23236877 | 23237366 | IGLC1 | Phased Variants |
| 1040 | chr22 | 23241762 | 23241835 | IGLJ2 | Genotyping |
| 1041 | chr22 | 23242602 | 23242981 | IGLC2 | Phased Variants |
| 1042 | chr22 | 23244157 | 23244373 | IGLC2 | Phased Variants |
| 1043 | chr22 | 23247137 | 23247209 | IGLJ3 | Genotyping |
| 1044 | chr22 | 23247257 | 23247444 | IGLJ3 | Phased Variants |
| 1045 | chr22 | 23247467 | 23247630 | IGLJ3 | Phased Variants |
| 1046 | chr22 | 23248182 | 23248404 | IGLC3 | Phased Variants |
| 1047 | chr22 | 23252687 | 23252824 | IGLJ4 | Genotyping |
| 1048 | chr22 | 23256362 | 23256504 | IGLJ5 | Genotyping |
| 1049 | chr22 | 23260267 | 23260399 | IGLJ6 | Genotyping |
| 1050 | chr22 | 23263507 | 23263653 | IGLJ7 | Genotyping |
| 1051 | chr22 | 23263872 | 23264263 | IGLJ7 | Phased Variants |
| 1052 | chr22 | 23278157 | 23278381 | IGLC7 | Phased Variants |
| 1053 | chr22 | 23282767 | 23282839 | IGLC7 | Phased Variants |
| 1054 | chr22 | 23282842 | 23282956 | IGLC7 | Phased Variants |
| 1055 | chr22 | 23523567 | 23524204 | BCR | Genotyping |
| 1056 | chr22 | 23524212 | 23524419 | BCR | Genotyping |
| 1057 | chr22 | 23610547 | 23610791 | BCR | Genotyping |
| 1058 | chr22 | 29191136 | 29191455 | XBP1 | Genotyping |
| 1059 | chr22 | 29191461 | 29191746 | XBP1 | Genotyping |
| 1060 | chr22 | 29192006 | 29192215 | XBP1 | Genotyping |
| 1061 | chr22 | 29193041 | 29193205 | XBP1 | Genotyping |
| 1062 | chr22 | 29196261 | 29196547 | XBP1 | Genotyping |
| 1063 | chr22 | 41513340 | 41513562 | EP300 | Genotyping |
| 1064 | chr22 | 41525845 | 41526047 | EP300 | Genotyping |
| 1065 | chr22 | 41527440 | 41527664 | EP300 | Genotyping |
| 1066 | chr22 | 41536110 | 41536291 | EP300 | Genotyping |
| 1067 | chr22 | 41545740 | 41545940 | EP300 | Genotyping |
| 1068 | chr22 | 41545995 | 41546223 | EP300 | Genotyping |
| 1069 | chr22 | 41565485 | 41565650 | EP300 | Genotyping |
| 1070 | chr22 | 41566385 | 41566592 | EP300 | Genotyping |
| 1071 | chr22 | 41568480 | 41568693 | EP300 | Genotyping |
| 1072 | chr22 | 41569600 | 41569814 | EP300 | Genotyping |
| 1073 | chr22 | 41572225 | 41572436 | EP300 | Genotyping |
| 1074 | chr22 | 41572800 | 41573022 | EP300 | Genotyping |
| 1075 | chr22 | 41573300 | 41573515 | EP300 | Genotyping |
| 1076 | chr22 | 41574255 | 41574486 | EP300 | Genotyping |
| 1077 | chr22 | 41574685 | 41574904 | EP300 | Genotyping |
| 1078 | chr22 | 47570209 | 47570414 | TBC1D22A | Phased Variants |
| 1079 | chrX | 1584324 | 1585521 | P2RY8 | Genotyping |
| 1080 | chrX | 1655789 | 1656029 | AKAP17A | Genotyping |
| 1081 | chrX | 12993264 | 12993539 | TMSB4X | Phased Variants |
| 1082 | chrX | 12993544 | 12994173 | TMSB4X | Phased Variants |
| 1083 | chrX | 12994289 | 12994397 | TMSB4X | Phased Variants |
| 1084 | chrX | 12994444 | 12994514 | TMSB4X | Phased Variants |
| 1085 | chrX | 33146106 | 33146490 | DMD | Phased Variants |
| 1086 | chrX | 35820576 | 35821268 | MAGEB16 | Genotyping |
| 1087 | chrX | 70347816 | 70348034 | MED12 | Genotyping |
| 1088 | chrX | 70612661 | 70612778 | TAF1 | Genotyping |
| 1089 | chrX | 73962123 | 73963110 | KIAA2022 | Genotyping |
| 1090 | chrX | 86772953 | 86773345 | KLHL4 | Genotyping |
| 1091 | chrX | 90026453 | 90026652 | PABPC5 | Phased Variants |
| 1092 | chrX | 100610984 | 100611308 | BTK | Genotyping |
| 1093 | chrX | 119509280 | 119509492 | ATP1B4 | Genotyping |
| 1094 | chrX | 141291052 | 141291326 | MAGEC2 | Genotyping |
| 1095 | chrX | 141291357 | 141291566 | MAGEC2 | Genotyping |
| 1096 | chrX | 153997383 | 153997622 | DKC1 | Genotyping |

TABLE 4

| # | Chromosome | Region Start | Region End | Number of 50 bp bins | Gene | Mean frac DLBCL with PV | Mean frac GCB with PV |
|---|---|---|---|---|---|---|---|
| 1 | chr22 | 23227063 | 23237340 | 135 | IGLL5 | 0.184 | 0.158 |
| 2 | chr18 | 60763830 | 60988465 | 104 | BCL2 | 0.111 | 0.165 |
| 3 | chr14 | 106239251 | 106241954 | 49 | IGHG3 | 0.193 | 0.155 |
| 4 | chr14 | 106092381 | 106095531 | 51 | IGHG4 | 0.179 | 0.155 |
| 5 | chr6 | 37138285 | 37141880 | 36 | PIM1 | 0.073 | 0.039 |
| 6 | chr22 | 22758648 | 22764603 | 22 | IGLV1-40 | 0.064 | 0.098 |
| 7 | chr2 | 89161240 | 89165610 | 66 | IGKJ1 | 0.144 | 0.134 |
| 8 | chr14 | 106829686 | 106831586 | 30 | IGHV4-34 | 0.077 | 0.049 |
| 9 | chr2 | 89158619 | 89160190 | 32 | IGKJ5 | 0.307 | 0.286 |
| 10 | chr22 | 23222928 | 23223998 | 22 | IGLV3-1 | 0.266 | 0.300 |
| 11 | chr14 | 106211961 | 106214011 | 39 | IGHG1 | 0.229 | 0.197 |
| 12 | chr14 | 106329751 | 106330201 | 10 | IGHJ5 | 0.320 | 0.261 |
| 13 | chr3 | 187957433 | 188471931 | 54 | LPP | 0.080 | 0.102 |
| 14 | chr2 | 89160890 | 89161190 | 7 | IGKJ2 | 0.151 | 0.096 |
| 15 | chr6 | 134491383 | 134495968 | 64 | SGK1 | 0.039 | 0.053 |
| 16 | chr6 | 150954421 | 150954821 | 9 | PLEKHG1 | 0.067 | 0.049 |
| 17 | chr2 | 89246682 | 89247982 | 18 | IGKV1-5 | 0.031 | 0.023 |
| 18 | chr8 | 128746808 | 128764273 | 164 | MYC | 0.037 | 0.047 |
| 19 | chr22 | 23040453 | 23041334 | 17 | IGLV2-23 | 0.051 | 0.073 |
| 20 | chr2 | 89160240 | 89160540 | 7 | IGKJ4 | 0.259 | 0.225 |
| 21 | chr22 | 22516708 | 22517100 | 8 | IGLV4-60 | 0.084 | 0.117 |
| 22 | chr12 | 122458782 | 122463132 | 48 | BCL7A | 0.091 | 0.106 |
| 23 | chr14 | 107178306 | 107179990 | 33 | IGHV2-70 | 0.224 | 0.242 |
| 24 | chr2 | 89160590 | 89160840 | 6 | IGKJ3 | 0.185 | 0.137 |
| 25 | chr22 | 22730453 | 22730938 | 7 | IGLV5-45 | 0.069 | 0.108 |
| 26 | chr22 | 23248183 | 23248383 | 5 | IGLC3 | 0.164 | 0.236 |
| 27 | chr2 | 89127262 | 89158569 | 66 | IGKC | 0.089 | 0.077 |
| 28 | chr9 | 37293170 | 37384885 | 18 | ZCCHC7 | 0.055 | 0.075 |
| 29 | chr14 | 106732971 | 106733441 | 9 | IGHV1-24 | 0.036 | 0.060 |
| 30 | chr2 | 89184967 | 89185677 | 15 | IGKV4-1 | 0.103 | 0.133 |
| 31 | chr2 | 59821915 | 60773435 | 12 | BCL11A | 0.035 | 0.053 |
| 32 | chr20 | 46131073 | 46131277 | 5 | NCOA3 | 0.071 | 0.102 |
| 33 | chr22 | 23165423 | 23165766 | 6 | IGLV2-8 | 0.045 | 0.022 |
| 34 | chr8 | 8748688 | 8750268 | 17 | MFHAS1 | 0.033 | 0.051 |
| 35 | chr19 | 52961147 | 52961549 | 9 | ZNF534 | 0.029 | 0.018 |
| 36 | chr9 | 16435499 | 16436299 | 17 | BNC2 | 0.034 | 0.049 |
| 37 | chr22 | 23264173 | 23282921 | 11 | IGLC7 | 0.041 | 0.061 |
| 38 | chr14 | 106318101 | 106325773 | 50 | IGHM | 0.181 | 0.175 |
| 39 | chr22 | 23235813 | 23235973 | 4 | IGLJ1 | 0.059 | 0.033 |
| 40 | chr16 | 11348521 | 11349221 | 15 | SOCS1 | 0.108 | 0.126 |
| 41 | chr16 | 10971441 | 10974194 | 56 | CIITA | 0.072 | 0.084 |
| 42 | chr5 | 13864466 | 13864666 | 5 | DNAH5 | 0.034 | 0.056 |
| 43 | chr6 | 27777784 | 27778062 | 6 | HIST1H3H | 0.041 | 0.025 |
| 44 | chr22 | 23192413 | 23214234 | 46 | IGLV4-3 | 0.061 | 0.074 |
| 45 | chr14 | 106330251 | 106330601 | 8 | IGHJ4 | 0.166 | 0.143 |
| 46 | chr14 | 106877716 | 106878731 | 18 | IGHV4-39 | 0.050 | 0.064 |
| 47 | chr10 | 90773867 | 90774067 | 5 | FAS | 0.042 | 0.066 |
| 48 | chr22 | 22723898 | 22724466 | 12 | IGLV7-46 | 0.057 | 0.081 |
| 49 | chr5 | 137801488 | 137801798 | 6 | EGR1 | 0.031 | 0.052 |
| 50 | chr22 | 23242603 | 23244358 | 13 | IGLC2 | 0.139 | 0.164 |
| 51 | chr22 | 22930853 | 22931153 | 7 | IGLV2-33 | 0.030 | 0.021 |
| 52 | chr14 | 106325852 | 106329701 | 73 | IGHJ6 | 0.474 | 0.471 |
| 53 | chr3 | 185697424 | 185697624 | 5 | TRA2B | 0.040 | 0.059 |
| 54 | chr6 | 26056035 | 26056539 | 11 | HIST1H1C | 0.059 | 0.079 |
| 55 | chr3 | 71551102 | 71551452 | 8 | FOXP1 | 0.015 | 0.006 |
| 56 | chr3 | 187440190 | 187661368 | 137 | BCL6 | 0.106 | 0.116 |
| 57 | chr11 | 128391384 | 128392103 | 15 | ETS1 | 0.061 | 0.059 |
| 58 | chr13 | 46959166 | 46962031 | 13 | KIAA0226L | 0.034 | 0.029 |
| 59 | chr11 | 118754794 | 118765389 | 17 | CXCR5 | 0.035 | 0.029 |
| 60 | chr17 | 62006521 | 62009656 | 27 | CD79B | 0.041 | 0.039 |
| 61 | chr1 | 2334442 | 2335149 | 15 | RER1 | 0.019 | 0.016 |
| 62 | chr8 | 139600458 | 139601543 | 20 | COL22A1 | 0.031 | 0.043 |
| 63 | chr1 | 34404023 | 34404123 | 3 | CSMD2 | 0.073 | 0.104 |
| 64 | chr6 | 26216780 | 26216880 | 3 | HIST1H2BG | 0.040 | 0.066 |
| 65 | chr19 | 52381612 | 52381762 | 4 | ZNF577 | 0.032 | 0.053 |
| 66 | chr11 | 65266553 | 65267598 | 13 | SCYL1 | 0.030 | 0.045 |
| 67 | chr22 | 23029498 | 23029739 | 5 | IGLV3-25 | 0.085 | 0.108 |
| 68 | chr9 | 78686580 | 78686830 | 6 | PCSK5 | 0.035 | 0.052 |
| 69 | chr14 | 106048956 | 106056101 | 25 | IGHA2 | 0.071 | 0.071 |
| 70 | chr14 | 69258239 | 69259639 | 29 | ZFP36L1 | 0.088 | 0.103 |
| 71 | chr5 | 75913717 | 75914417 | 15 | F2RL2 | 0.030 | 0.044 |
| 72 | chr14 | 106926181 | 106926381 | 5 | IGHV3-43 | 0.038 | 0.056 |
| 73 | chr6 | 27782719 | 27782919 | 5 | HIST1H2BM | 0.032 | 0.052 |
| 74 | chr2 | 100758484 | 100758634 | 4 | AFF3 | 0.037 | 0.025 |
| 75 | chr8 | 136569670 | 137528538 | 22 | KHDRBS3 | 0.029 | 0.041 |
| 76 | chr6 | 392761 | 395016 | 15 | IRF4 | 0.035 | 0.031 |

TABLE 4-continued

| | | | | | | | |
|---|---|---|---|---|---|---|---|
| 77 | chr8 | 3141725 | 4495082 | 9 | CSMD1 | 0.034 | 0.051 |
| 78 | chr14 | 106330651 | 106331101 | 10 | IGHJ3 | 0.057 | 0.075 |
| 79 | chr16 | 30093723 | 30093923 | 5 | PPP4C | 0.034 | 0.023 |
| 80 | chr12 | 92537876 | 92539341 | 28 | BTG1 | 0.058 | 0.057 |
| 81 | chr17 | 5366797 | 5366997 | 5 | DHX33 | 0.022 | 0.010 |
| 82 | chr22 | 22697728 | 22698078 | 8 | IGLV9-49 | 0.041 | 0.035 |
| 83 | chr22 | 23256363 | 23256463 | 3 | IGLJ5 | 0.059 | 0.082 |
| 84 | chr5 | 176522450 | 176522600 | 4 | FGFR4 | 0.037 | 0.025 |
| 85 | chr13 | 113516230 | 113516430 | 5 | ATP11A | 0.050 | 0.069 |
| 86 | chr14 | 106331551 | 106331651 | 3 | IGHJ1 | 0.046 | 0.033 |
| 87 | chr2 | 117951920 | 117952020 | 3 | DDX18 | 0.033 | 0.055 |
| 88 | chr14 | 107210956 | 107211156 | 5 | IGHV3-73 | 0.046 | 0.033 |
| 89 | chr12 | 6439714 | 6439914 | 5 | TNFRSF1A | 0.038 | 0.056 |
| 90 | chr2 | 136872526 | 136875621 | 28 | CXCR4 | 0.105 | 0.101 |
| 91 | chr3 | 165548199 | 165548649 | 10 | BCHE | 0.012 | 0.008 |
| 92 | chr4 | 188924115 | 188924865 | 16 | ZFP42 | 0.033 | 0.046 |
| 93 | chr20 | 25003527 | 25003727 | 5 | ACSS1 | 0.032 | 0.049 |
| 94 | chr14 | 106994301 | 106994899 | 11 | IGHV3-48 | 0.041 | 0.036 |
| 95 | chr16 | 3779107 | 3900912 | 82 | CREBBP | 0.035 | 0.043 |
| 96 | chr2 | 89544332 | 89544880 | 11 | IGKV2-30 | 0.029 | 0.042 |
| 97 | chr5 | 112176757 | 112176957 | 5 | APC | 0.028 | 0.046 |
| 98 | chr3 | 185146279 | 185198274 | 20 | MAP3K13 | 0.022 | 0.033 |
| 99 | chr11 | 129739779 | 129740079 | 7 | NFRKB | 0.037 | 0.030 |
| 100 | chr12 | 86198699 | 86199599 | 19 | RASSF9 | 0.035 | 0.047 |
| 101 | chr12 | 15813488 | 15813638 | 4 | EPS8 | 0.035 | 0.025 |
| 102 | chr2 | 63826278 | 63826428 | 4 | MDH1 | 0.017 | 0.008 |
| 103 | chr14 | 107083566 | 107083891 | 7 | IGHV4-59 | 0.040 | 0.054 |
| 104 | chr22 | 22735418 | 22735843 | 6 | IGLV1-44 | 0.059 | 0.079 |
| 105 | chr12 | 18891268 | 18891518 | 6 | CAPZA3 | 0.012 | 0.005 |
| 106 | chr14 | 106174971 | 106177526 | 44 | IGHA1 | 0.117 | 0.117 |
| 107 | chr13 | 58207132 | 58209082 | 40 | PCDH17 | 0.038 | 0.047 |
| 108 | chr6 | 26156650 | 26157350 | 15 | HIST1H1E | 0.064 | 0.077 |
| 109 | chr8 | 75898191 | 75898391 | 5 | CRISPLD1 | 0.012 | 0.007 |
| 110 | chr9 | 37024920 | 37033770 | 38 | PAX5 | 0.059 | 0.060 |
| 111 | chr17 | 18001530 | 18001680 | 4 | DRG2 | 0.015 | 0.008 |
| 112 | chr10 | 91092212 | 91092412 | 5 | IFIT3 | 0.026 | 0.016 |
| 113 | chr2 | 56149511 | 56150111 | 13 | EFEMP1 | 0.030 | 0.029 |
| 114 | chr6 | 26032015 | 26032215 | 5 | HIST1H3B | 0.030 | 0.046 |
| 115 | chrX | 1584325 | 1655990 | 29 | P2RY8 | 0.031 | 0.041 |
| 116 | chr4 | 187509885 | 187557980 | 16 | FAT1 | 0.028 | 0.039 |
| 117 | chr5 | 11110991 | 11411801 | 24 | CTNND2 | 0.031 | 0.040 |
| 118 | chr14 | 106110676 | 106114376 | 65 | IGHG2 | 0.213 | 0.210 |
| 119 | chr1 | 4472439 | 4476599 | 10 | AJAP1 | 0.030 | 0.026 |
| 120 | chr1 | 110561142 | 110561742 | 13 | AHCYL1 | 0.019 | 0.018 |
| 121 | chr14 | 106725296 | 106726174 | 14 | IGHV3-23 | 0.099 | 0.111 |
| 122 | chr1 | 111715728 | 111715878 | 4 | CEPT1 | 0.022 | 0.016 |
| 123 | chr11 | 118967324 | 118968024 | 15 | DPAGT1 | 0.032 | 0.044 |
| 124 | chr2 | 55237199 | 55237599 | 9 | RTN4 | 0.047 | 0.060 |
| 125 | chr11 | 111781037 | 111781637 | 13 | CRYAB | 0.025 | 0.037 |
| 126 | chr14 | 106573316 | 106574003 | 13 | IGHV3-11 | 0.041 | 0.054 |
| 127 | chr18 | 48231685 | 48232085 | 9 | MAPK4 | 0.022 | 0.020 |
| 128 | chr2 | 62934010 | 63217980 | 14 | EHBP1 | 0.030 | 0.042 |
| 129 | chr22 | 22677078 | 22677289 | 5 | IGLV1-51 | 0.046 | 0.066 |
| 130 | chr7 | 119915407 | 119915757 | 8 | KCND2 | 0.038 | 0.053 |
| 131 | chr22 | 23154348 | 23154798 | 8 | IGLV3-10 | 0.024 | 0.020 |
| 132 | chr6 | 26045745 | 26046045 | 7 | HIST1H3C | 0.030 | 0.026 |
| 133 | chr10 | 131640290 | 131640490 | 5 | EBF3 | 0.040 | 0.036 |
| 134 | chr1 | 109822182 | 109822782 | 13 | PSRC1 | 0.027 | 0.038 |
| 135 | chr17 | 18022120 | 18022770 | 14 | MYO15A | 0.039 | 0.036 |
| 136 | chr16 | 85933004 | 85954924 | 56 | IRF8 | 0.037 | 0.047 |
| 137 | chr2 | 89986777 | 89987085 | 7 | IGKV2D-29 | 0.024 | 0.021 |
| 138 | chr2 | 90249152 | 90249397 | 5 | IGKV1D-43 | 0.040 | 0.033 |
| 139 | chr2 | 242793233 | 242801088 | 24 | PDCD1 | 0.047 | 0.048 |
| 140 | chr6 | 27100080 | 27100180 | 3 | HIST1H2BJ | 0.033 | 0.027 |
| 141 | chr7 | 110545277 | 110698122 | 8 | IMMP2L | 0.004 | 0.002 |
| 142 | chr1 | 111441723 | 111442173 | 10 | CD53 | 0.027 | 0.038 |
| 143 | chrX | 70612662 | 70612762 | 3 | TAF1 | 0.007 | 0.000 |
| 144 | chr21 | 18981234 | 18981484 | 6 | BTG3 | 0.020 | 0.033 |
| 145 | chr14 | 107113406 | 107114196 | 10 | IGHV3-64 | 0.015 | 0.013 |
| 146 | chr22 | 22380473 | 22385883 | 18 | IGLV4-69 | 0.044 | 0.054 |
| 147 | chr9 | 5510590 | 5570130 | 34 | PDCD1LG2 | 0.026 | 0.028 |
| 148 | chr1 | 27059147 | 27106912 | 29 | ARID1A | 0.035 | 0.043 |
| 149 | chr13 | 32907207 | 32912827 | 17 | BRCA2 | 0.013 | 0.013 |
| 150 | chr18 | 48703170 | 48703920 | 16 | MEX3C | 0.022 | 0.023 |
| 151 | chr1 | 203274698 | 203276558 | 33 | BTG2 | 0.131 | 0.129 |
| 152 | chr8 | 128492948 | 128493298 | 8 | POU5F1B | 0.022 | 0.035 |
| 153 | chr6 | 27834969 | 27835069 | 3 | HIST1H1B | 0.043 | 0.038 |
| 154 | chr22 | 23010978 | 23011307 | 7 | IGLV3-27 | 0.045 | 0.059 |
| 155 | chr1 | 117078643 | 117087128 | 10 | CD58 | 0.022 | 0.021 |
| 156 | chr14 | 106380361 | 106381326 | 17 | IGHD3-3 | 0.040 | 0.040 |

TABLE 4-continued

| | | | | | | | |
|---|---|---|---|---|---|---|---|
| 157 | chr12 | 49415992 | 49447447 | 47 | KMT2D | 0.029 | 0.031 |
| 158 | chr22 | 22782038 | 22782288 | 6 | IGLV5-37 | 0.051 | 0.066 |
| 159 | chr8 | 18729446 | 18729896 | 10 | PSD3 | 0.036 | 0.048 |
| 160 | chr14 | 106552366 | 106552466 | 3 | IGHV3-9 | 0.020 | 0.011 |
| 161 | chrX | 35820577 | 35821227 | 14 | MAGEB16 | 0.021 | 0.032 |
| 162 | chr16 | 81946176 | 81962221 | 13 | PLCG2 | 0.027 | 0.028 |
| 163 | chr22 | 22712078 | 22712594 | 11 | IGLV1-47 | 0.050 | 0.063 |
| 164 | chr3 | 16419205 | 16419455 | 6 | RFTN1 | 0.050 | 0.046 |
| 165 | chr11 | 111613197 | 111613397 | 5 | PPP2R1B | 0.026 | 0.039 |
| 166 | chr14 | 106331151 | 106331501 | 8 | IGHJ2 | 0.048 | 0.047 |
| 167 | chr1 | 226923692 | 226925192 | 31 | ITPKB | 0.044 | 0.053 |
| 168 | chr6 | 27100940 | 27101260 | 5 | HIST1H2AG | 0.024 | 0.020 |
| 169 | chr10 | 91358987 | 91359287 | 7 | PANK1 | 0.021 | 0.019 |
| 170 | chr14 | 32615406 | 32615606 | 5 | ARHGAP5 | 0.020 | 0.033 |
| 171 | chrX | 119509281 | 119509481 | 5 | ATP1B4 | 0.016 | 0.013 |
| 172 | chr18 | 77794426 | 77795126 | 15 | RBFA | 0.014 | 0.014 |
| 173 | chr10 | 89624273 | 89720888 | 32 | PTEN | 0.015 | 0.016 |
| 174 | chr14 | 64330253 | 64330453 | 5 | SYNE2 | 0.006 | 0.003 |
| 175 | chr9 | 24545400 | 24905695 | 17 | IZUMO3 | 0.030 | 0.039 |
| 176 | chr5 | 54964699 | 54964899 | 5 | SLC38A9 | 0.002 | 0.000 |
| 177 | chr8 | 101730377 | 101730427 | 2 | PABPC1 | 0.015 | 0.008 |
| 178 | chr8 | 131373025 | 131373425 | 9 | ASAP1 | 0.030 | 0.040 |
| 179 | chr22 | 23101393 | 23101730 | 6 | IGLV2-14 | 0.048 | 0.044 |
| 180 | chr1 | 109649127 | 109649277 | 4 | C1orf194 | 0.047 | 0.045 |
| 181 | chr11 | 65623423 | 65623473 | 2 | CFL1 | 0.025 | 0.041 |
| 182 | chr22 | 22707428 | 22707793 | 7 | IGLV5-48 | 0.035 | 0.047 |
| 183 | chr14 | 106331701 | 106331801 | 3 | IGHD7-27 | 0.026 | 0.022 |
| 184 | chr14 | 96179593 | 96180293 | 15 | TCL1A | 0.050 | 0.050 |
| 185 | chr22 | 23063308 | 23063658 | 8 | IGLV3-19 | 0.031 | 0.029 |
| 186 | chr17 | 7576950 | 7579410 | 24 | TP53 | 0.040 | 0.051 |
| 187 | chr2 | 148680517 | 148680667 | 4 | ACVR2A | 0.025 | 0.037 |
| 188 | chr19 | 10334564 | 10341984 | 35 | S1PR2 | 0.064 | 0.077 |
| 189 | chr6 | 108040229 | 108042204 | 27 | SCML4 | 0.025 | 0.026 |
| 190 | chr6 | 27277285 | 27277485 | 5 | POM121L2 | 0.042 | 0.039 |
| 191 | chr3 | 186714605 | 186784290 | 33 | ST6GAL1 | 0.084 | 0.091 |
| 192 | chr19 | 12902575 | 12902825 | 6 | JUNE | 0.053 | 0.052 |
| 193 | chr14 | 107199021 | 107199172 | 4 | IGHV3-72 | 0.045 | 0.041 |
| 194 | chr11 | 102188382 | 102188932 | 12 | BIRC3 | 0.104 | 0.123 |
| 195 | chr1 | 185833556 | 186159096 | 32 | HMCN1 | 0.021 | 0.023 |
| 196 | chr12 | 18534683 | 18801013 | 30 | PIK3C2G | 0.017 | 0.020 |
| 197 | chrX | 100610985 | 100611285 | 7 | BTK | 0.021 | 0.021 |
| 198 | chr18 | 64172117 | 64239317 | 19 | CDH19 | 0.023 | 0.032 |
| 199 | chr2 | 1652011 | 1652811 | 17 | PXDN | 0.045 | 0.054 |
| 200 | chr11 | 111904097 | 111904247 | 4 | DLAT | 0.037 | 0.049 |
| 201 | chr22 | 22556228 | 22556628 | 9 | IGLV11-55 | 0.039 | 0.038 |
| 202 | chr2 | 103148734 | 103148934 | 5 | SLC9A4 | 0.024 | 0.036 |
| 203 | chr2 | 48027959 | 48028159 | 5 | MSH6 | 0.012 | 0.010 |
| 204 | chr4 | 134727699 | 134727899 | 5 | PABPC4L | 0.012 | 0.010 |
| 205 | chr11 | 134027790 | 134027940 | 4 | NCAPD3 | 0.047 | 0.061 |
| 206 | chr2 | 77746603 | 77746953 | 8 | LRRTM4 | 0.026 | 0.037 |
| 207 | chr1 | 160319284 | 160319484 | 5 | NCSTN | 0.044 | 0.039 |
| 208 | chr18 | 65179857 | 65181807 | 40 | DSEL | 0.021 | 0.029 |
| 209 | chr18 | 45003679 | 45008564 | 12 | B2M | 0.035 | 0.046 |
| 210 | chr1 | 29069532 | 29070182 | 14 | YTHDF2 | 0.043 | 0.052 |
| 211 | chr4 | 80327793 | 80328143 | 8 | GK2 | 0.030 | 0.041 |
| 212 | chr5 | 158527643 | 158527993 | 8 | EBF1 | 0.052 | 0.064 |
| 213 | chr1 | 3747621 | 3747771 | 4 | CEP104 | 0.025 | 0.037 |
| 214 | chr2 | 48059884 | 48066174 | 9 | FBXO11 | 0.014 | 0.015 |
| 215 | chrX | 33146107 | 33146457 | 8 | DMD | 0.059 | 0.059 |
| 216 | chr6 | 26124545 | 26124865 | 6 | HIST1H2AC | 0.051 | 0.063 |
| 217 | chr14 | 106791091 | 106791141 | 2 | IGHV3-30 | 0.045 | 0.041 |
| 218 | chr3 | 183209759 | 183273414 | 23 | KLHL6 | 0.036 | 0.036 |
| 219 | chr17 | 79478954 | 79479004 | 2 | ACTG1 | 0.005 | 0.000 |
| 220 | chr22 | 47570210 | 47570410 | 5 | TBC1D22A | 0.030 | 0.043 |
| 221 | chr6 | 27799169 | 27799369 | 5 | HIST1H4K | 0.022 | 0.033 |
| 222 | chr2 | 65258146 | 65258346 | 5 | SLC1A4 | 0.018 | 0.030 |
| 223 | chr14 | 106586201 | 106586301 | 3 | IGHV3-13 | 0.033 | 0.027 |
| 224 | chr6 | 26158530 | 26158790 | 4 | HIST1H2BD | 0.030 | 0.041 |
| 225 | chr14 | 106691756 | 106691856 | 3 | IGHV3-21 | 0.053 | 0.066 |
| 226 | chr10 | 90579967 | 90580317 | 8 | LIPM | 0.035 | 0.035 |
| 227 | chr7 | 82387831 | 82784641 | 19 | PCLO | 0.035 | 0.044 |
| 228 | chr22 | 23090123 | 23090338 | 4 | IGLV3-16 | 0.030 | 0.041 |
| 229 | chr2 | 89475782 | 89476114 | 7 | IGKV2-24 | 0.044 | 0.042 |
| 230 | chr2 | 90121892 | 90122155 | 6 | IGKV1D-17 | 0.030 | 0.041 |
| 231 | chr14 | 107034666 | 107035056 | 7 | IGHV5-51 | 0.038 | 0.049 |
| 232 | chr6 | 26217215 | 26217415 | 5 | HIST1H2AE | 0.024 | 0.023 |
| 233 | chr14 | 84420587 | 84420787 | 5 | FLRT2 | 0.000 | 0.000 |
| 234 | chr4 | 40198811 | 40201559 | 49 | RHOH | 0.062 | 0.068 |
| 235 | chr14 | 106539176 | 106539276 | 3 | IGHV1-8 | 0.040 | 0.038 |
| 236 | chr5 | 83258968 | 83259168 | 5 | EDIL3 | 0.022 | 0.033 |

TABLE 4-continued

| | | | | | | | |
|---|---|---|---|---|---|---|---|
| 237 | chrX | 70347817 | 70348017 | 5 | MED12 | 0.022 | 0.033 |
| 238 | chr18 | 48512955 | 48513305 | 8 | ELAC1 | 0.026 | 0.027 |
| 239 | chrX | 12993265 | 12994487 | 23 | TMSB4X | 0.098 | 0.108 |
| 240 | chr19 | 6586162 | 6591037 | 17 | CD70 | 0.052 | 0.064 |
| 241 | chr9 | 13222186 | 13222386 | 5 | MPDZ | 0.018 | 0.016 |
| 242 | chr19 | 8028409 | 8028559 | 4 | ELAVL1 | 0.037 | 0.049 |
| 243 | chr17 | 63010241 | 63052644 | 28 | GNA13 | 0.033 | 0.035 |
| 244 | chr6 | 75965847 | 75969257 | 10 | TMEM30A | 0.017 | 0.018 |
| 245 | chr2 | 61118795 | 61149620 | 27 | REL | 0.024 | 0.030 |
| 246 | chr8 | 103663492 | 103664142 | 14 | KLF10 | 0.032 | 0.034 |
| 247 | chr7 | 122634906 | 122635106 | 5 | TAS2R16 | 0.040 | 0.036 |
| 248 | chr7 | 106508491 | 106509141 | 14 | PIK3CG | 0.043 | 0.044 |
| 249 | chr19 | 1376441 | 1376641 | 5 | MUM1 | 0.053 | 0.066 |
| 250 | chr10 | 90074240 | 90074390 | 4 | RNLS | 0.012 | 0.012 |
| 251 | chr17 | 56408575 | 56409585 | 19 | BZRAP1 | 0.107 | 0.116 |
| 252 | chr18 | 48327695 | 48327895 | 5 | MRO | 0.034 | 0.033 |
| 253 | chr2 | 90212017 | 90212247 | 4 | IGKV3D-11 | 0.000 | 0.000 |
| 254 | chr3 | 164730701 | 164730851 | 4 | SI | 0.000 | 0.000 |
| 255 | chr18 | 75683735 | 75684485 | 16 | GALR1 | 0.025 | 0.026 |
| 256 | chr10 | 90699127 | 90699627 | 11 | ACTA2 | 0.022 | 0.030 |
| 257 | chr7 | 146997184 | 146997384 | 5 | CNTNAP2 | 0.020 | 0.030 |
| 258 | chr10 | 90537737 | 90537987 | 6 | LIPN | 0.021 | 0.022 |
| 259 | chr8 | 116616146 | 116616846 | 15 | TRPS1 | 0.033 | 0.042 |
| 260 | chr6 | 14117993 | 14135468 | 27 | CD83 | 0.061 | 0.069 |
| 261 | chr14 | 106610381 | 106610741 | 6 | IGHV3-15 | 0.036 | 0.046 |
| 262 | chr14 | 106962966 | 106963269 | 7 | IGHV1-45 | 0.023 | 0.023 |
| 263 | chr6 | 27833409 | 27833509 | 3 | HIST1H2AL | 0.017 | 0.027 |
| 264 | chr7 | 2963819 | 2987364 | 44 | CARD11 | 0.047 | 0.055 |
| 265 | chr11 | 134118685 | 134118835 | 4 | THYN1 | 0.017 | 0.016 |
| 266 | chr14 | 107258911 | 107282996 | 17 | IGHV7-81 | 0.031 | 0.040 |
| 267 | chrX | 73962124 | 73963074 | 20 | KIAA2022 | 0.020 | 0.028 |
| 268 | chr3 | 185236909 | 185237109 | 5 | LIPH | 0.022 | 0.033 |
| 269 | chr3 | 64547205 | 64580090 | 11 | ADAMTS9 | 0.028 | 0.030 |
| 270 | chr14 | 106405616 | 106405916 | 7 | IGHV6-1 | 0.028 | 0.037 |
| 271 | chr11 | 117712684 | 117712984 | 7 | FXYD6 | 0.035 | 0.035 |
| 272 | chr8 | 130692150 | 130760995 | 17 | GSDMC | 0.029 | 0.037 |
| 273 | chr22 | 22749603 | 22750309 | 14 | IGLV7-43 | 0.021 | 0.022 |
| 274 | chr22 | 23135153 | 23135508 | 7 | IGLV2-U | 0.020 | 0.021 |
| 275 | chr6 | 26234655 | 26234955 | 7 | HIST1H1D | 0.042 | 0.044 |
| 276 | chr11 | 112405017 | 112405578 | 12 | C11orf34 | 0.029 | 0.037 |
| 277 | chr1 | 2488007 | 2494707 | 36 | TNFRSF14 | 0.035 | 0.042 |
| 278 | chr18 | 48591760 | 48604805 | 16 | SMAD4 | 0.019 | 0.020 |
| 279 | chr18 | 55274406 | 55274556 | 4 | NARS | 0.015 | 0.025 |
| 280 | chrX | 90026454 | 90026604 | 4 | PABPC5 | 0.015 | 0.025 |
| 281 | chr8 | 623881 | 624081 | 5 | ERICH1 | 0.020 | 0.020 |
| 282 | chr18 | 1477566 | 1477666 | 3 | ADCYAP1 | 0.043 | 0.055 |
| 283 | chr12 | 48190732 | 48190982 | 6 | HDAC7 | 0.043 | 0.041 |
| 284 | chr14 | 106381486 | 106383981 | 18 | IGHD2-2 | 0.029 | 0.032 |
| 285 | chr5 | 135381970 | 135382170 | 5 | TGFBI | 0.034 | 0.030 |
| 286 | chr3 | 184580664 | 184580864 | 5 | VPS8 | 0.006 | 0.007 |
| 287 | chr14 | 106805291 | 106806190 | 8 | IGHV4-31 | 0.038 | 0.041 |
| 288 | chr22 | 23077338 | 23077588 | 4 | IGLV2-18 | 0.025 | 0.025 |
| 289 | chr11 | 134129470 | 134133940 | 40 | ACAD8 | 0.027 | 0.034 |
| 290 | chr1 | 190067140 | 190068190 | 22 | FAM5C | 0.028 | 0.035 |
| 291 | chr19 | 52403337 | 52403537 | 5 | ZNF649 | 0.026 | 0.026 |
| 292 | chr15 | 66727355 | 66729281 | 10 | MAP2K1 | 0.035 | 0.044 |
| 293 | chr6 | 94120220 | 94120720 | 11 | EPHA7 | 0.024 | 0.027 |
| 294 | chr20 | 23028373 | 23028823 | 10 | THBD | 0.044 | 0.052 |
| 295 | chr19 | 42599891 | 42600091 | 5 | POU2F2 | 0.038 | 0.049 |
| 296 | chrX | 86772954 | 86773304 | 8 | KLHL4 | 0.026 | 0.035 |
| 297 | chr9 | 37407370 | 37407570 | 5 | GRHPR | 0.046 | 0.056 |
| 298 | chr9 | 20820917 | 20946827 | 8 | FOCAD | 0.015 | 0.016 |
| 299 | chr6 | 91004619 | 91005994 | 10 | BACH2 | 0.051 | 0.061 |
| 300 | chr9 | 139390583 | 139402863 | 17 | NOTCH1 | 0.038 | 0.045 |
| 301 | chr14 | 106452661 | 106453001 | 7 | IGHV1-2 | 0.020 | 0.021 |
| 302 | chr6 | 26020710 | 26020910 | 5 | HIST1H3A | 0.036 | 0.036 |
| 303 | chr9 | 27950145 | 27950495 | 8 | LINGO2 | 0.022 | 0.031 |
| 304 | chr7 | 80285800 | 80286050 | 6 | CD36 | 0.013 | 0.022 |
| 305 | chr18 | 13825916 | 13826416 | 11 | MC5R | 0.035 | 0.043 |
| 306 | chr9 | 5450475 | 5468015 | 33 | CD274 | 0.026 | 0.029 |
| 307 | chr3 | 185446224 | 185538924 | 8 | IGF2BP2 | 0.019 | 0.027 |
| 308 | chr1 | 3800046 | 3800353 | 7 | DFFB | 0.042 | 0.044 |
| 309 | chr22 | 23055368 | 23055828 | 7 | IGLV3-21 | 0.034 | 0.035 |
| 310 | chr6 | 27114005 | 27114545 | 9 | HIST1H2BK | 0.023 | 0.031 |
| 311 | chr14 | 107013036 | 107013186 | 4 | IGHV3-49 | 0.020 | 0.029 |
| 312 | chr22 | 22453288 | 22453563 | 6 | IGLV8-61 | 0.053 | 0.055 |
| 313 | chr14 | 106357891 | 106357941 | 2 | IGHD6-19 | 0.000 | 0.000 |
| 314 | chr16 | 33523608 | 33523658 | 2 | IGHV3OR16-12 | 0.000 | 0.000 |
| 315 | chr7 | 151943422 | 151943472 | 2 | KMT2C | 0.000 | 0.000 |
| 316 | chr22 | 23114793 | 23115048 | 5 | IGLV3-12 | 0.018 | 0.026 |

TABLE 4-continued

| | | | | | | | |
|---|---|---|---|---|---|---|---|
| 317 | chr2 | 80801236 | 80801486 | 6 | CTNNA2 | 0.017 | 0.025 |
| 318 | chr22 | 23161918 | 23162288 | 8 | IGLV3-9 | 0.036 | 0.039 |
| 319 | chr12 | 113495365 | 113534745 | 80 | DTX1 | 0.058 | 0.065 |
| 320 | chr11 | 65190343 | 65190543 | 5 | FRMD8 | 0.050 | 0.049 |
| 321 | chr14 | 106967131 | 106967366 | 4 | IGHV1-46 | 0.022 | 0.033 |
| 322 | chr12 | 25205889 | 25207439 | 21 | LRMP | 0.038 | 0.041 |
| 323 | chr14 | 106780611 | 106780711 | 3 | IGHV4-28 | 0.036 | 0.038 |
| 324 | chr11 | 125472641 | 125472891 | 6 | STT3A | 0.046 | 0.055 |
| 325 | chr11 | 69346692 | 69346892 | 5 | CCND1 | 0.024 | 0.026 |
| 326 | chr13 | 51915234 | 51915534 | 7 | SERPINE3 | 0.035 | 0.044 |
| 327 | chr5 | 21783416 | 21783666 | 6 | CDH12 | 0.020 | 0.022 |
| 328 | chr12 | 25398219 | 25398269 | 2 | KRAS | 0.015 | 0.025 |
| 329 | chr1 | 85733208 | 85742033 | 19 | BCL10 | 0.021 | 0.025 |
| 330 | chr1 | 107866872 | 107867572 | 15 | NTNG1 | 0.013 | 0.015 |
| 331 | chr1 | 86591438 | 86591888 | 10 | COL24A1 | 0.029 | 0.036 |
| 332 | chr18 | 30349776 | 30350276 | 11 | KLHL14 | 0.033 | 0.036 |
| 333 | chr14 | 106641656 | 106642261 | 7 | IGHV1-18 | 0.023 | 0.026 |
| 334 | chr17 | 78343504 | 78343704 | 5 | RNF213 | 0.014 | 0.016 |
| 335 | chr1 | 120457961 | 120459261 | 27 | NOTCH2 | 0.036 | 0.039 |
| 336 | chr17 | 40467710 | 40491485 | 39 | STAT3 | 0.034 | 0.040 |
| 337 | chr9 | 19957357 | 19958157 | 17 | SLC24A2 | 0.027 | 0.031 |
| 338 | chr3 | 38180130 | 38182805 | 29 | MYD88 | 0.045 | 0.053 |
| 339 | chr18 | 73944894 | 73945344 | 10 | ZNF516 | 0.018 | 0.025 |
| 340 | chr7 | 140453013 | 140453254 | 5 | BRAF | 0.012 | 0.020 |
| 341 | chr6 | 159238416 | 159238766 | 8 | EZR | 0.050 | 0.057 |
| 342 | chr18 | 77092821 | 77093021 | 5 | ATP9B | 0.008 | 0.010 |
| 343 | chr22 | 23523568 | 23610748 | 22 | BCR | 0.038 | 0.045 |
| 344 | chrt2 | 22673243 | 22673593 | 8 | IGLV5-52 | 0.027 | 0.035 |
| 345 | chr4 | 88011078 | 88011278 | 5 | AFF1 | 0.014 | 0.016 |
| 346 | chr11 | 131747550 | 131748000 | 10 | NTM | 0.029 | 0.036 |
| 347 | chr2 | 90077982 | 90078316 | 6 | IGKV3D-20 | 0.025 | 0.033 |
| 348 | chr2 | 96809890 | 96810360 | 10 | DUSP2 | 0.063 | 0.066 |
| 349 | chr2 | 89265757 | 89265987 | 4 | IGKV1-6 | 0.010 | 0.012 |
| 350 | chr19 | 53598587 | 53599037 | 10 | ZNF160 | 0.024 | 0.031 |
| 351 | chr2 | 63335243 | 63631808 | 22 | WDPCP | 0.026 | 0.033 |
| 352 | chr9 | 21808815 | 21859450 | 9 | MTAP | 0.019 | 0.026 |
| 353 | chr6 | 27860480 | 27860895 | 7 | HIST1H2AM | 0.030 | 0.033 |
| 354 | chr6 | 27839659 | 27839759 | 3 | HIST1H3I | 0.036 | 0.038 |
| 355 | chr6 | 26252155 | 26252205 | 2 | HIST1H2BH | 0.015 | 0.016 |
| 356 | chr19 | 19256470 | 19293460 | 41 | MEF2B | 0.040 | 0.045 |
| 357 | chr14 | 107169646 | 107170861 | 21 | IGHV1-69 | 0.091 | 0.098 |
| 358 | chr8 | 113308015 | 113569195 | 15 | CSMD3 | 0.013 | 0.020 |
| 359 | chr22 | 22550338 | 22550788 | 10 | IGLV6-57 | 0.042 | 0.049 |
| 360 | chr4 | 153249286 | 153249486 | 5 | FBXW7 | 0.026 | 0.026 |
| 361 | chr11 | 120127164 | 120189629 | 22 | POU2F3 | 0.027 | 0.033 |
| 362 | chr12 | 57496553 | 57499113 | 13 | STAT6 | 0.046 | 0.054 |
| 363 | chr22 | 22937193 | 22937499 | 7 | IGLV3-32 | 0.018 | 0.026 |
| 364 | chr6 | 138188484 | 138202489 | 64 | TNFAIP3 | 0.024 | 0.028 |
| 365 | chr8 | 138849938 | 138850138 | 5 | FAM135B | 0.020 | 0.023 |
| 366 | chr14 | 107218756 | 107218856 | 3 | IGHV3-74 | 0.073 | 0.082 |
| 367 | chr14 | 23344698 | 23345198 | 11 | LRP10 | 0.059 | 0.063 |
| 368 | chr14 | 106866381 | 106866595 | 5 | IGHV3-38 | 0.032 | 0.033 |
| 369 | chr1 | 3547351 | 3547701 | 8 | WRAP73 | 0.024 | 0.027 |
| 370 | chr21 | 28213259 | 28216964 | 11 | ADAMTS1 | 0.028 | 0.036 |
| 371 | chr2 | 169781121 | 169781321 | 5 | ABCB11 | 0.016 | 0.023 |
| 372 | chr22 | 41513341 | 41574886 | 72 | EP300 | 0.031 | 0.037 |
| 373 | chr18 | 56054916 | 56063816 | 24 | NEDD4L | 0.016 | 0.020 |
| 374 | chr14 | 106845301 | 106846536 | 9 | IGHV3-35 | 0.055 | 0.064 |
| 375 | chr14 | 107136756 | 107136856 | 3 | IGHV3-66 | 0.030 | 0.038 |
| 376 | chr22 | 23047068 | 23047318 | 6 | IGLV3-22 | 0.043 | 0.049 |
| 377 | chr22 | 22786478 | 22786803 | 7 | IGLV1-36 | 0.040 | 0.047 |
| 378 | chr8 | 122626848 | 122627148 | 7 | HAS2 | 0.030 | 0.033 |
| 379 | chr5 | 131825018 | 131825218 | 5 | IRF1 | 0.026 | 0.030 |
| 380 | chr22 | 23252688 | 23252788 | 3 | IGLJ4 | 0.020 | 0.022 |
| 381 | chr14 | 107078456 | 107078606 | 4 | IGHV1-58 | 0.050 | 0.053 |
| 382 | chr4 | 154624671 | 154625021 | 8 | TLR2 | 0.017 | 0.020 |
| 383 | chr2 | 89196227 | 89215037 | 19 | IGKV5-2 | 0.024 | 0.028 |
| 384 | chr18 | 55319681 | 55359256 | 17 | ATP8B1 | 0.028 | 0.031 |
| 385 | chr1 | 61553803 | 61554303 | 11 | NFIA | 0.030 | 0.033 |
| 386 | chr10 | 89603603 | 89604053 | 10 | KLLN | 0.024 | 0.028 |
| 387 | chr22 | 23247138 | 23247609 | 9 | IGLJ3 | 0.165 | 0.169 |
| 388 | chr11 | 117101044 | 117101194 | 4 | PCSK7 | 0.042 | 0.049 |
| 389 | chr6 | 27861245 | 27861450 | 4 | HIST1H2BO | 0.037 | 0.045 |
| 390 | chrt2 | 61441170 | 61441870 | 15 | USP34 | 0.025 | 0.028 |
| 391 | chr11 | 111234537 | 111249512 | 16 | POU2AF1 | 0.030 | 0.034 |
| 392 | chr5 | 5182146 | 5182446 | 7 | ADAMTS16 | 0.038 | 0.044 |
| 393 | chr14 | 106667546 | 106667856 | 6 | IGHV3-20 | 0.021 | 0.025 |
| 394 | chr2 | 145162402 | 145693052 | 53 | ZEB2 | 0.041 | 0.046 |
| 395 | chr14 | 106494091 | 106494768 | 12 | IGHV2-5 | 0.027 | 0.034 |
| 396 | chr2 | 65593036 | 65593213 | 4 | SPRED2 | 0.057 | 0.061 |

TABLE 4-continued

| | | | | | | | |
|---|---|---|---|---|---|---|---|
| 397 | chr2 | 141245128 | 141245328 | 5 | LRP1B | 0.010 | 0.016 |
| 398 | chr22 | 23241763 | 23241813 | 2 | IGLJ2 | 0.030 | 0.033 |
| 399 | chrX | 153997384 | 153997584 | 5 | DKC1 | 0.042 | 0.046 |
| 400 | chr10 | 5755067 | 5755267 | 5 | FAM208B | 0.016 | 0.020 |
| 401 | chr1 | 35472493 | 35472693 | 5 | ZMYM6 | 0.016 | 0.020 |
| 402 | chr6 | 26250460 | 26250695 | 5 | HIST1H3F | 0.028 | 0.033 |
| 403 | chr3 | 176750700 | 176771710 | 17 | TBL1XR1 | 0.020 | 0.024 |
| 404 | chr18 | 77170716 | 77288591 | 29 | NFATC1 | 0.038 | 0.043 |
| 405 | chr13 | 41133663 | 41240784 | 49 | FOXO1 | 0.025 | 0.031 |
| 406 | chr8 | 128951725 | 128951875 | 4 | TMEM75 | 0.042 | 0.049 |
| 407 | chr22 | 22681928 | 22682198 | 5 | IGLV1-50 | 0.020 | 0.026 |
| 408 | chr2 | 89976277 | 89976377 | 3 | IGKV2D-30 | 0.066 | 0.071 |
| 409 | chr14 | 106757726 | 106758621 | 8 | IGHV2-26 | 0.026 | 0.033 |
| 410 | chr1 | 2306312 | 2306812 | 11 | MORN1 | 0.028 | 0.034 |
| 411 | chr14 | 106384031 | 106384926 | 9 | IGHD1-1 | 0.039 | 0.046 |
| 412 | chr8 | 104897562 | 104898462 | 19 | RWS2 | 0.030 | 0.036 |
| 413 | chr10 | 89500958 | 89501108 | 4 | PAPSS2 | 0.025 | 0.029 |
| 414 | chr1 | 201038553 | 201038753 | 5 | CACNA1S | 0.034 | 0.033 |
| 415 | chr13 | 84453543 | 84455243 | 35 | SLITRK1 | 0.034 | 0.039 |
| 416 | chr22 | 23263508 | 23264123 | 9 | IGLJ7 | 0.062 | 0.069 |
| 417 | chr5 | 140208034 | 140208834 | 17 | PCDHA6 | 0.026 | 0.031 |
| 418 | chr1 | 23885408 | 23885899 | 10 | ID3 | 0.015 | 0.020 |
| 419 | chr14 | 106518496 | 106519064 | 7 | IGHV3-7 | 0.035 | 0.040 |
| 420 | chr9 | 22005930 | 22009000 | 13 | CDKN2B | 0.031 | 0.035 |
| 421 | chr11 | 58978693 | 58979345 | 11 | MPEG1 | 0.032 | 0.036 |
| 422 | chr1 | 227842647 | 227842697 | 2 | ZNF678 | 0.010 | 0.016 |
| 423 | chr6 | 106534267 | 106555367 | 60 | PRDM1 | 0.031 | 0.036 |
| 424 | chr2 | 198950435 | 198950985 | 12 | PLCL1 | 0.021 | 0.027 |
| 425 | chr18 | 6947105 | 6980665 | 10 | LAMA1 | 0.027 | 0.033 |
| 426 | chr6 | 26197105 | 26197462 | 8 | HIST1H3D | 0.021 | 0.027 |
| 427 | chr19 | 51525627 | 51525927 | 7 | KLK11 | 0.028 | 0.033 |
| 428 | chr2 | 61719435 | 61719635 | 5 | XPO1 | 0.012 | 0.016 |
| 429 | chrX | 141291053 | 141291534 | 10 | MAGEC2 | 0.019 | 0.023 |
| 430 | chr14 | 35873672 | 35873822 | 4 | NFKBIA | 0.035 | 0.041 |
| 431 | chr2 | 89442292 | 89443217 | 19 | IGKV3-20 | 0.042 | 0.047 |
| 432 | chr1 | 72334892 | 72335098 | 5 | NEGR1 | 0.014 | 0.020 |
| 433 | chr1 | 9784433 | 9784533 | 3 | PIK3CD | 0.007 | 0.011 |
| 434 | chr2 | 170101186 | 170101386 | 5 | LRP2 | 0.032 | 0.036 |
| 435 | chr7 | 110737412 | 110764944 | 51 | LRRN3 | 0.019 | 0.024 |
| 436 | chr3 | 7620224 | 7620974 | 16 | GRM7 | 0.032 | 0.038 |
| 437 | chr22 | 22569333 | 22569633 | 7 | IGLV10-54 | 0.031 | 0.037 |
| 438 | chr17 | 75447869 | 75448419 | 12 | 9-Sep | 0.031 | 0.037 |
| 439 | chr7 | 148506319 | 148523734 | 19 | EZH2 | 0.019 | 0.025 |
| 440 | chr14 | 106621886 | 106622095 | 5 | IGHV3-16 | 0.024 | 0.030 |
| 441 | chr1 | 181452915 | 181453115 | 5 | CACNA1E | 0.032 | 0.036 |
| 442 | chr2 | 58520801 | 58521201 | 9 | FANCL | 0.029 | 0.035 |
| 443 | chr19 | 51559442 | 51561922 | 16 | KLK13 | 0.032 | 0.038 |
| 444 | chr16 | 2812097 | 2812747 | 14 | SRRM2 | 0.056 | 0.062 |
| 445 | chr6 | 41903612 | 41909397 | 26 | CCND3 | 0.041 | 0.047 |
| 446 | chr14 | 106068706 | 106071241 | 16 | IGHE | 0.118 | 0.124 |
| 447 | chr6 | 110777719 | 110778219 | 11 | SLC22A16 | 0.027 | 0.033 |
| 448 | chr9 | 21970835 | 21994385 | 37 | CDKN2A | 0.027 | 0.031 |
| 449 | chr2 | 90025207 | 90025522 | 6 | IGKV2D-26 | 0.012 | 0.016 |
| 450 | chr4 | 7728457 | 7728657 | 5 | SORCS2 | 0.034 | 0.039 |
| 451 | chr7 | 5569096 | 5569356 | 6 | ACTB | 0.048 | 0.055 |
| 452 | chr3 | 140281599 | 140281849 | 6 | CLSTN2 | 0.036 | 0.038 |
| 453 | chr2 | 89291907 | 89292182 | 4 | IGKV1-8 | 0.020 | 0.025 |
| 454 | chr22 | 23260268 | 23260368 | 3 | IGLJ6 | 0.043 | 0.049 |
| 455 | chr14 | 106815806 | 106815906 | 3 | IGHV3-33 | 0.059 | 0.066 |
| 456 | chr6 | 26123615 | 26124080 | 9 | HIST1H2BC | 0.031 | 0.036 |
| 457 | chr3 | 49397609 | 49413039 | 18 | RHOA | 0.030 | 0.035 |
| 458 | chr22 | 29191137 | 29196512 | 28 | XBP1 | 0.032 | 0.039 |
| 459 | chr14 | 106471396 | 106471580 | 4 | IGHV1-3 | 0.007 | 0.012 |
| 460 | chr17 | 41847059 | 41847209 | 4 | DUSP3 | 0.032 | 0.037 |
| 461 | chr17 | 51900442 | 51900892 | 10 | KIF2B | 0.035 | 0.039 |
| 462 | chr15 | 86312063 | 86312563 | 11 | KLHL25 | 0.032 | 0.037 |
| 463 | chr18 | 53804516 | 53804766 | 6 | TXNL1 | 0.036 | 0.041 |
| 464 | chr5 | 67590967 | 67591167 | 5 | PIK3R1 | 0.018 | 0.023 |
| 465 | chr5 | 124079828 | 124080678 | 18 | ZNF608 | 0.026 | 0.031 |
| 466 | chr1 | 90259932 | 90260232 | 5 | IGKV1D-8 | 0.034 | 0.039 |
| 467 | chr2 | 88906682 | 88906832 | 4 | EIF2AK3 | 0.059 | 0.066 |
| 468 | chr4 | 106157605 | 106157805 | 5 | TET2 | 0.018 | 0.023 |

| # | Mean frac ABC with PV | Mean frac PMBCL with PV | Mean frac cHL with PV | ranksumP ABCvsGCB | ranksumP PMBCLvsDLBCL | ranksumP cHLvsDLBCL |
|---|---|---|---|---|---|---|
| 1 | 0.224 | 0.242 | 0.088 | 0.00000 | 0.00003 | 0.00000 |
| 2 | 0.029 | 0.056 | 0.004 | 0.00000 | 0.00000 | 0.00000 |
| 3 | 0.251 | 0.105 | 0.032 | 0.00000 | 0.00000 | 0.00000 |

TABLE 4-continued

| | | | | | | |
|---|---|---|---|---|---|---|
| 4 | 0.217 | 0.136 | 0.056 | 0.00000 | 0.00000 | 0.00000 |
| 5 | 0.124 | 0.068 | 0.000 | 0.00000 | 0.00251 | 0.00000 |
| 6 | 0.013 | 0.102 | 0.000 | 0.00000 | 0.46986 | 0.00001 |
| 7 | 0.160 | 0.140 | 0.109 | 0.00000 | 0.00006 | 0.36296 |
| 8 | 0.121 | 0.100 | 0.012 | 0.00000 | 0.10144 | 0.01432 |
| 9 | 0.339 | 0.350 | 0.219 | 0.00000 | 0.28398 | 0.00000 |
| 10 | 0.215 | 0.429 | 0.208 | 0.00000 | 0.00000 | 0.22589 |
| 11 | 0.277 | 0.131 | 0.035 | 0.00000 | 0.00000 | 0.00000 |
| 12 | 0.410 | 0.375 | 0.148 | 0.00000 | 0.24822 | 0.00000 |
| 13 | 0.046 | 0.168 | 0.062 | 0.00001 | 0.00027 | 0.00345 |
| 14 | 0.236 | 0.116 | 0.062 | 0.00001 | 0.02569 | 0.00086 |
| 15 | 0.018 | 0.075 | 0.001 | 0.00002 | 0.58192 | 0.99403 |
| 16 | 0.094 | 0.063 | 0.000 | 0.00002 | 0.11666 | 0.00114 |
| 17 | 0.043 | 0.097 | 0.024 | 0.00003 | 0.01798 | 0.00005 |
| 18 | 0.021 | 0.039 | 0.001 | 0.00003 | 0.00000 | 0.86966 |
| 19 | 0.018 | 0.088 | 0.005 | 0.00003 | 0.77724 | 0.04594 |
| 20 | 0.311 | 0.241 | 0.130 | 0.00003 | 0.04157 | 0.00006 |
| 21 | 0.034 | 0.078 | 0.022 | 0.00003 | 0.17854 | 0.01628 |
| 22 | 0.068 | 0.173 | 0.041 | 0.00005 | 0.00033 | 0.01552 |
| 23 | 0.195 | 0.182 | 0.115 | 0.00006 | 0.00002 | 0.00004 |
| 24 | 0.258 | 0.135 | 0.109 | 0.00006 | 0.00291 | 0.00284 |
| 25 | 0.011 | 0.107 | 0.019 | 0.00010 | 0.70241 | 0.37522 |
| 26 | 0.055 | 0.113 | 0.035 | 0.00014 | 0.00837 | 0.00072 |
| 27 | 0.107 | 0.164 | 0.041 | 0.00022 | 0.00008 | 0.04625 |
| 28 | 0.025 | 0.069 | 0.002 | 0.00023 | 0.36871 | 0.42872 |
| 29 | 0.000 | 0.090 | 0.000 | 0.00026 | 0.33149 | 0.77291 |
| 30 | 0.057 | 0.133 | 0.078 | 0.00035 | 0.83189 | 0.36813 |
| 31 | 0.008 | 0.089 | 0.000 | 0.00075 | 0.19138 | 0.80319 |
| 32 | 0.025 | 0.025 | 0.009 | 0.00085 | 0.00670 | 0.02848 |
| 33 | 0.079 | 0.083 | 0.043 | 0.00090 | 0.90873 | 0.01148 |
| 34 | 0.004 | 0.055 | 0.000 | 0.00099 | 0.48925 | 0.69644 |
| 35 | 0.044 | 0.063 | 0.000 | 0.00113 | 0.75367 | 0.44231 |
| 36 | 0.012 | 0.077 | 0.000 | 0.00119 | 0.51920 | 0.84956 |
| 37 | 0.011 | 0.131 | 0.000 | 0.00129 | 0.00884 | 0.29860 |
| 38 | 0.190 | 0.139 | 0.024 | 0.00192 | 0.00000 | 0.00000 |
| 39 | 0.100 | 0.266 | 0.000 | 0.00225 | 0.00168 | 0.05724 |
| 40 | 0.080 | 0.292 | 0.046 | 0.00303 | 0.00000 | 0.07342 |
| 41 | 0.054 | 0.289 | 0.082 | 0.00307 | 0.00000 | 0.00000 |
| 42 | 0.000 | 0.088 | 0.000 | 0.00408 | 0.40676 | 0.90937 |
| 43 | 0.067 | 0.042 | 0.000 | 0.00488 | 0.21081 | 0.62256 |
| 44 | 0.042 | 0.162 | 0.025 | 0.00501 | 0.00000 | 0.65960 |
| 45 | 0.200 | 0.180 | 0.043 | 0.00606 | 0.43909 | 0.00002 |
| 46 | 0.028 | 0.059 | 0.053 | 0.00685 | 0.08333 | 0.00000 |
| 47 | 0.005 | 0.038 | 0.000 | 0.00715 | 0.19681 | 0.45229 |
| 48 | 0.021 | 0.094 | 0.000 | 0.00728 | 0.81618 | 0.00596 |
| 49 | 0.000 | 0.167 | 0.000 | 0.00799 | 0.01126 | 0.75859 |
| 50 | 0.100 | 0.163 | 0.094 | 0.00835 | 0.72971 | 0.51511 |
| 51 | 0.043 | 0.045 | 0.000 | 0.00870 | 0.55261 | 0.56841 |
| 52 | 0.478 | 0.470 | 0.362 | 0.00948 | 0.02862 | 0.00000 |
| 53 | 0.010 | 0.075 | 0.000 | 0.00954 | 0.90180 | 0.48859 |
| 54 | 0.027 | 0.017 | 0.000 | 0.00967 | 0.00022 | 0.00680 |
| 55 | 0.028 | 0.031 | 0.011 | 0.00999 | 0.57172 | 0.00116 |
| 56 | 0.089 | 0.126 | 0.044 | 0.01002 | 0.04210 | 0.00007 |
| 57 | 0.065 | 0.021 | 0.000 | 0.01042 | 0.00001 | 0.00039 |
| 58 | 0.042 | 0.067 | 0.000 | 0.01112 | 0.97915 | 0.84801 |
| 59 | 0.044 | 0.077 | 0.000 | 0.01378 | 0.40303 | 0.93788 |
| 60 | 0.044 | 0.083 | 0.002 | 0.01401 | 0.66941 | 0.59741 |
| 61 | 0.023 | 0.088 | 0.000 | 0.01514 | 0.02024 | 0.00677 |
| 62 | 0.011 | 0.078 | 0.000 | 0.01532 | 0.28495 | 0.48626 |
| 63 | 0.025 | 0.042 | 0.000 | 0.01556 | 0.06834 | 0.05288 |
| 64 | 0.000 | 0.063 | 0.000 | 0.01575 | 0.79954 | 0.58401 |
| 65 | 0.000 | 0.063 | 0.000 | 0.01627 | 0.93639 | 0.94029 |
| 66 | 0.008 | 0.048 | 0.003 | 0.01646 | 0.43210 | 0.34042 |
| 67 | 0.050 | 0.113 | 0.043 | 0.01712 | 0.97583 | 0.80122 |
| 68 | 0.008 | 0.073 | 0.000 | 0.01813 | 0.77106 | 0.87235 |
| 69 | 0.072 | 0.180 | 0.007 | 0.01828 | 0.00255 | 0.02269 |
| 70 | 0.065 | 0.159 | 0.013 | 0.01945 | 0.03212 | 0.00000 |
| 71 | 0.010 | 0.108 | 0.000 | 0.01980 | 0.01754 | 0.55332 |
| 72 | 0.010 | 0.038 | 0.000 | 0.01981 | 0.22178 | 0.96725 |
| 73 | 0.000 | 0.000 | 0.000 | 0.02014 | 0.01525 | 0.81176 |
| 74 | 0.056 | 0.078 | 0.033 | 0.02064 | 0.69126 | 0.04169 |
| 75 | 0.011 | 0.065 | 0.000 | 0.02090 | 0.60391 | 0.32890 |
| 76 | 0.042 | 0.021 | 0.000 | 0.02146 | 0.00420 | 0.95404 |
| 77 | 0.008 | 0.076 | 0.000 | 0.02188 | 0.57834 | 0.96296 |
| 78 | 0.030 | 0.150 | 0.009 | 0.02210 | 0.00851 | 0.25752 |
| 79 | 0.050 | 0.050 | 0.000 | 0.02254 | 0.59983 | 0.95843 |
| 80 | 0.059 | 0.074 | 0.012 | 0.02452 | 0.27041 | 0.12731 |
| 81 | 0.040 | 0.025 | 0.000 | 0.02494 | 0.30467 | 0.19851 |
| 82 | 0.050 | 0.047 | 0.000 | 0.02532 | 0.32106 | 0.47874 |
| 83 | 0.025 | 0.042 | 0.000 | 0.02682 | 0.15950 | 0.08878 |

TABLE 4-continued

| | | | | | | |
|---|---|---|---|---|---|---|
| 84 | 0.056 | 0.063 | 0.000 | 0.02722 | 0.79786 | 0.74613 |
| 85 | 0.020 | 0.113 | 0.000 | 0.02729 | 0.27017 | 0.10654 |
| 86 | 0.067 | 0.104 | 0.029 | 0.02734 | 0.59010 | 0.16336 |
| 87 | 0.000 | 0.063 | 0.000 | 0.02815 | 0.98381 | 0.97542 |
| 88 | 0.065 | 0.113 | 0.000 | 0.02872 | 0.30080 | 0.42892 |
| 89 | 0.010 | 0.050 | 0.000 | 0.02933 | 0.46779 | 0.82988 |
| 90 | 0.113 | 0.100 | 0.025 | 0.03071 | 0.00337 | 0.00000 |
| 91 | 0.018 | 0.081 | 0.000 | 0.03118 | 0.04749 | 0.00098 |
| 92 | 0.014 | 0.066 | 0.000 | 0.03190 | 0.74698 | 0.62135 |
| 93 | 0.005 | 0.138 | 0.000 | 0.03215 | 0.03660 | 0.87436 |
| 94 | 0.048 | 0.125 | 0.043 | 0.03245 | 0.00471 | 0.00001 |
| 95 | 0.022 | 0.070 | 0.001 | 0.03490 | 0.47515 | 0.61294 |
| 96 | 0.009 | 0.091 | 0.000 | 0.03816 | 0.14785 | 0.41409 |
| 97 | 0.000 | 0.088 | 0.000 | 0.03821 | 0.23210 | 0.50694 |
| 98 | 0.006 | 0.103 | 0.000 | 0.03855 | 0.00439 | 0.01617 |
| 99 | 0.046 | 0.054 | 0.000 | 0.03877 | 0.49619 | 0.72943 |
| 100 | 0.017 | 0.066 | 0.000 | 0.04167 | 0.79797 | 0.81991 |
| 101 | 0.050 | 0.031 | 0.000 | 0.04189 | 0.24118 | 0.93977 |
| 102 | 0.031 | 0.203 | 0.000 | 0.04203 | 0.00443 | 0.12932 |
| 103 | 0.018 | 0.179 | 0.043 | 0.04206 | 0.00035 | 0.00040 |
| 104 | 0.029 | 0.073 | 0.000 | 0.04311 | 0.62445 | 0.18113 |
| 105 | 0.021 | 0.125 | 0.000 | 0.04368 | 0.00589 | 0.00868 |
| 106 | 0.116 | 0.125 | 0.027 | 0.04581 | 0.05495 | 0.00009 |
| 107 | 0.024 | 0.092 | 0.000 | 0.04705 | 0.03043 | 0.23893 |
| 108 | 0.045 | 0.008 | 0.000 | 0.04776 | 0.00000 | 0.00658 |
| 109 | 0.020 | 0.050 | 0.000 | 0.04779 | 0.61717 | 0.01894 |
| 110 | 0.059 | 0.107 | 0.015 | 0.04840 | 0.84733 | 0.06185 |
| 111 | 0.025 | 0.031 | 0.000 | 0.04924 | 0.70570 | 0.06008 |
| 112 | 0.040 | 0.050 | 0.000 | 0.05027 | 0.89626 | 0.41400 |
| 113 | 0.031 | 0.115 | 0.000 | 0.05115 | 0.00217 | 0.49133 |
| 114 | 0.005 | 0.013 | 0.000 | 0.05360 | 0.05680 | 0.72269 |
| 115 | 0.016 | 0.093 | 0.001 | 0.05546 | 0.01173 | 0.29622 |
| 116 | 0.013 | 0.094 | 0.000 | 0.05661 | 0.05492 | 0.36536 |
| 117 | 0.016 | 0.060 | 0.000 | 0.05690 | 0.95068 | 0.19315 |
| 118 | 0.217 | 0.147 | 0.049 | 0.05698 | 0.00000 | 0.00000 |
| 119 | 0.035 | 0.031 | 0.000 | 0.05889 | 0.10905 | 0.59078 |
| 120 | 0.021 | 0.058 | 0.000 | 0.05908 | 0.58438 | 0.01312 |
| 121 | 0.080 | 0.027 | 0.000 | 0.05952 | 0.00000 | 0.00001 |
| 122 | 0.031 | 0.047 | 0.000 | 0.06085 | 0.91905 | 0.26127 |
| 123 | 0.013 | 0.046 | 0.000 | 0.06151 | 0.19789 | 0.69126 |
| 124 | 0.028 | 0.063 | 0.000 | 0.06231 | 0.41805 | 0.17702 |
| 125 | 0.008 | 0.082 | 0.000 | 0.06377 | 0.11838 | 0.14383 |
| 126 | 0.021 | 0.082 | 0.007 | 0.06792 | 0.84332 | 0.93964 |
| 127 | 0.025 | 0.021 | 0.000 | 0.07104 | 0.07945 | 0.10112 |
| 128 | 0.013 | 0.080 | 0.000 | 0.07190 | 0.51773 | 0.62080 |
| 129 | 0.015 | 0.113 | 0.000 | 0.07234 | 0.37625 | 0.20872 |
| 130 | 0.016 | 0.039 | 0.000 | 0.07723 | 0.12619 | 0.48614 |
| 131 | 0.028 | 0.102 | 0.000 | 0.07866 | 0.03037 | 0.15798 |
| 132 | 0.036 | 0.045 | 0.019 | 0.08101 | 0.47189 | 0.03046 |
| 133 | 0.045 | 0.100 | 0.000 | 0.08357 | 0.26942 | 0.76490 |
| 134 | 0.012 | 0.072 | 0.000 | 0.08367 | 0.51165 | 0.24502 |
| 135 | 0.043 | 0.085 | 0.000 | 0.08686 | 0.51095 | 0.37846 |
| 136 | 0.024 | 0.065 | 0.012 | 0.08712 | 0.41154 | 0.04982 |
| 137 | 0.029 | 0.045 | 0.000 | 0.09053 | 0.66530 | 0.22260 |
| 138 | 0.050 | 0.063 | 0.009 | 0.09076 | 0.87053 | 0.96927 |
| 139 | 0.046 | 0.083 | 0.000 | 0.09248 | 0.64737 | 0.01000 |
| 140 | 0.042 | 0.000 | 0.029 | 0.09735 | 0.05014 | 0.09524 |
| 141 | 0.006 | 0.063 | 0.000 | 0.10148 | 0.15804 | 0.00010 |
| 142 | 0.010 | 0.100 | 0.000 | 0.10715 | 0.04221 | 0.30553 |
| 143 | 0.017 | 0.063 | 0.000 | 0.10731 | 0.45417 | 0.02634 |
| 144 | 0.000 | 0.073 | 0.000 | 0.10744 | 0.29340 | 0.11987 |
| 145 | 0.018 | 0.050 | 0.000 | 0.10843 | 0.80649 | 0.00490 |
| 146 | 0.029 | 0.073 | 0.000 | 0.10860 | 0.97247 | 0.18279 |
| 147 | 0.024 | 0.057 | 0.000 | 0.11075 | 0.98596 | 0.05983 |
| 148 | 0.023 | 0.073 | 0.006 | 0.11182 | 0.58280 | 0.43378 |
| 149 | 0.013 | 0.088 | 0.000 | 0.11539 | 0.00502 | 0.00005 |
| 150 | 0.022 | 0.059 | 0.000 | 0.11749 | 0.74407 | 0.02655 |
| 151 | 0.133 | 0.133 | 0.012 | 0.11791 | 0.01136 | 0.00000 |
| 152 | 0.003 | 0.047 | 0.000 | 0.11971 | 0.87638 | 0.11243 |
| 153 | 0.050 | 0.042 | 0.000 | 0.12081 | 0.31080 | 0.40430 |
| 154 | 0.025 | 0.045 | 0.000 | 0.12123 | 0.15843 | 0.35845 |
| 155 | 0.023 | 0.025 | 0.000 | 0.12266 | 0.14627 | 0.06157 |
| 156 | 0.040 | 0.022 | 0.010 | 0.12443 | 0.00226 | 0.54240 |
| 157 | 0.026 | 0.097 | 0.000 | 0.12454 | 0.00102 | 0.09879 |
| 158 | 0.029 | 0.052 | 0.000 | 0.12900 | 0.22779 | 0.08945 |
| 159 | 0.018 | 0.100 | 0.000 | 0.12911 | 0.49227 | 0.67922 |
| 160 | 0.033 | 0.063 | 0.000 | 0.12919 | 0.69275 | 0.24178 |
| 161 | 0.005 | 0.080 | 0.000 | 0.13076 | 0.08392 | 0.03514 |
| 162 | 0.027 | 0.058 | 0.000 | 0.13686 | 0.98920 | 0.29436 |
| 163 | 0.032 | 0.108 | 0.000 | 0.13854 | 0.36497 | 0.04398 |

TABLE 4-continued

| | | | | | | |
|---|---|---|---|---|---|---|
| 164 | 0.054 | 0.063 | 0.000 | 0.14045 | 0.43890 | 0.10024 |
| 165 | 0.005 | 0.000 | 0.000 | 0.14058 | 0.02490 | 0.46424 |
| 166 | 0.050 | 0.102 | 0.027 | 0.14335 | 0.33135 | 0.15651 |
| 167 | 0.031 | 0.139 | 0.000 | 0.14412 | 0.00007 | 0.03739 |
| 168 | 0.030 | 0.038 | 0.000 | 0.14525 | 0.54138 | 0.28737 |
| 169 | 0.025 | 0.107 | 0.000 | 0.15224 | 0.01412 | 0.10864 |
| 170 | 0.000 | 0.100 | 0.000 | 0.15384 | 0.16273 | 0.16433 |
| 171 | 0.020 | 0.088 | 0.000 | 0.15508 | 0.23890 | 0.07712 |
| 172 | 0.013 | 0.075 | 0.000 | 0.15602 | 0.08296 | 0.00029 |
| 173 | 0.013 | 0.023 | 0.000 | 0.15663 | 0.04633 | 0.00000 |
| 174 | 0.010 | 0.025 | 0.000 | 0.15837 | 0.74245 | 0.00357 |
| 175 | 0.016 | 0.037 | 0.000 | 0.15955 | 0.10765 | 0.43759 |
| 176 | 0.005 | 0.013 | 0.000 | 0.16320 | 0.46997 | 0.00144 |
| 177 | 0.025 | 0.000 | 0.000 | 0.16445 | 0.26379 | 0.18377 |
| 178 | 0.014 | 0.028 | 0.000 | 0.16655 | 0.08650 | 0.59884 |
| 179 | 0.054 | 0.073 | 0.022 | 0.16893 | 0.83695 | 0.56495 |
| 180 | 0.050 | 0.078 | 0.022 | 0.17014 | 0.88867 | 0.40591 |
| 181 | 0.000 | 0.031 | 0.000 | 0.17060 | 0.58174 | 0.54924 |
| 182 | 0.018 | 0.071 | 0.000 | 0.17227 | 0.95304 | 0.82874 |
| 183 | 0.033 | 0.125 | 0.000 | 0.17412 | 0.05590 | 0.56584 |
| 184 | 0.050 | 0.071 | 0.000 | 0.17445 | 0.59106 | 0.01278 |
| 185 | 0.034 | 0.039 | 0.000 | 0.17496 | 0.31060 | 0.64225 |
| 186 | 0.023 | 0.107 | 0.000 | 0.17822 | 0.03641 | 0.51953 |
| 187 | 0.006 | 0.031 | 0.000 | 0.18073 | 0.41320 | 0.38140 |
| 188 | 0.044 | 0.104 | 0.002 | 0.18105 | 0.40386 | 0.00014 |
| 189 | 0.023 | 0.060 | 0.005 | 0.18315 | 0.54097 | 0.01195 |
| 190 | 0.045 | 0.050 | 0.000 | 0.18414 | 0.38135 | 0.41604 |
| 191 | 0.072 | 0.087 | 0.018 | 0.18556 | 0.01425 | 0.00007 |
| 192 | 0.054 | 0.010 | 0.000 | 0.18604 | 0.00259 | 0.04452 |
| 193 | 0.050 | 0.000 | 0.000 | 0.18636 | 0.00860 | 0.27305 |
| 194 | 0.075 | 0.104 | 0.043 | 0.18760 | 0.23061 | 0.02703 |
| 195 | 0.018 | 0.074 | 0.000 | 0.18799 | 0.04332 | 0.00092 |
| 196 | 0.013 | 0.054 | 0.000 | 0.18947 | 0.52931 | 0.00001 |
| 197 | 0.021 | 0.116 | 0.000 | 0.18957 | 0.01363 | 0.10957 |
| 198 | 0.009 | 0.072 | 0.002 | 0.19120 | 0.37384 | 0.02195 |
| 199 | 0.031 | 0.092 | 0.000 | 0.19342 | 0.57240 | 0.03398 |
| 200 | 0.019 | 0.016 | 0.000 | 0.19688 | 0.06546 | 0.70963 |
| 201 | 0.039 | 0.111 | 0.000 | 0.19910 | 0.04960 | 0.53925 |
| 202 | 0.005 | 0.063 | 0.000 | 0.20039 | 0.78808 | 0.29891 |
| 203 | 0.015 | 0.000 | 0.000 | 0.20189 | 0.09865 | 0.01894 |
| 204 | 0.015 | 0.150 | 0.000 | 0.20189 | 0.02007 | 0.01894 |
| 205 | 0.025 | 0.078 | 0.000 | 0.20429 | 0.99130 | 0.21830 |
| 206 | 0.009 | 0.047 | 0.000 | 0.20711 | 0.60835 | 0.35208 |
| 207 | 0.050 | 0.025 | 0.000 | 0.21582 | 0.05416 | 0.28073 |
| 208 | 0.009 | 0.073 | 0.000 | 0.21609 | 0.19591 | 0.00018 |
| 209 | 0.017 | 0.031 | 0.007 | 0.21616 | 0.04427 | 0.31773 |
| 210 | 0.030 | 0.040 | 0.006 | 0.21620 | 0.03795 | 0.84925 |
| 211 | 0.013 | 0.117 | 0.000 | 0.21872 | 0.01766 | 0.70075 |
| 212 | 0.034 | 0.055 | 0.000 | 0.22009 | 0.11870 | 0.13982 |
| 213 | 0.006 | 0.109 | 0.000 | 0.22034 | 0.26105 | 0.39687 |
| 214 | 0.014 | 0.063 | 0.000 | 0.22199 | 0.44292 | 0.00401 |
| 215 | 0.059 | 0.359 | 0.082 | 0.22404 | 0.00000 | 0.00004 |
| 216 | 0.033 | 0.010 | 0.000 | 0.22855 | 0.00394 | 0.11588 |
| 217 | 0.050 | 0.063 | 0.000 | 0.24046 | 0.72117 | 0.43844 |
| 218 | 0.036 | 0.052 | 0.006 | 0.24437 | 0.12177 | 0.41139 |
| 219 | 0.013 | 0.125 | 0.043 | 0.24604 | 0.05674 | 0.01689 |
| 220 | 0.010 | 0.175 | 0.000 | 0.24818 | 0.00334 | 0.70762 |
| 221 | 0.005 | 0.038 | 0.000 | 0.24870 | 0.54640 | 0.19851 |
| 222 | 0.000 | 0.050 | 0.000 | 0.25016 | 0.78384 | 0.08170 |
| 223 | 0.042 | 0.021 | 0.000 | 0.25073 | 0.17545 | 0.97542 |
| 224 | 0.013 | 0.016 | 0.000 | 0.25147 | 0.13295 | 0.69509 |
| 225 | 0.033 | 0.042 | 0.000 | 0.25208 | 0.23957 | 0.18828 |
| 226 | 0.034 | 0.047 | 0.000 | 0.25854 | 0.32941 | 0.85606 |
| 227 | 0.022 | 0.049 | 0.000 | 0.25896 | 0.17138 | 0.85294 |
| 228 | 0.013 | 0.063 | 0.065 | 0.26082 | 0.88005 | 0.00186 |
| 229 | 0.046 | 0.125 | 0.000 | 0.26354 | 0.03650 | 0.25182 |
| 230 | 0.013 | 0.083 | 0.000 | 0.26708 | 0.50393 | 0.47148 |
| 231 | 0.021 | 0.071 | 0.000 | 0.26981 | 0.83901 | 0.54622 |
| 232 | 0.025 | 0.038 | 0.000 | 0.26983 | 0.53539 | 0.29891 |
| 233 | 0.000 | 0.025 | 0.000 | 0.27098 | 0.90753 | 0.00089 |
| 234 | 0.053 | 0.028 | 0.015 | 0.27123 | 0.00000 | 0.12156 |
| 235 | 0.042 | 0.063 | 0.000 | 0.27246 | 0.79783 | 0.70059 |
| 236 | 0.005 | 0.063 | 0.000 | 0.27662 | 0.67082 | 0.19851 |
| 237 | 0.005 | 0.075 | 0.000 | 0.27662 | 0.38460 | 0.19851 |
| 238 | 0.025 | 0.102 | 0.000 | 0.27685 | 0.05340 | 0.35208 |
| 239 | 0.083 | 0.177 | 0.057 | 0.27705 | 0.03023 | 0.53439 |
| 240 | 0.035 | 0.121 | 0.000 | 0.27742 | 0.02768 | 0.05558 |
| 241 | 0.020 | 0.050 | 0.000 | 0.27845 | 0.92556 | 0.10149 |
| 242 | 0.019 | 0.094 | 0.000 | 0.28231 | 0.39328 | 0.68881 |
| 243 | 0.029 | 0.051 | 0.005 | 0.29192 | 0.20921 | 0.55174 |

TABLE 4-continued

| | | | | | | |
|---|---|---|---|---|---|---|
| 244 | 0.015 | 0.063 | 0.000 | 0.29877 | 0.61973 | 0.01289 |
| 245 | 0.014 | 0.053 | 0.006 | 0.29909 | 0.79282 | 0.00093 |
| 246 | 0.029 | 0.103 | 0.000 | 0.29943 | 0.04753 | 0.77217 |
| 247 | 0.045 | 0.050 | 0.000 | 0.30121 | 0.42497 | 0.50451 |
| 248 | 0.041 | 0.058 | 0.000 | 0.30584 | 0.28865 | 0.12742 |
| 249 | 0.035 | 0.063 | 0.000 | 0.30591 | 0.40617 | 0.10207 |
| 250 | 0.013 | 0.141 | 0.000 | 0.30697 | 0.04146 | 0.05611 |
| 251 | 0.095 | 0.122 | 0.050 | 0.31066 | 0.24386 | 0.00835 |
| 252 | 0.035 | 0.088 | 0.000 | 0.32051 | 0.36874 | 0.94107 |
| 253 | 0.000 | 0.063 | 0.000 | 0.32488 | 0.18259 | 0.00295 |
| 254 | 0.000 | 0.031 | 0.000 | 0.32488 | 0.89232 | 0.00295 |
| 255 | 0.023 | 0.055 | 0.000 | 0.32688 | 0.88862 | 0.08570 |
| 256 | 0.009 | 0.074 | 0.000 | 0.32826 | 0.22549 | 0.05225 |
| 257 | 0.005 | 0.063 | 0.000 | 0.33654 | 0.72508 | 0.12531 |
| 258 | 0.021 | 0.063 | 0.000 | 0.33950 | 0.63054 | 0.15262 |
| 259 | 0.020 | 0.088 | 0.000 | 0.34027 | 0.10857 | 0.96046 |
| 260 | 0.049 | 0.146 | 0.006 | 0.34145 | 0.00006 | 0.25221 |
| 261 | 0.021 | 0.042 | 0.000 | 0.34253 | 0.25513 | 0.68243 |
| 262 | 0.021 | 0.036 | 0.000 | 0.34439 | 0.45188 | 0.16111 |
| 263 | 0.000 | 0.042 | 0.000 | 0.34503 | 0.82367 | 0.13637 |
| 264 | 0.035 | 0.075 | 0.000 | 0.34677 | 0.68708 | 0.00272 |
| 265 | 0.019 | 0.094 | 0.000 | 0.35301 | 0.26225 | 0.10870 |
| 266 | 0.019 | 0.088 | 0.026 | 0.35469 | 0.15903 | 0.00002 |
| 267 | 0.009 | 0.103 | 0.000 | 0.35514 | 0.00284 | 0.00632 |
| 268 | 0.005 | 0.038 | 0.000 | 0.35786 | 0.57454 | 0.20093 |
| 269 | 0.025 | 0.091 | 0.000 | 0.35888 | 0.08153 | 0.38328 |
| 270 | 0.014 | 0.098 | 0.000 | 0.36129 | 0.28061 | 0.53891 |
| 271 | 0.036 | 0.045 | 0.000 | 0.36200 | 0.39501 | 0.93264 |
| 272 | 0.018 | 0.051 | 0.000 | 0.36490 | 0.59248 | 0.38946 |
| 273 | 0.018 | 0.067 | 0.000 | 0.36721 | 0.26604 | 0.01881 |
| 274 | 0.018 | 0.098 | 0.000 | 0.36740 | 0.03964 | 0.07222 |
| 275 | 0.039 | 0.018 | 0.000 | 0.36781 | 0.01092 | 0.23508 |
| 276 | 0.017 | 0.099 | 0.000 | 0.36795 | 0.03866 | 0.51208 |
| 277 | 0.024 | 0.082 | 0.000 | 0.37037 | 0.15033 | 0.73903 |
| 278 | 0.016 | 0.035 | 0.000 | 0.37088 | 0.36837 | 0.00422 |
| 279 | 0.000 | 0.047 | 0.000 | 0.37631 | 0.84014 | 0.07298 |
| 280 | 0.000 | 0.031 | 0.000 | 0.37790 | 0.70713 | 0.06008 |
| 281 | 0.020 | 0.025 | 0.000 | 0.38591 | 0.34374 | 0.13521 |
| 282 | 0.025 | 0.000 | 0.000 | 0.38723 | 0.02764 | 0.48180 |
| 283 | 0.046 | 0.021 | 0.000 | 0.38786 | 0.03107 | 0.34087 |
| 284 | 0.025 | 0.059 | 0.024 | 0.39142 | 0.82914 | 0.00001 |
| 285 | 0.040 | 0.038 | 0.000 | 0.39274 | 0.28309 | 0.98151 |
| 286 | 0.005 | 0.075 | 0.000 | 0.40112 | 0.15248 | 0.00357 |
| 287 | 0.034 | 0.117 | 0.000 | 0.40201 | 0.02655 | 0.49158 |
| 288 | 0.025 | 0.063 | 0.000 | 0.40450 | 0.82223 | 0.42774 |
| 289 | 0.016 | 0.063 | 0.000 | 0.40456 | 0.61602 | 0.02024 |
| 290 | 0.017 | 0.077 | 0.000 | 0.40678 | 0.18209 | 0.12955 |
| 291 | 0.025 | 0.075 | 0.000 | 0.41027 | 0.52307 | 0.41005 |
| 292 | 0.020 | 0.069 | 0.000 | 0.41169 | 0.93852 | 0.81159 |
| 293 | 0.020 | 0.119 | 0.000 | 0.41348 | 0.00251 | 0.10186 |
| 294 | 0.030 | 0.075 | 0.009 | 0.41401 | 0.97196 | 0.91852 |
| 295 | 0.020 | 0.125 | 0.000 | 0.41703 | 0.03149 | 0.68257 |
| 296 | 0.013 | 0.086 | 0.000 | 0.41822 | 0.64743 | 0.29530 |
| 297 | 0.030 | 0.113 | 0.000 | 0.42725 | 0.84925 | 0.34749 |
| 298 | 0.013 | 0.078 | 0.000 | 0.43273 | 0.41122 | 0.00842 |
| 299 | 0.038 | 0.100 | 0.017 | 0.43292 | 0.62927 | 0.61655 |
| 300 | 0.028 | 0.140 | 0.000 | 0.44217 | 0.00038 | 0.66264 |
| 301 | 0.018 | 0.080 | 0.000 | 0.44604 | 0.33603 | 0.09047 |
| 302 | 0.035 | 0.000 | 0.000 | 0.44876 | 0.01256 | 0.96541 |
| 303 | 0.009 | 0.117 | 0.000 | 0.45177 | 0.00957 | 0.11783 |
| 304 | 0.000 | 0.135 | 0.000 | 0.45506 | 0.00452 | 0.01644 |
| 305 | 0.023 | 0.085 | 0.000 | 0.45807 | 0.35320 | 0.85391 |
| 306 | 0.020 | 0.049 | 0.000 | 0.46045 | 0.38390 | 0.02293 |
| 307 | 0.006 | 0.102 | 0.000 | 0.47564 | 0.05373 | 0.03579 |
| 308 | 0.039 | 0.107 | 0.000 | 0.47590 | 0.23069 | 0.43666 |
| 309 | 0.032 | 0.107 | 0.000 | 0.47614 | 0.19555 | 0.90440 |
| 310 | 0.011 | 0.021 | 0.000 | 0.48388 | 0.09402 | 0.14560 |
| 311 | 0.006 | 0.109 | 0.000 | 0.48557 | 0.05983 | 0.17265 |
| 312 | 0.050 | 0.083 | 0.000 | 0.48567 | 0.96231 | 0.04559 |
| 313 | 0.000 | 0.000 | 0.000 | 0.48646 | 0.45288 | 0.03556 |
| 314 | 0.000 | 0.125 | 0.022 | 0.48646 | 0.05020 | 0.02436 |
| 315 | 0.000 | 0.125 | 0.000 | 0.48646 | 0.10655 | 0.03556 |
| 316 | 0.005 | 0.000 | 0.000 | 0.49420 | 0.05467 | 0.09497 |
| 317 | 0.004 | 0.146 | 0.000 | 0.50036 | 0.00472 | 0.03774 |
| 318 | 0.031 | 0.063 | 0.000 | 0.50251 | 0.65174 | 0.76665 |
| 319 | 0.047 | 0.075 | 0.000 | 0.50409 | 0.06246 | 0.00000 |
| 320 | 0.050 | 0.038 | 0.009 | 0.51163 | 0.10472 | 0.60740 |
| 321 | 0.006 | 0.063 | 0.000 | 0.51321 | 0.66087 | 0.32094 |
| 322 | 0.033 | 0.080 | 0.027 | 0.51555 | 0.36573 | 0.00948 |
| 323 | 0.033 | 0.125 | 0.000 | 0.51984 | 0.19368 | 0.92185 |

TABLE 4-continued

| | | | | | | |
|---|---|---|---|---|---|---|
| 324 | 0.033 | 0.052 | 0.000 | 0.52125 | 0.24640 | 0.20117 |
| 325 | 0.020 | 0.113 | 0.000 | 0.52233 | 0.04449 | 0.30659 |
| 326 | 0.021 | 0.152 | 0.000 | 0.53028 | 0.03239 | 0.74664 |
| 327 | 0.017 | 0.083 | 0.000 | 0.53207 | 0.16100 | 0.13344 |
| 328 | 0.000 | 0.000 | 0.000 | 0.53308 | 0.26379 | 0.18377 |
| 329 | 0.016 | 0.056 | 0.000 | 0.53493 | 0.60987 | 0.00831 |
| 330 | 0.010 | 0.063 | 0.000 | 0.53686 | 0.17297 | 0.00018 |
| 331 | 0.018 | 0.075 | 0.000 | 0.53874 | 0.54478 | 0.46033 |
| 332 | 0.030 | 0.091 | 0.000 | 0.53960 | 0.49213 | 0.94697 |
| 333 | 0.018 | 0.063 | 0.019 | 0.54851 | 0.55397 | 0.01550 |
| 334 | 0.010 | 0.038 | 0.000 | 0.54949 | 0.86764 | 0.04664 |
| 335 | 0.031 | 0.053 | 0.000 | 0.55999 | 0.22789 | 0.63380 |
| 336 | 0.023 | 0.059 | 0.000 | 0.56418 | 0.51376 | 0.71754 |
| 337 | 0.022 | 0.063 | 0.000 | 0.56498 | 0.75617 | 0.22788 |
| 338 | 0.033 | 0.073 | 0.000 | 0.56578 | 0.70668 | 0.03867 |
| 339 | 0.008 | 0.056 | 0.000 | 0.56926 | 0.67544 | 0.01359 |
| 340 | 0.000 | 0.075 | 0.000 | 0.56966 | 0.30182 | 0.01894 |
| 341 | 0.038 | 0.016 | 0.000 | 0.57311 | 0.00246 | 0.08463 |
| 342 | 0.005 | 0.075 | 0.000 | 0.57396 | 0.16232 | 0.00549 |
| 343 | 0.028 | 0.097 | 0.000 | 0.57399 | 0.04814 | 0.27043 |
| 344 | 0.016 | 0.117 | 0.000 | 0.57479 | 0.00701 | 0.30927 |
| 345 | 0.010 | 0.038 | 0.000 | 0.57733 | 0.89980 | 0.03303 |
| 346 | 0.018 | 0.119 | 0.000 | 0.57801 | 0.02773 | 0.42832 |
| 347 | 0.013 | 0.031 | 0.000 | 0.57996 | 0.26904 | 0.32350 |
| 348 | 0.060 | 0.006 | 0.000 | 0.58190 | 0.00002 | 0.00216 |
| 349 | 0.006 | 0.047 | 0.000 | 0.59812 | 0.84325 | 0.02299 |
| 350 | 0.013 | 0.063 | 0.000 | 0.60291 | 0.98122 | 0.12855 |
| 351 | 0.016 | 0.091 | 0.000 | 0.60661 | 0.01199 | 0.09457 |
| 352 | 0.008 | 0.042 | 0.000 | 0.61688 | 0.80480 | 0.03120 |
| 353 | 0.025 | 0.045 | 0.000 | 0.61920 | 0.45404 | 0.60865 |
| 354 | 0.033 | 0.021 | 0.000 | 0.62267 | 0.15955 | 0.75106 |
| 355 | 0.013 | 0.063 | 0.000 | 0.62577 | 0.55784 | 0.18377 |
| 356 | 0.032 | 0.091 | 0.000 | 0.62683 | 0.04274 | 0.29098 |
| 357 | 0.082 | 0.107 | 0.029 | 0.63032 | 0.38178 | 0.00266 |
| 358 | 0.003 | 0.046 | 0.000 | 0.63047 | 0.85436 | 0.00010 |
| 359 | 0.030 | 0.131 | 0.017 | 0.64049 | 0.04005 | 0.29687 |
| 360 | 0.025 | 0.038 | 0.000 | 0.64551 | 0.50853 | 0.39977 |
| 361 | 0.018 | 0.091 | 0.000 | 0.64824 | 0.02013 | 0.09628 |
| 362 | 0.035 | 0.072 | 0.013 | 0.65115 | 0.71967 | 0.94722 |
| 363 | 0.007 | 0.063 | 0.000 | 0.65348 | 0.49810 | 0.05644 |
| 364 | 0.018 | 0.035 | 0.004 | 0.65552 | 0.00591 | 0.00002 |
| 365 | 0.015 | 0.038 | 0.000 | 0.65643 | 0.70665 | 0.12531 |
| 366 | 0.058 | 0.104 | 0.058 | 0.66142 | 0.98960 | 0.26299 |
| 367 | 0.052 | 0.034 | 0.000 | 0.66215 | 0.00576 | 0.01137 |
| 368 | 0.030 | 0.163 | 0.000 | 0.66584 | 0.01626 | 0.86538 |
| 369 | 0.019 | 0.063 | 0.000 | 0.66789 | 0.68610 | 0.19690 |
| 370 | 0.016 | 0.108 | 0.012 | 0.67094 | 0.03930 | 0.06299 |
| 371 | 0.005 | 0.125 | 0.000 | 0.67664 | 0.00990 | 0.06041 |
| 372 | 0.022 | 0.067 | 0.000 | 0.67996 | 0.51033 | 0.09373 |
| 373 | 0.009 | 0.031 | 0.000 | 0.68133 | 0.24138 | 0.00003 |
| 374 | 0.042 | 0.097 | 0.000 | 0.68499 | 0.76566 | 0.05591 |
| 375 | 0.017 | 0.021 | 0.000 | 0.68512 | 0.22171 | 0.79848 |
| 376 | 0.033 | 0.042 | 0.014 | 0.68905 | 0.16524 | 0.80319 |
| 377 | 0.029 | 0.080 | 0.000 | 0.69080 | 0.82010 | 0.41665 |
| 378 | 0.025 | 0.063 | 0.000 | 0.70243 | 0.90117 | 0.66520 |
| 379 | 0.020 | 0.138 | 0.000 | 0.70868 | 0.00725 | 0.42851 |
| 380 | 0.017 | 0.021 | 0.000 | 0.71377 | 0.39782 | 0.24178 |
| 381 | 0.044 | 0.063 | 0.000 | 0.71737 | 0.53128 | 0.17192 |
| 382 | 0.013 | 0.125 | 0.000 | 0.72168 | 0.00257 | 0.03397 |
| 383 | 0.017 | 0.036 | 0.007 | 0.73228 | 0.12196 | 0.02080 |
| 384 | 0.024 | 0.044 | 0.000 | 0.73256 | 0.29761 | 0.29755 |
| 385 | 0.025 | 0.097 | 0.000 | 0.73331 | 0.11994 | 0.58902 |
| 386 | 0.018 | 0.044 | 0.000 | 0.73666 | 0.57207 | 0.12653 |
| 387 | 0.158 | 0.153 | 0.048 | 0.73794 | 0.02871 | 0.00093 |
| 388 | 0.031 | 0.016 | 0.000 | 0.73868 | 0.05815 | 0.47968 |
| 389 | 0.025 | 0.031 | 0.000 | 0.74033 | 0.21815 | 0.85767 |
| 390 | 0.020 | 0.042 | 0.000 | 0.74279 | 0.23146 | 0.11749 |
| 391 | 0.023 | 0.105 | 0.008 | 0.74326 | 0.02352 | 0.08875 |
| 392 | 0.029 | 0.107 | 0.000 | 0.75162 | 0.19189 | 0.54007 |
| 393 | 0.017 | 0.063 | 0.000 | 0.75404 | 0.64784 | 0.15262 |
| 394 | 0.032 | 0.048 | 0.008 | 0.76200 | 0.00643 | 0.47223 |
| 395 | 0.017 | 0.063 | 0.014 | 0.76623 | 0.78849 | 0.01259 |
| 396 | 0.050 | 0.250 | 0.033 | 0.77068 | 0.00195 | 0.40243 |
| 397 | 0.000 | 0.088 | 0.000 | 0.77497 | 0.10161 | 0.00830 |
| 398 | 0.025 | 0.094 | 0.000 | 0.77602 | 0.38252 | 0.80404 |
| 399 | 0.035 | 0.075 | 0.000 | 0.77946 | 0.93861 | 0.49207 |
| 400 | 0.010 | 0.000 | 0.000 | 0.77955 | 0.06988 | 0.04606 |
| 401 | 0.010 | 0.025 | 0.000 | 0.77955 | 0.46246 | 0.04606 |
| 402 | 0.020 | 0.013 | 0.000 | 0.78052 | 0.07461 | 0.50252 |
| 403 | 0.013 | 0.051 | 0.003 | 0.78556 | 0.88935 | 0.00559 |

TABLE 4-continued

| | | | | | | |
|---|---|---|---|---|---|---|
| 404 | 0.031 | 0.082 | 0.000 | 0.78831 | 0.61891 | 0.47180 |
| 405 | 0.016 | 0.042 | 0.000 | 0.78900 | 0.09626 | 0.00465 |
| 406 | 0.031 | 0.016 | 0.000 | 0.78980 | 0.05059 | 0.43332 |
| 407 | 0.010 | 0.088 | 0.000 | 0.79643 | 0.39142 | 0.12531 |
| 408 | 0.058 | 0.125 | 0.000 | 0.79654 | 0.28677 | 0.06295 |
| 409 | 0.016 | 0.039 | 0.000 | 0.80101 | 0.48691 | 0.27328 |
| 410 | 0.018 | 0.102 | 0.000 | 0.80151 | 0.03618 | 0.25568 |
| 411 | 0.028 | 0.132 | 0.024 | 0.81269 | 0.00673 | 0.00968 |
| 412 | 0.021 | 0.099 | 0.000 | 0.81294 | 0.04875 | 0.36772 |
| 413 | 0.019 | 0.047 | 0.000 | 0.81562 | 0.75051 | 0.38140 |
| 414 | 0.035 | 0.113 | 0.000 | 0.82537 | 0.08167 | 0.99310 |
| 415 | 0.026 | 0.073 | 0.000 | 0.82863 | 0.60871 | 0.95353 |
| 416 | 0.050 | 0.042 | 0.000 | 0.84212 | 0.02446 | 0.00290 |
| 417 | 0.019 | 0.051 | 0.000 | 0.84499 | 0.73711 | 0.13168 |
| 418 | 0.008 | 0.081 | 0.000 | 0.84648 | 0.06666 | 0.00452 |
| 419 | 0.029 | 0.054 | 0.000 | 0.84779 | 0.54879 | 0.79096 |
| 420 | 0.025 | 0.038 | 0.000 | 0.85460 | 0.20627 | 0.52500 |
| 421 | 0.025 | 0.080 | 0.000 | 0.85627 | 0.50475 | 0.70735 |
| 422 | 0.000 | 0.156 | 0.000 | 0.85664 | 0.04034 | 0.09510 |
| 423 | 0.023 | 0.065 | 0.000 | 0.86083 | 0.99103 | 0.15072 |
| 424 | 0.013 | 0.094 | 0.000 | 0.86126 | 0.14473 | 0.05072 |
| 425 | 0.018 | 0.094 | 0.000 | 0.86312 | 0.22629 | 0.28027 |
| 426 | 0.013 | 0.000 | 0.000 | 0.86864 | 0.00995 | 0.09168 |
| 427 | 0.021 | 0.089 | 0.000 | 0.87219 | 0.14799 | 0.45199 |
| 428 | 0.005 | 0.000 | 0.000 | 0.87795 | 0.09496 | 0.02531 |
| 429 | 0.013 | 0.081 | 0.000 | 0.88059 | 0.07959 | 0.02755 |
| 430 | 0.025 | 0.000 | 0.000 | 0.88119 | 0.02331 | 0.96205 |
| 431 | 0.036 | 0.148 | 0.050 | 0.88608 | 0.00002 | 0.00006 |
| 432 | 0.005 | 0.025 | 0.000 | 0.88638 | 0.51822 | 0.02712 |
| 433 | 0.000 | 0.083 | 0.000 | 0.89151 | 0.14993 | 0.02634 |
| 434 | 0.025 | 0.100 | 0.000 | 0.89564 | 0.18901 | 0.76737 |
| 435 | 0.011 | 0.086 | 0.002 | 0.90183 | 0.00080 | 0.00000 |
| 436 | 0.023 | 0.078 | 0.000 | 0.90333 | 0.28646 | 0.77891 |
| 437 | 0.021 | 0.063 | 0.000 | 0.90702 | 0.86839 | 0.77523 |
| 438 | 0.021 | 0.036 | 0.000 | 0.90976 | 0.14194 | 0.64487 |
| 439 | 0.011 | 0.082 | 0.000 | 0.91143 | 0.05741 | 0.00268 |
| 440 | 0.015 | 0.063 | 0.000 | 0.91521 | 0.67996 | 0.28737 |
| 441 | 0.025 | 0.025 | 0.000 | 0.91767 | 0.14135 | 0.76209 |
| 442 | 0.019 | 0.069 | 0.000 | 0.92005 | 0.73186 | 0.57669 |
| 443 | 0.023 | 0.113 | 0.000 | 0.92076 | 0.04033 | 0.89701 |
| 444 | 0.046 | 0.045 | 0.000 | 0.92192 | 0.02154 | 0.01164 |
| 445 | 0.033 | 0.058 | 0.000 | 0.92504 | 0.14949 | 0.21095 |
| 446 | 0.108 | 0.215 | 0.158 | 0.92648 | 0.00059 | 0.00000 |
| 447 | 0.018 | 0.034 | 0.000 | 0.92796 | 0.19315 | 0.23193 |
| 448 | 0.020 | 0.039 | 0.000 | 0.92888 | 0.04082 | 0.03393 |
| 449 | 0.004 | 0.031 | 0.000 | 0.92990 | 0.73921 | 0.01161 |
| 450 | 0.025 | 0.038 | 0.000 | 0.93035 | 0.30875 | 0.99310 |
| 451 | 0.038 | 0.208 | 0.007 | 0.93481 | 0.00069 | 0.95055 |
| 452 | 0.033 | 0.031 | 0.000 | 0.94099 | 0.11813 | 0.72422 |
| 453 | 0.013 | 0.047 | 0.022 | 0.94155 | 0.86146 | 0.00511 |
| 454 | 0.033 | 0.063 | 0.000 | 0.94574 | 0.74604 | 0.48180 |
| 455 | 0.050 | 0.063 | 0.043 | 0.94598 | 0.41907 | 0.10857 |
| 456 | 0.022 | 0.028 | 0.000 | 0.95616 | 0.07091 | 0.75304 |
| 457 | 0.022 | 0.045 | 0.000 | 0.95622 | 0.26281 | 0.40030 |
| 458 | 0.022 | 0.085 | 0.003 | 0.95630 | 0.05799 | 0.16891 |
| 459 | 0.000 | 0.141 | 0.000 | 0.95914 | 0.00935 | 0.01524 |
| 460 | 0.025 | 0.094 | 0.000 | 0.96078 | 0.74050 | 0.94029 |
| 461 | 0.028 | 0.088 | 0.000 | 0.96080 | 0.24029 | 0.71768 |
| 462 | 0.025 | 0.074 | 0.000 | 0.96521 | 0.83987 | 0.74482 |
| 463 | 0.029 | 0.115 | 0.000 | 0.96529 | 0.05667 | 0.84317 |
| 464 | 0.010 | 0.075 | 0.009 | 0.97792 | 0.39415 | 0.02207 |
| 465 | 0.019 | 0.063 | 0.000 | 0.98245 | 0.74836 | 0.14794 |
| 466 | 0.025 | 0.163 | 0.000 | 0.98690 | 0.17514 | 0.96394 |
| 467 | 0.050 | 0.063 | 0.000 | 0.98750 | 0.34568 | 0.07429 |
| 468 | 0.010 | 0.075 | 0.000 | 0.99542 | 0.34309 | 0.09635 |

TABLE 5

| Reference Coordinates | Nearest Gene | Percent Non-Reference | Total Non-Reference Bases | Plus Strand Oligonucleotide | SEQ ID NOS: |
|---|---|---|---|---|---|
| chr8:128,750,550-128,750,699 | MYC | 0 | 0 | CGACTACGACTCGGTGCAGCCGTATTTCTACTGCGACGAGGAGGAGAACTT CTACCAGCAGCAGCAGCGAGCTGCAGCCCGGCGCCCAGCGAGG ATATCTGGAAGAAATTCGAGCTGCTGCCCACCCCGCCCTGTCCCTAG | 1331 |
| chr8:128,750,550-128,750,699 | MYC | 2.5 | 4 | CGACTACGACTCGGTGCAGCCGTAGTTCTACTGCGACGAGGAGGAAAACT TCTACCAGCAGCAGCGAGCAGCGAGCTGCAGCCCTGCAGCCCCTGCAGCGAGG GATATCTGGAAGAACTTCGAGCTGCTGCCCACCCCGCCCTGTCCCTAG | 1332 |
| chr8:128,750,550-128,750,699 | MYC | 5 | 8 | CGACTACGACTCGGTGCAGCCGTAGTTCTACTGCGACGAGGAGAATACTT CTACCAGCAGCAGCCGCAGAGCGAGCTGCAGCCCTGGCGCCCAGCGAGG GTATCTGGAAGAACTACTGCCCACCCCCGCCCTGTCCCTAG | 1333 |
| chr8:128,750,550-128,750,699 | MYC | 7.5 | 11 | CGACTACGACTCGTTGCAGCCGTAGTTCTACTGCGACGAGGAGGAATACTT CTACCAGCAGCCGCAGAGCGAGCTGCAGCGCCTGGCGCCCAGCGAGG GTATCTGGAAGAACTTCGAGCTGCCACCCCGCCCTGTCCCTAG | 1334 |
| chr8:128,750,550-128,750,699 | MYC | 10 | 15 | CGACTACGACTCGTTGCAGCCGTAGATTCTACTGCGACGAGGAGGAATACTT CTACCTGCGACCAGCCCAGAGCGAGCTGCAGCGCCTGGCGCCGAGC GTATCTGGAAGAACTTCGAGCTGCTACAGCCCACCCCGCCCTTGTCCCTAG | 1335 |
| chr8:128,750,550-128,750,699 | MYC | 12.5 | 19 | CGACAACGACTCGTTGCACCCGTAGATCTACTGCGACGAGGAGGAATACTT CTACCTGCAGCAGCCCAGCGAGCGAGCTGCAGCCGCCTGGCGCCGAGC GTATCTGAAAGAACTTCGAGCTACAGCCCACCGCCCGCCCTTGTCCCTAG | 1336 |
| chr8:128,750,550-128,750,699 | MYC | 15 | 23 | CGACAACGACTCGTTGCACCCGTAGATCTACTGCGACGAGGAGGAATACTT CTACCTGCAGCAGCCCAGCGAGCGAGCTGCAGCCGCCTGGCGCCGAGC GTATCTGAAAGAACTTCGAGCTACAGCCCACCGCCCGCCCTTGTCCCTAG | 1337 |
| chr3:187,443,281-187,443,430 | BCL6 | 0 | 0 | GCTCACCTGTACAAATCTGGCTCCGCAGTTTCGCATTTGTAGGGCTTCTCT CCAGAGTGAATTCGAGTGTGGTTTTCAGTTGGCTGGCCGGTTGAACTGG GCCCCACAGATGTTGCAACGATAGGGTTTCTCACCTATTACCAAGAA | 1338 |
| chr3:187,443,281-187,443,430 | BCL6 | 2.5 | 4 | GCTCACCTGTACAAATCTGCCTCCGCAGTTTCGCATTTGTAGGGCTCTCT CCAGAGTGAATTCGAGTGTGGGTTTCAGTTGGCTGGCCGGTTGAACTGG GCCCCACAGATGTTGCAACGCTAGGGTTTCTCACCTATTACCAGAA | 1339 |
| chr3:187,443,281-187,443,430 | BCL6 | 5 | 8 | GCTCACCTGTACAAATCTGCCTCCGCAGTTTCGCCTTTGTAGGCTCCTCT CCAGAGTGAATTCGAGTGTAGGTTTTCAAGTTGGCTGGGCGGTTGAACTGG GCCCCACAGATGTTGCAACGCTAGGGTTTCTCACCTATTACCAAGAA | 1340 |
| chr3:187,443,281-187,443,430 | BCL6 | 7.5 | 11 | GCTCACCTGTACAAATCTGCCTCCGCCGTTTCGCCTTTTAGGGCTCCTCT CCAGAGTGAATTCGAGTGTAGGTTTCAAGTTGGCTGGGCGGTTGAACTGG CGCCCACCGATGTTGCAACGCTAGGGTTTCTCACCTATTTCCAAGAA | 1341 |
| chr3:187,443,281-187,443,430 | BCL6 | 10 | 15 | GCTCACCTGTACAAGTCTGCCTCCGCCGTTACGCCTTTTAGGGCTCCTCT CCAGATGAATTCGAGTGTAGGTTTCAAGTTGGCTGGGCGGTTGAACTGG GCTCCACCGACGTTGCAACGCTAGGGATTCTCACCTATTTCCAAGAA | 1342 |

TABLE 5-continued

| Reference Coordinates | Nearest Gene | Percent Non-Reference | Total Non-Reference Bases | Plus Strand Oligonucleotide | SEQ ID NOS: |
|---|---|---|---|---|---|
| chr3:187,443,281-187,443,430 | BCL6 | 12.5 | 19 | GCTCACCTGGACAAGTCTGCCTCCGCCGGTTACGACTTTTAGGGCTCCTCT CCAGAGTGAATTCGAGTGTAGGCTTTCAAGTTGGCTGGCGGTTGAACTGG GCTCCACGGCTGTTGCAACGCTAGGGATTCTCACCTATTTCCAAGAA | 1343 |
| chr3:187,443,281-187,443,430 | BCL6 | 15 | 23 | GCTCACCTGGACAAGTCTGCCTCCGCCGGTTACGACTTTTAGGGCACCTCT CCAGAGTGAATTCGAGTGTAGGCTTTCAAGTTGGCTGGGAGCTTGAACTGG GCTGCACGGCTGTTGCAACGCTAGGGATTCTCACCTATTTCCAAGAA | 1344 |
| — | — | — | — | Minus Strand Oligonucleotide | — |
| chr8:128,750,550-128,750,699 | MYC | 0 | 0 | CTAGGGACAGGGGCGGGTGGGCAGCAGCTCGAATTCTTCCAGATATC CTCGCTGGGCGCCCGGGGCTGCAGCTCGCTCTGCTGCTGCTGGTAGAA GTTCCTCCTCGTCGCAGTAGAAATACGCTCGCACCGAGTCGTAGTCG | 1345 |
| chr8:128,750,550-128,750,699 | MYC | 2.5 | 4 | CTAGGGACAGGGGCGGGTGGGCAGCAGCTCGAAGTTCTTCCAGATATC CTCGCTGGGCGCCAGGGCTGCAGCTCGCTCTGCTGCTGCTGGTAGAA GTTTTCCTCCTCGTCGCAGTAGAACTACGCTGCACCGAGTCGTAGTCG | 1346 |
| chr8:128,750,550-128,750,699 | MYC | 5 | 8 | CTAGGGACAGGGGCGGGTGGGCAGTAGCTCGAAGTTCTTCCAGATACC CTCGCTGGGCGCCAGGGCGCTGCAGCTCGCTCTGCCGCTGCTGGTAGAA GTATTCCTCCTCGTCGCAGTAGAACTACGGCTGCACCGAGTCGTAGTCG | 1347 |
| chr8:128,750,550-128,750,699 | MYC | 7.5 | 11 | CTAGGGACAGGGGCGGGTGGGCTGTAGCTCGAAGTTCTTCCAGATACC CTCGCTGGGCGCCAGGGCCTGCAGCTCGCTCCTGCCGCTGCTGGTAGAA GTATTCCTCCTCGTCGCAGTAGAACTACGGCTGCAACGAGTCGTAGTCG | 1348 |
| chr8:128,750,550-128,750,699 | MYC | 10 | 15 | CTAGGGACAAGGGCGGCGGGCTGGGCTGTAGCTCGAAGTTCTTCCAGATACG CTCGCTGGGCGCCAGGGCCTGCAGCTCGCTCCTGCCGCTGCAGGTAGAA GTATTCCTCCTCGTCGCAGTAGATCTACGGCTGCAACGAGTCGTAGTCG | 1349 |
| chr8:128,750,550-128,750,699 | MYC | 12.5 | 19 | CTAGGGACAAGGGCGGCGTGGGCTGTAGCTCGAAGTTCTTTCAGATACG CTCGCTGGGCGCCAGGGCCTGCAGCTCGCTCCTGCCGCTGCAGGTAGAA GTATTCCTCCTGCCGCAGTAGATCTACGGGCTGCAACGAGTCGTTGTCG | 1350 |
| chr8:128,750,550-128,750,699 | MYC | 15 | 23 | CTAGGCGACAAGGGCGGCGTGGGCTGTAGCTCGAAGTTCTTTCAGATACGC TCGGTGGGCGCCCAGGCGCTCCAGACGCTCGCCGCTGCAGTAGAA GTATTCCTCCTCGTCGCAGTAGATCTACGGGTGCAACGAGTCGCTGTCG | 1351 |
| chr3:187,443,281-187,443,430 | BCL6 | 0 | 0 | TTCTTGGTAATAGTGAGAACCTATCGTTGCAACATCGTGTGGGCCCAG TTCAACCGGCCAGCCAACCTGAAAACCCACACTCGAATTCACTCTGGAGAG AAGCCCTACAAATGCGAAACCTGCGGAGCCAGATTTGTACAGGTGAGC | 1352 |
| chr3:187,443,281-187,443,430 | BCL6 | 2.5 | 4 | TTCTTGGTAATAGTGAGAACCTGCAACATCTGTTCAACATCTGGGGCCCAG TTCAACCGCCCAGCCAACCTGAAAACCCAAATCGAATTCACTCTGGAGAG GAGCCCTACAAATGCGAAACCTGCGGAGGCCAGATTTGTACAGGTGAGC | 1353 |

TABLE 5-continued

| Reference Coordinates | Nearest Gene | Percent Non-Reference | Total Non-Reference Bases | Plus Strand Oligonucleotide | SEQ ID NOS: |
|---|---|---|---|---|---|
| chr3:187,443,281-187,443,430 | BCL6 | 5 | 8 | TTCTTGGTAATAGGTGAGAAACCCTAGCGTTGCAACATCCGTGGGGCCCAG<br>TTCAACCGCCCAGCCAACTTGAAAACCTACACTCGAATTCACTCTGGAGAG<br>GAGCCCTACAAAGGCGAAACCTGCGGAGGCAGATTTGTACAGGTGAGC | 1354 |
| chr3:187,443,281-187,443,430 | BCL6 | 7.5 | 11 | TTCTTGGAAATAGGTGAGAAACCCTAGCGTTGCAACATCCGTGGGGCCCAG<br>TTCAACCGCCCAGCCAACTCGAAAACCTACACTCGAATTCACTCTGGAGAG<br>GAGCCCTAAAAAGGCGAAACCGGCGGAGGCAGATTTGTACAGGTGAGC | 1355 |
| chr3:187,443,281-187,443,430 | BCL6 | 10 | 15 | TTCTTGGAAATAGGTGAGAATCCCTAGCGTTGCAACATCCGTGGAGCCCAG<br>TTCAACCGCCCAGCCAACTTGAAAACCTACACTCGAATTCACTCTGGAGAG<br>GAGCCCTAAAAAGGCGTAACCGGCGGAGGCAGACTTGTACAGGTGAGC | 1356 |
| chr3:187,443,281-187,443,430 | BCL6 | 12.5 | 19 | TTCTTGGAAATAGGTGAGAATCCCTAGCGTTGCAACAGCCGTGGAGCCCAG<br>TTCAACCGCCCAGCCAACTGAAAGCCTACACTCGAATTCACTCTGAGAG<br>GAGCCCTAAAAAGTCGTAACCGGCGGAGGCAGACTTGTCCAGGTGAGC | 1357 |
| chr3:187,443,281-187,443,430 | BCL6 | 15 | 23 | TTCTTGGAAATAGGTGAGAATCCCTAGCGTTGCAACAGCCGTGCAGCCCAG<br>TTCAAGTCCCAGCCAACTTGAAAGCCTACACTCGAATTCACTCTGAGAG<br>GTGCCCTAAAAAGTCGTAACCGGCGGAGGCAGACTTGTCCAGGTGAGC | 1358 |

TABLE 6

| Name | Sequence | SEQ ID NOs. |
|---|---|---|
| TNFRSF14_chr1:2488006-2488106 | TCTCTTCTGGCCCACAGCCGCAGCAATGGCGCTGAGTTCCTCTGCTGAGTTCATCCTGCTAGCTGGGTTC CCCAGCTGCCGGTCTGAGCCTGAGGCATG | 1 |
| TNFRSF14_chr1:2488106-2488206 | GAGCCTCCTGGAGACTGGGGGCCTCCTCGTCTCCGTCTGCTCGCA GCCCCGAGCCTCCTCTCCGTCTGCTCGCA | 2 |
| TNFRSF14_chr1:2488206-2488306 | GATCCCAGTTCTGACCCCAGGGCCTCCCACAGATCTCTTCCCCATGCCCCATGCCTGCCGTGTCTGCTC CGGCGTCCAGCCCGTCCCCTGCCTGCCTGG | 3 |
| CSMD2_chr1:34404022-34404122 | CCATGTTGCTGGCTTACTTGGCATTTCCCATGATCTCACACTGCTGCTCGGCTTATTTGGCATTTCCCATGATCCC CTGCTGCTGGTTTACTTGGCATTCCCTA | 4 |
| CSMD2_chr1:34404122-34404222 | TGATCCCATGTTGCTGGTTTACTTAGCATTTCCCATGATCATCCCATGTTGCTGGCTTACTTGGCATTTCCCATG ATACCATGTTGCTGGCTTACTTGGCATT | 5 |
| NEGR1_chr1:72334891-72334991 | ATAGATTAGAGGAAGAATTCTAGATGAAATTAAGTAAATGAGTTATTTAAGTCAACTAATACAAGTCCT CAAAACTTTGATTATAGAGAGCTAAACT | 6 |
| NEGR1_chr1:72334991-72335091 | GATAAATATAGACAAATATGAGCTATAAATAACTAGAGCTATACTATGATGAAAATAAATAATGAATAAT TGTGAAATAGCCAAAAATACTAAAATACAG | 7 |
| NEGR1_chr1:72335051-72335151 | AATGAATAATTGTGAAATAGCCAAAAATACTAGAGCTATAAGTTAAAAATAAATCTGAATAAAA AATGTAGGAGGGAAAAGTGATTACCTTACC | 8 |
| BCL10_chr1:85733207-85733307 | GACATGCATCAAATGTAAACAAAATGATTACAGCCATTTTATAAAAAGTCATATTCTTTAAAACATTTTTG TCATCATTAAAAAATTAAAGGCAATAAAG | 9 |
| BCL10_chr1:85733307-85733407 | TGTCATTGTCGTGAAACAGTACGTGATCTTAAGGAAGAAAACATCTCACTAGAGTTTGCACAAGTTCCTT CTTCTTCTAACTGTAGATCTGGTGGCAAAG | 10 |
| BCL10_chr1:85733407-85733507 | GAGGAGCCCCCTGGGTCCGTCTCCCAGTTCTGCTCGGAAGTGTAGTTGAAGAGAAGATGGTATTTCAGTTCTGCCTAC TTCTAGAACAGGCAAATTCAGAGAAGATT | 11 |
| BCL10_chr1:85733507-85733607 | AGTAGAAAAAAAAGGGCTCGTCTGCTGATTCTCCTTCTGGATGGTACATGACAGTGGATGCCCTCAGTTTT TCAGAGAAATTACTTCTCATCTGAATTTGAT | 12 |
| BCL10_chr1:85733607-85733707 | CTGGAGAGGTGTTCGTGGCTCCATCTGAAAAGGTTCACAACTGCTACATTTTAGTCCTACAATAAAATT ATTCAGATGTAAATGAAAAGTAACTAAA | 13 |
| BTG2_chr1:203274697-203274797 | ACCCGAGACCTTCACTGAGCCCGCGCCGCCGACATGAGCCACGGGAAGGGAACCGACATGCTCCC GGAGATCGCCGCCGTGCCGTGGGCTTCCTCTCC | 14 |
| BTG2_chr1:203274797-203274897 | AGCCTCCTTGAGGACCCGGGCTGCGTGAGCGAGCAGAGGCTTAAGGTCTTCAGCGGGGCGCTTCCAGGAG GCACTCACCAGGTGAGCGGCATGCCGAGGGCC | 15 |
| BTG2_chr1:203274897-203274997 | TGGCGCCACCGGGGTCGGCCCCATCCCTGCCAGGGCCGTCTTTCTTCTACTCCTGCGGCAGGGTGACCC ACGGGAGCAGCTTTGGGACTCGGTGGCCCT | 16 |

TABLE 6-continued

| Name | Sequence | SEQ ID NOs. |
|---|---|---|
| BTG2_chr1:203274997-203275097 | CCTCCGACCCCCGGGGCGGCCGCCCGAGTCCCCAGTTTCCTGGTCCTCCTCCCCAGCCTGTGCTCGGGTCTCGGCCGTGGCGGTTCTGATGGGGCGCGCC | 17 |
| BTG2_chr1:203275097-203275197 | CCTCTACGCTCTCGGAGGCGCAGACCCTGGTCCAGCCCAGTCCCCAGTCTTATGCCCCTGTCTCATTACGGGCTCGTCTCCCTGCTGAC | 18 |
| BTG2_chr1:203275197-203275297 | CCTCGAGATCTTAAGACCCTCGATGATGTTGTTGCGGGCCGCCCGTCCGAGGGTCCCGATGAGGGAAGAAGGTCAGTCGAGCCTTTTCAACAA | 19 |
| BTG2_chr1:203275297-203275397 | TTTGGAGTCCCAGTGCGGTTCTTCCTGCCGGTCGGGGTGCGTGTGCCTGGGTAGTCCACTGGTTGCTGACTGGCTTCAAGTTGGAATTTGGGCCCCCT | 20 |
| BTG2_chr1:203275397-203275497 | TTGTGTTATCTTTGGTTCCCCTTAGCCATCTGCCACCTATTGTGGTAGGGAGGAGAGCCTCGTAGCTCGTGACCCTGCCGTGCGGCCTTCAAGTTGGGA | 21 |
| BTG2_chr1:203275497-203275597 | GGTGAAGAGATAAGCAGCCCGCTCGCTGGCTGGGGAGAGACCTCTCCCAGCTGTTTCTAGCTGGTTACTGTCAGTTTTGGGAAGCGATAGCCATCTCG | 22 |
| BTG2_chr1:203275597-203275697 | GAACGACACCCACAGACCCTGCCTTTCTGAGGAAAAACAGATGTTTCATCAAAACAACCCAGTTTTCACTCCCTTAGGCACTGCTAAGGAAGGTTCTGA | 23 |
| BTG2_chr1:203275697-203275797 | CTCTTCTGAAGGAAGCAGAGGAACACAGGGTGGGAGGTCCAGTGACTTGCTGTGGACCCAACAATGTTGGCAGCCTTCCTGGCCCTGAAACTTCAGCTC | 24 |
| BTG2_chr1:203275797-203275897 | ACAGGTCTCCAGAGGCCCTGCCTGGACATGCCAGTCCAGTCACACCCTTGCTTGGGGTGTGCCAAAAGCAATAACTGGCCACTAGAGAGTA | 25 |
| BTG2_chr1:203275897-203275997 | CCCTAGAGCTCTAGAATCCCCTCCCAACAGCGCACACACACACACACACACTCTCTCTCCACACACACACTCAGTCACACACACACACAC | 26 |
| ITPKB_chr1:226923691-226923791 | CTTTCAGATCTTTCGCAGCGTCCCAACAGGGCAAAGGCTCCAGCATTCTGCCAGAAGGAATTCCCGCTCCACATTCCCGGTCCCCGGCTGTGCTGAGGG | 27 |
| ITPKB_chr1:226923791-226923891 | GCTGCCCCAAGCAAGCCCAGCGTTGGGAGACCCTCCCCTGCCCACTCTGTCGGAGAGCTGCCAACGCCCCCGCCCACGGGGGCCCACTTCGGGCCTCCTCA | 28 |
| ITPKB_chr1:226923891-226923991 | GGGCCTACGGAGGCCAGGCCCTGGGCAGCCTCGGACCAGCTCAGGGAATCAGAGGACTCTGCGCTTTGCACGCTCACAGTCGTCTCCTCTGGCCTTTTGC | 29 |
| ITPKB_chr1:226923991-226924091 | CCACTTCAGGCTCTCCCAGACCCGGCATGCCAGGCCACAGGGCCAGATATCCTTTCCCCATCTTCCCAGGGGGTTCTCCATGCGGGCCCGCCCTTTCTGGGGC | 30 |
| ITPKB_chr1:226924091-226924191 | TGGGCTTGTCTCACTGCCCAGAAACTGCCCCTGCCTCTCCACCAGGGCCTCTGGGGGCTGCAGGTCCTCAAGCTCACGGGCTCTTCCCAGACGGCTCAGTG | 31 |
| ITPKB_chr1:226924191-226924291 | AGGGCAAGATCCTGTGGACGGTGTGGCCCAGTGATGTAACTCTCGCTGCCACTTCCGTGGCCATCGTTAAGCTAGCTCCGAACAGCCCAATGAGGGAG | 32 |
| ITPKB_chr1:226924291-226924391 | CTAGGCAGCTCCCAGTTCCCGGGTAGGAGAGCCCCTTTGTCAATTCCATAGCTGGGGTGAGCCACAGCGGGGACTGGCAGGGATACCCTTCTCCAT | 33 |

TABLE 6-continued

| Name | Sequence | SEQ ID NOs. |
|---|---|---|
| ITPKB_chr1:226924391-226924491 | CCTTACAAAGCGGATGACCCTGAGCCTCTGATCCTGTAGGGCAGCCCGGCCGGGAAGAGAGTGGCATTCCTTTCTTCACCTGCGAGGAGCATAGGCTG | 34 |
| ITPKB_chr1:226924491-226924591 | GGCCCTCCTTTCCTCCCGGAGTCGGTTCCTGAAGTCTCTGGACATTGCTCCCCCAGGACTTTGTCTCCGTTCCTGCTCCGGGCGCCCTGAACCAGGA | 35 |
| ITPKB_chr1:226924591-226924691 | CCCTTCCAGGGGCTGACTGCTGCTGCGAAGGGCACGGGAGGGCGAGCGAGCCCTGCCCAAACGCGGGCTGCCGGGGCGCTTGAATGGCCGAGCTCTG | 36 |
| ITPKB_chr1:226924691-226924791 | TGCCTGGATGTGCGCCTCAAACATGCCCACTTTCTGGTTCACCTGCACTTCTGCAACTCGCGCTGCAAGATCCGCAGCTTCTCCTTGGCCTCCTCCGGC | 37 |
| ITPKB_chr1:226924791-226924891 | CCTGGCGGGGAGAGGGTACCGGCTGCCACCACCTGCTGCCGGTCCCCCTGCAGGGCGACCAGCCCAACTTGGGCTGCTCACGCTACTGCCGCTGCCGCC | 38 |
| ITPKB_chr1:226924891-226924991 | TGCCACTGCCGCTGCTACTATTCAGCCTGCGCCGGCCCTCCCCCAGCCCCCCGGGGCTCCGGGGCTCCTCGGGGACAGCGACTCGGCTGGGGGAAGAG | 39 |
| ITPKB_chr1:226924991-226925091 | GAAAGAGGCGCTCTCCCACTGGCCCTGAAAACGTGCCGGGCTCAGCACTGCCCTGCCTCTCCTCGGGGGCGGGGGCGTCTCGCTGCCACTGGGGCTCCCCCCGCGG | 40 |
| ITPKB_chr1:226925091-226925191 | CCGCTCTTCATCTCGTTGGCGTCGTCCGGCCGCCTCCCGGCTCTATTGAGCGCATAGCAGTACACAGCCATAGTACTGGGTCCCGCTGCCCGCGCCCG | 41 |
| ITPKB_chr1:226925191-226925291 | CTCCCGCTTCCTGCTCCCGCCGCCGCTCCTCCCGGCTCCCAGCCCCCGGAGGCCCGGCAGCCGCGGTTCCGCGCGATGGGGCGGCA | 42 |
| SLC1A4_chr2:65258145-65258245 | AAGTGCGAAGGAAGTGTCAGGCTGGATGTCAAAATGAACACCTTGGAGAACTGGATGATGAACAGACGGTAAAAATCAGCTAAACATCAGAGAAAATGG | 43 |
| SLC1A4_chr2:65258245-65258345 | AGGAAGAGAGGTCAAAACTGAACAGGAACTAGAAGAAGAGTGTAGCAGAAAAAGACTTGTCACAAACTTCGAGAGATTTGGAGAAAATGATGTCAAAACAC | 44 |
| SLC1A4_chr2:65258345-65258445 | ATCTTCCTCAAGCCCATGCTGAGTATCTCTGATTTGGTTAATTTCTTGGTAAGTGTTCCAAGTACAGACAACAAAGCAGAAAAGCACTGATTACAGGGAA | 45 |
| SPRED2_chr2:65593035-65593135 | TATGCAGAATGATCTTCAGATCATGTGAACGCTATAATTAAATGTTGCTACCAAATCCCCACTACCCTTTCTCCACCTAGAAAAGTTAATGCATGAA | 46 |
| SPRED2_chr2:65593135-65593235 | TTCAGTATGAGCAAATTGTGATTTATAAAACAAACAAACAAACAAAACCACCCTATTCACTCCGTAGGGGAATAAAGCTTTCTTGCATTA | 47 |
| SPRED2_chr2:65593180-65593280 | AACAAACAAAACCCCACCCTATTCACTCCGTAGGGGAATAAAGCTTTCTTGCATTAAGTCACGCATCATGGGGGTAGGAAAAAGCACAGTACTGAAAGAA | 48 |
| EIF2AK3_chr2:88906681-88906781 | GTGAAGTGATCCAAATGTAGCCCAGAGATCCTAAAGAAAAAACGATGCTCATGTGTTACAAAACAAAATTTTAAGGCAATCAGTGAGGAATCACAGACAA | 49 |

TABLE 6-continued

| Name | Sequence | SEQ ID NOs. |
|---|---|---|
| EIF2AK3_chr2:88906781-88906881 | ATTTCCTTAGTGTCTTTATCAAGGTTGAATCTGAATATAAATTACTAGAGGAAAGCAAATCAGATTTCACATCTGAAATTAAAACAAAATTCTTAGCT | 50 |
| IGKC_chr2:89127261-89127361 | AGGCAACAAAATGAGATCCTGTCCCTAGAAAAACATTTCAAAAAATTAACAGCATGGTGACGCACACTTGTAGCCCTAGCTACTTGGGAGGCTGAGTGGGA | 51 |
| IGKC_chr2:89127461-89127561 | AAGAACTTAAGCAGACTAGGATATAAAGTATAGGAGCGTATTGTGTACAGGAGGGAAATACTGTTTCCTGGATCTTTTGTTTCACTTACGCACACACC | 52 |
| IGKC_chr2:89127561-89127661 | CACACCCCGCCAGTAGTGTACCAGGTTGGCGATGGAAATCTCTCTTTCTGTGGATGAGTTTGTGGAAGCCCTTGCTCCAGCATGCCCCTTCCTTCTGCCCA | 53 |
| IGKC_chr2:89127661-89127761 | CCCCTGACCATTCCTTCCCTTCACAGACTGTCCCCATGGGTAGGCCACAGCCCAGCAGGCCCCAGCCTGGCGGCTGCAGCAGGAGCCCCATCCCAGG | 54 |
| IGKC_chr2:89127761-89127861 | GCCTGAGGGGCCATGCGGGGTCTGGGTGGGAGTGGGAACCGCTGAGGAAGGTGAAGGGAAATATGGTGAGATGACAGGCCCGTGTCAGGGAGAGTGGG | 55 |
| IGKC_chr2:89127861-89127961 | AGAGCCCCTGGAGTGCCCTACCTCTGTGGGCGTGGAACTTGTCGGGAACTTCCATCCAGCACTGGCCGACACTCCCGTCGCAGCTGATGCTACTACCCCAAGTGCCACAGTCCCAGCTGGAG | 56 |
| IGKC_chr2:89128431-89128531 | TCATCTCCACTGGATAACAGTGTTGTCGGAACTTGTCGGGACACTGGCCGACACTCCCGTCGCAGCTGCTCCTGACTGAGCAAGTCATTTAAGGGGG | 57 |
| IGKC_chr2:89128531-89128631 | TCCTTGGCACTCATAAGCACTCACAGAATGGGCTGGCAGTGCGCCCGGCCTCCCTGGGATGGGTCCAGAATGGAAGCCAGTCCGGGAGGGACCC | 58 |
| IGKC_chr2:89131726-89131826 | ACTGCTTAGAGCTCTCAGCCTAGATGGCGTATCACAGTTAATGCTCTATAAAACCATCATGGCTTTTCCCTAGTAAGCCTCAAATCGCTGCAAGCAAG | 59 |
| IGKC_chr2:89131826-89131926 | GCTTCATATATGAGAGTTTCTGCTGTCTCCTGGAGCCATCTCACCCAAAGCCACTGACTCTGGGAGACCAGCCCAGCCCACAAACCAGCAGAAGCACCAGT | 60 |
| IGKC_chr2:89131926-89132026 | TATAGTTAGAGCTGCATTATAAAGTGCCAGAGGACATTTCTTTGCAGTGAGATGTGTATCGTGAACGTTTGGGGCCTGTGCTCGCCTAGTCCTCATCTT | 61 |
| IGKC_chr2:89132026-89132126 | TGCTTTTCTAGTGACACAAAGCCATCCATGGCTGCAAATGTTAGCTGGGCTGGCTCCCTACTTGCCTCAAGCCCCTTCATAGACCCTTCAGGCACATG | 62 |
| IGKC_chr2:89132126-89132226 | CTTTTCTCTGGACGTTACAGACAGGTCCTCAGAGGTCAGAGACAGGTTGTCTCAGGGAGCAGGGAGGCTTCCTAGGGAGGTCAGACTCCAAATAGTGGAT | 63 |
| IGKC_chr2:89132226-89132326 | ATGGCAAAAATGCAGCTGCAGACTCATGAGGAGTCGCCCTGGCTGCCACTAGGGCTCCCACAGTGCGCTGCCAACCTGCTGCCCGTGCAGAAACTCT | 64 |
| IGKC_chr2:89140556-89140656 | CAACTGTGCCCTGCACTGTTAGGGCCCTTGTCAAAACAACACATTTCTCAGTGATTCTGAGACTCTTTCTCTTATCTATAGAAGTCATAACTCAAGAGTA | 65 |

TABLE 6-continued

| Name | Sequence | SEQ ID NOs. |
|---|---|---|
| IGKC_chr2:89140656-89140756 | AAATCATACCAATATTTTACATAAACCCTAGAATTTTTATAGATCTATTATTTCTTTTAGAGTACATATTG GAAGTAACTTCACAAGGAACATTTTCTT | 66 |
| IGKC_chr2:89140886-89140986 | TCTGGTCAAACCACTCCACAAATAAAGTGGACTGATCCTCTTGACTGTGTAAGTGCCCATTGTGT GCACAGAGCTGGTGAGAACGGGCCATGGTG | 67 |
| IGKC_chr2:89140986-89141086 | CTAGGTGGGGGTCGTGTTGGTGGAGTTCGACTAGATTATCTGGGATCATGCGAAATGAAATTCATTTCT AGCTGGCTGGCTTCAGAAGGTGCCATCTCC | 68 |
| IGKC_chr2:89141086-89141186 | TATTTTTATATGAGGCGTGCTTTTGGAACTCAGGGCAACGAAGGGTGGTGTGCACAAGGACAGCAGA AGAGTGAGCTGACTGGTCCCTGAAATCGCA | 69 |
| IGKC_chr2:89141186-89141286 | GTTGGAAAGTGGATTACCAGTGCAGTAGAACTCTTCACGGAGGCCTGACCATCAGGTCTAATGGTGTTG TTCCAGGTGGGTGGTCATGTGGAGCAAAAA | 70 |
| IGKC_chr2:89141286-89141386 | TATTTGAAATCAGCGAGCACGTACCTGAGAGATGACTTTTCCACTGGGCTAGTCTCTTGATATTTCTGGT CCTGTTTCTTCATCTGTAAACTGGGTTAG | 71 |
| IGKC_chr2:89157326-89157426 | AAGGAGACCAAGAGCGTATTAAAATCTTGATGTTTTCTTCCTAGCTTTTGAGTTTCTTCCTAGCTTCCCCCTATTCCTTAAT AAAGTTCTAAATTGTTTTGTTGGAGCTCT | 72 |
| IGKC_chr2:89157426-89157526 | TTGCAGCCATTCTGAGGGCTTTGCATGCTTTTCTGACCTTGCAGTAAACTCAATGCTTTAGGCAAAGAATG GCCACGTCATCCGACCCCCTCAGAGTTTA | 73 |
| IGKC_chr2:89157526-89157626 | GAATTCAGAACAGGTCTGAAGAAGACCAGGCAGCGGCTGAGTCAAGGAAAGCCTCCGTCCGCTTTTATTT CCCCTGTGCCTCTTCCAGGACTGTGCTGGG | 74 |
| IGKC_chr2:89157626-89157726 | ATAACAGGCTCCCGGGGTTACTTTGGCTGGGCTGGGCTAAAACCTCCCTGAGAGCAGGCCCTGAGCCC TGCCTCTGCGCCTGGGTGGTGTCAGCCCCT | 75 |
| IGKC_chr2:89157726-89157826 | CCACCTTCTGACTGTTCCAGCAACTCTCCAGCAACTCTCTAAGCCCTCCCAAAGGCCTGTAACCATATGCAGCA ATTTTCAGCCATACCAGGAGAGTCAACT | 76 |
| IGKC_chr2:89157826-89157926 | GTAATCTTGGCCACCTGCCTAAGAGGAAGTGCTAGCTTCACTTCTGACCCTTCAGCAACTGCCAGGTGGC CTCTTGGAAATCCCCCTCTGGGGGATTCCA | 77 |
| IGKC_chr2:89157926-89158026 | CCCGTTGGGTGGGAGAGCAGTAGTTAAAATGTAAAATAAGAATCTTTTGCTGGGAGAGTCAACAGATAG GGAGAAGTCAGCTGATAACAGAAATAGTTT | 78 |
| IGKC_chr2:89158036-89158136 | TAAAACTAACTTCACTGTTAACCAAGCAGTTCAACATGAAAGACTGAATCTCTTATGTTTAATATTTTCTT CTCTTTTAATCTTCATAACTAATTTTTTT | 79 |
| IGKC_chr2:89158136-89158236 | CAGATAATTGTATAAATAACCATGGTAGCAAAATAATGTGATCACTGGAAAATAAGCAGGGAAAAACA TGCTATGAAGATACTCCTATCTGGGTGAATT | 80 |
| IGKC_chr2:89158236-89158336 | CTTGATAGCTTTACATTTTCATCTGCATTTAAACATTAAACAGTTAATGTATTTGACATGAAATTATT TCAAGTTATCTTATTAGTTTTAATAGAGT | 81 |

TABLE 6-continued

| Name | Sequence | SEQ ID NOs. |
|---|---|---|
| IGKC_chr2:89158336-89158436 | TTAAAAAGTGTTTAAAAGAGTTTTCAAAAGGCTCTAAAAATCATTTTGAAATAGTTTAAAACAGTTTGAAT CGTTGTAAGTTAGTTTTAATAGAGCTTTA | 82 |
| IGKC_chr2:89158436-89158536 | AAAAGGCCCTAAAATAGTCCTATCAAGTTGTTGCAGACACCAAAATAATCTCCTTAAATATCACTTTTGAGAT CAGCTGGGTAAACAGCAGACAACACAATG | 83 |
| IGKC_chr2:89158536-89158636 | ACAAATCATTAAACTATTTTAGAGATTATGAAATTAAAAATACTCAGATTAAAATTTTCCTATCACAGAATT AAGGTACTGGAAAATATGTTTAAGTTTTT | 84 |
| IGKC_chr2:89158636-89158736 | ATTAATCACATTGCTATAGGTTTTAGATATTTTGTACAACTGAAATAAAATCACACACTGGCAGCTACATTT TTGAAAGTTAAAAACATGGTCACGAATAT | 85 |
| IGKJ5_chr2:89158736-89158836 | ATCTTATTTTAAAATCAGTTAATATACCTTAATGGTATTTAATGCCAAATTCAAAGTGAATTGATCAAGCC CTCAGTGGCCAGGTCATGGGTGTGATTTT | 86 |
| IGKJ5_chr2:89158836-89158936 | TACTCTGAAAGAATTACATATTTCTTTCTTTTTGGTTGAGCTTTTGTTATTTAAATACATTTGATGAGAGG ATATTGAAATAATTAAATAGCACTGAAAA | 87 |
| IGKJ5_chr2:89158936-89159036 | AAAAAAGCTTTAAATTATTTACAATCCCCTAATGGAAATTTTCACTAATGAGAATATCATAATGAATGTGA ATTTTATTTCTGAAATCTCTAATAAATCA | 88 |
| IGKJ5_chr2:89159036-89159041 | AAGCTTTAAATTATTATTACAATCCCCTAATGGAAATTTTCACTAATGAGAATATCATAATGAATGTGAATTTT ATTTCTGAAATCTCTAATAAATCAGTCTT | 89 |
| IGKJ5_chr2:89159041-89159141 | CTCCCTGGTTTTCCCAGCTCAGGCGCCCATTACGTTCTGTCTCTTTCCCCTTAGTGGCATTATTGTATCAC TGTGCATCAGGAAAGCTGGCTACGGCAG | 90 |
| IGKJ5_chr2:89159141-89159241 | CATCAATCGGGCAGACACAGGGTGGCCACGGCCACTAGCGCGCAAGGCCGGCTGCCCCAAGAGCGCGGTGG CATGGCCACCAAAGCCACTCAATCGAGAAAG | 91 |
| IGKJ5_chr2:89159241-89159341 | ACCGCGGCTCTGTCTACAGCTCGCGGTGCTCGCCACGGCCTTCTTGGCAGAGAATAAAAATGTAGACAAGTAATAA CAGAGAGATAATGAAAGAACATACTCTTTAA | 92 |
| IGKJ5_chr2:89159341-89159441 | AATATTTCCTATTTTTTTCACAGACCCACGGTCATTAAAAAATGCAATTATTACTTTTTTCATTTAAACA CATTTCTTTTGAGATTGAGCTTTTGGGAA | 93 |
| IGKJ5_chr2:89159441-89159541 | TAACCACCTTTCCACCATTACAATAAGAGATAATTTCACGTTTAGTCTAATGTACAAATTGGATTTTTAAA AAATGAGCTCTATCTGTGAAGCCCTTATT | 94 |
| IGKJ5_chr2:89159541-89159611 | AAAATGAGCTCTATCTGTGAAGCCCTTATTCCTATAGAATGTGTCTTTTTGAGTTTATTACTTATTACAGA CTCTAAAAACAACATTGCTCTGATTTTC | 95 |
| IGKJ5_chr2:89159611-89159711 | AAGTAAGCTGCCTCTTCTACATAGCAAATAGGTACACTTCACTTTTCCCTGATTTTTCTTAGGGCGTGCTA TTGATTTTTATTCTGTCTGACAAATAA | 96 |
| IGKJ5_chr2:89159711-89159811 | TTTATCAAACAAAAGGGAGAAAGACTAAAAATGTATTTTCCACTTTTCTGTATCATGCATAATCAGCAA CAACCAATACAATATTGGCAAGGAGTGAA | 97 |

TABLE 6-continued

| Name | Sequence | SEQ ID NOs. |
|---|---|---|
| IGKJ5_chr2:89159811-89159911 | CAAAAATAAATTTACTTTGCTCCTTAGAAATACAAGGGTTCCTTTTAGTTACACTTTTTTTTTTACTTT GTGTCATTCAGTTTAGAGCAATTAATC | 98 |
| IGKJ5_chr2:89159911-89160011 | TTTTTTCTCCAAATCCATTTTGAAGCTGAGTTTAACTTTTGCAACCCATGCAAATCTTAAATGCCCTCA TTTACCAATCTTTACCAAACTCCTATTT | 99 |
| IGKJ5_chr2:89160011-89160111 | AAGCCTCTAAAAGTCAATACTGGCCATCAGACCCAAATTTCAGAAGACAATAGTGAAAAATTACTTACGT TTAATCTCCAGTCGTGTCCCTTGGCCGAAG | 100 |
| IGKJ5_chr2:89160111-89160211 | GTGATCCACAGTGTTAACTTAATTACTTTCCCCTTAACAAAAATCTCTTTTGCTGTTAATATCACTAACCT GACCGATGCAGAGAAAATCTTGCAATTG | 101 |
| IGKJ4_chr2:89160211-89160311 | AGATGCCTCACTTAACTGGCTAGCGCTTGGCTGTTCCTTAAGATGAACTAAATTTTCTATCCCTTACTCATC TGACTTTTTGAAAGAATCTGGTACTCTTT | 102 |
| IGKJ4_chr2:89160311-89160411 | GGAATTGACCTGAGCTAATATCTCAAACACAAAAACGCTCCAAATTTAAAACCTTATAAGAAAAAGCATT AGGAAAGTGCACTTACGTTTGATCTCCACC | 103 |
| IGKJ4_chr2:89160411-89160511 | TTGGTCCCTCCGCCGAAAGTGAGCCACAGTGAGGATCTCACCCTTTCCCCTCAACAAAAACCTCTCTTGA AGCCAATCATATGAGATAGGCTGCTTGTT | 104 |
| IGKJ4_chr2:89160511-89160611 | CAGAGAAAAATTAGCTATTCTTCCCCATTTCCCCATGAATCCTATTCTCTCTCAAACCCAATGATTC GTCTATTTGCTCAGCTTTTTAAGTTCATT | 105 |
| IGKJ3_chr2:89160611-89160711 | TTCTGGTGTCCTGCTATTATTACTTCTGGGTCACCAGGTTTATTCAACCAAAATATCACAAAACTTGCAAAA TGATACAATGGCACTAAAATCTCACGAAT | 106 |
| IGKJ3_chr2:89160711-89160811 | AATTGAGACAGATGTACTTACGTTTGATATCCACTTTGGTCCCAGGGGCCGAAAGTGAATCACAGTGATTC GTCTTAACTTTTCCCTTTACAAAAACCTCC | 107 |
| IGKJ3_chr2:89160811-89160911 | CTGAAAGCTACCTACCTGGGAATGAAGTTTGTTAGATCCCTGGCATCCGACTTGGTCCCCTGGCCAAAGTGAATCACACAAAGG AACACAAAGTAAACTAATTAGCAACAGTGA | 108 |
| IGKJ2_chr2:89160911-89161011 | CTCTGTACCTACCTGGGAATGAAGTTTGTTAGATCCCTGGCATCCGACTAATGAAAATCCACACAAAGG AACACAAAGTAAACTAATTAGCAACAGTGA | 109 |
| IGKJ2_chr2:89161011-89161111 | AGAATCAGTGGAAAAAGTACTTACGTTTGATCTCCAGCTTGGTCCCCTGGCCAAAGTGTACACACAAT GGTTCCTCTTAACTTCCCTCCTATACAAAA | 110 |
| IGKJ2_chr2:89161111-89161211 | ACTCCCTTTCTGACAATGACCAAGGCTCTGTCCAGAGACATGTTATGTTCCCAGGACATTTCTGAAGCTA TTACTTAGACAAGTTATTCTCACCCAATG | 111 |
| IGKJ1_chr2:89161211-89161311 | ACTGAATCTTGCTTGCTTCTTCAAAGAAAAATGTGCAATCAATTCTGAGTTTGACTACAGACTTATCTTTAT CTTTTCCCTGAAGGATATCAGAGGCTGAT | 112 |
| IGKJ1_chr2:89161311-89161411 | TGCAGAGTCACCTTATAGATCACTTCATAGACACAGGGAACAGAAGACACAGACAACTGAGGAAGCAAA GTTTAAATTCTACTCACGTTTGATTTCCACC | 113 |

TABLE 6-continued

| Name | Sequence | SEQ ID NOs. |
|---|---|---|
| IGKJ1_chr2:89161411-89161511 | TTGGTCCCTTGGCCGAACGTCCACCACAGTGAGAGCTCTCCATTGTCTTGCTGAACAAAACCCTTCTCACCAAAGGGAACAGAGTCCTGGGTCAGCTG | 114 |
| IGKJ1_chr2:89161926-89162026 | ATCAACTTAAGGCTCATAACTTTGAAATGCATTTTGAAATGTAGCTCCAGATGGTATACGAACCAAAGTGAAGACTAATAGAGTAGAAAAGTAGACTTT | 115 |
| IGKJ1_chr2:89162026-89162126 | ACTTGGTTGGTTTGTCTGTTTCACAGACACAGAAGAGCTCAGCTCTTTACTGAGCTGACCAGGCGCATGCCATCTTTGGAGCTGCCATGGAGTCCCAGT | 116 |
| IGKJ1_chr2:89162126-89162226 | GTTCCATAGTGTGTTTCCATAGTAATCTCATCAACAACACTGAAGACCTTTTCAGTATTTTCTTTTGAGTCCAGCTCCATTTTTGCAGCCTTGTATCTCTCT | 117 |
| IGKJ1_chr2:89162776-89162876 | CCGCGCCCAGCCAGTCGCTGTTTATTTTACCTGCTTTCAGATTCTCTTCTACCCTTCTAAATTATAAGCTGTTTGATGTTTATTTGCCCTGTATTG | 118 |
| IGKJ1_chr2:89162876-89162976 | GGAGGCTCCGTCCAGTATCTTACTTAGCAAATGCTTAACAAACATTTTCAGAATAAACATCATAACTACACCTAATTGAAAGTCAATATAGATCAGAGA | 119 |
| IGKJ1_chr2:89162976-89163076 | TGCTATCATAGACCAAAGACTAATACTGCCCACACAGTAACTTTTACAACAGAGAAATCATAACTACAATTCTAAAGATTAGGGGTAGGTTTATTTGA | 120 |
| IGKJ1_chr2:89163076-89163176 | TTCTGTCACTGGACAGCTTTGCTAGTTGCCTTGAATAGCAGAATTAGACATTGTCTCACCAGAAGATGAGGAAGGAGAGGGATCAAGTTAGAGTGAGA | 121 |
| IGKJ1_chr2:89163176-89163276 | GTTAACATTGGCAAGTGAAATTTAATGCAAAATAGCTGACCAAGGCATAGTCCTTTTTTAAAGGGGACACAAAGTGATTTTCTGCAGACATAAC | 122 |
| IGKJ1_chr2:89163276-89163376 | GCAATACCAATCATAAAGGGTGACATTTATTGAGCACTTACTAAGTGCCAGACATTGTACATGATCATCACATTTAATTATTCCCAAGACTCTATGAACT | 123 |
| IGKJ1_chr2:89163306-89163406 | TGAGCACTTACTAAGTGCCAGACATTGTACATGATCATCACATTTAATTATTCCCAAGACTCTATGAACTAGGAACTAATATATCCCCTACTTTGTAG | 124 |
| IGKJ1_chr2:89163406-89163506 | GTGCAAAAACTTGAGGGCAGAGAGGTCAAGGAACTGGCTTATGGCAGTAAGTGGCAGAGCTGTGACCTAAACTCAGATCCCATGTTTTTAACTGAACTAT | 125 |
| IGKJ1_chr2:89163506-89163606 | ATCAGATTATACTCCAGAGTAAAGTCACTCAACGGAAGCAACAAGCTGACAGGGAATGCTGGGATGGGGGAAGGTAAAAGGAACTCCTTAGACTGGG | 126 |
| IGKJ1_chr2:89163606-89163706 | ATAAGTGTGTACAGACGTATGTATAAGACATGAAAAATATTGTTAAAGAGTGAAAATAACTAAAATCCTCATTAATAGGAGTTTGGTTAAACTG | 127 |
| IGKJ1_chr2:89163706-89163806 | TGCTAGAGCTTTACAATGTAGCACAAAGCAGACATTAAGGGGAAGAACGTAGACTTCTATATAGTTACGTGGAAGGTGTTTGTGAAAATGCAAGTCACTGA | 128 |
| IGKJ1_chr2:89163806-89163906 | AGAGTATGTGTGTGAGATATCATGATCCCATCTACATTGAATATATATGTATATATAAATACGGGCTGAATTTTAAAGACATAAATTGCTTGGTAGTT | 129 |

TABLE 6-continued

| Name | Sequence | SEQ ID NOs. |
|---|---|---|
| IGKJ1_chr2:89163861-89163961 | AAATACGGGCTGAATTTTAAAAGACATAAATTGTGCTTGGTAGTTATCTCCTGGGATTGCAGAGGAGAA<br>CAATGACACTTTATGCCATCTCCTCCTACT | 130 |
| IGKJ1_chr2:89163961-89164061 | CTTCTGTATGGTGATGTGAATATATTCATTTTATAGTTTTTAGAAATAATAAACTGTACTAATTTTGAAAA<br>AACAGTAAACTGACATTGCCTATTAGC | 131 |
| IGKJ1_chr2:89164061-89164161 | ATTCTCGATATTCCTGTGCAATGCATAAACATAACTTTTAAAAGATATGTACACACATGTGAGTTTTC<br>TTTGTCAAATACTTTTCTATAATCTTTAA | 132 |
| IGKJ1_chr2:89164161-89164261 | ATCAAGCATGCCAAAAAGGTAAAAGTTTCCTGTCTGTAGGAGATAGTCGTCTGCAAAGGAAAGAG<br>ATGTAGGGGATAGAAACAGGAATGAAAAAG | 133 |
| IGKJ1_chr2:89164261-89164361 | ATGACTGAGCTGTTTCGAGGGACTTATGTTCCTAAGTGAGCTAATTGGAAATCTAAATGAACAGTGCAAC<br>CGAATAACTATTGTAAAGCAGTATTTGTAA | 134 |
| IGKJ1_chr2:89164361-89164461 | ACAATAAAAGATGATTATCATAAGTACCATTGTTGCAAAAACTATTTTATTGATCACATGCAGTGGTGATC<br>TGTAGGAATGATTGTGTGATGTTTGCTG | 135 |
| IGKJ1_chr2:89164461-89164561 | TAACATAAATGAAACATGGGAAGTGGCTGAGATCTTTAGGATGCTGTGGTTCATTTTTGAAAGCAAA<br>TGTTGTCTCAGAAGCATCTGTGAGACTCTG | 136 |
| IGKJ1_chr2:89164561-89164661 | CCAGGATCCACCGTTCTACAAAATATCTGTGATGGACATTGATAAGATTGATCTGTTGAGGAAAGGCAAG<br>GTGTCAGTAAGATAGTCTGAGAGCTTCTG | 137 |
| IGKJ1_chr2:89164661-89164761 | GATTTCATGTAAAAGTGCTGAAATAGAATTTCTTGGGGACATTCCAACTAACTCATCACTGAAGGT<br>GCTTTACATTGAACCCTCAGCAAAGTTAGA | 138 |
| IGKJ1_chr2:89164761-89164861 | TTATCAGAAAAAAAATATAAACTGCTGTGAGGGCACAGGAAGGAAAGTCAGGGAGGAGGGGGCAA<br>GGAGAGAAAGAGCGAGAGAGGAGAGAAAGA | 139 |
| IGKJ1_chr2:89164866-89164966 | AGAGAGGAGGAGGAGAAGAAGTGCCAAGTACACACTTCAATGCACTCATATAAATCATCCTGAAAACTACTGATA<br>AATTATTTTAGCAATGTTCCTCAGATGTAA | 140 |
| IGKJ1_chr2:89164966-89165066 | CATTTCAAGAGAAATATCATTTTGCTTTTATTTGGCATAATTTACTAGCCAATTTAGGAAGTTCCCCTCACA<br>TCAGTAACATACAGTACATCACCCAGTA | 141 |
| IGKJ1_chr2:89165066-89165166 | TGTCAGAGGACACAATGGCATAAGTTTGCCTTTTGCAAGGTTTGCAGGGATGGCCATTTCCCTACCTGACTC<br>AGGAAAGTTCTGTAGCTGATATCCATCTTC | 142 |
| IGKJ1_chr2:89165166-89165266 | AAGTTTGGGTTCTTTCTCTATATATATATTTGAGCTCAGCAGTCATGCTGGAGTCCAGAGTAGGTGAT<br>TCTTTCTGCTTTAGCTTTGACTCCTTA | 143 |
| IGKJ1_chr2:89165191-89165291 | TATATATTTGAGCTCAGCAGTCATGCTGGAGTCCAGAGTAGGTGATTCTTTCTGCTTTAGCTTGACTCCTC<br>CTTAAGATTGTAACTCTCTCAGTTTTACA | 144 |
| IGKJ1_chr2:89165291-89165391 | TTTTTTGTCAGACGTAAGCTGACATTCCACAAGGAGGAGAAATTCTGTGTTCACATCCAGTGGTGC<br>TTGGAACCTGATTGGTTGTCATTCTTCCAG | 145 |

TABLE 6-continued

| Name | Sequence | SEQ ID NOs. |
|---|---|---|
| IGKJ1_chr2:89165391-89165491 | CTAGTTTGTCACGAGTGATATCTGTCCTGGATTCCAAGGATCAAGGCTGCCCATTAGCCAGGAAGTAGGGAGATAGAGGAGGTCACTTGAGAAAGAG | 146 |
| IGKJ1_chr2:89165491-89165591 | CTGCTTCTTTGCCGCCTCCAGGTTGTGTCTGTTTCCTCCATATCTGAAGACAGATGCTGGCAGAAGCAAAGTCCTTTGTCCGGCCACGTGCAAATGC | 147 |
| IGKJ1_chr2:89165591-89165691 | ATGGAACATAAATGAACAGAGATTCTTGTCCCACTCTAGAAAATGTAGAATGTTCATCTTGTTTCCAAGGGGACAGTGAAGGCTGCAGGTGTTTTTTGAC | 148 |
| IGKV4-1_chr2:89184966-89185066 | CTTTTGTACTCACTGGTTGTTTTTGCATAGGCCCCTCCAGGCCACGACCAGCTGTTTGGATTTTATAAACGGGCCGTTTGCATTGTGAACTGAGCTACAA | 149 |
| IGKV4-1_chr2:89185066-89185166 | CAGGCAGGCAGGGGCAGCAAGATGGTGTTGCAGACCCAGGTCTTCATTTCTCTGTTGCTCTCTGGATCTCTGGTGAGGAATTAAAAAGTGCCACAGTCTTTT | 150 |
| IGKV4-1_chr2:89185166-89185266 | CAGAGTAATATCTGTGTAGAAATAAAAAAATTAAGATATAGTTGGAAATAATGACTATTTCCAATATGGATCCAATTATCTGCTGACTTATAATACTAC | 151 |
| IGKV4-1_chr2:89185266-89185296 | ATTAAGATATAGTTGGAAATAATGACTATTTCCAATATGGATCCAATTATCTGCTGACTTATAATACTACTAGAAAGCAAATTTAAATGACATATTTCAA | 152 |
| IGKV4-1_chr2:89185296-89185396 | TTATATTGAGACAGCGTGTATAAGTTTATGTATAATCATTGTCCATTACTGACTACAGGTGCCTACGGGGACATCGTGATGACCCAGTCTCCAGACTCC | 153 |
| IGKV4-1_chr2:89185396-89185496 | CTGGCTGTGTCTCTGGGCGAGAGGGCCACCATCAACTGCAAGTCCAGCCAGTGTTTTATACAGCTCCAACAATAAGAACTACTTAGCTTGGTACCAGC | 154 |
| IGKV4-1_chr2:89185496-89185596 | AGAAACCAGGACAGCCTCCTAAGCTGCTCATTTACTGGGCATCTACCCGGGAATCCGGGGTCCCTGACCGATTCAGTGGCAGCGGGTCTGGGACAGATTT | 155 |
| IGKV4-1_chr2:89185596-89185696 | CACTCTCACCATCAGCAGCCTGCAGGCTGAAGATGTGGCAGTTTATTACTGTCAGCAATATTATAGTACTCCTCCCACAGTGCTTCCTCGTGTTCGAACACAA | 156 |
| IGKV4-1_chr2:89185696-89185796 | ACCTCCTCCCCCATACGTGGGCCAGTAGGTCTTTGCTGCAGCAGCTGCTTCCTCCTGCACAGCCCCAACATGCATGCTTCCTCTGTGTTGGGGAGG | 157 |
| IGKV5-2_chr2:89196226-89196326 | AATACATGAAAACAACTACCGAAATGTTATGAAATTATAGTTTAGTAGAACTAACAAGTGCATTAATGCAAAGAAAAGTAGGGCTCAGTAATCAGGGAA | 158 |
| IGKV5-2_chr2:89196326-89196426 | CCAAGTGTGCATTGTAAAAGTGCAGCCTCTCAACACTGGGTTTCATCACAAGTAACAGAACAGGATGCCTGATGCAGGGAAAAAAGAAAGGCAATTGTT | 159 |
| IGKV5-2_chr2:89196851-89196951 | GATCTCTGGTAAGAGAAACACTTCCTCTCCTCTGTGCCACCAAGTCCCCTGCATATCCACAAAAATAATATATTTTCATAAGGAATTGATTTTCCTCATT | 160 |
| IGKV5-2_chr2:89196951-89197051 | CTCTGCAAATAATGATGCATTTGATTTATGTTTTTACTTGCTCCATAATCAGATACCAGGGCAGAAACGACACTCACGGAGTCTCCAGCATTCATGTCA | 161 |

TABLE 6-continued

| Name | Sequence | SEQ ID NOs. |
|---|---|---|
| IGKV5-2_chr2:89197051-89197151 | GCGACTCCAGGAGACAAAGTCAACATCTCCTGCAAAGCCAGCCAAGACATTGATGATGATATGAACTGGTACCAACAGAAACCAGGAGAAGCTGCTATTT | 162 |
| IGKV5-2_chr2:89197151-89197251 | TCATTATTCAAGAAGCTACTACTTCTGTTCCTGGAATCCCACCTCGATTCAGTGGCTATGAACACAGATTTTACCCTCACAATTAATAACATAGA | 163 |
| IGKV5-2_chr2:89197251-89197351 | ACTGAGGATGCTGCATATTACTTCTGTCTACACAACATGATATAATTTCCCTCTCACAGTTGATACACCCTGTTACAAAAACCTCCAAGTTCTCTCAGTGGGAT | 164 |
| IGKV5-2_chr2:89214836-89214936 | GCCCTCTGTCCTGAGACACGGCCAAGGAGGCTGGAGACTGGGTCAGCACAATGTCCCCATTGCAGCCTGAAATGATAAAGACAGATAAATTATATCAGA | 165 |
| IGKV5-2_chr2:89214936-89215036 | TATACTGAGACTGTCCCCATGTAGGCCATGCATTGGTGACACTTGTAACCACAGTCATATGCAACATCTTGAGTAACCAGAAAACAAAAGATAACTGGGG | 166 |
| IGKV5-2_chr2:89215036-89215136 | AACTTACAACCTACAATGAGTGCCCTAAATCCAACAACCAAGAATCCAGAGACACAAAAAACAATGATGGCCACATGAGTTTGCCCGATGTTTCCCTATA | 167 |
| IGKV1-5_chr2:89246681-89246781 | TACCAACACCATCAGAGTGTGGCTGCATCTGAGGACCACTCTCAGCTGATGAGAGGCATCAGGAGGAGCAGCTGGGGCAGCCCTGCCTCACACATCTGCTT | 168 |
| IGKV1-5_chr2:89246786-89246886 | GGGGTTTATGTTCGGGTGTGATAACATGTGGGAGAATAACTATTATATACTGTTGGCAGTAATAAGTTGCAAAATCATCAGGCTGCAGCTGCTGATGGTGA | 169 |
| IGKV1-5_chr2:89246911-89247011 | GCCGCTGAACCTTGATGGGACCCCACTTCTAAACTAGAGCGCCTTATAGATCAGGAGCTTAGGGGCTTTCCCTGGTTTCTGCTGATACCAGGCCAACCAG | 170 |
| IGKV1-5_chr2:89247011-89247111 | CTACTAATACTCTGACTGGCCCCGGCAACCAAGTGATGACTGTGTCCTCCACAGATGCAGACAGGGTGGAAGGAGACTGGGTCATCTGGATGTCACATTTGG | 171 |
| IGKV1-5_chr2:89247096-89247196 | GGATGTCACATTTGGGCTGAGTAAATTCCTAGTGTCTCCCTTCCTTACCTGGGAGCCAGAGCAGCAGGAGCCCCAAAGCTTCCCTGAATAACCAGGCAGTACTG | 172 |
| IGKV1-5_chr2:89247196-89247296 | AGCACACTGGGCTGAGTAAATTCCTAGTGTCTCCTAGTTTTTTGAGAATTTAAATATTCCTCAGGAGCCGAGGAGCGAGCGGGGGACCCTCATGTCCATGC | 173 |
| IGKV1-5_chr2:89247526-89247626 | GGGACTATTTATTATGAGAAACAATTTTAGGTATTTTTGAGAATTTAAATATTCCTCAGGAGCCGATAGAGTAATGTATTTCATTGGTGTATCAG | 174 |
| IGKV1-5_chr2:89247626-89247726 | GATTATTTAGGAGAATATTCTTGTTTGTAGGAAACACATAGTAAAATGTTAGATGGTAGGATTCTCAAGTCTTCAAAAGACTCTCACTTCAAAAGACTCTTCATAAGATTCCGGGTA | 175 |
| IGKV1-5_chr2:89247641-89247741 | TATTCTTGTTTGTTGGAGAAACATAGTAAAATGTTAGATGGTAGGATTCTCAAGTCTTCAAAAGACTCTCATAAGATTCCGGGTAGGAAGGGGTAATT | 176 |
| IGKV1-5_chr2:89247831-89247931 | TGTAAGTATTAAGTAATGGTGTTATGCCTTTGTTCTTACTAGTATTAGATCAAGCAATTTATTACAGATATACAAAGATGATACCGTGTGTCTTCCATGC | 177 |

TABLE 6-continued

| Name | Sequence | SEQ ID NOs. |
|---|---|---|
| IGKV1-5_chr2:89247931-89248031 | ATGCAGCACTCACAGATCCACCACTATCAAGAGACTGCAGGTCTCTTTAATACCCAGAGACTAAATGAGGT GCACCTTATTCTTGTTTGTTTGGGTACCTTCAT | 178 |
| IGKV1-8_chr2:89291906-89292006 | TTGGGTGTGTAACACTGTGGGAGGGTAACTATAATACTGTTGACAGTAATAAGTGCAAAATCTTCAGAC TGCAGGCAGCTGATGGTGAGAGTGAAATCT | 179 |
| IGKV1-8_chr2:89292131-89292231 | CTGACTCGCCCGACAAGTGATGTGACTCTGTCTCCTGTAGATGCAGAGAATGAGGATGGAGACTGGGTC ATCCGGATGGCACATCTGGCACCTGAGATT | 180 |
| IGKV3-20_chr2:89442291-89442391 | CTTTCCCCTGGACAAAGACACAGGGTGCCTGGAGACTGCGTCAACACACAATTTCCCGTGTATCTGAGA TTGGAAATAAAACAGAGAAAGTCACCCATGT | 181 |
| IGKV3-20_chr2:89442391-89442491 | AATCTAAATCAAACCCATTGTCTTCCCAGAAGAGCCAGAATTATTGCTTTATATTGAGCTTTAATTATTGT ATTGACTGAGCAGAGTTGCCAGGTAACAG | 182 |
| IGKV3-20_chr2:89442491-89442591 | GACTTGAGAGGGTTTTCACTGACATGCAAAACCATTCCCCTCACCTGGGAGCCAGAGTAGCAG GAGGAAGAGAAGCTGCCTGGGGTTCCAT | 183 |
| IGKV3-20_chr2:89442616-89442716 | AGCTCTTCTCCAGAGCTCTGACCAGCATTGATATGGGCTCTGGACTGCAGGGCGGCTGGGAGGGACAT GCAAAGCAGCTGGGGCGGGTGCTGGGCTTG | 184 |
| IGKV3-20_chr2:89442716-89442816 | CAGCTGCAGAGACAATCTGCCTCCTCCCCTTTCTGCTCTCAGCAGCCCATGCCCAGGTGATCAGGCCAGAAAA GGCCGTTGGCTCAGTCTGAGGGTAGAACTT | 185 |
| IGKV3-20_chr2:89442816-89442916 | CTCCCCTGCGGCCACAGAATTAACCCCTGTGTCCTCTTGTTCCACCATCACCTAGATTGAGCCACGAAT GTTTGGTACAAGTCTGTTAGAAACAAAAT | 186 |
| IGKV3-20_chr2:89442916-89443016 | AGAAGGCTGTGGTTTCATTTTCTCTGCTCCAACTTGTGCCCAGTCAGCTCCCTAAATGCATGATGG ATCAGGTTGAAAGGAAGAGTCTATTACAA | 187 |
| IGKV3-20_chr2:89443016-89443116 | CTTTATCTTCCGGATATACTTGTATTTACTTGTTAGTGATCTTTCCTGAGGGTCCAGAAGCTGTCTCATTCT TTGCAGAAATTAAAGAGTAACATTTCAA | 188 |
| IGKV3-20_chr2:89443116-89443216 | TTAACCTTCAGCACTGTGGGTGTGAGGACTTTCACAACTGCACAGATAAGTGAGACCTGGGCTCCAAATCC TCAGGGTAGTGATACCATTTCCCTAAAGAC | 189 |
| IGKV3-20_chr2:89443216-89443316 | AGAAGATGGTTTTGTCCATGCAGGCAAAGAACTATTTCTTGGGTGATCCTCTAAACTATCCAGTCTTTTTA TTCTGTATAGCTGGTATAGTTTACCCTTA | 190 |
| IGKV2-30_chr2:89544656-89544756 | GGCTATATATGTATTTGTTCATATTTCAAAAATACACAGTTTCAAAATGGAACTCAAGGGATCCAAGGCTC AAAGGGGTCTCCAGAAGACCCCACACCAT | 191 |
| IGKV2-30_chr2:89544756-89544856 | CCCCTTTCTGTGTCAGTCTTCCCAGAGCACAGATCCTTGTTTGTTTCTGCTTGAATCTTCCTCACTCTCACAGAT CTGATCATCACATGCCCCACTCTGGAGG | 192 |
| IGKV2-30_chr2:89544856-89544956 | ACAACATGTCATGTCCAATACAGGAAAGGAACACACATAGAGTGTAGTGAGACCCCAGAGATCACT GTTGTTAGGGCAGTGGGCCCCAGAACTCA | 193 |

TABLE 6-continued

| Name | Sequence | SEQ ID NOs. |
|---|---|---|
| DUSP2_chr2:96810164-96810264 | GGAGCAGCAGCGGGTGAGAGACCCCATGGGCTGGCCGAGACAAGAGGACTCCTCAGCCAGTCCTCCTGACCTCAGACAGGTCTCAGGAATGTGCGAGGAC | 194 |
| DUSP2_chr2:96810264-96810364 | ACACCGGGACATACATTTCCCTTCATGCTCCCAACATACACATGCAAACATACACAGACCCATACAGGCACGCGCGAGCCAGCCATGCCCCACCCCCTCCC | 195 |
| DUSP2_chr2:96810364-96810464 | CCAACACACACACGTATAAAAGTGTGTATATGGGCAAACTGCTCCGATCCCCAAATGGAGGCTCTTTCCCTAGAGGCGCCCAGTCCGCGCGGGGAG | 196 |
| AFF3_chr2:100758483-100758583 | AAGCTCACTCACTGGGGCCATTGACTGGGATCCAGTCTGTGGCCATGTCATGTTTCTATTTTTGAGGTTATAGCTAATGAGCACATGAGGTTAAGACA | 197 |
| AFF3_chr2:100758583-100758683 | CACTTTTCATAAGGCCCCAGCAGCATCATAAATATGTGTGAGCATGTTCACACTTCAGGTTATGTCTTCTTTATGTGCACCCTCTACCACACACAC | 198 |
| DDX18_chr2:117951919-117952019 | GCCAAGAACCACGACTCTCTAATTTTACTTCCCAGCAGGTATTCAGTGCATAATAGTTCCTACTTAGAAGTATCATATTTGCCAAACACAAGTGATAC | 199 |
| DDX18_chr2:117952019-117952119 | CCAAAATGAGGTAAGTTCCTGTTTTCCAGTGAGATCTTTTGTTGTTGTTGTTGTTGTTGTTTGTTGTCGATGTTGTTGTTTTGGTTTTGGTCT | 200 |
| CXCR4_chr2:136874415-136874515 | CCGGGTCGTCCAGCCCGGGCCGCCGGCCGCTGCCCATACACCCACGCCAACCGCCCCGCAAGCAGCCTGCAGGGGCTCCGCGCTGGGCGACACGCCAGGCT | 201 |
| CXCR4_chr2:136874515-136874615 | CTGTCCCACAGGTGCTGGGGAGCGACTGGGCGGCTCCGCGCGAGCGTCTTTGAATTGCGCGCCTGCAGGAAACCAAAAACTCCCTAGCAAGAGGGT | 202 |
| CXCR4_chr2:136874615-136874715 | TTCAAAAGTTTCTGGAAACCACCGACGTTAAACATCACAACTGGACTCGGAGAGAGCCAAACGGTTTCCCCACTTGCACCTGCCAGTCTTCGCGCGG | 203 |
| CXCR4_chr2:136874715-136874815 | CGACCTGGCAGCCAGGTGCGGTCTTAACCGCCCCCGCCCCTCACCCGTACCCGCTCCTATCCCCGGAGCGCAAATCTCAGGGCTGGCAGCTGCGCGGT | 204 |
| CXCR4_chr2:136874920-136875020 | GGAAGGTTTTCCCCTCAAACCCAAAGCGCGGGCGGATCAACTCCTAGCTGCTGCCACCACTCGATCCCCTCAGAGGATCGGCGCGGTGGGTCCACCC | 205 |
| CXCR4_chr2:136875020-136875120 | GCCTCTCCCGCCCTCTGCCTACTGCTGGGAGACTGGCACAGCTCCGTCGGCCGCACAGAGTTTAACAAACACGCACCCAGTGTCAAGAACAGTCACCA | 206 |
| CXCR4_chr2:136875120-136875220 | GGGCTTAACCCGAAGTTAAAGCGGGCAATCTCCTCCTGGGAACTCAGCCCCAGGCACGCGCGCCCTCCGCCTCTAAATTCAGACACAATGTAACTCGCTC | 207 |
| CXCR4_chr2:136875220-136875320 | CAAGACATCCCCGCCTTCCCAAGGAAGAGACCCGGTTGTCGAGTCCCGAGGCAGCGCGCACGCCTTCTCTGCACTTGTGCACAGAATGTTCTTACGTTTG | 208 |
| CXCR4_chr2:136875320-136875420 | CAAACAGCGTGCAAGCCGCGCGCCGGGACTCAAGGGGAGACACATGAGCCACTGAACGCTCTTTCCAGTCGTTTCTCCTCGACTCACAGAGA | 209 |

TABLE 6-continued

| Name | Sequence | SEQ ID NOs. |
|---|---|---|
| CXCR4_chr2:136875420-136875520 | AAAAGATTCCAATCCTGCTCCCCCCACCCCGACTATATAGGCATGGTCAAGAAAACTCCTTTCGGTGACCCTTTTTGGAGTACGGGTACCTCC | 210 |
| CXCR4_chr2:136875520-136875620 | AATGTCCTGGCCGCTTCGCCCGCTTGCCCGTCGGAGAGGGGCTGCGCTTCAAGTTCAAACGTTTGTACATTTATGACAAGCAGGTTGAAACTGACTTACACTGA | 211 |
| CXCR4_chr2:136875620-136875720 | TCCCCTCCATGGTAACCGCTGGTTCTCCAGATGCGGTGGCTACTGGAGCACTTCAGGGCCCTCGGCGTCACTTTGCTACCTGCTGCCGCGCAGCCAACAAACTG | 212 |
| RFTN1_chr3:16419204-16419304 | CCCATTGCTGACATACTTACTCCCTGAGAGTGGCTCTTCATGCACCTCCAAGGGGTTGCTCTCCGGTCCATCCAGTGTCTTGCTCACCCCCTGTGGTGAA | 213 |
| RFTN1_chr3:16419304-16419404 | AGTTCTCCACCATCTCCCTCTCCGGAGGGTGAGCTGGGCTGGCTGCTTGGCGAGGGGCACCTCCCCTCTGGGGCCTGAGCTGGGGCTCTGGGCTTTGGTTTCTCC | 214 |
| RFTN1_chr3:16419404-16419504 | CAGCCGGAGCACTGCACACATCCCCAGTCCCCGGTTTCTCATTCTCCAGTGACGCGTGATCCCCACGTGCGTTTTTTGCATCTCTGGCATCTCGGTGCT | 215 |
| EIF4E3_chr3:71551101-71551201 | ATTTGCAGGTTATATCCTGATGTGGCACGACAGCCGCCTGGAACACAGAAGTTGGGAGGCTGACGCTCATCAGGAAGGCTCTTTTGGGGAGCCAGGA | 216 |
| EIF4E3_chr3:71551201-71551301 | AGAGTCCCCCAGAAGCCACTTGGCACCCTATCTATAACAAGTTGCTCTTTAAGAATCATGGGAACTCCAGAATCATTTTCACAAATACCTTCCACTCAT | 217 |
| EIF4E3_chr3:71551301-71551401 | GATTCAATTAAATGCAGAAAACACAAACCTTCCGTTCCCACTGGCAAACTGGGTCTAGCTAACTGAGCACAGCTAGCACAAGGCAGGCCCCTGCTAGC | 218 |
| EIF4E3_chr3:71551401-71551501 | AGGGCAAGTGGCCGCCCCGTCCCAAGGCCCAGGGAGCCTCTGCAGCTCCCTGCGGAAGGACCGTCAAGTGAACAGAGAGCTGGCTGCCATCTGGGTTCTT | 219 |
| KLHL6_chr3:183272308-183272408 | ATGAGATCACCAGTTTATCGTAACTAGAGGCCTCTCCCATCTAAAGCATCTTTGTAACTGCTTTCCCTTTCCCCACACTGCCTACACATAAAGAAGCCCC | 220 |
| KLHL6_chr3:183272408-183272508 | TAATTTGTAACAAGTCATTTGACAACTCCAGAGAGAGGGCCACATCCTTTTCTCTATGTCTGTTGATTAACAAAGACAACATTATGTTTCCAACACCAG | 221 |
| KLHL6_chr3:183272508-183272608 | TCAGACCAAGGGGGAAAAAAGTCCCCATGACTTCAGTAATTTTCCATCCTTTGGAACAAGGAAATATACACAAAAGGTTTACTATAGAATGTAAGCATTG | 222 |
| KLHL6_chr3:183273063-183273163 | AACTGTTCAAGATTGGGCTCTCACACTAACACACCTCTTCCTTGCAACTTGCACCCATTTGACTCTGGTCCTAGGCATGCTGACCTGAAATAGTTGCTG | 223 |
| KLHL6_chr3:183273163-183273263 | GCTGCGGCAAGCACCACCGCGGTGGCAGGAGAATTCCTGAATGTCCACACACAAGATGACATCTGTCAGAGCGTTTCCATTCCGCAGGGTTTCCAGGCCAT | 224 |
| KLHL6_chr3:183273263-183273363 | TCTGAAGAATTAAGGAGAGTCCCGCGTCGTCAAATTTGACCTTTTCCCCATTTAAGATCTCGACCAAGTCTCCTGTTTTCTGGGAGGGCTCATCTGTAGA | 225 |

TABLE 6-continued

| Name | Sequence | SEQ ID NOs. |
|---|---|---|
| KLHL6_chr3:183273363-183273463 | AGGTGCCAGGGGCCCTTCCAAACTCTTCTGACCACATCACCCATGGTCCAGGCGCCCCTTTGTCCTGCCATCAACATCGAGACTGAAGGAGCGCCCAAG | 226 |
| ST6GAL1_chr3:186714604-186714704 | CCTTCCTGTTGGCCACTACATACGTGTCCCCCGCTTCTTGCCCTCTGCTTGGGTCCCTGCTACACTGGTATCCTGCACTTTCCACCTTGTATTGCCA | 227 |
| ST6GAL1_chr3:186714704-186714804 | GTTTGTTTCCAAGGCCATCTCCACTTTGAGCTTGTTCATGACCACCTCACACAGCACACTTGGTCTGTGTGGTGGTTTGAGGGGTTCTGTCTGTACACTG | 228 |
| ST6GAL1_chr3:186714804-186714904 | TGCTTTGGCTGTCGTGTTGGAGGCGGGCAGGTGGGAAGGAAGAAATGTATTCTTGGGAGATTTGTTTTAGAGACATGAGACATGGAAATAGTTAAGTAAT | 229 |
| ST6GAL1_chr3:186714904-186715004 | AATATAATATGGAGGCATGGACTATCAGAGAGGCAGGCAGGACTGCCCAACCTCCTCACTGGGCACGTTACGCTACTTCCTCCTGACCTCTATAGTCC | 230 |
| ST6GAL1_chr3:186782529-186782629 | CTATCATTGCCCTTTCTTACCTTGATATCCTAAAAAGCTGGTGCGTCTGTCTTCTCTATCTTTTGTCCTGGTCAGTTATCCTAACTATTTTGTCTCTGTTT | 231 |
| ST6GAL1_chr3:186782629-186782729 | CTGTGGATTAGTAAACGGGTCCCCACCCCACTCCACAAGGAGAACATCTGCACCCAGAAGTCACTGAGAGAATAGCTGTTGCTTTGGTAGAATTCTG | 232 |
| ST6GAL1_chr3:186782729-186782829 | CCTCTGAGTGGGCTTGTTCTTTTCCCAGACGGAGAGGTCTCCTGACAGCAGCTCTCTTCTTCTTTTCTTTTTTTTTTTTCAGACGAGTTTTGCTCTTGC | 233 |
| ST6GAL1_chr3:186783389-186783489 | CTTCCTGTACCCTGTGGGCCTGAGAGAGAGACAATGGACAAGAAGACCCAGTGGCTTCCTTGGAAGCTTTGTGCTAGCTGGAGAGAAGACCTACTT | 234 |
| ST6GAL1_chr3:186783489-186783589 | CCTATATGCCTAGCAACAGTCCACACTGACTGGACTGCAACCAGGACATTTCCAGATTACTCAGTGGGCTTATCTTGAAATAATAGTTGATGCCATTTG | 235 |
| ST6GAL1_chr3:186783589-186783689 | TTAAATATTATTATATATACCATCTAAGGGTCTTACATGCCTTCTCTCATTGATCTTCATGGCAAACCCTGTGAGGTATGACCACCACCATTTTAC | 236 |
| ST6GAL1_chr3:186783689-186783789 | CTCAGAACTCAGGCTCCCAGAGTTTAAGTTGCTCACAGGAGCCCAGAAAGTAAGCGACAGAGGTGGGATTTGGTTCTAGGTGTTTGCCACCAGCACTTTA | 237 |
| ST6GAL1_chr3:186783789-186783889 | AATCACCCAAAGCTTTCTGGAAGCTCCAACTTTCTTCTTCAAGATACTGAAAGACAGGTATCTGGATGGGTTGGCAGGGCGGGTGGGAGGTGGGCGAGATT | 238 |
| ST6GAL1_chr3:186783889-186783989 | TCCATCACAACAGGGTCTAAAACCAGCAGCGATGGTGAGCTTGGGTGATTTTGATGAACCCCTGCCATACAGTCTATTAATATCATAATTGGAGCTAAAATTT | 239 |
| ST6GAL1_chr3:186783989-186784089 | AATCATGATGGCAATCATGAGTTCTGGGGCTTCTTGATTTGGGCCAGCAGACACAGTTCAGTCACTAGTTCTCCGAATCAGAGAAGGATGCCTTCAGG | 240 |
| ST6GAL1_chr3:186784089-186784189 | CTGTGTCTTCACATGGCTTTCCTCTGTGCGTGGTGGAAAGAGAGAGCTCTGCGGGTCTCTTCTTGTTGTAAGGACACTGGCCCCATTGGATTAGGGCCC | 241 |

TABLE 6-continued

| Name | Sequence | SEQ ID NOs. |
|---|---|---|
| ST6GAL1_chr3:186784189-186784289 | CACCACATGACACATTTAATCCTTAATTACCTCCCTCACAGCCCTATTTCCAAACAGGGTATTAGTCACATTAGGGATTAGGGCTTCAACATAGGAATTCT | 242 |
| ST6GAL1_chr3:186784289-186784389 | GGGGGCACACAATTCAGTCTATAACAGAGGGAAAACAGATTTGAGAGAGAAAAAGTCCAAATATGCACAGTGGTATATCTGAAGATGTGCGTGCGTGC | 243 |
| BCL6_chr3:187460134-187460234 | TCAAGGGCTCAGCAAACGACAACTTAAGCATTTAGAGTCCCATCCCTATCCACCAAACCCAGAGATAAGTTAGTCTTTTCAAGAAAAGCATTGTATAAAAC | 244 |
| BCL6_chr3:187460234-187460334 | CCTTCAAAACTGAAAAGAGAAGAGAAAAGGGGCAATTGGAGAATTCCCACTTTTTCGGCTGTCTCCTTCAAGTCGCCCAGTTTTATGAACAGCATCAGCCTT | 245 |
| BCL6_chr3:187460334-187460434 | ACTGTCACTATCAACAACCCTTAAAACTAGCCAATGCTTCGGCCTCTAGTATTGGAAAGTCTTCCAAATAGGATACTGGAAACTTCTATTTATAAGCTTG | 246 |
| BCL6_chr3:187460434-187460534 | GGGTGGCCGGCGGGCGGGGAGGTGGAGAGAGAGTTGCCATCTACACAGGTTTCTATTTTGGCCTGAAGACTCAACTGCAGTCATTAGAGTAAGGGAATGCC | 247 |
| BCL6_chr3:187460824-187460924 | TTATTTATTAAAACCACACACACCTTGCAAAGAGAAAAGGGAAACTGGAGTCTCTGTAGAGGAAGCCGTGGCATCGCTCAGAGCCACAAACTGTATTTC | 248 |
| BCL6_chr3:187460924-187461024 | TAAACAGCCCTTTCCCTGGTTCCCTCTCTCCTGCCCCACTTTTTTAAAATCCAGACTGTAAAAAACACATCTACTGACACTCACTTACTTTAAAAAA | 249 |
| BCL6_chr3:187461024-187461124 | GAAGAGAAAAGTAAAGCGTTACAAGACTTTCCTCCTGGAAACTATAAACTGAAAAAAAAATCCATAAAAGATTAAAATCCTGGCGGTTGTGGGGTGGCG | 250 |
| BCL6_chr3:187461124-187461224 | GGGGCCGGCGGGAGGGGCGCCGAGTGGAGATTGGCTCTCTGAGGTGGTCAGGGGCCCTGTGACAGCTTGGGACTTTCAGCAGGGTCTTGGGGTCATT | 251 |
| BCL6_chr3:187461224-187461324 | TATCTGCTCAACTGTCAGGACCCCCCCCCCAAACCCCAGCACCCCAGCCAACACACCATCGTAGAAGGGAACACAACAGAGGGTCTTTTTTCATTTTTT | 252 |
| BCL6_chr3:187461319-187461419 | TTTTTAAAAAATCGGTTTGGTTTGTGTTTTTGTTTTTCATGGGGAGCTTTAAAACTCATTATTGCAACATAGTTCCATTTTTCGCCAGGGTTCCAATAA | 253 |
| BCL6_chr3:187461454-187461554 | CAAGACATTTACCACGTCACTACATCCGGCAGCGGGGTGGCCTCCTAGCTCCTGCTGCCCCCGCCCTTTCTCCCCGCCCCGCCCCGGAGCTCAGCCGA | 254 |
| BCL6_chr3:187461554-187461654 | TTTCTGAGGCTCCAACTCTACCCACTCCCTCCCCGGGCCGCGGCCGCCTTCCCCCATTCTTACTCCCTCGAGGAGAGCCACAGGTTGCAAATCCA | 255 |
| BCL6_chr3:187461654-187461754 | ACCAACCTCGCATCTATTTTGCAAAATCACTCACAAAGATCTCCCTTTCGCGCCCCGCCTCCTCCGCGCCGGGTCCCCTCAGCCACGGCCACA | 256 |
| BCL6_chr3:187461754-187461854 | AAGTGCCCTTCTCCTCCTCGAGTCTTGCACATAAGGAACGCGGGCTGGGGCTCTGTTTCGTCTTTCCTCGCCCAAGGTAAGGACCTCGGGAATCTGAA | 257 |

TABLE 6-continued

| Name | Sequence | SEQ ID NOs. |
|---|---|---|
| BCL6_chr3:187461854-187461954 | GCCTGGCGTCCACTACGCTCAGGCCCGAGTTCCCTTTTACAGAGCTTGCACCATGGGAAAAAATAAAA<br>TAAAATTTAGGAAGGAGGCAACAGCCAT | 258 |
| BCL6_chr3:187461924-187462024 | TAAAATTTAGGAAGGAGGCAACAGCCATTGGGAGCCAACACAGAGTCACGCAGCGCCCAAATACAA<br>ACACCGCAGCGCCAGAAATCCCGCCACTT | 259 |
| BCL6_chr3:187462024-187462124 | TCTCGTTCTCCCAGGCTGTCTCTGCGAGGTTCCCTGAGTCCCCCGCACACTGAAAGGCATGCCAGGTGCA<br>GTGCGCACCCCTTTCCCACCCACCCCAAG | 260 |
| BCL6_chr3:187462124-187462224 | AAGCCCTGTCCCCCATCAGTCTCTCTCCTCGGGATGAGCAGGGAGAGCGCGCGGAGGTTCCCGACTCCC<br>TCGACTACAACCAAGAGAAGAATAATTTTCA | 261 |
| BCL6_chr3:187462224-187462324 | AAGTGTTCAACATCCCCGCCCCCAAGTCCCCAAAACACAGGGGCAGGGAACACCAAAACACTCGGCTCT<br>CATTAGGAAGATCACGGCTCTGAAAGGAAA | 262 |
| BCL6_chr3:187462324-187462424 | TAGTAGACACGATACTTCATCTCATCTGATTTATGACCAAAAAAACAAAAAACAAAACCCAAAGAGTTC<br>GCTTGCATTTTTCTTCCAAATCTCGTT | 263 |
| BCL6_chr3:187462424-187462524 | AACAAAAACCCAAAGAGTTCGCTTGCATTTTTTCTTCCAAATCTCGTTCGCTCGAAGGCAGGGAATCT<br>AAAAGACCCGAGGCCGATGGAAGAGCCA | 264 |
| BCL6_chr3:187462524-187462624 | GCCGGGGCGAGCCAGGGCCAGGAGCCGACGGAGCCAAGGAAACAGTTGCAAGCGAGAAGAGGGAAGGAA<br>GGAAGAGAGGCCAGGAAAAAGAGGAGGGAG | 265 |
| BCL6_chr3:187462624-187462724 | GGAAGCGGAGGCCAGGAGCCAGGAGCCGACGGAGCAAGGAAACAGTTGCAAGCGAGAAGAGGAAAAACAC<br>AGCCGCACGAATCCAGAGAGATCACAAGCCGT | 266 |
| BCL6_chr3:187462724-187462824 | ACGCAAGCAGCAGCAGAAAGAGCAGCAGAAGAGCGAGCGCGCGAGCGCGCCTCTCCGCGGTCTGGGGCCAGACAGCC<br>CCCAGACTAGCCCGAATCACCCCCCAAGCAC | 267 |
| BCL6_chr3:187462824-187462924 | TGTCTCGTCCTCTCTGTCTCCGGCCGCCCCCCCCTAATTCCCCCTCCTTCCCTCCTCCACCTCCTTTCCAAAAACC<br>AAAACAACAAGGAGGGTGGCAAAAG | 268 |
| BCL6_chr3:187462924-187463024 | CCTCCCAAACCGGCCGATTCACTCAAGACAACAATAATAATAATAACATAACAATCTATATCCTA<br>TGGTGGAGACGTGGGACTAATCTTCGG | 269 |
| BCL6_chr3:187463004-187463104 | ACATAACAATCTATATCCTATGGTGGGAGACGTGGGACTAATCTTCGGCATTATTTTAACACCTGACA<br>GCTAGAATAAATAAATATACATTTATA | 270 |
| BCL6_chr3:187463104-187463204 | AATAAAATATATACATTTATATCAATAGATACACATAGAAAACTTGGAGCCAAAGCATTTGGCAAGAGCGG<br>AAAAAAAAGAATTAAAAGGTAAAATAATG | 271 |
| BCL6_chr3:187463204-187463304 | ATCATGAGCAGCCGGCGGCGGCACCGGCCACCAGCGGCGCAACAGCCGGCGGCGCAGTAGCAGCAGC<br>GGCCGGCCAACAGCAATAATCACCTGTGT | 272 |
| BCL6_chr3:187463304-187463404 | CCGGCCCTTTCCTAGAAACTTCTTGCATCACCACTTCTAAGAACCCCAGTTCTAAGAATCAACAGAGCTCAA<br>TTCTCGGAATTTGAGCTTCGGACTTTACC | 273 |

TABLE 6-continued

| Name | Sequence | SEQ ID NOs. |
|---|---|---|
| BCL6_chr3:187463304-187463404 | ACTGCTACGTGGCAGGGAGGACTTGGTGTCAGCTCTCCGAGATTTTTACTGCCCCTGGCCAACCAAAAG CCCTCAAAGCCACAAGATTTTTCACTGC | 274 |
| BCL6_chr3:187463404-187463504 | CGGCATATTTCGAGGTCCTCATAAGCAGAGCGTCTCGGATTTGGAGGTTCCGTTCGAGGCTCGAGGGGC CTGAAGGTGGCTCTCCCCTCCCCGGGCCCAA | 275 |
| BCL6_chr3:187463504-187463604 | GACGATGTGTATGGCCTGCTCCCGCCACCATCACGTGGGCTCCTCCTCTGTGACGTCGGCGCCTCGTAG CAAAGCTCGGCCTCTGGAATTCTGAGAAC | 276 |
| BCL6_chr3:187463709-187463809 | GCACAAAAGGGAGCGAGAGGTTTGAACCACTGGGAAAAGTATGTTATATATAGTAGGGTTAGAGAGG CGAGTAAGAGAAAATAAAATAAAATAAACA | 277 |
| BCL6_chr3:187463794-187463894 | AAAATAAAATAAAACATCACAGTCTCTTCCAACTAGAATATTAGGCACCACAGAGAAAAATATTGCCAAGC AGTTTTCCGTGGGGTTCATTTGCTTTATTTT | 278 |
| BCL6_chr3:187463894-187463994 | TATTTAGGACAGGGGTTTTTGCTGTGTGTTCTGGGTTTTTTCTTTCTGGTGTGGCTTGGGATTTTTGGT TTCTGTATTTTGATGGTTTATGGATTTT | 279 |
| BCL6_chr3:187463994-187464094 | TGCTTCTGATTTTTGCCTTTTGCAAGTTGTGGTGTTACGTAAATCACAGGATCGGCATCGGTTGGATTT TTTTGTACGTGCCTTTTCTTTCCCTATCT | 280 |
| BCL6_chr3:187464094-187464194 | AATCCCTCAAGCGTTTAAAGATGTATTATTTCAATACTAATAATACTATTGAAAGAAGCTTAAATTTTTGGCC ATATGTAACAATCCCAGCCCCACTTTTT | 281 |
| BCL6_chr3:187619334-187619434 | ATTATCATCATCACCACCACAACATCCTCTGCCCTGGAGACCAAGAGAATTCAAACAGTCAGCACCTCTAA TGCTGTATAGAACATTGACCCTACTGTCT | 282 |
| BCL6_chr3:187619434-187619534 | CCCAGTTCCTGAGGATGGTGTGATAATAACATCTCAGAGTTCTGTAGTTTCTTCACCACTGTGCAGGTG TGGTTGGTGGGAGCAATGCCCTGGATGGA | 283 |
| BCL6_chr3:187619534-187619634 | TAAGCCAAGCTCTTGTGTCTCCGGCAGATAAAACAAGGTGAACCCTCAATCCGTGTAGCAGGAGTTTCCAGA CAAACTCACTTTGCATGGAAGGACACTAAC | 284 |
| BCL6_chr3:187619634-187619734 | CCTTCCAGGTGCATGGAGAAATATTTGTAGTTTTTACTGTCTCCCCCTTCCTCCACTGCCTCATCTTTTTGT TTTTTCCCCTGTGAGACTATTTGCTCTG | 285 |
| BCL6_chr3:187660817-187660917 | CCTTTCCAACACTGGCCTGCCTTAGGGACTCACCGTTCTACCTTTCGCCGTCGCACTGCACAGGTGGAACTGAGTTCAG ATGAGGGAGAATTGCTTTTCCATTGTTCAG | 286 |
| BCL6_chr3:187660917-187661017 | TAGGCTTTTGTAATTTCTAGTTTTGCTTACCTTTCCTTCCTACTCACCACACACAAAACAGTGTGAGCTTTCT CATTCTAGTGCATAAACACAGGTCGGTC | 287 |
| BCL6_chr3:187661017-187661117 | AATACCCACACAAGTGTTCAAAAGGTGAGCTGGCATTGCTGCCCAACTGCCCCATTATAGTCCCTTCTGTCCC TGCCCATCAGGCTGCCTTCCTCCGCAAC | 288 |
| BCL6_chr3:187661117-187661217 | CTTTTCTAGCTTGAATTGTACTGTGACTCCTTCTCACGGACCACTCCCGGAGACTGGTGAAAGTTGGGCCCA TTCTTGAAGCCTCTGCTTCTAAATCATGT | 289 |

TABLE 6-continued

| Name | Sequence | SEQ ID NOs. |
|---|---|---|
| BCL6_chr3:187661217-187661317 | TTTCCATAAAGTCTCCCTCATGCTGCTTCCACCTTCTCCTATTTGGAATTACTGTGGGCTCTTCCACTGTCCCATAGCAAGTGTTCTATACATTC | 290 |
| BCL6_chr3:187661317-187661417 | TGAAGGCACATTTGAATATATACTTTGTCATGGTTGCTTGGACCATGTCGTCTTTCCAAGTAGGCTGTGAACATTCAGTGCATGGATCATACCGTGC | 291 |
| AC022498.1_chr3:187957432-187957532 | CCCATTGTTCAAAGAAAGGCATTATGGAGTCTCCAAAAGCCATTGGCAGGTGCTGTCTGTGACTTCCTTAGCCTGGAAATAAACAAATAAACAAGCACAA | 292 |
| AC022498.1_chr3:187957532-187957612 | AAACAAATAAACAAGCACAAATTAGAAGTCTTTGCCCTATTACTGCACTATTAGTAGTTGATTGCGCAACATCATGCAAAAGTCACTTTAATTTATCTGG | 293 |
| AC022498.1_chr3:187957612-187957712 | CAGGTCTCTATGTAAACACCAATACAGTCAAGAGGGCTTGGATGGGTATTTGCTTTCATTTCTAATGAAATTTCAGGCCTCTAGGGTAGGATATCAAAATT | 294 |
| AC022498.1_chr3:187957712-187957812 | GGTAGATCATTTGCAATTTATTTTATCCCAAACACCCTCACTTTACAGTCAGAGAGAACTGAGGCCCAGAGAAGTAAAATGAGTTGCTCAAGGTCTCAGAGA | 295 |
| AC022498.1_chr3:187957812-187957867 | ACTGAGGCCCAGAGAAGTAAAATGAGTTGCTCAAGGTCTCAGAGAGCAAGAAGAAATAGAGATGGGACTTGAGCACCTAGAATCTCTGGTATTGCTGTCCTGTA | 296 |
| AC022498.1_chr3:187957867-187957967 | GTTCATGGAGCTGGCAGATGGATACATCTGTGACCTGGGATGATGGAGAGACTGCTGACCCTTCAGAGGATCTCATCCAAGGTGGGGTTTATGTGTAA | 297 |
| AC022498.1_chr3:187957967-187958067 | ATGATATCTGTGTTTCATTTTCCTTTCATAAAACTAATTTAAAAATCCTTTTGGTATCAAATTTTAAGCCAAAAAGTAGTGAGGGGAACATGGGTAGG | 298 |
| AC022498.1_chr3:187958067-187958167 | AATAGCTTACAGCTTGCCTAACAAGGTTGTTGACTGCATAAGAGTCAGGAGTTTGGGTAAGAGTGTGTGTGTGTGTGTGTGTGTGTGTGTGTGTGAG | 299 |
| AC022498.1_chr3:187958167-187958282 | CGTACTGAATTTGACTGCTTATTTTGTAGGGAAGGAACTGATGCCTAGAGTAGTGAGAGCTTTATTCAAACTCATTCCACTGTTATTGAGTAGTT | 300 |
| AC022498.1_chr3:187958282-187958382 | AGGATATTAGACCAGCAACATATTTGGGTAGAAACTTTCATATAAAAAGCTAAATCATAACTATCCAATCATGTCAACTAGTAAGGCTGCTCAGGTGGG | 301 |
| AC022498.1_chr3:187958382-187958482 | ATAACACATCAACCTTCTTTGGGATTCTTCCCTCAGACATGGTTTTGGTGGGAGGAGCATGGCAAGGGAGGGGCGAGCTCCAATGCAGGGCTGCTCTGT | 302 |
| AC022498.1_chr3:187958482-187958582 | CCTCGGCGACCTGAGCAGACACACAGCAGCAGAGATCAGAGATCAGAGACACTCTTAGTGAATGAACCTCCCTATTGGCTATATTAAAGTAATGCTTGAAAAGTTCC | 303 |
| AC022498.1_chr3:187958582-187958787 | TATGTATGCATAGTCTAAAGTGATGATTTTAGAGGTAGCAAGACAGTGAGAATGTCCCTACATGTGAAATGGGCACAGTTTTATCAGGGAAGTGTCAATA | 304 |
| AC022498.1_chr3:187958787-187958887 | GAGGGTTAATGTTCCACCTAGTTGCTCAAGAATGATTAAGTGGTCATGGGATAGCCTGACACTCTAGGAGCAGAAGGTGGTGGGTATGGATAGAACTAC | 305 |

TABLE 6-continued

| Name | Sequence | SEQ ID NOs. |
|---|---|---|
| AC022498.1_chr3:187958987-187959087 | TGATATAGCATGAATCAACCTGCTGTATCTGCGCAGGCCTCTCTGCAGCTGTTTGCCCTGAAGTACATGCTGCTACGTTTCTCCAGCTGATCCTGCATG | 306 |
| AC022498.1_chr3:187959087-187959187 | ACTGGGTATAAACGCCTGTCCGCTGTGTGCTGGACAGCCCCAGACACCCTCGGCAGCCTGCTGTGTTTGTGTGAGACATGCTGTGTTAGGGATTTAAGCA | 307 |
| AC022498.1_chr3:187959462-187959562 | ACAGCTTTCTCATCTACAATGGACAACCTATTTTTAAAGAATCTTCAGAGAGTCGTTGACTTTGTTTATAACTACTACTATATACGTAATTTCAGATGATAG | 308 |
| AC022498.1_chr3:187959562-187959662 | AATTGAAAATTTAACTTGTTTTTCTAGAAAGAGTTTATTTTCCCTATAACTTCAAAGAGTAATGGTGGGGAGTAGGACATTCTGAAAATAAGAGAAACA | 309 |
| AC022498.1_chr3:187959662-187959762 | TGTCAAATGAATTTCTGACTTCCAGCTAGGCATATGGAATAAAGGTCTTTATTCCAGTGACCTCTGCTCATTGGAAAAACTTTGGGCTGGTAGATTTCATG | 310 |
| LPP_chr3:188299217-188299317 | TCTCTTGCATTCTTAACTTGCAATTTAGTACTGTTTATATTCTGCTTGAAGGTTAGAGACATTCGACTAAATGGTCTTTTTCTCCACATTGCTGTCATTCA | 311 |
| LPP_chr3:188299317-188299417 | TTAATGTCCTGGTCCTGACTTTACTCATTGACCACAGGACAAGTGGCTCAACTCTCCTCCTGCCACTACCCAGGCTGTTAGTCCTGTTGGGAGGCTCAGG | 312 |
| LPP_chr3:188299417-188299517 | GCCCAACTCACTCACTCGTAACTCTGTAATCTGCATCTCCATTCAGCTGCAGCCTCCTACAGCCCCTGGTTATACCCTGGATCTTATCATTGCTTCGCTCTATTTTACC | 313 |
| LPP_chr3:188299517-188299617 | TCCTAAATCGTAAAAATTAAAACCAGCTCGGAACACAACCCCTCATTCTTCCAGCACTCTCTCTCATTCAGGTAACTCCTATTCTACTTTTCTTCAGCA | 314 |
| LPP_chr3:188471412-188471512 | TTGTTTTTTTTACTTTACCTTAATTCTCTTTTTGACTAAGATGTTAAAATGTTCTTAATGTGACTGTCTCCGAAACTGTTTTGTCTACCACTCA | 315 |
| LPP_chr3:188471512-188471612 | TCCTAGTGCAGTCATTGATCCTTCTTTCTGTTGCGAGTGTTTGAGTGTGTGAGTGTGTATATGTATTTGTAGAGGAAAAACAAGAGAGAGG | 316 |
| LPP_chr3:188471567-188471667 | TGTGAGTGTGTATATGTATTTGTAGAGGAAAAACAAGAGAGGGAAACAGACATTGGAGCCACCTTTCCCCACTAGCCACGTACCTGTTGAACCTTC | 317 |
| LPP_chr3:188471667-188471767 | AAGCCTCTCATAGAATCAGATATACACAAGCACAGTGACAGCACATGTCTCCTACAGTCCAGCTTTTAAGATATGATAAAACTCTTGTATTCACA | 318 |
| LPP_chr3:188471767-188471867 | GAGCTAAATGGCAATAACCATAGGAGATTGCATATTGCTACATTATGTAAAGACCAGAGTCCCAAGAAAATAGTGAGAACTCAGTTTGATGTATGATGTGA | 319 |
| LPP_chr3:188471867-188471967 | TATGTGATATCTTACTTTACATGGCTAACAGTTGACATTCTTTGTGGATTCTATATTGTCTAAGGCTACAGAAGAGCCATATGATAAATTCATCGGCAAC | 320 |
| N4BP2_chr4:40198810-40198910 | CAGTGAAAAGGCTTGGGCCGCTTTGTTTTCCCTGCTTTGTTGAACAAATTTGATTTCCGAGTCAGTCATTTTACTGTCAAGACATTTCTTCGGCAT | 321 |

TABLE 6-continued

| Name | Sequence | SEQ ID NOs. |
|---|---|---|
| N4BP2_chr4:40198910-40199010 | TCTGCAACAGGTAAGGATTTGCTTCCTTAAAGTATTTCTTTGGTGTCAAAAGAAATTTTCTAATTTTATTTAGCTTTACTCTAGGCCAAACATCGT | 322 |
| N4BP2_chr4:40199010-40199110 | AATGACTTCTGAGCTACCTGCTGTAAGGTGTAGAATCAATTTACAGGGGACGGGGTCGGGGGGTGAGTGTTGCTTTGATATTCACTGCCCCTCACCAC | 323 |
| N4BP2_chr4:40199110-40199210 | AGTCCTAACAAGATTTTGAAACATGAAAAGTTACAAATAGTTGGCTTTTGGTTTTCCAGATATTCTAGAGAATGCATATGCTTGTGACTGTGGCTGAGC | 324 |
| N4BP2_chr4:40199210-40199310 | TCAACTGTATGATGGGTAGTTTAAATACTACCAAGGTTTGATGAAGTAAATCTAAAGATGCTCTAAGTTGTGCAAATATGAATTTTAAAGTTGTCTAGTTCA | 325 |
| N4BP2_chr4:40199310-40199410 | GAAAAGAAACAGAACCGAAGTCTAAATGATGTAGATTTCAATCTGGAATTTCTAGCTTGTGTTTTTCACCTATTGCCAATGTTAATGACCATTTCCCAAA | 326 |
| N4BP2_chr4:40199410-40199510 | AGTGCTCTATGATGTATAACATGTATTTTTAATTAAATTTAATCTTTCTTCTGAGGTGGTTTGATTTGGAGATATGCTACGAGGTACCAGTCAGTAGCC | 327 |
| N4BP2_chr4:40199510-40199610 | TGAGTTGTAACTAAACAAAGTTTGGGAAATCACCCGGTTTTAGGTGTGCTTTACTAAATGAAAGTTGCCATTGACGTATTCAAGCAGGCAACAAGTAGTTGT | 328 |
| N4BP2_chr4:40199610-40199710 | GTCCCCCTTATTGGTTCTAAGCTGGTGCCGTGGAGGATATAAAGAGAAATATTTTAAAAATCTCTACTTGAAGGACCCCTATAATCTGGTAGTTGTGATAAG | 329 |
| N4BP2_chr4:40199710-40199760 | TTTAAAAATCTCTACTTTGAAGGACCCCTATAATCTGGTAGTTGTGATAAGAAGTAAAATTTAGGAAGCAATGCAAGATGAGAATTCAGTGATGAGTGGGG | 330 |
| N4BP2_chr4:40199760-40199860 | CAGCACAGGCTTGAAGAGTTCTGAATTCCATGGAGGGGGCCTGGGGCAAACTGGAGTTGTCAGGAAGATCTGGGCTTTGGAAGAGAATGCGAAGTGTCG | 331 |
| N4BP2_chr4:40199860-40199960 | GTAGAAGGAGAAGGGGCAGGTGCGATTTCAGACTGGGAGGAGGACCTTGTGGGCAAAGGCACAAAGGCGAGACTGACCTGGAGATGATAAGGCCAGTTGAAGAGA | 332 |
| N4BP2_chr4:40199960-40199990 | ACATTGCAGGAAATCAGATTAGACAGTTAGGGTGTGGACACAAAAGCGAGGACCTTGCAGGCACTGGGGAGAAGTGACCCCATTCAATAGTCCTTGGTCT | 333 |
| N4BP2_chr4:40199990-40200090 | CCTTCTGCCCTGCCTCGCTTCCTCCGGCTCTCCACGGCACCAGCAGAATTCCATGTGAGAGGGAGCTTGTCGAGCGTTGGCCTCTTCCCACTTGGGGCTG | 334 |
| N4BP2_chr4:40200090-40200190 | CTTTCTGCATCCCTGTGCCTGGCTGTGGGCCTTCCATTTGCCCTGCTCTTCCCTTAGGACATCATTTATGCAGAGAAAGGTTCGTGTGGCTCGGGGT | 335 |
| RHOH_chr4:40200505-40200605 | GGACGTTGTTTAGAGAGTCAGTAGATCAGTAGTCATAATAATTCAGACACTTTTTTTCTGGACCATAAAATATCTGAACCCATATAATAACAAACATACAGCACGGT | 336 |
| RHOH_chr4:40200605-40200705 | GAATAAGAACCAACTTTTGAGCCAGATCACTTTGCATGGAATCCCCATTCTATCATTCTATCATTTCTGGGCTGTGGGAACCTCAGACAAGTTACTTAA | 337 |

TABLE 6-continued

| Name | Sequence | SEQ ID NOs. |
|---|---|---|
| RHOH_chr4:40200705-40200805 | CTTCTTCAATGCTCAGATTAAAAAAAAATTCACAAAATATCTCTAATAACAGTAATAATAACTGAAAAT ACCTACCTCAGAGGGTTGTCGTAGAGATCA | 338 |
| RHOH_chr4:40200730-40200830 | AAAATTCACAAAATATCTCTAATAACAGTAATAATAACTGAAAAATACCTACCTCAGAGGGTTGTCGTAGA GATCAAATGAGATAAAAATATGTAAAGCAT | 339 |
| RHOH_chr4:40200830-40200930 | GTAGCCTAGTGCCTGACTGAAAAAAAAATCTCCAATAGATGCAACTCTTATGATTCTTATTAAGGACTTG GCTATTGCCACAAATGAAGGTGTTATGAG | 340 |
| RHOH_chr4:40200930-40201030 | CCCTGGCTTAAGAGCAAGAAGCCTGCAAAGCTAACTCTTCCTAATCCCAACATTCCTTTCCAGGGAAAGTA GGGTGACAGGTGAGGCTGGGAATTAACGT | 341 |
| RHOH_chr4:40201030-40201130 | TTTTTGAGCACCACCAAATATGGACAAGGCACAGGGGTTGGGTGTTTTCTAGTGAGAATACATATGAAAGAA GGAAAACAAACTTGGAAACCGCTATTTTAA | 342 |
| RHOH_chr4:40201130-40201230 | GCCATTTGGTAACAGTTTCTCTAGCTTATGAGATGAGAGAGGTTCCTCCAGTATCCGCTGCATTACTTGTG GGCCTCCTTGGTTGACGTCGCTCTCTGAA | 343 |
| RHOH_chr4:40201230-40201330 | CGCTTGGGGTGGAATTCTAGAGTGCTTTTCATTAGAGGCAGAGAGCATGATGACCTTTCTTCCTTGCCCAGTT TAAATTAAATTATTTATCTTACAATGTG | 344 |
| RHOH_chr4:40201330-40201430 | TTAATTTTAGTGCTAGCAAGGCACAGCTAAAATTCCATTTCTACTTAGGAGTGGGGATCATTGTGGCAGT GAGTGCTTATTTGGGTTTGGGATGCTTGGA | 345 |
| RHOH_chr4:40201430-40201530 | TCTGGGTGAAAGCCAGATTAAAAAGCATCCTCCTTCCCCATTCCACTCTCTAGGTTATAAATATTTTTTT GGATTAAAAGCCTCCTTTAAAAAAATGCA | 346 |
| RHOH_chr4:40201530-40201630 | AATCCACCTGGCATGTTAATTGTGCAGGGGATTCCTAATTATGTGCAGATGACGTGAGTCACACGGTG ATAGTGTTCCTTCTAGAGTCCCACTGTGT | 347 |
| PABPC4L_chr4:134727698-134727798 | ACTAGGCCTTCATCCTGTGTAATTGAAAAATATGTCACACGTGGTGATGAGAATCTATTTGAGGAACATG GGCAGTTTGAAATATATATGCAATGTATG | 348 |
| PABPC4L_chr4:134727798-134727898 | ACTAGTTTATATAATAATGAAAGGAAGTATTTAAAAGATAGAATGACATAGACTAATCTAATTGAGAATAT GAAAGTCTAACAGAAATGATTGCTTGTGAA | 349 |
| PABPC4L_chr4:134727898-134727998 | ATTTTATGAGAGAAAATCCACAGATAAATTCTCCACCTTGATCTATGTAATCCGAAATTTAGATGTTAAAAAT ATGTTGATTCTGAAAATTTATATTTATTC | 350 |
| SLC38A9_chr5:54964698-54964798 | TTTGGTATGAATAGGTCAAAACAAGTCACCATTAACTGACAGGAAGCACAGAGATTCTCAATTTAGTTTTG GCAAAGACATTATTTTATAAATATGAGTTT | 351 |
| SLC38A9_chr5:54964798-54964898 | TTAAATGATTCTTATGAAGAAACTAGCACCAAAGTGACCACTCTGCAAATAACTCCCAGCTTCTCTGA ATTTCAAAAGCAGCCACTAAAATTATTAG | 352 |
| SLC38A9_chr5:54964898-54964998 | CAAATCAATTTAGCTCAGAAAGCATGAATTACAGAAGTAAATCTTTAGGTACAAAGTAGACAGCTGACACA CATGTAGCATATACACACTAGTGATCTGCC | 353 |

TABLE 6-continued

| Name | Sequence | SEQ ID NOs. |
|---|---|---|
| ZNF608_chr5:124079827-124079927 | TTCCTTCTTTTACCAACATAGAGTTTCCCATGAGCCCTGAATCCGGGGCACTTTTGCTAACTTCCCCTGCAG CGGCGACGCTGCCACTCCCAGTGCCCCG | 354 |
| ZNF608_chr5:124079927-124080027 | CAGTGGAAGGGGCTCGCGCCACCTCCATTGCTTCTTGGCCCCAAAGCCATAGAGGTGCCCCCGGAAGGGG CCTGGCTGCCACTGCCATTCTGGTGGCCCT | 355 |
| ZNF608_chr5:124080027-124080127 | GAAGCAGGTCGTGCTGTTCCTTCCTGGATTTCCCCGCATCCTTATCCCGCTTGGCGCCTCGGCTGCTCTGG CTTTTACCTGGCTTCTCTCCTCTTTGCTTTT | 356 |
| ZNF608_chr5:124080127-124080227 | CCCACAGGAGCCTGCCCCCCGCGTGGGGCGGCAGAGGTGCTGGTGCTGGTGCTACTATTGCTGTTTGGGTTGCCG CTGCCGCCGCTGCTCACACTTTGACCCAGC | 357 |
| ZNF608_chr5:124080227-124080327 | GCTGAATTCATGCCAGTTGCCTCTCCAGGGCGCCCCTTGGACTTCCTGCCTCTTGCCAGTGCTGCTGATCTC GGGAATCCCATACAAGGCAGCAGAAGGCA | 358 |
| ZNF608_chr5:124080327-124080427 | GAGATTTATTAGCATCCTTAGAAGTTTTACTCCTTTTCACTTTTGATTTGCTGGTCTCTTTGTGTGAATTCC CCTGGGGAGCAGAGGCTGAACAGAAGC | 359 |
| ZNF608_chr5:124080427-124080527 | AAATTTTAGGCCATCAGCTAAGCTGCGTAGACACCAGCCCCACTGAGGGCCGGACTCCACAATCCTTG GAGTTGCTACTAGTGGTGGTGGTGGAA | 360 |
| ZNF608_chr5:124080527-124080627 | TTATTCATCTCAAATTTCTGTCTTTCTCCAAATCAGCCGTCCAAATCAATTATTAAATTCCAACCCCG ATTTCCCAATCATCGCCCACTGTCATAAG | 361 |
| ZNF608_chr5:124080627-124080727 | TATCAACTGTATTTGGATCCACACCTTTCCTGCAGTAGAAATGTTCACTGACATCCTGAAGATGAGCTCT CTAGAATAAAAATCCGATGAACTTTTCTT | 362 |
| EBF1_chr5:158527642-158527742 | TTCCTCAGGAATTTGAGCTGGGGATCTGCATCCTGGGCCATTGCAGTCTCTTTAGCATCCTCGCCGCCCCTG AGCGGCGCTGGAGGCTCGCAGGCTGCGCC | 363 |
| EBF1_chr5:158527742-158527842 | TCCCAGGGCTGCTGATGCCGCGTCCTGCTCCGCCGTTCTGGGACTGCTCGGGGGACAAAAGTGGAGGAGACGGGA GAGCCCGGGCAGAAAAGCAGGAGCGCGCGTC | 364 |
| EBF1_chr5:158527842-158527942 | CCAGGTGCCCACCTCTTCGCTTTGAGGCGGGGCGGTGGGATGGAATGGAATATGGGTGCGCGAGGTCGGGGCTG GTAACTCTCGGAGGGGCACGGCCTCCACGC | 365 |
| EBF1_chr5:158527942-158528042 | TGGGAGGGATGAATGAACGCGCTGGGCCTGGGCCTGCCAAATGAGGCGCTGTGGGTCCCCAGGAAGTGGGGTACCA GGCTCTACTCCCACCCCGGCCTCTGAAACGC | 366 |
| IRF4_chr6:392760-392860 | GGCCAGGAGGGGTGGCGGCTGGGTGGGAGAGAGGGTGCAAGACGAGCGGCGTCGGGAGCCTTTG GGCTGCGGGTGCGTTACAGGAGAGCAGGCGG | 367 |
| IRF4_chr6:392860-392960 | GTAGGAGGCCTTCGCGGGGCCGAGCTCGGAAGGCGGACACGGCTGTGCCCGCCCAGGGGATGCGCCGGGC CGGCCCGCGAAGGTGCCTTCTTCCGGGGCCC | 368 |
| IRF4_chr6:392960-393060 | GGACGACCCTGACACGCACGCGCGCCCTTCCGCAGCCTCAAAGACTCCGGGGCCTCGTGGTCACTGGCGC AGGGGATCGGGGCGGGGTGCCCGGAGTGCG | 369 |

TABLE 6-continued

| Name | Sequence | SEQ ID NOs. |
|---|---|---|
| IRF4_chr6:393090-393190 | CCCGCAGTTGCAGAGCAAGAGCGGCGGCGAGGACACCCCGGGCGCGGGCGCCGACGCGCGCGGGCATGAACCTGGAGGGCGGCGGCCGAGGCCGAGAGTTCGG | 370 |
| IRF4_chr6:393190-393290 | CATGAGCGCGGTGAGCTGCGGCAACGGAAGCTCCGCGGAACTGCTGATCGACCAGTCGACGCGGCAAGTACCCCGGGCTGGTGTGGAGAACGAGGAG | 371 |
| IRF4_chr6:393290-393390 | AAGAGCATCTTCCGCATCCCTGAAGGACACGCGGCAAGCAGGACTACAACCGCGAGGAGGACGCCGCGCTCTTCAAGGTCTCCGGCCTCGGGAGCCGGC | 372 |
| CD83_chr6:14117992-14118092 | CCCGCGCCCACAGTCTCTGCAGCTCGTGCAGCGGCGCAGCGCTCCAGCCATGTCGCGGCCTCCAGCTTCTGTCCTGAGCTGCGGTAGGGCTCGCGA | 373 |
| CD83_chr6:14118092-14118192 | GGGCCTGTCTCGCCCTGTCGCCCCCCGCCCCTCCACGACACCCCCTCCCGTCGTCGTTGCTCACGACGCGCTCTCTCTTTCTTGTAGCCTACAGCCTGG | 374 |
| CD83_chr6:14118192-14118292 | CTCCCGCGACGCCGGAGGTGAAGGTGGCTTGCTCCGAAGATGTGGACTTGCCCTGCACCGGGAACCATCTCTCCGCAGGTTCCCTACACGGTTCCTCTGGGT | 375 |
| CD83_chr6:14118292-14118392 | CAAGGTAGGTGCTGCGATACCCACGGGCTGCTCTCCCGCAGCTGAACTTGGAGTACACCCAGCCTCCCGTCGCGCCTCCCCCACCCCCTAGGCGTGGCGACCCCTCGTGTGCGCCA | 376 |
| CD83_chr6:14118392-14118492 | GGTGGGGGCGAGGGGCGTCTCTCCCAGTACAGGGCCGAATTAGCATCCGCATCCAGGTACAGGGCCGAATTAG | 377 |
| CD83_chr6:14118492-14118592 | GTTTTGCTCTCCCAGACCTCAATCCCCTTCCTGTCACTGAAGGTGGCTGAGATGATCCACTTAAGATGTTTTGGAAGGGCAGAGACTCTCATTT | 378 |
| CD83_chr6:14118592-14118692 | GGATTAATTCTGGAGGCCACCTGGTTGTGGCCAGCAGGTCAGGAAGAAAGCAACAGGGACCTAGATTTGGGCATTGGACAGGGGGAATGTCTCCAGA | 379 |
| HIST1H2BC_chr6:26123614-26123714 | CTCTCCAGTTCCTATATTCTAATACCCCTCCGCCGCCAAATAAAATTTGGCGTCTGCCCACAGCTCTTTTAGTGGTATCTGGGTGGCTCTTTAAAGAGC | 380 |
| HIST1H2BC_chr6:26123714-26123814 | CTTTGGGGTTAGGTGTTAAGACGCTTACTTGGAATGTTTACTTGGAGCTGGTTGTACTTGGTGACGGCTTGGTGCCCTCCGACACGGCCGTGCTTGGCCAG | 381 |
| HIST1H1E_chr6:26156649-26156749 | CTCCGGCCCCTGCCGAGAAGACTCCCGTGAAGAAGAAGGCCCCCAAGTCTGCCAGGTGCGGCCAAGCGCAAAGCGTCTGGGCCCCCGGTGTCCGAGCTCAT | 382 |
| HIST1H1E_chr6:26156749-26156849 | TACTAAAGCTGTTGCCGCCTCGAAGGAGGCCAGCGGCGTATCTTTGGCCGCTCTCAAGAAAGCGCTGCAGCCGCTGGCTATGACGTGGAGAAGAACAAC | 383 |
| HIST1H1E_chr6:26156849-26156949 | AGCCGCATCAAGCTGGGTCTCAAGAGCCTGGTGAGCAAGGGCCACCCTGGTGCAGACCAAGGGCACCCGGCGCTGCGGGTTCCTTCAAACTCAACAAGAAGG | 384 |
| HIST1H1E_chr6:26156949-26157049 | CGGCCTCTGGGAAGCCAAGCCTAAGCCTAAAAAGGCAGGCGCGGCCAAGGCCAAGAAGCCAGCAGGAGCGGCGAAGAAGCCCAAGAAGGCGACGCGGGGC | 385 |

TABLE 6-continued

| Name | Sequence | SEQ ID NOs. |
|---|---|---|
| HIST1H1E_chr6:26157049-26157149 | GGCCACCCCGAAGAGAGCGCCAAGAAGAGACCCAAAGAAGGCGAAGAGAGCCGCTGCAGCTGCTGAGC CAAAAAGCGAAAAGCCCGAAAAAGGCGAAA | 386 |
| HIST1H1E_chr6:26157149-26157249 | GCAGCCAAGCCAAAAAGGCGCCAAGAGCCCAGCGAAGCCCAAGGCCAAAGCAGTTAAACCCAAGGCGGCTAAA CCAAAGACCGCCAAGCCAAGGCAGCCAAGC | 387 |
| HIST1H1E_chr6:26157249-26157349 | CAAAGAAGGCGGAGCAGCCAAGAAAAAGTAGAAGAAGTTCCTTGGCCAACTGCTTAGAAGCCAACACACC CAAAGGCTCTTTTCAGAGCCACCACCCGCTC | 388 |
| HIST1H1E_chr6:26157349-26157449 | TCAGTAAAAGAGCTGTTCACTATTAGGGGGCTGGCTCGGGAAAAACGTGCTAAGCAGGCTGGGGTCT CCCGGACAAAGTCGGGGAGAGGAGTGGGA | 389 |
| HIST1H2BK_chr6:27114004-27114104 | CTCCTTAGCCAGATCGATTACAAGCACTGCATTACTCAGTGTGATAAGATCATGATAATCCCTTTA AAAAGATCGCCCGAATTTAAGCCTGGATT | 390 |
| HIST1H2BK_chr6:27114104-27114204 | AGGAACACGTGTTTACAGCTCTAATATCGATAATTTAAGTGGCTCTTAAAAGAGCCTTTGGGGTTGGGCT TTAAGACGCTTACTTGGCAAGTTTACTTAG | 391 |
| HIST1H2BK_chr6:27114204-27114304 | CGCTGGTGTACTTGGTGACGGCCTTGGTGCCCTTCGGACACGGCGTGTTGGCCAACTCCCCGGGCAGCAG CAGGCGCACGGCCCTCTCGATCTCCCTGGA | 392 |
| PIM1_chr6:37138284-37138384 | CCCCGGCCTTCTCCGGTCTCTGCGGCAGCTCCTCTGCCCGACCATCCTGGAGGTTGGGATG CTCTTGTCCAAATCAACTCGCTTGCCCAC | 393 |
| PIM1_chr6:37138384-37138484 | CTGCGCGCCCGCCCCTGCCAACGACCTGCACGCGCCACCAAGCTGGCGCGCCCGGTGAGAGCACCCCCGCCTCC GGCCCGGGATGCGGGGCCCCTGGCGGATC | 394 |
| PIM1_chr6:37138484-37138584 | TCCTGGGTGGGAGCTGGCGGCTCGCGGGCCGGCACTGAGTCCCCGTGCTCCCCCTTTCCTAGGCAAGG AGAAGGAGCCCCTGGAGTCCAGTACCAGG | 395 |
| PIM1_chr6:37138584-37138684 | TGGGCCCCTACTGGGCAGCAGCGGCGGCCACGGGCTGCTTCGGTCGTCTACTCAGGAGATCCGCGTCTCCGACAACTTGCC GGTGAGTGGCCCCCGCGGTGGGAGGGC | 396 |
| PIM1_chr6:37138684-37138784 | GCGCCGGGCGGGGGGCCATCAAACACGTGGAGAAGGACC CAGGTGGCCATCAAACACGTGGAGAAGGACC | 397 |
| PIM1_chr6:37138784-37138884 | GGATTTCCGACTGGGAGAGCTGGTGAGTGCCCTGCAGGAGCCCACCCCCAGGATGAGTGGGTGGGTGA GGGGCGCCCCCGACTCCCGCCTAACGCGGC | 398 |
| PIM1_chr6:37138884-37138984 | CCCCTCGCCCCTGCCAGCCTAATGCACTCGAGTGCCCATGGAAGTGGTCTCTGAAGAAGTGAGCTCG GGTTTCTCCGGCGTCATTAGGCTCCTGGAC | 399 |
| PIM1_chr6:37138984-37139084 | TGGTTCGAGAGGCCGACAGTTTCTGTCCTGATCCTGATCCTGGAGAGGCCCGGTGCAAGATCTCTTCGACT TCATCACGGAAAGGGGAGCCCTGCAAGAGG | 400 |
| PIM1_chr6:37139084-37139184 | AGCTGGCCGACGCTTCTTCTGCAGTGCTGCAGTGCGCCACTGCCACAACTGCGGGTGCTCCA CCCGACATCAAGGACGAAAACATCCTTAT | 401 |

TABLE 6-continued

| Name | Sequence | SEQ ID NOs. |
|---|---|---|
| PIM1_chr6:37139184-37139284 | CGACCTCAATCGGGCGAGCTCAAGCTCATCGACTTCGGGTCGGGGCGCTGCTCAAGGACACCGTCTAC ACGGACTTCGATGGTGAGCCAGGCCCGGGA | 402 |
| PIM1_chr6:37139284-37139384 | GGGAGCTGCCCAGTGACTCGGCCCGCCCCGGCGCCCAGTCCGGAGGCCTCGGCCAGTCCCGCGCCAGCC TTTTGTAAAGGTCATTGGGCGCCTGGCTC | 403 |
| PIM1_chr6:37139384-37139484 | GATGCTAGCCGGGGTGGGACAGGAGAGCCTCCCAGCGTAGTAAAGCCGGGATTTTCAGCCAGCTGA ACCTGTAATGTTTCTGCATGATTTATTCT | 404 |
| PIM1_chr6:37139484-37139584 | TCAAGTGGAATTCAGTTAGTTCCAGGCTTTCCCGATGAATAAGAGGTTGTGGGCAACCGGCGTAGCCCA GATTTTCTAAAGTCTGACCCAGTTTCCCC | 405 |
| MAP3K7_chr6:91004618-91004718 | CTCTAAACAGACAAAAGCAAAATATCTCATTAGGCATCATCTCCGCCAAGGTTCCCACTAGGCAGGAAAG GATTTTTATCTAAAGTAATTACCCTTTTA | 406 |
| MAP3K7_chr6:91004718-91004818 | GTTAAATACACTCAACAGATGAAATTTACAGAGAGTGAGAGACTGCAGCACTAGAGCGAAGGTGAAA ACCAGGAACGCGCGTCTCGCCGCCCGCGGG | 407 |
| MAP3K7_chr6:91004818-91004918 | CCCGCCGGAGACTGCGGGTCCGTCTCGCGGGTGGGGCGCGCCCCGGTCTCCCTCTCGTTTCCTGGAGGCCACA GGTCACGGCGACGGCGGTGACCGGAGAGC | 408 |
| MAP3K7_chr6:91005793-91005893 | CGGGTCTGACAGTGCTGCGGCTGCGCGGACGCGCGCCTCCTGCAGCCCGCCCCTCCCCATGCCTGACTT ATTACTCCTGCTCCTCCTCCCTGCTGT | 409 |
| MAP3K7_chr6:91005893-91005993 | TCCAAAACACCCTTCGACGCCAGCAAAATACAATGCCTCGGCCGCCGTAAACAGCCGGAGGGAGAG CACACATTCGGCGCGGCCGGCCGCCGGCTC | 410 |
| MAP3K7_chr6:91005993-91006093 | GGCTCCCACCCCCTTCCCGTTCCATGCTCTCCTTTATACCAAAACTGTAGCCTCGAAGAGCTCTCAGGCTTACCTAT GCCCGGGCCGGCCGGGGCTCCCCTTCCCGCGCC | 411 |
| SGK1_chr6:134493732-134493832 | TATGAAACAGCAGTGCTACGTCTCCTTTATACCAAAACTGTAGCCTCGAAGAGCTCTCAGGCTTACCTAT AAACGATGTTCAGTGAATGCAGTAGCCC | 412 |
| SGK1_chr6:134493832-134493932 | AAGGCACTGGCTATTTCAGCAGCATAGAAACGAGCCCGTGGTTCCAGGAAGCAGCGTTCCCTCTGGAGAT GGTAGAACAACTGCAGGAGACAGAACAAAG | 413 |
| SGK1_chr6:134493932-134494032 | TCATTCTGGGTTGCAAATGCAAATTAATTAGTTTTGACATACACAGCAAAAGAACAACTGCAGGAAGTGGC CCCAAGTAATCTATTAACTATAAACCTGAC | 414 |
| SGK1_chr6:134494032-134494132 | AGGTTGAAGGAAATGCTAATTCTGGTAACATTCTCCCCACCAAAAAATCTTTGAAAACTTTTTTCTCAAACT AAAACAAAGCAGGCTGTGCAGAGACACTA | 415 |
| SGK1_chr6:134494132-134494232 | AGAGTTGACTTCTATCCCCCCTGCTCACCTCTCCACCATTAATGTAGTCTAGGACAAAGTACAATTGTCA GCAGTCTGGAAAGAAGAAGTGAAGGCCCAC | 416 |
| SGK1_chr6:134494232-134494332 | CAGGAAAGGGTGCTTCACATTCTTCAACAGAACATTCCGCTCCGACATAATATGCTTCTCCTAGGAAAT GACGATTCAGATTTAGTGCATGTTTCAAC | 417 |

TABLE 6-continued

| Name | Sequence | SEQ ID NOs. |
|---|---|---|
| SGK1_chr6:134494552-134494652 | GAGGACATGAAGGAAGTGTACCAAAAGATCTTCAGATTTGAAATTACCTTTCCAAAACTGCCCTTTCCGATCACTTTCAAGAAGTGAAAGTCAGATGTT | 418 |
| SGK1_chr6:134494652-134494752 | TAGCATGAGGATTGGACGACGGCCAAGGTTGATTTGCTGAGAAGGACTTGGCTAGAAAAAAAAAAAGAATTTCTTTTAATACCATTGCTTCAAAGGA | 419 |
| SGK1_chr6:134494722-134494822 | AATTTCTTTAATACCATTGCTTCAAAGGACATCTATAACATAAACGATGTAGAAAATGTTACATCTACAAATGACTGATGCAAATGACCATACATC | 420 |
| SGK1_chr6:134494822-134494967 | AATAAAATAATACTCTGACTCAATACTTAAAATATTTATATCACTTGTTATGCCATAATGAAGCATTCCTGCCTTGATACTAATTTCTAGAAATGCTATTT | 421 |
| SGK1_chr6:134494967-134495067 | TAATCCATTAATGTAGGAATAATAACTGACTCCCTTACAGTTCTCCACAGATGCACGGCACATACAAAAACTTACTGGAGGAGAAGGGTTGGCATTCATA | 422 |
| SGK1_chr6:134495067-134495167 | AGCTCAGGCTCCTCGAGGTTGGGAGATCTTCAAGATGGACTGAACTTCAGGGCTGCAGGGAATAAAGGGCACGATTTAGAATCCAGCTCGCCACTAGGGGG | 423 |
| SGK1_chr6:134495167-134495267 | CACACCACATCAAAAGTGAGTTTCTGGCTCTACGACTTCTACCGACTTCTACCCCGATAATTCACTGTTTAAACTGAAAATACCCCAATACATTAGTCAGTTAAAGAA | 424 |
| SGK1_chr6:134495267-134495367 | AATAATAAACCCATTAAATACAGAAATAAGGATTGTTGCTCATGGAGAAAGGCCGTGAATTCGGCCAACACGAACCATTTATCTTACATCCAGTTCA | 425 |
| SGK1_chr6:134495367-134495467 | AGCCAAATCAGCACAAATTAACTTTAATGTTTAAAATGTCAAATATTAGAATTTAAGGAGAAATGAGATCCCCACCCCAGAAGAGTCTTCGCCTTCC | 426 |
| SGK1_chr6:134495467-134495567 | CGATAAAACGCCGTGATGAGAAATGTTTACCGCTGGCAAATTCAAACATTCAAACTACTAGTTATTTCCTCAAATCCGGTCAAACTTACTGTTTGCATGCATAGGAGT | 427 |
| SGK1_chr6:134495567-134495667 | TATTGGCAATCTTCTGAATAAAAGTCGTTCAGACCTAATCTGATCCGGGACTTTCAAAAAATTTCCACTTTGCGTCTCCTGGGGAGAAATAAAGAAACGTTTAGACGGCTT | 428 |
| SGK1_chr6:134495667-134495767 | CATAACGTTCCGGCGCGCCACACACTAATCTGATCCGGGACTTTCAAAAAATTTCCACTTTGCGTCTCCTGGAGCAGAAGTCCCCGCAAGATTCCTGCACTC | 429 |
| SGK1_chr6:134495767-134495867 | ACCGATGAGAATTGCCACCATGCCCCTCATCCTGGAGTAAGTGAGGGTGCCCTTAGCAGCCTCAGTTTTCACCGTCATCACCGCGGGGACAGAAA | 430 |
| SGK1_chr6:134495867-134495967 | GACGTTAGCGCTCAAAGACCGGCTCGGCGTATGCGCCAGGCCGTCGGCGCTCGGCCTTATAAAAAGGCACCGCCCGGGGGCGGGGCCTGCGCGACAG | 431 |
| PLEKHG1_chr6:150954420-150954520 | AGGGTGAGGAGGAGTCACCAGGTAAAGATGGGTTGGAAGGACCTGGCAGCAGGAGCAGGACCCCAGTCCAGGGCAGCAGGGAAGCGGGAGTCTG | 432 |
| PLEKHG1_chr6:150954520-150954620 | GGCAGAGCTGATTCCAGGCAGCTCAGTATTGCTGGCCTGTGCATCCTGAGACTTATCCGAGTCGCAGGTGAAGCTGGTGGGAATCAGGCAGAGTGCAGAG | 433 |

TABLE 6-continued

| Name | Sequence | SEQ ID NOs. |
|---|---|---|
| PLEKHG1_chr6:150954620-150954720 | CTTTAGCTGGGGCAGGGTTAGCCAAGAGCCTGTCATGGAGCTGCTCTCTGGGCACTGGAAACATAAGTCTGGAGGCCTTTGGCTGCAGCTGCAGATAAAG | 434 |
| PLEKHG1_chr6:150954720-150954820 | ATGCCAGGGCCCTCGACGATGGGGCCTTAGTCATCTCAGAGGTGGTGCAGAGGGTAGAGCCTGACTGGGGTCAGAGATGAGGAGGAGAGGGTCAGAA | 435 |
| PLEKHG1_chr6:150954820-150954920 | ACAGTGATTCTAAACCATTTGTTGAGGCAGAAGATACTAAATGGCCAGGAGTGCTAATGGGGAGAGAGGGAGCGTAGGCTCTAAAGGGGAAGCTTGTTAGGAATGA | 436 |
| EZR_chr6:159238415-159238515 | AGACAGAGGCGCAGGCACAGCCCTTTCATCAGCTGACCAGGAGTGCTCGGCCCGGCCTGCCAGGAACCTCTTATCAAACTCCACCGGCTGCCTGCATCTA | 437 |
| EZR_chr6:159238515-159238615 | CAATTCAAGTCCATGGCTAACCTTCTGTTAGAGACAGAAATTCTGCTGCAGCCAGCAAGTTTGCTGGTGTACAGGGCACCCGCTTTCATGGGCCTTAGTAGGA | 438 |
| EZR_chr6:159238615-159238715 | AGCGAAGCTGAAAGGCAACTTCCGAAAGCCAGTCTCTCCTCCCCAAACGCCCTTTAATATCTCCCCAGTTGGATCTGGGGCGCCTGTGGTTTCGGACCCTT | 439 |
| EZR_chr6:159238715-159238815 | AGGAGCTCTGAGAACTGTGTGTGGTGCGGAAGCCATCTGAGTCTCCCTGTGATTGGACTTTTTAAGAAACTTCTAAGTTGTATTACTATACCCTTTA | 440 |
| IMMP2L_chr7:110545276-110545376 | TTCCCTGTCATATGACTTCCATCCTAGCACTTCAGCACTACACAATATTATCATTAATGTTTAAATCATTGTCAAGTCTGTGATTGCCTTAGAGATTTATTAAGAAATA | 441 |
| IMMP2L_chr7:110545376-110545476 | ACATGCTAGGATTAGGAAAGTTTAACTTTTTACCATCCTTAAAATTAGATTTTGAAAACTGTCTTATCCCCATTAAAGAAAAAATAAAAGATGAAT | 442 |
| LRRN3_chr7:110697971-110698071 | TATACATACCTGCACATATATCAGCACATATGTATATGTCTGTATTATATGTATTAAATGAAAGATTATCCACATTTGTTCTTTAGGATCTTCAGCAG | 443 |
| LRRN3_chr7:110698071-110698171 | CTCTCTTCCCATCACAATAGAAAGGCCTGAGCTAACATTTCCATTTCTGCAAAAGGCAGATTTTGTTCAATTAAAATTATAATGCCTTAAATTTCCACA | 444 |
| LRRN3_chr7:110737411-110737511 | GACATTTAAGAGACTTCGTTTTCACTGTGATAAACAGGTTTGATTTGGACTTATAACTTTTTCTAAAATTATCAAATTAATAACGACTATAATGAAATA | 445 |
| LRRN3_chr7:110737511-110737611 | GAGGCAAATATTTTAGAGGATTCATTCCTTGGGGTAACATTTGTTCTATAATTTATAGTCTCATAATGTTGAGAGATTAAAGCATTTAAATAACATTGTC | 446 |
| LRRN3_chr7:110737611-110737711 | AACTAACTTCAGCTTACCTTTCTTAAGGAAAAAAAACAAAAAAATGTAAAAAAATAGACATGTATTTTCAAACATACAATTCATGTTTTTATGTCATTA | 447 |
| LRRN3_chr7:110746681-110746781 | AAGAGATGTGAGGGACTTATAAATAATTAAGATAACAGGAATTAAAGTCTCGGTGTGTGAAAATACTGTATATCTAGGATGCCACATAAAAACTGCCCT | 448 |
| LRRN3_chr7:110746781-110746881 | TACAGATCTTGCAGGGAAAGTACCTGACTATACTGTATAAGACTTCGTCTGCTACCATTTAATCATACCAAAAAAAATGAATCAACACCAAATAGATT | 449 |

TABLE 6-continued

| Name | Sequence | SEQ ID NOs. |
|---|---|---|
| LRRN3_chr7:110746881-110746981 | TCTTTTCCACTGTTCTCAATTTAAAAATAATTGGAGAAATGTGCTTTGTTTAGAAGAGTAAAGGAAAAC ATTCATTCAATAGTACCATGCAGAATGAT | 450 |
| KMT2C_chr7:151943421-151943521 | CAGAAAAATAGAAGATTATCATCGGATTTGGGAATCAAAGACAGCTCAGCAAAATACTAGGACATGGC TCATATAAGATGAATAAGCCTGGAAATACA | 451 |
| MYC_chr8:128750367-128750467 | CTTTAGGGGATAGCTCTCAAGGGGAGAGGTTCGGGACTGTGCGCGCACTGCGCGCTGCGCCAGGTTTC CGCACCAAGACCCCTTTAACTCAAGACTGC | 452 |
| MYC_chr8:128750467-128750567 | CTCCCGCTTTGTGTGCCCCGCTCCAGCAGCCCTCCCGGACGATGCCCCTCAACGTTAGCTTCACCAACAGG AACTATGACCTCGACTACGACTCGGTGCA | 453 |
| MYC_chr8:128750567-128750667 | GCCGTATTTCTACTGCGACGAGGAGGAGAACTTCTACCAGCAGCAGCAGAGCAGAGCTGCAGCCCCG GCGCCCAGCGAGGATATCTGGAAGAAATTC | 454 |
| MYC_chr8:128750667-128750767 | GAGCTGCTGCCCACCCCGCCCCTGTCCCCTAGCCGCCTCCCGGCTCTGCTCGCCCTCCACGTTGCGGT CACACCCTTCTCCCTTCGGGAGACAACG | 455 |
| MYC_chr8:128750767-128750867 | ACGGCGGTGGCGGGAGCTTCTCCACGGCCGACAGCTGGAGATGGTGACCGAGCTGCTGTGGAGGAGACA TGGTGAACCAGAGTTCATCTGCGACCCGGA | 456 |
| MYC_chr8:128750867-128750967 | CGACGAGACCTTCATCATAAAACATCATCAGGACTGTATGTGGAGCGGTTTCTGGCCCGCCGCCAAG CTCGTCTCAGAGAAGCTGGCCTCCTACCAG | 457 |
| MYC_chr8:128750967-128751067 | GCTGCCGGCAAAGACAGGCAGCCCCGAACCCCGCCACAGCGTCTGCTCCACCTCCAGCTTGT ACCTGCAGGATCTGAGCGCCGCCCTGCCTCAG | 458 |
| MYC_chr8:128751067-128751167 | AGTGCATCGACCCCTGCGTGGTCTTCCCCTACCCTCTCAACGACAGCAGCTCGCCCAAGTCCTGCGCCTCG CAAGACTCCAGCGCCTTCTCTCCGTCTC | 459 |
| MYC_chr8:128751167-128751267 | GGATTCTCTGCTCTCCTCGACGGAGTCTCCCCCGGCAGGGCAGCCCCCGAGCCCTGGTGCTGCTCCATGAGGAG ACACCGCCCACCAGCAGCGACTCTGT | 460 |
| PAX5_chr9:37024919-37025019 | GCTCCCCATCTGTCCCCACAGTTGCTCTTGGCTGAGCCAAGGGCTTGCTCACCTCTCAGAGACATTGCCCT AACTGGTTTGTTTTGGGCTTACATTGCAA | 461 |
| PAX5_chr9:37025019-37025119 | GATCAGTTCCTCCCCAGAGCCAGGCTGGAGTCCGAGGCAGAAAAGGCTGTGGAGGGCACTGGGGTCACC ACAGACTGGAAACCGGTTGGGCGCAGGCCCC | 462 |
| PAX5_chr9:37025119-37025219 | AAACCTTGAGGAATCGTTTGGGCTGGGACCAGAACACAGGGGGCTTCCTCTGCACAGAGAGCTCCCACCCGTTT GGTGGATTACTTCAGACTCAGAAAATTGAC | 463 |
| PAX5_chr9:37025219-37025319 | ACAAAGAGAAACTGACCTGCCCGCAGCCAGCCCTGGCTGCCTACACAGAGCTTTCCCCTGCTTGCCAGCC ACTCAGCACTGCCTGGCAGACACGGACATG | 464 |
| PAX5_chr9:37025319-37025419 | CTCGCCCCGGAAGCTCACCTTCACTCCAGCCGGGTCTCTGCTGCCTTTGTTAAATAGGGGACCTGCGGCT AGGAAAGCTGGATCCCAGGCTGTTGGGAT | 465 |

TABLE 6-continued

| Name | Sequence | SEQ ID NOs. |
|---|---|---|
| PAX5_chr9:37025419-37025519 | GGGGGGAGCGGGGTGGAGGACCAGGCATGGGGACGGCTCCTAGCCCGGGAGCAATCCCTGACCTGAAGCCCGAGAGACCCCGAGCGGCACCCGAGC | 466 |
| PAX5_chr9:37025519-37025619 | CGAGGCTGCCGAAGCCTGTCACCTTCCTCCAGCCTGGCTCTGCAGCAAACAGAAAGGAAACGCGATTCGTTCCACTTGGAATTTCCTTGAAATCTCCGAA | 467 |
| PAX5_chr9:37025619-37025719 | TCTAATCCGGCGTTAACTCACCGTGAGAGGAGCGCTCATCTCACAGGAGGCTGTGGTAATGGGTGAATTGGCAGGATCCCTGCGGGCCAGGCAGCCAGGC | 468 |
| PAX5_chr9:37025829-37025929 | TTTTCGTTTCTTTATCCTCTTTTTTTAAAGGGAGAAGCCATGAGAAAAGGCTCCTGCAGAGAAGGACCCCAATGGGGTCTTTAAGGGTCTCTGTATGAAC | 469 |
| PAX5_chr9:37025929-37026029 | TGGCCGGCTCCTAAGCAGAAGTGAACTGAGAAACCGCTACTTCCTTGATTTTTCAAAGCCCCCTCCTCAACTCCAGGACGCCTTTGGAGCCCTTAGCCCC | 470 |
| PAX5_chr9:37026269-37026369 | TGTCGCCCGCCGGAGCCTTGAAAGGCTCAGCTCGCTGCCCAAGCTACCGCGTTGCCGAGGCGGGATTCCCAGTGCCTCAGCCCGGGCGGCCAAGTGCGT | 471 |
| PAX5_chr9:37026369-37026469 | TGTTTCAGGTCCCCTGGGATCCCTGGAGAGTTAGCTGCGCGGCTGCAGAGGTCCGAGATCCTTCCGGCCTTAGTACCTGCTTACAGTGTATTTC | 472 |
| PAX5_chr9:37026469-37026569 | CGGCACCCCCAACCCGGTTCCCGGGAGAGTTGAAGAAGCAGCTCGCCGCCTCCCGGCGCCAAGGGCTGCCCAGGGCGTGCAAACGGTCGTCGTGCTTACAGTGTATTTC | 473 |
| PAX5_chr9:37026569-37026669 | CATCGGGGCGCTCCAGACTGCAGGCCGCCGCCCACCCGCGGCTTCGGGGTCTCTCTCAGAGCCTCCCTGCTGGAGACCGATAGGGAGCTCGCGCCACCAGGCCAGGCAC | 474 |
| PAX5_chr9:37026669-37026769 | TGTGCGAGCTGGGCTCAGAAAACACTGCTGGAGCTTCGGGGTCTCTCTCAGAGCCTCCCTGCTGGAGACCGCCCGGAGCTGCGCGGAGAGGCGGGAAATG | 475 |
| PAX5_chr9:37026769-37026869 | GTGCTAGCGCACCCGGGCTTCGGGGGCATAGCGTAGGGGCCCCGCCTCCGGGACAGCCAGCAGCCCCGGGCAGCTCCGGCCCCAGCCCGGGGTAGCTGC | 476 |
| PAX5_chr9:37026869-37026969 | GGCCAAGCGCCCCGCGCTTCGGGGGCATAGCTAGGGGCCCCGCCTCCGGGACAGCCAGCAGCCCCGGCCCCAGGAAGGAGCAGCTTTGAGGAGGCCGC | 477 |
| PAX5_chr9:37026969-37027069 | CGGAACAATCGGCCCCTTGACTTCACTCAGGGGCGGAGAGACCCGGGGCTGCCAGGCTGGTTCCGCGGCCTCGATGCTTCTGAGGTCCCTCCTCGACCC | 478 |
| PAX5_chr9:37033619-37033719 | CACACAGGCAAACAACTTTTGGACACAAACTCATATATTTTACATCTTTTAAAAATACATATACTGTAATGAACACACTGAGTCCCTTATATAAACACA | 479 |
| PAX5_chr9:37033719-37033819 | CAGGCCCTAACTTGCAGACCCCCGGAAGGACGCCAGCGTGAACATTCAGAAACAGAGAAAAACACAGACAAACTCACAGATATTTGGACTGATGCAGAAG | 480 |
| ZCCHC7_chr9:37293169-37293269 | ACAGTTTGAAGTGTGAGCCTGAACATGTTTGATCTAAGGTCTGGAGGAAGATGTGAAGCAAATCTGACCTAAAAAAATTATAGGAAAAAAGCAAATTGT | 481 |

TABLE 6-continued

| Name | Sequence | SEQ ID NOs. |
|---|---|---|
| ZCCHC7_chr9:37293269-37293369 | TCTGGATTTGTTCTTCACCAAGGACAAGTAAGCAGAGAACCAGACACTGGAGAAAAAAGGAGTCAGGAAGTAGACAAGGAAATGTTAAAAGAAATATAG | 482 |
| ZCCHC7_chr9:37293369-37293469 | GATAACTGAAAGAATGTAGCTTCCAGATTGCTTAGCTATCAGCAGATAGATAGAAACTTTTATACAGCCTTTAAATCTTCCCTAGAAACCTTTTAAAGT | 483 |
| ZCCHC7_chr9:37371494-37371594 | CAAGGGCCTGCCAGGATGAGAACGGGCAAAACCTGGCCAAGGTGACCCTAGGGACTACCCCTCCTAGGGACAGCACTCAGGGCCGTTCCCAATCACCCC | 484 |
| ZCCHC7_chr9:37371594-37371694 | GGATTTCCTGCTGTCTGTCTGCTCCTGCCACACCTCCTTTTGATCTACCCCCAAGACACACCCCTACCTTTTTATTCTGTGAAAATTTACTCATGCTGTGGGC | 485 |
| ZCCHC7_chr9:37371694-37371794 | CCTGCTGGAAATGCCCTCCTACTGTTTCCCCAAACCCGTCAGAAATTCCACGGGAAACTCCCTTCCCTTCTGCTGCAGGCACCGTCACTGTGTCTCTC | 486 |
| ZCCHC7_chr9:37371794-37371894 | AGCTCTGCCCCCCAGCCTCTGAGTCTCCAAGGCTCTGGGTCCTCAGAGGTCTCAGACTGGCTGAGTACTGGGGACCAAGGTCACGTTCTCAGCCTCCCACAGAAGCCTGGGA | 487 |
| ZCCHC7_chr9:37384684-37384784 | AGGCACACTCGCCCCCTGTCTCTCCAAGGCTCTGGGTCTGCAGTAGGCTCTCTCCCCCTGCCCCAGTCCACCGTCACTCAGACCAAGAAGCCCTAAACAAACGCTGCAGGTGA | 488 |
| ZCCHC7_chr9:37384784-37384884 | TTAGCAGAGCTCTCTCTGTCAAGACAGGTCAGGCTCTCGTCCTCCCCTGCCCCAGTCCACCGTCACTCAGAGGAGTGGCCTAAACAAACGCTGCAGGTGA | 489 |
| ZCCHC7_chr9:37384884-37384984 | GGCTCCCGAGCCCTGACATGATGTTTATGAAGAGGACTCTTGGCATCAGCACCTGGGCAAGGTGGGTAGAGGCAGGAGTGGGCAAATGGGAAAGTCT | 490 |
| GRHPR_chr9:37407369-37407469 | GGAGAGCCGTTTGAGATTCACCAGGTGAATGAACCCCCGGTTTTTTCTGGGTAACAGTCGAATGTGAATTACTTATTTTCACAAGCTCTTGACATGTTC | 491 |
| GRHPR_chr9:37407469-37407569 | CGTCAAATTGCTGTTCCCAAAGAGTCGACTCTGGTGACATATAAGTGTGTGGGACCATTGCATCTTACCCCAGAGATCCACTCCTGATCTGGCATTATT | 492 |
| GRHPR_chr9:37407569-37407669 | CAAAATCTGCTGAATTCAAAACGATCCTGTACTTCCTGCTCACCAGGTCTGAAAAGAAAAAAGAAAAAAGAAGAAGGAAAGACTACACCTGACAAAAGAC | 493 |
| FAM208B_chr10:5755066-5755166 | TTCACGGTTTCTTCTTTAGTTTATCTGAAATACATTTGTAAGCTTAGGGTGCAATTTGGATTAAAACAGTTTTCTTTAGTGTCAATAATGGCCTTTACTA | 494 |
| FAM208B_chr10:5755166-5755266 | GAGTGAATGGATATTTTTCCATTCTGGATTATCGTTTAATCGAAACTTTGTTTCCTGTGGAATTTTTCTGGTTTAAGTTATTTGATTTGGGAGATAAAT | 495 |
| FAM208B_chr10:5755266-5755366 | CATGTAACTTAATAAACTTTGGCATCCTGGTTAACTGAAATTGCTTCATTCAATATTTGAAGACTGAAATCTGTATTGTTGCCTGTACCTAAATTATGGG | 496 |
| FRMD8_chr11:65190342-65190442 | GGACAGACAGGAGGAGATGACTGAGTTAGATGAGACGAGGGGCGGGCTGGGGGTGCGAGAAGGAAGCTTGGCAAGGAGACTAGGTCTAGGGGGACCACA | 497 |

TABLE 6-continued

| Name | Sequence | SEQ ID NOs. |
|---|---|---|
| FRMD8_chr11:65190442-65190542 | GTGGGGCAGGCTGCATGGAAAATATCCGCAGGGTCCCCCAGGCAGAACAGCCACGCTCCAGGCCAGGCT GTCCCTACTGCCTGCCTGGTGAGGGGGAACTTGA | 498 |
| FRMD8_chr11:65190542-65190642 | CCTCTGGGAGGGCGCGCCTCTTGCATAGCTGAGCGAGCCCGGTGCCTGGTCTGTGTGGAAGGAGAA GGCAGGAGGAGGTAGAAGGGGTGGAGGAGTC | 499 |
| SCYL1_chr11:65266552-65266652 | GGGGCAGGCGGGAGCTTGAGGAAACCGCAGATAAGTTTTTTCTCTTGAAAGATAGAGATTAATACAACT ACTTAAAAAATATAGTCAATAGGTTACTAA | 500 |
| SCYL1_chr11:65266652-65266752 | GATATTGCTTAGCGTTAAGTTTTTAACGTAATTTTAAGATTTTAAGAGAAAAATATGAAGACTT AGAGAGTAGCATGAGGAAGGAAAAGATA | 501 |
| SCYL1_chr11:65266752-65266852 | AAAGGTTTCTAAAACATGACGGAGGTTGAGATGAAGCTTCTTCATGGAGTAAAAAAATGTATTTAAAGAA AATTGAGAGAAAGGACTACAGAGCCCCGAA | 502 |
| SCYL1_chr11:65266852-65266952 | TTAATACCAATAGAAGGGCAATGCTTTTAGATTAAAATGAAGTGACTTAAACAGCTTAAAGTTTAGTTT AAAAGTTGTAGGTGATTAAAATAATTTGAA | 503 |
| SCYL1_chr11:65267397-65267497 | TTGGAGAGTATAGAAGATAGAAAAATATAAGCCAAAAATTGGATAAATAGCACTGAAAAAATGAGG AAATTATTGGTAACCAATTTATTTAAAAGC | 504 |
| SCYL1_chr11:65267497-65267597 | CCATCAATTAATTTCTGGTGTGCAGAAGTTAGAAGTGTAAAGCTTAGAGAATGAGGGTGTTACGTAG ACCAGAACCAATTTAGAAGAATACTTGAAG | 505 |
| SCYL1_chr11:65267597-65267697 | CTAGAAGGGGAAGTTGTTAAAAATCACATCAAAAAGCTACTAAAAGGACTGGTGTAATTTAAAAAAAA CTAAGGCAGAAGGCTTTTGGAGAGTTAGAA | 506 |
| BIRC3_chr11:102188381-102188481 | TGGTGTAAGAGATGTGCCAGCGGCTGGCCGAGGGCCTTAGGGCTAGAGCCCGGGCGCTCAGAGT TGAGAGTTCAGTGGGTGGGGCCAGTTATCAA | 507 |
| BIRC3_chr11:102188481-102188581 | ACACCAGGGCCCAAAAGCAGGCTCTAGATAGTTCCAGGTAGTTCCAGGTGCTGCTCAATTTCTATTCACGTTTGGAGTGAG CCAGTGGAATTGTGAAGTTGTGCATTTTG | 508 |
| BIRC3_chr11:102188581-102188681 | ATTCGGTTGCCAAGAGTTATCACTGGGCCTTTGCCAGGTGCCAAATAAATTTCAGGACAGAGCCTAAGCA GAGCTCTGGCACAGGAAGGAAGTAAAACGT | 509 |
| BIRC3_chr11:102188681-102188781 | TTAATGAGCAAATGGACCCATGTTTCCAAGCGGTGGTAGGAACGGCTAGGAAGACAGCAGTTTTTGTGTCTTCCTGGT GATCAGCAGATGGAAACCTAGTAGTGCTCTTA | 510 |
| BIRC3_chr11:102188781-102188881 | CTCTGATCAATACATTGTCGAAGGCATGCATCCTGATGCTAACGGATTTACATGTAACACATAATATATTTTACGTTTAATTATCATAATC TTGCTATTATTATTGCTAACATTAAGTA | 511 |
| BIRC3_chr11:102188881-102188981 | CTGCTACCTGCTATGTGCTAGGTTTGTCTCTGAAGACTTTACATGTATTTTTCACGTTTAATTATCATAATC TTAAGAACCAGTACCATAATTATCTCC | 512 |
| POU2AF1_chr11:111249311-111249411 | GGGAAAAAGAATGACGAAAGGCAAGACGAAGTGAGCAAGTGAGGACACGCTTCACCGAGCCAGATCTCCA CTCCTCCCAGGGTATCCACAGGGACAAGTCA | 513 |

TABLE 6-continued

| Name | Sequence | SEQ ID NOs. |
|---|---|---|
| POU2AF1_chr11:111249411-111249511 | CACCTGGCAGAAAGCTAAGTCACTCAGTAGAAACAGGCCCAGGGAATTCAACAGAAGGCTGAAGAGCCACTGCTTATGGAAATAAAGCCCCTCCTGTAA | 514 |
| POU2AF1_chr11:111249511-111249611 | AGAACTGCATGGCTTTTCCCTCCCAACCCAAACCCCAAACCCATCTGGCTTTTGTTGTGTGAATCATAAACTGCCCTTTCTTCACCCAGTGATTCATG | 515 |
| CXCR5_chr11:118754793-118754893 | AATCCTCTCCACTGTGATCTGTAAAATCTAGACAGTCAGTCAGCTCCCGCCCTTTAAGAGTTTATTTTCCATTCTGTGAAGAAGCAGATAAGGAGA | 516 |
| CXCR5_chr11:118754893-118754993 | GCTGCTGTCCTTAGGAGACATCCTTTAGGAAGCTGAAGACACGGGTTCAGGCCCTGCATCCTCCTCTGAGTTGCTATGTGACTGGGAACAGGATACT | 517 |
| CXCR5_chr11:118754993-118755093 | TCACCTCTTCCATTCTTTCTCTCCTTTCTCTTAGGGTCGGAATATGAACTAGACAGGAAAGTACTTTGAAGGTTTTCTTACCGTAAGGAGGCTGGCATT | 518 |
| ETS1_chr11:128391383-128391483 | GGGCCCTCCACCCAGCTTCAGTTCTATGGGGGACGTGGAGTCAGGCGATGATGTCCTCGAGGCAGCGTCCATCTCCCCTTAACATTAAGGAATAAGGCC | 519 |
| ETS1_chr11:128391483-128391583 | AGAGGGTTCTCGCTCATTTGGGAAATAAAAAGCAGGAAATGGGGCGCTGGAAATTCTATAAGCTTTTCCCCACACTCACAAAAACACAGCTGTGAAA | 520 |
| ETS1_chr11:128391583-128391683 | ATAAATACCACACCCCCCAAACCAGGGTCTAGGGCCACCAACAGTCTCCTCCTCCTCCTCCTTCTCCTCCTCGTCCTCCAGATCCAGCTGCCAA | 521 |
| ETS1_chr11:128391648-128391748 | CCTTCTCCTCCTCGTCCTCCAGATCCAGCTGCCAACAGCATCCCCGCTCCTGAAGAAATGCACCGCCCAGAAGGGAACGGGAAAGGGGAAGAAGTCC | 522 |
| ETS1_chr11:128391748-128391848 | AGGGGACCCCCGGCCTCTGGCCCGAGAGCTTGGGTGGGGGCCTCGGCCCGTCGCCACTCACCCGGGGAGGGGAAAAGCTCCAGATCGACTTTTTCCGTCTTG | 523 |
| ETS1_chr11:128391848-128391948 | ATGATGGTGAGAGTCGGCTTGACGCTTGAGATCGACGGCCGCTTCATGTGCCAGGAGTGGGGACGTACGGGATGGTAGCAAGTTTGCAGTTACTGTGTTTTTC | 524 |
| ETS1_chr11:128391948-128392048 | TTTTTAATGAGAGATTAGTAACAGGGGGAAGGGACGGGGGAAATCCGACTTTCTTCCCAAAAATCTCAAATTCCCGCTGCCTTTCTTTCTTCCCCGCGCCCG | 525 |
| ETS1_chr11:128392048-128392148 | GACGGTGCGCGCGCCCGGCACTCCAGGGGAAGTTGGCACTTTGCGCGAAGTGACGCGCTCGGGTCCCAGCCTCGCCCGCGCCGCGCCCGCTCCTCCTGCC | 526 |
| LRMP_chr12:25205888-25205988 | GAGTGAGTAGCAAATATTCATTTATGACCCAGTTTTTGTCCACCCTGGCAATATTGTGGGGCTTTCAGAGGATACAGACATTTTTCTAGATTACAGCTAGGATATATT | 527 |
| LRMP_chr12:25205988-25206088 | CCTGAGTTTATGACAATGAAATGGTTGAAGAGGCAATATTGTGGGGCTTTCAGAGAGGTTTGCTGAGTGGCTAGGTGCATGGGTTTAACCATTAA | 528 |
| LRMP_chr12:25206088-25206188 | CTTCCCTTTTGCCTTTTATTATAAGCTGGTTTTGTCTGTGGCTGTTTTTCTTTTAAAATTAATTAAAACTTCTCAAAATTCTAAAGTAAACAAG | 529 |

TABLE 6-continued

| Name | Sequence | SEQ ID NOs. |
|---|---|---|
| LRMP_chr12:25206398-25206498 | GCATTCTCTACATACATCTACATACATATTTGCATTTTAAAAATTGAATATTTGTCATTTTTCTGTATTACCCAAAAGTATATAAACAGTTACCAGAG | 530 |
| LRMP_chr12:25206498-25206598 | ATTTATGTGAGAGACAGTTGTCACATTACAGATGTCAGATTAGCTATAAAATTGTTTCATTCTAGAAACCTAATATGTAAAAATAAACCTTACTTATT | 531 |
| LRMP_chr12:25206598-25206698 | TAGCCATTTATCAGACACAATTGCTTTTGTTCAGCCAGTTTCTTGTTCTTAGCAGTATAAATATTCTTTTTATAGAAAGTTACTTGTTTGAGAAATAAACAT | 532 |
| LRMP_chr12:25206698-25206848 | ATAAGCTTAAGGTAGGCTAGAGATGAAAAATTTCAGACTTGTGTTTGTTTTGATTTATTGTACCCTTTCTACTATTATCTGAGAAAGCTATTTAGGAGT | 533 |
| LRMP_chr12:25206848-25206948 | TTAAGAAATAGTCTAGTTTTAAAATAGCAATGTTTGCCGGACACAGTGGCTCACCCCTGTAATCCCAGCATTTTGGAGGCCGAGGTGGGCAGATTGCT | 534 |
| LRMP_chr12:25207088-25207188 | GAATTGCCAGTTTTCAATATTCTGATTCACTCTGTTAAGCTAGTAAGGCAGTCTTTAAATTACACAGTCTGTGTGTTATTTTACTACTGCTCAGAGGGC | 535 |
| LRMP_chr12:25207188-25207288 | ATTGGAGAGAGGTTCCCTTGTGATTAGAACTGTTCATGTTGAGACATGAATCATAAGGCATTCCAAAGTTGGTTTAAGGTGTGTCGCTTTAGACACTGTG | 536 |
| LRMP_chr12:25207288-25207388 | CCCAGGACTATTCTTTTGCTCCAGTTTGCCTTTTGATTAAATCAATATTATACCTGAGTTTTATAAACTACTAAGAATTTGTTCCCCTTCCTCACTGTG | 537 |
| LRMP_chr12:25207388-25207488 | ATTTTCTTGCAGTATTTCTTAGAAGAGTCAACTTTAATAACTTACCCCAAAGTGCACGTCTTGATATTATGAACTTGCTATTGTTGTCTTCCCAGTTT | 538 |
| BTG1_chr12:92537875-92537975 | TATTGTAGTTTTTGGAAGGGCTCGTTCTGCCCAAGAGAAGTTCCTCCTTACAGCTGATTCGGCTGTCTACCATTTGCACGTTGGTGCTGTTTTGAGTGCT | 539 |
| BTG1_chr12:92537975-92538075 | ACCTCCTCGTGGTGAGGCTTCATACAGCACACAGATGGAGCCATCCTCCCAATTCTGTAGGACACTTCATAGGGGTCAACCCAGAGTGTGAGTTCACTT | 540 |
| BTG1_chr12:92538075-92538175 | GGGAGAAGCCTGAACAGCTCCTGACTGCTCAGTCCAATCCGCTGTGCCTGTCCAATCAGGAGGATCCATTTTATGGTTGATGCGAATACAACGGTAAC | 541 |
| BTG1_chr12:92538175-92538275 | CCGATCCCTTGCATGGCTTTTCTGGGAACCAGTGATGTTTATAATGTCTATAGAAGAAAGAAGAACAGAGAAACACGCTTAGGATCGTTAGCTCCCA | 542 |
| BTG1_chr12:92538275-92538375 | CTGCGGATTCCTCCTACCCAGCTCCTTTGAGGAGCGAAAATGAAAACTATCAACTTTTAAAATGTCCAGGATTGCATCCGTTGTTGTGCATGTGCGG | 543 |
| BTG1_chr12:92538375-92538475 | GGATGCGAAAAAGCGGGCAGGGTTTTAGAAATAACACAGTAGTACCGGACAAAACAATCTCCAGGAACCAACCGGTTGAGCCGCCAAAACAGGAATCAGGC | 544 |
| BTG1_chr12:92538475-92538575 | GCGCAGCCTCGGCCAGTCGGGAAGCCACTGGCACCTATGGCCAGGCGAGAAACTGTTTACTTTCTCCACCCCACCCCAGATGCACACAATGGAGTTGATG | 545 |

TABLE 6-continued

| Name | Sequence | SEQ ID NOs. |
|---|---|---|
| BTG1_chr12:92538575-92538675 | GCTTTGGAGATAGAAGCGCCACCGGACTGTTAACCCCGAAGGGAAGAAAAACAAGCAACCCTAAACCA CGCTCTGGGCAGGGCTGTTAATTGTGCCGGT | 546 |
| BTG1_chr12:92538790-92538890 | ACGCAACGGTTGAGGGGGCTGAGGAAAGGGACGTCGAACCACCCCAGCCCACGGCTCCTTTGTCCC CAAATCCGCCGACGGTCCTCGGACCGCAGC | 547 |
| BTG1_chr12:92538890-92538990 | TCCCGCTTCGGTGCGCTTAAGTTTCTTTGTGCGTGTTGTCTTCCTCCGTTTTGCCAGCTGGGGGG AAGGGGCGCCCTCCGTCCAGCCCCTAA | 548 |
| BTG1_chr12:92538990-92539090 | AGCCTCGCGGGGAACCGCTGTTAGCGGCCACCCAGCGCAACCACACCGTCCCGCGGCGGGGCCCAAGC GCGACCCGGCCCCGGGGCGCTGCCGAGGTTCC | 549 |
| BTG1_chr12:92539090-92539190 | CGCAGCCCCGACGGCCGGACTCTGACCCAGGATGTGGGGCCCGGCGTCCCTCCGACCGCCCTGCCCTGCT CACCTGCCAGCTCCTGCAGGCTCTGGC | 550 |
| BTG1_chr12:92539190-92539290 | TGAAGGTCTGCAGCTGTCGCTCCTCGTGAGCCCCTTGGTGCCGGAGAAACTTGGAGATGAAGGACACGGC GGCGGCGATCTCGCCTATCATGTGGCGGC | 551 |
| BTG1_chr12:92539290-92539390 | CCGGGTGTAGAAGGGATGCATGGGGCGGCGTGCGGGGGCGGCGTGGGGCTCGGCGCGC GGCCCCGACGGCCGGACAGCCACCCCGGGCT | 552 |
| DTX1_chr12:113495364-113495464 | ACGCCGACACCCCCTCCCCGCGTTCTGCGCGCCCAGGCCTTCCAGGACACCGTGAGAGGGAAAAG GGGCAGGGACGCCCCCCTTCGCAGGAGCC | 553 |
| DTX1_chr12:113495464-113495564 | GTCGGAGAAGGGGCCCAGACGGAGGAGGCGAGAAGCCCACTGAAGCCCCGTGTCGGGGAAGAGGGACC CGCAGTTGGGAGTGCAAAGGGCTGGCTGAGAG | 554 |
| DTX1_chr12:113495564-113495664 | CCGCAGGAGCAGCAGGCCTGGGCCCAGGCCTCCTGGGTGACAGGCCCAAGGACTTTAGAGCTGTTTCCTCC AAGAGACAACACCGAAGAGGCTGGACCTCGA | 555 |
| DTX1_chr12:113495664-113495764 | ACAGGGGCGGCTGCCTCACTCCCTACCTGAGCCAGCCAGCCCGAGGGGGCCAAGGACTTTAGAGCTGTTTCCTCC GGCATAAGAGAGACACTTGCTTTCCAGGGC | 556 |
| DTX1_chr12:113495764-113495864 | AGCAACCCTTTATCGGAGAAGGCTCTACAGGGAAGGGGTCTCTTTGCAGCCTGGGATGGCCATCCCACATTCCT TTAACGGAGGTCTCTAGGCCTCAGAGAGAA | 557 |
| DTX1_chr12:113495864-113495964 | CCCAGAGTTAGAAAGGAGGCCAGACGTCCTTGCTGTCCCCCGGGAGAGGAAGTTGCCCCTGCTG CCAGGCCCAGGAGGAGCTGGGCCTGCAATA | 558 |
| DTX1_chr12:113495964-113496064 | GTGGGGGACCTGCCCCTGAGGCAGTGCGGCCATGTCACGGCCAGGCCACGTGGGCTGATGCCTGTG AATGGTCTGGGCTTCCACCGCAGAACGTGG | 559 |
| DTX1_chr12:113496064-113496164 | CCCGGGTGTGGTGTGGAGTGGCTGCTGAATGAGCACAGCCGCTGGCGCGCCTACACGGCCACCGTGCCA CCCACATTGAGAACGTCGTGAAGGAGGACGC | 560 |
| DTX1_chr12:113496164-113496264 | TCGCGGTTCCGTGGTCCTGGGCAGGTGGACGCCCAGCTTGTGCCCTACATCATCGACCTGCAGTCCATG CACCAGTTTCGCCAGGACACAGAGTGAGCAG | 561 |

TABLE 6-continued

| Name | Sequence | SEQ ID NOs. |
|---|---|---|
| DTX1_chr12:113496264-113496364 | ACACCCACCCATGCCACCCGCCCCGCCCCGGAGCCATCACTACCTTGCAGCGTAGGATGCTGAAAATCCCAG TAAATCTGCTGATGCCAAATCCCTTCCCA | 562 |
| DTX1_chr12:113496364-113496464 | TCTCCCTGCCTCACCTCCAGAAAAAACAGGGCAGTCTAACCTTGTCCAGTTTAAGACTTGGATTCCAATGCA GCCTCTGAGCAAGCTGTAGGGCCTTGAGC | 563 |
| DTX1_chr12:113496509-113496609 | GGGTAGATCAATATCTCCACAGCTGAGTGAGGATTAAATAAAATTGTCTCACTGAGCACAGAACCTAG AACAGCAGTAGCATGGGATTGTAGAATAAG | 564 |
| DTX1_chr12:113496609-113496709 | GGCTTTACATGCACTTCCTCATTTTGATTTTCCAAGAATCACCAGGCAGTAAGTCTCTGTATTGTTGTATT ATTATGAGTCCCATTTTATAGATGAAGAA | 565 |
| DTX1_chr12:113496694-113496794 | TTTATAGATGAAGAAACCGAGTCTCCCAGAAGCTGAGTGATTTAAACTCAGAGCTGGGATTTAAACCCAG GCGGTTGAGTTCCAGAACCAAAGTTCTTAA | 566 |
| DTX1_chr12:113496794-113496894 | CTGGTATCCTATACTGGCTCCAAGTGTTGGTTTGTGGGGTGGAGTCGTGCTGGTGTAATTAATTGGGGA TGGGGGGCCTTGGTGGTTGTGATGGTGGGG | 567 |
| DTX1_chr12:113496894-113496994 | TGAGGTGGCAATGATGGAGGAGACAGTGTTAGCGGTTGTGTGTTGGTGACTCAGTGATAGTATTGATGG TGGTGGGGTCTTGGTGACAATGGAGGGATG | 568 |
| DTX1_chr12:113497059-113497159 | TGTTGGTTGACATTGATAGTTGTTGGTGGTGGTGCTGGAAGTGGTGTGATGGGGTGGTGATGATGAAGA AATGAGAGAATGATTGGTGGTGCAGTCTT | 569 |
| DTX1_chr12:113497159-113497259 | CGTGGCCATGTGCTGGTGTGGCTGGTAGCCCTGTGTGGCCTGTTACTTAGTGGTATTGGTGATCCTGTTGTGG TTGTAATGATGGTGATGTTGATGGTTGCG | 570 |
| DTX1_chr12:113497259-113497359 | TTGGTGGTAATGTGATGGCTGATGATGGAGATAAAATCGATGAGGTCCCACTCTCAGGCCTACTCTCTTT GTTCTGGAGATTTGTCATCGTTGGGGAGA | 571 |
| BCL7A_chr12:122458781-122458881 | TGAAATGGCTGCTGTCGGGCTGCATCTCCAGGCCCGCGCTGACATTTGGGCGCTGACTCTCCGGTCTCCCT CTTCATTCTGGGCGCGCATTAGCTCTGGT | 572 |
| BCL7A_chr12:122458881-122458981 | CCGGCCCGTTCCGCTGCAGCTGAACACGCAAGATGCGCACCCAGGTTACCCTGATCATCGCAGATTTCTC CCCGGGGCTCTGTTCTGAGGCCTCAAAAGT | 573 |
| BCL7A_chr12:122458981-122459081 | GCTTCCTTGTAGATGGGACCAGGGGTCATTTGGGCAGTAGCAGCGCCCTCGGTCTCCAGTCTGGTACTGAAGTC AGGAATGGCTTAAGGTGAAATCGTGGTCCT | 574 |
| BCL7A_chr12:122459081-122459181 | CTGGTGAAGCTCAGCGAAGACCCCCTCGCCTTGTTTATGACAAGAGAGAACTCTCGGGGGCGGGAGGAGAG TCCCTGTTTACGATCGTGATCATCATTGAGC | 575 |
| BCL7A_chr12:122459181-122459281 | TTTTGCTGAGCAGAAAACTCTTTAGTACTCAAGGTCGAGAGTCTCTGTGGTCGTCGCCTGGCACCAGGCAC CTTCCTACCAACCCTAGTTTTCCAAAAGAC | 576 |
| BCL7A_chr12:122459281-122459381 | AAAGCCTGGGGACCAGGCAGCGACGTCCTAGCTCGCATTTGAACAGGGCGCGGGCCAGCAGAGATGCGCGATG CCCAACTCTTTCCAAGAGCACCTCGCGTCCC | 577 |

TABLE 6-continued

| Name | Sequence | SEQ ID NOs. |
|---|---|---|
| BCL7A_chr12:122459381-122459481 | GAACCGGTGCCTTCAACTCGGAGAAGTCAAGAGACCCGCAAGAAACTTGCAGACTGCACCCGCCGCCGC GCTCTGGGGGCTGGGCAGGGGCAGCTGGGC | 578 |
| BCL7A_chr12:122459481-122459581 | TGGCTCCCGGGAACGGACCCCCCGCGCCCCGCAGACCGGCTGTCTCCCATGGACCCCTCGGCACCTG CAGCCTCCGAGGAAGGGTCAGCGCGCTGT | 579 |
| BCL7A_chr12:122460811-122460911 | GGGGGCTCGGGCCAGCCGATGTTTTTGCGCAGAAGCCGTTCGTCTCTGGGCCGCGGCTGCCTCTCCACAC CGGGAGCTCGTGTTTGTTTTGCGAGGGAG | 580 |
| BCL7A_chr12:122460911-122461011 | CTGTTGTTTTTGTTCTCTGCACCGGGGAGAGGGGGGACTTGGTGGCGGCCGCGCGTGTTTTCGGATCAC ATTAGCGTCCGCCCGCGTGGCCCGGTCGA | 581 |
| BCL7A_chr12:122461011-122461111 | CATTAAGGGGATCGAACCTTTCCGCGCCTCGTCGGGGTCTGCTCGGAATCGGCCCTGGGCCAGGCCCG AGGCGCAACAGATCGCCAGGTTGGGTCAG | 582 |
| BCL7A_chr12:122461111-122461211 | AGTTGTTGAAAACTCCCCGCTGCTGATTTCAACTTTATTATTTTTTCCCACGCCTTCACTGGGGTCCCGG AGGGAGAGGAGCCGCCAACGCTGGCT | 583 |
| BCL7A_chr12:122461316-122461416 | AGTAGCGCCTCGGTTCTCTAAAAGCCACTGGGGGCTCCCGAGCCTCCGGTGTGGCGGTGTCACAAGTTAGCTGTC CTTTCTGAGTCAAACCCAACAAAAAGGCA | 584 |
| BCL7A_chr12:122461416-122461516 | AGAGGAAAATCAATAAAGTCCACGTGTCTCCCCGGCTCTCCTATGGAAAAGGGCTGGCTGCGATGCCGGATG CCCGCCCGTGGGTTTGGCTCCAGTG | 585 |
| BCL7A_chr12:122461516-122461616 | GGACAAAGAATTTTCAGAACCGTGAGAAGGGAGGCTTTCCAAAGTTGAGATCCAAGTCGTCGGTGTCTC GGGAGCTCCCCTGGTACACAGGGTGCCCGG | 586 |
| BCL7A_chr12:122461616-122461716 | TGCCCGACTGGAGCCATTTAAAAATGCAGAAACAGCTGCAGGCCAACACACACGCTGGAAAACAAC CCGCAGCCCCCTCTACTGTGGGATTCCCCGC | 587 |
| BCL7A_chr12:122461716-122461816 | GGGAAGCCCGGAGTTGCTCCCCTTCTCTGCTCAGCCCCTCGAGGAGGCGTGGGGCCTCCTACTCCAGGTTCCCGCT GTCCCTTCTGTCGCCGGCCTGGAGGTTGGG | 588 |
| BCL7A_chr12:122461816-122461916 | AAACAGCCGCAAGCCGCCCTTTCTCTGCTGAGGGAGACCAGGCTGTGGGGCCTGTAGTTGGAGCTTGAGGGGCTGTACCTCTG GGACAGAGGGCTCCTGCACCCTGACAGCTGC | 589 |
| BCL7A_chr12:122462001-122462101 | GGAGGCCTTCCTCCAGCCGCCGCCCGTGACCCGCGGGACCAGGCCTGGATCTCATGTCCAGCTTCCAGTTCCGCGACCT CGCCTCCCTGGGTTTGGGAAACAACAT | 590 |
| BCL7A_chr12:122462101-122462201 | CGTGTCTCTGAAGACCTCAGGCTTTCCTTGCTTCCCCAGTCTTCCAGTCCCAGCTTCACTTCGTTGCCGCGACCT TGGGCATATCATTGTCACTTCTCTAACCA | 591 |
| BCL7A_chr12:122462201-122462301 | TGGTGACCCGGGGTTTGTGTCTTCCAGTGTCCCCCTGCGGTTATTGAGGACGATTGAGGTCATGCCTC CGAGACACCCGCCCCTGGGCGCAGGAGG | 592 |
| BCL7A_chr12:122462716-122462816 | AATGCAAATTTAACAGGGCACCCTGTATTTTACCCAGAGGGAAGCCGAAGTGTTTGGCAGATCATTTGGC CCCATGAGCCTTGGGTGGGTTTCTCCTCAG | 593 |

TABLE 6-continued

| Name | Sequence | SEQ ID NOs. |
|---|---|---|
| BCL7A_chr12:122462816-122462916 | CCCTAGTGACCCCTAAATTACCCCCCGACCCACCCACTGTCCCCTGATGCTTCCCCACCCCGAAAA AGCTGTGGCCTCCCTCCTCATTTGGGCAG | 594 |
| BCL7A_chr12:122462916-122463016 | GCTGCCTCCTGTTCTCTTTTCTGGTGTTTCAGCAAGGCAGGCCAGTGGAGTGAGGTGACCAGAAGATG GCTAAGGGAAAACAAAATGGTGGGCCTCT | 595 |
| BCL7A_chr12:122463031-122463131 | CCAGGGTTTGGGGGCCCTGTCGTGGTGAGGAGAAGAACCCCAGGGCGATGGTAGGAGACGAAAGCTT GGGCTGCAGCGTAAGCTTGGAGGCCCGCTGC | 596 |
| BCL7A_chr12:122463131-122463231 | GGTGGCTCACGCCTGTAATCCCAGAGCTTTGGGAGGCTGAGACAGGAGGATTGCTTGAGCCCAGGAGTTT GAGACCAGCCTGGGTCTCAAACCAAAAAAA | 597 |
| KIAA0226L_chr13:46959165-46959265 | TAAATATAATTTAACGCCAATCTGAGAAAAAATGACTTATTAGCTGTGTGATTTTGAGCAATGCTCTTAAC CTCCCCATGAAGGATGGTGAGAACGA | 598 |
| KIAA0226L_chr13:46959265-46959365 | ACAGAATTGTAGCACGTGTATCAGTCTGGTACACAATGTCCTATGAAGGTTAGCTTTATTATCACCATCAT TATTATTGCAGAAGACTTTCAGTTCAGA | 599 |
| KIAA0226L_chr13:46959365-46959465 | ATAAGACACAGTTACAGAGACCTGTTTTATTTTCCAGCTTCTTAACTGAGTCATCTTTCAGCTCCTT TTAATTAAAAGAAAAAACAATCAGAGAT | 600 |
| KIAA0226L_chr13:46961680-46961780 | TCAAAGACCTGGCAGAATGACTTCCAACCCCAGATGCCCCAGCAGCAGTATTAGCAGTCATACAAT TGCCTGAAATGAAGAATGAGTAATCTGAT | 601 |
| KIAA0226L_chr13:46961780-46961880 | GAGTCGGCCGCCCTGAAATCGACCTGCAACTTACCCGGAACGTGAGCTCTCTCTCTGACCTCTGCTGGCTGC TTCACCTGGAGTCTGAGTCCGACTCATGT | 602 |
| KIAA0226L_chr13:46961880-46961980 | AGCACTTCACTGTCCGCGTTAGTTTAGCCTTCACTGTCAGCACAACTCGTCACCTTGTCCTCTTGCAGCGAAG GTTTGGAATCCCATCACGGGTGTGCAGTG | 603 |
| KIAA0226L_chr13:46961980-46962080 | GTTAGTCCTGAGATCATCGTGGTGCTAGGAGAACCTGCCAACCAATACAGAAAGTTGTCACGAATAGAAA CCTAAGCTCTGGCCGGTGCGCGGTGGTTCAA | 604 |
| ATP11A_chr13:113516229-113516329 | AGATATACTGTTCTAGACATGTCTGAAAGGAATCCTGCAAATTCTGTCTTATTGAACAGGCATAAGGT GTCACGTCAGGCGTAAGGTGTCACAGCAGG | 605 |
| ATP11A_chr13:113516329-113516429 | CGTAAGGCGTCACGTCAGGCGTAAGGTGTCACAGCAGGCGTAAGGCATCACGTCAGGCGTAAGGCGTCA CGTCAGGCGTAAGGCGTCACAAGCTCGGTGA | 606 |
| ATP11A_chr13:113516429-113516529 | ACGTCAGGGGTGTGCCTTGTGTTCTCTGTTCGTTGCTTCAGAAGCAGCATGTGGCAGCATCTCTGTG CCTATGACGATATTGCAGTGAATATGAGA | 607 |
| SYNE2_chr14:64330252-64330352 | AATTGTACATTTCAACAACATAAATAAGCTGTTCAAGACTGTCTCCCATGCCTCCAAAACAAATAAAAC CCCCACAACTCAAATGCATATAAGCTGTT | 608 |
| SYNE2_chr14:64330352-64330452 | ACTATAGTATAATGGTGAGTTATAGCACGTGTATGATGGGATTGTTGATAGAATAATGCATATTAGAGCT TTTAGTTCAAAAATTTGAGATAGTGATTCA | 609 |

TABLE 6-continued

| Name | Sequence | SEQ ID NOs. |
|---|---|---|
| SYNE2_chr14:64330452-64330552 | GAAAGAAAAAAGGAATGATTATCATGAATTCTGTTTATTAGAATTCTGTTTATTAAAGAGTTAAAGATATGTTTTATTTTTTATCTTTATTATTATCATTA | 610 |
| ZFP36L1_chr14:69258238-69258338 | AATTCTAATGTTGGTCCTTAGGATCAGCAGGGGGACCGGGAATCTGTAACTGCACCACCCCACCGAGAGGATTACAGGAGTCGAGAACCCAGTCGAGAGCTGG | 611 |
| ZFP36L1_chr14:69258338-69258438 | TTCCACAACAATGAGGTTCATTTAAAAAGTCTGAGGGGGGAGGGGAGGGGCCAAAGAAAGAAATAGATCAAAGAGCGGGAGAGTCGAGAAAAGAAGGAAGAAA | 612 |
| ZFP36L1_chr14:69258438-69258538 | TGTTGGGGAGCGCTGGCAGCCGCGGGCTGGCAAGTGAGTTTGGGAATGTGCAGGGAGGGAAGGAAGCTGAAAAATTCAAACTTTTTAAATGCTACTCTTCA | 613 |
| ZFP36L1_chr14:69258538-69258638 | GCTCCTCGGCGTCCCTGCACCCCAACCCTGCAGCCCTTGGGCGTTGGCAGCTGCACCAACAGGAGCAGCAAGCTGGGAAAACAGGAGCAACATGACCCGAC | 614 |
| ZFP36L1_chr14:69258638-69258738 | GTGTTAAGAGAAGGCAAAACACTTCAGCAATTAAACACCTTAAAAAGTAGCCCAGCAGCTTCACCCTTTCAAATTGGGAGGGGAGGTTGGAAAGAAATTTAACAACAT | 615 |
| ZFP36L1_chr14:69258738-69258838 | CCATAGACTTTTGCTACTACATTTAAACCGCAGTCCTGGAACATTCCGAGTTTAAAACTTGCTTTTTCAACACTGGCTGACAAGCAACATGTTTTAAGG | 616 |
| ZFP36L1_chr14:69258838-69258938 | AGCCCCCCCATTAAATCTTACTCGCGGACTCTCGAGTTCAAGCCACCAGCATTTTGTCGCACCCTCCCCCCCAACCCCGCCCCGCAATCGATGAGCGCAAT | 617 |
| ZFP36L1_chr14:69258938-69259038 | GCTCGGCAACAACAGGTAAGCGGGTCAACCTGCAAACTGTTCTGCAACATCTTTTTGAATCACAACTTGCCTTTCTTCCTCGTATCGCGGAAGAAGCCCAACGGAGCTAGG | 618 |
| ZFP36L1_chr14:69259038-69259138 | GCCGACTCAAGCCCCACTGCAAACTCCCCGAGGGAACCTCCCAACCCCACGGGTGGGTAATGCCCATATCCCCAGCTCCCCCAAAGAGTGAA | 619 |
| ZFP36L1_chr14:69259138-69259238 | GGAAAACATTGTCCCGAGACTCACTTCCCCGAGGGAACCTCCCAACCCCACGGGTGGGTAATGCCGCTGGACAGACCTAGGGCGCAGACTGGGAA | 620 |
| ZFP36L1_chr14:69259238-69259338 | CCCGATCAGACCAGCAACTCGGATCCAGCAGCACGTTACGTAAAACAGGATCGCCCAAAACTTGTCCCAATCCCAGCCCTCCCCCCGAAGCCCCGGG | 621 |
| ZFP36L1_chr14:69259338-69259438 | CTGCCCTGCCAGGCAAACTTCGCCCCTCAAAACCCTGGCCTCCAGATTCACATGTAATCCCCCAGCAACTGTTGAAACTCAAAGGGTGGGAAGGACGG | 622 |
| ZFP36L1_chr14:69259438-69259538 | GGCCAAATTCCTTCAAACTTGGGAGAAATGCCGAGGAGAAGAATCATCTCGCTGCACCACTTTTCCCCATTGCCTTCCAAGACCCAAACTTTTGGGGG | 623 |
| ZFP36L1_chr14:69259538-69259638 | TTCTTTCTTAAGGCAAAAGAAAAAGACTTTTGAAAAGCAAAATGCTCCGCCCCCCCTTTACCTTGCATAAAACTTCGCTCAAGTCGAAGATGGTGCAGAC | 624 |
| ZFP36L1_chr14:69259638-69259738 | ACGAGGTGGTGTCATCCTGCGTTCGCGCGAGCCAGGGCGAGGATCTGGTGTCGCGAAGGTCCCGGTGCGGGGAAGGCGCAGCCCTCTCCTGTCT | 625 |

TABLE 6-continued

| Name | Sequence | SEQ ID NOs. |
|---|---|---|
| FLRT2_chr14:84420586-84420686 | TTATTTTTTATATTAAGATTTATTCTAAATTTGATTCTTCTAAATATAGTATATATTAGTATATATA ATGCACCCTCTTCTTACCTAATGATCATTT | 626 |
| FLRT2_chr14:84420686-84420786 | CTAAATAATCATAACACATCGAGTAAAACATGTAATAACACATATTATTATTAAGATAAGTATAAGAA AATATAATAATAATTGTCCCTGTTCTAAAA | 627 |
| FLRT2_chr14:84420786-84420886 | GGTAATTATATATATGCTGAATGTGTCAGAGGCATTCGAACCAGAGTGACTCCATTTTGAGTGAGGGCTAG GAAAATGAGGCTGAGACTTGCTGGGATGCA | 628 |
| TCL1A_chr14:96179592-96179692 | TTTTAATTTTTATGCTTTCTTCTTCAGTGTATGTTTGGAGAGAGTTTGAACATTTTTTGACTCTTTTTCATTGAGT AAATCCAAATACTTGTAAAAGACTTATC | 629 |
| TCL1A_chr14:96179692-96179792 | TATTTCTTTAACAAAAACTAACATGGATTAAGGACCCATCTTAAGGCATCACACATTAAAAAAGTCAAT ATTGATTCAATACCGGCCTTATACTACGA | 630 |
| TCL1A_chr14:96179792-96179892 | CATCACTTGTTAAATTTGTTTCTAAATAAAGCCAGAGGTAGTGGAAAATACTTCACACTCTAGGCCAGT GTTTGCTATGCCTGGTTGACCCTAAACTG | 631 |
| TCL1A_chr14:96179892-96179992 | TTGAGGGTTCTTTTTAAAAATACAGATTTCTGGGACCCACCTGAGATGATTCCGATAATCGGCCATATGGA TGAGTCACTTAGAGATACCCATTTTTAAG | 632 |
| TCL1A_chr14:96179992-96180092 | GATTAGGACCCCAGAAGCCCAGAAAATGCCTGCTGTAGTCAACATTATAGTCACACTCCACAGGCACTGGG TCCACCCCTTTGACCGACATTCCTTTGCGG | 633 |
| TCL1A_chr14:96180092-96180192 | TTTTCCCACCCTTCTTCCCTGCCTGGAGAACTCCTATTCATCCTCCGAGCCCGGCTCAAAGTGGCTTCATC TGTGGGGATCCTCCCCTGCCCCATAGTGA | 634 |
| TCL1A_chr14:96180192-96180292 | GTGCTCCTTGAGTCCTCGCCTTCCGCCCTTCCTAGGGCATCCCAAATACACGAACTTCTCCCAGGCCCCATC CGCTCCAAAGCTGGCTGACCTCGATGT | 635 |
| TCL1A_chr14:96180292-96180392 | TAAGGGCAGCCAGGCGTCGTCGTCTTCTCGTCCAAATACACGAACTTCTCCCAGGCGGTCGGG TGGTGGTGACTGCCTCCCCGAGTGTCGGG | 636 |
| IGHA2_chr14:106048955-106049055 | AGGAATCAGATTTCAAAATGAATGATATAAGAAAAGAACCGGGGATCAGTGATCAGGAACAGGGGATCC ATGCATCTGGTCCAGGGCTCAGCCGGTCAGGAA | 637 |
| IGHE_chr14:106068705-106068805 | CCCTGGCCTGGAGTCCCAAGTCCCCAGCCCATCCTGCCCCTGGAGCCCCAGTTTAGCTTGGTCTTGAAGTCT GCTCTAGGTACCCCCAAAATCACAGTATC | 638 |
| IGHE_chr14:106068805-106068905 | CAGCCCCGCCTCTGCCCCACCGGGACAGCCAAGTTCAGCTGAGACTGGCCTACCGGGGAGTGCCCCTCTGA AGTTCACTCTAAGCCAGCCTGGTTCAGCCT | 639 |
| IGHE_chr14:106068905-106069005 | GGGCCAGGTCAGGCCAGGACCTCCCCTTGCAGGCAGCAAATCTTATTTCAGTCCAGCCAGCTCAACCAG CTTGCTTCTGACTCAGCTCCTCTTAGCCAG | 640 |
| IGHE_chr14:106069045-106069145 | TTAGCTCAGCAAAGCTGACCTAAAGTAGCCACCTCACCCCCAGCTTCATCCAGATGAATACAGTCCAGAT CAGCTTAGTCAGTTAAGCCTAGCCTAGTA | 641 |

TABLE 6-continued

| Name | Sequence | SEQ ID NOs. |
|---|---|---|
| IGHE_chr14:106069145-106069245 | GTTAAATCCAGTTACGACCAGTTCAACTAATCCTGCTCAGGCCTGCTCAGCCCCAGCTGAACCCAGTTTAGCCGAGGCCAGGCCAGCCCAGCCTGAA | 642 |
| IGHE_chr14:106069245-106069345 | TACAGTTGCCCAGTCTAGCTCAGCCCAGTCTCAGCCACTGCCCAGTTTAGCTGAGCTCAGCCTGCCCAGCCCAGCTCATATCAGCCCATTCAGCTGAAC | 643 |
| IGHE_chr14:106069345-106069445 | AGTTTGACCCAGTCTAACCCACCCGTCTAGCTCAGCTGAACCCAGCCCAGCCCAGCCCAGCAAACCCAGTTTAGCCTAGCTCAGCTCAGCCCATTTC | 644 |
| IGHE_chr14:106071060-106071160 | CCTGTCTCCTAGGGGTGGGCAGGCAGTCTGACCCCAGCCCTAGCCCTGCCCAGCCGTGGGGTCTCTGACCTTCTTGGTCTTGGGCCCCAGCCAAGATTCCCAGCCC | 645 |
| IGHE_chr14:106071190-106071290 | TTCTAGTTTCTGTGTCCCATGCAGGGAAGGATGCCTAGAGTCCACGCAGTGACCAAGAAGCTTGGTTGATGCTGTGAGGGTGGGCCCAGAGAGTCCCC | 646 |
| IGHG4_chr14:106095335-106095435 | CACCTGCTGTCTCCTTGGTCCTGGCTGAGAGGAGGGCCCTACGGCCAGCTCTGCTGACCCTGCCCTGGGCTCTGGTGATGCTGCCGGCCTGGACAAGCCCT | 647 |
| IGHG4_chr14:106095480-106095580 | GAGCTCAGGTGCTGTGCCCATCCTGCACAGGAGCCCACACCCCACAGCCGGTTCTGCCGCATCCCGTCATGTTCCTCGTGCTCCAGCCCCGGTCGTCCTGAGGCC | 648 |
| IGHG2_chr14:106110675-106110775 | TGAGCATGAGTGGGGCGGGCAGAGCCTCCGGTGAGGAGACAGATGGGGCTTGCCTTGCTGCCCTGGGCTGGGCTGCACAGCCGGGGTGCGTGCCTCCAGGC | 649 |
| IGHG2_chr14:106110775-106110875 | AGGAGGGCTGAGCTGCCTGGCTTCCAGCAGACACCCTCCCCTGAGCTGGCCTTCCACCAACTGTCTTGTCCACCTTGGTGTTGCTGGGCTTGTGATCTAC | 650 |
| IGHG2_chr14:106110830-106110930 | ACCAACTGTCTTGTCCACCTTGGTGTTGCTGGGCTTGTGATCTACGTTGCAGGTGTAGGTCAGGTGTGCCGAAGTTGCTGAGGGCACGGTCCTTGACCAGGCAG | 651 |
| IGHG2_chr14:106110950-106111050 | GGACTGTAGGACAGCCGGGAAGTGTGCACGCGCTGAGTTCCACGACCGTCACCGGTTCGGGGAAGTAGTCCTTGACCAGGCCG | 652 |
| IGHG2_chr14:106112335-106112435 | TGCTACACTGCCCTGCCACCACTCCAGCTTCATTGTGCTGGTGGCCCTGGCTCCTGGCAGCCCATCTTGCTCCTTCTGGGGCGCCAGCCTCAGAGG | 653 |
| IGHG2_chr14:106112435-106112535 | CCTTCCTGCCTAGGGTCCGCTGGGGCCAGCCCTGGGACACCCTCTGGTCTCAAGCACACATTCCCCTGCAGCCACACCTGCCCCTGCCTGAGAGCTCAGC | 654 |
| IGHG2_chr14:106112535-106112635 | CCCGAGCCCTGGAATGCTTCCCTTCTCCATCCCAGCTCACCCTTGCAACTGCTCAGTGGGATGGGCTCACACTCCCTTCCTGCACCAGGAGGCTGCA | 655 |
| IGHG2_chr14:106112635-106112735 | CTGCACTTTCACCAGCCCTGCTGTCTGCGCCAGCAACTACCCAGCTCCTGCCAAAATCTAGGAGCTGAGTGATGCCTCCCACCGGCCCTGCTCACCT | 656 |
| IGHG2_chr14:106112735-106112835 | GTGGTTGCCTTGCCCTGAGCTTCTAGTGCCTGTCCCCTGCTCGTCCTGCCTCCCACCGGCCCTGCTCACCTGTGGCTGCTCTGCTCTGATTCCCTGAGGCT | 657 |

TABLE 6-continued

| Name | Sequence | SEQ ID NOs. |
|---|---|---|
| IGHG2_chr14:106112835-106112935 | AAGCCTCAGTCCTGCTCACCTTCTGATGCTCTCCTCTGTCCCCTGAGCTCCAGGGGCTGTCCCCTGCTCGT<br>CCTGCCCTCCTACCTGCCCCTGCTTACCTG | 658 |
| IGHG2_chr14:106112935-106113035 | AGGGTGCTCTGCCCTGGTGCTCTGAGCTCCTGAGCTCCAGGGGCTGTCCCCTGCTTCCTCCTGTTCCTACCAGCCCCTG<br>CTCACCTGTGGCTGTCTGCCCTGGTCC | 659 |
| IGHG2_chr14:106113020-106113120 | CTCTGCCCTGGTCCTGCCCTGAGCTCCAGGGGCTCCCCCTGCTCTTCCTGCCCCCACCAGCCCCTGTTCACCTT<br>CAGATGCCCTCCCCTGGTCCCCTGAAGT | 660 |
| IGHG2_chr14:106113120-106113220 | CCCAGAGCTGCCCCCCTGTTCCTCCTGGCTCCACCAGCCCGTGCTCCTCACCTGCCTGCCTCTGCCCTGGTCC<br>CGAGTTCCAGGGGCTGCACCCTGTTCGCC | 661 |
| IGHG2_chr14:106113220-106113320 | CACCTCCCACTAGCCATGCCATGCTCAGCTCTTGATGCTCTGTCTGGTGCCCCTGAGCTCCAGGAGCTGTCCCCTA<br>CTCGTCCTGCCACCCACCAGCCCCTGCTC | 662 |
| IGHG2_chr14:106113320-106113420 | ACCTGAGGCCACCTGAGGCTGCTCTGCCCTGGTCCCCTGAGCTCCAGGGTCTTCCCCCTGCTCATCCTGCCT<br>CCCACCTGCCCTTGTTCACCTTCAGTTGC | 663 |
| IGHG2_chr14:106113420-106113520 | TCTGCCCTGGTCTGCTGCTGAGAGGTGCCCCCTGCTGCCCTGCTCACCTGTGGCTGCTCGGTACCCTGGTAGAACTCCA<br>GGTGCTCGGTCCTGGTACCCTGACTCC | 664 |
| IGHG2_chr14:106113450-106113550 | GCCCCCTGCTCTTCTGCCCCACCTGCCCTGCTCCACCTGTGGCTGCTCGGTCCTGTCCTGGCACCCCTGTCCAGGT<br>ATGCCCCCTGCTCACTCTGCCCTC | 665 |
| IGHG2_chr14:106113550-106113650 | CTCAACCCGGGCAGCAATGTCACTCAGGTCACTGTTGCCCCCTGCCTGTCCTGGTCCTGGGACCCCTGTCCAGGT<br>TTGGGCTGTTTTCTGGCCCTCATTTTGT | 666 |
| IGHG2_chr14:106113695-106113795 | TGTCCAGTCAGGTCTCCCAACAGAGCCCTTGCCTGTGCCCATGCCCTCTGCTGGGTGAGCTCCCAGAT<br>CCTCCCGTCCCTGCCCCAGGCCTGCT | 667 |
| IGHG2_chr14:106113795-106113895 | GAAGCCTTCCCAGAACCTCAGCTCCTCAGTGACTCTTCCCTCCCATCTGTCACTCAGCACAGCTCTCCCTGAACGCACGAG<br>CCTCACCCCCTCGCCCCAGGCCTGCT | 668 |
| IGHG2_chr14:106113895-106113995 | GCACTCTGGGCCTTTCTGGGCTTCCCTGGACTCTTCCCTCCCATCTGTCACTCAGCAGCTCTCCCCACTCCGC<br>TCCACTCCGCTGCTGACCACAGCCCTGC | 669 |
| IGHG2_chr14:106113905-106114005 | CCTTTCTGGGCCTCCCTGGACTCTTCCCCTCCTGGGCTCCTGGGCTGCCCTGGCACTGTGCACTCAGCACAGCTCTCCCCACTCCGC<br>TGCTGACCACAGCCCTGCTCCCCGCCAG | 670 |
| IGHG2_chr14:106114175-106114275 | CCCAGGCCAGACACTGTACCCTGCCCTGGCTGCCCTGGGCTCCAGTGATGCTGGCTGGACAAGCCCCTCCGTTC<br>ACCTGGGGCCTCTCCTCCTCCTGTTCT | 671 |
| IGHG2_chr14:106114275-106114375 | ACTGCCTCCTCCTCAGCTCAGGTCCTGCCTCCTGCCATGCTGGCATCACCCCACGGGCTGCTCGCCGATCCCGT<br>CAGGTTCCTGCTCCGTGCTCCCAGCCTGGTCGT | 672 |
| IGHG2_chr14:106114375-106114475 | CATGGAGGCCTCAGTCAGCCTTCTGGTGTGTCCCTGCCCTGTTGGCCTTGGAAGCCCCTGCCCACGGTCCCGT<br>CATCTTGCACTGGGCTGGGCGTTGGTGCCT | 673 |

TABLE 6-continued

| Name | Sequence | SEQ ID NOs. |
|---|---|---|
| IGHA1_chr14:106176375-106176475 | AGCTCAGCCCAGCCTAGTCAGCCCAGCCCAGCAGTCAGCCCAGCTTAGCCCAGTCAGTCC AGCTCAGTCAGTCCACTTAAGCTCACCCA | 674 |
| IGHA1_chr14:106176475-106176575 | GGTCAGCTTCCGTCCAGCCCAGCCCAGTCAGGCTCAGCCCAGCCCAACACAGTCAGCCCA GCTCAGCCTAGCCCAGCCCAGTCAGCACA | 675 |
| IGHA1_chr14:106176575-106176675 | GGTCAGACCCAGCTCAGTACAGCTCAGGTCAGCCCAGATCAGCCCAGCCAGTCCAACCCA GCCCAGCTCAGCTCATCCAAGCCTAGCTCA | 676 |
| IGHA1_chr14:106176675-106176775 | GCTCAGCCCAGCCCAGGTCAGCTCAGCCCTAGCCCAGCCAGCCGAACCCAGCTCAGCCCCAGGTCAACCCAATTCAGCTCA GCTCAGCCCAGGTCAACCCAACCAAGCTCA | 677 |
| IGHA1_chr14:106176775-106176875 | CAGCCTAGCCCAGTCAGCTCAGCCCAGCTCAGCCCAGTCAGCCCAGTCAGCTCAATCACCTAAGCTCAC CCAGCTCAGCCCAGTCTGGCTCAGCTTAG | 678 |
| IGHA1_chr14:106176875-106176975 | GTCAGCCCAGCCCAGCTTAGCCCAGATCAGTCCAGCTTAGCCCAGCTCAGCCCCAGGTCAG CCCAGCTCAGTCAGCCCAGCCCAGTCAG | 679 |
| IGHA1_chr14:106176985-106177085 | CCCAGCCCAGCTCAGCGCAGCCCAGCTAGCTCACCCCAGCTCAGGTCAGCTTAGCCAGCTCAGCCCAG CCCAACTCAGCTCAGCCCAGCTCAGCCCAA | 680 |
| IGHG1_chr14:106211960-106212060 | TCTGAGTCTCAGGGGCTGCCCACCTGCTCTCCCTGTCCCCTGAGCTCCAGGGCTCCCACCGGCCCTGCTTCCCACCGGGCCTGCTCACCTGCAGCTGCTCTGC CCTGGCTCCCTGAGGCTGAGCCTCAGTCC | 681 |
| IGHG1_chr14:106212060-106212160 | TGCTCACCTTCTGTGACTCTCTGATGCTCTCCCCTTGTCCCCTGAGTCCAGGGGCTGACCCCTGATCTTTCTGCTTCCTAC CTGCCCCTGCTTCACCTGGCTCTG | 682 |
| IGHG1_chr14:106212160-106212260 | CCCTGATCCCTGCTCGCCTGAGCTCCAGGAGCTCCTGCTCTTCCTGCCTCCCACCTGCTCACCTGCAG ATCTGCCCTGGCTCTCTGAGGTCCAGGG | 683 |
| IGHG1_chr14:106212260-106212360 | CTGCCCCCTCCTGCTCGCCCACCAGCCATGCTGACGTTGTGATGCTCTGCCCTGGTCTCTGAGGTC CAGGGGCTGTCCCCTGCTTATTCTGCCTC | 684 |
| IGHG1_chr14:106212360-106212460 | CCACCTGCCCCCTTCTCACCTGAGGCTCTTCTGCCCTGGTGCTCTGAGCTCCAAAAGCTGCCCACTTGCTCC TCCTGCTTCCTACCAGCCCCTGCTCTCCT | 685 |
| IGHG1_chr14:106212460-106212560 | GTGGATGATCTGCCTGGCTCTGAGCTCCAGGGGCTGCCCACCTGCTCCCCATGCTCCCACCTGCCCC TGCTGACCTGCGGCTGCTCTGCCTTGGCT | 686 |
| IGHG1_chr14:106212560-106212660 | CCCTGAGCTCCAGGAGCTTCCCCCTGCTCATCCTGCCTCATGGCCCCTGCTGTTCACCTTCAGATGCCTC CCTGGTCCCCTGAAGTCAGGAGCTGCCC | 687 |
| IGHG1_chr14:106212660-106212760 | CCTGTTCCTCCCCGCTCCCACCAGCCCGTGCTCACCTGCGGGCTGCTCTGCCCTGGTGCTCTGAGTTCCAGG GGCTGCCCCTCGCCCACCTCCCACT | 688 |
| IGHG1_chr14:106212760-106212860 | AGCCATGCTCACCTCCTGATGCTCTGTCCTGGTCCCCTGAGCTCCAGGGCTGCCCCCTGCTTGCCCATCT CCCACTAGCCATGCTCACCTTTGATGCT | 689 |

TABLE 6-continued

| Name | Sequence | SEQ ID NOs. |
|---|---|---|
| IGHG1_chr14:106212860-106212960 | CTGCCCCTGGTCTCCCTGAGCTCCAGGGTCTTCCCCCTGCTCATCCTGCGCCCAGCCCCTGCTCACCTGAGCTGCTCTGCCCTGGTCCCCTGAGCTC | 690 |
| IGHG1_chr14:106212870-106212970 | CCCCTGAGCTCCAGGGTCTTCCCCCTGCTCATCCTGCGCCCACCAGCCCCTGCTCACCTGAGGCTGCTCTGCCCTGGTCCCCTGAGCTCCAGGAGGTGC | 691 |
| IGHG1_chr14:106212980-106213080 | TTCTGCCCCCACCTGACCTCCACCTGTGGCTGCTGGTCCTGGTCCTGAGCTCCAATGCTGTCCCTGCTCACTCTGCCCTCCCTCAACCCGGGCA | 692 |
| IGHG1_chr14:106213080-106213180 | GCAATGTCACTCAGGTCACTGTTGCCCCCTGCCTGTCCCTGGCACCCTTCTGTCCAGGTTTGGGCTGTTTTTCTGCCCTCATTTTTGATTTTGCAGCACTT | 693 |
| IGHG1_chr14:106213125-106213225 | CCTCTGTCCAGGTTTGGGCTGTTTTTCTGCCCTCATTTTTGATTTTGCAGCACTTGGCGTGTTCCCTATGCTGTGGAGCAGCCCAGTGTCCAGTCAGGT | 694 |
| IGHG1_chr14:106213210-106213310 | AGTGTCCAGTCAGGTCTCCCAACAGAGCCCCTTGCCCTGCCCATGTCCCCTCTGAATGAGCTCCCGGATCCTCCTGTCCCTGACTGCTCCTGCTC | 695 |
| IGHG1_chr14:106213310-106213410 | TGGAAGCTCTCTGGAACCTCAGCTCTCCTCCAGTGGCCTCTCTGCTCTGTCTGGGTCAGTTCCCTGGTCAGTCCCTGAACGCACGGAGCCTCAGCCCCTTCCCCACTGCTGACCAGCCC | 696 |
| IGHG1_chr14:106213410-106213510 | GCTGCACTTCTGGGCCTTTCTGGGCCTCCCCAGTGCCCAACCCATCAGCTGGCTCTGAGCCCAGCCCCTGTGCCTCCCCTGTCCCCCCCTCCTCCACTGCTGACCAGCCC | 697 |
| IGHG1_chr14:106213510-106213610 | TGCTCCCCGCCAGCAGGTGCCCCAACCCATCAGCTGGCTCTGAGAGAGGGCCCACGGCCAGCACTGCTGACCCTGCCCTGGGCTCCTGCCCTCTGCCCTCTGGGCTTCC | 698 |
| IGHG1_chr14:106213660-106213760 | ACCTGCTGCTCCTTGGTCCTGGCTGAGAGAGGGCCCCACGGCCAGCACTGCTGACCCTGCCCTGGGCTCCGGTGATGCTGCCGGCCTGGACAAGCCCCTC | 699 |
| IGHG1_chr14:106213760-106213860 | CGTTCACCTGGGGCCCTCTCCTCCCTCGCTCGTCCTGGAGGCCTCAGTCAGCCTCTGGTGTGTCCTGCCCGCATCACCCCACCGCCCGGCTCTGCCCACGGTC | 700 |
| IGHG1_chr14:106213860-106213960 | CCAGTCATGTTCCTGCTCCGACTGGCTCCCAGCCCGGTCGTCCGGTCGTCCGGTCGTCCTGGAGGCCTCAGTCAGCCTCTGGTGTGTCCTGCCCTGTTGGCTTGGAAGCCCCCTGCCCCACGGTC | 701 |
| IGHG1_chr14:106213960-106214060 | CCCCTGTCTCGCACTGGGGTGGGCATCGGTGCCTGAAGGCTGCCACCTCCCCGTGCTGGCTCCGCTTGGGCCTCCATGTGGGGCCGGCCTGACCCCA | 702 |
| IGHG3_chr14:106239250-106239350 | CACTGCACTTTCACCAGCCTCAGCTGTCTGCTGTGCCGGCAACTACCCAGCTCTGCCAAAGTCTAGGAGCTGCGGCTGCCTCCTCCACCGTCCCTGCTCAC | 703 |
| IGHG3_chr14:106239350-106239450 | CTGTGGCTGCTCTGCCCTGGTGCTCTGAGCTCCAGGAGATGCCCCTGCTCTCCTCGCCCCCCACCTGCCCCTGCTCACCTGCAGCGGCTCTGCCCTGGT | 704 |
| IGHG3_chr14:106239455-106239555 | GAGCTCCAAGAGCTGCCCCTGCCCCTCTCCCCTGTCCCCTGACCCTGCTCCTCTGTTTGCCTATGGCTGCTCTGCCCTTGTCCCCTGAGCTCCAGGAGCTGCCCC | 705 |

TABLE 6-continued

| Name | Sequence | SEQ ID NOs. |
|---|---|---|
| IGHG3_chr14:106239555-106239655 | TGCTCATTCTGCGCCCACCTGCCCCTGTTCACCTGTGGCTGCTCTTCCCTGTGTCCTGAGCTCCATGAGCTGCCCCTTGCTCCTCCTGCTTCCACCA | 706 |
| IGHG3_chr14:106239655-106239755 | GCCCCTGCTCACCTACCGATGATCTTCCCGGCTCTCTGAGCTCCAGGGGCTGCCCACCTGCTACCCCTGCTTCCCACCAGCCTGCTTACCTGCAGCTG | 707 |
| IGHG3_chr14:106239755-106239855 | CTCTGCCCTGGCTGGCAGAGCTGCAGAAGCTGCCCCCTGCTCTGCAACCTCCCACCGCCCTTCTCATCTTCTGATGTTCCCCTGTTCCCTGAGCTCC | 708 |
| IGHG3_chr14:106239855-106239955 | AGGAGCTGCCCCCTACTCGTTCTACCTCCACCAAACCCGTGCTGCTCACCTGCGACTGCTGCTGCCCCTGGTCCCCTGAGCTCCAGGGGCTGCCCCCTGCTCCGCC | 709 |
| IGHG3_chr14:106239990-106240090 | TGCCCTGATCCCTGACTCCAGGACTGCCCCTGCCTCGTCGTTCCTGCCCCCTCACCTGCCCCTGCTCACCTGAGGCTGCTTGCCCTGGTCCCCTGAGCTAAA | 710 |
| IGHG3_chr14:106240090-106240190 | GGGGCTGCCCCTTACTCATCCTGCCTCCGCCCAGCCTTCCACCAGCCCCCTGCTCACCTTCTGATGCCCTCCCCTGGTCCCTGAGCTCCAGGGGCTGCCCCCTGAGCTGC | 711 |
| IGHG3_chr14:106240170-106240270 | GGGCTGCCCCCTGCTCCTGCCTCCCACCAGCCCCTGCTCACCTGCAGCTACACTGCCCCTGCTTGCCCTGGTTCCCTGAGCTCCAGGAGCTGCACCTGCCAGGAGCTCC | 712 |
| IGHG3_chr14:106240270-106240370 | GCCTTCCACCAGCCCCTGCTCACTGCAGCTACACTGCCCCCTGAGCTCCCTGAGCTCCGGGAGCTGCCGCCTGCTTGCTGCCTGCCCCACCAGCCCCTGCTC | 713 |
| IGHG3_chr14:106240370-106240470 | ACCTGTGGCTACACTGCCCTGGTGCCCCTGAGCTCCAGGAGCTGCCCCATCTTCCACTGAGCCCTGCTCACCTGCAACTGCTCTGCCCCTGG | 714 |
| IGHG3_chr14:106240470-106240570 | CTCTATAGAGCTCCAGGGGCTGCCCCTGGTCCTGCCTCCCACCTGCCCTGCGACTGTGGCTGCCTCCTCACCCTGTGGCTCCTCTGCCCCTGGTCCC | 715 |
| IGHG3_chr14:106240570-106240670 | CTCAGCTTCCAGGGTCTTCCTGCCTCCACCTGCCCTGCCCTGCACCTGTGGCTGCTGGTCCTGGTCCCCTGAACTCCAATGCGTGGTCCCTGAGCTCCAGGAGCTGCCC | 716 |
| IGHG3_chr14:106240670-106240770 | CCTGTTCTTCTGCCTCCCACTCGGTCCCCTGTGCACCTGTTGCCCCCTGCCTCGTCCTGGCACCCTCTGTCCAGGTTTCTGCCCCTGCTCACTCTGCCCCCTC | 717 |
| IGHG3_chr14:106240770-106240870 | AACCTGGGGCAGCAACGTCACTCGGTCCCCACTGTTCTTCTGCCTCATTTTGTTTAGGCTGTTTTCTTGCCTCATTTTGTTTAGGCACTGTTCCAG | 718 |
| IGHG3_chr14:106240820-106240920 | TGGCACCCTCTGTCCAGTTTAGGCTGTTTCTTGCAGCACTTGGCGTGTTCCCTATGCTGTGGAGCAGCCCCAGTGTCCAG | 719 |
| IGHG3_chr14:106240915-106241015 | TCCAGTCAGGTCTCCCAACAGAGCCCCTTGCCCTTGCCCATGCCCCTCCTGGATGAGCTCCGGATCCTCCCGTCCCTGCACTGCTCCTGCTCTGGA | 720 |
| IGHG3_chr14:106241015-106241115 | AGCCTCTCCAGAACCTCCAGTGCCTCTGCTCTGGGTCAGTTCCCTGAACGCACGAGCCTCAGCCCCTCCCCTTCGCCCCCAGGCCTGCTG | 721 |

TABLE 6-continued

| Name | Sequence | SEQ ID NOs. |
|---|---|---|
| IGHG3_chr14:106241115-106241215 | CACTCTGGGCCTTTCTGGGCCTCCCCTGGACTCTTCCCTCCTCCCGCCTCAGCACACAGCTCTCCCCT CCTCTCCGCTGCTGACCACCAGCCCTGCT | 722 |
| IGHG3_chr14:106241200-106241300 | GACCACAGCCCTGCTCCCCGGCCAGCAGGTGCCCAACCCATCAGCTGGCTCTGAGCCCAGCCCTGTGC CTCCCGTCCCCTGCCCTGCCTGCTGGGCT | 723 |
| IGHG3_chr14:106241345-106241445 | GCTCTGCTCCAGCTCACCTGCTGTCCTTGGTCCTGGCTGAGAGGAGGCCCCAGCCAGCTCTGCTGAC CCTGCCCTGGGCTCCGTGATGCTGCCGG | 724 |
| IGHG3_chr14:106241445-106241545 | CCTGGACAAGCCCCTCGGTTCACCTGGGACCCTCTCCTCCTCCCTCTGCCCTCCTGAGCTCAGGTC GGTCATGCCCATCCTGGCATCACCCCATG | 725 |
| IGHG3_chr14:106241545-106241645 | GCTGGCTCTGCCCCATCCGTCATGTTCCTCACACTCCCAGCCCGGTCGTCTTGGAGGCCTCAGTCAGCCT CTGGTGTGTCCTGCCCTGTTGGCTTGGAA | 726 |
| IGHM_chr14:106318100-106318200 | GGGTAGAGCCCCACCTCGTGGCCTGCAAGCCAGCCAGCCCCCTGCCGGTCGAGAAGGAAGCCTGTGAGA GCACACAACTGGAGGCCGGACGGGGAAGAGA | 727 |
| IGHM_chr14:106318200-106318300 | AACACGTGCCAACAGGCCACGCAGGCCCAGGACCCCAGAGACCCCAGATGCTGGCTCTGAGTTCCTCTCT CTGGTCTCCGATGTTCTTCGTTGGGATCA | 728 |
| IGHM_chr14:106318300-106318400 | TTTCACCTTACAGGCAACAAGAGACAGTGTGAAATGCTTTCCCTGTGGTCGGAGGAGCCGGGCAGAG ATGACCCAGTGGGGTGGTGTGGGGCTCCG | 729 |
| IGHM_chr14:106322055-106322155 | CTTTGCACACCACGTGTTCTCTGCCTGCCTGCATGACGTCCTTGGAAGGCAGCAGACCTGTGAGGTGGCT GCGTACTTGCCCCCTCTCAGGACTGATGG | 730 |
| IGHM_chr14:106322155-106322255 | GAAGCCCCGGTGCTGCTGATGTCAGAGTTGTTCTTGTATTTCCAGGAGACGAAGTGATGGAGTCGGGAAGG AAGTCCTGTGCGAGGCAGCCAACGGCCACG | 731 |
| IGHM_chr14:106322255-106322355 | CTGCTCGTATCCGACGGGGAATTCTCACAGGAGACGAGGCAGCAACCCAGGCCTGGGAGTGAGTATAGGGAGGGTGGGT GAGAGCCCGCAGACAAAAGAGAAGGAGG | 732 |
| IGHM_chr14:106322905-106323005 | ACTTCAGCTACCATCTATGTCCAACAAGATCATGAAGATTGGCCCAGCTGCCCAGTGCCCATGTCTCCCAGTTCATCCCAGCCC AGGCCAGCTCAATCCAGTTCATCCCAGCC | 733 |
| IGHM_chr14:106323005-106323105 | GGCTATCCATCTATGTCCAACAAGATCATGAAGATTGGCCCAGCTGCCCAGTGCCCATGTCTCCCAGTTCATCCCAGCCC AGGCCAGCTCAATCCAGTTCATCCCAGCC | 734 |
| IGHM_chr14:106323105-106323205 | CAGGCCAGCTCAATCCAGCCCAGCCCCAGCTCAGCTCAGCAAAGCCAAGCTCAGCCCAACT CAGATGAGCTCAGACCAGCTCAGCCC | 735 |
| IGHM_chr14:106323470-106323570 | CAGCTCAGCTCAGCCCCAGCCAGCTCGCTCAACCTTGCTCGGCTTAGCCTCAGCCAGCCCAGCCCA GCTCAATCCAGCCTGGCTCAGCCCAGCCC | 736 |
| IGHM_chr14:106323570-106323670 | AGCCCAGTTTGGCTCAACCCAGCTTGGCTCAGCCCAGGTCAGCCTCAGCCAGCCCAGCCCAACTCAGCCCAGCCCAGCCC AGCTCTGCTCAACCCAGCTCTGCTCAACTC | 737 |

TABLE 6-continued

| Name | Sequence | SEQ ID NOs. |
|---|---|---|
| IGHM_chr14:106323805-106323905 | AGCCCAGCTCATCCCAGCTCAGCCCAGCCCAGCCTAGCTTAGCTCAACCCAGCTCAGCTCAGTTCAGCTCA GCCCTGCTCAGCACAGCACAGCAGAGCCC | 738 |
| IGHM_chr14:106324010-106324110 | AGCCCGATCGGCTCAACCCAGCTCAGCCCAGCTCAGCCCAGCTTAACTCAGCCCAGTCAGCTCAGCCC AGCTTAACTCAGCCCAGCCCAGCCCAGCTC | 739 |
| IGHM_chr14:106324155-106324255 | TCAGCCCCAGTTCAGCCCAGCTCAGCCCCAGCCCAGCTTGGCTCAACACAGCTCAGCCTCAGCCAGCC CAGACCAGCTCAGCTCAGCCCAGTCCAGCT | 740 |
| IGHM_chr14:106324290-106324390 | CAACCCAGCCCAGCCCCAACCCAGCTCGGCTTAACCCAGCTCGGCCCCAGATCAGCCTGCTCAACT CAGCCCAGCCCAGCTCAACCCAGCCCAGTT | 741 |
| IGHM_chr14:106324490-106324590 | CAGCTCAGCTGAGCCCAGCCCAGTCCGGCTCAGCCCAGCTCAGCCCCGCCCCACTCAGCCCAGCTCAGCT CAGCCCAGCTCAGCCCAGCCTTAGCC | 742 |
| IGHM_chr14:106324750-106324850 | CAGCCCAGATCATCCCAGCTCAGCTCAGCTCGTTCAGTCAGCTCAGCCTCGGCTTAGCCCAGCTCAACCCAGTCC AGTCAGCCCAGCCTGGACCACCCAGCC | 743 |
| IGHM_chr14:106324850-106324950 | AGCTCAGCTCAGCCCAGCTCAGTCATCCCAGCACAGCAGCTCATTCAGCTCAGCTCAGCTCCAGTCTCTCAACCCA GCCCAAATCAGCTCAGCCCCAGGTC | 744 |
| IGHM_chr14:106324950-106325050 | ATCCCAGCTCAGCCCAGCCAGACAGCCTCAGTAGCCCAGCTCAGCCTAGTCAGCTCAGTTGAGTC AGTTCAACTCAGCCCAATCCAGCTGGCTC | 745 |
| IGHM_chr14:106325050-106325150 | AGCCCAGCTCACCCTAGCTCAGCTAGCCCAGCTTAGCCCCAACTCAACCCAGCCCAGCCTTGCCCAACCCAGCTCA GCTCAGCCCAGCCCAGTTAGCCAGCC | 746 |
| IGHM_chr14:106325150-106325250 | AGCCTCGGCTTAGCTCTGCTCAGTCGGCTCAGCCCCTCAGCCCCAGTTCAGCCCAGTTCAGCTCAGCTCA GCTCAGCCCAGTTCAGCCTCGGCTGTT | 747 |
| IGHM_chr14:106325250-106325350 | AGTCAGCCCAGCGTAGTCAGTCAGTTGAGCCCAGCCCAGGTTAGTCAGCCCAGTCAGCTCAGCTCAGCTCA ACCTGCTCAGCCCAGTTCAGCTCGGCTCA | 748 |
| IGHM_chr14:106325360-106325460 | GCCCAGCGTAGTCAGTTCAGTCAGCCCAGCCCAGCTGAGCCCAGCCCAGGTTAGTCAGCCCCAGTTCAGCTCAGTCAACTC AGCCCAAACCAGCTCGGCTCGGCCCAGTC | 749 |
| IGHM_chr14:106325460-106325560 | ACCCTAGTTCAGTTAGCTCAGCCCAGCCCAGCTCAGCCCAGCCTTAGCCTCTGCTCAGCCCCAGGTTA GCCCAGCCCAGCTCGGTTAGCTCTGCT | 750 |
| IGHM_chr14:106325515-106325615 | AGCCCAGCCCAGTTAGCCCAGCCAGCCCAGCTCGGCTTAGCCTTAGCTCTGCTCAGCTCGGCCCAGGTTAGCC CAGCCCAGCTCGGCTTAGCCTCTGCTCAGC | 751 |
| IGHM_chr14:106325615-106325715 | TCCGGCCCTGCTCCTCGCCTCAGCCCTGCCGTTCAGCCCAGTTCAGCTCAGCTCAGCCCAGCGCCC TGGTTAGCTCAGCCAGCTAAGCTCAGCT | 752 |
| IGHM_chr14:106325715-106325815 | CGGCTCAGCTCTGCTGAGCTCGCCCAGCTTGGCTCAGCCCGACACAGCCTGCTCAGCCCAGTTCAGCTC GGCTCAGCCCAGCCCAGCGTAGTC | 753 |

TABLE 6-continued

| Name | Sequence | SEQ ID NOs. |
|---|---|---|
| IGHJ6_chr14:106325820-106325920 | AGTTGAGCCCAGCCCAGGTTAGCTCAGCCCCAGGTTAGCTCAGCCCTGCCCAGGT TAGCTCAGCCCCAGTCCAGGTTAGCTCAGC | 754 |
| IGHJ6_chr14:106325920-106326020 | CCAGCTCAGCTCTGCCCCAGTTAGCTCAGCCCCCAGGTTAGCTCAGCCTTCAGCCTTGCCCAGG TTAGCTCAGCCCAGCTAAGCTCAACTTGG | 755 |
| IGHJ6_chr14:106326020-106326120 | CTCAGCTCAGCCTAGCTTGGCTCAGCCCAGCAGCACGCTCAGCCGTTCAGCTTGGCTCAGCCCAGC CCAGCCCAGCCTAGCTCAGCTCAGCCCGC | 756 |
| IGHJ6_chr14:106326245-106326345 | CCAGCTCAGCCAGCGCAGCCCAGCTCAGCTCAGCCTAGCTCAGCCTTGCTCGGCCCCAGCTCAGCTCAGCCCAGCT CAGCCTAGCCTTGCTCAGCCCAGCTCAGC | 757 |
| IGHJ6_chr14:106326450-106326550 | TCAGCCCAGCCTGCCCAGCTCAGCCCAGCTTAGTGCAGCCAAGCCCAGCTCAGCTCAGCTCACCTGTG CAACTTAGCCCAGCTCAGCTCAGCT | 758 |
| IGHJ6_chr14:106326550-106326650 | CAACCCAGTTCAACTCAGCCCAGTTCAGCTCAGCTCAGCCCCAGCTTCAGCCTTGTTTAGTCTAGGTCAGCTT AGTTCAGTTTTGCCCATTCAGCCCATTT | 759 |
| IGHJ6_chr14:106326650-106326750 | CTGAAAGCTGGATGGAGTTGTCATGGCCAGAAATGGTCAGCCCCACCAGACCTGCTTGTCTCAGCTAAAGC CATCTCATTGCCCAGGTTCCTGCACAGCCAG | 760 |
| IGHJ6_chr14:106326750-106326850 | GCTGGCTTCCATCTTTTGTCTCCCCTTACTTGATTACCCCCAGTTCCCTGCAGTCCTGCCCCAGCGCCACCTGG GTTTTGGTTCCAAAGCATTACCAATCAT | 761 |
| IGHJ6_chr14:106326850-106326950 | TACCACCCTCCACTACCTGGGTGGAATATTCTTTGTCTTTAAAGTCATTAAAACATCTTGAGAATGAG ACCAAGAATTTAGGAGCCTGTGCTGTGAT | 762 |
| IGHJ6_chr14:106326950-106327050 | AAAAATGAGCAGGTCCCCTTGCTCTAGAAGTGCAGCATATCTTCTGCACCAAGAGGAGGGTATTGAGAT GCTCAGAGCCTCCACCTTCCCGGAGCATCC | 763 |
| IGHJ6_chr14:106327050-106327150 | CCTCCCCTTCTGAGTCTGCAGTAAACCCCTGCCTTTAAATTCCCTCTAGAATAACAGTCATCATTGGAAACAA CCAGAAATGCATTTTATCTGAATTTGCC | 764 |
| IGHJ6_chr14:106327150-106327250 | ACTTAAAATTCTGCCATTTACCATAAATCGCTTTGGAAGGCATGGGTACTTTCAAGGGTGCGATGATGA CCTACAGTCAATGACTTAGACAAGGGCGAT | 765 |
| IGHJ6_chr14:106327250-106327350 | GCCAGTGGGGCTTGGTATGTTCAAGCATCATTACCCATGCCATCCCATTCAGAGGTTGTGAGCAGCT CGTGCGACCTCTCCTTCCAAATGGGCTTTA | 766 |
| IGHJ6_chr14:106327350-106327450 | GGGAAAGTTAAATGGAGTGACCCAGACAATGTCACTCAAAAGACTCACATAAATGAGTCTCCTGCTCT TCATCAAGCAATTAAGACCAGTTCCCCTTC | 767 |
| IGHJ6_chr14:106327450-106327550 | TAGTGGAAATAAGACGTCAAATACAAAGTTTAAGAGAAGCAAATGCAGCAGCGGCGCGCCGCTGCTGTCTCT TACCATGTCGGGCGCCTGGTCACTGCGAGC | 768 |
| IGHJ6_chr14:106327550-106327650 | CTTTGCAAAGCTTTGGCATGGAATCATTCCTCCAAGTCCATTAACAAGGGCTGGGGCCTGAGCAGCCAGTC GGCCCGGCCAGCAGAAGCCACGCATCCCAGC | 769 |

TABLE 6-continued

| Name | Sequence | SEQ ID NOs. |
|---|---|---|
| IGHJ6_chr14:106327650-106327750 | TCTGGGTAGTCCGGGAGACCCAAAGCCCAGGCCGGGCCTGGCAGCCACCCTCCCAGAGCCTCCGCTAGG CCAGTCCTGCTGACGCCGCCATCGGTGATTC | 770 |
| IGHJ6_chr14:106327750-106327850 | GGAACAGAATCTGTCCTTCTAAGGTGTCTCCACAGTCCTGCTTCAGCACTATCGATTGAGTTTTCTCTT ATGCCACAACTAACATGCTTAACTGAAA | 771 |
| IGHJ6_chr14:106327850-106327950 | TAATTCAGGATAATGATGCACATTTTACCTAAAACTATCCTAAAGTGAGTAGTTGAAAAGTGGTCTTGA AAAATACTAAAATGCTCTGAGGTATCGAAG | 772 |
| IGHJ6_chr14:106327950-106328050 | AATATCAAAGTGTTTCTCCTTAATCACAAAGAGAAAACGAGTTAACCTAAAAAGATTGTGAACACAGTCA TTATGAAAATAATGCTCTGAGGTATCGAAA | 773 |
| IGHJ6_chr14:106328050-106328150 | AAGTATTTGAGATTAGTTATCACATGAAGGAGTAACAAGCTAATTTAAAAAACTTTTTGAAATACAGTCAT AAACTCTCCCTAAGACTGTTTAATTTCTTA | 774 |
| IGHJ6_chr14:106328150-106328250 | AACATCTTACTTTAAAAATGAATGCAGTTTAGAAGTTGATATGCTGTTTGCACAAACTAGCAGTTGATAA GCTAAGATTGGAAATGAAATTCAGATAGTT | 775 |
| IGHJ6_chr14:106328250-106328350 | AAAAAAGCCTTTTCAGTTTCGTCAGCCTCCGCCTTATTTTAGAAACGCAAATTGTCCAGGTGTTGTTTTG CTCAGTAGAGCACTTTCAGATCTGGGCCT | 776 |
| IGHJ6_chr14:106328350-106328450 | GGGCAAAACCACCTTCTTCACAACCAGAAGTGATAAATTTACCAATTGTGTTTTTTGCTTCCTAAAATAGA CTCGCGGTGACCTGCTTCCTGCCACCT | 777 |
| IGHJ6_chr14:106328450-106328550 | GCTGTGGGTGCCGGAGACCCCCATGCAGCAGCCATCTTGACTCTCTAATTCATCATCTGCTTCCAGCTTCGCTCAA TTAATTAAAAAATAACTTGATTTATGA | 778 |
| IGHJ6_chr14:106328550-106328650 | TGGTCAAAACGCAGTCCCGCATCGGGGCCGACAGCACTGTGCTAGTATTTCTTAGCTGAGCTTGCTTTGGC CTCAATTCCAGACACATATCACTCATGGG | 779 |
| IGHJ6_chr14:106328650-106328750 | TGTTAATCAAATGATAAGAATTTCAAATACTTCAAATACTTGGACAGTTAAAAAAATTAATATACTTGAAAATCTCTCAC ATTTTAAGTACATAATTTTCTTAACCATT | 780 |
| IGHJ6_chr14:106328750-106328850 | TTTTCTCAGAAGCCACTTCAAACATATCCTGTCTTTAACAGTAAGCATGCCTTCCTAAGATAAACAATCCTT TTCTCTTGGAAACCAGCTTCAAGGCACTG | 781 |
| IGHJ6_chr14:106328850-106328950 | AGGTCCTGGAGCCTTCCCCTAAGCCCCTGTCAGGACGGCAGCCACCGTTTCTGGGCTACCCCTGCCCCAACC CTGCTCTCATCAGACGCGGGCTACGCGT | 782 |
| IGHJ6_chr14:106328950-106329050 | CCCTCCTCTGGCTGATTCACCCACCTCCGACAGTTCTCTCTTTCCAGCCAATAAAGAATTTAAGATGCAGGTTGA CACAGCGCACCTCATAATTCTAAAGAA | 783 |
| IGHJ6_chr14:106329050-106329150 | AATATTTCACGATTCGCTGCTGTGCAGCGATCTTGCAGTCCTACAGACACCGCTCCTGAGACACATTCCTC AGCCATCACTAAGACCCCTGGTTTGTTCA | 784 |
| IGHJ6_chr14:106329150-106329250 | GGGCATCTCGTCCAAATGGCTCCCCAAGCCCCCAGGCTCAGTTACTCCATCAGACGCACCCAACCTGAGT CCCATTTTTCCAAAGGCATCGGAAAATCCA | 785 |

TABLE 6-continued

| Name | Sequence | SEQ ID NOs. |
|---|---|---|
| IGHJ6_chr14:106329250-106329350 | CAGAGGGTTCCCAGATCTTCAAGGCACCTCAAGGCACCCCAGTGCCCGTCCCCTTCTGCCAGTCCGCCCAGGTCCCCTCGG AACATGCCCCGAGGACCAACCTGCAATGC | 786 |
| IGHJ6_chr14:106329350-106329450 | TCAGGAAACCCCACAGGCAGTAGCAGAGAAAACAAAGGCCCTAGAGTGGCCATTCTTACCTGAGGAGACGG TGACCGTGGTCCCTTTGCCCCGACGTCCAT | 787 |
| IGHJ6_chr14:106329450-106329550 | GTAGTAGTAGTAATCACAATGCAGAAGATGTCCATCCTCACCCCACACAAAACCCAGCCACCCAGA GACCTTCTGTCTCCGGGCGTCACATGGAAG | 788 |
| IGHJ6_chr14:106329550-106329650 | CTGACTGTCCGTGCCCTGTCTGCCCTTCTCATGGAACCCCTCTGCTGGCCTCCCACGTACCCCACATTCT GGCCCTGACCCCTCAGAAGCCAGACCACTG | 789 |
| IGHJ6_chr14:106329650-106329750 | TCGGCCTGGGAAGTCCAACTGCAAGCAGACAGAGCGGCTGCTAAGTCACCCCCAGGAGTCCAAAAACCCGGGG GGCACCCGTCCCAGAGAGCGGGTGCCTTGGA | 790 |
| IGHJ6_chr14:106329750-106329850 | GCGGGACAGAGTCCCACCACGCAATCATCACGACAGCCCCTGAGAATGCTCCAGGTGAAGCGGAGAGAG GTCACCCCAGACCAGCCGAAGGAGCCCCCA | 791 |
| IGHJ6_chr14:106329850-106329950 | GCTGCCGACATCTGTGGCCGGACTTGGGAGGACAGGCTGGGTTCCCATTCGAAGGGTCCCTCTCCCGG CTTTCTTTCCTGACCTCCAAAATGCCTCCA | 792 |
| IGHJ5_chr14:106329950-106330050 | AGACTCTGACCCTGAGACCCTGGCCAAGCTGAGTCTCCCTAAGTGGACTCAGAGAGGGGGTGGTGAGGACT CACCTGAGGAGACGGTGACCAGGGTTCCCT | 793 |
| IGHJ5_chr14:106330050-106330150 | GGCCCCGAGGGGTCGAACCAGTTGTCACATTGTGACAACAATGCCAGGACCCCAGGACGACTGGCGCCC CGCTACGTCCCTGGGACCCCTCTCAGACTGA | 794 |
| IGHJ5_chr14:106330150-106330250 | GCCCGGGGAGGGCCCGGGAGGGTTGTTGGGCATTGGACCCCAGAGGGCCTAGGGTGGCCTGGCCACAGAGA GACCCGTGCTGCTGGGCTCAGGAGGAAGGAG | 795 |
| IGHJ4_chr14:106330250-106330350 | CATCTGGAGCCCTTGCCCCTCGTCGTGTGGCCGCGTGTTGCCTCAGGGGCATCCTCCTGAGCCCCCCAGGAT GCTCCGGGGCTCTCTTGGCAGGAGACCCA | 796 |
| IGHJ4_chr14:106330350-106330450 | GCACCCTTATTCCCCCAGAATGCAGCAAGCAAAACCCTTCAGAGTTAAAGCAGGAGAGAGGTTGTGAGGAC TCACCTGAGGAGACGGTGACCAGGGTTCCC | 797 |
| IGHJ4_chr14:106330450-106330550 | TGGCCCCAGTAGTCAAAGTAGTCACATTGTGGGAGGCCCCATTAAGGGGTGCACAAAAACCTGACTCTCC GACTGTCCGGGCCGGCCGTGGCCAGCCAGC | 798 |
| IGHJ4_chr14:106330550-106330650 | CCCTGTCCCAAGGTCATTTTGTCCCCAGCACACAAGCATGACTCTGCCACCCTTTGCCCCAGCAGCAGAGT CCCAGTTCCCAAAGAAAGCCCTTCTGCTG | 799 |
| IGHJ3_chr14:106330650-106330750 | AACGTGGTCCCAAACAGCCGGAGAAGGAGCCCCGGAGGGCCCCACATGGCCCAGCGCAGACCCAAGGAGC CCCCGGACATTATCTCCCAGCTCCAGGACAG | 800 |
| IGHJ3_chr14:106330750-106330850 | AGGGACGCGTGGGCCCAGAGAAAGGAGGCAGAAGGAAAGCCATCTTACCTGAAGAGACGGTGACCATTGTC CCTTGGCCCCAGATATCAAAAGCATCACACA | 801 |

TABLE 6-continued

| Name | Sequence | SEQ ID NOs. |
|---|---|---|
| IGHJ3_chr14:106330850-106330950 | GGGACACAGTCCCTGTTCCTGCCCAGACACAAACCTGTGCCCGTGCAGGACACTCTGAATGGGTCACATGG CCCAAGCACAGAGCCAGAGGCAGGCAGCCGGCGTC | 802 |
| IGHJ3_chr14:106330950-106331050 | CCTGTCCCCAGCCACACAGACCCCTGCCCTGCCCCAGTGCTCCA GTGCCGGGCTGCCCTGGCCTGAGACCCAGGCGGGAGGGGTGACGTTCCAGGGAGACG | 803 |
| IGHJ3_chr14:106331050-106331150 | AGCACTTGTAGCCACACTAAAGCGCAGGCCTGTCCCCGGCACATGAACAGCGCCCAGCC CAGGCTCTGCCCACAACTTCTCCTTCCGT | 804 |
| IGHJ2_chr14:106331150-106331250 | CCCTGCCCTCCGGCCTGCTTGCTACCTGTGGAGGGTCCCTGACGGGGCTGAAGCCCAGCGGGGTCCCTGCC TGTCCTTGGGGGCTCCAGCTGCCCCAGGG | 805 |
| IGHJ2_chr14:106331250-106331350 | CTAAGTGACACAGCAGGGCTCTGGCATGCAGCCCATGGCGGAGACCCCAGGGATGGCAGCTGGTGTGGCCTC AGGCCAGACCCAGGCCGGCTGCAGACCCCA | 806 |
| IGHJ2_chr14:106331350-106331450 | GATACCTGGCCTGGTGCCTGGACAGAGAAGACTGGGAGGGGCTGCAGTGGGACTCACTGAGGAGACA GTGACCAGGGTGCCACGGCCCAGAGATCGA | 807 |
| IGHJ2_chr14:106331450-106331550 | AGTACCAGTAGCACAGCCTCTGCCTCTGCTTCTCCCATACAAAACACACCCTCGCCCCTCCTGCCGAC CTCCTTTGCTGACACCTGTCCCCAAGTC | 808 |
| IGHJ1_chr14:106331550-106331650 | TGAAGCCAAAGCCCTTGCCTGGCCAGTACACCTGGCTTCCCCGCTATCCCCAGACAGCAGACTCACCTGA GGAGACAGCGGTGACCAGGGTGCCCTGGCCCA | 809 |
| IGHJ1_chr14:106331650-106331750 | GTGCTGGAAGTATTCAGCCACCGTGAGTCAGCCCTGAGTCCTGAGCCAGGAGCCCTACAGAAACCCACGCCCGGGGTC CCGGGGAGCATGGTTTTTGTAGAGCTGCC | 810 |
| IGHD7-27_chr14:106331750-106331850 | AATCACTGTGTCCCCAGTTAGCACAGTGGTTCCAGCTCAGCCAAAACCCTGCGGCTGGTAGGGGGCCTG TGGGGCTGGGGGCTGATGTGGCTGCGGTCT | 811 |
| IGHD6-19_chr14:106357890-106357990 | TGCTGGGTCTGTCCTCTGTGGGAGGGGCTGCTACCCAGGCCCAGGACTGCAGTGGAGGGCTACTGAGGG GCTTTTGGGTCTGCCCTGAGCCGCTGTGGG | 812 |
| IGHD3-3_chr14:106380360-106380460 | GCTCTCAGGTCTACTGCGGGGACACTCGGGTTGCCCCTGGCTTAGGTGGACAGTGTCCGTGCCCACCTG TGCCCTGAGGCTCCATTTCAGGCTGATATC | 813 |
| IGHD3-3_chr14:106380460-106380560 | TGTCTGTATTGTCCCCAGCCGCTGCATGGCCATGTCCTTTTGGGTTTATAAATTGCCCCAAATCACCCAG GCATCATTCAGGCTTTTATATTCCCTGG | 814 |
| IGHD3-3_chr14:106380550-106380650 | TATTCCCTGGGCCACCAGGTGCCTCCACCCAGAAAGCTGAGATGTGGGAGGTTCTAGAGTCATTCTGCAA CCCTGGATGAGCCCCTGCAGCCTTCAGTGCT | 815 |
| IGHD3-3_chr14:106380650-106380750 | ACTGAGGTTCCAGCCAAGACCTGAGCAGGTGCAGATGAGGCCTGAGGCCCAGGTGAAGCCCAGGCCAGGT GAGGTCCAGGCCCAGTGAGGCCCAGGTCAGAT | 816 |
| IGHD3-3_chr14:106380750-106380850 | GAGGGCCCAGGTCAGGTGAAGCCCAGGTGAAACCCAGTCAGGTGAAGCCCAGGTCAGGTGAGGCCCAGATCATGTGAGCT CAGGACAGGCAAGGTCAAGTCAGGTGAGGC | 817 |

TABLE 6-continued

| Name | Sequence | SEQ ID NOs. |
|---|---|---|
| IGHD3-3_chr14:106380850-106380950 | CGAGCTCAGTGAAGCCCAGAGTGAGGTCAGGCCAGGTGAGTCTCAGGCCAGGTGAGGTCCAGGTCAGGTCAGGTGAGGCCCAGGTCAGGTCAAGGCTGAGGTA | 818 |
| IGHD3-3_chr14:106380910-106381010 | TCCAGGTCAGGTGAGGCCCAGGTCAGGCAAGGCTGAGGTAGATGTATGAGACTTCTGTAATTTTCAGTTGGTGCCAACCCTGCCTGGTGTCCCTGCCCT | 819 |
| IGHD3-3_chr14:106381010-106381110 | CCTCCCAGCCATGCTCTGTGCCTGCCAGAATGCCAGGCGGCCCCTGCACAGTGCTGCTGGCTGTGTGAGGAGCTGGGCTCTGCCTCCCTGTGCAGGGCGTCC | 820 |
| IGHD3-3_chr14:106381275-106381375 | GCCTGCAGCCTGTCGCGGGATGCCCAGGAGGTGAGTGCCACCACATATCAGGCCTTTTCTCTTTAAAGTCATTTCTTTGGGATACATCATCAATGTCT | 821 |
| IGHD3-3_chr14:106381485-106381585 | TCTAAACACAGTGTGTGCATTTTCCTCTTCTGCAATTTAGAATTTAACTGCTGTTTTCAAGGTACTGTAATGTATTTGTTCTCTTCTTGTAGGAGA | 822 |
| IGHD2-2_chr14:106381585-106381685 | CTTGCCAACCCTGTGTGTCTCAGTTCATACCCTCTTCCTCCCCAGTAGAAGTAACGACCACTGTGTTTATGTGATCATCCTTTTCTTGATTTTCCTTAT | 823 |
| IGHD2-2_chr14:106381655-106381755 | TGTGATCATCCTTTTCTTGATTTTCCTTATAGTTTCCTTCAGATGGCTGTTTGTTGCTTCATTCTCAGTTTGGGCTATGACAAATTTTGCCGGTGTAAATTTATTTAGAA | 824 |
| IGHD2-2_chr14:106381890-106381990 | CTGCCATCGTCTTATTGCCTGTTTTCCTTCAGATGGCTGGTGTTTGTTGCTTCATTCTCAGTTTGGGCTATGACAAACATATGTTCTGCACATCTTTGCCCATGA | 825 |
| IGHD2-2_chr14:106381990-106382090 | GGCTCTCAGGGAGGGCTCTGGAGCTGGGAGCTGGCATTGCCTGCAGGGCTCTGCTTTGTTGTTGCAGGGAGTTCCTGCCAAGGCTTTTCAGAGTGTCTGTGCCCAGCCTG | 826 |
| IGHD2-2_chr14:106382090-106382190 | AAGTACACACTGTACTTTGCCCTTGCATCAGGCACTTTCCTTGTGCTTGCTTCGTGTGGCTCCACATTCTGGAGAATTTATTCAGATCTGTGCTGCAA | 827 |
| IGHD2-2_chr14:106382325-106382425 | CTTCCCACACTGTCCTCCTCTGGGCTCACTCCCAGCCATCATCTCCCAGGCCATCCAGCAGCCATCGATCTTGAACACCAGTTATGAACTATCTGCACAGGAAAGCAGACAAGAAACAGCAAAAGCCCTG | 828 |
| IGHD2-2_chr14:106382905-106383005 | TTGCGTGGACCCTGTTTTGGTCAAGGGAAGTACTTGCTGGTGAAGGAGACCTCCCCTCCTTTCTTTCTCAGGAGCCCCCTCTGATGCCGTTGCCTGGTG | 829 |
| IGHD2-2_chr14:106383005-106383105 | TTTCTCAGGGCTGGTGCTGGGGGCTCAGCAGTGCTGCCCTGTTCTGCCAGTGGGAATGGGGTCTGTTCTGTTTCCAGTGGGAATGGGGTCTGTTCTGTTTCCACGCGGTGTTCTGGGGCGCCTTCCACGCGGTGTTCTGGGGATGTCAGCGGCTGG | 830 |
| IGHD2-2_chr14:106383030-106383130 | CAGCAGTGCTGCCCTGTTCCAGGTGGGAATGGGGTCTGTTCTGTTTCCACGCGGTGTTCTGGGGCGCCAGTGAGGGGCTCCGGATGTCAGCGGCTGG | 831 |
| IGHD2-2_chr14:106383130-106383230 | TCTCTGTCCTATGGTCTGGGCTCCGGTTCACTGCTCCGTGCTCGTCAGGTCGGTCGCTACTCAGTTACTATCCAGCGGGCTCCGTGGCTGTTCAGTG | 832 |
| IGHD2-2_chr14:106383980-106384080 | GGGAGCAAATGAGAGGAAGTGGCAGCGGCCCGAGTGCCAGGCGGTCCCAGGTTTGGGGTTGATCTTTGTGAACAGCTCCCTGGCCGTGTGTAAGTGG | 833 |

TABLE 6-continued

| Name | Sequence | SEQ ID NOs. |
|---|---|---|
| IGHD1-1_chr14:106384080-106384180 | TCGGGGGAGGCACGGAGTCTGAGCTACAAGCGGTGGCAGGAAGGCAGGTCCCAGTCTTGGGGTCTG GAGCTTATCTTCTTCCTGTGAACTGAGTGTG | 834 |
| IGHD1-1_chr14:106384630-106384730 | ATGGAGGACCTGCCTCGGATGACACCCCTATCTTAAGAAGGTCATGTGGGTTCCAGTGGGAGGAAGGG AAGTGGGCCACCTCCTGGGGGTCTTCACC | 835 |
| IGHD1-1_chr14:106384720-106384820 | GTCTTCACCCCACCCCACCTCAGCCTGGGGCCTCTGTGATTCCTCTGCACAGACCCCAAAGTCTGTGCT GCCGCAGGGCAGGAAGGAAGGGCTGTGG | 836 |
| IGHD1-1_chr14:106384825-106384925 | TCCAGGTTTGGGGCCACAGTGGTGTTCCCTAAGCCCGAGTCTCTGTCTCATGGGCCCCGCAGCAGGTCC TGAGTGAGGGACAGAGACCCGGGGCGGGTC | 837 |
| IGHD1-1_chr14:106384925-106385025 | TTTGGTCCTGGTGGACTCTGGGGTGGATTCCAGTGGGGAGTCATCAGGGTCCGTGTCCCCAGGGTACTG GGGTGTCCTGCTCCTGGAGTCGGCTCTGG | 838 |
| IGHV2-5_chr14:106494090-106494190 | CCTGGGTTTTTGTACAGGAGGTGCCCTCGGCTCTGCCTGTCTTTGTGGTCTGTGCAGTAATATGTGGCTGT GTCCACAGGGTCCATGTTGGTCATTGTAA | 839 |
| IGHV2-5_chr14:106494210-106494310 | GTGTCCTTGGTGATGGTGAGCCTGCTCTTCAGAGATGGGCTGTAGCGCTTATCATCATTCCAATAAATGAG TGCAAGCCACTCCAGGGCCTTTCCTGGGG | 840 |
| IGHV2-5_chr14:106494310-106494410 | GCTGACGGATCCAGCCAGCCACCACCCACTGTCTGAGTGAGAACCCAGAGAAGGTGCAGTCAGCGT GAGGGTCTGTGGGTTTCACCAGCGTAGG | 841 |
| IGHV2-5_chr14:106494445-106494545 | CTGTGGAGAAAGCATAAGAAGATGAAGCCCACAAACAAGAAAACTGATGTTTCACCCGTGAAGGAGTCC CTGACCAGCACTCACATGAAGGGGATGTC | 842 |
| IGHV2-5_chr14:106494545-106494645 | AGCAGCAGGACGTGGAGCAAAGTGTGTCCATGTGGGGCACAGAGGAGTCACTGAGCTGGGACCTGTGCT CGGCTTTTTCAACCCAGAGGAGGGTGGAGCT | 843 |
| IGHV2-5_chr14:106494565-106494665 | AAGTGTGTCCATGTGGGGCACAGGAGTCACTGAGCTGGGACCTGTGCTCGGCTTTTTCAACCCAGAGGA GGGTGGAGCTGGTGGAGATTTGCATTCCCC | 844 |
| IGHV2-5_chr14:106494650-106494750 | AGATTTGCATTCCCCTACTCTGTGCCCTACTCTATGGGATGGAGTCAGGTTTCAGGACTCAGGAGGGTGTT GCATCGTGGTGAGGACCAGTGATAGTAA | 845 |
| IGHV2-5_chr14:106494750-106494850 | CATGATCAGTGTAATTCAGATGGCATTAATCTAAGGCTGGGCAAGTAGATTCTGAGTAGAAGTCTTTCA GAAGTCATGATTATGAGGTCATGTTGGTCT | 846 |
| IGHV3-7_chr14:106518495-106518595 | GCCCTTCACAGAGTCCACATAGTATTCTCACTTCCATCTTGCTTTATGTTGGCCACCCACTTCCAGCCCCTT CCCTGGAGCCTGGCGGACCCCAGCTCATC | 847 |
| IGHV3-7_chr14:106518855-106518955 | TGAGTCCTCTGTGCTCAGTGCTGATCACCAAGTGGAAAAGGCCTTGAGTCCAGGGCTAAGGCTCCTCTCT GAGACCTGCAGGTCAGGTTGGGTTGGTT | 848 |
| IGHV3-7_chr14:106518955-106519055 | TTTCATCAGTAGAGGGAGGGCCCTATTTGCATGTCTCCTACTATATAAGAAGCTCTAGTGGGATGCTGGAG GAATAGGCTGTACCCATATAAGAAGACGGT | 849 |

TABLE 6-continued

| Name | Sequence | SEQ ID NOs. |
|---|---|---|
| IGHV3-7_chr14:106518970-106519070 | AGGGCCCTATTTGCATGTCTCCTACTATATAAGAAGCTCTAGTGGGATGCTGAGGAATAGGCTGTACCCATATAAGAAGACGGTGCTCTGCAGAAGTTT | 850 |
| IGHV3-7_chr14:106519070-106519170 | GCTGACAATGATGGTATTTGGAAAATATGCTGTCTTATGAAATTGTGCTGTGATAAACACTTTGCCCTGATCACCCTATTACATTTTTTAAAAATGTGT | 851 |
| IGHV3-11_chr14:106573540-106573640 | CAAACAGAGACAACCTAGTCAGAAACTGCCACATATATTCACTGCTTATCTCACTCACGTCCACTCAATGTCTCTAGTTCTCCATAAATCACCTTTTA | 852 |
| IGHV3-11_chr14:106573640-106573740 | TAATAGCAACAAGGAAAACCCAGCTGGGAAAACCCAGCCCCAAACTCCATGGTGAGTCCTCTGTGTTCAGTGCTGATCACCGAATGAAACTCCTGGGAATTCTGGGGCT | 853 |
| IGHV3-11_chr14:106573685-106573785 | GTCCTCTGTGTTCAGTGCTGATCACCGAATGCTGATCACCGAATGAAACTCCTGGGAATTCTGGGGCTCTTCTCCCAGAGCTGCAGGGTCTGGGCTCGGCTGGTTTT | 854 |
| IGHV3-11_chr14:106573785-106573885 | TATCAGCAGAGGAGGGCCCTATTTGCATGTCTCCTACTATATAGCAAGCTCTAGTGGGACGCTGGAGGAGAGGGCAGTGCCCAGAGCAGATGAGAGGGT | 855 |
| IGHV3-11_chr14:106573885-106573985 | CCCGAAAACACTGGAGGTAATCCTATCTCCAGGAAAAATATAACTTCAGATTTATGTGATTGTGACTTGATGATCAATTAGCAGTCATCATCTTATTTAA | 856 |
| IGHV3-11_chr14:106573985-106574085 | TGTTTACATATTTGCAGAATATATTCAGTGCAAGTGTCAATGTTACATTTTAGAGAAGATGAATTACATACATAACAGACAGTTGTCAATGTGTCCA | 857 |
| IGHV3-15_chr14:106610690-106610790 | ACTCACACTTAATCTCTCTAGTTCTCCATAAATCACCTTTAAAATAGCAGCAAGAAATACATGACACATACAGCTCAGCCCAAACTCCATGGTGAGTCCTCTGTGTC | 858 |
| IGHV1-18_chr14:106642110-106642210 | GATGCTATTTAATAGCCCAATTCCTGACCAGGATGAGCACCCATCCCTGAACTCTGTGTTGACAGAGCTTCCCCCACTGGAGAACATTGTAGAAGCTGAGGGTTCAAGCCGTAAT | 859 |
| IGHV1-18_chr14:106642210-106642310 | CCTGTTAGGGCCACGCATCCCATCCCTGACCAGGATGTGCTACCACCACTATAGTGAGACCCACTCCAGCCCAAGCTCCCCAGAGACACGCACCCTCACCTTA | 860 |
| IGHV3-23_chr14:106725295-106725395 | GGGCCCTTCACGAGTCTGCTGCTAAGGTGAATCCAGAGGCTGCACAGGAGAGTCTCAGGGACCCCCCAGGCTGTACCATTCCCTGGAGCCTGGCGACCCAGCTCAT | 861 |
| IGHV3-23_chr14:106725395-106725495 | GGCATAGCTGCTAAAGGTGAATCCAGAGGCTGCACAGGAGAGTCTCAGGGACCCCCCAGGCTGTACCAAGCCTCCCCCAGACTCCAACAGCTGCACCTCA | 862 |
| IGHV3-23_chr14:106725550-106725650 | ACTGTTCTCTCACTCTTATCCATTCACACTCAATTTTTCTATTTCTCCATGAATTACCTTTTAAAATAGCCACAAGAAAAAGCCAGCTCAGCCCAAACT | 863 |
| IGHV3-23_chr14:106725650-106725750 | CCATGGTGAGTTCTCTCTGTTCAGTCCTGATCACCAAATGAAAACACCTGAAAATCCCAGGGCTGGGCTCCTCTCTCAGAGCTGCAGGGTCAGGGCTGGG | 864 |
| IGHV3-23_chr14:106725780-106725880 | TTTGCATATCTCCTACTATATAGTAAGCTCTGGGGTGAGAGGCCTTTGGAGATAGTGGGGCTCAGAGCATGTCAGAATGTCCTCGGGAGATCTGTGATA | 865 |

TABLE 6-continued

| Name | Sequence | SEQ ID NOs. |
|---|---|---|
| IGHV3-23_chr14:106725880-106725980 | TTGAAAGCATTGGGAAATTGTGCTTTCCTATTGTCAGTTGTTTGTTTTGTGATAAACTTAAACCTAAAAATCTTATAATTTTGTAATTTTTATTT | 866 |
| IGHV3-23_chr14:106725995-106726095 | GAGGTACCATAGATCTACATAAACTGCATATTTTAAAGTAGCACCAATCATCTTTATTTTTACATACGCAGAGAAACCATGTATATAGTATCAATA | 867 |
| IGHV3-23_chr14:106726095-106726195 | TTATTTCCATGTTAAAGATGAAAAATTATCAGCAAAAGCACAGTGGGTTTTACAATGTCCCCAGTGCTCACTTTTGGTCAGAGTGAGCCTGGCATCTG | 868 |
| IGHV3-23_chr14:106732970-106733070 | TCCTACATAATGACAGTGTACACATCTTTCCATTGCTGTTTTACTCAATTACTCAACCCATTTTCTAAACAGATTTAAACTTCATAAATCCTGTCATCTC | 869 |
| IGHV1-24_chr14:106733070-106733170 | CTCAGCCTCAGCACAGCTGCCTCATTCCTCAGGGTTTCTGACGCTCCAGGATGTGGGTTTTCACACTGTGTCTGTTGCACAGTAATACACGGCCGTGTC | 870 |
| IGHV1-24_chr14:106733185-106733285 | GCTCAGCTCCATGTAGGCTGTGTCTGTAGATGTGTCCTGGTCATGTGACTCTGCCCTGGAACTCTGTGCGTAGATTGTTTCACCATCTTCAGGATCA | 871 |
| IGHV1-24_chr14:106733275-106733375 | TTCAGGATCAAAACCTCCATCCACTCCAAGCCCTTTTCCAGGAGCGCTGTCGCACCCAGTGCTGATGCATGGATAATTCAGTGAGGGTGTATCCGGAAACCTTGCAG | 872 |
| IGHV1-24_chr14:106733375-106733475 | GAGACCTTCACTGAGGCCCCAGGCTTCTTCACCTCAGCCCCCAGACTGTACCAGCTGGACCTGGGCGTGGGTGCCTGTGGAGAGGACAGAGGAGTGGATGA | 873 |
| IGHV1-24_chr14:106733475-106733575 | GACACCACTTAACTGGGACCCAGTGCCCCTCATCAGCCCTGGAACTCAGGATTCTCTTGCCTGTAGCTGCTGCCACCAAGAGAGATCCTCCAGTGCAGT | 874 |
| IGHV2-26_chr14:106758470-106758570 | GAGGGTGGGAATCTGGGAGAGCAAGGGCTTCCCATAAGTGTTCTGATAAAAATCCTCTTGTTTAGGGGGAAAGTGATGATTTTTTGAATGATAGAGA | 875 |
| IGHV2-26_chr14:106758570-106758670 | ATACATCACCCAAACATTTAAAAATGTATTGTGTAAAGAAGTGTAAATGGCATCTCAGCCATTTACACACTGCAAGACACACAGCTTATTAGTGTGCCTG | 876 |
| IGHV3-30_chr14:106791090-106791190 | TGGTGAATCGGCCCTTCACGGAGTCTGCATAGTATTTATTACTTCCATCATATGATATAACTGCCACCCACTCCAAGCCCCTTGCCTGAGCCTGGCGAC | 877 |
| IGHV4-31_chr14:106805945-106806045 | ACAATCACTTGAGTTCAGACACACCAGGATTCACTTAATGTTATTTTTAGTTCAGAACCTCTATCAGGTTTAGAGGGAATCGCTCTGTCCCAGGAGTGG | 878 |
| IGHV4-31_chr14:106806045-106806145 | ATCTTACAATAGCAAACGGTCTTAGAAAACCCAACATAATCTACAGCGAGACCTCAGCATGGCAAGCAAGGAATCACTAAAGCCACCAGGGAGATCCGG | 879 |
| IGHV4-31_chr14:106806120-106806220 | CACTAAAGCCACCAGGGAGATCCGGATGCACTGATACGATCCAGAAACATAGCGAGTCCGGGAACTGATGCCGACTTTGAGGCAGCCTCTTTTTTTTTTT | 880 |
| IGHV3-33_chr14:106815805-106815905 | GATGGTGAATCGGCCCTTCACGGAGTCTGCATAGTATTTATTACTTCCATCATACCATATAACTGCCACCCACTCCAGCCCCTTGCCTGAGCCTGGCGG | 881 |

TABLE 6-continued

| Name | Sequence | SEQ ID NOs. |
|---|---|---|
| IGHV3-33_chr14:106815905-106816005 | ACCCAGTGCATGCCATAGCTACTGAAGGTGAATCCAGACGCTGCACAGGAGAGTCTCAGGGACCTCCCAG GCTGGACCACGCCTCCCCAGACTCCACCA | 882 |
| IGHV4-34_chr14:106829685-106829785 | CTCGACTTCTTGAGGGACCGGTTGTAGTTGGTGCTTCCACTATGATTTGATTTCCCCATTCCACTCCAGCCCC TTCCCTGGGGGCTGGCGATCCAGCTCCA | 883 |
| IGHV4-34_chr14:106829765-106829865 | GGCTGGCGATCCAGCTCCAGTAGTAACCACTGAAGGACCCACCATAGACAGCGCAGTGAGGGACAGG GTCTCCGAAGGCTTCAACAGTCCTGCGCCC | 884 |
| IGHV4-34_chr14:106829865-106829965 | ACTGCTGTAGCTGCCACCTGGGACAGGACCCCCTGTGAACAGAGAAACCCACAGTGAGCCCTGGGATCAGA GGCGACATCTCATATCTTCATATCCGCATTC | 885 |
| IGHV4-34_chr14:106829965-106830065 | CTGAGACACTCACATCTGGGAGCTGCCACCAGGAGGAGAAGAACCACAGGTTGTTCATGTTCTTGTGCA GGAGGTCCATGACTCTCAGAAAGCACTTCC | 886 |
| IGHV4-34_chr14:106830125-106830225 | GAGGATTTGCATGTGGGTGCTTTGTATGGATAGGTAAAAAGGGATGAGGGAGGCCCCAGTCTTTTG GGCTCACCCTGGGAGGTGTATGCTGGCTGT | 887 |
| IGHV4-34_chr14:106830240-106830340 | AGTTCTCTTCTCTGGCCTCCCCTCACCAAACCCAGAGTCTCCTCTTCTTCCAGTAGGAAATGTGCTGAAGG AGCTGGTCTGGGAGACAAGTGTGATCATG | 888 |
| IGHV4-34_chr14:106830315-106830415 | GGTCTCCGGAGACAAGTGTGATCATGGATCAAAGACAGATTTTGGAATACAGTTAATACTGTTCTACATTT AAAGATTCATATAACACCAACCATACACCC | 889 |
| IGHV4-34_chr14:106830415-106830515 | AAGTTCACCTAAATTGTCATTTACCCCTTCAGACATATTTGAAACAGCTGCTGAGTGTAATAATCACAGTGA ATTGAGACAAACCTGGATCATGCAATGTG | 890 |
| IGHV4-34_chr14:106830515-106830615 | TACTGTAGTTCAGAACATCCATCATGGTTAGAAGGATGCTACCTGTCCCAGGAAGTGGTTATTTTTAAAT AGTACCTGAGAGCTGCCCTTCTGAGACCT | 891 |
| IGHV4-34_chr14:106830615-106830715 | TTTGAAATTTGAGATTGTGTGTGAGATCTCAGGAGATCTCAGGAGAAGGTAGTAGAATATATCTCCATCCTTCTCAATGTG TAACCCTGAGAATATGGCCTGACCTCTAA | 892 |
| IGHV4-34_chr14:106830715-106830815 | ACATTTCTGTGTGAAAAGATGTACATTGGGGATGACATTGGGGATGACAGCTTCAGATGAAAACTCTATAGTACAT CAGCACTGGAGGATAGTTCATCACCAAGA | 893 |
| IGHV4-34_chr14:106830815-106830915 | TTAGTGAAATTACCTTTCCTGGGAACCAGAGAGGACCTTCGTCTGAGCTCTACCCTCTGAGAGAACAAGGAA CTCTGGTTCTTCCCTGACAGGTCACACCTG | 894 |
| IGHV4-34_chr14:106831185-106831285 | AACAAGTGGGCTGGCCTTCTATGAGACAGACAGAGGGAAAGAGACAGAGACTCAATATCCAGAGCGAGGTGA GCTCCTTACCTACCTACCAGGTGGTCTCTGG | 895 |
| IGHV4-34_chr14:106831285-106831385 | GCCATTTGTTTGAGCAGACCCAGAAGTACCTTCCTCACCCTCAGGAGGAATTATGAACATTGAGAGAAACT GAGATACTTTTTTATTTACAGGGAATATT | 896 |
| IGHV4-34_chr14:106831385-106831485 | TCATCGGCGTGTTTACATCTACCTGGGTGTGTACAGGGATGCTAGGATGTGCTCATACAGAAGAGCAA GAATTATATTCTGGAAGAAAACCAAAG | 897 |

TABLE 6-continued

| Name | Sequence | SEQ ID NOs. |
|---|---|---|
| IGHV4-34_chr14:106831485-106831585 | AGTTTCTGAATTTGTAGTATTGTTTGCTGCAAATGTGTCAGTTCACTAGATCATGTTATGCTGCTAGAAG AAAAACTTCCCACATTGTCATGAGACA | 898 |
| IGHV4-34_chr14:106831585-106831685 | AAATGCAAAACAGTAAAGATTCAACTGAGATTCCCTTGAAAATCACCAGTAATGAACAGGCCAAAGAA ATCAACCATTGTGAAAGAGTGGTCATTAAG | 899 |
| IGHV3-35_chr14:106846385-106846485 | CCCAGTGTCACCTTACACATCTGCAGGTCACCTCACCCAAGGTCACACATCCACCATTATACCCCACAT CACCTCAGACACACCCTGGTCACCTCATA | 900 |
| IGHV3-35_chr14:106846485-106846585 | CATACGTCAGGTCACCTCACCTCACGCTCACCCAAGGTCACCTCACACATCCCGCAGGTCACCTCACCTCGTAAATCCCC AGGTCACCACATACATGCACCAGTTCACC | 901 |
| IGHV4-39_chr14:106877715-106877815 | CTCTTGAGGGACGGGTTGTAGTAGGTGCTCCCACTATAATAGATACTCCCAATCCACTCCAGCCCCTTCCC TGGGGGCTGGGCGATCCAGCCCCAGTAGT | 902 |
| IGHV4-39_chr14:106877815-106877915 | AACTACTACTGCTCGATGGAGCCACCAGAGACAGTGCAGGTGAGGGACAGGGTCTCCGAAGGCTTCACCA GTCCTGGGCCTGACTCCTGCAGCTGCAGCTG | 903 |
| IGHV4-39_chr14:106877915-106878030 | GAACAGAAAAACCCACAGTGAGCCCTGGGATCAGAGAGGCAGCCTCCCATATCTCCATGTCTGCATCCTAGA AACACTCACATCTGGGAGCCGCCACCAGCA | 904 |
| IGHV4-39_chr14:106878030-106878130 | GGAGGAAGAACCACAGGTGCTTCATTTTCTGCACATGAGATCCATGACTCTCAGAAAGCATTTCCCTTAT GAGTTGGACCTGAATTTAAGGAAATGTGT | 905 |
| IGHV4-39_chr14:106878130-106878230 | GGTGGCTTCCTGTGGGCCCTAAGTGAGGATTTGCATGGGGTGGTGCGTTTCTTCTTGGGCCTCCCCTCCAAGC GGATGAGAGAGGCGCCAGTCTTTTGAGCTC | 906 |
| IGHV4-39_chr14:106878230-106878330 | ACCCTGGGAGGAGAAATGCTGGCTGCCCTTTGAGAACTCAGTTCTCTCTTCTTGGATCAAGGACAGATTTTGGAATAGGGTCAG CCAGAGTCCTCTTCTTCCAGGTAAAGAGA | 907 |
| IGHV4-39_chr14:106878330-106878430 | TGTGCTGAAGGAGCTGGTCTGAGAGATGAGTGTGATCCTGGATCAAGGACAGATTTTGGAATAGGGTCAG TACTGTTCAACCCTTAAAGATTCATATAAA | 908 |
| IGHV4-39_chr14:106878430-106878530 | ACCCACCACACACCCAGGCACCTCATCTAAATAGTCATTTACCCTTTCAGCACACATTGAAACAACAGCTGAATGT AATAATGACAGTGACTTCAAACAATACTG | 909 |
| IGHV4-39_chr14:106878530-106878640 | ATGTTTATTGTAGTTCAGACATCCACCATGGTTACAGGGAAGCTCACTGTCCCTGGAAGTGGGTCATTTT TTAAAGCACCTGAGAGCTGTCCTTCTGT | 910 |
| IGHV4-39_chr14:106878640-106878780 | AAGGTAGTGGGACATATCTCCATACTTCTCAATGTGTGACCTTGAAGATGTGTCCTGCCCTCTAAACACTT CTGATTGAAAATATGTAGATTGGGGATTA | 911 |
| IGHV3-48_chr14:106994300-106994400 | GTGGAAATGCCTTGGAATCCAGGGCTAAGGCACCTCTCTGAGAGCTGCAGGGTCAGGGTTCAGGGGTTCGGGGTTCGGGGTTT TCATCAGTAGAGGGAGGGCCCTATTTGCAT | 912 |
| IGHV3-48_chr14:106994400-106994530 | GGACCCTTGAGGAGTAGGCTGTACCCAGATAAGACGACGGTGCCCTGTAGAAGTTTGCTGGCAATGATTG CATTTGGAAAATATGCTGTCTTATTATGAA | 913 |

TABLE 6-continued

| Name | Sequence | SEQ ID NOs. |
|---|---|---|
| IGHV3-48_chr14:106994530-106994630 | ATTGTGCTGTGATAAACACTTGCACTAATCACCCTATTTCATTTAAATATTCATGTAAACTATGTTCTGTAGGAGACAATATTTTCTCCATTTACAGA | 914 |
| IGHV3-48_chr14:106994545-106994645 | ACACTTTGCACTAATCACCCTATTTCATTTAAATATTCATGTAAACTATGTTCTGTAGGAGACAATATTTTCTCCATTTACAGAAGTGAAGTAAACCC | 915 |
| IGHV3-48_chr14:106994660-106994760 | CTGTATGCATCTAGGAGCTCATGTCTGGGATGAGTGAACCCCGGTACTGGGCCTGTCTTCATCACTGTCTCTGACATCCCCTAAACCACTCCAG | 916 |
| IGHV3-48_chr14:106994760-106994860 | GACAAAGCTGGATGTGTCTAGTGTTTTTATCAGAACCCACTTTCCGTAATAAGAGCATGTGTGGTTTTGCTGCCCTCCAGCACTCTTCTGAAAATATGGA | 917 |
| IGHV3-48_chr14:106994860-106994960 | GAGAACTAGGATCCAGGCACATTAATTTTCAGGTACTTCTGACATTGAACTTATTTTTCTATCTTTCTATTACTCTTTCCTTGTCTAAGTTTCCATTTG | 918 |
| IGHV4-59_chr14:107083565-107083665 | AGAGAGACCCACAGTGAGCCCTGGGATCAGAGAGCCACCTCCCATATCCCATGTCTGGATCCCTGAGATACTCACATCTGGGAGCTGCCACCAGGAGAAGG | 919 |
| IGHV4-59_chr14:107083665-107083765 | AAGAACCACAGATGTTTCATGTTCTGCACAGAGGTCCAGGACTCTCAGAAAGTATTTCCATGTGAGCTGGAACCTGAATTTAAGGAAATGTGTGGTG | 920 |
| IGHV4-59_chr14:107083790-107083890 | ATTTGCATGTGGGTGGTGCCTTTGTTGTATGGAGAGGTGAAAAAGGAGGAGGCCCCAGTCTTTTGGGCTCGCCCTGGGAGTAGGATCCTGGCTGTGCCC | 921 |
| IGHV4-59_chr14:107083890-107083990 | TTTGAGAACTCAGTTGTTCTTCTTGGGGTCTCCCCTCCAAGCCCAGAGTCCTCTCTTCAGGTAAAGAGACGTGCTGAAGGACCTGGTCTGGGAGATG | 922 |
| IGHV4-59_chr14:107113405-107113505 | CTGACAGTGGTGACCATGGTTGAGAACTTTCATCTCCTGTGAGGATCAATCTGCATTTCTGCATAGGAGAATAGGTTTTCATATTAAAAACAATCAT | 923 |
| IGHV3-64_chr14:107113505-107113605 | TTTAAAAATATGTAGAAATGACCCTAGTAATCACAGAGTCTGCATATATGTCTACCCCCATTACTACTAATAGCTGAAGAAGATGAAGTCCCACATCGTGACAGGAAA | 924 |
| IGHV3-64_chr14:107113820-107113920 | TGGAAGATGGTGAATCTGCCCTTCACAGATCTACTGAAGGTGAATCAGAGGCTGCACAGGAGAGTCCAGGGACCCACATATTCCAGTCCCCTTCCCTGGAGCCTG | 925 |
| IGHV3-64_chr14:107113920-107114020 | GCCGACCCAGTGCATAGCATAGCTCTCCCCTTCACACTCCAATATCTCTATTTCCTCATGAATCACCTTTAAAAATAGCAACAACCCAGGCTGACCAAGCCTTCAGCCCAAACTCCATC | 926 |
| IGHV3-64_chr14:107114095-107114195 | TTCTCCTCCATGTCCACTCACACTCCAATATCTCTATTTCCTCATGAATCACCTTTAAAAATAGCAACAAGGAAAACCCAGCTCAGCCCAAACTCCATC | 927 |
| IGHV3-64_chr14:107114195-107114295 | ATGACTCTTCTGTGTTCAGTGCTGATCACCAAATGAAAAACACCTGGGAATCCCAGGGCGGGGGCTCCTCTCCCAGAGCTGCGGAGTCGAGGTCTGGGCTGG | 928 |
| IGHV3-66_chr14:107136755-107136855 | TAGGGCAACATCCTTCCCATCCACTCAAGCCCTTGTGCATGGCCTGGCGCACCTAGTGCATAGAGTAACTGGTGAAGGTAGGTGTATCCACAAGTCTTGC | 929 |

TABLE 6-continued

| Name | Sequence | SEQ ID NOs. |
|---|---|---|
| IGHV3-66_chr14:107136855-107136955 | AGGAGACTTTCACTGATGCCCAGCCTTCTTCATCTCATCCCCAGACTGCACCTGGGACTGGGCACCCTGTGGAGAGGACACGGGAGTGGAT | 930 |
| IGHV1-69_chr14:107169645-107169745 | GAAAACTTGTTCACAGTAGCACCTTCATGGAATGTTTGTATCAACGTTATAGAGTGTGGCCTTTTCCACTCTGTGAATTTGGCTTATATTACGACTCTTG | 931 |
| IGHV1-69_chr14:107169745-107169845 | AATGGAATATTTATCTTAAAATTAGAGATGTACTTGTTCTTTTCTACTGTTCTTTTTTCTCAAATATATAACCCATTTTGTAAACAGCCTTAAACCTAATAA | 932 |
| IGHV1-69_chr14:107169970-107170070 | CTGCTCAGCTCTCATGTAGGCTGTGTCTGTGGATTTGTCCGCGTAATCGTGACTGTCCCCTGGAACTTCTGTGCGTAGTTTGCTGTACCAAAGATAGGGA | 933 |
| IGHV1-69_chr14:107170070-107170170 | TGATCCCTCCCATCCACTCAAGCCTTGTCCAGGGGCCTGTCGCACCCAGCTGATAGCATAGCTGCTGAAGGTGCCCTCCAGAAGCCTTGCAGGAGACCTT | 934 |
| IGHV1-69_chr14:107170170-107170270 | CACCGAGGACCCAGGCTTCTTCACCTCAGCCCCAGACTGCACCTGGGACTGGACACCTGTGGAGAGGACACAGGGGTGAATAAAATCTCT | 935 |
| IGHV1-69_chr14:107170220-107170320 | CCTGGGACTGGACACCTGTGGAGAGGACACAGGGGTGAATAAAATCTCTTTAACTAAACCAGGATCCCTTCCTCAGCCTTAGGACTAGGAGAAGCCCCTTA | 936 |
| IGHV1-69_chr14:107170320-107170420 | CCTGTAGCTGCTGCCACCACAAAGAGAGAACCTCCAGTCCATGGTCATGGTGATGAGCTGTGCTCCCAGGGGCTTCTTCAGAGGAGGAATGTGGTTGTTAT | 937 |
| IGHV1-69_chr14:107170420-107170520 | GTGATGCTCTCAGGGCACCAATATATCTATATTTATCTCAGAAGACCTCAGTGTATTTGCATATGCATGAGGCAGGGTATTTCACAGCTCAAAGCCTGAT | 938 |
| IGHV1-69_chr14:107170475-107170575 | TTTGCATATGCATGAGGCAGGGTATTTCACAGCTCAAAGCCTGATCTAGGATGAGAAAGAAAACACAGATGCCACATCAGCTGTACAAGTGTGGGATGCT | 939 |
| IGHV1-69_chr14:107170660-107170760 | CAGAACAAACCCAACCCAGGATGCACTCCTCACTGTGAACCCACATTTTATTGGCCTAAAGATTACCTGGGTTTTTGTGGGACCATTGCTGTCTCTG | 940 |
| IGHV1-69_chr14:107170760-107170860 | ACATTGAGCAGGCACCTAGACCCATCCTGTCCCATTAGGAACACTCAGAGTCACTGGTAACACTGAAAAGGTGGCCACTCGTTACCCTACATGAGTGT | 941 |
| IGHV1-69_chr14:107170860-107170960 | CCAGCAGGACCCATGGAGAGTTCTGAGATCTGCTGGGCACTCCCAAGACAGGGTCCCCAGCACTTTCCTGAGGGTCCTGACCTCGACTTCTTCAGTGG | 942 |
| IGHV2-70_chr14:107178305-107178405 | TTATCCATTTCTATGTGTCTTTTTGAAAAATGTCTACTCATGTCCTTTGCTCATTTTAACGGAGTTATTTGGTTCTTTGTTGCTGTTGTTGTTGTAGAGTTG | 943 |
| IGHV2-70_chr14:107178415-107178515 | TTGCAAATTCTTCATATTAGTTCCCGTGTCACAGGCAAAGTGTGCAAAAGTTTTCTGTCATTCTGTAAATTGCGTATTCACTCTGTGTTGTGAAAAAAT | 944 |
| IGHV2-70_chr14:107178515-107178615 | TATTTAGGTTAATTAAATCTCATCTGTCTATTTTTTTTAGGTAGCAGGACCTTCATGCTGAATCTTTGTCAAACAGGATACAGCTTCTGCTTGCATGA | 945 |

TABLE 6-continued

| Name | Sequence | SEQ ID NOs. |
|---|---|---|
| IGHV2-70_chr14:107178615-107178715 | ACCACTAACAGGGGACATGCCATTTATTAGTAAAGAAAAAGGAGGAAAACAAGGCTTGAGTCAGATGGGGATGGGAAACGCACGCCCTGGGCAGGAAAT | 946 |
| IGHV2-70_chr14:107178715-107178815 | GGCATCTCAGCCACCACTATCCTGTTCTGCAGAAGTGGGAGGGAGCACCACTGAAAAACACCTGGGTTCTTGTACAGGAAGCGCCCTGGGCTGTGTCT | 947 |
| IGHV2-70_chr14:107178815-107178915 | GTGTATCCGTGCACAATAATACGTGGCTGTGTCCACAGGGTCCATGTTGGTCATTGTAAGGACCACCTGGTTTTTGGAGGTGTCCTTGGAGATGGTGAG | 948 |
| IGHV2-70_chr14:107178880-107178980 | ACCTGGTTTTTGGAGGTGTCCTTGGAGATGGTGAGCCTGGTCTTCAGAGATGTGCTGTAGTATTTATCATCATCCAATCAATGAGTGCAAGCCACTCCA | 949 |
| IGHV2-70_chr14:107178980-107179080 | GGGCCTTCCCTGGGGGCTGACGATCCAGCTCACACACATTCCACTAGTGCTGAGTGAGAACCCAGAGAAGGTGCAGGTCAGTGTGAGGGTCTGTGTGGG | 950 |
| IGHV2-70_chr14:107179080-107179180 | TTTCACCAGCGCAGGACCAGACTCCCTCAAGGTGACCTGGGATAAGACCCCGTGGATAAGACATAAGAAGATGAAGCCACAAGGAGAGAATAGATTT | 951 |
| IGHV2-70_chr14:107179130-107179230 | CTGTGGAGAAGACATAAGAGATGAAGCCCACAAAGGAGAGAATAGATTTTTTGCTTCTGAAGTACTACCTGACCAGCACTCACAGGACGGGACAGTC | 952 |
| IGHV2-70_chr14:107179230-107179330 | AGTAGCAGGAGCGTGGAACAAAGTATGTCCATGGTGGAGAGAGCCAGGATTCACTGAGCGAGGCCCCTGTCCTCGTCTTTTGAACCCAGGGAGGGTGAGCTGA | 953 |
| IGHV2-70_chr14:107179330-107179430 | GTGGAGATTTGCATCCCCTCATCTGAGCCTACTCTATGGGTGCACTCAGGTCTCAGGACTCAGTAGGGGAGTGCATCTGTGGTGAGGAGCAGTGAGCC | 954 |
| IGHV2-70_chr14:107179430-107179560 | TACTCTATGGGGTGCACTCAGGTCTCAGGACTCAGTAGGGGAGTGCATCTGTGGTGAGGAGCAGTGAGCCCTCAGGTGTGGGGGTCCACGTGTGCTCTCC | 955 |
| IGHV2-70_chr14:107179460-107179560 | ATCAGGGAATCTATCTCATTTCAGCACCACCATGCCTCTCAGTCAGTAGGGCTCTCAGTCTTGACGCTCCTCCTGCTTCTACAGACAGGATCTTCTTGCGATGCTCCCGCACCGACA | 956 |
| IGHV2-70_chr14:107179560-107179660 | TGCAACCTTCTGTTTTAGTCCTAGAGATTAGAGTAGAAATCAAGAGAGCTGCCGTTCCTCCTCCCTTCAAGAATAATGATGGTGGGCATCTGGGGGGC | 957 |
| IGHV2-70_chr14:107179660-107179760 | AAGGGGCTCCCCACAAGCATTCTGATCAAAATCCTCTTTGATTATGGGAAAAGTGATGAATTTGTGTAAAAAATTGGAGAGAATAATAAGAAATAC | 958 |
| IGHV2-70_chr14:107179760-107179860 | AGTTACAGATAATTATGTAAAGAAGTGTGCTTAGCAGTGTGTGCACAGCTGCATTCCTAGAGGCATGTTCCATGAAAATCGATGTTGTCCTTG | 959 |
| IGHV2-70_chr14:107179860-107179960 | TGCCCCGTCAGTTCTGTGGAGAGTAGACTCCATGAATGACTTCCCTTTTCAGCCCATGAATGAATGACGGATGCTTTGGACAAGGGAATTGAAGACTC | 960 |
| IGHV2-70_chr14:107179960-107180060 | CTGAGGGAGCAGCAGGCTGACTGTTGCAGCCTTGCTCTGCACCTGCACCTGGATGTGTCTCTGTGCTCATAAGGCCGTGGAAACTCATCAATCCAGGTTC | 961 |

TABLE 6-continued

| Name | Sequence | SEQ ID NOs. |
|---|---|---|
| IGHV7-81_chr14:107258910-107259010 | CAAAAAGGGGTTAAATGATTTGGAAAAGTAAGTAGAAAATAAAAGAGGAGGAGTAAGAGCGGACAGAAGGGAAGGAAGCAAGCAATGATGAAC | 962 |
| IGHV7-81_chr14:107259010-107259110 | TGTGTAAAATTTCACTAATTAAAAGACTATTATATTGAAGAGGTGCCTATTAGGCAGCCTTTTGATGTTAACCATGTAATATACACCATGAACAACCTT | 963 |
| IGHV7-81_chr14:107259100-107259200 | GAACAACCTTGTAGAACACACAAGAGCCCCTCAGAGAACTGATGGTCAGTCTCCCATCCAGTTGCCTTAGGGGTTAAGAACGCTCCCATGTTGTTC | 964 |
| IGHV7-81_chr14:107259200-107259300 | TCTGGTTTTTGCTCCTGAGGACACAAACAGCCAGTGTTTCCTCCCCGATGAATAGAGAGGCCCCTGGGGAGGGTGTCTGCAGCTCACTCTGCACCT | 965 |
| IGHV7-81_chr14:107259235-107259335 | GTTTCCTCCCCGATGAATAGAGAGGCCCCTGGGGAGGGTGTGTCTGGCAGTCACTCTGCACCTGCACCGCGAAGGTTTAGAATGGTCCCTCTCACAC | 966 |
| IGHV7-81_chr14:107259335-107259435 | AATAATACATGGCGGCGTCCGAGGCCTTCAGGCTGCTCCACTCCAGGTAGGCCGTGCTGCTGGAGCTGTCGGCTGAGATGGTGACGTGGCCTTGGAAGGA | 967 |
| IGHV7-81_chr14:107259435-107259535 | TGGGCTGTATCTGGTATCAGAGTTCCCAGATAGAGATGCTCCCCATCCCAGTTCTTTCCCGGGCATCTGGCGCACCCAGTGGATCCAGTAGCTGGTA | 968 |
| IGHV7-81_chr14:107259535-107259655 | ACAGGAGATCCTCCAGAGACTCCCCGGGTCTTTTCACCTCTGCTGCAGACTGCAACAGCTGCACCTCCGCAAAGCACCCTGTGTGGAGACACAAATTTG | 969 |
| CIITA_chr16:10971440-10971540 | GTGTCTGGAGTATGAACCATGTATCAGCACCGAAAGGTTCTAGAAGTCAGACTTTCGGGCAGTGTGTCACTAACTCTCAGCATGCTGGCCTGGCCTGGCC | 970 |
| CIITA_chr16:10971540-10971640 | CACAGCAAGGTCTTCTCGCCTCCCTTTGGGTAAATACTGAGGGGTGCCTCTGCAGGACGGGACCTCTGCCAGACTCCACTCCATACCCAGAGAAGCAGGG | 971 |
| CIITA_chr16:10971640-10971740 | AAACCAAAATTGGAGTCAGCCTTGAGGTGTAGCTGTTGAGCCCTCAGCAGCTGGGGAGAGCTGGCGGATGCTGCTCCCCCCAGTTTCCTAATGTGTTT | 972 |
| CIITA_chr16:10971740-10971840 | GTTTAAAAGGGTCAGGGAGTCAGGGGACGGGGGAACAGATGGTGGGAAGAGCACAGTGCAGACACCTGGCACCGGCTCTGAAGGCAGCATGGCAGCTACACCGTTGG | 973 |
| CIITA_chr16:10971840-10971940 | CTGGAAGGGTGCCCCTGAAGAAGTCGTTTACATTCTGAGTCAATTTCCTGGAGTGTACAATGGACCTGTGGGAAAGCCTGTATGAAGGGTAATG | 974 |
| CIITA_chr16:10971940-10972040 | ATGAGGAGCCTAGCACAGTGTCCAATATTTTATAGGAACTGGAATTGAGCTCATAGGAGCTCAATTTTATTGGCATTGCTGTTGTTGGATGGTTAAAGGG | 975 |
| CIITA_chr16:10972040-10972140 | GTGGTATCCCTTTTCTAGACTCCCCTGAAATGTATGTTTGCTTTGAACCCAGAGACTGATGACAGGTCTGCCGGTGTGGTTGGGTGCAGCCTTAAGTT | 976 |
| CIITA_chr16:10972140-10972240 | GCTACGGAGAAAGTGTTGAGGGGAGAAGTCAGAGGTAACCTTGCCCCCTCCCTCAATTCCAGATGAGGAAATTCAGGCCTGAAAAGGGAAAGTGACCAC | 977 |

TABLE 6-continued

| Name | Sequence | SEQ ID NOs. |
|---|---|---|
| CIITA_chr16:10972240-10972340 | CTCAAAGTCTCATGCCTTGGAGGACCCAGCAGGAATCCAAGACCCTGAAAAGGACCGGCAGGGCTCTTG CCACGCCTGGGGGTGTGTCATGGTCATGGTAACAC | 978 |
| CIITA_chr16:10972340-10972440 | AGTTTTCCATCCATGGAAGGTACCTGAGGGATTTTCTTCTTCCCCTAGGGCCAGCATCAGAGGAGTGA ATAGCTCAGTTAGCTCATCTCAGGGGCCAT | 979 |
| CIITA_chr16:10972440-10972540 | GTGCCCTCGGAGGTGGTTTGCCACTTTCACGGTTGGACTGAGTTGGAGAGAAACAGAGACCCACCCAGGG GTGGGGACAAGCTCCCTGCAACTCAGGACT | 980 |
| CIITA_chr16:10972540-10972640 | TGCAGATCACTTGCCCCAAGTGGCTCCCTAGCTCCTCGGCCTCCTGGACTCTCCCCGAAGT GGGGGCTGGCCACTGTGAGGAACCGACTCG | 981 |
| CIITA_chr16:10972640-10972740 | AGGCAGGGACCCTCTTGGATGCCCCAGGCAGTTGGGATGCCACTTCTGATAAAGCACGTGGTGCCACAGT AGGTGCTTGGTTGCTCCACAGCCTGGCCCG | 982 |
| CIITA_chr16:10972740-10972840 | AGCTCAGCCCTGCAGAAAGAAAGTGAAAGGAAAAAGAACTGCGGGGAGGCGGGGAGGTAGGATGACC AGCGGACGAGCTGCCACAGACTTGCCGCGGCC | 983 |
| CIITA_chr16:10972840-10972940 | CCAGAGCTGGCGGAGGGAGAGCCACCAGCAGCCGCGCGGGAACCAGCGGGTAGGTGAC CAAAGTCTCCTCTGTAACCCCTAAGGTCGGGC | 984 |
| CIITA_chr16:10972940-10973040 | TGAGAATCGAGGCTCCAGACTGTCAGTTGCTCAAGGTCACACAGCAGTCTGGAGGATGGGGG GATGGAATATGCAAAATGTAGGGCCGGAAA | 985 |
| CIITA_chr16:10973040-10973140 | CACCTCGTTTCCAGCATCCCCGACTCTGCGCGGAACCAGGAGCCGGAACCCGGAGCTTGGCTT GCTGTGCCCAGAGCTCCACCCTTGGCCGACTCCG | 986 |
| CIITA_chr16:10973140-10973240 | GGTGGCAGGAAAGCCTGGCGGCAGCTTCTGCAGAGAAGCCGCAGACTGGGAGCGCGGAGCAGAC ACACTCCCCGCGGTCCCCTTGGCCGACTCC | 987 |
| CIITA_chr16:10973240-10973340 | CGCGCCCCGGGATCCGCAGAGGTGCGCGCCCTTCTTGTACGCCAGAGACTTTGGACCAGGGCCCGCCGTTCCC TGAGCTTCACTTTCCCTGTTGGGTCATATT | 988 |
| CIITA_chr16:10973340-10973440 | CCATCTCTTAACTCTGGAATCTTGGGTATTGGGCTCTCCAGGCGGGGGCCCTGCTCAGGGAGGCAGTAGG GAGCCAAACCTTTTAACCAGAGGATGGGATA | 989 |
| CIITA_chr16:10973440-10973540 | AGTCCTCAACTCTCGTTGAACATCTTGGCGAAGGTGTGTTGTTGGGAGGGGTGGGGAGGGATCCCCC CGGACTGAACCGATCTCTTGATCTCTCACT | 990 |
| CIITA_chr16:10973540-10973640 | TCTCTACCTCGCTTTGGGCCCTGAGTCACACCCCTCTAAGGAGAGAGGCTAAAGCGCCCGGAAAGCCAG CGTGCGAATGCCCGGGGTGGGAGTGGGAGAT | 991 |
| CIITA_chr16:10973640-10973740 | TGGAATCTCCCTGGGGTCAGGAAGACCCGGAATCGGAGCCACCATGCTTAGCTTAGCTTGGAACTCTTAAA AGCCGCGGTCCTCCTGAGTCCCACAGCCCC | 992 |
| CIITA_chr16:10973740-10973840 | TCTCCACCCTAGGTGGCACAGGAGAGTGGCAAAAGCCTAGAAGTTCAAGGCATGGCTCCCTCCCCAGCC GCAGCCTGGGAGTGTCTAACTTTGGCAGGAA | 993 |

TABLE 6-continued

| Name | Sequence | SEQ ID NOs. |
|---|---|---|
| CIITA_chr16:10973840-10973940 | GTCTTCCGTTTCTGCTCCCCATTCCAGAGAAAAAATAAATAATACTTCTCCGGAGTGAGATTAAGGAAACAGGTACTTCTTCCTCTTGGAGAAAGAGGA | 994 |
| CIITA_chr16:10973885-10973985 | CTTCTCCGGAGTGAGATTAAGGAAACAGGTACTTCTTCCTCTTGGAGAAAGAGGAGCCAAAGGAACTTGACTCCAACAAATGATCACCTTGCAAACCCCC | 995 |
| CIITA_chr16:10973985-10974085 | GGCTCCCTTAGGGGATGACCTGTCTCCAACAATCTCAGAGCGTTTGGAGGCAGGGTCTTTGAGATGACTGAGTGGGGAATCCCAGGCTCCCCACACAT | 996 |
| CIITA_chr16:10974085-10974185 | GAACATCACCTGGATGGATGATCAACCTGTTCAGGATGTAGGTTCCCGGGCTCACCCCCAGGCCCGGTTGCTAGGCCTGGGGTGAGGCTGAGATCCTGCAGG | 997 |
| CIITA_chr16:10974185-10974285 | TTAAACCATCTATCCAGGTGACTCCAATGTTCGTTTGTGGGGCAAAAGTCCCTCAAGTCAGAGACACTGGGAGGGCGTGATGTGGTCTCATCTCTTTAC | 998 |
| SOCS1_chr16:11348520-11348620 | CAAGAGGTGAGAAGGGGTCTGCGGCCTCGTCTCCAGCCCGAGGCGTGGGAGGCGCCTCGCCCTTACACCCATCCGCTCCCTCCAACCCAGGCCGGGAGGGT | 999 |
| SOCS1_chr16:11348620-11348720 | ACCCACATGGTTCCAGGCAAGTAATAACAAAATAACACGGCATCCCAGTTAATGCTGCGTGACGGCGGGCGCTGCCGGTCAAATCTGAAGGGAAGA | 1000 |
| SOCS1_chr16:11348720-11348820 | GCTTCAGGTAGTCGCGGACGACGGGGTTGAGGGGATGCGAGCCAGGTTCTCCGGCCCACGGTGGCCACGATGCGGCCTGGCGCACAGCTCCTCGCAGCGAC | 1001 |
| SOCS1_chr16:11348820-11348920 | CGCACGCGGCCTGGCGCCAGCGGGGCCCCAGCATGCGGCCGCACGTAGTGCTCCAGCGCTCGAAGAGGCAGTCGAAGCTCTGCGGCTGC | 1002 |
| SOCS1_chr16:11348920-11349020 | CATCCAGGTGAAAGCGGCCGGCTGAAAGTGCACGCGGATGCTCGTGGGTCCCGAGGCCATCTTCACGCTAAGGGCGAAAAAGCAGTTCCGCTGGCGCT | 1003 |
| SOCS1_chr16:11349020-11349120 | GTCGCGCACCAGGAAGGTGCCCACGGGCTCCGGCGGCCGCAGCCGCTCGTGCGCCCGTGCGAAGTGCGGAAGTGCGTGTCGCCGGGCCCCAGTAGAATCCGCAGGCGTCCAGGAGC | 1004 |
| SOCS1_chr16:11349120-11349220 | GCGCTGGCGCGCGGAAGGTGCGTGATGCGCCGGTAATCGGCGTGCAACGAATGTGCGGAAGTGCGTGTCGCCGGGGGCCGGGGACCGCGGGGGCACGGCCCGG | 1005 |
| SOCS1_chr16:11349220-11349320 | GGGCGCGGGGGCGCCCGGGGACTGCCATTGTCGGCTGCCACCTGCTGTGGAGGAGGAGGAAGGTTCTGGCCGCCGTCGGGGCTCTGCTG | 1006 |
| IGHV3OR16-12_chr16:33523607-33523707 | TTTAAAATCACCCAAATCAAAATAATTTATCTTCATTAATAAATAATCATCAGAAGTTTAACTAATTTTTACTTTATAATACTAGGTTTAAAAATTCTT | 1007 |
| IRF8_chr16:85933003-85933103 | AATCTGAATGCCCAAGTCGTTGATTGTCGTTTGCCTGTTTCCAAAGATTGGTAGATAGATGCCTTTTAAAAATCTCATTTTCTTTAAATCTGTTTAC | 1008 |
| IRF8_chr16:85933103-85933203 | ATGGAAAAACGTTAGGAGAGCTCATATAATGAACGGCAATAGCAACCCCCTATCTTGAAACGCGCTCTATCATCCCACTGAAATTCTACCACGTGGAATAA | 1009 |

TABLE 6-continued

| Name | Sequence | SEQ ID NOs. |
|---|---|---|
| IRF8_chr16:85933203-85933303 | TGCTTGGAGGGTCAGAGTTGTGGAACTGCCCAATAACCAGTCGTTACTGAGGGTTAGTTGTGAAGGAGGGGACAGACTGCTTCTAAAATTCTGTTTAAT | 1010 |
| IRF8_chr16:85933303-85933403 | GACAGTCAATTAAGATTTCTGAGTCTGCTTGAGGGCCTTTGCTTCCATCAGCCCAGTCGTCCTTGGCAAGAGAGTCGTATATGGGCCACAGCTCAC | 1011 |
| IRF8_chr16:85933403-85933503 | AAAAGCATTGTTTGAAAAAATTATTGAAAGAACATTGTTTGTAAAATGAGTCCCAATACATAGGACAGACTTTCCTAAGGTGAGATGTGTTACTTACCC | 1012 |
| IRF8_chr16:85933503-85933603 | AGAGCTGTGAAAGGCTTTACGATGGAAACTAGAGACTGAATTTTCAGAATTTTAAGAAGTCTCCCAACCAATGGCCCCCCACTTTCTTTTTTAAAC | 1013 |
| BZRAP1_chr17:56408574-56408674 | GGCGTGATCTCCGAAGCCCACAGTACACTCATCATCATAAAGTAGGAAACACTACACCCTCCAGTGCTGTTAGTAGTGCTTTCACTTTATGGGTGACTGCA | 1014 |
| BZRAP1_chr17:56408674-56408774 | TGTCTGTCTGTCCGTCGGCGTGTACTCTTCAGGCTGCCCAGGCCTCTCCTGACTCCTGCTCCAAGAGCCCCCCAGCCCCTTCCTTGGCTTCCTAAGATCCC | 1015 |
| BZRAP1_chr17:56408774-56408884 | CCCTCTTCCCTTCCCCCTAAAGGCTTCCAGCCACGCTAGCCACCACCCTCCAGCGTCCAAATGAGGCAGCCAGCCACAGCTCCCCCTCCGGAGGCCTCGGTCTCCCAGTCCACCCC | 1016 |
| BZRAP1_chr17:56408984-56409084 | AACCCCTGGCTGGCCGCTTCCAGCCACGCTAGCCACCACCCTCCAGCGTCCAAATGAGGCAGCCAGCCACAGCTCCCCTGCCAAGGTCTTGGTCTCCCAGTCCACCCC | 1017 |
| BZRAP1_chr17:56409084-56409184 | AACCGTGAGGTCCTGACTGCCCAGAGCCTCAGTCCCCACCCTTCAGCCTCCCCACCAGCCCCAAGATCCTGACCCCCCAGGGCCTAAGTCCCCAGCCTCCC | 1018 |
| BZRAP1_chr17:56409184-56409284 | CAACAGCCCAGGGTCCTGACCCCCCAGGGCCTCAGGGCCCTGGCCTCCCCACCAGCCCCAAGGTCTTGAACACACCAGGGCCTCAATTCCCAGCCTCCCCAC | 1019 |
| BZRAP1_chr17:56409284-56409384 | CAGCTCAAGGTCCTGACTCCCCAGAGCCTTGATTCTCGGCCTCCCCCACCAGCCCAAAGTCCTGACTCCCCCAGGGCCTCCCCACCAGCCTCCATAGCCAGCCCAAGTCCTGACCCCCCAGGGCCTCAGTCCCCAGTCCCAGCAGGAGCCCAA | 1020 |
| BZRAP1_chr17:56409384-56409484 | CCCAAAGTCCTGACTCCCCAGAGCCTTGATTCTCGGCCTCCCCCACCAGCCCAAAGTCCTGACTCCCTCACTGCCCTGCTTCCCCTGGCAGGAGCCCAA | 1021 |
| BZRAP1_chr17:56409484-56409584 | GGCTATCCCAACAAAAATGGTGGCCATGTGGGCGGAGGAAGAGGCTGGCGCCCCTTGAGACACTGGTCCCACTTCTCAGCCTCTGCGTACCCTCTGCCA | 1022 |
| BZRAP1_chr17:56409584-56409684 | TCCCCGCCTTACTCTCCAGCCTCTCCTTGGACACCTCTTTCCCCGCCTGGGGTCCCGGAGCCATTTTACCTTCCTTCACTAGAGAGGGTTTCAAGGCG | 1023 |
| GNA13_chr17:63010240-63010340 | CTAAGATTTTCAAGAAGTTAAACGTAGAATTAAGATTGTTCTAATTCTGGTGTGTAAACTGCTATTTAAAAAACAAAACAAAACAGAAAACATCAAAAACA | 1024 |
| GNA13_chr17:63010315-63010415 | AAACAAACAGAAAACATCAAAAACACAAAAAGATATTAAAACAGCAAGTCTTTTGTACATCACTGTAGCATAAGCTGCTTGAGGTTGTCATGCAGAATAG | 1025 |

TABLE 6-continued

| Name | Sequence | SEQ ID NOs. |
|---|---|---|
| GNA13_chr17:63010415-63010515 | TATCCTTCACGTCACGGAAAACAAGGCGGATGTTCTCCGTGTTGATAGCAGTGGTGAAGTGGTGGTATAAGGGCTTCTGTTGCTGGTCCCGGCGTTTGTT | 1026 |
| GNA13_chr17:63010515-63010615 | CCCGGAAACATTCCACCAGGAATTTTTGGACGTCTCTTAAGCAGTGGGGATCCCCTCAAATTCTAGGAAATAGTCTTTGATGCTCACAATTGCACCTTC | 1027 |
| GNA13_chr17:63010615-63010715 | TCCTCAAGCAAGTCTGTCTTGTTTAAGAACAGAATTATGGAGACATTGCTGAAAACCCGGTTATTGACGATTGTTCAAAAATGTTCAGAGACTCTGTAA | 1028 |
| GNA13_chr17:63010715-63010815 | GGCGATTGGTCAGTGCAGTCTTCCATAAGCACCTGGTCAAATTCACTTGAGGAGAAACAAGGAAAAAGTATTGATGTCACACTGTCGAAACATTCAAACCAACG | 1029 |
| GNA13_chr17:63010815-63010915 | TTTTCCTTTCTGATCTCTGACCACCTACATCAACCATTTTGAAAGGAAGACATTTTTATTTCAAAGTCGTATTCATGGATGCCTTTGGTGGGTCTTCTGGCA | 1030 |
| GNA13_chr17:63010915-63011015 | AGCAGAATATCTTGTTGTGATGGAATATAATCCTGGAAAAGAAAAAAACTTGTTTTATACCTATTAATCCCGAAGTAATGCGAATTTTTAATGGACTACTA | 1031 |
| 43717_chr17:75447868-75447968 | TGTAAATATTTGGCCAACTAAGCTGAGTGGCTAAGTTCTCCTGCTGCCCGGAGCTTCTTGGAACATGTTTCCTTTTCGCAAGGGGTTCCCTGGCTTCCA | 1032 |
| 43717_chr17:75447968-75448068 | GGAGGGCCAGGAGAGAAATTCGAATTGGCCACCGCTTTCTCTAAAATCACTCCGCTCAAGTTATCACCCCTCTGGGCTCCCGGAGACCCGGCTGCTGGAGG | 1033 |
| 43717_chr17:75448068-75448168 | CTGGAGATAGTCTCAATGCTCGAAATGCCGTAACCGAAGCTCCCCGCGGCCGGACTGGGATCCAGGGAGCTGCTGCCAGCGCAGCTCTGGATTCC | 1034 |
| 43717_chr17:75448168-75448268 | TGGATGTGTTGGATATGTGCAGGGCGTTCCTGGGAGGAGCGGGGAGGGAGGGTGCTGCTGGCGGGCTGGTCTGCCTGTGCTTTGCTTCTCTACAATGGC | 1035 |
| 43717_chr17:75448268-75448368 | ATGCTGCCTGTCCGCCATGCAGCCAACGGGGTGGTCTCCCGGCCTCAAAGCAGGAGGGGCGAGGAGCTTTGTTCAGAGGGTCTTTTCATGCTGGGAGAACC | 1036 |
| 43717_chr17:75448368-75448468 | CCAAGAGACTAAATCATGCAGCCAACGGGGTGTGCCCTTAGTAAGTACCGCCTTAGTAAGTACCACTTAGTTAGGCAATGCCATCTGCTCCTGAAACGCCGT | 1037 |
| ADCYAP1_chr18:1477565-1477665 | CAGCCTCCTTAGTAGCTACCGCCTTAGTAAGTACCACTTAGTACTACCACCGCCTGGCTAATTTCGTATTTTTTTTTTTAGAGTACCGGGGTTTCTCCATATTGGTCA | 1038 |
| ADCYAP1_chr18:1477665-1477765 | AAGTACCTCCTTAGTAGTAGTACCACTTAGTACTACCACCACGCCTGGCTAATTTCGTATTTTTTTTTTTAGTAGAGACGGGGTTTCTCCATATTGGTCA | 1039 |
| AC012123.1_chr18:30349775-30349875 | AGGTCAGGCGCATATGCCATGCGGCGGTCTCGCCGTCGTGCTCCAGCCACGACATCTGGAAGAGCGCCAGCTCCGACTCCACGGGGGCGGCAGCG | 1040 |
| AC012123.1_chr18:30349875-30349975 | AGTCCAGCAGGGCGCATCTCCTCGAAGTTGAGCAGCAGCACATCCTCCACCAGTACTTGTTGGCCAGCTTCTTGGTCTCCTCCAGGCCCGTGCAGCGC | 1041 |

TABLE 6-continued

| Name | Sequence | SEQ ID NOs. |
|---|---|---|
| KLHL14_chr18:30349975-30350075 | GGCGATCTTGCACACCTGCTTGTAGTTCTGCACCGAGATCTGTCGTTGAGGAACTGCACGCAGAGCTTG GTGACCTGGGGATGTGCAGGATCTTGCTG | 1042 |
| KLHL14_chr18:30350075-30350175 | ACCGACAGCACTTCCCTCCACCGTGTCCAGGGACAGGGTCACGTTGGCCGTGTAGAGGTACTCGAGCACCA GGCGCAGCCCGATGGACGAGCAGCCTGCA | 1043 |
| KLHL14_chr18:30350175-30350275 | GCACCAGGTTGTTGATGGCCCGGGGGCTGGTCAGCAGCTTGTCGTCGGGGAGGAAGAAGGAGTCCCGG GCTCCTCCTGCGGCGGCGGCTGCTGCTCTG | 1044 |
| KLHL14_chr18:30350275-30350375 | TGACGGCTGCTGTGCGGCGGCTGCTGTCGTCGGTCCTTGGGGGCCCCAGGCCCGTCCTGCCGCGCCGACCCCT CCCCCGAGGGGGGTGGCTGGAGAAGAGC | 1045 |
| BCL2_chr18:60806264-60806364 | GAGACTTCAGCGCCGGAGCTGGCTATTCCAGAGATGGACCTCAGAGGATTCCTTAGTCTAATTACCTTCTGG GCTGGGGTAGAAGATGTCTCGGAGGGAA | 1046 |
| BCL2_chr18:60806364-60806464 | GCACAGAACCAAGTTCCCTACTGCCGCACTAGCTATGCAAATACTGCAGGGCACCTGTGGGCTCATGTCC CTCCTGCAAGAAGGTGTGGTCAGTCCAGTA | 1047 |
| BCL2_chr18:60806464-60806564 | ATTCAAAAGACGTACTTCTGAAATAGGTGGAGAAATGCATTTATAGCAAATGTCTAAAATATGTTAA TAGTTATGCTATTTGGTTCACCAGGTTAGT | 1048 |
| BCL2_chr18:60806564-60806664 | GTAATAAACCATAACAAGAGAGACTAAAGGCCGTATCTATATGACCTTGAAATCTCATCTTCAGCGGCT TATTCATTCAGTAACCAAACTATTTTTGTA | 1049 |
| BCL2_chr18:60806664-60806764 | AGGTGCTGAGTATTAGCTTAAAGCTAAATAGACACATGCCCTGCCCTATAGTAACTGCTTGGTAATATT CCCAGTGGCTTCCATGGCCTCCTCTCAT | 1050 |
| BCL2_chr18:60806764-60806864 | TCTTAGTACTGAATTCAAAGCACTTTGTCTTGTCTGCAGGCCCATTTGCCCAGCAGTGGCTTGCCAGG AGAGAACAGGCCCATGCTCCTGTCCTCA | 1051 |
| BCL2_chr18:60983784-60983884 | CAAACAAACAATTCAAGAAGAAGGATTTAAATTTAGAAATTTAAATTGGGGCATTTAGTTAATCTTACTT TTAAACACCAAACAGTGGCATCAATATTT | 1052 |
| BCL2_chr18:60983884-60983984 | TGTCAACTTTGGTCAAATAAGATCAGATGTTCACATCAATCATCTACTTTTCTTGGCCTTTTCTCTATTGG CCTCCTAGTATGAGCACACTTTGTAAAA | 1053 |
| BCL2_chr18:60983984-60984084 | TGTAATAAAAACATGGTGTGCTTCTTGACATCTAATCCACTTGCAGTAATTTCTAGGCTTTTTGCTCCT GTTAGGTCCTATAAATAATGACATTAGT | 1054 |
| BCL2_chr18:60984454-60984554 | ATAGATACCTAGATGCAAATTTTTTCAGCCGACCACACAAATTAGGTCCACTCTGAGTGGTGAAAACAA AAGATTCTAACATTCTAGCAAACTGGTAAA | 1055 |
| BCL2_chr18:60984554-60984654 | CCATACACAAATTATAGATACAAAGAATGCAGCCGATGCAAATTCTGTCACTGACAAGGTAGCAAAGCC ATAGCCCTGATACTCCTCAGGACACCTCATC | 1056 |
| BCL2_chr18:60984654-60984754 | ACGCCCACTGGGAACATGGCACACACTGGAGATTCCAGTCCAAGGACTTTGGAATGTCAACTTAGCTCTT TACAAACACAACTAAGTTTTCAGGGAAA | 1057 |

TABLE 6-continued

| Name | Sequence | SEQ ID NOs. |
|---|---|---|
| BCL2_chr18:60984754-60984854 | AGACTTACATTGGTTTCCTCTTTTGGAAAATTTTACCGATTGATGATGCCCTTGGTCTTCTGTGGAGTCTATTCTTCTAATCGGGTTGTTCTCCAATTT | 1058 |
| BCL2_chr18:60984854-60984954 | TAGTGTACAACGGGCTTGTTTCAGGGGAGCTTGTTTGGGATGCAGACTGTCAAGACCCAACCTGGTATCTGGTTCATAAGCAGTCCCTGAAACCTCCCTC | 1059 |
| BCL2_chr18:60984954-60985054 | CGGTTCCAACAAGCTGCTCAAGCCAGGAAACGTGGTCTGCTGGGACTCCTGAGCTTCAGCTTGAGAAACACTGAAGGGGTACCATTTACCACCACATCC | 1060 |
| BCL2_chr18:60985054-60985154 | TACTGGATTACAAACGCTAGATCTTTGGATCTCCACGACTAGCAAGCAAGTAAAGACTTAAAGACTTTTAGATGCAGGGCTTATCGGTCAGGTTGGGAGTGAACGC | 1061 |
| BCL2_chr18:60985154-60985254 | TTTTGTCCAGAGAGGAGGTAGGGACGCCGGAAGCAACAACTCTGATTTATTTCGCCGGCTTCCACAGCCTCCCATTGCCCCAGGAGCCCACCCGCACTC | 1062 |
| BCL2_chr18:60985254-60985354 | CAACCCCCGCCATCTCGGACCTGTGGCCTTCAGCCCCAGACTCACATCACCCAAGTGCACCTACCCAGCCTCCGTTATCCTGGATCCAGGTGTGCAGGTGCCGG | 1063 |
| BCL2_chr18:60985354-60985454 | TTCAGGTACTCAGTCATCCACAGGGCGATGTTGTCCACCAGGGCGACATCTCCCGGTTGACGCTCTCCACACACATGACCCCACCGAACTCAAAGAAG | 1064 |
| BCL2_chr18:60985454-60985554 | CCACAATCCTCTCCCCCCAGTTCACCCCGTCCCTGAAAGACTCCTCCACCACCGTGGCAAAGCGTCCCCCGCGGTGAAGGGCGTCAGGTGCAGCTGGCTGGA | 1065 |
| BCL2_chr18:60985554-60985654 | CATCTCGGCGAAGTCGCCGGCGGTAGCGCGGGAGAAGTCGTCGCCGGACTGGCGGAGGGTCAGGTGGACCACAGGTGGACCACCGGGCTGAGCGCAGGCCCC | 1066 |
| BCL2_chr18:60985654-60985754 | GCCGCGGCGCCGCCCGGGGCAGCCGGGGTCTGCAGCGGCGAGGTCCTGGCGACCGGGTCCCGGGATGCGGCTGGATGGGGCGTGTGCCCGGGCTGGGAGGAGA | 1067 |
| BCL2_chr18:60985754-60985854 | AGATGCCCGGTGCGGGGTGCGGGCCGGGGCCGCGGCCCCCAGCTGCGCGCCATCCTTCCCAGAGAGAAAAGCAACGGGGCTGCGACAGCTTATAATGGATGTACTTCAT | 1068 |
| BCL2_chr18:60985854-60985954 | CACTATCTCCCGGTTATCGTACCCTGTTCTCCCAGCTGCGCCATCCTTCCCAGAGAGAAAAGCAACGGGGGCCAACGGCACCTTCGCCCCCAGCTCCCAC | 1069 |
| BCL2_chr18:60985954-60986054 | CCCACGCGCCCCCAGAGAAAGAAGAGAGTTATAATCCAGCTATTTTATTGGATGTGCTTGCATTCTTGGACGAGGGGGTGTCTTCAATCACGCGAACA | 1070 |
| BCL2_chr18:60986054-60986154 | CTTGATTCTGGTGTTTCCCCTTGGCATGAGATGCAGGAAATTTTATTCCAATTCTTTCGGATCTTTATTTCATGAGGCACGTTATTATTAGTAAGTA | 1071 |
| BCL2_chr18:60986154-60986254 | TTGTTAATATCAGTCACTTCCTCTGTGATGCTGAAAGGTTAAAGAAAAAACAAACTAATAAGTAAAAAATCAGGTGCGTTTCCCGTACACACTGAGTG | 1072 |
| BCL2_chr18:60986254-60986354 | AAAGCAGGGCATACACACTACAAGTAACACGGCTAAAAAGATGTATTAAGCTGCCTGGAAATTAAATTTACTCGAATGCACTTTAAGTAAAAATCTCA | 1073 |

TABLE 6-continued

| Name | Sequence | SEQ ID NOs. |
|---|---|---|
| BCL2_chr18:60986354-60986454 | AAGGTTTCCATTGAAAGTTACATTAAACCAATTTCCTGTGCAGAGAACTTACTTGTATTTTTAAGTACAGCATGATCCTCTGTCAAGTTTCCTTTTGT | 1074 |
| BCL2_chr18:60986454-60986554 | AAAACCAAAACAAATGCAAGCATAAGGCAACGATCCATCAATCTTCAGCACTCTCCAGTTATAGCTGATTTGAAACTTCCCAATGAATCAGGAGTCGCGGGGA | 1075 |
| BCL2_chr18:60986554-60986654 | GAGGGAGTAAAAATTAGGAGGATTTCCAGATCGATTCCCAGACTTCTGCCTTCACAGAAATGTCAATCCGCAGGAATCCCAACCGGAGATCTCAAGAGCTC | 1076 |
| BCL2_chr18:60986654-60986754 | GAGAAAAAAAAAGGCAGCGGCGGCGCAGATGAATTACAATTTTCAGTCCGTATTCGCAGAAGTCCTGTGATGTTTTCCCCTTCTCGGCAATTTACAC | 1077 |
| BCL2_chr18:60986844-60986944 | TGAAGGAGCCGGGGACGGGGACAGGAGGATCCTCTTCTGATTAAACTCCGAACAGCAAATGCATTTTCCGAAAAGCTGCTGGATAAATGAAGGCAGGACGCG | 1078 |
| BCL2_chr18:60986944-60987044 | CCTGGCCCCCGCGGTGCCCAGCGCTAGAAGCCCCGCTGTGTGGTGCGGCGAGGGGTGGGGAGAAGGAGGTGGTGGGGAGGGTTTTATTTTTCCCTC | 1079 |
| BCL2_chr18:60987044-60987144 | TTTTCCTAAAAGGATGACTGCTACGAAGTTCTCCCCCCTGGACCCCCTTCCGTCGCACCCCCACCGGCGCACCCCGCCTCCGGGCTGCGCACGCGCCTAC | 1080 |
| BCL2_chr18:60987964-60988064 | GTGTGTTCTCGCCTGACCTTTGTTTACTGCCGTATCACGCGCCCTGGACCCTTTCTAGCCGTGTATGAGAGTGTACACGCGCCTTTC | 1081 |
| BCL2_chr18:60988064-60988164 | ACACACACCGTTGTTGTTACCGGCGCTCGGCGCCGCGGGAGACCCAGGCCAATGCCGCCCCACCGCCCCAGCAGTGGACCTCAGCGTCCAGGCTGCCCTG | 1082 |
| BCL2_chr18:60988164-60988264 | CTGTGAAGACAGGTGACTCTGCACGTTTTAAGCAATGTCTAGGGACGCCCCAGCGTGGTGTTTACTTTCAAGTAGCTTCCTAGGTGTCCGGCACTACA | 1083 |
| BCL2_chr18:60988264-60988364 | CACGCACCGCATCCCCCGCCCCCGTGTCCCTAACACCTTTTACACTGGTTTAGTGCTACACGATGAGGCTCCAGGAAGGGGTTTATCAGGGCTTT | 1084 |
| BCL2_chr18:60988364-60988464 | ACGACAGTTAAGTCAATGTTTCCCTCTGTCCCTAACACCTTTTACACTGGTTTAGTGCTACACGATGAGGACTTCCATATAGTAACTTTCAGGCCCAC | 1085 |
| BCL2_chr18:60988464-60988564 | CGTCCTAACGCTGGGGTGGGTGGGCTCCTAAAGGTCTCCACCTTTGCCTGCCAATCCTAGTTGCCCGCACTTTCTCAAATGCCGGTATCCACGCTCGCTCGC | 1086 |
| S1PR2_chr19:10340823-10340923 | GTGTCTTCCATGGAGGATGGCAGCAGGACACCCCGTGCTGGCCCGACACTCTCGGCCTCCTTATCTGTTTAGGAATGCCGGTATCCACGCTCGC | 1087 |
| S1PR2_chr19:10340923-10341023 | GCGGGAGCCACGCCTCCTCCCCCCGCCCCCGAGACGCCACACGCGCGGGCCCCCAGTCTCCAAGCGGCACTGGAAGGATTCCTCTCCGTCCGC | 1088 |
| S1PR2_chr19:10341023-10341123 | CAGGGGTCCCGCCTCCGAGATTCTGGAAGACTGGGGGTGGGGACCAGATCGCAGCAGCAGCTGCACCGCGAGTTCCGGCCTGGCCGTGCGTCGCCCCACG | 1089 |

TABLE 6-continued

| Name | Sequence | SEQ ID NOs. |
|---|---|---|
| S1PR2_chr19:10341123-10341223 | AGGGGGACTGTGGGCTCAGCGCGTGGGCCCGGAGCATCTGACAAGGACAGAGACAGAGGAGGGGTG GAAATCCCCGGGTGAGTCAACCCGTGCTGAG | 1090 |
| S1PR2_chr19:10341223-10341323 | AAGGGGGCGAGTTCCGACGCTCCGCCCCGGCTCGGGGCTCCGGGGCCACGCGGAGGTCCGCGCCACGCGCGCCTTCACCC ACGACCCATCCCTGAGCCGGAGTTGAAAGA | 1091 |
| S1PR2_chr19:10341323-10341423 | GGAGGCGTCTGAGCCACCAGTCACTTTCTCTTTCCTTACAAAACAAAGCCACGCCCCCCGCCGGGGAC CGGAGGAGGCAAACAACTTGGGAAACCGA | 1092 |
| NCOA3_chr20:46131072-46131172 | CCCACTTTCCCCTTTCTGTCCCTAAAGTTTTTTCTTCCTCTTGCCTCCCCCAGCCCTTTTGAAAGCTCCCGC GTCTCCTCCTGCCCCGCCGCTCCTTA | 1093 |
| NCOA3_chr20:46131172-46131272 | GCAGCTTCTGGGACGCACGGAGGGAAAAAGCGCGCGGGGACCCCCCCACCCCAGCCTCCCAGCCGGGTG AGATTTGGTTGCTGTGTTTCCTCCTCACTTG | 1094 |
| NCOA3_chr20:46131217-46131317 | CCACCCCAGCCTCCCAGCCGGGTGAGATTTGGTTGCTGTGTTTCCTCCTCACTTGGGCATTTAAAAAATAT TTTAACACGAATTGTCCGCGACTTTTCA | 1095 |
| IGLV4-69_chr22:22380472-22380572 | CATGGCCTGACCCCCTCTCCTCCTCCAGCTTCTCCACCCTTCCACCCTCTGCTCAGTGACTGCCTGTGGAATGCCAAAG TGATTATTGGGGACACATGGGATGACTTT | 1096 |
| IGLV4-69_chr22:22380572-22380672 | TCTCTTATATTTTAAACATTGTGGGTGGGTAGTGAACCCAGACTCACCTCTCTGTGCCTGCCTCTCTGTT CCAGGGTCCTGGGCACAGTCTGCGCTGAC | 1097 |
| IGLV4-69_chr22:22380672-22380772 | CCAGGAAGCCTCGTGTCAGGGACCGTGGGACAGAAGGTCACCCTCCTGTACTGGAAACAGCAACAAC GTTGGAAGTTATGCTGTGGGCTGGTACCAA | 1098 |
| IGLV4-69_chr22:22380772-22380872 | CAGATTTCTCACCGTGCTCCCAAAACTGTGATGTTTGGAAATTCTCGCCCTCAGGGATCCCTGACCGCTT CTCTGGCTCAAAGTCTGGGACCACAGCCT | 1099 |
| IGLV4-69_chr22:22380872-22380972 | CCCTGACTATCTCGGGCCTCTAGCCTGCCTCTGAGGACCAGGCTTGATATTATTGTTCAACATGGGACTACAGCCTC AGTGCTTCACACAGTGCTGCAGGCACATGG | 1100 |
| IGLV4-69_chr22:22380972-22381072 | GGAACCGAGACAAAAACCTGCCCTTGCCCTGTCCCGAGGCTGATCACTCCATACTTGCCTATGACAAACA AAGAGGGTGCCTGGCCTGATCGTACAGTT | 1101 |
| IGLV4-60_chr22:22516707-22516807 | GAAATGTTGTTGCTCTTGTCCTTCTTCAGGCCATAATGAGCGTCTCTGTTTTCAGGGTCTCTCTCCCAGC CTGTGCTGACTCAATCATCCTCTGCCTC | 1102 |
| IGLV4-60_chr22:22516827-22516927 | TCAAGCTCACCTGCACTCTGAGCAGTGGGCACAGTGGGAGCGGAGTTCCTGATCGCTTCCAGGCTCCGATGCATGGCATCAGCAGCCAGG GAAGGCCCCTCCGGTACTTGATGAAGCTTGA | 1103 |
| IGLV4-60_chr22:22516927-22517027 | AGGTAGTGGAAGCTACAACAAGGGAGCGGAGTTCCTGATCGCTTCCAGGCTCCAGCTCTGGGGCTGAC CGCTACCTCACCCATCCAACCTCCAGTTT | 1104 |
| IGLV4-60_chr22:22517027-22517127 | GAGGATGAGGCTGATTATTACTGTGAGACCTGGGACACTAACTCACACAGTGATACAGGCAGATGAG GAAGTGGGACAAAATCCTCAACCTGCTGAGG | 1105 |

TABLE 6-continued

| Name | Sequence | SEQ ID NOs. |
|---|---|---|
| IGLV1-51_chr22:22677077-22677177 | AAGGTCACCATTCCTGCTCTGGAAGCAGCTCCAACATTGGGAATAATTATGTATCCTGGTACCAGCAGC TCCCAGGAACAGCCCCCAAACTCCTCATTT | 1106 |
| IGLV1-51_chr22:22677177-22677277 | ATGACAATAATAAGCGACCCTCAGGGATTCCTGACCGATTCTCTGGCTCCAAGTCTGGCACGTCAGCCAC CCTGGGCATCACCGGACTCCAGACTGGGGA | 1107 |
| IGLV5-48_chr22:22707517-22707617 | TCAGCCAGACTCACCTGACCTTGCGCAGTGGCATCAATCTTGGTAGCAGCTACAGGATATTCTGTACCAGC AGAAGCCAGAGAGCCCTCCCCGGTATCTCC | 1108 |
| IGLV5-48_chr22:22707617-22707717 | TGAGCTACTACTCAGACTCAAGTAAGCATCAGGGCTCTGGAGTCCCCAGCCGCTTCTCTGGATCCAAAGA TGCTTCGAGCAATGCAGGGATTTTAGTCAT | 1109 |
| IGLV1-47_chr22:22712077-22712177 | AGAGATCTGGGGAAGTCAGTTCAGCTGTGTAGAGAAGACAGGATTCAGGACAATCTCCAGCATGG CCGGCTTCCCCTCTCCCTCTCACCCTCCTCAC | 1110 |
| IGLV1-47_chr22:22712177-22712277 | TCACTGTGCAGGTGACAGGATGGGGACCAAGAGAGGGCCCTCGGGAAGCCCATGGGGCCCTGCTTTCTCC TCTTGTCTCCTTTCGTCTCTTGTCAATCAC | 1111 |
| IGLV1-47_chr22:22712277-22712377 | CATGTCTGTCTCTCACTTCCAGGTCTCTGGGCCCAGTCTGTGCTGACTCAGCCACCCTCAGCGTCTG GGACCCCCGGGCAGAGGGTCACCATCTCT | 1112 |
| IGLV1-47_chr22:22712377-22712477 | TGTTCTGAAGCAGCTCCAACATCGGAAGTAATTATGTATACTGGTACCAGCAGCTCCCAGGAACGGCCC CCAAACTCCTCATCTATAGTAATAATCAGC | 1113 |
| IGLV1-47_chr22:22712477-22712577 | GGCCCTCAGGGGTCCCTGACCGATTCTCTGGCTCCAAGTCTGGCACCTCAGCCTCTCCTGGCCATCAGTGGG CTCGGGTCCGAGGATGAGGCTGATTATTA | 1114 |
| IGLV7-46_chr22:22723897-22723997 | ATTTGCATAAAGCAGCACACAGACACCCCTCCGTGCGGAGAGCTCAATAGGAGATAAAGAGCCATCAG AATCCAGCCCCAGCTCTGGCACCAGGGTC | 1115 |
| IGLV7-46_chr22:22723997-22724097 | CCTTCCAATATCAGCACCACCATGGCCTGGACTCCTCCTCTTTCGTTCTTCCTCCTCACTCTGCTGCCCAGGTTAAGA GAGATTTCAAATACCAGCTTTGAGGGA | 1116 |
| IGLV7-46_chr22:22724097-22724197 | TCCCTTTTCTCCTTTCTAATTCCTAATATATGTCTGTTTTTTTTGTTTCAGGGTCCAATTCCCAGGCTGTG GTGACTCAGGAGCCCTCACTGACTGTG | 1117 |
| IGLV7-46_chr22:22724207-22724307 | GGACAGTCACTCTCCTCACCTGGCTCCAGCACTGGAGCTGTCACCAGTGGTCATTATCCCTACTGGTTCAG CAGAAGCCTGGCCAAGCCCCCAGGACACT | 1118 |
| IGLV7-46_chr22:22724307-22724407 | GATTTATGATACAAGCAACAACAAACACTCCTGACACCTGCCCGGTTCTCAGGCTCCTCCTTGGGGGCAAA GCTGCCCTGACCCTTTTGGGTGCGAGCCT | 1119 |
| IGLV7-46_chr22:22724407-22724507 | GAGGATGAGGCTGAGTATTACTGCCTTGCTTCTCCTATAGTGGTGCTCGGCACAGTGACAGACCCATGAGAG GAACCAAGACATAAACCTCCCTCGGCCTT | 1120 |
| IGLV5-45_chr22:22730452-22730552 | GGTCAGCCACCCAGCCTGATTCTGACTCTTCTGGCAAAGATCCCTGAAAAACTTACCCTGTTTCTGCCT TAGCACCCCATTAATGTCTGTTTCCAG | 1121 |

TABLE 6-continued

| Name | Sequence | SEQ ID NOs. |
|---|---|---|
| IGLV5-45_chr22:22730552-22730652 | TTCCCTCTTCGCAGGCTGTGCTGACTCAGCCGTCTTCCCTCTGCATCTCCTGGAGCATCAGCCAGTCTCACCTGCACCTTGCCAGTGCCAGTGGCATCAATGTT | 1122 |
| IGLV5-45_chr22:22730607-22730707 | GCATCAGCCAGTCTCACCTGCACCTTGCGCAGTGGCATCAATGTTGTGTACCTACAGGATATACTGGTACCAGCAGAAGCCAGGGAGTCCTCCCAGTATC | 1123 |
| IGLV5-45_chr22:22730707-22730807 | TCCTGAGTGACAAATCAGATCAGATAAGACAGAGGCTCTGAGTCCCCAGCCGCTTCTCTGATCAAAGATGCTTCGGCCAATGCAGGGATTTTACT | 1124 |
| IGLV5-45_chr22:22730887-22730987 | ACAGATGGGAAGTGGGACAAAAACCTCACCCTGTCTGTGCTCTGTACCAATTTTTAAATTTTAAAATAACTGCCTAGGCACACAAACTATATTT | 1125 |
| IGLV1-44_chr22:22735417-22735517 | GCCCAGTCTGTCTGCTGACTCAGCCACCCTCAGCGTCTGGGACCCCCGGGCAGAGGGTCACCATCTCTTGTTCTGGAAGCAGCTCCAACATCGGAAGTAATA | 1126 |
| IGLV1-44_chr22:22735517-22735617 | CTGTAAACTGGTACCAGCAGCTCCCAGGAACGGCCCCCAAACTCCTCATCTATAGTAATAATCAGCGGCCCTCAGGGGTCCCTGACCGATTCTCTGGCTC | 1127 |
| IGLV1-44_chr22:22735792-22735892 | TGCTGCTCCAGGCTGGCCTGTGCTCTGCTGCTGCAGCTTCCTCATGGGTCCCAGGGCATCCAGGGCCCTGCCTGAGAGTGGAGGCTCCTCTCCCCCT | 1128 |
| IGLV7-43_chr22:22749602-22749702 | TCCAGCACTGGAGCAGTCAGTCTGCCCTGACACTGTCAGGTGTGCAGCCTGAGGACGAGGCTGAGTATTACTGGGCCACTGATTTATAGTACAAGCAACAAAC | 1129 |
| IGLV7-43_chr22:22749732-22749832 | CCCTCCTTGGGGCAAAGCTGCCCTGACAGAAGAACCAAGACAATAAACCTCCCGGCCCTTGTGATGTGGAGATTGTGTGATCACCTGCTCTACTATGTGTGTCAAGCAGCCTACAG | 1130 |
| IGLV7-43_chr22:22749832-22749932 | TGACAGACTCATAAGAGAACAAGAACATAAACCTCCCGGCCCTTGTGATGTGGAGATTGTGATCATACACACCAGCTCTCAAGACACAGCCTATACACACCAGCCATAGAAAGGGAAGG | 1131 |
| IGLV7-43_chr22:22749857-22749957 | ACATAAACCTCCCTCGGCCCTTGTGATGTGGAGATTGTGATCATACACACCAGCTCTCAAGACACAGCCTACATGTGGACCAGCCATAGAAAGGGAAGG | 1132 |
| IGLV7-43_chr22:22749942-22750042 | ATAGAAAGGGAAGGAAGGAAAGGGTCTGAATTGATTTCTATCCCTCCTTGTGCCCTGAAGTGGAGGAAATGTGAGAGTGATTTGCAGTAATTGAATGAGACAA | 1133 |
| IGLV7-43_chr22:22750042-22750142 | AGCAAAAGTTATTTGTTTTATATGAAAAAAAAACAGAAACAGCAGGATCAGATCTAAAGGCTGAGTCTAAATGCATTTCCTCCAGACAGAAGCTTCTT | 1134 |
| IGLV7-43_chr22:22750092-22750192 | CAGATCTAAAGGCTGAGTCTAAATGCATTTCCTCCAGACAGAAGCTTCTTCAAACGATGGGCTTTCTGAGCTAAGAGCAAAGAAAATAAACTCTCCACGG | 1135 |
| IGLV7-43_chr22:22750192-22750292 | GTATATTATTAAAGTTTATTTATTGAGTTACTTTCAAAGCAATCCATGACTATTATATAAAGTCAGAAAGTATTAAAAATCACCAAGTTCTCTGCTAAG | 1136 |
| IGLV7-43_chr22:22750292-22750392 | CTACCTTATCCATGCAATCAAAATAAGTACTTTTCTTCATTTGGATGCATTTTTATTTCTGTTTTTAATATTTCCACAATGGTGATTAAACCTGGTGC | 1137 |

TABLE 6-continued

| Name | Sequence | SEQ ID NOs. |
|---|---|---|
| IGLV1-40_chr22:22758647-22758747 | ACAGGGTCAGGGAGGGGTCCAGGAAGCCCATGAGGCCCTGCTTTCTCCTTCTCTCTAGACCAAGAAT CACCGTGTCTGTCTCTCCTGCTTCCACG | 1138 |
| IGLV1-40_chr22:22758747-22758847 | GTCCTGGGCCCAGTCTGTGTTGACGCAGCCGCCTTCAGTGTCTGCGGCCCCAGGACAGAAGTCACCATC TCCTGCTCTGGAAGCAGCTCCGACATGGGG | 1139 |
| IGLV1-40_chr22:22758847-22758947 | AATTATGCGGTATCTGCTACCAGCAGCTCCCAGGAACAGCCCCCAAACTCCTCATCTATGAAAATAATA AGCGACCCTCAGGGATTCCTGACCGATTCT | 1140 |
| IGLV1-40_chr22:22758947-22759047 | CTGCTCTCCAAGTCTGGCACCTCAGCCACCCTGGGCATCACTGGCCTCTGGGCCTGAGGACTAGGCCGATTA TTACTGCTTAGCATGGGATACCAGCCTGAG | 1141 |
| IGLV1-40_chr22:22759047-22759147 | AGCTTGCACAGTGCTCCAGGCCAATGGGGAACTGAGACAAGAACCCTTCCTCCTCCGCCAGGAGGGTG AGTGCCTGCAGCTGCTGCTCACACCTGACC | 1142 |
| IGLV1-40_chr22:22759147-22759247 | TGTAGCTTCTGCTGCTGTAGCTTCCCCCATGGCCTCCGGGGCATCCAGGGCCTTGCCTAGGAGTGGAGGC TCCACCACTTTGTCCTCAGAGTCAGGAAC | 1143 |
| IGLV1-40_chr22:22759247-22759347 | AGGGACCCCAGGAGACAGAATATCCTGCTCCTCAGCTTGGGACACAGGGTCTCTGCACTGAAATCGTGGG CTGAGGTGCAGGTCCAACTGTGTCTTCAC | 1144 |
| IGLV1-40_chr22:22759297-22759397 | CTCTGCACTGAAATCGTGGGCTGAGGTGGCAGTCCAACTGTGTCTTCACAGTCCTTCCTGTGCCTGCCCA TGGTGTGGGGACGGAGTCGAGGAAGTGTGG | 1145 |
| IGLV1-40_chr22:22764167-22764267 | TCCTCACTCTCCTCGCTCGTCTCACTGGCACAGTCTGACTGGATACAGTTCCAGGGGAGGGCCCTGGGAAGCCTAT GGATTCTTGCTTTCTCCTGTTGTTCTAGA | 1146 |
| IGLV1-40_chr22:22764267-22764367 | AGCCGAATAATGATGCCTGTCTTCTCCACTTCCAGGGTCCTGGGCCCAGTCTGTGCTGACCCAGCCGCC CTCAGTGTCTGGGGCCCCAGGACAGAGGG | 1147 |
| IGLV1-40_chr22:22764367-22764467 | TCACCATCTCCTGCACTGGGAGCAGCTCCAACATCGGGGCAGGTTATGATGTACACTGGTACCAGCAGCT TCCAGGAACAGCCCCCAAACTCCTCATCTA | 1148 |
| IGLV1-40_chr22:22764552-22764652 | CTTCCAGGCTGAGGATGAGGCTGATTATTACTGCCAGTCCTATGACACAGCCTGAGTGGTTCCACAGTGC TCCAGGGCCCGGGGGAACTGAGACAAGAAC | 1149 |
| IGLV2-23_chr22:23040452-23040552 | GCTTCCTCACTCTCCTCACTCAGGACACAGGTGACGCCTTCCAGGGAAGGGGTCTTGGGGACCTCTGGGCTG ATCCTTGGTCTCTCCTGCTCCTCCAGGGTCACC | 1150 |
| IGLV2-23_chr22:23040592-23040692 | TTCCAGGGTCCTGGGCCCAGTCTGCCCTGACTCAGCCTGCCCTCCGTGTCTGGGTCTCCTGGACAGTCGATC ACCATCTCCTGCACTGGAACCAGCAGTGA | 1151 |
| IGLV2-23_chr22:23040692-23040792 | TGTTGGGAGTTATAACCTTGTCTCCTGGTACCAACAGCACCCAGGCAAAGCCCCCAAACTCATGATTTATG AGGGCAGTAAGCGGCCCTCAGGGGTTTCT | 1152 |
| IGLV2-23_chr22:23040792-23040892 | AATCGCTTCTCTGGCTCCAAGTCTGGCAACACGGCCTCCCTGACAATCTCTGGGCTCCAGGCTGAGGACG AGGCTGATTATTACTGCTGCTCATATGCAG | 1153 |

TABLE 6-continued

| Name | Sequence | SEQ ID NOs. |
|---|---|---|
| IGLV2-23_chr22:23040852-23040952 | GCTGAGGACGAGGCTGATTATTACTGCTGCTCATATGCAGGTAGTAGCACTTTCCACAGTGGTCCAAGTTCATGGGGAACTGAGACCAAAACCTGCCCAG | 1154 |
| IGLV2-23_chr22:23040952-23041052 | GGCCTTCAGACTTCCTCCTGCTCTGAAGATGCTTCCTCACCCGGTGCAAGAGGCTTGCTGCAGCGCGGCCTTGAGAATTCTTCTCTCCAGCTCCTTCC | 1155 |
| IGLV2-23_chr22:23041052-23041152 | CTTTCCACCATGAATTCAACAGGAAACCTGCCCTGTGGTTTCCCATCCAGGACAGGGACAGAGTTTCCTGATGCTTGTGTGCCTGTGCCTGAATGTGCA | 1156 |
| IGLV2-23_chr22:23041152-23041252 | ACTCTTCCAGCTCTTCAAATGCAGGGACAGTGACAAGGAGCTGCCTGATTGGTGCAGTCACTGCTTTTTTCAGGGATGTCTTCACCCTACACTATATCAT | 1157 |
| IGLV2-23_chr22:23041252-23041352 | CATCCCCTACACTGTGGGTAGAATTTTAGCAACTACATTCTAATGGTTATCGCCACAACTTTGATCTTTAGAAATAACAGTGCAGTGAACATCCCTATGCA | 1158 |
| IGLV2-23_chr22:23041352-23041452 | GGCTCCTTTGAGTTCCTGTGTGAATACGACACATAGGATTCATTTCTAAAAGTGAAATTGCGGGTCAGAAAGATGTGTTTGTGATTTTCACCCAATGTT | 1159 |
| IGLV3-21_chr22:23055497-23055597 | ACCAGCAGAAGCCAGGCCAGGCTCCTGTGCTCCTGTCGTCGTCGTCTATATGATGATAGCGACCGGCCCCTCAGGGATCCCTGAGCGATTCTCTGGCTCTGAGCCTTTCAGGTTG | 1160 |
| IGLV3-21_chr22:23055597-23055827 | CCCAGCTCGGTCACCCTCTTGCTCCAGCCCCGGGAAGCCTGTTGATAAAGCCATGAGTGAATCTGGCCCAGTTCACCTGGATCTGAGCCTTTCAGGTTG | 1161 |
| IGLV3-21_chr22:23055827-23055927 | CCCTTCCCTGGCCCCCTCCAGCCTCTCTACAGAAGATACATCAGGCATAAATATGGCTGGAAGGGCCAGAATCATCTGGTGACTTGGGCTGTTGT | 1162 |
| IGLV2-14_chr22:23101392-23101492 | GGTCCTGGGCCCAGTCTGCCTGACTCAGCCTGCCTCCGTGTCTGGGGTCTCGATCAGTGATCACCATCTCCTGCACTGGAACCAGCAGTGACGTTGG | 1163 |
| IGLV2-14_chr22:23101532-23101632 | AAAGCCCCCAAACTCATGCATTTATGAGGTCAGTAATCGGCCCTCAGGGGTTTCTAATCGCTTCTCTGGCTCCAAGTCTGCAACACGGCCTCCCTGACCA | 1164 |
| IGLV3-10_chr22:23154347-23154447 | AGGCTCAGTGCCCATAGACCCCAAGTTGGCCCTGCCCTGAACCCTGTGCAAAGCCCAGACACAGTCTTAGGGTAGGACCCCCTGGGAATGGGCTCTTGATC | 1165 |
| IGLV3-10_chr22:23154447-23154547 | TTCAAGCCCCCCTCCTCTGTTTTCCTTGCAGTCTCTGAGGCCTTCCTATGAGTCTGACACAGCCACCTCCGTGTCAGTGTCCCAGGACAAACGGCCAGGAT | 1166 |
| IGLV3-10_chr22:23154597-23154697 | AGAAGTCAGGCCAGGCCCCTGTGCTGGTCATCTATGAGGACAGCAAACGACCCTCCGGGATCCCTGAGAGATTCTCTGGCTCCAGCTCAGGGACAATGGC | 1167 |
| IGLV3-10_chr22:23154697-23154797 | CACCTTGACTATCAGTGGGGCCCAGGTGGAGGATGAAGCTGACTACTACTGTTACTCAACAGACAGCAGTGGTAATCATAGCACAGTGACACTGGCAGAT | 1168 |
| IGLV3-10_chr22:23154797-23154897 | GGGGAAGTGAGACACAAACCCCTTCTTCATCTATTTTACCCTCTCCCTCCCAGCCCCCAGGACCCGCTGTGGACCAACCCATAAGCAGGTCTGGCAGAATTCA | 1169 |

TABLE 6-continued

| Name | Sequence | SEQ ID NOs. |
|---|---|---|
| IGLV2-8_chr22:23165422-23165522 | AGGCTCACCTGGGCCCAGCACTGACTCACTAGACTGTGTTTCTCCCTTTCCAGGGTCTCTGGGCCCAGTCTG CCCTGACTCAGCCTCCCTCCGCGTCCGGG | 1170 |
| IGLV2-8_chr22:23165542-23165642 | CATCTCCTGCACTGGAACCAGCAGTGACGTTGGTGGTTATAACTATGTCTCCTGGTACCAACAGCACCCA GGCAAAGCCCCCAAACTCATGATTTATGAG | 1171 |
| IGLV2-8_chr22:23165642-23165742 | GTCAGTAAGCGGCCCTCAGGGGTCCCTGATCGTTCTCTGGCTCCAAGTCTGCAACTGGCCTCCCTGAC CGTCTCTGGGCTCCAGGCTGAGGATGAGG | 1172 |
| IGLV2-8_chr22:23165727-23165827 | AGGCTGAGGATGAGGCTGATTATTACTGCAGCTCATATGCAGGCAGCAACAATTTCCACAGTGTTTTAAG TCAATGAGGAAGTAAGATCAAAACCTGCCC | 1173 |
| IGLV4-3_chr22:23192412-23192512 | TCAGGCTCAGAACCCATAGGATCCTGAGCTGGGCCTGCCCAAACATGAGTTCATCCCAGGCACAACCTCA GGGTGGGACCCCCCTGGGAACAGATTCATCA | 1174 |
| IGLV4-3_chr22:23192512-23192612 | TTTACAAGCCTCTCTCTCCTGTCCTCTTGCAAGCTCCTATGAGCTTACACAGCCACCCTCAGTGTCAGTG TCACCAGGACAGGCAGCCATGATCACCTG | 1175 |
| IGLV4-3_chr22:23192612-23192712 | CTCTTGAGATAACCTCAAAGATGAGTATGTTTACTGGTTCTGGCAGAGACCAGACCAGGCCCATACTGGT GATATATGAAGGCAGCAAGCGGCCCTCAGG | 1176 |
| IGLV4-3_chr22:23192712-23192812 | AATTTCTGATTTTCTGAGTCCAGCTCAGGGAACATGGCCACCCTGACCATCAGCAGGCTCAGACTGAGG ACGAGCTGACTATTACTGTCACAGGTACA | 1177 |
| IGLV4-3_chr22:23192812-23192912 | ATAGAAACAGTGATGAGCCCACAGTGACACAGGCAGATTAGGAGTGAGACACAAACCCCTTCCCAATCT GTGTCACCCTCTTTCTCCAGCCCCAGGATG | 1178 |
| IGLV4-3_chr22:23197917-23198017 | GGGATGAGAAGGGACCAGGGGCTGGGATTGAGCTGTGAAGGGAACCAAAAGGCAGGAGGGACAGGGC AGGGGCTGTCAGCTATGACTCAGGGGAGGTTC | 1179 |
| IGLV4-3_chr22:23198017-23198117 | CTCGGGCCTTCAGGATCCTCCCTGGAGGCCACCAGGGGCGGGGGTGGCACATGCCTGGACCTGGGAGTC CCTGCTGGGCTTCACCCTGGGTGGGTCCTA | 1180 |
| IGLV4-3_chr22:23198067-23198167 | ATGCCTGGACCTGGGAGTCCCTGCTGGGCTTCACCCTGGGTGGGTCCTAGGAGTCTCTTCCTCCCTAAGTC CCCTAAAGAGACAGAGGCATTCTGGGGT | 1181 |
| IGLV4-3_chr22:23198167-23198267 | CCTAAATCTGTCATGCCCCCATAAATGCATTTCTACGAGGGCCAATAAATGAACTCCAGGTTTATCCAAGC AGCAGCTTCAGGCGCTGCAGACACAGAG | 1182 |
| IGLV4-3_chr22:23198267-23198367 | CGGGGAGGAATTAGCCAACCTGAGGCACCCTAGAAAGGGCTGAAGGGGCTGAAGGGGACTGAAGGGTCC CTGTGGGGCCGTGTGGTCCTGGGAGGGGAGA | 1183 |
| IGLV4-3_chr22:23198367-23198467 | GCTTGGGGTGTCTCCCAGCCACTCTGGGCCCTGTCCCTGACACTTCTCCCACAAAGAAGGGAAGGGAAATCC TGGGACCCCACAGCCAGGACCAACCGTGAA | 1184 |
| IGLV4-3_chr22:23198467-23198567 | CCCACAGGACAGGAAGGACAGGGACCCCCAAGGCTGGCTCCCATTTCCCAGGCACTGTCATGGGCTGAGTCT CAGGAAATCCAAGTCAAGGAGTTTCAATCC | 1185 |

TABLE 6-continued

| Name | Sequence | SEQ ID NOs. |
|---|---|---|
| IGLV4-3_chr22:23198587-23198687 | CCAAGGAAACAGAAGTCTACGGGCCCAGGCCCAGTGAGGGTAAGAGAGGAGCTTAGGATGCAGATTTGCATGGAGGCCCGCCCTCCTCTGAG | 1186 |
| IGLV4-3_chr22:23198687-23198787 | GCATCAGGGTAAGACAAGGCTGGGGGCAGGCCCAGTGCTGGGGTCTCAGGAGGCAGCGCTCTGGGACGTCTCCACATGGCCTGGCTCTGCTCTCCT | 1187 |
| IGLV4-3_chr22:23198797-23198897 | CTCAGGGCACAGGTGACGCTCCAGGAAGGGCCTCGGGGACCCTGGGCTGATCCTTGGTCTCCTGCTCCTCAGCCTCACCTGGGCCCAGCACTGACT | 1188 |
| IGLV4-3_chr22:23199022-23199122 | TTCGGAGTTATGACTATGTCTCCTGGTACCAACAGCACCCAGGCACAGTCCCCAAACCCATGATCTACAATGTCAATACTCAGCCTCAGGGGTCCCTGA | 1189 |
| IGLV4-3_chr22:23199122-23199222 | TCGTTTTCTCTGGCTCCAAGTCTGGCAATACGGCCTCATGACCATCTCTGGACTCCAGGCTGAGGACGAGGCTGATTATTAGTGCTGCTCATATACAAGC | 1190 |
| IGLV4-3_chr22:23199182-23199282 | TGAGGACCAGAGGCTGATTATTAGTGCTGCTCATATACAAGCAGTGCCACTTAACCACAGTGGTCCAAGTTCTTGGGGAACTGAGACGAAAACTGCCCTGG | 1191 |
| IGLV4-3_chr22:23199277-23199377 | CCTGGGCTCTCAGGCTGCTCCCTTTTGCTCTGAAGATGTTTCCTCACCCAGTGCAACGGGCTTCCTGAAGCACAGCCTTGAGAATTCTTCTCCCAGCAAC | 1192 |
| IGLV4-3_chr22:23199377-23199477 | TCTCTTTTTCCCACCATGAAATCAAAGGAAACCCTGCTCTCTGTGTTTCTCATCCAGGACAGGGACAGCTTCCTTTTGCTTGTGTGTTGGTCCCTGAGTG | 1193 |
| IGLV4-3_chr22:23199477-23199577 | GGTGCAACTCTTCCTAGCTTTTTAAATTATGGAGGGTGACAATGAGCTCCCTGACTGGTGCAGTCCCTGCTGTTTTCAGGAACATCCTCATCCTAAATG | 1194 |
| IGLV4-3_chr22:23199577-23199677 | CATCTGAATCTCCCACTGTGTGCAGACAATCTGGACAGATGTTATTAGGGGGAGTTTCAGAAGCCACATCTTACTCAACTCTGTATCCACCACTCT | 1195 |
| IGLV3-1_chr22:23222927-23223027 | TGCCTCAGCCATGGCATGATCCCTCTCTTCCTCGGGGTCTTGCTTACTGCACAGTGCTGCCCCTAGGGTCCTAGCCACTGGTCCCAGGGCTC | 1196 |
| IGLV3-1_chr22:23223027-23223127 | TGGGTCAGCCTGGCCTGACTCTGAGCTCAGCAGGGCCCCGCCTGTGGGCAGGATGCTCATGACCCTGCTGCAGGTGGATGGGCTCGGCGGGGCT | 1197 |
| IGLV3-1_chr22:23223077-23223177 | TGGGCAGGATGCTCATGACCCTGCTGCAGGTGGATGGGCTCGGCGGGGCTGAAATCCCCCACACAGTGCTCATGTGCTCACACTGCCTTAGGGCTCTTT | 1198 |
| IGLV3-1_chr22:23223177-23223277 | CATCCCTGATCTGTCCAGGCCAGGCACGTGGGAAGATTTACTTGGAGTTCAGTTTCAAGCCTTTTCTCTCCCGTTTCTCTCCTGTAGG | 1199 |
| IGLV3-1_chr22:23223277-23223377 | ATCCGTGGCCTCTATGAGCTGACTCAGCCACCCTCAGTGTCCGTGTCCCCAGGACAGACAGCCAGCATCACCTGCTCTGGAGATAAATTGGGGGATAAA | 1200 |
| IGLV3-1_chr22:23223327-23223427 | CAGGACAGACAGCCAGCATCACCTGCTCTGGAGATAAATTGGGGGATAAATGCTTGCTGTATCAGCAGAAGCCAGGCCAGTCCCCTGTCGTGGTCAT | 1201 |

TABLE 6-continued

| Name | Sequence | SEQ ID NOs. |
|---|---|---|
| IGLV3-1_chr22:23223427-23223527 | CTATCAAGATAGCAAGCGGCCTCAGGGATCCCTGAGCGATTCTCTGCTCCAACTCTGGGAACACAGCCACTCTGACCATCAGCGGGACCCAGGCTATG | 1202 |
| IGLV3-1_chr22:23223527-23223627 | GATGAGGCTGACTATTACTGTCAGGCGTGGGACAGCACTGCACACAGTGACACAGGCAGATGCGGAAGTGAGACAGAAACCAGCCACCTCGGCCTGG | 1203 |
| IGLV3-1_chr22:23223627-23223727 | CTCACAAGACCCTTCCCTCTCCTGCCCTGTCACACTGAGCAGGAGGGAGCCTTCATGTGAATGAAGTTTCCAGTCCTATCCCTGCCCTTATGTTC | 1204 |
| IGLV3-1_chr22:23223727-23223827 | CTCGAGAGACGGGAGCAAGTTCCTGCCCACCCTCTAGGCTCAGCTTATCCAGAATAAACTGAGCTAGTCATTTTGATGATCAAATGCCAGCTCCCAAAGA | 1205 |
| IGLV3-1_chr22:23223827-23223927 | CCCCAGAAACCCTGATATCTAAGTAGCACCGACTCTATTAGTATCAAGGGAGACTAGCCCCTAGGGTGAATCATTTTAGTGTCTCAGAAGGCACAGGCA | 1206 |
| IGLV3-1_chr22:23223927-23224027 | ATGGAAAGTGTTTATGAGGTTTCAGGATATGCACGTGAGCAGTTAAAGGCAGTCTTACAAGGAAGGAACCTACTAGAATTGGGGCCATCTGACATC | 1207 |
| IGLL5_chr22:23227062-23227162 | ACATCCCTGCTCTTGGGAGAGAAGGGCCAGGGCGGGACCCAGAGAGCTCTGCAGAGGCACCACAGACCCTCAGCAGGGGGTCGCAGCTGCAGCAGGACAGCT | 1208 |
| IGLL5_chr22:23227162-23227262 | GGACTTGGCTGCTTCTCGCCCAGGCCTGGATCCAGCCCTTGCACATCTCAGGGCAGGGGATAGGCCTGGGTGGCCAGAGCTGCAGCTGCACCTGCTGGGGA | 1209 |
| IGLL5_chr22:23227262-23227362 | GGCCTAGTCCAGTCCTCCAGGGTCCCCAGACAGACTCGGATTTCCGACTGCGCCACCATGGAAGGATGTGGTCTGCCGGTGACGATGTCTATCCAGAGGC | 1210 |
| IGLL5_chr22:23227567-23227667 | CCGAATATCCAAGGAGCCCAAGATCAGAGGCAGGAATAGGCCAAGCTCCCCAGTGGAGAAGCTGTGCTGGACCAGGGGTTTCCCAGGGCCCTCCCTTGTG | 1211 |
| IGLL5_chr22:23227667-23227767 | CCCTGAATGATGTCTGTTAGGGCACTTACCACCCTGTTACTGCTCAGTGCCTTGCCTATTTGAAGGACCAGGGATGTGTGGTGATTATTTGTATAATCCAG | 1212 |
| IGLL5_chr22:23227767-23227867 | CCCCCAGCACCTGGTCTCAAAAGTTACCCAAGCAATGTGTATAAAGATCCAGCCTGGAGATCTTTGAAAACCGATTCGATGAGTCGAACCATTAAGTCA | 1213 |
| IGLL5_chr22:23227867-23227967 | TGATCACCATCCTCAACTTCATCTCTTTCTTCCTCCTCATTATCACCTTCAAGAACTGTTAAGAGTCTGAGACTTCATCCTCTATTTGCAGACTAAGTCTGAGACTTCATCCTATTTGCAGAC | 1214 |
| IGLL5_chr22:23227897-23227997 | TCCTCCTCCTCCTCATTATCATCAACACCTTCAAGAACTTCAAGAACTGTTAAGAGTCTGAGAGTCTGAGACTTCATCCTCTATTTGCAGACTAAAAGTAAGCCTGCCACAGTGCCATGGA | 1215 |
| IGLL5_chr22:23227997-23228097 | TGCTGGGCAGAAGATACAAGACTCCTGGGTCAGAGAGACAACGAATAATCTGTTTTTCACAGCAATAGCAGTTGCCAAGGTATCAGCATTGTCTTGCCACCAGT | 1216 |
| IGLL5_chr22:23228097-23228197 | TCCACAAGGTGATGCAAAGAGGGCCAGTGACATCTGCATGCCAGAGCTCAGGGATCCAGAGCTCAGGGATCCCAAATATTCATACTTGACAGTAAGCATATATCTGTTTTG | 1217 |

TABLE 6-continued

| Name | Sequence | SEQ ID NOs. |
|---|---|---|
| IGLL5_chr22:23228197-23228297 | CTCCAAAGAGAGGCATTCTCTGTACCTTCCGAGGTTGTTCACTCCACAAAACACTCTTGAAAAGATAATCCACAATCAGTGCCTTTGCCCGAGAGACATGC | 1218 |
| IGLL5_chr22:23228297-23228397 | AGAAATGCAGAGATCCATAGTAGACCACTGTCTCCCACAACCATCAACTTTATCAATGAAATGAAGTCTCAGGCTATTTGTCTGTTACCATAGCCCACA | 1219 |
| IGLL5_chr22:23228397-23228497 | AAAATGTCTGGCTTGATTGTCACCAAATGTATCAAGGAAGTTAAGGAGTATCTGACACAAAATGTGAACCAAGCAATTCTCAAAGGAGGCCTCCCAGGAAA | 1220 |
| IGLL5_chr22:23228497-23228597 | TTCACTTTAGGAAGTCCTAGGAGGCTCTCTGAGAGTTGCTAAAACAAAACATTGAGAGTCCTAGAGGGCTGCAGATCTGAACTGAGCAGATATTTTTA | 1221 |
| IGLL5_chr22:23228597-23228697 | AAGATTTTGTGCAGAAAAGAAACTGAAAGCAAGAGGGCAGACCCTCATTGCAGTTCTGTAATGTAAGGGGGCAGAGCAGGGGCCTTTCTTCACCAGAG | 1222 |
| IGLL5_chr22:23229332-23229432 | GATATTGGACCCTGCATTCATCTTCTCTGGATGGTAATTTCTCACCTGTAAAACAGAGACACTGGCCCCAAGGACACCCCACAAGTAGTTGTGAATCCC | 1223 |
| IGLL5_chr22:23229432-23229532 | AAAGTAAGAGAAGAACAAAAAGAACAGAATTTATTCAAACACCCACTGAGTGCTTAGCAAACAGACAAACACATGGTTTCTTTAACTCTCATAAGCTTCATGCTGCC | 1224 |
| IGLL5_chr22:23229532-23229632 | AGAGGAACTCTCCCCATTTACAGATAAGGAGAACTGAGGCCCAGAGGTAACCTAGGTCTAGATAGACTCCACATTTATGACTTCACCACTCTTCCTTGCCT | 1225 |
| IGLL5_chr22:23229562-23229662 | AAACTGAGGCCCAGAGGTAACCTAGGTCTAGATAGACTCCACATTTATGACTTCACCACTCTTCCTTGCCTGAAGGATATAGAATCACTCCCTGCAGGC | 1226 |
| IGLL5_chr22:23229662-23229762 | TCTTGCCTGACTCAGGAAAGGCCACAGATAGCCAGCCAGGCTTAACCAACCAGCCAGCAAGAAAGGGCTGGTCCCAACTGGCTGAGTGCAGTGTACAGG | 1227 |
| IGLL5_chr22:23230012-23230112 | GTTGGTAGATGCCCCTCTGGGAGAGATCCCAGGGGTGACAGCCCATGCGACCCTGGAAGGGGCCTGGGCTAGGGACAGGGACCAGAGCCAGTCCAGGGAGAG | 1228 |
| IGLL5_chr22:23230112-23230212 | GACAGAGCCAATGGGGTTGGGGTGTACTGTAACAGCCCTGCTGGCGAGAGGGACCAGGGCACCGTCCTCCAGGGAGCCCATGCTGCAAGTCGGGCCAGAGG | 1229 |
| IGLL5_chr22:23230212-23230312 | TGCCCCTGAACCTGAAGGCCAATGAGACCCAAGACAGGCCAACTGGGTTGTGAGACCCCTGAGGAGCTGGCCCTGGTTCCCAGGCAGCGCTGGCCCCTGC | 1230 |
| IGLL5_chr22:23230312-23230412 | TGCTGCTGGGTCTGCGCCATGGCTCGCCCATGGCCTGCTGCGCCCAATGTTGCACCCGCAAGCGGGGACCCAGACCCTGGTCCTGGAGCCTCAGTTGGAAGCAGCCG | 1231 |
| IGLL5_chr22:23230412-23230512 | ATCCAGCCTGCGGAGCCTGTGGGGCAGCCTGTGAGGGGCAAGAGATTCCAGGGGATGTGGGGTCCTGCAGCAGAGCTGGGAAAGGGTGACCAAGGGAGACA | 1232 |
| IGLL5_chr22:23230512-23230612 | AGCCAGAGGAGTGAGGAGGAAGTTAACCCCTAAGAGGGGCTGGCTGACACTGGCTTTAGTAATGGGTTGATATTTTGTCCATCACAGATTTGTTTGA | 1233 |

TABLE 6-continued

| Name | Sequence | SEQ ID NOs. |
|---|---|---|
| IGLL5_chr22:23230612-23230712 | ATTACTGTTTTAATATCATATTACGATATATTTTTCTTGATTTCTGAGTTTTCTGCGCCACTTAAATTTTCACCAGGGTCAGTGCCTCAATCACCTA | 1234 |
| IGLL5_chr22:23230712-23230812 | GTCCTAGTCCTCTGGGTAGGGAGGAACAGAGGCAGGGACACATCCACAGGGGTGGTGCCACTGTCCCCACAGGGTGCCCAGGCCTGTTCCTCCC | 1235 |
| IGLL5_chr22:23230812-23230912 | CCTCCTCCTCTCTGCCCATGTGCCTCTGCCCAGTGAGGGCAGGGGCCACTCCCTGAGAAGGCAGCAAGGGCTTGGTTTGGTCTCCCCAAGGCTGTCT | 1236 |
| IGLL5_chr22:23230912-23231012 | GTTCACCAACTTGCACATAAATGCTTACTGGGGCCAGGCTCAAGGACACACAGGGAGGGTGGGATGAACCGAGGGGAGCTGTCCAGTCATTGGAACAGGCCC | 1237 |
| IGLL5_chr22:23231012-23231112 | ACGGCCCATGTTTGGAGCAATAAAGGGAGAGGGGATCTCCCTCTGGGATGATGCCCAGGCTGTCTCACAGATCGAGGGGCACTGGCTGGTGATGGGTGC | 1238 |
| IGLL5_chr22:23231072-23231172 | TGGTCTCACAGATCGAGGGGCACTGGCTGGTGATGGGTGCCCCCAAAAGACAGCAGCGTCAGAGGAGAGGAGACACAGATGAGGCTGGGAGCTCCT | 1239 |
| IGLL5_chr22:23231172-23231272 | GGGTGACTGGGAAGGGAGGCAAGAAGACACCATAGGGTCCGTGCACCATTCCCAGTCAGGACGAGTCCTTGGATGGATTTAGTGAGTAGATTATCAGAG | 1240 |
| IGLL5_chr22:23231272-23231372 | TCAGATTTGTGTTTTTTGAAAAATCAGCACCGATTGGAGGTGATGCGAACTCAGGATTAGGAGGAGGAGGAGAGGGGGTGATGGCCAAGTCCAGGGTAG | 1241 |
| IGLL5_chr22:23231372-23231472 | GTGGGGATCCTGGAGGAAGCCTGCCTTGGGATGGGGAGGACACTCAGATTCAGAGCCACCCAGGGGCCCAGTTTCCTATGAAATGGGAGCATGAAGTTG | 1242 |
| IGLL5_chr22:23231472-23231572 | AAGTGAGGGCTGAGCAGAGGGAGCAGACACGCTCGGGGACTGTCTCTATGGGCATTAAAAATGTATAACCATTTTAGCAACAGGCGCGAGTCAAAAAACA | 1243 |
| IGLL5_chr22:23231572-23231672 | AAGTGTGTTTATCTAAACTGGGCAATTCCACTTCTAGGAATTTATCCTAAGGGTTGTTGGGGAATAATCAAAGCTGTAACCAAATCTTTATACAAGG | 1244 |
| IGLL5_chr22:23231672-23231772 | GTGGTTAGCTCAGCATTATTAGTGATGGGAGAAAAACTGGAAAAAAATCCAAATATCTACCAGAAAGGGTGTGAAAAAACACAATTGTATTTGGGGGACTGT | 1245 |
| IGLL5_chr22:23231927-23232027 | TGGCTAATTTGATTAGGATTATTATTAGTTTAGAGACAGAGCCTCGCTATATTGCTCAGGCCTGTCTCAAATTCCTAAGCTCAAGCAATCTTTCTGCCT | 1246 |
| IGLL5_chr22:23232062-23232162 | ACTGCACCTGACCAACTGTGTTTTTAAAGTATATATGCATTTTCAAAAACCTGTCAGAAAATATAGAAAAATGTCAATGGTGTCTCGGCTGATG | 1247 |
| IGLL5_chr22:23232162-23232262 | GGATTTCACCTAATTTAATGTGGCTTTATAATTTTCTGGTTTTGTGAAGTGTTCACAAAAAGAGACATTTCTTCTAATAATTTTAATCACAACAGT | 1248 |
| IGLL5_chr22:23232262-23232362 | AATGTACTCATGTGCATTACTCTTTTTGTAATGAGTATATTACAAAATGTAATGACTTTTGTACATTACTCTTTTTCTTGCCAAAAAAAAGATTA | 1249 |

TABLE 6-continued

| Name | Sequence | SEQ ID NOs. |
|---|---|---|
| IGLL5_chr22:23232362-23232462 | AGCAGAGAAGTATATAAAGTAAAAGCAAGTGCTTCTGCTTACCATCTCTCACCTCTTCCCAGAGATAGCCACTGTCAGGTTGGTCAATATATACTTCCAGAA | 1250 |
| IGLL5_chr22:23232462-23232562 | CTTTTCCTGTGTGTGTGTGTGTCCCTGAAAACACACACACACACACACACAGTTGGTGCTGGGATTTTATTTTGCAAAGTAAGAGCC | 1251 |
| IGLL5_chr22:23232517-23232617 | CACACACAGTTGGTGCTGGGATTTTATTTTGCAAAAGTAAGAGCCATATTCTGCATATTACCAACTTTTAATCTATTATTGACACTTTCTGTATCAGTCC | 1252 |
| IGLL5_chr22:23232617-23232717 | ATATGGATTAACCACATTCATTGCTTATAAAACTTTGTTTTATAAGCAAAGTTTAGATGAGCCAGAGAATTTATTTCCACTAAAAATCTAAATGACAAATGA | 1253 |
| IGLL5_chr22:23232717-23232817 | TGCTGCAGTGGAAATTTGTGTGTGTGTGTGTGTGTGTGTGTGTGTGTGTGTATGTGTACAAAGTGCACTTATATATCTCCCAGGATA | 1254 |
| IGLL5_chr22:23234612-23234712 | TGACCTGGGTGTTTTCTTTTTCTCTGTAGGATGTTAATAGTATCTTGTCTAGGATGTCTAGGACAGAGGGCAATACAATGAGGGGAGGCATT | 1255 |
| IGLL5_chr22:23234712-23234812 | CTGCGATGTCCCCAGGCCTCTGCTTGAAGAGTAACTTGCTGAAGTGAGGACTCTGTGGAGGAGCAAGTTATACAGAAGAAGTTTAGTTGTGATCTGTT | 1256 |
| IGLJ1_chr22:23234812-23234912 | GAGTTGAGGTGTCTACAGGGCATCCAAGCAGACATAGGTTGAGGAGGCGCAGATATATATGTGAATCTGAAGCCAAGAGACAGAACCCAGGGTAAGGGCTGAAATAGG | 1257 |
| IGLJ1_chr22:23234912-23235012 | GATCTAAGACCCCTGGACAGTTGTGAGTGTGCACAATGAGGGTCAGATGCAGAGAAAATTAGGAGACTACAGAGACCAGAACCCAGGGTGGGATCTGGG | 1258 |
| IGLJ1_chr22:23235012-23235112 | AGTCAGCAGTTGGGCATGGCCTGGTAGAAAGGGAAGCCAAGGAGGAGGGGCAGTCTCAGACACCAAGGAGGGGAGAGTTGAGGGAGAGTGAGGCTG | 1259 |
| IGLJ1_chr22:23235112-23235212 | CTTCTTGCAGAGACATAGGGGATGGGGAAGAACTGCAGAGACTCCCACCAAAGGACTGTTGGCTTAACCAGAGATTTGAGGGAGAGATGAGGCTG | 1260 |
| IGLJ1_chr22:23235212-23235312 | AGAGCCAGGGGATCCTGCCATGTCCCAGCATAAAAACAGTACCTGACACAGATGGGTGCTTGGGAGCTGTTGTCGGATGAATGAGTGACAGATGCATGG | 1261 |
| IGLJ1_chr22:23235312-23235412 | ATGGACGGATGGAAGGATGGATGATAGATTGATGGACAAACAGATGAACAGATGAATAGCTGGATGGACAACTGGATGGATGGATAGCAGACAGACCCAGTGCT | 1262 |
| IGLJ1_chr22:23235412-23235512 | AGAGATCAGAAAAAGCTTCATGCACTAAGTGGGACTGAACCGCGTCTCCATGGGTAGAAAGCAGAGGAATCTTCCACTTGAGTCAGGAATGCAGACCCAGTGCT | 1263 |
| IGLJ1_chr22:23235512-23235612 | CTCAATCCAGGGAGAAAGCCAGCCTGGCTTCACTCTGTGTGGGGACACTTGTGTGGGGGACTCAGAGGCCCCTTTAAATGAGGCCAGACGACAGGTTGGACAGGTCCAA | 1264 |
| IGLJ1_chr22:23235612-23235712 | GCCAACTTCAGCACTCCTCTGCCACACTGCACAGGAGGGGATGTGTCACTCAGGGAGTTGCTGGGACCTATGGGTCCCAGTGTTGTCATCAGCACCGACAG | 1265 |

TABLE 6-continued

| Name | Sequence | SEQ ID NOs. |
|---|---|---|
| IGLJ1_chr22:23235712-23235812 | CCTCAGAGGAGGAAAGACACACACTGGGTAACTCCAAGGCTGTGTGTGGCACTTGCCTTGGACAGCAGACAGGCACAGGGACACCCTCAGGGGGCTGCC | 1266 |
| IGLJ1_chr22:23235812-23235912 | ACCCCCCTGCCTCATGTCTAGGTCCCAGCCCCGCCCACTGCAACCCTGTGCCGTCATGCCCAGCAGGCTCCTGCTCCAGCCCAGCCCCAGAGCAGA | 1267 |
| IGLJ1_chr22:23235847-23235947 | CACTGCAACCCTGTGCCGTCATGCCCAGCAGGCTCCTGCTCCAGCCCCAGAGAGACAGACCCCAGGTGTCGCCCCGGGGTTTTGCTCTGAGC | 1268 |
| IGLJ1_chr22:23235947-23236047 | CTCAGTCACTGTGTTATGTCTTCGGAACTGGGACTGGGACCAAGGTCACCCGTCCTAGGTAAGTGCCTCAACCTTTCCCAGCCTGTCTCACCCTCTGCTGTCCCT | 1269 |
| IGLJ1_chr22:23236047-23236147 | GGAAAATCTGTTTTCTCTCTGGGGTTCCTCCCCTCTGTCCTCCCAGCCTTAAGCACTGACCCTTACCTTTCTCCATGGGGCCTGGAGGAGGTGCATT | 1270 |
| IGLJ1_chr22:23236147-23236247 | AGTCTCCGGGTAACCGGCAGGAAGGGCCTCCACAGTGGGAGCAGCCGGATGCAGCCTGGTCCCGGGCCTGAGCTGGGATTGGGCAGGGTCAGGGCTCCT | 1271 |
| IGLJ1_chr22:23236247-23236347 | CCTCTCTTCCAGGGCAGATGTCTGAGTGAGGGACAGAGGCTGGTTCTGATGAGGGGCCCTGCAGTGTCCTTAGGGACATTGCCCAGTGACTCCTGGGGTC | 1272 |
| IGLJ1_chr22:23236277-23236377 | GGACAGAGGCTGGTTCTGATGAGGGGCCCTGCAGTGTCCTTAGGGACATTGCCCAGTGACTCCTGGGTCAAGGACAGAGGCTGCTGGGGTGGGCCTGGG | 1273 |
| IGLJ1_chr22:23236377-23236477 | AGCTGCTGAGTCTCATAGTCTAGGGGAGCAGCCCAAGAACAGTCTGAGGGTCTAGGCTGAGGACTGGATGCCAATCCAGCCTGGGAGGGCCACACGCCTGGTGACACAG | 1274 |
| IGLJ1_chr22:23236387-23236487 | TCTCATAGTCTAGGGGAGCAGCCCAAGAACAGTCTGAGGGTCTAGGCTGATGCCAATCCAGCCTGGGAGGGCCACACGCCTGTGACACAG | 1275 |
| IGLJ1_chr22:23236487-23236587 | AGTCACCCAAGGGAGACCATGGGGACACAGAGGGGACCGGCTGAGACTGGGTGAGGTGCCAGAATCCAAGGTGTCTGGTCTGGTCATGAGGACATGGGACACA | 1276 |
| IGLJ1_chr22:23236557-23236657 | TGTGCTGGGTCATGAGGACATGGGGACACAGAGGGGACCGGCTGAGACTGGGTGAGGTGCCAGAATCAACCCTCCCAGGACAGTCACCCAGAAAGGAGACACAG | 1277 |
| IGLJ1_chr22:23236657-23236757 | TCTCTTAGGGCAGAGATGTCTGTCCTGGAGCCCCCGTCACCCTTGGGCGCCCAGTGCTCTCTCTGTTCACGGATCGGCCTCCTGCCTTCACACAGGCA | 1278 |
| IGLC1_chr22:23236757-23236857 | TGTTAGACTCAGAAATGACCAGAGGGAGTGAATGAGGGGTGCAGAGAACTCCATGCTACCAGGTGAAGTTTGGGGTCATCACAGCTGCTGGGGTGG | 1279 |
| IGLC1_chr22:23236877-23236977 | CATAGTCTGTGGAGCAGCCCAGGAACAGCTGAGGTGAAGGGTTCTGTGGTCGGGCTTGTGAGACAGGAAACATCTCAGAGCCTCAGAGAGCCCTGA | 1280 |
| IGLC1_chr22:23236977-23237077 | GGCTTGTCTAGGTGGAGCCCACTCCTTGCCAGGAGAGCCAAGTGGGCTGGGGGCAGAGCCCGGTGCCTGTGAGGGATAGGAAGCTCCAGTTCAAAG | 1281 |

TABLE 6-continued

| Name | Sequence | SEQ ID NOs. |
|---|---|---|
| IGLC1_chr22:23237077-23237177 | CAGGCTTGGGTTCCCCACACACTGCCTGCCAGGACAGTCCTACAGGATGAGCAGGGACCCACAGTTCA CGGAGGAGGCTCTAGGTCCTGGAAGAATAA | 1282 |
| IGLC1_chr22:23237177-23237277 | AGTGGGTGATGAGGGGGTATAGGGATGGAAATGAGGGATCCAGGGGTCAAGGCCAGATTCTAAACTC AGACTCCAGAGATCAGAAGAAGGAACACA | 1283 |
| IGLC1_chr22:23237277-23237377 | GCCTGCCCTGGGTATATGGAGAATTGAGGCTGTAGGAGGAGGGGGTCTGGGCCAGGACACCTGAAAG GTGACTTGGGAGGGCTCCTAGGAAGGCACAG | 1284 |
| IGLC2_chr22:23242602-23242702 | TGAAAGCCCCACTGCTATGACCAGGTAGCCGGACGTGGGGTGATGCCAGAGAAAAGACTCCACGGAATA AGAGAGACCCAGGACAGCAGGCAGGCTCTC | 1285 |
| IGLC2_chr22:23242702-23242802 | CGATCCCCCCAGGCCCTTGCCCCATACACGGGCTCCAGAACACACATTTGGCTGGAACAGCCTGAGGGAC CAAAAGGCCCCAGTATCCCACAGAGCTGAG | 1286 |
| IGLC2_chr22:23242802-23242902 | GAGCCAGGCCAGAAAAGTAACCCCAGAGTTCGCTGTGCAGGGGAGACACAGAGCTCTCTTTATCTGTCAG GATGGCAGGAGGGGACAGGGTCAGGGCGCT | 1287 |
| IGLC2_chr22:23242902-23243002 | GAGGGTCAGATGTCGGTTGGGGGCCAAGGCCCCGAGAGATCTCAGGACAGAGCAGTGGTCAGGTGTCTAAG GTAAACAGCTCCCCGTCAGATCAGGGCAT | 1288 |
| IGLC2_chr22:23244157-23244257 | ATGCAGGACAGTCATGGTCTCAGCAGGAACACAGTTGAAATCCCCATTCCACACAAGACCGTTTAGCAGAA AGGAGTCCATACTTGTGCTGCCACCAGGAT | 1289 |
| IGLC2_chr22:23244257-23244357 | AGTCAAATGTCATGGTCTCAGCAGGAACACAGTTGAAATCCCCATTCCACACAAGACCGTTTAGCAGAA AGGAGTCCATACTTGTGCTGCCACCAGGAT | 1290 |
| IGLC2_chr22:23244357-23244457 | GTCCTGAGAAGCCTTGAGAGAATGAAACATACAGGTGCATTTCCTAGACTTGACAATGCACGTTAGCCAAG TAAAGGCAATGAAAAGTTCTCTACTAGGGA | 1291 |
| IGLJ3_chr22:23247257-23247357 | TTTGTTTGTTTTCTGTATCTTGTCTCAACTTGTGTCGTCAGCCTTTCTCCCTGCATCCCAGGCCTGAGCAAGGAC CTCTGCCCCCTGTTCAGACCCTTGCT | 1292 |
| IGLJ3_chr22:23247357-23247457 | TGCCTCAGCAGTTCACTACAACAACCACTTCACCTCTGACCGCAGGGGACAGGGGACTAGATAGAATGACTTAC TGAGCCTCGTCGTCTGTCTGTCTGTCTGT | 1293 |
| IGLJ3_chr22:23247457-23247567 | CTGTTTGTCTCTCTGTCTGTCTGACAGGCGCAGGCTGGGTCTTCTAAGCCTTGTTCTGTTCTGCCTCCTCA GTCTGGGTTCTTGTCGGAACAGCTTTGCC | 1294 |
| IGLJ3_chr22:23247567-23247667 | CTTGGGTTACCTGGGTTCCATCTCTGGGGAATTGGGAACAAGGGGTCTGAGGGAGGCTCAGGGAGGAGGCACCTCCTGGGAG ACTTTAGAAGGACCCCAGTGCCCTCGGGGCT | 1295 |
| IGLC3_chr22:23248182-23248282 | AGAGTTCCTCGTCAGGGGAGACACAGAGCTCTCTTTATCTGTCAGGATGGCAGGAGGGGACAGGGTCA GGGCGCTGAGGGTCAGATGTCGGTGTTGGGG | 1296 |
| IGLC3_chr22:23248282-23248382 | GCCAAGGCCCCGAGAGATCTCAGGACAGGTGGTCAGGTGTCTAAGGTAAAACAGCTCCCCGTGCAGATCA GGACATAGTGGAAAACACCCTGACCCTCT | 1297 |

TABLE 6-continued

| Name | Sequence | SEQ ID NOs. |
|---|---|---|
| IGLC3_chr22:23248382-23248482 | GCCTGGGCATAGACCTTCAGACACAGAGCCCCTGAACAAGGGCACCCAACACCTCATCATATACTGAGGT CAGGGGCTCCCCAGGTGGACACCAGGACTC | 1298 |
| IGLJ7_chr22:23263872-23263972 | AGAATATTCCGTGGAGAAGGTGGCCCCACAGCGCTGGGTCACGCGCCATCCCCCAAGACAGGCCAGGACACC ACAGACAGGGTGGTGGGTCTCAGAAAACTC | 1299 |
| IGLJ7_chr22:23263972-23264072 | AGGCCCTAAACGTGGATCCTTACCAATTCCTCCACTGAGGAAGACCTCAGAGACAGAGATGCCCAGGACAGG GACTTCTGGTAGGGACGGTGACTGGGACGG | 1300 |
| IGLJ7_chr22:23264072-23264172 | GTCCCTGTTTGTCAGGGAAAACCCACTGGAGAGTCAGATCCCCCAGATAACTTCTCACGACATGGAGACT CTTTCGAACACAGACAAAGCTCCACGTTCAGC | 1301 |
| IGLC7_chr22:23264172-23264272 | TCAGGGAGTAAAAAAAAAATGCTCAAATGGAGGCCTTTGATCTACTGGAATCCAGCCCCCAGGACTGAC ACCCTGTCTCACCAGGCAGCCCAGAGGGGT | 1302 |
| IGLC7_chr22:23278157-23278257 | CAGGGTCCACCAGAAGGCATCTCAGAACCAGCCAGCAGTTGGCCCTGATTGTCAGCAGGACCCCAGGGAG GGGGGTGGCCAGGACAGGGCTCTGAAGCCCC | 1303 |
| IGLC7_chr22:23278257-23278357 | CACCCCAGGACCTTCCCTGGGCAGAACGAGTTGGTGAGGGAGTGATGAGCAACCACAGGCCTCCTAACTT CCCAAGCTGGCGATTCTGAGAGGCCTCAAG | 1304 |
| IGLC7_chr22:23278357-23278457 | GCTGAGACACGGTTCAGCCTTTTAGGCCCTCTTGAACGTGTCCCCTGTCTCCACAGCCTGGAATGCACTC TCTTTTGACCCAGAAATCCTGCTCATAAG | 1305 |
| IGLC7_chr22:23282767-23282867 | CTGTCATTGTACAACACATCATTTCACTTGTTTTTCAAACATAGTGAATTCTTCCTAATTAAAGAAGAA AAGAGTATAAAGAGAAGAAAGTTTCCAGTGCA | 1306 |
| IGLC7_chr22:23282842-23282942 | GTATAAAGAGAAGAAAGTTTCCAGTGCAGCCTGGAGATCTGTACTGGTTGTATCTGGAATTCCAGACTCAGCC TTGCATTTCACATAGCAGATAGATGATGAT | 1307 |
| IGLC7_chr22:23282942-23283042 | GATGGAGGAGGAAGAAGAAGAGGAGGAGGAGGAGGAGGGAAAGAAGAAGAAGAAGAGAAGAGGAGGAGG AAGAAGAAGAACGAAGGGAAGAAGAAGAAGGATG | 1308 |
| TBC1D22A_chr22:47570209-47570309 | TCCAGGTCTGCCAGGTGTAGGGGAGGTTGACTGGTTCCATCATGGACCGGTTCCTCCATGGACCGGTTC CTCCGTGGACCGGTTCCCGCCCATGACCCGT | 1309 |
| TBC1D22A_chr22:47570309-47570409 | TCCGCCATGGACCACTCCTGCCCTGCCCTGGACCACTCCGCTGTCCTGCCGTGGACCGGTTCTGCCGTGGACTGGTTCCCGCC GTGGACCAGTTCCCGCTGTATACTGGTTC | 1310 |
| TBC1D22A_chr22:47570409-47570509 | TGCCCTGGACTGGTTCCCGCTGTCCCGCTGTGGACTGGTTCCTTGGGGCTCTAAGTGCGGAAGGGCCCAGAGCTGGTC CCTGCCCAGCGCCCCTGCTAGGGCTGTGTCC | 1311 |
| TMSB4X_chrX:12993264-12993364 | TCGTACTCGTGCGCCCTTCGTTCGGTGAGCCCCAGGGCGCCCCCTCCGTCCTCCGTCCTGCCTCCGT CCCCGCCCTTTCATCATCCGCGTCCCTGT | 1312 |
| TMSB4X_chrX:12993364-12993464 | GAAGGCATTCCCTAAATCCGAGCCCGAGTGGTTCTCCCCGGAAGGCTACTTTGGGGAGCTGGGGGGATG CGAAACACCCTAGATACTGGATAATGGGGT | 1313 |

TABLE 6-continued

| Name | Sequence | SEQ ID NOs. |
|---|---|---|
| TMSB4X_chrX:12993464-12993564 | GGGGAAATCGATGATTTAAGAACAAAACGAAAAACTGGCGTTTGCCGTGCGCTCGGAGGGACATTAAAAAATTCTTAGTGTTTGCCCGCCAAAGT | 1314 |
| TMSB4X_chrX:12993544-12993644 | TAGTGTTTGCCCGCCAAAGGTATTGTGCGTTGCCTTGGAGGCTGAGATATGGGGAATAGACAAGTCCTTTGTTCTGAGGTTCATCTTCCGAGCCCGAGC | 1315 |
| TMSB4X_chrX:12993644-12993744 | CTCCTCCCAGCCTCGGACGGCTCGCGCGGCTGCATCTGTGCCTGCGCGGCCGTGTGCTATGACATCTTTACAGTCCTTCTTGCAGAGACATG | 1316 |
| TMSB4X_chrX:12993744-12993844 | TGTGCCAGGGATGCCGAATTGCCGGAGAGCAGGCAAGACCGGCTTCCGGGGCGCGCGGGCCGCTTTGTGTGCGGGGCTGCATTGTGACGCGGGATG | 1317 |
| TMSB4X_chrX:12993844-12993944 | AAGCCGGTAGGGCGGTGTCGGAAGCTCCAGCCGCGGCCGCCGCCGCTTTGTGAGAGGACTAGAAAGCCGGATCCGGGCCCGCATCCTTGCGGAGGGCCGCG | 1318 |
| TMSB4X_chrX:12993944-12994044 | GCTAGGAAATGGAAACGCTTTTCCTACCTGGGCTCCATTTTAGGAATTCTTGCCGATTTTCCCACTTGAATTTTGGAAGTGGCTTTCCTTCTCTTTCCTT | 1319 |
| TMSB4X_chrX:12994044-12994144 | GTCCTAGCCAGCCTTTAATTTAAACGCTGTAATTAACAATTCGCAGTGGTCAATTCTGCAAGATTCGGCTTTGAGAGGCATCCGCCCTCT | 1320 |
| TMSB4X_chrX:12994144-12994244 | TTGGTCCACAGCGTTTGAAATATGGGAGGAGGGGGCGCGGGGGGTGTCGCCTCTTTTTCTGTAGAAAGAGGAAGCTCGTGAGCGCGGAACGGCAGCAGT | 1321 |
| TMSB4X_chrX:12994289-12994389 | AAGTGCAGTTCCCAGCCAGAGACAGCGGGGCGGGTGGCTCTTCCCTCACGCTCGCTCTTGGCTTGCTCCCTGCAGCTTTTCCTCCGACCACCATGTCTGAC | 1322 |
| TMSB4X_chrX:12994389-12994489 | AAACCCGATATGGCTGAGATCGAGAAATTCGAGAAAGTCGAAACTGAAGAAGACGCAAGAGAAAAATCCACTGCCTTCCAAAGAAAGTGAGCTCC | 1323 |
| TMSB4X_chrX:12994444-12994544 | AGACGCAAGAGAAAAATCCACTGCCTTCCAAAGAAAGTGAGCTCCGACCCACCCCCATCTTTAGAAAGGCTGGGTGGGAGCGGCCGGTGGGAGGGCGGGA | 1324 |
| DMD_chrX:3146106-3146206 | TTTATAGAAAGGCATATGGAACAGGAGTCATCCAAATATATCCCAGGGGTTGCAAATTGACCAAAAGAGTCACCTTTAGGGAAGCCTGCTTCTGAATGCT | 1325 |
| DMD_chrX:3146206-3146306 | TGTGGAATTTATCATTCTTCTGAATGGCTGTTGCATTTTATCTGCAGCTTTTACTCACCAGATGAGACCTCAGACATTTCAAATTCTGCGGAGCGTGGCTA | 1326 |
| DMD_chrX:3146306-3146406 | CACACCTTCATAGGAAAGCTTTTGCTGATTTCCCTGTTGTACTTTTCTCTTACACATTCTATGGGTATGGTAAACCTGGAGGTAGAGTCATAGCCAA | 1327 |

TABLE 6-continued

| Name | Sequence | SEQ ID NOs. |
|---|---|---|
| DMD_chrX:33146406-33146506 | GCACAGATAAAGCAGGCACAGAATCTCTGACCAGCCTCACAAAAGCAGACAAACACACAATCTTTTGCA CCTGTTTCTTCCACTCCGGTTGCCGTGAAT | 1328 |
| PABPC5_chrX:90026453-90026553 | TAGAAATGGTTCAACCAGTCCAATATCAATATAGCTGCTTATTACTCTTATTCACTTACTTCAAAGTGGCAT TTGTTTTGAGTAAGACTTTATTTAATTCT | 1329 |
| PABPC5_chrX:90026553-90026653 | TACCGTTAGCTTGAAACCATAGAGATCTTCTCTCTATTTGCCCTACTTCCTTCAAAAGTCAAATGACCTCC TACAAATAAAAGACGTTCTTATTTTCATT | 1330 |

What is claimed is:

1. A method comprising:
   (a) obtaining a biological sample from a subject;
   (b) selectively enriching the biological sample for at least 1,000 cell-free DNA molecules from genomic regions known to harbor phased variants;
   (c) obtaining, by a computer system, sequencing data for the at least 1,000 cell-free DNA molecules from a subject; and
   (d) processing, by the computer system, the sequencing data to identify one or more cell-free DNA molecules of the at least 1,000 cell-free DNA molecules, wherein identifying the one or more cell-free DNA molecules comprises aligning reads corresponding to each of the at least 1,000 cell-free DNA molecules to a reference human genome, wherein each of the one or more cell-free DNA molecules comprises a plurality of phased variants relative to a sequence from the reference genome, wherein at least 10% of the one or more cell-free DNA molecules comprises a first phased variant of the plurality of phased variants and a second phased variant of the plurality of phased variants that are separated by at least one nucleotide.

2. The method of claim 1, further comprising separating, in silico, (i) at least a portion of the identified one or more cell-free DNA molecules from (ii) one or more other cell-free DNA molecules of the plurality of cell-free DNA molecules that are not identified to comprise the plurality of phased variants.

3. The method of claim 1, wherein the method does not comprise barcode-mediated error suppression.

4. The method of claim 1, wherein at least 50% of the one or more cell-free DNA molecules comprise a first phased variant and a second phased variant that are separated by at least one nucleotide.

5. The method of claim 4, wherein 100% of the one or more cell-free DNA molecules comprise a first phased variant and a second phased variant that are separated by at least one nucleotide.

6. The method of claim 1, wherein the first and second phased variants are separated by at least 2 nucleotides.

7. The method of claim 1, wherein the first phased variant and the second phased variant are separated by at most 160 nucleotides.

8. The method of claim 1, further comprising sequencing the at least 1,000 cell-free DNA molecules from the subject.

9. The method of claim 1, wherein selectively enriching the biological sample for at least 1,000 cell-free DNA molecules from genomic regions known to harbor phased variants in a population of individuals or in a given individual comprises enriching from genomic regions that had been known to experience aberrant somatic hypermutation in a B-cell lymphoma.

10. The method of claim 9, wherein the aberrant somatic hypermutation is driven by activation-induced deamination.

11. The method of claim 9, wherein the genomic regions are genomic regions that had been identified as regions susceptible to APOBEC-mediated aberrant somatic hypermutation.

12. The method of claim 1, wherein the genomic regions are genomic regions known to harbor phased variants based on an evaluation of a population of individuals.

13. The method of claim 1, wherein the genomic regions are genomic regions known to harbor phased variants in a previously obtained sample from the subject.

14. The method of claim 13, wherein the previously obtained sample is a tumor DNA-containing sample.

\* \* \* \* \*